United States Patent
Daniels et al.

(10) Patent No.: US 12,162,867 B2
(45) Date of Patent: Dec. 10, 2024

(54) INHIBITORS OF RNA HELICASE DHX9 AND USES THEREOF

(71) Applicant: ACCENT THERAPEUTICS, INC., Lexington, MA (US)

(72) Inventors: Matthew H. Daniels, Somerville, MA (US); Kenneth W. Duncan, Westwood, MA (US); Brian Andrew Sparling, Saugus, MA (US); Andrew Stewart Tasker, Simi Valley, CA (US); Gavin Whitlock, Lexington, MA (US)

(73) Assignee: ACCENT THERAPEUTICS, INC., Lexington, MA (US)

( * ) Notice: Subject to any disclaimer, the term of this patent is extended or adjusted under 35 U.S.C. 154(b) by 22 days.

(21) Appl. No.: 18/620,036

(22) Filed: Mar. 28, 2024

(65) Prior Publication Data
US 2024/0279210 A1    Aug. 22, 2024

Related U.S. Application Data

(63) Continuation of application No. PCT/US2023/012929, filed on Feb. 13, 2023.

(60) Provisional application No. 63/309,917, filed on Feb. 14, 2022.

(51) Int. Cl.
| C07D 409/14 | (2006.01) |
| A61K 31/4436 | (2006.01) |
| A61K 31/506 | (2006.01) |
| C07D 409/04 | (2006.01) |

(52) U.S. Cl.
CPC ........ *C07D 409/14* (2013.01); *A61K 31/4436* (2013.01); *A61K 31/506* (2013.01); *C07D 409/04* (2013.01)

(58) Field of Classification Search
CPC ........... C07D 409/14; C07D 409/04; A61K 31/4436; A61K 31/506
See application file for complete search history.

(56) References Cited

FOREIGN PATENT DOCUMENTS

| WO | 2000/069849 A1 | 11/2000 | |
| WO | 2005/023761 A2 | 3/2005 | |
| WO | 2006/002421 A2 | 1/2006 | |
| WO | 2007/058990 A2 | 5/2007 | |
| WO | 2007/146712 A2 | 12/2007 | |
| WO | 2010/101964 A2 | 9/2010 | |
| WO | 2018/004290 A1 | 1/2018 | |
| WO | 2020/033413 A2 | 2/2020 | |
| WO | WO-2023154519 A1 * | 8/2023 | .............. A61P 35/00 |

OTHER PUBLICATIONS

U.S. Appl. No. 18/620,110, filed Mar. 28, 2024, Pending.
Gulliver et al., The enigmatic helicase DHX9 and its association with the hallmarks of cancer. Retrieved online at: https://www.future-science.com/doi/10.2144/fsoa-2020-0140. Future Sci OA. 2020:FSO650, 16 pages.
International Search Report and Written Opinion for Application No. PCT/US2023/012929, dated Apr. 6, 2023, 9 pages.

* cited by examiner

*Primary Examiner* — Kevin E Weddington
(74) *Attorney, Agent, or Firm* — McCarter & English, LLP; Xin Zhang; James M. Alburger

(57) ABSTRACT

Provided are compounds of the Formula (IIB):

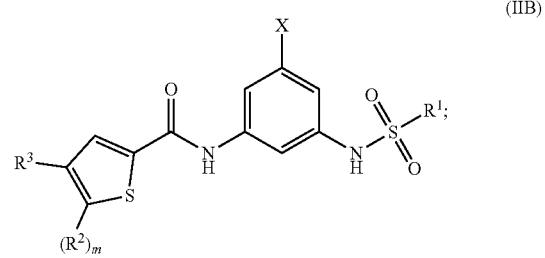

or pharmaceutically acceptable salts thereof, which are useful for the inhibition of DHX9 and in the treatment of a variety of DHX9 mediated conditions or diseases, such as cancer.

16 Claims, 9 Drawing Sheets
Specification includes a Sequence Listing.

SEQUENCE LISTING

```
Sequence total quantity: 11
SEQ ID NO: 1            moltype = RNA   length = 37
FEATURE                 Location/Qualifiers
misc_feature            1..37
                        note = Synthetic: Oligo1
source                  1..37
                        mol_type = other RNA
                        organism = synthetic construct
SEQUENCE: 1
gcctggtccc tgtccttgtt attttccttg gttaatt                             37

SEQ ID NO: 2            moltype = RNA   length = 37
FEATURE                 Location/Qualifiers
misc_feature            1..37
                        note = Synthetic: Oligo2
source                  1..37
                        mol_type = other RNA
                        organism = synthetic construct
SEQUENCE: 2
gaattaacca aggaaaataa caaggacagg gaccagg                             37
```

-continued

```
SEQ ID NO: 3              moltype = DNA   length = 20
FEATURE                   Location/Qualifiers
misc_feature              1..20
                          note = Synthetic: BRIP1-Circular-Forward
source                    1..20
                          mol_type = other DNA
                          organism = synthetic construct
SEQUENCE: 3
tctgtgtgcc agactgtgag                                                    20

SEQ ID NO: 4              moltype = DNA   length = 22
FEATURE                   Location/Qualifiers
misc_feature              1..22
                          note = Synthetic: BRIP1-Circular-Reverse
source                    1..22
                          mol_type = other DNA
                          organism = synthetic construct
SEQUENCE: 4
acaccaagtt ctgacgaaaa gg                                                 22

SEQ ID NO: 5              moltype = DNA   length = 20
FEATURE                   Location/Qualifiers
misc_feature              1..20
                          note = Synthetic: BRIP1-Linear-Forward
source                    1..20
                          mol_type = other DNA
                          organism = synthetic construct
SEQUENCE: 5
gtccatcctg aggtagtcgg                                                    20

SEQ ID NO: 6              moltype = DNA   length = 20
FEATURE                   Location/Qualifiers
misc_feature              1..20
                          note = Synthetic: BRIP1-Linear-Reverse
source                    1..20
                          mol_type = other DNA
                          organism = synthetic construct
SEQUENCE: 6
ttccccaggc tgacaagttc                                                    20

SEQ ID NO: 7              moltype = DNA   length = 22
FEATURE                   Location/Qualifiers
misc_feature              1..22
                          note = Synthetic: GAPDH-Forward
source                    1..22
                          mol_type = other DNA
                          organism = synthetic construct
SEQUENCE: 7
gtctcctctg acttcaacag cg                                                 22

SEQ ID NO: 8              moltype = DNA   length = 22
FEATURE                   Location/Qualifiers
misc_feature              1..22
                          note = Synthetic: GAPDH-Reverse
source                    1..22
                          mol_type = other DNA
                          organism = synthetic construct
SEQUENCE: 8
accaccctgt tgctgtagcc aa                                                 22

SEQ ID NO: 9              moltype = DNA   length = 23
FEATURE                   Location/Qualifiers
misc_feature              1..23
                          note = Synthetic: Forward Primer
source                    1..23
                          mol_type = other DNA
                          organism = synthetic construct
SEQUENCE: 9
gtgagccaag gaattttgtg ttt                                                23

SEQ ID NO: 10             moltype = DNA   length = 26
FEATURE                   Location/Qualifiers
misc_feature              1..26
                          note = Synthetic: Reverse Primer
source                    1..26
                          mol_type = other DNA
                          organism = synthetic construct
SEQUENCE: 10
ggtctgaact ttgccattaa tatctg                                             26
```

```
SEQ ID NO: 11          moltype = DNA  length = 18
FEATURE                Location/Qualifiers
misc_feature           1..18
                       note = Synthetic: Probe
source                 1..18
                       mol_type = other DNA
                       organism = synthetic construct
SEQUENCE: 11
ccatcttaca aggccttt                                                  18
```

INHIBITORS OF RNA HELICASE DHX9 AND USES THEREOF

RELATED APPLICATIONS

This application is a Continuation Application of PCT/US2023/012929, filed Feb. 13, 2023, which in turn claims priority to U.S. Provisional Application No. 63/309,917, filed on Feb. 14, 2022. The entire contents of the foregoing applications are expressly incorporated herein by reference.

SEQUENCE LISTING

The present application contains a Sequence Listing XML file, which has been submitted electronically in .xml format as part of the specification and is incorporate herein by reference in its entirety. Said XML file, created on Feb. 14, 2023, is named 130090-00420.xml, and is 14,841 bytes in size.

FIELD OF THE INVENTION

The present disclosure relates to inhibitors of RNA helicase DHX9, and pharmaceutically acceptable salts thereof, compositions of these compounds, processes for their preparation, and their use in the treatment of diseases.

BACKGROUND OF THE INVENTION

DHX9, also known as RNA Helicase A (RHA) or Nuclear DNA Helicase II (NDH II), is a DExH-box RNA helicase, which shuttles between nucleus and cytoplasm, and can use all four NTPs to power cycles of directional movement from 3' to 5'. Functionally, DHX9 can bind to and unwind or resolve dsDNA/RNA, ssDNA/RNA, DNA:RNA hybrids (such as R-loops), circular RNA, and DNA/RNA G quadruplexes. As such, DHX9 has regulatory roles in various RNA and DNA related cellular processes, such as transcription, translation, RNA splicing, editing, RNA transport and processing, microRNA genesis, and maintenance of genomic stability (Pan et al., 2021, *Current Protein & Peptide Science* (22), 29-40).

Due to its regulatory role in processes such as transcription and maintenance of genomic stability, DHX9 has shown to be a key regulator in a variety of cancer types (Gulliver et al., 2020, *Future Science OA* (2), FS0650). DHX9 has been shown to be involved in the regulation of genes associated with sustained proliferative signaling, evasion of growth suppressors, evasion of apoptosis, angiogenesis, and metastasis, all of which are hallmarks of cancer. Specifically, microsatellite instable cancers, such as Microsatellite Instable (MSI) colorectal cancer, and tumors with defective MisMatch Repair (MMR) exhibit a strong dependence on DHX9.

In addition to its role in cancer, DHX9 has been implicated in other diseases involving gene replication, translation or regulation. These diseases include viral infections and autoimmune disease.

Thus, there is a need for DHX9 inhibitors as potential therapeutic agents for treating diseases or disorders that are responsive to DHX9 inhibition.

SUMMARY OF THE INVENTION

The present disclosure provides compounds that are DHX9 inhibitors. In a first aspect, the present disclosure relates to compounds having the Formula I:

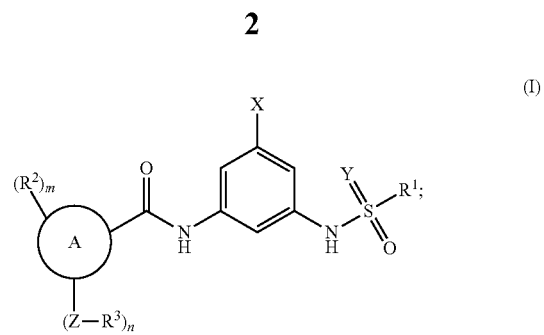

or a pharmaceutically acceptable salt thereof, wherein:

X is halo;
Y is O or $NR^y$;
$R^y$ is H or $C_{1-4}$alkyl;
$R^1$ is $C_{1-4}$alkyl or $C_{3-6}$cycloalkyl; wherein the $C_{1-4}$alkyl or $C_{3-6}$cycloalkyl are each optionally and independently substituted with 1 to 3 halo or —OH,
Ring A is a $C_{3-6}$cycloalkyl, 4 to 6-membered monocyclic heterocyclyl, 6 to 10 membered bicyclic heterocyclyl; phenyl, 5 to 6-membered monocyclic heteroaryl, or 8 to 10-membered bicyclic heteroaryl;
m is 0 to 3;
n is 0 or 2;
each $R^2$ is independently selected from $C_{1-4}$alkyl, $C_{3-6}$cycloalkyl, halo, $OR^{2a}$, cyano, $—NR^{2b}R^{2c}$, $—SO_2R^{2a}$, $—C(O)R^{2d}$, and $—C(O)NR^{2b}R^{2c}$ wherein the $C_{1-4}$alkyl and $C_{3-6}$cycloalkyl are optionally substituted with 1 to 4 $R^{2e}$; or 2 $R^2$ together form oxo;
$R^{2a}$ is H, $C_{1-4}$alkyl, $C_{1-4}$haloalkyl or $C_{1-4}$alkoxy $C_{1-4}$alkyl;
$R^{2d}$ is H, $C_{1-4}$alkyl, $C_{3-6}$cycloalkyl, $OR^{2a}$, phenyl, 4 to 6-membered monocyclic heterocyclyl, 6 to 8-membered bicyclic heterocyclyl, or 5 to 6-membered monocyclic heteroaryl, wherein the $C_{1-4}$alkyl is optionally substituted with 1 to 3 halo and the 5- to 6-membered monocyclic heteroaryl is optionally substituted with 1 to 3 $C_{1-4}$alkyl, $C_{1-4}$haloalkyl, or phenyl;
$R^{2b}$ and $R^{2c}$ are each independently selected from H, $C_{1-4}$alkyl, $C_{3-6}$cycloalkyl, phenyl, 4 to 6-membered monocyclic heterocyclyl and 5 to 6-membered monocyclic heteroaryl, wherein the $C_{1-4}$alkyl is optionally substituted with 1 to 3 substituents independently selected from halo and $C_{1-3}$alkoxy; or $R^{2b}$ and $R^{2c}$, together with the nitrogen to which they are attached form a 4 to 6 membered monocyclic heterocyclyl or 6 to 10 membered bicyclic heterocyclyl; wherein the 4 to 6 membered monocyclic heterocyclyl or 6 to 10 membered bicyclic heterocyclyl are each optionally substituted with 1 to 3 $R^{2d}$;
each $R^{2e}$ is independently selected from halo, cyano, $NR^{2b}R^{2c}$, $OR^{2a}$, phenyl, and 4 to 6 membered monocyclic heterocyclyl;
Z is a bond, $—CH_2—$, $—O—$, $—O—C_{1-4}$alkylene-*, $—C_{1-4}$alkylene-O—*, $—C(O)—$, $—C(O)O—$*, $—OC(O)—$*, $—S(O)_2—$, $—S(O)_2N(Z^a)—$*, $—N(Z^a)S(O)_2—$*, $—N(Z^a)—$, $—N(Z^a)—C_{1-4}$alkylene-*, $—C_{1-4}$ alkylene-N($Z^a$)—*, $—C(O)N(Z^a)—$*, $—N(Za)C(O)—$*, or $—C(O)N(Z^a)—C_{1-3}$alkylene-*, wherein indicates the attachment point to $R^3$;
$Z^a$ is H or $C_{1-4}$alkyl;
$R^3$ is $C_{3-6}$cycloalkyl, 7 to 10-membered bicyclic carbocyclyl, 4 to 6-membered monocyclic heterocyclyl, 6 to 10-membered bicyclic heterocyclyl, phenyl, 5 to 6-membered monocyclic heteroaryl, or 8 to 10-membered bicyclic heteroaryl, wherein the $C_{3-6}$cycloalkyl, 7 to 10-membered bicyclic carbocyclyl, 4 to 6-membered monocyclic heterocyclyl, 6 to 10-membered bicyclic heterocyclyl, phenyl, 5 to 6-membered monocyclic heteroaryl, or 8 to 10-membered bicyclic heteroaryl are each optionally and independently substituted with 1 to 4 $R^4$;

each $R^4$ is independently selected from $C_{1-4}$alkyl, $C_{2-4}$alkenyl, $C_{2-4}$alkynyl, halo, $OR^{4a}$ cyano, $-NR^{4b}R^{4c}$, $-C(O)R^{4a}$, $-C(O)OR^{4a}$, $-C(O)NR^{4b}R^{4c}$, $-NR^{4b}C(O)R^{4a}$, $-NR^{4b}C(O)OR^{4a}$, $-NR^{4b}SO_2R^{4a}$, $-SR^{4a}$, $-S(O)R^{4a}$, $-SO_2R^{4a}$, $SO_2NR^{4b}R^{4c}$, $-P(O)R^{4b}R^{4c}$, phenyl, 5 to 6-membered monocyclic heteroaryl, 4 to 6-membered monocyclic heterocyclyl, and 6 to 10-membered bicyclic heterocyclyl, wherein the $C_{1-4}$alkyl, $C_{2-4}$alkenyl, or $C_{2-4}$alkynyl is optionally substituted with 1 to 4 $R^{4d}$, and wherein the phenyl, 5 to 6-membered monocyclic heteroaryl, 4 to 6-membered monocyclic heterocyclyl and 6 to 10-membered bicyclic heterocyclyl are each optionally substituted with 1 to 3 $R^{4e}$ and further optionally substituted with 1 or 2 oxo; or two $R^4$ together form oxo;

$R^{4a}$ is H, $C_{1-4}$alkyl optionally substituted with 1 to 4 $R^{4d}$, $-NR^{4b}R^{4c}$, $C_{3-6}$cycloalkyl, 4 to 6-membered monocyclic heterocyclyl, phenyl, or 5 to 6-membered monocyclic heteroaryl; wherein the $C_{3-6}$cycloalkyl, 4 to 6-membered monocyclic heterocyclyl, phenyl or 5 to 6-membered monocyclic heteroaryl are each optionally and independently substituted with 1 to 3 $R^{4e}$;

$R^{4b}$ and $R^{4c}$ are each independently selected from H, phenyl, 4 to 6-membered monocyclic heterocyclyl, 5 to 6-membered monocyclic heteroaryl, and $C_{1-4}$alkyl optionally substituted with 1 to 4 $R^{4d}$; or $R^{4b}$ and $R^{4c}$ together with the nitrogen atom to which they are attached to form a 4 to 6-membered monocyclic heterocyclyl;

each $R^{4d}$ is independently selected from halo, $OR^{4f}$, $-C(O)C_{1-4}$alkyl, $-C(O)NR^{4b}R^{4c}$, $-C(O)C_{1-4}$haloalkyl, $-C(O)OR^{4f}$, $-NR^{4b}R^{4c}$, phenyl, and 5 to 6-membered monocyclic heteroaryl, wherein the phenyl and 5 to 6-membered monocyclic heteroaryl are each optionally substituted with 1 to 3 $R^{4g}$;

each $R^{4e}$ is independently selected from halo, $C_{1-4}$alkyl, cyano, $OR^{4f}$, $-NR^{4b}R^{4c}$, $-C(O)H$, $-C(O)R^{4h}$, $-SO_2C_{1-3}$alkyl, and $-C(O)NR^{4b}R^{4c}$, wherein $C_{1-4}$alkyl is optionally substituted with 1 to 3 substitutes independently selected from halo, $-SO_2C_{1-3}$alkyl and $-C(O)NR^{4b}R^{4c}$; and $-C(O)NR^{4b}R^{4c}$; or two $R^{4e}$ together form oxo;

$R^{4f}$ is H, $C_{1-4}$alkyl, $C_{1-4}$haloalkyl, phenyl or 5 to 6-membered monocyclic heteroaryl, wherein the phenyl and 5 to 6-membered monocyclic heteroaryl are each optionally substituted with one to three halo;

each $R^{4g}$ is independently selected from halo, $OR^{4f}$, $C_{1-4}$alkyl, $C_{1-4}$haloalkyl, halo, cyano, $-NR^{4b}R^{4c}$, $-C(O)H$, and $-C(O)OR^{4f}$; and each $R^{4h}$ is independently $C_{1-4}$alkyl, $C_{3-6}$cycloalkyl, $C_{1-3}$alkoxy or $-N(R^{4b})_2$.

Another aspect of the disclosure relates to pharmaceutical compositions comprising compounds of Formula (I) or pharmaceutically acceptable salts thereof, and a pharmaceutical carrier.

In yet another aspect, the present disclosure provides a method of treating a disease or disorder that is responsive to inhibition of DHX9 in a subject comprising administering to said subject an effective amount of at least one compound described herein or a pharmaceutically acceptable salt thereof. In some embodiments, the method is for the treatment of cancer.

Another aspect of the present disclosure relates to the use of at least one compound described herein or a pharmaceutically acceptable salt thereof, for the manufacture of a medicament for the treatment of a disease or disorder responsive to inhibition of DHX9. Also provided is a compound described herein or a pharmaceutically acceptable salt thereof for use in treating a disease or disorder responsive to inhibition of DHX9.

DETAILED DESCRIPTION OF THE INVENTION

Figure 1A:
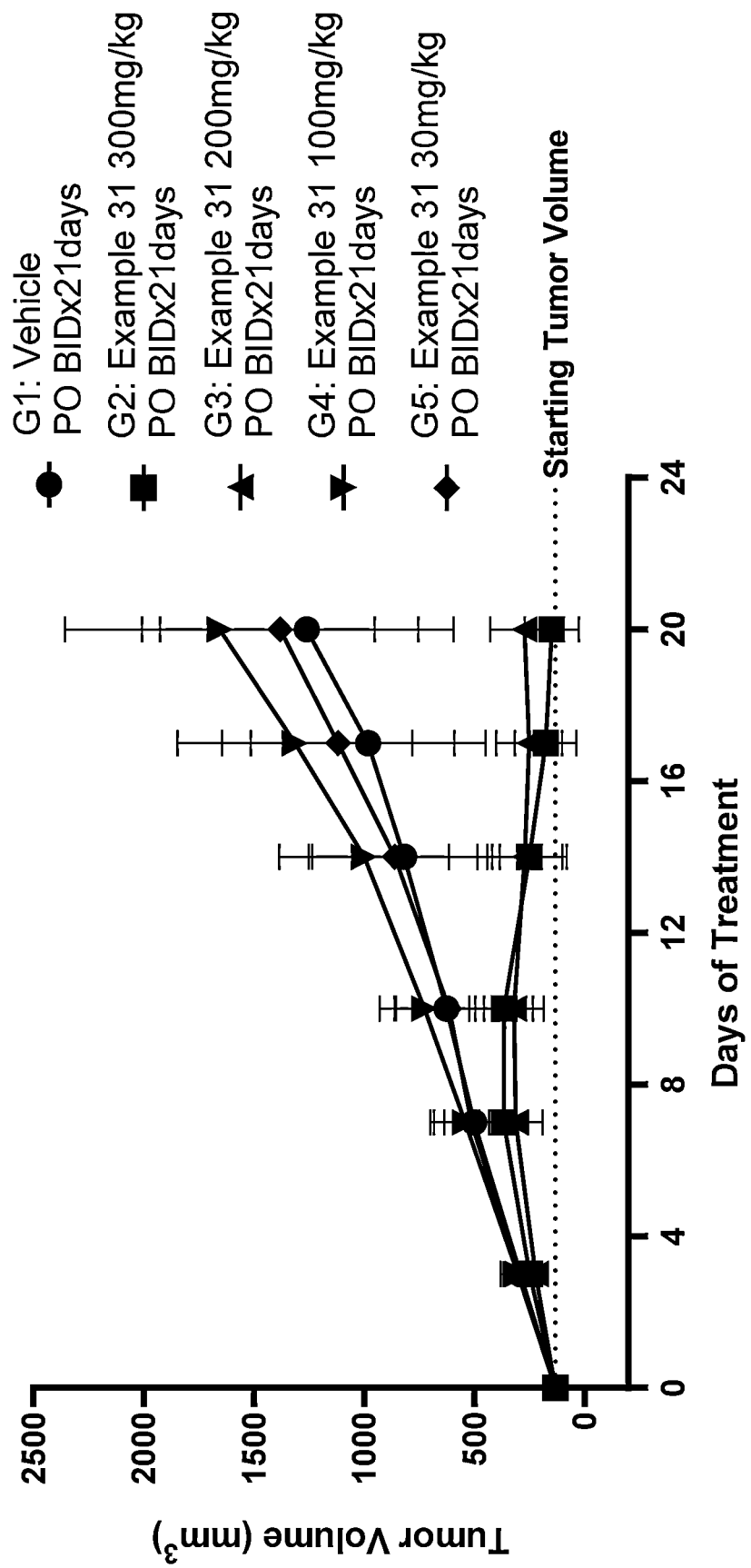
FIG. 1a and FIG. 1b show tumor volume over time for an in vivo efficacy study of compound of Example 31 in LS411N Xenografts.

The present disclosure provides compounds and pharmaceutical compositions thereof that may be useful in the treatment of diseases or disorders through mediation of DHX9 function/activity. In some embodiments, the compounds of present disclosure are DHX9 inhibitors.

COMPOUNDS AND COMPOSITIONS

In a first embodiment, the present disclosure provides a compound of Formula (I):

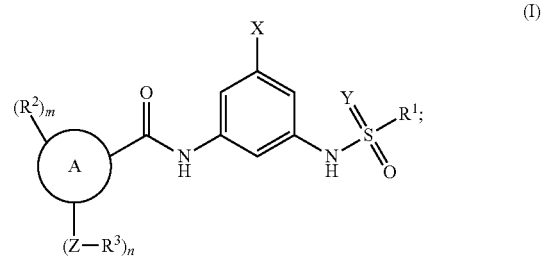

or a pharmaceutically acceptable salt thereof, wherein the variables in Formula (I) are as defined as follows:

X is halo;

Y is O or NR$^y$;

R$^y$ is H or C$_{1-4}$alkyl;

R$^1$ is C$_{1-4}$alkyl or C$_{3-6}$cycloalkyl; wherein the C$_{1-4}$alkyl or C$_{3-6}$cycloalkyl are each optionally and independently substituted with 1 to 3 halo;

Ring A is a C$_{3-6}$cycloalkyl, 4 to 6-membered monocyclic heterocyclyl, 6 to 10 membered bicyclic heterocyclyl; phenyl, 5 to 6-membered monocyclic heteroaryl, or 8 to 10-membered bicyclic heteroaryl;

m is 0 to 3;

n is 0 or 1;

each R$^2$ is independently selected from C$_{1-4}$alkyl, C$_{3-6}$cycloalkyl, halo, OR$^{2a}$, cyano, —NR$^{2b}$R$^{2c}$, —SO$_2$R$^{2a}$, —C(O)R$^{2d}$, and —C(O)NR$^{2b}$R$^{2c}$, wherein the C$_{1-4}$alkyl and C$_{3-6}$cycloalkyl are optionally substituted with 1 to 4 R$^{2e}$; or 2 R$^2$ together form oxo;

R$^{2a}$ is H, C$_{1-4}$alkyl, C$_{1-4}$haloalkyl or C$_{1-4}$alkoxyC$_{1-4}$alkyl;

R$^{2d}$ is H, C$_{1-4}$alkyl, C$_{3-6}$cycloalkyl, OR$^{2a}$, phenyl, 4 to 6-membered monocyclic heterocyclyl or 5 to 6-membered monocyclic heteroaryl, wherein the C$_{1-4}$alkyl is optionally substituted with 1 to 3 halo;

R$^{2b}$ and R$^{2c}$ are each independently selected from H, C$_{1-4}$alkyl, C$_{3-6}$cycloalkyl, phenyl, 4 to 6-membered monocyclic heterocyclyl and 5 to 6-membered monocyclic heteroaryl; or R$^{2b}$ and R$^{2c}$, together with the nitrogen to which they are attached form a 4 to 6 membered monocyclic heterocyclyl or 6 to 10 membered bicyclic heterocyclyl; wherein the 4 to 6 membered monocyclic heterocyclyl or 6 to 10 membered bicyclic heterocyclyl are each optionally substituted with 1 to 3 R$^{2d}$;

each R$^{2e}$ is independently selected from halo, cyano, NR$^{2b}$R$^{2c}$, OR$^{2a}$, phenyl, and 4 to 6 membered monocyclic heterocyclyl;

Z is a bond, —CH$_2$—, —O—, —O—C$_{1-4}$alkylene-*, —C$_{1-4}$alkylene-O—*, —C(O)—, —C(O)O—*, —OC(O)—*, —S(O)$_2$—, —S(O)$_2$N(Z$^a$)—*, —N(Z$^a$)S(O)$_2$—*, —N(Z$^a$)—, —N(Z$^a$)—C$_{1-4}$alkylene-*, —C$_{1-4}$alkylene-N(Z$^a$)—*, —C(O)N(Z$^a$)—*, or —C(O)N(Z$^a$)—C$_{1-3}$alkylene-*, wherein * indicates the attachment point to R$^3$;

Z$^a$ is H or C$_{1-4}$alkyl;

R$^3$ is C$_{3-6}$cycloalkyl, 7 to 10-membered bicyclic carbocyclyl, 4 to 6-membered monocyclic heterocyclyl, 6 to 10-membered bicyclic heterocyclyl, phenyl, 5 to 6-membered monocyclic heteroaryl, or 8 to 10-membered bicyclic heteroaryl, wherein the C$_{3-6}$cycloalkyl, 7 to 10-membered bicyclic carbocyclyl, 4 to 6-membered monocyclic heterocyclyl, 6 to 10-membered bicyclic heterocyclyl, phenyl, 5 to 6-membered monocyclic heteroaryl, or 8 to 10-membered bicyclic heteroaryl are each optionally and independently substituted with 1 to 4 R$^4$;

each R$^4$ is independently selected from C$_{1-4}$alkyl, halo, OR$^{4a}$, cyano, —NR$^{4b}$R$^{4c}$, —C(O)R$^{4a}$, —C(O)OR$^{4a}$, —C(O)NR$^{4b}$R$^{4c}$, —NR$^{4b}$C(O)R$^{4a}$, —NR$^{4b}$C(O)OR$^{4a}$, —SR$^{4a}$, —SO$_2$R$^{4a}$, —SO$_2$NR$^{4b}$R$^{4c}$, —P(O)R$^{4b}$R$^{4c}$, phenyl, 5 to 6-membered monocyclic heteroaryl, 4 to 6-membered monocyclic heterocyclyl, and 6 to 10-membered bicyclic heterocyclyl, wherein the C$_{1-4}$alkyl is optionally substituted with 1 to 4 R$^{4d}$, and wherein the phenyl, 5 to 6-membered monocyclic heteroaryl, 4 to 6-membered monocyclic heterocyclyl and 6 to 10-membered bicyclic heterocyclyl are each optionally substituted with 1 to 3 R$^{4e}$; or two R$^4$ together form oxo;

R$^{4a}$ is H, C$_{1-4}$alkyl optionally substituted with 1 to 4 R$^{4d}$, C$_{3-6}$cycloalkyl, 4 to 6-membered monocyclic heterocyclyl, phenyl, or 5 to 6-membered monocyclic heteroaryl; wherein the C$_{3-6}$cycloalkyl, 4 to 6-membered monocyclic heterocyclyl, phenyl or 5 to 6-membered monocyclic heteroaryl are each optionally and independently substituted with 1 to 3 R$^{4e}$;

R$^{4b}$ and R$^{4c}$ are each independently selected from H, phenyl, 4 to 6-membered monocyclic heterocyclyl, 5 to 6-membered monocyclic heteroaryl, and C$_{1-4}$alkyl optionally substituted with 1 to 4 R$^{4d}$;

each R$^{4d}$ is independently selected from halo, OR$^{4f}$, —C(O)C$_{1-4}$alkyl, —C(O)NR$^{4b}$R$^{4c}$, —C(O)C$_{1-4}$haloalkyl, phenyl, and 5 to 6-membered monocyclic heteroaryl, wherein the phenyl and 5 to 6-membered monocyclic heteroaryl are each optionally substituted with 1 to 3 R$^{4g}$;

each R$^{4e}$ is independently selected from halo, C$_{1-4}$alkyl optionally substituted with 1 to 3 halo, cyano, OR$^{4f}$, —NR$^{4b}$R$^{4c}$, —C(O)H, —C(O)C$_{1-4}$alkyl, —C$_{1-4}$alkylene-C(O)NR$^{4b}$R$^{4c}$, and —C(O)NR$^{4b}$R$^{4c}$; or two R$^{4c}$ together form oxo;

R$^{4f}$ is H, C$_{1-4}$alkyl, C$_{1-4}$haloalkyl, phenyl or 5 to 6-membered monocyclic heteroaryl, wherein the phenyl and 5 to 6-membered monocyclic heteroaryl are each optionally substituted with one to three halo;

each R$^{4g}$ is independently selected from halo, OR$^{4f}$, C$_{1-4}$alkyl, halo, cyano, —NR$^{4b}$R$^{4c}$, —C(O)H, and —C(O)OR$^{4f}$. In some embodiments, Y is O.

In a second embodiment, for the compound of Formula (I) described in the first aspect or the first embodiment, or a pharmaceutically acceptable salt thereof, X is Cl, Br, or F; and the remaining variables are as described in the first aspect or the first embodiment.

In a third embodiment, for the compound of Formula (I) described in the first aspect or the first embodiment, or a pharmaceutically acceptable salt thereof, X is Cl or Br; and the remaining variables are as described in the first aspect or the first embodiment.

In a fourth embodiment, for the compound of Formula (I) described in the first aspect or the first embodiment, or a pharmaceutically acceptable salt thereof, X is Cl; and the remaining variables are as described in the first aspect or the first embodiment.

In a fifth embodiment, for the compound of Formula (I) described in the first aspect or the first embodiment, or a pharmaceutically acceptable salt thereof, ring A is selected from phenyl, thiophenyl, pyrrolyl, pyrazoyl, furanyl, isothiazoyl, thiazoyl, imidazoyl, cyclobutyl, benzofuranyl, 2-oxo-2,3-dihydro-1H-benzo[d]imidazolyl, imidazo[1,2-a]pyridin-6-yl, 1,4,5,6-tetrahydrocyclopenta[c]pyrazolyl, 2-oxo-2,3-dihydro-1H-imidazolyl, indolizinyl, pyrrolo[1,2-a]pyrimidinyl, pyrrolo[1,2-c]pyrimidinyl, pyrrolo[1,2-a]pyraziny, 5,6-dihydro-4H-cyclopenta[b]thiophenyl, 5-oxo-5H-thiazolo[3,2-a]pyridinyl, thieno[3,2-b]pyridinyl, thieno[3,2-c]pyridinyl, thieno[2,3-c]pyridinyl, benzothiophenyl, thieno[3,2-d]pyrimidinyl, pyrrolo[1,2-b]pyridazinyl, pyrrolo[1,2-a]pyrazinyl, pyrrolo[1,2-a]pyrimidinyl, pyrrolo[1,2-b]pyrimidinyl, pyrrolo[1,2-c]pyrimidinyl, 1-oxo-1,2-dihydropyrrolo[1,2-a]pyrazinyl, pyrrolo[2,1-f][1,2,4]triazinyl, 4,5,6,7-tetrahydrothieno[2,3-c]pyridinyl, 5,6-dihydro-4H-cyclopenta[b]thiophenyl, and 4,7-dihydro-5H-thieno[2,3-c]pyranyl; and the remaining variables are as described in the first aspect or in the first, second, third, or fourth embodiment. In an alternative fifth embodiment, ring A is phenyl, thiophenyl, pyrrolyl, pyrazoyl, furanyl, isothiazoyl, thiazoyl, imidazoyl, cyclobutyl, benzofuranyl, 2-oxo-2,3-dihydro-1H-benzo[d]imidazolyl, imidazo[1,2-a]pyridin-6-yl, 1,4,5,6-tetrahydrocyclopenta[c]pyrazolyl, 2-oxo-2,3-dihydro-1H-imidazolyl, indolizinyl, pyrrolo[1,2-a]pyrimidinyl, pyrrolo[1,2-c]pyrimidinyl, pyrrolo[1,2-a]pyrazinly, 5-oxo-5H-thiazolo[3,2-a]pyridinyl, thieno[3,2-b]pyridinyl, thieno[3,2-c]pyridinyl, thieno[2,3-c]pyridinyl, benzothiophenyl, thieno[3,2-d]pyrimidinyl, pyrrolo[1,2-b]pyridazinyl, pyrrolo[1,2-a]pyrazinyl, pyrrolo[1,2-a]pyrimidinyl, pyrrolo[1,2-b]pyrimidinyl, pyrrolo[1,2-c]pyrimidinyl, 1-oxo-1,2-dihydropyrrolo[1,2-a]pyrazinyl, pyrrolo[2,1-f][1,2,4]triazinyl, 4,5,6,7-tetrahydrothieno[2,3-c]pyridinyl, 5,6-dihydro-4H-cyclopenta[b]thiophenyl, and 4,7-dihydro-5H-thieno[2,3-c]pyranyl; and the remaining variables are as described in the first aspect or in the first, second, third, or fourth embodiment.

In a sixth embodiment, for the compound of Formula (I) described in the first aspect or the first embodiment, or a pharmaceutically acceptable salt thereof, ring A is represented by the following formula:

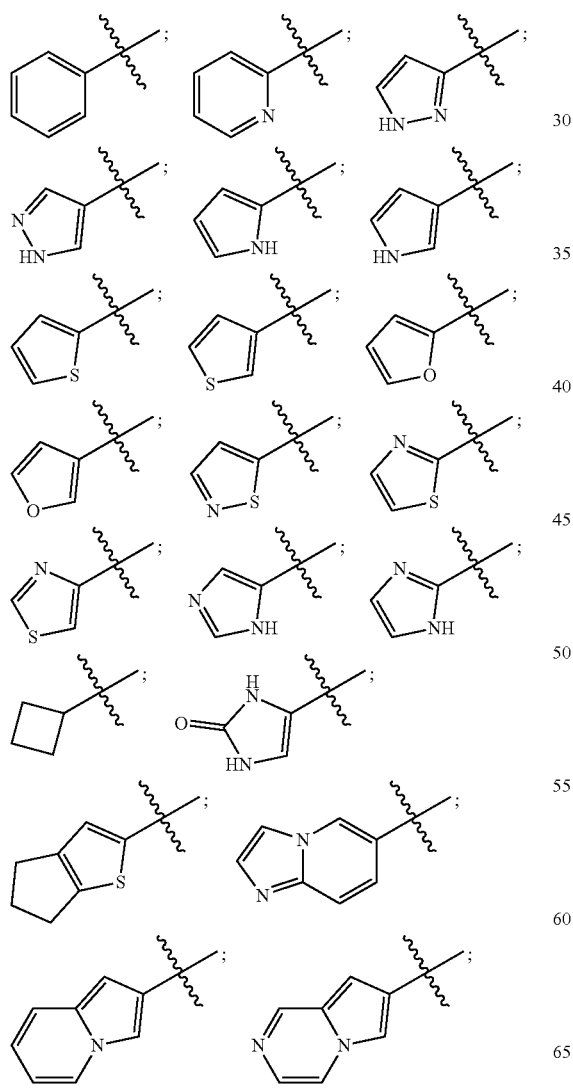

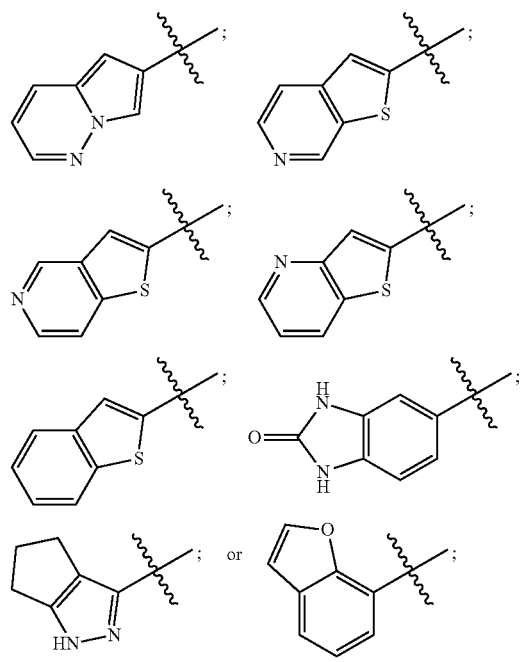

each of which is substituted with 0 to 2 $R^2$ and 0 to 1 $Z$—$R^3$; and the remaining variables are as described in the first aspect or the first, second, third, or fourth embodiment. In an alternative sixth embodiment, ring A is

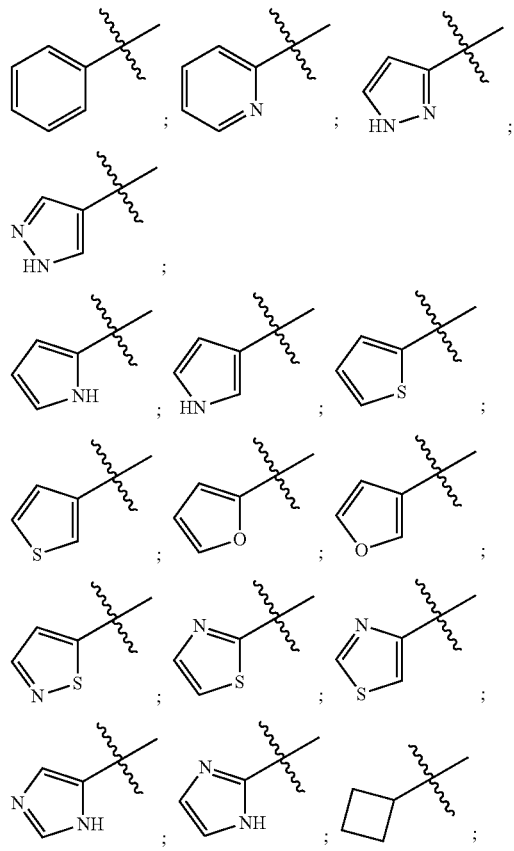

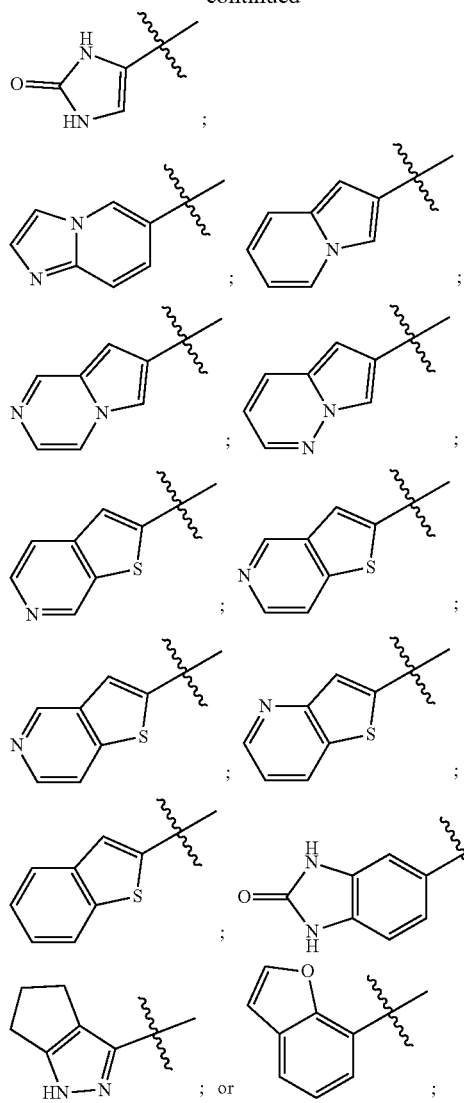

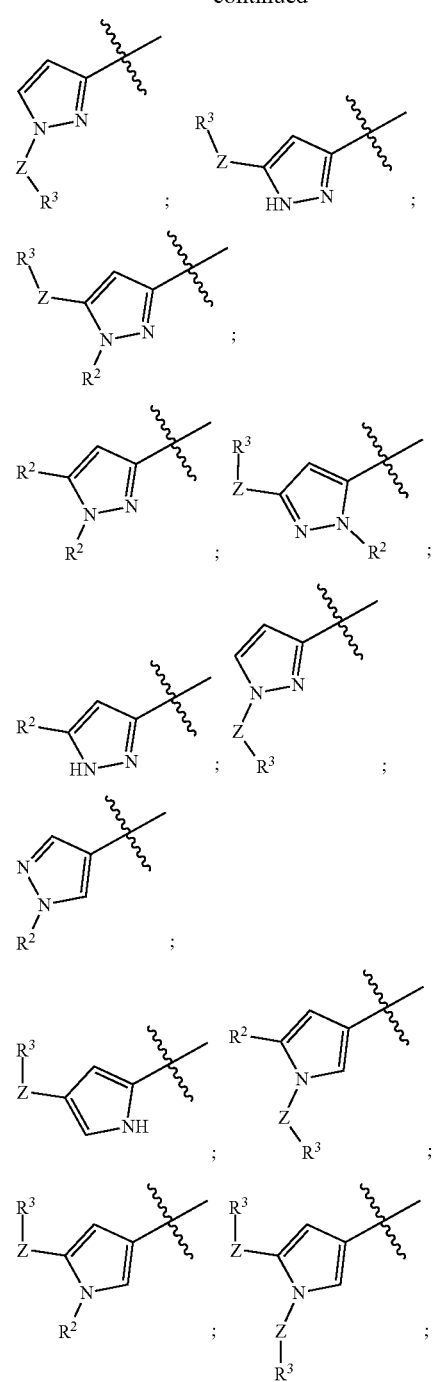

each of which is substituted with 0 to 2 $R^2$ and 0 to 1 $Z$—$R^3$; and the remaining variables are as described in the first aspect or the first, second, third, or fourth embodiment.

In a seventh embodiment, for the compound of Formula (I) described in the first aspect or in the first embodiment, or a pharmaceutically acceptable salt thereof, ring A is represented by the following formula:

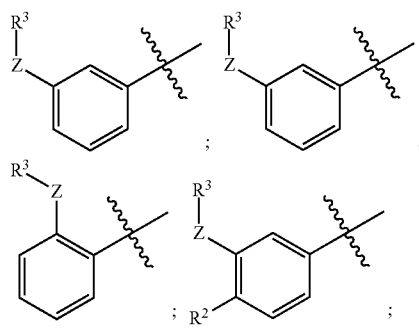

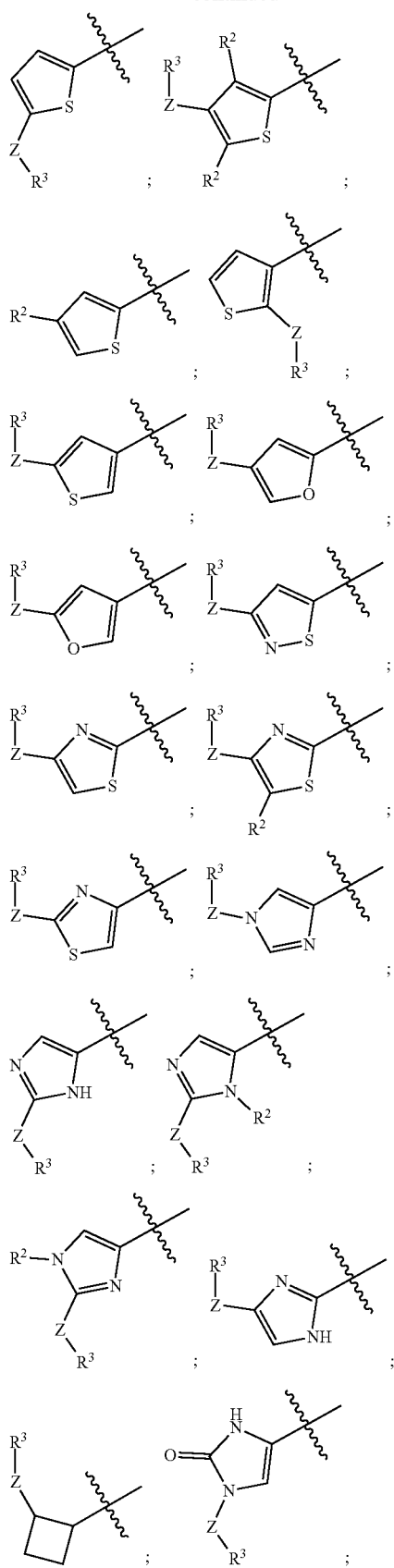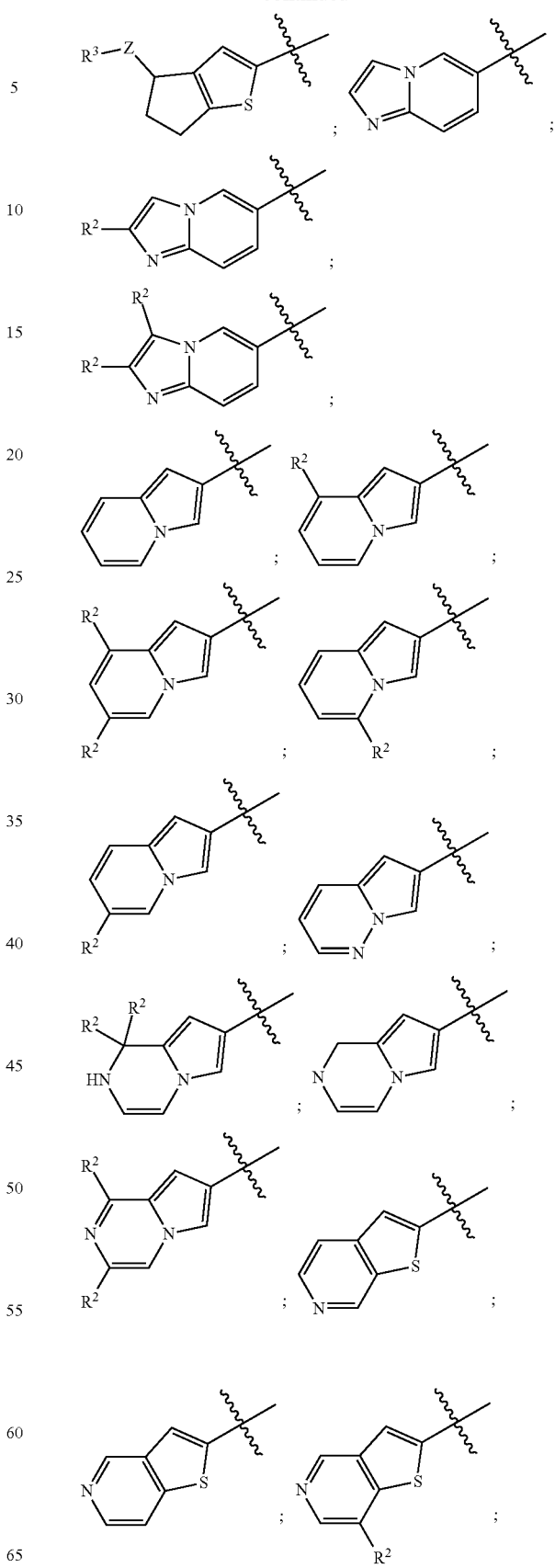

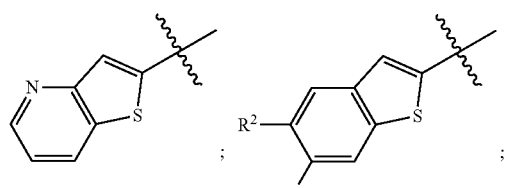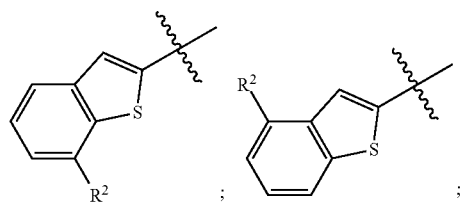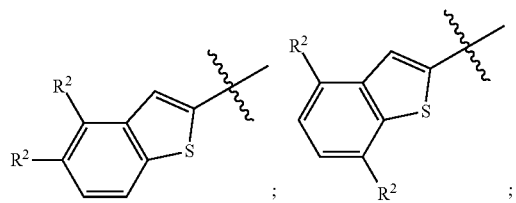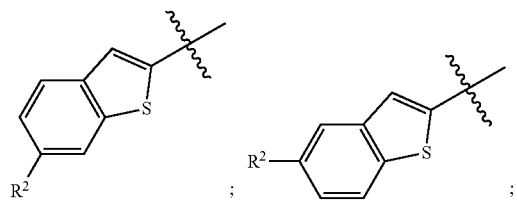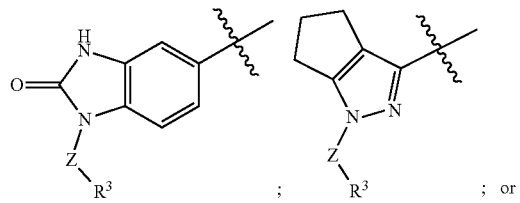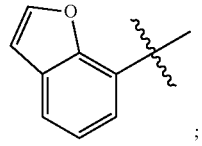
and the remaining variables are as described in the first aspect or in the first, second, third, or fourth embodiment. In an alternative seventh embodiment, ring A is
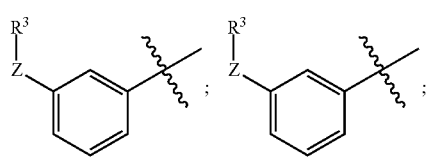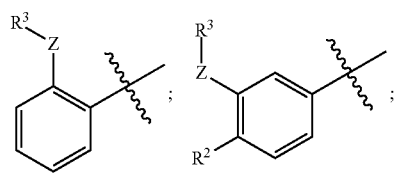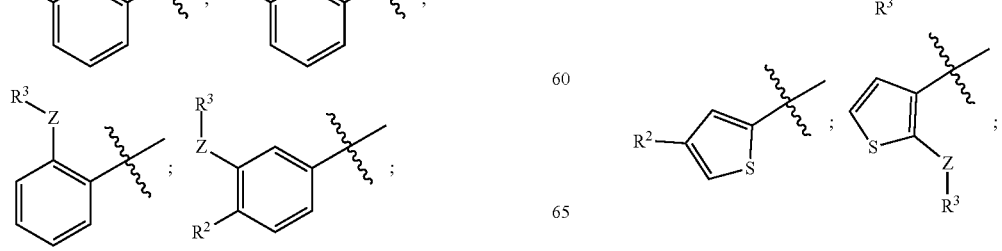

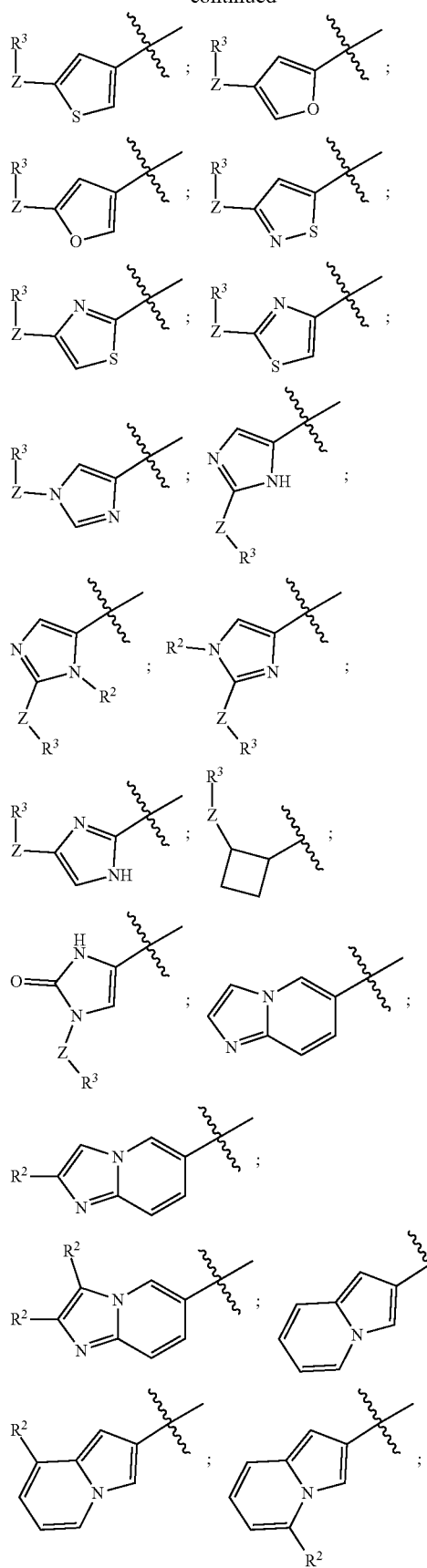
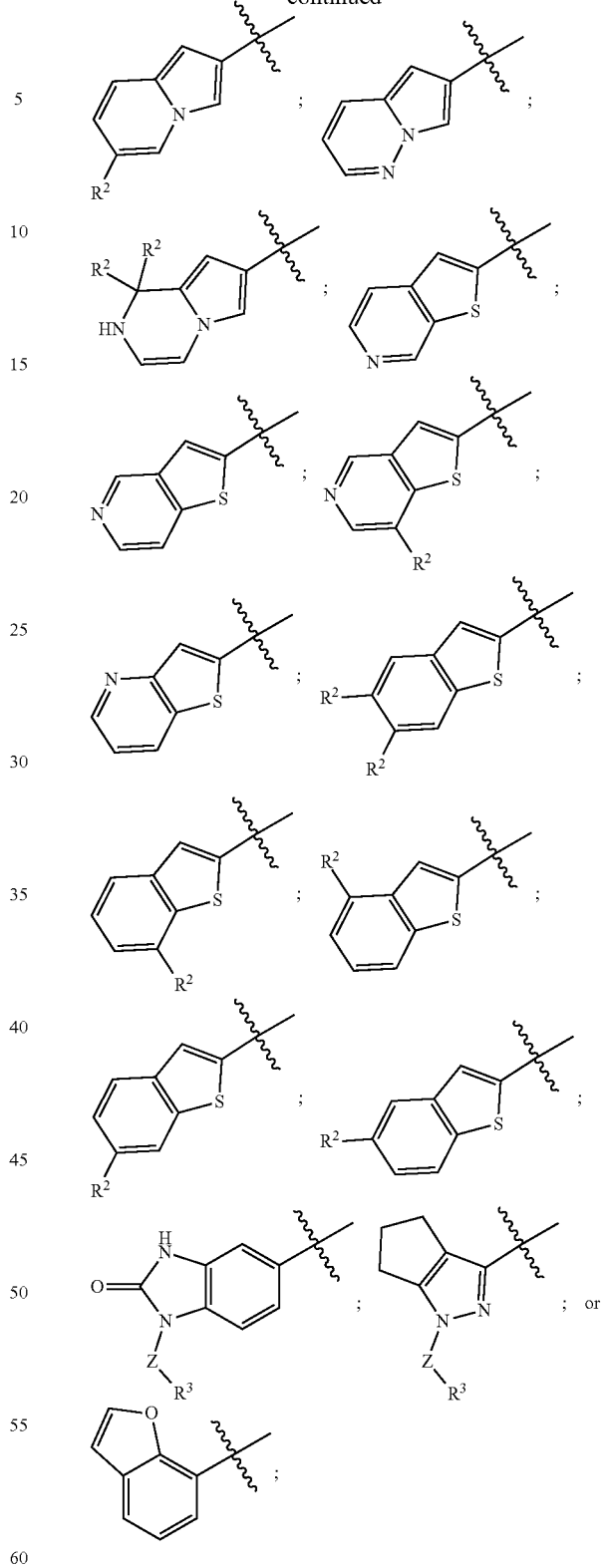
and the remaining variables are as described in the first aspect or in the first, second, third, or fourth embodiment.
In an eighth embodiment, for the compound of Formula (I) described in the first aspect or the first embodiment, or a pharmaceutically acceptable salt thereof, ring A is phenyl, thiophenyl, pyrrolyl, pyrazolyl, furanyl, isothiazoyl, and imidazolyl; and the remaining variables are as described in the first aspect or in the first, second, third, or fourth embodiment.

In a ninth embodiment, for the compound of Formula (I) described in the first aspect or in the first embodiment, or a pharmaceutically acceptable salt thereof, ring A is

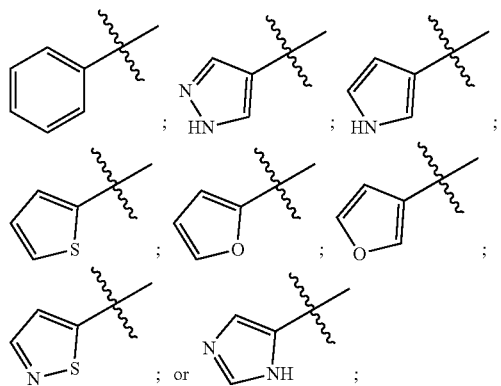

each of which is substituted with 0 to 1 R² and 1 R³; and the remaining variables are as described in the first, second, third, or fourth embodiment.

In a tenth embodiment, for the compound of Formula (I) described in the first aspect or in the first embodiment, or a pharmaceutically acceptable salt thereof, ring A is

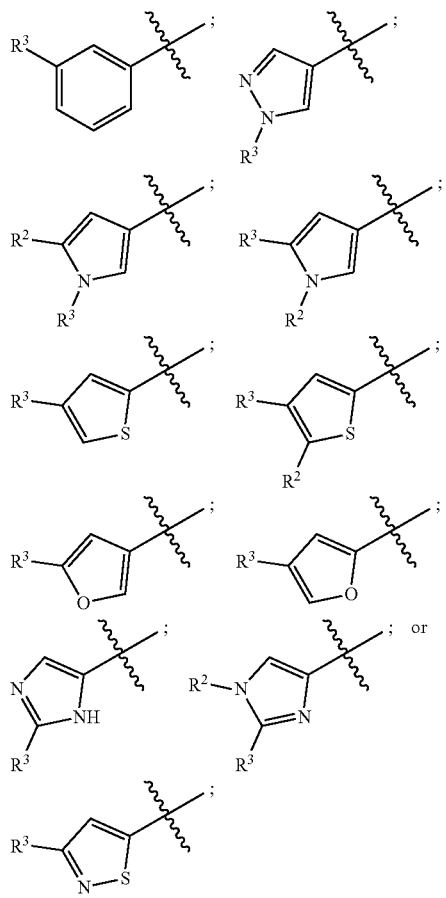

and the remaining variables are as described in the first aspect or in the first, second, third, or fourth embodiment.

In an eleventh embodiment, for the compound of Formula (I) described in first aspect or the first embodiment, R² is selected from —OCH₃, cyclopropyl, —CH₃, —CF₃, —CH₂CH₃, —CH(CH₃)₂, —CH(OH)CH₃, —C(CH₃)₂OH, —CH₂OCH₃, —CH₂OH, —CH₂CF₃, —CH₂CH₂OH, —CH₂CH₂CH₂OH, —CH₂CN, —CH₂CHF₂, —CH₂NH₂, —N(CH₃)₂, —SO₂CH₃, cyano, halo, —C(O)OH, —C(O)N(CH₃)₂, and —C(O)NHCH₃, or the following structural formula:

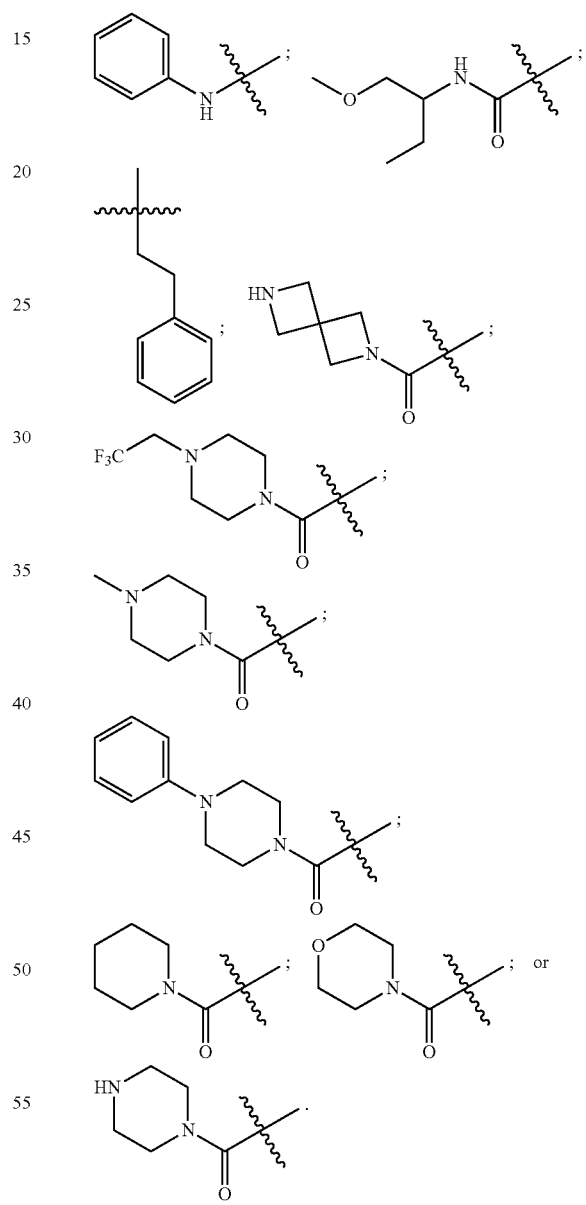

and the remaining variables are as described in the first aspect or in the first, second, third, fourth, fifth, sixth, seventh, eighth, ninth, or tenth embodiment or any alternative embodiments described therein. In alternative eleventh embodiment, R² is —CH₃, —CF₃, —CH₂CH₃, —CH(CH₃)₂, —CH(OH)CH₃, —CH₂OCH₃, —CH₂OH, —CH₂CF₃, —CH₂CH₂OH, —CH₂CH₂CH₂OH, —CH₂CN, —CH$_2$CHF$_2$, —CH$_2$NH$_2$, —N(CH$_3$)$_2$, cyano, halo, —C(O)OH, —C(O)N(CH$_3$)$_2$, —C(O)NHCH$_3$,

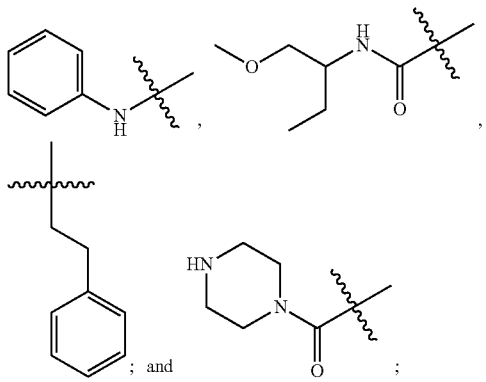

; and and the remaining variables are as described in the first aspect or in the first, second, third, fourth, fifth, sixth, seventh, eighth, ninth, or tenth embodiment or any alternative embodiments described therein.

In a twelfth embodiment, for the compound of Formula (I) described in the first aspect or in the first embodiment, or a pharmaceutically acceptable salt thereof, n is 1; and the remaining variables are as described in the first aspect or in the first, second, third, fourth, fifth, sixth, eighth, or eleventh embodiment or any alternative embodiments described therein.

In a thirteenth embodiment, for the compound of Formula (I) described in the first aspect or in the first embodiment, or a pharmaceutically acceptable salt thereof, n is 1 and Z is a bond; and the remaining variables are as described in the first aspect or in the first, second, third, fourth, fifth, sixth, seventh, eighth, eleventh, or twelfth embodiment.

In a fourteenth embodiment, for the compound of Formula (I) described in the first aspect or in the first embodiment, or a pharmaceutically acceptable salt thereof, n is 1 and Z is —CH$_2$—, —CH(CH$_3$)—, —O—, —N(H)—, —N(C$_{1-4}$alkyl)—, or —C(O)NH—*, wherein * indicates the attachment point to R$^3$; and the remaining variables are as described in the first aspect or in the first, second, third, fourth, fifth, sixth, seventh, eighth, eleventh or twelfth embodiment.

In a fifteenth embodiment, for the compound of Formula (I) described in the first aspect or in the first embodiment, or a pharmaceutically acceptable salt thereof, R$^3$ is selected from cyclopropyl, cyclobutyl, cyclopentyl, cyclohexyl, piperidinyl, piperazinyl, morpholinyl, pyrrolidinyl, phenyl, pyrrolyl, pyrazolyl, pyridyl, pyrimidyl, pyrazinyl, pyrazinyl, thiophenyl, tetrahydropyranyl, tetrahydrofuranyl, oxabicyclo[3.2.1]octanyl, thiazolyl, imidazoyl, triazolyl, tetrazolyl, oxadiazolyl, 3-oxo-2,3-dihydro-1H-pyrazoly, benzamidazolyl, indazolyl, indoyl, imidazolidinyl, azetidinyl, 2,3-dihydrobenzofuranyl, imidazo[1,2-a]pyridinyl, 2,3-dihydro-1H-indenyl, 2-oxo-2,3-dihydro-1H-benzo[d]imidazolyl, spiro[3.3]heptanyl, 2-azaspiro[3.3]heptanyl, and 2-oxaspiro[3.3]heptanyl, each of which is optionally substituted with 1 to 3 R$^4$; and the remaining variables are as described in the first aspect or in the first, second, third, fourth, fifth, sixth, seventh, eighth, ninth, tenth, eleventh, twelfth, thirteenth, or fourteenth embodiment or any alternative embodiments described therein. In an alternative fifteenth embodiment, R$^3$ is cyclopropyl, cyclobutyl, cyclohexyl, cyclopentyl, piperidinyl, piperazinyl, morpholinyl, pyrrolidinyl, phenyl, pyrrolyl, pyrazolyl, pyridyl, pyrimidyl, pyrazinyl, pyrazinyl, thiophenyl, tetrahydropyranyl, tetrahydrofuranyl, oxabicyclo[3.2.1]octanyl, thiazolyl, triazolyl, tetrazolyl, oxadiazolyl, 3-oxo-2,3-dihydro-1H-pyrazolyl, benzamidazolyl, indazolyl, indolyl, 2,3-dihydrobenzofuranyl, imidazo[1,2-a]pyridinyl, 2,3-dihydro-1H-indenyl, 2-oxo-2,3-dihydro-1H-benzo[d]imidazolyl, spiro[3.3]heptanyl, 2-azaspiro[3.3]heptanyl, and 2-oxaspiro[3.3]heptanyl, each of which is optionally substituted with 1 to 3 R$^4$; and the remaining variables are as described in the first aspect or in the first, second, third, fourth, fifth, sixth, seventh, eighth, ninth, tenth, eleventh, twelfth, thirteenth, or fourteenth embodiment or any alternative embodiments described therein. In some embodiments, R$^3$ is optionally substituted with 1 to 2 R$^4$. In some embodiments, R$^3$ is substituted with 1 R$^4$. In some embodiments, R$^3$ is unsubstituted.

In a sixteenth embodiment, for the compound of Formula (I) described in the first aspect or in the first embodiment, or a pharmaceutically acceptable salt thereof, Z is —CH$_2$—, R$^3$ is thiophenyl, pyrrolyl, and 2-oxo-2,3-dihydro-1H-benzo[d]imidazolyl, each of which is optionally substituted with 1 to 2 R$^4$; and the remaining variables are as described in the first aspect or in the first, second, third, fourth, fifth, sixth, seventh, eighth, ninth, tenth, eleventh, twelfth, thirteenth, or fourteenth embodiment or any alternative embodiments described therein.

In a seventeenth embodiment, for the compound of Formula (I) described in the first aspect or in the first embodiment, or a pharmaceutically acceptable salt thereof, R$^3$ is represented by the following structural formula:

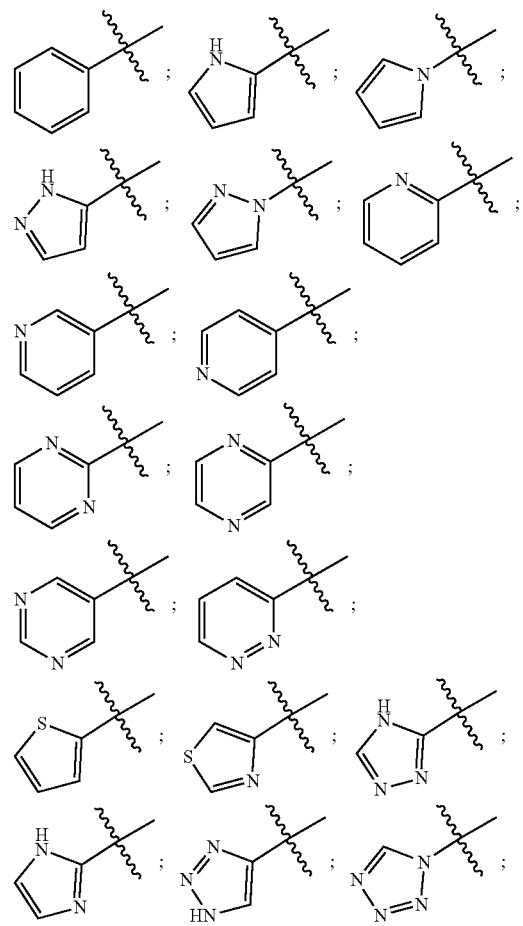

-continued

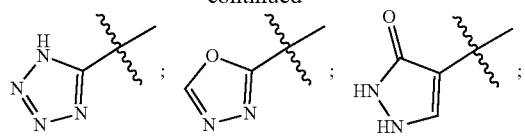
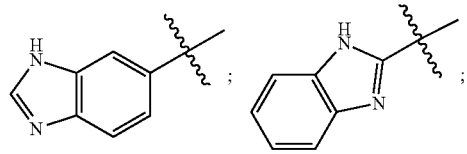
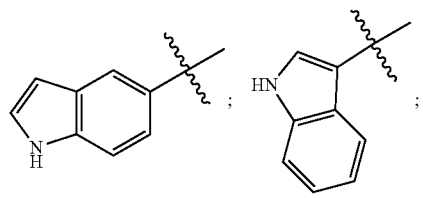
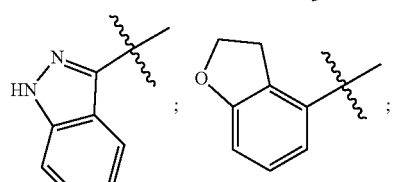
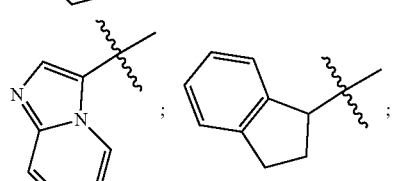
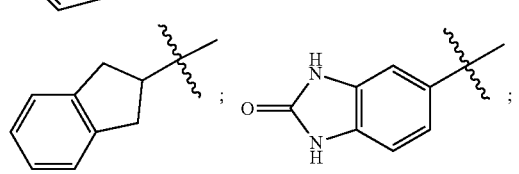
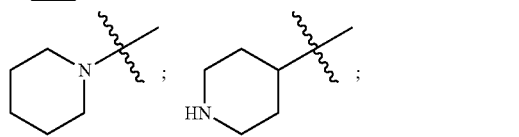
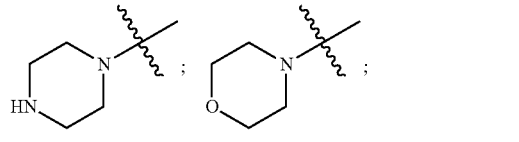
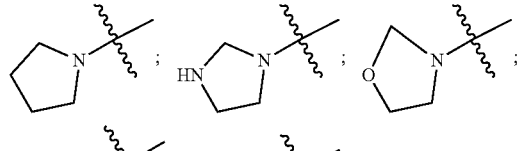
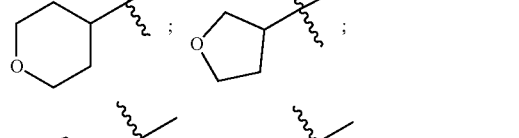
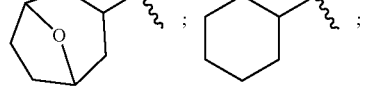

-continued

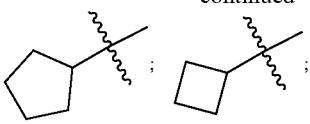
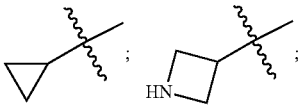
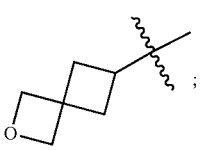

each of which is optionally substituted with 1 to 3 $R^4$; and the remaining variables are as described in the first, second, third, fourth, fifth, sixth, seventh, eighth, ninth, tenth, eleventh, twelfth, thirteenth, fourteenth, fifteenth, or sixteenth embodiment or any alternative embodiments described therein. In an alternative seventh embodiment. $R^3$ is

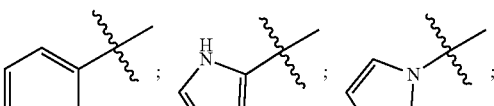
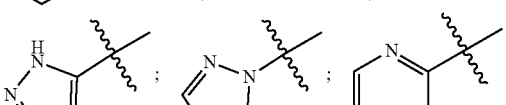
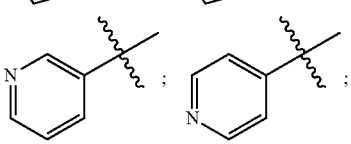
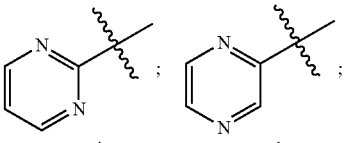
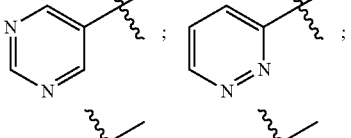
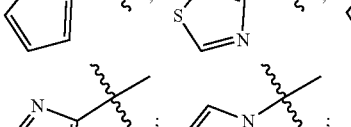
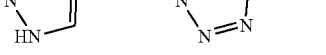

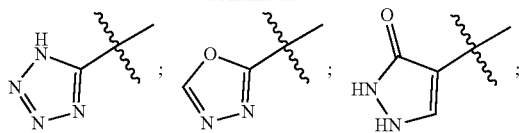
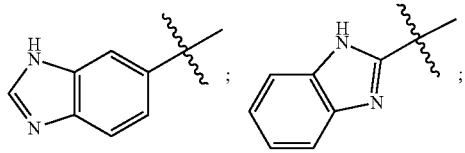
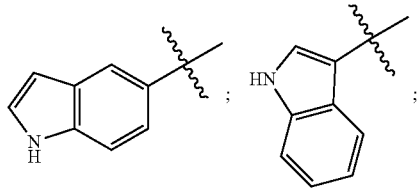
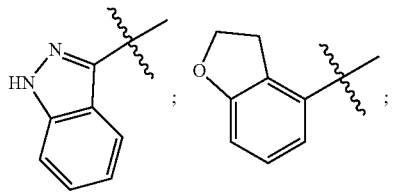
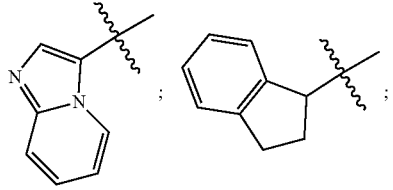
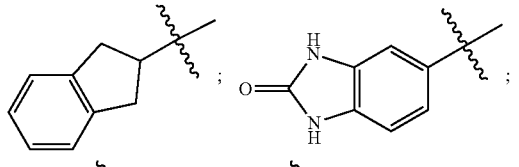
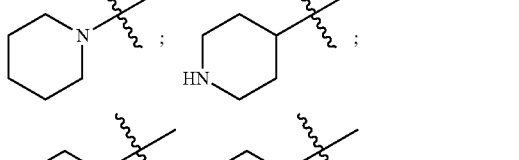
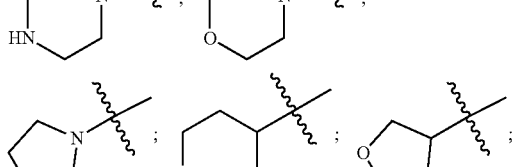
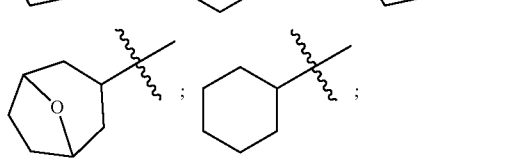
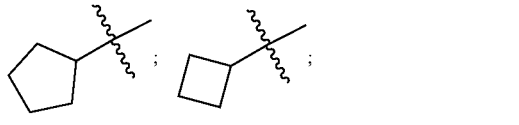

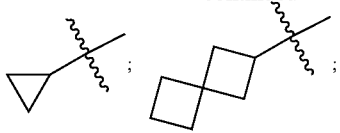
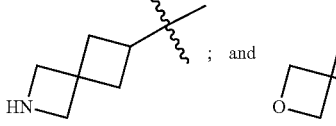
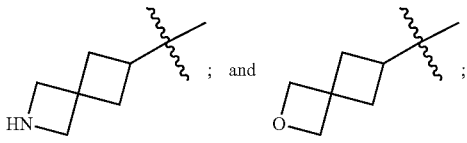

and each of which is optionally substituted with 1 to 3 $R^4$; and the remaining variables are as described in the first or in the first, second, third, fourth, fifth, sixth, seventh, eighth, ninth, tenth, eleventh, twelfth, thirteenth, fourteenth, fifteenth, or sixteenth embodiment or any alternative embodiments described therein. In some embodiments, $R^3$ is optionally substituted with 1 to 2 $R^4$. In some embodiments, $R^3$ is substituted with 1 $R^4$. In some embodiments, $R^3$ is unsubstituted.

In an eighteenth embodiment, for the compound of Formula (I) described in the first aspect or in the first embodiment, or a pharmaceutically acceptable salt thereof, $R^3$ is represented by the following structural formula:

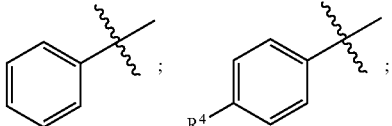
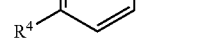
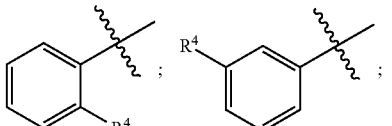
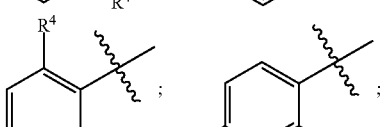
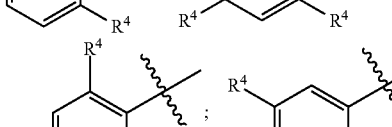
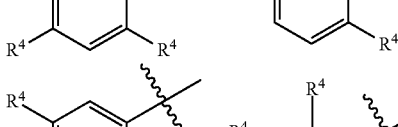
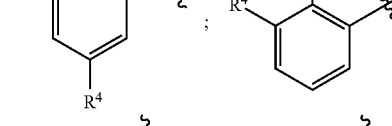
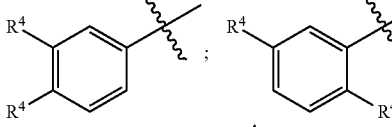
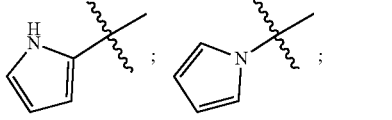

-continued
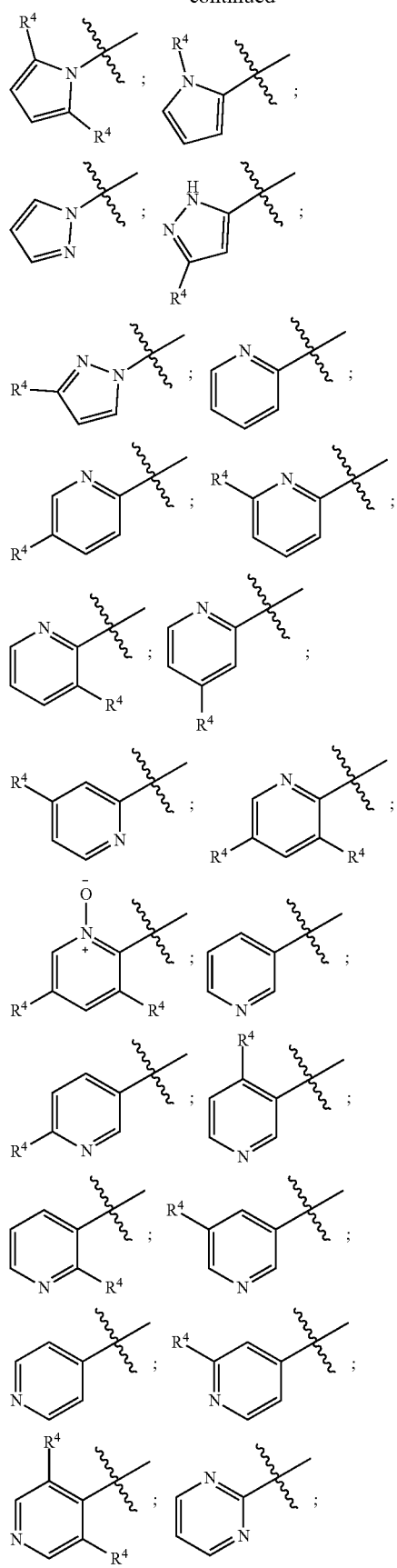
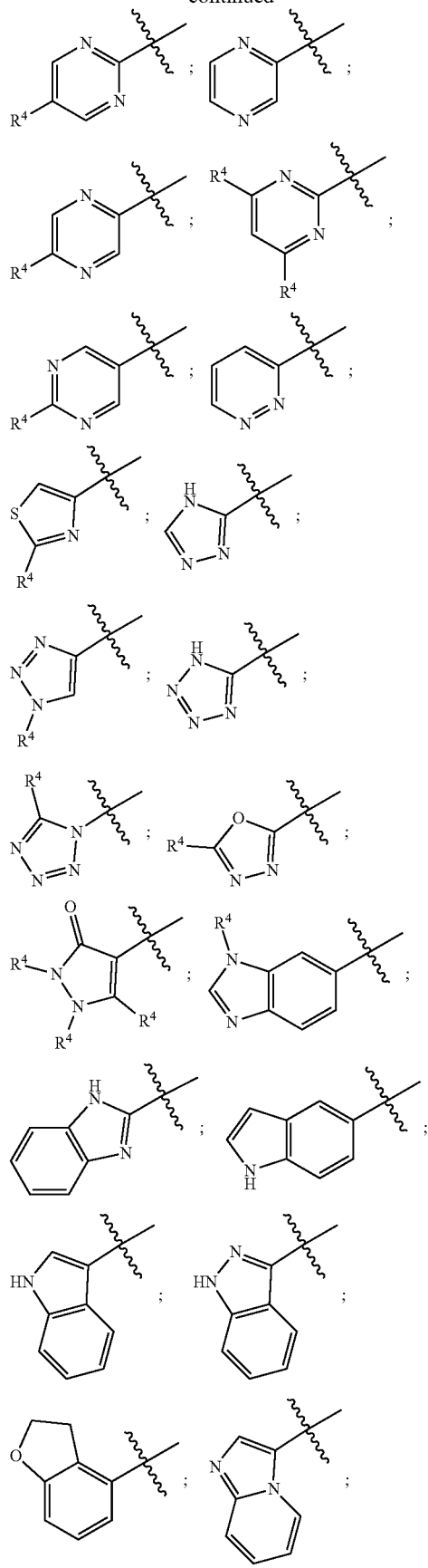

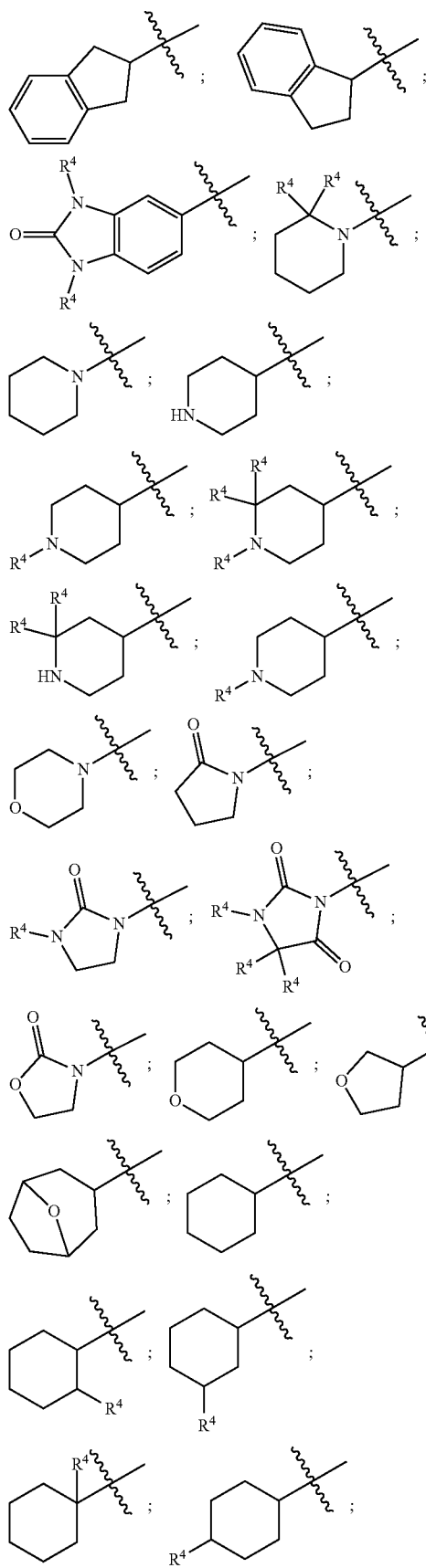
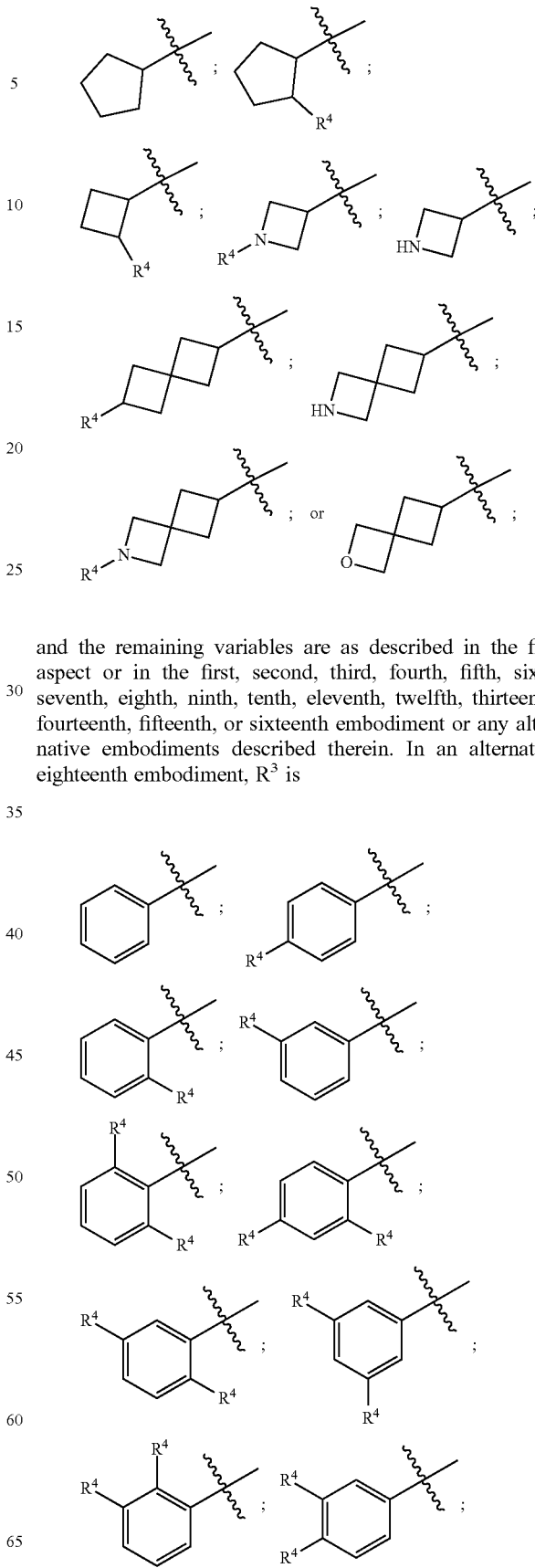
and the remaining variables are as described in the first aspect or in the first, second, third, fourth, fifth, sixth, seventh, eighth, ninth, tenth, eleventh, twelfth, thirteenth, fourteenth, fifteenth, or sixteenth embodiment or any alternative embodiments described therein. In an alternative eighteenth embodiment, $R^3$ is -continued
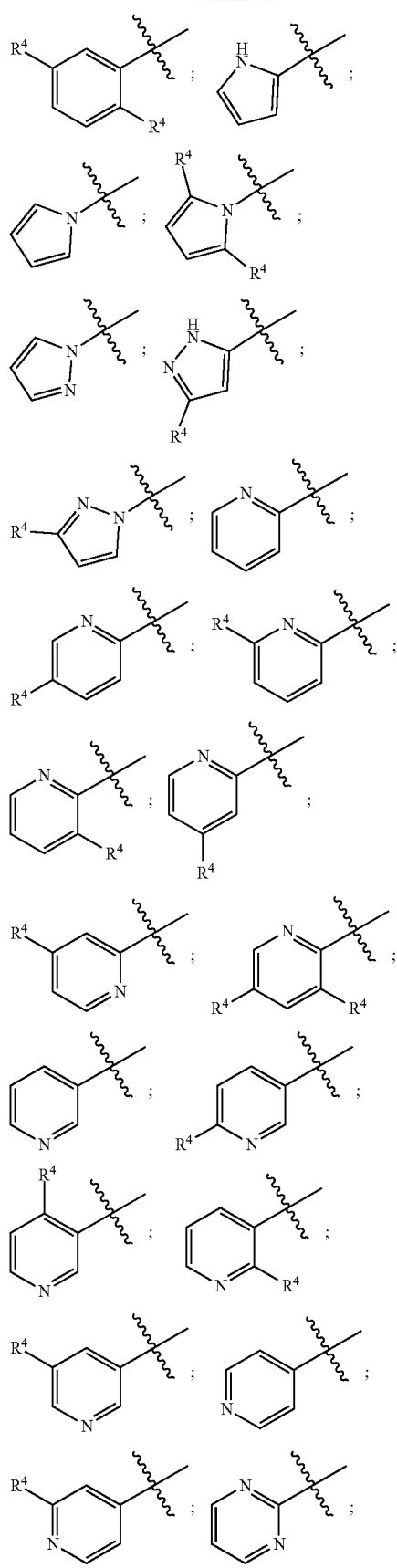
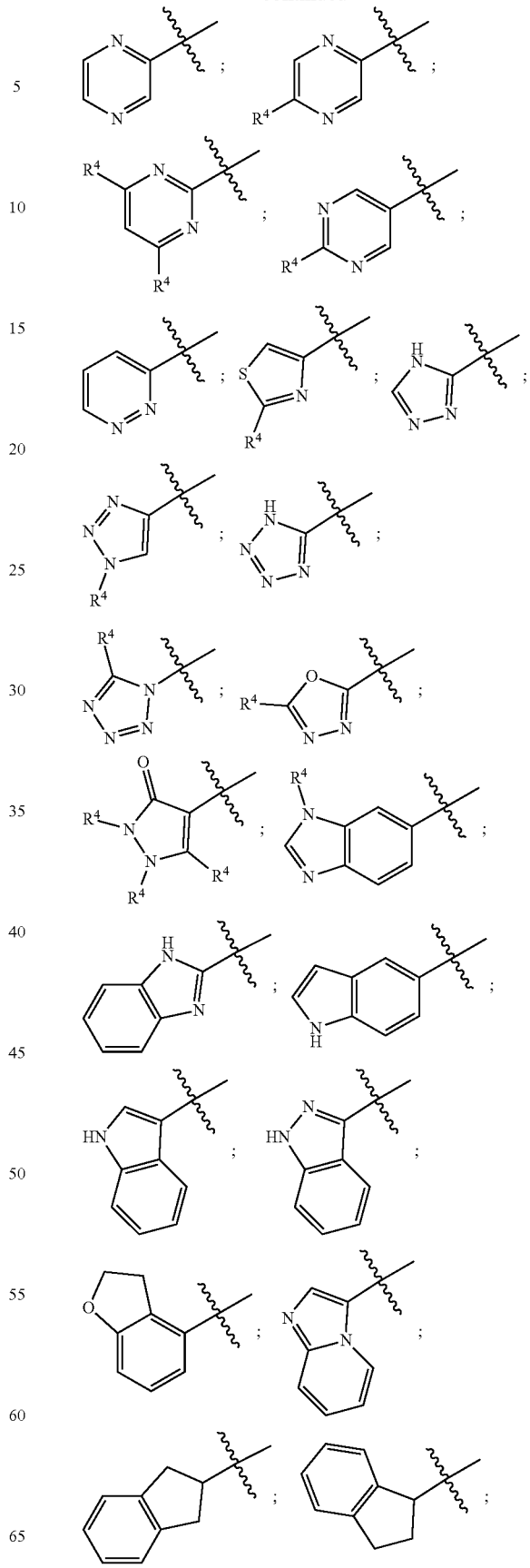

-continued

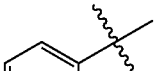

and the remaining variables are as described in the first aspect or in the first, second, third, fourth, fifth, sixth, seventh, eighth, ninth, tenth, eleventh, twelfth, thirteenth, fourteenth, fifteenth, or sixteenth embodiment or any alternative embodiments described therein.

In a nineteenth embodiment, for the compound of Formula (I) described in the first aspect or in the first embodiment, or a pharmaceutically acceptable salt thereof, $R^3$ is phenyl or 5 to 6-membered monocyclic heteroaryl, each of which is optionally substituted with 1 to 2 $R^4$; and the remaining variables are as described in the first aspect or in the first, second, third, fourth, fifth, sixth, seventh, eighth, ninth, tenth, eleventh, twelfth, thirteenth, or fourteenth embodiment or any alternative embodiments described therein.

In a twentieth embodiment, for the compound of Formula (I) described in the first aspect or in the first embodiment, or a pharmaceutically acceptable salt thereof, $R^3$ is phenyl, pyrazolyl, pyridyl, and pyrimidyl, each of which is optionally substituted with 1 to 2 $R^4$; and the remaining variables are as described in the first aspect or in the first, second, third, fourth, fifth, sixth, seventh, eighth, ninth, tenth, eleventh, twelfth, thirteenth, or fourteenth embodiment or any alternative embodiments described therein.

In a twenty-first embodiment, for the compound of Formula (I) described in the first aspect or in the first embodiment, or a pharmaceutically acceptable salt thereof, $R^3$ is

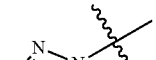

or each of which is optionally substituted with 1 to 2 $R^4$; and the remaining variables are as described in the first aspect or in the first, second, third, fourth, fifth, sixth, seventh, eighth, ninth, tenth, eleventh, twelfth, thirteenth, or fourteenth embodiment or any alternative embodiments described therein.

In a twenty-second embodiment, for the compound of Formula (I) described in the first aspect or in the first embodiment, or a pharmaceutically acceptable salt thereof, $R^3$ is represented by the following structural formula:

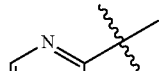

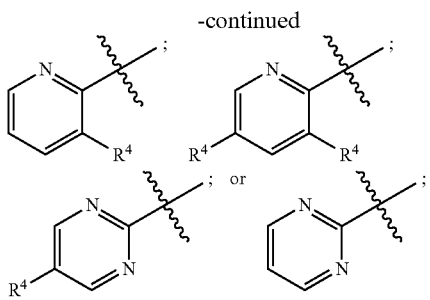

and the remaining variables are as described in the first aspect or in the first, second, third, fourth, fifth, sixth, seventh, eighth, ninth, tenth, eleventh, twelfth, thirteenth, or fourteenth embodiment or any alternative embodiments described therein. In an alternative twenty-second embodiment, $R^3$ is

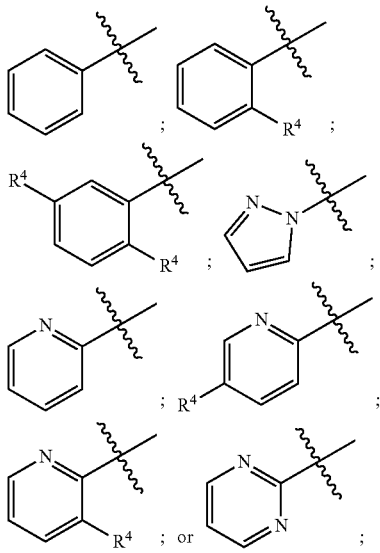

and the remaining variables are as described in the first aspect or in the first, second, third, fourth, fifth, sixth, seventh, eighth, ninth, tenth, eleventh, twelfth, thirteenth, or fourteenth embodiment or any alternative embodiments described therein.

In a twenty-third embodiment, for the compound of Formula (I) described in the first embodiment or in the first embodiment, or a pharmaceutically acceptable salt thereof, $R^4$ is selected from $C_{1-3}$alkyl, $C_{2-4}$alkenyl, $C_{2-4}$alkynyl, —$OR^{4a}$, —CN, —$NH_2$, —$NR^{4b}R^{4c}$, halo, —$C(O)R^{4a}$, —$NHC(O)R^{4a}$, —$NHC(O)OR^{4a}$, —$NR^{4b}SO_2R^{4a}$, —$SR^{4a}$, —$S(O)R^{4a}$, —$SO_2R^{4a}$, —$SO_2NR^{4b}R^{4c}$, —$P(O)R^{4b}R^{4c}$, —C(O)O—$C_{1-4}$alkyl, benzyl, phenyl, 5 to 6-membered monocyclic heteroaryl, 6 to 10-membered bicyclic heterocyclyl, and 4 to 6-membered monocyclic heterocyclyl, wherein the $C_{1-3}$alkyl, $C_{2-4}$alkenyl, or $C_{2-4}$alkynyl represented by $R^4$ is optionally substituted with 1 to 3 substituents independently selected from halo, phenyl, 5 to 6-membered monocyclic heteroaryl optionally substituted with 1 or 2 $R^{4g}$, and 4 to 6-membered monocyclic heterocyclyl optionally substituted with 1 or 2 $R^{4g}$, —$C(O)NR^{4b}R^{4c}$, —$C(O)R^{4a}$, and $OR^{4f}$; and the benzyl, phenyl, 5 to 6-membered monocyclic heteroaryl, 6 to 10-membered bicyclic heterocyclyl, and 4 to 6-membered monocyclic heterocyclyl represented by $R^4$ are each optionally substituted with 1 to 3 $R^{4e}$ and further optionally substituted with one or two oxo, or two $R^4$ together form an oxo; $R^{4a}$ is H, $C_{1-4}$alkyl optionally substituted with 1 to 4 $R^{4d}$, —$NR^{4b}R^{4c}$, $C_{3-6}$cycloalkyl, phenyl, 4- to 6-membered monocyclic heterocyclyl, or 5 to 6-membered monocyclic heteroaryl, wherein the phenyl, 4- to 6-membered monocyclic heterocyclyl, and 5 to 6-membered monocyclic heteroaryl are optionally substituted with 1 to 3 $R^{4e}$; each $R^{4b}$ is independently H or $C_{1-4}$alkyl; $R^{4c}$ is H, $C_{1-4}$alkyl optionally substituted with 1 to 4 $R^{4d}$, 4 to 6-membered monocyclic heterocyclyl, or 5 to 6-membered monocyclic heteroaryl; each $R^{4d}$ is independently selected from halo, —$OR^{4f}$, $C_{3-6}$ cycloalkyl, —C(O)OH, —$NR^{4b}R^{4c}$, phenyl, and 5 to 6-membered monocyclic heteroaryl, wherein the phenyl and 5 to 6-membered monocyclic heteroaryl are each optionally substituted with 1 to 3 substituents independently selected from $C_{1-3}$alkyl, $C_{1-3}$haloalkyl, halo, CN and OH; each $R^{4e}$ is independently selected from halo, —OH, $C_{1-4}$alkyl, $C_{1-4}$haloalkyl, $C_{1-4}$ alkoxy, —C(O)$R^{4h}$, —$SO_2C_{1-3}$alkyl, —$C_{1-3}$alkyl$SO_2C_{1-3}$alkyl, —C(O)N($C_{1-3}$alkyl)$_2$, and cyano; or two $R^{4e}$ together form an oxo; $R^{4f}$ is H, $C_{1-4}$alkyl, phenyl or 5 to 6-membered monocyclic heteroaryl, wherein phenyl and 5 to 6-membered monocyclic heteroaryl are each optionally substituted with 1 to 3 halo; each $R^{4g}$ is independently $C_{1-3}$alkyl or halo; and each $R^{4h}$ is independently $C_{1-4}$alkyl, $C_{3-6}$cycloalkyl, $C_{1-3}$alkoxyl or —N($R^{4b}$)$_2$; and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty second embodiment or any alternative embodiments described therein. In an alternative twenty-third embodiment, $R^4$ is $C_{1-3}$alkyl, —$OR^{4a}$, —CN, —$NH_2$, halo, —$C(O)R^{4a}$, —$NHC(O)R^{4a}$, —$NHC(O)OR^{4a}$, —$SR^{4a}$, —$SO_2R^{4a}$, —$SO_2NR^{4b}R^{4c}$, —$P(O)R^{4b}R^{4c}$, —C(O)O$C_{1-4}$alkyl, benzyl, phenyl, 5 to 6-membered monocyclic heteroaryl, and 4 to 6-membered monocyclic heterocyclyl, wherein the $C_{1-3}$alkyl represented by $R^4$ is optionally substituted with 1 to 3 substituents independently selected from halo, $OR^{4f}$, —$C(O)NR^{4b}R^{4c}$, phenyl, and 5 to 6-membered monocyclic heteroaryl; the benzyl, phenyl, 5 to 6-membered monocyclic heteroaryl, and 4 to 6-membered monocyclic heterocyclyl represented by $R^4$ are each optionally substituted with 1 to 3 $R^{4e}$, or two $R^4$ together form an oxo; $R^{4a}$ is H, $C_{1-4}$alkyl optionally substituted with 1 to 4 $R^{4d}$, —$NR^{4b}R^{4c}$phenyl, or 5 to 6-membered monocyclic heteroaryl, wherein the phenyl and 5 to 6-membered monocyclic heteroaryl are optionally substituted with 1 to 3 $R^{4e}$; $R^{4b}$ is H or $C_{1-4}$alkyl; $R^{4c}$ is H, $C_{1-4}$alkyl optionally substituted with 1 to 4 $R^{4d}$, 4 to 6-membered monocyclic heterocyclyl, or 5 to 6-membered monocyclic heteroaryl; each $R^{4d}$ is independently selected from $C_{1-3}$alkyl, halo, phenyl and 5 to 6-membered monocyclic heteroaryl, wherein the phenyl and 5 to 6-membered monocyclic heteroaryl are each optionally substituted with 1 to 3 substituents independently selected from halo, CN, and OH; each $R^{4e}$ is independently selected from halo, $C_{1-4}$alkyl, —C(O)$C_{1-3}$alkyl, —C(O)N($C_{1-3}$alkyl)$_2$, and cyano; or two $R^{4e}$ together form an oxo; $R^{4f}$ is H, $C_{1-4}$alkyl, phenyl or 5 to 6-membered monocyclic heteroaryl, wherein phenyl and 5 to 6-membered monocyclic heteroaryl are each optionally substituted with 1 to 3 halo; and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty second embodiment or any alternative embodiments described therein.

In a twenty-fourth embodiment, for the compound of Formula (I) described in the first aspect or in the first embodiment, or a pharmaceutically acceptable salt thereof, $R^4$ is represented by the following structural formula:

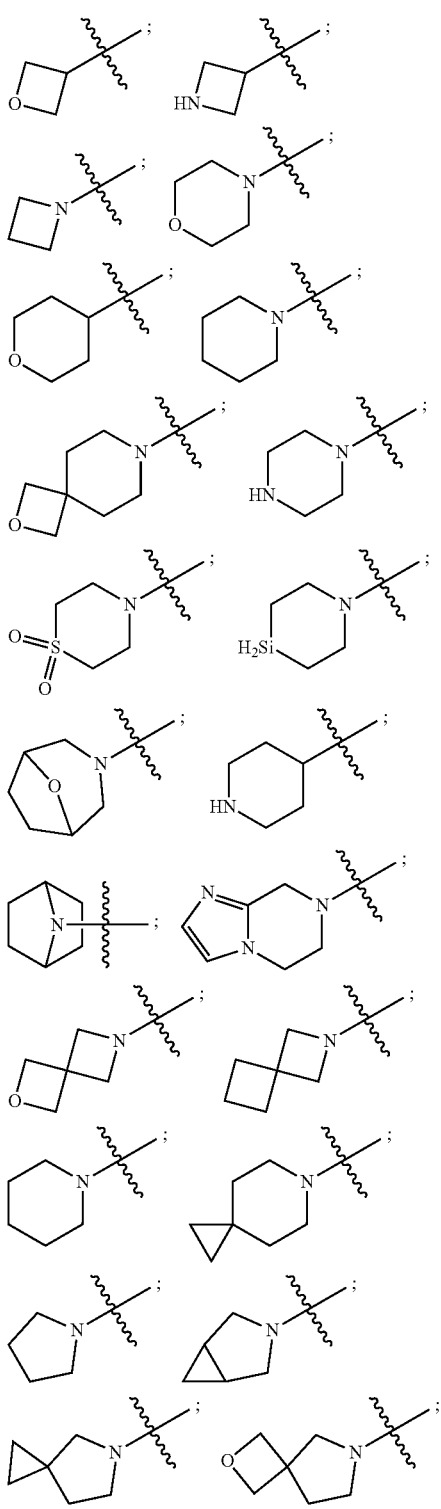

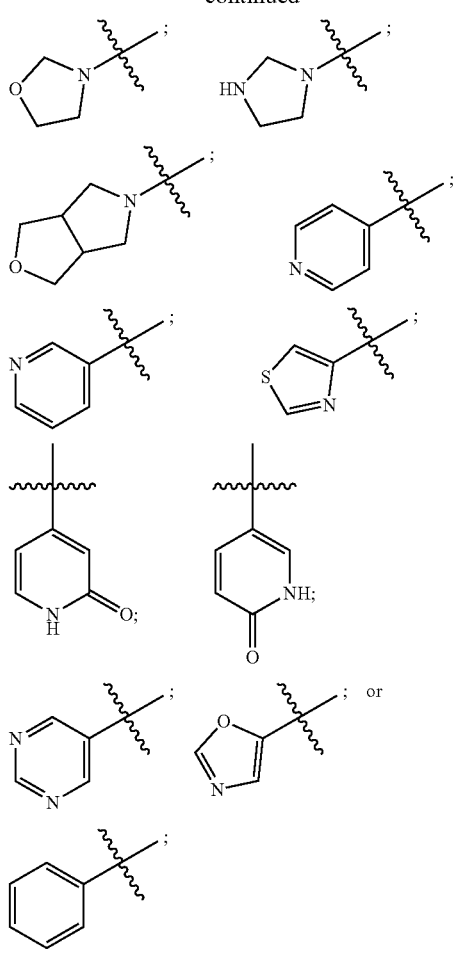

each of which is optionally substituted with 1 to 3 $R^{4e}$ and further optionally substituted with 1 or 2 oxo; and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment or any alternative embodiments described therein. In an alternative twenty-fourth embodiment, $R^4$ is

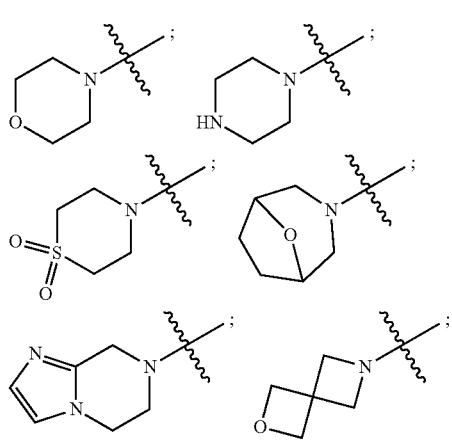

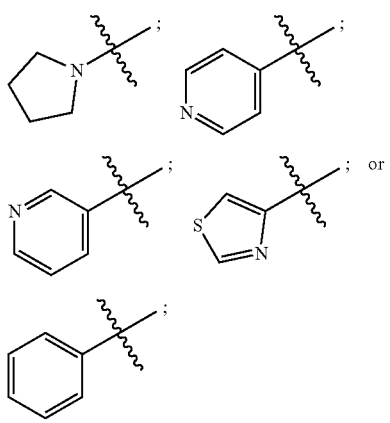

each of which is optionally substituted with 1 to 3 $R^{4e}$; and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment or any alternative embodiments described therein.

In a twenty-fifth embodiment, for the compound of Formula (I) described in the first aspect or in the first embodiment, or a pharmaceutically acceptable salt thereof, $R^4$ is represented by the following structural formula:

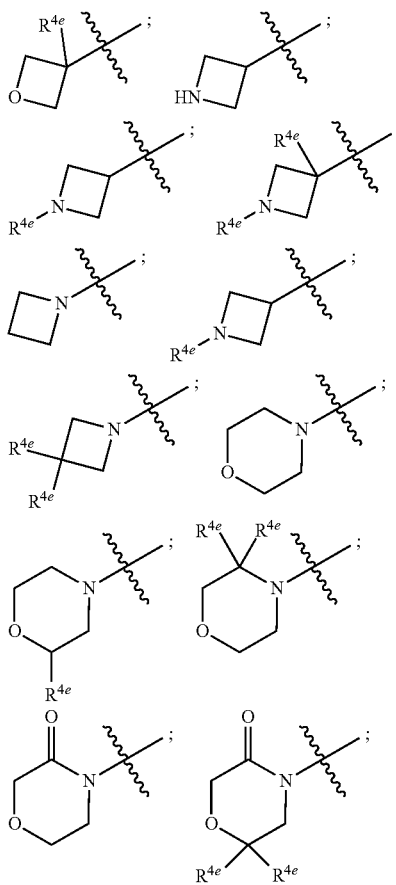
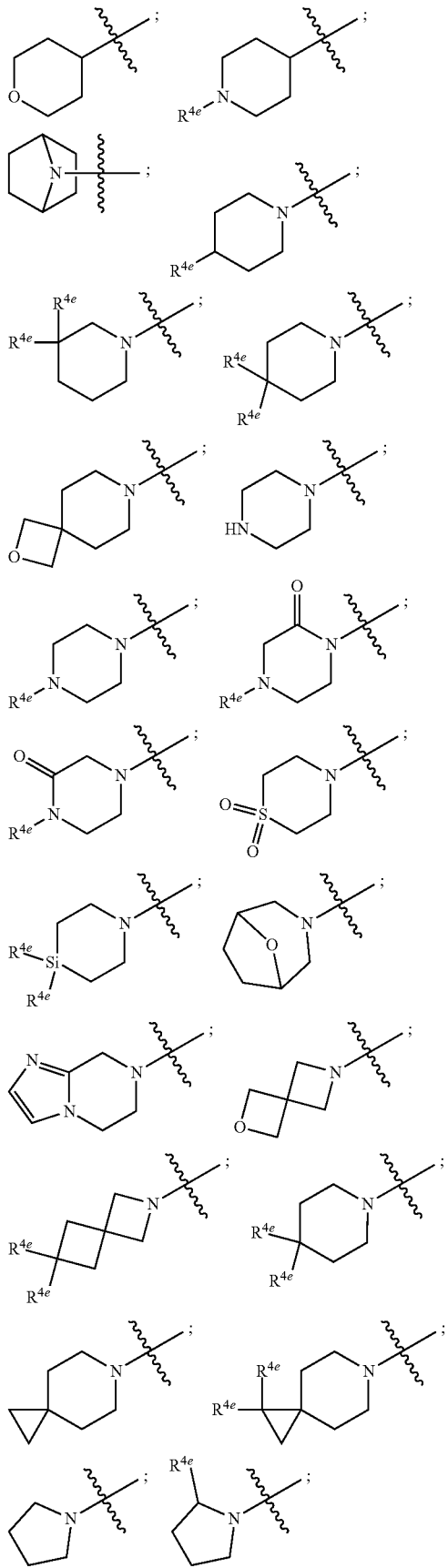

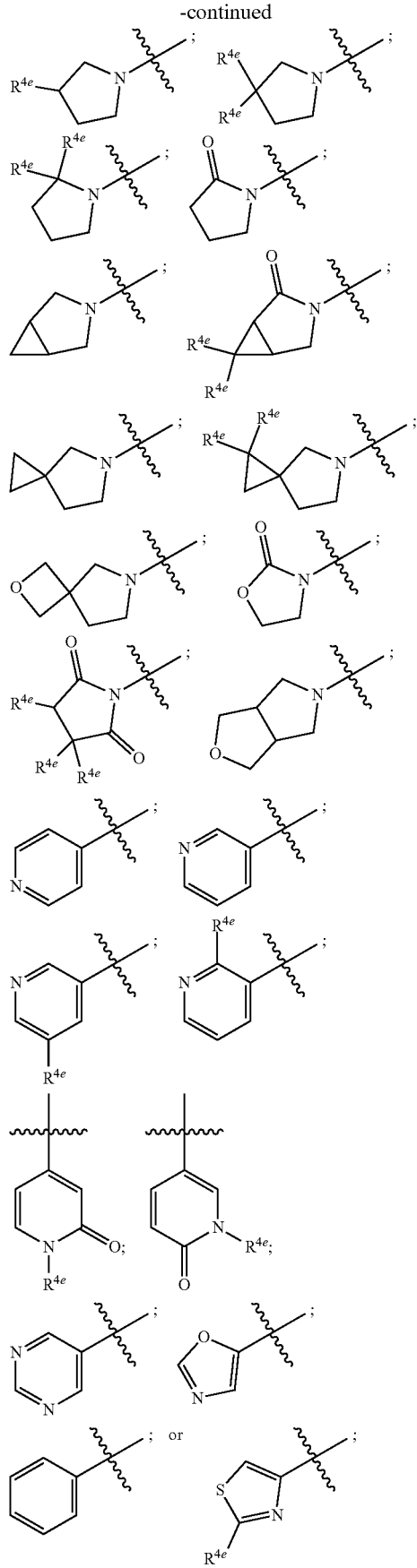

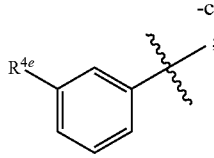

and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment or any alternative embodiments described therein. In an alternative twenty-fifth embodiment, $R^4$ is

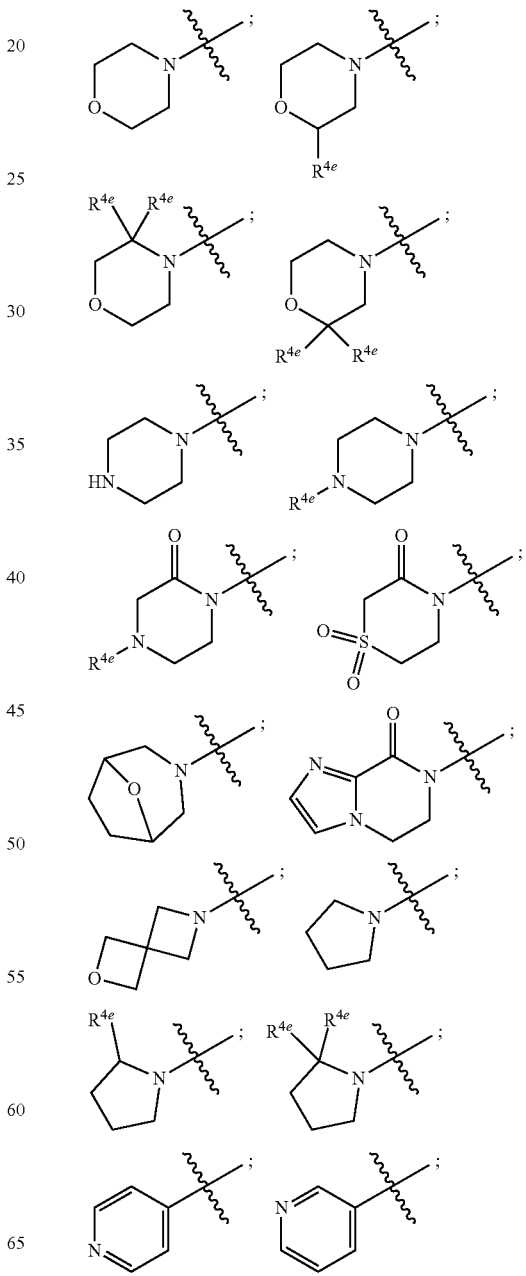

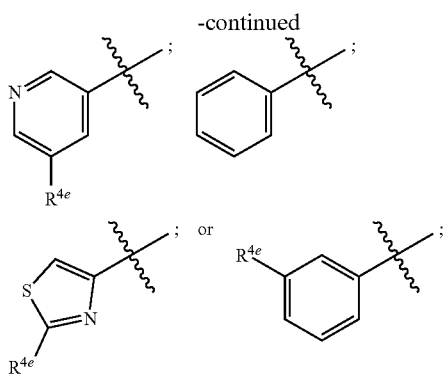

and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, or twenty-second embodiment or any alternative embodiments described therein.

In a twenty-sixth embodiment, for the compound of Formula (I) described in the first aspect or in the first embodiment, or a pharmaceutically acceptable salt thereof, each $R^{4e}$ is independently —F, —$CH_3$, —$CF_3$, —$CH_2CHF_2$, —$CH_2CF_3$, —$CH_2SO_2CH_3$, —OH, —$OCH_3$, —$SO_2CH_3$, —C(O)$CH_3$, —C(O)cyclopropyl, —C(O)cyclobutyl, —C(O)cyclopentyl, —C(O)CH$(CH_3)_2$, —C(O)C$(CH_3)_3$— C(O)N$(CH_3)_2$, —C(O)OCH$_3$, or cyano; and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth or twenty-fifth embodiment or any alternative embodiments described therein. In an alternative twenty-sixth embodiment, $R^{4e}$ is —$CH_3$, —C(O)$CH_3$, —C(O)CH$(CH_3)_2$—C(O)N$(CH_3)_2$, or cyano; and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth or twenty-fifth embodiment or any alternative embodiments described therein.

In a twenty-seventh embodiment, for the compound of Formula (I) described in the first aspect or in the first embodiment, or a pharmaceutically acceptable salt thereof, $R^4$ is —$OR^{4a}$; $R^{4a}$ is $C_{1-3}$alkyl optionally substituted with 1 to 3 $R^{4d}$ or 4- to 6-membered monocyclic heterocyclyl optionally substituted with 1 to 3 $R^{4e}$; each $R^{4d}$ is independently halo, $C_{1-2}$alkyl, phenyl or 5 to 6-membered monocyclic heteroaryl, provided when two or three $R^{4d}$ are present, one of the $R^{4d}$ is phenyl or 5 to 6-membered monocyclic heteroaryl, and the other $R^{4d}$ are each independently halo or $C_{1-2}$alkyl; wherein the phenyl and 5 to 6-membered monocyclic heteroaryl represented by $R^{4d}$ are each optionally substituted with 1 to 3 substituents independently selected from $C_{1-3}$alkyl, $C_{1-3}$haloalkyl and halo; each $R^{4e}$ is independently $C_{1-4}$alkyl, $C_{1-4}$haloalkyl, —$SO_2C_{1-3}$alkyl, or —C(O)$C_{3-6}$cycloalkyl; the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment or any alternative embodiments described therein. In an alternative twenty-seventh embodiment, $R^4$ is —$OR^{4a}$; $R^{4a}$ is $C_{1-3}$alkyl substituted with 1 to 3 $R^{4d}$; one of the $R^{4d}$ is phenyl or 5 to 6-membered monocyclic heteroaryl, and the other $R^{4d}$ are each independently halo or $C_{1-2}$alkyl; wherein the phenyl and 5 to 6-membered monocyclic heteroaryl represented by $R^{4d}$ are each optionally substituted with 1 to 3 halo; and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment or any alternative embodiments described therein.

In a twenty-eighth embodiment, for the compound of Formula (I) described in the first aspect or in the first embodiment, or a pharmaceutically acceptable salt thereof, $R^4$ is —$CH_3$, $CH_2OH$, —$CHF_2$, —$CF_3$, —CH$(CF_3)$OH, —$CH_2OCH_3$, —$CH_2CN$, —$CH_2CF_3$, —$CH_2CH_2OH$, —$CH_2C(O)N(CH_3)_2$, —C≡CC$(CH_3)_2$OH, —OH, —$OCH_3$, —$OCH_2CH_3$, —$OCH_2CH_2OCH_3$, —$OCH(CH_3)_2$, —$OCF_3$, —$OCHF_2$, —$OCH_2CF_3$, —O-cyclopropyl, —O-cyclobutyl, —OC$(CH_3)_3$, —OC$(CH_3)_2CH_2$OH, —OCH$(CH_3)$C(O)OH, —OC$(CH_3)_2$C(O)OH, —OCH$(CH_3)$CH$_2$OH, —OCH$_2$CH$_2$N$(CH_3)_2$, —CN, —$NH_2$, —NHCH$_3$, halo, —C(O)H, —C(O)CH$(CH_3)_2$, —C(O)OCH$_3$, —C(O)O-t-butyl, —N$(CH_3)SO_2CH_3$, —NHC(O)CH$_3$, —NHC(O)cyclopropyl, —NHC(O)OC$(CH_3)_3$, —C(O)CH$_3$, —C(O)OH, —C(O)NH$_2$, —C(O)NHCH$_3$, —C(O)N$(CH_3)_2$, —C(O)NC$(CH_3)_3$, —SCH$_3$, —S(O)CH$_3$, —SO$_2$CH$_3$, —SO$_2$N$(CH_3)_2$, —P(O)$(CH_3)_2$, phenyl, or $R^4$ is represented by the following structural formula:

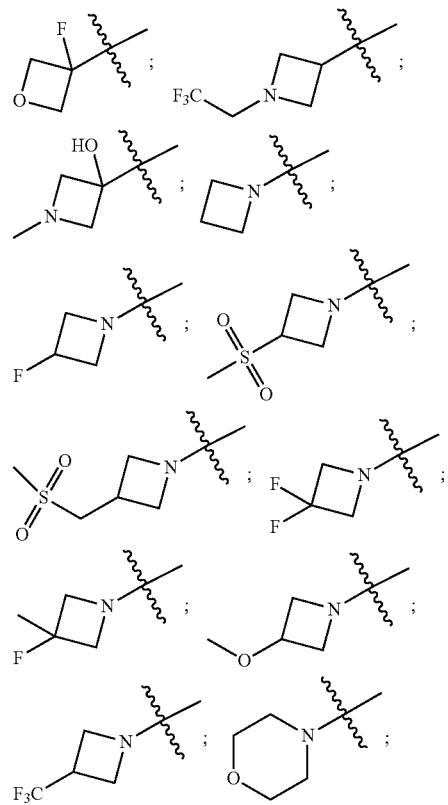

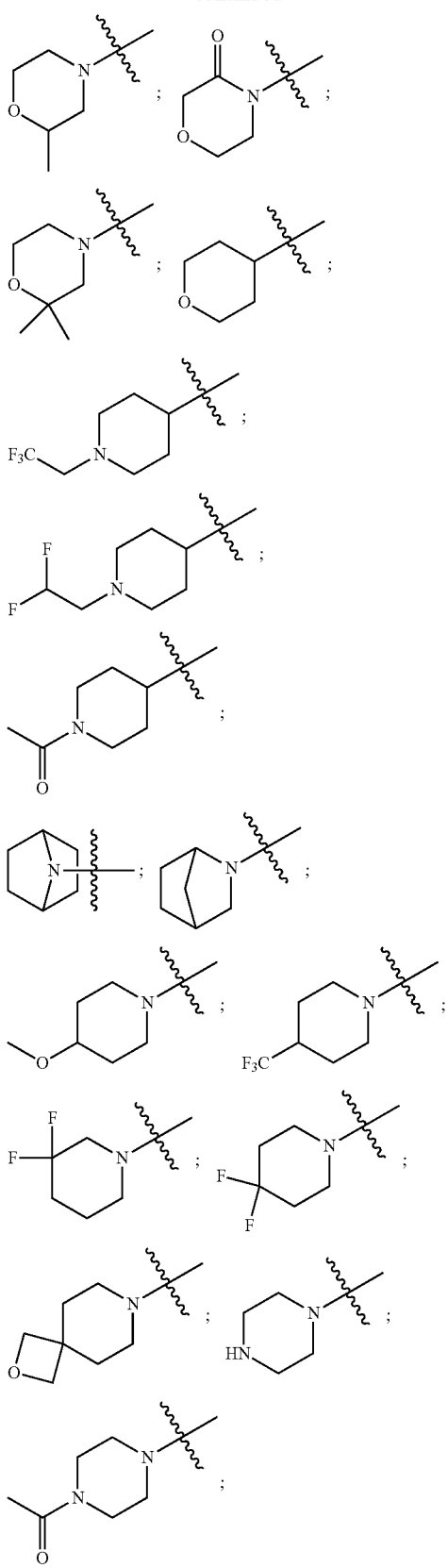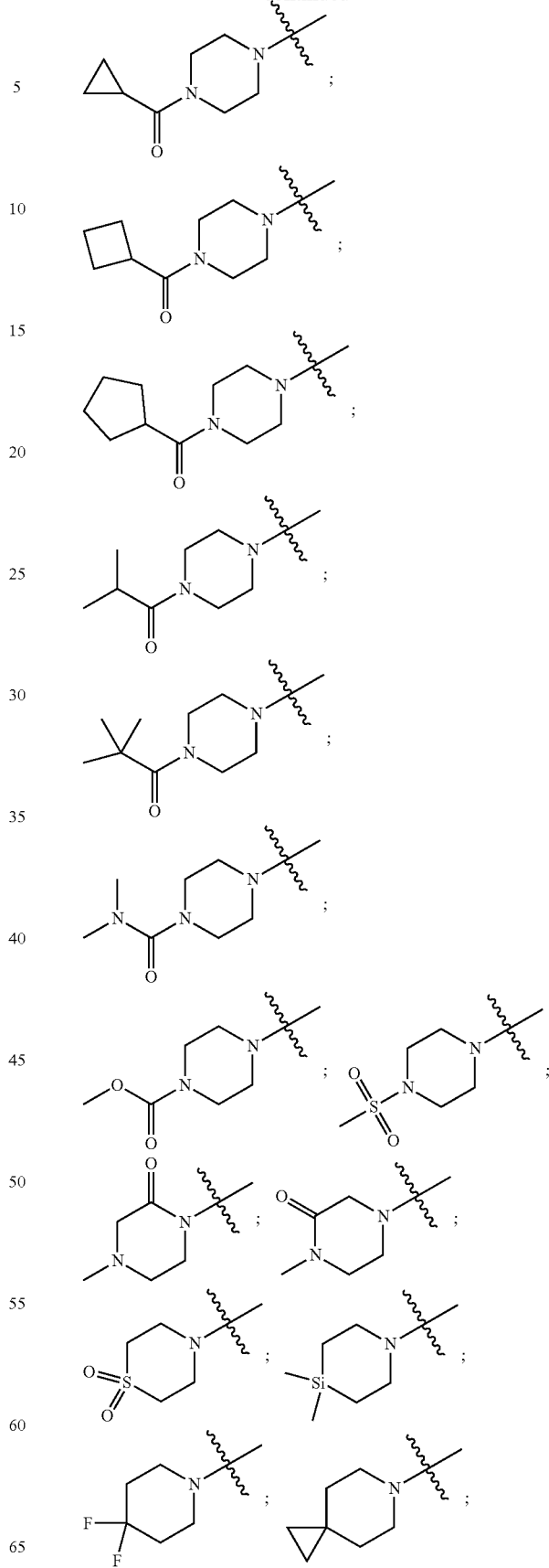

-continued
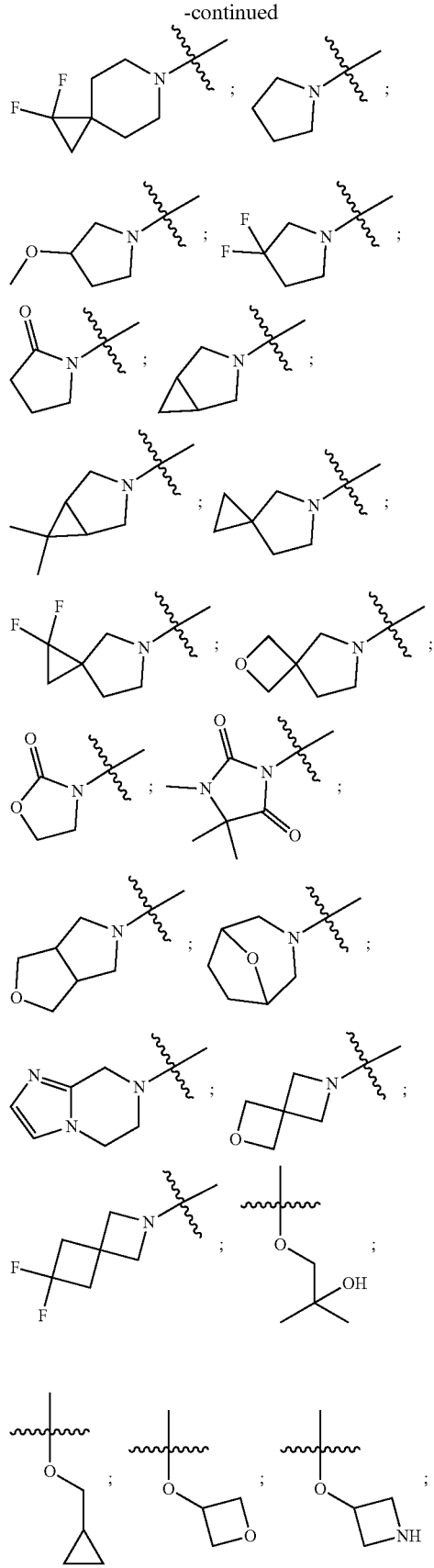
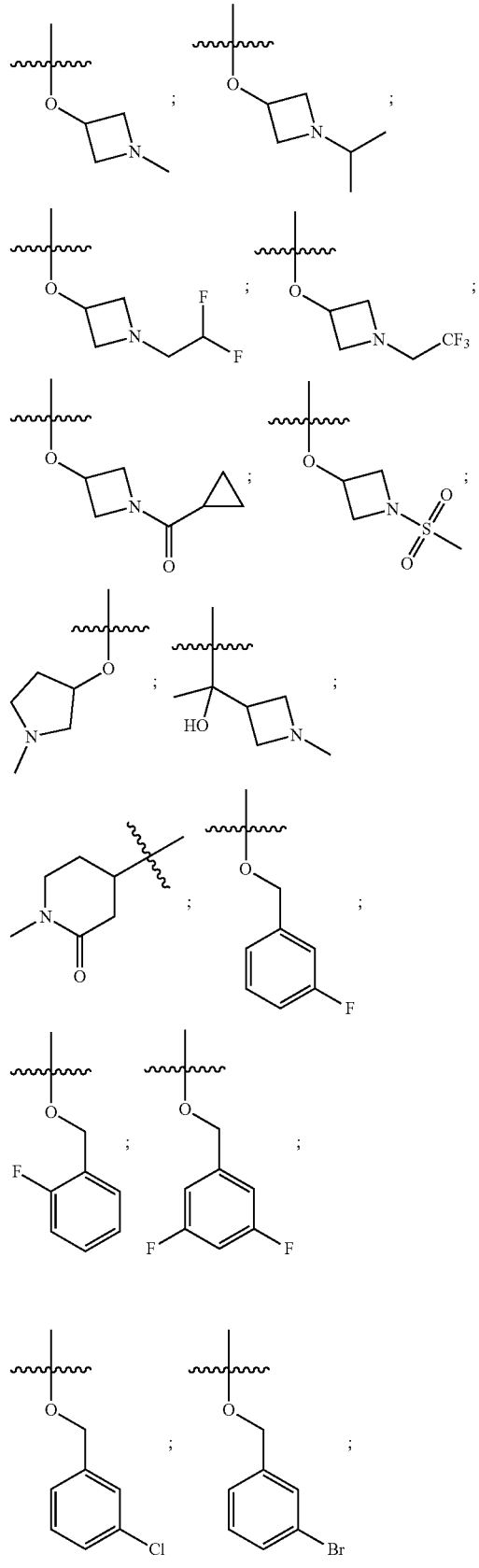

-continued
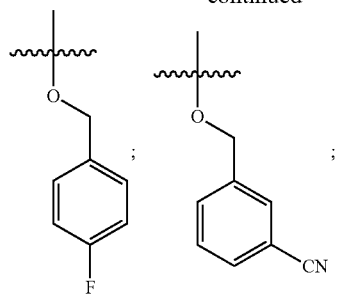
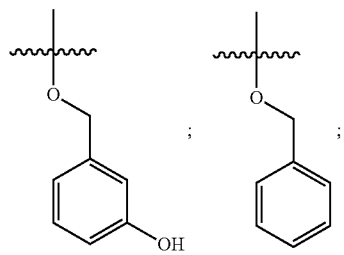
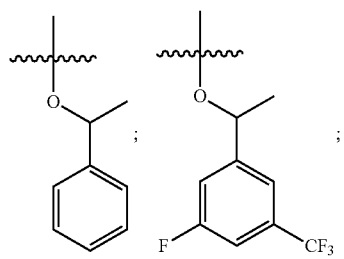
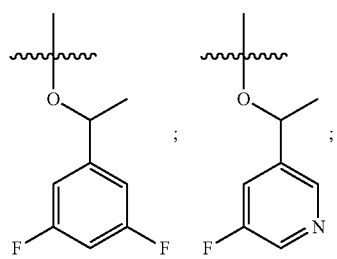
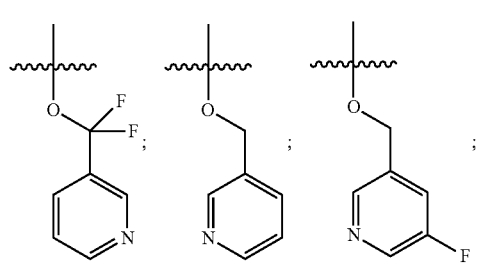
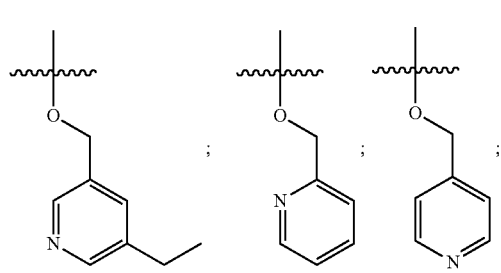
-continued
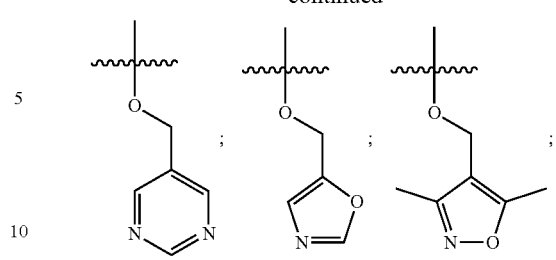
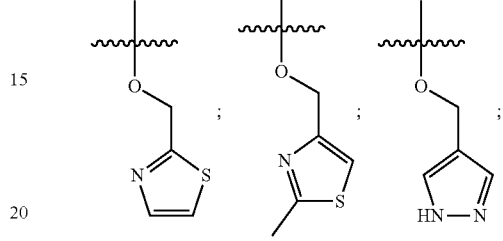
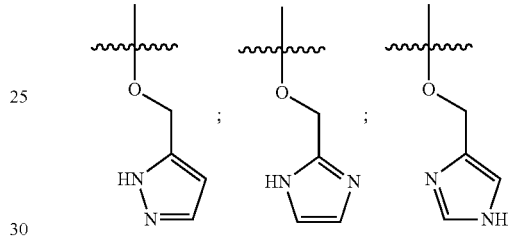
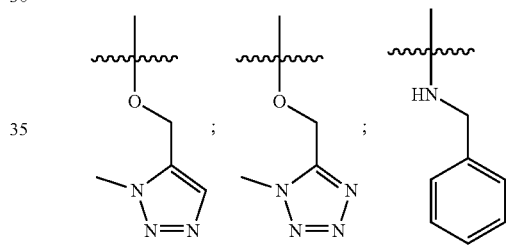
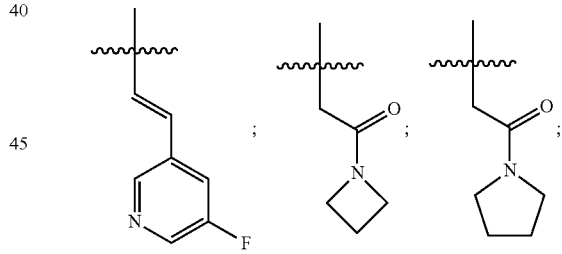
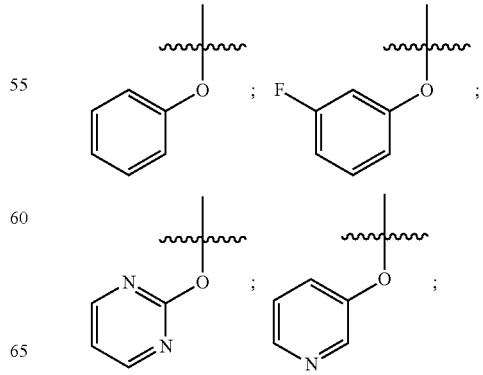

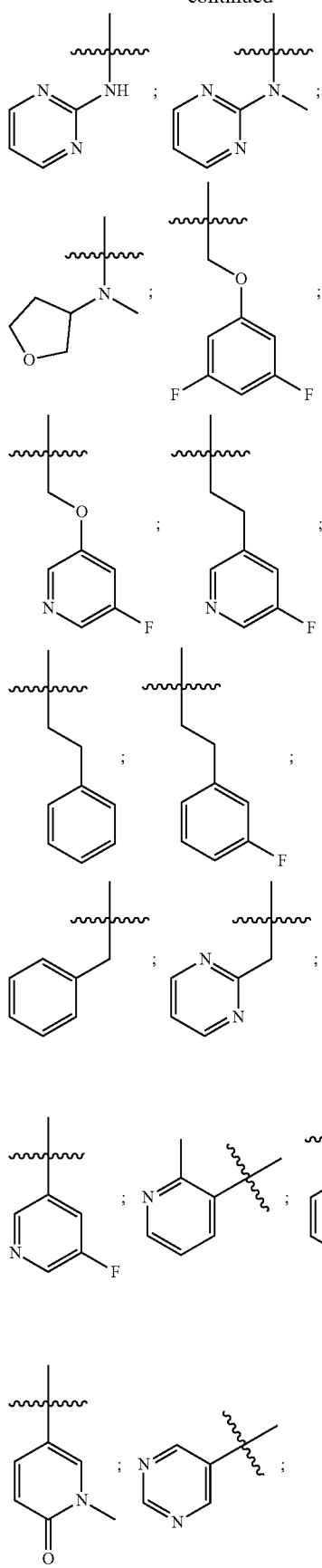

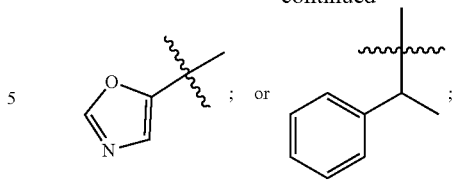

and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment or any alternative embodiments described therein. In an alternative twenty-eighth embodiment, $R^4$ is —CH$_3$, CH$_2$OH, —CHF$_2$, —CF$_3$, —CH(CF$_3$)OH, —CH$_2$OCH$_3$, —CH$_2$CN, —CH$_2$CF$_3$, —CH$_2$CH$_2$OH, —CH$_2$C(O)N(CH$_3$)$_2$, —OH, —OCH$_3$, —OCH$_2$CH$_3$, —OCH(CH$_3$)$_2$, —OCF$_3$, —CN, —NH$_2$, —NHR$^{4c}$, halo, —C(O)H, —C(O)CH(CH$_3$)$_2$, —C(O)OCH$_3$, —C(O)O-t-butyl, —NHC(O)CH$_3$, —NHC(O)cyclopropyl, —NHC(O)OC(CH$_3$)$_3$, —C(O)CH$_3$, —C(O)OH, —C(O)NH$_2$, —C(O)NHCH$_3$, —C(O)N(CH$_3$)$_2$, —C(O)NC(CH$_3$)$_3$, —SCH$_3$, —SO$_2$CH$_3$, —SO$_2$N(CH$_3$)$_2$, —P(O)(CH$_3$)$_2$, phenyl,

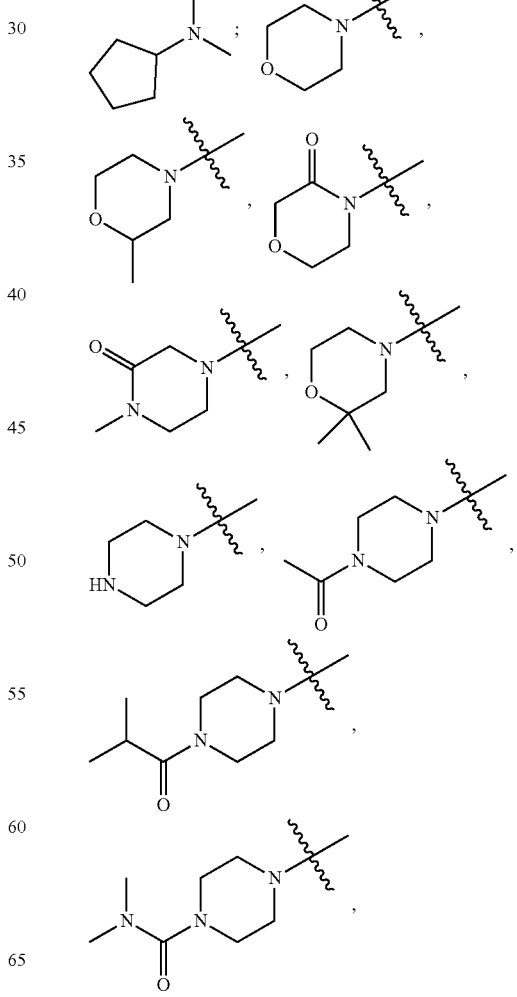

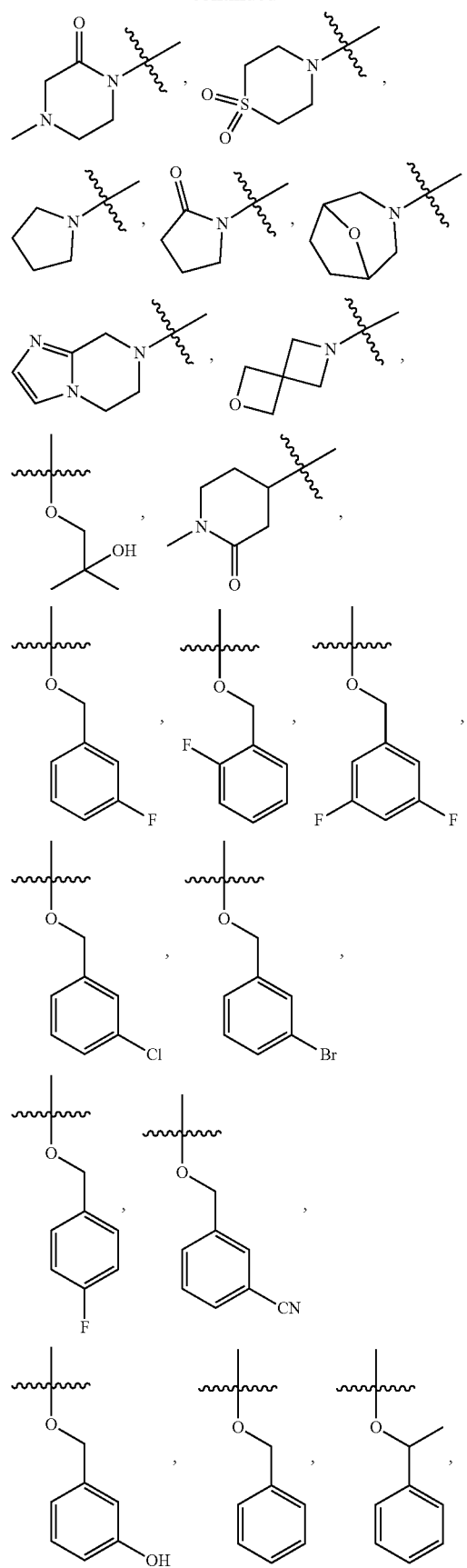
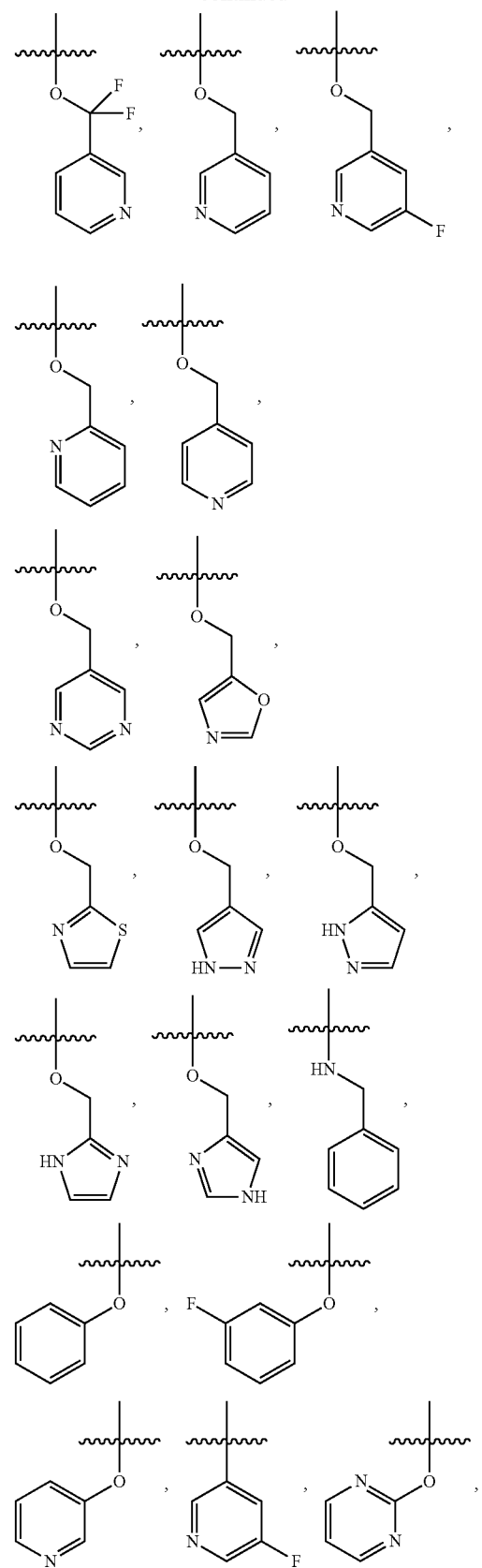

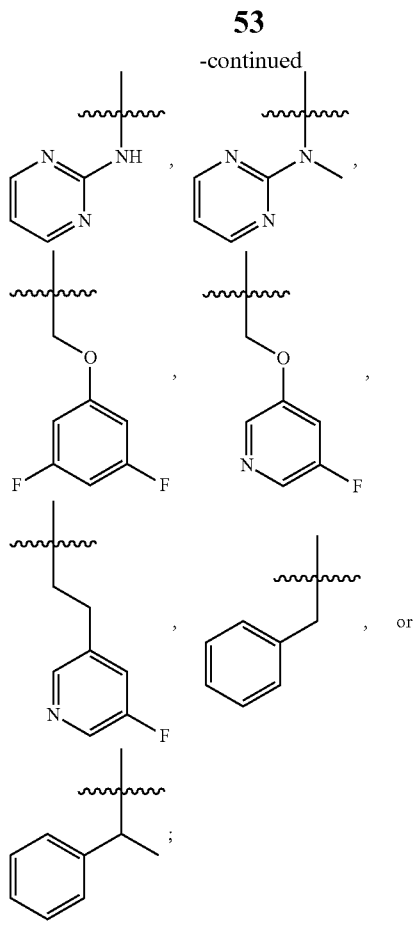

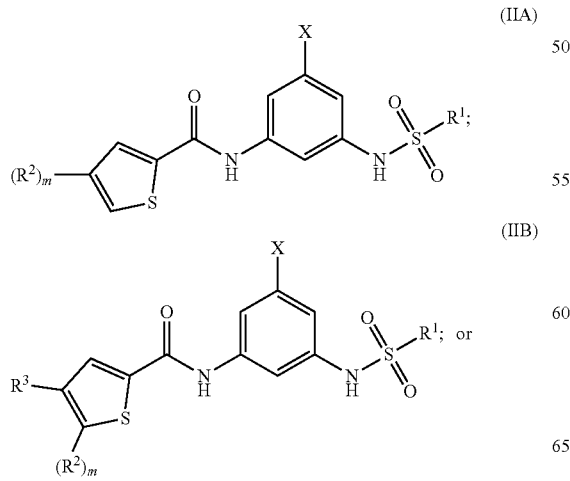

and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, or twenty-third embodiment or any alternative embodiments described therein.

In a twenty-ninth embodiment, the compound of the present disclosure is represented by Formula (IIA), (IIB), or (IIC):

(IIA)

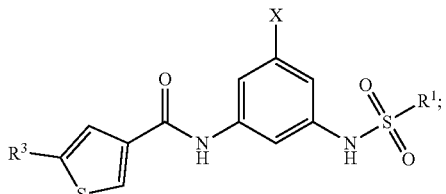

(IIC)

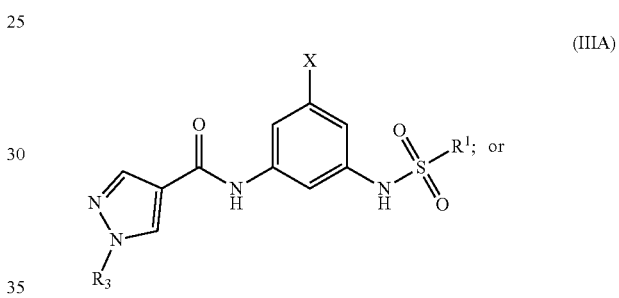

or a pharmaceutically acceptable salt thereof, wherein m is 0 or 1; and the variables X, R¹, R², and R³ depicted in Formula (IIA), (IIB), or (IIC) are as described in the first aspect or in the first, second, third, fourth, eleventh, fifteenth, seventeenth, eighteenth, nineteenth, twentieth, twenty-first, twenty-second, twenty-third, twenty-fourth, twenty-fifth, twenty-sixth, twenty-seventh, or twenty-eighth embodiment or any alternative embodiments described therein.

In a thirtieth embodiment, the compound of the present disclosure is represented by Formula (IIIA) or (IIIB):

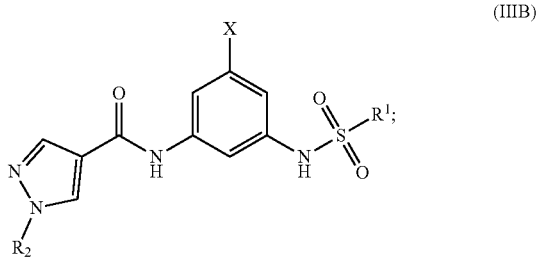

(IIIA)

(IIIB)

or a pharmaceutically acceptable salt thereof; where the variables X, R¹, R², and R³ depicted in Formula (IIIA) or (IIIB) are as described in the first aspect or in the first, second, third, fourth, eleventh, fifteenth, seventeenth, eighteenth, nineteenth, twentieth, twenty-first, twenty-second, twenty-third, twenty-fourth, twenty-fifth, twenty-sixth, twenty-seventh, or twenty-eighth embodiment or any alternative embodiments described therein.

In a thirty-first embodiment, the compound of the present disclosure is represented by Formula (IVA), (IVB), (IVC), or (IVD).

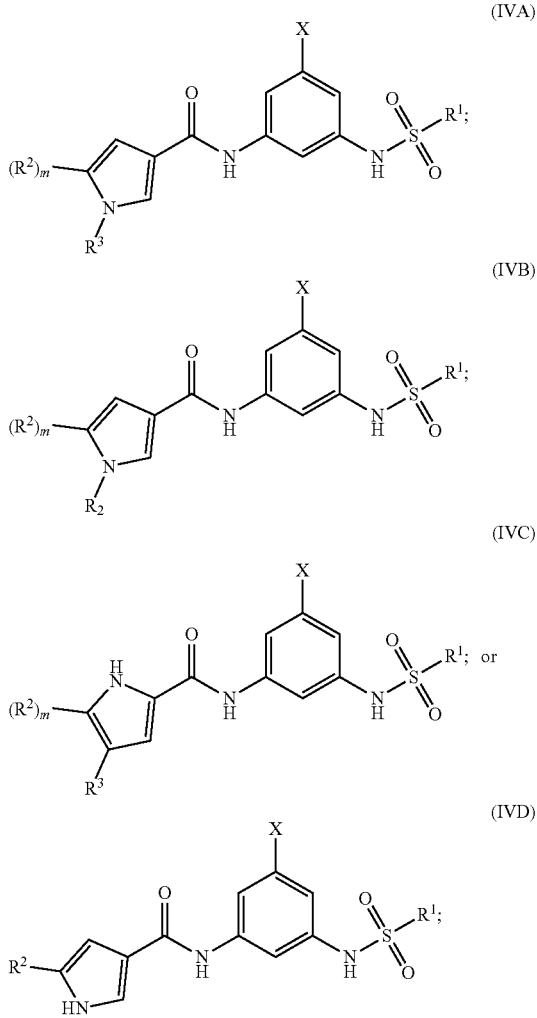

(IVA)
(IVB)
(IVC)
(IVD)

or a pharmaceutically acceptable salt thereof, wherein m is 0 or 1; and the variables X, $R^1$, $R^2$, and $R^3$ depicted in Formula (IVA), (IVB), (IVC), or (IVD) are as described in the first aspect or in the first, second, third, fourth, eleventh, fifteenth, seventeenth, eighteenth, nineteenth, twentieth, twenty-first, twenty-second, twenty-third, twenty-fourth, twenty-fifth, twenty-sixth, twenty-seventh, or twenty-eighth embodiment or any alternative embodiments described therein.

In a thirty-second embodiment, for compounds of Formula (I), (IIA), (IIB), (IIC), (IIIA), (IIIB), (IVA), (IVB), (IVC), or (IVD), or a pharmaceutically acceptable salt thereof, $R^1$ is —CH$_3$ or —CH$_2$CH$_3$; and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-first embodiment or any alternative embodiments described therein.

In a thirty-third embodiment, for compounds of Formula (I), (IIA), (IIB), (IIC), (IIIA), (IIIB), (IVA), (IVB), (IVC), or (IVD), or a pharmaceutically acceptable salt thereof, $R^1$ is —CH$_3$; and the remaining variables are as described in the first aspect or in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh, twenty-eighth, twenty-ninth, thirtieth, or thirty-first embodiment or any alternative embodiments described therein.

In a thirty-fourth embodiment, the compound of the present disclosure is represented by Formula (V):

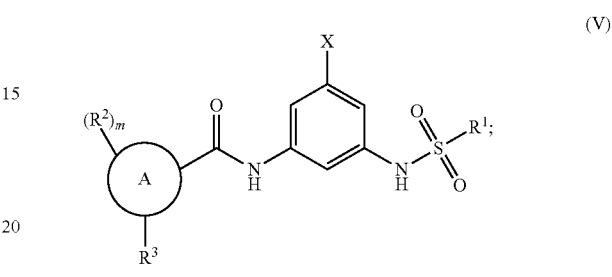

(V)

or a pharmaceutically acceptable salt thereof, wherein:
X is Cl or Br;
$R^1$ is —CH$_3$ or —CH$_2$CH$_3$;
ring A is selected from phenyl, thiophenyl, pyrrolyl, pyrazolyl, furanyl, isothiazolyl, and imidazolyl;
m is 0 or 1;
each $R^2$ is independently selected from C$_{1-3}$alkyl and —C(O)R$^{2d}$, wherein the C$_{1-3}$alkyl is optionally substituted with R$^{2g}$;
$R^{2d}$ is 4 to 6-membered monocyclic heterocyclyl;
$R^{2g}$ is cyano or OH;
$R^3$ is phenyl or 5 to 6-membered monocyclic heteroaryl, wherein the phenyl or 5 to 6-membered monocyclic heteroaryl are each optionally and independently substituted with 1 or 2 $R^4$;
each $R^4$ is independently selected from halo, C$_{1-4}$alkyl, —O-benzyl, —O—C$_{1-3}$alkyl, cyano, —NH$_2$, and 4 to 6-membered monocyclic heterocyclyl, wherein the benzyl is optionally substituted with 1 to 3 halo or C$_{1-3}$haloalkyl.

In an alternative thirty-fourth embodiment, for the compound of formula (V) or a pharmaceutically acceptable salt thereof, the definitions of variables are:
X is Cl or Br;
$R^1$ is —CH$_3$ or —CH$_2$CH$_3$;
ring A is selected from phenyl, thiophenyl, pyrrolyl, pyrazolyl, furanyl, isothiazolyl, and imidazolyl;
m is 0 or 1;
each $R^2$ is independently selected from C$_{1-3}$alkyl and —C(O)R$^{2d}$, wherein the C$_{1-3}$alkyl is optionally substituted with R$^{2g}$;
$R^{2d}$ is 4 to 6-membered monocyclic heterocyclyl;
$R^{2g}$ is cyano or OH;
$R^3$ is phenyl or 5 to 6-membered monocyclic heteroaryl, wherein the phenyl or 5 to 6-membered monocyclic heteroaryl are each optionally and independently substituted with 1 or 2 $R^4$;
each $R^4$ is independently selected from C$_{1-4}$alkyl, —O-benzyl, cyano, —NH$_2$, and 4 to 6-membered monocyclic heterocyclyl, wherein the benzyl is optionally substituted with halo.

In a thirty-fifth embodiment, for compounds of Formula (V), or a pharmaceutically acceptable salt thereof, ring A is

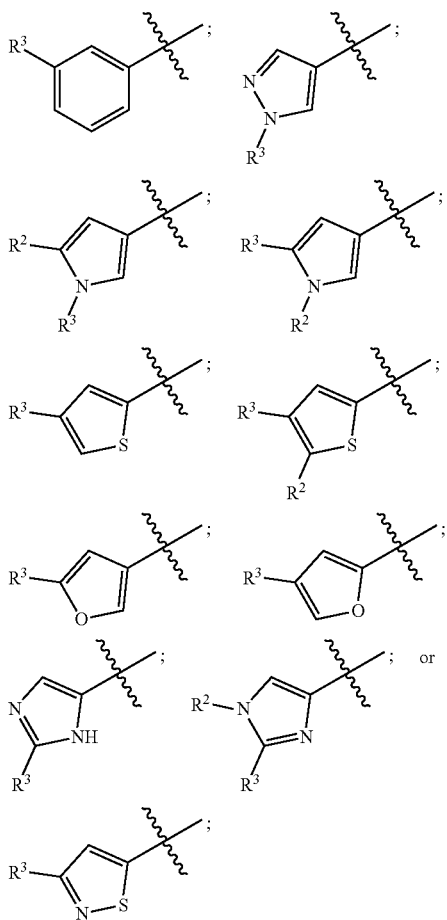

and the remaining variables are as described in the thirty-fourth embodiment or any alternative embodiments described therein.

In a thirty-sixth embodiment, the compound of the present disclosure is represented by Formula (IIB), (IIIA), (IVA); or (IVB):

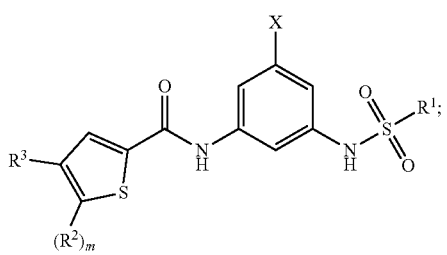

(IIB)

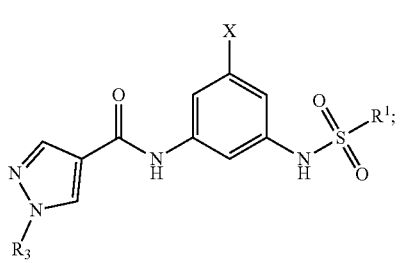

(IIIA)

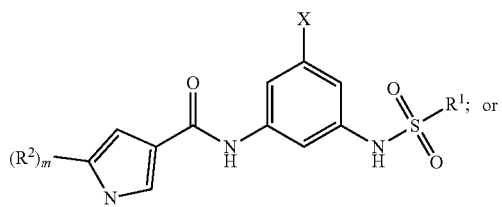

(IVA)

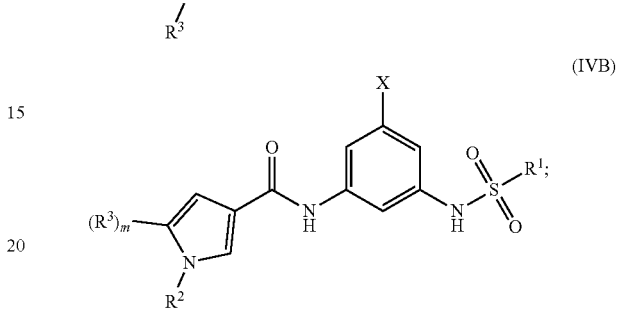

(IVB)

or a pharmaceutically acceptable salt thereof, wherein m is 0 or 1; and the variables X, $R^1$, $R^2$, and $R^3$ depicted in Formula (IIIA), (IVA), or (IVB) are as described in the thirty-fourth embodiment or any alternative embodiments described therein.

In a thirty-seventh embodiment, for compounds of Formula (V), (IIB), (IIIA), (IVA), or (IVB), or a pharmaceutically acceptable salt thereof, $R^3$ is phenyl, pyrazolyl, pyridyl, and pyrimidyl, each of which is optionally substituted with 1 to 2 $R^4$; and the remaining variables are as described in the thirty-fourth, thirty-fifth, or thirty-sixth embodiment or any alternative embodiments described therein.

In a thirty-eighth embodiment, for compounds of Formula (V), (IIB), (IIIA), (IVA), or (IVB) or a pharmaceutically acceptable salt thereof, $R^3$ is represented by the following structural formula:

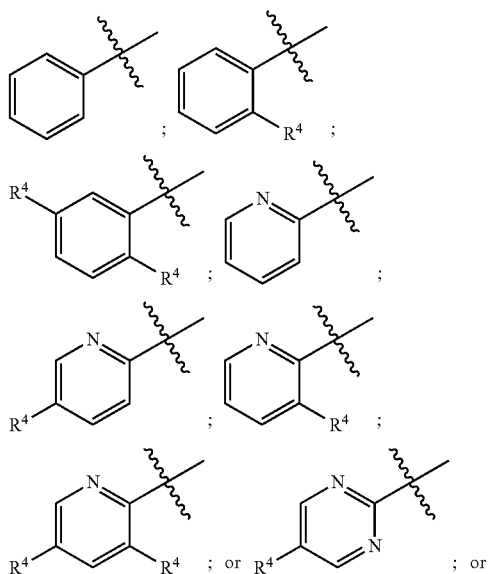

-continued

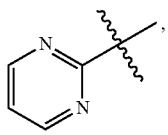

each of which is optionally substituted with 1 to 2 R⁴; and the remaining variables are as described in the thirty-fourth, thirty-fifth, or thirty-sixth embodiment or any alternative embodiments described therein. In an alternative thirty-eighth embodiment, R³ is

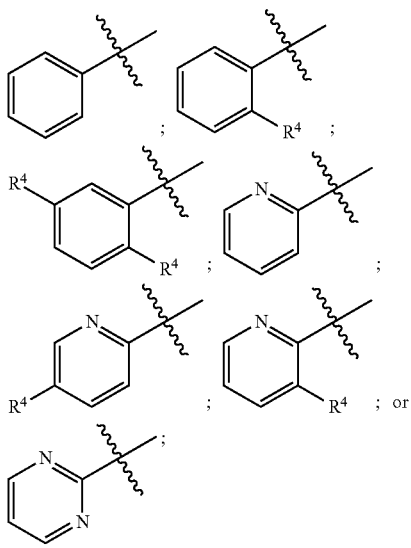

and the remaining variables are as described in the thirty-fourth, thirty-fifth, or thirty-sixth embodiment or any alternative embodiments described therein.

In a thirty-ninth embodiment, for compounds of Formula (V), (IIB), (IIIA), (IVA); or (IVB) or a pharmaceutically acceptable salt thereof, R⁴ is —F, —OCH(CH₃)₂, —OC(CH₃)₃, —CH₃, cyano, —NH₂, or R⁴ is represented by the following structural formula:

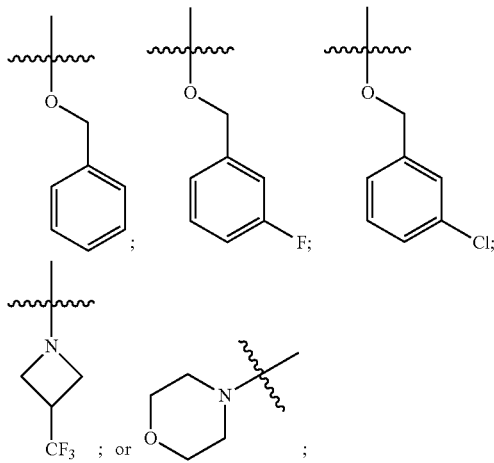

and the remaining variables are as described in the thirty-fourth, thirty-fifth, thirty-sixth, thirty-seventh, or thirty-eighth embodiment or any alternative embodiments described therein. In an alternative thirty-ninth embodiment, R⁴ is —CH₃, cyano, —NH₂,

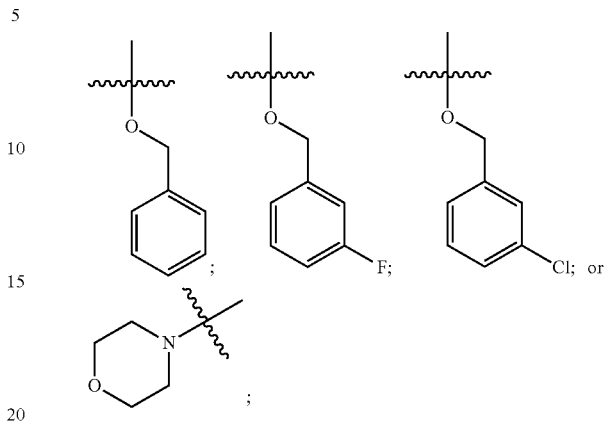

and the remaining variables are as described in the thirty-fourth, thirty-fifth, thirty-sixth, thirty-seventh, or thirty-eighth embodiment or any alternative embodiments described therein.

In a fortieth embodiment, for compounds of Formula (V), (IIB), (IIIA), (IVA), or (IVB) or a pharmaceutically acceptable salt thereof, R² is —CH₃, —CH₂CN, —CH₂OH,

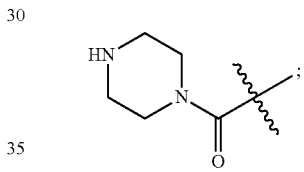

and the remaining variables are as described in the thirty-fourth, thirty-fifth, thirty-sixth, thirty-seventh, thirty-eighth, or thirty-ninth embodiment or any alternative embodiments described therein.

In a forty-first embodiment, the present disclosure provides a compound represented by Formula (IIB) or (IVB):

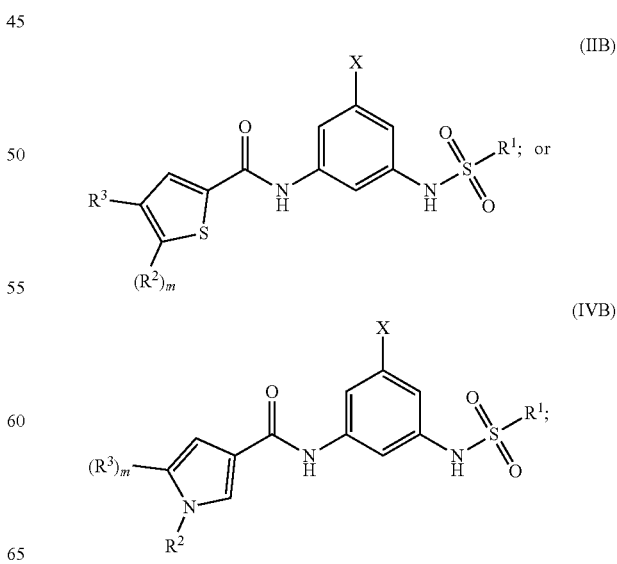

or a pharmaceutically acceptable salt thereof, wherein:
m is 1;
R¹ is —CH₃;
X is Cl;
R² is —CH₃;
R³ is pyrimidinyl or pyridinyl, each of which is optionally substituted with 1 or 2 R⁴;
R⁴ is halo, —OC$_{1-3}$alkyl, or 4- to 6-membered monocyclic heterocyclyl, wherein the 4 to 6-membered monocyclic heterocycyl is optionally substituted with 1 or 2 halo or C$_{1-3}$haloalkyl.

In a forty-second embodiment, for compounds of Formula (IIB) or (IVB), or a pharmaceutically acceptable salt thereof, R³ is represented by the following structural formula:

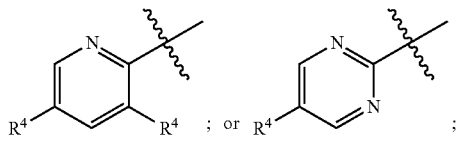

and the remaining variables are as described in the forty-first embodiment.

In a forty-third embodiment, for compounds of Formula (IIB) or (IVB), or a pharmaceutically acceptable salt thereof, each R⁴ is independently —F, —OCH(CH₃)₂, or —OC(CH₃)₃, or R⁴ is represented by the following structural formula:

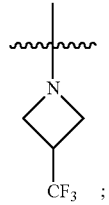 [SMILES: *N1CC(C(F)(F)F)C1]

and the remaining variables are as described in the forty-first or forty-second embodiment.

In a forty-fourth embodiment, the present disclosure provides a compound described herein (e.g., a compound of any one of Examples 1-736), or a pharmaceutically acceptable salt thereof.

In a forty-fifth embodiment, the present disclosure provides a compound selected from the group consisting of:
N-(3-chloro-5-(methylsulfonamido)phenyl)-1-phenyl-1H-imidazole-4-carboxamide;
5-bromo-N-(3-fluoro-5-(methylsulfonamido)phenyl)-1H-pyrrole-3-carboxamide;
N-(3-fluoro-5-(methylsulfonamido)phenyl)-5-methyl-1H-pyrazole-3-carboxamide;
5-bromo-N-(3-fluoro-5-(methylsulfonamido)phenyl)-1H-pyrazole-3-carboxamide;
N-(3-fluoro-5-(methylsulfonamido)phenyl)-5-methyl-1H-pyrrole-3-carboxamide;
N-(3-chloro-5-(methylsulfonamido)phenyl)-2-phenyl-1H-imidazole-4-carboxamide;
N-(3-chloro-5-(methylsulfonamido)phenyl)-4-phenylfuran-2-carboxamide;
N-(3-chloro-5-(methylsulfonamido)phenyl)-4-phenyl-1H-pyrrole-2-carboxamide;
N-(3-chloro-5-(methylsulfonamido)phenyl)-4-phenyl-1H-imidazole-2-carboxamide;
N-(3-bromo-5-(methylsulfonamido)phenyl)-4-methyl-3-(1H-pyrazol-1-yl)benzamide;
N-(3-chloro-5-(methylsulfonamido)phenyl)-5-methyl-4-phenylthiophene-2-carboxamide;
N-(3-bromo-5-(methylsulfonamido)phenyl)-2-phenylcyclobutane-1-carboxamide;
N-(3-chloro-5-(methylsulfonamido)phenyl)-3'-cyano-[1,1'-biphenyl]-3-carboxamide;
N-(3-chloro-5-(methylsulfonamido)phenyl)-3-(pyridin-4-yl)benzamide;
N-(3-bromo-5-(methylsulfonamido)phenyl)-4-phenylthiophene-2-carboxamide;
N-(3-iodo-5-(methylsulfonamido)phenyl)-4-phenylthiophene-2-carboxamide;
N-(3-bromo-5-(methylsulfonamido)phenyl)-4-(pyridin-2-yl)thiophene-2-carboxamide;
N-(3-bromo-5-(methylsulfonamido)phenyl)-4-(pyrazin-2-yl)thiophene-2-carboxamide;
N-(3-bromo-5-(methylsulfonamido)phenyl)-4-(2-hydroxy-6-methylphenyl)thiophene-2-carboxamide;
N-(3-bromo-5-(methylsulfonamido)phenyl)-4-(2-hydroxyphenyl)-5-methylthiophene-2-carboxamide;
N-(3-bromo-5-(methylsulfonamido)phenyl)-4-(2-hydroxyphenyl)thiophene-2-carboxamide;
N-(3-chloro-5-(methylsulfonamido)phenyl)-5-methyl-4-(pyrimidin-2-yl)thiophene-2-carboxamide;
N-(3-bromo-5-(methylsulfonamido)phenyl)-5-methyl-4-(pyridin-2-yl)thiophene-2-carboxamide;
N-(3-chloro-5-(methylsulfonamido)phenyl)-5-methyl-4-(pyridin-2-yl)thiophene-2-carboxamide;
N-(3-bromo-5-(methylsulfonamido)phenyl)-4-(pyrimidin-2-yl)thiophene-2-carboxamide;
N-(3-chloro-5-(methylsulfonamido)phenyl)-4-(pyrimidin-2-yl)thiophene-2-carboxamide;
N-(3-chloro-5-(ethylsulfonamido)phenyl)-5-methyl-4-(pyrimidin-2-yl)thiophene-2-carboxamide;
N-(3-chloro-5-(ethylsulfonamido)phenyl)-5-methyl-4-(pyridin-2-yl)thiophene-2-carboxamide;
4-(3-(benzyloxy)pyridin-2-yl)-N-(3-chloro-5-(methylsulfonamido)phenyl)thiophene-2-carboxamide;
4-(2-(benzyloxy)phenyl)-N-(3-bromo-5-(methylsulfonamido)phenyl)thiophene-2-carboxamide;
N-(3-chloro-5-(methylsulfonamido)phenyl)-4-(3-methylpyridin-2-yl)thiophene-2-carboxamide;
4-(3-(benzyloxy)pyridin-2-yl)-N-(3-bromo-5-(methylsulfonamido)phenyl)thiophene-2-carboxamide;
N-(3-bromo-5-(methylsulfonamido)phenyl)-4-(3-methylpyridin-2-yl)thiophene-2-carboxamide;
4-(3-(benzyloxy)pyridin-2-yl)-N-(3-chloro-5-(methylsulfonamido)phenyl)-5-methylthiophene-2-carboxamide;
N-(3-chloro-5-(methylsulfonamido)phenyl)-4-(5-fluoropyridin-2-yl)-5-methylthiophene-2-carboxamide;
N-(3-bromo-5-(methylsulfonamido)phenyl)-1-(pyridin-2-yl)-1H-pyrazole-4-carboxamide;
N-(3-chloro-5-(methylsulfonamido)phenyl)-1-(pyridin-2-yl)-1H-pyrazole-4-carboxamide;
N-(3-bromo-5-(methylsulfonamido)phenyl)-1-(4-cyanopyridin-2-yl)-1H-pyrazole-4-carboxamide;
N-(3-bromo-5-(methylsulfonamido)phenyl)-1-(5-fluoropyridin-2-yl)-1H-pyrazole-4-carboxamide;
N-(3-bromo-5-(methylsulfonamido)phenyl)-1-(pyrazin-2-yl)-1H-pyrazole-4-carboxamide;
N-(3-bromo-5-(methylsulfonamido)phenyl)-1-(5-cyanopyridin-2-yl)-1H-pyrazole-4-carboxamide;
N-(3-bromo-5-(methylsulfonamido)phenyl)-1-(5-methylpyridin-2-yl)-1H-pyrazole-4-carboxamide;

N-(3-bromo-5-(methylsulfonamido)phenyl)-1-(5-(trifluoromethyl)pyridin-2-yl)-1H-pyrazole-4-carboxamide;
N-(3-bromo-5-(methylsulfonamido)phenyl)-1-(2-cyano-6-methylphenyl)-1H-pyrazole-4-carboxamide;
N-(3-bromo-5-(methylsulfonamido)phenyl)-5-methyl-1-(3-methylpyridin-2-yl)-1H-pyrrole-3-carboxamide;
N-(3-chloro-5-(methylsulfonamido)phenyl)-1-(3-cyanopyridin-2-yl)-1H-pyrazole-4-carboxamide;
N-(3-chloro-5-(methylsulfonamido)phenyl)-1-(3-(trifluoromethyl)pyridin-2-yl)-1H-pyrazole-4-carboxamide;
N-(3-bromo-5-(methylsulfonamido)phenyl)-1-cyclohexyl-1H-pyrazole-4-carboxamide;
N-(3-bromo-5-(methylsulfonamido)phenyl)-1-(3-methylpyridin-2-yl)-1H-pyrazole-4-carboxamide;
N-(3-bromo-5-(methylsulfonamido)phenyl)-1-(pyrimidin-2-yl)-1H-pyrazole-4-carboxamide;
1-(2-(benzyloxy)phenyl)-N-(3-bromo-5-(methylsulfonamido)phenyl)-1H-pyrazole-4-carboxamide;
N-(3-bromo-5-(methylsulfonamido)phenyl)-1-(3-cyanophenyl)-1H-pyrazole-4-carboxamide;
N-(3-bromo-5-(methylsulfonamido)phenyl)-1-(5-cyano-2-methylphenyl)-1H-pyrazole-4-carboxamide;
N-(3-chloro-5-(methylsulfonamido)phenyl)-1-(3-methylpyridin-2-yl)-1H-pyrazole-4-carboxamide;
N-(3-bromo-5-(methylsulfonamido)phenyl)-1-(5-morpholinopyridin-2-yl)-1H-pyrazole-4-carboxamide;
N-(3-bromo-5-(methylsulfonamido)phenyl)-1-(6-(difluoromethyl)pyridin-2-yl)-1H-pyrazole-4-carboxamide;
N-(3-bromo-5-(methylsulfonamido)phenyl)-1-(6-(difluoromethoxy)pyridin-2-yl)-1H-pyrazole-4-carboxamide;
N-(3-bromo-5-(methylsulfonamido)phenyl)-1-(2-formylphenyl)-1H-pyrazole-4-carboxamide;
N-(3-chloro-5-(methylsulfonamido)phenyl)-5-methyl-1-(pyrimidin-2-yl)-1H-pyrrole-3-carboxamide;
N-(3-bromo-5-(methylsulfonamido)phenyl)-4-(1H-pyrazol-1-yl)thiophene-2-carboxamide;
N-(3-chloro-5-(methylsulfonamido)phenyl)-1-(3-(pyridin-3-ylmethoxy)pyridin-2-yl)-1H-pyrazole-4-carboxamide;
N-(3-chloro-5-(methylsulfonamido)phenyl)-1-(3-(1-phenylethoxy)pyridin-2-yl)-1H-pyrazole-4-carboxamide;
N-(3-chloro-5-(methylsulfonamido)phenyl)-1-(3-(pyridin-2-ylmethoxy)pyridin-2-yl)-1H-pyrazole-4-carboxamide;
N-(3-chloro-5-(methylsulfonamido)phenyl)-1-(3-(pyridin-4-ylmethoxy)pyridin-2-yl)-1H-pyrazole-4-carboxamide;
N-(3-chloro-5-(methylsulfonamido)phenyl)-1-(3-((3-fluorobenzyl)oxy)pyridin-2-yl)-1H-pyrazole-4-carboxamide;
N-(3-chloro-5-(methylsulfonamido)phenyl)-1-(3-(oxazol-5-ylmethoxy)pyridin-2-yl)-1H-pyrazole-4-carboxamide;
1-(2-(benzyloxy)-5-cyanophenyl)-N-(3-bromo-5-(methylsulfonamido)phenyl)-1H-pyrazole-4-carboxamide;
1-(3-(benzyloxy)pyridin-2-yl)-N-(3-chloro-5-(methylsulfonamido)phenyl)-1H-pyrazole-4-carboxamide;
N-(3-chloro-5-(methylsulfonamido)phenyl)-1-(3-((4-fluorobenzyl)oxy)pyridin-2-yl)-1H-pyrazole-4-carboxamide;
N-(3-chloro-5-(methylsulfonamido)phenyl)-1-(3-((3-chlorobenzyl)oxy)pyridin-2-yl)-1H-pyrazole-4-carboxamide;
4-bromo-N-(3-fluoro-5-(methylsulfonamido)phenyl)thiophene-2-carboxamide;
4-bromo-N-(3-(ethylsulfonamido)-5-fluorophenyl)thiophene-2-carboxamide;
N-(3-fluoro-5-(methylsulfonamido)phenyl)-4-phenylthiophene-2-carboxamide;
N-(3-(ethylsulfonamido)-5-fluorophenyl)-4-phenylthiophene-2-carboxamide;
N-(3-chloro-5-(methylsulfonamido)phenyl)-4-phenylthiophene-2-carboxamide;
N-(3-chloro-5-(methylsulfonamido)phenyl)-4-(pyridin-2-yl)thiophene-2-carboxamide;
N-(3-chloro-5-(ethylsulfonamido)phenyl)-4-(pyridin-2-yl)thiophene-2-carboxamide;
N-(3-bromo-5-(methylsulfonamido)phenyl)-4-(pyridin-3-yl)thiophene-2-carboxamide;
N-(3-chloro-5-(methylsulfonamido)phenyl)-1-ethyl-5-phenyl-1H-pyrrole-3-carboxamide;
N-(3-chloro-5-(methylsulfonamido)phenyl)-5-phenyl-1-(2,2,2-trifluoroethyl)-1H-pyrrole-3-carboxamide;
N-(3-chloro-5-(methylsulfonamido)phenyl)-1-methyl-5-(3-methylpyridin-2-yl)-1H-pyrrole-3-carboxamide;
N-(3-chloro-5-(methylsulfonamido)phenyl)-1-methyl-5-(pyrimidin-2-yl)-1H-pyrrole-3-carboxamide;
5-bromo-N-(3-chloro-5-(methylsulfonamido)phenyl)-1-methyl-1H-pyrrole-3-carboxamide;
N-(3-bromo-5-(methylsulfonamido)phenyl)-1-methyl-5-(3-methylpyridin-2-yl)-1H-pyrrole-3-carboxamide;
N-(3-bromo-5-(methylsulfonamido)phenyl)-1-cyclohexyl-5-methyl-1H-pyrrole-3-carboxamide;
1-(5-(4-acetylpiperazin-1-yl)pyridin-2-yl)-N-(3-bromo-5-(methylsulfonamido)phenyl)-1H-pyrazole-4-carboxamide;
1-(5-(4-acetylpiperazin-1-yl)-3-methylpyridin-2-yl)-N-(3-bromo-5-(methylsulfonamido)phenyl)-1H-pyrazole-4-carboxamide;
N-(3-bromo-5-(methylsulfonamido)phenyl)-1-(5-(4-methyl-3-oxopiperazin-1-yl)pyridin-2-yl)-1H-pyrazole-4-carboxamide;
4-(6-(4-((3-chloro-5-(methylsulfonamido)phenyl)carbamoyl)-1H-pyrazol-1-yl)pyridin-3-yl)-N,N-dimethylpiperazine-1-carboxamide;
N-(3-chloro-5-(methylsulfonamido)phenyl)-1-(5-(2-oxopyrrolidin-1-yl)pyridin-2-yl)-1H-pyrazole-4-carboxamide;
N-(3-chloro-5-(methylsulfonamido)phenyl)-1-(4-morpholinopyridin-2-yl)-1H-pyrazole-4-carboxamide;
N-(3-chloro-5-(methylsulfonamido)phenyl)-1-(5-(2-methylmorpholino)pyridin-2-yl)-1H-pyrazole-4-carboxamide;
N-(3-chloro-5-(methylsulfonamido)phenyl)-5-methyl-1-(5-morpholinopyridin-2-yl)-1H-pyrrole-3-carboxamide;
N-(3-chloro-5-(methylsulfonamido)phenyl)-5-methyl-1-(5-(4-methyl-3-oxopiperazin-1-yl)pyridin-2-yl)-1H-pyrrole-3-carboxamide;
N-(3-bromo-5-(methylsulfonamido)phenyl)-1-(cyanomethyl)-5-(pyridin-2-yl)-1H-pyrrole-3-carboxamide;
N-(3-bromo-5-(methylsulfonamido)phenyl)-1-methyl-2-(3-methylpyridin-2-yl)-1H-imidazole-4-carboxamide;
N-(3-chloro-5-(methylsulfonamido)phenyl)-1-(3-(difluoro(phenyl)methoxy)pyridin-2-yl)-1H-pyrazole-4-carboxamide;
N-(3-chloro-5-(methylsulfonamido)phenyl)-5-cyano-1-(pyridin-2-yl)-1H-pyrrole-3-carboxamide;
1-benzyl-N-(3-bromo-5-(methylsulfonamido)phenyl)-2-oxo-2,3-dihydro-1H-benzo[d]imidazole-5-carboxamide;
N-(3-chloro-5-(methylsulfonamido)phenyl)-3-(3-cyano-1H-pyrazol-1-yl)benzamide;
N-(3-bromo-5-(methylsulfonamido)phenyl)-2-oxo-1-phenyl-2,3-dihydro-1H-imidazole-4-carboxamide;
N-(3-chloro-5-(methylsulfonamido)phenyl)-3-(2-chloropyridin-4-yl)benzamide;
N-(3-bromo-5-(methylsulfonamido)phenyl)-1-(2-(2,2,2-trifluoro-1-hydroxyethyl)phenyl)-1H-pyrazole-4-carboxamide;
4-((1H-pyrrol-2-yl)methyl)-N-(3-bromo-5-(methylsulfonamido)phenyl)thiophene-2-carboxamide;
N-(3-fluoro-5-(methylsulfonamido)phenyl)-4-(pyridin-3-yl)thiophene-2-carboxamide;

N-(3-chloro-5-(methylsulfonamido)phenyl)-4-(2-hydroxyphenyl)thiophene-2-carboxamide;
N-(3-chloro-5-(methylsulfonamido)phenyl)-4-(2-methoxyphenyl)thiophene-2-carboxamide;
N-(3-chloro-5-(methylsulfonamido)phenyl)-4-(3-fluorophenyl)thiophene-2-carboxamide;
N-(3-chloro-5-(methylsulfonamido)phenyl)-1-methyl-5-phenyl-1H-pyrrole-3-carboxamide;
N-(3-chloro-5-(ethylsulfonamido)phenyl)-4-(pyridin-3-yl)thiophene-2-carboxamide;
4-(2-(benzyloxy)phenyl)-N-(3-chloro-5-(methylsulfonamido)phenyl)thiophene-2-carboxamide;
N-(3-fluoro-5-(methylsulfonamido)phenyl)-4-(pyridin-2-yl)thiophene-2-carboxamide;
N-(3-(ethylsulfonamido)-5-fluorophenyl)-4-(pyridin-2-yl)thiophene-2-carboxamide;
N-(3-fluoro-5-(methylsulfonamido)phenyl)-4-(2-hydroxyphenyl)thiophene-2-carboxamide;
N-(3-chloro-5-(methylsulfonamido)phenyl)-4-(2,6-difluorophenyl)thiophene-2-carboxamide;
N-(3-chloro-5-(methylsulfonamido)phenyl)-4-(pyridin-3-yl)thiophene-2-carboxamide;
N-(3-chloro-5-(methylsulfonamido)phenyl)-3-(1H-pyrazol-1-yl)benzamide;
N-(3-bromo-5-(methylsulfonamido)phenyl)-3-(1H-pyrazol-1-yl)benzamide;
1-ethyl-N-(3-fluoro-5-(methylsulfonamido)phenyl)-5-methyl-1H-pyrazole-3-carboxamide;
N-(3-chloro-5-(methylsulfonamido)phenyl)-5-(hydroxymethyl)-4-phenylthiophene-2-carboxamide;
N-(3-bromo-5-(methylsulfonoamidimidamido)phenyl)-4-(pyridin-2-yl)thiophene-2-carboxamide;
N-(3-bromo-5-(methylsulfonoamidimidamido)phenyl)-4-(3-methylpyridin-2-yl)thiophene-2-carboxamide;
N-(3-bromo-5-(methylsulfonoamidimidamido)phenyl)-5-methyl-4-(pyridin-2-yl)thiophene-2-carboxamide;
N-(3-chloro-5-(methylsulfonamido)phenyl)-5-phenylthiophene-3-carboxamide;
N-(3-chloro-5-(methylsulfonamido)phenyl)-5-phenylfuran-3-carboxamide;
N-(3-chloro-5-(methylsulfonamido)phenyl)-1-(3-hydroxypropyl)-1H-pyrazole-4-carboxamide;
N-(3-chloro-5-(methylsulfonamido)phenyl)-1-(2-hydroxyethyl)-1H-pyrazole-4-carboxamide;
N-(3-chloro-5-(methylsulfonamido)phenyl)-1-(2-oxaspiro[3.3]heptan-6-yl)-1H-pyrazole-4-carboxamide;
N-(3-chloro-5-(methylsulfonamido)phenyl)-5-methyl-1-phenyl-1H-pyrrole-3-carboxamide;
N-(3-chloro-5-(methylsulfonamido)phenyl)-5-methyl-1-(3-methylpyridin-2-yl)-1H-pyrrole-3-carboxamide;
N-(3-chloro-5-(methylsulfonamido)phenyl)-1-(tetrahydro-2H-pyran-4-yl)-1H-pyrazole-4-carboxamide;
N-(3-chloro-5-(methylsulfonamido)phenyl)-2-ethylimidazo[1,2-a]pyridine-6-carboxamide;
N-(3-chloro-5-(methylsulfonamido)phenyl)-3-(dimethylamino)-2-ethylimidazo[1,2-a]pyridine-6-carboxamide;
N-(3-chloro-5-(methylsulfonamido)phenyl)imidazo[1,2-a]pyridine-6-carboxamide;
N-(3-chloro-5-(methylsulfonamido)phenyl)benzofuran-7-carboxamide;
tert-butyl 4-(4-((3-chloro-5-(methylsulfonamido)phenyl)carbamoyl)-1H-pyrazol-1-yl)piperidine-1-carboxylate;
N-(3-chloro-5-(methylsulfonamido)phenyl)-3-(pyridin-2-yl)isothiazole-5-carboxamide;
5-(2-(benzyloxy)phenyl)-N-(3-chloro-5-(methylsulfonamido)phenyl)-1-methyl-1H-pyrazole-3-carboxamide;
3-(2-(benzyloxy)phenyl)-N-(3-chloro-5-(methylsulfonamido)phenyl)-1-methyl-1H-pyrazole-5-carboxamide;
N-(3-chloro-5-(methylsulfonamido)phenyl)-1-methyl-5-(pyridin-2-yl)-1H-pyrazole-3-carboxamide;
N-(3-chloro-5-(methylsulfonamido)phenyl)-1-methyl-3-(pyridin-2-yl)-1H-pyrazole-5-carboxamide;
N-(3-chloro-5-(methylsulfonamido)phenyl)-1-(1-phenylethyl)-1H-pyrazole-4-carboxamide;
N-(3-chloro-5-(methylsulfonamido)phenyl)-1-(2,2-difluoroethyl)-5-(3-methylpyridin-2-yl)-1H-pyrrole-3-carboxamide;
tert-butyl 6-(4-((3-chloro-5-(methylsulfonamido)phenyl)carbamoyl)-1H-pyrazol-1-yl)-2-azaspiro[3.3]heptane-2-carboxylate;
N-(3-chloro-5-(methylsulfonamido)phenyl)-1-(piperidin-4-yl)-1H-pyrazole-4-carboxamide;
N-(3-chloro-5-(methylsulfonamido)phenyl)-1-(2-azaspiro[3.3]heptan-6-yl)-1H-pyrazole-4-carboxamide;
N-(3-chloro-5-(methylsulfonamido)phenyl)-1-(4-(piperazin-1-yl)pyridin-2-yl)-1H-pyrazole-4-carboxamide;
1-(4-(4-acetylpiperazin-1-yl)pyridin-2-yl)-N-(3-chloro-5-(methylsulfonamido)phenyl)-1H-pyrazole-4-carboxamide;
N-(3-chloro-5-(methylsulfonamido)phenyl)-1-(5-(4-isobutyrylpiperazin-1-yl)pyridin-2-yl)-1H-pyrazole-4-carboxamide;
N-(3-chloro-5-(methylsulfonamido)phenyl)-1-(2-hydroxycyclohexyl)-1H-pyrazole-4-carboxamide;
N-(3-chloro-5-(methylsulfonamido)phenyl)-1-(4-hydroxycyclohexyl)-1H-pyrazole-4-carboxamide;
N-(3-chloro-5-(methylsulfonamido)phenyl)-1-(3-hydroxycyclohexyl)-1H-pyrazole-4-carboxamide;
N-(3-chloro-5-(methylsulfonamido)phenyl)-1-methyl-2-phenyl-1H-imidazole-4-carboxamide;
N-(3-chloro-5-(methylsulfonamido)phenyl)-1-methyl-2-(3-methylpyridin-2-yl)-1H-imidazole-4-carboxamide;
N-(3-bromo-5-(methylsulfonamido)phenyl)thiophene-2-carboxamide;
N-(3-chloro-5-(methylsulfonamido)phenyl)-1-methyl-5-(2-oxopiperidin-1-yl)-1H-pyrrole-3-carboxamide;
1-(2-(benzyloxy)cyclobutyl)-N-(3-chloro-5-(methylsulfonamido)phenyl)-1H-pyrazole-4-carboxamide;
N-(3-chloro-5-(methylsulfonamido)phenyl)-3-(3-(hydroxymethyl)-1H-pyrazol-1-yl)benzamide;
N-(3-bromo-5-(methylsulfonamido)phenyl)-1-(2-(hydroxymethyl)phenyl)-1H-pyrazole-4-carboxamide;
1-(3-aminopyridin-2-yl)-N-(3-bromo-5-(methylsulfonamido)phenyl)-1H-pyrazole-4-carboxamide;
N-(3-chloro-5-(methylsulfonamido)phenyl)-5-(hydroxymethyl)-4-(pyridin-2-yl)thiophene-2-carboxamide;
N-(3-chloro-5-(methylsulfonamido)phenyl)-3-(phenylamino)-1H-pyrazole-5-carboxamide;
N-(3-chloro-5-(methylsulfonamido)phenyl)-5-(piperazine-1-carbonyl)-1-(pyridin-2-yl)-1H-pyrrole-3-carboxamide;
N2-(3-chloro-5-(methylsulfonamido)phenyl)-N4-phenylthiophene-2,4-dicarboxamide;
N-(3-chloro-5-(methylsulfonamido)phenyl)-1-(3-(phenoxymethyl)pyridin-2-yl)-1H-pyrazole-4-carboxamide;
1-(3-(benzylamino)pyridin-2-yl)-N-(3-chloro-5-(methylsulfonamido)phenyl)-1H-pyrazole-4-carboxamide;
N-(3-chloro-5-(methylsulfonamido)phenyl)-5-(hydroxymethyl)-1-(pyridin-2-yl)-1H-pyrrole-3-carboxamide;
N-(3-chloro-5-(methylsulfonamido)phenyl)-5-methyl-1-(pyridin-2-yl)-1H-pyrrole-3-carboxamide;
N-(3-chloro-5-(methylsulfonamido)phenyl)-5-(5-fluoropyrimidin-2-yl)-1-methyl-1H-pyrrole-3-carboxamide;

N-(3-chloro-5-(methylsulfonamido)phenyl)-5-(5-ethoxypyrimidin-2-yl)-1-methyl-1H-pyrrole-3-carboxamide;
N-(3-chloro-5-(ethylsulfonamido)phenyl)-1-methyl-5-(pyrimidin-2-yl)-1H-pyrrole-3-carboxamide;
N-(3-chloro-5-(methylsulfonamido)phenyl)-5-(((5-fluoropyridin-3-yl)methoxy)pyridin-2-yl)-1-methyl-1H-pyrrole-3-carboxamide;
N-(3-chloro-5-(methylsulfonamido)phenyl)-1-(3-((5-fluoropyridin-3-yl)methoxy)pyridin-2-yl)-5-methyl-1H-pyrrole-3-carboxamide;
N-(3-chloro-5-(methylsulfonamido)phenyl)-4-(2-oxopyrrolidin-1-yl)thiophene-2-carboxamide;
N-(3-chloro-5-(methylsulfonamido)phenyl)-5-cyclopropyl-4-(pyridin-2-yl)thiophene-2-carboxamide;
N-(3-chloro-5-(methylsulfonamido)phenyl)-4-(3-(pyrimidin-2-yloxy)pyridin-2-yl)thiophene-2-carboxamide;
N-(3-chloro-5-(methylsulfonamido)phenyl)-1-(3-((3-hydroxybenzyl)oxy)pyridin-2-yl)-1H-pyrazole-4-carboxamide;
N-(3-chloro-5-(methylsulfonamido)phenyl)-1-(5-(3-oxomorpholino)pyridin-2-yl)-1H-pyrazole-4-carboxamide;
5-(aminomethyl)-N-(3-chloro-5-(methylsulfonamido)phenyl)-1-(pyridin-2-yl)-1H-pyrrole-3-carboxamide;
N-(3-chloro-5-(methylsulfonamido)phenyl)-1-(tetrahydrofuran-3-yl)-1H-pyrazole-4-carboxamide;
N-(3-chloro-5-(methylsulfonamido)phenyl)-1-(5-(4-methyl-3-oxopiperazin-1-yl)pyrimidin-2-yl)-1H-pyrazole-4-carboxamide;
N-(3-chloro-5-(methylsulfonamido)phenyl)-1-(5-(4-methyl-3-oxopiperazin-1-yl)pyrazin-2-yl)-1H-pyrazole-4-carboxamide;
N-(3-chloro-5-(methylsulfonamido)phenyl)-5-(3-(pyridin-3-ylmethoxy)pyridin-2-yl)-1-(2,2,2-trifluoroethyl)-1H-pyrrole-3-carboxamide;
N-(3-chloro-5-(methylsulfonamido)phenyl)-1-(3-((5-fluoropyridin-3-yl)methoxy)pyridin-2-yl)-1H-pyrazole-4-carboxamide;
N-(3-chloro-5-(methylsulfonamido)phenyl)-1-(3-((3,5-difluorobenzyl)oxy)pyridin-2-yl)-1H-pyrazole-4-carboxamide;
N-(3-chloro-5-(methylsulfonamido)phenyl)-1-(3-(pyrimidin-5-ylmethoxy)pyridin-2-yl)-1H-pyrazole-4-carboxamide;
N-(3-chloro-5-(methylsulfonamido)phenyl)-1-(3-((2-fluorobenzyl)oxy)pyridin-2-yl)-1H-pyrazole-4-carboxamide;
N-(3-chloro-5-(methylsulfonamido)phenyl)-1-(5-(tetrahydro-2H-pyran-4-yl)pyridin-2-yl)-1H-pyrazole-4-carboxamide;
1-(5-(8-oxa-3-azabicyclo[3.2.1]octan-3-yl)pyridin-2-yl)-N-(3-chloro-5-(methylsulfonamido)phenyl)-1H-pyrazole-4-carboxamide;
N-(3-chloro-5-(methylsulfonamido)phenyl)-1-(5-(5,6-dihydroimidazo[1,2-a]pyrazin-7(8H)-yl)pyridin-2-yl)-1H-pyrazole-4-carboxamide;
N-(3-chloro-5-(methylsulfonamido)phenyl)-1-(5-(4-methyl-3-oxopiperazin-1-yl)-3-(pyridin-3-ylmethoxy)pyridin-2-yl)-1H-pyrazole-4-carboxamide;
N-(3-chloro-5-(methylsulfonamido)phenyl)-1-(5-morpholino-3-(pyridin-3-ylmethoxy)pyridin-2-yl)-1H-pyrazole-4-carboxamide;
N-(3-chloro-5-(methylsulfonamido)phenyl)-1-(3-(2-hydroxy-2-methylpropoxy)pyridin-2-yl)-1H-pyrazole-4-carboxamide;
N-(3-chloro-5-(methylsulfonamido)phenyl)-1-(3-(pyrimidin-2-yloxy)pyridin-2-yl)-1H-pyrazole-4-carboxamide;
N-(3-chloro-5-(methylsulfonamido)phenyl)-1-(5-methoxypyridin-2-yl)-1H-pyrazole-4-carboxamide;
N-(3-chloro-5-(methylsulfonamido)phenyl)-1-(5-(methylsulfonyl)pyridin-2-yl)-1H-pyrazole-4-carboxamide;
N-(3-chloro-5-(methylsulfonamido)phenyl)-1-(3-(methylsulfonyl)pyridin-2-yl)-1H-pyrazole-4-carboxamide;
N-(3-chloro-5-(methylsulfonamido)phenyl)-1-(5-(N,N-dimethylsulfamoyl)pyridin-2-yl)-1H-pyrazole-4-carboxamide;
N-(3-chloro-5-(methylsulfonamido)phenyl)-1-(3-(dimethylphosphoryl)pyridin-2-yl)-1H-pyrazole-4-carboxamide;
N-(3-chloro-5-(methylsulfonamido)phenyl)-1-(5-fluoro-3-((3-fluorobenzyl)oxy)pyridin-2-yl)-1H-pyrazole-4-carboxamide;
N-(3-chloro-5-(methylsulfonamido)phenyl)-1-(3-((3-cyanobenzyl)oxy)-5-fluoropyridin-2-yl)-1H-pyrazole-4-carboxamide;
N-(3-chloro-5-(methylsulfonamido)phenyl)-1-(3-((3-fluorobenzyl)oxy)-6-methylpyridin-2-yl)-1H-pyrazole-4-carboxamide;
N-(3-chloro-5-(methylsulfonamido)phenyl)-1-(3-(thiazol-2-ylmethoxy)pyridin-2-yl)-1H-pyrazole-4-carboxamide;
1-(3-((1H-pyrazol-4-yl)methoxy)pyridin-2-yl)-N-(3-chloro-5-(methylsulfonamido)phenyl)-1H-pyrazole-4-carboxamide;
N-(3-chloro-5-(methylsulfonamido)phenyl)-1-(5-fluoropyrimidin-2-yl)-5-methyl-1H-pyrrole-3-carboxamide;
N-(3-chloro-5-(methylsulfonamido)phenyl)-1-(5-ethoxypyrimidin-2-yl)-5-methyl-1H-pyrrole-3-carboxamide;
N-(3-chloro-5-(methylsulfonamido)phenyl)indolizine-2-carboxamide;
N-(3-chloro-5-(methylsulfonamido)phenyl)-1-(2-((3-fluorobenzyl)oxy)phenyl)-1H-pyrazole-4-carboxamide;
N-(3-chloro-5-(methylsulfonamido)phenyl)-1-(2-fluoro-6-((3-fluorobenzyl)oxy)phenyl)-1H-pyrazole-4-carboxamide;
3-(3-(benzyloxy)pyridin-2-yl)-N5-(3-chloro-5-(methylsulfonamido)phenyl)-N2-methylthiophene-2,5-dicarboxamide;
3-(3-(benzyloxy)pyridin-2-yl)-N5-(3-chloro-5-(methylsulfonamido)phenyl)-N2,N2-dimethylthiophene-2,5-dicarboxamide;
4-(3-(benzyloxy)pyridin-2-yl)-N-(3-fluoro-5-(methylsulfonamido)phenyl)thiophene-2-carboxamide;
N-(3-chloro-5-(methylsulfonamido)phenyl)-4-(3-(oxazol-5-ylmethoxy)pyridin-2-yl)thiophene-2-carboxamide;
4-(3-(benzyloxy)pyridin-2-yl)-N-(3-chloro-5-(methylsulfonamido)phenyl)-5-(hydroxymethyl)thiophene-2-carboxamide;
N-(3-chloro-5-(methylsulfonamido)phenyl)-4-(3-(pyridin-3-ylmethoxy)pyridin-2-yl)thiophene-2-carboxamide;
N-(3-chloro-5-(methylsulfonamido)phenyl)-1-(5-(methylthio)pyridin-2-yl)-1H-pyrazole-4-carboxamide;
N-(3-chloro-5-(methylsulfonamido)phenyl)-1-(3-(methylthio)pyridin-2-yl)-1H-pyrazole-4-carboxamide;
N-(3-chloro-5-(methylsulfonamido)phenyl)-4-(3-(cyclopropanecarboxamido)pyridin-2-yl)thiophene-2-carboxamide;
N-(3-chloro-5-(methylsulfonamido)phenyl)-4-(3-(2-(dimethylamino)-2-oxoethyl)pyridin-2-yl)thiophene-2-carboxamide;
2-(5-((3-chloro-5-(methylsulfonamido)phenyl)carbamoyl)thiophen-3-yl)-N,N-dimethylnicotinamide;
N-(3-chloro-5-(methylsulfonamido)phenyl)-4-(3-(trifluoromethyl)pyridin-2-yl)thiophene-2-carboxamide;
N-(3-chloro-5-(ethylsulfonamido)phenyl)-4-(3-methylpyridin-2-yl)thiophene-2-carboxamide;

N-(3-chloro-5-(methylsulfonamido)phenyl)-4-(5-fluoro-3-((5-fluoropyridin-3-yl)methoxy)pyridin-2-yl)thiophene-2-carboxamide;
N-(3-chloro-5-(ethylsulfonamido)phenyl)-4-(5-fluoro-3-methylpyridin-2-yl)thiophene-2-carboxamide;
N-(3-chloro-5-(methylsulfonamido)phenyl)-4-(3-hydroxypyridin-2-yl)-5-methylthiophene-2-carboxamide;
N-(3-chloro-5-(methylsulfonamido)phenyl)-4-(3-((3,5-difluorophenoxy)methyl)pyridin-2-yl)thiophene-2-carboxamide;
N-(3-chloro-5-(methylsulfonamido)phenyl)-4-(5'-fluoro-[3,3'-bipyridin]-2-yl)-5-methylthiophene-2-carboxamide;
N-(3-chloro-5-(methylsulfonamido)phenyl)thieno[2,3-c]pyridine-2-carboxamide;
1-(3-((3-bromobenzyl)oxy)pyridin-2-yl)-N-(3-chloro-5-(methylsulfonamido)phenyl)-1H-pyrazole-4-carboxamide;
N-(3-chloro-5-(methylsulfonamido)phenyl)-5-ethyl-4-(pyridin-2-yl)thiophene-2-carboxamide;
N-(3-chloro-5-(methylsulfonamido)phenyl)-5-isopropyl-4-(pyridin-2-yl)thiophene-2-carboxamide;
N-(3-chloro-5-(methylsulfonamido)phenyl)-5-(methoxymethyl)-4-(pyridin-2-yl)thiophene-2-carboxamide;
4-(1-benzyl-1H-1,2,3-triazol-4-yl)-N-(3-chloro-5-(methylsulfonamido)phenyl)-5-methylthiophene-2-carboxamide;
N-(3-chloro-5-(methylsulfonamido)phenyl)-5-methyl-4-(1-phenyl-1H-1,2,3-triazol-4-yl)thiophene-2-carboxamide;
N-(3-chloro-5-(methylsulfonamido)phenyl)-4-(3-(pyrimidin-2-ylamino)pyridin-2-yl)thiophene-2-carboxamide;
N-(3-chloro-5-(methylsulfonamido)phenyl)-4-(3-(methyl(pyrimidin-2-yl)amino)pyridin-2-yl)thiophene-2-carboxamide;
N-(3-chloro-5-(methylsulfonamido)phenyl)-4-(3-(pyridin-3-yloxy)pyridin-2-yl)thiophene-2-carboxamide;
4-(2-(benzyloxy)-6-fluorophenyl)-N-(3-chloro-5-(methylsulfonamido)phenyl)-5-methylthiophene-2-carboxamide;
4-bromo-N-(3-chloro-5-(methylsulfonamido)phenyl)thiophene-2-carboxamide;
methyl (5-((3-chloro-5-(methylsulfonamido)phenyl)carbamoyl)thiophen-3-yl)prolinate;
N-(3-chloro-5-(methylsulfonamido)phenyl)-4-(piperidin-4-yl)thiophene-2-carboxamide;
N-(3-chloro-5-(methylsulfonamido)phenyl)-4-(piperazin-1-yl)thiophene-2-carboxamide;
N-(3-chloro-5-(methylsulfonamido)phenyl)-4-morpholinothiophene-2-carboxamide;
N-(3-chloro-5-(methylsulfonamido)phenyl)-4-(4-(2,2,2-trifluoroethyl)piperazin-1-yl)thiophene-2-carboxamide;
N-(3-chloro-5-(cyclopropanesulfonamido)phenyl)-5-methyl-1-(5-morpholinopyridin-2-yl)-1H-pyrrole-3-carboxamide;
N-(3-chloro-5-((difluoromethyl)sulfonamido)phenyl)-5-methyl-1-(5-morpholinopyridin-2-yl)-1H-pyrrole-3-carboxamide;
N-(3-chloro-5-(ethylsulfonamido)phenyl)-5-methyl-1-(5-morpholinopyridin-2-yl)-1H-pyrrole-3-carboxamide;
1-(8-oxabicyclo[3.2.1]octan-3-yl)-N-(3-chloro-5-(methylsulfonamido)phenyl)-1H-pyrazole-4-carboxamide;
N-(3-chloro-5-(methylsulfonamido)phenyl)-1-(5-fluoro-3-(3-fluorophenethyl)pyridin-2-yl)-1H-pyrazole-4-carboxamide;
1-(3-((1H-imidazol-2-yl)methoxy)pyridin-2-yl)-N-(3-chloro-5-(methylsulfonamido)phenyl)-1H-pyrazole-4-carboxamide;
1-(3-(((1H-pyrazol-5-yl)methoxy)pyridin-2-yl)-N-(3-chloro-5-(methylsulfonamido)phenyl)-1H-pyrazole-4-carboxamide;
1-(3-((1H-imidazol-4-yl)methoxy)pyridin-2-yl)-N-(3-chloro-5-(methylsulfonamido)phenyl)-1H-pyrazole-4-carboxamide;
N-(3-chloro-5-(methylsulfonamido)phenyl)-1-(2-((3-fluorobenzyl)oxy)-6-methylphenyl)-1H-pyrazole-4-carboxamide;
N-(3-chloro-5-(methylsulfonamido)phenyl)-1-(3-((3,5-difluorophenoxy)methyl)pyridin-2-yl)-1H-pyrazole-4-carboxamide;
N-(3-chloro-5-(methylsulfonamido)phenyl)-1-(2-(5-fluoropyridin-3-yl)phenyl)-1H-pyrazole-4-carboxamide;
N-(3-chloro-5-(methylsulfonamido)phenyl)-1-(3-((3,5-difluorobenzyl)oxy)-5-(2-oxa-6-azaspiro[3.3]heptan-6-yl)pyridin-2-yl)-1H-pyrazole-4-carboxamide;
N-(3-chloro-5-(methylsulfonamido)phenyl)-1-(2-phenoxycyclopentyl)-1H-pyrazole-4-carboxamide;
N-(3-chloro-5-(methylsulfonamido)phenyl)-1-(2-phenylcyclopentyl)-1H-pyrazole-4-carboxamide;
N-(3-chloro-5-(methylsulfonamido)phenyl)-1-(5-methyl-3-(oxazol-5-ylmethoxy)pyridin-2-yl)-1H-pyrazole-4-carboxamide;
N-(3-chloro-5-(methylsulfonamido)phenyl)-1-(3-(((5-fluoropyridin-3-yl)oxy)methyl)pyridin-2-yl)-1H-pyrazole-4-carboxamide;
N-(3-chloro-5-(methylsulfonamido)phenyl)-1-(2-(pyrimidin-2-yloxy)phenyl)-1H-pyrazole-4-carboxamide;
N-(3-chloro-5-(methylsulfonamido)phenyl)-1-(2-(pyridin-3-yloxy)phenyl)-1H-pyrazole-4-carboxamide;
N-(3-chloro-5-(methylsulfonamido)phenyl)-1-(2-(3-fluorophenoxy)phenyl)-1H-pyrazole-4-carboxamide;
N-(3-chloro-5-(methylsulfonamido)phenyl)-1-(5-(1-methyl-2-oxopiperidin-4-yl)pyridin-2-yl)-1H-pyrazole-4-carboxamide;
N-(3-chloro-5-(methylsulfonamido)phenyl)-1-(5-fluoropyridin-2-yl)-5-(trifluoromethyl)-1H-pyrrole-3-carboxamide;
N-(3-chloro-5-(methylsulfonamido)phenyl)-5-(5-fluoro-3-(oxazol-5-ylmethoxy)pyridin-2-yl)-1-methyl-1H-pyrrole-3-carboxamide;
N-(3-chloro-5-(methylsulfonamido)phenyl)-5-methyl-1-(5-(methyl(tetrahydrofuran-3-yl)amino)pyridin-2-yl)-1H-pyrrole-3-carboxamide;
N-(3-chloro-5-(methylsulfonamido)phenyl)-5-methyl-1-(5-(pyrrolidin-1-yl)pyridin-2-yl)-1H-pyrrole-3-carboxamide;
N-(3-chloro-5-(methylsulfonamido)phenyl)-1-(5-morpholinopyridin-2-yl)-5-(trifluoromethyl)-1H-pyrrole-3-carboxamide;
N-(3-chloro-5-(methylsulfonamido)phenyl)-1-(5-(2,2-dimethylmorpholino)pyridin-2-yl)-5-methyl-1H-pyrrole-3-carboxamide;
N-(3-chloro-5-(methylsulfonamido)phenyl)-1-methyl-5-(5-morpholinopyridin-2-yl)-1H-pyrrole-3-carboxamide;
N-(3-chloro-5-(methylsulfonamido)phenyl)-1-ethyl-5-(5-morpholinopyridin-2-yl)-1H-pyrrole-3-carboxamide;
N-(3-chloro-5-(methylsulfonamido)phenyl)-5-(5-morpholinopyridin-2-yl)-1-(2,2,2-trifluoroethyl)-1H-pyrrole-3-carboxamide;
1-(5-(2-oxa-6-azaspiro[3.3]heptan-6-yl)pyridin-2-yl)-N-(3-chloro-5-(methylsulfonamido)phenyl)-5-methyl-1H-pyrrole-3-carboxamide;
5-(5-(2-oxa-6-azaspiro[3.3]heptan-6-yl)pyridin-2-yl)-N-(3-chloro-5-(methylsulfonamido)phenyl)-1-methyl-1H-pyrrole-3-carboxamide;
5-(5-(2-oxa-6-azaspiro[3.3]heptan-6-yl)pyridin-2-yl)-N-(3-chloro-5-(methylsulfonamido)phenyl)-1-(2,2,2-trifluoroethyl)-1H-pyrrole-3-carboxamide;

N-(3-chloro-5-(methylsulfonamido)phenyl)-1-methyl-5-(3-(thiazol-2-ylmethoxy)pyridin-2-yl)-1H-pyrrole-3-carboxamide;

N-(3-chloro-5-(methylsulfonamido)phenyl)-5-methyl-1-(3-(thiazol-2-ylmethoxy)pyridin-2-yl)-1H-pyrrole-3-carboxamide;

N-(3-chloro-5-(methylsulfonamido)phenyl)-1-(3-hydroxypyridin-2-yl)-5-methyl-1H-pyrrole-3-carboxamide;

N-(3-chloro-5-(methylsulfonamido)phenyl)-1-cyclopentyl-5-methyl-1H-pyrrole-3-carboxamide;

N-(3-chloro-5-(methylsulfonamido)phenyl)-1-(5-(4-isobutyrylpiperazin-1-yl)pyridin-2-yl)-5-methyl-1H-pyrrole-3-carboxamide;

4-(6-(4-((3-chloro-5-(methylsulfonamido)phenyl)carbamoyl)-2-methyl-1H-pyrrol-1-yl)pyridin-3-yl)-N,N-dimethylpiperazine-1-carboxamide;

N-(3-chloro-5-(methylsulfonamido)phenyl)-1-(5-(1,1-dioxidothiomorpholino)pyridin-2-yl)-5-methyl-1H-pyrrole-3-carboxamide;

N-(3-chloro-5-(methylsulfonamido)phenyl)-1-(2,2-difluoroethyl)-5-(5-fluoropyridin-2-yl)-1H-pyrrole-3-carboxamide;

N-(3-chloro-5-(methylsulfonamido)phenyl)-5-(1-hydroxyethyl)-1-(pyridin-2-yl)-1H-pyrrole-3-carboxamide;

N-(3-chloro-5-(methylsulfonamido)phenyl)thieno[3,2-c]pyridine-2-carboxamide;

N-(3-chloro-5-(methylsulfonamido)phenyl)thieno[3,2-b]pyridine-2-carboxamide;

N-(3-chloro-5-(methylsulfonamido)phenyl)-7-methylthieno[3,2-c]pyridine-2-carboxamide;

N-(3-chloro-5-(methylsulfonamido)phenyl)-5,6-dimethoxybenzo[b]thiophene-2-carboxamide;

N-(3-chloro-5-(methylsulfonamido)phenyl)pyrrolo[1,2-b]pyridazine-6-carboxamide;

6-chloro-N-(3-chloro-5-(methylsulfonamido)phenyl)benzo[b]thiophene-2-carboxamide;

N-(3-chloro-5-(methylsulfonamido)phenyl)-6-fluorobenzo[b]thiophene-2-carboxamide;

N-(3-chloro-5-(methylsulfonamido)phenyl)-5-fluorobenzo[b]thiophene-2-carboxamide;

N-(3-chloro-5-(methylsulfonamido)phenyl)-4-fluorobenzo[b]thiophene-2-carboxamide;

N-(3-chloro-5-(methylsulfonamido)phenyl)-7-fluorobenzo[b]thiophene-2-carboxamide;

5-chloro-N-(3-chloro-5-(methylsulfonamido)phenyl)benzo[b]thiophene-2-carboxamide;

6-chloro-N-(3-chloro-5-(methylsulfonamido)phenyl)indolizine-2-carboxamide;

N-(3-chloro-5-(methylsulfonamido)phenyl)-6-methylindolizine-2-carboxamide;

N-(3-chloro-5-(methylsulfonamido)phenyl)-1-oxo-1,2-dihydropyrrolo[1,2-a]pyrazine-7-carboxamide;

N-(3-chloro-5-(methylsulfonamido)phenyl)-8-(trifluoromethyl)indolizine-2-carboxamide;

N-(3-chloro-5-(methylsulfonamido)phenyl)-7-methoxybenzo[b]thiophene-2-carboxamide;

N-(3-chloro-5-(methylsulfonamido)phenyl)-5-methylindolizine-2-carboxamide;

N-(3-chloro-5-(methylsulfonamido)phenyl)-8-fluoroindolizine-2-carboxamide;

N-(3-chloro-5-(methylsulfonamido)phenyl)-1-(2-hydroxycyclobutyl)-1H-pyrazole-4-carboxamide;

N-(3-chloro-5-(methylsulfonamido)phenyl)-1-(1-methyl-2-oxopiperidin-4-yl)-1H-pyrazole-4-carboxamide;

N-(3-chloro-5-(methylsulfonamido)phenyl)-1-phenethyl-1H-pyrazole-4-carboxamide;

N-(3-chloro-5-(methylsulfonamido)phenyl)-1-cyclopentyl-1H-pyrazole-4-carboxamide;

1-(6-acetamidospiro[3.3]heptan-2-yl)-N-(3-chloro-5-(methylsulfonamido)phenyl)-1H-pyrazole-4-carboxamide;

N-(3-chloro-5-(methylsulfonamido)phenyl)-1-(2-methyl-2-azaspiro[3.3]heptan-6-yl)-1H-pyrazole-4-carboxamide;

N-(3-chloro-5-(methylsulfonamido)phenyl)-1-(2-(2,2,2-trifluoroethyl)-2-azaspiro[3.3]heptan-6-yl)-1H-pyrazole-4-carboxamide;

1-(2-acetyl-2-azaspiro[3.3]heptan-6-yl)-N-(3-chloro-5-(methylsulfonamido)phenyl)-1H-pyrazole-4-carboxamide;

N-(3-bromo-5-(methylsulfonamido)phenyl-2,4,6-d3)-4-phenylthiophene-2-carboxamide;

N-(3-chloro-5-(methylsulfonamido)phenyl)-1-(2,2-dimethylpiperidin-4-yl)-1H-pyrazole-4-carboxamide;

N-(3-chloro-5-(methylsulfonamido)phenyl)-1-(1-(2,2,2-trifluoroethyl)piperidin-4-yl)-1H-pyrazole-4-carboxamide;

1-(1-acetylpiperidin-4-yl)-N-(3-chloro-5-(methylsulfonamido)phenyl)-1H-pyrazole-4-carboxamide;

tert-butyl (6-(4-((3-chloro-5-(methylsulfonamido)phenyl)carbamoyl)-1H-pyrazol-1-yl)spiro[3.3]heptan-2-yl)carbamate;

1-(6-aminospiro[3.3]heptan-2-yl)-N-(3-chloro-5-(methylsulfonamido)phenyl)-1H-pyrazole-4-carboxamide; and 1-(3-fluoro-5-morpholinopyridin-2-yl)-5-methyl-N-(3-(methylsulfonamido)phenyl)-1H-pyrrole-3-carboxamide;

N-(3-chloro-5-(methylsulfonamido)phenyl)-1-(3-fluoro-5-morpholinopyridin-2-yl)-5-methyl-1H-pyrrole-3-carboxamide;

N-(3-chloro-5-(methylsulfonamido)phenyl)-5-(5-fluoropyridin-2-yl)-1-(2-hydroxyethyl)-1H-pyrrole-3-carboxamide;

N-(3-chloro-5-(methylsulfonamido)phenyl)-4-(4-methyl-3-oxopiperazin-1-yl)thiophene-2-carboxamide;

N-(3-chloro-5-(methylsulfonamido)phenyl)-1-(5-morpholinopyrimidin-2-yl)-1H-pyrazole-4-carboxamide;

N-(3-chloro-5-(methylsulfonamido)phenyl)-1-(5'-fluoro-[3,3'-bipyridin]-2-yl)-1H-pyrazole-4-carboxamide;

N-(3-chloro-5-(methylsulfonamido)phenyl)-4-(3-methyl-2-oxoimidazolidin-1-yl)thiophene-2-carboxamide;

N-(3-chloro-5-(methylsulfonamido)phenyl)-4-methoxybenzo[b]thiophene-2-carboxamide;

N-(3-chloro-5-(methylsulfonamido)phenyl)-1,3-dimethylpyrrolo[1,2-a]pyrazine-7-carboxamide;

N-(3-chloro-5-(methylsulfonamido)phenyl)-5-(4-phenylpiperazine-1-carbonyl)-1-(pyridin-2-yl)-1H-pyrrole-3-carboxamide;

N-(3-chloro-5-(methylsulfonamido)phenyl)-4-(trifluoromethyl)benzo[b]thiophene-2-carboxamide;

N-(3-chloro-5-(methylsulfonamido)phenyl)-4,5-difluorobenzo[b]thiophene-2-carboxamide;

N-(3-chloro-5-(methylsulfonamido)phenyl)-4,7-difluorobenzo[b]thiophene-2-carboxamide;

N-(3-chloro-5-(methylsulfonamido)phenyl)-5-(trifluoromethyl)benzo[b]thiophene-2-carboxamide;

N-(3-chloro-5-(methylsulfonamido)phenyl)-1-(3-(pyrimidin-5-yl)pyridin-2-yl)-1H-pyrazole-4-carboxamide;

N-(3-chloro-5-(methylsulfonamido)phenyl)-6-methoxybenzo[b]thiophene-2-carboxamide;

N-(3-chloro-5-(methylsulfonamido)phenyl)-5-(piperidine-1-carbonyl)-1-(pyridin-2-yl)-1H-pyrrole-3-carboxamide;

N-(3-chloro-5-(methylsulfonamido)phenyl)-5-(morpholine-4-carbonyl)-1-(pyridin-2-yl)-1H-pyrrole-3-carboxamide;

N-(3-chloro-5-(methylsulfonamido)phenyl)-4-(3,4,4-trimethyl-2,5-dioxoimidazolidin-1-yl)thiophene-2-carboxamide;

4-(3-(2-(azetidin-1-yl)-2-oxoethyl)pyridin-2-yl)-N-(3-chloro-5-(methylsulfonamido)phenyl)thiophene-2-carboxamide;

N-(3-chloro-5-(methylsulfonamido)phenyl)-4-(2-oxooxazolidin-3-yl)thiophene-2-carboxamide;

N-(3-chloro-5-(methylsulfonamido)phenyl)-1-(5-morpholinopyrazin-2-yl)-1H-pyrazole-4-carboxamide;

N-(3-chloro-5-(methylsulfonamido)phenyl)-4-(3-(pyrimidin-2-ylmethyl)pyridin-2-yl)thiophene-2-carboxamide;

N-(3-chloro-5-(methylsulfonamido)phenyl)-1-(pyridin-2-yl)-5-(4-(2,2,2-trifluoroethyl)piperazine-1-carbonyl)-1H-pyrrole-3-carboxamide;

N-(3-chloro-5-(methylsulfonamido)phenyl)-5-methyl-4-(2-oxopyrrolidin-1-yl)thiophene-2-carboxamide;

N-(3-chloro-5-(methylsulfonamido)phenyl)-1-(3-hydroxy-5-(2-oxa-6-azaspiro[3.3]heptan-6-yl)pyridin-2-yl)-1H-pyrazole-4-carboxamide;

N-(3-chloro-5-(methylsulfonamido)phenyl)-4-(3-(2-oxo-2-(pyrrolidin-1-yl)ethyl)pyridin-2-yl)thiophene-2-carboxamide;

N-(3-fluoro-5-(methylsulfonamido)phenyl)-5-methyl-4-(3-methylpyridin-2-yl)thiophene-2-carboxamide;

N-(3-chloro-5-(methylsulfonamido)phenyl)-5-(4-methylpiperazine-1-carbonyl)-1-(pyridin-2-yl)-1H-pyrrole-3-carboxamide;

N-(3-chloro-5-(methylsulfonamido)phenyl)-1-(3-(pyridin-3-yloxy)pyridin-2-yl)-1H-pyrazole-4-carboxamide;

N-(3-chloro-5-(methylsulfonamido)phenyl)-1-methyl-5-(3-(pyridin-3-yloxy)pyridin-2-yl)-1H-pyrrole-3-carboxamide;

N-(3-chloro-5-(methylsulfonamido)phenyl)-4-(3-(2-(dimethylamino)-2-oxoethyl)pyridin-2-yl)-5-methylthiophene-2-carboxamide;

N-(3-chloro-5-(methylsulfonamido)phenyl)-5-(2-hydroxypropan-2-yl)-1-(pyridin-2-yl)-1H-pyrrole-3-carboxamide;

N-(3-chloro-5-(methylsulfonamido)phenyl)-6,8-dimethylindolizine-2-carboxamide;

N-(3-fluoro-5-(methylsulfonamido)phenyl)-4-(3-methylpyridin-2-yl)thiophene-2-carboxamide;

N-(3-chloro-5-(methylsulfonamido)phenyl)-1-(pyridin-2-yl)-5-(2,6-diazaspiro[3.3]heptane-2-carbonyl)-1H-pyrrole-3-carboxamide;

N-(3-chloro-5-(methylsulfonamido)phenyl)-8-methylindolizine-2-carboxamide;

N-(3-chloro-5-(methylsulfonamido)phenyl)pyrrolo[1,2-a]pyrazine-7-carboxamide;

N-(3-chloro-5-(methylsulfonamido)phenyl)-5-(3,5-difluoropyridin-2-yl)-1-methyl-1H-pyrrole-3-carboxamide;

N-(3-chloro-5-(methylsulfonamido)phenyl)-5-(5-fluoro-3-methoxypyridin-2-yl)-1-methyl-1H-pyrrole-3-carboxamide;

N-(3-chloro-5-(methylsulfonamido)phenyl)-1-methyl-5-(5-(trifluoromethyl)pyridin-2-yl)-1H-pyrrole-3-carboxamide;

N-(3-chloro-5-(methylsulfonamido)phenyl)-5-(5-cyanopyridin-2-yl)-1-methyl-1H-pyrrole-3-carboxamide;

N-(3-chloro-5-(methylsulfonamido)phenyl)-5-methylbenzo[b]thiophene-2-carboxamide;

N-(3-chloro-5-(methylsulfonamido)phenyl)-4-(5-ethoxypyrimidin-2-yl)-5-methylthiophene-2-carboxamide;

N-(3-chloro-5-(methylsulfonamido)phenyl)-5-methyl-4-(1-(tetrahydro-2H-pyran-4-yl)-1H-1,2,3-triazol-4-yl)thiophene-2-carboxamide;

N-(3-chloro-5-(methylsulfonamido)phenyl)-1-methyl-5-(5-(trifluoromethyl)pyrimidin-2-yl)-1H-pyrrole-3-carboxamide;

N-(3-chloro-5-(methylsulfonamido)phenyl)-5-(5-ethoxypyridin-2-yl)-1-methyl-1H-pyrrole-3-carboxamide;

N-(3-chloro-5-(methylsulfonamido)phenyl)-5-(5-methoxypyridin-2-yl)-1-methyl-1H-pyrrole-3-carboxamide;

N-(3-chloro-5-(methylsulfonamido)phenyl)-5-(5-(methoxymethyl)pyridin-2-yl)-1-methyl-1H-pyrrole-3-carboxamide;

N-(3-chloro-5-(methylsulfonamido)phenyl)-4-(5-fluoropyrimidin-2-yl)-5-methylthiophene-2-carboxamide;

N-(3-chloro-5-(methylsulfonamido)phenyl)-4-(5-ethoxypyridin-2-yl)-5-methylthiophene-2-carboxamide;

N-(3-chloro-5-(methylsulfonamido)phenyl)-5-(5-fluoropyridin-2-yl)-1-methyl-1H-pyrrole-3-carboxamide;

N-(3-chloro-5-(methylsulfonamido)phenyl)-4-(5-fluoropyrimidin-2-yl)thiophene-2-carboxamide;

N-(3-chloro-5-(methylsulfonamido)phenyl)-4-(5-ethoxypyridin-2-yl)thiophene-2-carboxamide;

N-(3-chloro-5-(methylsulfonamido)phenyl)-1-(5-chloropyridin-2-yl)-5-methyl-1H-pyrrole-3-carboxamide;

N-(3-chloro-5-(methylsulfonamido)phenyl)-1-(5-methoxypyridin-2-yl)-5-methyl-1H-pyrrole-3-carboxamide;

N-(3-chloro-5-(methylsulfonamido)phenyl)-4-(pyridin-3-yloxy)-5,6-dihydro-4H-cyclopenta[b]thiophene-2-carboxamide;

4-chloro-N-(3-chloro-5-(methylsulfonamido)phenyl)benzo[b]thiophene-2-carboxamide;

N-(3-chloro-5-(methylsulfonamido)phenyl)-1-(3-(3-fluorophenoxy)pyridin-2-yl)-1H-pyrazole-4-carboxamide;

N-(3-chloro-5-(methylsulfonamido)phenyl)-4-(4-methoxy-1H-pyrazol-1-yl)thiophene-2-carboxamide;

N-(3-chloro-5-(methylsulfonamido)phenyl)-1-(5-fluoropyridin-2-yl)-5-methyl-1H-pyrrole-3-carboxamide;

N-(3-chloro-5-(methylsulfonamido)phenyl)-5-methyl-4-(1-phenethyl-1H-imidazol-2-yl)thiophene-2-carboxamide;

N-(3-chloro-5-(methylsulfonamido)phenyl)-4-(4-methoxy-1H-pyrazol-1-yl)-5-methylthiophene-2-carboxamide;

N-(3-chloro-5-(methylsulfonamido)phenyl)-5-(5-(methoxymethyl)pyrimidin-2-yl)-1-methyl-1H-pyrrole-3-carboxamide;

N-(3-chloro-5-(methylsulfonamido)phenyl)-1-(5-cyanopyridin-2-yl)-5-methyl-1H-pyrrole-3-carboxamide;

N-(3-chloro-5-(methylsulfonamido)phenyl)-5-(5-chloropyridin-2-yl)-1-methyl-1H-pyrrole-3-carboxamide;

N-(3-chloro-5-(methylsulfonamido)phenyl)-5-(5-chloropyrimidin-2-yl)-1-methyl-1H-pyrrole-3-carboxamide;

N-(3-chloro-5-(methylsulfonamido)phenyl)-1-(5-(3-fluoroazetidine-1-yl)pyridin-2-yl)-5-methyl-1H-pyrrole-3-carboxamide;

N-(3-chloro-5-(methylsulfonamido)phenyl)-1-(3-fluoropyridin-2-yl)-5-(methoxymethyl)-1H-pyrrole-3-carboxamide;

N-(3-chloro-5-(methylsulfonamido)phenyl)-1-(5-ethoxypyridin-2-yl)-5-methyl-1H-pyrrole-3-carboxamide;

N-(3-chloro-5-(methylsulfonamido)phenyl)-4-(4-ethoxy-1H-pyrazol-1-yl)-5-methylthiophene-2-carboxamide;

N-(3-chloro-5-(methylsulfonamido)phenyl)-4-(4-fluoro-1H-pyrazol-1-yl)-5-methylthiophene-2-carboxamide;

N-(3-chloro-5-(methylsulfonamido)phenyl)-4-(4-fluoro-1H-pyrazol-1-yl)thiophene-2-carboxamide;

N-(3-chloro-5-(methylsulfonamido)phenyl)-1-(5-methoxypyrimidin-2-yl)-5-methyl-1H-pyrrole-3-carboxamide;

N-(3-chloro-5-(methylsulfonamido)phenyl)-1-(5-(methoxymethyl)pyridin-2-yl)-5-methyl-1H-pyrrole-3-carboxamide;

N-(3-chloro-5-(methylsulfonamido)phenyl)-4-(5-methoxypyrimidin-2-yl)thiophene-2-carboxamide;

5-(5-(azetidin-1-yl)pyridin-2-yl)-N-(3-chloro-5-(methylsulfonamido)phenyl)-1-methyl-1H-pyrrole-3-carboxamide;

N-(3-chloro-5-(methylsulfonamido)phenyl)-4-(5-methoxypyrimidin-2-yl)-5-methylthiophene-2-carboxamide;

N-(3-chloro-5-(methylsulfonamido)phenyl)-1-(5-(3,3-difluoropyrrolidin-1-yl)pyridin-2-yl)-5-methyl-1H-pyrrole-3-carboxamide;

N-(3-chloro-5-(methylsulfonamido)phenyl)-5-(5-(3,3-difluoroazetidin-1-yl)pyridin-2-yl)-1-methyl-1H-pyrrole-3-carboxamide;

N-(3-chloro-5-(methylsulfonamido)phenyl)-5-methyl-1-(5-(methyl(tetrahydrofuran-3-yl)amino)pyridin-2-yl)-1H-pyrrole-3-carboxamide;

N-(3-chloro-5-(methylsulfonamido)phenyl)-5-methyl-1-(5-(methyl(tetrahydrofuran-3-yl)amino)pyridin-2-yl)-1H-pyrrole-3-carboxamide;

N-(3-chloro-5-(methylsulfonamido)phenyl)-5-methyl-1-(5-(trifluoromethyl)pyrimidin-2-yl)-1H-pyrrole-3-carboxamide;

N-(3-chloro-5-(methylsulfonamido)phenyl)-1-(5-(2-methoxyethoxy)pyridin-2-yl)-5-methyl-1H-pyrrole-3-carboxamide;

N-(3-chloro-5-(methylsulfonamido)phenyl)-4-(5-ethoxypyrimidin-2-yl)thiophene-2-carboxamide;

1-(5-(azetidin-1-yl)pyridin-2-yl)-N-(3-chloro-5-(methylsulfonamido)phenyl)-5-methyl-1H-pyrrole-3-carboxamide;

N-(3-chloro-5-(methylsulfonamido)phenyl)-5-(3-(cyclopropylmethoxy)pyridin-2-yl)-1-methyl-1H-pyrrole-3-carboxamide;

N-(3-chloro-5-(methylsulfonamido)phenyl)-5-cyclopropyl-4-(5-fluoropyrimidin-2-yl)thiophene-2-carboxamide;

1-(5-(azetidin-1-yl)pyrimidin-2-yl)-N-(3-chloro-5-(methylsulfonamido)phenyl)-5-methyl-1H-pyrrole-3-carboxamide;

N-(3-chloro-5-(methylsulfonamido)phenyl)-5-(5-(3-fluoroazetidin-1-yl)pyridin-2-yl)-1-methyl-1H-pyrrole-3-carboxamide;

N-(3-chloro-5-(ethylsulfonamido)phenyl)-4-(5-fluoropyrimidin-2-yl)thiophene-2-carboxamide;

N-(3-chloro-5-(methylsulfonamido)phenyl)-1-(5-chloropyrimidin-2-yl)-5-methyl-1H-pyrrole-3-carboxamide;

5-chloro-N-(3-chloro-5-(methylsulfonamido)phenyl)-1-(5-fluoropyrimidin-2-yl)-1H-pyrrole-3-carboxamide;

N-(3-chloro-5-(methylsulfonamido)phenyl)-5-methyl-1-(5-(2-oxopyrrolidin-1-yl)pyridin-2-yl)-1H-pyrrole-3-carboxamide;

N-(3-chloro-5-(methylsulfonamido)phenyl)-5-(5,5'-difluoro-[3,3'-bipyridin]-2-yl)-1-methyl-1H-pyrrole-3-carboxamide;

N-(3-chloro-5-(methylsulfonamido)phenyl)-4-(5-fluoro-1'-methyl-2'-oxo-1',2'-dihydro-[3,4'-bipyridin]-2-yl)-5-methylthiophene-2-carboxamide;

N-(3-chloro-5-(methylsulfonamido)phenyl)-4-(5-fluoro-1'-methyl-6'-oxo-1',6'-dihydro-[3,3'-bipyridin]-2-yl)-5-methylthiophene-2-carboxamide;

N-(3-chloro-5-(methylsulfonamido)phenyl)-4-(5,5'-difluoro-[3,3'-bipyridin]-2-yl)-5-methylthiophene-2-carboxamide;

N-(3-chloro-5-(methylsulfonamido)phenyl)-1-(5-(3,3-difluoroazetidin-1-yl)pyrimidin-2-yl)-5-methyl-1H-pyrrole-3-carboxamide;

N-(3-chloro-5-(methylsulfonamido)phenyl)-5-methyl-1-(5-(methylsulfonyl)pyrimidin-2-yl)-1H-pyrrole-3-carboxamide;

N-(3-chloro-5-(methylsulfonamido)phenyl)-5-methyl-1-(5-(trifluoromethyl)pyridin-2-yl)-1H-pyrrole-3-carboxamide;

N-(3-chloro-5-(methylsulfonamido)phenyl)-1-(3-(cyclopropylmethoxy)pyridin-2-yl)-5-methyl-1H-pyrrole-3-carboxamide;

tert-butyl 3-(4-((3-chloro-5-(methylsulfonamido)phenyl)carbamoyl)-2-(5-fluoropyrimidin-2-yl)-1H-pyrrol-1-yl)azetidine-1-carboxylate;

1-(5-(3-azabicyclo[3.1.0]hexan-3-yl)pyridin-2-yl)-N-(3-chloro-5-(methylsulfonamido)phenyl)-5-methyl-1H-pyrrole-3-carboxamide;

N-(3-chloro-5-(ethylsulfonamido)phenyl)-4-(5-fluoropyrimidin-2-yl)-5-methylthiophene-2-carboxamide;

N-(3-chloro-5-(ethylsulfonamido)phenyl)-5-cyclopropyl-4-(5-fluoropyrimidin-2-yl)thiophene-2-carboxamide;

N-(3-chloro-5-(methylsulfonamido)phenyl)-5-methyl-1-(5-(methylthio)pyrimidin-2-yl)-1H-pyrrole-3-carboxamide;

N-(3-chloro-5-(methylsulfonamido)phenyl)-5-methyl-1-(5-(methylsulfinyl)pyrimidin-2-yl)-1H-pyrrole-3-carboxamide;

N-(3-chloro-5-(methylsulfonamido)phenyl)-1-methyl-5-(5-(pyrrolidin-1-yl)pyrimidin-2-yl)-1H-pyrrole-3-carboxamide;

N-(3-chloro-5-(methylsulfonamido)phenyl)-5-cyclopropyl-1-(5-fluoropyrimidin-2-yl)-1H-pyrrole-3-carboxamide;

5-(5-(azetidin-1-yl)pyrimidin-2-yl)-N-(3-chloro-5-(methylsulfonamido)phenyl)-1-methyl-1H-pyrrole-3-carboxamide;

N-(3-chloro-5-(methylsulfonamido)phenyl)-4-(4,4-dimethyl-2,5-dioxo-3-(pyridin-2-yl)imidazolidin-1-yl)-5-methylthiophene-2-carboxamide;

N-(3-chloro-5-(methylsulfonamido)phenyl)-4-(5-fluoro-2'-methyl-[3,3'-bipyridin]-2-yl)-5-methylthiophene-2-carboxamide;

N-(3-chloro-5-(methylsulfonamido)phenyl)-4-(5-fluoro-3-(oxazol-5-yl)pyridin-2-yl)-5-methylthiophene-2-carboxamide;

N-(3-chloro-5-(methylsulfonamido)phenyl)-5-methyl-1-(5-(oxetan-3-yloxy)pyrimidin-2-yl)-1H-pyrrole-3-carboxamide;

N-(3-chloro-5-(methylsulfonamido)phenyl)-1-(5-(3,3-difluoroazetidin-1-yl)pyridin-2-yl)-5-methyl-1H-pyrrole-3-carboxamide;

N-(3-chloro-5-(methylsulfonamido)phenyl)-1-(5-ethoxypyrimidin-2-yl)-5-(trifluoromethyl)-1H-pyrrole-3-carboxamide;

N-(3-chloro-5-(methylsulfonamido)phenyl)-4-(5-(difluoromethoxy)pyrimidin-2-yl)-5-methylthiophene-2-carboxamide;

N-(3-chloro-5-(methylsulfonamido)phenyl)-1-(5-fluoro-3-methoxypyridin-2-yl)-5-methyl-1H-pyrrole-3-carboxamide;

N-(3-chloro-5-(methylsulfonamido)phenyl)-1-(3,5-difluoropyridin-2-yl)-5-methyl-1H-pyrrole-3-carboxamide;

5-chloro-N-(3-chloro-5-(methylsulfonamido)phenyl)-4-(5-fluoropyrimidin-2-yl)thiophene-2-carboxamide;

N-(3-chloro-5-(ethylsulfonamido)phenyl)-5-(5-fluoropyridin-2-yl)-1-methyl-1H-pyrrole-3-carboxamide;

N-(3-chloro-5-(methylsulfonamido)phenyl)-5-ethyl-4-(5-fluoropyrimidin-2-yl)thiophene-2-carboxamide;

1-(5-(5-azaspiro[2.4]heptan-5-yl)pyridin-2-yl)-N-(3-chloro-5-(methylsulfonamido)phenyl)-5-methyl-1H-pyrrole-3-carboxamide;

N-(3-chloro-5-(methylsulfonamido)phenyl)-1-(5-(3-fluoroazetidin-1-yl)pyrimidin-2-yl)-5-methyl-1H-pyrrole-3-carboxamide;

N-(3-chloro-5-(methylsulfonamido)phenyl)-5-methyl-4-(5-(N-methylmethylsulfonamido)pyrimidin-2-yl)thiophene-2-carboxamide;

N-(3-chloro-5-(methylsulfonamido)phenyl)-1-cyclopropyl-5-(5-fluoropyrimidin-2-yl)-1H-pyrrole-3-carboxamide;

N-(3-chloro-5-(methylsulfonamido)phenyl)-5-methyl-1-(5-(2-oxopyrrolidin-1-yl)pyrimidin-2-yl)-1H-pyrrole-3-carboxamide;

N-(3-chloro-5-(methylsulfonamido)phenyl)-5-(5-fluoropyrimidin-2-yl)-1-isopropyl-1H-pyrrole-3-carboxamide;

N-(3-chloro-5-(methylsulfonamido)phenyl)-5-methyl-4-(5-(methylsulfonyl)pyrimidin-2-yl)thiophene-2-carboxamide;

N-(3-chloro-5-(methylsulfonamido)phenyl)-1-(5,5'-difluoro-[3,3'-bipyridin]-2-yl)-5-methyl-1H-pyrrole-3-carboxamide;

N-(3-chloro-5-(methylsulfonamido)phenyl)-4-(3,4-dimethyl-2,5-dioxo-4-(pyridin-2-yl)imidazolidin-1-yl)-5-methylthiophene-2-carboxamide;

N-(3-chloro-5-(ethylsulfonamido)phenyl)-4-(5-fluoropyridin-2-yl)-5-methylthiophene-2-carboxamide;

N-(3-chloro-5-(methylsulfonamido)phenyl)-5-(3-fluoro-5-methylpyridin-2-yl)-1-methyl-1H-pyrrole-3-carboxamide;

methyl 4-(6-(4-((3-chloro-5-(methylsulfonamido)phenyl)carbamoyl)-1-methyl-1H-pyrrol-2-yl)pyridin-3-yl)piperazine-1-carboxylate;

N-(3-chloro-5-(methylsulfonamido)phenyl)-5-(5-(3,3-difluoroazetidin-1-yl)pyrimidin-2-yl)-1-methyl-1H-pyrrole-3-carboxamide;

N-(3-chloro-5-(methylsulfonamido)phenyl)-1-methyl-5-(5-((1-methylazetidin-3-yl)oxy)pyridin-2-yl)-1H-pyrrole-3-carboxamide;

methyl 4-(6-(5-((3-chloro-5-(methylsulfonamido)phenyl)carbamoyl)-2-methylthiophen-3-yl)-5-methylpyridin-3-yl)piperazine-1-carboxylate;

N-(3-chloro-5-(ethylsulfonamido)phenyl)-4-(3,5-difluoropyridin-2-yl)-5-methylthiophene-2-carboxamide;

N-(3-chloro-5-(ethylsulfonamido)phenyl)-5-(5-fluoropyrimidin-2-yl)-1-methyl-1H-pyrrole-3-carboxamide;

N-(3-chloro-5-(methylsulfonamido)phenyl)-5-(5-(3-fluoroazetidin-1-yl)pyrimidin-2-yl)-1-methyl-1H-pyrrole-3-carboxamide;

N-(3-chloro-5-(methylsulfonamido)phenyl)-4-(5-fluoro-3-methylpyridin-2-yl)-5-methylthiophene-2-carboxamide;

N-(3-chloro-5-(methylsulfonamido)phenyl)-4-(3,5-difluoropyridin-2-yl)-5-methylthiophene-2-carboxamide;

N-(3-chloro-5-(ethylsulfonamido)phenyl)-4-(5-fluoro-3-methylpyridin-2-yl)-5-methylthiophene-2-carboxamide;

N-(3-chloro-5-(methylsulfonamido)phenyl)-4-(5-fluoro-3-methoxypyridin-2-yl)-5-methylthiophene-2-carboxamide;

N-(3-chloro-5-(ethylsulfonamido)phenyl)-1-(3-chloro-5-fluoropyridin-2-yl)-5-methyl-1H-pyrrole-3-carboxamide;

N-(3-chloro-5-(methylsulfonamido)phenyl)-4-(5-methoxypyridin-2-yl)-5-methylthiophene-2-carboxamide;

N-(3-chloro-5-(methylsulfonamido)phenyl)-5-methyl-1-(5-(oxetan-3-yloxy)pyridin-2-yl)-1H-pyrrole-3-carboxamide;

N-(3-chloro-5-(ethylsulfonamido)phenyl)-5-(3,5-difluoropyridin-2-yl)-1-methyl-1H-pyrrole-3-carboxamide;

N-(3-chloro-5-(methylsulfonamido)phenyl)-1-methyl-5-(5-(pyrrolidin-1-yl)pyridin-2-yl)-1H-pyrrole-3-carboxamide;

N-(3-chloro-5-(methylsulfonamido)phenyl)-1-methyl-5-(5-(tetrahydro-2H-pyran-4-yl)pyridin-2-yl)-1H-pyrrole-3-carboxamide;

N-(3-chloro-5-(methylsulfonamido)phenyl)-5-(3-chloro-5-fluoropyridin-2-yl)-1-methyl-1H-pyrrole-3-carboxamide;

N-(3-chloro-5-(methylsulfonamido)phenyl)-5-(5-fluoro-3-methylpyridin-2-yl)-1-methyl-1H-pyrrole-3-carboxamide;

N-(3-chloro-5-(ethylsulfonamido)phenyl)-1-(3,5-difluoropyridin-2-yl)-5-methyl-1H-pyrrole-3-carboxamide;

1-(azetidin-3-yl)-N-(3-chloro-5-(methylsulfonamido)phenyl)-5-(5-fluoropyrimidin-2-yl)-1H-pyrrole-3-carboxamide;

N-(3-chloro-5-(methylsulfonamido)phenyl)-5-(3-cyano-5-fluoropyridin-2-yl)-1-methyl-1H-pyrrole-3-carboxamide;

N-(3-chloro-5-(ethylsulfonamido)phenyl)-4-(5-methoxypyrimidin-2-yl)-5-methylthiophene-2-carboxamide;

N-(3-chloro-5-(ethylsulfonamido)phenyl)-4-(5-fluoro-3-methoxypyridin-2-yl)-5-methylthiophene-2-carboxamide;

N-(3-chloro-5-(ethylsulfonamido)phenyl)-4-(3-chloro-5-fluoropyridin-2-yl)-5-methylthiophene-2-carboxamide;

N-(3-chloro-5-(methylsulfonamido)phenyl)-5-methyl-4-(5-(methylamino)pyrimidin-2-yl)thiophene-2-carboxamide;

N-(3-chloro-5-(methylsulfonamido)phenyl)-5-methyl-1-(5-(2-oxooxazolidin-3-yl)pyridin-2-yl)-1H-pyrrole-3-carboxamide;

N-(3-chloro-5-(methylsulfonamido)phenyl)-1-methyl-5-(2,4,6-trifluorophenyl)-1H-pyrrole-3-carboxamide;

N-(3-chloro-5-(ethylsulfonamido)phenyl)-5-(3-fluoro-5-methylpyridin-2-yl)-1-methyl-1H-pyrrole-3-carboxamide;

N-(3-chloro-5-(methylsulfonamido)phenyl)-5-methyl-4-(2,4,6-trifluorophenyl)thiophene-2-carboxamide;

N-(3-chloro-5-(methylsulfonamido)phenyl)-5-methyl-1-(5-(2-oxooxazolidin-3-yl)pyridin-2-yl)-1H-pyrrole-3-carboxamide;

N-(3-chloro-5-(methylsulfonamido)phenyl)-4-(5-(4-(cyclopropanecarbonyl)piperazin-1-yl)pyridin-2-yl)-5-methylthiophene-2-carboxamide;

N-(3-chloro-5-(methylsulfonamido)phenyl)-1-methyl-5-(5-(1-(2,2,2-trifluoroethyl)piperidin-4-yl)pyridin-2-yl)-1H-pyrrole-3-carboxamide;

N-(3-chloro-5-(methylsulfonamido)phenyl)-5-methyl-4-(5-(trifluoromethyl)pyridin-2-yl)thiophene-2-carboxamide;

N-(3-chloro-5-(ethylsulfonamido)phenyl)-5-(5-(3,3-difluoroazetidin-1-yl)pyrimidin-2-yl)-1-methyl-1H-pyrrole-3-carboxamide;

N-(3-chloro-5-(methylsulfonamido)phenyl)-5-methyl-4-(5-(trifluoromethyl)pyrimidin-2-yl)thiophene-2-carboxamide;

N-(3-chloro-5-(methylsulfonamido)phenyl)-4-(3-fluoro-5-methoxypyridin-2-yl)-5-methylthiophene-2-carboxamide;

N-(3-chloro-5-(methylsulfonamido)phenyl)-4-(3-chloro-5-fluoropyridin-2-yl)-5-methylthiophene-2-carboxamide;

N-(3-chloro-5-(methylsulfonamido)phenyl)-1-methyl-5-(5-(4-pivaloylpiperazin-1-yl)pyridin-2-yl)-1H-pyrrole-3-carboxamide;

N-(3-chloro-5-(methylsulfonamido)phenyl)-5-(5-methoxypyrimidin-2-yl)-1-methyl-1H-pyrrole-3-carboxamide;

N-(3-chloro-5-(methylsulfonamido)phenyl)-5-(5-(4-(cyclopentanecarbonyl)piperazin-1-yl)pyridin-2-yl)-1-methyl-1H-pyrrole-3-carboxamide;

1-(5-(7-azabicyclo[2.2.1]heptan-7-yl)pyridin-2-yl)-N-(3-chloro-5-(methylsulfonamido)phenyl)-5-methyl-1H-pyrrole-3-carboxamide;

N-(3-chloro-5-(methylsulfonamido)phenyl)-1-(5-(3-methoxyazetidin-1-yl)pyrimidin-2-yl)-5-methyl-1H-pyrrole-3-carboxamide;

N-(3-chloro-5-(methylsulfonamido)phenyl)-4-(5-(3,3-difluoroazetidin-1-yl)-3-fluoropyridin-2-yl)-5-methylthiophene-2-carboxamide;

N-(3-chloro-5-(methylsulfonamido)phenyl)-5-(2-cyano-4-fluoro-6-methylphenyl)-1-methyl-1H-pyrrole-3-carboxamide;

N-(3-chloro-5-(methylsulfonamido)phenyl)-5-(5-(3,3-difluoroazetidin-1-yl)-3-methylpyridin-2-yl)-1-methyl-1H-pyrrole-3-carboxamide;

N-(3-chloro-5-(ethylsulfonamido)phenyl)-4-(3-fluoro-5-methoxypyridin-2-yl)-5-methylthiophene-2-carboxamide;

N-(3-chloro-5-(ethylsulfonamido)phenyl)-5-methyl-4-(3-methyl-5-(trifluoromethyl)pyridin-2-yl)thiophene-2-carboxamide;

N-(3-chloro-5-(methylsulfonamido)phenyl)-4-(3-methoxy-5-(trifluoromethyl)pyridin-2-yl)-5-methylthiophene-2-carboxamide;

N-(3-chloro-5-(methylsulfonamido)phenyl)-5-(5-(4-(cyclobutanecarbonyl)piperazin-1-yl)pyridin-2-yl)-1-methyl-1H-pyrrole-3-carboxamide;

N-(3-chloro-5-(methylsulfonamido)phenyl)-4-(5-(4,4-difluoropiperidin-1-yl)-3-methylpyridin-2-yl)-5-methylthiophene-2-carboxamide;

N-(3-chloro-5-(methylsulfonamido)phenyl)-5-methyl-1-(5-(tetrahydro-1H-furo[3,4-c]pyrrol-5(3H)-yl)pyridin-2-yl)-1H-pyrrole-3-carboxamide;

N-(3-chloro-5-(methylsulfonamido)phenyl)-4-(5-(3,3-difluoroazetidin-1-yl)pyridin-2-yl)-5-methylthiophene-2-carboxamide;

N-(3-chloro-5-(methylsulfonamido)phenyl)-5-(6-(3,3-difluoroazetidin-1-yl)pyridin-2-yl)-1-methyl-1H-pyrrole-3-carboxamide;

N-(3-chloro-5-(methylsulfonamido)phenyl)-4-(5-methoxy-3-methylpyridin-2-yl)-5-methylthiophene-2-carboxamide;

N-(3-chloro-5-(methylsulfonamido)phenyl)-4-(3,5-difluoropyridin-4-yl)-5-methylthiophene-2-carboxamide;

N-(3-chloro-5-(methylsulfonamido)phenyl)-1-(5-(3,3-difluoroazetidin-1-yl)-3-methylpyridin-2-yl)-5-methyl-1H-pyrrole-3-carboxamide;

N-(3-chloro-5-(methylsulfonamido)phenyl)-1-(3-cyano-5-(3,3-difluoroazetidin-1-yl)pyridin-2-yl)-5-methyl-1H-pyrrole-3-carboxamide;

N-(3-chloro-5-(methylsulfonamido)phenyl)-5-(5-(4-(cyclopropanecarbonyl)piperazin-1-yl)pyridin-2-yl)-1-methyl-1H-pyrrole-3-carboxamide;

N-(3-chloro-5-(methylsulfonamido)phenyl)-1-(5-(3,3-difluoroazetidin-1-yl)-3-fluoropyridin-2-yl)-5-methyl-1H-pyrrole-3-carboxamide;

N-(3-chloro-5-(methylsulfonamido)phenyl)-5-(5-(3,3-difluoroazetidin-1-yl)-3-fluoropyridin-2-yl)-1-methyl-1H-pyrrole-3-carboxamide;

1-(3-chloro-5-(3,3-difluoroazetidin-1-yl)pyridin-2-yl)-N-(3-chloro-5-(methylsulfonamido)phenyl)-5-methyl-1H-pyrrole-3-carboxamide;

N-(3-chloro-5-(methylsulfonamido)phenyl)-4-(5-isopropoxypyrimidin-2-yl)-5-methylthiophene-2-carboxamide;

N-(3-chloro-5-(methylsulfonamido)phenyl)-5-(5-(4,4-difluoropiperidin-1-yl)-3-methylpyridin-2-yl)-1-methyl-1H-pyrrole-3-carboxamide;

N-(3-chloro-5-(methylsulfonamido)phenyl)-5-(3-(difluoromethoxy)-5-fluoropyridin-2-yl)-1-methyl-1H-pyrrole-3-carboxamide;

N-(3-chloro-5-(ethylsulfonamido)phenyl)-1-(5-(3,3-difluoroazetidin-1-yl)pyrimidin-2-yl)-5-methyl-1H-pyrrole-3-carboxamide;

N-(3-chloro-5-(methylsulfonamido)phenyl)-5-(4-(3,3-difluoroazetidin-1-yl)pyridin-2-yl)-1-methyl-1H-pyrrole-3-carboxamide;

N-(3-chloro-5-(methylsulfonamido)phenyl)-4-(3-chloro-5-methoxypyridin-2-yl)-5-methylthiophene-2-carboxamide;

N-(3-chloro-5-(methylsulfonamido)phenyl)-1-(5-(3,3-difluoroazetidin-1-yl)-3-methoxypyridin-2-yl)-5-methyl-1H-pyrrole-3-carboxamide;

N-(3-chloro-5-(methylsulfonamido)phenyl)-5-methyl-4-(5-(2,2,2-trifluoroethoxy)pyrimidin-2-yl)thiophene-2-carboxamide;

N-(3-chloro-5-(methylsulfonamido)phenyl)-1-(5-(3,3-difluoroazetidin-1-yl)-3-(trifluoromethyl)pyridin-2-yl)-5-methyl-1H-pyrrole-3-carboxamide;

N-(3-chloro-5-(methylsulfonamido)phenyl)-4-(5-(3,3-difluoroazetidin-1-yl)-3-isopropoxypyridin-2-yl)-5-methylthiophene-2-carboxamide;

N-(3-chloro-5-(methylsulfonamido)phenyl)-4-(5-cyclobutoxypyrimidin-2-yl)-5-methylthiophene-2-carboxamide;

N-(3-chloro-5-(ethylsulfonamido)phenyl)-4-(5-ethoxypyrimidin-2-yl)-5-methylthiophene-2-carboxamide;

N-(3-chloro-5-(methylsulfonamido)phenyl)-4-(5-(3,3-difluoroazetidin-1-yl)-3-methoxypyridin-2-yl)-5-methylthiophene-2-carboxamide;

N-(3-chloro-5-(methylsulfonamido)phenyl)-5-(5-(3,3-difluoroazetidin-1-yl)-3-methoxypyridin-2-yl)-1-methyl-1H-pyrrole-3-carboxamide;

N-(3-chloro-5-(methylsulfonamido)phenyl)-1-methyl-5-(5-(3,4,4-trimethyl-2,5-dioxoimidazolidin-1-yl)pyridin-2-yl)-1H-pyrrole-3-carboxamide;

N-(3-chloro-5-(methylsulfonamido)phenyl)-5-(5-(difluoromethoxy)pyrimidin-2-yl)-1-methyl-1H-pyrrole-3-carboxamide;

N-(3-chloro-5-(ethylsulfonamido)phenyl)-4-(5-(3,3-difluoroazetidin-1-yl)pyrimidin-2-yl)-5-methylthiophene-2-carboxamide;

N-(3-chloro-5-(methylsulfonamido)phenyl)-5-(3-fluoro-5-(trifluoromethyl)pyridin-2-yl)-1-methyl-1H-pyrrole-3-carboxamide;

N-(3-chloro-5-(ethylsulfonamido)phenyl)-4-(5-(3-fluoroazetidin-1-yl)pyrimidin-2-yl)-5-methylthiophene-2-carboxamide;

N-(3-chloro-5-(methylsulfonamido)phenyl)-5-(5-ethoxy-3-fluoropyridin-2-yl)-1-methyl-1H-pyrrole-3-carboxamide;

N-(3-chloro-5-(ethylsulfonamido)phenyl)-5-methyl-4-(5-(trifluoromethyl)pyrimidin-2-yl)thiophene-2-carboxamide;

N-(3-chloro-5-(methylsulfonamido)phenyl)-4-(5-(3-fluorooxetan-3-yl)pyrimidin-2-yl)-5-methylthiophene-2-carboxamide;

N-(3-chloro-5-(methylsulfonamido)phenyl)-5-(5-fluoropyridin-2-yl)-1-(methylsulfonyl)-1H-pyrrole-3-carboxamide;

N-(3-chloro-5-(methylsulfonamido)phenyl)-5-(3-fluoro-5-methoxypyridin-2-yl)-1-methyl-1H-pyrrole-3-carboxamide;

4-(5-(1-acetylpiperidin-4-yl)pyrimidin-2-yl)-N-(3-chloro-5-(methylsulfonamido)phenyl)-5-methylthiophene-2-carboxamide;

N-(3-chloro-5-(cyclopropanesulfonamido)phenyl)-5-(5-(3,3-difluoroazetidin-1-yl)pyridin-2-yl)-1-methyl-1H-pyrrole-3-carboxamide;

N-(3-chloro-5-(propylsulfonamido)phenyl)-5-(5-(3,3-difluoroazetidin-1-yl)pyridin-2-yl)-1-methyl-1H-pyrrole-3-carboxamide;

methyl 4-(6-(4-(((3-chloro-5-(methylsulfonamido)phenyl)carbamoyl)-1-methyl-1H-pyrrol-2-yl)-5-fluoropyridin-3-yl)piperazine-1-carboxylate;

N-(3-chloro-5-(methylsulfonamido)phenyl)-5-(5-(4-methoxypiperidin-1-yl)pyridin-2-yl)-1-methyl-1H-pyrrole-3-carboxamide;

N-(3-chloro-5-(methylsulfonamido)phenyl)-4-(3-cyano-5-(3,3-difluoroazetidin-1-yl)pyridin-2-yl)-5-methylthiophene-2-carboxamide;

N-(3-chloro-5-(methylsulfonamido)phenyl)-4-(5-(3,3-difluoroazetidin-1-yl)-3-(2,2,2-trifluoroethoxy)pyridin-2-yl)-5-methylthiophene-2-carboxamide;

N-(3-chloro-5-(methylsulfonamido)phenyl)-1-(5-(3,3-difluoroazetidin-1-yl)-3-(2,2,2-trifluoroethoxy)pyridin-2-yl)-5-methyl-1H-pyrrole-3-carboxamide;

N-(3-chloro-5-(methylsulfonamido)phenyl)-4-(3-cyclobutoxy-5-(3,3-difluoroazetidin-1-yl)pyridin-2-yl)-5-methylthiophene-2-carboxamide;

N-(3-chloro-5-(methylsulfonamido)phenyl)-5-methyl-4-(5-((1-methylazetidin-3-yl)oxy)pyrimidin-2-yl)thiophene-2-carboxamide;

N-(3-chloro-5-(methylsulfonamido)phenyl)-4-(5-(3,3-difluoroazetidin-1-yl)-3-(difluoromethoxy)pyridin-2-yl)-5-methylthiophene-2-carboxamide;

4-(5-(tert-butoxy)pyrimidin-2-yl)-N-(3-chloro-5-(methylsulfonamido)phenyl)-5-methylthiophene-2-carboxamide;

N-(3-chloro-5-(methylsulfonamido)phenyl)-5-(5-(4-(cyclopropanecarbonyl)piperazin-1-yl)-3-fluoropyridin-2-yl)-1-methyl-1H-pyrrole-3-carboxamide;

N-(3-chloro-5-(methylsulfonamido)phenyl)-5-(3-ethoxy-5-fluoropyridin-2-yl)-1-methyl-1H-pyrrole-3-carboxamide;

N-(3-chloro-5-(methylsulfonamido)phenyl)-5-(5-(3-fluoro-3-methylazetidin-1-yl)pyridin-2-yl)-1-methyl-1H-pyrrole-3-carboxamide;

N-(3-chloro-5-(methylsulfonamido)phenyl)-1-(3-cyclobutoxy-5-(3,3-difluoroazetidin-1-yl)pyridin-2-yl)-5-methyl-1H-pyrrole-3-carboxamide;

N-(3-chloro-5-(methylsulfonamido)phenyl)-1-methyl-5-(5-(3-(methylsulfonyl)azetidin-1-yl)pyridin-2-yl)-1H-pyrrole-3-carboxamide;

N-(3-chloro-5-(methylsulfonamido)phenyl)-5-(5-(3-methoxyazetidin-1-yl)pyridin-2-yl)-1-methyl-1H-pyrrole-3-carboxamide;

N-(3-chloro-5-(methylsulfonamido)phenyl)-5-(3-fluoro-5-(3-fluoroazetidin-1-yl)pyridin-2-yl)-1-methyl-1H-pyrrole-3-carboxamide;

N-(3-chloro-5-(methylsulfonamido)phenyl)-4-(3-fluoro-5-(6-azaspiro[2.5]octan-6-yl)pyridin-2-yl)-5-methylthiophene-2-carboxamide;

N-(3-chloro-5-(methylsulfonamido)phenyl)-5-(3-fluoro-5-(6-azaspiro[2.5]octan-6-yl)pyridin-2-yl)-1-methyl-1H-pyrrole-3-carboxamide;

N-(3-chloro-5-(methylsulfonamido)phenyl)-4-(3-fluoro-5-(2-oxa-6-azaspiro[3.4]octan-6-yl)pyridin-2-yl)-5-methylthiophene-2-carboxamide;

N-(3-chloro-5-(methylsulfonamido)phenyl)-5-(5-(4,4-difluoropiperidin-1-yl)-3-fluoropyridin-2-yl)-1-methyl-1H-pyrrole-3-carboxamide;

N-(3-chloro-5-(methylsulfonamido)phenyl)-5-(5-(4,4-dimethyl-1,4-azasilinan-1-yl)-3-fluoropyridin-2-yl)-1-methyl-1H-pyrrole-3-carboxamide;

N-(3-chloro-5-(methylsulfonamido)phenyl)-4-(5-(6,6-difluoro-2-azaspiro[3.3]heptan-2-yl)-3-fluoropyridin-2-yl)-5-methylthiophene-2-carboxamide;

N-(3-chloro-5-(methylsulfonamido)phenyl)-4-(5-(4,4-difluoropiperidin-1-yl)-3-fluoropyridin-2-yl)-5-methylthiophene-2-carboxamide;

N-(3-chloro-5-(methylsulfonamido)phenyl)-4-(5-(3,3-difluoroazetidin-1-yl)pyrimidin-2-yl)-5-methylthiophene-2-carboxamide;

N-(3-chloro-5-(methylsulfonamido)phenyl)-1-methyl-5-(5-(3-((methylsulfonyl)methyl)azetidin-1-yl)pyridin-2-yl)-1H-pyrrole-3-carboxamide;

N-(3-chloro-5-(methylsulfonamido)phenyl)-5-(3-fluoro-5-(4-(trifluoromethyl)piperidin-1-yl)pyridin-2-yl)-1-methyl-1H-pyrrole-3-carboxamide;

N-(3-chloro-5-(methylsulfonamido)phenyl)-4-(5-(4,4-dimethyl-1,4-azasilinan-1-yl)-3-fluoropyridin-2-yl)-5-methylthiophene-2-carboxamide;

N-(3-chloro-5-(methylsulfonamido)phenyl)-4-(3-fluoro-5-(2-oxa-7-azaspiro[3.5]nonan-7-yl)pyridin-2-yl)-5-methylthiophene-2-carboxamide;

N-(3-chloro-5-(methylsulfonamido)phenyl)-5-(3-fluoro-5-(2-oxa-7-azaspiro[3.5]nonan-7-yl)pyridin-2-yl)-1-methyl-1H-pyrrole-3-carboxamide;

N-(3-chloro-5-(methylsulfonamido)phenyl)-4-(5-(6,6-dimethyl-3-azabicyclo[3.1.0]hexan-3-yl)-3-fluoropyridin-2-yl)-5-methylthiophene-2-carboxamide;

N-(3-chloro-5-(methylsulfonamido)phenyl)-1-(5-(3,3-difluoroazetidin-1-yl)-3-isopropoxypyridin-2-yl)-5-methyl-1H-pyrrole-3-carboxamide;

N-(3-chloro-5-(methylsulfonamido)phenyl)-4-(3-fluoro-5-(3-(trifluoromethyl)azetidin-1-yl)pyridin-2-yl)-5-methylthiophene-2-carboxamide;

N-(3-chloro-5-(methylsulfonamido)phenyl)-5-(5-(1,1-difluoro-5-azaspiro[2.4]heptan-5-yl)-3-fluoropyridin-2-yl)-1-methyl-1H-pyrrole-3-carboxamide;

N-(3-chloro-5-(methylsulfonamido)phenyl)-5-(5-(3,3-difluoropyrrolidin-1-yl)-3-fluoropyridin-2-yl)-1-methyl-1H-pyrrole-3-carboxamide;

N-(3-chloro-5-(methylsulfonamido)phenyl)-5-(5-(6,6-dimethyl-3-azabicyclo[3.1.0]hexan-3-yl)-3-fluoropyridin-2-yl)-1-methyl-1H-pyrrole-3-carboxamide;

N-(3-chloro-5-((2-hydroxyethyl)sulfonamido)phenyl)-5-(5-(3,3-difluoroazetidin-1-yl)pyridin-2-yl)-1-methyl-1H-pyrrole-3-carboxamide;

N-(3-chloro-5-(methylsulfonamido)phenyl)-5-(5-(6,6-difluoro-2-azaspiro[3.3]heptan-2-yl)-3-fluoropyridin-2-yl)-1-methyl-1H-pyrrole-3-carboxamide;

N-(3-chloro-5-(ethylsulfonamido)phenyl)-5-(5-(3,3-difluoroazetidin-1-yl)-3-fluoropyridin-2-yl)-1-methyl-1H-pyrrole-3-carboxamide;

N-(3-chloro-5-(methylsulfonamido)phenyl)-4-(5-(1,1-difluoro-6-azaspiro[2.5]octan-6-yl)-3-fluoropyridin-2-yl)-5-methylthiophene-2-carboxamide;

N-(3-chloro-5-(methylsulfonamido)phenyl)-4-(5-(3,3-difluoropyrrolidin-1-yl)pyrimidin-2-yl)-5-methylthiophene-2-carboxamide;

N-(3-chloro-5-(methylsulfonamido)phenyl)-5-(5-((1-(cyclopropanecarbonyl)azetidin-3-yl)oxy)-3-fluoropyridin-2-yl)-1-methyl-1H-pyrrole-3-carboxamide;

N-(3-chloro-5-(methylsulfonamido)phenyl)-4-(5-(1,1-difluoro-5-azaspiro[2.4]heptan-5-yl)-3-fluoropyridin-2-yl)-5-methylthiophene-2-carboxamide;

N-(3-chloro-5-(methylsulfonamido)phenyl)-5-(5-(3,3-difluoroazetidin-1-yl)-3-isopropoxypyridin-2-yl)-1-methyl-1H-pyrrole-3-carboxamide;

N-(3-chloro-5-(methylsulfonamido)phenyl)-4-(3-fluoro-5-(4-(trifluoromethyl)piperidin-1-yl)pyridin-2-yl)-5-methylthiophene-2-carboxamide;

N-(3-chloro-5-(methylsulfonamido)phenyl)-4-(5-(3,3-difluoropiperidin-1-yl)-3-fluoropyridin-2-yl)-5-methylthiophene-2-carboxamide;

N-(3-chloro-5-(methylsulfonamido)phenyl)-5-(5-(1,1-difluoro-6-azaspiro[2.5]octan-6-yl)-3-fluoropyridin-2-yl)-1-methyl-1H-pyrrole-3-carboxamide;

N-(3-chloro-5-(methylsulfonamido)phenyl)-5-(5-(3,3-difluoropiperidin-1-yl)-3-fluoropyridin-2-yl)-1-methyl-1H-pyrrole-3-carboxamide;

N-(3-chloro-5-(methylsulfonamido)phenyl)-5-methyl-4-(5-(1-(2,2,2-trifluoroethyl)azetidin-3-yl)pyridin-2-yl)thiophene-2-carboxamide;

N-(3-chloro-5-(methylsulfonamido)phenyl)-5-(5-(1-(2,2-difluoroethyl)piperidin-4-yl)pyridin-2-yl)-1-methyl-1H-pyrrole-3-carboxamide;

N-(3-chloro-5-(methylsulfonamido)phenyl)-4-(5-(3,3-difluoropyrrolidin-1-yl)-3-fluoropyridin-2-yl)-5-methylthiophene-2-carboxamide;

N-(3-chloro-5-(methylsulfonamido)phenyl)-4-(3-cyano-5-(trifluoromethyl)pyridin-2-yl)-5-methylthiophene-2-carboxamide;

N-(3-chloro-5-(methylsulfonamido)phenyl)-4-(5-(3,3-difluoropyrrolidin-1-yl)pyridin-2-yl)-5-methylthiophene-2-carboxamide;

N-(3-chloro-5-(methylsulfonamido)phenyl)-5-(3-fluoro-5-(3-(trifluoromethyl)azetidin-1-yl)pyridin-2-yl)-1-methyl-1H-pyrrole-3-carboxamide;

N-(3-chloro-5-(methylsulfonamido)phenyl)-4-(3-fluoro-5-(trifluoromethyl)pyridin-2-yl)-5-methylthiophene-2-carboxamide;

N-(3-chloro-5-(methylsulfonamido)phenyl)-4-(3-fluoro-5-(1-(2,2,2-trifluoroethyl)piperidin-4-yl)pyridin-2-yl)-5-methylthiophene-2-carboxamide;

N-(3-chloro-5-(methylsulfonamido)phenyl)-5-(3-fluoro-5-((1-methylazetidin-3-yl)oxy)pyridin-2-yl)-1-methyl-1H-pyrrole-3-carboxamide;

N-(3-chloro-5-(methylsulfonamido)phenyl)-4-(5-cyanopyridin-2-yl)-5-methylthiophene-2-carboxamide;

N-(3-chloro-5-(methylsulfonamido)phenyl)-4-(3-fluoro-5-isopropoxypyridin-2-yl)-5-methylthiophene-2-carboxamide;

N-(3-chloro-5-(methylsulfonamido)phenyl)-4-(5-ethoxy-3-fluoropyridin-2-yl)-5-methylthiophene-2-carboxamide;

N-(3-chloro-5-(methylsulfonamido)phenyl)-4-(5-(3,3-difluoroazetidin-1-yl)-3-methylpyridin-2-yl)-5-methylthiophene-2-carboxamide;

N-(3-chloro-5-(methylsulfonamido)phenyl)-4-(5-isopropoxypyrimidin-2-yl)thiophene-2-carboxamide;

N-(3-chloro-5-(methylsulfonamido)phenyl)-4-(3-fluoro-5-isopropoxypyridin-2-yl)thiophene-2-carboxamide;

N-(3-chloro-5-(methylsulfonamido)phenyl)-4-(5-(trifluoromethyl)pyrimidin-2-yl)thiophene-2-carboxamide;

N-(3-chloro-5-(methylsulfonamido)phenyl)-4-(5-cyano-3-methylpyridin-2-yl)-5-methylthiophene-2-carboxamide;

N-(3-chloro-5-(methylsulfonamido)phenyl)-4-(5-cyanopyrimidin-2-yl)-5-methylthiophene-2-carboxamide;

N-(3-chloro-5-(methylsulfonamido)phenyl)-4-(5-(trifluoromethyl)pyridin-2-yl)thiophene-2-carboxamide;

N-(3-chloro-5-(methylsulfonamido)phenyl)-4-(5-cyano-3-fluoropyridin-2-yl)-5-methylthiophene-2-carboxamide;

N-(3-chloro-5-(methylsulfonamido)phenyl)-4-(5-(3,3-difluoroazetidin-1-yl)pyrimidin-2-yl)thiophene-2-carboxamide;

N-(3-chloro-5-(methylsulfonamido)phenyl)-4-(5-isopropoxypyridin-2-yl)thiophene-2-carboxamide;

N-(3-chloro-5-(methylsulfonamido)phenyl)-1-(5-(3,3-difluoropyrrolidin-1-yl)-3-fluoropyridin-2-yl)-5-methyl-1H-pyrrole-3-carboxamide;

N-(3-chloro-5-(methylsulfonamido)phenyl)-4-(5-(3,3-difluoroazetidin-1-yl)pyridin-2-yl)thiophene-2-carboxamide;

N-(3-chloro-5-(methylsulfonamido)phenyl)-1-(5-(3,3-difluoropyrrolidin-1-yl)pyrimidin-2-yl)-5-methyl-1H-pyrrole-3-carboxamide;

N-(3-chloro-5-(methylsulfonamido)phenyl)-4-(5-(3,3-difluoroazetidin-1-yl)-3-fluoropyridin-2-yl)thiophene-2-carboxamide;

N-(3-chloro-5-(methylsulfonamido)phenyl)-5-methyl-4-(5-(3-(trifluoromethyl)azetidin-1-yl)pyrimidin-2-yl)thiophene-2-carboxamide;

N-(3-chloro-5-(methylsulfonamido)phenyl)-5-(5-(3,3-difluoropyrrolidin-1-yl)pyrimidin-2-yl)-1-methyl-1H-pyrrole-3-carboxamide;

N-(3-chloro-5-(methylsulfonamido)phenyl)-5-(5-(3,3-difluoropyrrolidin-1-yl)pyridin-2-yl)-1-methyl-1H-pyrrole-3-carboxamide;

N-(3-chloro-5-(methylsulfonamido)phenyl)-4-(5-(6,6-difluoro-2-azaspiro[3.3]heptan-2-yl)pyrimidin-2-yl)-5-methylthiophene-2-carboxamide;

N-(3-chloro-5-(methylsulfonamido)phenyl)-1-(5-(6,6-difluoro-2-azaspiro[3.3]heptan-2-yl)pyrimidin-2-yl)-5-methyl-1H-pyrrole-3-carboxamide;

N-(3-chloro-5-(methylsulfonamido)phenyl)-4-(5-(1,1-difluoro-5-azaspiro[2.4]heptan-5-yl)pyrimidin-2-yl)-5-methylthiophene-2-carboxamide;

N-(3-chloro-5-(methylsulfonamido)phenyl)-1-(5-(1,1-difluoro-5-azaspiro[2.4]heptan-5-yl)-3-fluoropyridin-2-yl)-5-methyl-1H-pyrrole-3-carboxamide;

N-(3-chloro-5-(methylsulfonamido)phenyl)-5-(5-(6,6-difluoro-2-azaspiro[3.3]heptan-2-yl)pyrimidin-2-yl)-1-methyl-1H-pyrrole-3-carboxamide;

N-(3-chloro-5-(methylsulfonamido)phenyl)-4-(5-((1-hydroxy-2-methylpropan-2-yl)oxy)pyrimidin-2-yl)-5-methylthiophene-2-carboxamide;

N-(3-chloro-5-(methylsulfonamido)phenyl)-5-ethyl-4-(3-fluoropyridin-2-yl)thiophene-2-carboxamide;

N-(3-chloro-5-(methylsulfonamido)phenyl)-4-(3-fluoro-5-(trifluoromethyl)pyridin-2-yl)thiophene-2-carboxamide;

N-(3-chloro-5-(methylsulfonamido)phenyl)-1-methyl-5-(5-(3-(trifluoromethyl)azetidin-1-yl)pyrimidin-2-yl)-1H-pyrrole-3-carboxamide;

4-(5-(tert-butoxy)-3-fluoropyridin-2-yl)-N-(3-chloro-5-(methylsulfonamido)phenyl)-5-methylthiophene-2-carboxamide;

N-(3-chloro-5-(methylsulfonamido)phenyl)-4-(5-(dimethylphosphoryl)pyridin-2-yl)-5-methylthiophene-2-carboxamide;

N-(3-chloro-5-(methylsulfonamido)phenyl)-4-(3,5-difluoropyridin-2-yl)-5-ethylthiophene-2-carboxamide;

N-(3-chloro-5-(methylsulfonamido)phenyl)-5-(5-(1,1-difluoro-5-azaspiro[2.4]heptan-5-yl)pyrimidin-2-yl)-1-methyl-1H-pyrrole-3-carboxamide;

N-(3-chloro-5-((2-hydroxyethyl)sulfonamido)phenyl)-4-(5-(3,3-difluoroazetidin-1-yl)-3-methoxypyridin-2-yl)-5-methylthiophene-2-carboxamide;

N-(3-chloro-5-(methylsulfonamido)phenyl)-5-(5-(1,1-difluoro-5-azaspiro[2.4]heptan-5-yl)pyridin-2-yl)-1-methyl-1H-pyrrole-3-carboxamide;

N-(3-chloro-5-(methylsulfonamido)phenyl)-5-methyl-4-(5-(3-(trifluoromethyl)azetidin-1-yl)pyridin-2-yl)thiophene-2-carboxamide;

N-(3-chloro-5-(methylsulfonamido)phenyl)-1-methyl-5-(5-(3-(trifluoromethyl)azetidin-1-yl)pyridin-2-yl)-1H-pyrrole-3-carboxamide;

N-(3-chloro-5-(methylsulfonamido)phenyl)-5-ethyl-4-(5-fluoropyridin-2-yl)thiophene-2-carboxamide;

4-(5-(tert-butoxy)pyrimidin-2-yl)-N-(3-chloro-5-(methylsulfonamido)phenyl)thiophene-2-carboxamide;

N-(3-chloro-5-(methylsulfonamido)phenyl)-4-(5-(dimethylphosphoryl)pyrimidin-2-yl)-5-methylthiophene-2-carboxamide;

4-(5-(tert-butoxy)pyridin-2-yl)-N-(3-chloro-5-(methylsulfonamido)phenyl)-5-methylthiophene-2-carboxamide;

N-(3-chloro-5-(methylsulfonamido)phenyl)-5-(5-(6,6-difluoro-2-azaspiro[3.3]heptan-2-yl)pyridin-2-yl)-1-methyl-1H-pyrrole-3-carboxamide;

N-(3-chloro-5-(methylsulfonamido)phenyl)-4-(5-(6,6-difluoro-2-azaspiro[3.3]heptan-2-yl)pyridin-2-yl)-5-methylthiophene-2-carboxamide;

N-(3-chloro-5-(methylsulfonamido)phenyl)-4-(5-(1,1-difluoro-5-azaspiro[2.4]heptan-5-yl)pyridin-2-yl)-5-methylthiophene-2-carboxamide;

1-(5-(tert-butoxy)-3-fluoropyridin-2-yl)-N-(3-chloro-5-(methylsulfonamido)phenyl)-5-methyl-1H-pyrrole-3-carboxamide;

1-(5-(tert-butoxy)pyridin-2-yl)-N-(3-chloro-5-(methylsulfonamido)phenyl)-5-methyl-1H-pyrrole-3-carboxamide;

5-(5-(tert-butoxy)pyridin-2-yl)-N-(3-chloro-5-(methylsulfonamido)phenyl)-1-methyl-1H-pyrrole-3-carboxamide;

N-(3-chloro-5-(propylsulfonamido)phenyl)-4-(3-methylpyridin-2-yl)thiophene-2-carboxamide;

N-(3-chloro-5-(methylsulfonamido)phenyl)-5-(3,5-difluoropyridin-2-yl)-1H-pyrrole-3-carboxamide;

4-(5-(tert-butoxy)pyrimidin-2-yl)-N-(3-chloro-5-(methylsulfonamido)phenyl)-5-(hydroxymethyl)thiophene-2-carboxamide;

N-(3-chloro-5-((1-methylethyl)sulfonamido)phenyl)-4-(3-methylpyridin-2-yl)thiophene-2-carboxamide;

5-(5-(tert-butoxy)pyrimidin-2-yl)-N-(3-chloro-5-(methylsulfonamido)phenyl)-1-methyl-1H-pyrrole-3-carboxamide;

N-(3-chloro-5-(methylsulfonamido)phenyl)-5-(3-methylpyridin-2-yl)thiophene-2-carboxamide;

N-(3-chloro-5-(N-methylmethylsulfonamido)phenyl)-4-(3-methylpyridin-2-yl)thiophene-2-carboxamide;

1-(5-(tert-butoxy)pyrimidin-2-yl)-N-(3-chloro-5-(methylsulfonamido)phenyl)-5-methyl-1H-pyrrole-3-carboxamide;

5-(5-(tert-butoxy)-3-fluoropyridin-2-yl)-N-(3-chloro-5-(methylsulfonamido)phenyl)-1-methyl-1H-pyrrole-3-carboxamide;

5-(3,5-difluoropyridin-2-yl)-N-(3-fluoro-5-(methylsulfonamido)phenyl)-1-methyl-1H-pyrrole-3-carboxamide;

N-(3-chloro-5-((2-hydroxyethyl)sulfonamido)phenyl)-5-(3,5-difluoropyridin-2-yl)-1-methyl-1H-pyrrole-3-carboxamide;

N-(3-chloro-5-(methylsulfonamido)phenyl)-3-fluoro-4-(5-isopropoxypyrimidin-2-yl)-5-methylthiophene-2-carboxamide;

N-(3-chloro-5-(methylsulfonamido)phenyl)-3-methyl-4-(3-methylpyridin-2-yl)thiophene-2-carboxamide;

4-(3-fluoro-5-(3-(trifluoromethyl)azetidin-1-yl)pyridin-2-yl)-N-(3-fluoro-5-(methylsulfonamido)phenyl)-5-methylthiophene-2-carboxamide;

N-(3-chloro-5-(methylsulfonamido)phenyl)-4-(5-fluoropyridin-2-yl)-5-methylthiazole-2-carboxamide;

N-(3-chloro-5-(ethylsulfonamido)phenyl)-4-(3-fluoro-5-(3-(trifluoromethyl)azetidin-1-yl)pyridin-2-yl)-5-methylthiophene-2-carboxamide;

N-(3-chloro-5-((2-hydroxyethyl)sulfonamido)phenyl)-4-(3-fluoro-5-(3-(trifluoromethyl)azetidin-1-yl)pyridin-2-yl)-5-methylthiophene-2-carboxamide;

N-(3-chloro-5-(methylsulfonamido)phenyl)-4-(3-fluoro-5-((1-methylazetidin-3-yl)oxy)pyridin-2-yl)-5-methylthiophene-2-carboxamide;

4-(5-(azetidin-3-yloxy)-3-fluoropyridin-2-yl)-N-(3-chloro-5-(methylsulfonamido)phenyl)-5-methylthiophene-2-carboxamide;

N-(3-chloro-5-(methylsulfonamido)phenyl)-4-(3-(1,1-dioxidothiomorpholino)-5-fluoropyridin-2-yl)-5-methylthiophene-2-carboxamide;

4-(3-(4-acetylpiperazin-1-yl)-5-fluoropyridin-2-yl)-N-(3-chloro-5-(methylsulfonamido)phenyl)-5-methylthiophene-2-carboxamide;

N-(3-chloro-5-(methylsulfonamido)phenyl)-4-(5-fluoro-3-(3-methoxypyrrolidin-1-yl)pyridin-2-yl)-5-methylthiophene-2-carboxamide;

N-(3-chloro-5-((methyl)sulfonamido-1,1,1-d3)phenyl)-4-(5-isopropoxypyrimidin-2-yl)-5-methylthiophene-2-carboxamide;

N-(3-chloro-5-(methylsulfonamido)phenyl)-4-(5-fluoro-3-(4-(methylsulfonyl)piperazin-1-yl)pyridin-2-yl)-5-methylthiophene-2-carboxamide;

N-(3-chloro-5-(methylsulfonamido)phenyl)-4-(5-fluoro-3-(6-azaspiro[2.5]octan-6-yl)pyridin-2-yl)-5-methylthiophene-2-carboxamide;

N-(3-chloro-5-(methylsulfonamido)phenyl)-5-methyl-1-(5-(3-(trifluoromethyl)azetidin-1-yl)pyrimidin-2-yl)-1H-pyrrole-3-carboxamide;

2-(5-((3-chloro-5-(methylsulfonamido)phenyl)carbamoyl)-2-methylthiophen-3-yl)-3,5-difluoropyridine 1-oxide;

4-(5-(azetidin-3-yloxy)pyrimidin-2-yl)-N-(3-chloro-5-(methylsulfonamido)phenyl)-5-methylthiophene-2-carboxamide;

N-(3-chloro-5-(methylsulfonamido)phenyl)-4-(5-fluoro-3-(3-hydroxy-3-methylbut-1-yn-1-yl)pyridin-2-yl)-5-methylthiophene-2-carboxamide;

N-(3-chloro-5-(methylsulfonamido)phenyl)-4-(3-fluoro-5-(3-hydroxy-1-methylazetidin-3-yl)pyridin-2-yl)-5-methylthiophene-2-carboxamide;

N-(2-fluoro-3-(methylsulfonamido)phenyl)-4-(3-(pyridin-3-ylmethoxy)pyridin-2-yl)thiophene-2-carboxamide;

1-(2-(benzyloxy)cyclopentyl)-N-(3-chloro-5-(methylsulfonamido)phenyl)-1H-pyrazole-4-carboxamide;

N-(3-chloro-5-(methylsulfonamido)phenyl)-1-(2-(((5-fluoropyridin-3-yl)oxy)methyl)phenyl)-1H-pyrazole-4-carboxamide;

N-(3-chloro-5-(methylsulfonamido)phenyl)-1-(2-fluoro-6-((5-fluoropyridin-3-yl)methoxy)phenyl)-1H-pyrazole-4-carboxamide;

N-(3-chloro-5-(methylsulfonamido)phenyl)-1-(2-(dimethylcarbamoyl)-6-((3-fluorobenzyl)oxy)phenyl)-1H-pyrazole-4-carboxamide;

N-(3-chloro-5-(methylsulfonamido)phenyl)-1-(2,4-difluoro-6-(oxazol-5-ylmethoxy)phenyl)-1H-pyrazole-4-carboxamide;

N-(3-chloro-5-(methylsulfonamido)phenyl)-1-(5-fluoro-3-(oxazol-5-ylmethoxy)pyridin-2-yl)-1H-pyrazole-4-carboxamide;

N-(3-chloro-5-(methylsulfonamido)phenyl)-4-(3-((5-fluoropyridin-3-yl)methoxy)pyridin-2-yl)thiophene-2-carboxamide;

1-(2-(benzyloxy)phenyl)-N-(3-fluoro-5-(methylsulfonamido)phenyl)-1H-pyrazole-4-carboxamide;

N-(3-chloro-5-(methylsulfonamido)phenyl)-1-(2-fluoro-6-(oxazol-5-ylmethoxy)phenyl)-1H-pyrazole-4-carboxamide;

N-(3-chloro-5-(methylsulfonamido)phenyl)-1-(2-((3-fluorobenzyl)oxy)-4-(2-oxa-6-azaspiro[3.3]heptan-6-yl)phenyl)-1H-pyrazole-4-carboxamide;

N-(3-chloro-5-(methylsulfonamido)phenyl)-4-(3-((5-fluoropyridin-3-yl)methoxy)pyridin-2-yl)-5-methylthiophene-2-carboxamide;

N-(3-chloro-5-(methylsulfonamido)phenyl)-1-(3-((5-fluoropyridin-3-yl)methoxy)pyridin-2-yl)-5-(hydroxymethyl)-1H-pyrrole-3-carboxamide;

N-(3-chloro-5-(ethylsulfonamido)phenyl)-4-(5-fluoro-3-(thiazol-2-ylmethoxy)pyridin-2-yl)-5-methylthiophene-2-carboxamide;

N-(3-chloro-5-(methylsulfonamido)phenyl)-5-(5-fluoro-3-((2-methylthiazol-4-yl)methoxy)pyridin-2-yl)-1-methyl-1H-pyrrole-3-carboxamide;

N-(3-chloro-5-(methylsulfonamido)phenyl)-5-(3-((3,5-dimethylisoxazol-4-yl)methoxy)-5-fluoropyridin-2-yl)-1-methyl-1H-pyrrole-3-carboxamide;

N-(3-chloro-5-(ethylsulfonamido)phenyl)-4-(5-fluoro-3-(pyrimidin-5-ylmethoxy)pyridin-2-yl)-5-methylthiophene-2-carboxamide;

N-(3-chloro-5-(methylsulfonamido)phenyl)-5-(2-((5-fluoropyridin-3-yl)methoxy)-4-methylpyridin-3-yl)-1-methyl-1H-pyrrole-3-carboxamide;

N-(3-chloro-5-(methylsulfonamido)phenyl)-5-(5-fluoro-3-((1-methyl-1H-1,2,3-triazol-5-yl)methoxy)pyridin-2-yl)-1-methyl-1H-pyrrole-3-carboxamide;

(E)-N-(3-chloro-5-(methylsulfonamido)phenyl)-5-(2-(2-(5-fluoropyridin-3-yl)vinyl)phenyl)-1-methyl-1H-pyrrole-3-carboxamide;

N-(3-chloro-5-(methylsulfonamido)phenyl)-5-(5-fluoro-3-((1-methyl-1H-tetrazol-5-yl)methoxy)pyridin-2-yl)-1-methyl-1H-pyrrole-3-carboxamide;

N-(3-chloro-5-(methylsulfonamido)phenyl)-5-(5-fluoro-3-(2-(5-fluoropyridin-3-yl)ethyl)pyridin-2-yl)-1-methyl-1H-pyrrole-3-carboxamide;

(E)-N-(3-chloro-5-(methylsulfonamido)phenyl)-5-(5-fluoro-3-(2-(5-fluoropyridin-3-yl)vinyl)pyridin-2-yl)-1-methyl-1H-pyrrole-3-carboxamide;

4-(3-((5-fluoropyridin-3-yl)methoxy)pyridin-2-yl)-5-methyl-N-(3-(methylsulfonamido)phenyl)thiophene-2-carboxamide;

N-(3-chloro-5-(methylsulfonamido)phenyl)-5-(3-(1-(3-fluoro-5-(trifluoromethyl)phenyl)ethoxy)pyridin-2-yl)-1-methyl-1H-pyrrole-3-carboxamide;

N-(3-chloro-5-(methylsulfonamido)phenyl)-5-(3-((1S)-1-(3-fluoro-5-(trifluoromethyl)phenyl)ethoxy)pyridin-2-yl)-1-methyl-1H-pyrrole-3-carboxamide;

N-(3-chloro-5-(methylsulfonamido)phenyl)-5-(3-((1R)-1-(3-fluoro-5-(trifluoromethyl)phenyl)ethoxy)pyridin-2-yl)-1-methyl-1H-pyrrole-3-carboxamide;

N-(3-chloro-5-(methylsulfonamido)phenyl)-5-(3-((5-ethylpyridin-3-yl)methoxy)pyridin-2-yl)-1-methyl-1H-pyrrole-3-carboxamide;

N-(3-chloro-5-(methylsulfonamido)phenyl)-4-(3-(1-(5-fluoropyridin-3-yl)ethoxy)pyridin-2-yl)-5-methylthiophene-2-carboxamide;

(R)-N-(3-chloro-5-(methylsulfonamido)phenyl)-4-(3-(1-(5-fluoropyridin-3-yl)ethoxy)pyridin-2-yl)-5-methylthiophene-2-carboxamide;

(S)-N-(3-chloro-5-(methylsulfonamido)phenyl)-4-(3-(1-(5-fluoropyridin-3-yl)ethoxy)pyridin-2-yl)-5-methylthiophene-2-carboxamide;

N-(3-chloro-5-((2-hydroxyethyl)sulfonamido)phenyl)-4-(3-((5-fluoropyridin-3-yl)methoxy)pyridin-2-yl)-5-methylthiophene-2-carboxamide;

N-(3-chloro-5-(methylsulfonamido)phenyl)-4-(5-fluoro-3-(oxazol-5-ylmethoxy)pyridin-2-yl)-5-methylthiophene-2-carboxamide;

N-(3-chloro-5-(methylsulfonamido)phenyl)-5-(5-(3,3-difluoroazetidin-1-yl)-3-(oxazol-5-ylmethoxy)pyridin-2-yl)-1-methyl-1H-pyrrole-3-carboxamide;

N-(3-chloro-5-(methylsulfonamido)phenyl)-5-(5-((3,5-difluorobenzyl)oxy)-2-methylpyrimidin-4-yl)-1-methyl-1H-pyrrole-3-carboxamide;

N-(3-chloro-5-(methylsulfonamido)phenyl)-5-(5-fluoro-3-(pyrimidin-5-ylmethoxy)pyridin-2-yl)-1-(2,2,2-trifluoroethyl)-1H-pyrrole-3-carboxamide;

5-(3-((6-(2-hydroxypropan-2-yl)pyridin-2-yl)methoxy)pyridin-2-yl)-1-methyl-N-(3-(methylsulfonamido)phenyl)-1H-pyrrole-3-carboxamide;

5-(3-((3-hydroxybenzyl)oxy)pyridin-2-yl)-1-methyl-N-(3-(methylsulfonamido)phenyl)-1H-pyrrole-3-carboxamide;

N-(3-chloro-5-(methylsulfonamido)phenyl)-4-(3-(1-(3,5-difluorophenyl)ethoxy)pyridin-2-yl)-5-methylthiophene-2-carboxamide;

(S)-N-(3-chloro-5-(methylsulfonamido)phenyl)-4-(3-(1-(3,5-difluorophenyl)ethoxy)pyridin-2-yl)-5-methylthiophene-2-carboxamide;

(R)-N-(3-chloro-5-(methylsulfonamido)phenyl)-4-(3-(1-(3,5-difluorophenyl)ethoxy)pyridin-2-yl)-5-methylthiophene-2-carboxamide;

N-(3-chloro-5-(methylsulfonamido)phenyl)-5-(5-((3,5-difluorobenzyl)oxy)pyrimidin-4-yl)-1-methyl-1H-pyrrole-3-carboxamide;

N-(3-chloro-5-(methylsulfonamido)phenyl)-5-(5-((1-isopropylazetidin-3-yl)oxy)pyrimidin-2-yl)-1-(2,2,2-trifluoroethyl)-1H-pyrrole-3-carboxamide;

(S)-N-(3-chloro-5-(methylsulfonamido)phenyl)-5-(5-((1-methylpyrrolidin-3-yl)oxy)pyrimidin-2-yl)-1-(2,2,2-trifluoroethyl)-1H-pyrrole-3-carboxamide;

(R)-N-(3-chloro-5-(methylsulfonamido)phenyl)-5-(5-((1-methylpyrrolidin-3-yl)oxy)pyrimidin-2-yl)-1-(2,2,2-trifluoroethyl)-1H-pyrrole-3-carboxamide;

N-(3-chloro-5-(methylsulfonamido)phenyl)-1-(2,2-difluoroethyl)-5-(5-((1-methylazetidin-3-yl)oxy)pyrimidin-2-yl)-1H-pyrrole-3-carboxamide;

N-(3-chloro-5-(methylsulfonamido)phenyl)-5-(5-((1-(methylsulfonyl)azetidin-3-yl)oxy)pyrimidin-2-yl)-1-(2,2,2-trifluoroethyl)-1H-pyrrole-3-carboxamide;

(R)-N-(3-chloro-5-(methylsulfonamido)phenyl)-5-(3-fluoro-5-((1-methylpyrrolidin-3-yl)oxy)pyridin-2-yl)-1-methyl-1H-pyrrole-3-carboxamide;

(S)-N-(3-chloro-5-(methylsulfonamido)phenyl)-5-(3-fluoro-5-((1-methylpyrrolidin-3-yl)oxy)pyridin-2-yl)-1-methyl-1H-pyrrole-3-carboxamide;

2-((2-(5-((3-chloro-5-(methylsulfonamido)phenyl)carbamoyl)-2-methylthiophen-3-yl)pyrimidin-5-yl)oxy)propanoic acid;

N-(3-chloro-5-((2-hydroxyethyl)sulfonamido)phenyl)-4-(5-isopropoxypyrimidin-2-yl)-5-methylthiophene-2-carboxamide;

N-(3-chloro-5-(methylsulfonamido)phenyl)-4-(5-hydroxypyrimidin-2-yl)-5-methylthiophene-2-carboxamide;

4-(5-(tert-butoxy)pyrimidin-2-yl)-N-(3-chloro-5-(ethylsulfonamido)phenyl)-5-methylthiophene-2-carboxamide;

2-((2-(5-((3-chloro-5-(methylsulfonamido)phenyl)carbamoyl)-2-methylthiophen-3-yl)pyrimidin-5-yl)oxy)-2-methylpropanoic acid;

N-(3-chloro-5-(methylsulfonamido)phenyl)-4-(5-((1-hydroxypropan-2-yl)oxy)pyrimidin-2-yl)-5-methylthiophene-2-carboxamide;

N-(3-chloro-5-(methylsulfonamido)phenyl)-5-(5-(2-(dimethylamino)ethoxy)-3-fluoropyridin-2-yl)-1-methyl-1H-pyrrole-3-carboxamide;

N-(3-chloro-5-(methylsulfonamido)phenyl)-4-(3-fluoro-5-(1-hydroxy-1-(1-methylazetidin-3-yl)ethyl)pyridin-2-yl)-5-methylthiophene-2-carboxamide;

N-(3-chloro-5-(ethylsulfonamido)phenyl)-4-(5-isopropoxypyrimidin-2-yl)-5-methylthiophene-2-carboxamide;

N-(3-chloro-5-(methylsulfonamido)phenyl)-5-(3-fluoro-5-((1-(2,2,2-trifluoroethyl)azetidin-3-yl)oxy)pyridin-2-yl)-1-methyl-1H-pyrrole-3-carboxamide;

2-(4-((3-chloro-5-(methylsulfonamido)phenyl)carbamoyl)-1-methyl-1H-pyrrol-2-yl)-3,5-difluoropyridine 1-oxide;

N-(3-chloro-5-(methylsulfonamido)phenyl)-5-(3-fluoro-5-((1-isopropylazetidin-3-yl)oxy)pyridin-2-yl)-1-methyl-1H-pyrrole-3-carboxamide;

N-(3-chloro-5-(methylsulfonamido)phenyl)-5-(5-((1-(2,2-difluoroethyl)azetidin-3-yl)oxy)-3-fluoropyridin-2-yl)-1-methyl-1H-pyrrole-3-carboxamide;

N-(3-chloro-5-(methylsulfonamido)phenyl)-1-(2,2-difluoroethyl)-5-(5-(3-(trifluoromethyl)azetidin-1-yl)pyrimidin-2-yl)-1H-pyrrole-3-carboxamide;

N-(3-chloro-5-(methylsulfonamido)phenyl)-5-(3-fluoro-6-methoxypyridin-2-yl)-1-methyl-1H-pyrrole-3-carboxamide;

N-(3-chloro-5-(methylsulfonamido)phenyl)-5-(3-fluoropyridin-2-yl)-1-(2,2,2-trifluoroethyl)-1H-pyrrole-3-carboxamide;

N-(3-chloro-5-(methylsulfonamido)phenyl)-5-(5-methoxypyrimidin-2-yl)-1-(2,2,2-trifluoroethyl)-1H-pyrrole-3-carboxamide;

N-(3-chloro-5-(methylsulfonamido)phenyl)-5-(5-fluoropyrimidin-2-yl)-1-(2,2,2-trifluoroethyl)-1H-pyrrole-3-carboxamide; and N-(3-chloro-5-(methylsulfonamido)phenyl)-5-(5-((1-methylazetidin-3-yl)oxy)pyrimidin-2-yl)-1-(2,2,2-trifluoroethyl)-1H-pyrrole-3-carboxamide;

or a pharmaceutically acceptable salt thereof.

The compounds and intermediates described herein may be isolated and used as the compound per se. Alternatively, when a moiety is present that is capable of forming a salt, the compound or intermediate may be isolated and used as its corresponding salt. As used herein, the terms "salt" or "salts" refers to an acid addition or base addition salt of a compound described herein. "Salts" include in particular "pharmaceutical acceptable salts". The term "pharmaceutically acceptable salts" refers to salts that retain the biological effectiveness and properties of the compounds described herein and, which typically are not biologically or otherwise undesirable. In many cases, the compounds of the present disclosure are capable of forming acid and/or base salts by virtue of the presence of amino and/or carboxyl groups or groups similar thereto.

Pharmaceutically acceptable acid addition salts can be formed with inorganic acids or organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The salts can be synthesized by conventional chemical methods from a compound containing a basic or acidic moiety. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Isotopically-labeled compounds of Formula (I) can generally be prepared by conventional techniques known to those skilled in the art or by processes analogous to those described in the accompanying Examples and Preparations using an appropriate isotopically-labeled reagents in place of the non-labeled reagent previously employed. In one embodiment, the present disclosure provides deuterated compounds described herein or a pharmaceutically acceptable salt thereof.

Pharmaceutically acceptable solvates in accordance with the disclosure include those wherein the solvent of crystallization may be isotopically substituted, e.g. $D_2O$, $d_6$-acetone, $d_6$-DMSO.

It will be recognized by those skilled in the art that the compounds of the present disclosure may contain chiral centers and as such may exist in different stereoisomeric forms. As used herein, the term "an optical isomer" or "a stereoisomer" refers to any of the various stereo isomeric configurations which may exist for a given compound of the present disclosure. It is understood that a substituent may be attached at a chiral center of a carbon atom. Therefore, the disclosure includes enantiomers, diastereomers or racemates of the compound.

"Enantiomers" are a pair of stereoisomers that are non-superimposable mirror images of each other. A 1:1 mixture of a pair of enantiomers is a "racemic" mixture. The term "racemic" or "rac" is used to designate a racemic mixture where appropriate. When designating the stereochemistry for the compounds of the present disclosure, a single stereoisomer with known relative and absolute configuration of the two chiral centers is designated using the conventional RS system (e.g., (1S,2S)). "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Alternatively, the resolved compounds can be defined by the respective retention times for the corresponding enantiomers/diastereomers via chiral HPLC.

Certain of the compounds described herein contain one or more asymmetric centers or axes and may thus give rise to enantiomers, diastereomers, and other stereoisomeric forms that may be defined, in terms of absolute stereochemistry, as (R)- or (S)—.

Unless specified otherwise, the compounds of the present disclosure are meant to include all such possible stereoisomers, including racemic mixtures, optically pure forms and intermediate mixtures. Optically active (R)- and (S)-stereoisomers may be prepared using chiral synthons or chiral reagents, or resolved using conventional techniques (e.g., separated on chiral SFC or HPLC chromatography columns, such as CHIRALPAK® and CHIRALCEL® available from DAICEL Corp. using the appropriate solvent or mixture of solvents to achieve good separation). If the compound contains a double bond, the substituent may be E or Z configuration. If the compound contains a disubstituted cycloalkyl, the cycloalkyl substituent may have a cis- or trans-configuration. All tautomeric forms are also intended to be included.

The present disclosure also provides a pharmaceutical composition comprising a compound described herein (e.g., a compound according to any one of the preceding embodiments), or a pharmaceutically acceptable salt thereof, and one or more pharmaceutically acceptable carriers.

METHODS OF USE

The compounds described herein have DHX9 inhibitory activity. As used herein, "DHX9 inhibitory activity" refers to the ability of a compound or composition to induce a detectable decrease in DHX9 activity in vivo or in vitro (e.g., at least 10% decrease in DHX9 activity as measured by a given assay such as the bioassay described in the examples and known in the art).

In certain embodiments, the present disclosure provides a method of treating a disease or disorder responsive to inhibition of DHX9 activity (referred herein as "DHX9 mediated disease or disorder") in a subject in need of the treatment. The method comprises administering to the subject a compound described herein (e.g., a compound described in any one of the first to forty-fifth embodiments) or a pharmaceutically acceptable salt thereof or a pharmaceutical composition thereof.

In certain embodiments, the present disclosure provides the use of a compound described herein (e.g., a compound described in any one of the first to forty-fifth embodiments) or a pharmaceutically acceptable salt thereof or a pharmaceutical composition comprising a compound described herein or a pharmaceutically acceptable salt thereof for the manufacture of a medicament for the treatment of a DHX9 mediated disorder or disease in a subject in need of the treatment.

In certain embodiments, the present disclosure provides a compound described herein (e.g., a compound described in any one of the first to forty-fifth embodiments) or a pharmaceutically acceptable salt thereof or a pharmaceutical composition comprising a compound described herein or a pharmaceutically acceptable salt thereof for use in the treatment of a DHX9 mediated disorder or disease in a subject in need of the treatment.

In certain embodiments, the DHX9 mediated disease or disorder is selected from cancer, viral infections, and autoimmune disease.

In some embodiments, the present disclosure provides a method of treating cancer. In some embodiments, the cancer is selected from colorectal, endometrial, ovarian, gastric, hematopoietic, breast, brain, skin, lung, blood, prostate, head and neck, pancreatic, bladder, bone, soft-tissue, kidney, and liver cancer. In some embodiments the cancer is selected from colorectal, endometrial, ovarian, hematopoietic, and gastric cancer. In some embodiments, the cancer is colorectal cancer. In some embodiments, the cancer is Ewing's Sarcoma.

In some embodiments, the cancer is a microsatellite instable (MSI) cancer. In some embodiments, the cancer is MSI-high cancer. In other embodiments, the cancer is MSI-low cancer. MSI is determined by PCR analysis of 5 different nucleotide repeats, which is dependent on the cancer type. MSI-low cancers are characterized by instability at only 1 of the 5 sites; while MSI-high cancers are characterized by instability at 2 or more of the 5 sites (G. Yang et al. Correlations between microsatellite instability and the biological behavior of tumors. *Journal of Cancer Research and Clinical Oncology*, 2019).

MSI-high cancer is additionally characterized by defective mismatch repair (dMMR) (M. Lorenzi, et al. Epidemiology of Microsatellite Instability High (MSI-H) and Deficient Mismatch Repair (dMMR) in Solid Tumors: A Structured Literature Review. *Journal of Oncology*, Volume 2020, Article ID 1897929). For example, dMMR in colorectal cancer can be determined by MLH1 promoter hypermethylation, rendering MLH1 inactive, which comprises about 80-90% of MSI-high colorectal cancers. MSI-high colorectal cancer with inactivated MLH1 is also named sporadic MSI-high colorectal cancer. Alternatively, dMMR can be determined by immunohistochemistry mutation status of MLH1, MSH2, MSH6, MSH3, PMS1 and/or PMS2 mismatch repair (MMR) proteins. In MSI-high colorectal cancer, MLH1 and MSH2 are the 2 predominantly mutated MMR proteins. They are mutated in about 10-20% of MSI-high colorectal cancers. MSI-high colorectal cancers with these mutations are also known as Lynch Syndrome cancers.

In some embodiments, the cancer is a MSI cancer and/or has mutations or defects in DNA mis-match repair (MMR), and/or mutations or defects in RNA splicing and the kinetochore complex.

The compounds, or pharmaceutically acceptable salts thereof described herein may be used to decrease the expression or activity of DHX9, or to otherwise affect the properties and/or behavior of DHX9 in a cell.

One embodiment of the present disclosure includes a method of decreasing the expression or activity of DHX9, or to otherwise affect the properties and/or behavior of DHX9 in a subject comprising administering to said subject an effective amount of at least one compound described herein, or a pharmaceutically acceptable salt thereof.

In certain embodiments, the present disclosure relates to the aforementioned methods, wherein said subject is a mammal.

In certain embodiments, the present disclosure relates to the aforementioned methods, wherein said subject is a primate.

In certain embodiments, the present disclosure relates to the aforementioned methods, wherein said subject is a human.

As used herein, an "effective amount" and a "therapeutically effective amount" can used interchangeably. It means an amount effective for treating or lessening the severity of one or more of the diseases, disorders or conditions as recited herein. In some embodiments, the effective dose can be between 10 µg and 500 mg.

The compounds and compositions, according to the methods of the present disclosure, may be administered using any amount and any route of administration effective for treating or lessening the severity of one or more of the diseases, disorders or conditions recited above.

In certain embodiments, the present disclosure relates to the aforementioned methods, wherein said compound is administered parenterally.

In certain embodiments, the present disclosure relates to the aforementioned methods, wherein said compound is administered intramuscularly, intravenously, subcutaneously, orally, pulmonary, rectally, intrathecally, topically or intranasally.

In certain embodiments, the present disclosure relates to the aforementioned methods, wherein said compound is administered systemically.

The compounds of the present disclosure are typically used as a pharmaceutical composition (e.g., a compound of the present disclosure and at least one pharmaceutically acceptable carrier). As used herein, the term "pharmaceutically acceptable carrier" includes generally recognized as safe (GRAS) solvents, dispersion media, surfactants, antioxidants, preservatives (e.g., antibacterial agents, antifungal agents), isotonic agents, salts, preservatives, drug stabilizers, buffering agents (e.g., maleic acid, tartaric acid, lactic acid, citric acid, acetic acid, sodium bicarbonate, sodium phosphate, and the like), and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. For purposes of this disclosure, solvates and hydrates are considered pharmaceutical compositions comprising a compound of the present disclosure and a solvent (i.e., solvate) or water (i.e., hydrate).

The formulations may be prepared using conventional dissolution and mixing procedures. For example, the bulk drug substance (i.e., compound of the present disclosure or stabilized form of the compound (e.g., complex with a cyclodextrin derivative or other known complexation agent)) is dissolved in a suitable solvent in the presence of one or more of the excipients described above. The compound of the present disclosure is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition comprising a compound of the present disclosure is generally formulated for use as a parenteral or oral administration or alternatively suppositories.

For example, the pharmaceutical oral compositions of the present disclosure can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethylene glycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include a compound of the disclosure in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The parenteral compositions (e.g, intravenous (IV) formulation) are aqueous isotonic solutions or suspensions. The parenteral compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are generally prepared according to conventional mixing, granulating or coating methods, respectively, and contain about 0.1-75%, or contain about 1-50%, of the active ingredient.

The compound of the present disclosure or pharmaceutical composition thereof for use in a subject (e.g., human) is typically administered orally or parenterally at a therapeutic dose. When administered intravenously via infusion, the dosage may depend upon the infusion rate at which an IV formulation is administered. In general, the therapeutically effective dosage of a compound, the pharmaceutical composition, or the combinations thereof, is dependent on the species of the subject, the body weight, age and individual condition, the disorder or disease or the severity thereof being treated. A physician, pharmacist, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present disclosure can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations.

Definitions

As used herein, a "patient," "subject" or "individual" are used interchangeably and refer to either a human or non-human animal. The term includes mammals such as humans. Typically, the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In some embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease, condition or disorder, refers to the management and care of a patient for the purpose of combating the disease, condition, or disorder and includes the administration of a compound of the present disclosure to obtaining desired pharmacological and/or physiological effect. The effect can be therapeutic, which includes achieving, partially or substantially, one or more of the following results: partially or totally reducing the extent of the disease, condition or disorder; ameliorating or improving a clinical symptom, complications or indicator associated with the disease, condition or disorder; or delaying, inhibiting or decreasing the likelihood of the progression of the disease, condition or disorder; or eliminating the disease, condition or disorder. In certain embodiments, the effect can be to prevent the onset of the symptoms or complications of the disease, condition or disorder.

As used herein the term "cancer" has the meaning normally accepted in the art. The term can broadly refer to abnormal cell growth.

As used herein, a subject is "in need of" a treatment if such subject would benefit biologically, medically or in quality of life from such treatment (in some embodiments, a human).

As used herein, the phrase "optionally substituted" is used interchangeably with the phrase "substituted or unsubstituted." In general the term "optionally substituted" refers to the replacement of hydrogen radicals in a given structure with the radical of a specified substituent. Specific substituents are described in the definitions and in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position.

As used herein, the term "alkyl" refers to a fully saturated branched or unbranched hydrocarbon moiety. The term "$C_{1-4}$alkyl" refers to an alkyl having 1 to 4 carbon atoms. The terms "$C_{1-3}$alkyl" and "$C_{1-2}$alkyl" are to be construed accordingly. Representative examples of "$C_{1-4}$alkyl" include, but are not limited to, methyl, ethyl, n-propyl, iso-propyl, n-butyl, sec-butyl, iso-butyl, and tert-butyl. Similarly, the alkyl portion (i.e., alkyl moiety) of an alkoxy have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls).

As used herein, the term "alkylene" refers to a fully saturated branched or unbranched divalent hydrocarbon radical. The term "C1-4alkylene" refers to an alkylene having 1 to 4 carbon atoms. The terms "C1-3alkylene" and "C1-2alkylene" are to be construed accordingly. Representative examples of "C1-4alkylene" include, but are not limited to, methylene, ethylene, n-propylene, iso-propylene, n-butylene, sec-butylene, iso-butylene, and tert-butylene.

As used herein, the term "alkoxy" refers to a fully saturated branched or unbranched alkyl moiety attached through an oxygen bridge (i.e. a —O—$C_{1-4}$ alkyl group wherein $C_{1-4}$ alkyl is as defined herein). Representative examples of alkoxy include, but are not limited to, methoxy, ethoxy, propoxy, 2-propoxy, butoxy, tert-butoxy and the like. In some embodiments, alkoxy groups have about 1-4 carbons, and in some embodiments about 1-2 carbons. The term "$C_{1-2}$ alkoxy" is to be construed accordingly.

As used herein, the term "$C_{1-4}$ alkoxyC1-4alkyl" refers to a $C_{1-4}$ allkyl group as defined herein, wherein at least of the hydrogen atoms is replaced by an $C_{1-4}$ alkoxy. The $C_{1-4}$alkoxy$C_{1-4}$ alkyl group is connected through the rest of the molecule described herein through the alkyl group.

The number of carbon atoms in a group is specified herein by the prefix "$C_{x-xx}$", wherein x and xx are integers. For example, "$C_{1-3}$ alkyl" is an alkyl group which has from 1 to 3 carbon atoms.

"Halogen" or "halo" may be fluorine, chlorine, bromine or iodine.

As used herein, the term "halo-substituted-$C_{1-4}$alkyl" or "$C_{1-4}$haloalkyl" refers to a $C_{1-4}$alkyl group as defined herein, wherein at least one of the hydrogen atoms is replaced by a halo atom. The $C_{1-4}$haloalkyl group can be monohalo-$C_{1-4}$alkyl, dihalo-$C_{1-4}$alkyl or polyhalo-$C_{1-4}$ alkyl including perhalo-$C_{1-4}$alkyl. A monohalo-$C_{1-4}$alkyl can have one iodo, bromo, chloro or fluoro within the alkyl group. Dihalo-$C_{1-4}$alkyl and polyhalo-$C_{1-4}$alkyl groups can have two or more of the same halo atoms or a combination of different halo groups within the alkyl. Typically the polyhalo-$C_{1-4}$alkyl group contains up to 9, or 8, or 7, or 6, or 5, or 4, or 3, or 2 halo groups. Non-limiting examples of $C_{1-4}$haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-$C_{1-4}$alkyl group refers to a $C_{1-4}$alkyl group having all hydrogen atoms replaced with halo atoms.

The term "aryl" refers to an aromatic carbocyclic single ring or two fused ring system containing 6 to 10 carbon atoms. Examples include phenyl, indanyl, tetrahydronaphthalene, and naphthyl.

The term "heteroaryl" refers to a 5- to 12-membered aromatic radical containing 1-4 heteroatoms selected from N, O, and S. In some instances, nitrogen atoms in a heteroaryl may be quaternized. The term "heteroaryl" may be used interchangeably with the terms "heteroaryl ring", "heteroaryl group", or "heteroaromatic". A heteroaryl group may be mono- or bi-cyclic. Monocyclic heteroaryl includes, for example, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, 30 triazinyl, tetrazinyl, and the like. Bi-cyclic heteroaryls include groups in which a monocyclic heteroaryl ring is fused to one or more aryl or heteroaryl rings. Non-limiting examples include indolyl, indazoyl, benzofuranyl, benzimidazolyl, and imidazo[1,2-a]pyridine.

The term "carbocyclic ring" or "carbocyclyl" refers to a 4- to 12-membered saturated or partially unsaturated hydrocarbon ring and may exist as a single ring, bicyclic ring (including fused, spiro or bridged carbocyclic rings) or a spiro ring. Bi-cyclic carbocyclyl groups include, e.g., unsaturated carbocyclic radicals fused to another unsaturated carbocyclic radical, cycloalkyl, or aryl, such as, for example, cyclohexyl, cyclohexenyl, 2,3-dihydroindenyl, decahydronaphthalenyl, and 1,2,3,4-tetrahydronaphthalenyl. Unless specified otherwise, the carbocyclic ring generally contains 4- to 10-ring members.

The term "$C_{3-6}$ cycloalkyl" refers to a carbocyclic ring which is fully saturated (e.g., cyclopropyl, cyclobutyl, cyclopentyl, and cyclohexyl).

The term "heterocycle" or "heterocyclyl" refers to a 4- to 12-membered saturated or partially unsaturated heterocyclic ring containing 1 to 4 heteroatoms independently selected from N, O, and S. A heterocyclyl group may be mono- or bicyclic (e.g., a bridged, fused, or spiro bicyclic ring). Examples of monocyclic saturated or partially unsaturated heterocyclic radicals include, without limitation, piperdinyl, piperazinyl, tetrahydropyranyl, morpholinyl, and pyrrolidinyl. Bi-cyclic heterocyclyl groups include, e.g., unsaturated heterocyclic radicals fused to another unsaturated heterocyclic radical, cycloalkyl, aryl, or heteroaryl ring, such as, for example, 2-oxo-2,3-dihydro-1H-benzo[d]imidazolyl, 1,4,5,6-tetrahydrocyclopenta[c]pyrazolyl, 4,5,6,7-tetrahydrothieno[2,3-c]pyridinyl, 5,6-dihydro-4H-cyclopenta[b]thiophenyl, and 4,7-dihydro-5H-thieno[2,3-c]pyranyl. In some embodiments, the heterocyclyl group is a 4 to 6 membered monocyclic heterocyclyl group. In some embodiments, the heterocyclyl group is a 8 to 10 membered bicyclic heterocyclyl group.

As used herein the term "spiro" ring means a two-ring system wherein both rings share one common atom. Examples of spiro rings include 5-oxaspiro[2.3]hexane, oxaspiro[2.4]heptanyl, 5-oxaspiro[2.4]heptanyl, 4-oxaspiro[2.4]heptane, 4-oxaspiro[2.5]octanyl, 6-oxaspiro[2.5]octanyl, oxaspiro[2.5]octanyl, oxaspiro[3.4]octanyl, oxaspiro[bicyclo[2.1.1]hexane-2,3'-oxetan]-1-yl, oxaspiro[bicyclo[3.2.0]heptane-6,1'-cyclobutan]-7-yl, 2,6-diazaspiro[3.3]heptanyl, -oxa-6-azaspiro[3.3]heptane, 2,2,6-diazaspiro[3.3] heptane, 3-azaspiro[5.5]undecanyl, 3,9-diazaspiro[5.5] undecanyl, 7-azaspiro[3.5]nonane, 2,6-diazaspiro[3.4] octane, 8-azaspiro[4.5]decane, 1,6-diazaspiro[3.3]heptane, 5-azaspiro[2.5]octane, 4,7-diazaspiro[2.5]octane, 5-oxa-2-azaspiro[3.4]octane, 6-oxa-1-azaspiro[3.3]heptane, 3-azaspiro[5.5]undecanyl, 3,9-diazaspiro[5.5]undecanyl, and the like.

The term "fused" ring refers to two ring systems share two adjacent ring atoms. Fused heterocycles have at least one the ring systems contain a ring atom that is a heteroatom selected from O, N and S (e.g., 3-oxabicyclo[3.1.0]hexane).

As used herein the term "bridged" refers to a 5 to 10 membered cyclic moiety connected at two non-adjacent ring atoms (e.g. bicyclo[1.1.1]pentane, bicyclo [2.2.1] heptane and bicyclo [3.2.1] octane).

The phrase "pharmaceutically acceptable" indicates that the substance, composition or dosage form must be compatible chemically and/or toxicologically, with the other ingredients comprising a formulation, and/or the mammal being treated therewith.

Unless specified otherwise, the term "compounds of the present disclosure" refers to compounds of Formula (I), as well as all stereoisomers (including diastereoisomers and enantiomers), rotamers, tautomers, isotopically labeled compounds (including deuterium substitutions). When a moiety is present that is capable of forming a salt, then salts are included as well, in particular pharmaceutically acceptable salts.

As used herein, the term "a," "an," "the" and similar terms used in the context of the present disclosure (especially in the context of the claims) are to be construed to cover both the singular and plural unless otherwise indicated herein or clearly contradicted by the context. The use of any and all examples, or exemplary language (e.g. "such as") provided herein is intended merely to better illuminate the disclosure and does not pose a limitation on the scope of the disclosure otherwise claimed.

It is also possible that the intermediates and compounds of the present disclosure may exist in different tautomeric forms, and all such forms are embraced within the scope of the disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

In one embodiment, the present disclosure relates to a compound of the Formula (I) as defined herein, in free form. In another embodiment, the present disclosure relates to a compound of the Formula (I) as defined herein, in salt form. In another embodiment, the present disclosure relates to a compound of the Formula (I) as defined herein, in acid addition salt form. In a further embodiment, the present disclosure relates to a compound of the Formula (I) as defined herein, in pharmaceutically acceptable salt form. In yet a further embodiment, the present disclosure relates to a compound of the Formula (I) as defined herein, in pharmaceutically acceptable acid addition salt form. In yet a further embodiment, the present disclosure relates to any one of the compounds of the Examples in free form. In yet a further embodiment, the present disclosure relates to any one of the compounds of the Examples in salt form. In yet a further embodiment, the present disclosure relates to any one of the compounds of the Examples in acid addition salt form. In yet a further embodiment, the present disclosure relates to any one of the compounds of the Examples in pharmaceutically acceptable salt form. In still another embodiment, the present disclosure relates to any one of the compounds of the Examples in pharmaceutically acceptable acid addition salt form.

Compounds of the present disclosure may be synthesized by synthetic routes that include processes analogous to those well-known in the chemical arts, particularly in light of the description contained herein. The starting materials are generally available from commercial sources such as Sigma-Aldrich or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present disclosure as well as key intermediates. For a more detailed description of the individual reaction steps, see the Examples section below. Although specific starting materials and reagents are depicted in the schemes and discussed below, other starting materials and reagents can be easily substituted to provide a variety of derivatives and/or reaction conditions.

EXEMPLIFICATION

Abbreviation

PE=petroleum ether
EtOAc=EA=ethyl acetate
ESI=electrospray ionisation
MeOH=methanol
EtOH=ethanol
DCM=dichloromethane
DIAD=Diisopropyl azodicarboxylate
DMF=dimethylformamide
DPPA=Diphenylphosphoryl azide
EDCI=1-Ethyl-3-(3-dimethylaminopropyl)carbodiimide
HATU=Hexafluorophosphate Azabenzotriazole Tetramethyl Uronium
HCl=hydrochloric acid
$H_2O$=water
NBS=N-bromosuccinimide
LCMS=liquid chromatography mass spectrometry
HPLC=high pressure liquid chromatography
THF=tetrahydrofuran
MeCN=ACN=acetonitrile
DMSO=dimetylsulfoxide
PhMe=Toluene
AcOH=acetic acid
CDI=carbonyldiimidazole
TFA=trifluoroacetic acid
DIPEA=DIEA=diisopropylethyl amine
TLC=Thin Layer Chromatography
$N_2$=Nitrogen
KOH=Potassium Hydroxide
$NH_4HCO_3$=Ammonium Bicarbonate
t-BuOH=tert-butanol
$NH_4Cl$=ammonium chloride
t-BuOK=potassium tert-butoxide
NaH=sodium hydride
Xantphos=4,5-Bis(diphenylphosphino)-9,9-dimethylxanthene
$Na_2SO_4$=sodium sulfate
$K_2CO_3$=potassium carbonate
$K_3PO_4$=potassium phosphate
$Cs_2CO_3$=cesium carbonate
$NaHCO_3$=sodium bicarbonate
$Pd(OAc)_2$=Palladium (II) Acetate
$Pd_2(dba)_3$=tris(dibenzylideneacetone)dipalladium(0)
NaOH=Sodium Hydroxide
TCFH=N'-tetramethylformamidinium hexafluorophosphate
NMI=1-Methylimidazole
Xantphos=4,5-Bis(diphenylphosphino)-9,9-dimethylxanthene
$XantPhosPdG_3$=[(4,5-Bis(diphenylphosphino)-9,9-dimethylxanthene)-2-(2'-amino-1,1'-biphenyl)]palladium (II) methanesulfonate
RuPhos=2-Dicyclohexylphosphino-2',6'-diisopropoxybiphenyl
RuPhos Pd $G_3$=(2-Dicyclohexylphosphino-2',6'-diisopropoxy-1,1'-biphenyl)[2-(2'-amino-1,1'-biphenyl)]palladium(II) methanesulfonate
Pd/C=Palladium on Carbon
$Pd(dppf)Cl_2$ DCM=[1,1'-Bis(diphenylphosphino)ferrocene]dichloropalladium(II), complex with dichloromethane
$Pd(dppf)Cl_2$=[1,1'-Bis(diphenylphosphino)ferrocene]dichloropalladium(II)
$Pd(PPh_3)_4$=Tetrakis(triphenylphosphine)palladium(0)
$Pd(PPh_3)_2Cl_2$=Bis(triphenylphosphine)palladium(II) dichloride
STAB=$NaBH(AcO)_3$=sodium triacetoxyborohydride
$AlMe_3$=$Al(CH_3)_3$=trimethylaluminum
DIAD=diisopropyl azodicarboxylate
PEPPSI-IHeptCl=(SP-4-1)-[1,3-Bis[2,6-bis(1-propylbutyl)phenyl]-4,5-dichloro-1,3-dihydro-2H-imidazol-2-ylidene]dichloro(3-chloropyridine-κN)-Palladium
$Er(OTf)_3$=erbium(III) triflate
$Br_2$=bromine
KOAc=potassium acetate
TEBAc=benzyltriethylammonium chloride
$B_2pin_2$=bis(pinacolato)diboron BINAP=2,2'-bis(diphenylphosphino)-1,1'-binaphthyl
BPO=benzoyl peroxide
Py=pyridine
LiAlH$_4$=lithium aluminum hydride General Methods 1. $^1$H NMR spectra were recorded on:
NMR10 Bruker AVANCE III HD 300 MHz
NMR16 Bruker AVANCE III HD 300 MHz
NMR19 Bruker AVANCE III HD 400 MHz
NMR24 Bruker AVANCE NEO 400 MHz
NMR30 Bruker AVANCE NEO 400 MHz
2. LCMS measurement was run on SHIMADZU LCMS-2020 using the follow conditions:
Method A: Mobile Phase: A: Water (0.05% TFA) B: Acetonitrile (0.05% TFA); Gradient Phase: 5% B to 100% B within 2.0 min, 100% B with 0.7 min (total runtime: 2.8 min); Flow Rate: 1.5 mL/min; Column: HALO C$_{18}$, 3.0*30 mm, 2.0 μm; Column Temperature: 40° C. Detectors: AD2 ELSD, PDA (220 nm and 254 nm), ESI.
Method B: Mobile Phase: A: Water (0.1% FA) B: Acetonitrile (0.1% FA); Gradient Phase: 5% B to 100% B within 2.0 min, 100% B with 0.7 min (total runtime: 2.8 min); Flow Rate: 1.5 mL/min; Column: HALO C$_{18}$, 3.0*30 mm, 2.0 μm; Column Temperature: 40° C. Detectors: AD2 ELSD, PDA (220 nm and 254 nm), ESI.
Method C: Mobile Phase: A: Water (5 mM NH$_4$HCO$_3$) B: Acetonitrile; Gradient Phase: 10% B to 95% B within 2.0 min, 100% B with 0.6 min (total runtime: 2.8 min); Flow Rate: 1.5 mL/min; Column: Poroshell HPH-C$_{18}$, 3.0*50 mm, 4.0 μm; Column Temperature: 40° C. Detectors: AD2 ELSD, PDA (220 nm and 254 nm), ESI.

PREPARATION OF INTERMEDIATES

The compounds claimed herein were prepared following the procedures outlined in the following schemes. Compound names were generated using the software built into ChemDraw. To the extent that there are discrepancies between the name of a compound and its depicted structure, the depicted chemical structure is to be taken as the appropriate compound.

Intermediate A:
N-(3-amino-5-chlorophenyl)methanesulfonamide

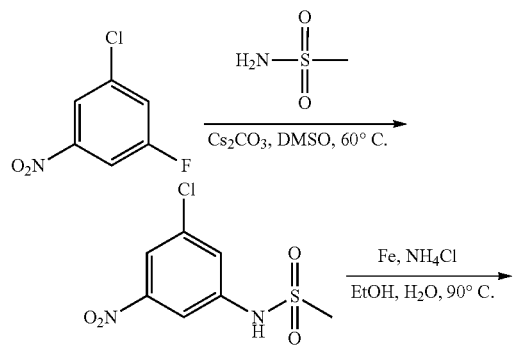

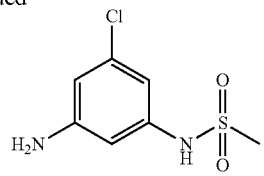

Step 1: To a stirred mixture of 1-chloro-3-fluoro-5-nitrobenzene (45 g, 256.35 mmol, 1.00 equiv) and methane sulfonamide (24.38 g, 256.35 mmol, 1.00 equiv), Cs$_2$CO$_3$ (250.57 g, 769.05 mmol, 3.00 equiv) in 500 mL of DMSO, the resulted solution was stirred for 2 h at 60° C. The mixture was cooled then quenched with 1000 mL of water and extracted with 3×1000 mL of ethyl acetate and dried over anhydrous Na$_2$SO$_4$ and concentrated and the residue was purified onto silica gel column eluted with 50% of ethyl acetate in petroleum ether to afford N-(3-chloro-5-nitrophenyl) methane sulfonamide (41 g, 63.81%) as a light yellow solid. LCMS (ESI) [M+H]+: 249.9

Step 2: To a stirred solution of N-(3-chloro-5-nitrophenyl) methanesulfonamide (41.00 g, 163.57 mmol, 1.00 equiv) and Fe (91.35 g, 1635.75 mmol, 10.00 equiv), NH$_4$Cl (87.50 g, 1635.75 mmol, 10.00 equiv) in 500 mL of ethanol and 300 mL of water, this was stirred for 2 h at 90° C. The resulting mixture was filtered, the filter cake was washed with 6×50 mL of methanol. The filtrate was concentrated under reduced pressure. The residue was purified onto silica gel column eluted with 50% of ethyl acetate in petroleum ether to afford N-(3-amino-5-chlorophenyl) methanesulfonamide (25.3 g, 70.1%) as a light yellow solid.

LCMS (ESI) [M+H]+: 220.01. $^1$H NMR (300 MHz, DMSO-d$_6$) δ 9.64 (s, 1H), 6.41-6.31 (m, 3H), 5.54 (s, 2H), 2.98 (s, 3H)

Intermediate E:
N-(3-amino-5-chlorophenyl)propane-1-sulfonamide

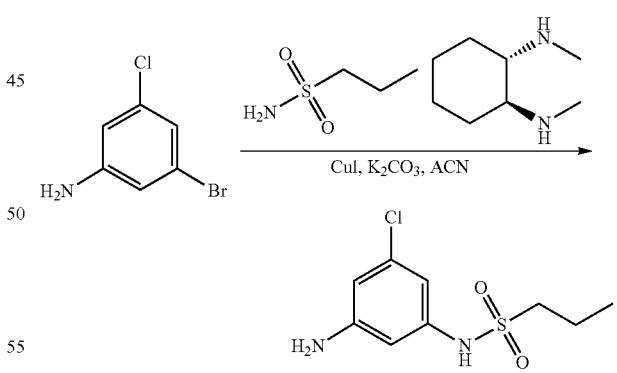

A solution of 3-bromo-5-chloroaniline (1 g, 4.843 mmol, 1 equiv), propane-1-sulfonamide (1.19 g, 9.686 mmol, 2 equiv), (1S,2S)-N$^1$,N$^2$-dimethylcyclohexane-1,2-diamine (2.07 g, 14.529 mmol, 3 equiv), CuI (2.77 g, 14.529 mmol, 3 equiv) and K$_2$CO$_3$ (2.01 g, 14.529 mmol, 3 equiv) in ACN (10 mL) was stirred for 2 hours at 110° C. under nitrogen atmosphere.

The resulting mixture was concentrated under reduced pressure. The residue was purified by silica gel column chromatography, eluted with PE/EA (1:1) to afford N-(3- amino-5-chlorophenyl)propane-1-sulfonamide (540 mg, 45% yield) as a yellow solid.
LCMS (ESI) [M+H]+: 249

Intermediate H.
N-3-amino-5-chlorophenyl)cyclopropanesulfonamide

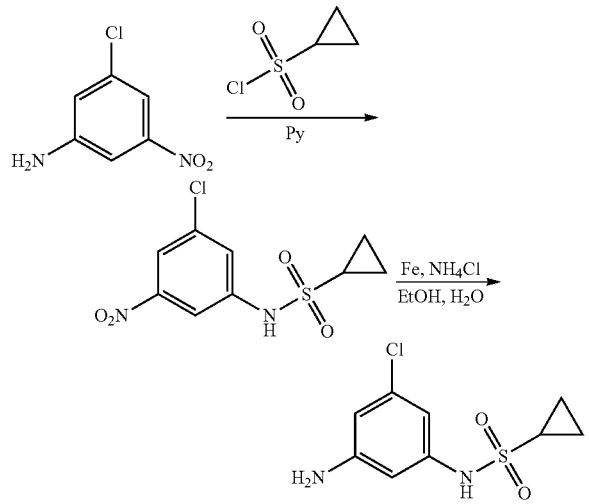

Step 1: A solution of 3-chloro-5-nitroaniline (300 mg, 1.738 mmol, 1 equiv) and cyclopropan esulfonyl chloride (244 mg, 1.738 mmol, 1 equiv) in pyridine (5 ml) was stirred for 2 hours at room temperature. The resulting mixture was concentrated under reduced pressure. The resid ue was purified by silica gel column chromatography, eluted with PE/EA (5:1) to afford N-(3-chloro-5-nitrophenyl)cyclopropanesulfonamide (255 mg, 53% yield) as a white solid. LCMS (ESI) [M+1$^+$]H: 277

Step 2: A solution of N-(3-chloro-5-nitrophenyl)cyclopropanesulfonamide (235 mg, 0.849 mmol, 1 equiv), Fe (474 mg 8490 mmol, 10 equiv) and N4Cl (136 mg, 2.547 mmol, 3 equiv) in ethanol(5 ml) and $H_2O$ (1 mL) was stirred for 2 hours at 80° C. under nitrogen atmosphere. The mixture was allowed to cool down to room temperature. The resulting mixture was filtered, the filter cake was washed with ethanol (3×10 ml). The filtrate was concentrated under reduced pressure. The residue was purified by silica gel column chromatography, eluted with PE/EA (1:1) to afford N-(3-amino-5-chlorophenyl)cyclopropanesulfonamide (190 mg, 91% yield) as a white solid. LCMS (ESI) [M+H]+: 247

The following intermediates were prepared using experimental procedures similar for intermediates A E or H:

| Structure | Intermediate | MS (ESI) [M + H]+ | $^1$H NMR |
|---|---|---|---|
| ![B structure] | B | 205 | $^1$H NMR (400 MHz, DMSO-d6) δ 9.63 (s, 1H), 6.26 (t, J = 1.9 Hz, 1H), 6.12 (dt, J = 10.8, 2.1 Hz, 1H), 6.04 (dt, J = 11.5, 2.1 Hz, 1H), 5.52 (s, 2H), 2.98 (s, 3H). |
| ![C structure] | C | 265 | $^1$H NMR (300 MHz, DMSO-d$_6$) δ 9.63 (s, 1H), 6.58-6.36 (m, 3H), 5.53 (s, 2H), 2.98 (s, 3H) |
| ![D structure] | D | 313 | $^1$H NMR (400 MHz, DMSO-d6) δ 9.39 (s, 1H), 6.66 (q, J = 1.6 Hz, 2H), 6.46 (t, J = 1.6 Hz, 1 H), 5.42 (s, 2H) 2.96 (s, 3H) |
| ![F structure] | F | 249 | |

| Structure | Intermediate | MS (ESI) [M + H]+ | 1H NMR |
|---|---|---|---|
| 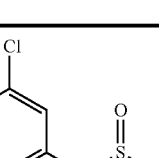 | G | 220 | |
| 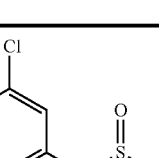 | I | 251 | |

Intermediate J: 2-bromo-5-(tert-butoxy)pyrimidine

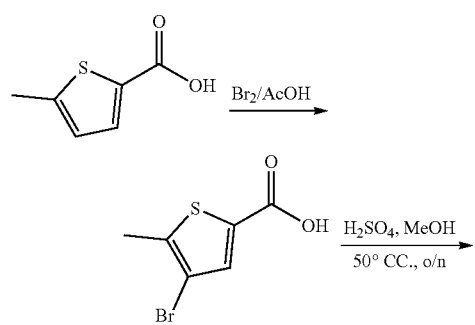

A mixture of 2-bromopyrimidin-5-ol (2.5 g, 14.3 mmol, 1 equiv) and Er(OTf)₃ (0.44 g, 0.7 mmol, 0.05 equiv) in Boc₂O (60 mL) was stirred for overnight at 50° C. The resulting mixture was concentrated under reduced pressure. The residue was purified by silica gel column chromatography, eluted with PE/EA (5:1) to afford 2-bromo-5-(tert-butoxy)pyrimidine (400 mg, 6% yield) as a yellow oil. This reaction was repeated 13 times and to afford 2.9 g of the desired product in total. LCMS (ESI) [M+H]+: 231

Intermediate K: 5-methyl-4-(4,4,5,5-tetramethyl-],3,2-dioxaborolan-2-yl)thiophene-2-carboxylate

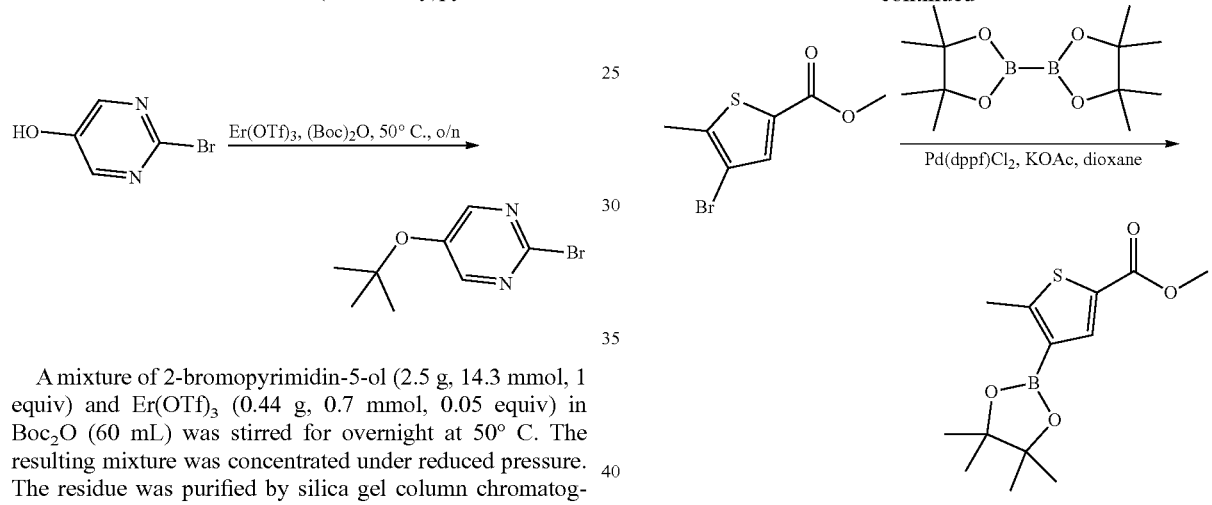

Step 1: A mixture of 5-methylthiophene-2-carboxylic acid (100 g, 703.383 mmol, 1 equiv) and Br₂ (123.65 g, 773.721 mmol, 1.1 equiv) in AcOH (1 L) was stirred for 2 hours at 60° C. The product was precipitated by the addition of water (500 mL) at 0° C. The precipitated solids were collected by filtration and washed with water to afford 4-bromo-5-methylthiophene-2-carboxylic acid (130 g, 84%) as a yellow solid. LCMS (ESI) [M+H]+: 221

Step 2: A mixture of 4-bromo-5-methylthiophene-2-carboxylic acid (100 g, 452.345 mmol, 1 equiv) and H₂SO₄ (100 mL, 1876.211 mmol, 4.15 equiv) in MeOH (1 L) was stirred for overnight at 50° C. The resulting mixture was concentrated under vacuum. The resulting mixture was diluted with water (200 mL). The aqueous layer was extracted with EtOAc (3×300 mL), dried over anhydrous Na₂SO₄. After filtration, the filtrate was concentrated under reduced pressure. The residue was purified by silica gel column chromatography, eluted with PE/EA (10:1) to afford methyl 4-bromo-5-methylthiophene-2-carboxylate (80 g, 74% yield) as a light yellow solid. GCMS: 234. ¹H NMR (300 MHz, DMSO-d₆) δ 7.70 (s, 1H), 3.82 (s, 3H), 2.43 (s, 3H).

Step 3: A mixture of methyl 4-bromo-5-methylthiophene-2-carboxylate (80 g, 340.281 mmol, 1 equiv), bis(pinacolato)diboron (172.82 g, 680.562 mmol, 2 equiv) Pd(dppf)Cl₂

(12.45 g, 17.014 mmol, 0.05 equiv) and KOAc (100.19 g, 1020.843 mmol, 3 equiv) in 1,4-dioxane (800 mL) was stirred for overnight at 80° C. under nitrogen atmosphere. The resulting mixture was filtered and the filter cake was washed with EtOAc. The filtrate was concentrated under reduced pressure. The residue was purified by silica gel column chromatography, eluted with PE/EA (15:1) to afford methyl 5-methyl-4-(4,4,5,5-tetramethyl-1,3,2-dioxaborolan-2-yl)thiophene-2-carboxylate (90 g, crude). The crude product was re-crystallized from hexane to afford methyl 5-methyl-4-(4,4,5,5-tetramethyl-1,3,2-dioxaborolan-2-yl)thiophene-2-carboxylate (35 g, 36% yield) as a white solid. LCMS (ESI) [M+H]$^+$: 283. $^1$H NMR (400 MHz, DMSO-d$_6$) δ 7.70 (s, 1H), 3.79 (s, 3H), 2.65 (s, 3H), 1.28 (s, 12H)

Intermediate L: methyl 5-methyl-1H-pyrrole-3-carboxylate

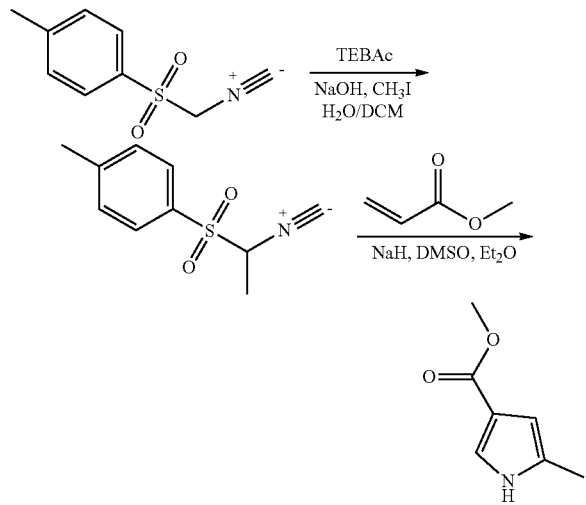

Step 1: Tosyl methylisocyanide (200 g, 1.03 mol, 1 equiv) was dissolved in dichloromethane 1.5 L and cooled to 0° C. Benzyltriethylammonium chloride (46.62 g, 2.05 mol, 2 equiv.), methyl iodide 126.3 mL (2.05 mol, 2 equiv) and 1.5 L of 30% aqueous sodium hydroxide solution were added. The mixture was stirred for 3 hours at 0° C. Water (4 L) was added to the reaction mixture, extracted with dichloromethane (1.5 L×3). The organic layer was dried over sodium sulfate and concentrated under reduced pressure. The residue was purified by silica gel column chromatography, eluted with PE/EA (4:1) to afford 1-((1-isocyanoethyl)sulfonyl)-4-methylbenzene(167 g, 78.0% yield) as a brown oil. .Step 2: A solution of methyl acrylate (138.2 mL, 1.55 mol, 0.97 equiv) and 1-(1-isocyanoethylsulfonyl)-4-methylbenzene (335 g, 1.60 mol, 1 equiv) in diethyl ether (3 L) and DMSO (1.5 L) were added dropwise to a stirred suspension of sodium hydride (60% purity) (99.7 g, 2.49 mol, 1.55 equiv) in diethyl ether (4 L) under nitrogen. The resulting suspension was stirred at room temperature for 4 hours. The reaction mixture was poured into sodium chloride solution (5 L), layers separated and the aqueous extracted with EA (3×5 L), the organic layers were combined and washed with water (5 L), dried over Na$_2$SO$_4$, filtered and evaporated to afford beige solid. The crude product was purified by flash silica chromatography, elution gradient 0 to 40% ethyl acetate to afford methyl 5-methyl-1H-pyrrole-3-carboxylate (105.6 g, 47.4% yield) as a white solid. LCMS (ESI) [M+H]$^+$: 140. $^1$H NMR (400 MHz, DMSO-d$_6$) δ 11.18 (s, 1H), 7.24 (dd, J=3.0, 1.7 Hz, 1H), 6.10 (dt, J=2.7, 1.4 Hz, 1H), 3.66 (s, 3H), 2.15 (d, J=1.0 Hz, 3H).

Intermediate M: 1-methyl-5-(4,4,5,5-tetramethyl-1, 3,2-dioxaborolan-2-yl)pyrrole-3-carboxylate

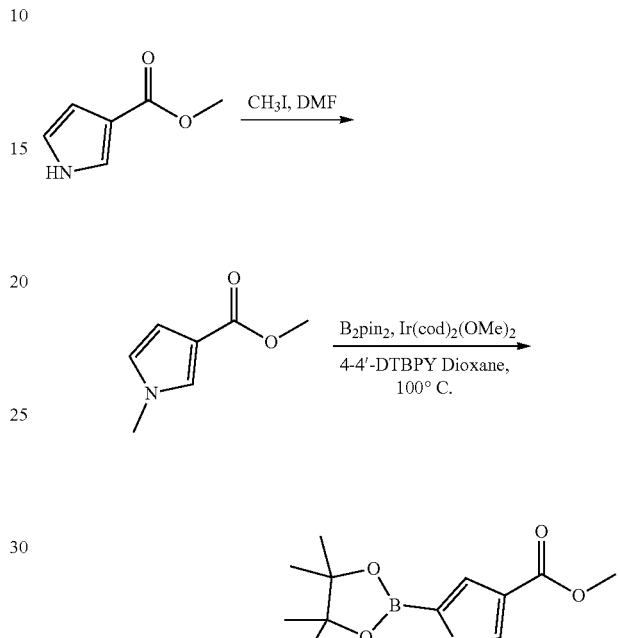

Step 1: To a stirred solution of methyl 1H-pyrrole-3-carboxylate (100 g, 800 mmol, I equiv) and NaH (60%) (64 g, 1.6 mol, 2 equiv) in DMF (1 L) was added CH$_3$I (227.2 g, 1.6 mol, 2 equiv) dropwise at 0° C. The resulting mixture was stirred for additional 3 hours at room temperature. The reaction was quenched by the addition of water (5 L) at 0° C. The resulting mixture was extracted with EtOAc (3×5 L). The combined organic layers were washed with brine (3×5 L), dried over anhydrous Na$_2$SO$_4$. After filtration, the filtrate was concentrated under reduced pressure. The residue was purified by silica gel column chromatography, eluted with PE/EA (5:1) to afford methyl 1-methylpyrrole-3-carboxylate (95 g, 85.6%) as a white solid. LCMS (ESI) [M+H]$^+$: 140

Step 2: A solution of methyl 1-methylpyrrole-3-carboxylate (95 g, 683. 5 mmol, 1 equiv), B$_2$Pin$_2$ (138.9 g, 546.7 mmol, 0.8 equiv), Di-mu-methoxobis(1,5-cyclooctadiene) diiridium(I) (6.7 g, 10.3 mmol, 0.015 equiv) and 4,4'-Di-tert-butyl-2,2'-bipyridine (5.49 g, 20.5 mmol, 0.03 equiv) in 1,4-dioxane(IL) was stirred for 3 hours at 100° C. under nitrogen atmosphere. The mixture was concentrated under reduced pressure. The residue was purified by silica gel column chromatography, eluted with PE/EA (2/1) to afford crude product. The crude product was triturated with PE for 12 hours at RT and filtered to afford 1-methyl-5-(4,4,5,5-tetramethyl-1,3,2-dioxaborolan-2-yl)pyrrole-3-carboxylate (105 g, 57.8% yield) as a white solid. LCMS (ESI) [M+H]$^+$: 266. $^1$H NMR (300 MHz, Chloroform-d) δ 7.37 (d, J=1.6 Hz, 1H), 7.21 (d, J=1.6 Hz, 1H), 3.82 (s, 3H), 3.78 (s, 3H), 1.31 (s, 12H).

The following intermediates were prepared using experimental procedures similar for intermediate M:

| Structure | Intermediate | MS (ESI) [M + H]⁺ | ¹H NMR |
|---|---|---|---|
| 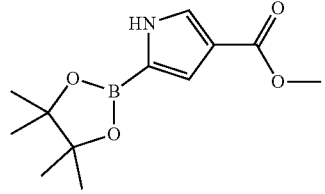 | N | 252 | |
| 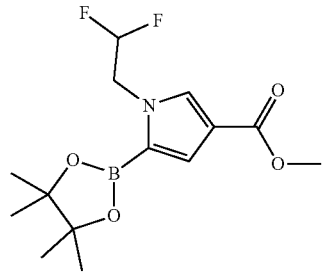 | O | 316 | |
| 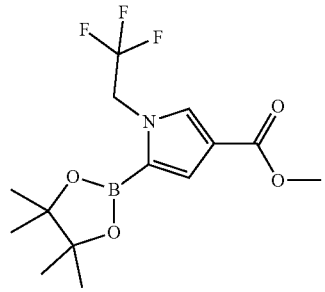 | P | 334 | ¹H NMR (400 MHz, DMSO-d6) δ 7.80 (d, 1H), 6.99 (d, 1H), 5.08 (m, 2H), 3.72 (s, 3H), 1.26 (s, 12H). |

GENERAL SCHEMES

Compounds described below can be prepared through, for example, the following general schemes, among other methods known to those skilled in the art:

General Scheme A

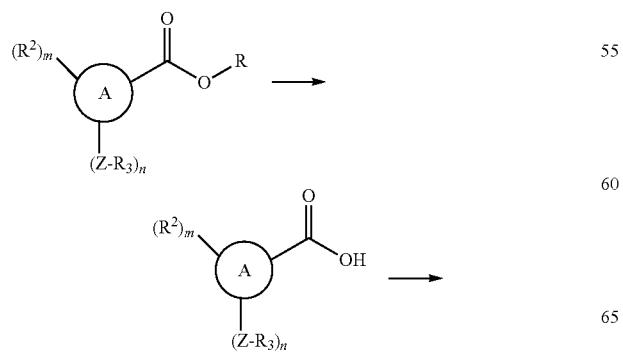

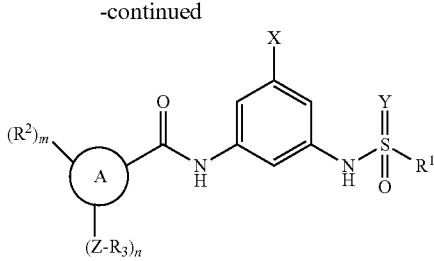

A carboxylic acid ester, either commercially available or prepare through various means (e.g. Suzuki coupling, Buchwald coupling, alkylation, SNAr, ring condensation, or multistep syntheses) is hydrolyzed with various reagents (e.g. lithium hydroxide) to yield a carboxylic acid. The carboxylic acid is then coupled with an appropriate reagent (e.g. one of the above-described anilines or other amine) using various reagents to provide the desired product.

General Scheme B

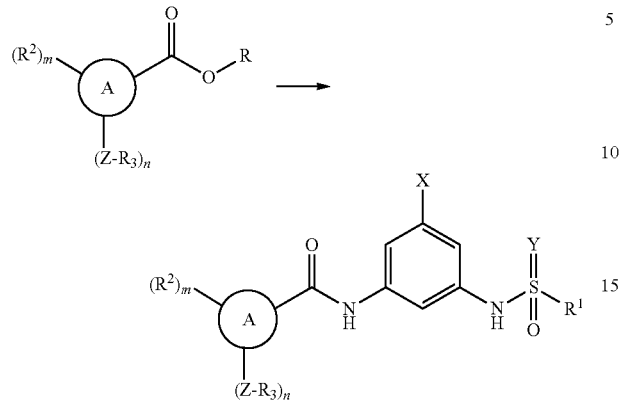

A carboxylic acid ester, either commercially available or prepared through various means (e.g. Suzuki coupling, Buchwald coupling, alkylation, SNAr, ring condensation, or multistep syntheses) is reacted with an appropriate reagent (e.g. one of the above-described anilines or other amine) in the presence of trimethylaluminum or other appropriate reagent to provide the desired product.

In general, either method is suitable for obtaining the examples shown below and can be considered interchangeable. For the examples shown below, one skilled in the art can identify alternative conditions for individual steps, such as alkylations, hydrolysis, displacements, cross-coupling or other chemical transformations.

EXAMPLES

Example 1: N-(3-chloro-5-(methylsulfonamido)phenyl)-1-phenyl-1H-imidazole-4-carboxamide To a mixture of 1-phenyl-1H-imidazole-4-carboxylic acid (70 mg, 0.371 mmol) and N-(3-amino-5-chlorophenyl)methanesulfonamide (81.8 mg, 0.371 mmol) in ACN (1 mL) was added TCFH (103 mg, 0.371 mmol) and NMI (30.4 mg, 0.371 mmol), the resulting mixture was stirred for two hours at room temperature. Then it was concentrated, the residue was purified by reverse phase flash chromatography eluting with 60% of acetonitrile in water (0.1% $NH_4HCO_3$) to afford N-(3-chloro-5-methanesulfonamidophenyl)-1-phenyl-1H-imidazole-4-carboxamide (47.2 mg, 32.4%) as a white solid. LCMS [M+H]$^+$: 391. $^1$H NM/R (400 MHz, DMSO-d$_6$) δ 10.27 (s, 1H), 10.05 (s, 1H), 8.53-8.44 (m, 2H), 7.83-7.74 (m, 4H), 7.57 (dd, J=8.6, 7.2 Hz, 2H), 7.48-7.39 (m, 1H), 6.92 (t, J=2.0 Hz, 1H), 3.10 (s, 3H).

Example 2-14 and 321-332

The compounds listed in the following table were prepared using a procedure similar to that described for example 1:

| Structure | Example No. | MS (ESI) [M + H]$^+$ | $^1$H NMR |
|---|---|---|---|
| 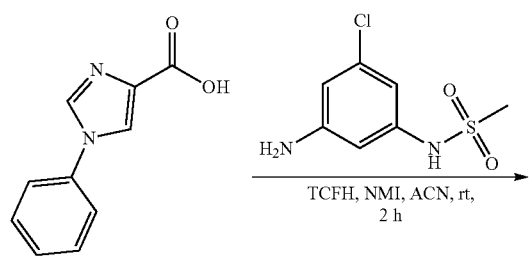 | 2 | 376 | $^1$H NMR (300 MHz, DMSO-d6) δ 12.10 (s, 1H), 10.02 (s, 1H), 9.78 (s, 1H), 7.56 (s, 1H), 7.52-7.39 (m, 2H), 6.73 (s, 1H), 6.67 (dt, J = 10.4, 2.2 Hz, 1H), 3.06 (s, 3H). |

| Structure | Example No. | MS (ESI) [M + H]+ | 1H NMR |
|---|---|---|---|
| 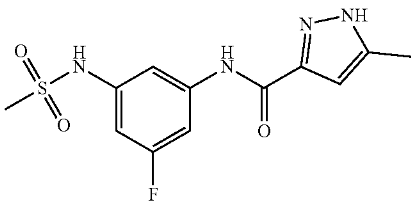 | 3 | 313 | 1H NMR (300 MHz, DMSO-d6) δ 13.12 (s, 1H), 10.24 (s, 1H), 10.04 (s, 1H), 7.61 (s, 1H), 7.48 (dt, J = 11.4, 2.1 Hz, 1H), 6.69 (dt, J = 10.5, 2.2 Hz, 1H), 6.53 (s, 1H), 3.09 (s, 3H), 2.30 (s, 3H). |
| 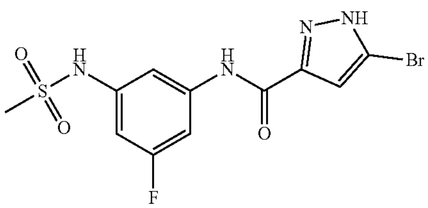 [SMILES: CS(=O)(=O)Nc1cc(F)cc(NC(=O)c2cc(Br)[nH]n2)c1] | 4 | 377 | 1H NMR (300 MHz, DMSO-d6) δ 10.45 (s, 1H), 7.45 (d, J = 11.1 Hz, 2H), 7.17 (s, 1H), 6.75 (d, J = 10.6 Hz, 1H), 3.08 (s, 3H) |
| 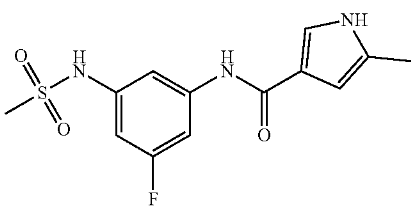 | 5 | 312 | 1H NMR (300 MHz, DMSO-d6) δ 11.11 (s, 1H), 9.99 (s, 1H), 9.62 (s, 1H), 7.58-7.29 (m, 3H), 6.64 (dt, J = 10.5, 2.2 Hz, 1H), 6.33 (dt, J = 2.6, 1.3 Hz, 1H), 3.06 (s, 3H), 2.19 (s, 3H). |
| 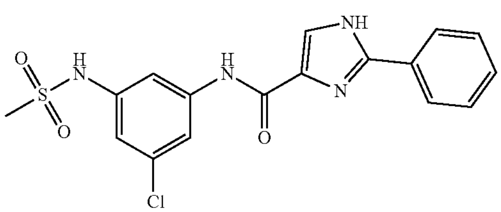 [SMILES: CS(=O)(=O)Nc1cc(Cl)cc(NC(=O)c2c[nH]c(-c3ccccc3)n2)c1] | 6 | 391 | 1H NMR (300 MHz, DMSO-d6) δ 13.19 (s, 1H), 10.03 (s, 1H), 8.09 (d, J = 7.6 Hz, 2H), 7.99 (s, 1H), 7.77 (s, 2H), 7.52 (t, J = 7.5 Hz, 2H), 7.43 (t, J = 7.2 Hz, 1H), 6.92 (t, J = 2.0 Hz, 1H), 3.10 (s, 3H). |
| 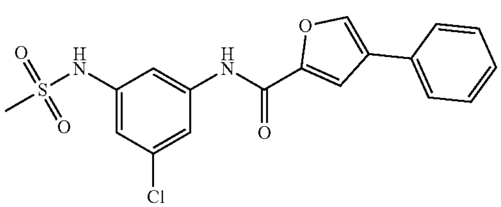 [SMILES: CS(=O)(=O)Nc1cc(Cl)cc(NC(=O)c2cc(-c3ccccc3)co2)c1] | 7 | 391 | 1H NMR (400 MHz, DMSO-d6) δ 10.49 (s, 1H), 10.08 (s, 1H), 8.49 (d, J = 1.0 Hz, 1H), 7.84 (d, J = 1.0 Hz, 1H), 7.74-7.65 (m, 4H), 7.44 (t, J = 7.7 Hz, 2H), 7.37-7.29 (m, 1H), 6.96 (t, J = 2.0 Hz, 1H), 3.08 (s, 3H). |
| 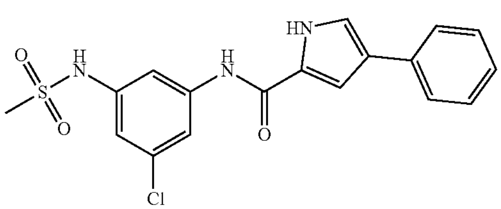 [SMILES: CS(=O)(=O)Nc1cc(Cl)cc(NC(=O)c2cc(-c3ccccc3)c[nH]2)c1] | 8 | 390 | 1H NMR (300 MHz, DMSO-d6) δ 11.93 (s, 1H), 10.06 (d, J = 3.7 Hz, 2H), 7.70 (dt, J = 13.2, 1.9 Hz, 2H), 7.60 (dt, J = 8.2, 1.7 Hz, 2H), 7.49 (q, J = 2.2, 1.7 Hz, 2H), 7.37 (t, J = 7.7 Hz, 2H), 7.24-7.12 (m, 1H), 6.92 (t, J = 1.9 Hz, 1H), 3.09 (s, 3H). |
| 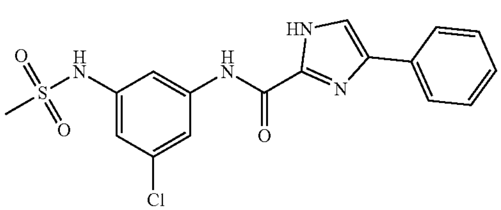 [SMILES: CS(=O)(=O)Nc1cc(Cl)cc(NC(=O)c2nc(-c3ccccc3)c[nH]2)c1] | 9 | 391 | 1H NMR (300 MHz, DMSO-d6) δ 13.56 (d, J = 74.4 Hz, 1H), 10.60 (d, J = 58.3 Hz, 1H), 10.10 (s, 1H), 7.99-7.87 (m, 3H), 7.74 (dd, J = 31.7, 18.6 Hz, 2H), 7.41 (t, J = 7.5 Hz, 2H), 7.27 (t, J = 7.4 Hz, 1H), 6.95 (s, 1H), 3.11 (s, 3H). |

-continued

| Structure | Example No. | MS (ESI) [M + H]⁺ | ¹H NMR |
|---|---|---|---|
| 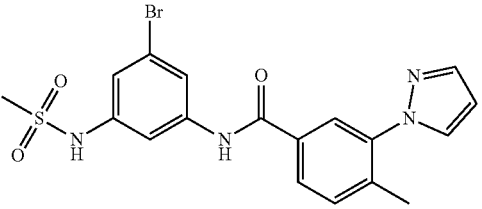 [SMILES: Cc1ccc(C(=O)Nc2cc(Br)cc(NS(C)(=O)=O)c2)cc1-n1cccn1] | 10 | 449 | ¹H NMR (300 MHz, DMSO-d6) δ 10.68 (s, 1H), 9.64 (d, J = 0.8 Hz, 1H), 8.27 (dd, J = 8.2, 7.2 Hz, 1H), 8.26-8.17 (m, 1H), 8.17-8.09 (m, 2H), 7.82-7.69 (m, 4H), 3.23 (s, 3H), 3.07-3.00 (m, 3H). |
| 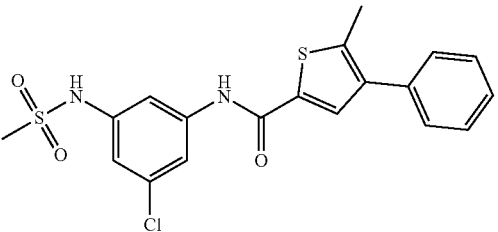 | 11 | 421 | ¹H NMR (400 MHz, DMSO-d6) δ 10.33 (s, 1H), 10.07 (s, 1H), 8.09 (s, 1H), 7.67 (t, J = 1.9 Hz, 1H), 7.61 (t, J = 1.9 Hz, 1H), 7.54-7.45 (m, 4H), 7.40 (dq, J = 8.8, 4.4 Hz, 1H), 6.95 (t, J = 2.0 Hz, 1H), 3.06 (s, 3H), 2.53 (s, 3H). |
| 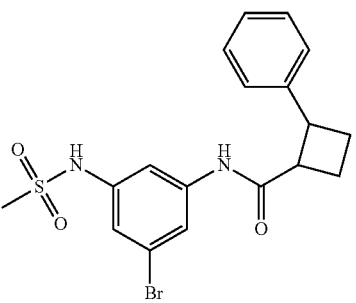 [SMILES: CS(=O)(=O)Nc1cc(Br)cc(NC(=O)C2CCC2c2ccccc2)c1] | 12 | 423 | ¹H NMR (300 MHz, DMSO-d6) δ 9.91 (s, 1H), 9.74 (s, 1H), 7.35 (t, J = 1.8 Hz, 1H), 7.26-7.18 (m, 4H), 7.18-7.13 (m, 1H), 7.08 (ddd, J = 8.5, 5.3, 2.4 Hz, 1H), 6.92 (t, J = 1.9 Hz, 1H), 3.98 (q, J = 8.7 Hz, 1H), 3.62-3.54 (m, 1H), 2.98 (s, 3H), 2.49-2.43 (m, 1H), 2.33-2.21 (m, 2H), 2.19-2.09 (m, 1H). |
| 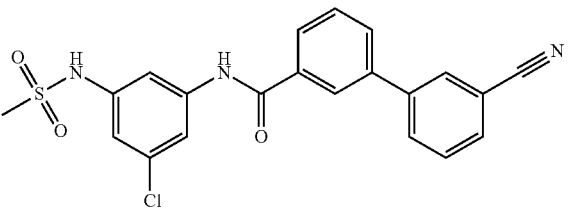 [SMILES: CS(=O)(=O)Nc1cc(Cl)cc(NC(=O)c2cccc(-c3cccc(C#N)c3)c2)c1] | 13 | 426 | ¹H NMR (300 MHz, DMSO-d6) δ 10.56 (s, 1H), 10.10 (s, 1H), 8.30 (dt, J = 4.1, 1.8 Hz, 2H), 8.15 (dt, J = 8.1, 1.4 Hz, 1H), 8.06-7.94 (m, 2H), 7.90 (dt, J = 7.7, 1.3 Hz, 1H), 7.81-7.63 (m, 4H), 6.99 (t, J = 1.9 Hz, 1H), 3.09 (s, 3H). |
| 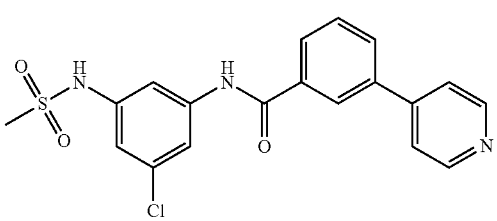 [SMILES: CS(=O)(=O)Nc1cc(Cl)cc(NC(=O)c2cccc(-c3ccncc3)c2)c1] | 14 | 402 | ¹H NMR (300 MHz, DMSO-d6) δ 10.60 (s, 1H), 10.10 (s, 1H), 8.79-8.63 (m, 2H), 8.33 (t, J = 1.8 Hz, 1H), 8.05 (ddt, J = 8.2, 3.6, 1.5 Hz, 2H), 7.89-7.79 (m, 2H), 7.72 (q, J = 3.4, 2.9 Hz, 3H), 6.99 (t, J = 1.9 Hz, 1H), 3.09 (s, 3H). |
| 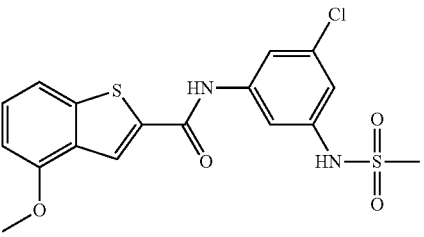 [SMILES: COc1cccc2sc(C(=O)Nc3cc(Cl)cc(NS(C)(=O)=O)c3)cc12] | 321 | 411.1 | ¹H NMR (400 MHz, DMSO-d6) δ 10.71 (d, J = 11.3 Hz, 1H), 10.11 (d, J = 11.3 Hz, 1H), 8.54 (d, J = 11.5 Hz, 1H), 7.78-7.66 (m, 2H), 7.62 (dd, J = 11.5, 8.0 Hz, 1H), 7.48 (dt, J = 11.6, 8.0 Hz, 1H), 7.04-6.94 (m, 2H), 4.00 (d, J = 11.6 Hz, 3H), 3.10 (d, J = 11.6 Hz, 3H) |

-continued

| Structure | Example No. | MS (ESI) [M + H]+ | 1H NMR |
|---|---|---|---|
| (structure) | 322 | 393.2 | 1H NMR (400 MHz, DMSO-d6) δ 10.24 (s, 1H), 10.05 (s, 1H), 8.19 (d, J = 1.6 Hz, 1H), 8.02 (s, 1H), 7.73 (d, J = 1.9 Hz, 1H), 7.66 (d, J = 2.0 Hz, 1H), 7.39 (s, 1H), 6.93 (d, J = 2.0 Hz, 1H), 3.07 (s, 3H), 2.59 (s, 3H), 2.29 (d, J = 1.1 Hz, 3H). |
| (structure) | 323 | 446.9 [M − H]− | 1H NMR (400 MHz, DMSO-d6) δ 10.89 (d, J = 3.3 Hz, 1H), 10.10 (d, J = 3.0 Hz, 1H), 8.62-8.56 (m, 1H), 8.44 (dd, J = 8.3, 3.6 Hz, 1H), 7.89 (dd, J = 7.5, 3.6 Hz, 1H), 7.68 (tq, J = 5.8, 3.9, 3.0 Hz, 3H), 7.01 (dt, J = 3.8, 1.9 Hz, 1H), 3.08 (d, J = 3.2 Hz, 3H) |
| (structure) | 324 | 414.9 [M −H]− | 1H NMR (400 MHz, DMSO-d6) δ 10.84 (s, 1H), 10.17 (s, 1H), 8.58 (d, J = 3.3 Hz, 1H), 7.71 (t, J = 1.8 Hz, 1H), 7.65 (t, J = 1.9 Hz, 1H), 7.46 (td, J = 9.0, 3.6 Hz, 1H), 7.37 (td, J = 9.1, 3.5 Hz, 1H), 7.00 (t, J = 1.9 Hz, 1H), 3.09 (s, 3H) |
| (structure) | 325 | 414.9 [M − H]− | 1H NMR (400 MHz, DMSO-d6) δ 10.84 (s, 1H), 10.13 (s, 1H), 8.58 (d, J = 3.4 Hz, 1H), 7.72 (t, J = 1.9 Hz, 1H), 7.65 (t, J = 1.9 Hz, 1H), 7.46 (td, J = 9.0, 3.7 Hz, 1H), 7.37 (td, J = 9.1, 3.6 Hz, 1H), 7.00 (t, J = 2.0 Hz, 1H), 3.08 (s, 3H) |
| (structure) | 326 | 446.9 [M −H]− | 1H NMR (400 MHz, DMSO-d6) δ 10.89 (s, 1H), 10.11 (s, 1H), 8.48 (d, J = 10.0 Hz, 2H), 8.34 (d, J = 8.6 Hz, 1H), 7.80 (dd, J = 8.6, 1.9 Hz, 1H), 7.72 (t, J = 1.9 Hz, 1H), 7.67 (t, J = 2.0 Hz, 1H), 7.00 (t, J = 2.0 Hz, 1H), 3.09 (s, 3H) |
| (structure) | 327 | 408.9 [M − H]− | 1H NMR (400 MHz, DMSO-d6) δ 10.61 (s, 1H), 10.08 (s, 1H), 8.30 (s, 1H), 7.90 (d, J = 8.8 Hz, 1H), 7.70 (d, J = 1.7 Hz, 1H), 7.68-7.60 (m, 2H), 7.09 (dd, J = 8.9, 2.4 Hz, 1H), 6.96 (q, J = 1.7 Hz, 1H), 3.86 (s, 3H), 3.08 (s, 3H) |

-continued

| Structure | Example No. | MS (ESI) [M + H]+ | 1H NMR |
|---|---|---|---|
| (6,8-dimethylindolizine-2-carboxamide with 3-chloro-5-methylsulfonamido phenyl) | 328 | 391.95 | 1H NMR (400 MHz, DMSO-d6) δ 10.09 (s, 1H), 9.97 (s, 1H), 8.06 (d, J = 1.8 Hz, 1H), 8.01-7.96 (m, 1H), 7.75 (t, J = 1.8 Hz, 1H), 7.69 (q, J = 1.6 Hz, 1H), 6.94 (dt, J = 12.8, 1.6 Hz, 2H), 6.48 (t, J = 1.4 Hz, 1H), 3.07 (s, 3H), 2.35 (s, 3H), 2.17 (d, J = 1.2 Hz, 3H) |
| (8-methylindolizine-2-carboxamide with 3-chloro-5-methylsulfonamido phenyl) | 329 | 378 | 1H NMR (400 MHz, DMSO-d6) δ 10.14 (s, 1H), 10.03 (s, 1H), 8.18 (dd, J = 14.1, 3.3 Hz, 2H), 7.75 (d, J = 2.0 Hz, 1H), 7.69 (t, J = 2.0 Hz, 1H), 7.00 (s, 1H), 6.92 (t, J = 2.0 Hz, 1H), 6.63-6.55 (m, 2H), 3.07 (s, 3H), 2.38 (s, 3H) |
| (pyrrolo[1,2-a]pyrazine-3-carboxamide with 3-chloro-5-methylsulfonamido phenyl) | 330 | 364.95 | 1H NMR (400 MHz, DMSO-d6) δ 10.33 (s, 1H), 10.06 (s, 1H), 8.96 (d, J = 1.5 Hz, 1H), 8.35-8.29 (m, 2H), 7.74 (t, J = 1.9 Hz, 1H), 7.67 (t, J = 1.9 Hz, 1H), 7.57 (d, J = 4.9 Hz, 1H), 7.43 (d, J = 1.3 Hz, 1H), 6.95 (t, J = 2.0 Hz, 1H), 3.07 (s, 3H). |
| (5-methylbenzothiophene-2-carboxamide with 3-chloro-5-methylsulfonamido phenyl) | 331 | 394.95 | 1H NMR (400 MHz, DMSO-d6) δ 10.69 (s, 1H), 10.09 (s, 1H), 8.31 (d, J = 2.0 Hz, 1H), 7.94 (d, J = 8.2 Hz, 1H), 7.81 (s, 1H), 7.75-7.69 (m, 1H), 7.73-7.64 (m, 1H), 7.35 (d, J = 8.3 Hz, 1H), 6.97 (q, J = 2.1 Hz, 1H), 3.11-3.06 (m, 3H), 2.46 (d, J = 1.9 Hz, 3H) |
| (4-chlorobenzothiophene-2-carboxamide with 3-chloro-5-methylsulfonamido phenyl) | 332 | 414.9 | 1H NMR (400 MHz, DMSO-d6) δ 10.84 (s, 1H), 10.10 (s, 1H), 8.54 (d, J = 0.9 Hz, 1H), 8.08 (dd, J = 8.0, 1.0 Hz, 1H), 7.70 (dt, J = 9.2, 1.8 Hz, 2H), 7.59 (dd, J = 7.7, 1.0 Hz, 1H), 7.52 (t, J = 7.9 Hz, 1H), 7.00 (t, J = 1.9 Hz, 1H), 3.08 (s, 3H) |

Example 15: N-(3-bromo-5-(methylsulfonamido)phenyl)-4-phenylthiophene-2-carboxamide

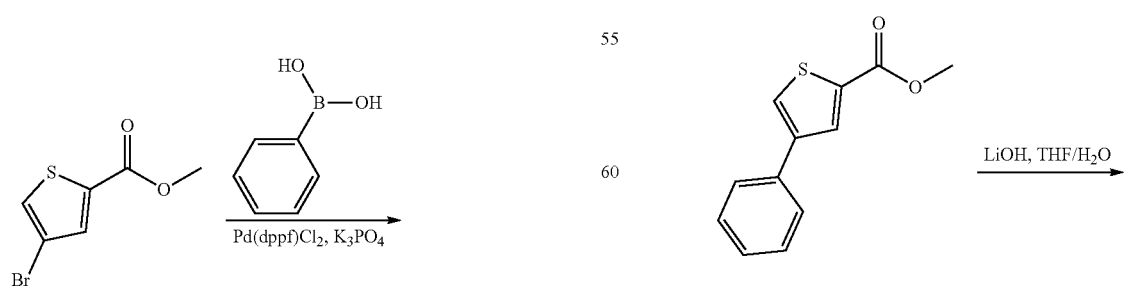

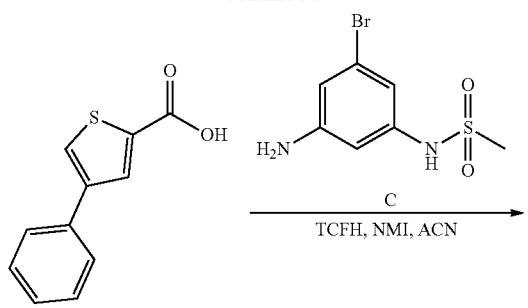

methanesulfonamide (11 g, 41.4 mmol) in ACN (110 mL) was added TCFH (17.3 g, 62.1 mmol) and NMI (10.1 g, 124 mmol) at room temperature. The resulting mixture was stirred overnight, Then it was concentrated, the residue was purified by reverse phase flash chromatography eluting with 60% of acetonitrile in water (0.1% FA) to afford N-(3-bromo-5-methanesulfonamidophenyl)-4-phenylthiophene-2-carboxamide (11.0519 g, 24.486 mmol) as a light yellow solid. LCMS (ESI) [M−H]⁻: 449. ¹H NMR (300 MHz, DMSO-d₆) δ 10.46 (s, 1H), 10.09 (s, 1H), 8.49 (d, J=1.5 Hz, 1H), 8.23 (d, J=1.4 Hz, 1H), 7.96-7.60 (m, 4H), 7.57-7.24 (m, 3H), 7.11 (t, J=1.9 Hz, 1H), 3.08 (s, 3H).

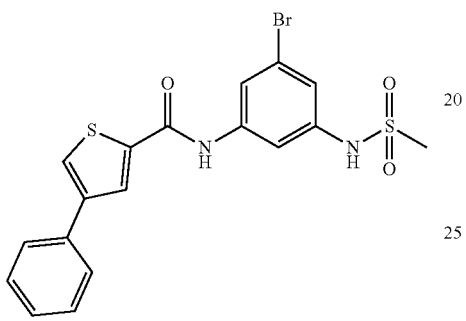

Examples 16

The compounds listed in the following table were prepared using a procedure similar to that described for example 15:

| Structure | Example No. | MS (ESI) [M + H]⁺ | ¹H NMR |
|---|---|---|---|
| 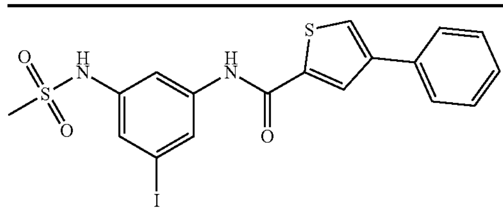 | 16 | 499 | ¹H NMR (300 MHz, DMSO-d6) δ 10.39 (s, 1H), 10.00 (s, 1H), 8.49 (d, J = 1.5 Hz, 1H), 8.22 (d, J = 1.4 Hz, 1H), 7.96 (t, J = 1.7 Hz, 1H), 7.75 (dt, J = 5.8, 1.4 Hz, 3H), 7.49 (t, J = 7.5 Hz, 2H), 7.36 (t, J = 7.4 Hz, 1H), 7.28 (t, J = 1.8 Hz, 1H), 3.07 (s, 3H). |

Step 1: To a mixture of methyl 4-bromothiophene-2-carboxylate (30 g, 135 mmol), phenylboronic acid (32.9 g, 270 mmol), Pd(dppf)Cl₂ (11.0 g, 13.5 mmol) and K₃PO₄ (85.8 g, 405 mmol) was added dioxane (300 mL) and H₂O (30 mL). The resulting mixture was stirred for 2 hours at 80° C. under N₂ atmosphere. The reaction mixture was extracted with ethyl acetate. The organic phase was concentrated under reduced pressure. The residue was purified by flash chromatography on silica gel eluting with 20% of ethyl acetate in petroleum ether to afford methyl 4-phenylthiophene-2-carboxylate (27.1 g, 124 mmol) as a light yellow solid.

Step 2: To a stirred solution of methyl 4-phenylthiophene-2-carboxylate (26.1 g, 119 mmol) in 260 mL of THF and 260 mL of water was added LiOH (24.9 g, 595 mmol). The resulting mixture was stirred overnight at room temperature. Then it was concentrated, and the pH value of the residue solution was adjusted to 3 with 1M HCl (aq). The product was precipitated from the solution. After filtration, obtained 4-phenylthiophene-2-carboxylic acid (24.4 g, 119 mmol) as a white solid.

Step 3: To a mixture of 4-phenylthiophene-2-carboxylic acid (10.1 g, 49.6 mmol) and N-(3-amino-5-bromophenyl)

Example 17: N-(3-bromo-5-(methylsulfonamido) phenyl)-4-(pyridin-2-yl)thiophene-2-carboxamide

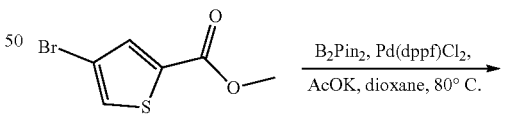

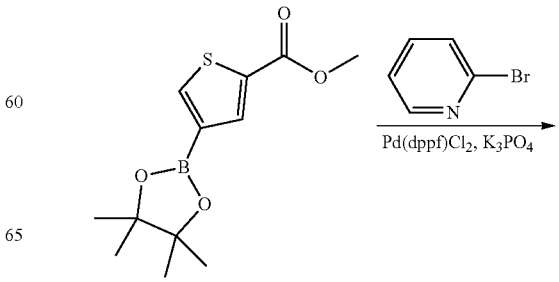

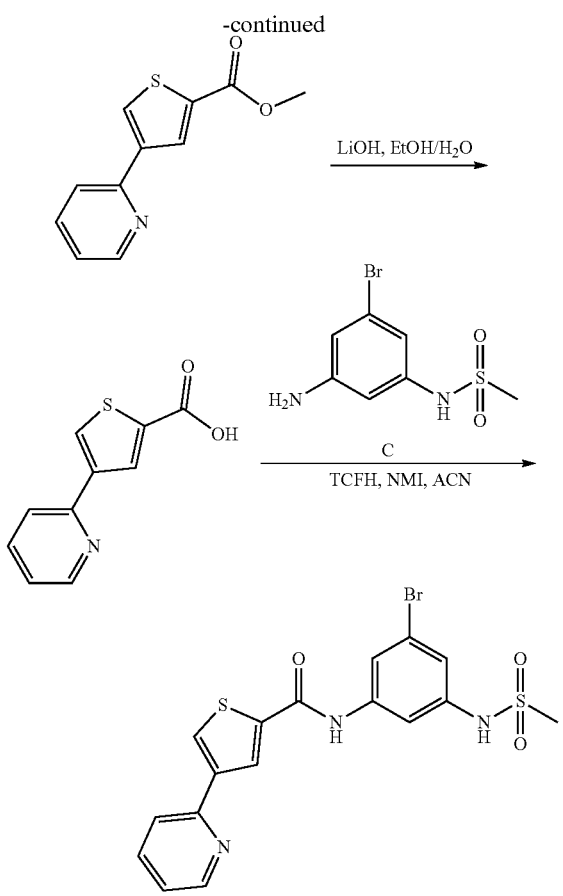

Step 1: A mixture of ethyl 4-bromothiophene-2-carboxylate (250 g, 1063.37 mmol, 1.00 equiv) and bis(pinacolato)diboron (810.10 g, 3190.13 mmol, 3.00 equiv) and Pd(dppf)Cl₂ (38.90 g, 53.17 mmol, 0.05 equiv) and AcOK (313.09 g, 3190.13 mmol, 3.00 equiv) in 1500 mL of 1,4-dioxane, the resulted solution was stirred for 2 h at 80° C. under nitrogen atmosphere. The resulting mixture was concentrated under reduced pressure. The residue was purified onto silica gel column eluted with 50% of ethyl acetate in petroleum ether to afford ethyl 4-(4,4,5-trimethyl-1,3,2-dioxaborolan-2-yl)thiophene-2-carboxylate (231.02 g, 81.0%) as a yellow solid.

Step 2: A mixture of methyl 4-(4,4,5,5-tetramethyl-1,3,2-dioxaborolan-2-yl)thiophene-2-carboxylate (231.00 g, 861.52 mmol, 1.00 equiv) and 2-bromopyridine (163.34 g, 1033.83 mmol, 1.20 equiv) and Pd(dppf)Cl₂ (31.52 g, 43.076 mmol, 0.05 equiv) and K₂CO₃ (357.20 g, 2584.57 mmol, 3.00 equiv) in 1000 mL of 1,4-dioxane and 100 mL of water, the resulted solution was stirred for 2 h at 90° C. under nitrogen atmosphere. The resulting mixture was concentrated under reduced pressure. The residue was purified onto silica gel column eluted with 50% of ethyl acetate in petroleum ether to afford methyl 4-(pyridin-2-yl)thiophene-2-carboxylate (196.12 g, 103.8%) as a white solid. LCMS (ESI). [M+H]⁺: 219

Step 3: A mixture of methyl 4-(pyridin-2-yl)thiophene-2-carboxylate (186.00 g, 848.31 mmol, 1.00 equiv) and LiOH (60.95 g, 2544.924 mmol, 3.00 equiv) in 1000 mL of ethanol and 100 mL of water, this was stirred for 1 h at 60° C. The mixture was adjusted pH to 6 with HCl (aq.). The precipitated solids were collected by filtration and washed with 3×100 mL of water. This resulted in 4-(pyridin-2-yl)thiophene-2-carboxylic acid (133.12 g, 76.4%) as a white solid. LCMS (ESI) [M+H]⁺: 206

Step 4: A mixture of 4-(pyridin-2-yl)thiophene-2-carboxylic acid (133.12 g, 648.05 mmol, 1.00 equiv) and N-(3-amino-5-bromophenyl)methanesulfonamide (171.82 g, 648.05 mmol, 1.00 equiv) and TCFH (272.75 g, 972.08 mmol, 1.50 equiv) and NMI (159.63 g, 1944.159 mmol, 3 equiv) in 800 mL of acetonitrile, this was stirred for 2 h at room temperature. The residue was purified onto silica gel column eluted with 10% of methanol in dichloromethane to afford 75 g (95% purity) of the desired product. The desired product was purified by trituration with 300 mL of 30% of methanol in dichloromethane. This resulted in N-(3-bromo-5-methanesulfonamidophenyl)-4-(pyridin-2-yl)thiophene-2-carboxamide (54.8097 g, 18.7%) as a white solid. LCMS (ESI) [M+H]⁺: 452. ¹H NMR (300 MHz, DMSO-d₆) δ 10.61 (s, 1H), 10.08 (s, 1H), 8.75 (d, J=1.4 Hz, 1H), 8.65 (m, J=4.8, 1.4 Hz, 1H), 8.52 (d, J=1.3 Hz, 1H), 7.92 (m, J=2.9, 1.4 Hz, 2H), 7.84 (t, J=1.8 Hz, 1H), 7.75 (t, J=1.9 Hz, 1H), 7.36 (td, J=5.3, 3.1 Hz, 1H), 7.10 (t, J=1.8 Hz, 1H), 3.08 (s, 3H).

Example 31: N-(3-chloro-5-methanesulfonamidophenyl)-4-(3-methylpyridin-2-yl)thiophene-2-carboxamide

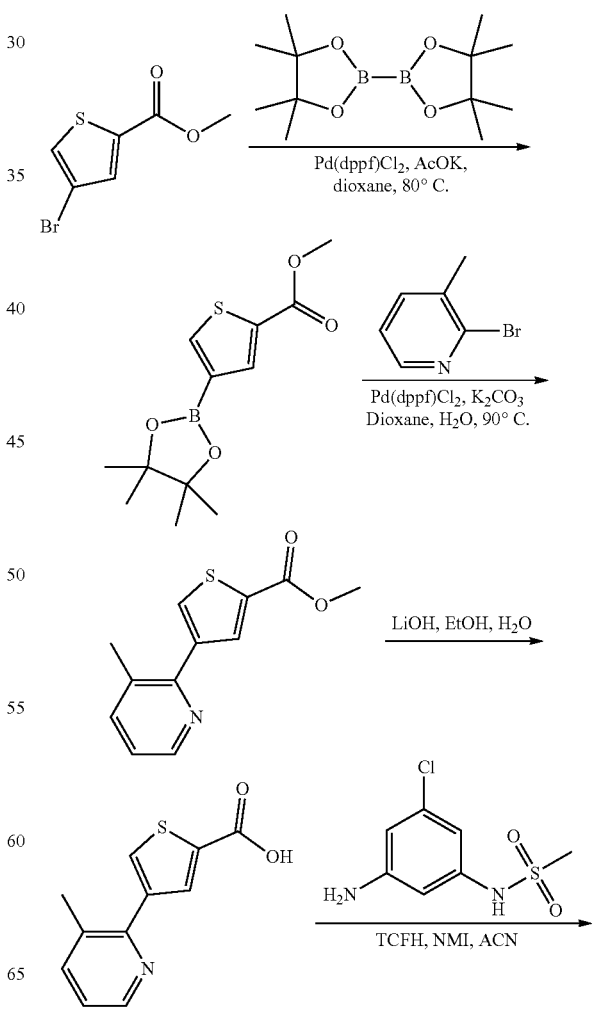

-continued

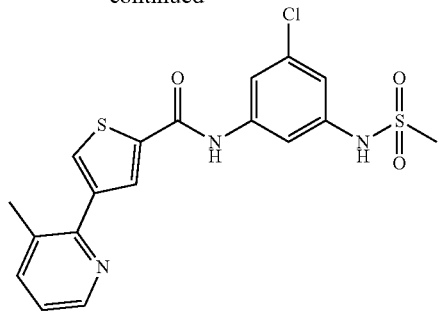

Step 1: A solution of methyl 4-bromothiophene-2-carboxylate (150 g, 678.52 mmol, 1.00 equiv), Pd(dppf)Cl$_2$ (24.82 g, 33.93 mmol, 0.05 equiv), AcOK (199.77 g, 2035.55 mmol, 3.00 equiv) and bis(pinacolato)diboron (206.76 g, 814.22 mmol, 1.2 equiv) in 1000 mL of dioxane. This was stirred for 2 hours at 80° C. under nitrogen atmosphere. The resulting mixture was cooled and concentrated. The residue was purified onto silica gel column eluted with 10% of ethyl acetate in petroleum ether to afford methyl 4-(4,4,5,5-tetramethyl-1,3,2-dioxaborolan-2-yl)thiophene-2-carboxylate (170 g, 92.5%) as a yellow solid.

Step 2: A solution of methyl 4-(4,4,5,5-tetramethyl-1,3,2-dioxaborolan-2-yl)thiophene-2-carboxylate (170 g, 634.02 mmol, 1.00 equiv), Pd(dppf)Cl$_2$ (23.20 g, 31.70 mmol, 0.05 equiv), K$_2$CO$_3$ (262.87 g, 1902.06 mmol, 3.00 equiv) and 2-bromo-3-methylpyridine (109.07 g, 634.02 mmol, 1.00 equiv) in 1000 mL of 1,4-dioxane and 200 mL of water, this was stirred for 2 hours at 90° C. under nitrogen atmosphere. The resulting mixture was cooled and concentrated. The residue was purified onto silica gel column chromatography, eluted with 50% of ethyl acetate in petroleum ether to afford methyl 4-(3-methylpyridin-2-yl)thiophene-2-carboxylate (115 g, 77%) as a yellow solid. LCMS (ESI) [M+H]+: 234

Step 3: To a stirred solution of methyl 4-(3-methylpyridin-2-yl)thiophene-2-carboxylate (115 g, 492.95 mmol, 1.00 equiv), LiOH (118.06 g, 4929.49 mmol, 10.00 equiv) in 250 mL of ethanol and 250 mL of water. Then the mixture was stirred for 2 hours at room temperature. The mixture was adjusted pH to 5 with citric acid. The precipitated solids were collected by filtration and washed with water. The resulted solid was dried under vacuum to afford 4-(3-methylpyridin-2-yl)thiophene-2-carboxylic acid (60 g, 54.9%) as a yellow solid.

LCMS (ESI) [M+H]+: 220

Step 4: To a stirred solution of 4-(3-methylpyridin-2-yl)thiophene-2-carboxylic acid (60 g, 273.65 mmol, 1.00 equiv), TCFH (115.17 g, 410.47 mmol, 1.50 equiv) and NMI (67.40 g, 820.94 mmol, 3.00 equiv) in 1000 mL of acetonitrile, to this was added N-(3-amino-5-chlorophenyl)methanesulfonamide (50 g, 226.58 mmol, 0.83 equiv). Then the mixture was stirred for 2 hours at room temperature. The mixture was concentrated and purified by reverse flash chromatography eluting with 56% acetonitrile in water (0.05% FA) to afford N-(3-chloro-5-methanesulfonamidophenyl)-4-(3-methylpyridin-2-yl)thiophene-2-carboxamide (49.6634 g, 42.8%) as a white solid. LCMS (ESI) [M+H]+: 422. $^1$H NMR (300 MHz, Methanol-d4) δ 8.49-8.41 (m, 1H), 8.21 (d, J=1.4 Hz, 1H), 7.99 (d, J=1.4 Hz, 1H), 7.85-7.75 (m, 1H), 7.69 (t, J=1.9 Hz, 1H), 7.60 (t, J=1.9 Hz, 1H), 7.35 (dd, J=7.7, 4.9 Hz, 1H), 7.05 (t, J=2.0 Hz, 1H), 3.06 (s, 3H), 2.50 (s, 3H).

Example 18-35 and 333-386

The compounds listed in the following table were prepared using a procedure similar to that described for example 17:

| Structure | Example No. | MS (ESI) [M + H]+ | $^1$H NMR |
|---|---|---|---|
| 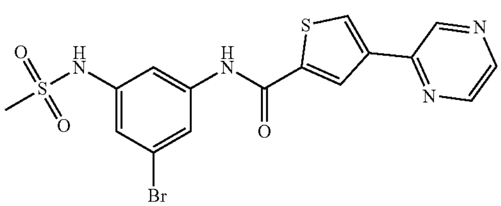 [SMILES: CS(=O)(=O)Nc1cc(Br)cc(NC(=O)c2cc(-c3cnccn3)cs2)c1] | 18 | 453 | $^1$H NMR (300 MHz, DMSO-d6) δ 10.63 (s, 1H), 9.24 (s, 1H), 8.74 (d, J = 21.9 Hz, 3H), 8.61 (d, J = 2.5 Hz, 1H), 7.83 (s, 1H), 7.73 (s, 1H), 7.10 (s, 1H), 3.08 (s, 3H) |
| 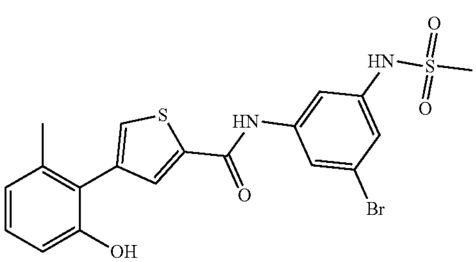 [SMILES: Cc1cccc(O)c1-c1csc(C(=O)Nc2cc(Br)cc(NS(C)(=O)=O)c2)c1] | 19 | 479 | $^1$H NMR (300 MHz, DMSO-d6) δ 10.32 (s, 1H), 9.35 (s, 1H), 8.02 (s, 1H), 7.80 (s, 1H), 7.73-7.63 (m, 2H), 7.06 (d, J = 8.4 Hz, 2H), 6.76 (t, J = 8.4 Hz, 3H), 3.05 (s, 3H), 2.12 (s, 3H). |

| Structure | Example No. | MS (ESI) [M + H]+ | 1H NMR |
|---|---|---|---|
| 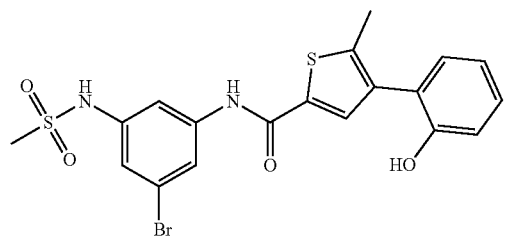 [SMILES: Cc1sc(C(=O)Nc2cc(Br)cc(NS(C)(=O)=O)c2)cc1-c1ccccc1O] | 20 | 481 | 1H NMR (300 MHz, DMSO-d6) δ 10.26 (s, 1H), 10.04 (s, 1H), 9.61 (s, 1H), 7.98 (s, 1H), 7.81 (t, J = 1.8 Hz, 1H), 7.67 (t, J = 2.0 Hz, 1H), 7.27-7.14 (m, 2H), 7.07 (t, J = 1.8 Hz, 1H), 6.97 (d, J = 8.0 Hz, 1H), 6.88 (t, J = 7.4 Hz, 1H), 3.06 (s, 3H), 2.37 (s, 3H). |
| 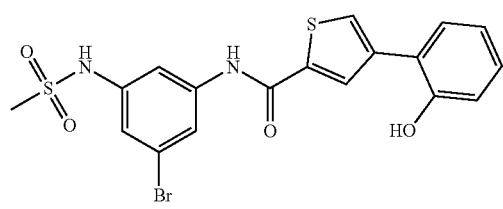 | 21 | 467 | 1H NMR (400 MHz, DMSO-d6) δ 10.44 (s, 1H), 9.95 (s, 2H), 8.47 (d, J = 1.4 Hz, 1H), 8.14 (d, J = 1.4 Hz, 1H), 7.81 (t, J = 1.8 Hz, 1H), 7.70 (t, J = 1.9 Hz, 1H), 7.53 (dd, J = 7.7, 1.7 Hz, 1H), 7.17 (td, J = 7.7, 1.7 Hz, 1H), 7.09 (t, J = 1.9 Hz, 1H), 6.98 (dd, J = 8.1, 1.2 Hz, 1H), 6.90 (td, J = 7.5, 1.2 Hz, 1H), 3.07 (s, 3H). |
| 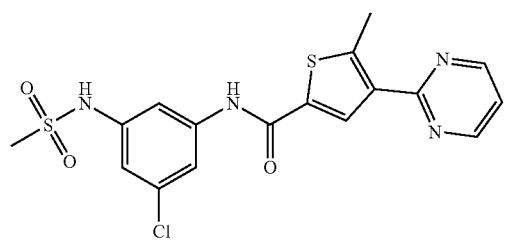 [SMILES: Cc1sc(C(=O)Nc2cc(Cl)cc(NS(C)(=O)=O)c2)cc1-c1ncccn1] | 22 | 423 | 1H NMR (300 MHz, DMSO-d6) δ 10.60 (s, 1H), 10.08 (s, 1H), 8.93 (d, J = 4.9 Hz, 2H), 8.73 (s, 1H), 7.70 (dt, J = 5.1, 1.9 Hz, 2H), 7.44 (t, J = 4.9 Hz, 1H), 6.95 (t, J = 1.9 Hz, 1H), 3.08 (s, 3H), 2.88 (s, 3H). |
| 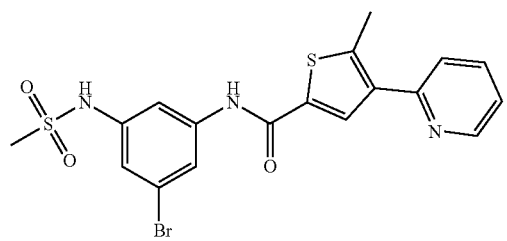 [SMILES: Cc1sc(C(=O)Nc2cc(Br)cc(NS(C)(=O)=O)c2)cc1-c1ccccn1] | 23 | 466 | 1H NMR (400 MHz, DMSO-d6) δ 10.43 (s, 1H), 10.04 (s, 1H), 8.72-8.66 (m, 1H), 8.40 (s, 1H), 7.93 (td, J = 7.7, 1.9 Hz, 1H), 7.81 (t, J = 1.8 Hz, 1H), 7.73-7.66 (m, 2H), 7.41-7.33 (m, 1H), 7.08 (t, J = 1.9 Hz, 1H), 3.06 (s, 3H), 2.71 (s, 3H). |
| 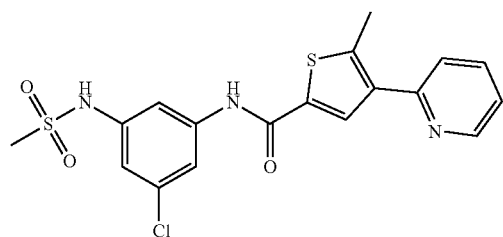 [SMILES: Cc1sc(C(=O)Nc2cc(Cl)cc(NS(C)(=O)=O)c2)cc1-c1ccccn1] | 24 | 422 | 1H NMR (400 MHz, DMSO-d6) δ 10.45 (s, 1H), 10.09 (s, 1H), 8.69 (s, 1H), 8.40 (s, 1H), 7.93 (s, 1H), 7.73-7.53 (m, 3H), 7.37 (s, 1H), 6.95 (s, 1H), 3.07 (s, 3H), 2.71 (s, 3H). |
| 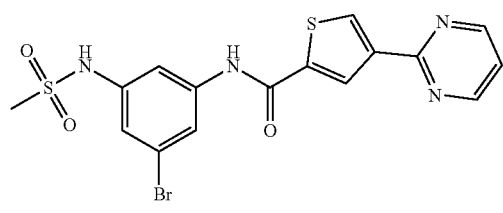 [SMILES: CS(=O)(=O)Nc1cc(Br)cc(NC(=O)c2cc(-c3ncccn3)cs2)c1] | 25 | 453 | 1H NMR (400 MHz, DMSO-d6) δ 10.66 (s, 1H), 10.07 (s, 1H), 8.90 (d, J = 4.9 Hz, 2H), 8.84 (d, J = 1.3 Hz, 1H), 8.67 (s, 1H), 7.84 (d, J = 1.8 Hz, 1H), 7.75 (t, J = 1.9 Hz, 1H), 7.45 (t, J = 4.9 Hz, 1H), 7.10 (t, J = 1.9 Hz, 1H), 3.08 (s, 3H). |

-continued

| Structure | Example No. | MS (ESI) [M + H]+ | 1H NMR |
|---|---|---|---|
| 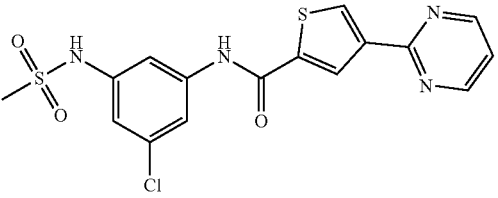 [SMILES: CS(=O)(=O)Nc1cc(Cl)cc(NC(=O)c2cc(-c3ncccn3)cs2)c1] | 26 | 409 | 1H NMR (400 MHz, DMSO-d6) δ 10.68 (s, 1H), 10.09 (s, 1H), 8.90 (d, J = 4.9 Hz, 2H), 8.85 (d, J = 1.3 Hz, 1H), 8.67 (d, J = 1.3 Hz, 1H), 7.71 (dt, J = 4.8, 1.9 Hz, 2H), 7.46 (t, J = 4.9 Hz, 1H), 6.97 (t, J = 1.9 Hz, 1H), 3.08 (s, 3H). |
| 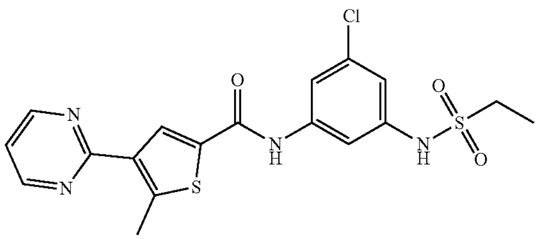 [SMILES: CCS(=O)(=O)Nc1cc(Cl)cc(NC(=O)c2cc(-c3ncccn3)c(C)s2)c1] | 27 | 437 | 1H NMR (300 MHz, DMSO-d6) δ 10.59 (s, 1H), 10.14 (s, 1H), 8.93 (d, J = 4.9 Hz, 2H), 8.73 (s, 1H), 7.69 (d, J = 2.0 Hz, 2H), 7.44 (t, J = 4.9 Hz, 1H), 6.96 (t, J = 1.9 Hz, 1H), 3.18 (q, J = 7.3 Hz, 2H), 2.88 (s, 3H), 1.22 (t, J = 7.3 Hz, 3H). |
| 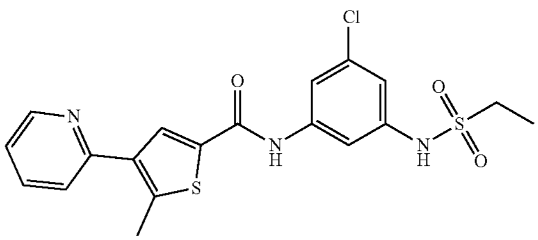 [SMILES: CCS(=O)(=O)Nc1cc(Cl)cc(NC(=O)c2cc(-c3ccccn3)c(C)s2)c1] | 28 | 436 | 1H NMR (300 MHz, DMSO-d6) δ 10.45 (s, 1H), 10.18 (s, 1H), 8.84-8.56 (m, 1H), 8.41 (s, 1H), 8.07-7.84 (m, 1H), 7.68 (dd, J = 14.5, 7.8 Hz, 3H), 7.49-7.20 (m, 1H), 6.96 (d, J = 2.2 Hz, 1H), 3.17 (q, J = 7.2 Hz, 2H), 2.71 (s, 3H), 1.22 (t, J = 7.2 Hz, 3H). |
| 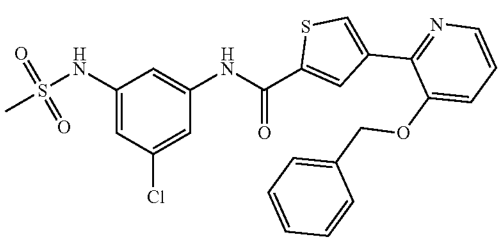 [SMILES: CS(=O)(=O)Nc1cc(Cl)cc(NC(=O)c2cc(-c3ncccc3OCc3ccccc3)cs2)c1] | 29 | 514 | 1H NMR (300 MHz, DMSO-d6) δ 10.65 (s, 1H), 10.09 (s, 1H), 8.84 (d, J = 1.3 Hz, 1H), 8.47 (d, J = 1.3 Hz, 1H), 8.33-8.18 (m, 1H), 7.77-7.64 (m, 3H), 7.54 (d, J = 7.2 Hz, 2H), 7.47-7.31 (m, 4H), 6.96 (t, J = 1.9 Hz, 1H), 5.37 (s, 2H), 3.08 (s, 3H). |
| 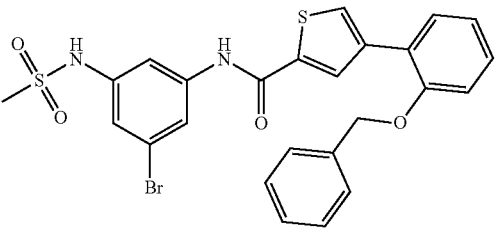 [SMILES: CS(=O)(=O)Nc1cc(Br)cc(NC(=O)c2cc(-c3ccccc3OCc3ccccc3)cs2)c1] | 30 | 557 | 1H NMR (300 MHz, DMSO-d6) δ 10.43 (s, 1H), 10.09 (s, 1H), 8.45 (d, J = 1.4 Hz, 1H), 8.10 (d, J = 1.3 Hz, 1H), 7.80 (t, J = 1.8 Hz, 1H), 7.70 (t, J = 1.9 Hz, 1H), 7.60 (dd, J = 7.7, 1.7 Hz, 1H), 7.49 (d, J = 7.3 Hz, 2H), 7.42-7.20 (m, 5H), 7.15-7.02 (m, 2H), 5.24 (s, 2H), 3.08 (s, 3H). |
| 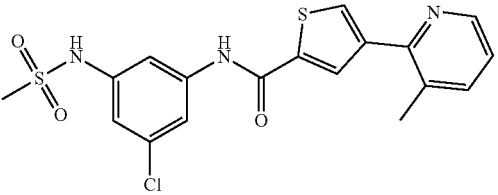 [SMILES: Cc1cccnc1-c1csc(C(=O)Nc2cc(Cl)cc(NS(C)(=O)=O)c2)c1] | 31 | 422 | 1H NMR (400 MHz, DMSO-d6) δ 10.57 (s, 1H), 10.08 (s, 1H), 8.58-8.45 (m, 2H), 8.20 (d, J = 1.3 Hz, 1H), 7.75 (dd, J = 7.7, 1.6 Hz, 1H), 7.69 (dt, J = 10.2, 1.9 Hz, 2H), 7.31 (dd, J = 7.7, 4.7 Hz, 1H), 6.97 (t, J = 1.9 Hz, 1H), 3.08 (s, 3H), 2.51 (s, 3H). |

| Structure | Example No. | MS (ESI) [M + H]⁺ | ¹H NMR |
|---|---|---|---|
| 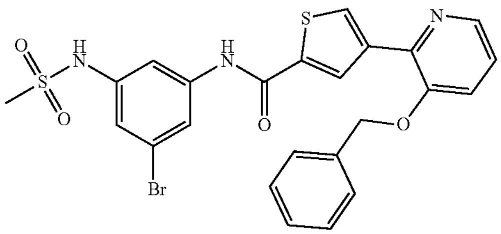 [SMILES: CS(=O)(=O)Nc1cc(Br)cc(NC(=O)c2cc(-c3ncccc3OCc3ccccc3)cs2)c1] | 32 | 558 | ¹H NMR (400 MHz, DMSO-d6) δ 10.63 (s, 1H), 10.06 (s, 1H), 8.83 (d, J = 1.4 Hz, 1H), 8.47 (d, J = 1.3 Hz, 1H), 8.27 (dd, J = 4.6, 1.3 Hz, 1H), 7.83 (t, J = 1.8 Hz, 1H), 7.75 (t, J = 1.9 Hz, 1H), 7.69 (dd, J = 8.5, 1.2 Hz, 1H), 7.59-7.49 (m, 2H), 7.46-7.39 (m, 2H), 7.39-7.31 (m, 2H), 7.09 (t, J = 1.9 Hz, 1H), 3.07 (s, 3H). |
| 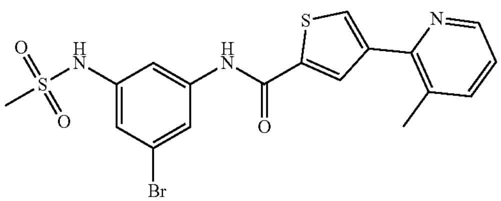 [SMILES: Cc1cccnc1-c1csc(C(=O)Nc2cc(Br)cc(NS(C)(=O)=O)c2)c1] | 33 | 466 | ¹H NMR (400 MHz, DMSO-d6) δ 10.55 (s, 1H), 10.06 (s, 1H), 8.51 (d, J = 1.5 Hz, 2H), 8.19 (d, J = 1.3 Hz, 1H), 7.83 (t, J = 1.8 Hz, 1H), 7.76 (dd, J = 8.1, 1.5 Hz, 1H), 7.72 (t, J = 1.9 Hz, 1H), 7.31 (dd, J = 7.7, 4.7 Hz, 1H), 7.10 (t, J = 1.9 Hz, 1H), 3.07 (s, 3H), 2.50 (s, 3H). |
| 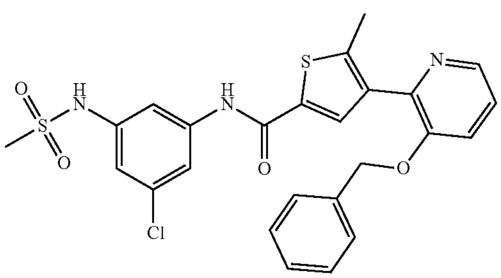 [SMILES: Cc1sc(C(=O)Nc2cc(Cl)cc(NS(C)(=O)=O)c2)cc1-c1ncccc1OCc1ccccc1] | 34 | 528 | ¹H NMR (300 MHz, DMSO-d6) δ 10.36 (s, 1H), 10.10 (s, 1H), 8.31-8.25 (m, 1H), 8.18 (s, 1H), 7.73-7.60 (m, 3H), 7.46-7.38 (m, 3H), 7.33 (q, J = 7.4, 6.7 Hz, 3H), 6.95 (t, J = 2.0 Hz, 1H), 5.22 (s, 2H), 3.07 (s, 3H), 2.41 (s, 3H). |
| 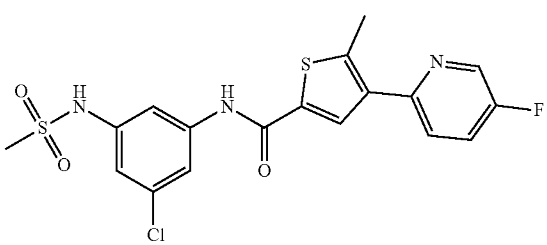 | 35 | 440 | ¹H NMR (400 MHz, DMSO-d6) δ 10.44 (s, 1H), 10.06 (s, 1H), 8.69 (d, J = 2.9 Hz, 1H), 8.36 (s, 1H), 7.88 (td, J = 8.7, 3.0 Hz, 1H), 7.77 (dd, J = 8.8, 4.4 Hz, 1H), 7.68 (t, J = 1.8 Hz, 1H), 7.64 (t, J = 1.9 Hz, 1H), 6.95 (t, J = 1.9 Hz, 1H), 3.07 (s, 3H), 2.69 (s, 3H). |
| 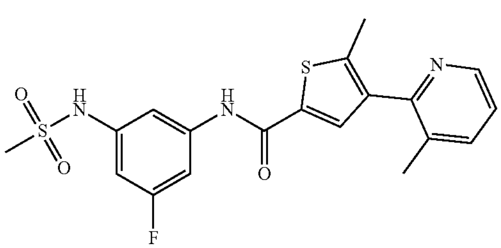 [SMILES: Cc1cccnc1-c1cc(C(=O)Nc2cc(F)cc(NS(C)(=O)=O)c2)sc1C] | 333 | 420.05 | ¹H NMR (300 MHz, DMSO-d6) δ 10.34 (s, 1H), 10.11 (s, 1H), 8.50 (dd, J = 4.9, 1.7 Hz, 1H), 8.00 (s, 1H), 7.81-7.75 (m, 1H), 7.46 (dd, J = 9.9, 2.1 Hz, 2H), 7.35 (dd, J = 7.7, 4.8 Hz, 1H), 6.72 (dt, J = 10.5, 2.2 Hz, 1H), 3.07 (s, 3H), 2.35 (s, 3H), 2.24 (s, 3H). |
| 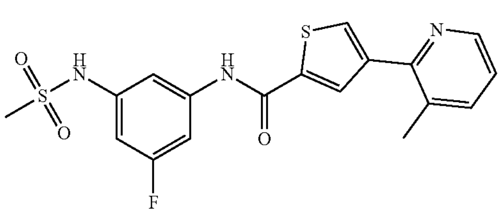 [SMILES: Cc1cccnc1-c1csc(C(=O)Nc2cc(F)cc(NS(C)(=O)=O)c2)c1] | 334 | 405.8 | ¹H NMR (300 MHz, Methanol-d4) δ 8.45 (d, J = 4.5 Hz, 1H), 8.21 (d, J = 1.4 Hz, 1H), 7.99 (d, J = 1.4 Hz, 1H), 7.80 (d, J = 7.7 Hz, 1H), 7.55-7.49 (m, 1H), 7.42-7.31 (m, 2H), 6.81 (dt, J = 10.3, 2.2 Hz, 1H), 3.06 (s, 3H), 2.50 (s, 3H) |

| Structure | Example No. | MS (ESI) [M + H]+ | ¹H NMR |
|---|---|---|---|
| 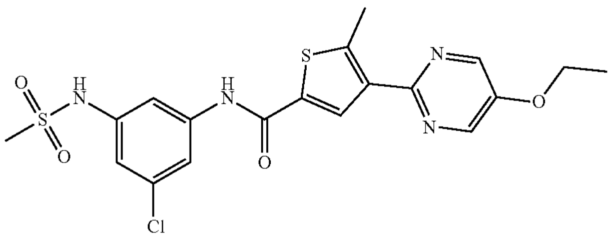 [SMILES: CCOc1cnc(-c2cc(C(=O)Nc3cc(Cl)cc(NS(C)(=O)=O)c3)sc2C)nc1] | 335 | 467 | ¹H NMR (300 MHz, DMSO-d6) δ 10.57 (s, 1H), 10.07 (s, 1H), 8.65 (s, 3H), 7.72- 7.63 (m, 2H), 6.95 (s, 1H), 4.27 (q, J = 6.9 Hz, 2H), 3.08 (s, 3H), 2.84 (s, 3H), 1.40 (t, J = 7.0 Hz, 3H). |
| 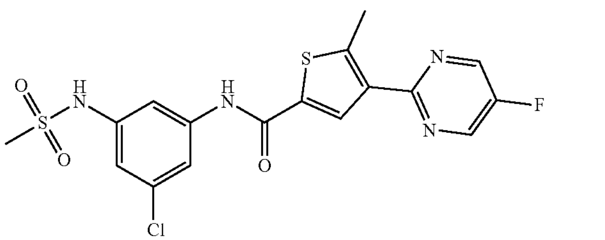 [SMILES: Cc1sc(C(=O)Nc2cc(Cl)cc(NS(C)(=O)=O)c2)cc1-c1ncc(F)cn1] | 336 | 440.85 | ¹H NMR (400 MHz, DMSO-d6) δ 10.58 (s, 1H), 10.08 (s, 1H), 9.01 (s, 2H), 8.68 (s, 1H), 7.68 (dt, J = 7.0, 2.0 Hz, 2H), 6.95 (t, J = 2.0 Hz, 1H), 3.07 (s, 3H), 2.85 (s, 3H). |
| 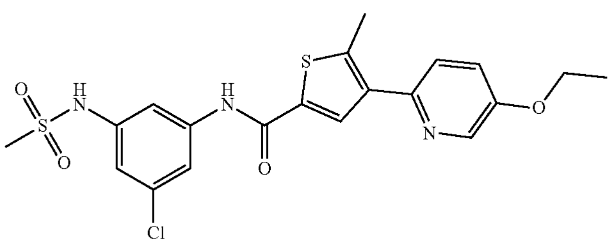 [SMILES: CCOc1ccc(-c2cc(C(=O)Nc3cc(Cl)cc(NS(C)(=O)=O)c3)sc2C)nc1] | 337 | 465.95 | ¹H NMR (400 MHz, DMSO-d6) δ 10.42 (s, 2H), 8.42-8.30 (m, 2H), 7.70-7.60 (m, 3H), 7.50 (dd, J = 8.7, 3.0 Hz, 1H), 6.94 (t, J = 2.0 Hz, 1H), 4.16 (q, J = 6.9 Hz, 2H), 3.06 (s, 3H), 2.67 (s, 3H), 1.38 (t, J = 6.9 Hz, 3H). |
| 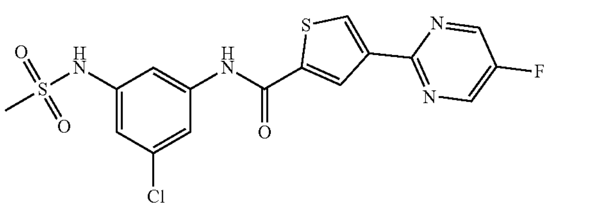 [SMILES: CS(=O)(=O)Nc1cc(Cl)cc(NC(=O)c2cc(-c3ncc(F)cn3)cs2)c1] | 338 | 426.85 | ¹H NMR (400 MHz, DMSO-d6) δ 10.68 (s, 1H), 10.09 (s, 1H), 8.99 (s, 2H), 8.80 (s, 1H), 8.63 (s, 1H), 7.74-7.66 (m, 2H), 6.97 (d, J = 2.1 Hz, 1H), 3.08 (s, 3H). |
| 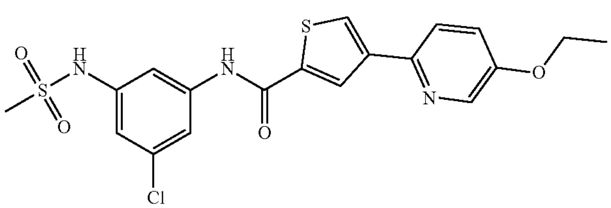 [SMILES: CCOc1ccc(-c2csc(C(=O)Nc3cc(Cl)cc(NS(C)(=O)=O)c3)c2)nc1] | 339 | 452.05 | ¹H NMR (400 MHz, DMSO-d6) δ 10.57 (s, 1H), 10.08 (s, 1H), 8.67 (d, J = 1.4 Hz, 1H), 8.33 (dd, J = 5.8, 2.1 Hz, 2H), 7.85 (d, J = 8.7 Hz, 1H), 7.69 (dt, J = 6.3, 1.9 Hz, 2H), 7.50 (dd, J = 8.8, 3.0 Hz, 1H), 6.96 (t, J = 2.0 Hz, 1H), 4.16 (q, J = 6.9 Hz, 2H), 3.08 (s, 3H), 1.37 (t, J = 7.0 Hz, 3H). |
| 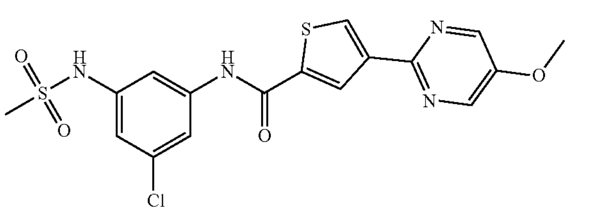 | 340 | 439.05 | ¹H NMR (400 MHz, DMSO-d6) δ 10.65 (s, 1H), 10.06 (s, 1H), 8.76 (d, J = 1.3 Hz, 1H), 8.63 (s, 2H), 8.50 (d, J = 1.3 Hz, 1H), 7.70 (t, J = 1.8 Hz, 2H), 6.96 (t, J = 2.0 Hz, 1H), 3.97 (s, 3H), 3.07 (s, 3H). |

| Structure | Example No. | MS (ESI) [M + H]+ | ¹H NMR |
|---|---|---|---|
| 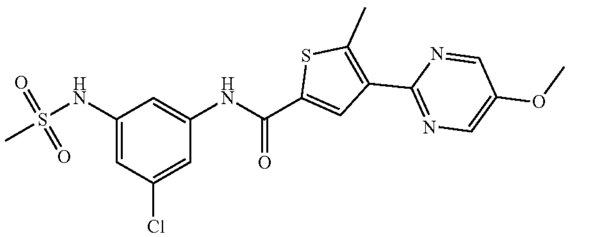 | 341 | 453.05 | ¹H NMR (400 MHz, DMSO-d6) δ 10.56 (s, 1H), 10.05 (s, 1H), 8.65 (d, J = 8.1 Hz, 3H), 7.68 (dt, J = 6.0, 1.8 Hz, 2H), 6.95 (t, J = 1.9 Hz, 1H), 3.97 (s, 3H), 3.07 (d, J = 1.3 Hz, 3H), 2.83 (s, 3H). |
| 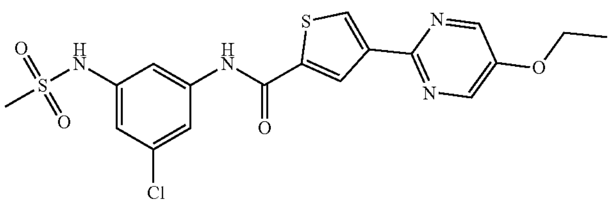 [SMILES: CCOc1cnc(-c2csc(C(=O)Nc3cc(Cl)cc(NS(C)(=O)=O)c3)c2)nc1] | 342 | 452.9 | ¹H NMR (400 MHz, DMSO-d6) δ 10.64 (s, 1H), 10.08 (s, 1H), 8.76 (s, 1H), 8.62 (s, 2H), 8.49 (s, 1H), 7.70 (s, 2H), 6.96 (d, J = 2.3 Hz, 1H), 4.26 (q, J = 6.9 Hz, 2H), 3.08 (s, 3H), 1.39 (t, J = 6.9 Hz, 3H). |
| 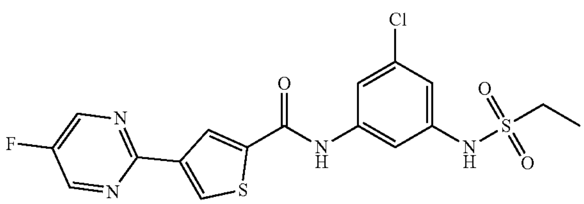 [SMILES: CCS(=O)(=O)Nc1cc(Cl)cc(NC(=O)c2cc(-c3ncc(F)cn3)cs2)c1] | 343 | 440.9 | ¹H NMR (300 MHz, DMSO-d6) δ 10.67 (s, 1H), 10.13 (s, 1H), 8.99 (d, J = 0.8 Hz, 2H), 8.80 (d, J = 1.3 Hz, 1H), 8.63 (d, J = 1.3 Hz, 1H), 7.70 (d, J = 2.0 Hz, 2H), 6.98 (t, J = 2.0 Hz, 1H), 3.19 (q, J = 7.3 Hz, 2H), 1.23 (t, J = 7.3 Hz, 3H). |
| 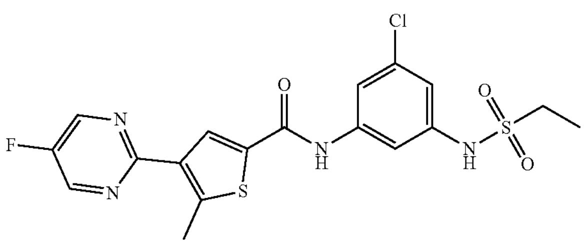 | 344 | 454.85 | ¹H NMR (400 MHz, DMSO-d6) δ 10.58 (s, 1H), 10.12 (s, 1H), 9.00 (s, 2H), 8.67 (s, 1H), 7.67 (d, J = 2.0 Hz, 2H), 6.95 (t, J = 1.7 Hz, 1H), 3.18 (q, J = 7.3 Hz, 2H), 2.85 (s, 3H), 1.22 (t, J = 7.3 Hz, 3H). |
| 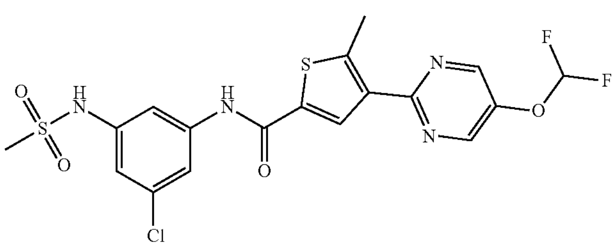 [SMILES: Cc1sc(C(=O)Nc2cc(Cl)cc(NS(C)(=O)=O)c2)cc1-c1ncc(OC(F)F)cn1] | 345 | 488.9 | ¹H NMR (300 MHz, DMSO-d6) δ 10.61 (s, 1H), 10.07 (s, 1H), 8.89 (s, 2H), 8.70 (s, 1H), 7.74-7.17 (m, 3H), 6.96 (t, J = 1.9 Hz, 1H), 3.08 (s, 3H), 2.86 (s, 3H). |
| 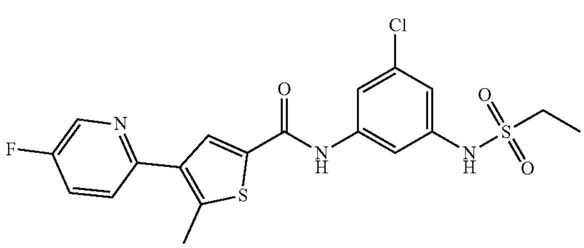 [SMILES: CCS(=O)(=O)Nc1cc(Cl)cc(NC(=O)c2cc(-c3ccc(F)cn3)c(C)s2)c1] | 346 | 454 | ¹H NMR (300 MHz, DMSO-d6) δ 10.44 (s, 1H), 10.13 (s, 1H), 8.69 (d, J = 3.0 Hz, 1H), 8.37 (s, 1H), 7.89 (td, J = 8.7, 3.0 Hz, 1H), 7.77 (dd, J = 8.9, 4.4 Hz, 1H), 7.65 (dt, J = 8.3, 1.9 Hz, 2H), 6.96 (t, J = 1.9 Hz, 1H), 3.18 (q, J = 7.3 Hz, 2H), 2.69 (s, 3H), 1.22 (t, J = 7.3 Hz, 3H). |

-continued

| Structure | Example No. | MS (ESI) [M + H]+ | 1H NMR |
|---|---|---|---|
| (structure) | 347 | 472 | 1H NMR (400 MHz, DMSO-d6) δ 10.44 (s, 1H), 10.15 (s, 1H), 8.66 (d, J = 2.5 Hz, 1H), 8.24-8.07 (m, 2H), 7.71-7.57 (m, 2H), 6.95 (t, J = 2.0 Hz, 1H), 3.16 (q, J = 7.2 Hz, 2H), 2.52 (d, J = 1.5 Hz, 3H), 1.21 (t, J = 7.3 Hz, 3H). |
| (structure) | 348 | 453.85 | 1H NMR (400 MHz, DMSO-d6) δ 10.31 (s, 1H), 10.07 (s, 1H), 8.50 (d, J = 2.8 Hz, 1H), 7.97 (s, 1H), 7.78 (dd, J = 9.5, 2.8 Hz, 1H), 7.66 (t, J = 1.8 Hz, 1H), 7.59 (t, J = 1.9 Hz, 1H), 6.94 (t, J = 1.9 Hz, 1H), 3.05 (s, 3H), 2.33 (s, 3H), 2.26 (s, 3H). |
| (structure) | 349 | 458 | 1H NMR (400 MHz, DMSO-d6) δ 10.44 (s, 1H), 10.07 (s, 1H), 8.66 (d, J = 2.4 Hz, 1H), 8.18 (d, J = 1.7 Hz, 1H), 8.14 (ddd, J = 10.4, 8.9, 2.4 Hz, 1H), 7.66 (t, J = 1.9 Hz, 1H), 7.62 (t, J = 1.9 Hz, 1H), 6.95 (t, J = 1.9 Hz, 1H), 3.06 (s, 3H), 2.52 (s, 3H). |
| (structure) | 350 | 468 | 1H NMR (400 MHz, DMSO-d6) δ 10.30 (s, 1H), 10.13 (s, 1H), 8.50 (d, J = 2.9 Hz, 1H), 7.97 (s, 1H), 7.78 (dd, J = 9.7, 2.9 Hz, 1H), 7.64 (t, J = 1.9 Hz, 1H), 7.59 (t, J = 1.9 Hz, 1H), 6.94 (t, J = 2.0 Hz, 1H), 3.16 (q, J = 7.3 Hz, 2H), 2.33 (s, 3H), 2.26 (s, 3H), 1.20 (t, J = 7.3 Hz, 3H). |
| (structure) | 351 | 470 | 1H NMR (300 MHz, DMSO-d6) δ 10.37 (s, 1H), 10.08 (s, 1H), 8.28 (d, J = 2.3 Hz, 1H), 8.09 (s, 1H), 7.67 (ddd, J = 7.4, 4.8, 2.4 Hz, 2H), 7.63 (t, J = 1.9 Hz, 1H), 6.94 (t, J = 1.9 Hz, 1H), 3.89 (s, 3H), 3.07 (s, 3H), 2.41 (s, 3H). |
| (structure) | 352 | 452 | 1H NMR (300 MHz, DMSO-d6) δ 10.43 (s, 1H), 10.11 (s, 1H), 8.40 (d, J = 2.9 Hz, 1H), 8.34 (s, 1H), 7.71-7.61 (m, 3H), 7.53 (dd, J = 8.7, 3.0 Hz, 1H), 6.95 (t, J = 1.9 Hz, 1H), 3.89 (s, 3H), 3.07 (s, 3H), 2.67 (s, 3H). |

-continued

| Structure | Example No. | MS (ESI) [M + H]+ | 1H NMR |
|---|---|---|---|
| 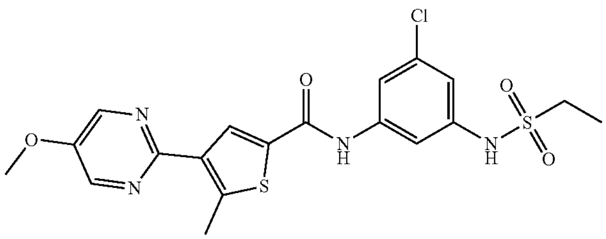 [SMILES: CCS(=O)(=O)Nc1cc(Cl)cc(NC(=O)c2cc(-c3ncc(OC)cn3)c(C)s2)c1] | 353 | 467 | 1H NMR (300 MHz, DMSO-d6) δ 10.57 (s, 1H), 10.11 (s, 1H), 8.66 (d, J = 6.6 Hz, 3H), 7.68 (d, J = 2.0 Hz, 2H), 6.95 (t, J = 2.0 Hz, 1H), 3.98 (s, 3H), 3.18 (q, J = 7.3 Hz, 2H), 2.84 (s, 3H), 1.22 (t, J = 7.3 Hz, 3H). |
| 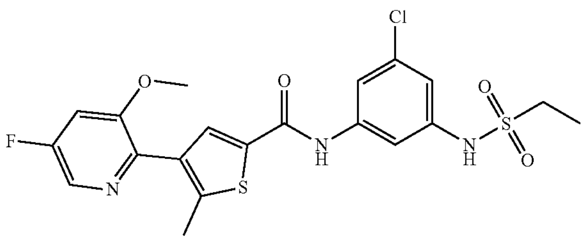 [SMILES: CCS(=O)(=O)Nc1cc(Cl)cc(NC(=O)c2cc(-c3ncc(F)cc3OC)c(C)s2)c1] | 354 | 484 | 1H NMR (300 MHz, DMSO-d6) δ 10.36 (s, 1H), 10.11 (s, 1H), 8.28 (d, J = 2.3 Hz, 1H), 8.09 (s, 1H), 7.72-7.56 (m, 3H), 6.95 (t, J = 2.0 Hz, 1H), 3.89 (s, 3H), 3.17 (q, J = 7.3 Hz, 2H), 2.40 (s, 3H), 1.21 (t, J = 7.3 Hz, 3H). |
| 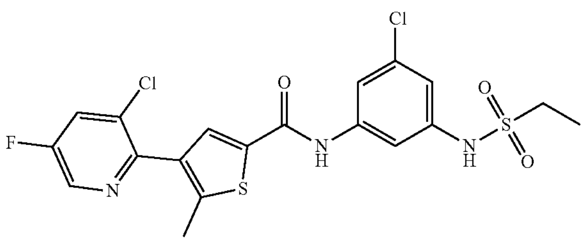 | 355 | 487.95 | 1H NMR (300 MHz, DMSO-d6) δ 10.38 (s, 1H), 10.11 (s, 1H), 8.73 (d, J = 2.6 Hz, 1H), 8.30 (dd, J = 8.5, 2.6 Hz, 1H), 8.08 (s, 1H), 7.63 (dt, J = 16.4, 1.9 Hz, 2H), 6.95 (t, J = 2.0 Hz, 1H), 3.17 (q, J = 7.3 Hz, 2H), 2.40 (s, 3H), 1.20 (t, J = 7.3 Hz, 3H). |
| 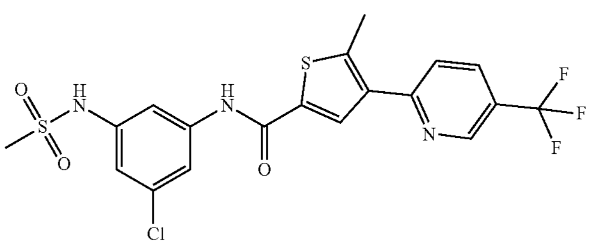 [SMILES: Cc1sc(C(=O)Nc2cc(Cl)cc(NS(C)(=O)=O)c2)cc1-c1ccc(C(F)(F)F)cn1] | 356 | 489.9 | 1H NMR (300 MHz, DMSO-d6) δ 10.51 (s, 1H), 10.09 (s, 1H), 9.07 (s, 1H), 8.48 (s, 1H), 8.40-8.33 (m, 1H), 7.93 (d, J = 8.4 Hz, 1H), 7.68 (d, J = 1.9 Hz, 1H), 7.64 (s, 1H), 6.96 (t, J = 2.0 Hz, 1H), 3.08 (s, 3H), 2.77 (s, 3H). |
| 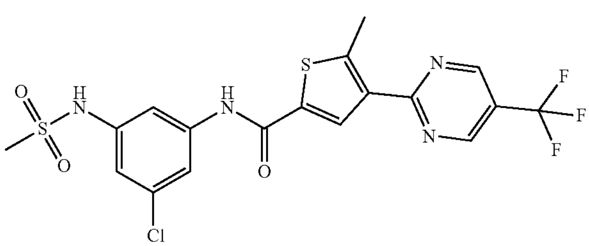 [SMILES: Cc1sc(C(=O)Nc2cc(Cl)cc(NS(C)(=O)=O)c2)cc1-c1ncc(C(F)(F)F)cn1] | 357 | 490.9 | 1H NMR (400 MHz, DMSO-d6) δ 10.67 (s, 1H), 10.11 (s, 1H), 9.35 (s, 2H), 8.78 (s, 1H), 7.68 (dt, J = 10.4, 1.9 Hz, 2H), 6.95 (t, J = 2.0 Hz, 1H), 3.07 (s, 3H), 2.91 (s, 3H). |
| 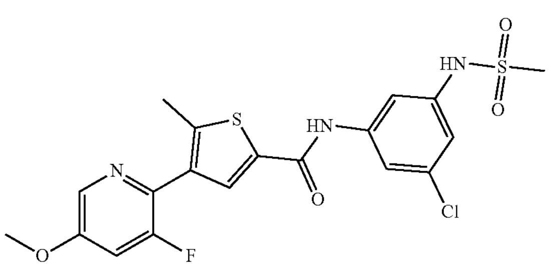 | 358 | 469.95 | 1H NMR (400 MHz, Chloroform-d) δ 8.33 (s, 1H), 8.23 (s, 1H), 7.85 (s, 1H), 7.63 (s, 1H), 7.50 (d, J = 19.4 Hz, 2H), 7.19 (d, J = 10.8 Hz, 1H), 6.97 (t, J = 1.7 Hz, 1H), 3.94 (s, 3H), 3.04 (s, 3H), 2.52 (d, J = 1.8 Hz, 3H). |

| Structure | Example No. | MS (ESI) [M + H]+ | ¹H NMR |
|---|---|---|---|
| 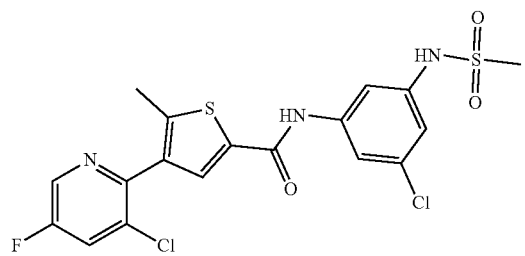 [SMILES: Cc1sc(C(=O)Nc2cc(Cl)cc(NS(C)(=O)=O)c2)cc1-c1ncc(F)cc1Cl] | 359 | 473.9 | ¹H NMR (300 MHz, DMSO-d6) δ 10.39 (s, 1H), 10.07 (s, 1H), 8.73 (d, J = 2.6 Hz, 1H), 8.30 (dd, J = 8.5, 2.6 Hz, 1H), 8.08 (s, 1H), 7.63 (dt, J = 19.9, 1.9 Hz, 2H), 6.94 (t, J = 2.0 Hz, 1H), 3.06 (s, 3H), 2.40 (s, 3H). |
| 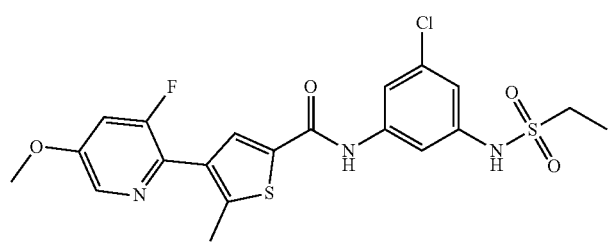 [SMILES: CCS(=O)(=O)Nc1cc(Cl)cc(NC(=O)c2cc(-c3ncc(OC)cc3F)c(C)s2)c1] | 360 | 483.9 | ¹H NMR (400 MHz, Chloroform-d) δ 8.25 (s, 2H), 7.85 (s, 1H), 7.54 (d, J = 1.8 Hz, 1H), 7.47 (s, 1H), 7.22 (s, 1H), 7.19 (s, 1H), 6.98 (t, J = 1.8 Hz, 1H), 3.95 (s, 3H), 3.17 (q, J = 7.3 Hz, 2H), 2.54 (d, J = 1.8 Hz, 3H), 1.37 (t, J = 7.3 Hz, 3H). |
| 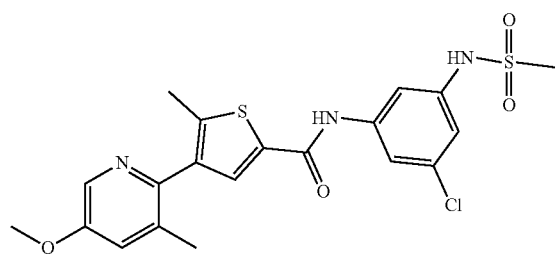 | 361 | 465.9 | ¹H NMR (400 MHz, DMSO-d6) δ 10.29 (s, 1H), 10.09 (s, 1H), 8.21 (d, J = 2.9 Hz, 1H), 7.95 (s, 1H), 7.71-7.54 (m, 2H), 7.39 (d, J = 2.9 Hz, 1H), 6.94 (t, J = 2.0 Hz, 1H), 3.87 (s, 3H), 3.05 (s, 3H), 2.32 (s, 3H), 2.22 (s, 3H). |
| 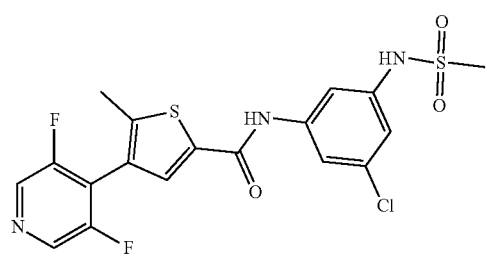 [SMILES: Cc1sc(C(=O)Nc2cc(Cl)cc(NS(C)(=O)=O)c2)cc1-c1c(F)cncc1F] | 362 | 458 | ¹H NMR (300 MHz, DMSO-d6) δ 10.44 (s, 1H), 10.09 (s, 1H), 8.72 (s, 2H), 8.06 (s, 1H), 7.67 (t, J = 1.9 Hz, 1H), 7.60 (t, J = 1.9 Hz, 1H), 6.96 (t, J = 1.9 Hz, 1H), 3.07 (s, 3H), 2.41 (s, 3H). |
| 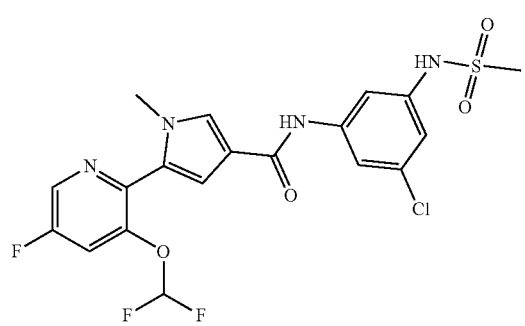 [SMILES: Cn1cc(C(=O)Nc2cc(Cl)cc(NS(C)(=O)=O)c2)cc1-c1ncc(F)cc1OC(F)F] | 363 | 488.9 | ¹H NMR (400 MHz, DMSO-d6) δ 10.00 (s, 1H), 9.87 (s, 1H), 8.60 (d, J = 2.4 Hz, 1H), 7.90 (dd, J = 9.6, 2.5 Hz, 1H), 7.77-7.69 (m, 2H), 7.63 (t, J = 1.9 Hz, 1H), 7.37 (s, 1H), 7.08 (d, J = 1.9 Hz, 1H), 6.91 (t, J = 1.9 Hz, 1H), 3.78 (s,3H), 3.06 (s, 3H). |

-continued

| Structure | Example No. | MS (ESI) [M + H]+ | 1H NMR |
|---|---|---|---|
| 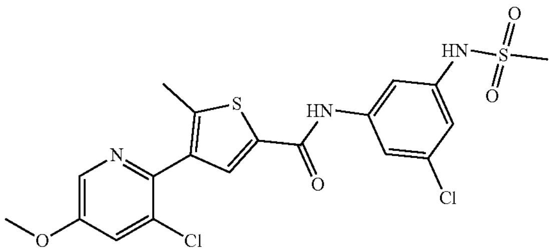 | 364 | 485.95 | 1H NMR (300 MHz, DMSO-d6) δ 10.37 (s, 1H), 10.06 (s, 1H), 8.39 (d, J = 2.6 Hz, 1H), 8.05 (s, 1H), 7.76 (d, J = 2.6 Hz, 1H), 7.67 (t, J = 1.8 Hz, 1H), 7.61 (t, J = 1.9 Hz, 1H), 6.94 (t, J = 1.9 Hz, 1H), 3.92 (s, 3H), 3.06 (s, 3H), 2.38 (s, 3H). |
| 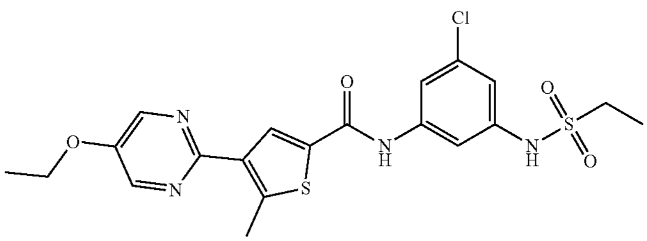 [SMILES: CCOc1cnc(-c2cc(C(=O)Nc3cc(Cl)cc(NS(=O)(=O)CC)c3)sc2C)nc1] | 365 | 481 | 1H NMR (400 MHz, DMSO-d6) δ 10.55 (s, 1H), 10.12 (s, 1H), 8.64 (d, J = 2.1 Hz, 3H), 7.67 (d, J = 2.0 Hz, 2H), 6.94 (t, J = 2.0 Hz, 1H), 4.26 (q, J = 7.0 Hz, 2H), 3.17 (q, J = 7.3 Hz, 2H), 2.83 (s, 3H), 1.39 (t, J = 6.9 Hz, 3H), 1.21 (t, J =7.3 Hz, 3H). |
| 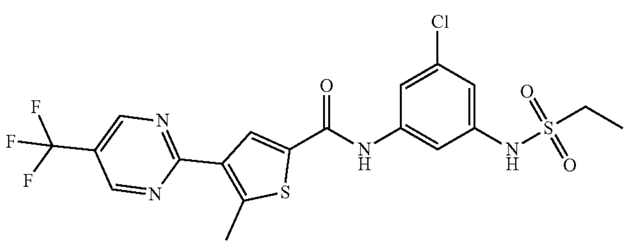 [SMILES: CCS(=O)(=O)Nc1cc(Cl)cc(NC(=O)c2cc(-c3ncc(C(F)(F)F)cn3)c(C)s2)c1] | 366 | 505 | 1H NMR (400 MHz, DMSO-d6) δ 10.65 (s, 1H), 10.11 (s, 1H), 9.35 (s, 2H), 8.78 (s, 1H), 7.67 (dd, J = 4.6, 2.2 Hz, 2H), 6.96 (t, J = 2.0 Hz, 1H), 3.18 (q, J = 7.3 Hz, 2H), 2.91 (s, 3H), 1.22 (t, J = 7.3 Hz, 3H). |
| 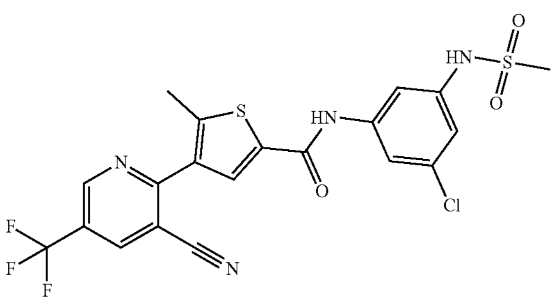 [SMILES: Cc1sc(C(=O)Nc2cc(Cl)cc(NS(C)(=O)=O)c2)cc1-c1ncc(C(F)(F)F)cc1C#N] | 367 | 514.8 | 1H NMR (300 MHz, DMSO-d6) δ 10.54 (s, 1H), 10.07 (s, 1H),9.38 (dd, J = 2.2, 0.9 Hz, 1H), 9.09 (d, J = 2.3 Hz, 1H), 8.27 (s, 1H), 7.75-7.34 (m, 2H), 6.96 (t, J = 1.9 Hz, 1H), 3.07 (s, 3H), 2.58 (s, 3H). |
| 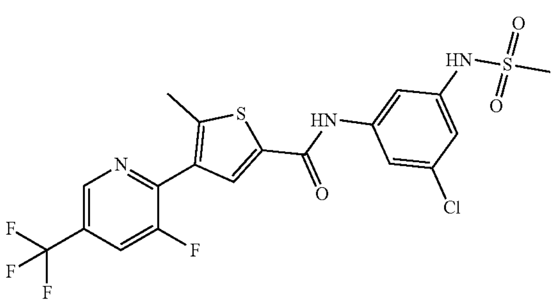 [SMILES: Cc1sc(C(=O)Nc2cc(Cl)cc(NS(C)(=O)=O)c2)cc1-c1ncc(C(F)(F)F)cc1F] | 368 | 507.8 | 1H NMR (400 MHz, DMSO-d6) δ 10.51 (s, 1H), 10.08 (s, 1H), 8.98 (d, J = 1.8 Hz, 1H), 8.51 (dd, J = 10.3, 1.9 Hz, 1H), 8.27 (d, J = 1.9 Hz, 1H), 7.65 (dt, J = 17.9, 1.9 Hz, 2H), 6.96 (t, J = 1.9 Hz, 1H), 3.06 (s, 3H), 2.60 (d, J = 1.5 Hz, 3H). |
| 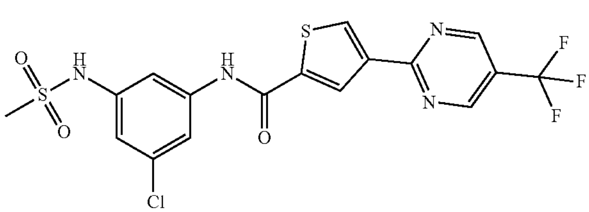 | 369 | 476.85 | 1H NMR (400 MHz, DMSO-d6) δ 10.74 (s, 1H), 10.11 (s, 1H), 9.34 (t, J = 0.9 Hz, 2H), 8.87 (dd, J = 16.7, 1.2 Hz, 2H), 7.71 (dt, J = 6.6, 1.9 Hz, 2H), 6.97 (t, J = 1.9 Hz, 1H), 3.09 (s, 3H). |

| Structure | Example No. | MS (ESI) [M + H]+ | 1H NMR |
|---|---|---|---|
| 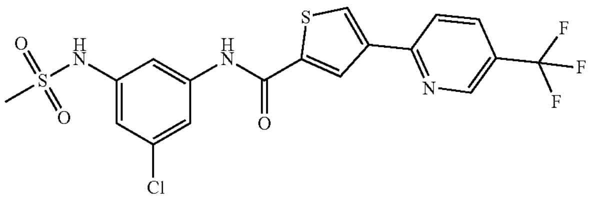 [SMILES: CS(=O)(=O)Nc1cc(Cl)cc(NC(=O)c2cc(-c3ccc(C(F)(F)F)cn3)cs2)c1] | 370 | 476 | 1H NMR (400 MHz, DMSO-d6) δ 10.67 (s, 1H), 10.10 (s, 1H), 9.08-8.98 (m, 1H), 8.80 (d, J = 1.4 Hz, 1H), 8.72 (d, J = 1.3 Hz, 1H), 8.34 (dd, J = 8.5, 2.4 Hz, 1H), 8.15 (d, J = 8.4 Hz, 1H), 7.69 (dt, J = 11.0, 1.9 Hz, 2H), 6.97 (t, J = 1.9 Hz, 1H), 3.08 (s, 3H). |
| 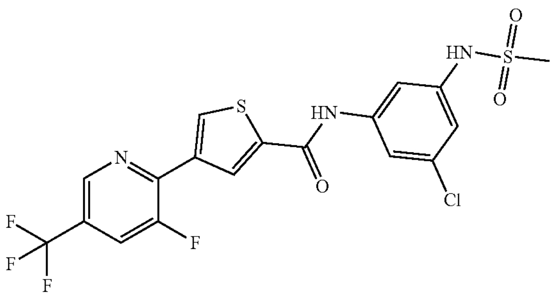 [SMILES: CS(=O)(=O)Nc1cc(Cl)cc(NC(=O)c2cc(-c3ncc(C(F)(F)F)cc3F)cs2)c1] | 371 | 493.9 | 1H NMR (400 MHz, DMSO-d6) δ 10.74 (s, 1H), 10.09 (s, 1H), 8.94 (s, 1H), 8.81 (d, J = 1.4 Hz, 1H), 8.63 (t, J = 1.6 Hz, 1H), 8.48 (dd, J = 11.4, 1.9 Hz, 1H), 7.69 (dt, J = 7.5, 1.9 Hz, 2H), 6.97 (t, J = 1.9 Hz, 1H), 3.08 (s, 3H). |
| 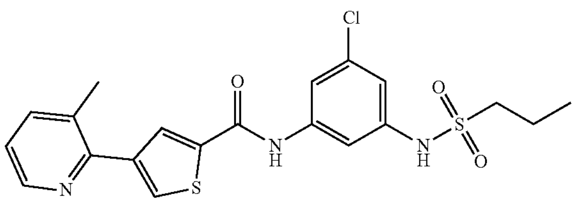 [SMILES: CCCS(=O)(=O)Nc1cc(Cl)cc(NC(=O)c2cc(-c3ncccc3C)cs2)c1] | 372 | 450 | 1H NMR (400 MHz, Methanol-d4) δ 8.49-8.40 (m, 1H), 8.18 (d, J = 1.4 Hz, 1H), 7.97 (d, J = 1.4 Hz, 1H), 7.78 (ddd, J = 7.8, 1.8, 0.9 Hz, 1H), 7.66 (t, J = 1.9 Hz, 1H), 7.55 (t, J = 1.9 Hz, 1H), 7.33 (dd, J = 7.7, 4.9 Hz, 1H), 7.02 (t, J = 1.9 Hz, 1H), 3.21-3.09 (m, 2H), 2.48 (s, 3H), 1.91-1.71 (m, 2H), 1.03 (t, J = 7.5 Hz, 3H). |
| 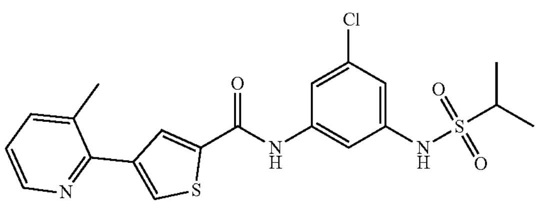 [SMILES: Cc1cccnc1-c1csc(C(=O)Nc2cc(Cl)cc(NS(=O)(=O)C(C)C)c2)c1] | 373 | 450 | 1H NMR (400 MHz, Methanol-d4) δ 8.43 (dd, J = 4.7, 1.7 Hz, 1H), 8.18 (d, J = 1.4 Hz, 1H), 7.97 (d, J = 1.4 Hz, 1H), 7.78 (dd, J = 7.7, 1.4 Hz, 1H), 7.68 (t, J = 1.9 Hz, 1H), 7.54 (t, J = 1.8 Hz, 1H), 7.33 (dd, J = 7.7, 4.9 Hz, 1H), 7.04 (t, J = 1.9 Hz, 1H), 3.40-3.33 (m, 1H), 2.48 (s, 3H), 1.36 (d, J = 6.8 Hz, 6H). |
| 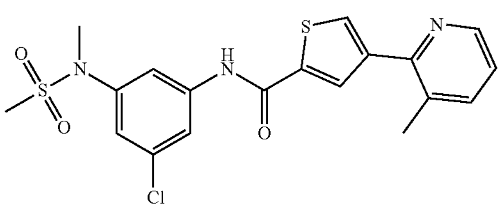 [SMILES: Cc1cccnc1-c1csc(C(=O)Nc2cc(Cl)cc(N(C)S(C)(=O)=O)c2)c1] | 374 | 436 | 1H NMR (400 MHz, DMSO-d6) δ 10.61 (s, 1H), 8.59-8.45 (m, 2H), 8.21 (d, J = 1.3 Hz, 1H), 7.92 (d, J = 2.0 Hz, 1H), 7.79-7.68 (m, 2H), 7.31 (dd, J = 7.7, 4.7 Hz, 1H), 7.28 (d, J = 1.9 Hz, 1H), 3.26 (s, 3H), 3.02 (s, 3H), 2.51 (s, J = 2.1 Hz, 3H). |
| 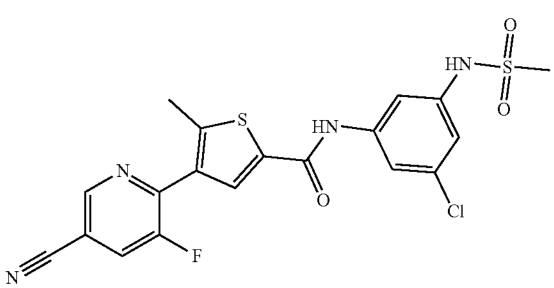 | 375 | 465 | 1H NMR (400 MHz, DMSO-d6) δ 10.51 (s, 1H), 10.07 (s, 1H), 9.03 (t, J = 1.5 Hz, 1H), 8.60 (dd, J = 10.4, 1.7 Hz, 1H), 8.28 (d, J = 2.1 Hz, 1H), 7.65 (dt, J = 15.0, 1.9 Hz, 2H), 6.96 (t, J = 1.9 Hz, 1H), 3.07 (s, 3H), 2.60 (d, J = 1.5 Hz, 3H). |

| Structure | Example No. | MS (ESI) [M + H]+ | 1H NMR |
|---|---|---|---|
| 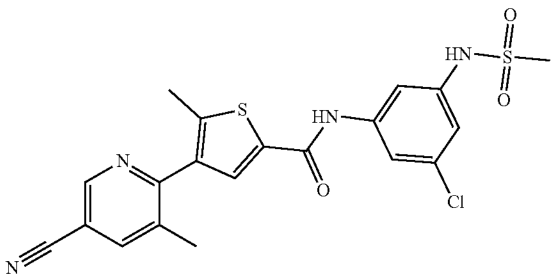 [SMILES: Cc1cc(C#N)cnc1-c1cc(C(=O)Nc2cc(Cl)cc(NS(C)(=O)=O)c2)sc1C] | 376 | 461 | 1H NMR (400 MHz, DMSO-d6) δ 10.35 (s, 1H), 10.08 (s, 1H), 8.95 (d, J = 2.0 Hz, 1H), 8.35 (d, J = 2.1 Hz, 1H), 8.03 (s, 1H), 7.67-7.62 (m, 1H), 7.59 (t, J = 2.0 Hz, 1H), 6.95 (t, J = 2.0 Hz, 1H), 3.06 (s, 3H), 2.38 (s, 3H), 2.31 (s, 3H). |
| 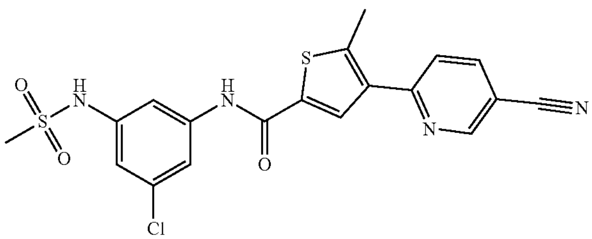 [SMILES: Cc1sc(C(=O)Nc2cc(Cl)cc(NS(C)(=O)=O)c2)cc1-c1ccc(C#N)cn1] | 377 | 447 | 1H NMR (400 MHz, DMSO-d6) δ 10.50 (s, 1H), 10.09 (s, 1H), 9.12 (dd, J = 2.2, 0.9 Hz, 1H), 8.60-8.30 (m, 2H), 7.90 (dd, J = 8.3, 0.9 Hz, 1H), 7.66 (dt, J = 15.7, 1.9 Hz, 2H), 6.96 (t, J = 2.0 Hz, 1H), 3.08 (s, 3H), 2.76 (s, 3H). |
| 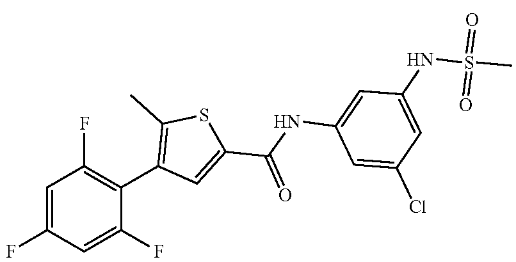 [SMILES: Cc1sc(C(=O)Nc2cc(Cl)cc(NS(C)(=O)=O)c2)cc1-c1c(F)cc(F)cc1F] | 378 | 475 | 1H NMR (300 MHz, DMSO-d6) δ 10.37 (s, 1H), 10.09 (s, 1H), 7.98 (s, 1H), 7.67 (t, J = 1.8 Hz, 1H), 7.59 (t, J = 1.9 Hz, 1H), 7.41 (t, J = 8.6 Hz, 2H), 6.95 (t, J = 1.9 Hz, 1H), 3.06 (s, 3H), 2.35 (s, 3H). |
| 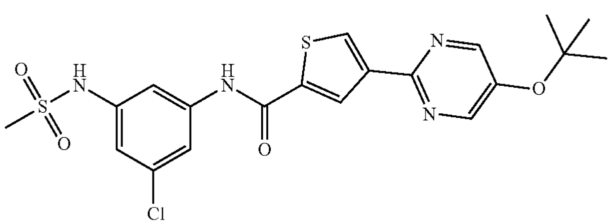 [SMILES: CC(C)(C)Oc1cnc(-c2csc(C(=O)Nc3cc(Cl)cc(NS(C)(=O)=O)c3)c2)nc1] | 379 | 481 | 1H NMR (400 MHz, DMSO-d6) δ 10.66 (s, 1H), 10.09 (s, 1H), 8.78 (d, J = 1.3 Hz, 1H), 8.62 (s, 2H), 8.55 (d, J = 1.3 Hz, 1H), 7.70 (dd, J = 4.7, 2.9 Hz, 2H), 6.96 (t, J = 2.0 Hz, 1H), 3.08 (s, 3H), 1.38 (s, 9H). |
| 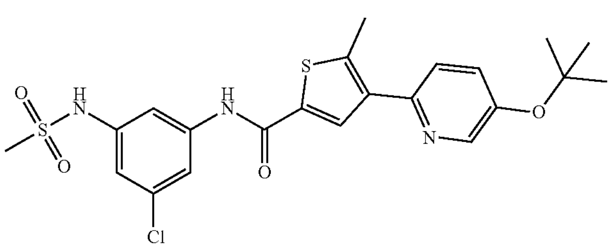 [SMILES: Cc1sc(C(=O)Nc2cc(Cl)cc(NS(C)(=O)=O)c2)cc1-c1ccc(OC(C)(C)C)cn1] | 380 | 494 | 1H NMR (400 MHz, DMSO-d6) δ 10.42 (s, 1H), 10.07 (s, 1H), 8.56-8.25 (m, 2H), 7.72-7.61 (m, 3H), 7.57 (dd, J = 8.6, 2.8 Hz, 1H), 6.94 (t, J = 2.0 Hz, 1H), 3.06 (s, 3H), 2.69 (s, 3H), 1.36 (s, 9H). |
| 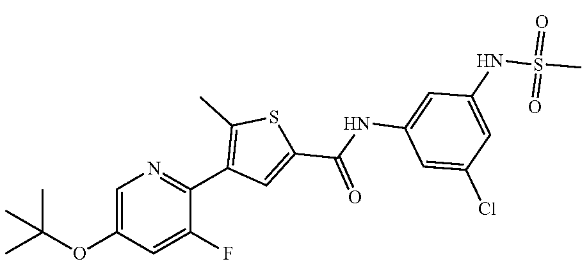 [SMILES: Cc1sc(C(=O)Nc2cc(Cl)cc(NS(C)(=O)=O)c2)cc1-c1ncc(OC(C)(C)C)cc1F] | 381 | 512 | 1H NMR (400 MHz, DMSO-d6) δ 10.42 (s, 1H), 10.07 (s, 1H), 8.28 (dd, J = 2.3, 1.3 Hz, 1H), 8.19 (d, J = 1.6 Hz, 1H), 7.70-7.59 (m, 3H), 6.94 (t, J = 2.0 Hz, 1H), 3.06 (s, 3H), 2.53 (d, J = 1.5 Hz, 3H), 1.40 (s, 9H). |

| Structure | Example No. | MS (ESI) [M + H]+ | 1H NMR |
|---|---|---|---|
| 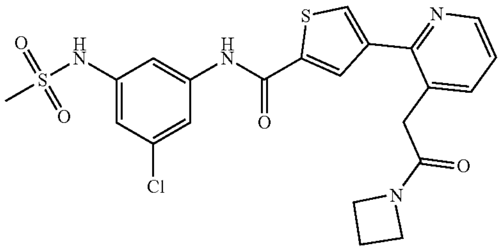 [SMILES: CS(=O)(=O)Nc1cc(Cl)cc(NC(=O)c2cc(-c3ncccc3CC(=O)N3CCC3)cs2)c1] | 382 | 505 | 1H NMR (300 MHz, DMSO-d6) δ 10.54 (s, 1H), 8.60-8.49 (m, 1H), 8.34 (d, J = 1.4 Hz, 1H), 8.05 (d, J = 1.3 Hz, 1H), 7.74 (d, J = 6.3 Hz, 1H), 7.68 (s, 1H), 7.63 (s, 1H), 7.38 (dd, J = 7.7, 4.6 Hz, 1H), 6.94 (s, 1H), 4.08 (t, J = 7.5 Hz, 2H), 3.85 (t, J = 7.7 Hz, 2H), 3.58 (s, 2H), 3.05 (s, 3H), 2.22-2.10 (m, 2H). |
| 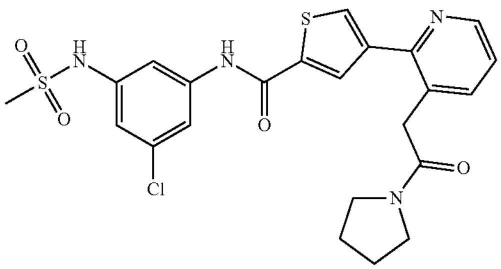 [SMILES: CS(=O)(=O)Nc1cc(Cl)cc(NC(=O)c2cc(-c3ncccc3CC(=O)N3CCCC3)cs2)c1] | 383 | 519 | 1H NMR (300 MHz, DMSO-d6) δ 10.54 (s, 1H), 8.55 (dd, J = 4.8, 1.7 Hz, 1H), 8.33 (d, J = 1.4 Hz, 1H), 7.97 (d, J = 1.3 Hz, 1H), 7.76-7.62 (m, 3H), 7.37 (dd, J = 7.8, 4.7 Hz, 1H), 6.95 (t, J = 2.0 Hz, 1H), 3.80 (s, 2H), 3.40 (t, J = 6.7 Hz, 2H), 3.28 (d, J = 6.7 Hz, 2H), 3.06 (s, 3H), 1.80 (dp, J = 26.7, 6.8 Hz, 4H). |
| 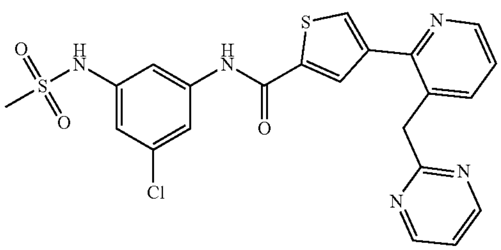 [SMILES: CS(=O)(=O)Nc1cc(Cl)cc(NC(=O)c2cc(-c3ncccc3Cc3ncccn3)cs2)c1] | 384 | 500 | 1H NMR (400 MHz, DMSO-d6) δ 10.51 (s, 1H), 10.02 (s, 1H), 8.73 (d, J = 4.9 Hz, 2H), 8.56 (dd, J = 4.7, 1.7 Hz, 1H), 8.39 (d, J = 1.4 Hz, 1H), 8.19 (d, J = 1.3 Hz, 1H), 7.78 (dd, J = 7.8, 1.7 Hz, 1H), 7.66 (dt, J = 14.8, 1.9 Hz, 2H), 7.40-7.32 (m, 2H), 6.95 (t, J = 2.0 Hz, 1H), 4.48 (s, 2H), 3.06 (s, 3H). |
| 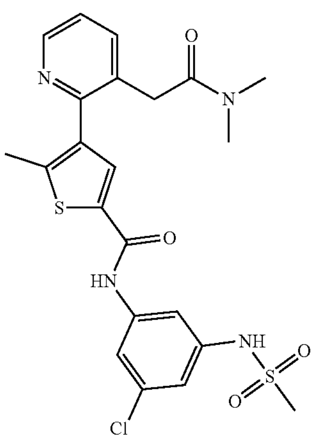 [SMILES: Cc1sc(C(=O)Nc2cc(Cl)cc(NS(C)(=O)=O)c2)cc1-c1ncccc1CC(=O)N(C)C] | 385 | 509 | 1H NMR (300 MHz, DMSO-d6) δ 10.33 (s, 1H), 10.06 (s, 1H), 8.54 (dd, J = 4.8, 1.7 Hz, 1H), 7.90 (s, 1H), 7.77-7.66 (m, 2H), 7.60 (t, J = 1.9 Hz, 1H), 7.40 (dd, J = 7.8, 4.7 Hz, 1H), 6.94 (t, J = 2.0 Hz, 1H), 3.62 (s, 2H), 3.06 (s, 3H), 2.82 (s, 3H), 2.75 (s, 3H), 2.28 (s, 3H). |
| 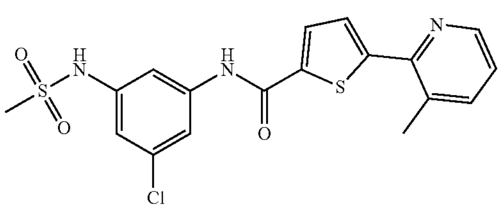 [SMILES: Cc1cccnc1-c1ccc(C(=O)Nc2cc(Cl)cc(NS(C)(=O)=O)c2)s1] | 386 | 422 | 1H NMR (400 MHz, DMSO-d6) δ 10.47 (s, 1H), 10.07 (s, 1H), 8.54-8.41 (m, 1H), 8.05 (d, J = 4.1 Hz, 1H), 7.83-7.54 (m, 4H), 7.32 (dd, J = 7.7, 4.7 Hz, 1H), 6.97 (t, J = 2.0 Hz, 1H), 3.08 (s, 3H), 2.59 (s, 3H). |

Example 36: N-(3-bromo-5-(methylsulfonamido)phenyl)-1-(pyridin-2-yl)-1H-pyrazole-4-carboxamide

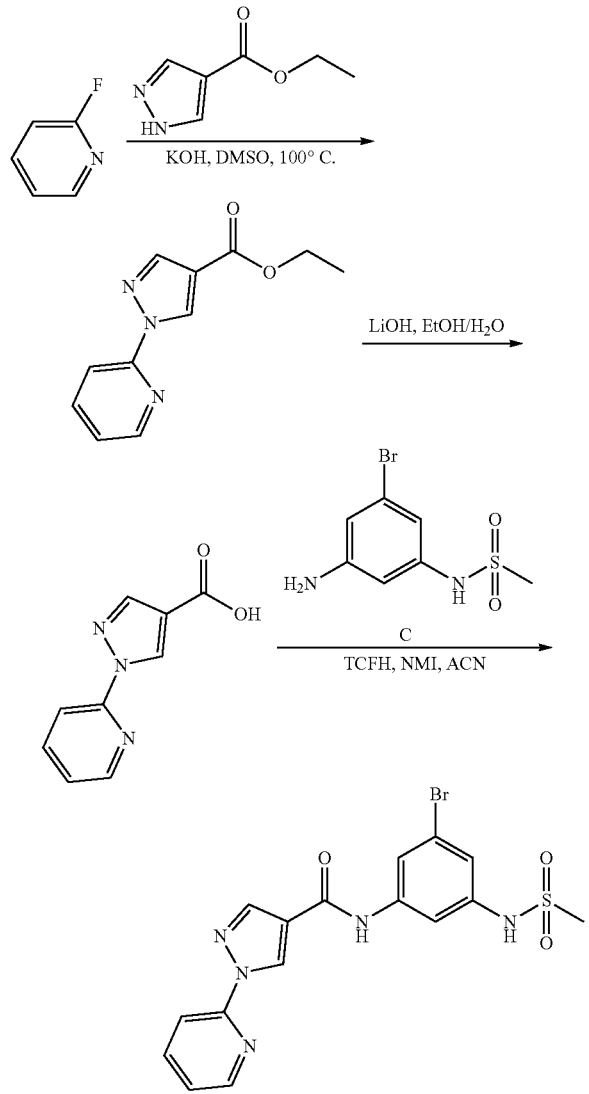

Step 1: To a stirred solution of 2-fluoropyridine (150 g, 1.54 mol), KOH (260 g, 4.62 mol), ethyl 1H-pyrazole-4-carboxylate (258.7 g, 1.85 mol) in 3500 mL of DMSO. Then the mixture was stirred for 2 h at 100'° C. The mixture was cooled then quenched with 3000 mL of water. The aqueous layer was extracted with 3×1000 mL of ethyl acetate. The mixture was concentrated and purified onto silica gel eluting with 35% of ethyl acetate in petroleum ether to afford ethyl 1-(pyridin-2-yl)-1H-pyrazole-4-carboxylate (168 g, 49.5%) as a yellow solid. LCMS (ESI) [M+H]⁺: 218

Step 2: To a stirred solution of ethyl 1-(pyridin-2-yl)-1H-pyrazole-4-carboxylate (168 g, 0.77 mol), LiOH (53 g, 2.32 mol) in 1000 mL of water and 3000 mL of tetrahydrofuran Then the mixture was stirred for 2 h at room temperature. the mixture was adjusted pH 6 with conc. HCl. The aqueous layer was extracted with 3×500 mL of ethyl acetate. This was concentrated and purified by reverse flash chromatography eluting with 50% acetonitrile in water (0.05% FA) to afford 1-(pyridin-2-yl)-1H-pyrazole-4-carboxylic acid (116 g, 80.5%) as an off-white solid. LCMS (ESI) [M+H]⁺: 190

Step 4: To a stirred solution of 1-(pyridin-2-yl)-1H-pyrazole-4-carboxylic acid (95 g, 0.51 mol), TCFH (211 g, 0.75 mol), NMI (246 g, 3.03 mol), N-(3-amino-5-bromophenyl)methanesulfonamide (134 g, 0.51 mol) in 300 mL of acetonitrile. Then the mixture was stirred for 2 h at room temperature. The mixture was concentrated and purified by reverse flash chromatography eluting with 50% acetonitrile in water (0.05% FA) to afford N-(3-bromo-5-methanesulfonamidophenyl)-1-(pyridin-2-yl)-1H-pyrazole-4-carbo xamide (51.5 g, 23.6%) as a white solid. LCMS (ESI) [M+H]⁺: 436. ¹H NMR (300 MHz, Acetone-d₆) δ 9.67 (s, 1H), 9.29 (d, J=0.9 Hz, 1H), 8.83 (s, 1H), 8.54 (dt, J=4.8, 1.4 Hz, 1H), 8.26 (d, J=0.8 Hz, 1H), 8.13-8.01 (m, 2H), 7.99 (dt, J=2.5, 1.2 Hz, 1H), 7.80 (dt, J=2.9, 1.4 Hz, 1H), 7.44 (h, J=4.7 Hz, 1H), 7.26 (t, J=1.9 Hz, 1H), 3.11 (s, 3H).

Examples 37-49 and 387

The compounds listed in the following table were prepared using a procedure similar to that described for example 36:

| Structure | Example No. | MS (ESI) [M + H]⁺ | ¹H NMR |
|---|---|---|---|
| (3-chloro-5-methanesulfonamidophenyl structure) | 37 | 392 | ¹H NMR (300 MHz, DMSO-d6) δ 10.31 (s, 1H), 10.08 (s, 1H), 9.43 (d, J = 0.8 Hz, 1H), 8.56 (ddd, J = 4.8, 1.8, 0.9 Hz, 1H), 8.30 (d, J = 0.8 Hz, 1H), 8.16-7.90 (m, 2H), 7.73 (t, J = 1.9 Hz, 1H), 7.64 (t, J = 1.9 Hz, 1H), 7.47 (ddd, J = 7.2, 4.8, 1.2 Hz, 1H), 6.95 (t, J = 1.9 Hz, 1H), 3.07 (s, 3H). |

| Structure | Example No. | MS (ESI) [M + H]+ | 1H NMR |
|---|---|---|---|
| 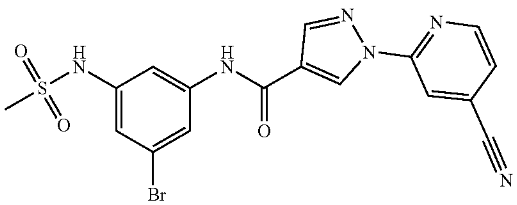 [SMILES: CS(=O)(=O)Nc1cc(Br)cc(NC(=O)c2cnn(-c3cc(C#N)ccn3)c2)c1] | 38 | 461 | 1H NMR (300 MHz, DMSO-d6) δ 10.34 (s, 1H), 10.08 (s, 1H), 9.44 (s, 1H), 8.81 (d, J = 5.1 Hz, 1H), 8.37 (d, J = 3.8 Hz, 2H), 7.93 (dd, J = 5.0, 1.4 Hz, 1H), 7.85 (t, J = 1.8 Hz, 1H), 7.68 (t, J = 1.9 Hz, 1H), 7.09 (t, J = 1.9 Hz, 1H), 3.07 (s, 3H). |
| 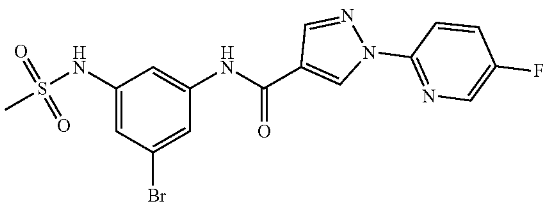 [SMILES: CS(=O)(=O)Nc1cc(Br)cc(NC(=O)c2cnn(-c3ccc(F)cn3)c2)c1] | 39 | 454 | 1H NMR (300 MHz, DMSO-d6) δ 10.29 (s, 1H), 10.06 (s, 1H), 9.36 (d, J = 0.8 Hz, 1H), 8.61 (t, J = 1.7 Hz, 1H), 8.31 (d, J = 0.8 Hz, 1H), 8.17-7.91 (m, 2H), 7.85 (t, J = 1.8 Hz, 1H), 7.69 (t, J = 1.9 Hz, 1H), 7.08 (t, J = 1.9 Hz, 1H), 3.07 (s, 3H). |
| 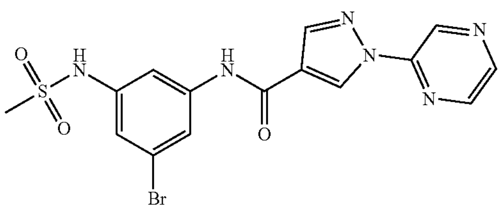 [SMILES: CS(=O)(=O)Nc1cc(Br)cc(NC(=O)c2cnn(-c3cnccn3)c2)c1] | 40 | 437 | 1H NMR (300 MHz, DMSO-d6) δ 10.34 (s, 1H), 10.07 (s, 1H), 9.42 (s, 1H), 9.29 (d, J = 1.5 Hz, 1H), 8.74 (d, J = 2.6 Hz, 1H), 8.66 (dd, J = 2.6, 1.4 Hz, 1H), 8.40 (s, 1H), 7.85 (t, J = 1.8 Hz, 1H), 7.68 (t, J = 1.9 Hz, 1H), 7.09 (t, J = 1.9 Hz, 1H), 3.08 (s, 3H). |
| 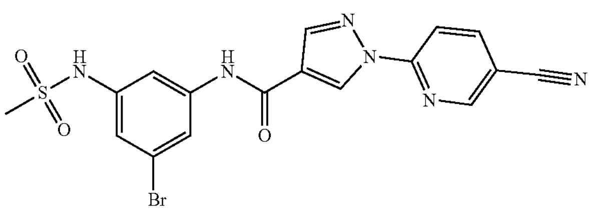 [SMILES: CS(=O)(=O)Nc1cc(Br)cc(NC(=O)c2cnn(-c3ccc(C#N)cn3)c2)c1] | 41 | 459 [M − H] | 1H NMR (300 MHz, DMSO-d6) δ 10.35 (s, 1H), 10.08 (s, 1H), 9.49 (s, 1H), 9.08 (dd, J = 2.2, 0.8 Hz, 1H), 8.55 (dd, J = 8.6, 2.2 Hz, 1H), 8.39 (s, 1H), 8.14 (d, J = 8.6 Hz, 1H), 7.85 (t, J = 1.8 Hz, 1H), 7.69 (d, J = 2.0 Hz, 1H), 7.09 (t, J = 1.9 Hz, 1H), 3.08 (s, 3H). |
| 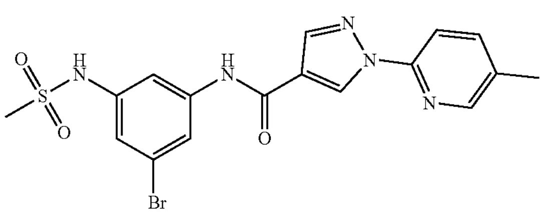 | 42 | 450 | 1H NMR (300 MHz, DMSO-d6) δ 10.27 (s, 1H), 10.06 (s, 1H), 9.40 (s, 1H), 8.39 (s, 1H), 8.27 (s, 1H), 8.03-7.79 (m, 3H), 7.69 (d, J = 1.9 Hz, 1H), 7.08 (t, J = 1.9Hz, 1H), 3.07 (s, 3H), 2.38 (s, 3H). |
| 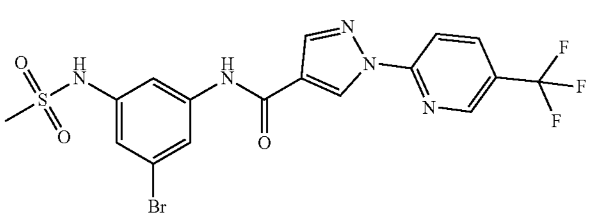 [SMILES: CS(=O)(=O)Nc1cc(Br)cc(NC(=O)c2cnn(-c3ccc(C(F)(F)F)cn3)c2)c1] | 43 | 504 | 1H NMR (300 MHz, DMSO-d6) δ 10.37 (s, 1H), 10.08 (s, 1H), 9.50 (d, J = 0.8 Hz, 1H), 9.14-8.84 (m, 1H), 8.56-8.42 (m, 1H), 8.38 (d, J = 0.8 Hz, 1H), 8.18 (d, J = 8.6 Hz, 1H), 7.86 (t, J = 1.8 Hz, 1H), 7.69 (t, J = 1.9 Hz, 1H), 7.09 (t, J = 1.9 Hz, 1H), 3.08 (s, 3H). |
| 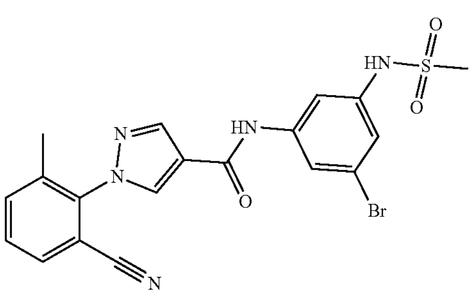 [SMILES: Cc1cccc(C#N)c1-n1cc(C(=O)Nc2cc(Br)cc(NS(C)(=O)=O)c2)cn1] | 44 | 474 | 1H NMR (300 MHz, DMSO-d6) δ 10.24 (s, 1H), 10.10 (s, 1H), 8.78 (s, 1H), 8.41 (s, 1H), 7.94 (d, J = 7.6 Hz, 1H), 7.83 (dd, J = 5.0, 3.1 Hz, 2H), 7.73-7.62 (m, 2H), 7.08 (t, J = 1.9 Hz, 1H), 3.07 (s, 3H), 2.14 (s, 3H). |

-continued

| Structure | Example No. | MS (ESI) [M + H]+ | 1H NMR |
|---|---|---|---|
| 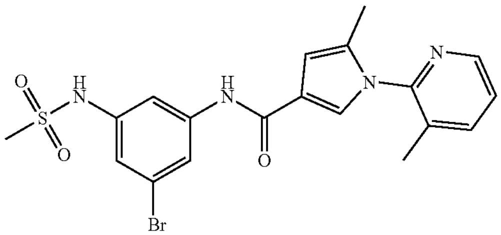 [SMILES: Cc1cccnc1-n1cc(C(=O)Nc2cc(Br)cc(NS(C)(=O)=O)c2)cc1C] | 45 | 463 | 1H NMR (400 MHz, Chloroform-d) δ 8.45 (d, J = 4.6 Hz, 1H), 7.89-7.73 (m, 2H), 7.58 (t, J = 9.8 Hz, 3H), 7.48-7.34 (m, 2H), 7.16 (d, J = 1.8 Hz, 1H), 6.37 (s, 1H), 3.00 (s, 3H), 2.16 (s, 3H), 2.07 (s, 3H). |
| 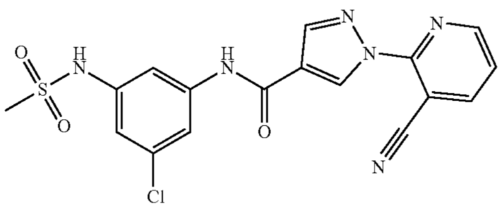 [SMILES: CS(=O)(=O)Nc1cc(Cl)cc(NC(=O)c2cnn(-c3ncccc3C#N)c2)c1] | 46 | 417 | 1H NMR (400 MHz, DMSO-d6) δ 10.38 (s, 1H), 10.10 (s, 1H), 9.39 (s, 1H), 8.84 (dd, J = 4.8, 1.7 Hz, 1H), 8.57 (dd, J = 7.9, 1.7 Hz, 1H), 8.40 (s, 1H), 7.72 (t, J = 1.9 Hz, 1H), 7.67 (dd, J = 7.9, 4.8 Hz, 1H), 7.63 (t, J = 1.9 Hz, 1H), 6.95 (t, J = 1.9 Hz, 1H), 3.07 (s, 3H). |
| 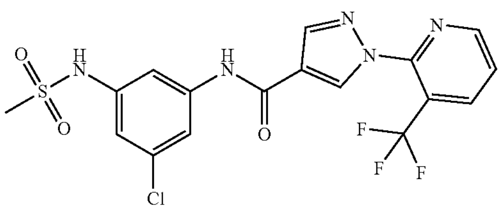 [SMILES: CS(=O)(=O)Nc1cc(Cl)cc(NC(=O)c2cnn(-c3ncccc3C(F)(F)F)c2)c1] | 47 | 460 | 1H NMR (400 MHz, DMSO-d6) δ 10.32 (s, 1H), 10.08 (s, 1H), 9.09 (s, 1H), 8.93-8.84 (m, 1H), 8.54 (dd, J = 7.9, 1.6 Hz, 1H), 8.32 (s, 1H), 7.82 (dd, J = 7.9, 4.8 Hz, 1H), 7.71 (t, J = 1.8 Hz, 1H), 7.61 (t, J = 1.9 Hz, 1H), 6.95 (t, J = 1.9 Hz, 1H), 3.07 (s, 3H). |
| 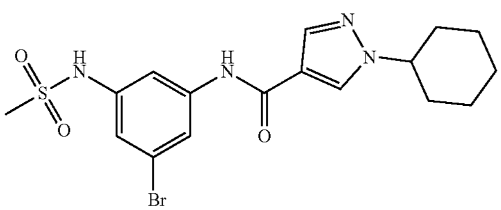 [SMILES: CS(=O)(=O)Nc1cc(Br)cc(NC(=O)c2cnn(C3CCCCC3)c2)c1] | 48 | 441 | 1H NMR (300 MHz, DMSO-d6) δ 10.03 (s, 1H), 9.97 (s, 1H), 8.40 (s, 1H), 8.03 (s, 1H), 7.80 (t, J = 1.8 Hz, 1H), 7.63 (t, J = 1.9 Hz, 1H), 7.05 (t, J = 1.9 Hz, 1H), 4.31-4.06 (m, 1H), 3.06 (s, 3H), 2.14-1.94 (m, 2H), 1.81 (t, J = 10.7 Hz, 2H), 1.69 (td, J = 11.9, 3.5 Hz, 3H), 1.41 (q, J = 12.7 Hz, 2H), 1.22 (q, J = 13.5, 13.0 Hz, 1H). |
| 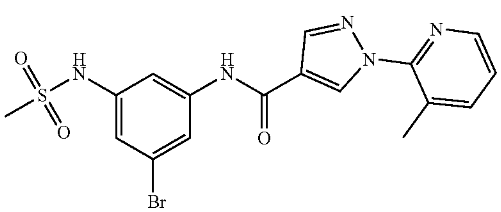 [SMILES: Cc1cccnc1-n1cc(C(=O)Nc2cc(Br)cc(NS(C)(=O)=O)c2)cn1] | 49 | 450 | 1H NMR (300 MHz, DMSO-d6) δ 10.25 (s, 1H), 10.06 (s, 1H), 9.10 (d, J = 0.8 Hz, 1H), 8.43 (dd, J = 4.8, 1.7 Hz, 1H), 8.28 (d, J = 0.8 Hz, 1H), 8.02-7.91 (m, 1H), 7.85 (t, J = 1.8 Hz, 1H), 7.68 (t, J = 1.9 Hz, 1H), 7.47 (dd, J = 7.6, 4.7 Hz, 1H), 7.08 (t, J = 1.9 Hz, 1H), 3.07 (s, 3H), 2.51 (dd, J = 3.9, 2.0 Hz, 3H). |
| 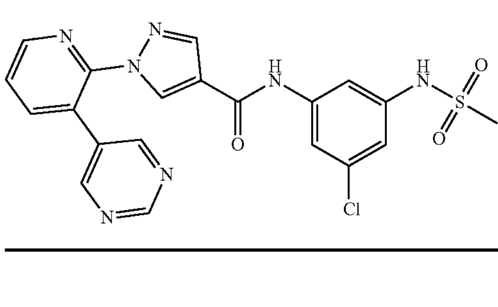 | 387 | 470.05 | 1H NMR (300 MHz, DMSO-d6) δ 10.27 (s, 1H), 10.06 (s, 1H), 9.15 (d, J = 8.9 Hz, 2H), 8.82-8.64 (m, 3H), 8.23 (dd, J = 7.7, 1.7 Hz, 1H), 8.00 (s, 1H), 7.80-7.67 (m, 2H), 7.60 (t, J = 1.9 Hz, 1H), 6.94 (t, J = 2.0 Hz, 1H), 3.07 (s, 3H). |

Example 50: N-(3-bromo-5-(methylsulfonamido)phenyl)-1-(pyrimidin-2-yl)-1H-pyrazole-4-carboxamide

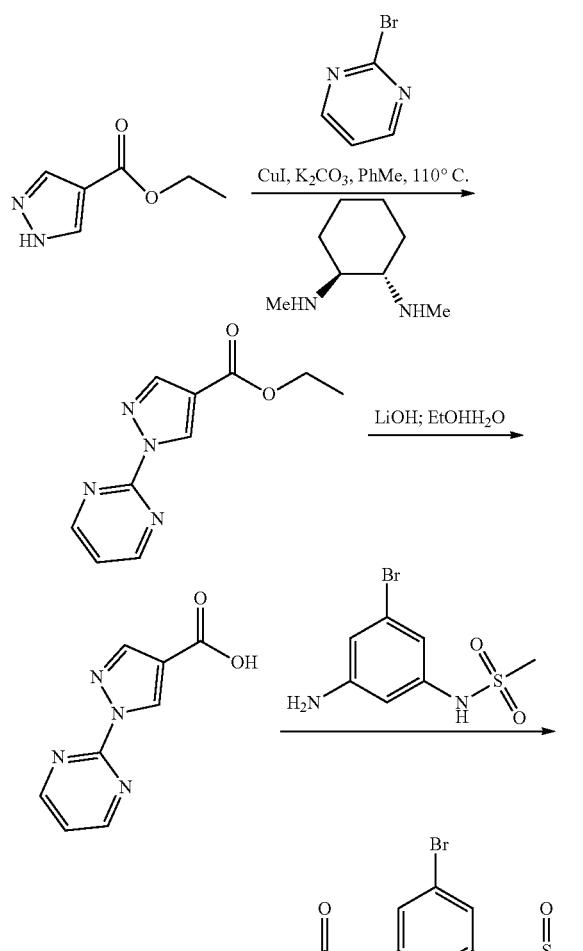

Step 1: A solution of ethyl 1H-pyrazole-4-carboxylate (500 mg, 3.568 mmol, 1 equiv) and pyrimidine, 2-bromo- (567.23 mg, 3.568 mmol, 1equiv) and (1S,2S)-N1, N2-dimethylcyclohexane-1,2-diamine (101.50 mg, 0.714 mmol, 0.2 equiv) and CuI (67.95 mg, 0.357 mmol, 0.1 equiv) and $K_2CO_3$ (1479.27 mg, 10.704 mmol, 3 equiv) in Toluene (5 mL) was stirred for 2 h at 110° C. under nitrogen atmosphere. The aqueous layer was extracted with EtOAc (3×30 mL). The residue was purified by silica gel column chromatography, eluted with Petroleum ether/EtOAc (1:1) to afford ethyl 1-(pyrimidin-2-yl) pyrazole-4-carboxylate (440 mg, 56.52%) as a white solid. LCMS (ESI) $[M+H]^+$: 219

Step 2: A solution of ethyl 1-(pyrimidin-2-yl) pyrazole-4-carboxylate (440 mg, 2.016 mmol, 1 equiv) and LiOH (144.87 mg, 6.048 mmol, 3 equiv) in EtOH (4 mL) and $H_2O$ (1.5 mL) was stirred for 1 h at 60° C. The mixture was acidified to pH 6 with HCl (aq.). The residue was purified by reverse phase flash chromatography with the following conditions: column, silica gel; mobile phase, MeCN in water, 0% to 100% gradient in 20 min; detector, UV 254 nm. This resulted in 11-(pyrimidin-2-yl) pyrazole-4-carboxylic acid (380 mg, 99.10%) as a white solid. LCMS (ESI) $[M+H]^+$: 191

Step 3: To a stirred solution of 1-(pyrimidin-2-yl) pyrazole-4-carboxylic acid (80 mg, 0.421 mmol, 1 equiv) and N-(3-amino-5-bromophenyl) methanesulfonamide (111.54 mg, 0.421 mmol, 1 equiv) in DMSO (4 mL) were added NMI (103.62 mg, 1.263 mmol, 3 equiv) and NMI (103.62 mg, 1.263 mmol, 3 equiv) in portions at room temperature. The residue was purified by reverse phase flash chromatography with the following conditions: column, silica gel; mobile phase, MeCN in water, 000 to 10000 gradient in 20 min; detector, UV 254 nm. This resulted in N-(3-bromo-5-methanesulfonamidophenyl)-1-(pyrimidin-2-yl) pyrazole-4-carboxamide (19.3 mg, 10.490) as a white solid. LCMS (ESI) $[M+H]^+$: 436. $^1$H NMR (300 MHz, DMSO-$d_6$) δ 10.34 (s, 1H), 10.07 (s, 1H), 9.46 (s, 1H), 8.96 (d, J=4.8 Hz, 2H), 8.33 (s, 1H), 7.86 (t, J=1.8 Hz, 1H), 7.69 (t, J=1.8 Hz, 1H), 7.59 (t, J=4.8 Hz, 1H), 7.09 (t, J=1.9 Hz, 1H), 3.08 (s, 3H).

Examples 51-60 and 388-393

The compounds listed in the following table were prepared using a procedure similar to that described for example 50:

| Structure | Example No. | MS (ESI) $[M + H]^+$ | $^1$H NMR |
|---|---|---|---|
| (structure shown) | 51 | 541 | $^1$H NMR (300 MHz, DMSO-d6) δ 10.14 (s, 1H), 10.06 (s, 1H), 8.83 (d, J = 0.6 Hz, 1H), 8.29 (d, J = 0.6 Hz, 1H), 7.82 (t, J = 1.8 Hz, 1H), 7.72-7.59 (m, 2H), 7.39 (dddd, J = 18.5, 11.4, 8.6, 4.3 Hz, 7H), 7.20-7.02 (m, 2H), 5.29 (s, 2H), 3.07 (s, 3H). |

| Structure | Example No. | MS (ESI) [M + H]+ | 1H NMR |
|---|---|---|---|
| 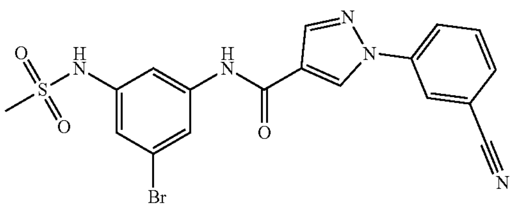 [SMILES: CS(=O)(=O)Nc1cc(Br)cc(NC(=O)c2cnn(-c3cccc(C#N)c3)c2)c1] | 52 | 460 | 1H NMR (300 MHz, DMSO-d6) δ 10.23 (s, 1H), 10.09(s, 1H),9.23 (s, 1H), 8.41 (d, J = 2.6 Hz, 2H), 8.33-8.18 (m, 1H), 7.95-7.71 (m, 3H), 7.65 (t, J = 1.9 Hz, 1H), 7.09 (t, J = 1.9 Hz, 1H), 3.07 (s, 3H). |
| 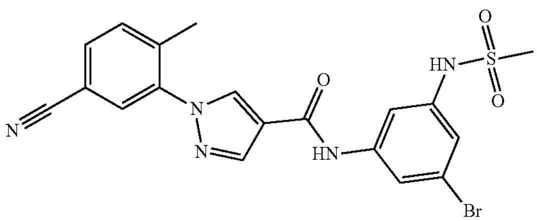 [SMILES: Cc1ccc(C#N)cc1-n1cc(C(=O)Nc2cc(Br)cc(NS(C)(=O)=O)c2)cn1] | 53 | 474 | 1H NMR (300 MHz, DMSO-d6) δ 10.18 (s, 1H), 10.07 (s, 1H), 8.76 (s, 1H), 8.34 (s, 1H), 8.02 (d, J = 1.7 Hz, 1H), 7.91 (dd, J = 7.9, 1.8 Hz, 1H), 7.83 (d, J = 1.9 Hz, 1H), 7.72-7.60 (m, 2H), 7.08 (t, J = 1.9 Hz, 1H), 3.07 (s, 3H), 2.35 (s, 3H). |
| 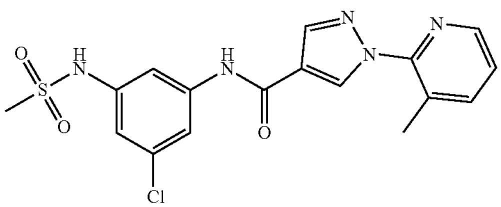 [SMILES: Cc1cccnc1-n1cc(C(=O)Nc2cc(Cl)cc(NS(C)(=O)=O)c2)cn1] | 54 | 406 | 1H NMR (300 MHz, Methanol-d4) δ 8.87 (d, J = 0.8 Hz, 1H), 8.40 (d, J = 4.8 Hz, 1H), 8.29 (d, J = 0.8 Hz, 1H), 7.99-7.84 (m, 1H), 7.70 (t, J = 1.9 Hz, 1H), 7.61 (t, J = 1.9 Hz, 1H), 7.45 (dd, J = 7.6, 4.7 Hz, 1H), 7.04 (t, J = 2.0 Hz, 1H), 3.06 (s, 3H), 2.51 (s, 3H). |
| 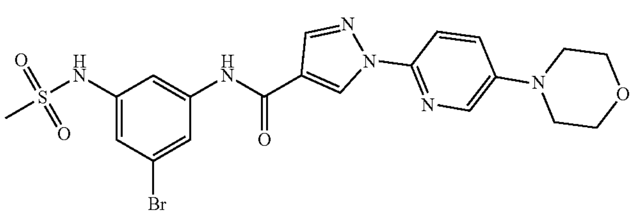 [SMILES: CS(=O)(=O)Nc1cc(Br)cc(NC(=O)c2cnn(-c3ccc(N4CCOCC4)cn3)c2)c1] | 55 | 521 | 1H NMR (300 MHz, DMSO-d6) δ 10.24 (s, 1H), 10.06 (s, 1H), 9.28 (d, J = 0.8 Hz, 1H), 8.32-8.14 (m, 2H), 7.91-7.76 (m, 2H), 7.74-7.53 (m, 2H), 7.08 (t, J = 1.8 Hz, 1H), 3.78 (t, J = 4.7 Hz, 4H), 3.25 (t, J = 4.9 Hz, 4H), 3.07 (s, 3H). |
| 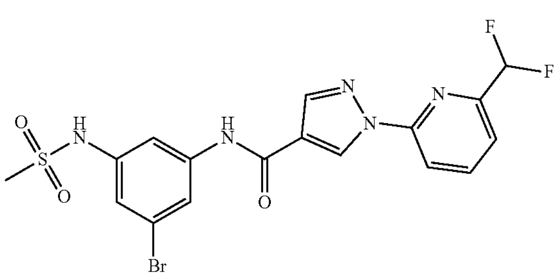 [SMILES: CS(=O)(=O)Nc1cc(Br)cc(NC(=O)c2cnn(-c3cccc(C(F)F)n3)c2)c1] | 56 | 486 | 1H NMR (300 MHz, DMSO-d6) δ 10.42 (s, 1H), 10.07 (s, 1H), 9.39 (d, J = 0.8 Hz, 1H), 8.35 (d, J = 0.8 Hz, 1H), 8.32-8.22 (m, 1H), 8.17 (dd, J = 8.3, 1.0 Hz, 1H), 7.86 (t, J = 1.8 Hz, 1H), 7.76 (d, J = 7.4 Hz, 1H), 7.69 (t, J = 1.9 Hz, 1H), 7.31-6.86 (m, 2H), 3.08 (s, 3H). |

| Structure | Example No. | MS (ESI) [M + H]+ | 1H NMR |
|---|---|---|---|
| 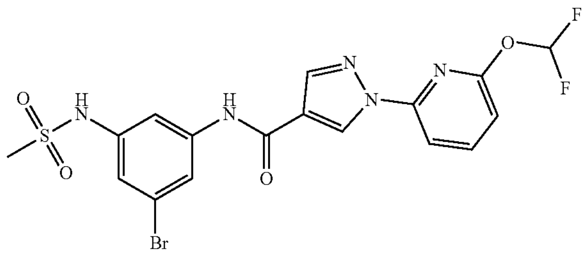 [SMILES: CS(=O)(=O)Nc1cc(Br)cc(NC(=O)c2cnn(-c3cccc(OC(F)F)n3)c2)c1] | 57 | 502 | 1H NMR (300 MHz, DMSO-d6) δ 10.34 (s, 1H), 10.08 (s, 1H), 9.31 (s, 1H), 8.39 (s, 1H), 8.28-7.97 (m, 2H), 7.89-7.72 (m, 2H), 7.68 (d, J = 1.9 Hz, 1H), 7.19-7.01 (m, 2H), 3.07 (s, 3H). |
| 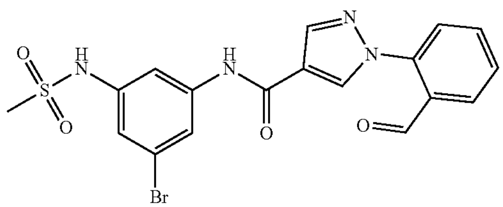 [SMILES: CS(=O)(=O)Nc1cc(Br)cc(NC(=O)c2cnn(-c3ccccc3C=O)c2)c1] | 58 | 463 | 1H NMR (300 MHz, DMSO-d6) δ 10.24 (s, 1H), 10.08 (s, 1H), 9.97 (s, 1H), 9.02 (s, 1H), 8.40 (s, 1H), 7.94 (dd, J = 7.7, 1.5 Hz, 1H), 7.91-7.77 (m, 3H), 7.72-7.63 (m, 2H), 7.09 (t, J = 1.9 Hz, 1H), 3.08 (s, 3H). |
| 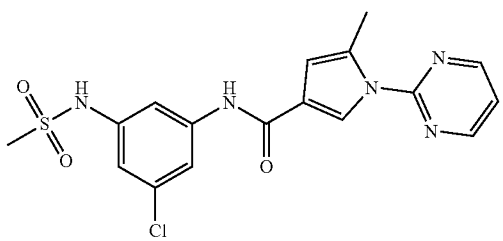 [SMILES: Cc1cc(C(=O)Nc2cc(Cl)cc(NS(C)(=O)=O)c2)cn1-c1ncccn1] | 59 | 406 | 1H NMR (300 MHz, DMSO-d6) δ 10.03 (s, 2H), 8.89 (d, J = 4.8 Hz, 2H), 8.51 (d, J = 2.1 Hz, 1H), 7.72 (t, J = 1.8 Hz, 1H), 7.66 (t, J = 1.8 Hz, 1H), 7.48 (t, J = 4.9 Hz, 1H), 6.90 (t, J = 1.9 Hz, 1H), 6.58 (dd, J = 1.8, 1.0 Hz, 1H), 3.06 (s, 3H), 2.61 (d, J = 1.0 Hz, 3H). |
| 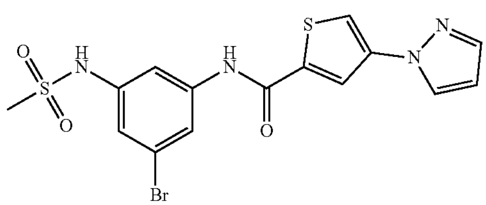 [SMILES: CS(=O)(=O)Nc1cc(Br)cc(NC(=O)c2cc(-n3cccn3)cs2)c1] | 60 | 441 | 1H NMR (300 MHz, DMSO-d6) δ 10.60 (s, 1H), 10.08 (s, 1H), 8.53 (d, J = 1.5 Hz, 1H), 8.40 (d, J = 2.5 Hz, 1H), 8.06 (d, J = 1.5 Hz, 1H), 7.82 (t, J = 1.8 Hz, 1H), 7.78-7.62 (m, 2H), 7.10 (t, J = 1.9 Hz, 1H), 6.71-6.31 (m, 1H), 3.07 (s, 3H) |
| 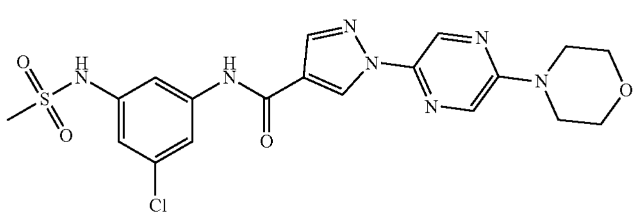 [SMILES: CS(=O)(=O)Nc1cc(Cl)cc(NC(=O)c2cnn(-c3cnc(N4CCOCC4)cn3)c2)c1] | 388 | 478.05 | 1H NMR (400 MHz, DMSO-d6) δ 10.24 (s, 1H), 10.07 (s, 1H), 9.18 (s, 1H), 8.72 (d, J = 1.3 Hz, 1H), 8.36-8.09 (m, 2H), 7.70 (t, J = 1.9 Hz, 1H), 7.61 (t, J = 1.9 Hz, 1H), 6.93 (t, J = 2.0 Hz, 1H), 3.75 (dd, J = 5.9, 3.8 Hz, 4H), 3.60 (t, J = 4.9 Hz, 4H), 3.06 (s, 3H). |

| Structure | Example No. | MS (ESI) [M + H]+ | 1H NMR |
|---|---|---|---|
| 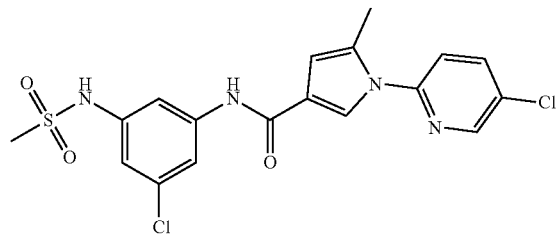 [SMILES: Cc1cc(C(=O)Nc2cc(Cl)cc(NS(C)(=O)=O)c2)cn1-c1ccc(Cl)cn1] | 389 | 438.9 | 1H NMR (400 MHz, DMSO-d6) δ 10.02 (s, 1H), 9.88 (s, 1H), 8.64 (d, J = 2.6 Hz, 1H), 8.16 (dd, J = 8.7, 2.6 Hz, 1H), 7.99 (d, J = 2.0 Hz, 1H), 7.73-7.65 (m, 2H), 7.62 (t, J = 1.9 Hz, 1H), 6.90 (t, J = 2.0 Hz, 1H), 6.59 (dd, J = 2.1, 1.1 Hz, 1H), 3.05 (s, 3H), 2.41-2.36 (m, 3H). |
| 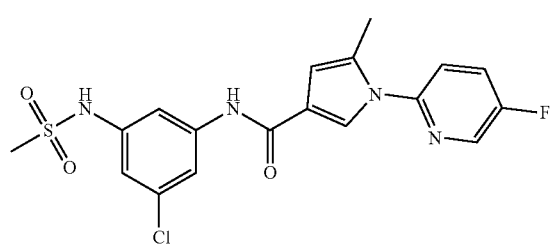 [SMILES: Cc1cc(C(=O)Nc2cc(Cl)cc(NS(C)(=O)=O)c2)cn1-c1ccc(F)cn1] | 390 | 422.9 | 1H NMR (400 MHz, DMSO-d6) δ 9.92 (d, J = 57.4 Hz, 2H), 8.59 (d, J = 3.0 Hz, 1H), 8.04-7.90 (m, 2H), 7.76-7.68 (m, 2H), 7.63 (t, J = 2.0 Hz, 1H), 6.90 (t, J = 1.9 Hz, 1H), 6.58 (s, 1H), 3.06 (s, 3H), 2.35 (s, 3H). |
| 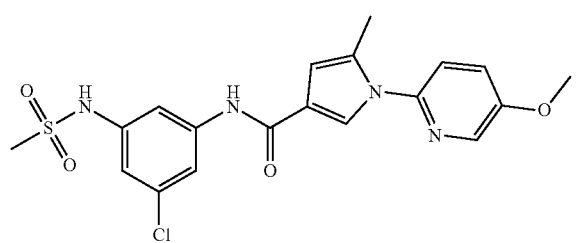 | 391 | 435 | 1H NMR (400 MHz, DMSO-d6) δ 10.00 (s, 1H), 9.81 (s, 1H), 8.28 (d, J = 3.0 Hz, 1H), 7.86 (d, J = 2.0 Hz, 1H), 7.70 (t, J = 1.9 Hz, 1H), 7.66-7.52 (m, 3H), 6.88 (t, J = 2.0 Hz, 1H), 6.54 (t, J = 1.6 Hz, 1H), 3.90 (s, 3H), 3.04 (s, 3H), 2.31 (d, J = 1.0 Hz, 3H). |
| 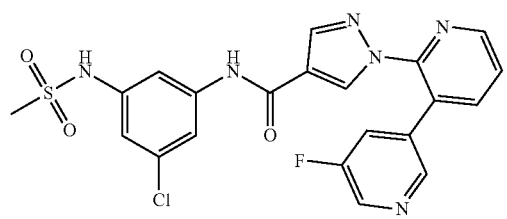 [SMILES: CS(=O)(=O)Nc1cc(Cl)cc(NC(=O)c2cnn(-c3ncccc3-c3cncc(F)c3)c2)c1] | 392 | 487 | 1H NMR (400 MHz, DMSO-d6) δ 10.20 (s, 1H), 9.07 (s, 1H), 8.68 (dd, J = 4.8, 1.7 Hz, 1H), 8.55 (d, J = 2.8 Hz, 1H), 8.27 (t, J = 1.8 Hz, 1H), 8.18 (dd, J = 7.7, 1.7 Hz, 1H), 7.99 (s, 1H), 7.78-7.64 (m, 2H), 7.59 (t, J = 1.9 Hz, 1H), 7.47 (t, J = 1.9 Hz, 1H), 6.87 (t, J = 2.0 Hz, 1H), 2.96 (s, 3H). |
| 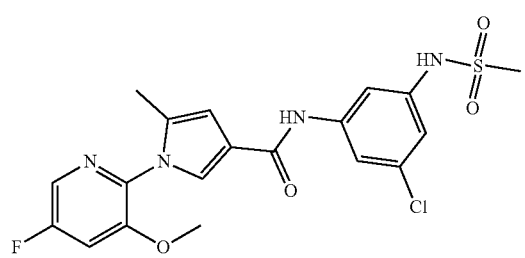 [SMILES: COc1cc(F)cnc1-n1cc(C(=O)Nc2cc(Cl)cc(NS(C)(=O)=O)c2)cc1C] | 393 | 453 | 1H NMR (300 MHz, DMSO-d6) δ 9.99 (s, 1H), 9.78 (s, 1H), 8.19 (d, J = 2.5 Hz, 1H), 7.86 (dd, J = 10.3, 2.4 Hz, 1H), 7.71 (d, J = 1.9 Hz, 1H), 7.66-7.59 (m, 2H), 6.89 (t, J = 2.0 Hz, 1H), 6.53 (d, J = 1.7 Hz, 1H), 3.90 (s, 3H), 3.06 (s, 3H), 2.07 (d, J = 1.0 Hz, 3H). |

Example 61: N-(3-chloro-5-(methylsulfonamido) phenyl)-1-(3-(pyridin-3-ylmethoxy)pyridin-2-yl)- 1H-pyrazole-4-carboxamide

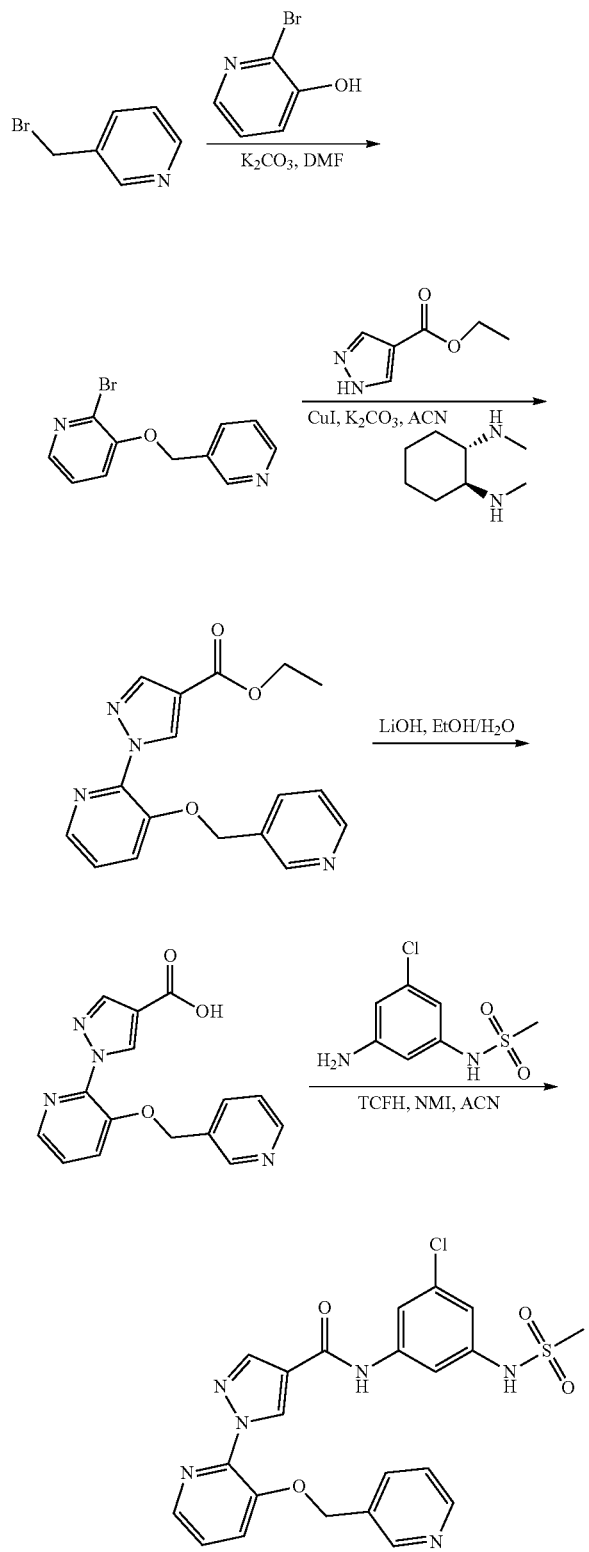

Step 1: To a mixture of 3-(bromomethyl)pyridine (520 mg, 3.02 mmol), 2-bromopyridin-3-ol (629 mg, 3.62 mmol), K$_2$CO$_3$ (1.25 g, 9.06 mmol) was added DMF (5 mL). The resulting mixture was stirred for 2 hours at 60° C. under N$_2$ atmosphere. The reaction mixture was extracted with ethyl acetate. The organic phase was concentrated under reduced pressure. The residue was purified by flash chromatography on silica gel eluting with 15% of ethyl acetate in petroleum ether to afford 2-bromo-3-[(pyridin-3-yl) methoxy]pyridine (550 mg, 68.6%) as a white solid. LCMS [M+H]$^+$: 265

Step 2: To a mixture of 2-bromo-3-[(pyridin-3-yl) methoxy]pyridine (550 mg, 2.07 mmol), (1S,2S)-N1,N2-di methylcyclohexane-1,2-diamine (117 mg, 0.828 mmol), ethyl 1H-pyrazole-4-carboxylate (434 mg, 3.10 mmol), CuI (78.8 mg, 0.414 mmol) and K$_2$CO$_3$ (855 mg, 6.20 mmol) was added ACN (6 mL). The resulting mixture was stirred for 2 hours at 90° C. under N$_2$ atmosphere. The reaction mixture was extracted with ethyl acetate. The organic phase was concentrated under reduced pressure. The residue was purified by flash chromatography on silica gel eluting with 95% of ethyl acetate in petroleum ether to afford ethyl 1-{3-[(pyridin-3-yl)methoxy]pyridin-2-yl}-1H-pyrazole-4-carboxylate (450 mg, 66.9%) as a yellow solid. LCMS [M+H]$^+$: 325

Step 3: To a stirred solution of ethyl 1-{3-[(pyridin-3-yl) methoxy]pyridin-2-yl}-1H-pyrazole-4-carboxy late (450 mg, 1.38 mmol) in 4 mL of EtOH and 4 mL of water was added LiOH (289 mg, 6.89 mmol). The resulting mixture was stirred for two hours at room temperature. Then it was concentrated, and the PH value of the residue solution was adjusted to 3 with 1M HCl(aq). The product was precipitated from the solution. After filtration, the filter cake was washed with water and dried under vacuum. This resulted in 1-{3-[(pyridin-3-yl)methoxy]pyridin-2-yl}-1H-pyrazole-4-carboxylic acid (260 mg, 63.2%) as a white solid. LCMS [M+H]$^+$: 297

Step 4: To a mixture of 1-{3-[(pyridin-3-yl)methoxy] pyridin-2-yl}-1H-pyrazole-4-carboxylic acid (120 mg, 0.405 mmol) and N-(3-amino-5-chlorophenyl)methanesulfonamide (107 mg, 0.485 mmol) in ACN (1 mL) was added TCFH (169 mg, 0.607 mmol) and NMI (99.2 mg, 1.21 mmol) at room temperature for two hours. Then it was concentrated, the residue was purified by reverse phase flash chromatography eluting with 65% of acetonitrile in water (0.1% NH$_4$HCO$_3$) to afford N-(3-chloro-5-methanesulfonamidophenyl)-1-{3-[(pyridin-3-yl)methoxy]pyridin-2-yl}-1H-pyrazole-4-carboxamide (27.0 mg, 13.3%) as a white solid. LCMS [M+H]$^+$: 499. $^1$H NMR (300 MHz, DMSO-d$_6$) δ 10.21 (s, 1H), 10.08 (s, 1H), 8.91 (d, J=0.7 Hz, 1H), 8.70-8.63 (m, 1H), 8.53 (dd, J=4.8, 1.7 Hz, 1H), 8.30 (d, J=0.7 Hz, 1H), 8.21 (dd, J=4.6, 1.3 Hz, 1H), 7.96-7.81 (m, 2H), 7.70 (t, J=1.9 Hz, 1H), 7.65-7.53 (m, 2H), 7.47-7.37 (m, 1H), 6.94 (t, J=2.0 Hz, 1H), 5.36 (s, 2H), 3.07 (s, 3H).

Examples 62-70

The compounds listed in the following table were prepared using a procedure similar to that described for example 61:

| Structure | Example No. | MS (ESI) [M + H]+ | ¹H NMR |
|---|---|---|---|
| 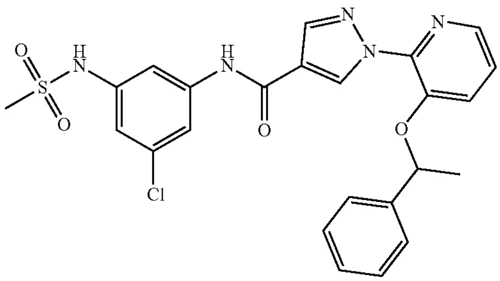 [SMILES: CC(Oc1cccnc1-n1cc(C(=O)Nc2cc(Cl)cc(NS(C)(=O)=O)c2)cn1)c1ccccc1] | 62 | 512 | ¹H NMR (400 MHz, DMSO-d6) δ 10.23 (s, 1H), 10.07 (s, 1H), 8.89 (s, 1H), 8.33 (s, 1H), 8.10 (d, J = 4.6 Hz, 1H), 7.72 (t, J = 1.9 Hz, 1H), 7.69-7.60 (m, 2H), 7.46-7.36 (m, 3H), 7.37-7.30 (m, 2H), 7.29-7.23 (m, 1H), 6.95 (t, J = 2.0 Hz, 1H), 3.08 (s, 3H), 1.53 (d, J = 6.3 Hz, 3H). |
| 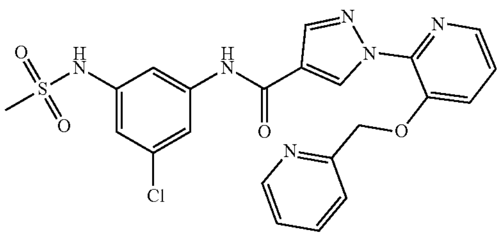 [SMILES: CS(=O)(=O)Nc1cc(Cl)cc(NC(=O)c2cnn(-c3ncccc3OCc3ccccn3)c2)c1] | 63 | 499 | ¹H NMR (300 MHz, DMSO-d6) δ 10.23 (s, 1H), 10.07 (s, 1H), 8.98 (s, 1H), 8.58 (dt, J = 4.7, 1.5 Hz, 1H), 8.32 (s, 1H), 8.19 (dd, J = 4.6, 1.3 Hz, 1H), 7.93-7.79 (m, 2H), 7.72 (t, J = 1.9 Hz, 1H), 7.62 (t, J = 1.9 Hz, 1H), 7.59-7.49 (m, 2H), 7.34 (ddd, J = 7.6, 4.9, 1.2 Hz, 1H), 6.95 (t, J = 1.9 Hz, 1H), 5.39 (s, 2H), 3.08 (s, 3H). |
| 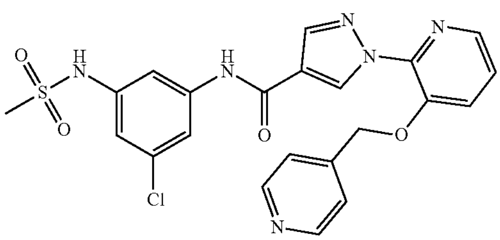 [SMILES: CS(=O)(=O)Nc1cc(Cl)cc(NC(=O)c2cnn(-c3ncccc3OCc3ccncc3)c2)c1] | 64 | 499 | ¹H NMR (300 MHz, DMSO-d6) δ 10.24 (s, 1H), 10.08 (s, 1H), 8.96 (d, J = 0.7 Hz, 1H), 8.73-8.46 (m, 2H), 8.34 (d, J = 0.7 Hz, 1H), 8.21 (dd, J = 4.6, 1.3 Hz, 1H), 7.83 (dd, J = 8.4, 1.4 Hz, 1H), 7.72 (t, J = 1.9 Hz, 1H), 7.62 (t, J = 1.9 Hz, 1H), 7.57 (dd, J = 8.3, 4.7 Hz, 1H), 7.46-7.35 (m, 2H), 6.95 (t, J = 1.9 Hz, 1H), 5.39 (s, 2H), 3.08 (s, 3H). |
| 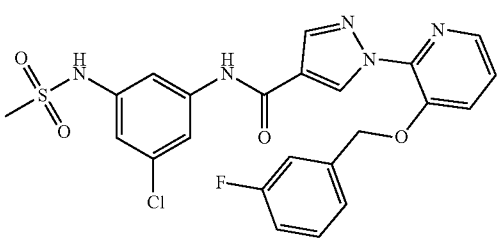 [SMILES: CS(=O)(=O)Nc1cc(Cl)cc(NC(=O)c2cnn(-c3ncccc3OCc3cccc(F)c3)c2)c1] | 65 | 516 | ¹H NMR (300 MHz, DMSO-d6) δ 10.22 (s, 1H), 10.08 (s, 1H), 8.93 (d, J = 0.7 Hz, 1H), 8.32 (d, J = 0.7 Hz, 1H), 8.20 (dd, J = 4.6, 1.3 Hz, 1H), 7.86 (dd, J = 8.4, 1.4 Hz, 1H), 7.71 (t, J = 1.8 Hz, 1H), 7.62 (t, J = 1.9 Hz, 1H), 7.57 (dd, J = 8.3, 4.6 Hz, 1H), 7.43 (td, J = 8.0, 6.0 Hz, 1H), 7.29 (t, J = 6.8 Hz, 2H), 7.15 (td, J = 8.5, 2.1 Hz, 1H), 6.95 (t, J = 1.9 Hz, 1H), 5.34 (s, 2H), 3.08 (s, 3H). |
| 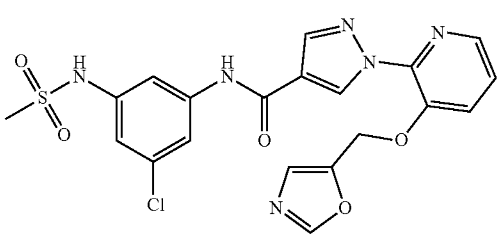 [SMILES: CS(=O)(=O)Nc1cc(Cl)cc(NC(=O)c2cnn(-c3ncccc3OCc3cnco3)c2)c1] | 66 | 489 | ¹H NMR (400 MHz, DMSO-d6) δ 10.20 (s, 1H), 10.09 (s, 1H), 8.81 (s, 1H), 8.40 (s, 1H), 8.27 (s, 1H), 8.21 (dd, J = 4.6, 1.3 Hz, 1H), 7.98 (dd, J = 8.4, 1.4 Hz, 1H), 7.70 (t, J = 1.9 Hz, 1H), 7.62-7.54 (m, 2H), 7.35 (s, 1H), 6.94 (t, J = 2.0 Hz, 1H), 5.39 (s, 2H), 3.07 (s, 3H). |

| Structure | Example No. | MS (ESI) [M + H]+ | 1H NMR |
|---|---|---|---|
| 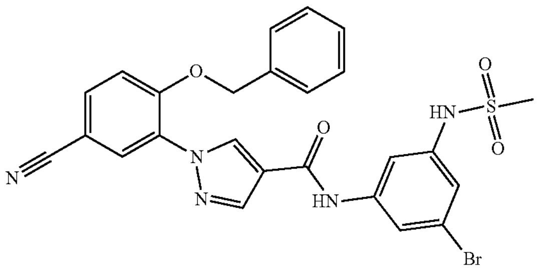 [SMILES: CS(=O)(=O)Nc1cc(Br)cc(NC(=O)c2cnn(-c3cc(C#N)ccc3OCc3ccccc3)c2)c1] | 67 | 566 | 1H NMR (300 MHz, DMSO-d6) δ 10.19 (s, 1H), 10.06 (s, 1H), 8.87 (s, 1H), 8.35 (s, 1H), 8.16 (d, J = 2.1 Hz, 1H), 7.95 (dd, J = 8.7, 2.2 Hz, 1H), 7.81 (t, J = 1.8 Hz, 1H), 7.65 (d, J = 1.9 Hz, 1H), 7.56 (d, J = 8.8 Hz, 1H), 7.46 (d, J = 7.2 Hz, 2H), 7.43-7.27 (m, 3H), 7.08 (t, J = 1.9 Hz, 1H), 5.42 (s, 2H), 3.07 (s, 3H). |
| 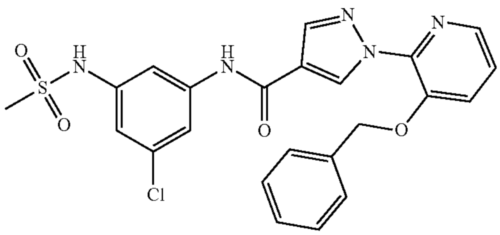 [SMILES: CS(=O)(=O)Nc1cc(Cl)cc(NC(=O)c2cnn(-c3ncccc3OCc3ccccc3)c2)c1] | 68 | 498 | 1H NMR (300 MHz, DMSO-d6) δ 10.21 (s, 1H), 10.08 (s, 1H), 8.90 (d, J = 0.7 Hz, 1H), 8.30 (d, J = 0.7 Hz, 1H), 8.18 (dd, J = 4.6, 1.3 Hz, 1H), 7.86 (dd, J = 8.4, 1.4 Hz, 1H), 7.71 (t, J = 1.9 Hz, 1H), 7.61 (t, J = 1.9 Hz, 1H), 7.55 (dd, J = 8.3, 4.7 Hz, 1H), 7.49-7.42 (m, 2H), 7.42-7.27 (m, 3H), 6.95 (t, J = 1.9 Hz, 1H), 5.31 (s, 2H), 3.08 (s, 3H). |
| 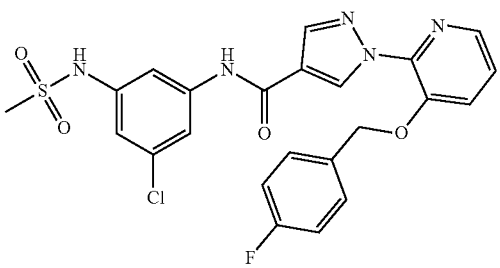 [SMILES: CS(=O)(=O)Nc1cc(Cl)cc(NC(=O)c2cnn(-c3ncccc3OCc3ccc(F)cc3)c2)c1] | 69 | 516 | 1H NMR (400 MHz, DMSO-d6) δ 10.21 (s, 1H), 10.08 (s, 1H), 8.89 (s, 1H), 8.29 (s, 1H), 8.18 (dd, J = 4.6, 1.3 Hz, 1H), 7.86 (dd, J = 8.4, 1.3 Hz, 1H), 7.71 (t, J = 1.9 Hz, 1H), 7.61 (t, J = 1.9 Hz, 1H), 7.56 (dd, J = 8.3, 4.6 Hz, 1H), 7.53-7.43 (m, 2H), 7.30-7.14 (m, 2H), 6.94 (t, J = 2.0 Hz, 1H), 5.29 (s, 2H), 3.07 (s, 3H). |
| 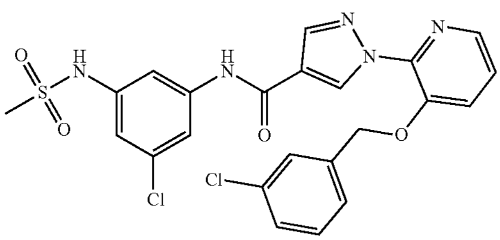 [SMILES: CS(=O)(=O)Nc1cc(Cl)cc(NC(=O)c2cnn(-c3ncccc3OCc3cccc(Cl)c3)c2)c1] | 70 | 532 | 1H NMR (400 MHz, DMSO-d6) δ 10.21 (s, 1H), 10.05 (s, 1H), 8.93 (s, 1H), 8.30 (s, 1H), 8.20 (d, J = 4.6 Hz, 1H), 7.85 (d, J = 8.3 Hz, 1H), 7.70 (t, J = 1.8 Hz, 1H), 7.61 (t, J = 1.9 Hz, 1H), 7.57 (dd, J = 8.3, 4.7 Hz, 1H), 7.54 (s, 1H), 7.46-7.31 (m, 3H), 6.94 (t, J = 1.9 Hz, 1H), 5.32 (s, 2H), 3.07 (s, 3H). |

Example 71: 4-bromo-N-(3-fluoro-5-(methylsulfonamido)phenyl)thiophene-2-carboxamide

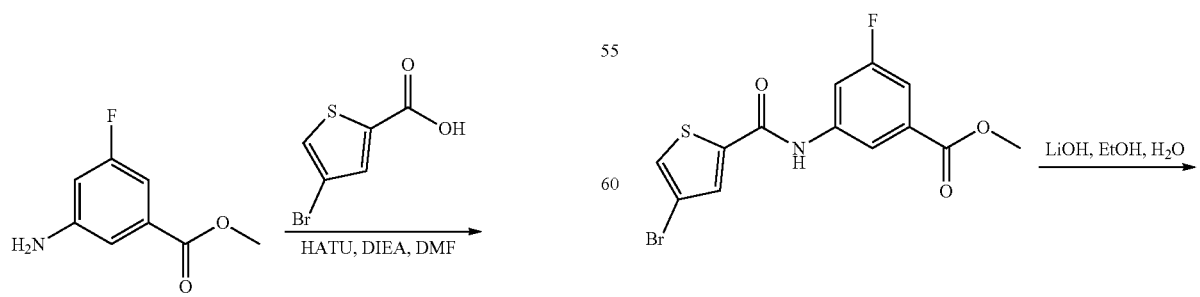

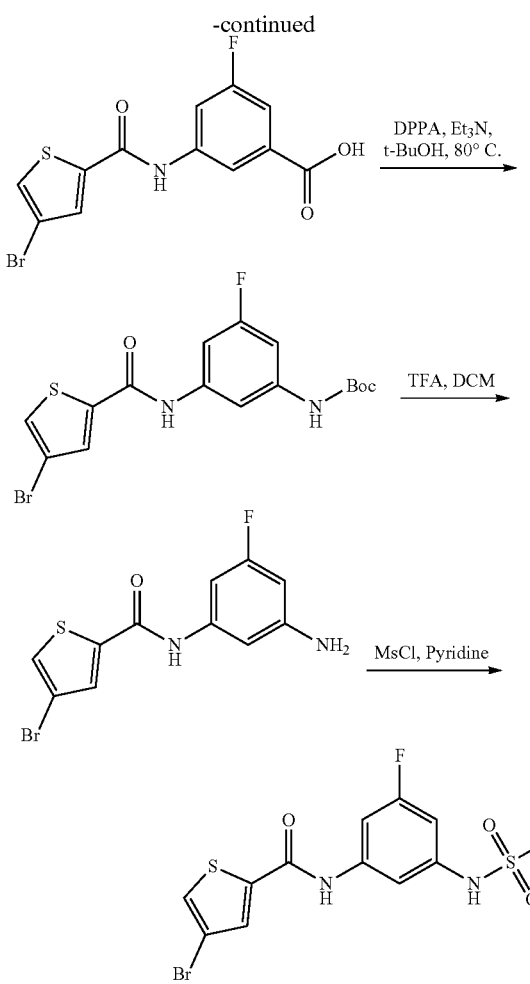

Step 1: To a stirred solution of methyl 3-amino-5-fluorobenzoate (1 g, 5.91 mmol), HATU (2.92 g, 7.68 mmol) and DIEA (2.28 g, 17.7 mmol) in DMF (10 mL) was added 4-bromothiophene-2-carboxylic acid (1.3 4 g, 6.50 mmol). Then the mixture was stirred for 1 h at room temperature. The mixture was concentrated and purified by reverse phase flash chromatography eluting with ACN/H₂O (5-95%, acidic system) to afford methyl 3-(4-bromothiophene-2-amido)-5-fluorobenzoate (1.28 g, 3.59 mmol) as a yellow solid. LCMS (ESI) [M+H]⁺: 358

Step 2: To a stirred solution of methyl 3-(4-bromothiophene-2-amido)-5-fluorobenzoate (1.25 g, 3.48 mmol) in EtOH (10 mL) and H₂O (10 mL) was added LiOH (416 mg, 17.4 mmol). Then the mixture was stirred for 2 h at room temperature. The mixture was acidified to pH 5 with citric acid. The precipitated solids were collected by filtration and washed with water. The resulting solid was dried under vacuum to afford 3-(4-bromothiophene-2-amido)-5-fluorobenzoic acid (1.02 g, 2.98 mmol) as a white solid. LCMS (ESI) [M+H]⁺: 344

Step 3: To a stirred solution of 3-(4-bromothiophene-2-amido)-5-fluorobenzoic acid (1 g, 2.906 mmol, 1 equiv) and DPPA (1.04 g, 3.778 mmol, 1.3 equiv) in t-BuOH (20 mL) was added Et3N (0.88 g, 8.718 mmol, 3 equiv) at 80° C. under nitrogen atmosphere for 6 h. The resulting mixture was concentrated under reduced pressure. The residue was purified by silica gel column chromatography, eluted with Petroleum ether/EtOAc (2:1) to afford tert-butyl N-[3-(4-bromothiophene-2-amido)-5-fluorophenyl]carbamate (750 mg, 61.53%) as a light yellow solid. LCMS (ESI) [M+H]⁺: 415

Step 4: To a stirred solution of tert-butyl N-[3-(4-bromothiophene-2-amido)-5-fluorophenyl]carbamate (700 mg, 1.68 mmol) in DCM (10 mL) was added TFA (1.91 g, 16.8 mmol) dropwise at 0° C. for 1 h. The resulting mixture was concentrated under vacuum. The mixture was basified to pH 9 with NaOH. The mixture was concentrated and purified by flash chromatography on silica gel eluting with EtOAc/Petroleum ether (0-100%) to afford N-(3-amino-5-fluorophenyl)-4-bromothiophene-2-carboxamide (513 mg, 1.62 mmol) as a yellow solid. LCMS (ESI) [M+H]⁺: 315

Step 5: To a stirred solution of N-(3-amino-5-fluorophenyl)-4-bromothiophene-2-carboxamide (100 mg, 0.317 mmol) in Pyridine (5 mL) was added MsCl (39.8 mg, 0.348 mmol) dropwise at 0° C. Then the mixture was stirred for 1 h at room temperature. The mixture was concentrated and purified by flash chromatography on silica gel eluting with EtOAc/Petroleum ether (0-100%) to afford 4-bromo-N-(3-fluoro-5-methanesulfonamidophenyl)thiophene-2-carboxamide (25.3 mg, 0.0643 mmol) as a white solid. LCMS (ESI) [M+H]⁺: 393. ¹H NMR (300 MHz, DMSO-d₆) δ 10.52 (s, 1H), 10.12 (s, 1H), 8.11 (d, J=1.5 Hz, 1H), 8.05 (d, J=1.4 Hz, 1H), 7.46 (dd, J=10.4, 2.1 Hz, 2H), 6.75 (dt, J=10.5, 2.2 Hz, 1H), 3.08 (s, 3H).

Examples 72-78

The compounds listed in the following table were prepared using a procedure similar to that described for example 71:

| Structure | Example No. | MS (ESI) [M + H]⁺ | ¹H NMR |
|---|---|---|---|
| 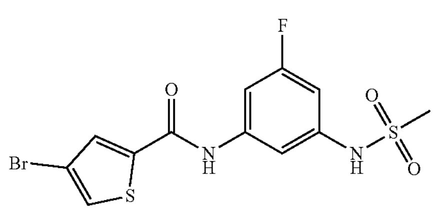 [SMILES: CS(=O)(=O)Nc1cc(F)cc(NC(=O)c2cc(Br)cs2)c1] | 72 | 407 | ¹H NMR (300 MHz, DMSO-d6) δ 10.51 (s, 1H), 10.15 (s, 1H), 8.11 (d, J = 1.5 Hz, 1H), 8.04 (d, J = 1.4 Hz, 1H), 7.45 (dt, J = 9.7, 2.2 Hz, 2H), 6.76 (dt, J = 10.5, 2.2 Hz, 1H), 3.19 (q, J = 7.3 Hz, 2H), 1.22 (t, J = 7.3 Hz, 3H). |

-continued

| Structure | Example No. | MS (ESI) [M + H]⁺ | ¹H NMR |
|---|---|---|---|
| (structure with methylsulfonamide, fluoro, phenyl-thiophene carboxamide) | 73 | 391 | ¹H NMR (300 MHz, DMSO-d6) δ 10.51 (s, 1H), 10.12 (s, 1H), 8.49 (d, J = 1.5 Hz, 1H), 8.22 (d, J = 1.4 Hz, 1H), 7.85-7.67 (m, 2H), 7.57-7.42 (m, 4H), 7.42-7.29 (m, 1H), 6.76 (dt, J = 10.5, 2.2 Hz, 1H), 3.09 (s, 3H). |
| (structure with ethylsulfonamide, fluoro, phenyl-thiophene carboxamide) | 74 | 405 | ¹H NMR (300 MHz, DMSO-d6) δ 10.50 (s, 1H), 10.15 (s, 1H), 8.49 (d, J = 1.5 Hz, 1H), 8.22 (d, J = 1.4 Hz, 1H), 7.82-7.70 (m, 2H), 7.55-7.43 (m, 4H), 7.42-7.32 (m, 1H), 6.76 (dt, J = 10.4, 2.2 Hz, 1H), 3.20 (q, J = 7.3 Hz, 2H), 1.23 (t, J = 7.3 Hz, 3H). |
| (structure with methylsulfonamide, chloro, phenyl-thiophene carboxamide) | 75 | 407 | ¹H NMR (300 MHz, DMSO-d6) δ 10.47 (s, 1H), 10.11 (s, 1H), 8.49 (d, J = 1.5 Hz, 1H), 8.23 (d, J = 1.4 Hz, 1H), 7.80-7.72 (m, 2H), 7.66 (dt, J = 12.1, 1.9 Hz, 2H), 7.49 (t, J = 7.6 Hz, 2H), 7.42-7.30 (m, 1H), 6.98 (t, J = 1.9 Hz, 1H), 3.08 (s, 3H). |
| (structure with methylsulfonamide, chloro, pyridyl-thiophene carboxamide) | 76 | 408 | ¹H NMR (400 MHz, DMSO-d6) δ 10.61 (s, 1H), 10.14 (s, 1H), 8.75 (d, J = 1.3 Hz, 1H), 8.64 (dt, J = 4.8, 1.5 Hz, 1H), 8.51 (d, J = 1.3 Hz, 1H), 7.96-7.86 (m, 2H), 7.72-7.66 (m, 2H), 7.36 (ddd, J = 6.2, 4.8, 2.5 Hz, 1H), 6.97 (t, J = 2.0 Hz, 1H), 3.18 (q, J = 7.3 Hz, 2H), 1.22 (t, J = 7.3 Hz, 3H). |
| (structure with ethylsulfonamide, chloro, pyridyl-thiophene carboxamide) | 77 | 422 | ¹H NMR (300 MHz, DMSO-d6) δ 10.61 (s, 1H), 10.14 (s, 1H), 8.75 (d, J = 1.4 Hz, 1H), 8.65 (dt, J = 4.8, 1.4 Hz, 1H), 8.52 (d, J = 1.3 Hz, 1H), 7.97-7.85 (m, 2H), 7.69 (d, J = 2.0 Hz, 2H), 7.36 (td, J = 5.3, 2.9 Hz, 1H), 6.97 (t, J = 1.9 Hz, 1H), 3.18 (dd, J = 8.1, 6.6 Hz, 2H), 1.23 (t, J = 7.3 Hz, 3H). |
| (structure with methylsulfonamide, bromo, pyridyl-thiophene carboxamide) | 78 | 452 | ¹H NMR (300 MHz, DMSO-d6) δ 10.46 (s, 1H), 9.00 (d, J = 2.3 Hz, 1H), 8.60-8.50 (m, 2H), 8.38 (d, J = 1.4 Hz, 1H), 8.14 (dt, J = 8.0, 2.0 Hz, 1H), 7.78 (t, J = 1.8 Hz, 1H), 7.66 (t, J = 1.9 Hz, 1H), 7.52 (dd, J = 8.0, 4.7 Hz, 1H), 7.09 (t, J = 1.9 Hz, 1H), 3.05 (s, 3H). |

Example 79: N-(3-chloro-5-(methylsulfonamido)phenyl)-1-ethyl-5-phenyl-1H-pyrrole-3-carboxamide

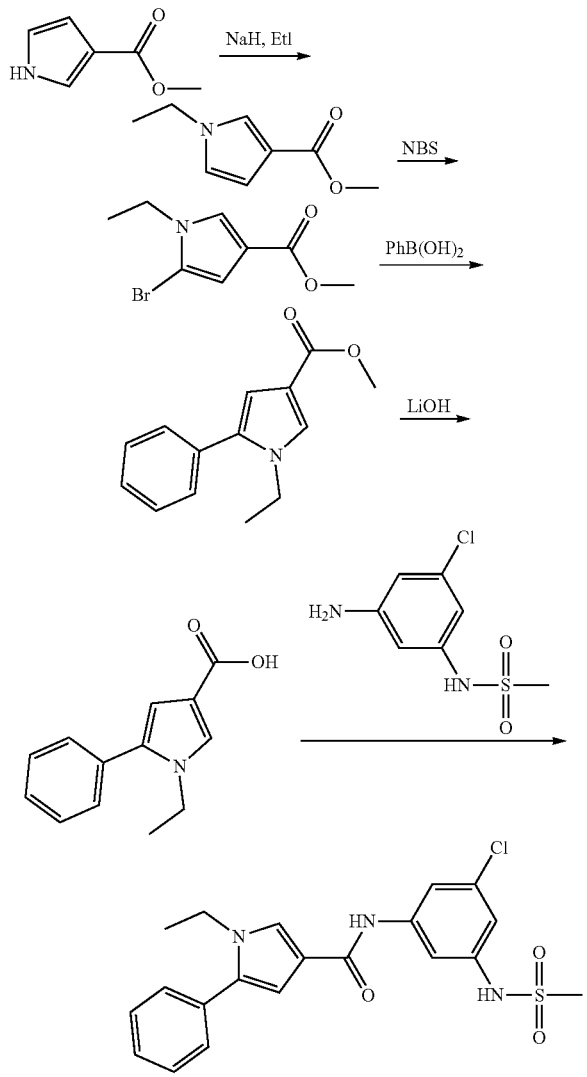

Step 1: To a solution of methyl 1H-pyrrole-3-carboxylate (2.0 g, 15.9 mmol) in DMF (20 mL) was added NaH (791 mg, 19.8 mmol, 60% purity) at 0° C. The mixture was stirred at 0-5° C. for 15 min, MeI (3.37 g, 23.8 mmol) was added to the above mixture at 0-5° C. The mixture was stirred at 25° C. for 1.5 h. The mixture was poured into water (20 mL) and extracted with EA (30 mL*3). The combined organic layers were washed with brine (15 mL*2) and dried over Na$_2$SO$_4$. The mixture was filtered, and the filtrate was concentrated in vacuo to give a crude. The crude product was pre-purified by column chromatography on silica gel eluted with PE:EA=100:1 to 5:1. Methyl 1-ethyl-1H-pyrrole-3-carboxylate (1.2 g, 7.83 mmol, 98.3% yield) was obtained as yellow oil. LCMS: MS (ESI) Retention time: 0.654 min, (M+1)+=154.0. $^1$H NMR (400 MHz, CHLOROFORM-d) δ=7.24 (t, J=2.0 Hz, 1H) 6.52-6.56 (m, 1H) 6.50 (dd, J=2.8, 1.6 Hz, 1H) 3.86 (q, J=7.2 Hz, 2H) 3.72 (s, 3H) 1.37 (t, J=7.2 Hz, 3H).

Step 2: To a solution of Methyl 1-ethyl-1H-pyrrole-3-carboxylate (1.2 g, 7.83 mmol) in THF (20 mL) was added NBS (1.43 g, 8.06 mmol) at 0° C. The mixture was stirred at 25° C. for 1 h. The mixture was poured into water (25 mL), and was extracted with EtOAc (30 mL*3). The combined organic layers were washed with brine (20 mL*3), dried over Na$_2$SO$_4$, and concentrated in vacuum to give a residue. The residue was purified by silica gel column chromatography (Petroleum ether/Ethyl acetate=10/1). Methyl 5-bromo-1-ethyl-1H-pyrrole-3-carboxylate (1.8 g, 7.75 mmol, 99.4% yield) was obtained as colorless oil. LCMS: MS (ESI) Retention time: 0.783 min, (M+1)+ =233.9. $^1$H NMR (400 MHz, CHLOROFORM-d) δ=7.37 (d, J=1.6 Hz, 1H) 6.59 (d, J=1.6 Hz, 1H) 3.96 (q, J=7.2 Hz, 2H) 3.75-3.84 (m, 3H) 1.40 (t, J=7.2 Hz, 3H).

Step 3: To a solution of methyl 5-bromo-1-ethyl-1H-pyrrole-3-carboxylate (1.8 g, 7.75 mmol) and phenylboronic acid (1.2 g, 9.84 mmol) in MeOH (4 mL) and toluene (30 mL) was added tetrakis(triphenylphosphane) palladium (716 mg, 620 μmol) and 2.0 M aq. Solution of disodium carbonate (7.75 ul, 15.5 mmol). The mixture was stirred under a nitrogen atmosphere at 80° C. for 3 h. The mixture was cooled to 25° C. poured into water (20 mL) and extracted with EA (30 mL*3). The combined organic layers were washed with brine (15 mL*2) and dried over Na$_2$SO$_4$. The mixture was filtered, and the filtrate was concentrated in vacuo to give residue. The resulting oil was purified by flash chromatography eluting with 5% ethyl acetate/hexanes. Compound 4 (1.1 g, 4.79 mmol, 62.1% yield) was obtained as colorless oil. LCMS: MS (ESI) Retention time: 0.830 min, (M+1)+=230.0. $^1$H NMR (400 MHz, CHLOROFORM-d) δ=7.26-7.40 (m, 6H) 6.50-6.52 (m, 1H) 3.86-3.93 (m, 2H) 3.73-3.79 (m, 3H) 1.26 (t, J=7.2 Hz, 3H).

Step 4: To a solution of methyl 1-ethyl-5-phenyl-1H-pyrrole-3-carboxylate (1 g, 3.53 mmol) in THF (10 mL), MeOH (10 mL) and H$_2$O (10 mL) was added LiOH—H$_2$O (545 mg, 13.0 mmol). The mixture was stirred at 25° C. for 2 h. The mixture was cooled to 25° C., and poured into water (20 mL). The pH of mixture was adjusted to 3-4 by 1 N HCl. And the mixture was extracted with EA (30 mL*3). The combined organic layers were washed with brine (15 mL*2) and dried over Na$_2$SO$_4$. The mixture was filtered, and the filtrate was concentrated in vacuo to give 1-ethyl-5-phenyl-1H-pyrrole-3-carboxylic acid (850 mg, 3.94 mmol, 90.6% yield) was obtained as white solid. LCMS: MS (ESI) Retention time: 0.766 min, (M+1)+=216.0. $^1$H NMR (400 MHz, METHANOL-d4) δ=7.51 (d, J=2.0 Hz, 1H) 7.35-7.48 (m, 5H) 6.42-6.55 (m, 1H) 4.01-4.10 (m, 2H) 1.28 (t, J=7.3 Hz, 3H)

Step 5: To a solution of 1-ethyl-5-phenyl-1H-pyrrole-3-carboxylic acid (250 mg, 1.16 mmol) and N-(3-amino-5-chlorophenyl)methanesulfonamide (300 mg, 1.35 mmol) in pyridine (5 mL) was added EDCI (667 mg, 3.48 mmol). The mixture was stirred at 25° C. for 15 h. The mixture was partitioned between water (30 mL) and EtOAc (30 mL). The aqueous layer was separated and extracted with EtOAc (30 mL*2). The combined organic phases were washed with 1N HCl (20 mL*4) and brine (25 mL*2), dried over anhydrous Na$_2$SO$_4$, filtered, and the 5 filtrate was evaporated in vacuo to give a residue. The residue was purified by Prep-HPLC (Column: Unisil 3-100 C18 Ultra 150*50 mm*3 um, mobile phase: [water (0.225%$_0$FA)-ACN]; B %: 36%-~66%, 10 min) and lyophilized. N-(3-chloro-5-(methylsulfonamido)phenyl)-1-ethyl-5-phenyl-7H-pyrrole-3-carboxamide (286.74 mg, 98.487 Purity, 0.675 mmol, 58.2 yield) was obtained as off-white solid. LCMS: MS (ESI) Retention time: 0.920 min (M+1)+=417.9. $^1$H NMR (400 MHz, DMSO-d$_6$) δ=9.93-10.26 (7, 1H) 9.77 (s, 1H) 7.72 (d, J=1.6 Hz, 2H) 7.58-7.66 (i, 1H) 7.34-7.54 (m, 5H) 6.88 (s, 1H) 6.74 (d, J=1.6 Hz, 1H) 4.02 (q, J=7.2 Hz, 2H) 2.94-3.12 (m, 3H) 1.25 (t, J=7.2 Hz, 3H)

Examples 80-82

The compounds listed in the following table were prepared using a procedure similar to that described for example 79:

| Structure | Example No. | MS (ESI) [M + H]+ | 1H NMR |
|---|---|---|---|
| (structure 80) | 80 | 472 | 1H NMR (400 MHz, DMSO-d6) δ 9.91 (s, 1H) 7.74-7.83 (m, 1H) 7.65-7.71 (m, 1H) 7.57-7.63 (m, 1H) 7.37-7.54 (m, 5H) 6.79-6.95 (m, 2H) 4.86-5.08 (m, 2H) 3.03 (s, 3H). |
| (structure 81) | 81 | 419 | 1H NMR (400 MHz, DMSO-d6) δ 9.80 (s, 2H), 8.50 (br d, J = 4.6 Hz, 1H), 8.27 (s, 1H), 7.80-7.62 (m, 4H), 7.34-7.22 (m, 1H), 6.91 (dd, J = 1.6, 6.4 Hz, 2H), 3.69 (d, J = 0.8 Hz, 3H), 3.06 (d, J = 1.2 Hz, 3H), 2.40 (s, 3H) |
| (structure 82) | 82 | 406 | 1H NMR (400 MHz, DMSO-d6) δ 9.96 (s, 2H), 8.81 (d, J = 4.8 Hz, 2H), 7.79-7.71 (m, 3H), 7.68 (s, 1H), 7.30 (t, J = 4.8 Hz, 1H), 6.90 (s, 1H), 4.10 (s, 3H), 3.07 (s, 3H) |

Example 83: 5-bromo-N-(3-chloro-5-(methylsulfonamido)phenyl)-1-methyl-1H-pyrrole-3-carboxamide

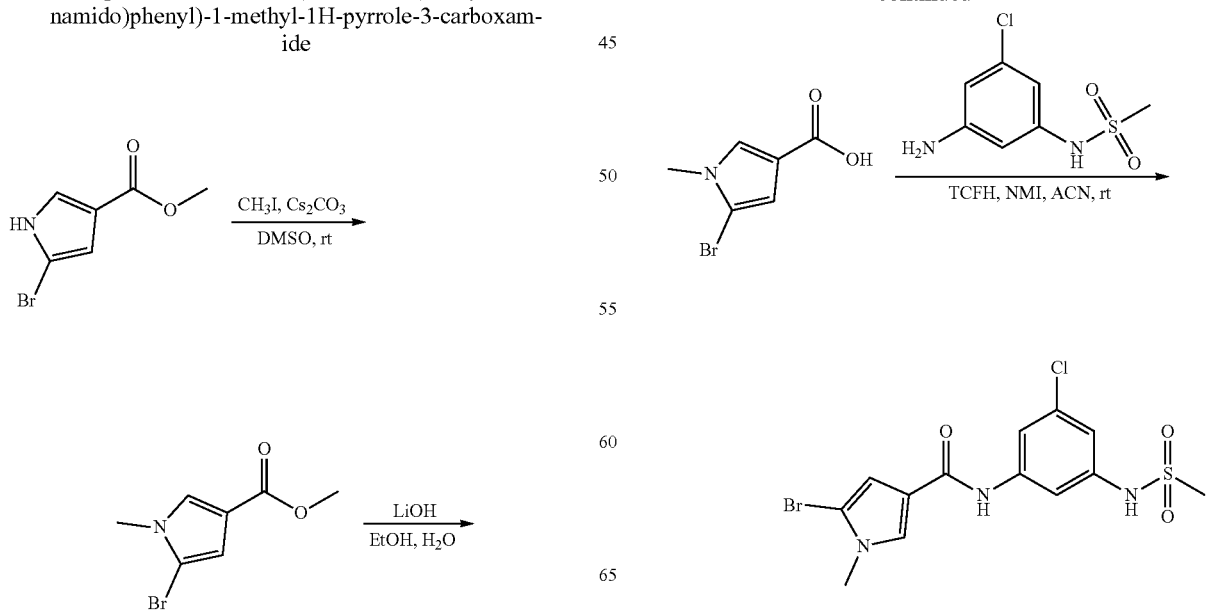

Step 1: To a stirred solution of methyl 5-bromo-1H-pyrrole-3-carboxylate (500 mg, 2.45 mmol), CH3I (521 mg, 3.67 mmol) and Cs$_2$CO$_3$ (2.38 g, 7.35 mmol) was added DMSO (10 mL). Then the mixture was stirred for 2 h at room temperature. The mixture was concentrated and purified by flash chromatography eluting with Petroleum ether/EtOAc (0-100%, acidic system) to afford methyl 5-bromo-1-methyl-1H-pyrrole-3-carboxylate (500 mg, 2.29 mmol) as a yellow solid. LCMS (ESI) [M+H]$^+$: 217.97

Step 2: To a stirred solution of methyl 5-bromo-1-methyl-1H-pyrrole-3-carboxylate (500 mg, 2.29 mmol) in EtOH (6 mL) and H$_2$O (2 mL) was added LiOH (164 mg, 6.86 mmol). Then the mixture was stirred for 2 h at room temperature. The mixture was concentrated and purified by reverse phase flash chromatography eluting with ACN/H$_2$O (0-100%, acidic system) to afford 5-bromo-1-methyl-1H-pyrrole-3-carboxylic acid (453 mg, 2.22 mmol) as an off-white solid. LCMS (ESI) [M+H]$^+$: 203.96

Step 3: To a stirred solution of 5-bromo-1-methyl-1H-pyrrole-3-carboxylic acid (203 mg, 0.994 mmol), TCFH (417 mg, 1.49 mmol) and N-(3-amino-5-chlorophenyl)methanesulfonamide (219 mg, 0.993 mmol), NMI (407 mg, 4.97 mmol) was added ACN (10 mL). Then the mixture was stirred for 2 h at room temperature. The mixture was concentrated and purified by reverse phase flash chromatography eluting with ACN/H$_2$O (0-100%, acidic system) to afford 5-bromo-N-(3-chloro-5-methanesulfonamidophenyl)-1-methyl-1H-pyrrole-3-carboxamide (31.9 mg, 0.0782 mmol) as an off-white solid. LCMS (ESI) [M+H]$^+$: 405.95. $^1$H NMR (300 MHz, DMSO-d$_6$) δ 10.04 (s, 1H), 9.78 (s, 1H), 7.72-7.65 (m, 2H), 7.59 (t, J=1.9 Hz, 1H), 6.89 (t, J=2.0 Hz, 1H), 6.83 (d, J=2.1 Hz, 1H), 3.63 (s, 3H), 3.05 (s, 3H).

Example 84: N-(3-bromo-5-(methylsulfonamido)phenyl)-1-methyl-5-(3-methylpyridin-2-yl)-1H-pyrrole-3-carboxamide

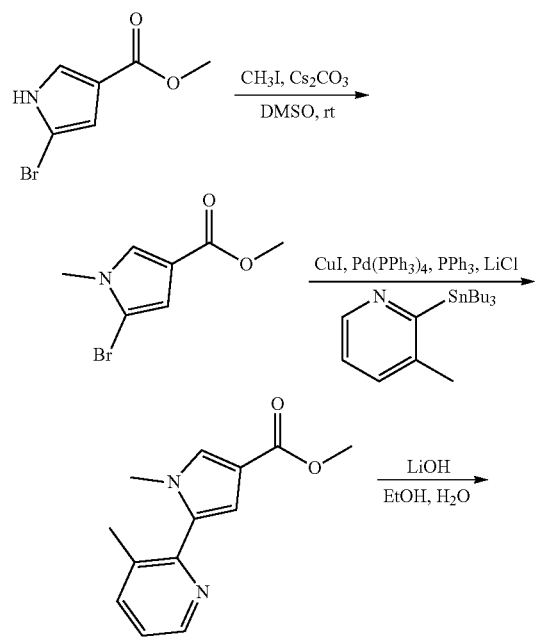

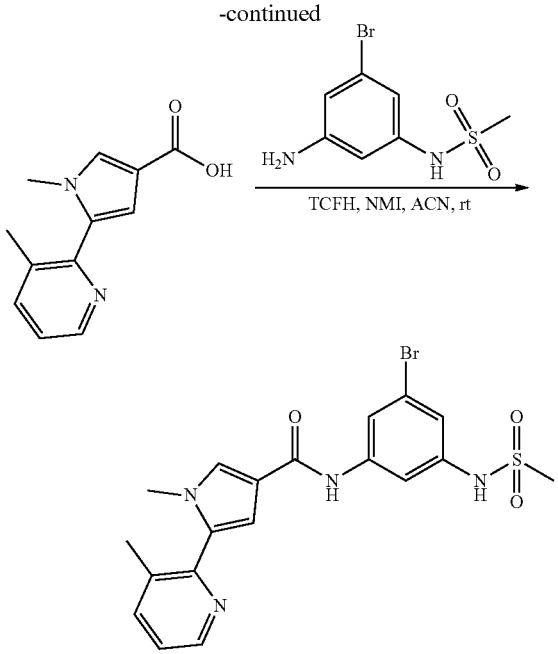

Step 1: To a stirred solution of methyl 5-bromo-1H-pyrrole-3-carboxylate (450 mg, 2.20 mmol) and iodomethane (374 mg, 2.64 mmol) in DMSO (10 mL). Then the mixture was stirred for 2 h at room temperature. The mixture was concentrated and purified by reverse flash chromatography eluting with ACN/H$_2$O (5-95%, acidic system) to afford methyl 5-bromo-1-methyl-1H-pyrrole-3-carboxylate (380 mg, 1.74 mmol) as a white solid.

Step 2: To a stirred solution of methyl 5-bromo-1-methyl-1H-pyrrole-3-carboxylate (380 mg, 1.74 mmol) and 3-methyl-2-(tributylstannyl)pyridine (1.99 g, 5.22 mmol) in DMSO (5 mL) was added CuI (66.2 mg, 348 µmol), Pd(PPh$_3$)$_4$ (402 mg, 348 µmol), PPh$_3$ (684 mg, 2.61 mmol) and LiCl (95.8 mg, 2.26 mmol) at 100° C. for 12 h. The reaction mixture was then cooled to RT, diluted with ethyl acetate (75 ml), then transferred to a separatory funnel, and washed with 10% aqueous ammonium chloride. The aqueous phase was extracted with ethyl acetate (3 times 60 ml). The combined organic phases were washed with water (3 times 75 ml), brine, and dried over magnesium sulfate. The mixture was concentrated and purified by flash chromatography on silica gel eluting with EA/PE (0-100%) to afford methyl 1-methyl-5-(3-methylpyridin-2-yl)-1H-pyrrole-3-carboxylate (346 mg, 1.50 mmol) as a white solid.

Step 3: To a stirred solution of methyl 1-methyl-5-(3-methylpyridin-2-yl)-1H-pyrrole-3-carboxylate (200 mg, 868 µmol) in EtOH (3 mL) and H$_2$O (3 mL) was added LiOH (207 mg, 8.68 mmol). Then the mixture was stirred for 2 h at room temperature. The mixture was acidified to pH 5 with citric acid. The precipitated solids were collected by filtration and washed with water. The resulting solid was dried under vacuum to afford 1-methyl-5-(3-methylpyridin-2-yl)-1H-pyrrole-3-carboxylic acid (150 mg, 693 µmol) as a white solid.

Step 4: To a stirred solution of 1-methyl-5-(3-methylpyridin-2-yl)-1H-pyrrole-3-carboxylic acid (100 mg, 462 µmol), TCFH (168 mg, 600 µmol) and NMI (113 mg, 1.38 mmol) in ACN (5 mL) was added N-(3-amino-5-bromophenyl)methanesulfonamide (134 mg, 508 µmol). Then the mixture was stirred for 1 h at room temperature. The mixture was concentrated and purified by reverse flash chromatography eluting with ACN/H₂O (5-95%,acidic system) to afford N-(3-bromo-5-methanesulfonamidophenyl)-1-methyl-5-(3-methylpyridin-2-yl)-1H-pyrrole-3-carboxamide (24.8 mg, 53.6 μmol) as a white solid. LCMS (ESI): [M+H]⁺: 463. ¹H NMR (300 MHz, DMSO-d₆) δ 9.99 (s, 1H), 9.78 (s, 1H), 8.56-8.44 (m, 1H), 7.84 (t, J=1.8 Hz, 1H), 7.77 (d, J=7.8 Hz, 1H), 7.72-7.64 (m, 2H), 7.29 (dd, J=7.7, 4.7 Hz, 1H), 7.03 (t, J=1.9 Hz, 1H), 6.91 (d, J=1.9 Hz, 1H), 3.69 (s, 3H), 3.06 (s, 3H), 2.40 (s, 3H).

Example 85: N-(3-bromo-5-(methylsulfonamido)phenyl)-1-cyclohexyl-5-methyl-1H-pyrrole-3-carboxamide

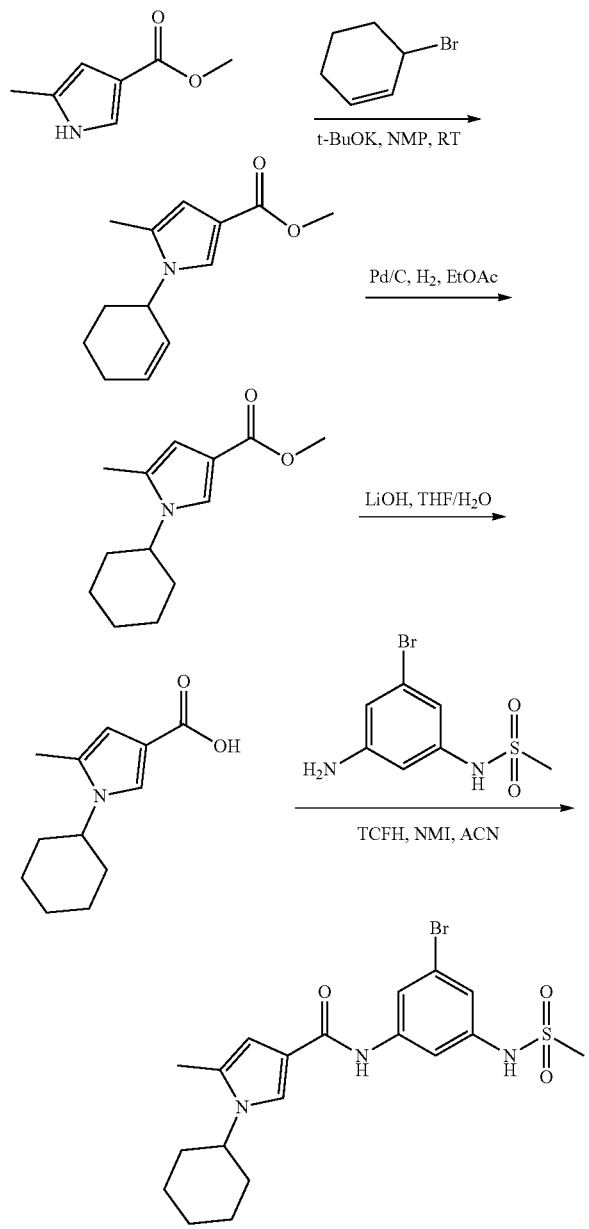

Step 1: To a mixture of methyl 5-methyl-1H-pyrrole-3-carboxylate (210 mg, 1.50 mmol), t-BuOK (252 mg, 2.25 mmol), 3-bromocyclohex-1-ene (288 mg, 1.79 mmol) was added NMP (2 mL). The resulting mixture was stirred for 2 hours at room temperature under N₂ atmosphere. The reaction mixture was extracted with ethyl acetate. The organic phase was concentrated under reduced pressure. The residue was purified by flash chromatography on silica gel eluting with 30% of ethyl acetate in petroleum ether to afford methyl 1-(cyclohex-2-en-1-yl)-5-methyl-1H-pyrrole-3-carboxylate (175 mg, 52.8%) as a light yellow solid. LCMS [M+H]⁺: 220

Step 2: To a mixture of methyl 1-(cyclohex-2-en-1-yl)-5-methyl-1H-pyrrole-3-carboxylate (175 mg, 0.798 mmol), Pd/C (84.9 mg, 0.798 mmol) was added EtOAc (2 mL). The resulting mixture was stirred for 2 hours at room temperature under H₂ atmosphere. The reaction mixture was filtered. Then the reaction mixture was concentrated under reduced pressure. The residue was purified by flash chromatography on silica gel eluting with 30% of ethyl acetate in petroleum ether to afford methyl 1-cyclohexyl-5-methyl-1H-pyrrole-3-carboxylate (145 mg, 82.1%) as a yellow solid. LCMS [M+H]⁺: 222

Step 3: To a stirred solution of methyl 1-cyclohexyl-5-methyl-1H-pyrrole-3-carboxylate (145 mg, 0.656 mmol) in 2 mL of THF and 2 mL of water was added LiOH (137.7 mg, 3.27 mmol). The resulting mixture was stirred overnight at 50° C. Then it was concentrated, and the PH value of the residue solution was adjusted to 3 with 1M HCl (aq). The product was precipitated from the solution. After filtration, the filter cake was washed with water (2 mL) and dried under vacuum. This resulted in 1-cyclohexyl-5-methyl-1H-pyrrole-3-carboxylic acid (60 mg, 43.9%) as a white solid. LCMS [M+H]⁺: 207

Step 4: To a mixture of 1-cyclohexyl-5-methyl-1H-pyrrole-3-carboxylic aid (60 mg, 0.289 mmol) and N-(3-amino-5-bromophenyl)methanesulfonamide (91.7 mg, 0.346 mmol) in ACN (1 mL) was added TCFH (121 mg, 0.433 mmol) and NMI (71.0 mg, 0.867 mmol) at room temperature. The resulting mixture was stirred for two hours, Then it was concentrated, the residue was purified by reverse phase flash chromatography eluting with 93% of acetonitrile in water (0.1% FA) to afford N-(3-bromo-5-methanesulfonamidophenyl)-1-cyclohexyl-5-methyl-1H-pyrrole-3-carboxamide (45.6 mg, 34.6%) as a white solid. LCMS [M+H]⁺: 454. ¹H NMR (300 MHz, DMSO-d₆) δ 9.96 (s, 1H), 9.56 (s, 1H), 7.81 (t, J=1.8 Hz, 1H), 7.66 (t, J=1.9 Hz, 1H), 7.57 (d, J=2.0 Hz, 1H), 7.00 (t, J=1.9 Hz, 1H), 6.34 (s, 1H), 3.87 (s, 1H), 3.05 (s, 3H), 2.26-2.13 (m, 3H), 1.88 (dd, J=25.6, 12.1 Hz, 4H), 1.51 (dd, J=46.0, 12.5 Hz, 6H).

Example 86: 1-(5-(4-acetylpiperazin-1-yl)pyridin-2-yl)-N-(3-bromo-5-(methylsulfonamido)phenyl)-1H-pyrazole-4-carboxamide

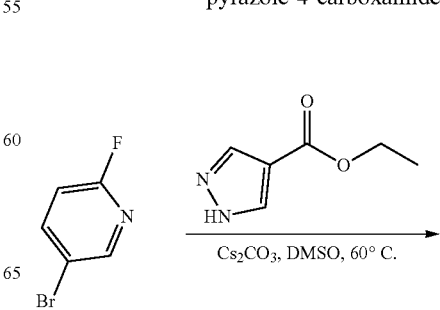

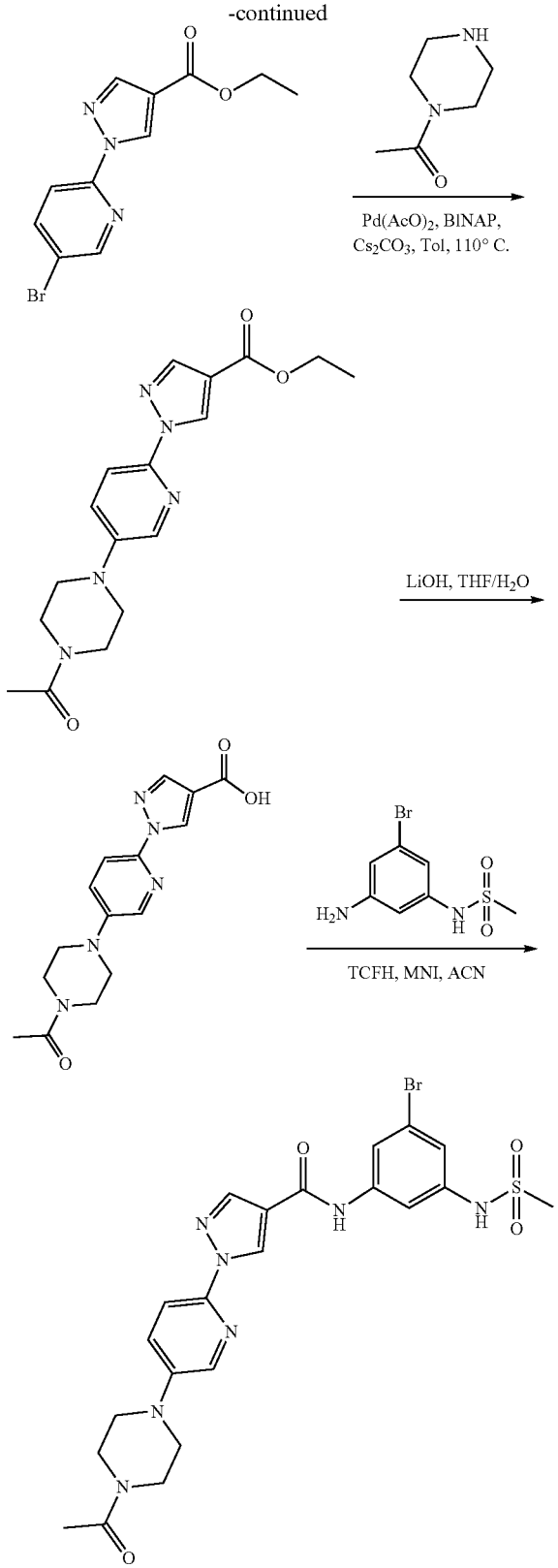

temperature. The resulting solution was stirred for two hours at 60° C. The reaction was quenched with water. The reaction mixture was diluted with water (50 mL). The resulting solution was extracted with EtOAc (50*3 mL) and the organic layers were combined. The organic layer was dried over anhydrous sodium sulfate and concentrated under vacuum. The residue was purified by flash chromatography on silica gel eluting with EtOAc/Petroleum ether (42%) to afford ethyl 1-(5-bromopyridin-2-yl)pyrazole-4-carboxylate (300 mg, 84.69%) as a yellow solid LCMS (ESI): [M+H]$^+$: 296

Step 2: To a solution of ethyl 1-(5-bromopyridin-2-yl) pyrazole-4-carboxylate (200 mg, 0.675 mmol, 1 equiv), 1-(piperazin-1-yl) ethanone (129.8 mg, 1.013 mmol, 1.50 equiv), Pd(AcO)$_2$ (15.2 mg, 0.068 mmol, 0.10 equiv) and BINAP (84.1 mg, 0.135 mmol, 0.20 equiv) in toluene (5 mL) was added Cs$_2$CO$_3$ (660.2 mg, 2.026 mmol, 3.00 equiv) at room temperature under nitrogen. The resulting solution was stirred for two hours at 100° C. The resulting solution was concentrated under vacuum. The residue was purified by flash chromatography on silica gel eluting with EtOAc/ Petroleum ether (45%) to afford ethyl 1-[5-(4-acetylpiperazin-1-yl) pyridin-2-yl] pyrazole-4-carboxylate (130 mg, 53.81%) as a yellow solid. LCMS (ESI): [M+H]$^+$:344

Step 3: To a solution of ethyl 1-[5-(4-acetylpiperazin-1-yl)pyridin-2-yl]pyrazole-4-carboxylate (135 mg, 0.393 mmol, 1 equiv) in THE (2 mL) and H$_2$O (2 mL) was added LiOH (47.1 mg, 1.967 mmol, 5.00 equiv) at room temperature. The resulting solution was stirred for one hour at room temperature. The residue was purified by flash chromatography on C18 column gel eluting with ACN/water(0.1% FA) (35%) to afford 1-[5-(4-acetylpiperazin-1-yl) pyridin-2-yl] pyrazole-4-carboxylic acid (95 mg, 70.50%) as a white solid. LCMS (ESI): [M+H]$^+$:316

Step 4: To a solution of 1-[5-(4-acetylpiperazin-1-yl) pyridin-2-yl]pyrazole-4-carboxylic acid (95 mg, 0.301 mmol, 1 equiv), NMI (49.5 mg, 0.603 mmol, 2.00 equiv) and TCFH (126.8 mg, 0.452 mmol, 1.50 equiv) in ACN (2 mL) at room temperature. The resulting solution was stirred for 10 minus at room temperature. Then N-(3-amino-5-bromophenyl) methanesulfonamide (119.8 mg, 0.452 mmol, 1.50 equiv) was added and stirred for one hours at room temperature. The residue was purified by Pre-HPLC on condition: Column: Sunfire prep C18 column, 30*150 mm, 5 µm; Mobile Phase A: Water (0.1% FA), Mobile Phase B: ACN; Flow rate: 60 mL/min; Gradient: 33% B to 47% B in 7 min, 47% B; Wave Length: 254/220 nm; RT1(min): 6.28 to afford 1-[5-(4-acetylpiperazin-1-yl)pyridin-2-yl]-N-(3-bromo-5-methanesulfonamidophenyl)pyrazole-4-carboxami de (19.7 mg, 11.37%) as a white solid. LCMS (ESI): [M+H]$^+$:562. $^1$H NMR (300 MHz, DMSO-d$_6$) δ 10.24 (s, 1H), 10.06 (s, 1H), 9.28 (d, J=0.8 Hz, 1H), 8.33-8.16 (m, 2H), 7.96-7.78 (m, 2H), 7.76-7.54 (m, 2H), 7.08 (t, J=1.9 Hz, 1H), 3.62 (t, J=5.2 Hz, 4H), 3.25 (t, J=5.3 Hz, 4H), 3.07 (s, 3H), 2.07 (s, 3H).

Example 87-94 and 394-423

The compounds listed in the following table were prepared using a procedure similar to that described for example 86:

Step 1: A solution of 5-bromo-2-fluoropyridine (200 mg, 1.136 mmol, 1 equiv) and ethyl 1H-pyrazole-4-carboxylate (238.9 mg, 1.705 mmol, 1.50 equiv) in DMSO (5 mL) was added Cs$_2$CO$_3$ (1110.8 mg, 3.409 mmol, 3.00 equiv) at room

| Structure | Example No. | MS (ESI) [M + H]+ | 1H NMR |
|---|---|---|---|
| 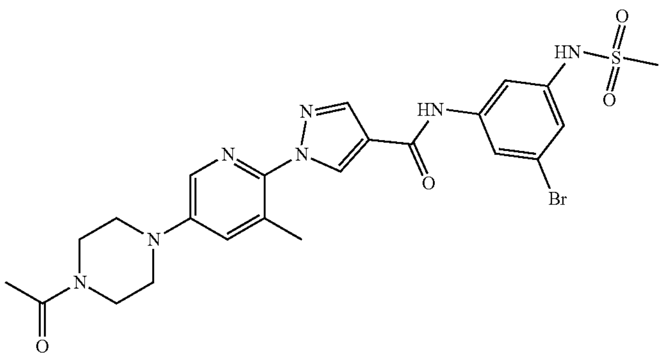 [SMILES: CC(=O)N1CCN(c2cnc(-n3cc(C(=O)Nc4cc(Br)cc(NS(C)(=O)=O)c4)cn3)c(C)c2)CC1] | 87 | 576 | 1H NMR (300 MHz, DMSO-d6) δ 10.16 (s, 1H), 10.05 (s, 1H), 8.87 (s, 1H), 8.21 (s, 1H), 8.10 (d, J = 2.8 Hz, 1H), 7.80 (t, J = 1.8 Hz, 1H), 7.63 (t, J = 1.9 Hz, 1H), 7.48 (d, J = 2.8 Hz, 1H), 7.05 (t, J = 1.9 Hz, 1H), 3.62 (t, J = 5.3 Hz, 4H), 3.27 (t, J = 5.2 Hz, 4H), 3.04 (s, 3H), 2.37 (s, 3H), 2.07 (s, 3H). |
| 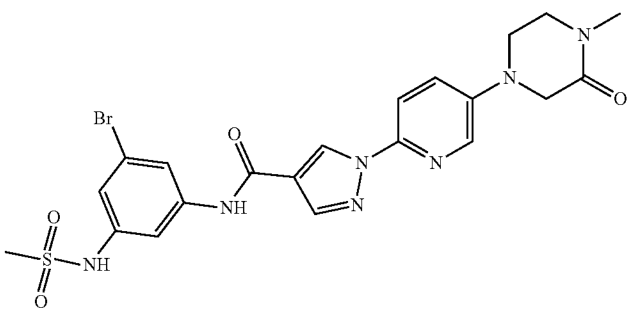 [SMILES: CN1CCN(c2ccc(-n3cc(C(=O)Nc4cc(Br)cc(NS(C)(=O)=O)c4)cn3)nc2)CC1=O] | 88 | 548 | 1H NMR (300 MHz, DMSO-d6) δ 10.22 (s, 1H), 9.28 (d, J = 0.8 Hz, 1H), 8.38-8.12 (m, 2H), 7.95-7.73 (m, 2H), 7.63 (dd, J = 9.1, 2.8 Hz, 2H), 7.05 (t, J = 1.9 Hz, 1H), 3.92 (s, 2H), 3.67-3.54 (m, 2H), 3.48 (dd, J = 6.6, 4.3 Hz, 2H), 3.04 (s, 3H), 2.93 (s, 3H). |
| 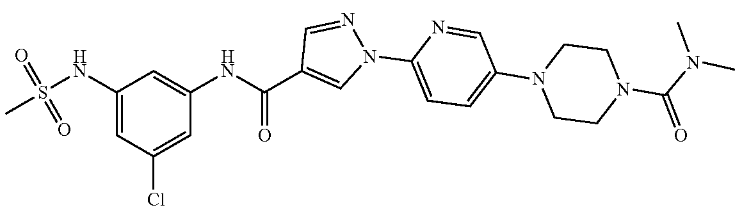 | 89 | 547 | 1H NMR (300 MHz, DMSO-d6) δ 10.26 (s, 1H), 10.08 (s, 1H), 9.29 (d, J = 0.8 Hz, 1H), 8.23 (s, 2H), 7.84 (d, J = 9.0 Hz, 1H), 7.73 (t, J = 1.8 Hz, 1H), 7.68-7.60 (m, 2H), 6.94 (t, J = 2.0 Hz, 1H), 3.28 (s, 8H), 3.08 (s, 3H), 2.80 (s, 6H). |
| 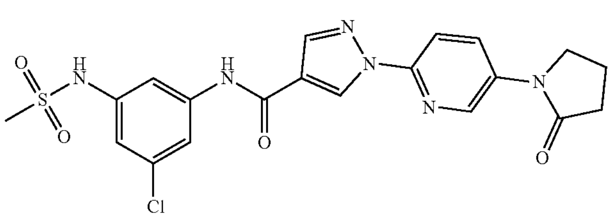 [SMILES: CS(=O)(=O)Nc1cc(Cl)cc(NC(=O)c2cnn(-c3ccc(N4CCCC4=O)cn3)c2)c1] | 90 | 475 | 1H NMR (300 MHz, DMSO-d6) δ 10.31 (s, 1H), 10.09 (s, 1H), 9.37 (s, 1H), 8.84 (d, J = 2.6 Hz, 1H), 8.39 (dd, J = 9.0, 2.7 Hz, 1H), 8.29 (s, 1H), 8.01 (d, J = 9.0 Hz, 1H), 7.73 (t, J = 1.9 Hz, 1H), 7.64 (t, J = 1.9 Hz, 1H), 6.95 (t, J = 1.9 Hz, 1H), 3.94 (t, J = 7.0 Hz, 2H), 3.08 (s, 3H), 2.60-2.52 (m, 2H), 2.15 (q, J = 7.5 Hz, 2H). |

| Structure | Example No. | MS (ESI) [M + H]+ | ¹H NMR |
|---|---|---|---|
| 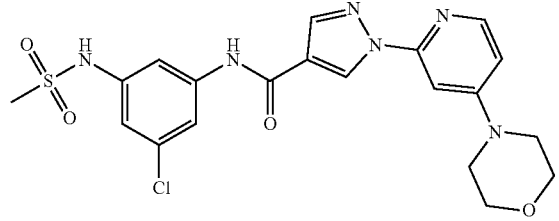 [SMILES: CS(=O)(=O)Nc1cc(Cl)cc(NC(=O)c2cnn(-c3cc(N4CCOCC4)ccn3)c2)c1] | 91 | 477 | ¹H NMR (300 MHz, DMSO-d6) δ 10.27 (s, 1H), 10.08 (s, 1H), 9.37 (s, 1H), 8.25 (s, 1H), 8.15 (d, J = 5.9 Hz, 1H), 7.73 (t, J = 1.9 Hz, 1H), 7.64 (t, J = 1.9 Hz, 1H), 7.36 (d, J = 2.3 Hz, 1H), 6.93 (dt, J = 6.2, 2.2 Hz, 2H), 3.75 (t, J = 4.7 Hz, 4H), 3.40 (t, J = 4.9 Hz, 4H), 3.08 (s, 3H). |
| 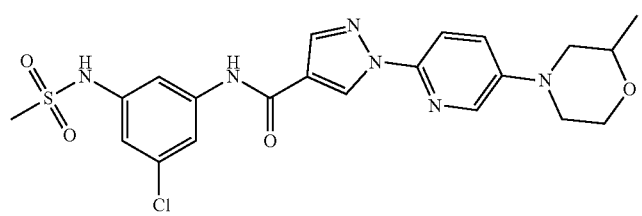 | 92 | 491 | ¹H NMR (300 MHz, DMSO-d6) δ 10.26 (s, 1H), 10.08 (s, 1H), 9.28 (s, 1H), 8.28-8.17 (m, 2H), 7.84 (d, J = 9.1 Hz, 1H), 7.72 (t, J = 1.8 Hz, 1H), 7.67-7.57 (m, 2H), 6.94 (t, J = 1.9 Hz, 1H), 3.96 (d, J = 11.7 Hz, 1H), 3.69 (q, J = 13.0, 11.4 Hz, 4H), 3.07 (s, 3H), 2.82-2.72 (m, 1H), 2.48-2.41 (m, 1H), 1.18 (d, J = 6.1 Hz, 3H). |
| 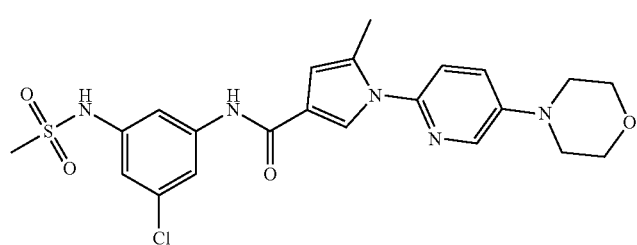 [SMILES: Cc1cc(C(=O)Nc2cc(Cl)cc(NS(C)(=O)=O)c2)cn1-c1ccc(N2CCOCC2)cn1] | 93 | 490 | ¹H NMR (300 MHz, DMSO-d6) δ 10.01 (s, 1H), 9.82 (s, 1H), 8.26 (d, J = 2.9 Hz, 1H), 7.84 (d, J = 2.0 Hz, 1H), 7.72 (t, J = 1.9 Hz, 1H), 7.64 (t, J = 1.9 Hz, 1H), 7.56 (dd, J = 8.9, 3.0 Hz, 1H), 7.46 (d, J = 8.8 Hz, 1H), 6.89 (t, J = 1.9 Hz, 1H), 6.54 (dd, J = 2.1, 1.1 Hz, 1H), 3.78 (t, J = 4.9 Hz, 4H), 3.25 (t, J = 4.9 Hz, 4H), 3.06 (s, 3H), 2.30 (s, 3H). |

-continued

| Structure | Example No. | MS (ESI) [M + H]+ | 1H NMR |
|---|---|---|---|
| 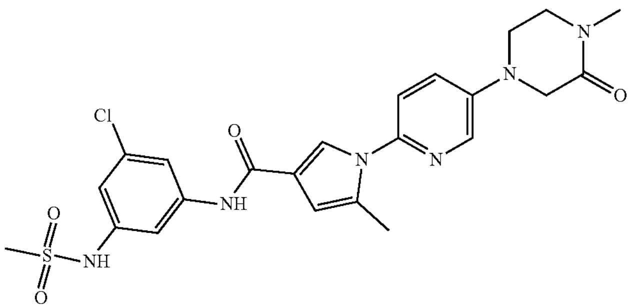 [SMILES: Cc1cc(C(=O)Nc2cc(Cl)cc(NS(C)(=O)=O)c2)cn1-c1ccc(N2CCN(C)C(=O)C2)cn1] | 94 | 517 | 1H NMR (300 MHz, DMSO-d6) δ 10.01 (s, 1H), 9.82 (s, 1H), 8.25 (d, J = 2.9 Hz, 1H), 7.84 (d, J = 2.0 Hz, 1H), 7.72 (t, J = 1.9 Hz, 1H), 7.64 (t, J = 1.9 Hz, 1H), 7.57 (dd, J = 9.1, 3.0 Hz, 1H), 7.46 (d, J = 8.8 Hz, 1H), 6.89 (t, J = 1.9 Hz, 1H), 6.54 (s, 1H), 3.92 (s, 2H), 3.63 (t, J = 5.4 Hz, 2H), 3.48 (t, J = 5.5 Hz, 2H), 3.06 (s, 3H), 2.93 (s, 3H), 2.30 (s, 3H). |
| 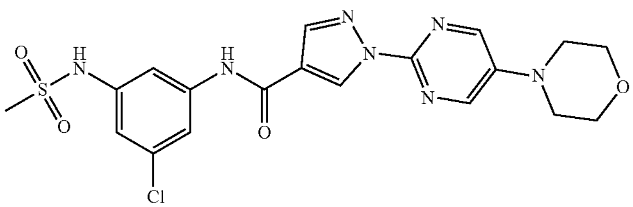 [SMILES: CS(=O)(=O)Nc1cc(Cl)cc(NC(=O)c2cnn(-c3ncc(N4CCOCC4)cn3)c2)c1] | 394 | 477.95 | 1H NMR (400 MHz, DMSO-d6) δ 10.27 (s, 1H), 10.12 (s, 1H), 9.29 (s, 1H), 8.60 (s, 2H), 8.24 (s, 1H), 7.66 (dt, J = 34.4, 1.9 Hz, 2H), 6.94 (d, J = 2.0 Hz, 1H), 3.79 (t, J = 4.8 Hz, 4H), 3.33 (s, 4H), 3.06 (s, 3H). |
| 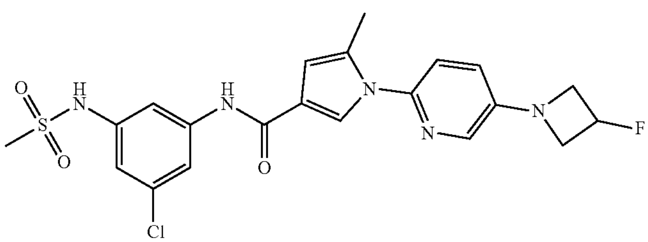 [SMILES: Cc1cc(C(=O)Nc2cc(Cl)cc(NS(C)(=O)=O)c2)cn1-c1ccc(N2CC(F)C2)cn1] | 395 | 478.2 | 1H NMR (300 MHz, DMSO-d6) δ 10.02 (s, 1H), 9.79 (s, 1H), 7.81 (dd, J = 7.7, 2.5 Hz, 2H), 7.71 (t, J = 1.9 Hz, 1H), 7.62 (t, J = 1.9 Hz, 1H), 7.42 (d, J = 8.6 Hz, 1H), 7.11 (dd, J = 8.7, 3.0 Hz, 1H), 6.88 (t, J = 1.9 Hz, 1H), 6.53 (d, J = 1.8 Hz, 1H), 5.84-5.32 (m, 1H), 4.29 (ddd, J = 21.0, 9.8, 5.6 Hz, 2H), 4.14-3.88 (m, 2H), 3.05 (s, 3H), 2.28 (d, J = 1.0 Hz, 3H). |
| 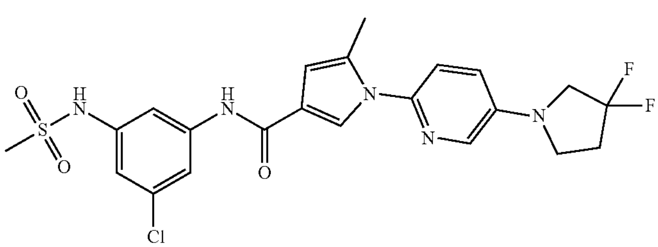 [SMILES: Cc1cc(C(=O)Nc2cc(Cl)cc(NS(C)(=O)=O)c2)cn1-c1ccc(N2CCC(F)(F)C2)cn1] | 396 | 510 | 1H NMR (300 MHz, DMSO-d6) δ 10.08 (s, 1H), 9.80 (s, 1H), 7.95 (d, J = 3.0 Hz, 1H), 7.85-7.58 (m, 3H), 7.44 (d, J = 8.7 Hz, 1H), 7.22 (dd, J = 8.9, 3.0 Hz, 1H), 6.88 (t, J = 2.0 Hz, 1H), 6.53 (s, 1H), 3.82 (t, J = 13.3 Hz, 2H), 3.59 (t, J = 7.2 Hz, 2H), 3.05 (s, 3H), 2.59 (dq, J = 14.4, 7.1 Hz, 2H), 2.27 (s, 3H). |

| Structure | Example No. | MS (ESI) [M + H]+ | ¹H NMR |
|---|---|---|---|
| 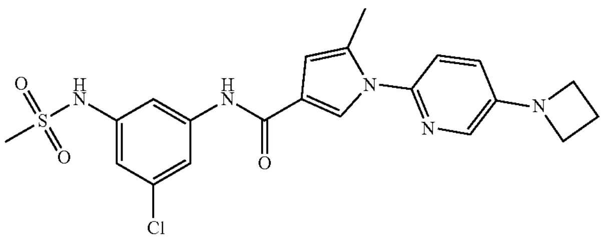 [SMILES: Cc1cc(C(=O)Nc2cc(Cl)cc(NS(C)(=O)=O)c2)cn1-c1ccc(N2CCC2)cn1] | 397 | 460 | ¹H NMR (400 MHz, DMSO-d6) δ 9.96 (s, 1H), 9.76 (s, 1H), 7.77 (d, J = 2.0 Hz, 1H), 7.73 (d, J = 2.9 Hz, 1H), 7.70 (s, 1H), 7.61 (s, 1H), 7.37 (d, J = 8.6 Hz, 1H), 7.00 (dd, J = 8.6, 2.9 Hz, 1H), 6.87 (d, J = 2.0 Hz, 1H), 6.51 (d, J = 1.9 Hz, 1H), 3.94 (t, J = 7.3 Hz, 4H), 3.04 (s, 3H), 2.38 (p, J = 7.2 Hz, 2H), 2.26 (s, 3H). |
| 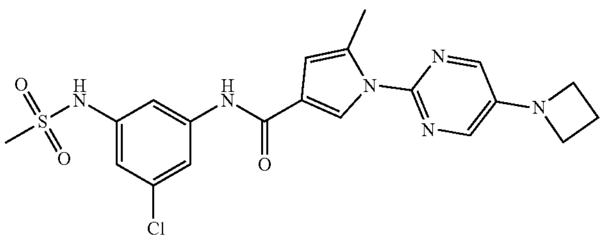 [SMILES: Cc1cc(C(=O)Nc2cc(Cl)cc(NS(C)(=O)=O)c2)cn1-c1ncc(N2CCC2)cn1] | 398 | 461 | ¹H NMR (400 MHz, DMSO-d6) δ 9.91 (s, 2H), 8.24 (d, J = 2.1 Hz, 1H), 8.09 (d, J = 2.0 Hz, 2H), 7.71 (t, J = 1.6 Hz, 1H), 7.65 (t, J = 1.7 Hz, 1H), 6.89 (t, J = 1.5 Hz, 1H), 6.51 (dd, J = 2.1, 1.1 Hz, 1H), 4.03-3.94 (m, 4H), 3.05 (s, 3H), 2.49 (s, 3H), 2.41 (p, J = 7.4 Hz, 2H). |
| 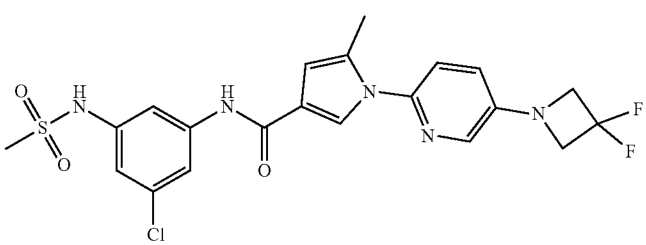 [SMILES: Cc1cc(C(=O)Nc2cc(Cl)cc(NS(C)(=O)=O)c2)cn1-c1ccc(N2CC(F)(F)C2)cn1] | 399 | 496.05 | ¹H NMR (400 MHz, DMSO-d6) δ 9.99 (s, 1H), 9.80 (s, 1H), 7.91 (d, J = 2.9 Hz, 1H), 7.81 (d, J = 2.0 Hz, 1H), 7.71 (d, J = 1.9 Hz, 1H), 7.63 (t, J = 2.0 Hz, 1H), 7.47 (d, J = 8.6 Hz, 1H), 7.21 (dd, J = 8.6, 3.0 Hz, 1H), 6.88 (d, J = 2.1 Hz, 1H), 6.53 (s, 1H), 4.43 (t, J = 12.3 Hz, 4H), 3.06 (s, 3H), 2.28 (s, 3H). |
| 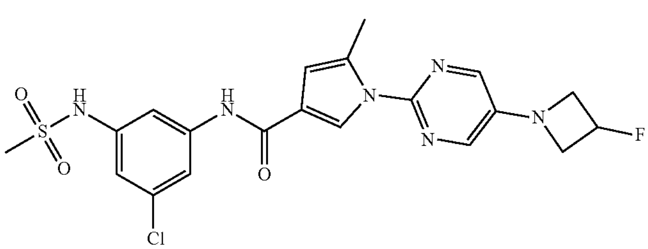 [SMILES: Cc1cc(C(=O)Nc2cc(Cl)cc(NS(C)(=O)=O)c2)cn1-c1ncc(N2CC(F)C2)cn1] | 400 | 468.9 | ¹H NMR (400 MHz, DMSO-d6) δ 9.92 (s, 1H), 9.80 (s, 1H), 8.27 (d, J = 2.1 Hz, 1H), 8.18 (d, J = 1.2 Hz, 2H), 7.67 (dd, J = 25.7, 1.9 Hz, 2H), 6.89 (t, J = 1.9 Hz, 1H), 6.52 (d, J = 2.1 Hz, 1H), 5.54 (dt, J = 57.3, 2.9 Hz, 1H), 4.46-4.21 (m, 2H), 4.20-3.88 (m, 2H), 3.05 (d, J = 1.4 Hz, 3H), 2.51 (s, 3H). |

-continued
| Structure | Example No. | MS (ESI) [M + H]+ | ¹H NMR |
|---|---|---|---|
| 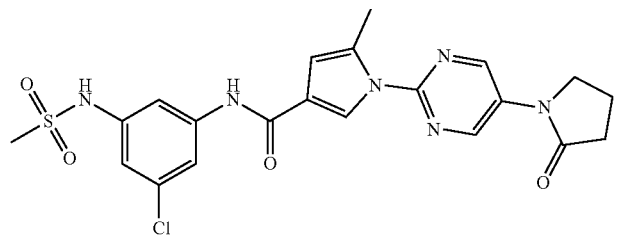 [SMILES: Cc1cc(C(=O)Nc2cc(Cl)cc(NS(C)(=O)=O)c2)cn1-c1ncc(N2CCCC2=O)cn1] | 401 | 488.95 | ¹H NMR (400 MHz, DMSO-d6) δ 10.01 (s, 2H), 9.18 (s, 2H), 8.43 (d, J = 2.1 Hz, 1H), 7.69 (dt, J = 27.7, 1.9 Hz, 2H), 6.90 (t, J = 1.9 Hz, 1H), 6.60-6.54 (m, 1H), 3.94 (t, J = 7.1 Hz, 2H), 3.06 (s, 3H), 2.60-2.51 (m, 5H), 2.15 (p, J = 7.6 Hz, 2H). |
| 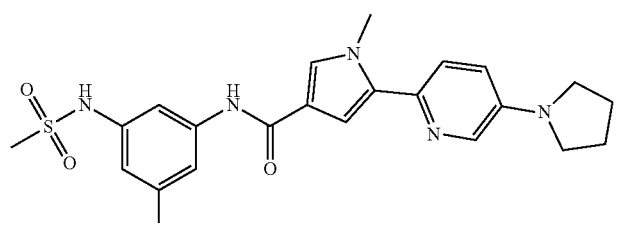 | 402 | 473.95 | ¹H NMR (400 MHz, DMSO-d6) δ 9.98 (s, 1H), 9.76 (s, 1H), 7.96 (d, J = 3.0 Hz, 1H), 7.72 (t, J = 1.9 Hz, 1H), 7.67-7.53 (m, 2H), 7.48 (d, J = 8.6 Hz, 1H), 7.07-6.75 (m, 3H), 3.90 (s, 3H), 3.29 (s, 4H), 3.06 (s, 3H), 2.02-1.94 (m, 4H). |
| 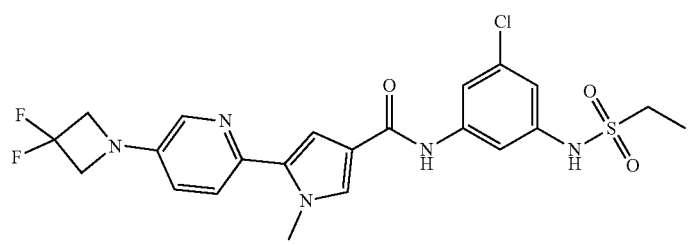 [SMILES: CCS(=O)(=O)Nc1cc(Cl)cc(NC(=O)c2cc(-c3ccc(N4CC(F)(F)C4)cn3)n(C)c2)c1] | 403 | 510.1 | ¹H NMR (400 MHz, DMSO-d6) δ 10.04 (s, 1H), 9.79 (s, 1H), 7.99 (d, J = 2.9 Hz, 1H), 7.71 (t, J = 2.0 Hz, 1H), 7.66-7.49 (m, 3H), 7.11 (dd, J = 8.8, 3.0 Hz, 1H), 7.03 (d, J = 2.0 Hz, 1H), 6.89 (t, J = 2.0 Hz, 1H), 4.40 (t, J = 12.3 Hz, 4H), 3.91 (s, 3H), 3.17 (q, J = 7.3 Hz, 2H), 1.21 (t, J = 7.3 Hz, 3H). |
| 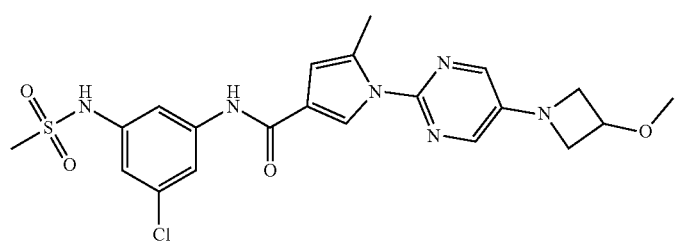 | 404 | 490.95 | ¹H NMR (400 MHz, DMSO-d6) δ 10.12-9.89 (m, 2H), 8.26 (d, J = 2.1 Hz, 1H), 8.13 (s, 2H), 7.68 (d, J = 26.7 Hz, 2H), 6.89 (t, J = 1.9 Hz, 1H), 6.55-6.49 (m, 1H), 4.42-4.35 (m, 1H), 4.21 (dd, J = 8.4, 6.2 Hz, 2H), 3.81 (dd, J = 8.5, 4.2 Hz, 2H), 3.30 (s, 3H), 3.26 (s, 3H), 3.05 (s, 3H). |

| Structure | Example No. | MS (ESI) [M + H]+ | 1H NMR |
|---|---|---|---|
| 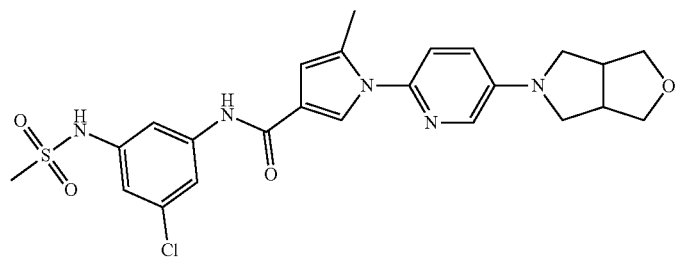 [SMILES: Cc1cc(C(=O)Nc2cc(Cl)cc(NS(C)(=O)=O)c2)cn1-c1ccc(N2CC3COCC3C2)cn1] | 405 | 516 | 1H NMR (400 MHz, DMSO-d6) δ 10.01 (s, 1H), 9.78 (s, 1H), 7.93 (d, J = 3.0 Hz, 1H), 7.78 (d, J = 2.1 Hz, 1H), 7.66 (dt, J = 34.9, 1.9 Hz, 2H), 7.39 (d, J = 8.7 Hz, 1H), 7.19 (dd, J = 8.9, 3.0 Hz, 1H), 6.88 (t, J = 2.0 Hz, 1H), 6.51 (dd, J = 2.1, 1.1 Hz, 1H), 3.87 (dd, J = 8.8, 6.5 Hz, 2H), 3.58 (dd, J = 8.8, 3.4 Hz, 2H), 3.45 (dd, J = 9.7, 7.2 Hz, 2H), 3.29 (dd, J = 10.2, 2.9 Hz, 2H), 3.05 (s, 5H), 2.29-2.24 (m, 3H). |
| 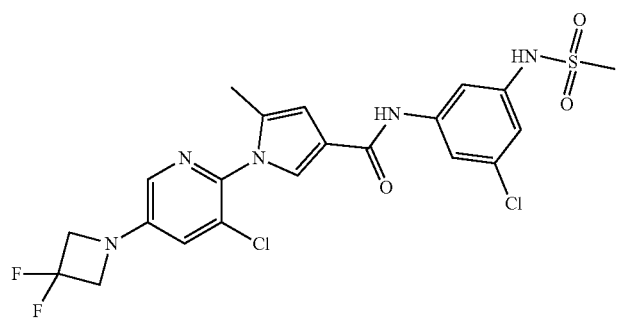 | 406 | 529.95 | 1H NMR (400 MHz, DMSO-d6) δ 9.99 (s, 1H), 9.78 (s, 1H), 7.90 (d, J = 2.6 Hz, 1H), 7.70 (d, J = 2.2 Hz, 1H), 7.59 (d, J = 14.6 Hz, 2H), 7.42 (d, J = 2.5 Hz, 1H), 6.88 (d, J = 2.2 Hz, 1H), 6.54 (s, 1H), 4.50 (t, J = 12.3 Hz, 4H), 3.05 (d, J = 1.7 Hz, 3H), 2.05 (d, J = 22.9 Hz, 3H). |
| 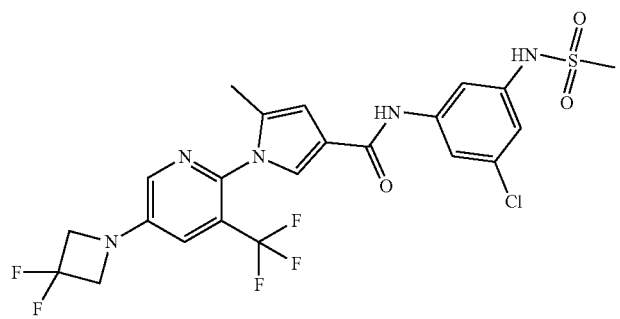 [SMILES: Cc1cc(C(=O)Nc2cc(Cl)cc(NS(C)(=O)=O)c2)cn1-c1ncc(N2CC(F)(F)C2)cc1C(F)(F)F] | 407 | 563.9 | 1H NMR (400 MHz, DMSO-d6) δ 10.03 (s, 1H), 9.79 (d, J = 2.4 Hz, 1H), 8.17 (d, J = 2.9 Hz, 1H), 7.70 (q, J = 2.0 Hz, 1H), 7.63 (t, J = 2.3 Hz, 1H), 7.55 (s, 1H), 7.51 (d, J = 2.9 Hz, 1H), 6.90 (p, J = 1.9 Hz, 1H), 6.64-6.41 (m, 1H), 4.58 (t, J = 12.3 Hz, 4H), 3.06 (d, J = 1.6 Hz, 3H), 1.96 (s, 3H). |

-continued

| Structure | Example No. | MS (ESI) [M + H]+ | ¹H NMR |
|---|---|---|---|
| 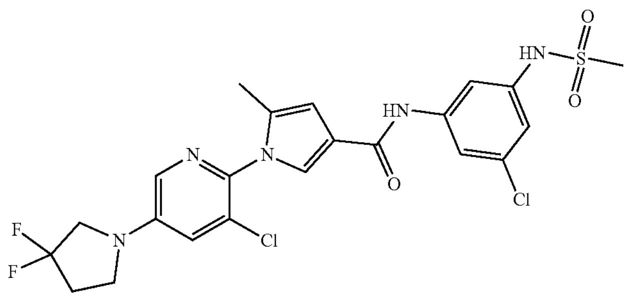 [SMILES: Cc1cc(C(=O)Nc2cc(Cl)cc(NS(C)(=O)=O)c2)cn1-c1ncc(N2CCC(F)(F)C2)cc1Cl] | 408 | 528.05 | ¹H NMR (400 MHz, DMSO-d6) δ 10.00 (s, 1H), 9.81 (s, 1H), 7.84 (d, J = 2.4 Hz, 1H), 7.70 (d, J = 1.9 Hz, 1H), 7.65-7.55 (m, 2H), 7.26 (dd, J = 12.5, 2.5 Hz, 1H), 6.88 (d, J = 2.0 Hz, 1H), 6.55 (s, 1H), 3.86 (t, J = 13.1 Hz, 2H), 3.62 (t, J = 7.3 Hz, 2H), 3.05 (s, 3H), 2.70-2.56 (m, 2H), 2.10 (s, 3H). |
| 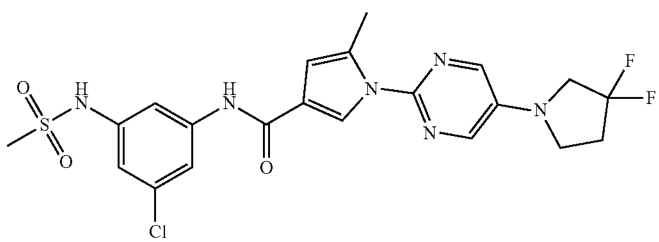 [SMILES: Cc1cc(C(=O)Nc2cc(Cl)cc(NS(C)(=O)=O)c2)cn1-c1ncc(N2CCC(F)(F)C2)cn1] | 409 | 511.05 | ¹H NMR (400 MHz, DMSO-d6) δ 8.28 (d, J = 10.7 Hz, 3H), 7.69 (dq, J = 23.3, 2.2 Hz, 2H), 6.89 (t, J = 2.0 Hz, 1H), 6.53 (dd, J = 2.2, 1.2 Hz, 1H), 3.86 (t, J = 13.2 Hz, 2H), 3.63 (t, J = 7.3 Hz, 2H), 3.38 (s, 3H), 3.06 (s, 3H), 2.59 (td, J = 14.5, 7.2 Hz, 2H). |
| 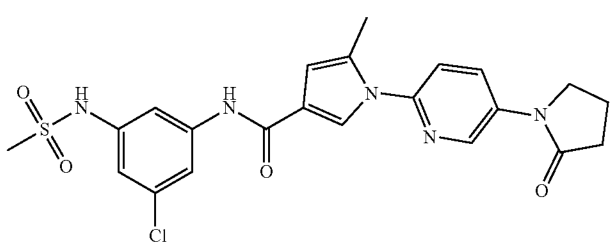 [SMILES: Cc1cc(C(=O)Nc2cc(Cl)cc(NS(C)(=O)=O)c2)cn1-c1ccc(N2CCCC2=O)cn1] | 410 | 487.95 | ¹H NMR (300 MHz, DMSO-d6) δ 10.00 (s, 1H), 9.86 (s, 1H), 8.84 (d, J = 2.7 Hz, 1H), 8.36 (dd, J = 8.9, 2.8 Hz, 1H), 7.95 (d, J = 2.0 Hz, 1H), 7.75-7.59 (m, 3H), 6.89 (t, J = 1.9 Hz, 1H), 6.61-6.50 (m, 1H), 3.94 (t, J = 7.0 Hz, 2H), 3.05 (s, 3H), 2.57 (d, J = 7.9 Hz, 2H), 2.37 (d, J = 1.0 Hz, 3H), 2.13 (p, J = 7.5 Hz, 2H). |

| Structure | Example No. | MS (ESI) [M + H]+ | ¹H NMR |
|---|---|---|---|
| 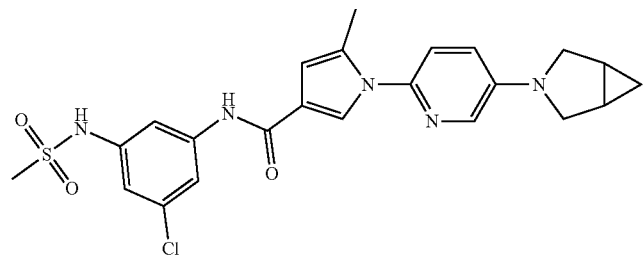 [SMILES: Cc1cc(C(=O)Nc2cc(Cl)cc(NS(C)(=O)=O)c2)cn1-c1ccc(N2CC3CC3C2)cn1] | 411 | 486.05 | ¹H NMR (300 MHz, DMSO-d6) δ 10.03 (s, 1H), 9.78 (s, 1H), 7.86 (d, J = 3.0 Hz, 1H), 7.76 (d, J = 2.0 Hz, 1H), 7.71 (t, J = 1.9 Hz, 1H), 7.62 (t, J = 1.9 Hz, 1H), 7.36 (d, J = 8.8 Hz, 1H), 7.12 (dd, J = 8.9, 3.0 Hz, 1H), 6.88 (t, J = 1.9 Hz, 1H), 6.51 (dd, J = 2.0, 1.1 Hz, 1H), 3.59 (d, J = 9.4 Hz, 2H), 3.33-3.24 (m, 2H), 3.05 (s, 3H), 2.26 (d, J = 1.0 Hz, 3H), 1.79-1.70 (m, 2H), 0.82-0.70 (m, 1H), 0.28 (d, J = 4.2 Hz, 1H). |
| 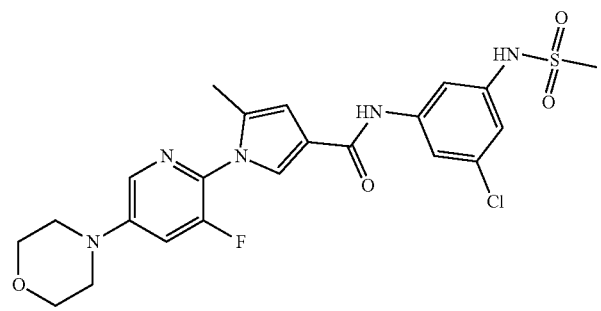 [SMILES: Cc1cc(C(=O)Nc2cc(Cl)cc(NS(C)(=O)=O)c2)cn1-c1ncc(N2CCOCC2)cc1F] | 412 | 508.1 | ¹H NMR (300 MHz, DMSO-d6) δ 10.00 (s, 1H), 9.82 (s, 1H), 8.16 (d, J = 2.4 Hz, 1H), 7.80-7.43 (m, 4H), 6.89 (t, J = 2.0 Hz, 1H), 6.56 (dd, J = 1.9, 1.1 Hz, 1H), 3.77 (t, J = 4.9 Hz, 4H), 3.34 (s, 1H), 3.32 (s, 3H), 3.06 (s, 3H), 2.19-2.07 (m, 3H). |
| 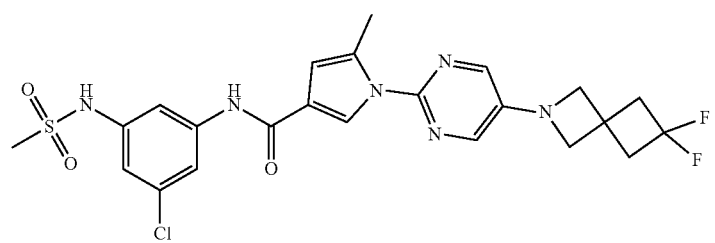 [SMILES: Cc1cc(C(=O)Nc2cc(Cl)cc(NS(C)(=O)=O)c2)cn1-c1ncc(N2CC3(C2)CC(F)(F)C3)cn1] | 413 | 537.2 | ¹H NMR (300 MHz, DMSO-d6) δ 8.19 (d, J = 2.1 Hz, 1H), 8.09 (s, 2H), 7.71-7.50 (m, 2H), 6.88 (s, 1H), 6.50 (s, 1H), 4.07 (s, 4H), 3.02 (s, 3H), 2.86 (t, J = 12.5 Hz, 5H), 2.46 (s, 3H). |
| 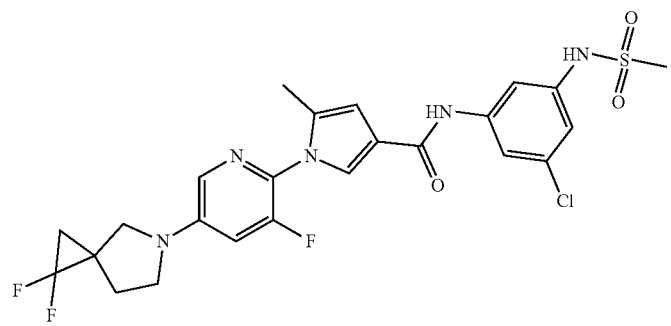 [SMILES: Cc1cc(C(=O)Nc2cc(Cl)cc(NS(C)(=O)=O)c2)cn1-c1ncc(N2CCC3(C2)CC3(F)F)cc1F] | 414 | 554.15 | ¹H NMR (400 MHz, DMSO-d6) δ 10.01 (s, 1H), 9.80 (s, 1H), 7.79 (d, J = 2.5 Hz, 1H), 7.70 (t, J = 1.9 Hz, 1H), 7.62 (dt, J = 8.4, 1.7 Hz, 2H), 7.17 (dd, J = 12.6, 2.5 Hz, 1H), 6.88 (t, J = 2.0 Hz, 1H), 6.54 (dd, J = 2.0, 1.1 Hz, 1H), 3.68-3.43 (m, 4H), 3.05 (s, 3H), 2.25 (dt, J = 13.2, 6.8 Hz, 1H), 2.09 (s, 4H), 1.74-1.62 (m, 2H). |

| Structure | Example No. | MS (ESI) [M + H]+ | ¹H NMR |
|---|---|---|---|
| 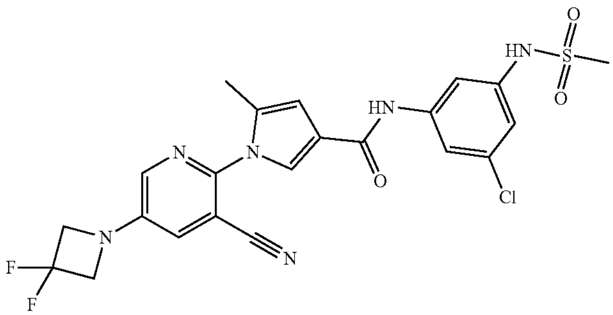 [SMILES: Cc1cc(C(=O)Nc2cc(Cl)cc(NS(C)(=O)=O)c2)cn1-c1ncc(N2CC(F)(F)C2)cc1C#N] | 415 | 520.95 | ¹H NMR (400 MHz, DMSO-d6) δ 10.03 (s, 1H), 9.85 (s, 1H), 8.18 (d, J = 3.0 Hz, 1H), 7.77 (d, J = 3.0 Hz, 1H), 7.74 (d, J = 1.8 Hz, 1H), 7.70 (s, 1H), 7.62 (s, 1H), 6.90 (s, 1H), 6.62 (s, 1H), 4.52 (t, J = 12.2 Hz, 4H), 3.05 (s, 3H), 2.10 (d, J = 23.6 Hz, 3H). |
| 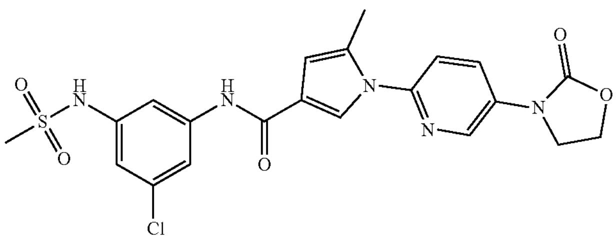 [SMILES: Cc1cc(C(=O)Nc2cc(Cl)cc(NS(C)(=O)=O)c2)cn1-c1ccc(N2CCOC2=O)cn1] | 416 | 489.9 | ¹H NMR (300 MHz, DMSO-d6) δ 10.34-9.76 (m, 2H), 8.72 (d, J = 2.8 Hz, 1H), 8.26 (dd, J = 8.9, 2.8 Hz, 1H), 7.94 (d, J = 2.0 Hz, 1H), 7.76-7.56 (m, 3H), 6.89 (t, J = 2.0 Hz, 1H), 6.58 (dd, J = 2.0, 1.1 Hz, 1H), 4.52 (dd, J = 9.1, 6.8 Hz, 2H), 4.17 (dd, J = 9.1, 6.9 Hz, 2H), 3.06 (s, 3H), 2.39-2.33 (m, 3H). |
| 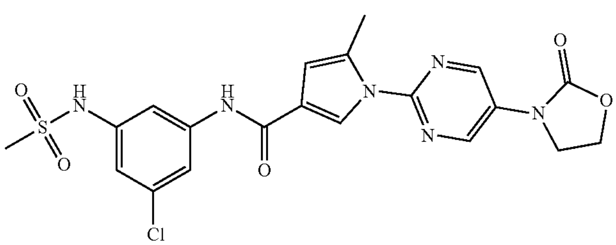 [SMILES: Cc1cc(C(=O)Nc2cc(Cl)cc(NS(C)(=O)=O)c2)cn1-c1ncc(N2CCOC2=O)cn1] | 417 | 491.05 | ¹H NMR (300 MHz, DMSO-d6) δ 10.22-9.96 (m, 2H), 9.08 (s, 2H), 8.43 (d, J = 2.1 Hz, 1H), 7.73 (t, J = 1.9 Hz, 1H), 7.65 (t, J = 1.9 Hz, 1H), 6.91 (t, J = 1.9 Hz, 1H), 6.58 (dd, J = 2.1, 1.2 Hz, 1H), 4.56 (dd, J = 9.1, 6.8 Hz, 2H), 4.18 (dd, J = 9.1, 6.9 Hz, 2H), 3.06 (s, 3H), 2.59 (d, J = 1.0 Hz, 3H). |
| 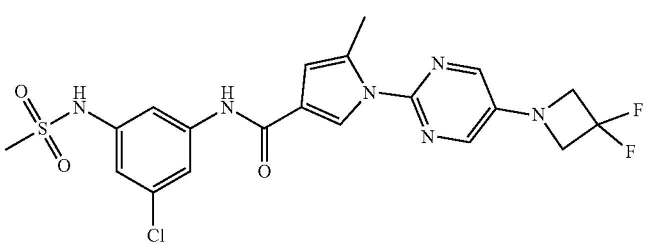 [SMILES: Cc1cc(C(=O)Nc2cc(Cl)cc(NS(C)(=O)=O)c2)cn1-c1ncc(N2CC(F)(F)C2)cn1] | 418 | 497 | ¹H NMR (300 MHz, DMSO-d6) δ 9.96 (s, 2H), 8.30 (d, J = 2.1 Hz, 1H), 8.27 (s, 2H), 7.72 (t, J = 1.9 Hz, 1H), 7.66 (t, J = 1.9 Hz, 1H), 6.89 (t, J = 1.9 Hz, 1H), 6.53 (dd, J = 2.2, 1.1 Hz, 1H), 4.48 (t, J = 12.3 Hz, 4H), 3.06 (s, 3H), 2.52 (s, 3H). |

-continued
| Structure | Example No. | MS (ESI) [M + H]+ | 1H NMR |
|---|---|---|---|
| 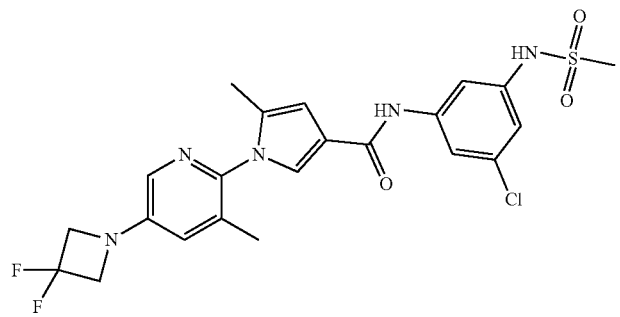 | 419 | 509.95 | 1H NMR (400 MHz, DMSO-d6) δ 10.00 (s, 1H), 9.74 (s, 1H), 7.77 (d, J = 2.8 Hz, 1H), 7.69 (t, J = 1.9 Hz, 1H), 7.61 (t, J = 1.9 Hz, 1H), 7.51 (d, J = 2.0 Hz, 1H), 7.10 (d, J = 2.9 Hz, 1H), 6.88 (t, J = 1.9 Hz, 1H), 6.53 (t, J = 1.5 Hz, 1H), 4.43 (t, J = 12.3 Hz, 4H), 3.05 (s, 3H), 2.03 (s, 3H), 1.99-1.93 (m, 3H). |
| 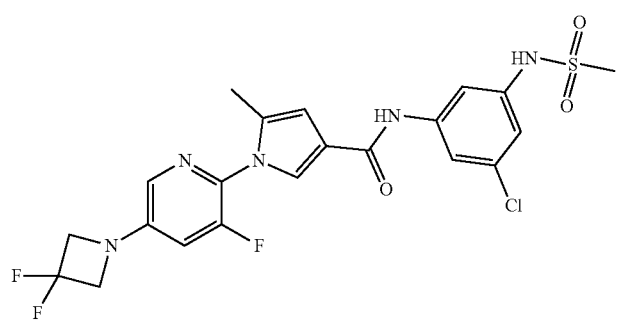 [SMILES: Cc1cc(C(=O)Nc2cc(Cl)cc(NS(C)(=O)=O)c2)cn1-c1ncc(N2CC(F)(F)C2)cc1F] | 420 | 513.9 | 1H NMR (400 MHz, DMSO-d6) δ 10.00 (s, 1H), 9.81 (s, 1H), 7.79 (d, J = 2.5 Hz, 1H), 7.70 (t, J = 1.9 Hz, 1H), 7.64 (dt, J = 12.5, 1.8 Hz, 2H), 7.29 (dd, J = 11.7, 2.5 Hz, 1H), 6.89 (t, J = 2.0 Hz, 1H), 6.56 (d, J = 1.8 Hz, 1H), 4.48 (t, J = 12.3 Hz, 4H), 3.05 (s, 3H), 2.11 (s, 3H). |
| 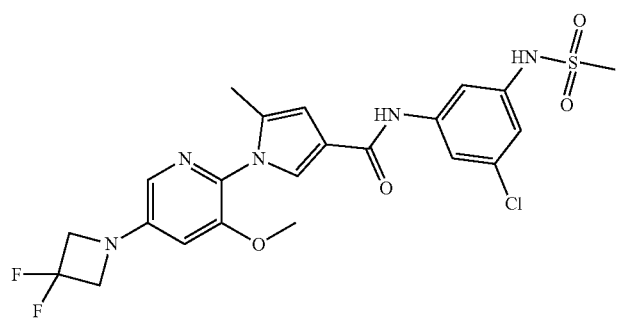 [SMILES: COc1cc(N2CC(F)(F)C2)cnc1-n1cc(C(=O)Nc2cc(Cl)cc(NS(C)(=O)=O)c2)cc1C] | 421 | 526 | 1H NMR (400 MHz, DMSO-d6) δ 9.98 (s, 1H), 9.73 (s, 1H), 7.66 (dd, J = 33.7, 2.1 Hz, 2H), 7.50 (dd, J = 19.8, 2.1 Hz, 2H), 6.88 (q, J = 2.3 Hz, 2H), 6.47 (d, J = 2.1 Hz, 1H), 4.46 (t, J = 12.3 Hz, 4H), 3.83 (s, 3H), 3.12-2.94 (m, 3H), 2.01 (s, 3H). |
| 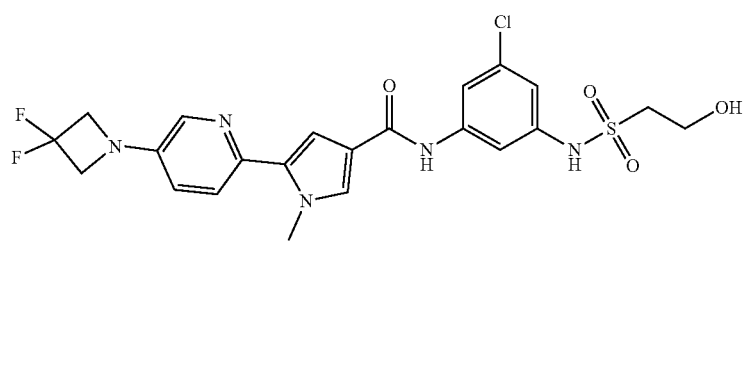 [SMILES: Cn1cc(C(=O)Nc2cc(Cl)cc(NS(=O)(=O)CCO)c2)cc1-c1ccc(N2CC(F)(F)C2)cn1] | 422 | 554 | 1H NMR (400 MHz, DMSO-d6) δ 9.79 (s, 1H), 7.98 (d, J = 2.9 Hz, 1H), 7.69 (t, J = 1.9 Hz, 1H), 7.64-7.51 (m, 3H), 7.09 (dd, J = 8.7, 2.9 Hz, 1H), 7.03 (d, J = 2.0 Hz, 1H), 6.88 (t, J = 2.0 Hz, 1H), 4.39 (t, J = 12.3 Hz, 4H), 3.91 (s, 3H), 3.76 (t, J = 6.6 Hz, 2H), 3.30 (t, J = 6.6 Hz, 2H). |

| Structure | Example No. | MS (ESI) [M + H]+ | ¹H NMR |
|---|---|---|---|
| (structure with difluoroazetidine-pyrimidine-pyrrole-carboxamide-chlorophenyl-ethylsulfonamide) | 423 | 511 | ¹H NMR (400 MHz, DMSO-d6) δ 10.04 (s, 1H), 9.95 (s, 1H), 8.29 (d, J = 11.0 Hz, 3H), 7.75-7.55 (m, 2H), 6.90 (d, J = 2.0 Hz, 1H), 6.53 (s, 1H), 4.48 (t, J = 12.3 Hz, 4H), 3.16 (q, J = 7.3 Hz, 2H), 2.52 (s, 3H), 1.21 (t, J = 7.3 Hz, 3H). |

Example 95: N-(3-bromo-5-(methylsulfonamido)phenyl)-1-methyl-2-(3-methylpyridin-2-yl)-1H-imidazole-4-carboxamide

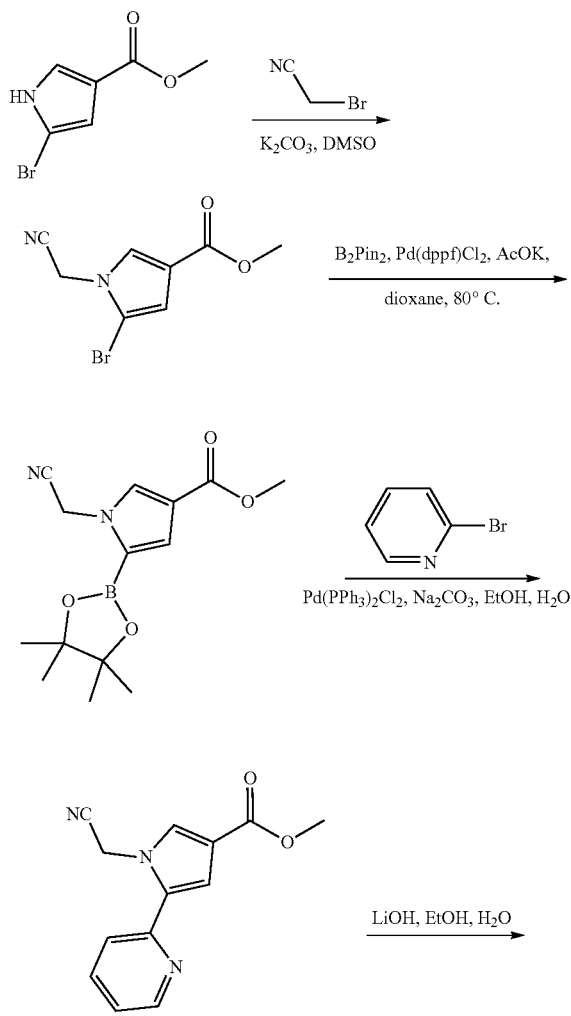

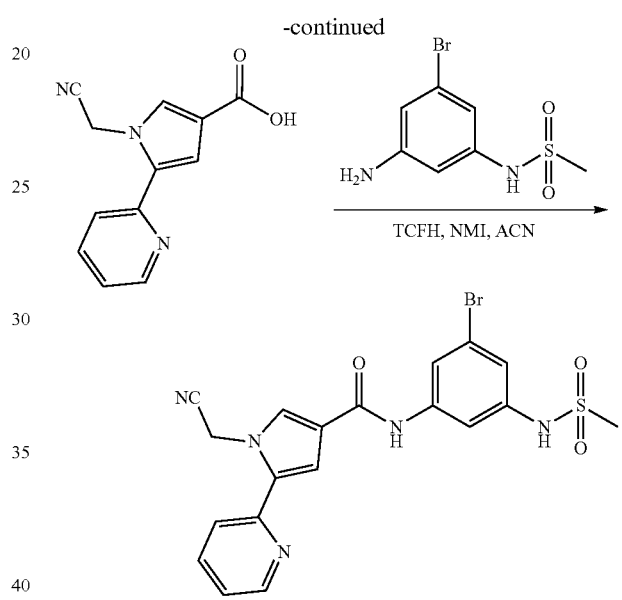

Step 1: To a stirred solution of methyl 5-bromo-1H-pyrrole-3-carboxylate (600 mg, 2.94 mmol), $K_2CO_3$ (812 mg, 5.88 mmol) and 2-bromoacetonitrile (705 mg, 5.88 mmol) in DMSO (10 mL). Then the mixture was stirred for 4 h at room temperature. The mixture was concentrated and purified by reverse phase flash chromatography eluting with ACN/$H_2O$ (5-95%, acidic system) to afford methyl 5-bromo-1-(cyanomethyl)-1H-pyrrole-3-carboxylate (693 mg, 2.85 mmol) as a white solid.

Step 2: A solution of methyl 5-bromo-1-(cyanomethyl)-1H-pyrrole-3-carboxylate (700 mg, 2.87 mmol), Pd(dppf)Cl₂ (420 mg, 0.574 mmol), KOAc (844 mg, 8.61 mmol) and B₂Pin₂ (3.63 g, 14.3 mmol) in dioxane (10 mL) was stirred for 2 h at 80° C. under nitrogen atmosphere. The resulting mixture was concentrated under reduced pressure. The residue was purified by silica gel column chromatography, eluted with Petroleum ether/EtOAc (0-100%) to afford methyl 1-(cyanomethyl)-5-(4,4,5,5-tetramethyl-1,3,2-dioxaborolan-2-yl)-1H-pyrrole-3-carboxylate (326 mg, 1.12 mmol) as a yellow solid.

Step 3: A solution of methyl 1-(cyanomethyl)-5-(4,4,5,5-tetramethyl-1,3,2-dioxaborolan-2-yl)-1H-pyrrole-3-carboxylate (330 mg, 1.13 mmol), Pd(PPh₃)₂Cl₂ (158 mg, 0.226 mmol), Na₂CO₃ (358 mg, 3.38 mmol) and 2-bromopyridine (213 mg, 1.35 mmol) in EtOH (4 mL) and H₂O (1 mL) was stirred for 2 h at 80° C. under nitrogen atmosphere. The resulting mixture was concentrated under reduced pressure. The residue was purified by silica gel column chromatography, eluted with Petroleum ether/EtOAc (0-100%) to afford methyl 1-(cyanomethyl)-5-(pyridin-2-yl)-1H-pyrrole-3-carboxylate (148 mg, 0.615 mmol) as a white solid. LCMS (ESI) [M+H]+: 242

Step 4: To a stirred solution of methyl 1-(cyanomethyl)-5-(pyridin-2-yl)-1H-pyrrole-3-carboxylate (150 mg, 0.621 mmol) in H$_2$O (5 mL) and EtOH (5 mL) was added LiOH (148 mg, 6.21 mmol). Then the mixture was stirred for 2 h at room temperature. The mixture was acidified to pH 5 with citric acid. The precipitated solids were collected by filtration and washed with water. The resulting solid was dried under vacuum to afford 1-(cyanomethyl)-5-(pyridin-2-yl)-1H-pyrrole-3-carboxylic acid (108 mg, 0.479 mmol) as a yellow solid. LCMS (ESI) [M+H]+: 228

Step 5: To a stirred solution of 1-(cyanomethyl)-5-(pyridin-2-yl)-1H-pyrrole-3-carboxylic acid (110 mg, 0.484 mmol), TCFH (176 mg, 0.629 mmol) and NMI (119 mg, 1.45 mmol) in ACN (5 mL) was added N-(3-amino-5-bromophenyl) methanesulfonamide (153 mg, 0.580 mmol). Then the mixture was stirred for 1 h at room temperature. The mixture was concentrated and purified by reverse phase flash chromatography eluting with ACN/H$_2$O (5-95%, acidic system) to afford N-(3-bromo-5-methanesulfonamidophenyl)-1-(cyanomethyl)-5-(pyridin-2-yl)-1H-pyrrole-3-carboxamide (47.6 mg, 0.1004 mmol) as a white solid. LCMS (ESI) [M+H]+: 474. $^1$H NMR (300 MHz, DMSO-d$_6$) δ10.09 (s, 1H), 10.01 (s, 1H), 8.62 (d, J=4.8 Hz, 1H), 7.96-7.75 (m, 4H), 7.67 (t, J=1.9 Hz, 1H), 7.42 (d, J=1.9 Hz, 1H), 7.32 (ddd, J=6.4, 5.0, 1.3 Hz, 1H), 7.05 (t, J=1.9 Hz, 1H), 5.78 (s, 2H), 3.06 (s, 3H).

Example 96: N-(3-bromo-5-(methylsulfonamido)phenyl)-1-methyl-2-(3-methylpyridin-2-yl)-1H-imidazole-4-carboxamide

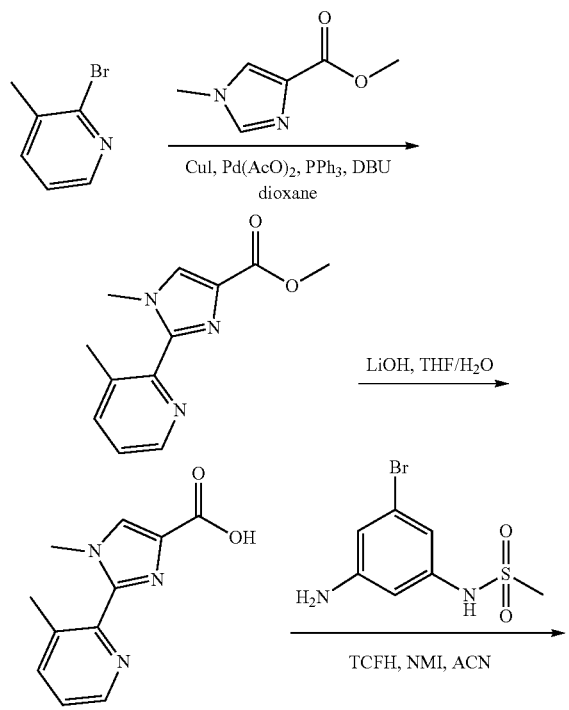

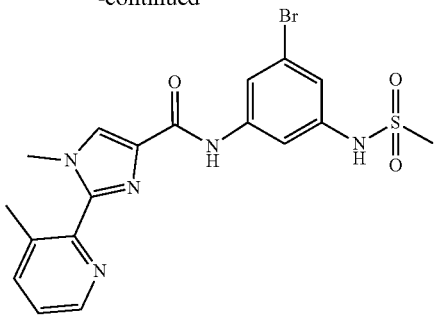

Step 1: To a mixture of 2-bromo-3-methylpyridine (51 mg, 2.96 mmol), CuI (1.12 g, 5.92 mmol), Pd(AcO)$_2$ (132 mg, 0.592 mmol), PPh$_3$ (309 mg, 1.18 mmol), DBU (901 mg, 5.92 mmol), methyl 1-methyl-1H-imidazole-4-carboxylate (497 mg, 3.55 mmol) was added Dioxane (5 mL). The resulting mixture was stirred for 2 hours at 140° C. under N$_2$ atmosphere. The reaction mixture was concentrated under reduced pressure. The residue was purified by flash chromatography on silica gel eluting with 35% of ethyl acetate in petroleum ether to afford methyl 1-methyl-2-(3-methylpyridin-2-yl)-1H-imidazole-4-carboxylate (320 mg, 46.7%) as a white solid. LCMS [M+H]+: 232

Step 2: To a stirred solution of methyl 1-methyl-2-(3-methylpyridin-2-yl)-1H-imidazole-4-carboxylate (150 mg, 0.648 mmol) in 2 mL of THF and 2 mL of water was added LiOH (135 mg, 3.23 mmol). The resulting mixture was stirred for two hours at room temperature. Then it was concentrated, and the PH value of the residue solution was adjusted to 3 with 1M HCl(aq). The product was precipitated from the solution. After filtration, the filter cake was washed with water and dried under vacuum. This resulted in 1-methyl-2-(3-methylpyridin-2-yl)-1H-imidazole-4-carboxylic acid (110 mg, 78.0%) as a white solid. LCMS [M+H]+: 218

Step 3: To a mixture of 1-methyl-2-(3-methylpyridin-2-yl)-1H-imidazole-4-carboxylic acid (110 mg, 0.506 mmol) and N-(3-amino-5-bromophenyl)methanesulfonamide (160 mg, 0.607 mmol) in ACN (1 mL) was added TCFH (212 mg, 0.759 mmol) and NMI (123 mg, 1.51 mmol) at room temperature for two hours. Then it was concentrated, the residue was purified by reverse phase flash chromatography eluting with 60% of acetonitrile in water (0.1% NH$_4$HCO$_3$) to afford N-(3-bromo-5-methanesulfonamidophenyl)-1-methyl-2-(3-methylpyridin-2-yl)-1H-imidazole-4-carboxamide (25.9 mg, 11.0%) as a light pink solid. LCMS [M+H]+: 464 $^1$H NMR (300 MHz, DMSO-d$_6$) δ 10.00 (s, 2H), 8.54 (d, J=4.6 Hz, 1H), 8.03 (s, 1H), 7.91-7.76 (m, 3H), 7.43 (dd, J=7.8, 4.8 Hz, 1H), 7.04 (s, 1H), 3.76 (s, 3H), 3.08 (s, 3H), 2.48 (s, 3H).

Example 97: N-(3-chloro-5-(methylsulfonamido)phenyl)-1-(3-(difluoro(phenyl)methoxy)pyridin-2-yl)-1H-pyrazole-4-carboxamide

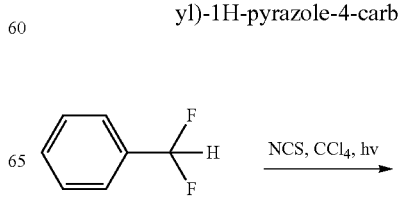

-continued

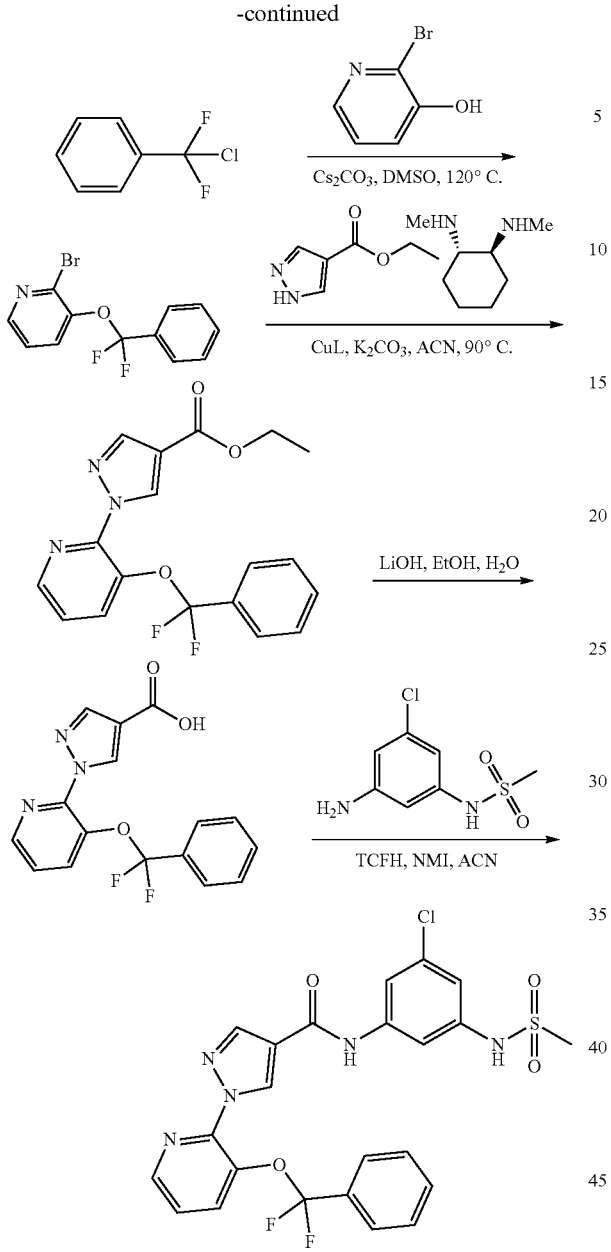

Step 1: To a stirred solution of (difluoromethyl)benzene (1.2 g, 9.36 mmol) and NCS (1.36 g, 10.2 mmol) in CCl4 (20 mL). The magnetically stirred mixture was exposed to sunlight during the daytime and a sunlamp at night for 50 h at room temperature. The resulting mixture was concentrated under reduced pressure at 0° C. to afford (chlorodifluoromethyl)benzene (350 mg, 2.15 mmol, low boiling point) as a yellow oil.

Step 2: To a stirred solution of (chlorodifluoromethyl)benzene (350 mg, 2.15 mmol), Cs₂CO₃ (1.40 g, 4.30 mmol) and 2-bromopyridin-3-ol (410 mg, 2.36 mmol) in DMSO (5 mL). Then the mixture was stirred for 3 h at 120° C. The mixture was concentrated and purified by reverse phase flash chromatography eluting with ACN/H₂O (5-95%, acidic system) to afford 2-bromo-3-[difluoro(phenyl) methoxy]pyridine (50.0 mg, 0.166 mmol) as a yellow solid. LCMS (ESI) [M+H]⁺: 300

Step 3: A solution of 2-bromo-3-[difluoro(phenyl) methoxy]pyridine (50 mg, 0.166 mmol), CuI (6.32 mg, 0.0332 mmol), K₂CO₃ (68.8 mg, 0.498 mmol), ethyl 1H-pyrazole-4-carboxylate (25.5 mg, 0.182 mmol) and (1S, 2S)-N1, N2-dimethylcyclohexane-1,2-diamine (9.44 mg, 0.0664 mmol) in ACN (5 mL) was stirred for 2 h at 90° C. under nitrogen atmosphere. The resulting mixture was concentrated under reduced pressure. The residue was purified by silica gel column chromatography, eluted with Petroleum ether/EtOAc (0-100%) to afford ethyl 1-{3-[difluoro(phenyl)methoxy]pyridin-2-yl}-1H-pyrazole-4-carboxylate (40.0 mg, 0.111 mmol) as a yellow solid. LCMS (ESI) [M+H]⁺: 360

Step 4: To a stirred solution of ethyl 1-{3-[difluoro(phenyl)methoxy]pyridin-2-yl}-1H-pyrazole-4-carboxylate (40 mg, 0.111 mmol) in EtOH (3 mL) and H₂O (3 mL) was added LiOH (26.5 mg, 1.11 mmol). Then the mixture was stirred for 2 h at room temperature. The mixture was acidified to pH 5 with citric acid. The precipitated solids were collected by filtration and washed with water. The resulting solid was dried under vacuum to afford 1-{3-[difluoro(phenyl)methoxy]pyridin-2-yl}-1H-pyrazole-4-carboxylic acid (28.0 mg, 0.0845 mmol) as a yellow solid. LCMS (ESI) [M+H]⁺: 332

Step 5: To a stirred solution of 1-{3-[difluoro(phenyl)methoxy]pyridin-2-yl}-1H-pyrazole-4-carboxylic acid (28 mg, 0.0845 mmol), TCFH (23.7 mg, 0.0845 mmol) and NMI (6.93 mg, 0.0845 mmol) in ACN (5 mL) was added N-(3-amino-5-chlorophenyl)methanesulfonamide (20.5 mg, 0.0929 mmol). Then the mixture was stirred for 1 h at room temperature. The mixture was concentrated and purified by reverse phase flash chromatography eluting with ACN/H₂O (5-95%, acidic system) to afford N-(3-chloro-5-methanesulfonamidophenyl)-1-{3-[difluoro(phenyl)methoxy]pyridin-2-yl}-1H-pyrazole-4-carboxamide (6.4 0 mg, 0.0119 mmol) as an orange solid. LCMS (ESI) [M+H]⁺: 534. H NMR (300 MHz, DMSO-d₆) δ 10.27 (s, 1H), 10.11 (s, 1H), 9.07 (s, 1H), 8.58 (dd, J=4.6, 1.5 Hz, 1H), 8.34 (s, 1H), 8.24-8.15 (m, 1H), 7.79-7.66 (m, 4H), 7.66-7.50 (m, 4H), 6.94 (t, J=1.9 Hz, 1H), 3.07 (s, 3H).

Example 98: N-(3-chloro-5-(methylsulfonamido)phenyl)-5-cyano-1-(pyridin-2-yl)-1H-pyrrole-3-carboxamide

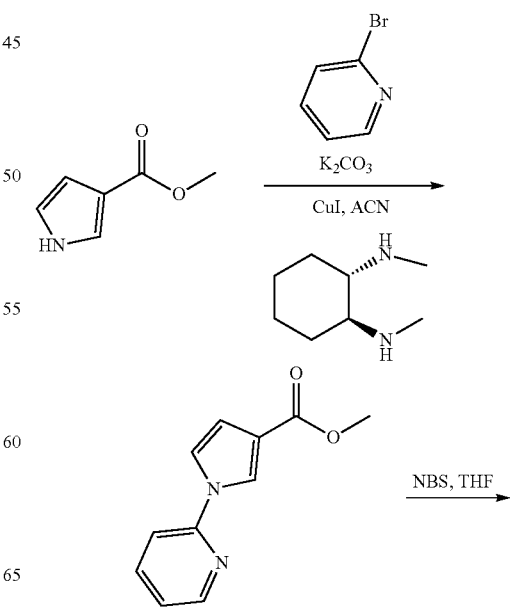

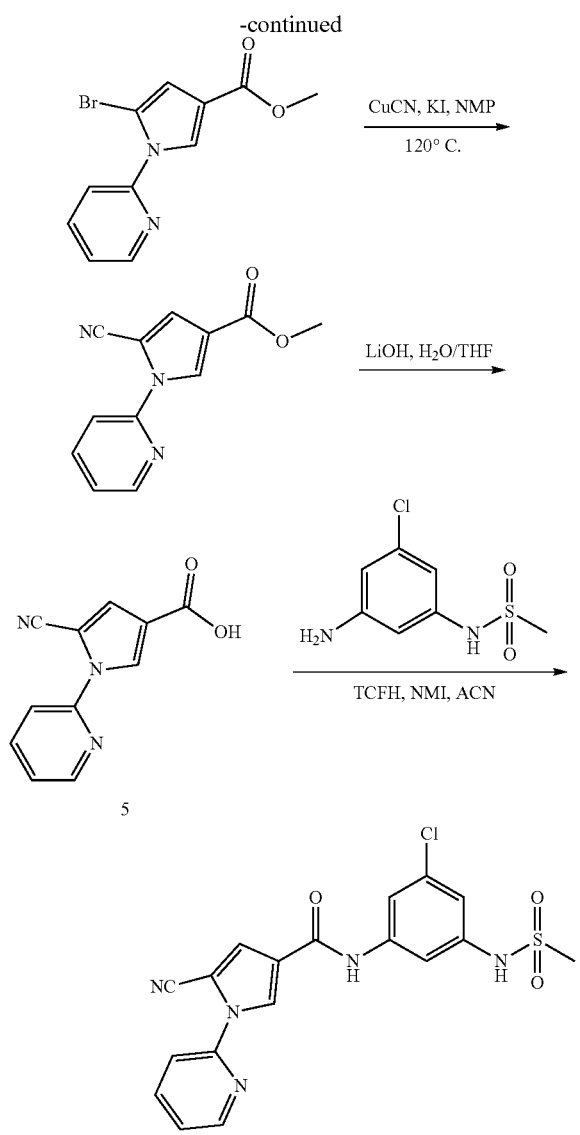

Step 1: Under nitrogen, a solution of methyl 1H-pyrrole-3-carboxylate (1 g, 7.992 mmol, 1 equiv), 2-bromo pyridine (1.89 g, 11.988 mmol, 1.5 equiv), CuI (304.4 mg, 1.598 mmol, 0.20 equiv) and (1S,2S)-N1, N2-dimethylcyclohexane-1,2-diamine (454.7 mg, 3.197 mmol, 0.40 equiv) in ACN (10 mL) was added $K_2CO_3$ (3.34 g, 23.992 mmol, 3.00 equiv) at room temperature. The resulting solution was stirred for two hours at 90° C. The resulting solution was concentrated under vacuum. The residue was purified by flash chromatography on silica gel eluting with EtOAc/Petroleum ether (26%) to afford methyl 1-(pyridin-2-yl) pyrrole-3-carboxylate (1.2 g, 68.69%) as a yellow solid. LCMS: (ESI): [M+H]$^+$:203

Step 2: To a solution of methyl 1-(pyridin-2-yl) pyrrole-3-carboxylate (850 mg, 4.203 mmol, 1 equiv) in THF (10 mL) was added NBS (897.79 mg, 5.044 mmol, 1.2 equiv) at room temperature. The resulting solution was stirred for two hours at room temperature. The residue was purified by flash chromatography on silica gel eluting with column gel eluting with EtOAc/Petroleum ether (28%) to afford methyl 5-bromo-1-(pyridin-2-yl) pyrrole-3-carboxylate (410 mg, 33.31%) as a yellow solid. LCMS: (ESI): [M+H]$^+$:281

Step 3: Under nitrogen, a solution of methyl 5-bromo-1-(pyridin-2-yl) pyrrole-3-carboxylate (410 mg, 1.459 mmol, 1 equiv) and CuCN (261.3 mg, 2.917 mmol, 2.00 equiv) in NMP (5 mL) was added KI (242.1 mg, 1.458 mmol, 1.00 equiv) at room temperature. The resulting solution was stirred for two hours at 120° C. The reaction mixture was diluted with water (50 mL). The resulting solution was extracted with EtOAc (50×3 mL) and the organic layers were combined. The organic layer was dried over anhydrous sodium sulfate and concentrated under vacuum. The residue was purified by flash chromatography on silica gel eluting with EtOAc/Petroleum ether (35%) to afford methyl 5-cyano-1-(pyridin-2-yl) pyrrole-3-carboxylate (180 mg, 46.71%) as a yellow solid. LCMS: (ESI): [M+H]$^+$:228

Step 4: To a solution of methyl 5-cyano-1-(pyridin-2-yl) pyrrole-3-carboxylate (180 mg, 0.753 mmol, 1 equiv, 95%) in THF (4 mL) and $H_2O$ (2 mL) was added LiOH (90.1 mg, 3.762 mmol, 5.00 equiv) at room temperature. The resulting solution was stirred for one hour at room temperature. The residue was purified by flash chromatography on C18 column gel eluting with ACN/water (0.1% FA) (45%) to afford 5-cyano-1-(pyridin-2-yl) pyrrole-3-carboxylic acid (150 mg, 86.01%) as a yellow solid. LCMS: (ESI): [M+H]$^+$:214

Step 5: A solution of 5-cyano-1-(pyridin-2-yl) pyrrole-3-carboxylic acid (150 mg, 0.704 mmol, 1 equiv), NMI (115.5 mg, 1.407 mmol, 2.00 equiv) and TCFH (296.1 mg, 1.055 mmol, 1.50 equiv) in ACN (5 mL) at room temperature. The resulting solution was stirred for 10 minus at room temperature. Then N-(3-amino-5-chlorophenyl) methanesulfonamide (186.3 mg, 0.844 mmol, 1.20 equiv) was added and stirred for one hours at room temperature. The residue was purified by Pre-HPLC on condition: Column: Sunfire prep C18 column, 30*150 mm, 5 μm; Mobile Phase A: Water (0.1% FA), Mobile Phase B: ACN; Flow rate: 60 mL/min; Gradient: 40% B to 60% B in 7 min, 60% B; Wave Length: 254/220 nm; RT1(min): 5.72 to afford N-(3-chloro-5-methanesulfonamidophenyl)-5-(phenylamino)-2H-pyrazole-3-carboxamide (29.6 mg, 48.73%) as a white solid. LCMS: (ESI): [M+H]$^+$:416. $^1$H NMR (300 MHz, DMSO-$d_6$) δ 10.21 (s, 1H), 10.10 (s, 1H), 8.63 (d, J=4.8 Hz, 1H), 8.56 (d, J=1.8 Hz, 1H), 8.19-8.08 (m, 1H), 7.89 (d, J=8.2 Hz, 1H), 7.81 (d, J=1.8 Hz, 1H), 7.71 (t, J=1.9 Hz, 1H), 7.62 (d, J=2.0 Hz, 1H), 7.57 (dd, J=7.4, 4.7 Hz, 1H), 6.95 (t, J=2.0 Hz, 1H), 3.08 (s, 3H).

Example 99: 1-benzyl-N-(3-bromo-5-(methylsulfonamido)phenyl)-2-oxo-2,3-dihydro-1H-benzo[d]imidazole-5-carboxamide

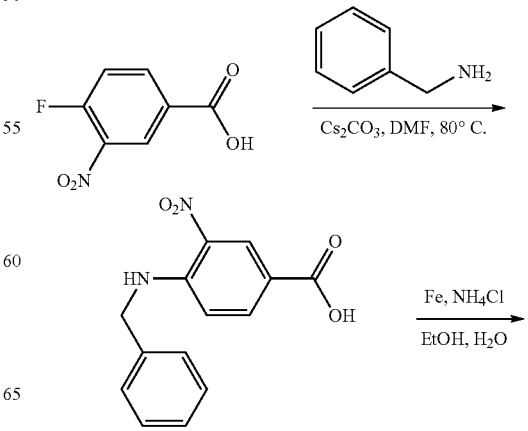

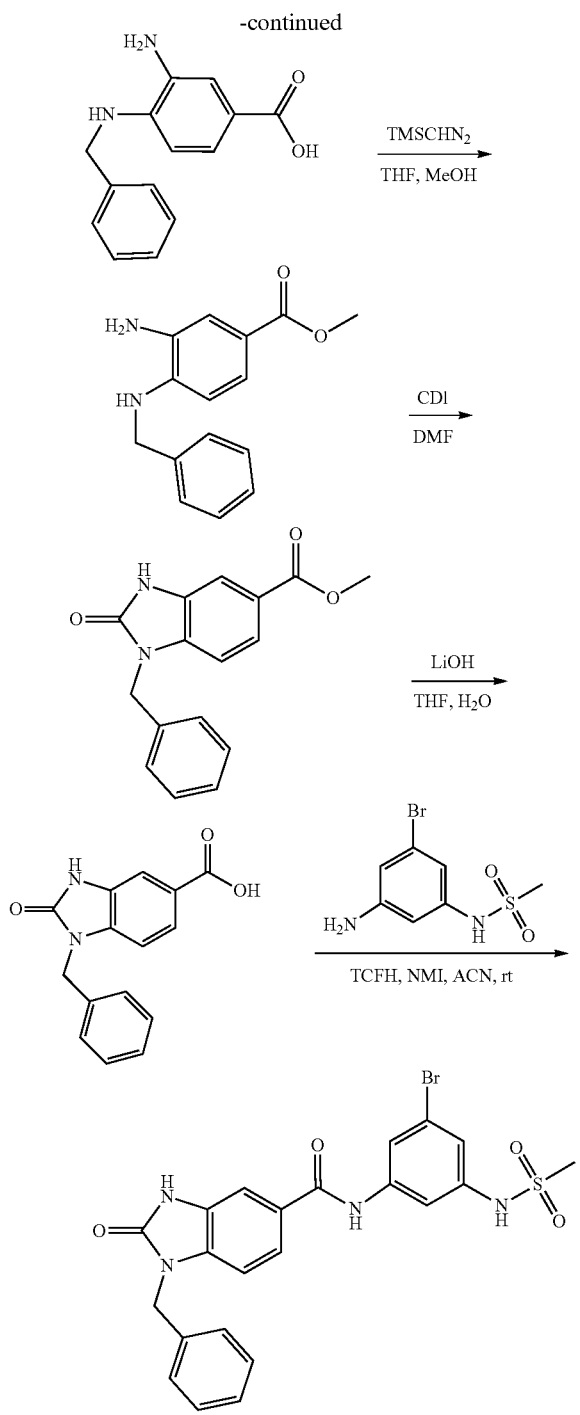

Fe (1.43 g, 25.6 mmol). Then the mixture was stirred for 2 h at 90° C. The mixture was concentrated and purified by flash chromatography eluting with EtOAc/Petroleum ether (0-100%, acidic system) to afford 3-amino-4-(benzylamino) benzoic acid (330 mg, 1.36 mmol) as an yellow solid. LCMS (ESI) [M+H]$^+$: 243.11

Step 3: To a stirred solution of 3-amino-4-(benzylamino) benzoic acid (330 mg, 1.36 mmol) in THF (6 mL) and MeOH (2 mL) was added a solution of (trimethylsilyl) diazomethane (4.08 mmol) in hexane dropwise under $N_2$ atmosphere. Then the mixture was stirred for 2 h at room temperature. The mixture was concentrated and purified by reverse phase flash chromatography eluting with ACN/H$_2$O (0-100%, acidic system) to afford methyl 3-amino-4-(benzylamino)benzoate (265 mg, 1.03 mmol) as a yellow solid. LCMS (ESI) [M+H]$^+$: 357.12

Step 4: To a stirred solution of methyl 3-amino-4-(benzylamino)benzoate (265 mg, 1.03 mmol) in DMF (5 mL) was added CDI (225 mg, 3.09 mmol). Then the mixture was stirred for 2 h at 60° C. The mixture was concentrated and purified by reverse phase flash chromatography eluting with ACN/H$_2$O (0-100%, acidic system) to afford methyl 1-benzyl-2-oxo-2,3-dihydro-1H-1,3-benzodiazole-5-carboxylate (100 mg, 0.354 mmol) as an off-white solid. LCMS (ESI) [M+H]$^+$: 283.02

Step 5: To a stirred solution of methyl 1-benzyl-2-oxo-2,3-dihydro-1H-1,3-benzodiazole-5-carboxylate (100 mg, 0.354 mmol) in THF (3 mL) and H$_2$O (1 mL) was added LiOH (25.3 mg, 1.06 mmol). Then the mixture was stirred for 2 h at room temperature. The mixture was concentrated and purified by reverse phase flash chromatography eluting with ACN/H$_2$O (0-100%, acidic system) to afford 1-benzyl-2-oxo-2,3-dihydro-1H-1,3-benzodiazole-5-carboxylic acid (76.0 mg, 0.283 mmol) as an off-white solid. LCMS (ESI) [M+H]$^+$: 269.04 Step 6: To a stirred solution of 1-benzyl-2-oxo-2,3-dihydro-1H-1,3-benzodiazole-5-carboxylic acid (76 mg, 0.283 mmol), NMI (115 mg, 1.41 mmol) and TCFH (118 mg, 0.424 mmol) in ACN (5 mL) was added N-(3-amino-5-bromophenyl) methane sulfonamide (75.0 mg, 0.283 mmol). Then the mixture was stirred for 2 h at room temperature. The mixture was concentrated and purified by reverse phase flash chromatography eluting with ACN/H$_2$O (0-100%, acidic system) to afford 1-benzyl-N-(3-bromo-5-methanesulfonamido phenyl)-2-oxo-2,3-dihydro-1H-1,3-benzodiazole-5-car boxamide (21.1 mg, 0.039.5 mmol) as a white solid. LCMS (ESI) [M+H]$^+$: 515.3. $^1$H NMR (300 MHz, DMSO-d$_6$) δ 10.61 (s, 1H), 8.52 (d, J=2.6 Hz, 1H), 8.34 (s, 1H), 8.03 (d, J=8.1 Hz, 1H), 7.84 (d, J=7.7 Hz, 1H), 7.71 (d, J=1.9 Hz, 2H), 7.65 (t, J=7.8 Hz, 1H), 6.98 (t, J=2.0 Hz, 1H), 6.55 (d, J=2.5 Hz, 1H), 5.26 (s, 1H), 4.55 (s, 2H), 3.08 (s, 3H).

Example 100: N-(3-chloro-5-(methylsulfonamido) phenyl)-3-(3-cyano-1H-pyrazol-1-yl)benzamide

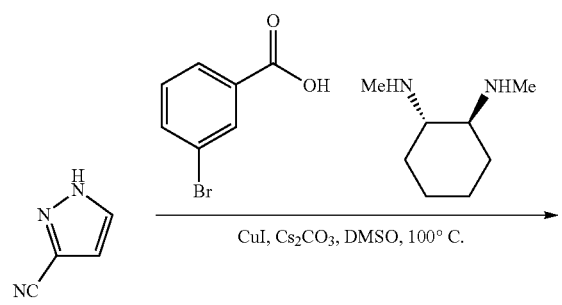

Step 1: To a stirred solution of 4-fluoro-3-nitrobenzoic acid (1 g, 5.40 mmol) and 1-phenylmethanamine (578 mg, 5.40 mmol) in DMF (15 mL) was added Cs$_2$CO$_3$ (5.26 g, 16.2 mmol). Then the mixture was stirred for 2 h at 80° C. The mixture was concentrated and purified by reverse phase flash chromatography eluting with ACN/H$_2$O (0-100%, acidic system) to afford 4-(benzylamino)-3-nitrobenzoic acid (700 mg, 2.57 mmol) as a yellow solid. LCMS (ESI) [M+H]$^+$: 273.08

Step 2: To a stirred solution of 4-(benzylamino)-3-nitrobenzoic acid (700 mg, 2.57 mmol) and NH$_4$Cl (1.08 g, 20.5 mmol) in EtOH (10 mL) and H$_2$O (3 mL) was added -continued

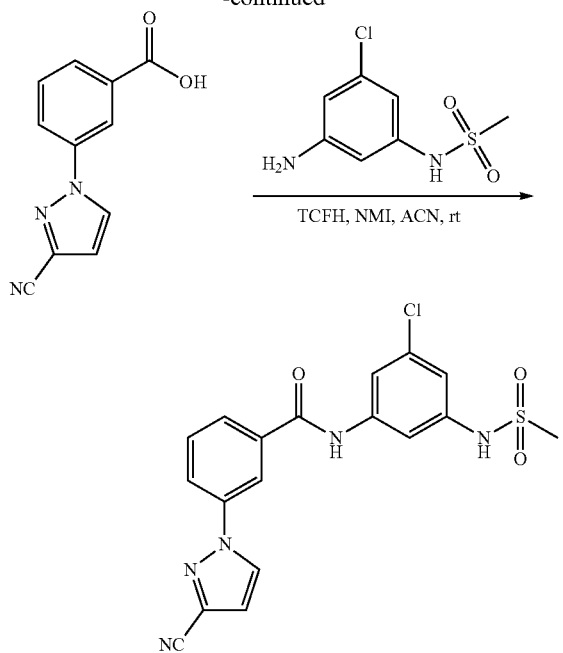

Step 1: To a stirred solution of 1H-pyrazole-3-carbonitrile (260 mg, 2.79 mmol), CuI (106 mg, 0.558 mmol), (1S,2S)-N1,N2-dimethylcyclohexane-1,2-diamine (157 mg, 1.11 mmol) and 3-bromobenzoic acid (560 mg, 2.79 mmol) in DMSO (10 mL) was added $Cs_2CO_3$ (2.72 g, 8.37 mmol). Then the mixture was stirred for 2 h at 100° C. under $N_2$ atmosphere. The mixture was concentrated and purified by reverse phase flash chromatography eluting with $ACN/H_2O$ (0-100%, acidic system) to afford 3-(3-cyano-1H-pyrazol-1-yl)benzoic acid (85.0 mg, 0.398 mmol) as a yellow solid. LCMS (ESI) [M+H]$^+$: 214.05

Step 2: To a stirred solution of 3-(3-cyano-1H-pyrazol-1-yl)benzoic acid (85 mg, 0.398 mmol), TCFH (167 mg, 0.597 mmol) and NMI (163 mg, 1.99 mmol) in ACN (5 mL) was added N-(3-amino-5-chlorophenyl)methanesulfonamide (87.8 mg, 0.398 mmol). Then the mixture was stirred for 2 h at room temperature. The mixture was concentrated and purified by reverse phase flash chromatography eluting with $ACN/H_2O$ (0-100%, acidic system) to afford N-(3-chloro-5-methane sulfonamidophenyl)-3-(3-cyano-1H-pyrazol-1-yl)benzamide (24.3 mg, 0.0570 mmol) as a white solid. LCMS (ESI) [M+H]$^+$: 416.05. $^1$H NMR (300 MHz, DMSO-$d_6$) δ 10.66 (s, 1H), 10.12 (s, 1H), 8.92 (d, J=2.7 Hz, 1H), 8.43 (d, J=2.2 Hz, 1H), 8.19-8.09 (m, 1H), 8.01 (d, J=7.8 Hz, 1H), 7.81-7.68 (m, 3H), 7.35 (d, J=2.6 Hz, 1H), 6.99 (t, J=2.0 Hz, 1H), 3.09 (s, 3H).

Example 101: N-(3-bromo-5-(methylsulfonamido)phenyl)-2-oxo-1-phenyl-2,3-dihydro-1H-imidazole-4-carboxamide

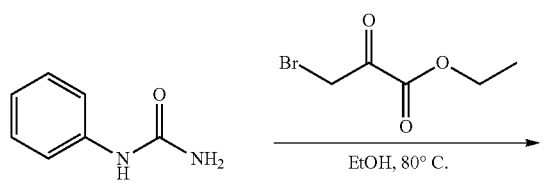

-continued

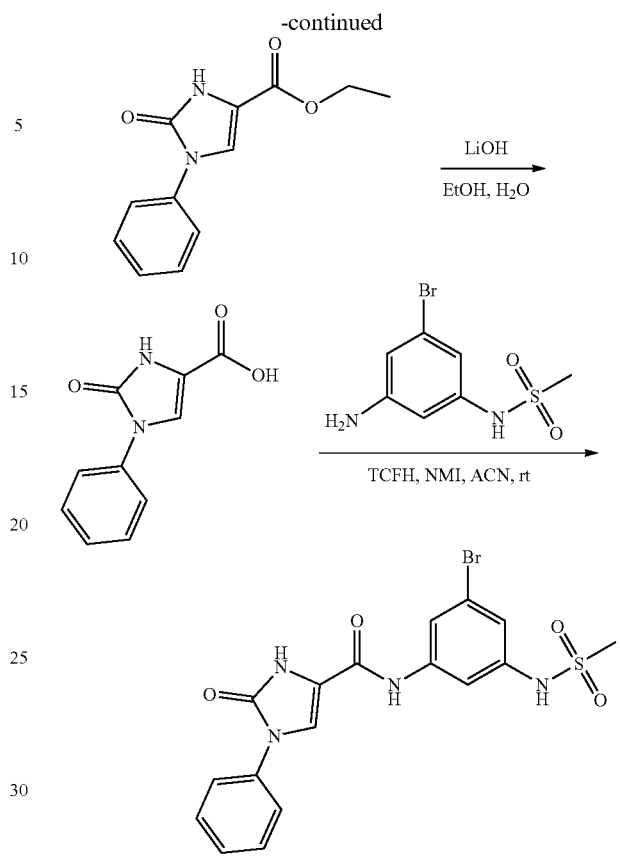

Step 1: A mixture of phenylurea (500 mg, 3.67 mmol) and ethyl 3-bromo-2-oxopropanoate 5 (715 mg, 3.67 mmol) in EtOH (10 mL) was stirred for 2 h at 80° C. The mixture was concentrated and purified by reverse phase flash chromatography eluting with $ACN/H_2O$ (0-100%, acidic system) to afford ethyl 2-oxo-1-phenyl-2,3-dihydro-1H-imidazole-4-carboxylate (235 mg, 1.01 mmol) as a yellow solid. LCMS (ESI) [M+H]$^+$: 233.08

Step 2: To a stirred solution of ethyl 2-oxo-1-phenyl-2,3-dihydro-1H-imidazole-4-carboxylate (235 mg, 1.01 mmol) in EtOH (3 mL) and $H_2O$ (1 mL) was added LiOH (72.5 mg, 3.03 mmol). Then the mixture was stirred for 2 h at room temperature. The mixture was concentrated and purified by reverse phase flash chromatography eluting with $ACN/H_2O$ (0-100%, acidic system) to afford 2-oxo-1-phenyl-2,3-dihydro-1H-imidazole-4-carboxylic acid (180 mg, 0.881 mmol) as a yellow solid. LCMS (ESI) [M+H]$^+$: 205.05

Step 3: To a stirred solution of 2-oxo-1-phenyl-2,3-dihydro-1H-imidazole-4-carboxylic acid (180 mg, 0.881 mmol), TCFH (369 mg, 1.32 mmol) and NMI (360 mg, 4.40 mmol) in ACN (10 mL) was added N-(3-amino-5-bromophenyl)methanesulfonamide (233 mg, 0.881 mmol). Then the mixture was stirred for 2 h at room temperature. The mixture was concentrated and purified by reverse phase flash chromatography eluting with $ACN/H_2O$ (0-100%, acidic system) to afford N-(3-bromo-5-methanesulfonamidophenyl)-2-oxo-1-phenyl-2,3-dihydro-1H-imidazole-4-carboxamide (21.1 mg, 0.0466 mmol) as a white solid. LCMS (ESI) [M+H]$^+$: 451. $^1$H NMR (300 MHz, DMSO-$d_6$) δ 10.38 (s, 1H), 10.05 (d, J=7.7 Hz, 2H), 8.33 (s, 1H), 7.83 (s, 1H), 7.81-7.71 (m, 3H), 7.35 (t, J=7.8 Hz, 2H), 7.12 (s, 1H), 7.00 (t, J=7.3 Hz, 1H), 3.09 (s, 3H).

217
Example 102: N-(3-chloro-5-(methylsulfonamido) phenyl)-3-(2-chloropyridin-4-yl)benzamide

218
Example 103: N-(3-bromo-5-(methylsulfonamido) phenyl)-1-(2-(2,2,2-trifluoro-1-hydroxyethyl)phenyl)-1H-pyrazole-4-carboxamide

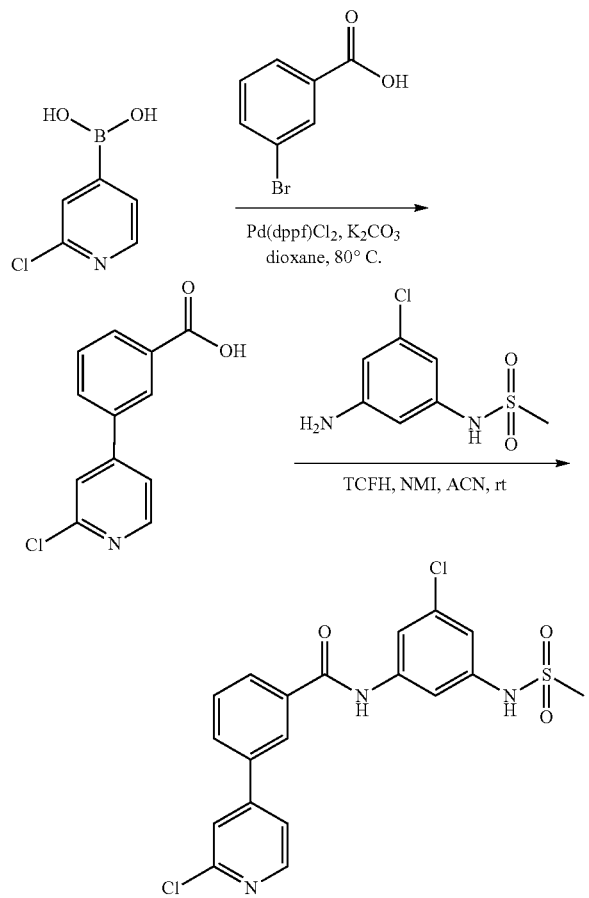

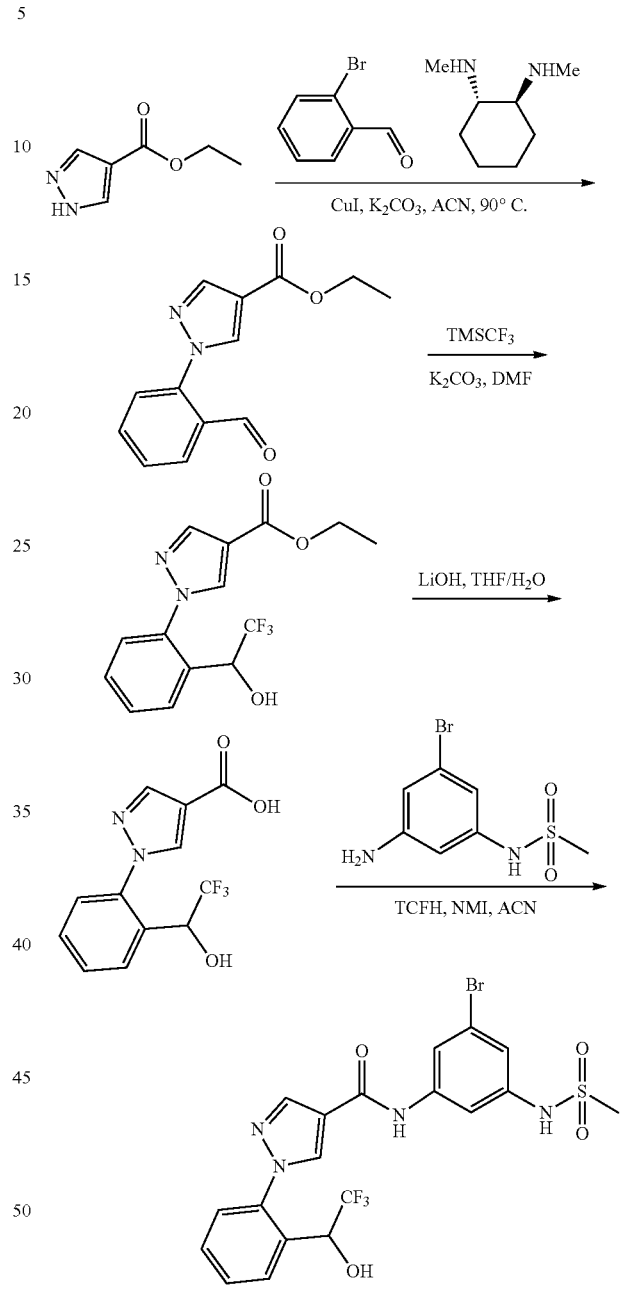

Step 1: To a stirred solution of (2-chloropyridin-4-yl) boronic acid (500 mg, 3.17 mmol), Pd(dppf)Cl$_2$ (347 mg, 0.475 mmol) and 3-bromobenzoic acid (637 mg, 3.17 mmol) in dioxane (15 mL) was added K$_2$CO$_3$ (1.32 g, 9.51 mmol). Then the mixture was stirred for 2 h at 80° C. The mixture was concentrated and purified by reverse phase flash chromatography eluting with ACN/H$_2$O (0-100%, acidic system) to afford 3-(2-chloropyridin-4-yl)benzoic acid (210 mg, 0.898 mmol) as a yellow solid. LCMS (ESI) [M+H]$^+$: 234.02

Step 2: To a stirred solution of 3-(2-chloropyridin-4-yl) benzoic acid (200 mg, 0.855 mmol), TCFH (358 mg, 1.28 mmol) and NMI (350 mg, 4.27 mmol) in ACN (5 mL) was added N-(3-amino-5-chlorophenyl)methanesulfonamide (188 mg, 0.855 mmol). Then the mixture was stirred for 2 h at room temperature. The mixture was concentrated and purified by reverse phase flash chromatography eluting with ACN/H$_2$O (0-100%, acidic system) to afford N-(3-chloro-5-methanesulfonamidophenyl)-3-(2-chloropyridin-4-yl) benzamide (24.8 mg, 0.0566 mmol) as a white solid. LCMS (ESI) [M+H]$^+$: 436.02. $^1$H NMR (300 MHz, DMSO-d$_6$) δ 10.59 (s, 1H), 10.11 (s, 1H), 8.54 (d, J=5.3 Hz, 1H), 8.37 (s, 1H), 8.10 (d, J=7.7 Hz, 1H), 8.06 (d, J=7.8 Hz, 1H), 8.00 (d, J=1.6 Hz, 1H), 7.96-7.78 (m, 1H), 7.77-7.66 (m, 3H), 6.99 (t, J=1.9 Hz, 1H), 3.09 (s, 3H).

Step 1: To a stirred solution of ethyl 1H-pyrazole-4-carboxylate (310 mg, 2.21 mmol), 2-bromobenzaldehyde (490 mg, 2.65 mmol), (1S,2S)-N1,N2-dimethylcyclohexane-1,2-diamine (125 mg, 0.884 mmol), CuI (83.9 mg, 0.442 mmol) and K$_2$CO$_3$ (914 mg, 6.63 mmol) in ACN (10.00 mL). Then the mixture was stirred for 4 h at 90° C. under N2. The mixture was concentrated and purified by reverse phase flash chromatography eluting with ACN/H$_2$O (5-95%, acidic system) to afford ethyl 1-(2-formylphenyl)-1H-pyrazole-4-carboxylate (332 mg, 1.36 mmol, 95%) as a yellow solid. LCMS (ESI) [M+H]$^+$: 245

Step 2: To a stirred solution of ethyl 1-(2-formylphenyl)-1H-pyrazole-4-carboxylate (350 mg, 1.43 mmol), trimethyl (trifluoromethyl)silane (813 mg, 5.72 mmol) and K$_2$CO$_3$ (592 mg, 4.29 mmol) in DMF (10.00 mL). Then the mixture was stirred for 4 h at room temperature. The mixture was concentrated and purified by reverse phase flash chromatography eluting with ACN/H$_2$O (5-95%, acidic system) to afford ethyl 1-[2-(2,2,2-trifluoro-1-hydroxyethyl)phenyl]-1H-pyrazole-4-carboxylate (209 mg, 95%) as a yellow solid. LCMS (ESI) [M+H]$^+$: 315

Step 3: To a stirred solution of ethyl 1-[2-(2,2,2-trifluoro-1-hydroxyethyl)phenyl]-1H-pyrazole-4-carboxylate (220 mg, 0.700 mmol) and LiOH (10 mg, 2.5 mmol) in THF (10.00 mL) was added H$_2$O (2.00 mL). Then the mixture was stirred for 2 h at room temperature. The mixture was acidified to pH 5 with citric acid. The precipitated solids were collected by filtration and washed with water. The resulting solid was dried under vacuum to afford 1-[2-(2,2,2-trifluoro-1-hydroxyethyl)phenyl]-1H-pyrazole-4-carboxylic acid (104 mg, 95%) as a white solid. LCMS (ESI) [M+H]$^+$: 310

Step 4: To a stirred solution of 1-[2-(2,2,2-trifluoro-1-hydroxyethyl)phenyl]-1H-pyrazole-4-carboxylic acid (110 mg, 0.384 mmol), TCFH (107 mg, 0.384 mmol) and NMI (31.3 mg, 0.384 mmol) in ACN (10.00 mL) was added N-(3-amino-5-bromophenyl)methanesulfonamide (101 mg, 0.384 mmol). Then the mixture was stirred for 4 h at room temperature. The mixture was concentrated and purified by reverse phase flash chromatography eluting with ACN/H$_2$O (5-95%, acidic system) to afford N-(3-bromo-5-methanesulfonamidophenyl)-1-[2-(2,2,2-trifluoro-1-hydroxyethyl)phenyl]-1H-pyrazole-4-carboxamide (3 4.4 mg, 96.918%) as a white solid. LCMS (ESI) [M+H]$^+$: 534. $^1$H NMR (400 MHz, DMSO-d$_6$) δ 10.17 (s, 1H), 10.09-10.04 (m, 1H), 8.70 (s, 1H), 8.34 (d, J=0.6 Hz, 1H), 7.88-7.81 (m, 2H), 7.69-7.58 (m, 3H), 7.58-7.51 (m, 1H), 7.11-7.05 (m, 2H), 5.61 (p, J=6.9 Hz, 1H), 3.07 (s, 3H).

Example 104: 4-((1H-pyrrol-2-yl)methyl)-N-(3-bromo-5-(methylsulfonamido)phenyl)-thiophene-2-carboxamide

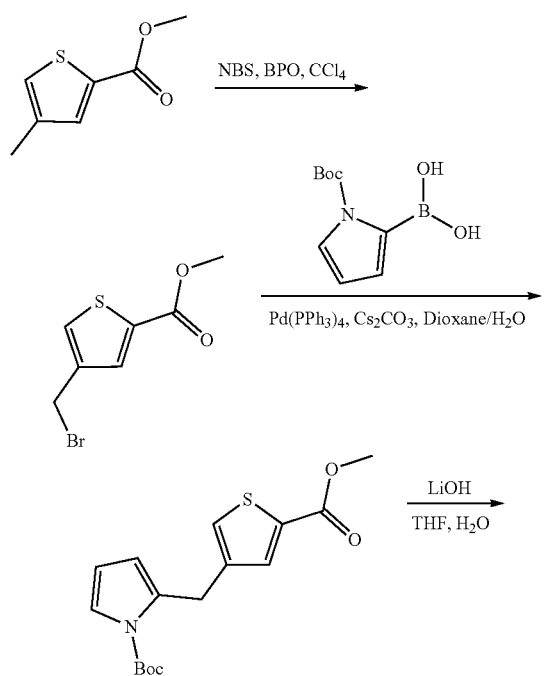

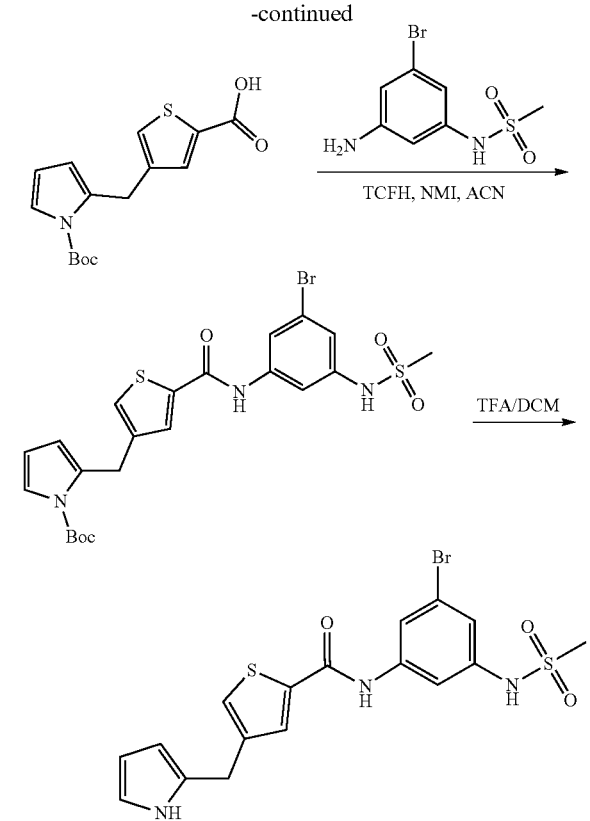

Step 1: To a solution of methyl 4-methylthiophene-2-carboxylate (500 mg, 3.201 mmol, 1 equiv) and NBS (854.6 mg, 4.802 mmol, 1.50 equiv) in CCl$_4$ (10 mL) was added BPO (1640.6 mg, 6.402 mmol, 2.00 equiv) at room temperature under nitrogen. The resulting solution was stirred overnight at 80° C. The resulting solution was concentrated under vacuum. The residue was purified by flash chromatography on silica gel eluting with EtOAc/Petroleum ether (26%) to afford methyl 4-(bromomethyl)thiophene-2-carboxylate (200 mg, 26.5%) as a yellow oil. LCMS: (ESI): [M+H]$^+$:235

Step 2: To a solution of methyl 4-(bromomethyl)thiophene-2-carboxylate (200 mg, 0.851 mmol, 1 equiv), Pd(PPh$_3$)$_4$(98.3 mg, 0.085 mmol, 0.10 equiv) and 1-(tert-butoxycarbonyl)pyrrol-2-ylboronic acid (269.3 mg, 1.276 mmol, 1.50 equiv) in Dioxane (5 mL) and H$_2$O (0.5 mL) was added Cs$_2$CO$_3$ (831.5 mg, 2.552 mmol, 3.00 equiv) at room temperature under nitrogen. The resulting solution was stirred for 2 hours at 90° C. The reaction mixture was diluted with water (50 mL). The resulting solution was extracted with EtOAc (50×3 mL) and the organic layers were combined. The organic layer was dried over anhydrous sodium sulfate and concentrated under vacuum. The residue was purified by flash chromatography on silica gel eluting with EtOAc/Petroleum ether (42%) to afford tert-butyl 2-{[5-(methoxycarbonyl)thiophen-3-yl]methyl}pyrrole-1-carboxylate (80 mg, 27.50%) as a yellow oil. LCMS: (ESI): [M+H]$^+$:322

Step 3: To a solution of tert-butyl 2-{[5-(methoxycarbonyl)thiophen-3-yl]methyl}pyrrole-1-carboxylate (80 mg, 0.249 mmol, 1 equiv) in THF (2 mL) and H$_2$O (1 mL) was added LiOH (29.8 mg, 1.244 mmol, 5.00 equiv) at room temperature. The resulting solution was stirred for one hour at room temperature. The residue was purified by flash chromatography on C18 column gel eluting with ACN/water (0.1% FA) (33%) to afford 4-{[1-(tert-butoxycarbonyl)pyrrol-2-yl]methyl}thiophene-2-carboxylic acid (60 mg, 75.29%) as a white solid. LCMS: (ESI): [M+H]+:308

Step 4: A solution of 4-{[1-(tert-butoxycarbonyl)pyrrol-2-yl]methyl}thiophene-2-carboxylic acid (50 mg, 0.163 mmol, 1 equiv), NMI (26.7 mg, 0.325 mmol, 2.00 equiv) and TCFH (68.5 mg, 0.244 mmol, 1.50 equiv) in ACN (2 mL) at room temperature. The resulting solution was stirred for 10 minus at room temperature. Then N-(3-amino-5-bromophenyl) methanesulfonamide (64.7 mg, 0.244 mmol, 1.50 equiv) was added and stirred at room temperature for one hours. The residue was purified by C18 column gel eluting with ACN/water (0.05 NH$_4$HCO$_3$) (65%) to afford tert-butyl 2-({5-[(3-bromo-5-methanesulfonamidophenyl)carbamoyl]thiophen-3-yl}methyl)pyrrole-1-carboxylate (55 mg, 59.93%) as a white solid. LCMS: (ESI): [M+H]+: 554

Step 5: To a solution of tert-butyl 2-({5-[(3-bromo-5-methanesulfonamidophenyl)carbamoyl]thiophen-3-yl}methyl)pyrrole-1-carboxylate (55 mg, 0.099 mmol, 1 equiv) in DCM (2 mL) was added TFA (1 mL) at 0° C. The mixture was stirred for one hour at room temperature. The residue was purified by Pre-HPLC on condition: Column: YMC-Actus Triart C18 ExRS, 30*150 mm, 5 µm; Mobile Phase A: Water (10 mmol/L NH$_4$HCO$_3$), Mobile Phase B: ACN; Flow rate: 60 mL/min; Gradient: 40% B to 60% B in 7 min, 60% B; Wave Length: 254/220 nm; RT1(min): 9.28/11.57 to afford N-(3-bromo-5-methanesulfonamidophenyl)-4-(1H-pyrrol-2-ylmethyl) thiophene-2-carboxamide (16.0 mg, 34.8 9%) as a white solid. LCMS: (ESI): [M+H]+:454

$^1$H NMR (300 MHz, DMSO-d$_6$) δ 10.65 (s, 1H), 10.36 (s, 1H), 10.08 (s, 1H), 7.89 (s, 1H), 7.77 (s, 1H), 7.65 (s, 1H), 7.50 (s, 1H) 7.06 (s, 1H), 6.63 (s, 1H), 5.93 (d, 1H), 5.78 (s, 1H), 3.90 (s, J=5.2 Hz, 2H), 2.95 (s, 3H).

Example 105: N-(3-fluoro-5-(methylsulfonamido)phenyl)-4-(pyridin-3-yl)thiophene-2-carboxamide

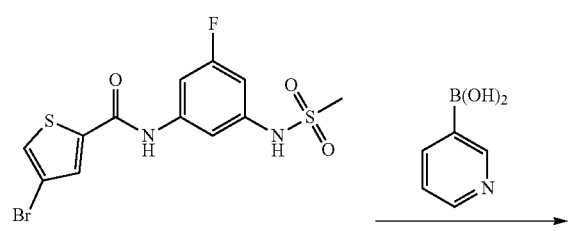

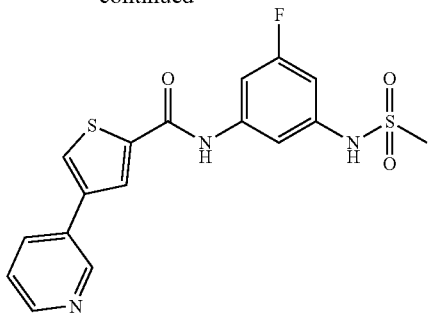

Step 1: To a solution of 4-bromo-N-(3-fluoro-5-methanesulfonamidophenyl)thiophene-2-carboxamide (100 mg, 0.254 mmol, 1 equiv) and pyridin-3-ylboronic acid (46.89 mg, 0.381 mmol, 1.5 equiv) and Pd(PPh$_3$)$_2$Cl$_2$ (17.85 mg, 0.025 mmol, 0.1 equiv) and Na$_2$CO$_3$ (80.86 mg, 0.762 mmol, 3 equiv) in EtOH (3 mL) and H$_2$O (1 mL) was stirred for 2 h at 90° C. under nitrogen atmosphere. The residue was purified by reverse phase flash chromatography with the following conditions: column, silica gel; mobile phase, MeCN in water, 0% to 100% 20 gradient in 20 min; detector, UV 254 nm. This resulted in N-(3-fluoro-5-methanesulfonamidophenyl)-4-(pyridin-3-yl)thiophene-2-carboxamide (27.8 mg, 27.93%) as a light green solid. LCMS: (ESI): LCMS (ESI) [M+H]+: 392. $^1$H NMR (300 MHz, DMSO-d$_6$) δ 10.61 (s, 1H), 10.14 (s, 1H), 9.11 (s, 1H), 8.66 (d, J=21.6 Hz, 2H), 8.48 (s, 2H), 7.75 (s, 2H), 7.49 (s, 2H), 6.76 (d, J=10.4 Hz, 1H), 3.09 (s, 3H).

Examples 108-111

The compounds listed in the following table were prepared using a procedure similar to that described for example 105:

| Structure | Example No. | MS (ESI) [M + H]+ | $^1$H NMR |
|---|---|---|---|
| (structure with methylsulfonamide, Cl, thiophene, phenol substituents) | 106 | 423 | $^1$H NMR (300 MHz, DMSO-d6) δ 10.47 (s, 1H), 10.09 (s, 1H), 9.95 (s, 1H), 8.47 (d, J = 1.4 Hz, 1H), 8.15 (d, J = 1.3 Hz, 1H), 7.67 (dt, J = 11.3, 1.9 Hz, 2H), 7.54 (dd, J = 7.8, 1.7 Hz, 1H), 7.24-7.12 (m, 1H), 7.03-6.93 (m, 2H), 6.91 (td, J = 7.4, 1.2 Hz, 1H), 3.08 (s, 3H). |

| Structure | Example No. | MS (ESI) [M + H]+ | ¹H NMR |
|---|---|---|---|
| 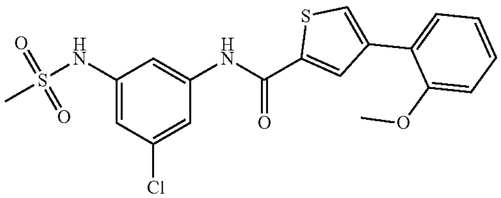 [SMILES: COc1ccccc1-c1csc(C(=O)Nc2cc(Cl)cc(NS(C)(=O)=O)c2)c1] | 107 | 437 | ¹H NMR (400 MHz, DMSO-d6) δ 10.45 (s, 1H), 10.08 (s, 1H), 8.41 (d, J = 1.4 Hz, 1H), 8.09 (d, J = 1.3 Hz, 1H), 7.66 (dt, J = 15.8, 1.9 Hz, 2H), 7.57 (dd, J = 7.5, 1.7 Hz, 1H), 7.36 (t, J = 8.1 Hz, 1H), 7.15 (d, J = 8.2 Hz, 1H), 7.06 (t, J = 7.4 Hz, 1H), 6.97 (t, J = 1.9 Hz, 1H), 3.87 (s, 3H), 3.07 (s, 3H). |
| 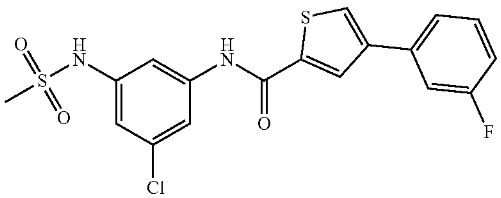 [SMILES: CS(=O)(=O)Nc1cc(Cl)cc(NC(=O)c2cc(-c3cccc(F)c3)cs2)c1] | 108 | 425 | ¹H NMR (300 MHz, DMSO-d6) δ 10.47 (s, 1H), 10.12 (s, 1H), 8.51 (d, J = 1.4 Hz, 1H), 8.33 (d, J = 1.4 Hz, 1H), 7.71-7.47 (m, 6H), 7.20 (dd, J = 9.7, 7.3 Hz, 1H), 6.98 (t, J = 1.9 Hz, 1H), 3.09 (s, 3H). |
| 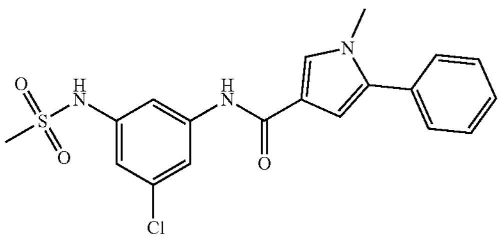 [SMILES: Cn1cc(C(=O)Nc2cc(Cl)cc(NS(C)(=O)=O)c2)cc1-c1ccccc1] | 109 | 404 | ¹H NMR (400 MHz, DMSO-d6) δ 9.80 (s, 1H), 7.73 (t, J = 1.9 Hz, 1H), 7.67-7.61 (m, 2H), 7.54-7.47 (m, 2H), 7.51-7.43 (m, 2H), 7.42-7.33 (m, 1H), 6.90 (t, J = 1.9 Hz, 1H), 6.81 (d, J = 2.0 Hz, 1H), 3.71 (s, 3H), 3.06 (s, 3H). |
| 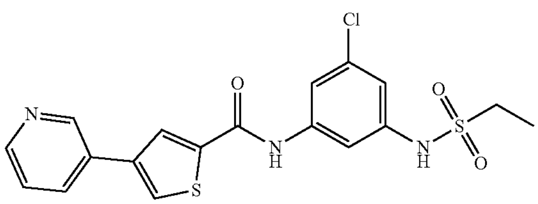 [SMILES: CCS(=O)(=O)Nc1cc(Cl)cc(NC(=O)c2cc(-c3cccnc3)cs2)c1] | 110 | 422 | ¹H NMR (400 MHz, DMSO-d6) δ 10.49 (s, 1H), 10.15 (s, 1H), 9.00 (s, 1H), 8.59-8.50 (m, 2H), 8.37 (s, 1H), 8.13 (d, J = 8.0 Hz, 1H), 7.65 (d, J = 11.2 Hz, 2H), 7.51 (t, J = 6.6 Hz, 1H), 6.98 (s, 1H), 3.19 (q, J = 7.2 Hz, 2H), 1.22 (t, J = 7.2 Hz, 3H). |
| 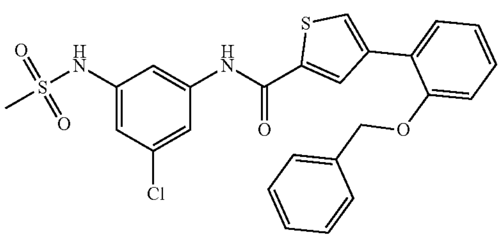 [SMILES: CS(=O)(=O)Nc1cc(Cl)cc(NC(=O)c2cc(-c3ccccc3OCc3ccccc3)cs2)c1] | 111 | 513 | 1H NMR (300 MHz, DMSO-d6) δ 10.45 (s, 1H), 10.09 (s, 1H), 8.45 (s, 1H), 8.10 (d, J = 1.4 Hz, 1H), 7.63 (dd, J = 18.6, 7.5 Hz, 3H), 7.48 (d, J = 7.2 Hz, 2H), 7.41-7.16 (m, 5H), 7.08 (s, 1H), 6.97 (s, 1H), 5.24 (s, 2H), 3.08 (s, 3H). |

Example 112: N-(3-fluoro-5-(methylsulfonamido)phenyl)-4-(pyridin-2-yl)thiophene-2-carboxamide

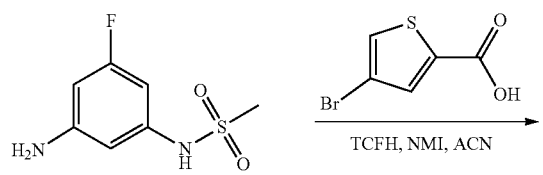

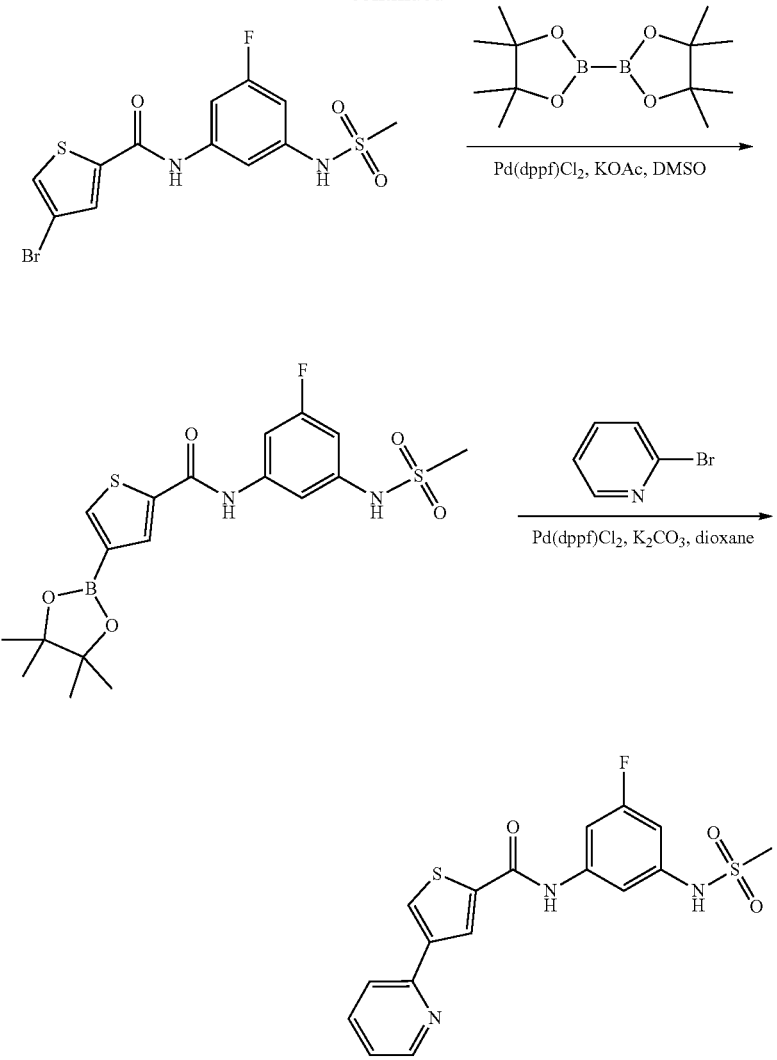

Step 1: To a stirred solution of N-(3-amino-5-fluorophenyl)methanesulfonamide (100 mg, 0.489 mmol), TCFH (178 mg, 0.635 mmol) and NMI (119 mg, 1.46 mmol) in ACN (5 mL) was added 4-bromothiophene-2-carboxylic acid (111 mg, 0.537 mmol). Then the mixture was stirred for 1 h at room temperature. The mixture was concentrated and purified by reverse phase flash chromatography eluting with ACN/H$_2$O (5-95%, acidic system) to afford 4-bromo-N-(3-fluoro-5-methanesulfonamidophenyl) thiophene-2-carboxamide (128 mg, 0.327 mmol) as a yellow solid. LCMS (ESI) [M+H]$^+$: 393

Step 2: A solution of 4-bromo-N-(3-fluoro-5-methanesulfonamidophenyl)thiophene-2-carboxamide (130 mg, 0.330 mmol), Pd(dppf)Cl$_2$ (24.1 mg, 0.0330 mmol), KOAc (97.1 mg, 0.990 mmol) and 4,4,5,5-tetramethyl-2-(4,4,5,5-tetramethyl-1,3,2-dioxaborolan-2-yl)-1,3,2-dioxaborolane (335 mg, 1.32 mmol) in DMSO (10 mL) was stirred for 2 h at 80° C. under nitrogen atmosphere. The mixture was concentrated and purified by reverse phase flash chromatography eluting with ACN/H$_2$O (5-95%, acidic system) to afford N-(3-fluoro-5-methanesulfonamidophenyl)-4-(4,4,5,5-tetramethyl-1,3,2-dioxaborolan-2-yl)thiophene-2-carboxamide (69.3 mg, 0.157 mmol) as a yellow solid. LCMS (ESI) [M+H]: 441

Step 3: A solution of N-(3-fluoro-5-methanesulfonamidophenyl)-4-(4,4,5,5-tetramethyl-1,3,2-dioxaborolan-2-yl)thiophene-2-carboxamide (70 mg, 0.158 mmol), Pd(dppf)Cl$_2$ (11.5 mg, 0.0158 mmol), K$_2$Cl$_3$ (65.5 mg, 0.474 mmol) and 2-bromopyridine (49.9 mg, 0.316 mmol) in dioxane (5 mL) was stirred for 2 h at 80° C. under nitrogen atmosphere. The resulting mixture was concentrated under reduced pressure. The residue was purified by silica gel column chromatography, eluted with Petroleum ether/EtOAc (0-100%) to afford N-(3-fluoro-5-methanesulfonamidophenyl)-4-(pyridin-2-yl)thiophene-2-carboxamide (26.7 mg, 0.0682 mmol) as a white solid. LCMS (ESI) [M+H$^+$: 392. $^1$HNMR (300 MHz, DMSO-d$_6$) δ 10.64 (s, 1H), 10.13 (s, 1H), 8.75 (d, J=1.4 Hz, 1H), 8.65 (dt, J=4.8, 1.5 Hz, 1H), 8.52 (d, J=1.3 Hz, 1H), 7.98-17.85 (m, 2H), 7.56-7.43 (m, 2H), 7.41-7.31 (m, 1H), 6.75 (dt, J=10.5, 2.2 Hz, 1H), 3.09 (s, 3H).

Examples 113 and 114

The compounds listed in the following table were prepared using a procedure similar to that described for example 112:

| Structure | Example No. | MS (ESI) [M + H]+ | ¹H NMR |
|---|---|---|---|
| 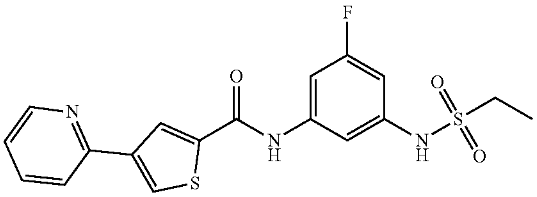 [SMILES: CCS(=O)(=O)Nc1cc(F)cc(NC(=O)c2cc(-c3ccccn3)cs2)c1] | 113 | 406 | ¹H NMR (400 MHz, DMSO-d6) δ 10.63 (s, 1H), 10.13 (s, 1H), 8.75 (d, J = 1.4 Hz, 1H), 8.64 (dt, J = 4.7, 1.5 Hz, 1H), 8.51 (d, J = 1.3 Hz, 1H), 8.02-7.86 (m, 2H), 7.56-7.42 (m, 2H), 7.36 (ddd, J = 6.3, 4.8, 2.4 Hz, 1H), 6.75 (dt, J = 10.5, 2.2 Hz, 1H), 3.18 (t, J = 7.3 Hz, 2H), 1.22 (t, J = 7.3 Hz, 3H) |
| 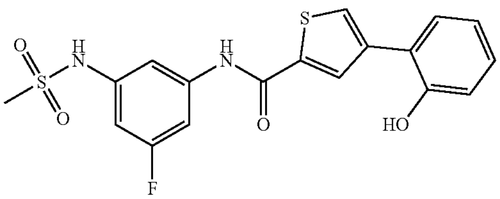 | 114 | 407 | ¹H NMR (300 MHz, DMSO-d6) δ 10.49 (s, 1H), 10.10 (s, 1H), 9.95 (s, 1H), 8.47 (d, J = 1.4 Hz, 1H), 8.14 (d, J = 1.3 Hz, 1H), 7.54 (dd, J = 7.7, 1.7 Hz, 1H), 7.47 (d, J = 9.0 Hz, 2H), 7.22-7.13 (m, 1H), 6.99 (dd, J = 8.2, 1.2 Hz, 1H), 6.96-6.87 (m, 1H), 6.74 (dd, J = 10.5, 2.2 Hz, 1H), 3.08 (s, 3H). |

Example 115: N-(3-chloro-5-(methylsulfonamido)phenyl)-4-(2,6-difluorophenyl)thiophene-2-carboxamide

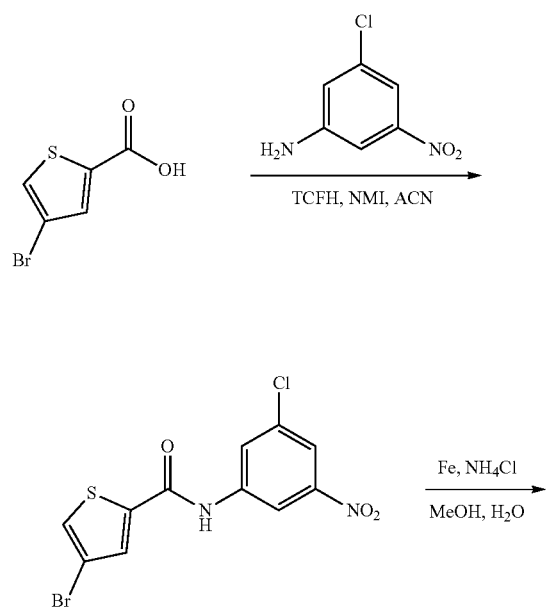

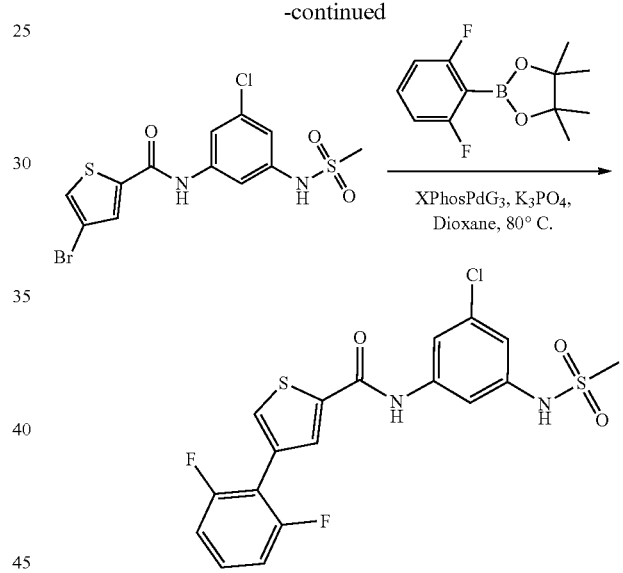

Step 1: To a stirred solution of 4-bromothiophene-2-carboxylic acid (2.02 g, 9.75 mmol), TCFH (4.11 g, 14.6 mmol) and NMI (2.3 g, 29.25 mmol) in ACN (50.00 mL) was added 3-chloro-5-nitroaniline (1.68 g, 9.75 mmol). Then the mixture was stirred for 4 h at room temperature. The mixture was concentrated and purified by flash chromatography on silica gel eluting with EtOAc/Petroleum ether (0-100%) to afford 4-bromo-N-(3-chloro-5-nitrophenyl)thiophene-2-carboxamide (3.2 g, 95%) as a yellow solid. LCMS (ESI) [M+H]+: 361

Step 2: To a solution of 4-bromo-N-(3-chloro-5-nitrophenyl) thiophene-2-carboxamide (3.2 g, 8.84 mmol) in a solution of methanol and water (50 mL) was added Fe (2.4 g, 44 mmol) and NH₄Cl (4.7 g, 88 mmol). The resulting mixture was stirred for 2 hours at 80° C. under N₂ atmosphere. The resulting mixture was filtered. The filtrate was concentrated under reduced pressure to give the crude product which was purified by flash chromatography on silica gel eluting with EtOAc/Petroleum ether (0-100%) to afford N-(3-amino-5-chlorophenyl)-4-bromothiophene-2-carboxamide (2.93 g, 95%) as a yellow solid. LCMS (ESI) [M+H]+: 331

Step 3: To a stirred solution of N-(3-amino-5-chlorophenyl)-4-bromothiophene-2-carboxamide (1.02 g, 3.07 mmol) in Pyridine (15.00 mL) was added methanesulfonyl chloride (703 mg, 6.14 mmol) dropwise at 0° C. Then the mixture was stirred for 4 h at room temperature. The mixture was concentrated and purified by flash chromatography on silica gel eluting with EtOAc/Petroleum ether (0-100%) to afford 4-bromo-N-(3-chloro-5-methanesulfonamidophenyl) thiophene-2-carboxamide (800 mg, 95%) as a yellow solid. LCMS (ESI) [M+H]+: 409

Step 4: To a stirred solution of 4-bromo-N-(3-chloro-5-methanesulfonamidophenyl) thiophene-2-carboxamide (100 mg, 0.244 mmol), 2-(2,6-difluorophenyl)-4,4,5,5-tetramethyl-1,3,2-dioxaborolane (117 mg, 0.488 mmol), XPhos-PdG$_3$ (21 mg, 0.0244 mmol) and K$_3$PO$_4$ (155 mg, 0.732 mmol) in 1,4-dioxane (5.00 mL). Then the mixture was stirred for 8 h at 80° C. The mixture was concentrated and purified by reverse phase flash chromatography eluting with ACN/H$_2$O (5-95%, acidic system) to afford N-(3-chloro-5-methanesulfonamidophenyl)-4-(2,6-difluorophenyl) thiophene-2-carboxamide (31.3 mg, 98.180%) as an off-white solid. LCMS (ESI) [M+H]+: 443. $^1$H NMR (300 MHz, DMSO-d$_6$) δ 10.52 (s, 1H), 10.10 (s, 1H), 8.31 (s, 1H), 8.15 (s, 1H), 7.66 (d, J=13.3 Hz, 2H), 7.50 (q, J=7.4 Hz, 1H), 7.28 (t, J=8.2 Hz, 2H), 6.98 (s, 1H), 3.08 (s, 3H).

Example 116: N-(3-chloro-5-(methylsulfonamido)phenyl)-4-(pyridin-3-yl)thiophene-2-carboxamide

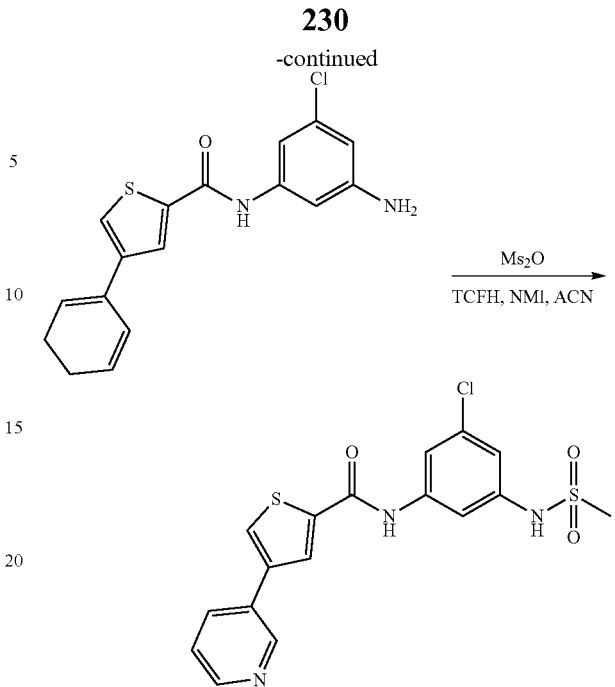

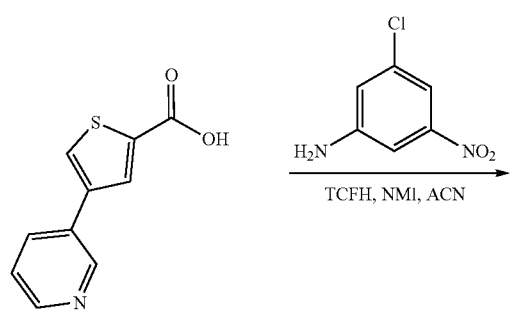

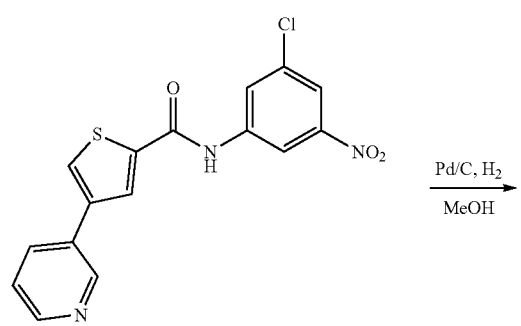

Step 1: To a mixture of 4-(pyridin-3-yl)thiophene-2-carboxylic acid (280 mg, 1.36 mmol) and 3-chloro-5-nitroaniline (281 mg, 1.63 mmol) in ACN (3 mL) was added TCFH (571 mg, 2.04 mmol) and NMI (334 mg, 4.08 mmol) at room temperature for two hours. Then it was concentrated, the residue was purified by reverse phase flash chromatography eluting with 50% of acetonitrile in water (0.1% NH$_4$HCO$_3$) to afford N-(3-chloro-5-nitrophenyl)-4-(pyridin-3-yl)thiophene-2-carboxamide (212 mg,) as a white solid.

Step 2: To a mixture of N-(3-chloro-5-nitrophenyl)-4-(pyridin-3-yl)thiophene-2-carboxamide (212 mg, 589 μmol), Fe powder (164 mg, 2.94 mmol), ethyl 1H-pyrazole-4-carboxylate (434 mg, 3.10 mmol), NH$_4$Cl (157 mg, 2.94 mmol) was added EtOH (2 mL) and H$_2$O (0.2 mL). The resulting mixture was stirred for 2 hours at 80° C. under N$_2$ atmosphere. The reaction mixture was extracted with ethyl acetate. The organic phase was concentrated under reduced pressure. The residue was purified by flash chromatography on silica gel eluting with 30% of ethyl acetate in petroleum ether to afford N-(3-amino-5-chlorophenyl)-4-(pyridin-3-yl) thiophene-2-carboxamide (156 mg) as a yellow solid.

Step 3: A solution of N-(3-amino-5-chlorophenyl)-4-(pyridin-3-yl)thiophene-2-carboxamide (156 mg, 473 μmol) and Et$_3$N (142 mg, 1.41 mmol) in DCM (1 mL) was stirred at room temperature. Then Ms$_2$O (123 mg, 709 μmol) was added into the solution at 0° C. and the resulting mixture was stirred at room temperature for 3 hours/The solvent was concentrated under vacuum. The residue was purified onto silica gel column eluting with 60% of ethyl acetate in petroleum ether to afford N-(3-chloro-5-methanesulfonamidophenyl)-4-(pyridin-3-yl)thiophene-2-carboxamide (9.6 mg,) as a white solid. LCMS [M+H]+: 408. $^1$H NMR (300 MHz, DMSO-d$_6$) δ 10.49 (s, 1H), 9.00 (d, J=2.2 Hz, 1H), 8.60-8.50 (m, 2H), 8.38 (d, J=1.4 Hz, 1H), 8.14 (dt, J=7.9, 2.0 Hz, 1H), 7.64 (dt, J=14.6, 1.9 Hz, 2H), 7.52 (dd, J=7.9, 4.8 Hz, 1H), 6.97 (t, J=1.9 Hz, 1H), 3.07 (s, 3H).

Examples 117 and 118

The compounds listed in the following table were prepared using a procedure similar to that described for Example 116:

| Structure | Example No. | MS (ESI) [M + H]+ | 1H NMR |
|---|---|---|---|
| (structure with Cl) | 117 | 391 | 1H NMR (300 MHz, DMSO-d6) δ 10.62 (s, 1H), 10.10 (s, 1H), 8.63 (dd, J = 2.5, 0.6 Hz, 1H), 8.38 (t, J = 2.0 Hz, 1H), 8.08 (ddd, J = 8.1, 2.3, 1.0 Hz, 1H), 7.91-7.79 (m, 2H), 7.75-7.62 (m, 3H), 6.99 (t, J = 2.0 Hz, 1H), 6.61 (dd, J = 2.5, 1.7 Hz, 1H), 3.09 (s, 3H). |
| (structure with Br) | 118 | 435 | 1H NMR (300 MHz, DMSO-d6) δ 10.59 (s, 1H), 10.10 (s, 1H), 8.62 (d, J = 2.5 Hz, 1H), 8.38 (t, J = 2.0 Hz, 1H), 8.08 (ddd, J = 8.1, 2.3, 1.0 Hz, 1H), 7.85 (ddd, J = 9.7, 7.7, 1.6 Hz, 3H), 7.76 (t, J = 1.9 Hz, 1H), 7.67 (t, J = 7.9 Hz, 1H), 7.11 (t, J = 1.9 Hz, 1H), 6.61 (dd, J = 2.5, 1.8 Hz, 1H), 3.08 (s, 3H). |

Example 119: 1-ethyl-N-(3-fluoro-5-(methylsulfonamido)phenyl)-5-methyl-1H-pyrazole-3-carboxamide

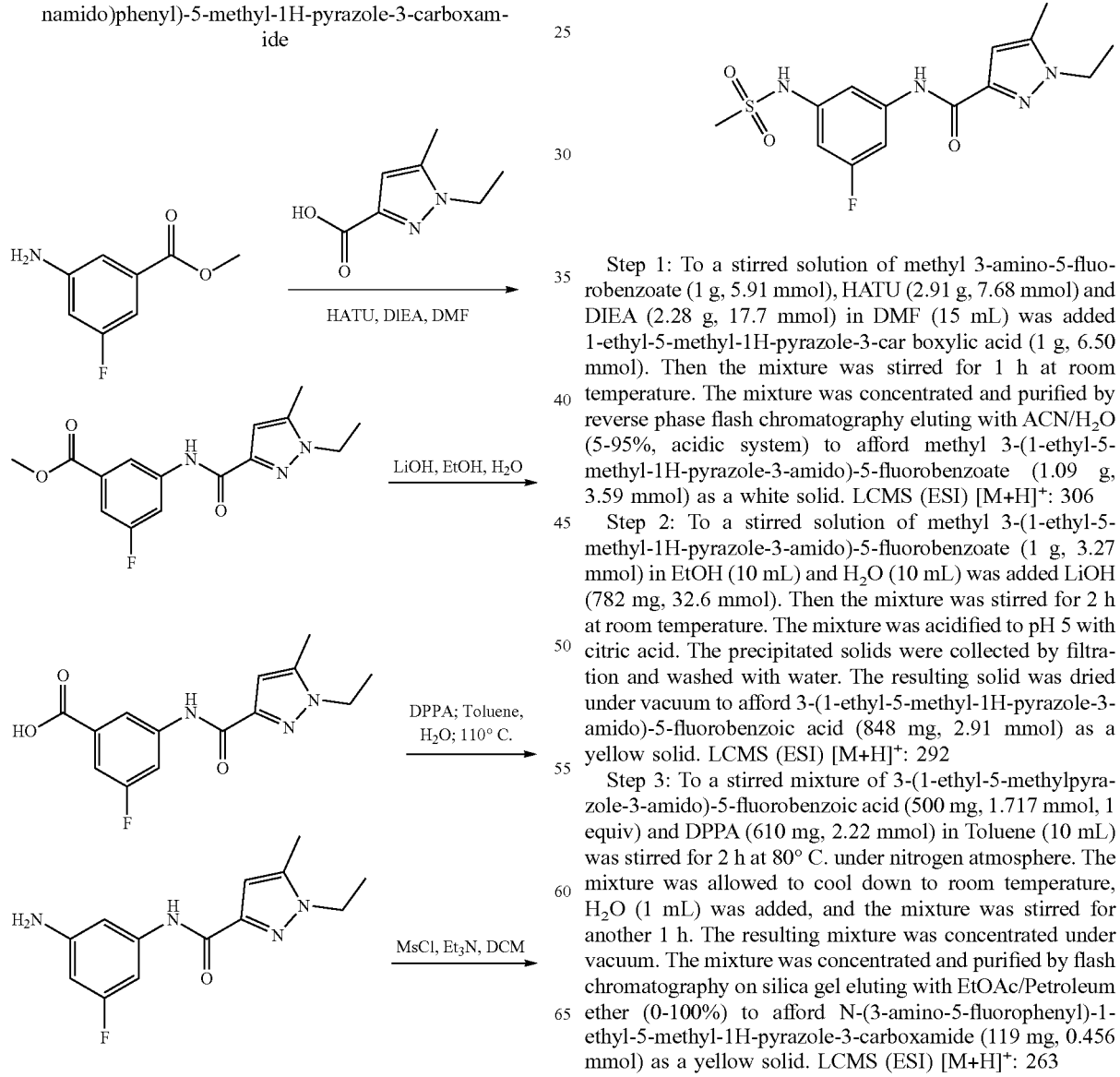

Step 1: To a stirred solution of methyl 3-amino-5-fluorobenzoate (1 g, 5.91 mmol), HATU (2.91 g, 7.68 mmol) and DIEA (2.28 g, 17.7 mmol) in DMF (15 mL) was added 1-ethyl-5-methyl-1H-pyrazole-3-car boxylic acid (1 g, 6.50 mmol). Then the mixture was stirred for 1 h at room temperature. The mixture was concentrated and purified by reverse phase flash chromatography eluting with ACN/H$_2$O (5-95%, acidic system) to afford methyl 3-(1-ethyl-5-methyl-1H-pyrazole-3-amido)-5-fluorobenzoate (1.09 g, 3.59 mmol) as a white solid. LCMS (ESI) [M+H]+: 306

Step 2: To a stirred solution of methyl 3-(1-ethyl-5-methyl-1H-pyrazole-3-amido)-5-fluorobenzoate (1 g, 3.27 mmol) in EtOH (10 mL) and H$_2$O (10 mL) was added LiOH (782 mg, 32.6 mmol). Then the mixture was stirred for 2 h at room temperature. The mixture was acidified to pH 5 with citric acid. The precipitated solids were collected by filtration and washed with water. The resulting solid was dried under vacuum to afford 3-(1-ethyl-5-methyl-1H-pyrazole-3-amido)-5-fluorobenzoic acid (848 mg, 2.91 mmol) as a yellow solid. LCMS (ESI) [M+H]+: 292

Step 3: To a stirred mixture of 3-(1-ethyl-5-methylpyrazole-3-amido)-5-fluorobenzoic acid (500 mg, 1.717 mmol, 1 equiv) and DPPA (610 mg, 2.22 mmol) in Toluene (10 mL) was stirred for 2 h at 80° C. under nitrogen atmosphere. The mixture was allowed to cool down to room temperature, H$_2$O (1 mL) was added, and the mixture was stirred for another 1 h. The resulting mixture was concentrated under vacuum. The mixture was concentrated and purified by flash chromatography on silica gel eluting with EtOAc/Petroleum ether (0-100%) to afford N-(3-amino-5-fluorophenyl)-1-ethyl-5-methyl-1H-pyrazole-3-carboxamide (119 mg, 0.456 mmol) as a yellow solid. LCMS (ESI) [M+H]+: 263

Step 4: To a stirred solution of N-(3-amino-5-fluorophenyl)-1-ethyl-5-methyl-1H-pyrazole-3-carboxamide (100 mg, 0.381 mmol) and Et₃N (115 mg, 1.14 mmol) in DCM (10 mL) was added MsCl (47.7 mg, 0.419 mmol) dropwise at 0° C. Then the mixture was stirred for 1 h at room temperature. The mixture was concentrated and purified by flash chromatography on silica gel eluting with EtOAc/Petroleum ether (0-100%) to afford 1-ethyl-N-(3-fluoro-5-methanesulfonamidophenyl)-5-methyl-1H-pyrazole-3-carboxami de (54.7 mg, 0.1607 mmol) as an off-white solid. LCMS (ESI) [M+H]⁺: 341. ¹H NMR (400 MHz, DMSO-d₆) δ 10.16 (d, J=2.1 Hz, 1H), 10.04 (d, J=2.2 Hz, 1H), 7.59 (d, J=2.1 Hz, 1H), 7.48 (dt, J=11.5, 2.2 Hz, 1H), 6.68 (dt, J=10.4, 2.3 Hz, 1H), 6.57 (d, J=2.1 Hz, 1H), 4.18 (qd, J=7.2, 2.1 Hz, 2H), 3.09 (d, J=2.1 Hz, 3H), 2.33 (d, J=2.1 Hz, 3H), 1.37 (td, J=7.3, 2.1 Hz, 3H).

Example 120: N-(3-chloro-5-(methylsulfonamido)phenyl)-5-(hydroxymethyl)-4-phenylthiophene-2-carboxamide

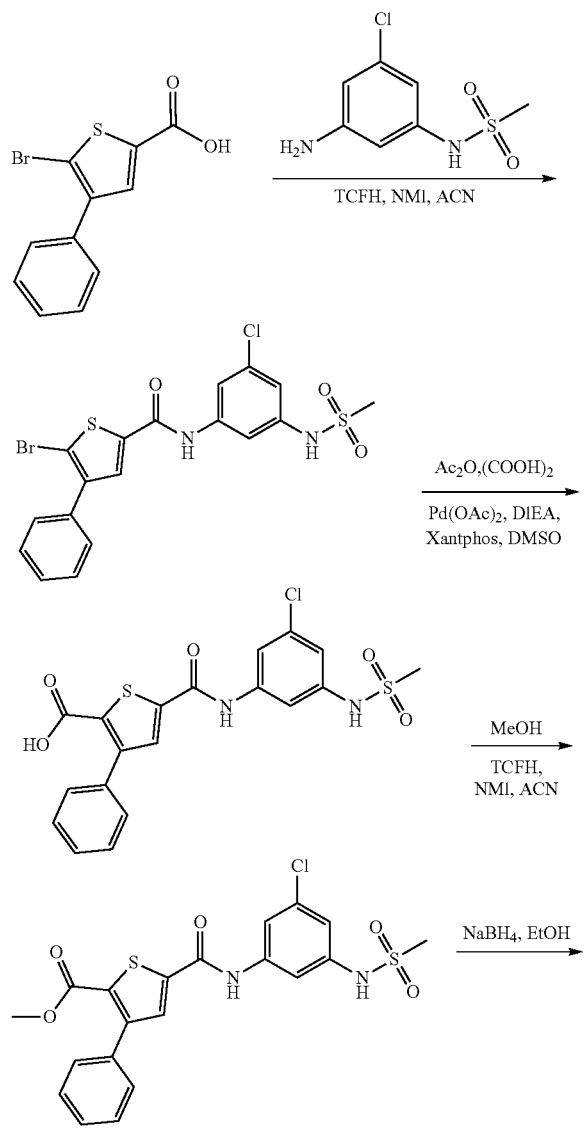

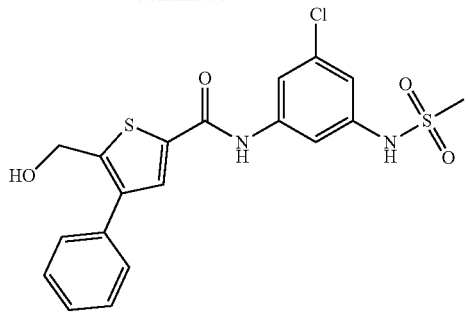

Step 1: To a stirred solution of N-(3-amino-5-chlorophenyl)methanesulfonamide (155 mg, 0.706 mmol), TCFH (297 mg, 1.059 mmol) and NMI (172 mg, 2.118 mmol) in ACN (15.00 mL) was added 5-bromo-4-phenylthio phene-2-carboxylic acid (200 mg, 0.706 mmol). Then the mixture was stirred for 4 h at room temperature. The mixture was concentrated and purified by reverse phase flash chromatography eluting with ACN/H₂O (5-95%, acidic system) to afford 5-bromo-N-(3-chloro-5-methane sulfonamidophenyl)-4-phenylthiophene-2-carboxamide (350 mg, 95%) as a white solid. LCMS (ESI) [M+H]⁺: 485

Step 2: To a stirred solution of 5-bromo-N-(3-chloro-5-methanesulfonamidophenyl)-4-phenylthiophene-2-car boxamide (350 mg, 0.720 mmol), Ac2O (140 mg, 1.37 mmol), Pd(OAc)₂ (16 mg, 0.071 mmol), Xantphos (80 mg, 0.138 mmol) and (COOH)₂ (129 mg, 1.44 mmol) and DIEA (266 mg, 2.06 mmol) in DMSO (10.00 mL). Then the mixture was stirred for 4 h at 90° C. under N₂ atmosphere. The mixture was concentrated and purified by reverse phase flash chromatography eluting with ACN/H₂O (5-95%, acidic system) to afford 5-[(3-chloro-5-methanesulfonamidophenyl)carbamoyl]-3-phenylthiophene-2-carboxylic acid (210 mg, 95%) as a yellow solid. LCMS (ESI) [M+H]⁺: 451

Step 3: To a stirred solution of 5-[(3-chloro-5-methanesulfonamidophenyl)carbamoyl]-3-phenylthiophene-2-carboxylic acid (210 mg, 0.465 mmol), TCFH (196 mg, 0.6975 mmol) and NMI (115 mg, 1.395 mmol) in ACN (5.00 mL) was added methanol (5 ml). Then the mixture was stirred for 4 h at room temperature. The mixture was concentrated and purified by reverse phase flash chromatography eluting with ACN/H₂O (5-95%, acidic system) to afford methyl 5-[(3-chloro-5-methanesulfonamidophenyl)carbamoyl]-3-phenylthiophene-2-carboxylate (180 mg, 95%) as a white solid. LCMS (ESI) [M+H]⁺: 465

Step 4: To a stirred solution of methyl 5-[(3-chloro-5-methanesulfonamidophenyl)carbamoyl]-3-phenylthi ophene-2-carboxylate (180 mg, 0.387 mmol) and NaBH₄ (44 mg, 1.16 mmol) in EtOH (10.00 mL) at 0° C. Then the mixture was stirred for 1 h at room temperature. The mixture was acidified to pH 5 with citric acid. The precipitated solids were collected by filtration and washed with water. The resulting solid was dried under vacuum to afford N-(3-chloro-5-methanesulfona midophenyl)-5-(hydroxymethyl)-4-phenylthiophene-2-carboxamide (37.2 mg, 98.340%) as a white solid. LCMS (ESI) [M+H]⁺: 437. ¹H NMR (300 MHz, DMSO-d₆) δ 10.38 (s, 1H), 10.08 (s, 1H), 8.14 (s, 1H), 7.66 (dt, J=15.7, 1.9 Hz, 2H), 7.54-7.44 (m, 4H), 7.41 (dt, J=5.7, 3.4 Hz, 1H), 6.96 (t, J=2.0 Hz, 1H), 5.88 (t, J=5.4 Hz, 1H), 4.74 (d, J=5.4 Hz, 2H), 3.08 (s, 3H).

Example 121: N-(3-bromo-5-(methylsulfonoamidimidamido)phenyl)-4-(pyridin-2-yl)thiophene-2-carboxamide

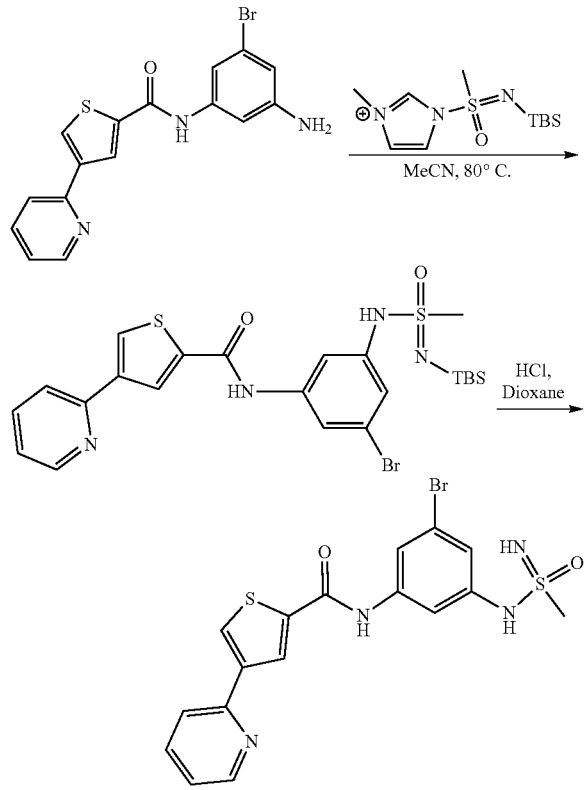

Step 1: A solution of N-(3-amino-5-bromophenyl)-4-(pyridin-2-yl) thiophene-2-carboxamide (180 mg, 0.481 mmol, 1 equiv) and 3-{[(tert-butyldimethylsilyl)imino](methyl)oxo-lambda6-sulfanyl}-1-methylimidazol-1-ium (158.41 mg, 0.577 mmol, 1.2 equiv) in MeCN (3 mL) was stirred for 1 h at room temperature. The residue was purified by reverse phase flash chromatography with the following conditions: column, C18 silica gel; mobile phase, MeCN in Water (0.1% FA), 0% to 100% gradient in 10 min; detector, UV 254 nm. This resulted in N-{3-bromo-5-[N-(tert-butyldimethylsilyl)methanesulfonoimidamido]phenyl}-4-(pyridin-2-yl)thiophene-2-carboxamide (170 mg, 62.49%) as a white solid. LCMS: (ESI): LCMS (ESI) [M+H]$^+$: 565

Step 2: N-{3-bromo-5-[N-(tert-butyldimethylsilyl)methanesulfonoimidamido]phenyl}-4-(pyridin-2-yl)thiophene-2-carboxamide (170 mg, 0.301 mmol, 1 equiv) was dissolved in a solution of HCl in 1,4-dioxane (3 mL, 1 N) and it was stirred for 1 h at room temperature. The residue was purified by reverse phase flash chromatography with the following conditions: column, C18 silica gel; mobile phase, MeCN in Water (0.1% FA), 0% to 100% gradient in 20 min; detector, UV 254 nm. This resulted in N-(3-bromo-5-methanesulfonoimidamidophenyl)-4-(pyridin-2-yl)thiophene-2-carboxamide (14.3 mg, 10.54%) as a white solid. LCMS: (ESI): LCMS (ESI) [M+H]$^+$: 451. $^1$H NMR (300 MHz, DMSO-$d_6$) δ 10.38 (s, 1H), 8.74 (d, J=1.3 Hz, 1H), 8.64 (dt, J=4.8, 1.4 Hz, 1H), 8.49 (d, J=1.3 Hz, 1H), 7.95-7.88 (m, 2H), 7.58 (t, J=1.8 Hz, 1H), 7.44-7.33 (m, 2H), 6.98-6.78 (m, 3H), 3.17 (s, 3H).

Examples 122 and 123

The compounds listed in the following table were prepared using a procedure similar to that described for example 120:

| Structure | Example No. | MS (ESI) [M + H]$^+$ | $^1$H NMR |
|---|---|---|---|
| (structure with HN=S(O)(Me)-NH-phenyl(Br)-NH-C(O)-thiophene-pyridine with methyl) | 122 | 465 | $^1$H NMR (300 MHz, DMSO-$d_6$) δ 10.33 (s, 1H), 8.64-8.47 (m, 2H), 8.17 (d, J = 1.4 Hz, 1H), 7.76 (dd, J = 7.8, 1.6 Hz, 1H), 7.57 (t, J = 1.9 Hz, 1H), 7.39 (t, J = 1.9 Hz, 1H), 7.32 (dd, J = 7.7, 4.7 Hz, 1H), 6.94 (t, J = 1.9 Hz, 1H), 6.87 (s, 2H), 3.16 (s, 3H), 2.51 (s, 3H). |
| (structure with HN=S(O)(Me)-NH-phenyl(Br)-NH-C(O)-methylthiophene-pyridine) | 123 | 465 | $^1$H NMR (300 MHz, DMSO-$d_6$) δ 10.21 (s, 1H), 8.69 (ddd, J = 4.8, 1.8, 0.8 Hz, 1H), 8.39 (s, 1H), 7.93 (td, J = 7.7, 1.9 Hz, 1H), 7.69 (d, J = 8.0 Hz, 1H), 7.56 (t, J = 1.9 Hz, 1H), 7.37 (dt, J = 6.5, 2.9 Hz, 2H), 6.92 (t, J = 1.9 Hz, 1H), 6.87 (s, 2H), 3.16 (s, 3H), 2.71 (s, 3H). |

Example 125: N-(3-chloro-5-(methylsulfonamido)phenyl)-5-phenylthiophene-3-carboxamide

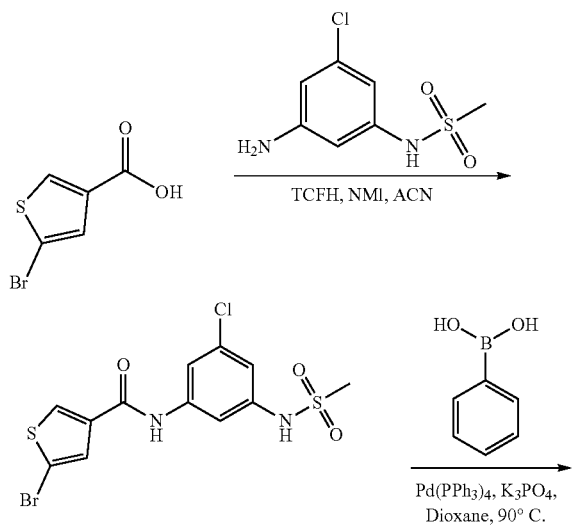

Step 1: To a stirred solution of 5-bromothiophene-3-carboxylic acid (100 mg, 0.482 mmol), TCFH (204 mg, 0.723 mmol) and NMI (119 mg, 1.446 mmol) in ACN (5.00 mL) was added N-(3-amino-5-chlorophenyl)methanesulfonamide (106 mg, 0.482 mmol). Then the mixture was stirred for 4 h at room temperature. The mixture was concentrated and purified by revere phase flash chromatography eluting with ACN/H$_2$O (5-95%, acidic system) to afford 5-bromo-N-(3-chloro-5-methanesulfonamidophenyl)thiophene-3-carboxamide (150 mg, 95%) as a yellow solid.

LCMS (ESI) [M+H]$^+$: 409.

Step 2: To a stirred solution of 5-bromo-N-(3-chloro-5-methanesulfonamidophenyl)thiophene-3-carboxamide (90 mg, 0.219 mmol), phenylboronic acid (26.7 mg, 0.219 mmol), Pd(PPh$_3$)$_4$(24 mg, 0.0219 mmol) and K$_3$PO$_4$ (139 mg, 0.657 mmol) in dioxane (10.00 mL) was added H$_2$O (3.00 mL). Then the mixture was stirred for 4 h at 90° C. under nitrogen. The mixture was concentrated and purified by reverse phase flash chromatography eluting with ACN/H$_2$O (5-95%, acidic system) to afford N-(3-chloro-5-methanesulfonamidophenyl)-5-phenylthiophene-3-carboxamide (45 mg, 99.350%) as a white solid. LCMS (ESI) [M+H]$^+$: 407. $^1$H NMR (300 MHz, DMSO-d$_6$) δ 10.31 (s, 1H), 10.09 (s, 1H), 8.35 (d, J=1.4 Hz, 1H), 8.00 (d, J=1.4 Hz, 1H), 7.71 (ddt, J=10.6, 8.6, 1.7 Hz, 4H), 7.54-7.43 (m, 2H), 7.43-7.32 (m, 1H), 6.97 (t, J=1.9 Hz, 1H), 3.08 (s, 3H).

Example 125

The compounds listed in the following table were prepared using a procedure similar to that described for example 123:

| Structure | Example No. | MS (ESI) [M + H]$^+$ | $^1$H NMR |
|---|---|---|---|
| 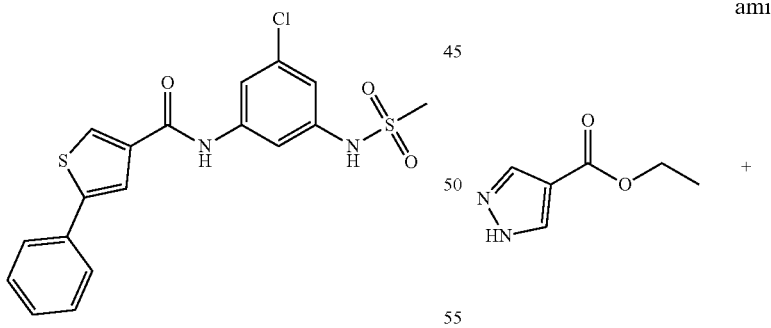 | 125 | 391 | $^1$H NMR (300 MHz, DMSO-d$_6$) δ 10.24 (s, 1H), 10.09 (s, 1H), 8.48 (d, J = 0.8 Hz, 1H), 7.81-7.73 (m, 2H), 7.70 (t, J = 1.8 Hz, 1H), 7.62 (t, J = 1.9 Hz, 1H), 7.54-7.32 (m, 4H), 6.96 (t, J = 2.0 Hz, 1H), 3.08 (s, 3H). |

Example 126: N-(3-chloro-5-(methylsulfonamido)phenyl)-1-(3-hydroxypropyl)-1H-pyrazole-4-carboxamide

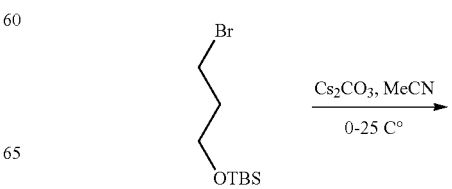

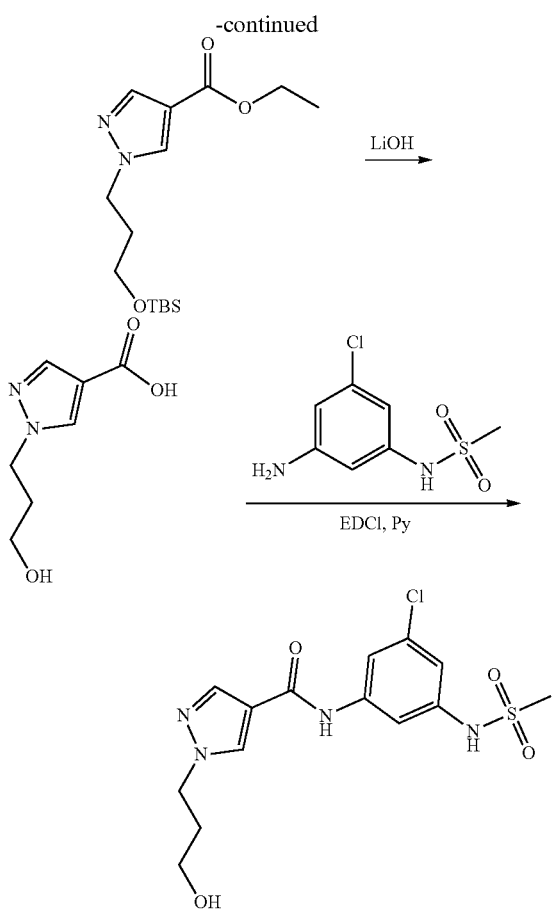

Step 1: To a solution of ethyl 1H-pyrazole-4-carboxylate (200 mg, 1.42 mmol) and $Cs_2CO_3$ (693 mg, 2.13 mmol) in MeCN (5 mL) was added (3-bromopropoxy)(tert-butyl)dimethylsilane (377 mg, 1.49 mmol) at 0° C., The mixture was stirred at 25° C. for 5 h. The mixture was poured into water (20 mL) and extracted with EA (30 mL*3). The combined organic layers were washed with brine (15 mL*2) and dried over $Na_2SO_4$. The mixture was filtered, and the filtrate was concentrated in vacuo to give a crude. ethyl 1-(3-((tert-butyldimethylsilyl)oxy)propyl)-1H-pyrazole-4-carboxylate (440 mg, 1.40 mmol, 99.3% yield) was obtained as colorless oil. LCMS: MS (ESI) Retention time: 0.972 min, (M)+=313.2. $^1$H NMR (400 MHz, CHLOROFORM-d) δ=7.85 (d, J=8.8 Hz, 2H), 4.33-4.14 (m, 4H), 3.52 (t, J=5.6 Hz, 2H), 2.06-1.95 (m, 2H), 1.30 (t, J=7.2 Hz, 3H), 0.86 (s, 9H), 0.08-0.11 (m, 6H).

Step 2: To a solution of ethyl 1-(3-((tert-butyldimethylsilyl)oxy)propyl)-1H-pyrazole-4-carboxylate (440 mg, 1.47 mg) in THF (5 mL) and MeOH (5 mL) was added a solution of LiOH·$H_2O$ (185 mg, 4.41 mmol) in water (5 mL). The mixture was stirred at 25° C. for 14 h. The mixture was poured into water (20 mL) and extracted with EA (30 mL*3). The combined organic layers were washed with brine (15 mL*2) and dried over $Na_2SO_4$. The mixture was filtered, and the filtrate was concentrated in vacuo to give residue. The residue was purified by prep-HPLC and lyophilized. 1-(3-hydroxypropyl)-1H-pyrazole-4-carboxylic acid (160 mg, 0.592 mmol, 40.3% yield) was obtained as white solid. LCMS: MS (ESI) Retention time: 0.115 min, (M+1)+=171.0. $^1$H NMR (400 MHz, DMSO-$d_6$) δ=8.22 (s, 1H), 7.78 (s, 1H), 4.60 (br s, 1H), 4.18 (t, J=6.8 Hz, 2H), 3.40-3.35 (m, 2H), 1.91 (quin, J=6.8 Hz, 2H) Step 3: To a solution of 1-(3-hydroxypropyl)-1H-pyrazole-4-carboxylic acid (75 mg, 0.441 mmol) and N-(3-amino-5-chlorophenyl)methanesulfonamide (106 mg, 484 μmol) in pyridine (2 mL) was added EDCI (168 mg, 881 μmol). The mixture was stirred at 25° C. for 3 h. The mixture was poured into water (20 mL) and extracted with EA (25 mL*3). The combined organic layers were washed with 0.5 N HCl (15 mL*2), brine (15 mL*2) and dried over $Na_2SO_4$. The mixture was filtered, and the filtrate was concentrated in vacuo to give residue.

The residue was purified by prep-HPLC and lyophilized. N-(3-chloro-5-(methylsulfonamido)phenyl)-1-(3-hydroxypropyl)-1H-pyrazole-4-carboxamide (102.45 mg, 0.269 mmol, 97.96% purity, 60.9% yield) was obtained as white solid. LCMS: MS (ESI) Retention time: 0.718 min, (M+1)+=373.0. $^1$H NMR (400 MHz, DMSO-$d_6$) δ=10.00 (s, 1H), 8.36 (s, 1H), 8.03 (s, 1H), 7.66 (t, J=1.6 Hz, 1H), 7.56 (t, J=1.6 Hz, 1H), 6.90 (t, J=2.0 Hz, 1H), 4.63 (br s, 1H), 4.21 (t, J=6.8 Hz, 2H), 3.41-3.37 (m, 2H), 3.05 (s, 3H), 1.93 (quin, J=6.4 Hz, 2H)

Example 127-128

The compounds listed in the following table were prepared using a procedure similar to that described for example 125:

| Structure | Example No. | MS (ESI) [M + H]+ | $^1$H NMR |
|---|---|---|---|
| HO–pyrazole-CONH-phenyl(Cl)-NHSO2Me | 127 | 359 | $^1$H NMR (400 MHz, DMSO-$d_6$) δ 10.05 (d, J = 4.8 Hz, 2H), 8.37 (s, 1H), 8.03 (s, 1H), 7.79-7.53 (m, 2H), 6.92 (t, J = 1.8 Hz, 1H), 4.99 (br t, J = 5.0 Hz, 1H), 4.20 (t, J = 5.2 Hz, 2H), 3.76 (q, J = 5.0 Hz, 2H), 3.07 (s, 3H) |

-continued

| Structure | Example No. | MS (ESI) [M + H]+ | 1H NMR |
|---|---|---|---|
| (structure with oxetane-spiro-cyclobutane-pyrazole-carboxamide-chlorophenyl-methanesulfonamide) | 128 | 411 | 1H NMR (400 MHz, DMSO-d6) δ 10.01 (s, 2H), 8.41 (s, 1H), 8.06 (s, 1H), 7.66 (t, J = 1.8 Hz, 1H), 7.56 (t, J = 1.8 Hz, 1H), 6.91 (t, J = 1.8 Hz, 1H), 4.79 (t, J = 8.0 Hz, 1H), 4.68 (s, 2H), 4.58 (s, 2H), 3.05 (s, 3H), 2.81-2.74 (m, 2H), 2.70-2.62 (m, 2H) |

Example 129: N-(3-chloro-5-(methylsulfonamido)phenyl)-5-methyl-1-phenyl-1H-pyrrole-3-carboxamide

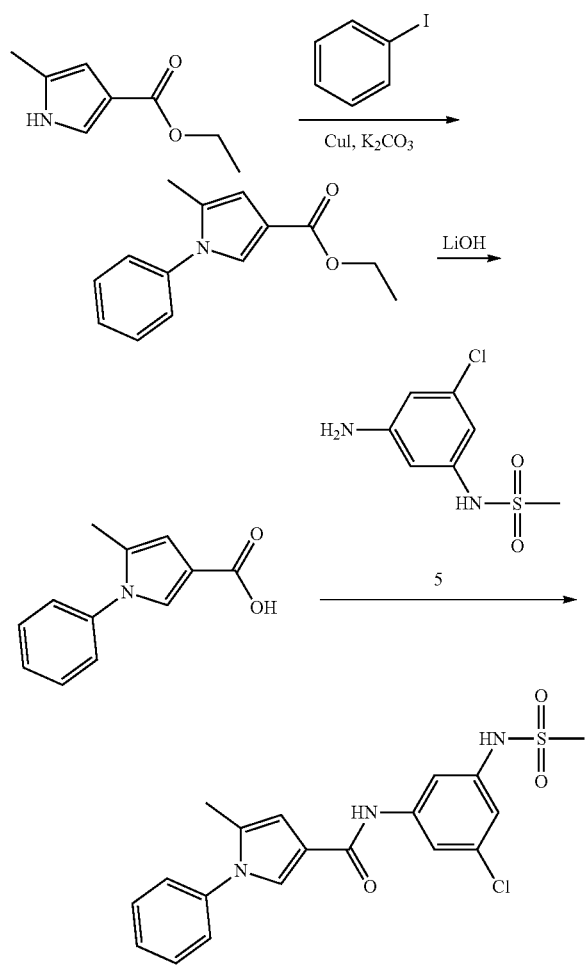

Step 1: To a solution of ethyl 5-methyl-1H-pyrrole-3-carboxylate (100 mg, 652 μmol) and iodobenzene (199 mg, 978 μmol) in DMSO (2 mL) was added 1-hydroxypyrrolidine-2,5-dione (7.5 mg, 65.2 μmol), dipotassium carbonate (179 mg, 1.3 mmol) and λ¹-copper (1+) iodide (12.4 mg, 65.2 μmol) at 25° C. The mixture was stirred at 90° C. for 16 h. The mixture was poured to H₂O (50 mL). The mixture was extracted with EA (30 mL*2). The combined organic layers were washed with brine (30 mL), dried over Na₂SO₄, filtered and concentrated under reduced pressure to give a residue. The residue was purified by column chromatography (PE:EA=10:1~1:1) to afford ethyl 5-methyl-1-phenyl-1H-pyrrole-3-carboxylate (430 mg, 1.87 mmol) as colorless oil. ¹H NMR (400 MHz, CHLOROFORM-d) δ=7.58-7.38 (m, 4H), 7.35-7.29 (m, 2H), 6.48 (dd, J=0.8, 1.8 Hz, 1H), 4.31 (q, J=7.2 Hz, 2H), 1.36 (t, J=7.2 Hz, 3H)

Step 2: To a solution of ethyl 5-methyl-1-phenyl-1H-pyrrole-3-carboxylate (420 mg, 1.83 mmol) in MeOH (3 mL), THF (2 mL) and H₂O (1 mL) was added lithium (1+) hydrate hydroxide (230 mg, 5.49 mmol) at 25° C. The mixture was stirred at 60° for 16 h. The mixture was poured to 1N HCl (20 mL). The mixture was extracted with EA (30 mL*2). The combined organic layers were washed with brine (30 mL), dried over Na₂SO₄, filtered and concentrated under reduced pressure to give 5-methyl-1-phenyl-1H-pyrrole-3-carboxylic acid (360 mg, 1.83 mmol, crude) as brown solid. LCMS: MS (ESI) Retention time: 0.747 min, (M)+=202.0

Step 3: To a solution of 5-methyl-1-phenyl-1H-pyrrole-3-carboxylic acid (330 mg, 1.63 mmol) and N-(3-amino-5-chlorophenyl)methanesulfonamide (538 mg, 2.44 mmol) in pyridine (3 mL) was added EDCI (624 mg, 3.26 mmol) at 25° C. The mixture was stirred at 25° C. for 2 h. The mixture was poured to 1N HCl (20 mL). The mixture was extracted with EA (50 mL*2). The combined organic layers were washed with brine (30 mL), dried over Na₂SO₄, filtered and concentrated under reduced pressure to give a residue. The residue was purified by prep-HPLC and lyophilized. 5-(2-(benzyloxy)phenyl)-N-(3-chloro-5-(methylsulfonamido)phenyl)-1-methyl-1H-pyrazole-3-carboxamide (282.58 mg, 0.553 mmol, 98.80% purity, 84.2% yield) was obtained as off-white solid. LCMS: MS (ESI) Retention time: 0.916 min, (M+1)+=511.2. ¹H NMR (400 MHz, DMSO-d₆) δ=10.33 (s, 1H) 9.89-10.21 (m, 1H) 7.68-7.78 (m, 2H) 7.46-7.54 (m, 1H) 7.25-7.41 (m, 7H) 7.10 (t, J=7.6 Hz, 1H) 6.91 (t, J=1.6 Hz, 1H) 6.79 (s, 1H) 5.18 (s, 2H) 3.74 (s, 3H) 3.08 (s, 3H).

Example 130

The compounds listed in the following table were prepared using a procedure similar to that described for example 129:

| Structure | Example No. | MS (ESI) [M + H]+ | ¹H NMR |
|---|---|---|---|
| (structure 130) | 130 | 419 | ¹H NMR (400 MHz, DMSO-d6) δ 9.78 (s, 2H) 8.35-8.55 (m, 1H) 7.94 (d, J = 7.6 Hz, 1H) 7.70 (s, 1H) 7.62 (d, J = 1.6 Hz, 2H) 7.50 (dd, J = 7.8, 4.8 Hz, 1H) 6.76-6.99 (m, 1H) 6.57 (s, 1H) 3.06 (s, 3H) 2.12 (s, 3H) 1.88-2.06 (m, 3H). |

Example 131: N-(3-chloro-5-(methylsulfonamido)phenyl)-1-(tetrahydro-2H-pyran-4-yl)-1H-pyrazole-4-carboxamide

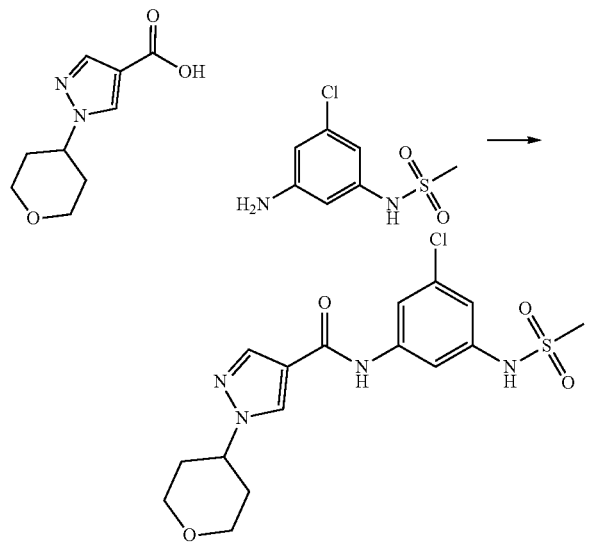

To a solution of 1-(tetrahydro-2H-pyran-4-yl)-1H-pyrazole-4-carboxylic acid (50 mg, 254 mol) and N-(3-amino-5-chlorophenyl)methanesulfonamide (61.5 mg, 279 μmol) in pyridine (1 mL) was added EDCI (97.3 mg, 508 μmol) at 25° C. The mixture was stirred at 25° C. for 12 h. The mixture was poured into H2O (50 mL). The mixture was extracted with EA (30 mL*2). The combined organic layers were washed with brine (30 mL), dried over $Na_2SO_4$, filtered and concentrated under reduced pressure to give a residue. The residue was purified by prep-HPLC (FA) to afford N-(3-chloro-5-(methylsulfonamido)phenyl)-1-(tetrahydro-2H-pyran-4-yl)-1H-pyrazole-4-carboxamide (54.68 mg, 137 μmol) as off-white solid. LCMS: MS (ESI) Retention time: 0.738 min, (M+1)+=399.1. ¹H NMR (400 MHz, DMSO-d6) δ=10.02 (s, 2H), 8.44 (s, 1H), 8.07 (s, 1H), 7.76-7.45 (m, 2H), 6.92 (t, J=1.8 Hz, 1H), 4.60-4.39 (m, 1H), 3.98 (br dd, J=2.4, 11.8 Hz, 2H), 3.50-3.44 (m, 2H), 3.06 (s, 3H), 2.06-1.89 (m, 4H).

Examples 132-136

The compounds listed in the following table were prepared using a procedure similar to that described for Example:

| Structure | Example No. | MS (ESI) [M + H]+ | ¹H NMR |
|---|---|---|---|
| (structure 132) | 132 | 393 | ¹H NMR (400 MHz, DMSO-d6) δ 10.51 (s, 1H), 10.22-9.93 (m, 1H), 9.17 (d, J = 0.6 Hz, 1H), 7.85 (s, 1H), 7.74-7.62 (m, 3H), 7.56 (d, J = 9.4 Hz, 1H), 6.97 (t, J = 1.8 Hz, 1H), 3.07 (s, 3H), 2.74 (q, J = 7.6 Hz, 2H), 1.28 (t, J = 7.6 Hz, 3H) |
| (structure 133) | 133 | 436 | ¹H NMR (400 MHz, DMSO-d6) δ 10.58 (s, 1H) 8.79 (s, 1H) 8.26 (s, 1H) 7.62-7.75 (m, 3H) 7.49 (d, J = 9.4 Hz, 1H) 6.97 (t, J = 2.0 Hz, 1H) 3.01-3.12 (m, 3H) 2.81-2.92 (m, 6H) 2.76 (q, J = 7.6 Hz, 2H) 1.26 (t, J = 7.6 Hz, 3H) |

-continued
| Structure | Example No. | MS (ESI) [M + H]+ | ¹H NMR |
|---|---|---|---|
| 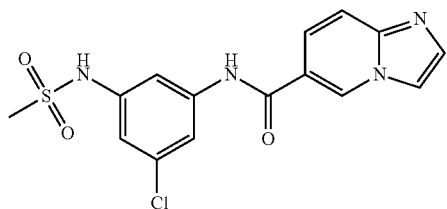 [SMILES: CS(=O)(=O)Nc1cc(Cl)cc(NC(=O)c2ccc3nccn3c2)c1] | 134 | 365 | ¹H NMR (400 MHz, DMSO-d6) δ 10.57 (s, 2H), 9.26 (s, 1H), 8.12 (s, 1H), 7.89-7.58 (m, 5H), 7.12-6.78 (m, 1H), 3.08 (s, 3H) |
| 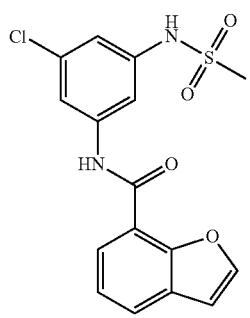 [SMILES: CS(=O)(=O)Nc1cc(Cl)cc(NC(=O)c2cccc3ccoc23)c1] | 135 | 365 | ¹H NMR (400 MHz, DMSO-d6) δ 10.57 (s, 1H) 10.10 (br s, 1H) 8.15 (d, J = 2.0 Hz, 1H) 7.88 (d, J = 7.6 Hz, 1H) 7.62-7.75 (m, 3H) 7.40 (t, J = 7.6 Hz, 1H) 7.10 (d, J = 2.0 Hz, 1H) 6.98 (t, J = 1.6 Hz, 1H) 3.08 (s, 3H) |
| 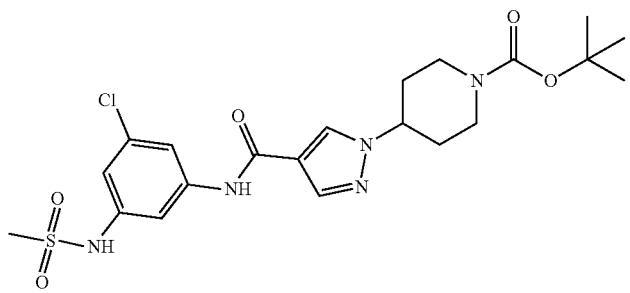 [SMILES: CC(C)(C)OC(=O)N1CCC(n2cc(C(=O)Nc3cc(Cl)cc(NS(C)(=O)=O)c3)cn2)CC1] | 136 | 442 | ¹H NMR (400 MHz, DMSO-d6) δ 9.98 (s, 1H), 8.44 (s, 1H), 8.05 (s, 1H), 7.74-7.47 (m, 2H), 6.91 (t, J = 1.8 Hz, 1H), 4.50-4.37 (m, 1H), 4.05 (br d, J = 11.4 Hz, 2H), 3.04 (s, 3H), 2.99-2.78 (m, 2H), 2.09-2.00 (m, 2H), 1.86-1.72 (m, 2H), 1.43 (s, 9H) |
Example 137: N-(3-chloro-5-(methylsulfonamido)phenyl)-3-(pyridin-2-yl)isothiazole-5-carboxamide
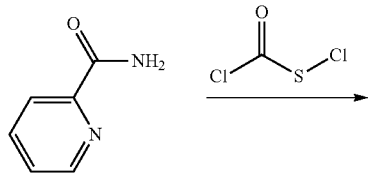
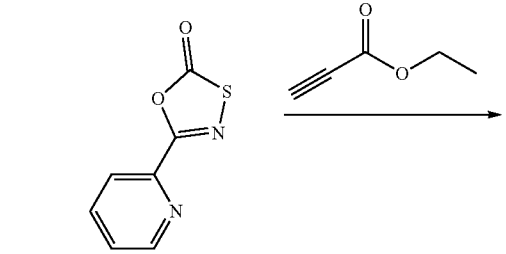
-continued
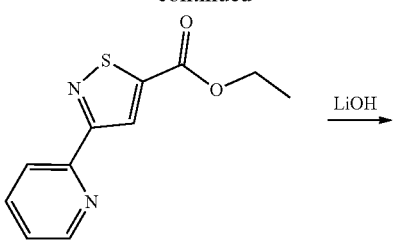
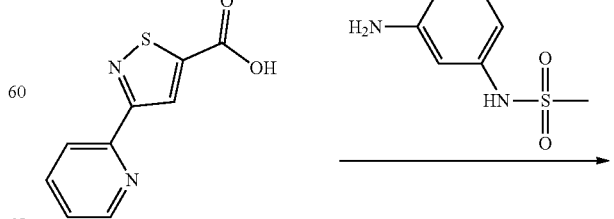

-continued

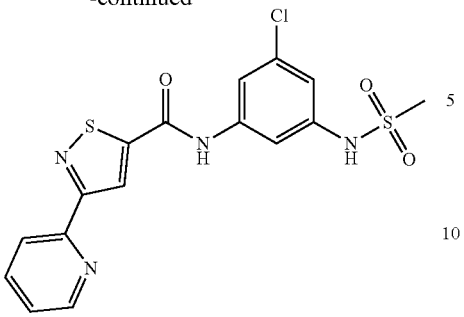

Step 1: To a solution of picolinamide (1.5 g, 12.2 mmol) in toluene (15 mL) was added carbonochloridic hypochlorous thioanhydride (2.38 g, 18.2 mmol) at 25° C. The mixture was stirred at 60° C. for 16 h. The mixture was concentrated under reduced pressure to give a residue. The residue was purified by column chromatography (PE: EA=10:1~1:1) to afford desired compound. 5-(pyridin-2-yl)-1,3,4-oxathiazol-2-one (550 mg, 3.05 mmol) was obtained as white solid. $^1$H NMR (400 MHz, DMSO-d6) δ=8.85-8.72 (m, 1H), 8.16-7.98 (m, 2H), 7.67 (ddd, J=1.8, 4.9, 6.9 Hz, 1H)

Step 2: To a solution of 5-(pyridin-2-yl)-1,3,4-oxathiazol-2-one (450 mg, 2.49 mmol) in xylene (5 mL) was added ethyl prop-2-ynoate (1.21 g, 12.4 mmol). The mixture was stirred at 160° C. for 16 h. The mixture was concentrated in vacuo to afford a residue. The residue was purified by column chromatography (PE:EA=10:1~1:1) to afford desired compound. Ethyl 3-(pyridin-2-yl)isothiazole-5-carboxylate (330 mg, 1.4 mmol) was obtained as brown solid. LCMS: MS (ESI) Retention time: 0.761 min, (M)+=235.0. $^1$H NMR (400 MHz, CHLOROFORM-d) δ=8.78-8.65 (m, 1H), 8.56 (s, 1H), 8.24 (d, J=7.8 Hz, 1H), 7.84 (dt, J=1.8, 7.8 Hz, 1H), 7.35 (ddd, J=1.0, 4.9, 7.5 Hz, 1H), 4.48-4.40 (m, 2H), 1.44 (t, J=7.2 Hz, 3H)

Step 3: To a solution of ethyl 3-(pyridin-2-yl)isothiazole-5-carboxylate (320 mg, 1.36 mmol) in a mixture of MeOH (5 mL), THF (3 mL) and H2O (1 mL) was added LiOH. H2O (285 mg, 6.8 mmol). The mixture was stirred at 25° C. for 2 h. The mixture was poured into 1N HCl solution (10 mL). The mixture was extracted with EA (30 mL*2). The combined organic layers were washed with brine (30 mL), dried over Na$_2$SO$_4$, filtered and concentrated under reduced pressure to give crude product. 3-(pyridin-2-yl)isothiazole-5-carboxylic acid (200 mg, 969 μmol, crude) was obtained as yellow solid.

Step 4: To a solution of 3-(pyridin-2-yl)isothiazole-5-carboxylic acid (50 mg, 242 μmol) and compound 7 (69.2 mg, 314 μmol) in pyridine (1 mL) was added EDCI (92.7 mg, 484 μmol) at 25° C. The mixture was stirred at 25° C. for 2 h. The mixture was poured into H$_2$O (50 mL) and extracted with EA (30 mL*2). The combined organic layers were washed with brine (30 mL), dried over Na$_2$SO$_4$, filtered and concentrated under reduced pressure to give a residue. The residue was purified by prep-HPLC (TFA) to afford N-(3-chloro-5-(methylsulfonamido)phenyl)-3-(pyridin-2-yl)isothiazole-5-carboxamide (57.79 mg, 141 mol) as yellow solid. LCMS: MS (ESI) Retention time: 0.793 min, (M+1)+=409.0. $^1$H NMR (400 MHz, DMSO-d6) δ=10.94 (s, 1H), 10.15 (s, 1H), 8.94 (s, 1H), 8.74 (d, J=4.6 Hz, 1H), 8.23 (d, J=7.8 Hz, 1H), 8.01 (dt, J=1.8, 7.6 Hz, 1H), 7.78-7.67 (m, 2H), 7.54 (dd, J=5.4, 7.0 Hz, 1H), 7.13-6.91 (m, 1H), 3.09 (s, 3H)

Example 138: N-(3-chloro-5-(methylsulfonamido) phenyl)-3-(pyridin-2-yl)isothiazole-5-carboxamide

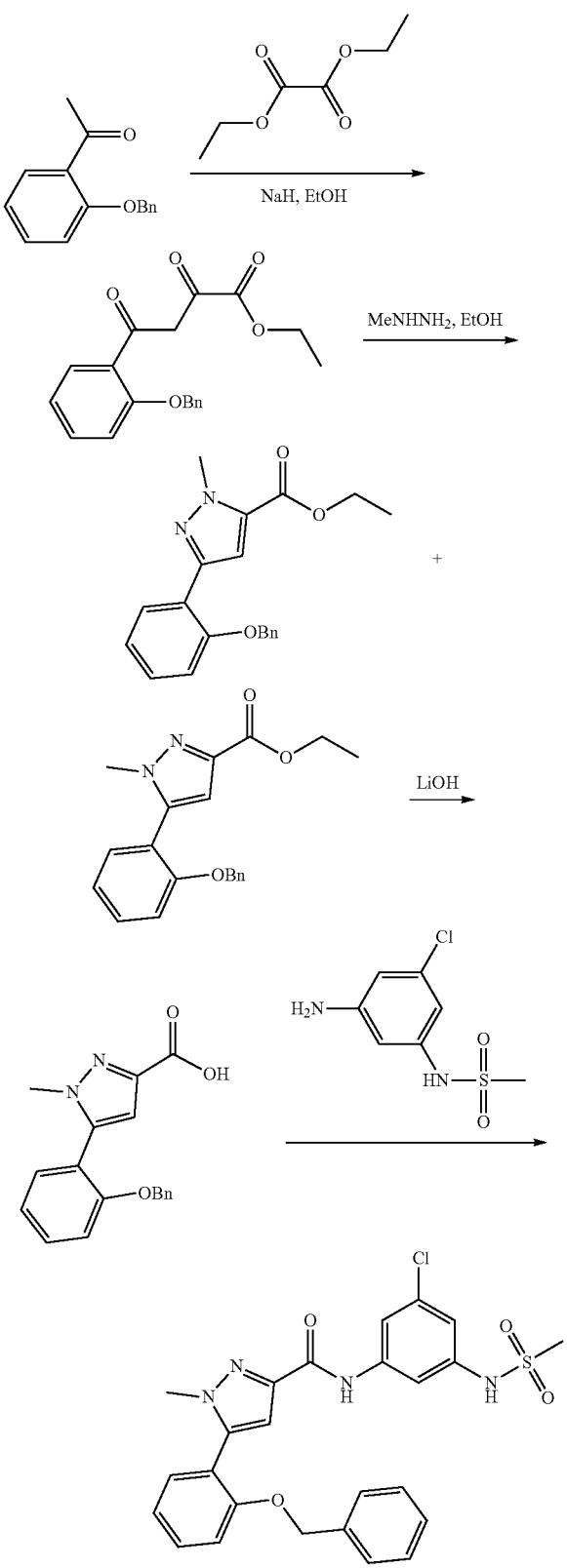

Step 1: Sodium hydride (723 mg, 18.1 mmol) was added to EtOH (150 mL) at 0° C., followed by diethyl oxalate (2.41 g, 16.5 mmol). Then, a solution of 1-(2-(benzyloxy)phenyl)ethan-1-one (3.75 g, 16.5 mmol) in EtOH (20 mL) was added to the reaction dropwise at 0° C., after the addition, the reaction was stirred at 25° C. for 16 hr. The reaction mixture was concentrated to remove solvent, the residue was diluted with water (100 mL), extracted with EA (50 mL*3), washed with brine (50 mL), dried over Na$_2$SO$_4$, and concentrated. ethyl 4-(2-(benzyloxy)phenyl)-2,4-dioxobutanoate (4 g, 11.8 mmol) was obtained as colorless oil. LCMS: MS (ESI) Retention time: 0.982, (M+1)+=326.9

Step 2: To a solvent of EtOH (30 mL) was added NaH (183 mg, 60% purity, 4.59 mmol) at 0° C., the mixture was stirred at 25° C. for 5 min. Then ethyl 4-(2-(benzyloxy)phenyl)-2,4-dioxobutanoate (1.5 g, 4.59 mmol) was added to above mixture, followed by methyl 15 hydrazine sulfate (661 mg, 4.59 mmol). The mixture was stirred at 25° C. for 25 min, and 60° C. for 2 h. The mixture was cooled to 25° C. and poured into water (35 mL). The pH value of mixture was adjusted to 4-5 by 1 N (HCl) and the mixture was extracted with EA (40 mL*3). The combined organic layers were washed with brine (25 mL*2) and dried over Na$_2$SO$_4$. The mixture was filtered, and the filtrate was concentrated in vacuo to give a residue. The residue was purified by silica gel column chromatography (Petroleum ether/Ethyl acetate=100/1 to 1/1). ethyl 3-(2-(benzyloxy)phenyl)-1-methyl-1H-pyrazole-5-carboxylate (0.9 g, 2.67 mmol, 58.4% yield) was obtained as lightly yellow oil. Also obtained ethyl 5-(2-(benzyloxy)phenyl)-1-methyl-1H-pyrazole-3-carboxylate. LCMS: MS (ESI) Retention time: 0.947 min, (M+1)+=337.2. $^1$H NMR (400 MHz, CHLOROFORM-d) δ=7.32-7.39 (m, 1H) 7.15-7.29 (m, 6H) 6.95-7.04 (m, 2H) 6.74 (s, 1H) 5.01 (s, 2H) 4.35 (q, J=7.1 Hz, 2H) 3.71 (s, 3H) 1.34 (t, J=7.2 Hz, 3H).

Step 3: To a solution of ethyl 3-(2-(benzyloxy)phenyl)-1-methyl-1H-pyrazole-5-carboxylate (500 mg, 1.48 mmol) in a mixed solvent (MeOH:THF:H2O=1:1:1, 15 mL) was added LiOH (185 mg, 4.43 mmol). The mixture was stirred at 25° C. for 2 h. The pH value of mixture was adjusted to 3-4. The mixture was partitioned between water (20 mL) and EtOAc (30 mL). The aqueous layer was separated and extracted with EtOAc (30 mL*2). The combined organic phases were washed with brine (25 mL*2), dried over anhydrous Na$_2$SO$_4$, filtered, and the filtrate was evaporated in vacuo to give 5-(2-(benzyloxy)phenyl)-1-methyl-1H-pyrazole-3-carboxylic acid (450 mg, 1.45 mmol, 98.6% yield) as yellow solid. $^1$H NMR (400 MHz, METHANOL-d4) δ=7.45-7.56 (m, 1H) 7.22-7.39 (m, 7H) 7.07-7.15 (m, 1H) 6.76 (s, 1H) 5.16 (s, 2H) 3.72 (s, 3H).

Step 4: To a solution of 5-(2-(benzyloxy)phenyl)-1-methyl-1H-pyrazole-3-carboxylic acid (220 mg) in Py (6 mL) was added N-(3-amino-5-chlorophenyl)methanesulfonamide (188 mg, 856 ummol) and EDCI (272 mg, 1.42 mmol). The mixture was stirred at 25° C. for 15 h. The mixture was partitioned between water (30 mL) and EtOAc (30 mL). The aqueous layer was separated and extracted with EtOAc (30 mL*2). The combined organic phases were washed with 1 N HCl (20 mL*3) and brine (25 mL*2), dried over anhydrous Na$_2$SO$_4$, filtered, and the filtrate was evaporated in vacuo to give a residue. The residue was purified by Prep-HPLC and lyophilized. 5-(2-(benzyloxy)phenyl)-N-(3-chloro-5-(methylsulfonamido)phenyl)-1-methyl-1H-pyrazole-3-carboxamide (282.58 mg, 0.553 mmol, 98.80% purity, 84.2% yield) was obtained as off-white solid. LCMS: MS (ESI) Retention time: 0.916 min, (M+1)+=511.2. $^1$H NMR (400 MHz, DMSO-d6) δ=10.33 (s, 1H) 9.89-10.21 (m, 1H) 7.68-7.78 (m, 2H) 7.46-7.54 (m, 1H) 7.25-7.41 (m, 7H) 7.10 (t, J=7.6 Hz, 1H) 6.91 (t, J=1.6 Hz, 1H) 6.79 (s, 1H) 5.18 (s, 2H) 3.74 (s, 3H) 3.08 (s, 3H).

Examples 139-141

The compounds listed in the following table were prepared using a procedure similar to that described for example 138:

| Structure | Example No. | MS (ESI) [M + H]+ | $^1$H NMR |
|---|---|---|---|
| 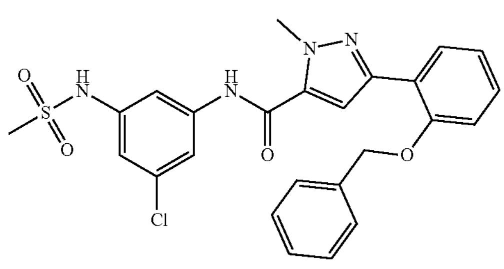 [SMILES: Cn1nc(-c2ccccc2OCc2ccccc2)cc1C(=O)Nc1cc(Cl)cc(NS(C)(=O)=O)c1] | 139 | 511 | $^1$H NMR (400 MHz, DMSO-d$_6$) δ 10.51 (s, 2H), 7.91 (dd, J = 1.4, 7.6 Hz, 1H), 7.64 (d, J = 1.6 Hz, 2H), 7.58-7.47 (m, 3H), 7.38 (t, J = 7.6 Hz, 2H), 7.33-7.25 (m, 2H), 7.17 (d, J = 8.4 Hz, 1H), 7.07-6.94 (m, 2H), 5.32 (s, 2H), 4.14 (s, 3H), 3.07 (s, 3H) |
| 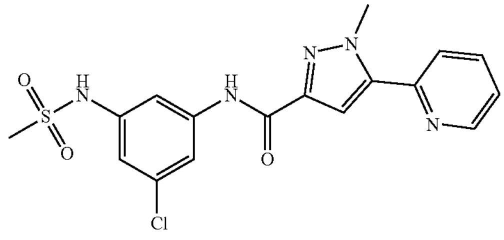 [SMILES: Cn1nc(C(=O)Nc2cc(Cl)cc(NS(C)(=O)=O)c2)cc1-c1ccccn1] | 140 | 406 | $^1$H NMR (400 MHz, DMSO-d$_6$) δ 10.41 (s, 1H) 8.73 (d, J = 4.4 Hz, 1H) 7.86-8.09 (m, 2H) 7.69-7.81 (m, 2H) 7.42-7.51 (m, 1H) 7.35 (s, 1H) 6.93 (t, J = 1.6 Hz, 1H) 4.28 (s, 3H) 3.10 (s, 3H) |

| Structure | Example No. | MS (ESI) [M + H]+ | 1H NMR |
|---|---|---|---|
| (structure shown) | 141 | 406 | 1H NMR (400 MHz, DMSO-d6) δ 10.54 (s, 2H), 8.63 (d, J = 4.4 Hz, 1H), 7.97 (d, J = 7.8 Hz, 1H), 7.92-7.84 (m, 1H), 7.77 (s, 1H), 7.71 (br d, J = 5.8 Hz, 2H), 7.40-7.33 (m, 1H), 6.98 (s, 1H), 4.19 (s, 3H), 3.08 (s, 3H) |

Example 142: N-(3-chloro-5-(methylsulfonamido)phenyl)-1-(1-phenylethyl)-1H-pyrazole-4-carboxamide

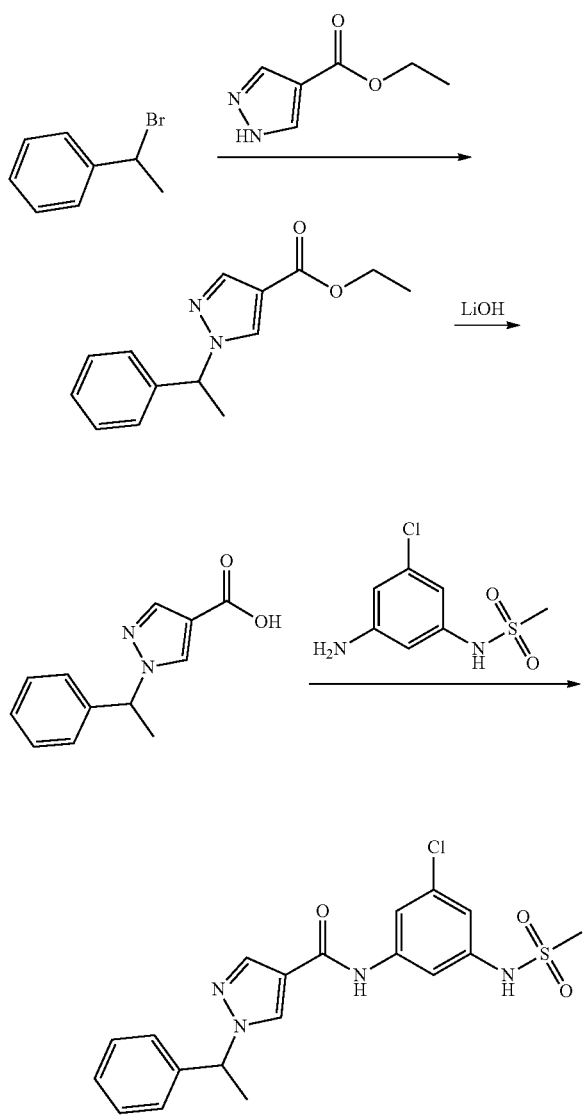

Step 1: To a solution of ethyl 1H-pyrazole-4-carboxylate (1.0 g, 7.13 mmol) in DMF (15 mL) 5 was added NaH (355 mg, 8.91 mmol, 60% purity) at 0° C. The mixture was stirred at 0° C. for 0.5 h. (1-bromoethyl)benzene (1.64 g, 8.91 mmol) was added above mixture at 0° C. The mixture was stirred at 25° C. for 2 h. The mixture was poured into water (80 mL) was extracted with EA (40 mL*3). The combined organic phase was washed with brine (25 mL*3), dried with anhydrous Na2SO4, filtered and concentrated in vacuum to give a residue. The residue was purified by silica gel column chromatography (Petroleum ether/Ethyl acetate=5/1). Compound 3 (1.67 g, 6.83 mmol, 95.9% yield) was obtained as colorless oil. LCMS: MS (ESI) Retention time: 0.819 min, (M)+=245.0. 1H NMR (400 MHz, CHLOROFORM-d) δ=7.85 (d, J=16.4 Hz, 2H), 7.33-7.21 (m, 3H), 7.17-7.12 (m, 2H), 5.45 (q, J=7.2 Hz, 1H), 4.20 (q, J=7.2 Hz, 2H), 1.84 (d, J=7.2 Hz, 3H), 1.26 (t, J=7.2 Hz, 3H) Step 2: To a solution of ethyl 1-(1-phenylethyl)-1H-pyrazole-4-carboxylate (1.0 g, 4.09 mmol) in a mixture solvent (15 mL, THF/MeOH/H2O=1:1:1) was added lithium (1+) hydrate hydroxide (551 mg, 12.2 mmo). The mixture was stirred at 60° C. for 15 h. The mixture was cooled to 25° C. and poured into water (20 mL). The pH value of mixture was adjusted to 3-4 by 1 N HCl and it was extracted with EA (30 mL*3). The combined organic layers were washed with brine (15 mL*2) and dried over Na2SO4. The mixture was filtered, and the filtrate was concentrated in vacuo to give a crude. The crude was used in next step without further purification. 1-(1-phenylethyl)-1H-pyrazole-4-carboxylic acid (880 mg, 4.06 mmol, 99.5% yield) was obtained as white solid. LCMS: MS (ESI) Retention time: 0.715 min, (M+1)+=217.1

Step 3: To a solution of 1-(1-phenylethyl)-1H-pyrazole-4-carboxylic acid (150 mg, 0.694 mol) and in N-(3-amino-5-chlorophenyl)methanesulfonamide (183 mg, 832 ummol) in pyridine (5 mL) was added EDCI (264 mg, 1.38 mmol). The mixture was stirred at 25° C. for 5 h. The mixture was poured into water (40 mL), and was extracted with EtOAc (30 mL*3). The combined organic layers were washed with brine (15 mL*3) and dried over Na2SO4. The filtrate was filtered and concentrated in vacuum to give a residue. The residue was purified by silica gel column chromatography (Petroleum ether/Ethyl acetate=50/1-1/1). The crude was re-purified by reversed-phase chromatography (H2O—0.225% FA-MeCN condition) and lyophilized. N-(3-chloro-5-(methylsulfonamido)phenyl)-1-(1-phenylethyl)-1H-pyrazole-4-carboxamide (188.2 mg, 0.454 mmol, 99.77% purity, 64.4% yield) was obtained as white solid. LCMS: MS (ESI) Retention time: 0.812 min, (M+1)+=419.2. 1H NMR (400 MHz, DMSO-d6) δ=10.04 (s, 1H), 8.51 (s, 1H), 8.07 (s, 1H), 7.65 (d, J=1.6 Hz, 1H), 7.55 (d, J=1.6 Hz, 1H), 7.40-7.24 (m, 5H), 6.91 (d, J=1.6 Hz, 1H), 5.69 (q, J=7.2 Hz, 1H), 3.05 (s, 3H), 1.94-1.73 (m, 3H)

Example 143: N-(3-chloro-5-(methylsulfonamido)phenyl)-1-(2,2-difluoroethyl)-5-(3-methylpyridin-2-yl)-1H-pyrrole-3-carboxamide

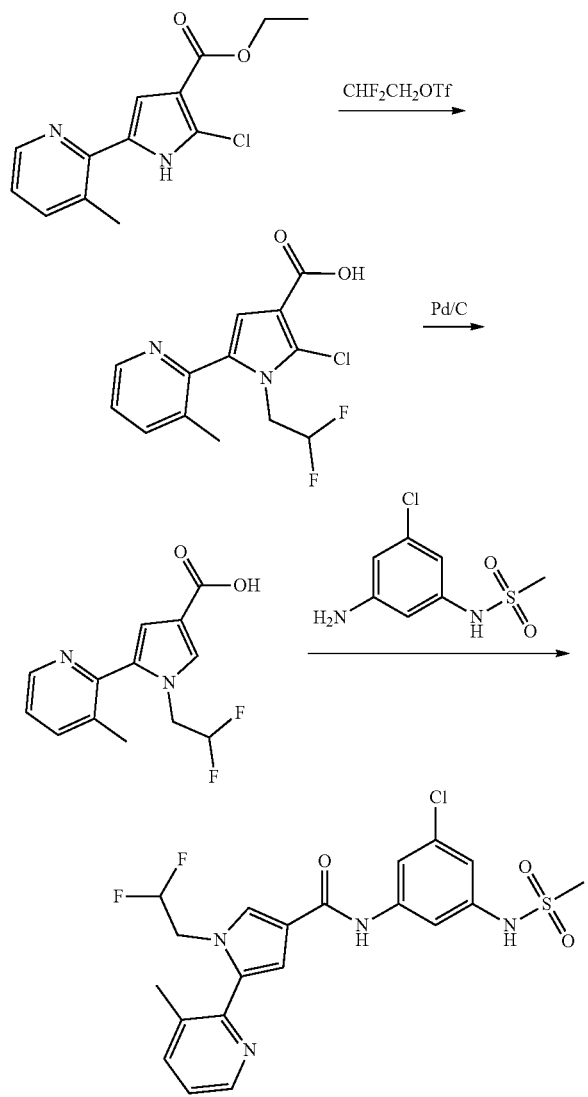

Step 1: To a solution of ethyl 2-chloro-5-(3-methylpyridin-2-yl)-1H-pyrrole-3-carboxylate (650 mg, 2.45 mmol) in DMF (6 mL) was added sodium hydride (146 mg, 3.67 mmol) at 0° C. The mixture was stirred at 0° C. for 0.5 h. To the mixture was added 2, 2-difluoroethyl trifluoromethanesulfonate (575 mg, 2.69 mmol) at 0° C. The mixture was stirred at 25° C. for 1 h. The mixture was poured to H₂O (50 mL). The mixture was extracted with EA (30 mL*2).

The combined organic layers were washed with brine (30 mL), dried over Na₂SO₄, filtered and concentrated under reduced pressure to give a residue. The residue was purified by column chromatography (PE:EA=10:1-0:1) to afford desired compound. 2-chloro-1-(2,2-difluoroethyl)-5-(3-methylpyridin-2-yl)-1H-pyrrole-3-carboxylic acid (300 mg, 1 mmol) was obtained as yellow solid. LCMS: MS (ESI) Retention time: 0.634 min, (M)+=301.0. ¹H NMR (400 MHz, DMSO-d₆) δ=12.77-12.24 (m, 1H), 8.49 (d, J=3.6 Hz, 1H), 7.79 (d, J=7.4 Hz, 1H), 7.32 (dd, J=4.8, 7.7 Hz, 1H), 6.82 (s, 1H), 6.52-6.01 (m, 1H), 4.73 (dt, J=3.2, 15.2 Hz, 2H), 2.37 (s, 3H)

Step 2: To a solution of 2-chloro-1-(2,2-difluoroethyl)-5-(3-methylpyridin-2-yl)-1H-pyrrole-3-carboxylic acid (300 mg, 997 μmol) in MeOH (5 mL) was added Pd/C (200 mg, 187 μmol) at 25° C. The mixture was stirred at 25° C. for 14 h under hydrogen (15 Psi). The mixture was filtered and filter cake was washed with MeOH (50 mL). The filtrate was concentrated in vacuo to afford crude product. 1-(2,2-difluoroethyl)-5-(3-methylpyridin-2-yl)-1H-pyrrole-3-carboxylic acid (280 mg) was obtained as colorless oil. LCMS: MS (ESI) Retention time: 0.354 min, (M)+=267.0

Step 3: To a solution of 1-(2,2-difluoroethyl)-5-(3-methylpyridin-2-yl)-1H-pyrrole-3-carboxylic acid (100 mg, 375 μmol) and 1-(2,2-difluoroethyl)-5-(3-methylpyridin-2-yl)-1H-pyrrole-3-carboxylic acid (99.3 mg, 450 μmol) in pyridine (1 mL) was added EDCI (143 mg, 750 μmol) at 25° C. The mixture was stirred at 25° C. for 14 h. The mixture was poured to H₂O (50 mL). The mixture was extracted with EA (30 mL*2). The combined organic layers were washed with brine (30 mL), dried over Na₂SO₄, filtered and concentrated under reduced pressure to give a residue. The residue was purified by prep-HPLC and lyophilized. N-(3-chloro-5-(methylsulfonamido)phenyl)-5-(hydroxymethyl)-1-(pyridin-2-yl)-1H-pyrrole-3-carboxamide (95.7 mg, 0.226 mmol, 99.4 purity, 61.7% yield) was obtained as white solid. LCMS: MS (ESI) Retention time: 0.683 min, (M−1)−=419.0. ¹H NMR (400 MHz, DMSO-d₆) δ=9.95 (s, 1H), 8.69-8.49 (m, 1H), 8.18-8.14 (m, 1H), 8.11-8.00 (m, 1H), 7.84 (d, J=8.4 Hz, 1H), 7.77-7.70 (m, 1H), 7.65 (s, 1H), 7.51-7.41 (m, 1H), 6.91 (t, J=1.6 Hz, 1H), 6.83 (d, J=1.6 Hz, 1H), 5.32 (br t, J=5.6 Hz, 1H), 4.60 (br d, J=4.8 Hz, 2H), 3.06 (s, 3H)

Example 144: tert-butyl 6-(4-((3-chloro-5-(methylsulfonamido)phenyl)carbamoyl)-1H-pyrazol-1-yl)-2-azaspiro[3.3]heptane-2-carboxylate

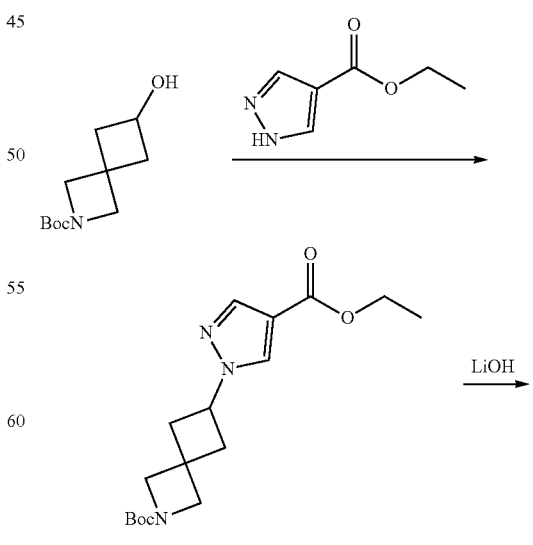

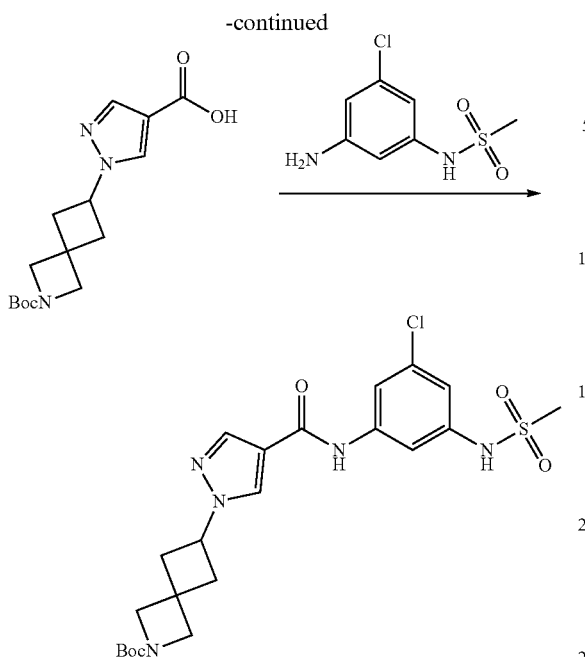

Step 1: To a solution of ethyl 1H-pyrazole-4-carboxylate (100 mg, 0.713 mmol) and tert-butyl 6-hydroxy-2-azaspiro[3.3]heptane-2-carboxylate (174 mg, 820 μmol) in THF (2 mL) was added PPh3 (243 mg, 927 μmol) and DIAD (187 mg, 927 μmol) at 0° C. slowly. The mixture was stirred at 25° C. for 15 h. The mixture was poured into water (20 mL) and extracted with EA (30 mL*3). The combined organic layers were washed with brine (15 mL*2) and dried over Na₂SO₄. The mixture was filtered, and the filtrate was concentrated in vacuo to give a residue. The residue was purified by column chromatography on silica gel using petroleum ether/ethylacetate (10:1 to 2:1) as eluent. tert-butyl 6-(4-(ethoxycarbonyl)-1H-pyrazol-1-yl)-2-azaspiro[3.3]heptane-2-carboxylate (170 mg, 0.507 mmol, 71.1% yield) was obtained as colorless oil. LCMS: MS (ESI) Retention time: 0.899 min, (M+1)+=336.3. ¹H NMR (400 MHz, CHLOROFORM-d) δ=7.98 (s, 1H), 7.85 (s, 1H), 7.81 (s, 1H), 4.65-4.50 (m, 1H), 4.30-4.18 (m, 3H), 3.96 (s, 2H), 3.89 (s, 2H), 2.67 (d, J=8.0 Hz, 4H), 1.37 (s, 9H), 1.32-1.23 (m, 4H)

Step 2: To a solution of tert-butyl 6-(4-(ethoxycarbonyl)-1H-pyrazol-1-yl)-2-azaspiro[3.3]heptane-2-carboxylate (170 mg, 0.506 mmol) in THF (2 mL) and MeOH (2 mL) was added a solution of lithium hydroxide hydrate (63.7 mg, 1.52 mmol) in water (2 mL). The mixture was stirred at 25° C. for 15 h. The mixture was poured into water (20 mL). The pH value of mixture was adjusted to 3-4 by 0.5 N HCl aqueous solution. It was extracted with EA (30 mL*3). The combined organic layers were washed with brine (15 mL*2) and dried over Na₂SO₄. The mixture was filtered, and the filtrate was concentrated in vacuo to give a crude. 1-(2-(tert-butoxycarbonyl)-2-azaspiro[3.3]heptan-6-yl)-1H-pyrazole-4-carboxylic acid (140 mg, 0.455 mmol, 90.3% yield) was obtained as white solid. LCMS: MS (ESI) Retention time: 0.818 min, (M+1)+=308.2

Step 3: To a solution of 1-(2-(tert-butoxycarbonyl)-2-azaspiro[3.3]heptan-6-yl)-1H-pyrazole-4-carboxylic acid (140 mg, 0.455 mmol) and N-(3-amino-5-chlorophenyl)methanesulfonamide (110 mg, 501 μmol) in pyridine (4 mL) was added EDCI (200 mg, 1.04 mmol). The mixture was stirred at 25° C. for 3 h. The mixture was poured into water (20 mL) and extracted with EA (25 mL*3). The combined organic layers were washed with 0.5 N HCl (15 mL*2), brine (15 mL*2) and dried over Na₂SO₄. The mixture was filtered, and the filtrate was concentrated in vacuo to give residue. The residue was purified by prep-HPLC and lyophilized. tert-butyl 6-(4-((3-chloro-5-(methylsulfonamido)phenyl)carbamoyl)-1H-pyrazol-1-yl)-2-azaspiro[3.3]heptane-2-carboxylate (150 mg, 0.294 mmol, 99.59% purity, 64.2% yield) was obtained as white solid. LCMS: MS (ESI) Retention time: 0.840 min, (M+1)+=510.2. ¹H NMR (400 MHz, DMSO-d₆) δ=10.01 (s, 1H), 8.42 (s, 1H), 8.06 (s, 1H), 7.64 (t, J=1.6 Hz, 1H), 7.54 (t, J=1.6 Hz, 1H), 6.90 (t, J=2.0 Hz, 1H), 4.97-4.70 (m, 1H), 4.05-3.72 (m, 4H), 3.04 (s, 3H), 2.73-2.59 (m, 4H), 1.37 (s, 9H).

Example 145: N-(3-chloro-5-(methylsulfonamido)phenyl)-1-(piperidin-4-yl)-1H-pyrazole-4-carboxamide

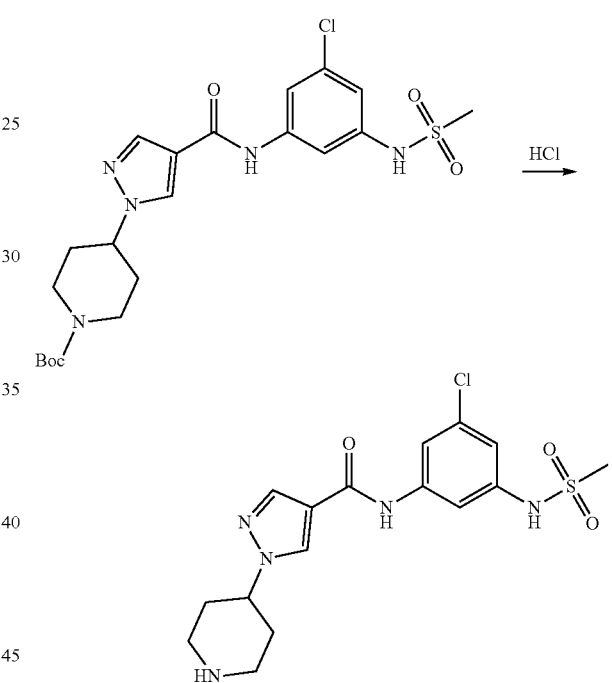

To a solution of tert-butyl 4-(4-((3-chloro-5-(methylsulfonamido)phenyl)carbamoyl)-1H-pyrazol-1-yl)piperidine-1-carboxylate (200 mg, 401 μmol) in DCM (4 mL) was added trifluoroacetic acid (744 mg, 6.52 mmol) at 25° C. The mixture was stirred at 25° C. for 2 h. The mixture was concentrated in vacuo to afford a residue. The residue was purified by prep-HPLC (NH₄HCO₃) to afford desired compound. N-(3-chloro-5-(methylsulfonamido)phenyl)-1-(piperidin-4-yl)-1H-pyrazole-4-carboxamide (41.59 mg, 104 μmol) was obtained as white solid. LCMS: MS (ESI) Retention time: 0.722 min, (M+1)+=425.2. H NMR (400 MHz, DMSO-d₆) δ=9.97 (s, 1H), 8.41 (s, 1H), 8.04 (s, 1H), 7.62 (t, J=1.8 Hz, 1H), 7.52 (t, J=1.8 Hz, 1H), 6.89 (t, J=1.8 Hz, 1H), 4.29 (br s, 1H), 3.02 (s, 5H), 2.82-2.58 (m, 2H), 2.00 (br d, J=10.6 Hz, 2H), 1.881-1.73 (m, 2H)

Examples 146-147

The compounds listed in the following table were prepared using a procedure similar to that described for example 145:

| Structure | Example No. | MS (ESI) [M + H]+ | 1H NMR |
|---|---|---|---|
| (structure with azaspiro, pyrazole, chloroaryl, methylsulfonamide) | 146 | 410 | 1H NMR (400 MHZ, DMSO-d6) δ 10.12 (s, 1H) 8.45 (s, 2H) 8.06 (s, 1H) 7.47-7.70 (m, 2H) 6.89 (t, J = 1.8 Hz, 1H) 4.75-4.90 (m, 1H) 4.01 (br s, 4H) 3.02 (s, 3H) 2.71-2.83 (m, 2H) 2.57-2.70 (m, 2H) |
| (piperazinyl-pyridine-pyrazole carboxamide structure) | 147 | 476 | 1H NMR (400 MHZ, DMSO-d6) δ 10.28 (s, 1H), 9.36 (s, 1H), 8.25 (s, 1H), 8.21 (s, 1H), 8.13 (d, J = 6.0 Hz, 1H), 7.72 (t, J = 1.8 Hz, 1H), 7.64 (t, J = 1.9 Hz, 1H), 7.34 (d, J = 2.4 Hz, 1H), 6.94 (t, J = 2.0 Hz, 1H), 6.90 (dd, J = 6.1, 2.4 Hz, 1H), 3.43 (t, J = 5.2 Hz, 4H), 3.07 (s, 3H), 2.92 (t, J = 5.1 Hz, 4H). |

Example 148: 1-(4-(4-acetylpiperazin-1-yl)pyridin-2-yl)-N-(3-chloro-5-ID-6,R(methylsulfonamido)phenyl)-1H-pyrazole-4-carboxamide

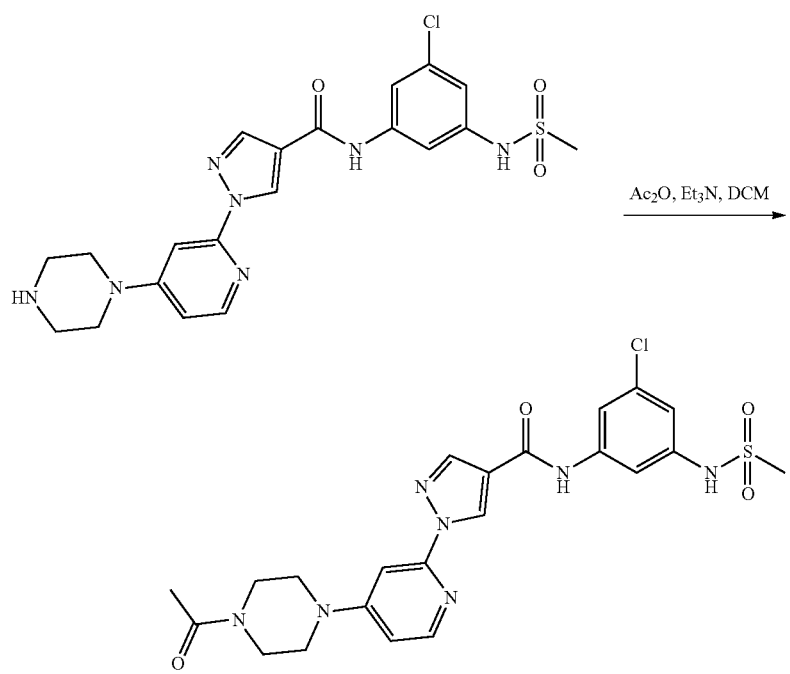

To a stirred solution of N-(3-chloro-5-methanesulfonamidophenyl)-1-[4-(piperazin-1-yl)pyridin-2-yl]-1H-pyrazole-4-carboxamide (90 mg, 0.189 mmol) and Ac2O (21.1 mg, 0.206 mmol) in DCM (5 mL) was added Et3N (57.3 mg, 0.567 mmol) dropwise at 0° C. Then the mixture was stirred for 1 h at room temperature. The mixture was concentrated and purified by flash chromatography on silica gel eluting with EtOAc/Petroleum ether (0-100%) to afford 1-[4-(4-acetylpiperazin-1-yl)pyridin-2-yl]-N-(3-chloro-5-methanesulfonamidophenyl)-1H-pyrazole-4-carboxamide (14.6 mg, 0.0282 mmol) as a white solid. LCMS (ESI) [M+H]+: 518. H NMR (400 MHz, DMSO-d6) δ 10.25 (s, 1H), 9.36 (s, 1H), 8.25 (s, 1H), 8.14 (d, J=6.0 Hz, 1H), 7.69 (t, J=1.9 Hz, 1H), 7.60 (t, J=1.9 Hz, 1H), 7.34 (d, J=2.4 Hz, 1H), 6.95-6.87 (m, 2H), 3.60 (s, 4H), 3.52 (d, J=5.7 Hz, 2H), 3.46 (t, J=5.5 Hz, 2H), 3.04 (s, 3H), 2.05 (s, 3H).

Example 149: N-(3-chloro-5-(methylsulfonamido)phenyl)-1-(5-(4-isobutyrylpiperazin-1-yl)pyridin-2-yl)-1H-pyrazole-4-carboxamide

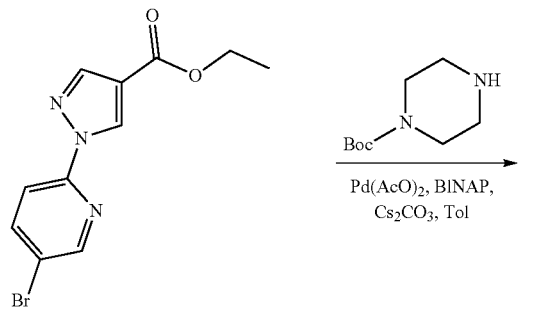

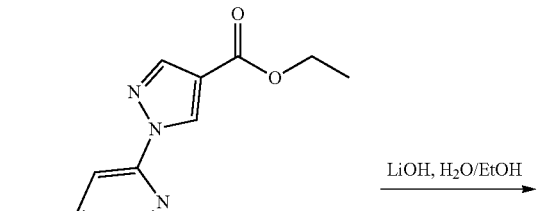

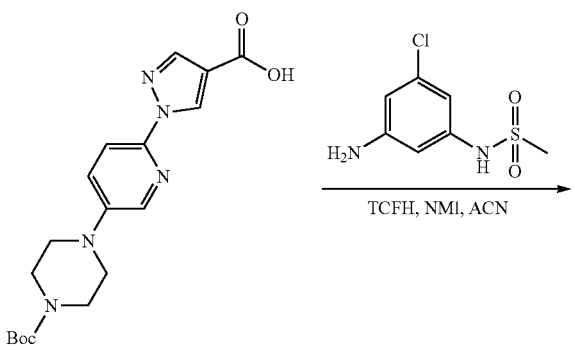

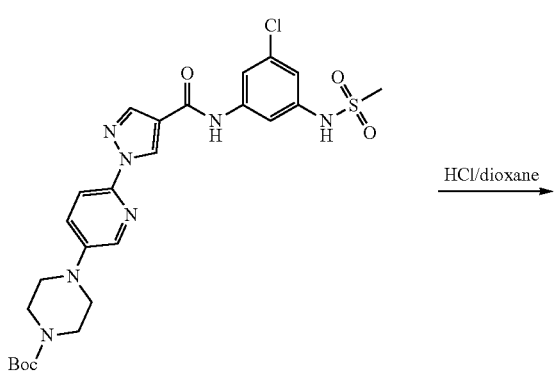

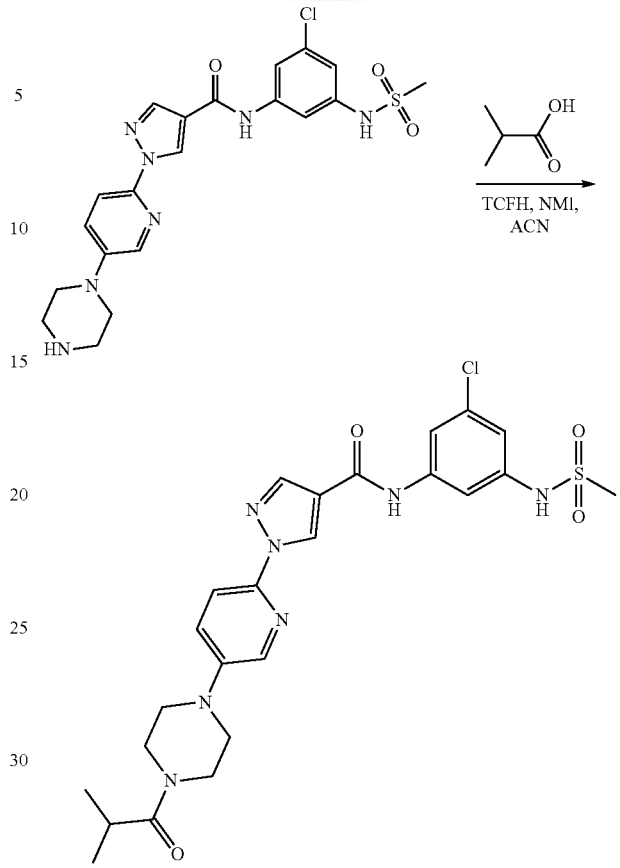

Step 1: A solution of ethyl 1-(5-bromopyridin-2-yl)-1H-pyrazole-4-carboxylate (350 mg, 1.18 mmol), Pd(AcO)$_2$ (52.9 mg, 0.236 mmol), BINAP (293 mg, 0.472 mmol), Cs$_2$CO$_3$ (1.15 g, 3.54 mmol) and tert-butyl piperazine-1-carboxylate (240 mg, 1.29 mmol) in Toluene (5 mL) was stirred for 2 h at 110° C. under nitrogen atmosphere. The resulting mixture was concentrated under reduced pressure. The residue was purified by silica gel column chromatography, eluted with Petroleum ether/EtOAc (0-100%) to afford tert-butyl 4-{6-[4-(ethoxycarbonyl)-1H-pyrazol-1-yl]pyridin-3-yl} piperazine-1-carboxylate (270 mg, 0.672 mmol) as a yellow solid. LCMS (ESI) [M+H]$^+$: 402

Step 2: To a stirred solution of tert-butyl 4-{6-[4-(ethoxycarbonyl)-1H-pyrazol-1-yl]pyridin-3-yl}piperazine-1-carboxylate (270 mg, 0.672 mmol) in EtOH (3 mL) and H$_2$O (3 mL) was added LiOH (160 mg, 6.71 mmo 1). Then the mixture was stirred for 2 h at room temperature. The mixture was acidified to pH 5 with citric acid. The precipitated solids were collected by filtration and washed with water. The resulting solid was dried under vacuum to afford 1-(5-{4-[(tert-butoxy) carbonyl]piperazin-1-yl} pyridin-2-yl)-1H-pyrazole-4-carboxylic acid (180 mg, 0.482 mmol) as a yellow solid. LCMS (ESI) [M+H]$^+$: 374

Step 3: To a stirred solution of 1-(5-{4-[(tert-butoxy) carbonyl]piperazin-1-yl}pyridin-2-yl)-1H-pyrazole-4-carboxylic acid (180 mg, 0.482 mmol), TCFH (270 mg, 0.964 mmol) and NMI (118 mg, 1.44 mmol) in ACN (5 mL) was added N-(3-amino-5-chlorophenyl)methanesulfonamide (116 mg, 0.530 mmol). Then the mixture was stirred for 1 h at room temperature. The mixture was concentrated and purified by reverse phase flash chromatography eluting with ACN/H$_2$O (5-95%, acidic system) to afford tert-butyl 4-(6-

{4-[(3-chloro-5-methanesulfonamidophenyl)carbamoyl]-1H-pyrazol-1-yl}pyridin-3-yl) piperazine-1-carboxylate (220 mg, 0.381 mmol) as a yellow solid. LCMS (ESI) [M+H]⁺: 576

Step 4: To a stirred solution of tert-butyl 4-(6-{4-[(3-chloro-5-methanesulfonamidophenyl)carbamoyl]-1H-pyrazol-1-yl} pyridin-3-yl)piperazine-1-carboxylate (220 mg, 0.381 mmol) in HCl/dioxane (5 mL) at 0° C. for 1 h. The resulting mixture was concentrated under vacuum. The mixture was basified to pH 9 with NaOH. The mixture was concentrated and purified by flash chromatography on silica gel eluting with EtOAc/Petroleum ether (0-100%) to afford N-(3-chloro-5-methanesulfonamidophenyl)-1-[5-(piperazin-1-yl)pyridin-2-yl]-1H-pyrazole-4-carboxamide (140 mg, 0.294 mmol) as a yellow solid. LCMS (ESI) [M+H]⁺: 476

Step 5: To a stirred solution of N-(3-chloro-5-methanesulfonamidophenyl)-1-[5-(piperazin-1-yl)pyridin-2-yl]-1H-pyrazole-4-carboxamide (140 mg, 0.294 mmol), TCFH (164 mg, 0.588 mmol) and NMI (72.4 mg, 0.882 mmol) in ACN (5 mL) was added 2-methylpropanoic acid (28.4 mg, 0.323 mmol). Then the mixture was stirred for 1 h at room temperature. The mixture was concentrated and purified by reverse phase flash chromatography eluting with ACN/H₂O (5-95%, acidic system) to afford N-(3-chloro-5-methanesulfonamidophenyl)-1-{5-[4-(2-methylpropanoyl)piperazin-1-yl]pyridin-2-yl}-1H-pyrazole-4-carboxamide (13.5 mg, 0.0247 mmol) as a white solid. LCMS (ESI) [M+H]⁺: 546. H NMR (300 MHz, DMSO-d₆) δ 10.26 (s, 1H), 10.08 (s, 1H), 9.28 (s, 1H), 8.24 (d, J=3.1 Hz, 2H), 7.84 (d, J=8.9 Hz, 1H), 7.72 (t, J=1.9 Hz, 1H), 7.69-7.60 (m, 2H), 6.94 (t, J=1.9 Hz, 1H), 3.67 (s, 4H), 3.26 (s, 4H), 3.07 (s, 3H), 2.94 (p, J=6.7 Hz, 1H), 1.03 (d, J=6.7 Hz, 6H).

Example 150: N-(3-chloro-5-(methylsulfonamido)phenyl)-1-(trans-2-hydroxycyclohexyl)-1H-pyrazole-4-carboxamide

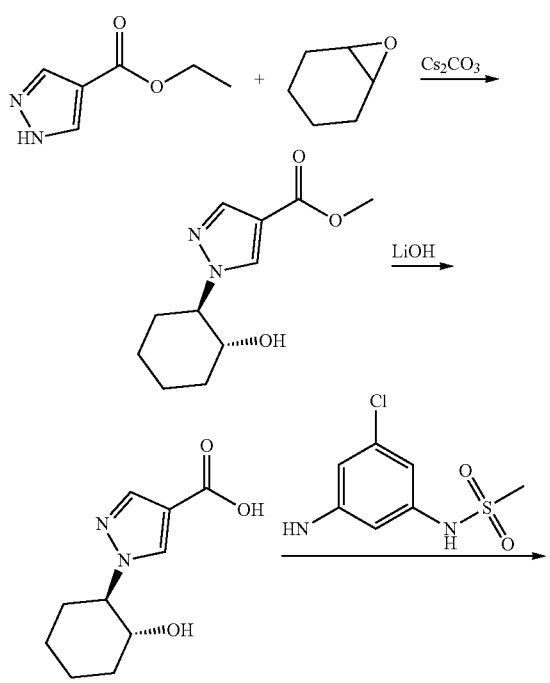

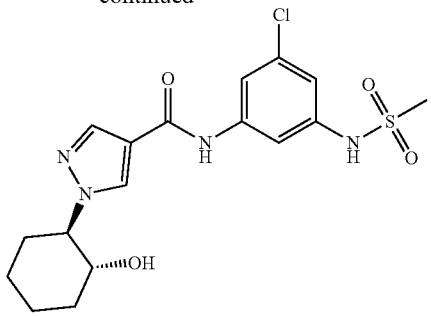

Stereochemistry Arbitrarly Assigned

Step 1: To a solution of ethyl 1H-pyrazole-4-carboxylate (2 g, 14.2 mmol) and 7-oxabicyclo[4.1.0]heptane (2.09 g, 21.3 mmol) in DMF (20 mL) was added cesium carbonate (13.8 g, 42.6 mmol) at 25° C. The mixture was stirred at 100° C. for 16 h. The mixture was poured to H₂O (50 mL). The mixture was extracted with EA (30 mL*2). The combined organic layers were washed with brine (30 mL), dried over Na₂SO₄, filtered and concentrated under reduced pressure to give a residue. The residue was purified by column chromatography (PE:EA=10:1~1:1) to afford ethyl 1-(trans-2-hydroxycyclohexyl)-1H-pyrazole-4-carboxylate (1.8 g, 7.55 mmol) as colorless oil. LCMS: MS (ESI) Retention time: 0.706 min, (M)+=239.0. ¹H NMR (400 MHz, DMSO-d₆) δ=8.24 (s, 1H), 7.83 (s, 1H), 4.81 (d, J=5.8 Hz, 1H), 4.21 (q, J=7.0 Hz, 2H), 3.93 (ddd, J=4.4, 9.8, 11.8 Hz, 1H), 3.68 (td, J=4.6, 9.8 Hz, 1H), 2.05-1.61 (m, 6H), 1.30-1.24 (m, 5H) Step 2: To a solution of ethyl 1-(trans-2-hydroxycyclohexyl)-1H-pyrazole-4-carboxylate (200 mg, 839 µmol) in MeOH (3 mL) and THF (2 mL) and H₂O (1 mL) was added lithium hydroxide hydrate (105 mg, 2.51 mmol) at 25° C. The mixture was stirred at 25° C. for 16 h.

The mixture was poured into 1N HCl (20 mL). The mixture was extracted with EA (30 mL*2). The combined organic layers were washed with brine (30 mL), dried over Na₂SO₄, filtered and concentrated under reduced pressure to give 1-(trans-2-hydroxycyclohexyl)-1H-pyrazole-4-carboxylic acid (150 mg, 713 µmol) as white solid. LCMS: MS (ESI) Retention time: 0.512 min, (M)+=211.0

Step 3: To a solution of 1-trans-2-hydroxycyclohexyl)-1H-pyrazole-4-carboxylic acid (80 mg, 380 µmol) and N-(3-amino-5-chlorophenyl)methanesulfonamide (100 mg, 455 µmol) in pyridine (2 mL) was added EDCI (145 mg, 760 µmol) at 25° C. The mixture was stirred at 25° C. for 14 h. The mixture was poured to H₂O (50 mL). The mixture was extracted with EA (30 mL*2). The combined organic layers were washed with brine (30 mL), dried over Na₂SO₄, filtered and concentrated under reduced pressure to give a residue. The residue was purified by prep-HPLC to afford desired compound. N-(3-chloro-5-(methylsulfonamido)phenyl)-1-trans-2-hydroxycyclohexyl)-1H-pyrazole-4-carboxamide (113.15 mg, 274 µmol) was obtained as yellow solid. LCMS: MS (ESI) Retention time: 0.749 min, (M+1)+=413.1. ¹H NMR (400 MHz, DMSO-d₆) δ=10.03 (d, J=17.0 Hz, 2H), 8.34 (s, 1H), 8.04 (s, 1H), 7.80-7.47 (m, 2H), 6.92 (t, J=1.8 Hz, 1H), 4.03-3.87 (m, 1H), 3.75-3.59 (m, 1H), 3.07 (s, 3H), 2.01-1.64 (m, 5H), 1.32 (br s, 3H)

Example 151: N-(3-chloro-5-(methylsulfonamido)phenyl)-1-((1s,4s)-4-hydroxycyclohexyl)-1H-pyrazole-4-carboxamide

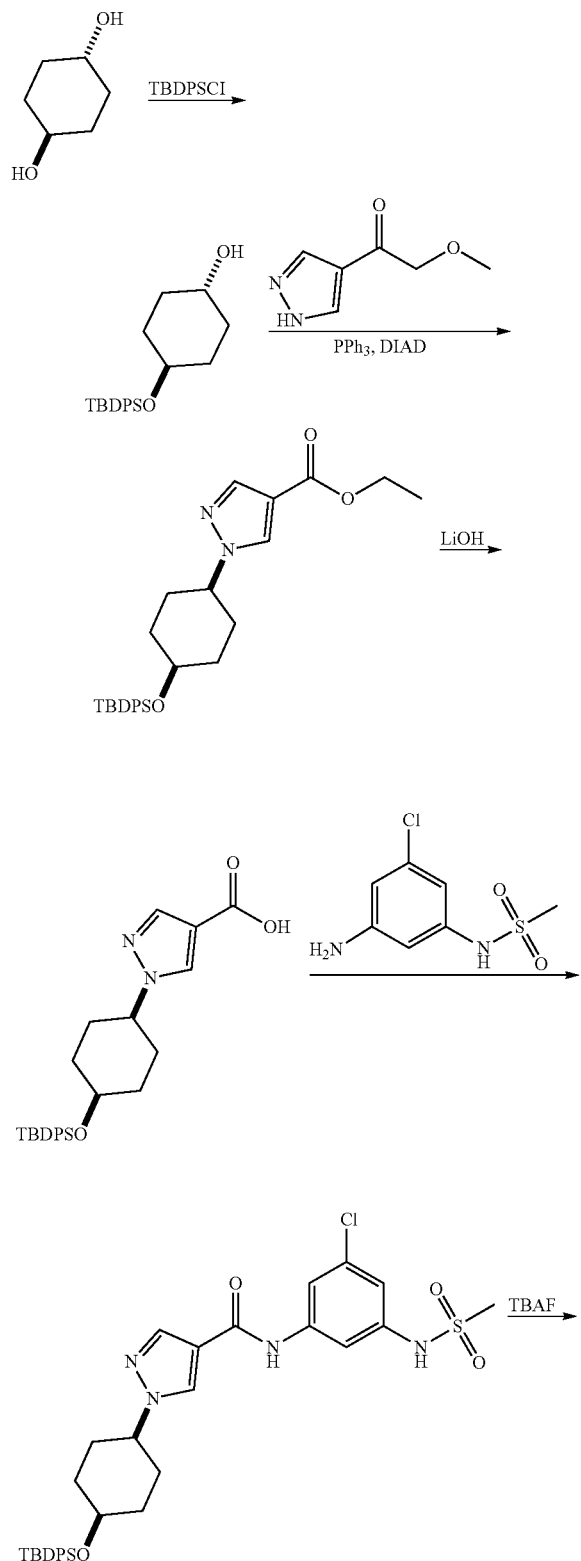

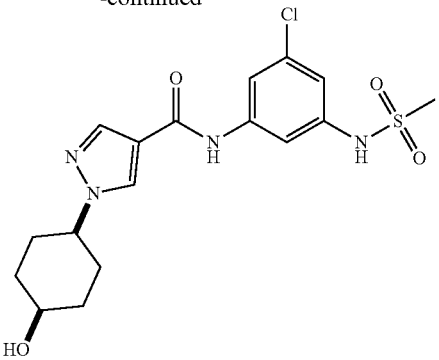

Step 1: To a solution of (1r,4r)-cyclohexane-1,4-diol (1 g, 8.6 mmol) and 1H-imidazole (614 mg, 9.03 mmol) in DMF (10 mL) and DCM (20 mL) was added a solution of tert-butyl(chloro) diphenylsilane (2.36 g, 8.6 mmol) in DCM (5 mL). The mixture was stirred at 25° C. for 16 h. The mixture was poured into water (20 mL) and extracted with EA (30 mL*3). The combined organic layers were washed with brine (15 mL*2) and dried over $Na_2SO_4$. The mixture was filtered, and the filtrate was concentrated in vacuo to give residue. The residue was purified by column chromatography on silica gel using petroleum ether/ethylacetate (10:1 to 2:1) as eluent. (1r,4r)-4-((tert-butyldiphenylsilyl)oxy)cyclohexan-1-ol (1.4 g, 3.94 mmol, 46% yield) was obtained as colorless oil. LCMS: MS (ESI) Retention time: 1.031 min, (M+1)+=337.4. $^1$H NMR (400 MHz, CHLOROFORM-d) δ=7.69 (d, J=7.2 Hz, 4H), 7.50-7.34 (m, 6H), 3.79-3.62 (m, 2H), 1.97-1.87 (m, 2H), 1.82 (br dd, J=3.6, 13.2 Hz, 2H), 1.51-1.39 (m, 2H), 1.32-1.15 (m, 3H), 1.07 (s, 9H).

Step 2: To a solution of ethyl 1H-pyrazole-4-carboxylate (0.4 g, 2.85 mmol, 1 eq) and (1r,4r)-4-((tert-butyldiphenylsilyl)oxy)cyclohexan-1-ol (1.1 g, 3.13 mmol) in THF (15 mL) was added triphenylphosphine (1.15 g, 3.56 mol), DIAD (0.719 g, 3.56 mmol) at 0° C. The mixture was stirred at 25° C. for 15 h. The mixture was extracted with EtOAc (40 mL*3). The combined organic layers were washed with brine (25 mL*2), dried over $Na_2SO_4$. The mixture was cooled to 25° C. and concentrated in vacuo to give a residue. The residue was purified by flash silica gel chromatography. ethyl 1-((1s,4s)-4-((tert-butyldiphenylsilyl)oxy)cyclohexyl)-1H-pyrazole-4-carboxylate (0.82 g, 1.72 mmol, 60.7% yield) was obtained as colorless oil. $^1$H NMR (400 MHz, CHLOROFORM-d) δ=7.92 (s, 1H) 7.82-7.88 (m, 1H) 7.60 (dd, J=7.6, 1.2 Hz, 4H) 7.25-7.43 (m, 6H) 4.24 (q, J=7.2 Hz, 2H) 3.92-4.04 (m, 1H) 2.21 (qd, J=12.4, 3.2 Hz, 2H) 1.91 (br dd, J=12.4, 3.2 Hz, 2H) 1.76 (br dd, J=12.8, 2.8 Hz, 2H) 1.36-1.47 (m, 1H) 1.35-1.38 (m, 1H) 1.29 (t, J=7.1 Hz, 3H) 1.03 (s, 9H).

Step 3: To a solution of ethyl 1-((1s,4s)-4-((tert-butyldiphenylsilyl)oxy)cyclohexyl)-1H-pyrazole-4-carboxylate (810 mg, 1.69 mmol) in THF (5 mL) and MeOH (5 mL) was added a solution of LiOH·H₂O (212 mg, 5.06 mmol) in $H_2O$ (5 mL). The mixture was stirred at 60° C. for 15 h. The mixture was cooled to 25° C., the pH of the mixture was adjusted to 3-4 by 2 N HCl. The mixture was extracted with EtOAc (30 mL*3). The combined organic layers were washed with brine (15 mL*2), dried over $Na_2SO_4$. And the filtrate was concentrated in vacuo to give 1-((1s,4s)-4-((tert-butyldiphenylsilyl)oxy)cyclohexyl)-1H-pyrazole-4-carboxylic acid (730 mg, 1.62 mmol, 96.3% yield) as white solid. LCMS: MS (ESI) Retention time: 0.826 min, (M+1)+

=449.1. ¹H NMR (400 MHz, CHLOROFORM-d) δ=8.24 (s, 1H), 7.83 (s, 1H), 7.69-7.56 (m, 4H), 7.52-7.33 (m, 6H), 4.21 (tt, J=3.6, 11.2 Hz, 1H), 4.01-3.98 (m, 1H), 2.37-2.20 (m, 2H), 1.84-1.76 (m, 2H), 1.69 (br dd, J=2.4, 13.2 Hz, 2H), 1.57-1.44 (m, 2H), 1.08-0.99 (m, 9H) Step 4: To a solution of 1-((1s,4s)-4-((tert-butyldiphenylsilyl)oxy)cyclohexyl)-1H-pyrazole-4-carboxylic acid (240 mg, 0.535 mmol) and N-(3-amino-5-chlorophenyl)methanesulfonamide (129 mg, 588 μmol) in pyridine (5 mL) was added EDCI (203 mg, 1.06 mmol). The mixture was stirred at 25° C. for 3 h. The mixture was poured into water (20 mL) and extracted with EA (25 mL*3). The combined organic layers were washed with 0.5 N HCl (15 mL*2), brine (15 mL*2) and dried over Na₂SO₄. The mixture was filtered, and the filtrate was concentrated in vacuo to give residue. The residue was purified by column chromatography on silica gel using petroleum ether/ethylacetate (50:1 to 2:1) as eluent. 1-((1s,4s)-4-((tert-butyldiphenylsilyl)oxy)cyclohexyl)-N-(3-chloro-5-(methylsulfonamido)phenyl)-1H-pyrazole-4-carboxamide (300 mg, 0.461 mmol, 86.4% yield) was obtained as colorless oil. LCMS: MS (ESI) Retention time: 1.075 min, (M+1)+=651.3. ¹H NMR (400 MHz, DMSO-d₆) δ=10.21-9.91 (m, 2H), 8.42 (s, 1H), 8.06 (s, 1H), 7.70-7.39 (m, 12H), 6.93 (t, J=1.6 Hz, 1H), 4.24 (ddd, J=3.6, 7.6, 11.1 Hz, 1H), 3.06 (s, 3H), 2.37-2.13 (m, 2H), 1.92-1.82 (m, 2H), 1.72 (br d, J=10.6 Hz, 2H), 1.65-1.47 (m, 2H), 1.06 (s, 9H).

Step 5: To a solution of 1-((1s,4s)-4-((tert-butyldiphenylsilyl)oxy)cyclohexyl)-N-(3-chloro-5-(methylsulfonamido)phenyl)-1H-pyrazole-4-carboxamide (200 mg, 0.307 mmol) in THF (5 mL) was added TBAF (399 ul, 1 M in THF) dropwise at 25° C. slowly. The mixture was stirred at 60° C. for 18 h. The mixture was poured into water (20 mL) and extracted with EA (20 mL*3). The combined organic layers were washed with 0.5 N HCl (10 mL), brine (25 mL*2) and dried over Na₂SO₄. The mixture was filtered, and the filtrate was concentrated in vacuo to give residue. The residue was purified by flash chromatography (silica gel, PE/EA=30:1 to 1:0) to give desired product. N-(3-chloro-5-(methylsulfonamido)phenyl)-1-((1s,4s)-4-hydroxycyclohexyl)-1H-pyrazole-4-carboxamide (94.13 mg, 0.228 mmol, 100% puity, 74.6% yield) was obtained as white solid. LCMS: MS (ESI) Retention time: 0.820 min, (M+1)+=413.1. ¹H NMR (400 MHz, DMSO-d₆) δ=9.85-10.19 (m, 2H) 8.38-8.57 (m, 1H) 8.01 (s, 1H) 7.66 (t, J=1.8 Hz, 1H) 7.57 (t, J=1.8 Hz, 1H) 6.92 (t, J=1.8 Hz, 1H) 4.51 (d, J=3.2 Hz, 1H) 4.22 (tt, J=10.8, 3.6 Hz, 1H) 3.85 (br d, J=2.4 Hz, 1H) 3.06 (s, 3H) 2.06-2.24 (m, 2H) 1.68-1.86 (m, 4H) 1.49-1.67 (m, 2H)

Example 152

The compounds listed in the following table were prepared using a procedure similar to that described for example 151:

| Structure | Example No. | MS (ESI) [M + H]⁺ | ¹H NMR |
|---|---|---|---|
| *stereochemistry arbitrarly assigned* | 152a | 413 | ¹H NMR (400 MHZ, DMSO-d₆) δ 9.78-10.17 (m, 2H) 8.40 (s, 1H) 8.01 (s, 1H) 7.66 (t, J = 1.6 Hz, 1H) 7.56 (t, J = 1.6 Hz, 1H) 6.91 (t, J = 1.6 Hz, 1H) 4.66 (d, J = 3.2 Hz, 1H) 4.45-4.59 (m, 1H) 4.08 (br d, J = 2.8 Hz, 1H) 3.05 (s, 3H) 1.87-2.07 (m, 3H) 1.52-1.84 (m, 4H) 1.38-1.50 (m, 1H) |
| *stereochemistry arbitrarly assigned* | 152b | 413 | ¹H NMR (400 MHZ, DMSO-d₆) δ = 9.83-10.29 (m, 2H) 8.39 (s, 1H) 8.01 H) 7.56 (t, J = 1.8 Hz, 1H) (d, J = 4.4 Hz, 1H) 4.17-6.91 (t, J = 1.8 Hz, 1H) 4.82 (s, 1H) 7.65 (t, J = 1.8 Hz, 1 4.32 (m, 1H) 3.47-3.64 (m, 1H) 3.05 (s, 3H) 2.14-2.28 (m, 1H) 1.73-2.02 (m, 3H) 1.50-1.68 (m, 2 H) 1.27-1.47 (m, 1H) 1.06-1.19 (m, 1H) |

Example 153: N-(3-chloro-5-(methylsulfonamido)phenyl)-1-(2-cis-hydroxycyclohexyl)-1H-pyrazole-4-carboxamide

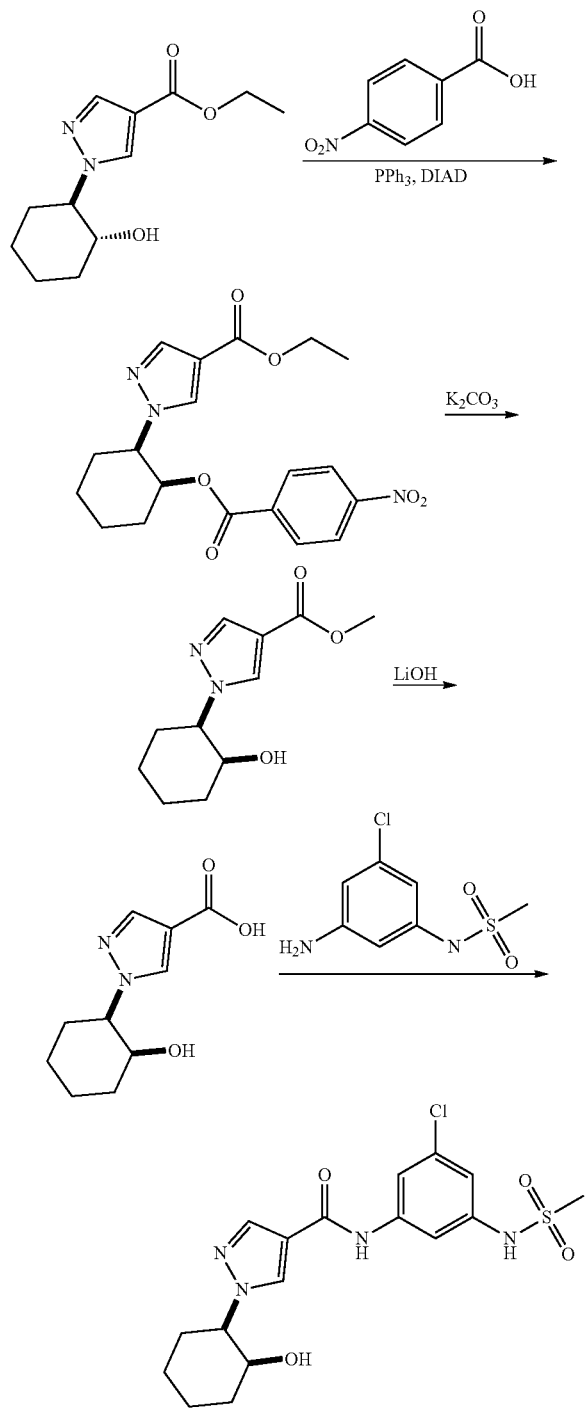

Stereochemistry Arbitrarly Assigned

Step 1: To a solution of ethyl 1-(trans-2-hydroxycyclohexyl)-1H-pyrazole-4-carboxylate (1 g, 4.19 mmol) and 4-nitrobenzoic acid (1.04 g, 6.28 mmol) and PPh₃ (2.19 g, 8.38 mmol) was added DIAD (1.69 g, 8.38 mmol) at 0° C. The mixture was stirred at 25° C. for 16 h. The 10 mixture was poured to H₂O (20 mL). The mixture was extracted with EA (30 mL*2). The combined organic layers were washed with brine (30 mL), dried over Na₂SO₄, filtered and concentrated under reduced pressure to give a residue. The residue was purified by column chromatography (PE:EA=10:1~1:1) to afford ethyl 1-(cis-2-((4-nitrobenzoyl)oxy)cyclohexyl)-1H-pyrazole-4-carboxylate (1.6 g, 4.13 mmol) as white solid. LCMS: MS (ESI) Retention time: 0.883 min, (M+1)+=388.1

Step 2: To a solution of ethyl 1-(cis-2-((4-nitrobenzoyl)oxy)cyclohexyl)-1H-pyrazole-4-carboxylate (1.6 g, 4.13 mmol) in MeOH (20 mL) was added dipotassium carbonate (1.14 g, 8.26 mmol) at 25° C. The mixture was stirred at 25° C. for 2 h. The mixture was poured to H₂O (50 mL). The mixture was extracted with EA (30 mL*2). The combined organic layers were washed with brine (30 mL), dried over Na₂SO₄, filtered and concentrated under reduced pressure to give a residue. The residue was purified by column chromatography (PE:EA=10:1~1:1) to afford ethyl 1-(cis-2-hydroxycyclohexyl)-1H-pyrazole-4-carboxylate (900 mg, 3.77 mmol) as white solid. LCMS: MS (ESI) Retention time: 0.802 min, (M+1)+=239.2. ¹H NMR (400 MHz, DMSO-d₆) δ=8.19 (s, 1H), 7.85 (s, 1H), 4.83 (d, J=4.4 Hz, 1H), 4.81-4.77 (m, 2H), 4.24 (td, J=3.0, 12.2 Hz, 1H), 2.10 (br dd, J=3.6, 12.2 Hz, 1H), 1.84-1.71 (m, 3H), 1.67-1.51 (m, 2H), 1.47-1.33 (m, 2H), 1.12 (br s, 3H)

Step 3: To a solution of ethyl 1-(cis-2-hydroxycyclohexyl)-1H-pyrazole-4-carboxylate (200 mg, 893 μmol) in MeOH (3 mL) and THF (2 mL) and H₂O (1 mL) was added LiOH·H₂O (105 mg, 2.51 mmol) at 25° C. The mixture was stirred at 25° C. for 16 h. The mixture was poured to 0.5N HCl (10 mL). The mixture was extracted with EA (30 mL*2). The combined organic layers were washed with brine (30 mL), dried over Na₂SO₄, filtered and concentrated under reduced pressure to give 1-(cis-2-hydroxycyclohexyl)-1H-pyrazole-4-carboxylic acid (150 mg, 713 μmol) as white solid. LCMS: MS (ESI) Retention time: 0.475 min, (M+1)+=211.0

Step 4: To a solution of 1-(cis-2-hydroxycyclohexyl)-1H-pyrazole-4-carboxylic acid (100 mg, 475 μmol) and N-(3-amino-5-chlorophenyl)methanesulfonamide (115 mg, 522 μmol) in pyridine (2 mL) was added EDCI (182 mg, 950 μmol) at 25° C. The mixture was stirred at 2 h. The mixture was poured to H₂O (50 mL). The mixture was extracted with EA (30 mL*2). The combined organic layers were washed with brine (30 mL), dried over Na₂SO₄, filtered and concentrated under reduced pressure to give a residue. The residue was purified by prep-HPLC to give N-(3-chloro-5-(methylsulfonamido)phenyl)-1-(cis-2-hydroxycyclohexyl)-1H-pyrazole-4-carboxamide (60.96 mg, 147 μmol) as white solid. LCMS: MS (ESI) Retention time: 0.760 min, (M+1)+=413.0. ¹H NMR (400 MHz, DMSO-d₆) δ=9.99 (s, 1H), 8.41 (s, 1H), 7.99 (s, 1H), 7.76-7.47 (m, 2H), 6.91 (t, J=1.8 Hz, 1H), 4.89 (br s, 1H), 4.29-4.18 (m, 1H), 4.04 (br s, 1H), 3.05 (s, 3H), 2.16-2.03 (m, 1H), 1.91-1.74 (m, 3H), 1.69-1.53 (m, 2H), 1.49-1.34 (m, 2H)

Example 154

The compounds listed in the following table were prepared using a procedure similar to that described for example 153:

| Structure | Example No. | MS (ESI) [M + H]+ | 1H NMR |
|---|---|---|---|
| (Structure: HO-cyclohexyl-pyrazole-C(O)NH-phenyl(Cl)-NHS(O)2Me) *stereochemistry arbitrarly assigned* | 154 | 413 | 1H NMR (400 MHZ, DMSO-d6) δ (400 MHZ, DMSO-d6) δ 9.88-10.26 (m, 2H) 8.38 (s, 1H) 8.02 (s, 1H) 7.65 (s, 1H) 7.55 (s, 1H) 6.90 (s, 1H) 4.68 (d, J = 4.0 Hz, 1H) 4.19 (tt, J = 11.6, 3.6 Hz, 1H) 3.42-3.57 (m, 1H) 3.04 (s, 3H) 1.86-2.09 (m, 4H) 1.69-1.85 (m, 2H) 1.27-1.46 (m, 2H). |

Example 155: N-(3-chloro-5-(methylsulfonamido)phenyl)-1-methyl-2-phenyl-1H-imidazole-4-carboxamide

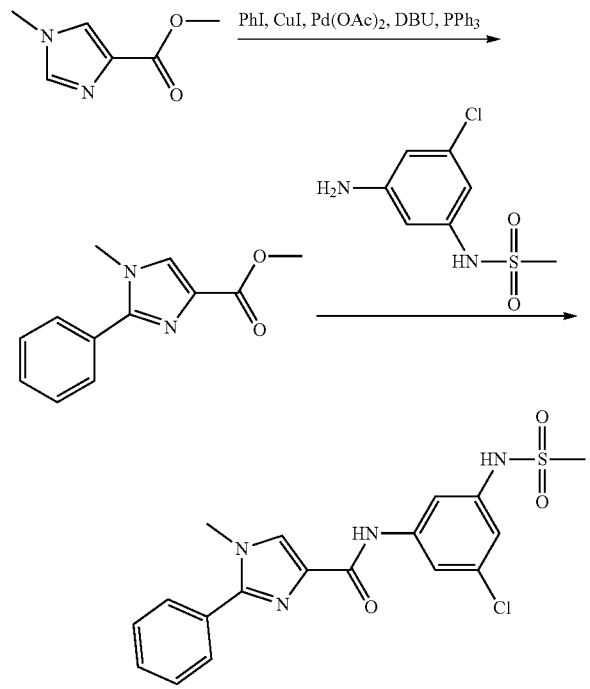

Step 1: To a solution of methyl 1-methyl-1H-imidazole-4-carboxylate (100 mg, 713 μmol) and iodobenzene (188 mg, 926 μmol) in dioxane (2 mL) was added triphenylphosphine (37.2 mg, 142 μmol), DBU (216 mg, 1.42 mmol), Pd(OAc)2 (16 mg, 71.3 μmol) and CuI (270 mg, 1.42 mmol) at 25° C. The mixture was stirred at 120° C. under microwave for 2 h. The mixture was filtered and filter cake was washed with EA (20 mL). The filtrate was concentrated in vacuo to afford a residue. The residue was purified by column chromatography (PE:EA=10:1~0:1) to afford desired compound. methyl 1-methyl-2-phenyl-1H-imidazole-4-carboxylate (900 mg, 4.16 mmol) was obtained as brown oil. LCMS: MS (ESI) Retention time: 0.816 min, (M)+=217.1. 1H NMR (400 MHz, CHLOROFORM-d) δ=7.72-7.69 (m, 1H), 7.69-7.65 (m, 2H), 7.48 (dd, J=1.8, 5.1 Hz, 3H), 3.93 (s, 3H), 3.79 (s, 3H)

Step 2: To a solution of methyl methyl 1-methyl-2-phenyl-1H-imidazole-4-carboxylate (370 mg, 1.71 mmol) and N-(3-amino-5-chlorophenyl)methanesulfonamide (564 mg, 2.56 mmol) in toluene (5 mL) was added LiHMDS (4.27 mmol) at 20° C. The mixture was stirred at 20° C. for 2 h. The mixture was poured into H2O (50 mL) and extracted with EA (50 mL*2). The combined organic layers were washed with brine (30 mL), dried over Na2SO4, filtered and concentrated under reduced pressure to give a residue. The residue was purified by column chromatography (PE:EA=10:1~1:1) to afford desired compound. N-(3-chloro-5-(methylsulfonamido)phenyl)-1-methyl-2-phenyl-1H-imidazole-4-carboxamide (49.96 mg, 123 μmol) was obtained as yellow solid. LCMS: MS (ESI) Retention time: 0.759 min, (M+1)+=405.0. 1H NMR (400 MHz, DMSO-d6) δ=10.17 (s, 1H), 10.04 (s, 1H), 8.08 (s, 1H), 7.86-7.69 (m, 4H), 7.59-7.51 (m, 3H), 6.92 (t, J=1.8 Hz, 1H), 3.83 (s, 3H), 3.09 (s, 3H)

Example 156

The compounds listed in the following table were prepared using a procedure similar to that described for example 155:

| Structure | Example No. | MS (ESI) [M + H]+ | 1H NMR |
|---|---|---|---|
| (Structure: MeS(O)2NH-phenyl(Cl)-NHC(O)-imidazole(NMe)-pyridyl(Me)) | 156 | 420 | 1H NMR (400 MHZ, DMSO-d6) δ 9.81-10.22 (m, 2H) 8.54 (d, J = 4.4 Hz, 1H) 8.01-8.07 (m, 1H) 7.84 (d, J-7.6 Hz, 1H) 7.74 (d, J = 1.2 Hz, 2H) 7.43 (dd, J = 7.6, 4.8 Hz, 1H) 6.91 (t, J = 1.6 Hz, 1H) 3.76 (s, 3H) 3.00-3.13 (m, 1H) 3.08 (s, 2H) 2.48 (s, 3H) |

Example 157: N-(3-bromo-5-(methylsulfonamido) phenyl)thiophene-2-carboxamide

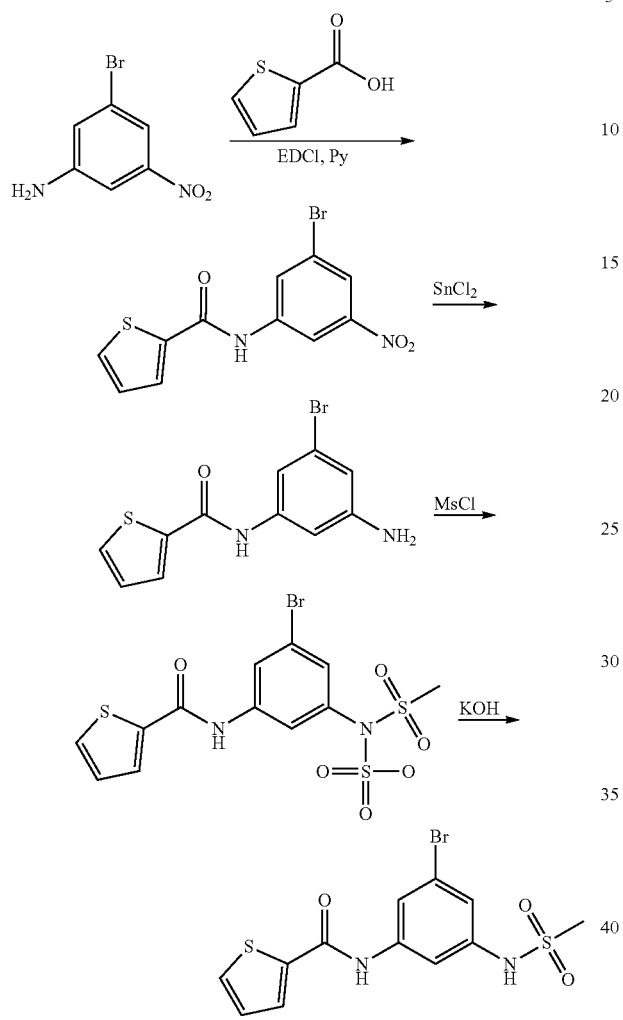

Step 1: To a solution of 3-bromo-5-nitroaniline (500 mg, 2.3 mmol) and thiophene-2-carboxylic acid (589 mg, 4.6 mmol) in pyridine (5 mL) was added EDCI (881 mg, 4.6 mmol) at 20° C. The mixture was stirred at 20° C. for 2 h. The mixture was poured into 1 N HCl (100 mL). Then the aqueous layer was extracted with EA (2×100 mL). The combined organic layers were washed with brine (100 mL), dried over Na$_2$SO$_4$, filtered and concentrated under reduced pressure to give N-(3-bromo-5-nitrophenyl)thiophene-2-carboxamide (3 g, 9.17 mmol) as yellow solid.

LCMS: MS (ESI) Retention time: 0.876 min, (M)+=328.9

Step 2: To a solution of N-(3-bromo-5-nitrophenyl)thiophene-2-carboxamide (3 g, 9.17 mmol) in EA (20 mL) and EtOH (10 mL) was added λ$^2$-tin (2+) dichloride (13.8 g, 73.3 mmol) at 20° C. The mixture was stirred at 60° C. for 16 h. The mixture was poured to aq·K$_2$CO$_3$ (100 mL). Then the aqueous layer was extracted with EA (2×200 mL). The combined organic layers were washed with brine (200 mL), dried over Na$_2$SO$_4$, filtered and concentrated under reduced pressure to give a residue. The residue was purified by column chromatography (PE:EA=5:1~0:1) to afford N-(3-amino-5-bromophenyl)thiophene-2-carboxamide (1.7 g, 5.72 mmol) was obtained as brown oil. LCMS: MS (ESI) Retention time: 0.728 min, (M)+=264.0

$^1$H NMR (400 MHz, DMSO-d$_6$) δ=10.03 (s, 1H), 8.00 (dd, J=1.2, 3.8 Hz, 1H), 7.85 (dd, J=1.2, 4.9 Hz, 1H), 7.22 (dd, J=3.8, 5.0 Hz, 1H), 7.09 (t, J=1.8 Hz, 1H), 7.00 (t, J=1.8 Hz, 1H), 6.49 (t, J=1.8 Hz, 1H), 5.73-5.15 (m, 2H)

Step 3: To a solution of N-(3-amino-5-bromophenyl)thiophene-2-carboxamide (300 mg, 1.00 mmol) in THF (3 mL) was added triethylamine (202 mg, 2.00 mmol) and methanesulfonyl chloride (598 mg, 5.22 mmol) at 0° C. The mixture was stirred at 0° C. for 1 h. The mixture was poured to aq. NaHCO$_3$ (20 mL). Then the aqueous layer was extracted with EA (2×20 mL). The combined organic layers were washed with brine (20 mL), dried over Na$_2$SO$_4$, filtered and concentrated under reduced pressure to give N-(3-bromo-5-(N-(methylsulfonyl)methylsulfonamido)phenyl)thiophene-2-carboxamide (300 mg, 661 μmol) as white solid.

Step 4: To a solution of N-(3-bromo-5-(N-(methylsulfonyl)methylsulfonamido)phenyl)thiophene-2-carboxamide (270 mg, 595 μmol) in THF (8 mL) was added a solution of KOH (220 mg, 3.92 mmol) in H$_2$O (4 mL) at 25° C. The mixture was stirred at 25° C. for 3 h. To the mixture was added 1N HCl (10 mL), extracted with EA (20 mL*3), washed with brine (20 mL), dried over Na$_2$SO$_4$, concentrated in vacuo to afford a residue. The residue was purified by prep-HPLC to afford N-(3-bromo-5-(methylsulfonamido)phenyl)thiophene-2-carboxamide (95.56 mg, 254 μmol) as white solid. LCMS: MS (ESI) Retention time: 0.777 min, (M+1)+=374.9

$^1$H NMR (400 MHz, DMSO-d$_6$) δ=10.41 (s, 1H), 10.08 (ddd, J=2.2, 5.2, 11.2 Hz, 1H), 8.04 (dd, J=1.2, 3.8 Hz, 1H), 7.90 (dd, J=1.2, 4.8 Hz, 1H), 7.79 (t, J=1.8 Hz, 1H), 7.67 (t, J=1.8 Hz, 1H), 7.24 (dd, J=3.8, 5.0 Hz, 1H), 7.09 (t, J=1.8 Hz, 1H), 3.06 (s, 3H)

Example 158: N-(3-chloro-5-(methylsulfonamido) phenyl)-1-methyl-5-(2-oxopiperidin-1-yl)-1H-pyrrole-3-carboxamide

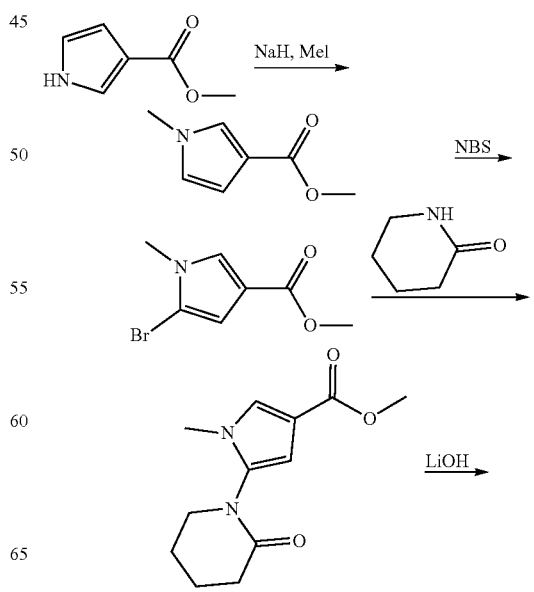

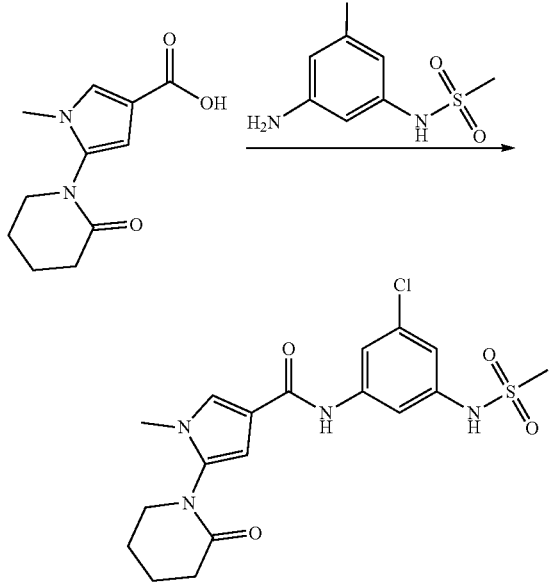

Step 1: To a solution of methyl 1H-pyrrole-3-carboxylate (2 g, 15.9 mmol) in DMF (20 mL) was added sodium hydride (951 mg, 23.8 mmol) at 0° C. The mixture was stirred at 0° C. for 0.5 h. To the mixture was added iodomethane (3.37 g, 23.8 mmol) at 0° C. The mixture was stirred at 25° C. for 2 h. The mixture was poured into H₂O (50 mL). Then the aqueous layer was extracted with EA (2×50 mL). The combined organic layers were washed with brine (50 mL), dried over Na₂SO₄, filtered and concentrated under reduced pressure to give methyl 1-methyl-1H-pyrrole-3-carboxylate (1.8 g, 12.9 mmol, crude) as colorless oil.

Step 2: To a solution of methyl 1-methyl-1H-pyrrole-3-carboxylate (1.8 g, 12.9 mmol) in THF (18 mL) was added 1-bromopyrrolidine-2, 5-dione (2.27 g, 12.8 mmol) slowly at 0° C. The mixture was stirred at 25° C. for 0.5 h. The mixture was poured to aq·Na2SO3 (40 mL). Then the aqueous layer was extracted with EA (2×40 mL). The combined organic layers were washed with brine (40 mL), dried over Na₂SO₄, filtered and concentrated under reduced pressure to give a residue. The residue was purified by column chromatography (PE:EA=20:1~1:1) to afford methyl 5-bromo-1-methyl-1H-pyrrole-3-carboxylate (2.4 g, 11 mmol) as white solid.

Step 3: To a solution of methyl 5-bromo-1-methyl-1H-pyrrole-3-carboxylate (1.3 g, 5.96 mmol) and piperidin-2-one (1.17 g, 11.9 mmol) in DMF (10 mL) was added rac-(2R)-pyrrolidine-2-carboxylic acid (137 mg, 1.19 mmol) and V-copper (1+) iodide (226 mg, 1.19 mmol) and dicaesium (1+) carbonate (5.79 g, 17.8 mmol) at 25° C. The mixture was stirred at 140° C. for 2 h under microwave. The mixture was poured into H₂O (50 mL). The mixture was extracted with EA (30 mL*2). The combined organic layers were washed with brine (30 mL), dried over Na₂SO₄, filtered and concentrated under reduced pressure to give a residue. The residue was purified by column chromatography (PE:EA=10:1~1:1) to afford methyl 1-methyl-5-(2-oxopiperidin-1-yl)-1H-pyrrole-3-carboxylate (300 mg, 1.26 mmol) was obtained as white solid.

LCMS: MS (ESI) Retention time: 0.636 min, (M)+=237.0

Step 4: To a solution of methyl 1-methyl-5-(2-oxopiperidin-1-yl)-1H-pyrrole-3-carboxylate 5 (200 mg, 846 μmol) in MeOH (5 mL) and THF (3 mL) and H₂O (1 mL) was added lithium (1+) hydrate hydroxide (177 mg, 4.22 mmol) at 25° C. The mixture was stirred at 15 h. The mixture was poured into 1N HCl (20 mL). The mixture was extracted with EA (30 mL*2). The combined organic layers were washed with brine (30 mL), dried over Na₂SO₄, filtered and concentrated under reduced pressure to give 1-methyl-5-(2-oxopiperidin-1-yl)-1H-pyrrole-3-carboxylic acid (180 mg, 809 μmol) was obtained as white solid.

LCMS: MS (ESI) Retention time: 0.372 min, (M)+=222.9

Step 5: To a solution of 1-methyl-5-(2-oxopiperidin-1-yl)-1H-pyrrole-3-carboxylic acid (75 mg, 337 μmol) and N-(3-amino-5-chlorophenyl)methanesulfonamide (81.6 mg, 370 μmol) in pyridine (3 mL) was added EDCI (129 mg, 674 μmol) at 25° C. The mixture was stirred at 25° C. for 1 h. The mixture was poured into H₂O (20 mL). The mixture was extracted with EA (30 mL*2). The combined organic layers were washed with brine (30 mL), dried over Na₂SO₄, filtered and concentrated under reduced pressure to give a residue. The residue was purified by prep-HPLC to afford N-(3-chloro-5-(methylsulfonamido)phenyl)-1-methyl-5-(2-oxopiperidin-1-yl)-1H-pyrrole-3-carboxamide (68.57 mg, 161 μmol) as off-white solid.

LCMS: MS (ESI) Retention time: 0.722 min, (M+1)+=425.2

¹H NMR (400 MHz, DMSO-d₆) δ=9.72 (s, 2H), 7.69 (t, J=1.8 Hz, 1H), 7.58 (t, J=1.8 Hz, 1H), 7.46 (d, J=2.0 Hz, 1H), 6.87 (t, J=1.8 Hz, 1H), 6.49 (d, J=2.0 Hz, 1H), 3.52 (br t, J=5.4 Hz, 2H), 3.41 (s, 3H), 3.05 (s, 3H), 2.42 (br t, J=6.0 Hz, 2H), 1.94-1.80 (m, 4H)

Example 159: 1-(2-trans-(benzyloxy)cyclobutyl)-N-(3-chloro-5-(methylsulfonamido)phenyl)-1H-pyrazole-4-carboxamide

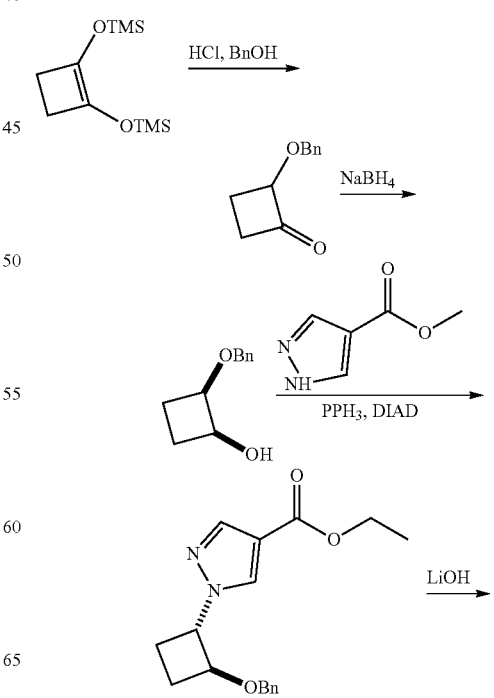

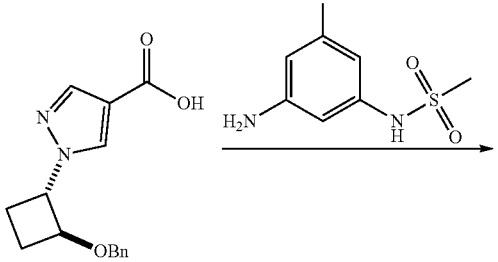

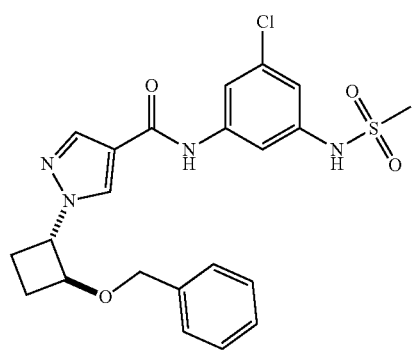

Stereochemistry Arbitrarly Assigned

Step 1: To a solution of 1,2-bis((trimethylsilyl)oxy)cyclobut-1-ene (5 g, 21.6 mmol) in HCl/dioxane (20 mL, 4M) was added phenylmethanol (2.8 g, 25.9 mmol) at 25° C. The mixture was stirred at 80° C. for 16 h. The mixture was concentrated in vacuo to afford a residue. The residue was purified by column chromatography (PE:EA=10:1~1:1) to afford 2-(benzyloxy)cyclobutan-1-one (2.1 g, 11.9 mmol) as colorless oil. $^1$H NMR (400 MHz, CHLOROFORM-d) δ=7.52-7.29 (m, 5H), 4.83-4.71 (m, 2H), 4.69-4.60 (m, 1H), 2.88-2.70 (m, 2H), 2.42-2.23 (m, 1H), 2.04-1.87 (m, 1H)

Step 2: To a solution of 2-(benzyloxy)cyclobutan-1-one (2.1 g, 11.9 mmol) in MeOH (20 mL) was added sodium boranuide (900 mg, 23.8 mmol) at 0° C. The mixture was stirred at 25° C. for 2 h. The mixture was quenched with sat·NH$_4$Cl (20 mL) and stirred at 25° C. for 15 min. The mixture was extracted with EA (30 mL*3). The combined organic phase was washed with brine (15 mL*2), dried with anhydrous Na$_2$SO$_4$, filtered and concentrated in vacuum to give a residue. The residue was purified by silica gel column chromatography (Petroleum ether/Ethyl acetate=20/1-1/1) to afford desired compound. cis-2-(benzyloxy)cyclobutan-1-ol (690 mg, 3.87 mmol) was obtained as colorless oil, which was determined by $^1$H NMR. Trans-2-(benzyloxy)cyclobutan-1-ol (690 mg, 3.87 mmol) was obtained as colorless oil, which was determined by $^1$H NMR.

cis-2-(benzyloxy)cyclobutan-1-ol:
$^1$H NMR (400 MHz, CHLOROFORM-d) δ=7.43-7.30 (m, 4H), 4.65-4.48 (m, 2H), 4.31 (br dd, J=2.2, 4.6 Hz, 1H), 4.18-4.11 (m, 1H), 2.13-1.97 (m, 4H), 1.28 (t, J=7.2 Hz, 1H)
trans-2-(benzyloxy)cyclobutan-1-ol $^1$H NMR (400 MHz, CHLOROFORM-d) δ=7.44-7.29 (m, 5H), 4.68-4.49 (m, 2H), 4.21-3.99 (m, 1H), 3.90-3.71 (m, 1H), 2.21 (s, 1H), 2.11-1.91 (m, 2H), 1.49-1.29 (m, 2H)

Step 3: To a solution of cis-2-(benzyloxy)cyclobutan-1-ol (690 mg, 3.87 mmol) and ethyl 1H-pyrazole-4-carboxylate (812 mg, 5.8 mmol) and triphenylphosphane (2.03 g, 7.74 mmol) in THF (10 mL) was added DIAD (1.56 g, 774 mmol) at 0° C. The mixture was stirred at 25° C. for 16 h. The mixture was poured to H$_2$O (50 mL). The mixture was extracted with EA (30 mL*2). The combined organic layers were washed with brine (30 mL), dried over Na$_2$SO$_4$, filtered and concentrated under reduced pressure to give a residue. The residue was purified by column chromatography (PE:EA=10:1~1:1) to afford ethyl 1-(trans-2-(benzyloxy)cyclobutyl)-1H-pyrazole-4-carboxylate (690 mg, 2.13 mmol) as colorless oil. LCMS: MS (ESI) Retention time: 0.833 min, (M+1)+=301.1 $^1$H NMR (400 MHz, CHLOROFORM-d) δ=8.01-7.92 (m, 1H), 7.79 (s, 1H), 7.35-7.19 (m, 5H), 4.66-4.56 (m, 1H), 4.48 (d, J=1.8 Hz, 2H), 4.45-4.38 (m, 1H), 4.32 (q, J=7.2 Hz, 2H), 2.39-2.18 (m, 2H), 1.88-1.74 (m, 2H), 1.41-1.33 (m, 3H)

Step 4: To a solution of ethyl 1-(trans-2-(benzyloxy)cyclobutyl)-1H-pyrazole-4-carboxylate (120 mg, 399 µmol) in THF (2 mL) and MeOH (3 mL) and H$_2$O (1 mL) was added lithium hydroxide hydrate (83.5 mg, 1.99 mmol) at 25° C. The mixture was stirred at 25° C. for 16 h. The mixture was poured to 1N HCl (15 mL). The mixture was extracted with EA (30 mL*2). The combined organic layers were washed with brine (30 mL), dried over Na$_2$SO$_4$, filtered and concentrated under reduced pressure to give 1-(trans-2-(benzyloxy)cyclobutyl)-1H-pyrazole-4-carboxylic acid (100 mg, 367 µmol) as colorless oil. LCMS: MS (ESI) Retention time: 0.748 min, (M+1)+=273.1

Step 5: To a solution of 1-(trans-2-(benzyloxy)cyclobutyl)-1H-pyrazole-4-carboxylic acid (70 mg, 257 µmol) and N-(3-amino-5-chlorophenyl)methanesulfonamide (62.2 mg, 282 µmol) in pyridine (2 mL) was added EDCI (98.5 mg, 514 µmol) at 25° C. The mixture was stirred at 25° C. for 16 h. The mixture was poured to H$_2$O (20 mL). Then the aqueous layer was extracted with EA (2×20 mL). The combined organic layers were washed with brine (20 mL), dried over Na$_2$SO$_4$, filtered and concentrated under reduced pressure to give a residue. The residue was purified by prep-HPLC to afford 1-(trans-2-(benzyloxy)cyclobutyl)-N-(3-chloro-5-(methylsulfonamido)phenyl)-1H-pyrazole-4-carboxamide (28.48 mg, 59.9 µmol) as white solid.

LCMS: MS (ESI) Retention time: 0.845 min, (M+1)+=475.2 $^1$H NMR (400 MHz, DMSO-d$_6$) δ=10.04 (s, 1H), 8.46 (s, 1H), 8.09 (s, 1H), 7.71-7.51 (m, 2H), 7.34-7.19 (m, 5H), 6.92 (t, J=1.8 Hz, 1H), 4.80 (br d, J=7.4 Hz, 1H), 4.47-4.31 (m, 3H), 3.05 (s, 3H), 2.28-2.13 (m, 2H), 1.99 (br t, J=9.4 Hz, 1H), 1.76-1.62 (m, 1H)

Example 424

The compounds listed in the following table were prepared using a procedure similar to that described for example 159:

| Structure | Example No. | MS (ESI) [M + H]+ | 1H NMR |
|---|---|---|---|
| (structure with pyrazole, cyclopentyl-O-benzyl, amide linker to chlorophenyl methylsulfonamide) | 424 | 489 | 1H NMR (400 MHZ, DMSO-d6) δ 10.03 (s, 2H), 8.47 (d, J = 3.5 Hz, 1H), 8.07 (d, J = 3.4 Hz, 1H), 7.75-7.55 (m, 3H), 7.37-7.13 (m, 6H), 6.97-6.71 (m, 1H), 4.74 (td, J = 8.0, 5.2 Hz, 1H), 4.44 (d, J = 3.8 Hz, 2H), 4.18 (q, J = 6.0 Hz, 2H), 3.06 (d, J = 3.0 Hz, 4H), 2.28-2.16 (m, 2H), 2.16-1.95 (m, 3H), 1.89-1.50 (m, 4H). |

Example 160: N-(3-chloro-5-(methylsulfonamido)phenyl)-3-(3-(hydroxymethyl)-1H-pyrazol-1-yl)benzamide

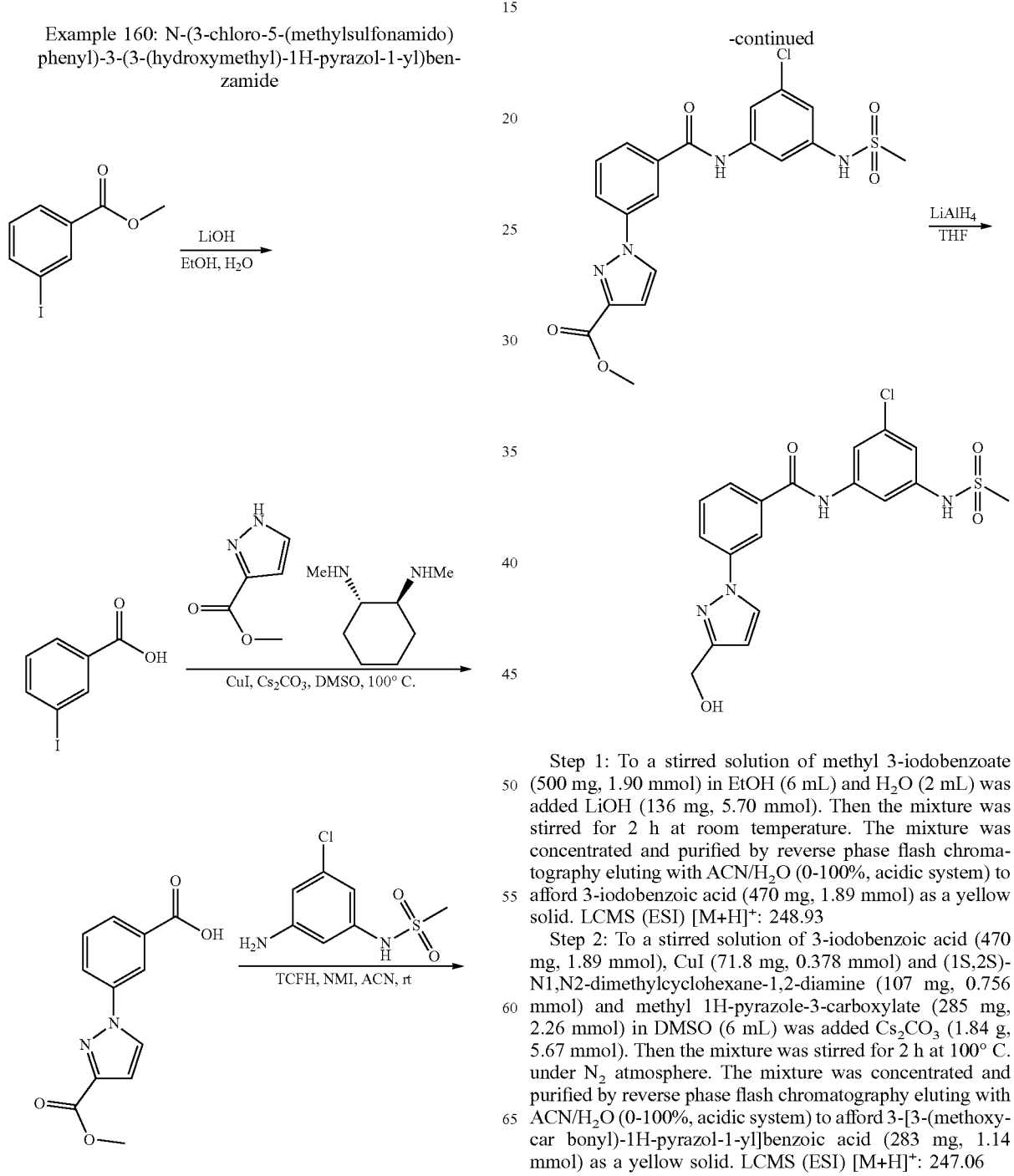

Step 1: To a stirred solution of methyl 3-iodobenzoate (500 mg, 1.90 mmol) in EtOH (6 mL) and H₂O (2 mL) was added LiOH (136 mg, 5.70 mmol). Then the mixture was stirred for 2 h at room temperature. The mixture was concentrated and purified by reverse phase flash chromatography eluting with ACN/H₂O (0-100%, acidic system) to afford 3-iodobenzoic acid (470 mg, 1.89 mmol) as a yellow solid. LCMS (ESI) [M+H]⁺: 248.93

Step 2: To a stirred solution of 3-iodobenzoic acid (470 mg, 1.89 mmol), CuI (71.8 mg, 0.378 mmol) and (1S,2S)-N1,N2-dimethylcyclohexane-1,2-diamine (107 mg, 0.756 mmol) and methyl 1H-pyrazole-3-carboxylate (285 mg, 2.26 mmol) in DMSO (6 mL) was added Cs₂CO₃ (1.84 g, 5.67 mmol). Then the mixture was stirred for 2 h at 100° C. under N₂ atmosphere. The mixture was concentrated and purified by reverse phase flash chromatography eluting with ACN/H₂O (0-100%, acidic system) to afford 3-[3-(methoxycarbonyl)-1H-pyrazol-1-yl]benzoic acid (283 mg, 1.14 mmol) as a yellow solid. LCMS (ESI) [M+H]⁺: 247.06

Step 3: To a stirred solution of 3-[3-(methoxycarbonyl)-1H-pyrazol-1-yl]benzoic acid (283 mg, 1.14 mmol), TCFH (478 mg, 1.71 mmol) and NMI (467 mg, 5.70 mmol) in ACN (5 mL) was added N-(3-amino-5-chlorophenyl) methanesulfonamide (251 mg, 1.14 mmol). Then the mixture was stirred for 2 h at room temperature. The mixture was concentrated and purified by reverse phase flash chromatography eluting with ACN/H$_2$O (0-100%, acidic system) to afford methyl 1-{3-[(3-chloro-5-methanesulfonamidophenyl)carbamoyl]phenyl}-1H-pyrazole-3-carboxylate (230 mg, 0.512 mmol) as an off-white solid. LCMS (ESI) [M+H]$^+$: 449.06

Step 4: To a stirred solution of methyl 1-{3-[(3-chloro-5-methanesulfonamidophenyl)carbamoyl]phenyl}-1H-pyrazole-3-carboxylate (230 mg, 0.512 mmol) in THF (5 mL) was added LiAlH$_4$ (110 mg, 1.53 mmol) under N$_2$ atmosphere. Then the mixture was stirred for 2 h at room temperature. The mixture was concentrated and purified by reverse phase flash chromatography eluting with ACN/H$_2$O (0-100%, acidic system) to afford N-(3-chloro-5-methanesulfonamidophenyl)-3-[3-(hydroxymethyl)-1H-pyrazol-1-yl] benzamide (14.6 mg, 0.0344 mmol) as a white solid. LCMS (ESI) [M+H]$^+$: 421.07 $^1$H NMR (300 MHz, DMSO-d$_6$) δ 10.61 (s, 1H), 8.52 (d, J=2.6 Hz, 1H), 8.34 (s, 1H), 8.03 (d, J=8.1 Hz, 1H), 7.84 (d, J=7.7 Hz, 1H), 7.71 (d, J=1.9 Hz, 2H), 7.65 (t, J=7.8 Hz, 1H), 6.98 (t, J=2.0 Hz, 1H), 6.55 (d, J=2.5 Hz, 1H), 5.26 (s, 1H), 4.55 (s, 2H), 3.08 (s, 3H).

Example 161: N-(3-bromo-5-(methylsulfonamido)phenyl)-1-(2-(hydroxymethyl)phenyl)-1H-pyrazole-4-carboxamide

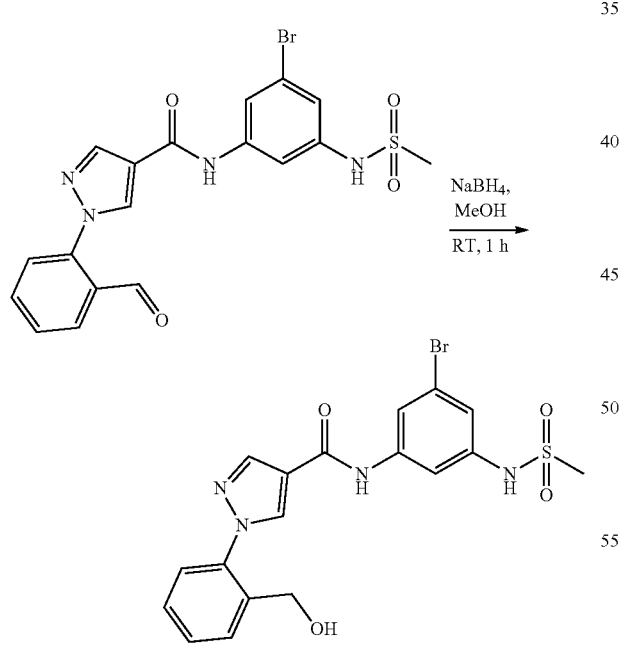

To a stirred solution of N-(3-bromo-5-methanesulfonamidophenyl)-1-(2-formylphenyl)-1H-pyrazole-4-carboxamide (200 mg, 0.431 mmol) in MeOH (5 mL) was added NaBH4 (21.1 mg, 0.560 mmol) at 0° C. Then the mixture was stirred for 1 h at room temperature. The mixture was concentrated and purified by flash chromatography on silica gel eluting with EtOAc/Petroleum ether (0-100%) to afford N-(3-bromo-5-methanesulfonamidophenyl)-1-[2-(hydroxymethyl)phenyl]-1H-pyrazole-4-carboxamide (25.6 mg, 0.055 mmol) as a white solid.
LCMS (ESI) [M+H]$^+$: 465 $^1$H NMR (300 MHz, DMSO-d$_6$) δ 10.15 (s, 1H), 10.09 (s, 1H), 8.73 (s, 1H), 8.29 (s, 1H), 7.82 (t, J=1.8 Hz, 1H), 7.74-7.61 (m, 2H), 7.59-7.40 (m, 3H), 7.07 (t, J=1.9 Hz, 1H), 5.34 (t, J=5.6 Hz, 1H), 4.47 (d, J=5.2 Hz, 2H), 3.06 (s, 3H).

Example 162: 1-(3-aminopyridin-2-yl)-N-(3-bromo-5-(methylsulfonamido)phenyl)-1H-pyrazole-4-carboxamide

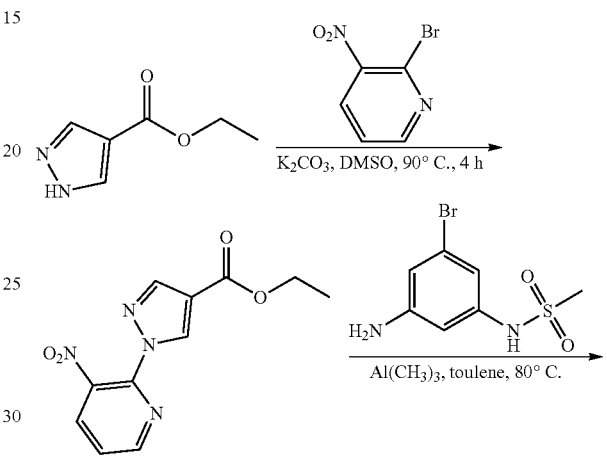

Step 1: To a stirred solution of ethyl 1H-pyrazole-4-carboxylate (150 mg, 1.07 mmol), 2-bromo-3-nitropyridine (259 mg, 1.28 mmol) and K$_2$CO$_3$ (529 mg, 3.84 mmol) in DMSO (10.00 mL). Then the mixture was stirred for 4 h at 90° C. under nitrogen. The mixture was concentrated and purified by reverse phase flash chromatography eluting with ACN/H$_2$O (5-95%, acidic system) to afford ethyl 1-(3-nitropyridin-2-yl)-1H-pyrazole-4-carboxylate (110 mg, 95%) as a yellow solid. LCMS (ESI) [M+H]$^+$: 263

Step 2: To a stirred solution of ethyl 1-(3-nitropyridin-2-yl)-1H-pyrazole-4-carboxylate (110 mg, 0.419 mmol), N-(3- amino-5-bromophenyl) methanesulfonamide (111 mg, 0.419 mmol) and Al(CH3)$_3$ (0.5 ml) in toluene (5.00 mL). Then the mixture was stirred for 1.5 h at 80° C. under nitrogen. The mixture was concentrated and purified by reverse phase flash chromatography eluting with ACN/H$_2$O (5-95%, acidic system) to afford N-(3-bromo-5-methanesulfonamidophenyl)-1-(3-nitropyridin-2-yl)-1H-pyrazole-4-carboxamide (120 mg, 95%) as a white solid. LCMS (ESI) [M+H]$^+$: 481

Step 3: To a solution of N-(3-bromo-5-methanesulfonamidophenyl)-1-(3-nitropyridin-2-yl)-1H-pyrazole-4-carboxamide (120 mg, 0.249 mmol) in a solution of methanol and water (15 mL) was added Fe (70 mg, 1.245 mmol) and NH$_4$Cl (131 mg, 2.49 mmol). The resulting mixture was stirred for 1 hour at 80° C. under N$_2$ atmosphere. The resulting mixture was filtered. The filtrate was concentrated under reduced pressure to give the crude product. The mixture was concentrated and purified by flash chromatography on silica gel eluting with EtOAc/Petroleum ether (0-100%) to afford 1-(3-aminopyridin-2-yl)-N-(3-bromo-5-methanesulfonamidophenyl)-1H-pyrazole-4-carboxamide (45.9 mg, 97.661%) as a white solid. LCMS (ESI) [M+H]$^+$: 451

$^1$H NMR (300 MHz, DMSO-d$_6$) δ 10.28 (s, 1H), 10.06 (s, 1H), 9.31 (d, J=0.8 Hz, 1H), 8.29 (d, J=0.8 Hz, 1H), 7.86 (t, J=1.8 Hz, 1H), 7.77 (dd, J=4.4, 1.5 Hz, 1H), 7.70 (t, J=1.9 Hz, 1H), 7.35 (dd, J=8.1, 1.6 Hz, 1H), 7.21 (dd, J=8.1, 4.4 Hz, 1H), 7.08 (t, J=1.9 Hz, 1H), 6.41 (s, 2H), 3.07 (s, 3H).

Example 163: N-(3-chloro-5-(methylsulfonamido)phenyl)-5-(hydroxymethyl)-4-(pyridin-2-yl)thiophene-2-carboxamide

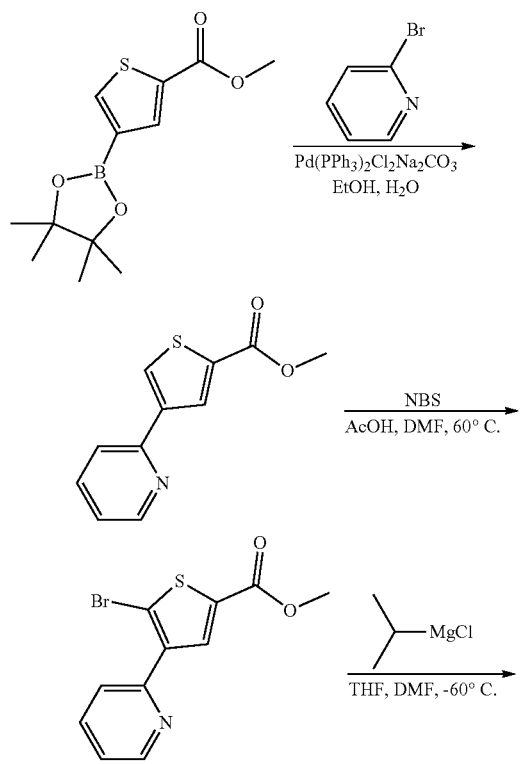

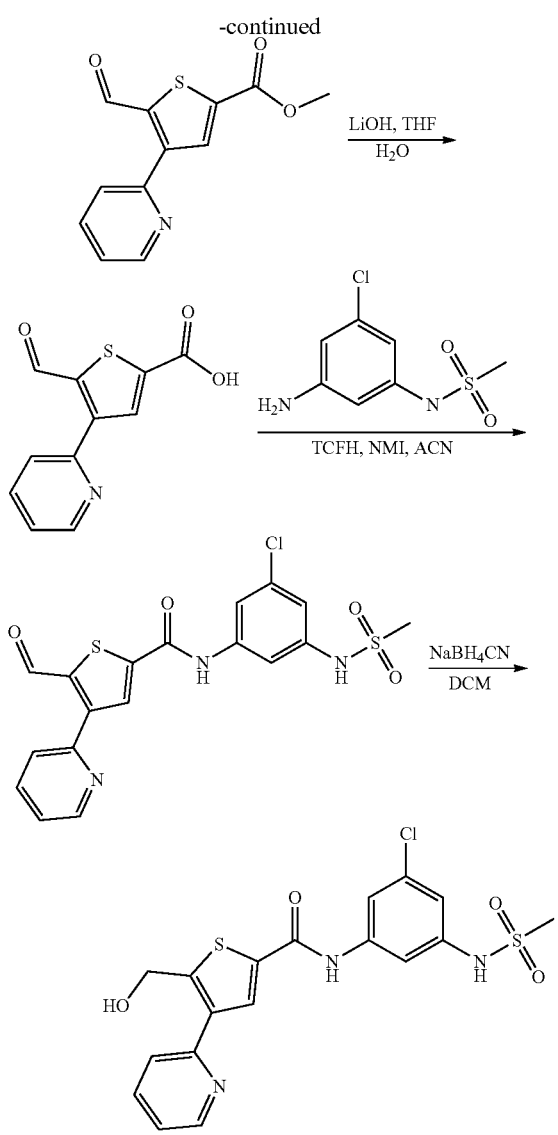

Step 1: To a stirred solution of methyl 4-(4,4,5,5-tetramethyl-1,3,2-dioxaborolan-2-yl)thiophene-2-carboxylate (600 mg, 2.23 mmol), 2-bromopyridine (527 mg, 3.34 mmol), Pd(PPh$_3$)Cl$_2$ (156 mg, 0.223 mmol) and Na$_2$CO$_3$ (709 mg, 6.69 mmol) in EtOH (10.00 mL) was added H$_2$O (2.00 mL). Then the mixture was stirred for 4 h at 80° C. under N$_2$ atmosphere. The mixture was concentrated and purified by reverse phase flash chromatography eluting with ACN/H$_2$O (5-95%, acidic system) to afford methyl 4-(pyridin-2-yl)thiophene-2-carboxylate (456 mg, 95%) as a white solid. LCMS (ESI) [M+H]$^+$: 220

Step 2: To a solution of methyl 4-(pyridin-2-yl)thiophene-2-carboxylate (480 mg, 2.18 mmol) in DMF (15 mL) was added N-Bromosuccinimide (1.75 g, 9.81 mmol) and AcOH (392 mg, 6.54 mmol). The resulting mixture was stirred for 4 hours at 60° C. under N$_2$ atmosphere. The mixture was concentrated and purified by flash chromatography on silica gel eluting with EtOAc/Petroleum ether (0-100%) to afford methyl 5-bromo-4-(pyridin-2-yl)thiophene-2-carboxylate (294 mg, 95%) as a yellow solid. LCMS (ESI) [M+H]$^+$: 299

Step 3: To a stirred solution of methyl 5-bromo-4-(pyridin-2-yl)thiophene-2-carboxylate (310 mg, 1.03 mmol) in THF (15.00 mL) was added chloro(propan-2-yl) magnesium (126 mg, 1.23 mmol) dropwise at −60° C. under N₂ atmosphere. Then the mixture was stirred for 3 h at −60° C. After that the mixture was added DMF (751 mg, 10.3 mmol) dropwise at −60° C. Then the mixture was stirred for 8 h at room temperature. The mixture was concentrated and purified by flash chromatography on silica gel eluting with EtOAc/Petroleum ether (0-100%) to afford methyl 5-formyl-4-(pyridin-2-yl) thiophene-2-carboxylate (142 mg, 95%) as a yellow solid.

LCMS (ESI) [M+H]⁺: 248

Step 4: To a stirred solution of methyl 5-formyl-4-(pyridin-2-yl)thiophene-2-carboxylate (150 mg, 0.606 mmol) and LiOH (10 mg, 2.5 mmol) in THF (10.00 mL) was added H₂O (2.00 mL) dropwise. Then the mixture was stirred for 2 h at room temperature. The mixture was acidified to pH 5 with citric acid. The precipitated solids were collected by filtration and washed with water. The resulting solid was dried under vacuum to 5-formyl-4-(pyridin-2-yl)thiophene-2-carboxylic acid (104 mg, 95%) as a yellow solid. LCMS (ESI) [M+H]⁺: 234

Step 5: To a stirred solution of 5-formyl-4-(pyridin-2-yl)thiophene-2-carboxylic acid (110 mg, 0.471 mmol), TCFH (198 mg, 0.706 mmol) and NMI (115 mg, 1.41 mmol) in ACN (5.00 mL) was added N-(3-amino-5-chlorophenyl)methanesulfonamide (103 mg, 0.471 mmol). Then the mixture was stirred for 4 h at room temperature. The mixture was concentrated and purified by reverse phase flash chromatography eluting with ACN/H₂O (5-95%, acidic system) to afford N-(3-chloro-5-methanesulfonamidophenyl)-5-formyl-4-(pyridin-2-yl)thiophene-2-carboxamide (85.5 mg, 95%) as a white solid. LCMS (ESI) [M+H]⁺: 437

Step 6: To a stirred solution of N-(3-chloro-5-methanesulfonamidophenyl)-5-formyl-4-(pyridin-2-yl)thiophene-2-carboxamide (90 mg, 0.206 mmol) in DCM (10.00 mL) was added NaBH₃CN (12.9 mg, 0.206 mmol) dropwise at 0° C. Then the mixture was stirred for 30 minutes at room temperature. The mixture was concentrated and purified by reverse phase flash chromatography eluting with ACN/H₂O (5-95%, acidic system) to afford N-(3-chloro-5-methanesulfonamidophenyl)-5-(hydroxymethyl)-4-(pyridin-2-yl)thiophene-2-carboxamide (9.6 mg, 97.816%) as an off-white solid. LCMS (ESI) [M+H]⁺: 439

¹H NMR (400 MHz, DMSO-d₆) δ 10.44 (s, 1H), 10.07 (s, 1H), 8.67 (ddd, J=4.8, 1.8, 0.9 Hz, 1H), 8.48 (s, 1H), 7.94 (td, J=7.7, 1.8 Hz, 1H), 7.76-7.67 (m, 2H), 7.65 (t, J=1.9 Hz, 1H), 7.35 (ddd, J=7.5, 4.8, 1.1 Hz, 1H), 6.96 (t, J=2.0 Hz, 1H), 6.04 (t, J=5.6 Hz, 1H), 4.99 (d, J=5.6 Hz, 2H), 3.07 (s, 3H).

Example 164: N-(3-chloro-5-(methylsulfonamido)phenyl)-3-(phenylamino)-1H-pyrazole-5-carboxamide

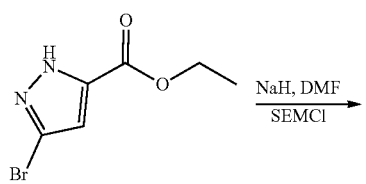

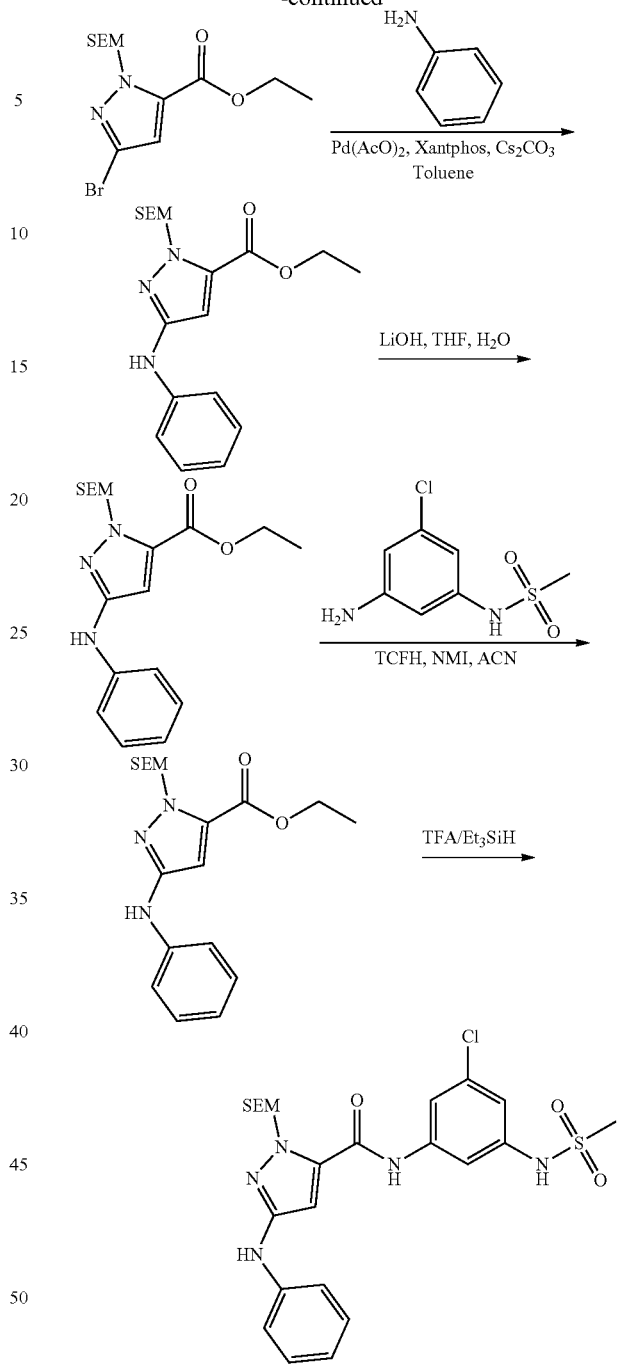

Step 1: Under nitrogen, a solution of ethyl 5-bromo-2H-pyrazole-3-carboxylate (1 g, 4.565 mmol, 1 equiv) in DMF (15 mL) was added NaH (164 mg, 6.834 mmol, 1.50 equiv) at 0° C. The resulting solution was stirred for half an hour at room temperature. Then [2-(chloromethoxy)ethyl]trimethylsilane (910 mg, 5.458 mmol, 1.20 equiv) was added and stirred for one hour at room temperature. The reaction was quenched with water (2 mL). The reaction mixture was diluted with water (50 mL). The resulting solution was extracted with EtOAc (3×50 mL) and the organic layers were combined. The organic layer was dried over anhydrous sodium sulfate and concentrated under vacuum. The residue was purified by flash chromatography on silica gel eluting with EtOAc/Petroleum ether (23%) to afford ethyl 5-bromo-2-{[2-(trimethylsilyl)ethoxy]methyl}pyrazole-3-carboxylate (1.2 g, 75.25%) as a yellow oil. LCMS: (ESI): [M+H]⁺: 349

Step 2: Under nitrogen, a solution of ethyl 5-bromo-2-{[2-(trimethylsilyl)ethoxy]methyl}pyrazole-3-carboxylate (500 mg, 1.431 mmol, 1 equiv), aniline (266.62 mg, 2.862 mmol, 2 equiv), Pd(OAc)₂ (16.07 mg, 0.072 mmol, 0.05 equiv) and XantPhos (82.8 mg, 0.143 mmol, 0.10 equiv) in Toluene (5 mL) was added Cs₂CO₃ (1.4 g, 4.297 mmol, 3.00 equiv) at room temperature. The resulting solution was stirred for two hours at 100° C. The resulting solution was concentrated under vacuum. The residue was purified by flash chromatography on silica gel eluting with EtOAc/Petroleum ehter (45%) to afford ethyl 5-(phenylamino)-2-{[2-(trimethylsilyl)ethoxy]methyl}pyrazole-3-carboxylate (230 mg, 44.45%) as a yellow oil. LCMS: (ESI): [M+H]⁺: 362

Step 3: To a solution of ethyl 5-(phenylamino)-2-{[2-(trimethylsilyl)ethoxy]methyl}pyrazole-3-carboxylate (230 mg, 0.636 mmol, 1 equiv) in THE (5 mL) and H₂O (2 mL) was added LiOH (76.2 mg, 3.182 mmol, 5.00 equiv) at room temperature. The resulting solution was stirred for one hour at room temperature. The residue was purified by flash chromatography on C18 column gel eluting with ACN/water (0.1% FA) (37%) to afford 5-(phenylamino)-2-{[2-(trimethylsilyl)ethoxy]methyl}pyrazole-3-carboxylic acid (130 mg, 61.28%) as a yellow solid. LCMS: (ESI): [M+H]⁺:334

Step 4: A solution of 5-(phenylamino)-2-{[2-(trimethylsilyl)ethoxy]methyl}pyrazole-3-carboxylic acid (130 mg, 0.390 mmol, 1 equiv), NMI (64 mg, 0.779 mmol, 2.00 equiv) and TCFH (164.1 mg, 0.585 mmol, 1.50 equiv) in ACN (5 mL) at room temperature. The resulting solution was stirred for 10 minus at room temperature. Then N-(3-amino-5-chlorophenyl)methanesulfonamide (103.2 mg, 0.468 mmol, 1.20 equiv) was added and stirred for one hours at room temperature. The residue was purified by C18 column gel eluting with ACN/water (0.05 NH₄HCO₃) (68%) to afford N-(3-chloro-5-methanesulfonamidophenyl)-5-(phenylamino)-2-{[2-(trimethylsilyl)ethoxy]methyl}pyrazole-3-carboxamide (80 mg, 38.28%) as a yellow solid. LCMS: (ESI): [M+H]⁺:536

Step 5: To a solution of N-(3-chloro-5-methanesulfonamidophenyl)-5-(phenylamino)-2-{[2-(trimethylsilyl)ethoxy]methyl}pyrazole-3-carboxamide (80 mg, 0.149 mmol, 1 equiv) in Et₃SiH (1 mL, 6.192 mmol, 41.50 equiv) was added TFA (1 mL) at 0° C. The mixture was stirred for one hour at room temperature. The residue was purified by Pre-HPLC on condition: Column: Sunfire prep C18 column, 30*150 mm, 5 μm; Mobile Phase A: Water (0.1% FA), Mobile Phase B: ACN; Flow rate: 60 mL/min; Gradient: 40% B to 52% B in 7 min, 52% B; Wave Length: 254/220 nm; RT1(min): 6.62 to afford N-(3-chloro-5-methanesulfonamidophenyl)-5-(phenylamino)-2H-pyrazole-3-carboxamide (29.6 mg, 48.73%) as a white solid. LCMS: (ESI): [M+H]⁺:406. ¹H NMR (300 MHz, DMSO-d₆) δ 12.98 (s, 1H), 10.21 (d, J=75.1 Hz, 2H), 8.57 (s, 1H), 7.68 (s, 2H), 7.32 (s, 1H), 7.22 (t, J=7.6 Hz, 2H), 6.96 (s, 1H), 6.75 (d, J=9.1 Hz, 2H), 3.08 (s, 3H).

Example 165: N-(3-chloro-5-(methylsulfonamido)phenyl)-5-(piperazine-1-carbonyl)-1-(pyridin-2-yl)-1H-pyrrole-3-carboxamide

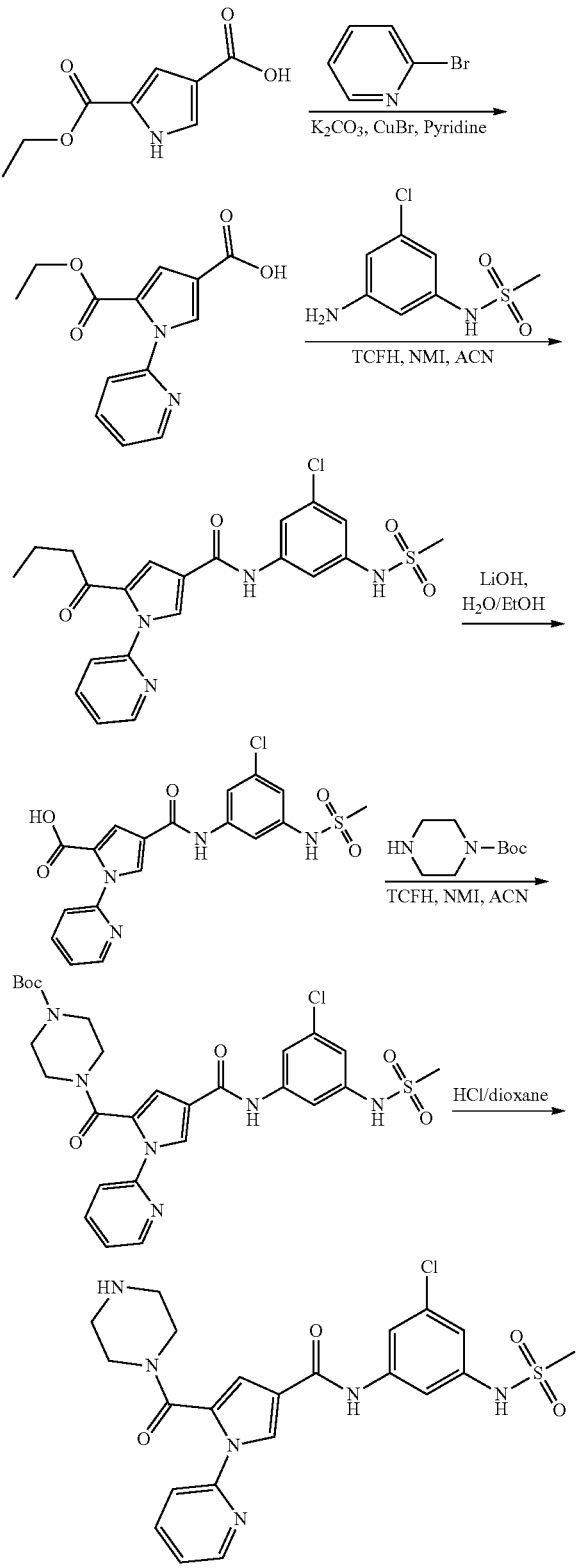

Step 1: To a stirred solution of 5-(ethoxycarbonyl)-1H-pyrrole-3-carboxylic acid (320 mg, 1.74 mmol), K$_2$CO$_3$ (721 mg, 5.22 mmol), CuBr (249 mg, 1.74 mmol) and 2-bromopyridine (301 mg, 1.91 mmol) in Pyridine (5 mL). Then the mixture was stirred for 5 h at 110° C. The mixture was concentrated and purified by reverse phase flash chromatography eluting with ACN/H$_2$O (5-95%, acidic system) to afford 5-(ethoxycarbonyl)-1-(pyridin-2-yl)-1H-pyrrole-3-carboxylic acid (120 mg, 0.461 mmol) as a yellow solid. LCMS (ESI) [M+H]$^+$: 261

Step 2: To a stirred solution of 5-(ethoxycarbonyl)-1-(pyridin-2-yl)-1H-pyrrole-3-carboxylic acid (120 mg, 0.461 mmol), TCFH (193 mg, 0.691 mmol) and NMI (113 mg, 1.3 mmol) in ACN (5 mL) was added N-(3-amino-5-chlorophenyl)methanesulfonamide (111 mg, 0.507 mmol). Then the mixture was stirred for 2 h at room temperature. The mixture was concentrated and purified by reverse phase flash chromatography eluting with ACN/H$_2$O (5-95%, acidic system) to afford ethyl 4-[(3-chloro-5-methanesulfonamidophenyl)carbamoyl]-1-(pyridin-2-yl)-1H-pyrrole-2-carboxylate (130 mg, 0.280 mmol) as a yellow solid. LCMS (ESI) [M+H]$^+$: 463

Step 3: To a stirred solution of ethyl 4-[(3-chloro-5-methanesulfonamidophenyl)carbamoyl]-1-(pyridin-2-yl)-1H-pyrrole-2-carboxylate (130 mg, 0.280 mmol) in EtOH (3 mL) and H$_2$O (3 mL) was added LiOH (66.8 mg, 2.79 mmol). Then the mixture was stirred for 2 h at room temperature. The mixture was acidified to pH 5 with citric acid. The precipitated solids were collected by filtration and washed with water. The resulting solid was dried under vacuum to afford 4-[(3-chloro-5-methanesulfonamidophenyl)carbamoyl]-1-(pyridin-2-yl)-1H-pyrrole-2-carboxylic acid (90.0 mg, 0.206 mmol) as a yellow solid. LCMS (ESI) [M+H]$^+$: 435

Step 4: To a stirred solution of 4-[(3-chloro-5-methanesulfonamidophenyl)carbamoyl]-1-(pyridin-2-yl)-1H-pyrrole-2-carboxylic acid (90 mg, 0.206 mmol), TCFH (86.6 mg, 0.309 mmol) and NMI (50.7 mg, 0.618 mmol) in ACN (5 mL) was added tert-butyl piperazine-1-carboxylate (42.0 mg, 0.226 mmol). Then the mixture was stirred for 1 h at room temperature. The mixture was concentrated and purified by reverse phase flash chromatography eluting with ACN/H$_2$O (5-95%, acidic system) to afford tert-butyl 4-{4-[(3-chloro-5-methanesulfonamidophenyl) carbamoyl]-1-(pyridin-2-yl)-1H-pyrrole-2-carbonyl}piperazine-1-carboxylate (80.0 mg, 0.132 mmol) as a yellow solid. LCMS (ESI) [M+H]$^+$: 603

Step 5: To a stirred solution of tert-butyl 4-{4-[(3-chloro-5-methanesulfonamidophenyl)carbamoyl]-1-(pyridin-2-yl)-1H-pyrrole-2-carbonyl}piperazine-1-carboxylate (80 mg, 0.132 mmol) in HCl/dioxane (5 mL) at 0° C. for 1 h. The resulting mixture was concentrated under vacuum. The mixture was basified to pH 9 with NaOH. The mixture was concentrated and purified by reverse phase flash chromatography eluting with ACN/H$_2$O (5-95%, acidic system) to afford N-(3-chloro-5-methanesulfonamidophenyl)-5-(piperazine-1-carbonyl)-1-(pyridin-2-yl)-1H-pyrrole-3-carboxamide (19.1 mg, 0.0379 mmol) as a light yellow solid. LCMS (ESI) [M+H]$^+$: 503. $^1$H NMR (300 MHz, DMSO-d$_6$) δ 10.05 (s, 1H), 8.55-8.46 (m, 1H), 8.31-8.20 (m, 2H), 8.02 (td, J=7.8, 1.9 Hz, 1H), 7.71 (t, J=1.9 Hz, 1H), 7.63 (t, J=1.9 Hz, 1H), 7.55 (d, J=8.2 Hz, 1H), 7.48-7.38 (m, 1H), 6.99 (d, J=1.8 Hz, 1H), 6.92 (t, J=1.9 Hz, 1H), 3.44 (s, 4H), 3.07 (s, 3H), 2.67 (s, 4H), 1.24 (s, 1H).

Example 166: N2-(3-chloro-5-(methylsulfonamido)phenyl)-N4-phenylthiophene-2,4-dicarboxamide

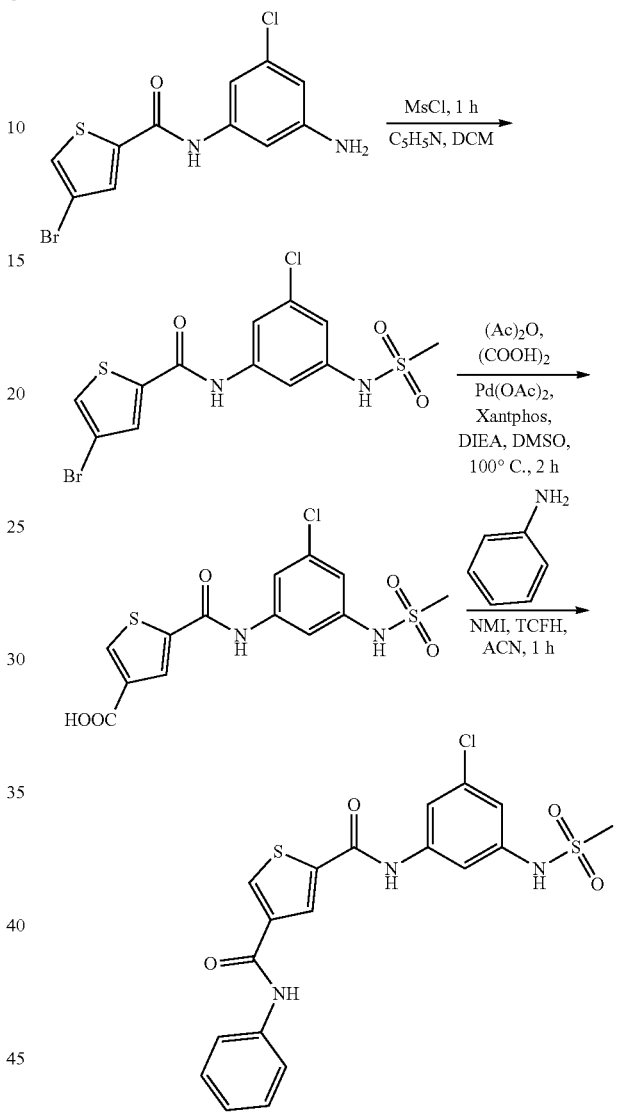

Step 1: To a stirred solution of N-(3-amino-5-chlorophenyl)-4-bromothiophene-2-carboxamide (100.0 mg, 0.49 mmol, 1.00 equiv) in a mixture of 2 mL DCM and 2 mL C$_5$H$_5$N was added MsCl (83.8 mg, 0.74 mmol, 1.50 equiv) dropwise, the resulting solution was stirred for 2 h at room temperature. Then it was quenched with the addition of 10 mL of water and extracted with 3×20 mL of ethyl acetate and the organic phase was dried over anhydrous Na$_2$SO$_4$. After filtration, the filtrate was concentrated under reduced pressure. The residue was purified onto silica gel column chromatography, eluted with 50% of ethyl acetate in petroleum ether to afford 4-bromo-N-(3-chloro-5-methanesulfonamidophenyl) thiophene-2-carboxamide (90.0 mg, 73.1%) as a white solid. LCMS (ESI) [M+H]$^+$: 408.90

Step 2: Into an 8-mL sealed tube, was placed 4-bromo-N-(3-chloro-5-methanesulfonamidophenyl) thiophene-2-carboxamide (90.0 mg, 0.40 mmol, 1.00 equiv), (Ac)$_2$O (20.0 mg, 0.08 mmol, 0.20 equiv), (COOH)$_2$ (20.0 mg, 0.08 mmol, 0.20 equiv), Pd(OAc)$_2$ (12.4 mg, 0.08 mmol, 0.20 equiv), Xantphos (16.3 mg, 0.08 mmol, 0.20 equiv), DIEA (100.0 mg, 1.20 mmol, 3.00 equiv) in 4 mL of DMSO, the mixture was stirred for 2 h at 100° C. under N$_2$ atmosphere. The mixture was purified onto silica gel column chromatography, eluted with 50% of ethyl acetate in petroleum ether to afford 5-[(3-chloro-5-methanesulfonamidophenyl) carbamoyl]thiophene-3-carboxylic acid (60.0 mg, 73.1%) as a white solid. LCMS (ESI) [M+H]$^+$: 374.98

Step 3: Into an 8-mL sealed tube, was placed 5-[(3-chloro-5-methanesulfonamidophenyl) carbamoyl]thiophene-3-carboxylic acid (60.0 mg, 0.36 mmol, 1.00 equiv) and aniline (14.9 mg, 0.36 mmol, 1.00 equiv), NMI (54 mg, 1.08 mmol, 3.00 equiv) in 4 mL of ACN, to this was added TCFH (266.7 mg, 0.7 mmol, 1.30 equiv) and the resulting mixture was stirred for 1 h at room temperature. Then it was quenched with the addition of 10 mL of water and extracted with 3×20 mL of ethyl acetate and the combined organic phase was dried over anhydrous Na$_2$SO$_4$. After filtration, the filtrate was concentrated under reduced pressure. The residue was purified onto silica gel column chromatography, eluted with 50% of ethyl acetate in petroleum ether to afford N2-(3-chloro-5-methanesulfonamidophenyl)-N4-phenylthiophene-2,4-dicarboxamide (10.8 mg, 14.8%) as a white solid. LCMS (ESI) [M+H]$^+$: 450.03. H NMR (400 MHz, DMSO-d$_6$) δ 10.64 (s, 1H), 10.25 (s, 1H), 10.10 (s, 1H), 8.66 (s, 1H), 8.53 (s, 1H), 7.74 (s, 3H), 7.68 (d, J=17.7 Hz, 1H), 7.37 (s, 2H), 7.12 (s, 1H), 6.97 (s, 1H), 3.39 (s, 1H), 3.08 (s, 3H), 2.69 (s, 1H).

Example 167: N-(3-chloro-5-(methylsulfonamido)phenyl)-1-(3-(phenoxymethyl)pyridin-2-yl)-1H-pyrazole-4-carboxamide

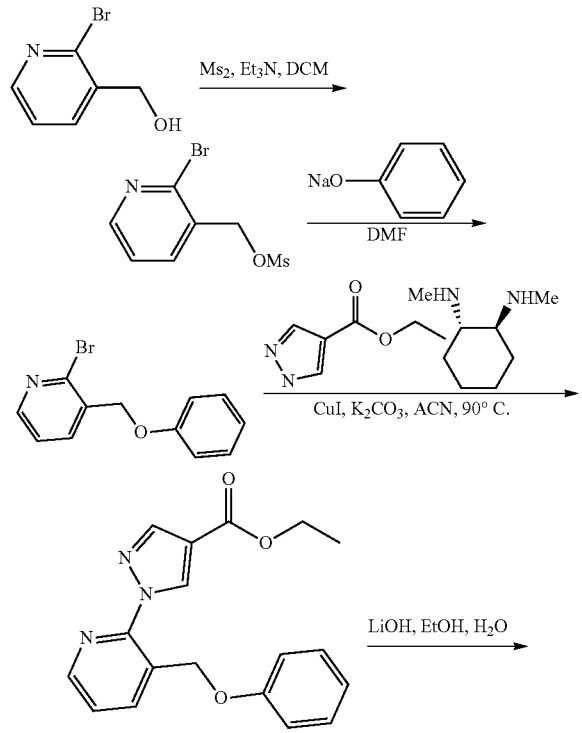

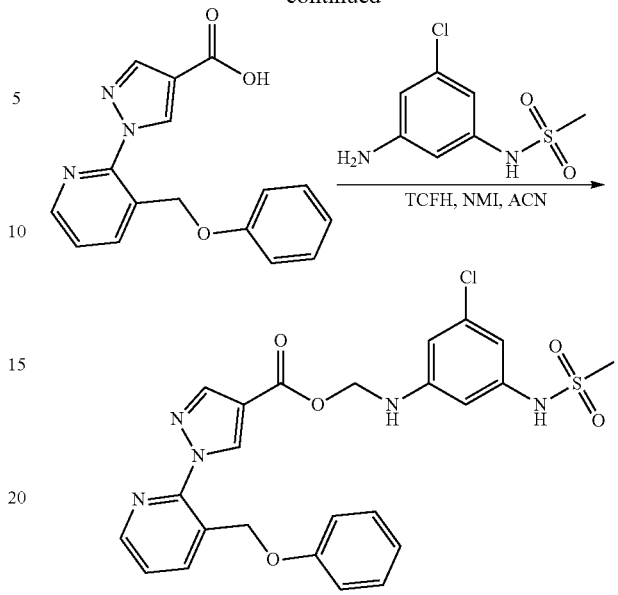

Step 1: To a stirred solution of (2-bromopyridin-3-yl)methanol (500 mg, 2.65 mmol) and Ms$_2$O (923 mg, 5.30 mmol) in DCM (20 mL) was added Et$_3$N (804 mg, 7.95 mmol) dropwise at 0° C. Then the mixture was stirred for 2 h at room temperature. The mixture was concentrated and purified by flash chromatography on silica gel eluting with EtOAc/Petroleum ether (0-100%) to afford (2-bromopyridin-3-yl)methyl methanesulfonate (544 mg, 2.04 mmol) as a yellow solid. LCMS (ESI) [M+H]$^+$: 266

Step 2: To a stirred solution of (2-bromopyridin-3-yl)methyl methanesulfonate (550 mg, 2.06 mmol) and Phenoxysodium (262 mg, 2.26 mmol) in DMF (10 mL). Then the mixture was stirred for 2 h at room temperature. The mixture was concentrated and purified by flash chromatography on silica gel eluting with EtOAc/Petroleum ether (0-100%) to afford 2-bromo-3-(phenoxymethyl)pyridine (465 mg, 1.76 mmol) as a yellow solid. LCMS (ESI) [M+H]$^+$: 264

Step 3: To a stirred solution of 2-bromo-3-(phenoxymethyl)pyridine (470 mg, 1.77 mmol), K$_2$CO$_3$ (733 mg, 5.31 mmol), CuI (67.4 mg, 0.354 mmol), ethyl 1H-pyrazole-4-carboxylate (322 mg, 2.30 mmol) and (1S,2S)-N1,N2-dimethylcyclohexane-1,2-diamine (100 mg, 0.708 mmol) in ACN (5 mL). Then the mixture was stirred for 2 h at 90° C. The mixture was concentrated and purified by reverse phase flash chromatography eluting with ACN/H$_2$O (5-95%, acidic system) to afford ethyl 1-[3-(phenoxymethyl) pyridin-2-yl]-1H-pyrazole-4-carboxylate (356 mg, 1.10 mmol) as a yellow solid. LCMS (ESI) [M+H]$^+$: 324

Step 4: To a stirred solution of ethyl 1-[3-(phenoxymethyl)pyridin-2-yl]-1H-pyrazole-4-carboxylate (360 mg, 1.11 mmol) in EtOH (5 mL) and H$_2$O (5 mL) was added LiOH (265 mg, 11.1 mmol). Then the mixture was stirred for 2 h at room temperature. The mixture was acidified to pH 5 with citric acid. The precipitated solids were collected by filtration and washed with water. The resulting solid was dried under vacuum to afford 1-[3-(phenoxymethyl)pyridin-2-yl]-1H-pyrazole-4-carboxylic acid (257 mg, 0.871 mmol) as a yellow solid. LCMS (ESI) [M+H]$^+$: 296

Step 5: To a stirred solution of 1-[3-(phenoxymethyl)pyridin-2-yl]-1H-pyrazole-4-carboxylic acid (170 mg, 0.575 mmol), TCFH (209 mg, 0.747 mmol) and NMI (141 mg, 1.72 mmol) in ACN (5 mL) was added N-(3-amino-5-chlorophenyl) methanesulfonamide (139 mg, 0.632 mmol). Then the mixture was stirred for 1 h at room temperature. The mixture was concentrated and purified by reverse phase flash chromatography eluting with ACN/H₂O (5-95%, acidic system) to afford N-(3-chloro-5-methanesulfonamidophenyl)-1-[3-(phenoxymethyl) pyridin-2-yl]-1H-pyrazole-4-carboxamide (183.0 mg, 0.3675 mmol) as an off-white solid. LCMS (ESI) [M+H]⁺: 498. ¹H NMR (300 MHz, DMSO-d₆) δ 10.32 (s, 1H), 10.09 (s, 1H), 9.29 (s, 1H), 8.56 (dd, J=4.7, 1.7 Hz, 1H), 8.31 (s, 1H), 8.23 (dd, J=7.8, 1.7 Hz, 1H), 7.73 (t, J=1.9 Hz, 1H), 7.64 (t, J=1.9 Hz, 1H), 7.58 (dd, J=7.8, 4.7 Hz, 1H), 7.30 (dd, J=8.6, 7.3 Hz, 2H), 6.96 (ddd, J=7.0, 4.2, 2.5 Hz, 4H), 5.52 (s, 2H), 3.08 (s, 3H).

Example 168: 1-(3-(benzylamino)pyridin-2-yl)-N-(3-chloro-5-(methylsulfonamido)phenyl)-1H-pyrazole-4-carboxamide

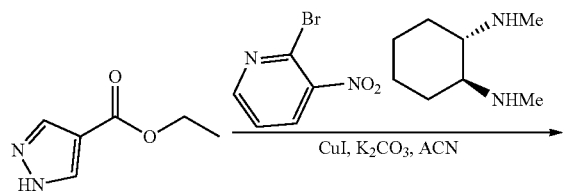

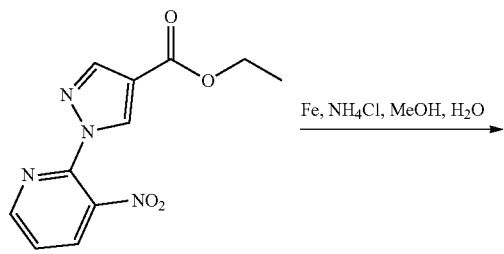

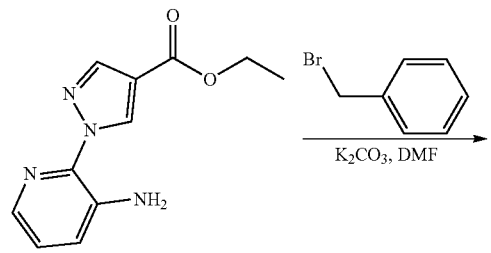

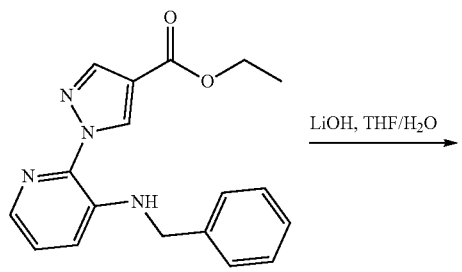

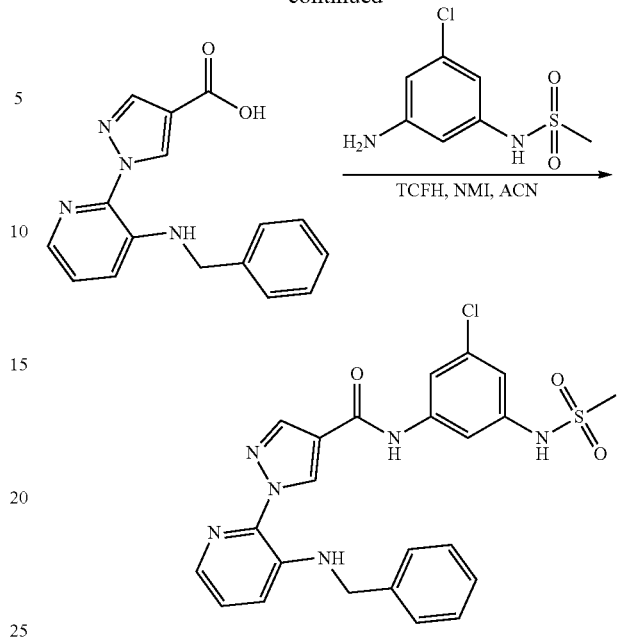

Step 1: To a stirred solution of ethyl 1H-pyrazole-4-carboxylate (200 mg, 1.42 mmol), 2-bromo-3-nitropyridine (288 mg, 1.42 mmol), (1S,2S)-N1, N2-dimethylcyclohexane-1,2-diamine (40.3 mg, 0.284 mmol), CuI (107 mg, 0.568 mmol) and K₂CO₃ (587 mg, 4.26 mmol) in ACN (10.00 mL). Then the mixture was stirred for 4 h at 90° C. under N₂ atmosphere. The mixture was concentrated and purified by reverse phase flash chromatography eluting with ACN/H₂O (5-95%, acidic system) to afford ethyl 1-(3-nitropyridin-2-yl)-1H-pyrazole-4-carboxylate (237 mg, 95%) as a yellow solid. LCMS (ESI) [M+H]⁺: 263 Step 2: To a solution of ethyl 1-(3-nitropyridin-2-yl)-1H-pyrazole-4-carboxylate (250 mg, 0.953 mmol) in a solution of methanol and water (15 mL) was added Fe (266 mg, 4.76 mmol) and NH₄Cl (505 mg, 9.53 mmol). The resulting mixture was stirred for 2 hours at 80° C. under N₂ atmosphere. The resulting mixture was filtered. The filtrate was concentrated under reduced pressure to give the crude product. The mixture was concentrated and purified by flash chromatography on silica gel eluting with EtOAc/Petroleum ether (0-100%) to afford ethyl 1-(3-aminopyridin-2-yl)-1H-pyrazole-4-carboxylate (209 mg, 90%) as a yellow solid. LCMS (ESI) [M+H]⁺: 233

Step 3: To a stirred solution of ethyl 1-(3-aminopyridin-2-yl)-1H-pyrazole-4-carboxylate (220 mg, 0.947 mmol), (bromomethyl)benzene (161 mg, 0.947 mmol), K₂CO₃ (130 mg, 0.947 mmol) in DMF (10.00 mL). Then the mixture was stirred for 4 h at room temperature. The mixture was concentrated and purified by reverse phase flash chromatography eluting with ACN/H₂O (5-95%, acidic system) to afford ethyl 1-[3-(benzylamino)pyridin-2-yl]-1H-pyrazole-4-carboxylate (142 mg, 95%) as a yellow solid. LCMS (ESI) [M+H]⁺: 323

Step 4: To a stirred solution of ethyl 1-[3-(benzylamino) pyridin-2-yl]-1H-pyrazole-4-carboxylate (150 mg, 0.465 mmol) and LiOH (10 mg, 2.5 mmol) in THF (10.00 mL) was added H₂O (2.00 mL). Then the mixture was stirred for 2 h at room temperature. The mixture was acidified to pH 5 with citric acid. The precipitated solids were collected by filtration and washed with water. The resulting solid was dried under vacuum to afford 1-[3-(benzylamino) pyridin-2-yl]-

1H-pyrazole-4-carboxylic acid (95.0 mg, 95%) as a yellow solid. LCMS (ESI) [M+H]+: 295

Step 5: To a stirred solution of 1-[3-(benzylamino)pyridin-2-yl]-1H-pyrazole-4-carboxylic acid (100 mg, 0.339 mmol), TCFH (142 mg, 0.508 mmol) and NMI (82.8 mg, 1.01 mmol) in ACN (5.00 mL) was added N-(3-amino-5-chlorophenyl)methanesulfonamide (74.8 mg, 0.339 mmol). Then the mixture was stirred for 4 h at room temperature. The mixture was concentrated and purified by reverse phase flash chromatography eluting with ACN/H$_2$O (5-95%, acidic system) to afford 1-[3-(benzylamino)pyridin-2-yl]-N-(3-chloro-5-methanesulfonamidophenyl)-1H-pyrazole-4-carboxamide (38.5 mg, 98.283%) as a white solid. LCMS (ESI) [M+H]+: 498. $^1$H NMR (300 MHz, DMSO-d$_6$) δ 10.33 (s, 1H), 10.08 (s, 1H), 9.37 (d, J=0.9 Hz, 1H), 8.33 (d, J=0.8 Hz, 1H), 7.95 (t, J=6.0 Hz, 1H), 7.82-7.70 (m, 2H), 7.65 (t, J=1.9 Hz, 1H), 7.43-7.31 (m, 4H), 7.31-7.17 (m, 3H), 6.95 (t, J=1.9 Hz, 1H), 4.53 (d, J=5.9 Hz, 2H), 3.08 (s, 3H).

Example 169: N-(3-chloro-5-(methylsulfonamido)phenyl)-5-(hydroxymethyl)-1-(pyridin-2-yl)-1H-pyrrole-3-carboxamide

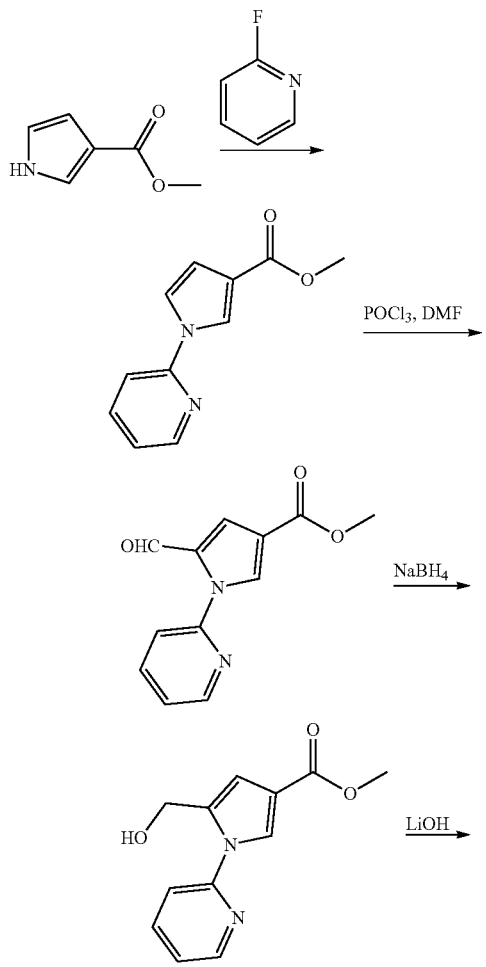

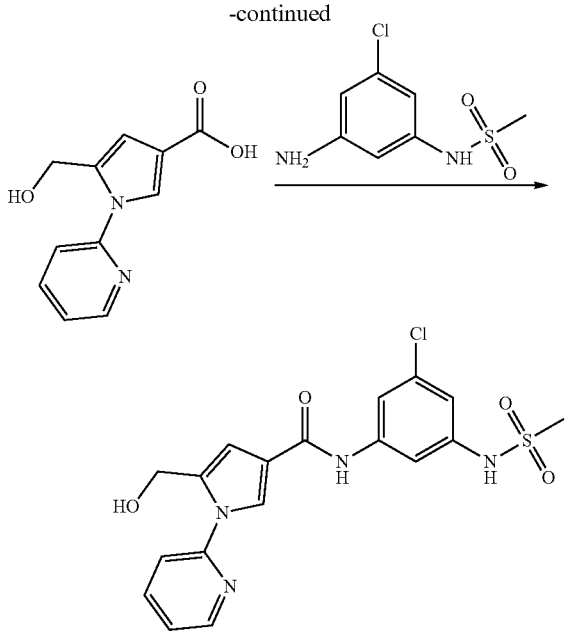

Step 1: To solution of methyl 1H-pyrrole-3carboxylate (1.0 g, 7.99 mmol) and Cs$_2$CO$_3$ (3.87 g, 11.9 mmol) in DMF (10 mL) was added 2-fluoropyridine (1.93 g, 19.9 mmol). The mixture was stirred at 100° C. for 2 h. The mixture was cooled to 25° C. and poured into water (40 mL), and was extracted with EtOAc (30 mL*3). The combined organic layers were washed with brine (20 mL*3), dried over Na$_2$SO$_4$. And the filtrate was concentrated in vacuo to give residue. The residue was purified by column chromatography on silica gel using petroleum ether/ethylacetate (100:1 to 3:1) as eluent. methyl 1-(pyridin-2-yl)-1H-pyrrole-3-carboxylate (1.57 g, 7.76 mmol, 97.5% yield) was obtained as white solid. $^1$H NMR (400 MHz, CHLOROFORM-d) δ=8.36-8.69 (m, 1H) 8.07-8.25 (m, 1H) 7.82 (ddd, J=8.4, 7.6, 2.0 Hz, 1H) 7.51 (dd, J=3.2, 2.4 Hz, 1H) 7.39 (d, J=8.4 Hz, 1H) 7.22 (ddd, J=7.6, 4.8, 0.8 Hz, 1H) 6.78 (dd, J=3.2, 1.6 Hz, 1H) 3.87 (s, 3H)

Step 2: The Vilsmeier reagent was prepared by adding POCl$_3$ (1.13 g, 7.4 mmol) dropwise to ice cold dry DMF (4 mL) under stirring. The mixture was then stirred for 15 min at 0° C. To the above Vilsmeier reagent was added methyl 1-(pyridin-2-yl)-1H-pyrrole-3-carboxylate (300 mg, 1.48 mmol) as a solution in DCE (15 mL). Then the mixture was allowed to warm to 100° C. and was stirred for 1.0 h. The reaction mixture was poured into saturated sodium chloride aqueous (30 mL). The mixture was extracted with dichloromethane (3×30 mL), the combined organic phase was washed with water (3×20 mL), dried over Na$_2$SO$_4$, filtered, and concentrated in vacuo. The crude product was purified by flash chromatography (silica gel, PE/EA=30:1 to 4:1) to give desired product. methyl 5-formyl-1-(pyridin-2-yl)-1H-pyrrole-3-carboxylate (400 mg, 0.98 mmol, 24.5% yield) was obtained as yellow solid. $^1$H NMR (400 MHz, DMSO-d6) δ=9.80 (s, 1H), 8.64-8.53 (m, 1H), 8.20 (d, J=1.6 Hz, 1H), 8.05 (dt, J=1.6, 8.0 Hz, 1H), 7.75 (d, J=8.0 Hz, 1H), 7.60-7.43 (m, 2H), 3.80 (s, 3H).

Step 3: To a solution of methyl 5-formyl-1-(pyridin-2-yl)-1H-pyrrole-3-carboxylate (400 mg, 1.73 mmol) in MeOH (10 mL) was added NaBH$_4$ (196 mg, 5.19 mmol) at 0° C. slowly. The mixture was stirred at 25° C. for 1 h. The reaction mixture was poured into saturated NH$_4$Cl aqueous (30 mL) and stirred at 25° C. for 0.5 h. The mixture was extracted with EA (3×30 mL), the combined organic phase was washed with brine (2×20 mL), dried over Na$_2$SO$_4$, filtered, and concentrated in vacuo to give a crude. The crude was purified by silica gel column chromatography (Petroleum ether/Ethyl acetate=5/1). methyl 5-(hydroxymethyl)-1-(pyridin-2-yl)-1H-pyrrole-3-carboxylate (270 mg, 1.16 mmol, 67.3% yield) was obtained as white solid. $^1$H NMR (400 MHz, CHLOROFORM-d) δ=8.58-8.48 (m, 1H), 8.04-7.91 (m, 1H), 7.74 (d, J=1.6 Hz, 1H), 7.47 (d, J=8.0 Hz, 1H), 7.39-7.31 (m, 1H), 6.72 (d, J=1.6 Hz, 1H), 4.54 (s, 2H), 3.85 (s, 3H).

Step 4: To a solution of methyl 5-(hydroxymethyl)-1-(pyridin-2-yl)-1H-pyrrole-3-carboxylate (270 mg, 1.16 mmol) in THF (5 mL) and MeOH (5 mL) was added a solution of LiOH·H$_2$O in water (5 mL). The mixture was stirred at 60° C. for 15 h. The mixture was cooled to 25° C., the pH value of the mixture was adjusted to 3-4 by 2 N HCl. The mixture was extracted with EtOAc (30 mL*3). The combined organic layers were washed with brine (10 mL*2), dried over Na$_2$SO$_4$. And the filtrate was concentrated in vacuo to give a crude. 5-(hydroxymethyl)-1-(pyridin-2-yl)-1H-pyrrole-3-carboxylic acid (230 mg, 1.05 mmol, 90.9% yield) was obtained as white solid. LCMS: MS (ESI) Retention time: 0.508 min, (M−17)+=201.2. $^1$H NMR (400 MHz, DMSO-d6) δ=12.05 (br s, 1H), 8.53 (dd, J=1.2, 4.8 Hz, 1H), 8.07-7.95 (m, 1H), 7.89-7.72 (m, 2H), 7.46-7.37 (m, 1H), 6.55 (d, J=2.0 Hz, 1H), 5.22 (t, J=5.6 Hz, 1H), 4.55 (d, J=5.6 Hz, 2H)

Step 5: To a solution of 5-(hydroxymethyl)-1-(pyridin-2-yl)-1H-pyrrole-3-carboxylic acid (80 mg, 0.3666 mmol) and N-(3-amino-5-chlorophenyl)methanesulfonamide (88.9 mg, 403 μmol) in Py (2 mL) was added EDCI (140 mg, 733 μmol). The mixture was stirred at 25° C. for 3 h. The mixture was poured into water (20 mL) and extracted with EA (25 mL*3). The combined organic layers were washed with 0.5 N HCl (15 mL*2), brine (15 mL*2) and dried over Na$_2$SO$_4$. The mixture was filtered, and the filtrate was concentrated in vacuo to give residue. The residue was purified by prep-HPLC and lyophilized. N-(3-chloro-5-(methylsulfonamido)phenyl)-5-(hydroxymethyl)-1-(pyridin-2-yl)-1H-pyrrole-3-carboxamide (95.7 mg, 0.226 mmol, 99.4 purity, 61.7% yield) was obtained as white solid. LCMS: MS (ESI) Retention time: 0.683 min, (M−1)−=419.0. $^1$H NMR (400 MHz, DMSO-d6) δ=9.95 (s, 1H), 8.69-8.49 (m, 1H), 8.18-8.14 (m, 1H), 8.11-8.00 (m, 1H), 7.84 (d, J=8.4 Hz, 1H), 7.77-7.70 (m, 1H), 7.65 (s, 1H), 7.51-7.41 (m, 1H), 6.91 (t, J=1.6 Hz, 1H), 6.83 (d, J=1.6 Hz, 1H), 5.32 (br t, J=5.6 Hz, 1H), 4.60 (br d, J=4.8 Hz, 2H), 3.06 (s, 3H)

Example 170: N-(3-chloro-5-(methylsulfonamido)phenyl)-5-methyl-1-(pyridin-2-yl)-1H-pyrrole-3-carboxamide

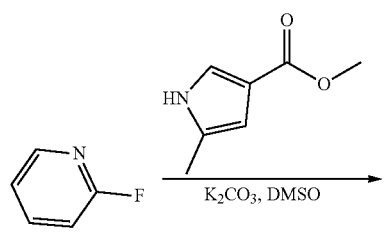

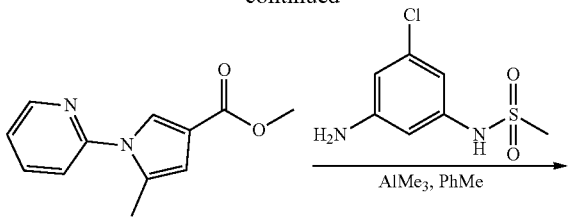

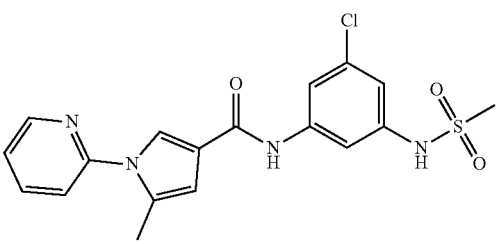

Step 1: A solution of 2-fluoropyridine (300 mg, 3.090 mmol, 1 equiv), methyl 5-methyl-1H-pyrrole-3-carboxylate (430 mg, 3.090 mmol, 1 equiv) and K$_2$CO$_3$ (1279 mg, 9.270 mmol, 3 equiv) in DMSO (5 ml) was stirred for 1 h at 60° C. The mixture was allowed to cool down to room temperature. The reaction mixture was diluted with water (50 mL). The resulting mixture was extracted with EtOAc (3*50 mL). The combined organic layers were washed with EtOAc (100 mL), dried over anhydrous Na$_2$SO$_4$. After filtration, the filtrate was concentrated under reduced pressure. The residue was purified by silica gel column chromatography, eluted with Petroleum ether/EtOAc (1:1) to afford methyl 5-methyl-1-(pyridin-2-yl)pyrrole-3-carboxylate (280 mg, 41.91%) as a white solid. LCMS (ESI) [M+H]$^+$: 217.09.

Step 2: To a stirred solution of methyl 5-methyl-1-(pyridin-2-yl)pyrrole-3-carboxylate (50 m g, 0.231 mmol, 1 equiv) and N-(3-amino-5-chlorophenyl)methanesulfonamide (51 mg, 0.231 mmol, 1 equiv) in PhMe (2 ml) was added Al(Me)$_3$ (0.6 ml) at 0° C. The resulting mixture was stirred for 1 h at 80° C. The mixture was allowed to cool down to room temperature. The reaction was quenched by the addition of Water (2 mL) at 0'° C. The precipitated solids were collected by filtration and washed with acetonitrile (3*6 mL). The resulting mixture was concentrated under reduced pressure. The residue was purified by reverse phase flash chromatography with the following conditions:C18 column; mobile phase, MeCN in Water (0.1% FA), 1 0% to 50% gradient in 10 min; detector, UV 254 nm.35% to afford N-(3-chloro-5-methanesulfonamidophenyl)-5-methyl-1-(pyridin-2-yl)pyrrole-3-carboxamide (30.7 mg, 32.75% id) as a white solid. LCMS (ESI) [M+H]D: 405.10. $^1$H NMR (400 MHz, DMSO-d$_6$) δ 10.02 (s, 1H), 9.87 (s, 1H), 8.58 (dt, J=4.8, 1.5 Hz, 1H), 8.03 (td, J=7.8, 2.0 Hz, 2H), 7.72 (t, J=1.9 Hz, 1H), 7.67-7.60 (m, 2H), 7.49-7.42 (m, 1H), 6.89 (t, J=2.0 Hz, 1H), 6.58 (dd, J=2.1, 1.1 Hz, 1H), 3.06 (s, 3H), 2.39 (d, J=1.0 Hz, 3H).

Examples 425-426

The compounds listed in the following table were prepared using a procedure similar to that described for example 170:

| Structure | Example No. | MS (ESI) [M + H]+ | 1H NMR |
|---|---|---|---|
| 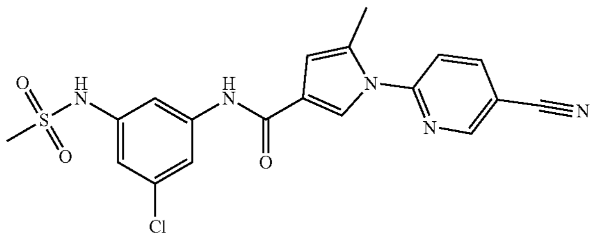 [SMILES: Cc1cc(C(=O)Nc2cc(Cl)cc(NS(C)(=O)=O)c2)cn1-c1ccc(C#N)cn1] | 425 | 429.95 | 1H NMR (400 MHZ, DMSO-d6) δ 10.02 (s, 1H), 9.93 (s, 1H), 9.04 (d, J = 2.2 Hz, 1H), 8.52 (dd, J = 8.6, 2.3 Hz, 1H), 8.14 (d, J = 2.0 Hz, 1H), 7.87 (d, J = 8.5 Hz, 1H), 7.67 (dt, J = 29.8, 1.9 Hz, 2H), 6.91 (t, J = 2.0 Hz, 1H), 6.64 (d, J = 1.8 Hz, 1H), 3.06 (s, 3H), 2.46 (s, 3H). |
| 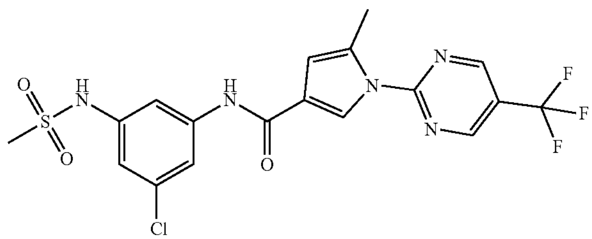 [SMILES: Cc1cc(C(=O)Nc2cc(Cl)cc(NS(C)(=O)=O)c2)cn1-c1ncc(C(F)(F)F)cn1] | 426 | 473.95 | 1H NMR (400 MHZ, DMSO-d6) δ 10.07 (d, J = 37.7 Hz, 2H), 9.32 (d, J = 0.9 Hz, 2H), 8.57 (d, J = 2.1 Hz, 1H), 7.73 (t, J = 1.9 Hz, 1H), 7.66 (t, J = 1.9 Hz, 1H), 6.91 (t, J = 2.0 Hz, 1H), 6.63 (t, J = 1.7 Hz, 1H), 3.06 (s, 3H), 2.63 (d, J = 1.0 Hz, 3H). |

Example 171: N-(3-chloro-5-(methylsulfonamido)phenyl)-5-(5-fluoropyrimidin-2-yl)-1-methyl-1H-pyrrole-3-carboxamide

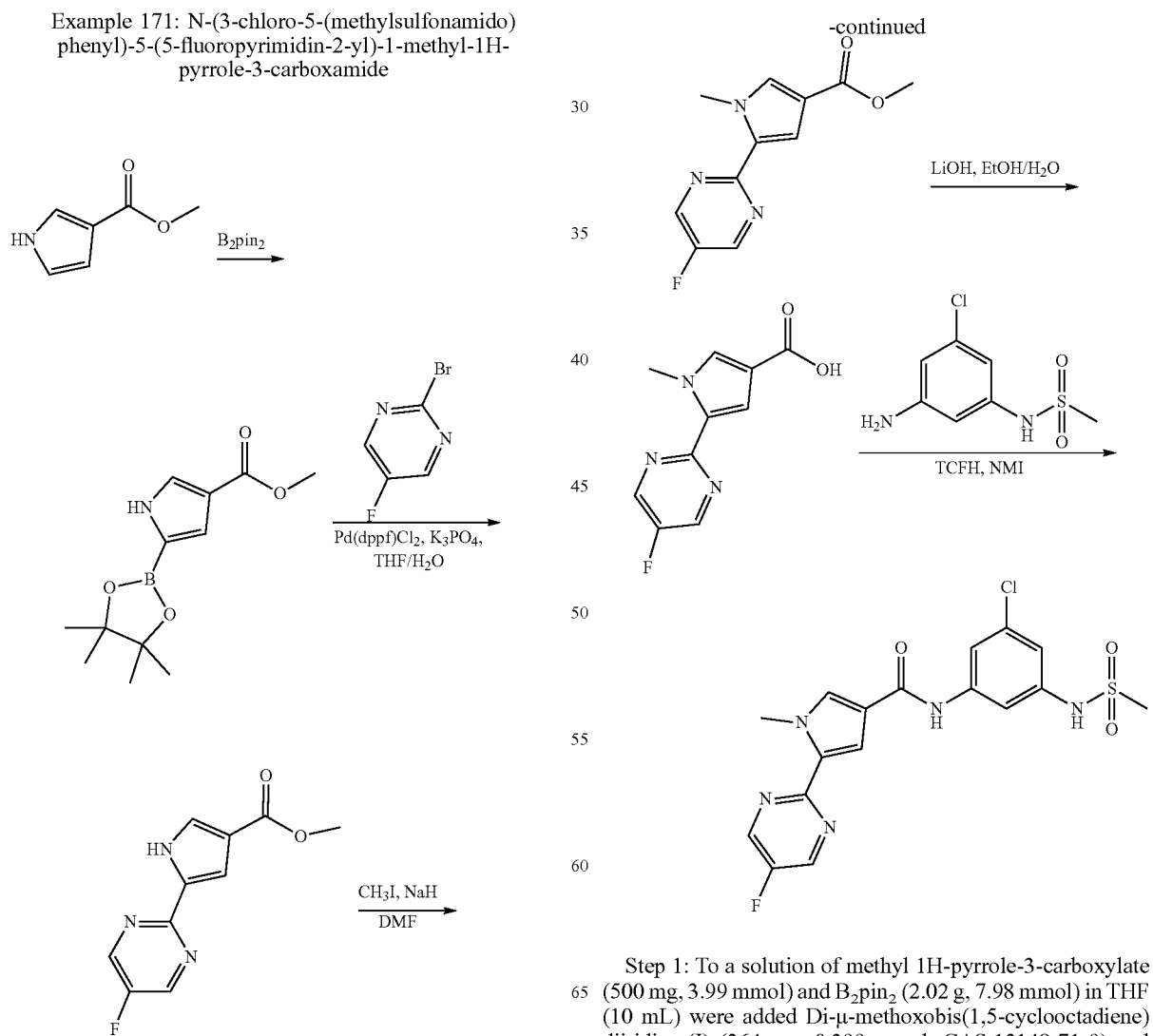

Step 1: To a solution of methyl 1H-pyrrole-3-carboxylate (500 mg, 3.99 mmol) and B₂pin₂ (2.02 g, 7.98 mmol) in THF (10 mL) were added Di-μ-methoxobis(1,5-cyclooctadiene)diiridium(I) (264 mg, 0.399 mmol, CAS:12148-71-9) and 4,4'-Di-tert-butyl-2,2'-bipyridine (107 mg, 0.399 mmol). After stirring for 2 h at 100° C. under a nitrogen atmosphere, the resulting mixture was concentrated under reduced pressure. The residue was purified by silica gel column chromatography, eluted with Petroleum ether/EtOAc (1/1) to afford methyl 5-(4,4,5,5-tetramethyl-1,3,2-dioxaborolan-2-yl)-1H-pyrrole-3-carboxylate (350 mg, 1.39 mmol) as a brown solid. LCMS (ESI) [M+H]$^+$:252.

Step 2: A mixture of methyl 5-(4,4,5,5-tetramethyl-1,3,2-dioxaborolan-2-yl)-1H-pyrrole-3-carboxylate (200 mg, 0.796 mmol), 2-bromo-5-fluoropyrimidine (169 mg, 0.955 mmol), Pd(dp pf)Cl$_2$ (65.0 mg, 0.0796 mmol) and K$_3$PO$_4$ (504 mg, 2.38 mmol) in THE (2 mL) and H$_2$O (0.2 mL) was stirred for 2 hours at 80° C. under N$_2$ atmosphere. The reaction mixture was extracted with ethyl acetate. The organic phase was concentrated under reduced pressure. The residue was purified by flash chromatography on silica gel eluting with 30% f ethyl acetate in petroleum ether to afford methyl 5-(5-fluoropyrimidin-2-yl)-1H-pyrrole-3-carboxylate (135 mg, 76.7%) as a white solid. LCMS [M+H]$^+$: 222

Step 3: To a stirred solution of methyl 5-(5-fluoropyrimidin-2-yl)-1H-pyrrole-3-carboxylate (135 mg, 0.610 mmol), CH$_3$I (129 mg, 0.915 mmol) in DMF (1 ml) was added NaH (73.2 mg, 1.83 mmol) at 0° C. The resulting mixture was stirred for 2 hours at room temperature. Then it was quenched with water, the mixture was concentrated and the residue was purified by reverse phase flash chromatography eluting with 60% f acetonitrile in water (0.1% NH$_4$H CO$_3$) to afford methyl 5-(5-fluoropyrimidin-2-yl)-1-methyl-1H-pyrrole-3-carboxylate (60.0 mg, 41.9%) as a white solid. LCMS [M+H]$^+$: 236

Step 4: To a stirred solution of methyl 5-(5-fluoropyrimidin-2-yl)-1-methyl-1H-pyrrole-3-carboxylate (60 mg, 0.255 mmol) in EtOH (1 mL) and water (1 mL) was added LiOH (53.3 mg, 1.27 mmol). The resulting mixture was stirred for 2 hours at room temperature. Then it was concentrated, and the pH value of the residue solution was adjusted to 3 with 1M HCl (aq). The product was precipitated from the solution. The mixture was filtered and the filter cake was washed with water (2 mL) to afford 5-(5-fluoropyrimidin-2-yl)-1-methyl-1H-pyrrole-3-carb oxylic acid (35.0 mg, 62.3%) as a white solid. LCMS [M+H]$^+$: 222

Step 5: To a mixture of 5-(5-fluoropyrimidin-2-yl)-1-methyl-1H-pyrrole-3-carboxylic acid (3 5 mg, 0.158 mmol) and N-(3-amino-5-chlorophenyl)methanesulfonamide (41.7 mg, 0.189 m mol) in ACN (0.5 mL) was added TCFH (66.3 mg, 0.237 mmol) and NMI (38.8 mg, 0.474 m mol) at room temperature for 2 hours. Then it was concentrated, the residue was purified by reverse phase flash chromatography eluting with 50% f acetonitrile in water (0.1% FA) to afford N-(3-chloro-5-(methylsulfonamido)phenyl)-5-(5-fluoropyrimidin-2-yl)-1-methyl-1H-pyrrole-3-carboxamide (11.8 mg, 17.6%) as a white solid. LCMS [M+H]$^+$: 424. $^1$H NMR (300 M Hz, DMSO-d$_6$) δ 10.02 (s, 1H), 8.98 (d, J=0.8 Hz, 2H), 7.80 (t, J=1.7 Hz, 2H), 7.77-7.69 (m, 2H), 6.97 (t, J=1.9 Hz, 1H), 4.14 (s, 3H), 3.13 (s, 3H).

Example 172

The compounds listed in the following table were prepared using a procedure similar to that described for example 171:

| Structure | Example No. | MS (ESI) [M + H]$^+$ | $^1$H NMR |
|---|---|---|---|
| ![structure] | 172 | 450 | $^1$H NMR (400 MHZ, DMSO-d$_6$) δ 9.90 (s, 1H), 8.56 (s, 2H), 7.69 (d, J = 26.9 Hz, 3H), 7.55 (d, J = 2.1 Hz, 1H), 6.89 (s, 1H), 4.22 (q, J = 6.9 Hz, 2H), 4.05 (s, 3H), 3.06 (s, 3H), 1.38 (t, J = 6.9 Hz, 3H). |

Example 173: N-(3-chloro-5-(ethylsulfonamido)phenyl)-1-methyl-5-(pyrimidin-2-yl)-1H-pyrrole-3-carboxamide

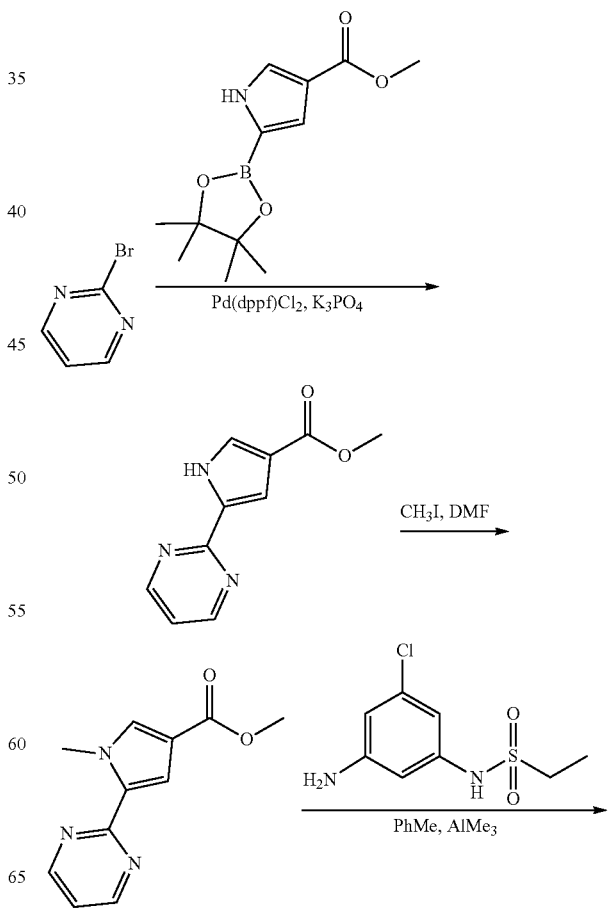

-continued

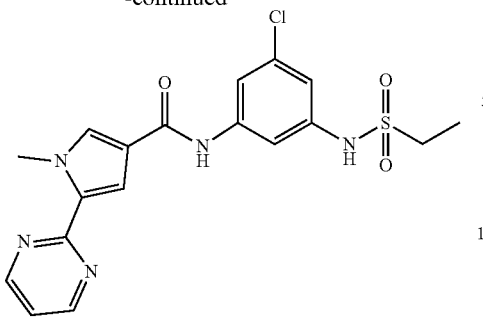

Step 1: A solution of 2-bromopyrimidine (500 mg, 3.145 mmol, 1 equiv), methyl 5-(4,4,5,5-tetramethyl-1,3,2-dioxaborolan-2-yl)-1H-pyrrole-3-carboxylate (790 mg, 3.145 nmol, 1 equiv), Pd(dppf)Cl$_2$ (257 mg, 0.315 mmol, 0.1 equiv) and K$_3$PO$_4$ (2003 mg, 9.435 mmol, 3 equiv) in 1,4-dioxane (10 ml) and H$_2$O (2 ml) was stirred for 2 h at 80° C. under nitrogen atmosphere. The mixture was allowed to cool down to room temperature. The reaction mixture was diluted with water (50 mL). The resulting mixture was extracted with EtOAc (3*50 mL). The combined organic layers were washed with (100 mL), dried over anhydrous Na$_2$SO$_4$. After filtration, the filtrate was concentrated under reduced pressure. The residue was purified by silicagel column chromatography, eluted with Petroleum ether/EtOAc (1:1) to afford methyl 5-(pyrimidin-2-yl)-1H-pyrrole-3-carboxylate (480 mg, 75.11%) as a white solid. LCMS (ESI) [M+H]$^+$: 204.07.

Step 2: To a stirred solution of methyl 5-(pyrimidin-2-yl)-1H-pyrrole-3-carboxylate (460 mg, 2.264 mmol, 1 equiv) and NaH (163 mg, 6.792 mmol, 3 equiv) in DMF (5 ml) was added CH$_3$I (643 mg, 4.528 mmol, 2 equiv) dropwise 0° C. The reaction was quenched by the addition of Water (2 mL) at 0° C. The resulting mixture was extracted with EtOAc (3*50 mL). The combined organic layers were washed with water (100 mL), dried over anhydrous Na$_2$SO$_4$. After filtration, the filtrate was concentrated under reduced pressure. The residue was purified by silica gel column chromatography, eluted with Petroleum ether/EtOAc (3:1) to afford methyl 1-methyl-5-(pyrimidin-2-yl)pyrrole-3-carboxylate (390 mg, 79.31%) as a white solid. LCM S (ESI) [M+H]$^+$: 218.09.

Step 3: To a stirred solution of methyl 1-methyl-5-(pyrimidin-2-yl)pyrrole-3-carboxylate (80 mg, 0.368 mmol, 1 equiv) and N-(3-amino-5-chlorophenyl)ethanesulfonamide (87 mg, 0.368 mmol, 1 equiv) in PhMe (2 ml) were added Al(Me)$_3$ at 0° C. The resulting mixture was stirred for additional 1.5 h at 80° C. The mixture was allowed to cool down to room temperature. The reaction was quenched by the addition of Water (1.5 mL) at 0° C. The resulting mixture w as concentrated under reduced pressure. The residue was purified by reverse phase flash chromatography with the following conditions: column, C18 silica gel; mobile phase, MeCN in Water (0.1% FA), 10% to 80% gradient in 10 min; detector, UV 254 nm. 45% to afford N-(3-chloro-5-ethanesulfonamidophenyl)-1-methyl-5-(pyrimidin-2-yl)pyrrole-3-carboxamide (21.7 mg, 13.90%) as a white solid. LCMS (ESI) [M+H]$^+$: 419.95. $^1$H NMR (400 MHz, DMSO-d$_6$) δ 9.95-10.04 (dd, 2H), 8.81 (dd, J=4.8, 1.0 Hz, 2H), 7.67-7.73 (m, J=1.5 Hz, 4H), 7.30 (td, J=4.9, 1.0 Hz, 1H), 6.90 (q, J=1.5, 1.1 Hz, 1 Hz), 4.09 (s, 311), 3.17 (q, J=7.3 Hz, 211), 1.22 (t, J=7.3 Hz, 3H).

Example 174: N-(3-chloro-5-(methylsulfonamido)phenyl)-5-(3-((5-fluoropyridin-3-yl)methoxy)pyridin-2-yl)-1-methyl-1H-pyrrole-3-carboxamide

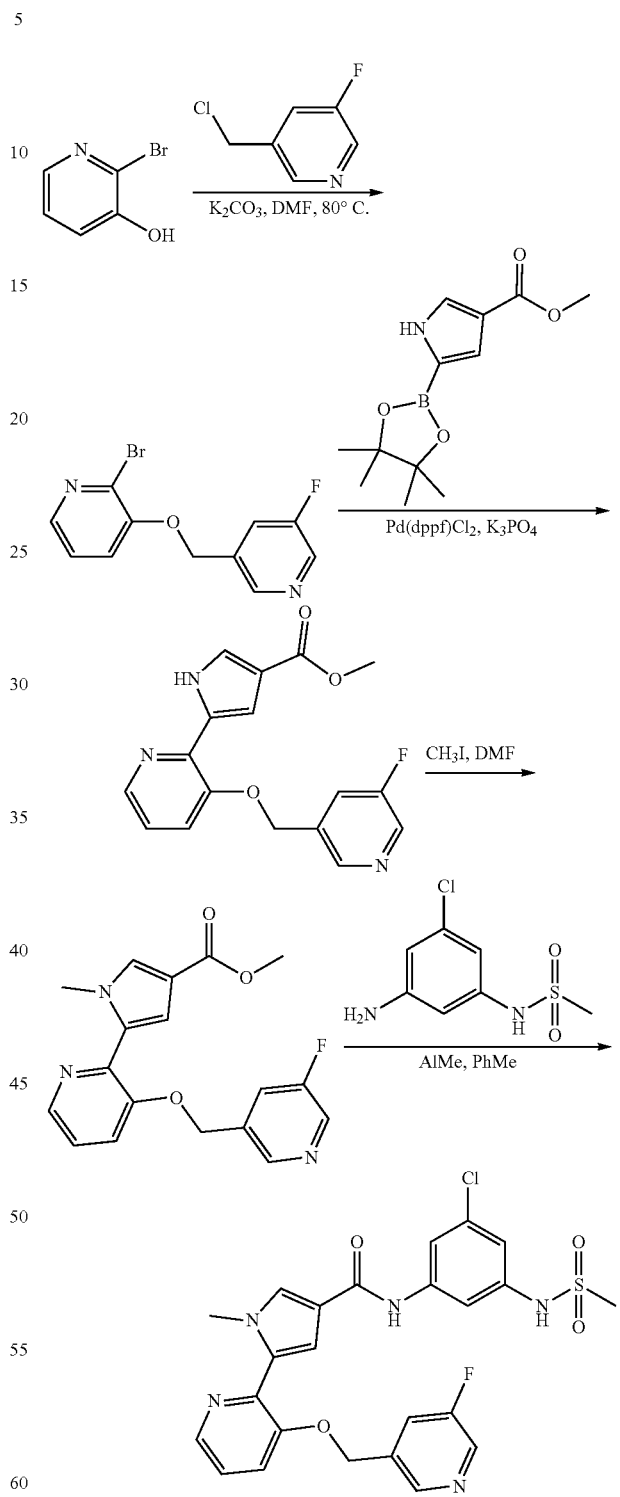

Step 1: A solution of 2-bromopyridin-3-ol (370 mg, 2.126 mmol, 1 equiv), 3-(chloromethyl)-5-fluoropyridine (310 mg, 2.126 mmol, 1 equiv) and K$_2$CO$_3$ (880 mg, 6.378 mmol, 3 equiv) in DMF (5 ml) was stirred for 2 hours at 80° C. The mixture was allowed to cool down to room temperature. The reaction mixture was diluted with water (50 mL). The resulting mixture was extracted with EtOAc (3*50 mL). The combined organic layers were washed with water (100 mL), dried over anhydrous Na₂SO₄. After filtration, the filtrate was concentrated under reduced pressure. The residue was purified by silica gel column chromatography, eluted with Petroleum ether/EtOAc (5:1) to afford 2-bromo-3-[(5-fluoropyridin-3-yl)methoxy]pyridine (380 mg, 63.12%) as a white solid. LCMS (ESI) [M+H]⁺: 283.

Step 2: A solution of 2-bromo-3-[(5-fluoropyridin-3-yl)methoxy]pyridine (360 mg, 1.272 mmol, 1 equiv), methyl 5-(4,4,5,5-tetramethyl-1,3,2-dioxaborolan-2-yl)-1H-pyrrole-3-carboxylate (319 mg, 1.272 mmol, 1 equiv), Pd(dppf)Cl₂ (104 mg, 0.127 mmol, 0.1 equiv) and K₃PO₄ (810 mg, 3.816 mmol, 3 equiv) in 1,4-dioxane (5 ml) and H₂O (1 ml) was stirred for 2 hours at 80° C. under nitrogen atmosphere. The mixture was allowed to cool down to room temperature. The reaction mixture was diluted with water (50 mL). The resulting mixture was extracted with EtOAc (3*50 mL). The combined organic layers were washed with water (100 mL), dried over anhydrous Na₂SO₄. After filtration, the filtrate was concentrated under reduced pressure. The residue was purified by silica gel column chromatography, eluted with Petroleum ether/EtOAc (1:1) to afford methyl 5-{3-[(5-fluoropyridin-3-yl)methoxy]pyridin-2-yl}-1H-pyrrole-3-carboxylate (280 mg, 67.27%) as a white solid. LCMS (ESI) [M+H]⁺: 329.

Step 3: To a stirred solution of methyl 5-{3-[(5-fluoropyridin-3-yl)methoxy]pyridin-2-yl}-1H-pyrrole-3-carboxylate (260 mg, 0.794 mmol, 1 equiv) and NaH (57 mg, 2.382 mmol, 3 equiv) in DMF (5 ml) was added CH₃I (226 mg, 1.588 mmol, 2 equiv) dropwise at 0° C. The reaction was quenched by the addition of water (2 mL) at 0° C. The reaction mixture was diluted with water (50 mL). The resulting mixture was extracted with EtOAc (3*50 mL). The combined organic layers were washed with water (100 mL), dried over anhydrous Na₂SO₄. After filtration, the filtrate was concentrated under reduced pressure. The residue was purified by silica gel column chromatography, eluted with Petroleum ether/EtOAc (1:1) to afford methyl 5-{3-[(5-fluoropyridin-3-yl)methoxy]pyridin-2-yl}-1-methylpyrrole-3-carboxylate (112 mg, 41.31%) as a white solid. LCMS (ESI) [M+H]⁺: 342.

Step 4: To a stirred solution of methyl 5-{3-[(5-fluoropyridin-3-yl)methoxy]pyridin-2-yl}-1-methylpyrrole-3-carboxylate (102 mg, 0.299 mmol, 1 equiv) and N-(3-amino-5-chlorophenyl)methanesulfonamide (66 mg, 0.299 mmol, 1 equiv) in PhMe (2 ml) was added Al(Me)₃ (0.8 ml) dropwise at room temperature. The resulting mixture was stirred for additional 1.5 hours at 80° C. The mixture was allowed to cool down to room temperature. The reaction was quenched by the addition of Water (1.5 mL) at 0° C. The resulting mixture was concentrated under reduced pressure. The crude product (50 mg) was purified by Prep-HPLC with the following conditions (Column: Sunfire prep C18 column, 30*150 mm, 5 m; Mobile Phase A: Water(0.1% FA), Mobile Phase B: ACN; Flow rate: 60 mL/min; Gradient: 33% B to 49% B in 8 min, 49% B; Wave Length: 254/220 nm; RT1(min): 7.27 to afford N-(3-chloro-5-methanesulfonamidophenyl)-5-{3-[(5-fluoropyridin-3-yl)methoxy]pyridin-2-yl}-1-methylpyrrole-3-carboxamide (23.9 mg, 15.09%) as a white solid. LCMS (ESI) [M+H]⁺: 486. ¹H NMR (300 MHz, DMSO-d6) δ 9.80 (s, 1H), 8.55 (d, J=2.5 Hz, 2H), 8.28 (dd, J=4.7, 1.3 Hz, 1H), 7.80 (dt, J=9.6, 2.3 Hz, 1H), 7.72-7.59 (m, 4H), 7.36 (dd, J=8.4, 4.7 Hz, 1H), 7.18 (d, J=1.9 Hz, 1H), 6.90 (t, J=1.9 Hz, 1H), 5.35 (s, 2H), 3.80 (s, 3H), 3.06 (s, 3H).

Example 427

The compounds listed in the following table were prepared using a procedure similar to that described for example 174:

| Structure | Eample No. | MS (ESI) [M + H]⁺ | ¹H NMR |
|---|---|---|---|
| 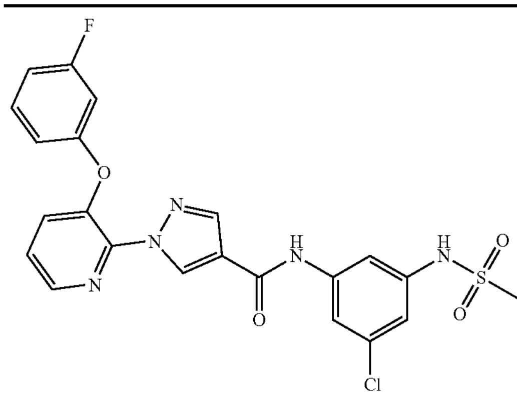 | 427 | 502 | ¹H NMR (300 MHz, DMSO-d6) δ 10.24 (s, 1H), 10.08 (s, 1H), 9.03 (s, 1H), 8.47 (dd, J = 4.6, 1.5 Hz, 1H), 8.21 (s, 1H), 7.82 (dd, J = 8.2, 1.5 Hz, 1H), 7.69 (t, J = 1.9 Hz, 1H), 7.66-7.56 (m, 2H), 7.40 (td, J = 8.2, 6.8 Hz, 1H), 7.06-6.91 (m, 3H), 6.85 (dd, J = 8.0, 2.3 Hz, 1H), 3.07 (s, 3H). |

Example 175: N-(3-chloro-5-(methylsulfonamido)phenyl)-1-(3-((5-fluoropyridin-3-yl)methoxy)pyridin-2-yl)-5-methyl-1H-pyrrole-3-carboxamide

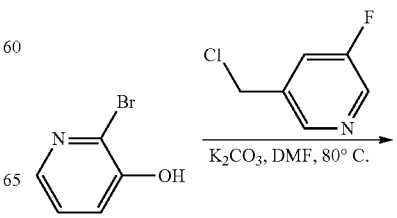

-continued

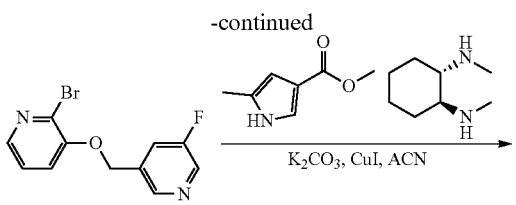

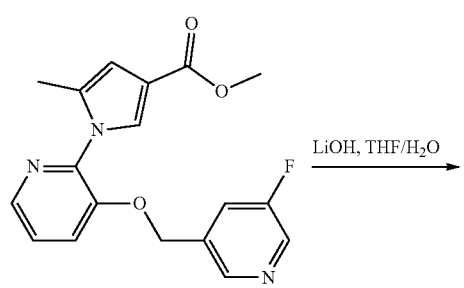

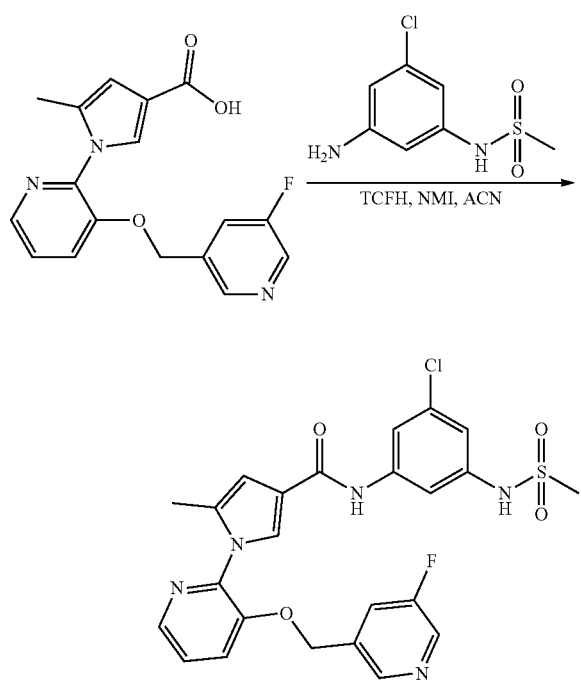

Step 1: A solution of 2-bromopyridin-3-ol (300 mg, 1.724 mmol, 1 equiv), 3-(chloromethyl)-5-fluoropyridine (251 mg, 1.724 mmol, 1 equiv) and K₂CO₃ (714 mg, 5.172 mmol, 3 equiv) in DMF (5 ml) was stirred for 1.5 hours at 80° C. The mixture was allowed to cool down to room temperature. The reaction mixture was diluted with water (50 mL). The resulting mixture was extracted with EtOAc (3*50 mL). The combined organic layers were washed with water (100 mL), dried over anhydrous Na₂SO₄. After filtration, the filtrate was concentrated under reduced pressure. The residue was purified by silica gel column chromatography, eluted with EtOAc/Petroleum ether (25%) to afford 2-bromo-3-[(5-fluoropyridin-3-yl)methoxy]pyridine (220 mg, 45.07%) as a white solid. LCMS (ESI) [M+H]⁺: 282.98.

Step 2: A solution of 2-bromo-3-[(5-fluoropyridin-3-yl)methoxy]pyridine (200 mg, 0.706 mmol, 1 equiv), methyl 5-methyl-1H-pyrrole-3-carboxylate (98 mg, 0.706 mmol, 1 equiv), (1S,2S)-N1,N2-dimethylcyclohexane-1,2-diamine (40 mg, 0.282 mmol, 0.4 equiv) and CuI (27 mg, 0.141 mmol, 0.2 equiv) in acetonitrile (5 ml) was stirred for 2 hours at 90° C. under nitrogen atmosphere. The mixture was allowed to cool down to room temperature. The resulting mixture was extracted with EtOAc (3*50 mL). The combined organic layers were washed with water (100 mL), dried over anhydrous Na₂SO₄. After filtration, the filtrate was concentrated under reduced pressure. The residue was purified by silica gel column chromatography, eluted with EtOAc/Petroleum ether (35%) to afford methyl 1-{3-[(5-fluoropyridin-3-yl)methoxy]pyridin-2-yl}-5-methylpyrrole-3-carboxylate (115 mg, 47.69%) as a white solid. LCMS (ESI) [M+H]⁺: 342.12.

Step 3: A solution of methyl 1-{3-[(5-fluoropyridin-3-yl)methoxy]pyridin-2-yl}-5-methylpyrrole-3-carboxylate (95 mg, 0.278 mmol, 1 equiv) and LiOH (20 mg, 0.834 mmol, 3 equiv) in THF (4 ml) and H₂O (1 ml) was stirred for 2 hours at room temperature. The mixture was acidified to pH 7 with HCl (aq.). The precipitated solids were collected by filtration and washed with water (50 mL). The residue was purified by silica gel column chromatography, eluted with EtOAc/Petroleum ether (75%) to afford 1-{3-[(5-fluoropyridin-3-yl)methoxy]pyridin-2-yl}-5-methylpyrrole-3-carboxylic acid (73 mg, 80.14%) as a white solid. LCMS (ESI) [M+H]⁺: 328.10.

Step 4: A solution of 1-{3-[(5-fluoropyridin-3-yl)methoxy]pyridin-2-yl}-5-methylpyrrole-3-carboxylic acid (54 mg, 0.165 mmol, 1 equiv), N-(3-amino-5-chlorophenyl)methanesulfonamide (37 mg, 0.165 mmol, 1 equiv), TCFH (69 mg, 0.247 mmol, 1.5 equiv) and NMI (68 mg, 0.825 mmol, 5 equiv) in acetonitrile (2 ml) was stirred for 2 hours at room temperature. The residue solution was purified by Prep-HPLC with the following conditions: Sunfire prep C18 column, 30*150 mm, 5 µm; Mobile Phase A: Water(0.1% FA), Mobile Phase B: ACN; Flow rate: 60 mL/min; Gradient: 31% B to 55% B in 8 min, 55% B; Wave Length: 254/220 nm; RT1(min): 7.65 to afford N-(3-chloro-5-methanesulfonamidophenyl)-1-{3-[(5-fluoropyridin-3-yl)methoxy]pyridin-2-yl}-5-methylpyrrole-3-carboxamide (23.3 mg, 26.47%) as a white solid. LCMS (ESI) [M+H]⁺: 530.25. ¹H NMR (300 MHz, DMSO-d6) δ 9.78 (s, 1H), 8.54 (d, J=2.8 Hz, 1H), 8.44 (d, J=1.8 Hz, 1H), 8.23 (dd, J=4.7, 1.3 Hz, 1H), 7.89 (dd, J=8.3, 1.4 Hz, 1H), 7.78-7.69 (m, 2H), 7.69-7.53 (m, 3H), 6.89 (t, J=2.0 Hz, 1H), 6.55 (d, J=1.7 Hz, 1H), 5.34 (s, 2H), 3.05 (s, 3H), 2.12-2.06 (m, 3H).

Examples 428-430

The compounds listed in the following table were prepared using a procedure similar to that described for example 175:

| Structure | Example No. | MS (ESI) [M + H]⁺ | ¹H NMR |
|---|---|---|---|
| 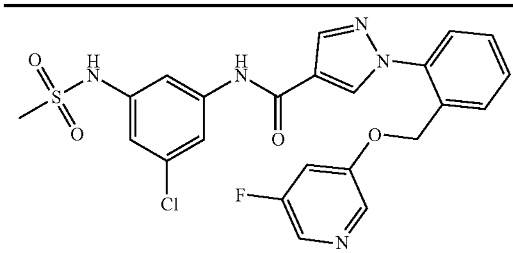 | 428 | 516 | ¹H NMR (400 MHz, DMSO-d6) δ 10.13 (s, 1H), 10.07 (s, 1H), 8.75 (d, J = 2.3 Hz, 1H), 8.27 (d, J = 2.2 Hz, 1H), 8.23-8.01 (m, 2H), 7.81-7.68 (m, 2H), 7.59 (dq, J = 8.1, 1.9 Hz, 4H), 7.41 (dt, J = 11.1, 2.4 Hz, 1H), 6.94 (t, J = 1.9 Hz, 1H), 5.27 (s, 2H), 3.07 (d, J = 2.1 Hz, 3H). |
| 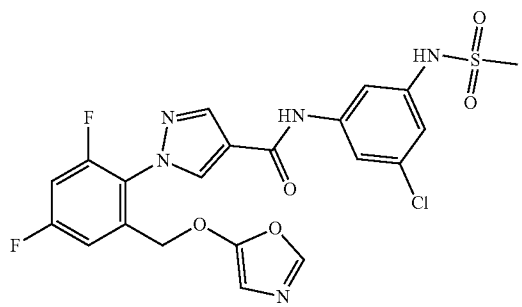 [SMILES: CS(=O)(=O)Nc1cc(Cl)cc(NC(=O)c2cnn(-c3c(F)cc(F)cc3COc3cnco3)c2)c1] | 429 | 524 | ¹H NMR (400 MHz, DMSO-d6) δ 10.13 (s, 2H), 8.50 (s, 1H), 8.39 (s, 1H), 8.26 (s, 1H), 7.66 (t, J = 1.9 Hz, 1H), 7.56 (t, J = 1.9 Hz, 1H), 7.36 (dt, J = 10.9, 2.2 Hz, 1H), 7.31 (s, 1H), 7.20 (td, J = 9.5, 2.6 Hz, 1H), 6.93 (t, J = 2.0 Hz, 1H), 5.34 (s, 2H), 3.05 (s, 3H). |
| 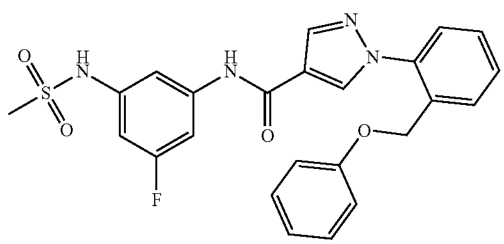 [SMILES: CS(=O)(=O)Nc1cc(F)cc(NC(=O)c2cnn(-c3ccccc3COc3ccccc3)c2)c1] | 430 | 481 | ¹H NMR (300 MHz, DMSO-d6) δ 10.18 (s, 1H), 10.09 (s, 1H), 8.84 (s, 1H), 8.30 (s, 1H), 7.68 (dd, J = 7.9, 1.6 Hz, 1H), 7.50-7.26 (m, 9H), 7.24-7.04 (m, 1H), 6.73 (dt, J = 10.4, 2.2 Hz, 1H), 5.29 (s, 2H), 3.08 (s, 3H). |

Example 176: N-(3-chloro-5-(methylsulfonamido)phenyl)-4-(2-oxopyrrolidin-1-yl)thiophene-2-carboxamide

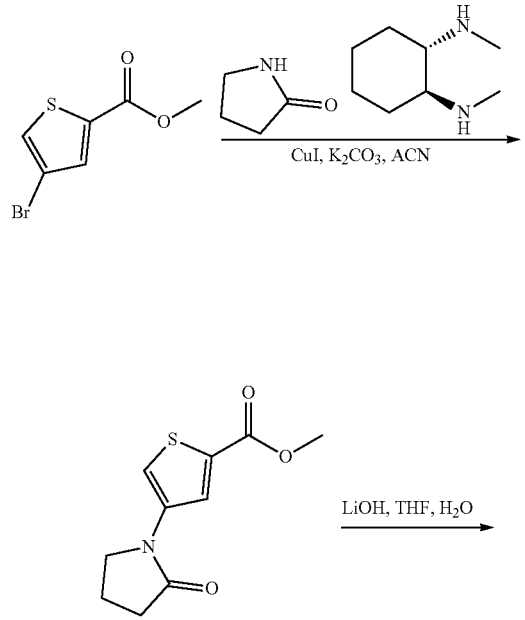

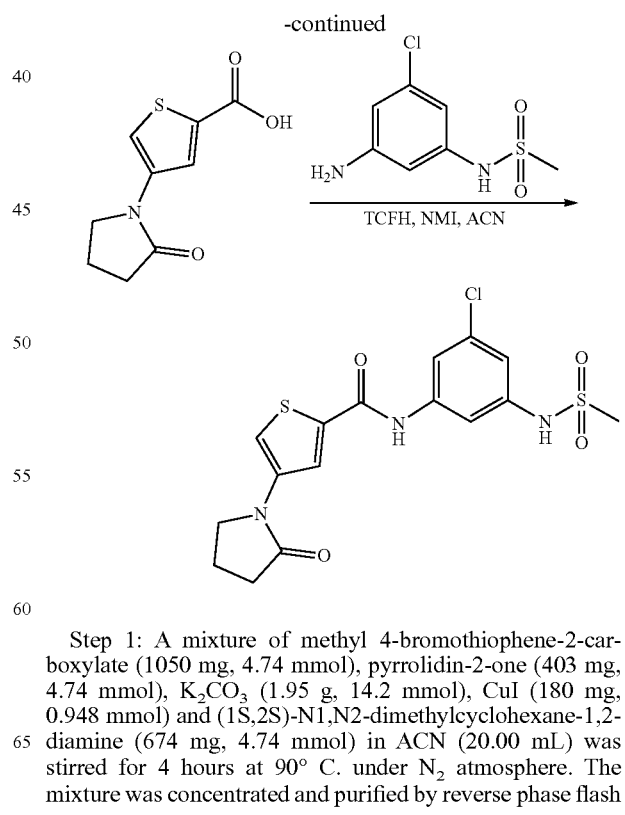

Step 1: A mixture of methyl 4-bromothiophene-2-carboxylate (1050 mg, 4.74 mmol), pyrrolidin-2-one (403 mg, 4.74 mmol), K₂CO₃ (1.95 g, 14.2 mmol), CuI (180 mg, 0.948 mmol) and (1S,2S)-N1,N2-dimethylcyclohexane-1,2-diamine (674 mg, 4.74 mmol) in ACN (20.00 mL) was stirred for 4 hours at 90° C. under N₂ atmosphere. The mixture was concentrated and purified by reverse phase flash chromatography eluting with ACN/H₂O (5-95%, acidic system) to afford methyl 4-(2-oxopyrrolidin-1-yl)thiophene-2-carboxylate (665 mg, 2.95 mmol) as a yellow solid. LCMS (ESI) [M+H]⁺: 226

Step 2: To a stirred solution of methyl 4-(2-oxopyrrolidin-1-yl)thiophene-2-carboxylate (250 mg, 1.10 mmol) and LiOH (2.5 mg, 0.5 mmol) in THF (2.50 mL) was added H₂O (0.50 mL). Then the mixture was stirred for 2 h at room temperature. The mixture was acidified to pH 5 with citric acid. The precipitated solids were collected by filtration and washed with water. The resulting solid was dried under vacuum to afford 4-(2-oxopyrrolidin-1-yl)thiophene-2-carboxylic acid (171 mg, 0.809 mmol) as a yellow solid. LCMS (ESI) [M+H]⁺: 212.24

Step 3: To a stirred solution of 4-(2-oxopyrrolidin-1-yl)thiophene-2-carboxylic acid (120 mg, 0.568 mmol), TCFH (239 mg, 0.851 mmol) and NMI (139 mg, 1.70 mmol) in ACN (5.00 mL) was added N-(3-amino-5-chlorophenyl)methanesulfonamide (125 mg, 0.568 mmol). Then the mixture was stirred for 4 hours at room temperature. The mixture was concentrated and purified by reverse phase flash chromatography eluting with ACN/H₂O (5-95%, acidic system) to afford N-(3-chloro-5-methanesulfonamidophenyl)-4-(2-oxopyrrolidin-1-yl)thiophene-2-carboxamide (58.9 mg, 99.018%) as a white solid. LCMS (ESI) [M+H]⁺: 414.89. ¹H NMR (400 MHz, DMSO-d6) δ 10.56 (s, 1H), 10.07 (s, 1H), 8.49 (d, J=1.5 Hz, 1H), 7.67 (dd, J=12.3, 1.7 Hz, 3H), 6.96 (t, J=2.0 Hz, 1H), 3.84 (t, J=7.1 Hz, 2H), 3.07 (s, 3H), 2.51 (d, J=16.2 Hz, 1H), 2.18-2.05 (m, 2H).

Examples 431-447

The compounds listed in the following table were prepared using a procedure similar to that described for example 177:

| Structure | Compound No. | MS (ESI) [M + H]⁺ | ¹H NMR |
|---|---|---|---|
| 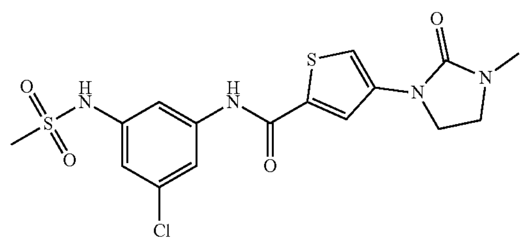 | 431 | 427 [M − H]⁻ | ¹H NMR (400 MHz, DMSO-d6) δ 10.53 (s, 1H), 10.11 (s, 1H), 8.41 (d, J = 1.6 Hz, 1H), 7.64 (d, J = 2.0 Hz, 2H), 7.30 (d, J = 1.5 Hz, 1H), 6.95 (t, J = 2.0 Hz, 1H), 3.78 (dd, J = 9.2, 6.7 Hz, 2H), 3.48 (dd, J = 9.2, 6.6 Hz, 2H), 3.06 (s, 3H), 2.78 (s, 3H). |
| 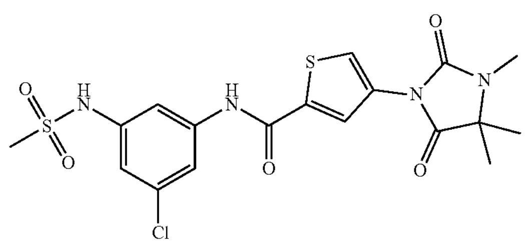 | 432 | 469 [M − H]⁻ | ¹H NMR (400 MHz, DMSO-d6) δ 10.58 (s, 1H), 10.07 (s, 1H), 8.36 (d, J = 1.5 Hz, 1H), 8.01 (d, J = 1.4 Hz, 1H), 7.66 (dt, J = 6.7, 1.9 Hz, 2H), 6.96 (t, J = 2.0 Hz, 1H), 3.07 (s, 3H), 2.90 (s, 3H), 1.43 (s, 6H). |
| 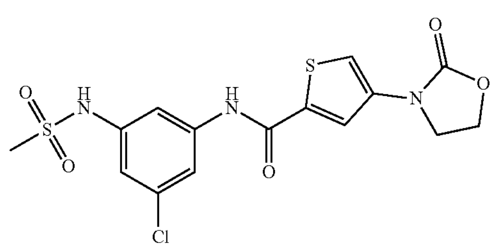 [SMILES: CS(=O)(=O)Nc1cc(Cl)cc(NC(=O)c2cc(N3CCOC3=O)cs2)c1] | 433 | 414 [M − H]⁻ | ¹H NMR (400 MHz, DMSO-d6) δ 10.59 (s, 1H), 10.06 (s, 1H), 8.39 (d, J = 1.6 Hz, 1H), 7.65 (d, J = 2.0 Hz, 2H), 7.50 (d, J = 1.5 Hz, 1H), 6.97 (d, J = 2.1 Hz, 1H), 4.49 (dd, J = 9.1, 6.9 Hz, 2H), 4.05 (dd, J = 9.1, 6.9 Hz, 2H), 3.06 (s, 3H). |
| 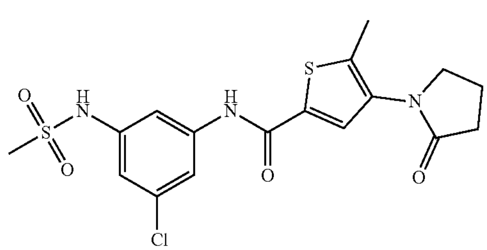 [SMILES: Cc1sc(C(=O)Nc2cc(Cl)cc(NS(C)(=O)=O)c2)cc1N1CCCC1=O] | 434 | 426 [M − H]⁻ | ¹H NMR (400 MHz, DMSO-d6) δ 10.35 (s, 1H), 10.08 (s, 1H), 7.92 (s, 1H), 7.62 (dt, J = 22.1, 1.9 Hz, 2H), 6.94 (t, J = 1.9 Hz, 1H), 3.72 (t, J = 7.0 Hz, 2H), 3.06 (s, 3H), 2.43 (t, J = 8.0 Hz, 2H), 2.32 (s, 3H), 2.18-2.06 (m, 2H). |

| Structure | Compound No. | MS (ESI) [M + H]+ | 1H NMR |
|---|---|---|---|
| 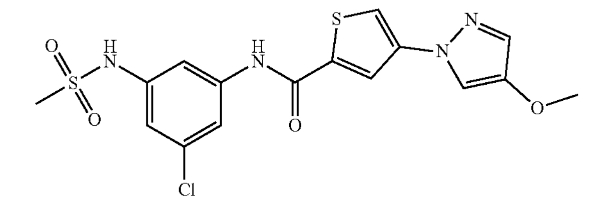 | 435 | 427 | 1H NMR (300 MHz, DMSO-d6) δ 10.61 (s, 1H), 10.12 (s, 1H), 8.49 (d, J = 1.5 Hz, 1H), 8.19 (s, 1H), 7.92 (d, J = 1.5 Hz, 1H), 7.67 (dt, J = 8.4, 1.9 Hz, 2H), 7.56 (s, 1H), 6.97 (t, J = 1.9 Hz, 1H), 3.78 (s, 3H), 3.08 (s, 3H). |
| 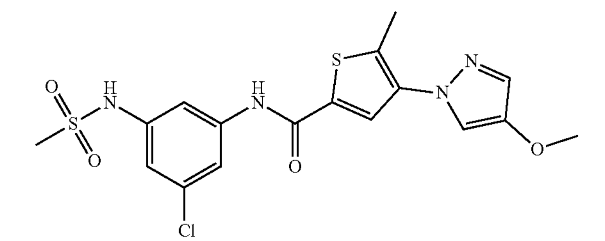 | 436 | 441 | 1H NMR (400 MHz, DMSO-d6) δ 10.43 (s, 1H), 10.15 (s, 1H), 8.18 (s, 1H), 7.92 (s, 1H), 7.65 (d, J = 1.9 Hz, 1H), 7.60 (d, J = 2.0 Hz, 1H), 7.56 (s, 1H), 6.94 (t, J = 2.0 Hz, 1H), 3.76 (s, 3H), 3.04 (s, 3H), 2.54 (s, 3H). |
| 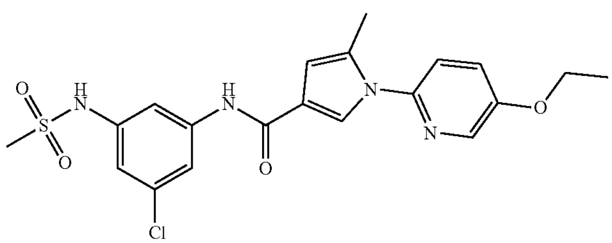 [SMILES: CCOc1ccc(-n2cc(C(=O)Nc3cc(Cl)cc(NS(C)(=O)=O)c3)cc2C)nc1] | 437 | 449 | 1H NMR (400 MHz, DMSO-d6) δ8 9.98 (s, 1H), 9.80 (s, 1H), 8.25 (d, J = 3.0 Hz, 1H), 7.86 (d, J = 1.9 Hz, 1H), 7.70 (s, 1H), 7.60 (dd, J = 8.8, 3.4 Hz, 2H), 7.54 (d, J = 8.8 Hz, 1H), 6.88 (d, J = 2.7 Hz, 1H), 6.54 (s, 1H), 4.18 (q, J = 6.9 Hz, 2H), 3.04 (d, J = 4.4 Hz, 2H), 2.30 (s, 3H), 1.38 (t, J = 7.0 Hz, 3H). |
| 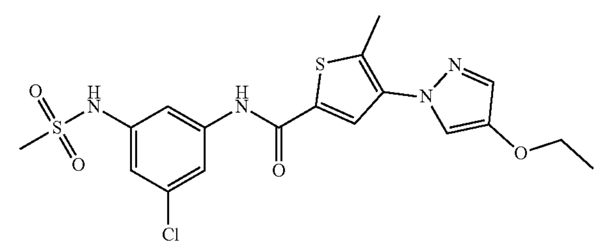 [SMILES: CCOc1cnn(-c2cc(C(=O)Nc3cc(Cl)cc(NS(C)(=O)=O)c3)sc2C)c1] | 438 | 455 | 1H NMR (400 MHz, DMSO-d6) δ 10.44 (s, 1H), 10.06 (s, 1H), 8.17 (s, 1H), 7.90 (s, 1H), 7.67 (t, J = 1.9 Hz, 1H), 7.62 (t, J = 1.9 Hz, 1H), 7.55 (s, 1H), 6.96 (t, J = 2.0 Hz, 1H), 3.99 (q, J = 7.0 Hz, 2H), 3.06 (s, 3H), 2.53 (s, 3H), 1.32 (t, J = 7.0 Hz, 3H). |
| 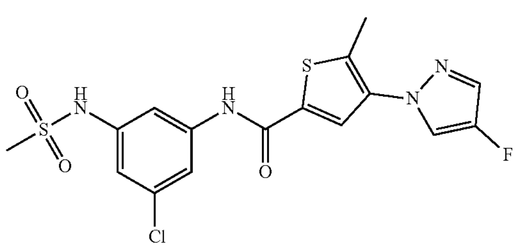 [SMILES: Cc1sc(C(=O)Nc2cc(Cl)cc(NS(C)(=O)=O)c2)cc1-n1cc(F)cn1] | 439 | 429 | 1H NMR (400 MHz, DMSO-d6) δ 10.46 (s, 1H), 10.07 (s, 1H), 8.36 (d, J = 4.5 Hz, 1H), 8.18 (s, 1H), 7.85 (d, J = 4.0 Hz, 1H), 7.66 (d, J = 1.9 Hz, 1H), 7.61 (t, J = 1.9 Hz, 1H), 6.96 (t, J = 1.9 Hz, 1H), 3.06 (s, 3H), 2.52 (s, 3H). |
| 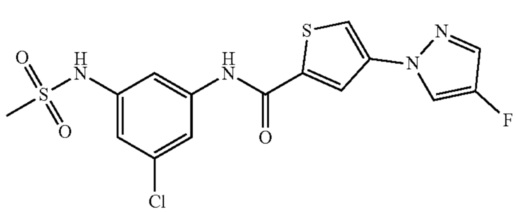 [SMILES: CS(=O)(=O)Nc1cc(Cl)cc(NC(=O)c2cc(-n3cc(F)cn3)cs2)c1] | 440 | 415 | 1H NMR (400 MHz, DMSO-d6) δ 10.61 (s, 1H), 10.08 (s, 1H), 8.60 (d, J = 4.5 Hz, 1H), 8.49 (d, J = 1.5 Hz, 1H), 8.01 (d, J = 1.6 Hz, 1H), 7.85 (d, J = 4.1 Hz, 1H), 7.67 (dt, J = 12.4, 1.9 Hz, 2H), 6.97 (t, J = 1.9 Hz, 1H), 3.07 (s, 3H). |

-continued

| Structure | Compound No. | MS (ESI) [M + H]+ | 1H NMR |
|---|---|---|---|
| 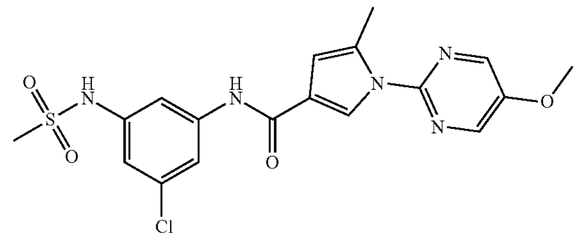 | 441 | 436 | 1H NMR (400 MHz, DMSO-d6) δ 9.97 (s, 2H), 8.64 (s, 2H), 8.35 (d, J = 2.1 Hz, 1H), 7.71 (d, J = 1.9 Hz, 1H), 7.68-7.62 (m, 1H), 6.90 (t, J = 2.0 Hz, 1H), 6.55 (dd, J = 2.1, 1.1 Hz, 1H), 3.97 (s, 3H), 3.05 (s, 3H), 2.55 (s, 3H). |
| 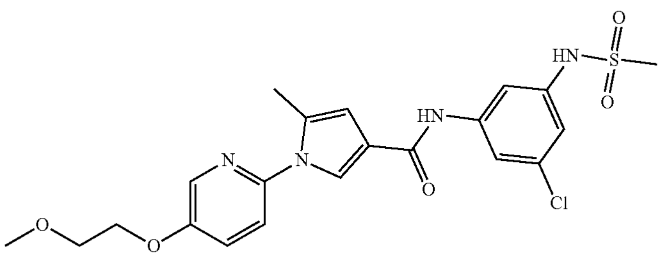 | 442 | 479 | 1H NMR (400 MHz, DMSO-d6) δ 10.11-9.73 (m, 2H), 8.28 (d, J = 3.0 Hz, 1H), 7.87 (d, J = 2.1 Hz, 1H), 7.72 (t, J = 1.8 Hz, 1H), 7.67-7.60 (m, 2H), 7.55 (d, J = 8.8 Hz, 1H), 6.89 (t, J = 1.9 Hz, 1H), 6.55 (d, J = 2.0 Hz, 1H), 4.29-4.22 (m, 2H), 3.74-3.67 (m, 2H), 3.33 (s, 3H), 3.06 (s, 3H), 2.31 (s, 3H). |
| 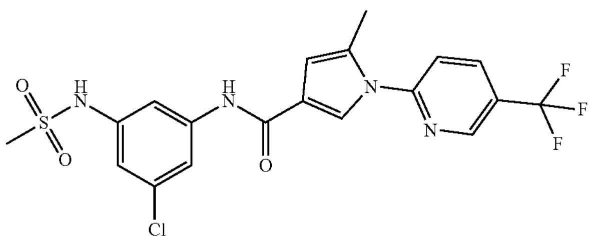 [SMILES: Cc1cc(C(=O)Nc2cc(Cl)cc(NS(C)(=O)=O)c2)cn1-c1ccc(C(F)(F)F)cn1] | 443 | 473 | 1H NMR (300 MHz, DMSO-d6) δ 10.03 (s, 1H), 9.93 (s, 1H), 9.02-8.95 (m, 1H), 8.44 (dd, J = 9.0, 2.5 Hz, 1H), 8.13 (d, J = 2.0 Hz, 1H), 7.89 (d, J = 8.6 Hz, 1H), 7.72 (t, J = 1.9 Hz, 1H), 7.63 (t, J = 1.9 Hz, 1H), 6.91 (t, J = 2.0 Hz, 1H), 6.65 (dd, J = 2.0, 1.1 Hz, 1H), 3.06 (s, 3H), 2.47 (d, J = 1.0 Hz, 3H). |
| 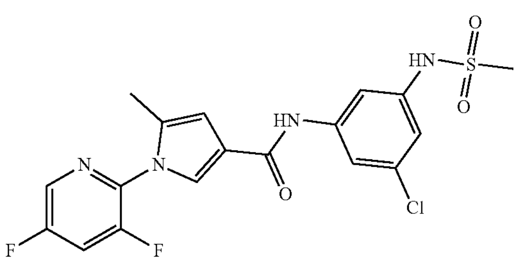 [SMILES: Cc1cc(C(=O)Nc2cc(Cl)cc(NS(C)(=O)=O)c2)cn1-c1ncc(F)cc1F] | 444 | 441 | 1H NMR (300 MHz, DMSO-d6) δ 10.03 (s, 1H), 9.88 (s, 1H), 8.59 (d, J = 2.5 Hz, 1H), 8.45-8.24 (m, 1H), 7.77 (t, J = 1.9 Hz, 1H), 7.71 (t, J = 1.9 Hz, 1H), 7.62 (t, J = 1.9 Hz, 1H), 6.90 (t, J = 1.9 Hz, 1H), 6.66-6.59 (m, 1H), 3.06 (s, 3H), 2.18 (s, 3H). |
| 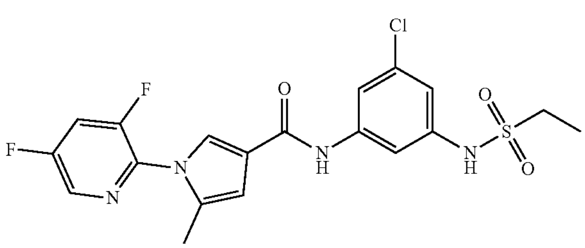 [SMILES: CCS(=O)(=O)Nc1cc(Cl)cc(NC(=O)c2cc(C)n(-c3ncc(F)cc3F)c2)c1] | 445 | 455 | 1H NMR (300 MHz, DMSO-d6) δ 10.08 (s, 1H), 9.87 (s, 1H), 8.59 (d, J = 2.5 Hz, 1H), 8.35 (ddd, J = 9.9, 8.3, 2.5 Hz, 1H), 7.77 (t, J = 1.9 Hz, 1H), 7.69 (t, J = 1.8 Hz, 1H), 7.62 (t, J = 1.9 Hz, 1H), 6.90 (t, J = 1.9 Hz, 1H), 6.62 (dd, J = 1.9, 1.1 Hz, 1H), 3.16 (q, J = 7.3 Hz, 2H), 2.18 (s, 3H), 1.21 (t, J = 7.3 Hz, 3H). |

| Structure | Compound No. | MS (ESI) [M + H]+ | 1H NMR |
|---|---|---|---|
| (structure with 3-chloro-5-fluoropyridinyl pyrrole carboxamide, chlorophenyl, ethylsulfonamide) | 446 | 471 | 1H NMR (300 MHz, DMSO-d6) δ 10.05 (s, 1H), 9.84 (s, 1H), 8.69 (d, J = 2.7 Hz, 1H), 8.48 (dd, J = 8.0, 2.7 Hz, 1H), 7.74-7.67 (m, 2H), 7.62 (t, J = 1.9 Hz, 1H), 6.90 (t, J = 1.9 Hz, 1H), 6.60 (dd, J = 1.9, 1.1 Hz, 1H), 3.17 (q, J = 7.3 Hz, 2H), 2.07 (d, J = 1.0 Hz, 3H), 1.21 (t, J = 7.3 Hz, 3H). |
| (structure with methylsulfonamide chlorophenyl pyrrole carboxamide pyridine methoxymethyl) | 447 | 449 | 1H NMR (300 MHz, DMSO-d6) δ 9.95 (d, J = 52.6 Hz, 2H), 8.52 (d, J = 2.3 Hz, 1H), 8.03-7.92 (m, 2H), 7.78-7.54 (m, 3H), 6.89 (t, J = 1.9 Hz, 1H), 6.58 (dd, J = 2.0, 1.1 Hz, 1H), 4.52 (s, 2H), 3.35 (s, 3H), 3.05 (s, 3H), 2.38 (d, J = 1.0 Hz, 3H). |

Example 177: N-(3-chloro-5-(methylsulfonamido)phenyl)-5-cyclopropyl-4-(pyridin-2-yl)thiophene-2-carboxamide

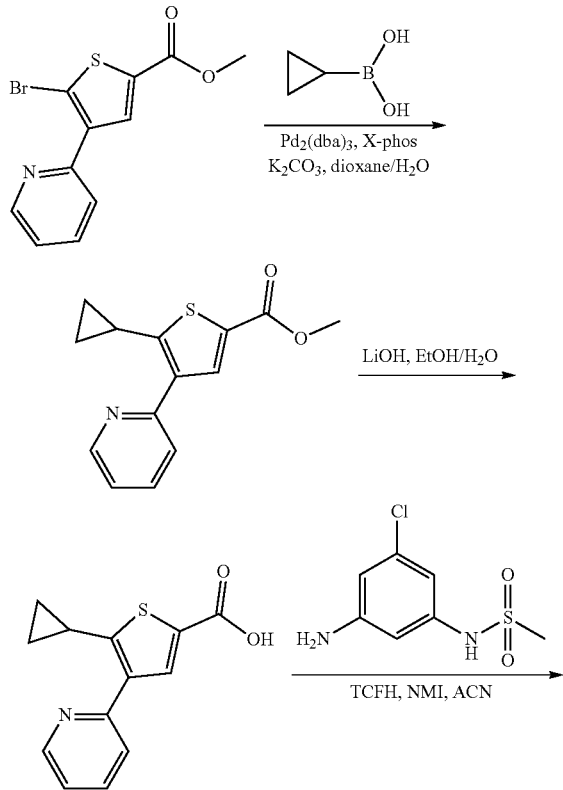

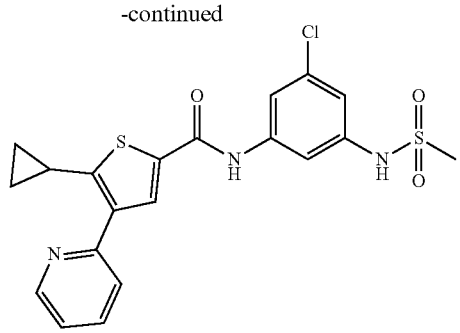

Step 1: A solution of methyl 5-bromo-4-(pyridin-2-yl)thiophene-2-carboxylate (30 mg, 1.00 mmol), Pd$_2$(dba)$_3$ (183 mg, 0.200 mmol), X-phos (190 mg, 0.400 mmol), K$_2$CO$_3$ (414 mg, 3.00 mmol) and cyclopropylboronic acid (128 mg, 1.50 mmol) in dioxane (5 mL) and H$_2$O (1 mL) was stirred for 2 hours at 80° C. under nitrogen atmosphere. The resulting mixture was concentrated under reduced pressure. The residue was purified by silica gel column chromatography, eluted with Petroleum ether/EtOAc (0-100%) to afford methyl 5-cyclopropyl-4-(pyridin-2-yl)thiophene-2-carboxylate (165 mg, 0.636 mmol) as a white solid. LCMS (ESI) [M+H]+: 260.

Step 2: To a stirred solution of methyl 5-cyclopropyl-4-(pyridin-2-yl)thiophene-2-carboxylate (165 mg, 0.636 mmol) in EtOH (3 mL) and H$_2$O (3 mL) was added LiOH (152 mg, 6.35 mmol). Then the mixture was stirred for 2 hours at room temperature. The mixture was acidified to pH 5 with citric acid. The precipitated solids were collected by filtration and washed with water. The resulting solid was dried under vacuum to afford 5-cyclopropyl-4-(pyridin-2-yl)thiophene-2-carboxylic acid (130 mg, 0.529 mmol) as a white solid. LCMS (ESI) [M+H]+: 246.

Step 3: To a stirred solution of 5-cyclopropyl-4-(pyridin-2-yl)thiophene-2-carboxylic acid (130 mg, 0.529 mmol), TCFH (294 mg, 1.05 mmol) and NMI (260 mg, 3.17 mmol) in ACN (5 mL) was added N-(3-amino-5-chlorophenyl)methanesulfonamide (128 mg, 0.581 mmol). Then the mixture was stirred for 1 hour at room temperature. The mixture was concentrated and purified by reverse phase flash chromatography eluting with ACN/H₂O (5-95%, acidic system) to afford N-(3-chloro-5-methanesulfonamidophenyl)-5-cyclopropyl-4-(pyridin-2-yl)thiophene-2-carboxamide (56.2 mg, 0.125 mmol) as a white solid. LCMS (ESI) [M+448. ¹H NMR (400 MHz, DMSO-d6) δ 10.46 (s, 1H), 10.10 (s, 1H), 8.69 (dt, J=4.6, 1.6 Hz, 1H), 8.40 (s, 1H), 7.94 (td, J=7.7, 1.9 Hz, 1H), 7.85 (dd, J=8.0, 1.2 Hz, 1H), 7.65 (dt, J=17.3, 1.9 Hz, 2H), 7.38 (ddd, J=7.6, 4.8, 1.2 Hz, 1H), 6.94 (t, J=2.0 Hz, 1H), 3.07 (s, 3H), 2.68 (tt, J=8.4, 5.2 Hz, 1H), 1.25-1.14 (m, 2H), 0.85-70.76 (i, 2H).

Examples 448-451

The compounds listed in the following table were prepared using a procedure similar to that described for example 177:

| Structure | Compound No. | MS (ESI) [M + H]⁺ | ¹H NMR |
|---|---|---|---|
| 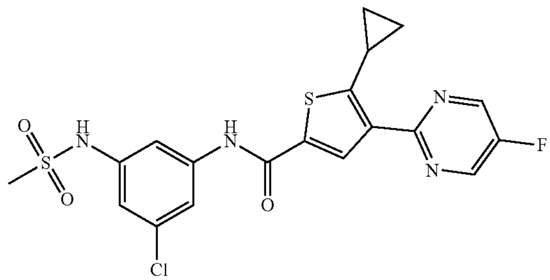 [SMILES: CS(=O)(=O)Nc1cc(Cl)cc(NC(=O)c2cc(-c3ncc(F)cn3)c(C3CC3)s2)c1] | 448 | 466.9 | ¹H NMR (400 MHz, DMSO-d6) δ 10.56 (s, 1H), 10.05 (s, 1H), 9.00 (s, 2H), 8.62 (s, 1H), 7.66 (dt, J = 10.7, 2.0 Hz, 2H), 6.94 (d, J = 2.1 Hz, 1H), 3.42 (tt, J = 8.5, 5.2 Hz, 1H), 3.06 (s, 3H), 1.24 (h, J = 4.5 Hz, 2H), 0.83 (q, J = 5.1 Hz, 2H). |
| 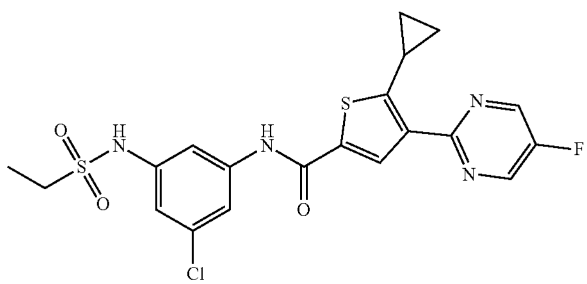 [SMILES: CCS(=O)(=O)Nc1cc(Cl)cc(NC(=O)c2cc(-c3ncc(F)cn3)c(C3CC3)s2)c1] | 449 | 480.9 | ¹H NMR (400 MHz, DMSO-d6) δ 10.56 (s, 1H), 10.11 (s, 1H), 9.00 (s, 2H), 8.62 (s, 1H), 7.69-7.62 (m, 2H), 6.95 (d, J = 1.9 Hz, 1H), 3.41 (td, J = 8.5, 4.3 Hz, 1H), 3.17 (q, J = 7.3 Hz, 2H), 1.22 (q, J = 7.4 Hz, 5H), 0.86-0.77 (m, 2H). |
| 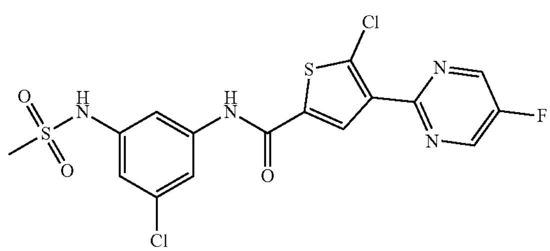 [SMILES: CS(=O)(=O)Nc1cc(Cl)cc(NC(=O)c2cc(-c3ncc(F)cn3)c(Cl)s2)c1] | 450 | 460.85 | ¹H NMR (400 MHz, DMSO-d6) δ 10.73 (s, 1H), 10.08 (s, 1H), 9.07 (s, 2H), 8.69 (s, 1H), 7.71-7.61 (m, 2H), 6.97 (t, J = 1.9 Hz, 1H), 3.07 (s, 3H). |
| 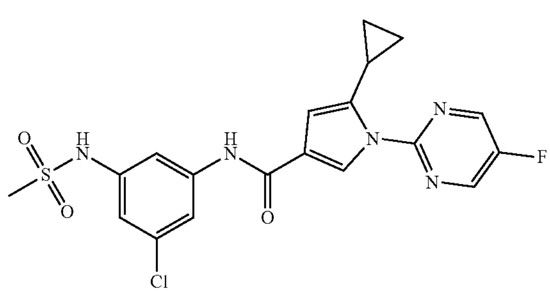 [SMILES: CS(=O)(=O)Nc1cc(Cl)cc(NC(=O)c2cc(C3CC3)n(-c3ncc(F)cn3)c2)c1] | 451 | 450 | ¹H NMR (300 MHz, DMSO-d6) δ 10.34-9.92 (m, 2H), 9.01 (s, 2H), 8.35 (d, J = 2.1 Hz, 1H), 7.67 (dt, J = 17.9, 1.9 Hz, 2H), 6.90 (t, J = 1.9 Hz, 1H), 6.50 (dd, J = 2.1, 1.0 Hz, 1H), 3.06 (s, 3H), 2.61-2.51 (m, 1H), 0.93-0.81 (m, 2H), 0.67-0.56 (m, 2H). |

Example 178: N-(3-chloro-5-(methylsulfonamido)phenyl)-4-(3-(pyrimidin-2-yloxy)pyridin-2-yl)thiophene-2-carboxamide

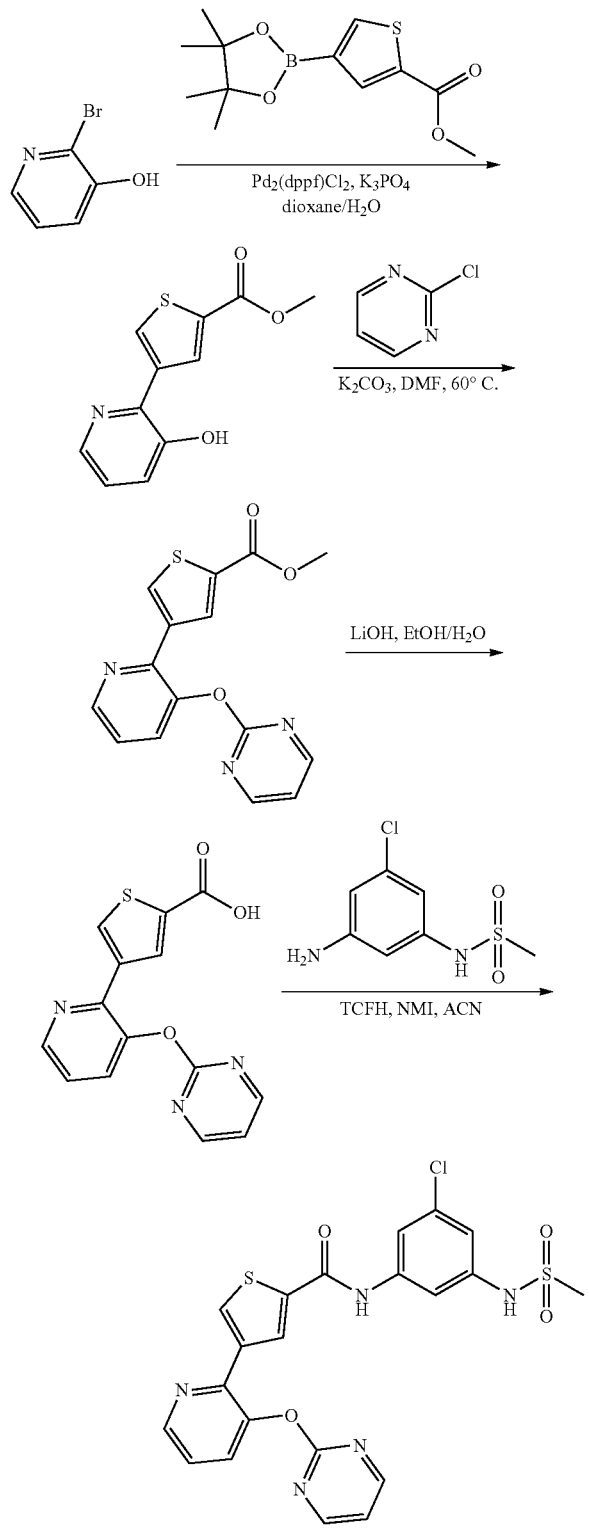

Step 1: A solution of 2-bromopyridin-3-ol (520 mg, 2.98 mmol), Pd(dppf)Cl$_2$ (218 mg, 0.298 mmol), K$_3$PO$_4$ (1.89 g, 8.94 mmol) and methyl 4-(4,4,5,5-tetramethyl-1,3,2-dioxaborolan-2-yl)thiophene-2-carboxylate (957 mg, 3.57 mmol) in dioxane (10 mL) and H$_2$O (1 mL) was stirred for 2 h at 80° C. under nitrogen atmosphere. The resulting mixture was concentrated under reduced pressure. The residue was purified by silica gel column chromatography, eluted with EtOAc/Petroleum ether (0-100%) to afford methyl 4-(3-hydroxypyridin-2-yl)thiophene-2-carboxylate (510 mg, 2.16 mmol) as a white solid. LCMS (ESI) [M+H]$^+$: 236.

Step 2: A mixture of methyl 4-(3-hydroxypyridin-2-yl)thiophene-2-carboxylate (250 mg, 1.0 6 mmol), K$_2$CO$_3$ (439 mg, 3.18 mmol) and 2-chloropyrimidine (121 mg, 1.06 mmol) in DMF (5 mL) was stirred for 5 h at room temperature. The mixture was concentrated and purified by reverse phase flash chromatography eluting with ACN/H$_2$O (5-95%, acidic system) to afford methyl 4-[3-(pyrimidin-2-yloxy)pyridin-2-yl]thiophene-2-carboxylate (210 mg, 0.670 mmol) as a white solid. LCMS (ESI) [M+H]$^+$: 314.

Step 3: To a stirred solution of methyl 4-[3-(pyrimidin-2-yloxy)pyridin-2-yl]thiophene-2-carboxylate (150 mg, 0.478 mmol) in EtOH (4 mL) and H$_2$O (4 mL) was added LiOH (114 mg, 4.77 mmol). Then the mixture was stirred for 2 h at room temperature. The mixture was acidified to pH 5 with citric acid. The precipitated solids were collected by filtration and washed with water. The resulting solid was dried under vacuum to afford 4-[3-(pyrimidin-2-yloxy)pyridin-2-yl]thiophene-2-carboxylic acid (108 mg, 0.360 mmol) as a white solid. LCMS (ESI) [M+H]$^+$: 300.

Step 4: To a stirred solution of 4-[3-(pyrimidin-2-yloxy)pyridin-2-yl]thiophene-2-carboxylic acid (110 mg, 0.367 mmol), TCFH (205 mg, 0.734 mmol) and NMI (90.2 mg, 1.10 mmol) in ACN (5 mL) was added N-(3-amino-5-chlorophenyl)methanesulfonamide (80.9 mg, 0.367 m mol). Then the mixture was stirred for 1 h at room temperature. The mixture was concentrated and purified by reverse phase flash chromatography eluting with ACN/H$_2$O (5-95%, acidic system) to afford N-(3-chloro-5-methanesulfonamidophenyl)-4-[3-(pyrimidin-2-yloxy)pyridin-2-yl]thiophene-2-carboxamide (56.3 mg, 0.112 mmol) as a white solid. LCMS (ESI) [M+H]$^+$: 502. $^1$H NMR (400 MHz, DMSO-d$_6$) δ 10.64 (s, 1H), 10.08 (s, 1H), 8.72 (d, J=1.4 Hz, 1H), 8.63 (dd, J=18.2, 4.7 Hz, 3H), 8.23 (d, J=1.3 Hz, 1H), 7.85 (dd, J=8.2, 1.4 Hz, 1H), 7.67 (dt, J=6.6, 1.9 Hz, 2H), 7.51 (dd, J=8.2, 4.6 Hz, 1H), 7.30 (t, J=4.8 Hz, 1H), 6.96 (t, J=2.0 Hz, 1H), 3.07 (s, 3H).

Examples 452-459

The compounds listed in the following table were prepared using a procedure similar to that described for example 178:

| Structure | Compound No. | MS (ESI) [M + H]+ | 1H NMR |
|---|---|---|---|
| 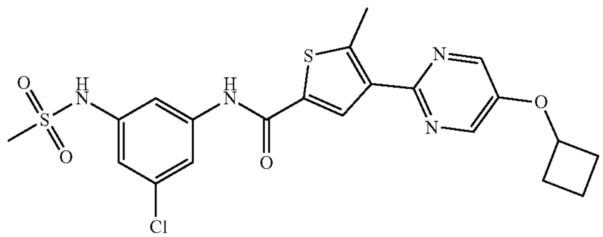 [SMILES: Cc1sc(C(=O)Nc2cc(Cl)cc(NS(C)(=O)=O)c2)cc1-c1ncc(OC2CCC2)cn1] | 452 | 492.9 | 1H NMR (400 MHz, DMSO-d6) δ 10.56 (s, 1H), 10.06 (s, 1H), 8.63 (s, 1H), 8.55 (s, 2H), 7.69 (dt, J = 7.0, 1.9 Hz, 2H), 6.94 (t, J = 2.0 Hz, 1H), 4.94 (p, J = 7.1 Hz, 1H), 3.07 (s, 3H), 2.83 (s, 3H), 2.54 (s, 1H), 2.50 (s, 1H), 2.11 (dd, J = 11.1, 8.7 Hz, 2H), 1.84 (q, J = 10.3 Hz, 1H), 1.68 (p, J = 9.3 Hz, 1H). |
| 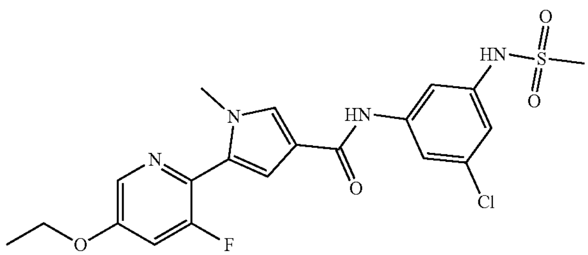 [SMILES: CCOc1cnc(-c2cc(C(=O)Nc3cc(Cl)cc(NS(C)(=O)=O)c3)cn2C)c(F)c1] | 453 | 466.95 | 1H NMR (400 MHz, DMSO-d6) δ 10.00 (s, 1H), 9.85 (s, 1H), 8.31-8.16 (m, 1H), 7.75-7.67 (m, 2H), 7.64 (t, J = 1.8 Hz, 1H), 7.57 (dd, J = 12.6, 2.5 Hz, 1H), 7.07 (dd, J = 3.2, 1.9 Hz, 1H), 6.89 (t, J = 1.9 Hz, 1H), 4.18 (q, J = 6.9 Hz, 2H), 3.84 (s, 3H), 3.06 (s, 3H), 1.37 (t, J = 6.9 Hz, 3H). |
| 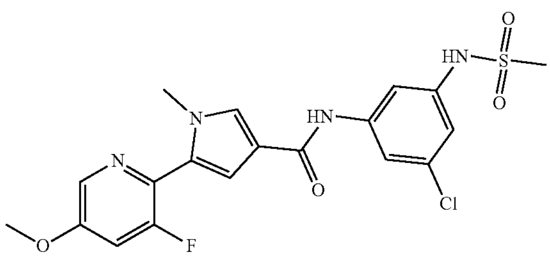 | 454 | 452.95 | 1H NMR (400 MHz, DMSO-d6) δ 10.00 (s, 1H), 9.85 (s, 1H), 8.27 (dd, J = 2.5, 1.1 Hz, 1H), 7.77-7.66 (m, 2H), 7.66-7.51 (m, 2H), 7.08 (dd, J = 3.3, 2.0 Hz, 1H), 6.90 (t, J = 2.0 Hz, 1H), 3.87 (d, J = 23.9 Hz, 6H), 3.06 (s, 3H). |
| 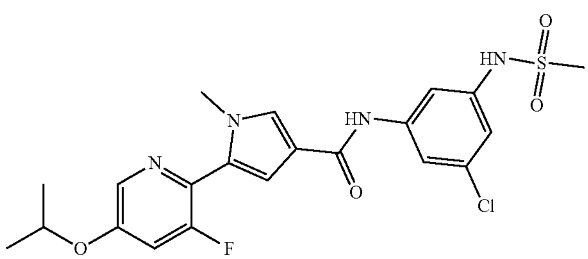 [SMILES: CC(C)Oc1cnc(-c2cc(C(=O)Nc3cc(Cl)cc(NS(C)(=O)=O)c3)cn2C)c(F)c1] | 455 | 497.85 | 1H NMR (400 MHz, Methanol-d4) δ 8.17 (dd, J = 2.5, 1.0 Hz, 1H), 7.96 (d, J = 1.5 Hz, 1H), 7.64 (t, J = 1.9 Hz, 1H), 7.55 (t, J = 1.9 Hz, 1H), 7.39 (dd, J = 11.9, 2.5 Hz, 1H), 7.02 (t, J = 1.9 Hz, 1H), 4.75 (hept, J = 6.1 Hz, 1H), 3.03 (s, 3H), 2.53 (d, J = 1.3 Hz, 3H), 1.39 (d, J = 6.0 Hz, 6H). |
| 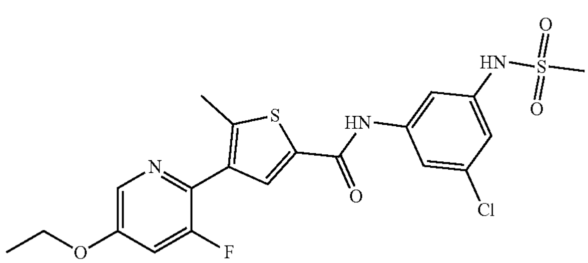 [SMILES: CCOc1cnc(-c2cc(C(=O)Nc3cc(Cl)cc(NS(C)(=O)=O)c3)sc2C)c(F)c1] | 456 | 484.2 | 1H NMR (400 MHz, Methanol-d4) δ 8.20 (dd, J = 2.4, 1.0 Hz, 1H), 7.96 (d, J = 1.5 Hz, 1H), 7.64 (t, J = 1.9 Hz, 1H), 7.55 (t, J = 1.9 Hz, 1H), 7.38 (dd, J = 11.7, 2.4 Hz, 1H), 7.01 (t, J = 1.9 Hz, 1H), 4.19 (q, J = 7.0 Hz, 2H), 3.03 (s, 3H), 2.52 (d, J = 1.3 Hz, 3H), 1.46 (t, J = 7.0 Hz, 3H). |
| 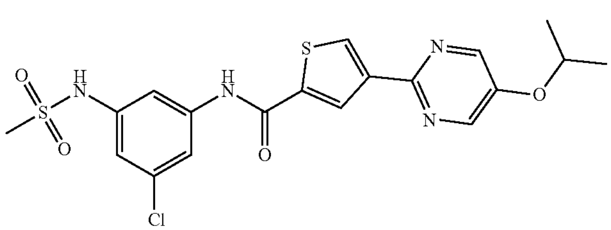 [SMILES: CC(C)Oc1cnc(-c2csc(C(=O)Nc3cc(Cl)cc(NS(C)(=O)=O)c3)c2)nc1] | 457 | 466.9 | 1H NMR (400 MHz, DMSO-d6) δ 10.65 (s, 1H), 10.09 (s, 1H), 8.76 (d, J = 1.4 Hz, 1H), 8.61 (s, 2H), 8.49 (d, J = 1.4 Hz, 1H), 7.70 (p, J = 1.8 Hz, 2H), 6.96 (t, J = 1.9 Hz, 1H), 4.88 (hept, J = 6.0 Hz, 1H), 3.08 (s, 3H), 1.34 (d, J = 6.0 Hz, 6H). |

-continued

| Structure | Compound No. | MS (ESI) [M + H]+ | 1H NMR |
|---|---|---|---|
| (structure with isopropoxy-fluoro-pyridine-thiophene-carboxamide-chlorophenyl-methylsulfonamide) | 458 | 483.85 | 1H NMR (400 MHz, DMSO-d6) δ 10.64 (s, 1H), 10.09 (s, 1H), 8.68 (d, J = 1.4 Hz, 1H), 8.37-8.20 (m, 2H), 7.68 (dt, J = 5.4, 1.8 Hz, 2H), 7.61 (dd, J = 13.5, 2.4 Hz, 1H), 6.95 (t, J = 2.0 Hz, 1H), 4.80 (hept, J = 6.1 Hz, 1H), 3.07 (s, 3H), 1.33 (d, J = 6.0 Hz, 6H). |
| (structure with methylsulfonamide-chlorophenyl-carboxamide-thiophene-pyridine-isopropoxy) | 459 | 466.1 | 1H NMR (400 MHz, DMSO-d6) δ 10.57 (s, 1H), 10.23-9.78 (m, 1H), 8.66 (d, J = 1.4 Hz, 1H), 8.31 (dd, J = 16.8, 2.1 Hz, 2H), 7.84 (d, J = 8.8 Hz, 1H), 7.69 (dt, J = 6.8, 1.9 Hz, 2H), 7.51 (dd, J = 8.8, 3.0 Hz, 1H), 6.96 (t, J = 1.9 Hz, 1H), 4.76 (hept, J = 6.1 Hz, 1H), 3.08 (s, 3H), 1.31 (d, J = 6.0 Hz, 6H). |

Example 460: N-(3-chloro-5-(methylsulfonamido)phenyl)-4-(3-fluoro-5-(3-(trifluoromethyl)azetidin-1-yl)pyridin-2-yl)-5-methylthiophene-2-carboxamide

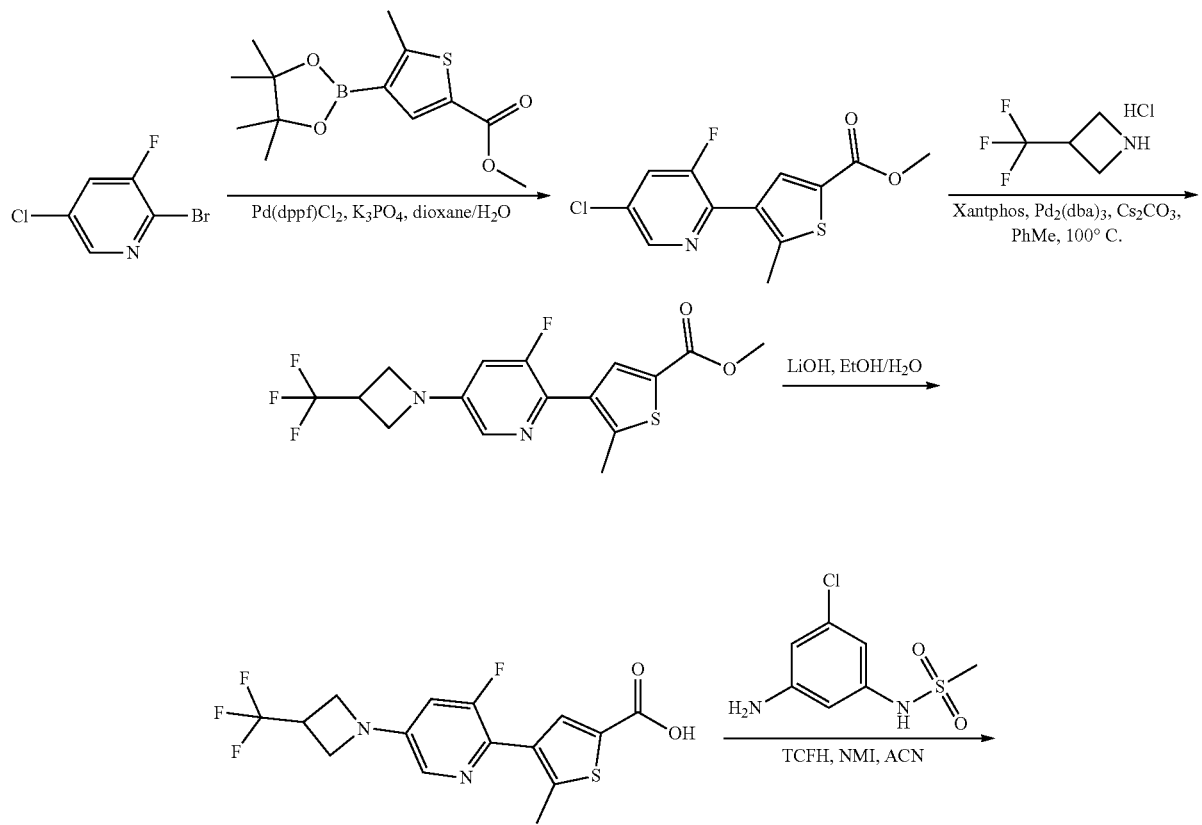

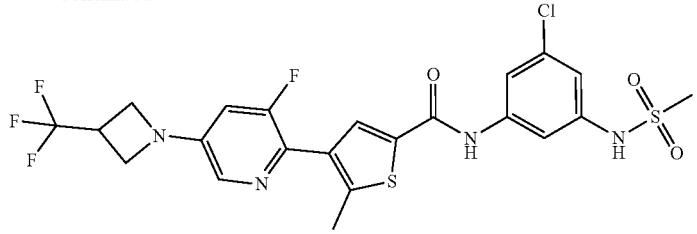

Step 1: A solution of 2-bromo-5-chloro-3-fluoropyridine (14 g, 66.5 mmol, 1 equiv), Pd(dppf)Cl₂ (3.40 g, 4.65 mmol, 0.07 equiv), K₃PO₄ (42.1 g, 199 mmol, 3 equiv) and methyl 5-methyl-4-(4,4,5,5-tetramethyl-1,3,2-dioxaborolan-2-yl)thiophene-2-carboxylate (16.8 g, 59.8 mmol, 0.9 equiv) in dioxane (140 mL) and H₂O (14 mL) was stirred for 2 hours at 80° C. under nitrogen atmosphere. The resulting mixture was concentrated under reduced pressure. The residue was purified by silica gel column chromatography, eluted with PE/EA (2:1) to afford methyl 4-(5-chloro-3-fluoropyridin-2-yl)-5-methylthiophene-2-carboxylate (11.9 g, 62.6% yield) as a white solid. LCMS (ESI) [M+H]⁺: 286

Step 2: A solution of methyl 4-(5-chloro-3-fluoropyridin-2-yl)-5-methylthiophene-2-carboxylate (11.9 g, 41.6 mmol, 1 equiv), Cs₂CO₃ (40.4 g, 124 mmol, 3 equiv), Xantphos (4.81 g, 8.32 mmol, 0.2 equiv), Pd₂(dba)₃ (3.80 g, 4.16 mmol, 0.1 equiv) and 3-(trifluoromethyl)azetidine hydrochloride (8.06 g, 49.9 mmol, 1.2 equiv) in PhMe (120 mL) was stirred for 5 hours at 100° C. under nitrogen atmosphere. The resulting mixture was concentrated under reduced pressure. The residue was purified by silica gel column chromatography, eluted with PE/EA (1:1) to afford methyl 4-(3-fluoro-5-(3-(trifluoromethyl) azetidin-1-yl)pyridin-2-yl)-5-methylthiophene-2-carboxylate (8.20 g, 52.9% yield) as a white solid. LCMS (ESI) [M+H]⁺: 375

Step 3: To a stirred solution of 4-(3-fluoro-5-(3-(trifluoromethyl)azetidin-1-yl)pyridin-2-yl)-5-methylthiophene-2-carboxylate (8.2 g, 21.9 mmol, 1 equiv) in EtOH (82 mL) and H₂O (82 mL) was added LiOH (5.24 g, 219 mmol, 10 equiv) at 0° C. Then the mixture was stirred for 4 hours at room temperature. The mixture was acidified to pH 5 with 1 M HCl (aq.). The precipitated solids were collected by filtration and washed with water. The resulting solid was dried under vacuum to afford 4-{3-fluoro-5-[3-(trifluoromethyl)azetidin-1-yl]pyridin-2-yl}-5-methylthiophene-2-carboxylic acid (5.60 g, 70.9% yield) as a white solid. LCMS (ESI) [M+H]⁺: 361

Step 4: To a stirred solution of 4-{3-fluoro-5-[3-(trifluoromethyl)azetidin-1-yl]pyridin-2-yl}-5-methylthio phene-2-carboxylic acid (5.6 g, 15.5 mmol, 1 equiv), TCFH (13.0 g, 46.5 mmol, 3 equiv) and NMI (5.08 g, 62.0 mmol, 4 equiv) in ACN (56 mL) was added N-(3-amino-5-chlorophenyl)methanesulfonamide (4.08 g, 18.5 mmol, 1.2 equiv) at room temperature. Then the mixture was stirred for 3 hours at room temperature. The mixture was concentrated under reduced pressure. The residue was purified by reversed-phase flash chromatography with the following conditions: column, C18 silica gel; mobile phase, MeCN in water (0.1% formic acid), 0% to 50% gradient in 20 min; detector, UV 254 nm. This resulted in N-(3-chloro-5-methanesulfonamidophenyl)-4-{3-fluoro-5-[3-(trifluoromethyl)azetidin-1-yl]pyridin-2-yl}-5-methylthiophene-2-carboxamide (4.8783 g, 55.8% yield) as a white solid. LCMS (ESI) [M+H]⁺: 563.10. ¹H NMR (300 MHz, DMSO-d₆) δ 10.42 (s, 1H), 10.07 (s, 1H), 8.12 (s, 1H), 7.87 (s, 1H), 7.65 (d, J=12.0 Hz, 2H), 7.03 (dd, J=12.4, 2.3 Hz, 1H), 6.94 (d, J=2.0 Hz, 1H), 4.22 (t, J=8.6 Hz, 2H), 4.09-3.98 (m, 2H), 3.79 (s, 1H), 3.06 (s, 3H), 2.48 (s, 3H).

Examples 461-514

The compounds listed in the following table were prepared using a procedure similar to that described for example A:

| Structure | Compound No. | MS (ESI) [M + H]⁺ | ¹H NMR |
|---|---|---|---|
| 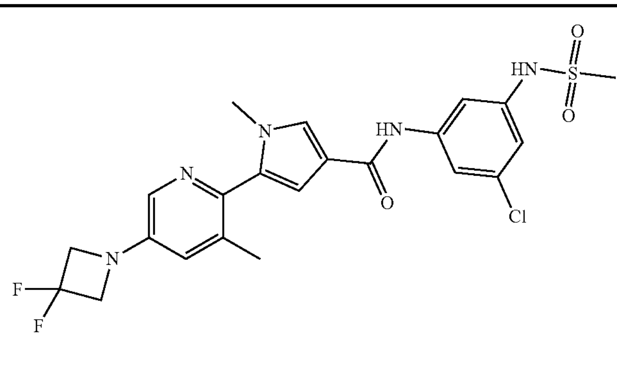 | 461 | 510.05 | ¹H NMR (300 MHz, DMSO-d6) δ 10.01 (s, 1H), 9.75 (s, 1H), 7.90 (d, J = 2.7 Hz, 1H), 7.71 (t, J = 1.9 Hz, 1H), 7.67-7.59 (m, 2H), 6.98 (d, J = 2.7 Hz, 1H), 6.90 (t, J = 1.9 Hz, 1H), 6.76 (d, J = 1.9 Hz, 1H), 4.40 (t, J = 12.3 Hz, 4H), 3.61 (s, 3H), 3.07 (s, 3H), 2.32 (s, 3H). |

-continued

| Structure | Compound No. | MS (ESI) [M + H]+ | 1H NMR |
|---|---|---|---|
| 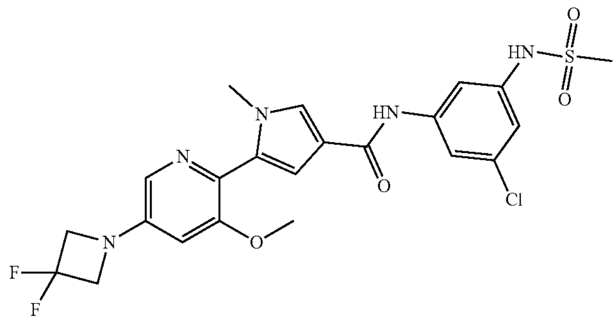 [SMILES: COc1cc(N2CC(F)(F)C2)cnc1-c1cc(C(=O)Nc2cc(Cl)cc(NS(C)(=O)=O)c2)cn1C] | 462 | 525.95 | 1H NMR (400 MHz, DMSO-d6) δ 9.98 (s, 1H), 9.76 (s, 1H), 7.72 (t, J = 1.9 Hz, 1H), 7.67-7.51 (m, 3H), 7.00-6.80 (m, 2H), 6.74 (d, J = 2.3 Hz, 1H), 4.42 (t, J = 12.3 Hz, 4H), 3.86 (s, 3H), 3.69 (s, 3H), 3.06 (s, 3H). |
| 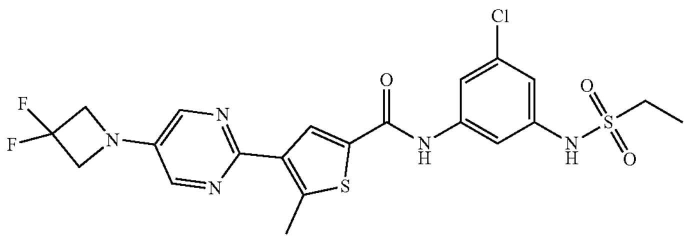 [SMILES: CCS(=O)(=O)Nc1cc(Cl)cc(NC(=O)c2cc(-c3ncc(N4CC(F)(F)C4)cn3)c(C)s2)c1] | 463 | 527.9 | 1H NMR (400 MHz, DMSO-d6) δ 10.55 (s, 1H), 10.09 (s, 1H), 8.61 (s, 1H), 8.29 (s, 2H), 7.68 (d, J = 2.0 Hz, 2H), 6.95 (t, J = 1.9 Hz, 1H), 4.50 (t, J = 12.3 Hz, 4H), 3.18 (q, J = 7.3 Hz, 2H), 2.82 (s, 3H), 1.22 (t, J = 7.3 Hz, 3H). |
| 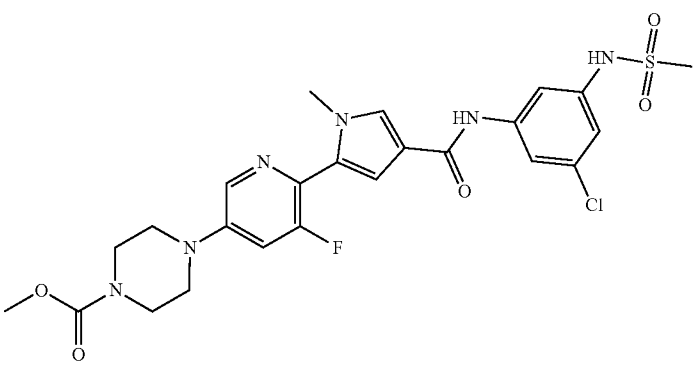 | 464 | 565.15 | 1H NMR (400 MHz, DMSO-d6) δ 9.98 (s, 1H), 9.82 (s, 1H), 8.25 (t, J = 2.0 Hz, 1H), 7.78-7.54 (m, 3H), 7.40 (dd, J = 14.1, 2.5 Hz, 1H), 7.02 (dd, J = 3.3, 2.0 Hz, 1H), 6.89 (t, J = 2.0 Hz, 1H), 3.84 (s, 3H), 3.64 (s, 3H), 3.52 (t, J = 5.2 Hz, 4H), 3.34 (d, J = 6.1 Hz, 4H), 3.06 (s, 3H). |
| 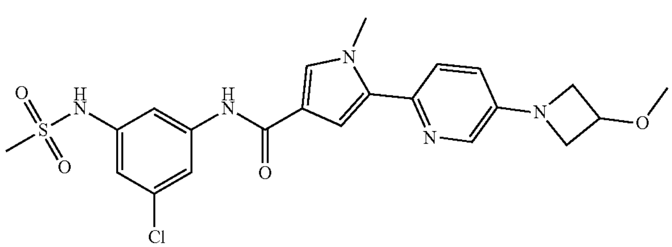 | 465 | 490.15 | 1H NMR (300 MHz, DMSO-d6) δ 10.01 (s, 1H), 9.79 (s, 1H), 7.86 (d, J = 2.8 Hz, 1H), 7.73 (t, J = 1.9 Hz, 1H), 7.68-7.56 (m, 2H), 7.50 (d, J = 8.5 Hz, 1H), 7.04-6.84 (m, 3H), 4.37 (ddd, J = 10.4, 6.1, 4.2 Hz, 1H), 4.15 (dd, J = 8.2, 6.2 Hz, 2H), 3.91 (s, 3H), 3.72 (dd, J = 8.5, 4.1 Hz, 2H), 3.26 (s, 3H), 3.07 (s, 3H). |

-continued

| Structure | Compound No. | MS (ESI) [M + H]+ | 1H NMR |
|---|---|---|---|
| 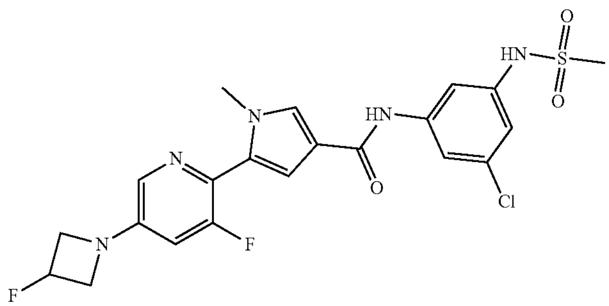 [SMILES: Cn1cc(C(=O)Nc2cc(Cl)cc(NS(C)(=O)=O)c2)cc1-c1ncc(N2CC(F)C2)cc1F] | 466 | 496 | 1H NMR (400 MHz, DMSO-d6) δ 9.99 (s, 1H), 9.82 (s, 1H), 7.84-7.76 (m, 1H), 7.75-7.54 (m, 3H), 7.04-6.81 (m, 3H), 5.73-5.28 (m, 1H), 4.38-4.17 (m, 2H), 4.05 (dddd, J = 24.1, 9.8, 3.1, 1.4 Hz, 2H), 3.81 (s, 3H), 3.06 (s, 3H). |
| 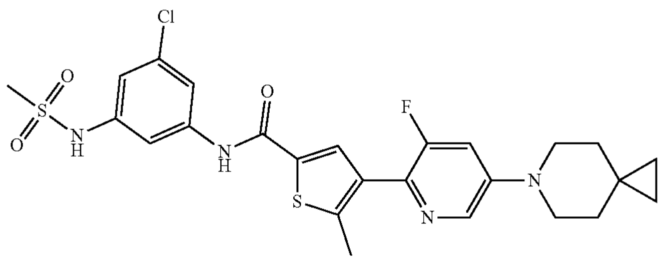 [SMILES: Cc1sc(C(=O)Nc2cc(Cl)cc(NS(C)(=O)=O)c2)cc1-c1ncc(N2CCC3(CC2)CC3)cc1F] | 467 | 549.1 | 1H NMR (300 MHz, DMSO-d6) δ 10.42 (s, 1H), 10.07 (s, 1H), 8.30 (s, 1H), 8.15 (s, 1H), 7.72-7.59 (m, 2H), 7.46-7.33 (m, 1H), 6.95 (t, J = 2.0 Hz, 1H), 3.42 (t, J = 5.5 Hz, 4H), 3.07 (s, 3H), 2.52 (s, 3H), 1.46 (t, J = 5.5 Hz, 4H), 0.37 (s, 4H). |
| 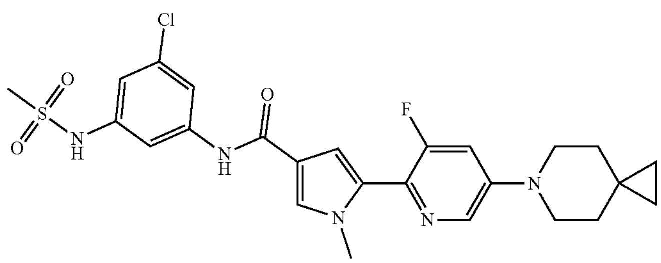 [SMILES: Cn1cc(C(=O)Nc2cc(Cl)cc(NS(C)(=O)=O)c2)cc1-c1ncc(N2CCC3(CC2)CC3)cc1F] | 468 | 532.15 | 1H NMR (300 MHz, DMSO-d6) δ 10.01 (s, 1H), 9.83 (s, 1H), 8.25 (t, J = 2.0 Hz, 1H), 7.73 (t, J = 1.8 Hz, 1H), 7.68-7.57 (m, 2H), 7.38 (dd, J = 14.5, 2.4 Hz, 1H), 7.00 (dd, J = 3.2, 1.9 Hz, 1H), 6.90 (t, J = 1.9 Hz, 1H), 3.84 (s, 3H), 3.40 (dd, J = 6.7, 4.4 Hz, 4H), 3.07 (s, 3H), 1.50-1.41 (m, 4H), 0.37 (s, 4H). |
| 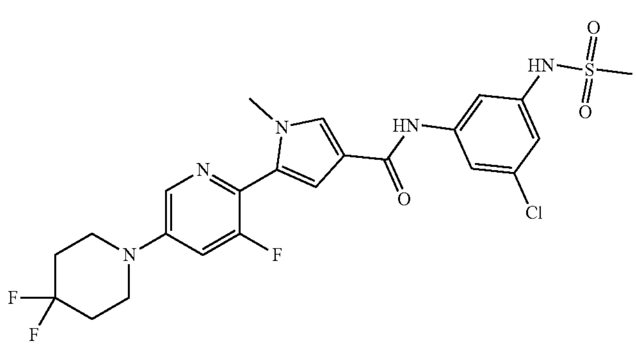 [SMILES: Cn1cc(C(=O)Nc2cc(Cl)cc(NS(C)(=O)=O)c2)cc1-c1ncc(N2CCC(F)(F)CC2)cc1F] | 469 | 541.95 | 1H NMR (300 MHz, DMSO-d6) δ 10.02 (s, 1H), 9.84 (s, 1H), 8.31 (t, J = 2.0 Hz, 1H), 7.80-7.59 (m, 3H), 7.49 (dd, J = 14.2, 2.5 Hz, 1H), 7.03 (dd, J = 3.3, 1.9 Hz, 1H), 6.89 (t, J = 1.9 Hz, 1H), 3.85 (s, 3H), 3.52 (t, J = 5.8 Hz, 4H), 3.06 (s, |

| Structure | Compound No. | MS (ESI) [M + H]+ | 1H NMR |
|---|---|---|---|
| | | | 3H), 2.13 (d, J = 6.3 Hz, 1H), 2.08 (s, 1H), 2.06-1.98 (m, 2H). |
| 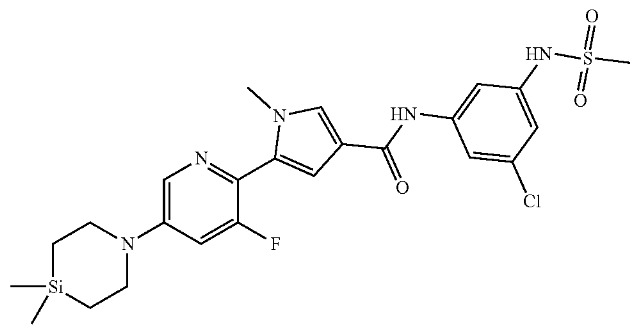 | 470 | 550 | 1H NMR (300 MHz, DMSO-d6) δ 10.02 (s, 1H), 9.82 (s, 1H), 8.14 (t, J = 2.1 Hz, 1H), 7.72 (t, J = 1.9 Hz, 1H), 7.65 (d, J = 1.8 Hz, 2H), 7.24 (dd, J = 14.5, 2.4 Hz, 1H), 6.97 (dd, J = 3.2, 1.9 Hz, 1H), 6.90 (t, J = 2.0 Hz, 1H), 3.85 (s, 3H), 3.73 (t, J = 6.3 Hz, 4H), 3.07 (s, 3H), 0.77 (dd, J = 7.4, 4.6 Hz, 4H), 0.11 (s, 6H). |
| 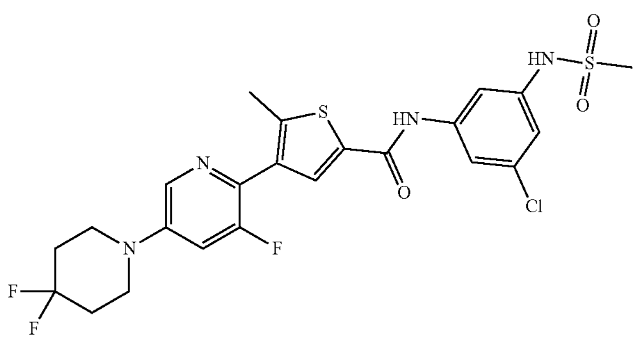 [SMILES: Cc1sc(C(=O)Nc2cc(Cl)cc(NS(C)(=O)=O)c2)cc1-c1ncc(N2CCC(F)(F)CC2)cc1F] | 471 | 559.05 | 1H NMR (300 MHz, DMSO-d6) δ 10.43 (s, 1H), 10.07 (s, 1H), 8.36 (t, J = 2.0 Hz, 1H), 8.15 (d, J = 1.6 Hz, 1H), 7.66 (dt, J = 10.7, 1.9 Hz, 2H), 7.50 (dd, J = 13.9, 2.4 Hz, 1H), 6.95 (t, J = 2.0 Hz, 1H), 3.54 (t, J = 5.8 Hz, 4H), 3.07 (s, 3H), 2.51 (s, 3H), 2.10 (td, J = 13.5, 12.8, 7.3 Hz, 4H). |
| 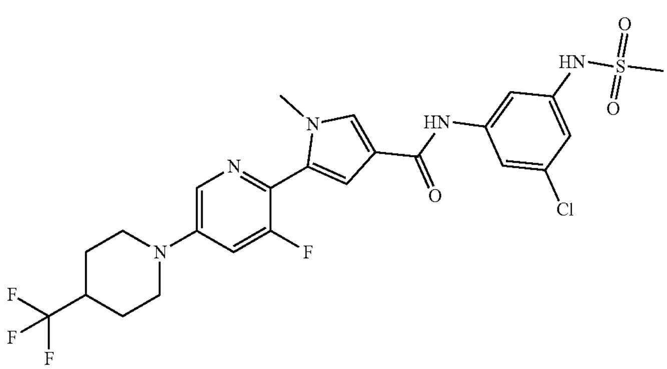 [SMILES: Cn1cc(C(=O)Nc2cc(Cl)cc(NS(C)(=O)=O)c2)cc1-c1ncc(N2CCC(C(F)(F)F)CC2)cc1F] | 472 | 574.2 | 1H NMR (300 MHz, DMSO-d6) δ 10.01 (s, 1H), 9.83 (s, 1H), 8.25 (d, J = 2.1 Hz, 1H), 7.72 (t, J = 1.9 Hz, 1H), 7.70-7.56 (m, 2H), 7.42 (dd, J = 14.3, 2.4 Hz, 1H), 7.02 (dd, J = 3.3, 1.9 Hz, 1H), 6.89 (t, J = 1.9 Hz, 1H), 4.00 (d, J = 13.0 Hz, 2H), 3.84 (s, 3H), 3.06 (s, 3H), 2.89 (t, J = 12.5 Hz, 2H), 2.60 (d, J = 8.7 Hz, 1H), 1.89 (d, J = 12.9 Hz, 2H), 1.55 (tt, J = 13.1, 6.5 Hz, 2H). |

-continued

| Structure | Compound No. | MS (ESI) [M + H]+ | 1H NMR |
|---|---|---|---|
| 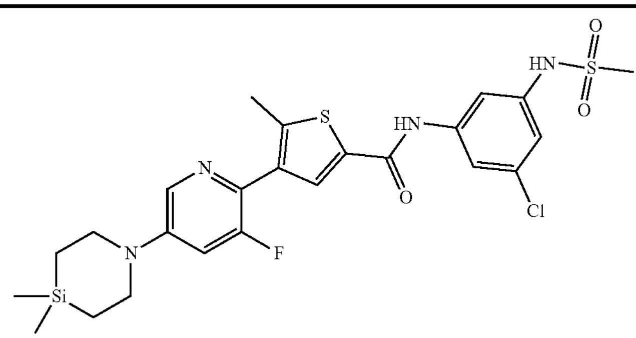 | 473 | 567.2 | 1H NMR (400 MHz, DMSO-d6) δ 10.29 (s, 1H), 9.95 (s, 1H), 8.22-7.96 (m, 2H), 7.54 (dt, J = 14.9, 1.9 Hz, 2H), 7.14 (dd, J = 14.5, 2.5 Hz, 1H), 6.84 (t, J = 1.9 Hz, 1H), 3.63 (t, J = 6.3 Hz, 4H), 2.96 (s, 3H), 2.42 (S, 3H), 0.66 (dd, J = 7.5, 4.9 Hz, 4H), 0.00 (s, 6H). |
| 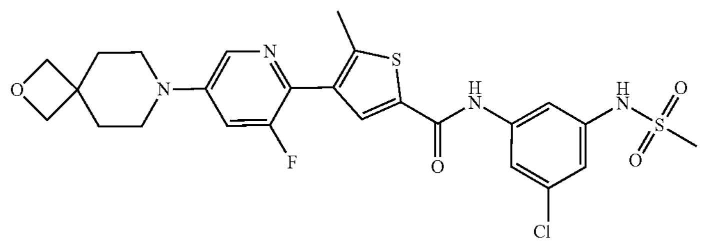 [SMILES: Cc1sc(C(=O)Nc2cc(Cl)cc(NS(C)(=O)=O)c2)cc1-c1ncc(N2CCC3(CC2)COC3)cc1F] | 474 | 565.15 [M − H]− | 1H NMR (400 MHz, DMSO-d6) δ 10.41 (s, 1H), 10.06 (s, 1H), 8.28 (t, J = 2.1 Hz, 1H), 8.13 (d, J = 1.6 Hz, 1H), 7.65 (dt, J = 14.5, 1.9 Hz, 2H), 7.39 (dd, J = 14.1, 2.5 Hz, 1H), 6.94 (t, J = 1.9 Hz, 1H), 4.36 (s, 4H), 3.32-3.28 (m, 4H), 3.06 (s, 3H), 2.51 (s, 3H), 1.96-1.83 (m, 4H). |
| 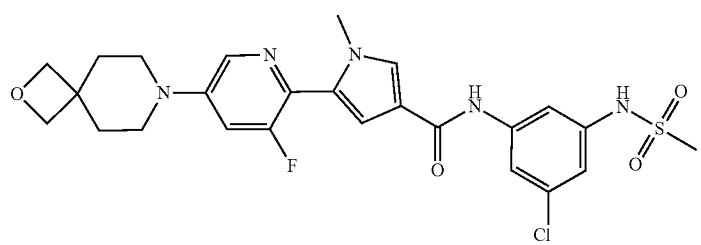 [SMILES: Cn1cc(C(=O)Nc2cc(Cl)cc(NS(C)(=O)=O)c2)cc1-c1ncc(N2CCC3(CC2)COC3)cc1F] | 475 | 548.15 | 1H NMR (400 MHz, DMSO-d6) δ 10.02 (s, 1H), 9.82 (s, 1H), 8.23 (d, J = 2.1 Hz, 1H), 7.86-7.53 (m, 3H), 7.38 (dd, J = 14.4, 2.4 Hz, 1H), 7.06-6.78 (m, 2H), 4.35 (s, 4H), 3.83 (s, 3H), 3.31-3.16 (m, 4H), 3.05 (s, 3H), 2.01-1.68 (m, 4H). |
| 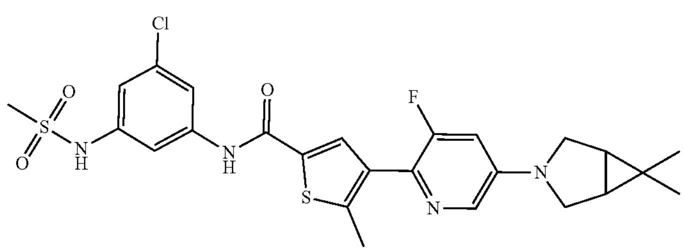 | 476 | 549.1 | 1H NMR (400 MHz, DMSO-d6) δ 10.40 (s, 1H), 10.05 (s, 1H), 8.10 (s, 1H), 7.85 (s, 1H), 7.65 (d, J = 14.4 Hz, 2H), 6.94 (s, 1H), 6.87 (d, J = 13.5 Hz, 1H), 3.49 (d, J = 10.2 Hz, 2H), 3.28 (s, 2H), 3.06 (s, 3H), 2.48 (s, 3H), 1.59 (s, 2H), 1.07 (s, 3H), 0.83 (s, 3H). |

-continued

| Structure | Compound No. | MS (ESI) [M + H]+ | 1H NMR |
|---|---|---|---|
| 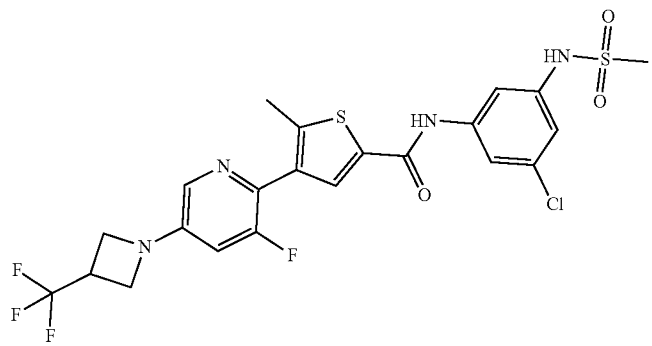 [SMILES: Cc1sc(C(=O)Nc2cc(Cl)cc(NS(C)(=O)=O)c2)cc1-c1ncc(N2CC(C(F)(F)F)C2)cc1F] | 477 | 563.1 | 1H NMR (400 MHz, DMSO-d6) δ 10.40 (s, 1H), 10.05 (s, 1H), 8.12 (d, J = 1.6 Hz, 1H), 7.87 (t, J = 2.0 Hz, 1H), 7.65 (dt, J = 14.8, 1.9 Hz, 2H), 7.02 (dd, J = 12.4, 2.3 Hz, 1H), 6.94 (t, J = 1.9 Hz, 1H), 4.22 (t, J = 8.6 Hz, 2H), 4.03 (dd, J = 8.7, 5.1 Hz, 2H), 3.79 (d, J = 9.3 Hz, 1H), 3.06 (s, 3H), 2.48 (d, J = 1.3 Hz, 3H). |
| 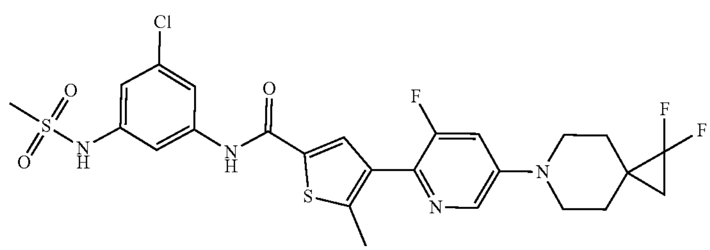 [SMILES: Cc1sc(C(=O)Nc2cc(Cl)cc(NS(C)(=O)=O)c2)cc1-c1ncc(N2CCC3(CC2)CC3(F)F)cc1F] | 478 | 585.1 | 1H NMR (400 MHz, DMSO-d6) δ 10.42 (s, 1H), 10.06 (s, 1H), 8.41-8.27 (m, 1H), 8.14 (d, J = 1.6 Hz, 1H), 7.65 (dt, J = 14.9, 1.9 Hz, 2H), 7.43 (dd, J = 14.1, 2.5 Hz, 1H), 6.94 (t, J = 2.0 Hz, 1H), 3.47 (ddd, J = 10.8, 6.7, 3.9 Hz, 2H), 3.43-3.35 (m, 2H), 3.06 (s, 3H), 2.51 (s, 3H), 1.83-1.71 (m, 2H), 1.64 (s, 2H), 1.37 (t, J = 8.7 Hz, 2H). |
| 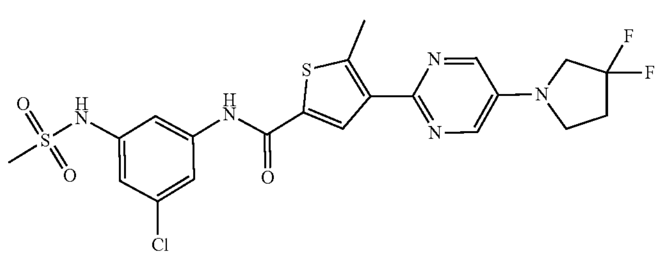 [SMILES: Cc1sc(C(=O)Nc2cc(Cl)cc(NS(C)(=O)=O)c2)cc1-c1ncc(N2CCC(F)(F)C2)cn1] | 479 | 528.05 | 1H NMR (400 MHz, DMSO-d6) δ 10.55 (s, 1H), 10.06 (s, 1H), 8.60 (s, 1H), 8.32 (s, 2H), 7.69 (p, J = 1.9 Hz, 2H), 6.94 (t, J = 1.9 Hz, 1H), 3.87 (t, J = 13.2 Hz, 2H), 3.64 (t, J = 7.3 Hz, 2H), 3.07 (s, 3H), 2.82 (s, 3H), 2.58 (dp, J = 14.8, 7.4 Hz, 2H). |

| Structure | Compound No. | MS (ESI) [M + H]+ | 1H NMR |
|---|---|---|---|
| 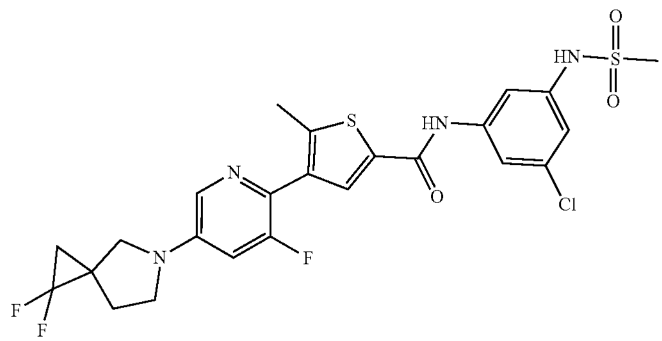 [SMILES: Cc1sc(C(=O)Nc2cc(Cl)cc(NS(C)(=O)=O)c2)cc1-c1ncc(N2CCC3(C2)CC3(F)F)cc1F] | 480 | 571.1 | 1H NMR (400 MHz, DMSO-d6) δ 10.41 (s, 1H), 10.06 (s, 1H), 8.13 (d, J = 1.6 Hz, 1H), 7.95 (t, J = 2.1 Hz, 1H), 7.66 (dt, J = 14.2, 1.9 Hz, 2H), 7.02 (dd, J = 13.4, 2.4 Hz, 1H), 6.94 (t, J = 1.9 Hz, 1H), 3.63-3.50 (m, 3H), 3.46 (dd, J = 10.3, 4.9 Hz, 1H), 3.06 (s, 3H), 2.49 (s, 3H), 2.25 (dt, J = 13.4, 6.8 Hz, 1H), 2.15 (dt, J = 12.7, 6.4 Hz, 1H), 1.69 (dd, J = 11.2, 7.3 Hz, 2H). |
| 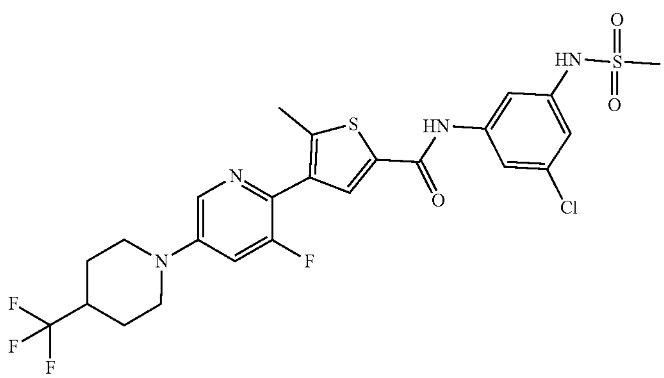 [SMILES: Cc1sc(C(=O)Nc2cc(Cl)cc(NS(C)(=O)=O)c2)cc1-c1ncc(N2CCC(C(F)(F)F)CC2)cc1F] | 481 | 591.05 | 1H NMR (300 MHz, DMSO-d6) δ 10.42 (s, 1H), 10.07 (s, 1H), 8.31 (d, J = 2.4 Hz, 1H), 8.15 (d, J = 1.6 Hz, 1H), 7.66 (dt, J = 11.4, 1.9 Hz, 2H), 7.43 (dd, J = 14.1, 2.4 Hz, 1H), 6.95 (t, J = 1.9 Hz, 1H), 4.03 (d, J = 13.1 Hz, 2H), 3.07 (s, 3H), 2.91 (t, J = 12.1 Hz, 2H), 2.70-2.57 (m, 1H), 2.52 (s, 3H), 1.91 (d, J = 12.8 Hz, 2H), 1.65-1.44 (m, 2H). |
| 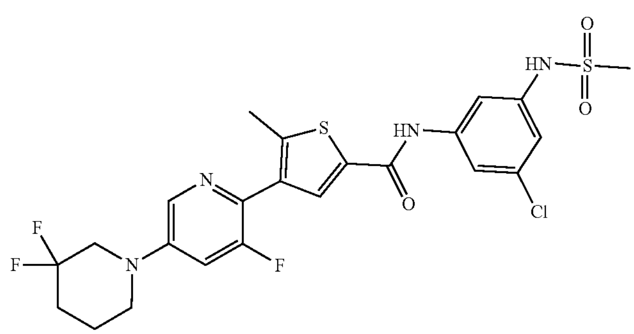 [SMILES: Cc1sc(C(=O)Nc2cc(Cl)cc(NS(C)(=O)=O)c2)cc1-c1ncc(N2CCCC(F)(F)C2)cc1F] | 482 | 559.05 | 1H NMR (300 MHz, DMSO-d6) δ 10.42 (s, 1H), 10.07 (s, 1H), 8.34 (s, 1H), 8.15 (s, 1H), 7.73-7.61 (m, 2H), 7.50 (dd, J = 13.9, 2.4 Hz, 1H), 6.95 (t, J = 1.9 Hz, 1H), 3.75 (t, J = 11.9 Hz, 2H), 3.46 (s, 2H), 3.07 (s, 3H), 2.52 (s, 3H), 2.10 (dt, J = 14.4, 7.4 Hz, 2H), 1.81 (s, 2H). |

| Structure | Compound No. | MS (ESI) [M + H]+ | 1H NMR |
|---|---|---|---|
| 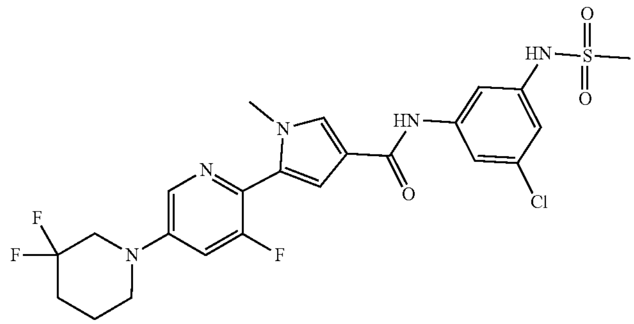 [SMILES: Cn1cc(C(=O)Nc2cc(Cl)cc(NS(C)(=O)=O)c2)cc1-c1ncc(N2CCCC(F)(F)C2)cc1F] | 483 | 542.2 | 1H NMR (300 MHz, DMSO-d6) δ 10.02 (s, 1H), 9.84 (s, 1H), 8.29 (d, J = 2.0 Hz, 1H), 7.72 (t, J = 1.9 Hz, 1H), 7.69-7.60 (m, 2H), 7.49 (dd, J = 14.3, 2.4 Hz, 1H), 7.02 (dd, J = 3.2, 1.9 Hz, 1H), 6.89 (t, J = 1.9 Hz, 1H), 3.84 (s, 3H), 3.81-3.66 (m, 2H), 3.44 (t, J = 5.4 Hz, 2H), 3.06 (s, 3H), 2.08 (dp, J = 18.1, 6.3 Hz, 2H), 1.79 (s, 2H). |
| 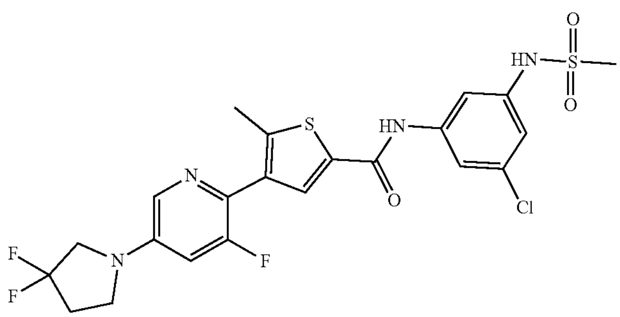 [SMILES: Cc1sc(C(=O)Nc2cc(Cl)cc(NS(C)(=O)=O)c2)cc1-c1ncc(N2CCC(F)(F)C2)cc1F] | 484 | 545 | 1H NMR (400 MHz, DMSO-d6) δ 10.41 (s, 1H), 10.08 (s, 1H), 8.13 (d, J = 1.6 Hz, 1H), 7.99 (t, J = 2.0 Hz, 1H), 7.64 (dt, J = 15.3, 1.9 Hz, 2H), 7.10 (dd, J = 13.3, 2.4 Hz, 1H), 6.94 (t, J = 1.9 Hz, 1H), 3.85 (t, J = 13.2 Hz, 2H), 3.61 (t, J = 7.3 Hz, 2H), 3.05 (s, 3H), 2.71-2.52 (m, 2H), 2.49 (s, 3H). |
| 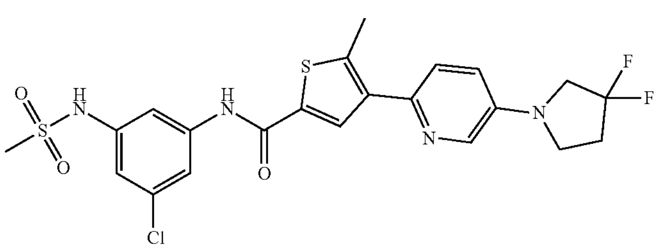 [SMILES: Cc1sc(C(=O)Nc2cc(Cl)cc(NS(C)(=O)=O)c2)cc1-c1ccc(N2CCC(F)(F)C2)cn1] | 485 | 527.05 | 1H NMR (400 MHz, DMSO-d6) δ10.41 (s, 1H), 10.07 (s, 1H), 8.32 (s, 1H), 8.10 (d, J = 3.0 Hz, 1H), 7.66 (dt, J = 12.3, 1.9 Hz, 2H), 7.53 (d, J = 8.7 Hz, 1H), 7.14 (dd, J = 8.7, 3.0 Hz, 1H), 6.94 (t, J = 1.9 Hz, 1H), 3.82 (t, J = 13.3 Hz, 2H), 3.59 (t, J = 7.2 Hz, 2H), 3.07 (s, 3H), 2.66 (s, 3H), 2.58 (dq, J = 14.5, 7.2 Hz, 2H). |

| Structure | Compound No. | MS (ESI) [M + H]+ | 1H NMR |
|---|---|---|---|
| 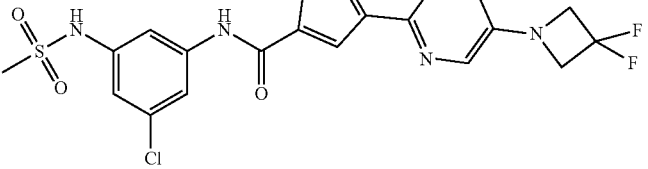 | 486 | 500.05 | 1H NMR (400 MHz, DMSO-d6) δ 10.64 (s, 1H), 10.08 (s, 1H), 8.74 (d, J = 1.3 Hz, 1H), 8.43 (d, J = 1.2 Hz, 1H), 8.26 (s, 2H), 7.70 (p, J = 1.9 Hz, 2H), 6.96 (t, J = 1.9 Hz, 1H), 4.50 (t, J = 12.3 Hz, 4H), 3.08 (s, 3H). |
| 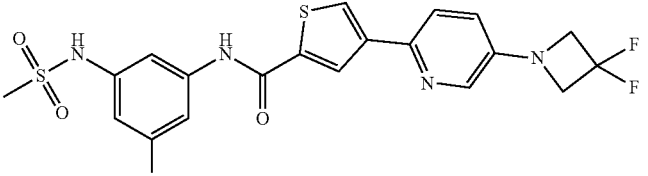 | 487 | 498.9 | 1H NMR (400 MHz, DMSO-d6) δ 10.58 (s, 1H), 10.09 (s, 1H), 8.64 (d, J = 1.4 Hz, 1H), 8.28 (d, J = 1.3 Hz, 1H), 7.99 (d, J = 2.8 Hz, 1H), 7.78 (d, J = 8.5 Hz, 1H), 7.73-7.62 (m, 2H), 7.11 (dd, J = 8.6, 2.9 Hz, 1H), 6.96 (t, J = 2.0 Hz, 1H), 4.41 (t, J = 12.3 Hz, 4H), 3.08 (s, 3H). |
| 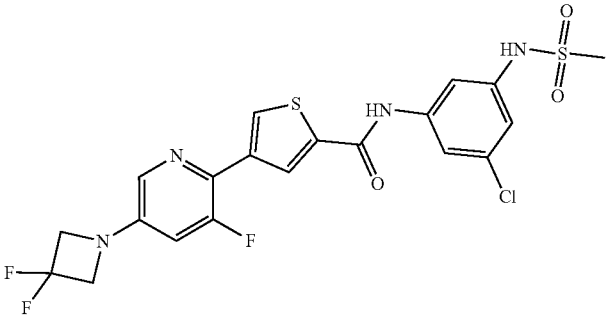 [SMILES: CS(=O)(=O)Nc1cc(Cl)cc(NC(=O)c2cc(-c3ncc(N4CC(F)(F)C4)cc3F)cs2)c1] | 488 | 516.85 | 1H NMR (400 MHz, DMSO-d6) δ 10.64 (s, 1H), 10.13 (s, 1H), 8.65 (d, J = 1.4 Hz, 1H), 8.20 (t, J = 1.5 Hz, 1H), 7.90 (t, J = 2.0 Hz, 1H), 7.68 (p, J = 1.9 Hz, 2H), 7.12 (dd, J = 13.3, 2.4 Hz, 1H), 6.95 (t, J = 2.0 Hz, 1H), 4.46 (t, J = 12.3 Hz, 4H), 3.07 (s, 3H). |
| 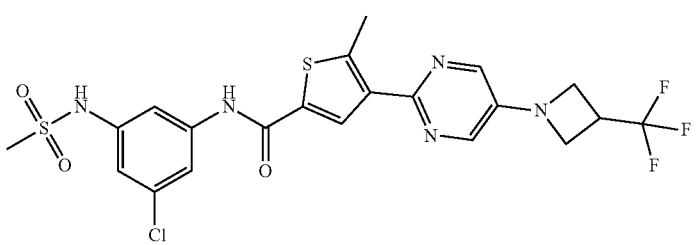 [SMILES: Cc1sc(C(=O)Nc2cc(Cl)cc(NS(C)(=O)=O)c2)cc1-c1ncc(N2CC(C(F)(F)F)C2)cn1] | 489 | 546.15 | 1H NMR (400 MHz, DMSO-d6) δ 10.55 (s, 1H), 10.05 (s, 1H), 8.60 (s, 1H), 8.23 (s, 2H), 7.68 (dt, J = 4.8, 1.9 Hz, 2H), 6.94 (t, J = 2.0 Hz, 1H), 4.26 (t, J = 8.6 Hz, 2H), 4.07 (dd, J = 8.6, 5.1 Hz, 2H), 3.80 (dt, J = 9.4, 4.8 Hz, 1H), 3.07 (s, 3H), 2.81 (s, 3H). |

-continued
| Structure | Compound No. | MS (ESI) [M + H]+ | 1H NMR |
|---|---|---|---|
| 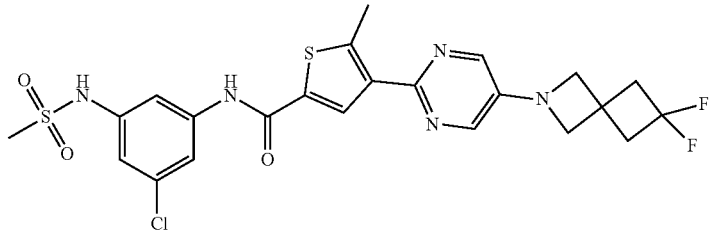 [SMILES: Cc1sc(C(=O)Nc2cc(Cl)cc(NS(C)(=O)=O)c2)cc1-c1ncc(N2CC3(C2)CC(F)(F)C3)cn1] | 490 | 533.9 | 1H NMR (400 MHz, DMSO-d6) δ 10.54 (s, 1H), 10.05 (s, 1H), 8.59 (s, 1H), 8.16 (s, 2H), 7.68 (dt, J = 5.4, 1.9 Hz, 2H), 6.94 (t, J = 1.9 Hz, 1H), 4.11 (s, 4H), 3.07 (s, 3H), 2.89 (t, J = 12.5 Hz, 4H), 2.80 (s, 3H). |
| 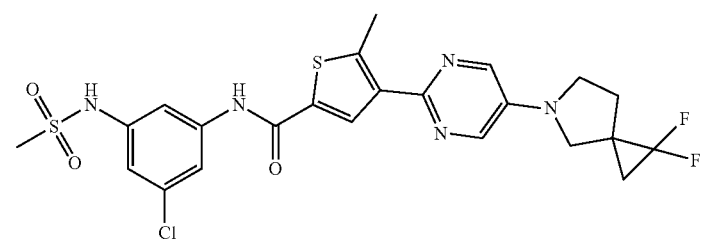 [SMILES: Cc1sc(C(=O)Nc2cc(Cl)cc(NS(C)(=O)=O)c2)cc1-c1ncc(N2CCC3(C2)CC3(F)F)cn1] | 491 | 544.15 | 1H NMR (400 MHz, DMSO-d6) δ 10.55 (s, 1H), 10.05 (s, 1H), 8.60 (s, 1H), 8.27 (s, 2H), 7.69 (dt, J = 5.2, 1.9 Hz, 2H), 6.94 (t, J = 1.9 Hz, 1H), 3.68-3.53 (m, 3H), 3.47 (dd, J = 10.2, 4.8 Hz, 1H), 3.07 (s, 3H), 2.81 (s, 3H), 2.20 (ddt, J = 44.1, 12.2, 6.4 Hz, 2H), 1.69 (dd, J = 11.2, 7.4 Hz, 2H). |
| 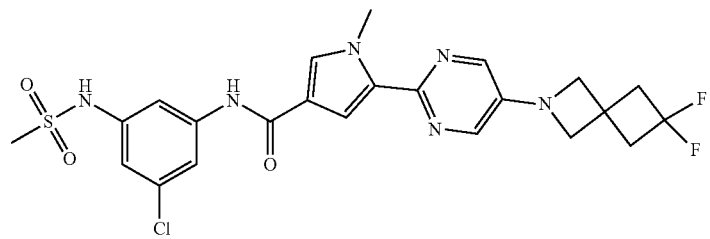 [SMILES: Cn1cc(C(=O)Nc2cc(Cl)cc(NS(C)(=O)=O)c2)cc1-c1ncc(N2CC3(C2)CC(F)(F)C3)cn1] | 492 | 537.15 | 1H NMR (400 MHz, DMSO-d6) δ 9.99 (s, 1H), 9.88 (s, 1H), 8.19-7.94 (m, 2H), 7.84-7.53 (m, 3H), 7.45 (t, J = 1.7 Hz, 1H), 6.98-6.62 (m, 1H), 4.25-3.82 (m, 7H), 3.06 (d, J = 1.0 Hz, 3H), 2.88 (t, J = 12.5 Hz, 4H). |
| 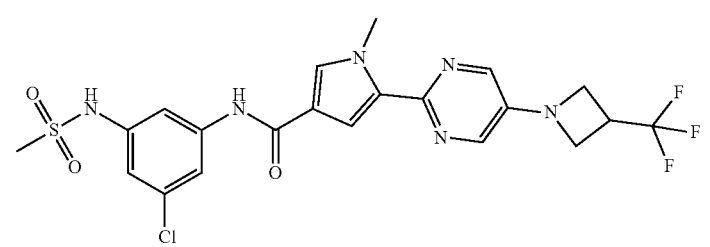 [SMILES: Cn1cc(C(=O)Nc2cc(Cl)cc(NS(C)(=O)=O)c2)cc1-c1ncc(N2CC(C(F)(F)F)C2)cn1] | 493 | 529.05 | 1H NMR (400 MHz, DMSO-d6) δ 9.90 (d, J = 2.2 Hz, 2H), 8.17 (d, J = 1.3 Hz, 2H), 7.75 (h, J = 1.3 Hz, 1H), 7.68 (q, J = 1.7 Hz, 1H), 7.62 (d, J = 2.1 Hz, 1H), 7.48 (d, J = 2.2 Hz, 1H), 6.90 (q, J = 2.3 Hz, 1H), 4.23 (t, J = 8.6 Hz, 2H), 4.04 (d, J = 9.5 Hz, 5H), 3.80 (dtt, J = 14.1, 9.3, 5.4 Hz, 1H), 3.07 (d, J = 2.3 Hz, 3H). |

-continued

| Structure | Compound No. | MS (ESI) [M + H]+ | 1H NMR |
|---|---|---|---|
| 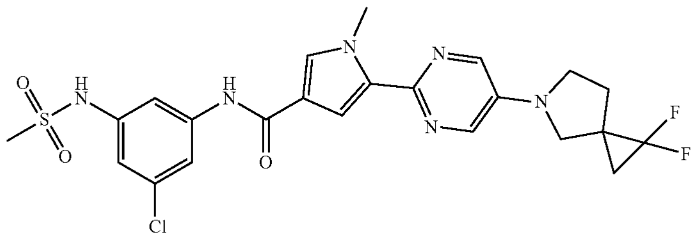 [SMILES: Cn1cc(C(=O)Nc2cc(Cl)cc(NS(C)(=O)=O)c2)cc1-c1ncc(N2CCC3(C2)CC3(F)F)cn1] | 494 | 537.05 | 1H NMR (400 MHz, DMSO-d6) δ 10.02 (s, 1H), 9.87 (s, 1H), 8.22 (s, 2H), 7.70 (dt, J = 27.3, 1.9 Hz, 2H), 7.60 (d, J = 2.1 Hz, 1H), 7.43 (d, J = 2.1 Hz, 1H), 6.88 (t, J = 2.0 Hz, 1H), 4.03 (s, 3H), 3.61-3.49 (m, 3H), 3.47-3.40 (m, 1H), 3.06 (s, 3H), 2.25 (dt, J = 13.3, 6.9 Hz, 1H), 2.12 (ddd, J = 16.4, 11.6, 5.1 Hz, 1H), 1.77-1.56 (m, 2H). |
| 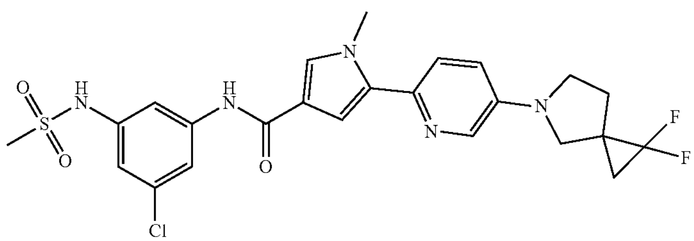 [SMILES: Cn1cc(C(=O)Nc2cc(Cl)cc(NS(C)(=O)=O)c2)cc1-c1ccc(N2CCC3(C2)CC3(F)F)cn1] | 495 | 536.2 | 1H NMR (400 MHz, DMSO-d6) δ 10.01 (s, 1H), 9.77 (s, 1H), 8.00 (d, J = 2.9 Hz, 1H), 7.72 (t, J = 1.9 Hz, 1H), 7.66-7.56 (m, 2H), 7.51 (d, J = 8.7 Hz, 1H), 7.06 (dd, J = 8.8, 2.9 Hz, 1H), 6.97 (d, J = 2.0 Hz, 1H), 6.88 (t, J = 1.9 Hz, 1H), 3.91 (s, 3H), 3.61-3.38 (m, 4H), 3.06 (s, 3H), 2.24 (dt, J = 13.3, 6.7 Hz, 1H), 2.16-2.08 (m, 1H), 1.75-1.56 (m, 2H). |
| 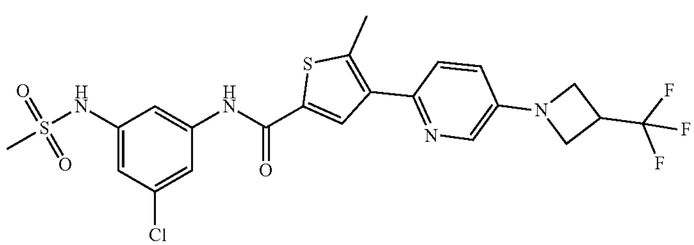 [SMILES: Cc1sc(C(=O)Nc2cc(Cl)cc(NS(C)(=O)=O)c2)cc1-c1ccc(N2CC(C(F)(F)F)C2)cn1] | 496 | 545.15 | 1H NMR (400 MHz, DMSO-d6) δ 10.41 (s, 1H), 10.07 (s, 1H), 8.31 (s, 1H), 7.98 (d, J = 2.9 Hz, 1H), 7.66 (dt, J = 13.1, 1.9 Hz, 2H), 7.52 (d, J = 8.5 Hz, 1H), 7.04 (dd, J = 8.6, 2.9 Hz, 1H), 6.94 (t, J = 2.0 Hz, 1H), 4.18 (t, J = 8.5 Hz, 2H), 4.00 (dd, J = 8.5, 5.1 Hz, 2H), 3.86-3.68 (m, 1H), 3.06 (s, 3H), 2.65 (s, 3H). |

| Structure | Compound No. | MS (ESI) [M + H]+ | 1H NMR |
|---|---|---|---|
| 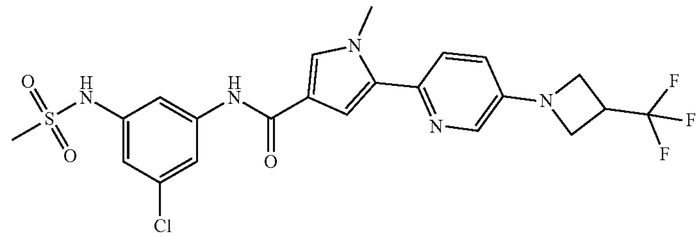 [SMILES: Cn1cc(C(=O)Nc2cc(Cl)cc(NS(C)(=O)=O)c2)cc1-c1ccc(N2CC(C(F)(F)F)C2)cn1] | 497 | 528.05 | 1H NMR (400 MHz, DMSO-d6) δ 10.00 (s, 1H), 9.78 (s, 1H), 7.92 (d, J = 2.9 Hz, 1H), 7.78-7.38 (m, 4H), 7.07-6.95 (m, 2H), 6.89 (t, J = 1.9 Hz, 1H), 4.16 (t, J = 8.4 Hz, 2H), 3.97 (dd, J = 8.4, 5.2 Hz, 2H), 3.91 (s, 3H), 3.76 (ddq, J = 14.1, 9.4, 5.0 Hz, 1H), 3.06 (s, 3H). |
| 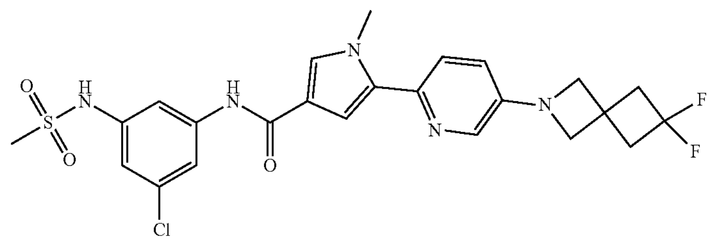 | 498 | 536.05 | 1H NMR (400 MHz, DMSO-d6) δ 10.02 (s, 1H), 9.77 (s, 1H), 7.86 (d, J = 2.8 Hz, 1H), 7.72 (t, J = 1.9 Hz, 1H), 7.65-7.56 (m, 2H), 7.49 (d, J = 8.6 Hz, 1H), 7.01-6.84 (m, 3H), 4.01 (s, 4H), 3.90 (s, 3H), 3.06 (s, 3H), 2.88 (t, J = 12.5 Hz, 4H). |
| 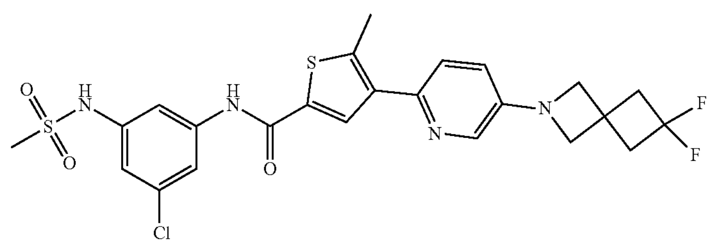 [SMILES: Cc1sc(C(=O)Nc2cc(Cl)cc(NS(C)(=O)=O)c2)cc1-c1ccc(N2CC3(C2)CC(F)(F)C3)cn1] | 499 | 553.05 | 1H NMR (400 MHz, DMSO-d6) δ 10.40 (s, 1H), 10.09 (s, 1H), 8.29 (s, 1H), 7.98-7.84 (m, 1H), 7.65 (dt, J = 12.9, 1.9 Hz, 2H), 7.53-7.44 (m, 1H), 7.04-6.87 (m, 2H), 4.03 (s, 4H), 3.06 (s, 3H), 2.89 (t, J = 12.5 Hz, 4H), 2.64 (s, 3H). |
| 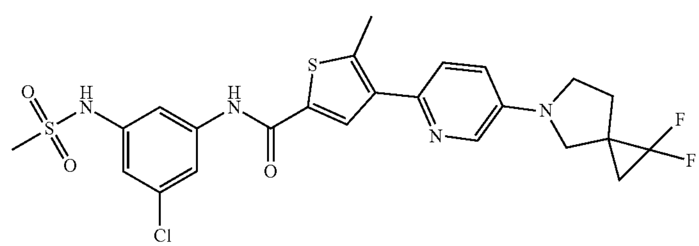 [SMILES: Cc1sc(C(=O)Nc2cc(Cl)cc(NS(C)(=O)=O)c2)cc1-c1ccc(N2CCC3(C2)CC3(F)F)cn1] | 500 | 533.05 | 1H NMR (400 MHz, DMSO-d6) δ 10.41 (s, 1H), 10.07 (s, 1H), 8.31 (s, 1H), 8.06 (d, J = 3.0 Hz, 1H), 7.66 (dt, J = 12.4, 1.9 Hz, 2H), 7.51 (d, J = 8.7 Hz, 1H), 7.09 (dd, J = 8.7, 3.0 Hz, 1H), 6.94 (t, J = 1.9 Hz, 1H), 3.61-3.48 (m, 3H), 3.43 (dd, J = 10.1, 4.9 Hz, 1H), 3.07 (s, 3H), 2.66 (s, 3H), 2.25 (dt, J = 12.8, 6.7 Hz, |

| Structure | Compound No. | MS (ESI) [M + H]+ | 1H NMR |
|---|---|---|---|
| | | | 1H), 2.13 (dq, J = 12.7, 6.4 Hz, 1H), 1.68 (dq, J = 13.1, 8.2, 6.5 Hz, 2H). |
| 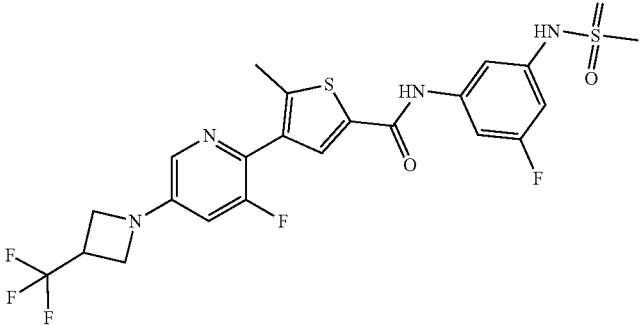 | 501 | 547.05 | 1H NMR (400 MHz, DMSO-d6) δ 10.43 (s, 1H), 10.07 (s, 1H), 8.12 (d, J = 1.6 Hz, 1H), 7.86 (d, J = 2.0 Hz, 1H), 7.45 (dd, J = 10.2, 2.1 Hz, 2H), 7.02 (dd, J = 12.5, 2.3 Hz, 1H), 6.72 (dt, J = 10.4, 2.2 Hz, 1H), 4.22 (t, J = 8.6 Hz, 2H), 4.03 (dd, J = 8.7, 5.1 Hz, 2H), 3.79 (ddq, J = 14.2, 9.5, 5.1 Hz, 1H), 3.06 (s, 3H), 2.49-2.47 (S, 3H). |
| 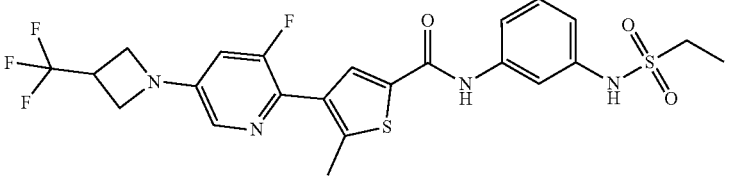 | 502 | 557.1 | 1H NMR (400 MHz, DMSO-d6) δ 10.40 (s, 1H), 10.09 (s, 1H), 8.12 (s, 1H), 7.86 (d, J = 2.3 Hz, 1H), 7.72-7.59 (m, 2H), 7.02 (dd, J = 12.4, 2.3 Hz, 1H), 6.95 (d, J = 2.2 Hz, 1H), 4.22 (t, J = 8.6 Hz, 2H), 4.03 (dd, J = 8.7, 5.1 Hz, 2H), 3.79 (ddq, J = 14.2, 9.5, 5.1 Hz, 1H), 3.17 (q, J = 7.3 Hz, 2H), 2.48 (s, 3H), 1.21 (t, J = 7.3 Hz, 3H). |
| 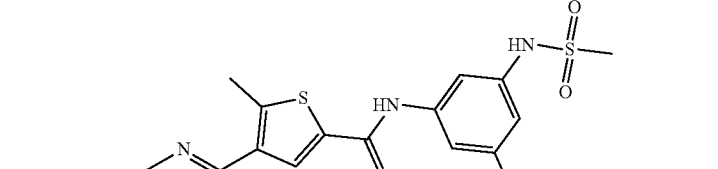 | 503 | 573.3 | 1H NMR (400 MHz, DMSO-d6) δ 10.36 (s, 1H), 10.08 (s, 1H), 8.35 (d, J = 2.4 Hz, 1H), 8.21 (s, 1H), 7.66 (tt, J = 11.6, 2.4 Hz, 3H), 6.94 (d, J = 2.2 Hz, 1H), 3.38-3.31 (m, 4H), 3.10 (d, J = 5.3 Hz, 4H), 3.06 (s, 3H), 2.44 (s, 3H). |

| Structure | Compound No. | MS (ESI) [M + H]+ | 1H NMR |
|---|---|---|---|
| 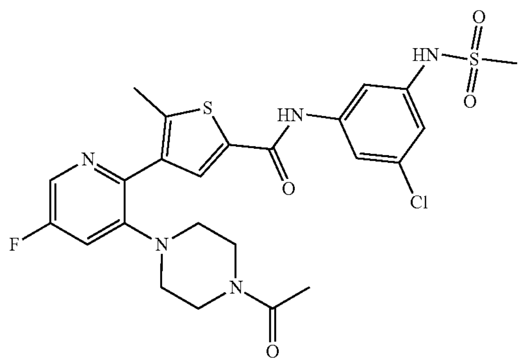 [SMILES: CC(=O)N1CCN(c2cc(F)cnc2-c2cc(C(=O)Nc3cc(Cl)cc(NS(C)(=O)=O)c3)sc2C)CC1] | 504 | 566.05 | 1H NMR (400 MHz, DMSO-d6) δ 10.36 (s, 1H), 10.07 (s, 1H), 8.31 (d, J = 2.4 Hz, 1H), 8.20 (s, 1H), 7.67 (t, J = 1.8 Hz, 1H), 7.62 (t, J = 1.9 Hz, 1H), 7.48 (dd, J = 10.9, 2.5 Hz, 1H), 6.94 (t, J = 1.9 Hz, 1H), 3.45 (d, J = 10.4 Hz, 1H), 3.38 (d, J = 9.9 Hz, 1H), 3.05 (s, 3H), 2.81 (p, J = 4.6 Hz, 4H), 2.44 (s, 3H), 1.96 (s, 3H). |
| 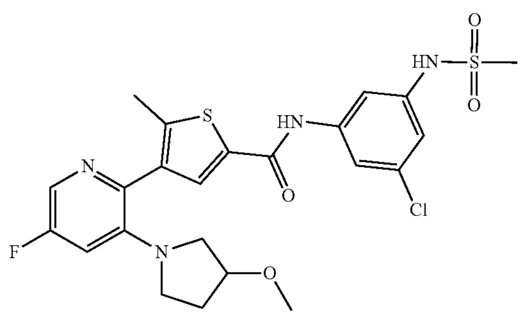 [SMILES: COC1CCN(c2cc(F)cnc2-c2cc(C(=O)Nc3cc(Cl)cc(NS(C)(=O)=O)c3)sc2C)C1] | 505 | 539.1 | 1H NMR (400 MHz, DMSO-d6) δ 10.36 (s, 1H), 10.10 (s, 1H), 8.07-7.98 (m, 2H), 7.67 (t, J = 1.9 Hz, 1H), 7.61 (d, J = 2.0 Hz, 1H), 7.16 (dd, J = 12.1, 2.5 Hz, 1H), 6.93 (d, J = 2.0 Hz, 1H), 3.95-3.90 (m, 1H), 3.16 (s, 3H), 3.05 (s, 4H), 3.11-3.00 (m, 1H), 3.00-2.91 (m, 1H), 2.84 (dd, J = 10.9, 2.0 Hz, 1H), 2.23 (s, 3H), 1.92 (td, J = 8.5, 8.0, 4.3 Hz, 2H). |
| 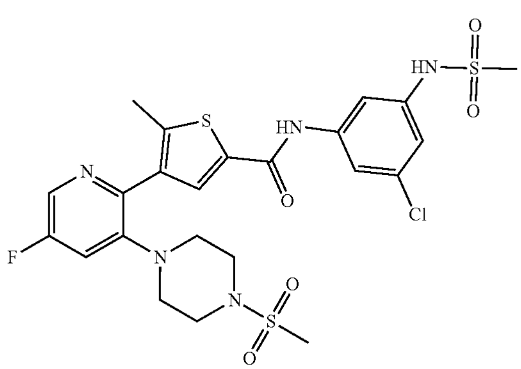 [SMILES: Cc1sc(C(=O)Nc2cc(Cl)cc(NS(C)(=O)=O)c2)cc1-c1ncc(F)cc1N1CCN(S(C)(=O)=O)CC1] | 506 | 602 | 1H NMR (400 MHz, DMSO-d6) δ 10.32 (s, 1H), 9.99 (s, 1H), 8.26 (d, J = 2.4 Hz, 1H), 8.13 (s, 1H), 7.62 (t, J = 1.9 Hz, 1H), 7.54 (t, J = 1.9 Hz, 1H), 7.47 (dd, J = 10.9, 2.6 Hz, 1H), 6.87 (t, J = 2.0 Hz, 1H), 3.07-3.00 (m, 4H), 2.99 (s, 3H), 2.87 (t, J = 4.9 Hz, 4H), 2.80 (s, 3H), 2.37 (s, 3H). |

-continued

| Structure | Compound No. | MS (ESI) [M + H]+ | 1H NMR |
|---|---|---|---|
| 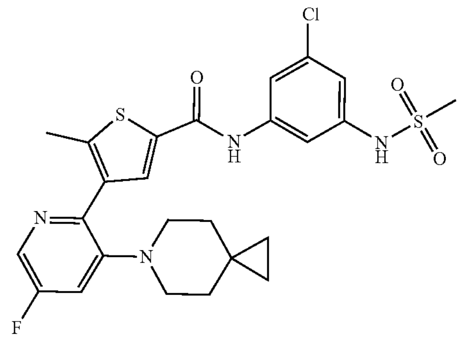 [SMILES: Cc1sc(C(=O)Nc2cc(Cl)cc(NS(C)(=O)=O)c2)cc1-c1ncc(F)cc1N1CCC2(CC1)CC2] | 507 | 549.15 | 1H NMR (400 MHz, DMSO-d6) δ 10.37 (s, 1H), 10.06 (s, 1H), 8.25 (d, J = 2.4 Hz, 1H), 8.19 (s, 1H), 7.65 (dt, J = 16.8, 1.7 Hz, 2H), 7.47 (dd, J = 11.1, 2.5 Hz, 1H), 6.94 (q, J = 1.7 Hz, 1H), 3.06 (s, 3H), 2.86 (t, J = 5.2 Hz, 4H), 2.45 (s, 3H), 1.30 (t, J = 5.0 Hz, 4H), 0.26 (s, 4H). |
| 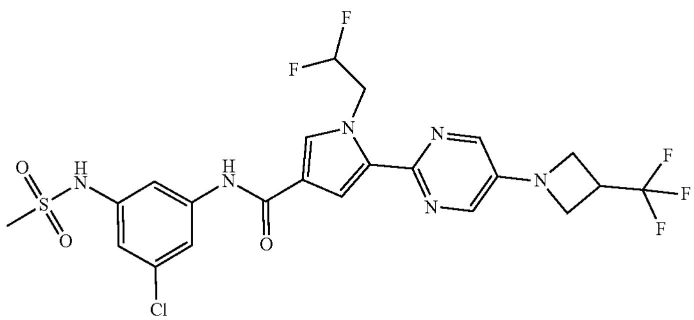 [SMILES: CS(=O)(=O)Nc1cc(Cl)cc(NC(=O)c2cc(-c3ncc(N4CC(C(F)(F)F)C4)cn3)n(CC(F)F)c2)c1] | 508 | 579.1 | 1H NMR (300 MHz, DMSO-d6) δ 9.99 (s, 2H), 8.18 (s, 2H), 7.74 (t, J = 1.9 Hz, 1H), 7.72-7.66 (m, 2H), 7.57 (d, J = 2.1 Hz, 1H), 6.91 (t, J = 1.9 Hz, 1H), 6.59 6.13 (m, 1H), 5.08 (td, J = 14.5, 3.9 Hz, 2H), 4.24 (t, J = 8.6 Hz, 2H), 4.06 (dd, J = 8.6, 5.1 Hz, 2H), 3.80 (ddq, J = 13.9, 9.2, 5.0 Hz, 1H), 3.07 (s, 3H). |
| 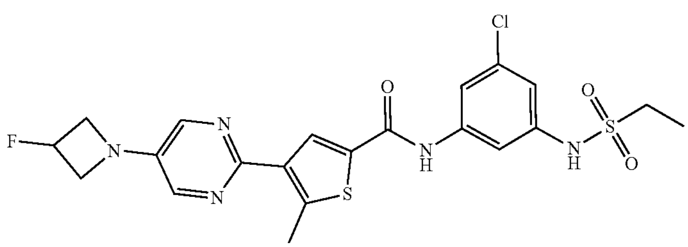 [SMILES: CCS(=O)(=O)Nc1cc(Cl)cc(NC(=O)c2cc(-c3ncc(N4CC(F)C4)cn3)c(C)s2)c1] | 509 | 510 | 1H NMR (400 MHz, DMSO-d6) δ 10.54 (s, 1H), 10.08 (s, 1H), 8.59 (s, 1H), 8.20 (s, 2H), 7.68 (d, J = 1.9 Hz, 2H), 6.95 (t, J = 1.9 Hz, 1H), 5.54 (ddt, J = 60.6, 6.1, 3.1 Hz, 1H), 4.48-4.25 (m, 2H), 4.21-4.02 (m, 2H), 3.17 (q, J = 7.3 Hz, 2H), 2.81 (s, 3H), 1.22 (t, J = 7.3 Hz, 3H). |
| 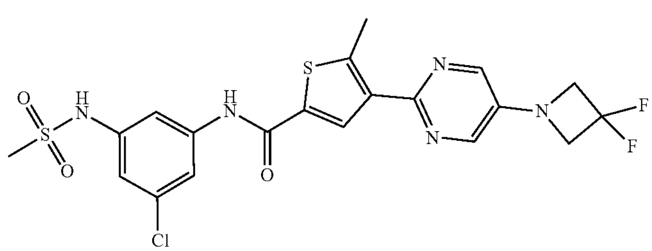 [SMILES: Cc1sc(C(=O)Nc2cc(Cl)cc(NS(C)(=O)=O)c2)cc1-c1ncc(N2CC(F)(F)C2)cn1] | 510 | 514 | 1H NMR (400 MHz, DMSO-d6) δ 10.56 (s, 1H), 10.06 (s, 1H), 8.61 (s, 1H), 8.29 (s, 2H), 7.69 (dt, J = 5.0, 1.9 Hz, 2H), 6.94 (t, J = 1.9 Hz, 1H), 4.50 (t, J = 12.3 Hz, 4H), 3.07 (s, 3H), 2.82 (s, 3H). |

-continued

| Structure | Compound No. | MS (ESI) [M + H]+ | ¹H NMR |
|---|---|---|---|
| 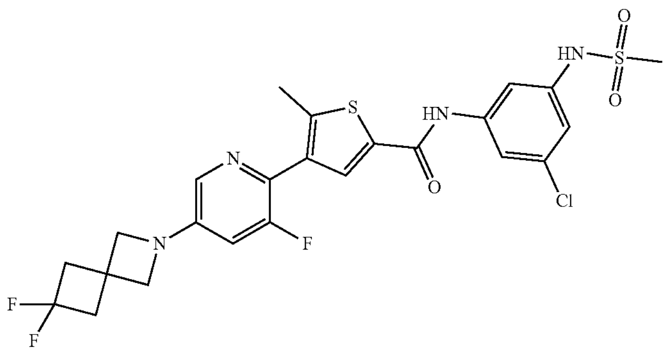 [SMILES: Cc1sc(C(=O)Nc2cc(Cl)cc(NS(C)(=O)=O)c2)cc1-c1ncc(N2CC3(C2)CC(F)(F)C3)cc1F] | 511 | 571 | ¹H NMR (300 MHz, DMSO-d6) δ 10.41 (s, 1H), 10.07 (s, 1H), 8.12 (d, J = 1.6 Hz, 1H), 7.80 (t, J = 2.0 Hz, 1H), 7.66 (dt, J = 11.2, 1.9 Hz, 2H), 7.00-6.88 (m, 2H), 4.08 (s, 4H), 3.07 (s, 3H), 2.90 (t, J = 12.5 Hz, 4H), 2.48 (d, J = 1.5 Hz, 3H). |
| 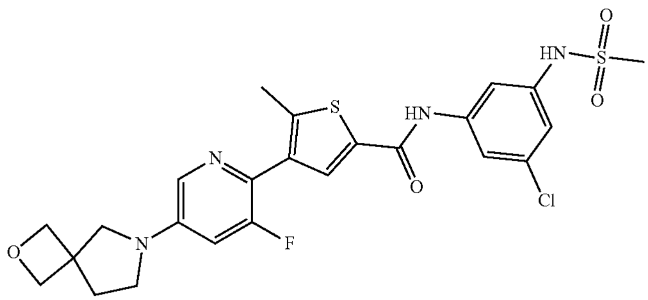 [SMILES: Cc1sc(C(=O)Nc2cc(Cl)cc(NS(C)(=O)=O)c2)cc1-c1ncc(N2CCC3(COC3)C2)cc1F] | 512 | 551 | ¹H NMR (300 MHz, DMSO-d6) δ 10.42 (s, 1H), 10.04 (s, 1H), 8.12 (d, J = 1.6 Hz, 1H), 7.92 (t, J = 2.1 Hz, 1H), 7.66 (dt, J = 10.5, 1.9 Hz, 2H), 7.04-6.82 (m, 2H), 4.75-4.43 (m, 4H), 3.63 (s, 2H), 3.38 (d, J = 7.0 Hz, 2H), 3.07 (s, 3H), 2.49 (d, J = 1.4 Hz, 3H), 2.30 (t, J = 6.9 Hz, 2H). |
| 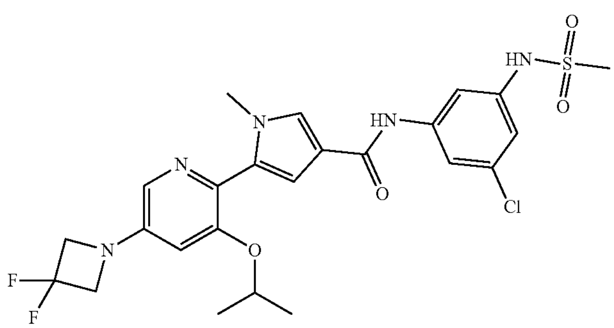 [SMILES: CC(C)Oc1cc(N2CC(F)(F)C2)cnc1-c1cc(C(=O)Nc2cc(Cl)cc(NS(C)(=O)=O)c2)cn1C] | 513 | 554 | ¹H NMR (400 MHz, DMSO-d6) δ 9.99 (s, 1H), 9.79 (s, 1H), 7.71 (t, J = 1.9 Hz, 1H), 7.62 (q, J = 2.0 Hz, 3H), 6.89 (dd, J = 5.2, 2.0 Hz, 2H), 6.79 (s, 1H), 4.73 (p, J = 5.8 Hz, 1H), 4.43 (dd, J = 13.4, 10.6 Hz, 4H), 3.68 (s, 3H), 3.06 (s, 3H), 1.28 (d, J = 5.9 Hz, 6H). |
| 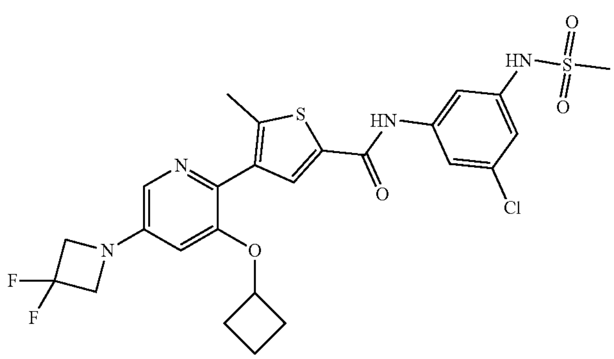 [SMILES: Cc1sc(C(=O)Nc2cc(Cl)cc(NS(C)(=O)=O)c2)cc1-c1ncc(N2CC(F)(F)C2)cc1OC1CCC1] | 514 | 583 | ¹H NMR (300 MHz, DMSO-d6) δ 10.36 (s, 1H), 10.06 (s, 1H), 8.06 (s, 1H), 7.67 (t, J = 1.9 Hz, 1H), 7.63 (dd, J = 4.8, 2.2 Hz, 2H), 6.94 (t, J = 1.9 Hz, 1H), 6.51 (d, J = 2.3 Hz, 1H), 4.78 (p, J = 7.1 Hz, 1H), 4.42 (t, J = 12.3 Hz, 4H), 3.07 (s, 3H), 2.45 (d, J = 7.7 Hz, 2H), 2.40 (s, 3H), 2.12-1.94 (m, |

| Structure | Compound No. | MS (ESI) [M + H]+ | 1H NMR |
|---|---|---|---|
| | | | 2H), 1.79 (q, J = 10.2 Hz, 1H), 1.65 (p, J = 9.1 Hz, 1H). |

Example 515: N-(3-chloro-5-methanesulfona midophenyl)-5-[5-(4-methoxypiperidin-1-yl)pyridin-2-yl]-1-methyl-1H-pyrrole-3-carboxamide

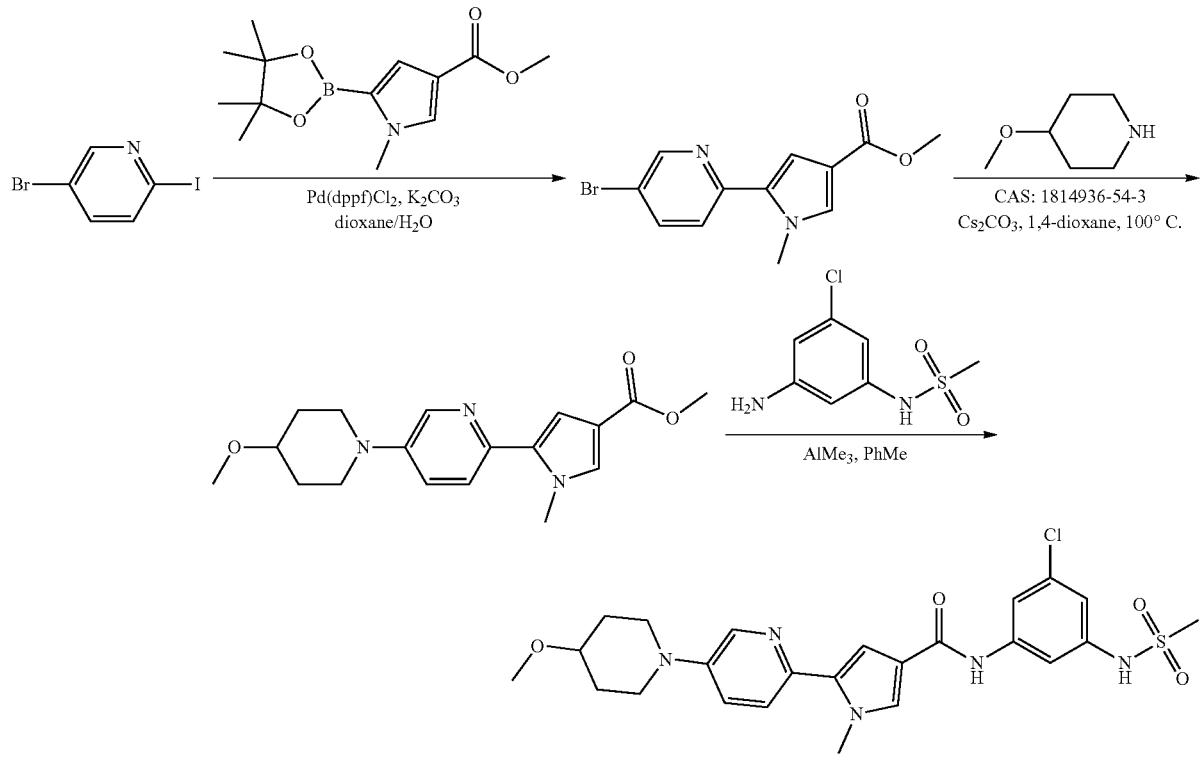

Step 1: To a stirred solution of 5-bromo-2-iodopyridine (320 mg, 1.12 mmol), Pd(dppf)Cl₂ (122 mg, 168 μmol) and K₂CO₃ (467 mg, 3.36 mmol) in dioxane (9 mL) and H₂O (3 mL) was added methyl 1-methyl-5-(4,4,5,5-tetramethyl-1,3,2-dioxaborolan-2-yl)-1H-pyrrole-3-carboxylate (296 mg, 1.12 mmol). Then the mixture was stirred for 1 hour at 90° C. The mixture was concentrated and purified by normal phase flash chromatography eluting with PE/EA (70%) to afford methyl 5-(5-bromopyridin-2-yl)-1-methyl-1H-pyrrole-3-carboxylate (255 mg, 864 μmol) as an off yellow solid. LCMS (ESI) [M+H]+: 295

Step 2: To a stirred solution of methyl 5-(5-bromopyridin-2-yl)-1-methyl-1H-pyrrole-3-carboxylate (255 mg, 864 μmol) and Cs₂CO₃ (841 mg, 2.59 mmol) in dioxane (10 mL) was added 4-ethylpiperidine (97.8 mg, 864 μmol) and {1,3-bis[2,6-bis(heptan-4-yl)phenyl]-4,5-dichloro-2,3-dihydro-1H-imidazol-2-yl}dichloro(3-chloro-λ4-pyridin-1-yl)palladium (33.5 mg, 8.64 μmol). Then the mixture was stirred for 1 hour at 100° C. The mixture was concentrated and purified by normal phase flash chromatography eluting with PE/EA (81%) to afford methyl 5-[5-(4-methoxypiperidin-1-yl)pyridin-2-yl]-1-methyl-1H-pyrrole-3-carboxylate (150 mg, 455 μmol) as an off white solid. LCMS (ESI) [M+H]+: 330.17

Step 3: To a stirred solution of methyl 5-[5-(4-methoxypiperidin-1-yl)pyridin-2-yl]-1-methyl-1H-pyrrole-3-carboxylate (130 mg, 394 μmol) and N-(3-amino-5-chlorophenyl)methanesulfonamide (86.9 mg, 394 μmol) in PhMe (6 mL) was added Al(CH₃)₃(36 mg, 1.195 mmol). Then the mixture was stirred for 1 hour at 80'° C. The mixture was concentrated and purified by reverse phase flash chromatography eluting with ACN/H₂O (4200, acidic system) to afford N-(3-chloro-5-methanesulfona midophenyl)-5-[5-(4-methoxypiperidin-1-yl)pyridin-2-yl]-1-methyl-1H-pyrrole-3-carboxamide (122 mg, 229 μmol) as a white solid. LCMS (ESI) [M+H]+: 517.95. ¹H NMR (400 MHz, DMSO-d₆) δ 10.02 (s, 1H), 9.78 (s, 1H), 8.31 (d, J=2.9 Hz, 1H), 7.72 (t, J=1.9 Hz, 1H), 7.66-97.57 (s, 2H), 7.51 (d, J=8.8 Hz, H), 7.41 (dd, J=8.9, 3.0 Hz, H), 7.01 (d, J=2.0 Hz, 1H), 6.89 (t, J=2.0 Hz, 1H), 3.92 (s, 3H), 3.58 (dt, J=13.1, 4.8 Hz, 2H), 3.38 (tt, J=8.1, 3.7 Hz, 1H), 3.28 (s, 3H), 3.06 (s, 3H), 3.00 (ddd, J=12.7, 9.5, 3.2 Hz, 2H), 1.99-1.90 (m, 2H), 1.53 (dtd, J=12.8, 9.0, 3.8 Hz, 2H).

Example 516-523

The compounds listed in the following table were prepared using a procedure similar to that described for example 515;

| Structure | Compound No. | MS (ESI) [M + H]+ | 1H NMR |
|---|---|---|---|
| (structure for compound 516) | 516 | 532.2 | 1H NMR (300 MHz, DMSO-d6) δ 10.01 (s, 1H), 9.81 (s, 1H), 7.82 (s, 1H), 7.71 (t, J = 1.9 Hz, 1H), 7.63 (d, J = 1.8 Hz, 2H), 6.95-6.72 (m, 3H), 3.80 (s, 3H), 3.48 (d, J = 10.3 Hz, 2H), 3.28 (d, J = 10.4 Hz, 2H), 3.06 (s, 3H), 1.58 (d, J = 3.6 Hz, 2H), 1.07 (s, 3H), 0.83 (s, 3H). |
| (structure for compound 517) | 517 | 528.15 | 1H NMR (300 MHz, DMSO-d6) δ 10.05 (s, 1H), 9.83 (s, 1H), 7.89 (dd, J = 2.4, 1.4 Hz, 1H), 7.75-7.53 (m, 3H), 7.12 (dd, J = 12.6, 2.4 Hz, 1H), 7.02 (dd, J = 3.3, 2.0 Hz, 1H), 6.89 (t, J = 1.9 Hz, 1H), 4.44 (t, J = 12.3 Hz, 4H), 3.82 (s, 3H), 3.16 (q, J = 7.2 Hz, 2H), 1.21 (t, J = 7.3 Hz, 3H). |
| (structure for compound 518) | 518 | 568.15 | 1H NMR (300 MHz, DMSO-d6) δ 10.02 (s, 1H), 9.84 (s, 1H), 8.27 (t, J = 2.0 Hz, 1H), 7.78-7.68 (m, 1H), 7.70-7.56 (m, 2H), 7.42 (dt, J = 14.0, 1.9 Hz, 1H), 7.12-6.96 (m, 1H), 6.90 (t, J = 1.9 Hz, 1H), 3.85 (s, 3H), 3.44 (tdd, J = 12.7, 7.3, 4.2 Hz, 4H), 3.07 (s, 3H), 1.76 (ddd, J = 11.9, 7.4, 3.9 Hz, 2H), 1.70-1.50 (m, 2H), 1.37 (t, J = 8.7 Hz, 2H). |

| Structure | Compound No. | MS (ESI) [M + H]+ | 1H NMR |
|---|---|---|---|
| 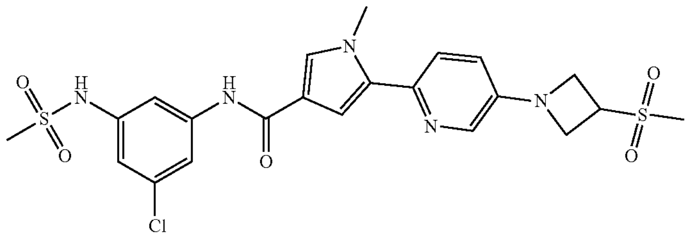 | 519 | 538.05 | 1H NMR (300 MHz, DMSO-d6) δ 10.05 (s, 1H), 9.83 (d, J = 5.8 Hz, 1H), 7.96-7.88 (m, 1H), 7.73 (p, J = 1.7 Hz, 1H), 7.63 (dt, J = 4.5, 2.3 Hz, 2H), 7.54 (dd, J = 8.6, 0.7 Hz, 1H), 7.11-6.95 (m, 2H), 6.93-6.83 (m, 1H), 4.47 (td, J = 8.1, 4.1 Hz, 1H), 4.31-4.07 (m, 4H), 3.91 (s, 3H), 3.07 (d, J = 4.3 Hz, 6H). |
| 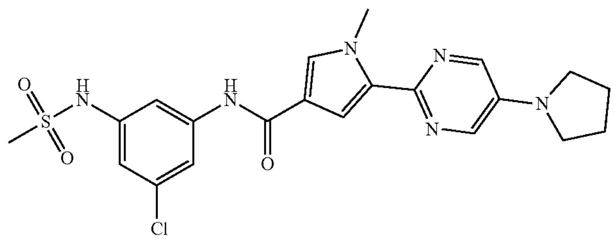 [SMILES: Cn1cc(C(=O)Nc2cc(Cl)cc(NS(C)(=O)=O)c2)cc1-c1ncc(N2CCCC2)cn1] | 520 | 475.05 | 1H NMR (300 MHz, DMSO-d6) δ 10.05 (s, 1H), 9.86 (s, 1H), 8.16 (s, 2H), 7.73 (t, J = 1.9 Hz, 1H), 7.66 (t, J = 1.9 Hz, 1H), 7.58 (d, J = 2.1 Hz, 1H), 7.39 (d, J = 2.2 Hz, 1H), 6.88 (t, J = 1.9 Hz, 1H), 4.02 (s, 3H), 3.25 (s, 4H), 3.05 (s, 3H), 2.03-1.93 (m, 4H). |
| 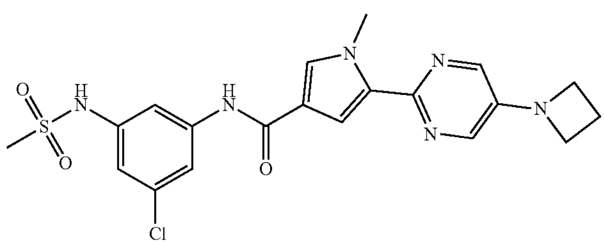 [SMILES: Cn1cc(C(=O)Nc2cc(Cl)cc(NS(C)(=O)=O)c2)cc1-c1ncc(N2CCC2)cn1] | 521 | 460.95 | 1H NMR (400 MHz, DMSO-d6) δ 9.99 (s, 1H), 9.88 (s, 1H), 8.05 (s, 2H), 7.74 (d, J = 2.2 Hz, 1H), 7.68 (d, J = 2.2 Hz, 1H), 7.60 (d, J = 2.2 Hz, 1H), 7.44 (d, J = 2.2 Hz, 1H), 6.89 (t, J = 2.1 Hz, 1H), 4.02 (s, 3H), 3.97 (t, J = 7.3 Hz, 4H), 3.07 (s, 3H), 2.40 (p, J = 7.3 Hz, 2H). |
| 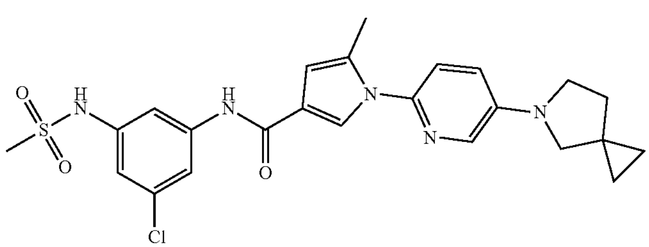 [SMILES: Cc1cc(C(=O)Nc2cc(Cl)cc(NS(C)(=O)=O)c2)cn1-c1ccc(N2CCC3(CC3)C2)cn1] | 522 | 500 | 1H NMR (400 MHz, DMSO-d6) δ 9.92 (s, 1H), 9.78 (s, 1H), 7.82 (d, J = 3.0 Hz, 1H), 7.77 (d, J = 2.0 Hz, 1H), 7.71 (t, J = 1.9 Hz, 1H), 7.63 (t, J = 1.9 Hz, 1H), 7.36 (d, J = 8.8 Hz, 1H), 7.06 (dd, J = 8.8, 3.1 Hz, 1H), 6.88 (t, J = 1.9 Hz, 1H), |

| Structure | Compound No. | MS (ESI) [M + H]+ | 1H NMR |
|---|---|---|---|
| | | | 6.51 (dd, J = 2.0, 1.1 Hz, 1H), 3.48 (t, J = 6.8 Hz, 2H), 3.25 (s, 2H), 3.05 (s, 3H), 2.25 (d, J = 0.9 Hz, 3H), 1.95 (t, J = 6.7 Hz, 2H), 0.66 (dt, J = 6.9, 1.8 Hz, 4H). |
| 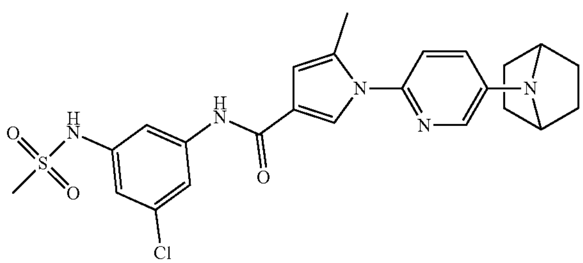 [SMILES: Cc1cc(C(=O)Nc2cc(Cl)cc(NS(C)(=O)=O)c2)cn1-c1ccc(N2C3CCC2CC3)cn1] | 523 | 500.05 | 1H NMR (400 MHz, DMSO-d6) δ 10.00 (s, 1H), 9.79 (s, 1H), 8.23 (d, J = 3.0 Hz, 1H), 7.83 (d, J = 2.0 Hz, 1H), 7.72 (t, J = 1.9 Hz, 1H), 7.63 (t, J = 1.9 Hz, 1H), 7.53 (dd, J = 8.8, 3.0 Hz, 1H), 7.38 (d, J = 8.7 Hz, 1H), 6.88 (t, J = 1.9 Hz, 1H), 6.51 (s, 1H), 4.41 (t, J = 2.6 Hz, 2H), 3.06 (s, 3H), 2.29 (s, 3H), 1.71-1.65 (m, 4H), 1.47 (t, J = 6.4 Hz, 4H). |
Example 524: N-(3-chloro-5-methanesulfo namidophenyl)-5-{3-fluoro-5-[3-(trifluoromethyl)azetidin-1-yl] pyridin-2-yl}-1-methyl-1H-pyrrole-3-carboxamide
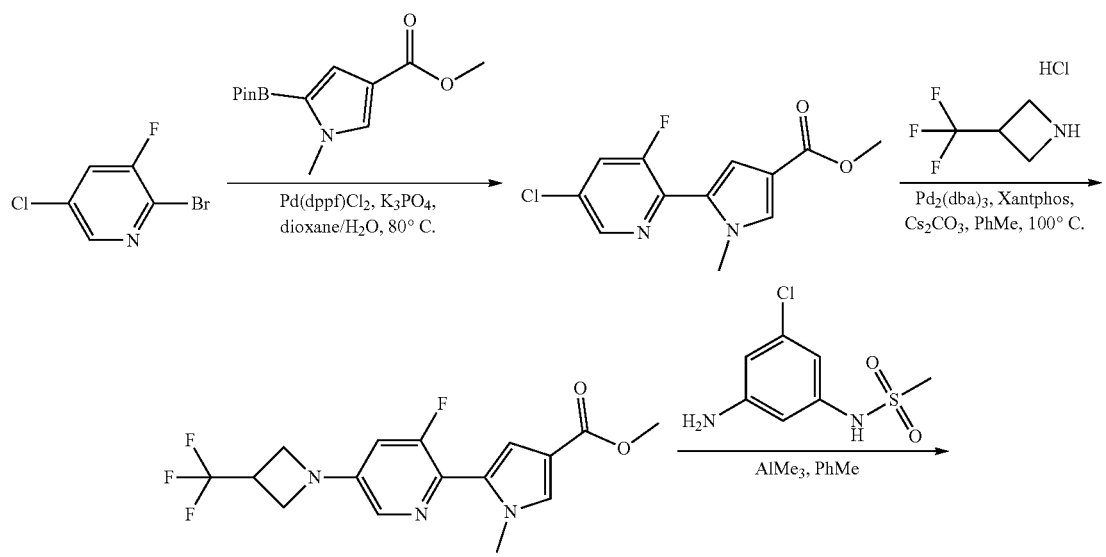

-continued

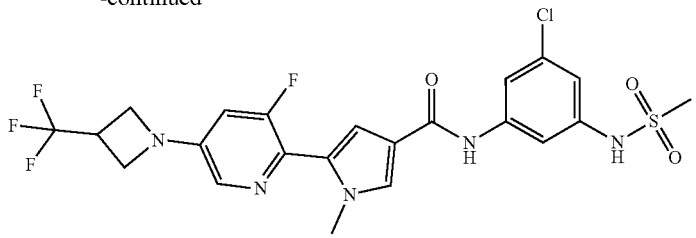

Step 1: To a mixture of 2-bromo-5-chloro-3-fluoropyridine (520 mg, 2.47 mmol), methyl 1-methyl-5-(4,4,5,5-tetramethyl-1,3,2-dioxaborolan-2-yl)-1H-pyrrole-3-carboxylate (784 mg, 2.96 mmol), Pd(dppf)Cl$_2$ (201 mg, 247 µmol) and K$_3$PO$_4$ (1.57 g, 7.41 mmol) was added dioxane (5 mL) and H$_2$O (0.5 mL). The resulting mixture was stirred for 2 hours at 80° C. under N$_2$ atmosphere. The reaction mixture was extracted with ethyl acetate. The organic phase was concentrated under reduced pressure. The residue was purified by flash chromatography on silica gel eluting with 0-100% f ethyl acetate in petroleum ether to afford methyl 5-(5-chloro-3-fluoropyridin-2-yl)-1-methyl-1H-pyrrole-3-carboxylate (310 mg, 47.6% yield) as a white solid. LCMS [M+H]$^+$:269

Step 2: To a mixture of methyl 5-(5-chloro-3-fluoropyridin-2-yl)-1-methyl-1H-pyrrole-3-carboxylate (310 mg, 1.15 mmol), 3-(trifluoromethyl)azetidine hydrochloride (277 mg, 1.72 mmol), Pd$_2$(dba)$_3$ (105 mg, 115 µmol), Xantphos (132 mg, 230 µmol) and Cs$_2$CO$_3$ (1.12 g, 3.44 mmol) was added PhMe (3 mL). The resulting mixture was stirred for 2 hours at 100° C. under N$_2$ atmosphere. The reaction mixture was extracted with ethyl acetate. The organic phase was concentrated under reduced pressure. The residue was purified by flash chromatography on silica gel eluting with 0-100% f ethyl acetate in petroleum ether to afford methyl 5-{3-fluoro-5-[3-(trifluoromethyl)azetidin-1-yl]pyridin-2-yl}-1-methyl-1H-pyrrole-3-carboxylate (133 mg, 32.4% yield) as a yellow solid. LCMS [M+H]$^+$: 358

Step 3: To a mixture of methyl 5-{3-fluoro-5-[3-(trifluoromethyl)azetidin-1-yl]pyridin-2-yl}-1-methyl-1H-pyrrole-3-carboxylate (133 mg, 372 µmol), N-(3-amino-5-chlorophenyl)methanesulfonamide (82.0 mg, 372 µmol) in toluene (0.8 mL) was stirred at room temperature. Then AlMe$_3$ (0.5 mL) in Toluene (0.7 mL) was added into the solution and the resulting mixture was stirred at 80° C. for 2 hours. The reaction mixture was quenched with water. The reaction mixture was extracted with ethyl acetate. The organic phase was concentrated under reduced pressure, The residue was purified by reverse phase flash chromatography eluting with 7000 of acetonitrile in water (0.1% NH$_4$HCO$_3$) to afford N-(3-chloro-5-methanesulfo namidophenyl)-5-{3-fluoro-5-[3-(trifluoromethyl)azetidin-1-yl]pyridin-2-yl}-1-methyl-1H-pyrrole-3-carboxamide (114.1 mg, 56.1% yield) as a light yellow solid. LCMS [M–H]$^−$: 544.15. $^1$H NM/R (400 MHz, DMSO-d$_6$) δ 9.99 (s, 1H), 9.82 (s, 1H), 7.87-7.80 (m, 1H), 7.76-7.59 (m, 3H), 7.07-6.96 (m, 2H), 6.89 (t, J=1.9 Hz, 1H), 4.21 (t, J=8.6 Hz, 2H), 4.02 (dd, J=8.7, 5.1 Hz, 2H), 3.81 (s, 4H), 3.06 (s, 3H).

Examples 525-531

The compounds listed in the following table were prepared using a procedure similar to that described for example 524:

| Structure | Compound No. | MS (ESI) [M + H]$^+$ | $^1$H NMR |
|---|---|---|---|
| 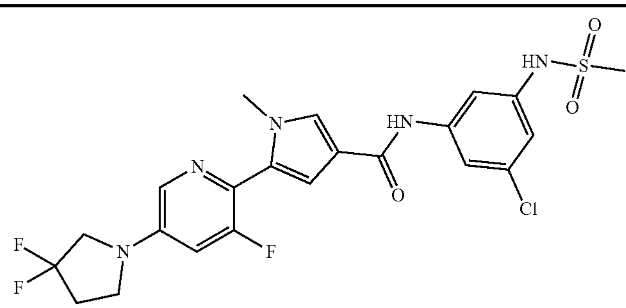 | 525 | 527.9 | $^1$H NMR (400 MHz, DMSO-d6) δ 10.03 (s, 1H), 9.83 (s, 1H), 7.95 (d, J = 2.1 Hz, 1H), 7.72 (d, J = 1.9 Hz, 1H), 7.70-7.49 (m, 2H), 7.09 (dd, J = 13.4, 2.4 Hz, 1H), 6.99 (dd, J = 3.4, 1.9 Hz, 1H), 6.89 (q, J = 1.9 Hz, 1H), 4.01-3.68 (m, |

-continued

| Structure | Compound No. | MS (ESI) [M + H]+ | 1H NMR |
|---|---|---|---|
| | | | 5H), 3.60 (t, J = 7.2 Hz, 2H), 3.06 (d, J = 1.7 Hz, 3H), 2.59 (dq, J = 14.5, 7.1 Hz, 2H). |
| 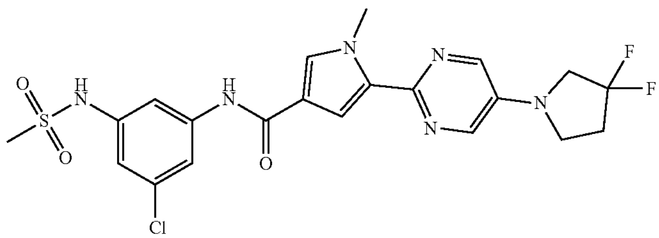 [SMILES: Cn1cc(C(=O)Nc2cc(Cl)cc(NS(C)(=O)=O)c2)cc1-c1ncc(N2CCC(F)(F)C2)cn1] | 526 | 511.05 | 1H NMR (400 MHz, DMSO-d6) δ 10.00 (s, 1H), 9.88 (s, 1H), 8.26 (s, 2H), 7.74 (t, J = 1.9 Hz, 1H), 7.67 (t, J = 1.9 Hz, 1H), 7.61 (d, J = 2.1 Hz, 1H), 7.45 (d, J = 2.1 Hz, 1H), 6.89 (t, J = 1.9 Hz, 1H), 4.03 (s, 3H), 3.84 (t, J = 13.2 Hz, 2H), 3.62 (t, J = 7.2 Hz, 2H), 3.06 (d, J = 1.5 Hz, 3H), 2.58 (dq, J = 14.5, 7.1 Hz, 2H). |
| 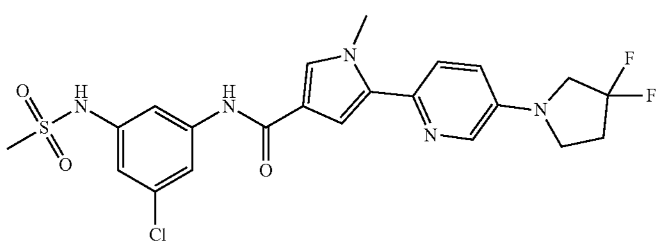 [SMILES: Cn1cc(C(=O)Nc2cc(Cl)cc(NS(C)(=O)=O)c2)cc1-c1ccc(N2CCC(F)(F)C2)cn1] | 527 | 510.15 | 1H NMR (400 MHz, DMSO-d6) δ 9.99 (s, 1H), 9.78 (s, 1H), 8.04 (d, J = 2.9 Hz, 1H), 7.72 (d, J = 2.1 Hz, 1H), 7.64-7.57 (m, 2H), 7.54 (d, J = 8.7 Hz, 1H), 7.11 (dd, J = 8.8, 3.0 Hz, 1H), 6.99 (d, J = 2.0 Hz, 1H), 6.88 (d, J = 2.2 Hz, 1H), 3.91 (s, 3H), 3.79 (t, J = 13.2 Hz, 2H), |

-continued

| Structure | Compound No. | MS (ESI) [M + H]+ | 1H NMR |
|---|---|---|---|
| | | | 3.57 (t, J = 7.2 Hz, 2H), 3.06 (s, 3H), 2.57 (dq, J = 14.6, 7.2 Hz, 2H). |
| 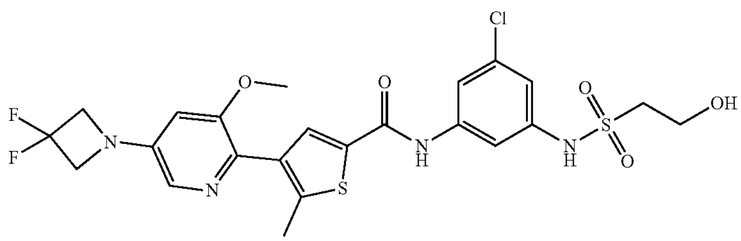 [SMILES: COc1cc(N2CC(F)(F)C2)cnc1-c1cc(C(=O)Nc2cc(Cl)cc(NS(=O)(=O)CCO)c2)sc1C] | 528 | 573.05 | 1H NMR (400 MHz, Methanol-d4) δ 7.84 (s, 1H), 7.58 (dt, J = 36.1, 2.0 Hz, 3H), 7.02 (t, J = 2.0 Hz, 1H), 6.75 (d, J = 2.0 Hz, 1H), 4.39 (t, J = 11.9 Hz, 4H), 3.94 (t, J = 6.3 Hz, 2H), 3.88 (s, 3H), 3.34 (d, J = 6.3 Hz, 2H), 2.39 (s, 3H). |
| 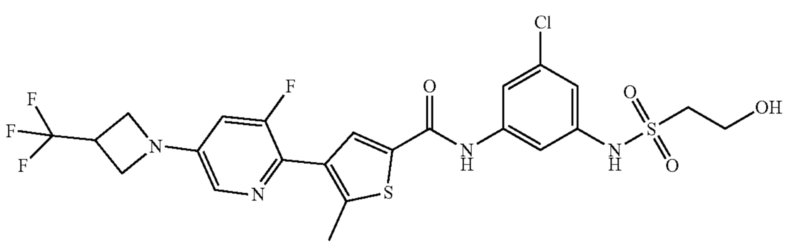 [SMILES: Cc1sc(C(=O)Nc2cc(Cl)cc(NS(=O)(=O)CCO)c2)cc1-c1ncc(N2CC(C(F)(F)F)C2)cc1F] | 529 | 593.1 | 1H NMR (400 MHz, DMSO-d6) δ 10.41 (s, 1H), 10.04 (s, 1H), 8.12 (d, J = 1.6 Hz, 1H), 7.87 (t, J = 1.9 Hz, 1H), 7.67 (t, J = 1.9 Hz, 1H), 7.63 (t, J = 1.9 Hz, 1H), 7.02 (dd, J = 12.5, 2.3 Hz, 1H), 6.94 (t, J = 1.9 Hz, 1H), 4.94 (t, J = 5.7 Hz, 1H), 4.22 (t, J = 8.6 Hz, 2H), 4.03 (dd, J = 8.7, 5.1 Hz, 2H), 3.89-3.60 (m, 3H), 3.30 (s, 2H), 2.49-2.47 (s, |

| Structure | Compound No. | MS (ESI) [M + H]+ | 1H NMR |
|---|---|---|---|
| 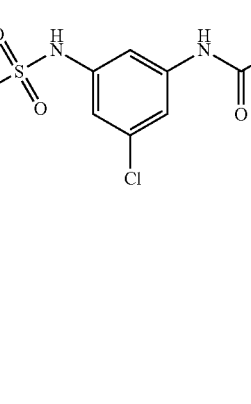 | 530 | 522 | 1H NMR (400 MHz, DMSO-d6) δ 10.00 (s, 1H), 9.79 (s, 1H), 7.98 (d, J = 2.9 Hz, 1H), 7.70 (dt, J = 4.3, 1.9 Hz, 2H), 7.61 (d, J = 2.0 Hz, 1H), 7.57 (d, J = 8.6 Hz, 1H), 7.06 (s, 1H), 7.03 (d, J = 2.1 Hz, 1H), 6.91 (t, J = 2.0 Hz, 1H), 4.39 (t, J = 12.3 Hz, 4H), 3.92 (s, 3H), 2.69 (tt, J = 7.8, 5.0 Hz, 1H), 0.99 (ddt, J = 10.7, 8.0, 2.5 Hz, 4H). |
| 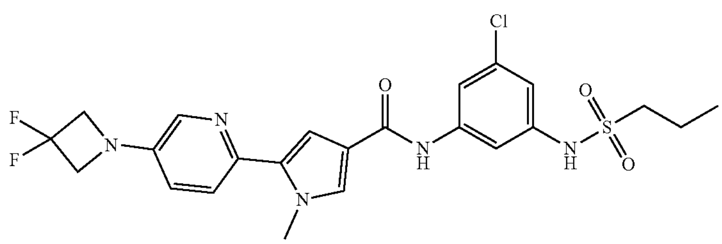 [SMILES: CCCS(=O)(=O)Nc1cc(Cl)cc(NC(=O)c2cc(-c3ccc(N4CC(F)(F)C4)cn3)n(C)c2)c1] | 531 | 524 | 1H NMR (300 MHz, DMSO-d6) δ 10.08 (s, 1H), 9.81 (s, 1H), 7.99 (d, J = 2.9 Hz, 1H), 7.73 (t, J = 1.9 Hz, 1H), 7.62 (s, 2H), 7.57 (d, J = 8.6 Hz, 1H), 7.17-6.97 (m, 2H), 6.90 (t, J = 2.0 Hz, 1H), 4.40 (t, J = 12.3 Hz, 4H), 3.92 (s, 3H), 3.18-2.98 (m, 2H), 1.87-1.52 (m, 2H), 0.96 (t, J = 7.4 Hz, 3H). |

Example 532: N-(3-chloro-5-methanesulfonamid-ophenyl)-4-[5-(3,3-difluoroazetidin-1-yl)-3-fluoro-pyridin-2-yl]-5-methylthiophene-2-carboxamide

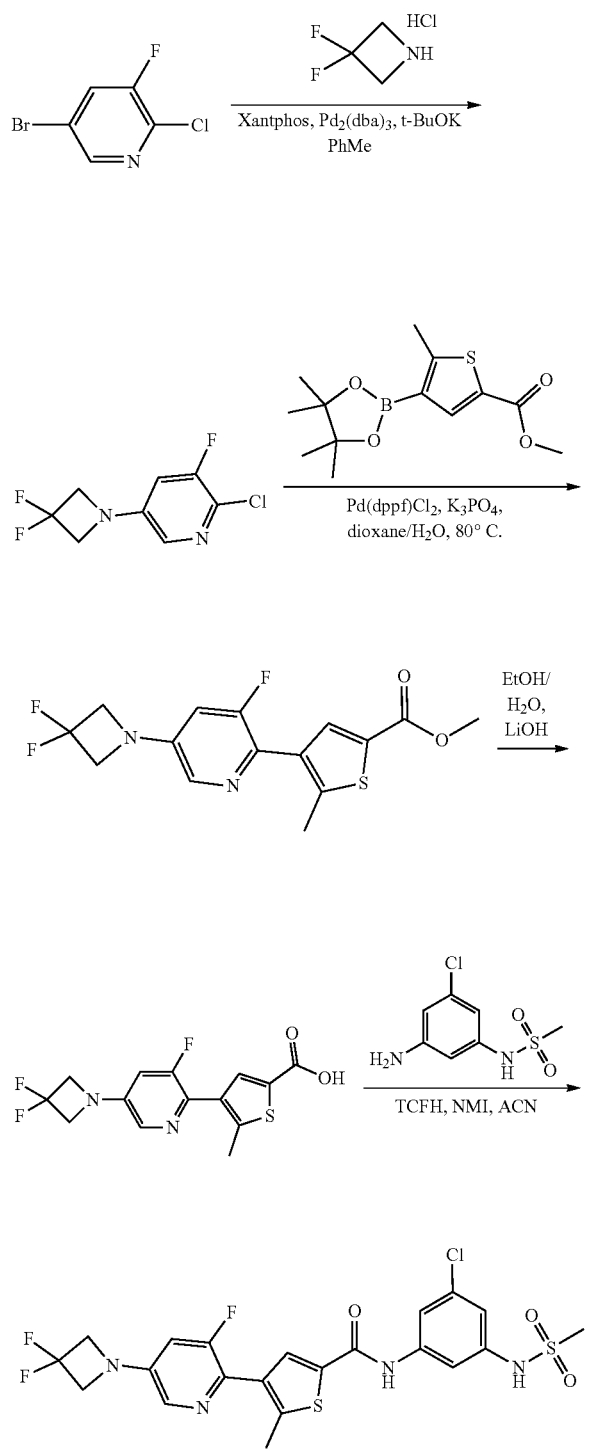

Step 1: To a stirred solution of 5-bromo-2-chloro-3-fluoropyridine (1.03 g, 4.89 mmol), Xantphos (565 mg, 0.978 mmol), Pd$_2$(dba)$_3$ (447 mg, 0.489 mmol), 3,3-difluoroazetidine hydrochloride (695 mg, 5.37 mmol) and t-BuOK (1.63 g, 14.6 mmol) in PhMe (25 mL) at room temperature. Then the mixture was stirred for 5 hours at 110° C. under nitrogen atmosphere. The mixture was concentrated under reduced pressure. The residue was purified by reversed-phase flash chromatography with the following conditions: column, C18 silica gel; mobile phase, MeCN in water (0.1% formic acid), 0% to 45% gradient in 20 min; detector, UV 254 nm. This resulted in 2-chloro-5-(3,3-difluoroazetidin-1-yl)-3-fluoropyridine (180 mg, 0.808 mmol) as a white solid. LCMS (ESI) [M+H]$^+$: 223.

Step 2: A solution of 2-chloro-5-(3,3-difluoroazetidin-1-yl)-3-fluoropyridine (180 mg, 0.808 mmol), Pd(dppf)Cl$_2$ (66 mg, 0.0808 mmol), K$_3$PO$_4$ (513 mg, 2.42 mmol) and methyl 5-methyl-4-(4,4,5,5-tetra methyl-1,3,2-dioxaborolan-2-yl) thiophene-2-carboxylate (250 mg, 0.888 mmol) in dioxane (10 mL) and H$_2$O (1 mL) was stirred for 2 hours at 80° C. under nitrogen atmosphere. The resulting mixture was concentrated under reduced pressure. The residue was purified by silica gel column chromatography, eluted with PE/EA (1:2) to afford methyl 4-[5-(3,3-difluoroazetidin-1-yl)-3-fluoropyridin-2-yl]-5-methylthiophene-2-carboxylate (180 mg, 0.525 mmol) as a white solid. LCMS (ESI) [M+H]$^+$: 343.

Step 3: To a stirred solution of methyl 4-[5-(3,3-difluoroazetidin-1-yl)-3-fluoropyridin-2-yl]-5-methylthiophene-2-carboxylate (160 mg, 0.467 mmol) in EtOH (5 mL) and H$_2$O (1 mL) was added LiOH (111 mg, 4.67 mmol) at 0° C. Then the mixture was stirred for 2 hours at room temperature. The mixture was acidified to pH 5 with citric acid. The precipitated solids were collected by filtration and washed with water. The resulting solid was dried under vacuum to afford 4-[5-(3,3-difluoroazetidin-1-yl)-3-fluoropyridin-2-yl]-5-methylthiophene-2-carboxylic acid (160 mg, 0.487 mmol) as a yellow solid. LCMS (ESI) [M+H]$^+$: 329.

Step 4: To a stirred solution of 4-[5-(3,3-difluoroazetidin-1-yl)-3-fluoropyridin-2-yl]-5-methylthiophene-2-carboxylic acid (160 mg, 0.487 mmol), TCFH (408 mg, 1.46 mmol) and NMI (80 mg, 0.974 mmol) in ACN (5 mL) was added N-(3-amino-5-chlorophenyl)methanesulfonamide (128 mg, 0.584 mmol) at room temperature. Then the mixture was stirred for 1 hour at room temperature. The mixture was concentrated under reduced pressure. The residue was purified by reversed-phase flash chromatography with the following conditions: column, C18 silica gel; mobile phase, MeCN in water (0.1% formic acid), 0% to 50% gradient in 20 min; detector, UV 254 nm. This resulted in N-(3-chloro-5-methanesulfonamidophenyl)-4-[5-(3,3-difluoroazetidin-1-yl)-3-fluoropyridin-2-yl]-5-methylthiophene-2-carboxamide (75.6 mg, 0.142 mmol) as a white solid. LCMS (ESI) [M+H]$^+$: 530.95. $^1$H NMR (400 MHz, DMSO-d$_6$) δ 10.41 (s, 1H), 9.78 (s, 1H), 8.13 (d, J=1.6 Hz, 1H), 7.93 (t, J=2.0 Hz, 1H), 7.65 (dt, J=14.9, 1.9 Hz, 2H), 7.12 (dd, J=12.3, 2.3 Hz, 1H), 6.94 (t, J=1.9 Hz, 1H), 4.46 (t, J=12.3 Hz, 4H), 3.06 (s, 3H), 2.49 (s, 3H).

Examples 533-539

The compounds listed in the following table were prepared using a procedure similar to that described for example 532:

| Structure | Compound No. | MS (ESI) [M + H]+ | 1H NMR |
|---|---|---|---|
| 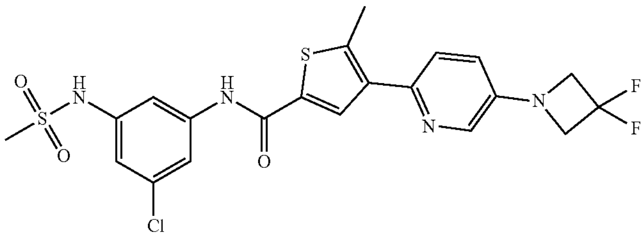 [SMILES: Cc1sc(C(=O)Nc2cc(Cl)cc(NS(C)(=O)=O)c2)cc1-c1ccc(N2CC(F)(F)C2)cn1] | 533 | 512.85 | 1H NMR (400 MHz, DMSO-d6) δ 10.42 (s, 1H), 10.06 (s, 1H), 8.31 (s, 1H), 8.05 (d, J = 2.9 Hz, 1H), 7.66 (dt, J = 12.9, 1.9 Hz, 2H), 7.56 (d, J = 8.6 Hz, 1H), 7.12 (dd, J = 8.6, 3.0 Hz, 1H), 6.94 (t, J = 1.9 Hz, 1H), 4.42 (t, J = 12.3 Hz, 4H), 3.07 (s, 3H), 2.66 (s, 3H). |
| 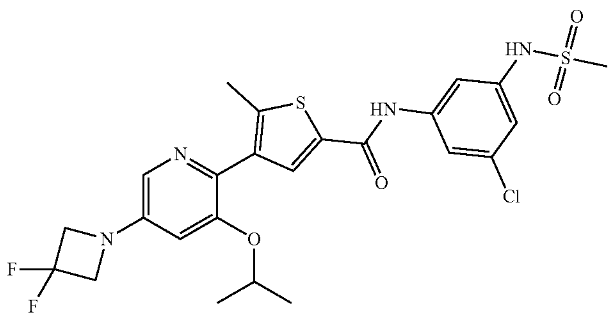 [SMILES: Cc1sc(C(=O)Nc2cc(Cl)cc(NS(C)(=O)=O)c2)cc1-c1ncc(N2CC(F)(F)C2)cc1OC(C)C] | 534 | 571.15 | 1H NMR (400 MHz, DMSO-d6) δ 10.33 (s, 1H), 10.05 (s, 1H), 8.02 (s, 1H), 7.63 (dd, J = 13.3, 2.2 Hz, 3H), 6.93 (t, J = 1.9 Hz, 1H), 6.73 (d, J = 2.2 Hz, 1H), 4.66 (p, J = 5.9 Hz, 1H), 4.41 (t, J = 12.3 Hz, 4H), 3.05 (s, 3H), 2.39 (s, 3H), 1.24 (d, J = 6.0 Hz, 6H). |
| 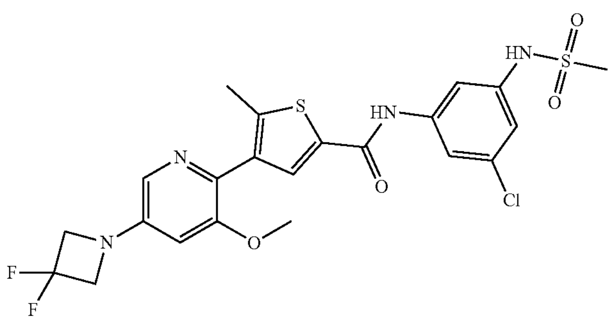 [SMILES: COc1cc(N2CC(F)(F)C2)cnc1-c1cc(C(=O)Nc2cc(Cl)cc(NS(C)(=O)=O)c2)sc1C] | 535 | 543.1 | 1H NMR (300 MHz, DMSO-d6) δ 10.34 (s, 1H), 10.11 (s, 1H), 8.05 (s, 1H), 7.65 (dt, J = 13.3, 2.2 Hz, 3H), 6.93 (t, J = 1.9 Hz, 1H), 6.77 (d, J = 2.3 Hz, 1H), 4.44 (t, J = 12.3 Hz, 4H), 3.85 (s, 3H), 3.06 (s, 3H), 2.38 (s, 3H). |
| 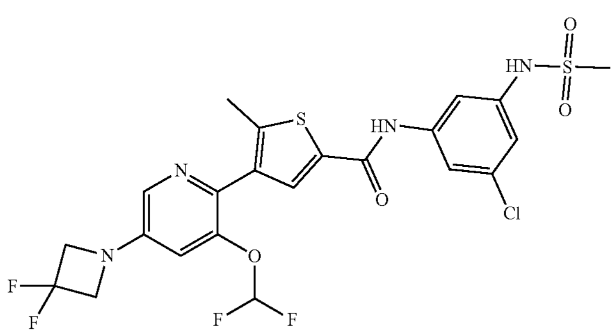 [SMILES: Cc1sc(C(=O)Nc2cc(Cl)cc(NS(C)(=O)=O)c2)cc1-c1ncc(N2CC(F)(F)C2)cc1OC(F)F] | 536 | 579 | 1H NMR (300 MHz, DMSO-d6) δ 10.39 (s, 1H), 10.07 (s, 1H), 8.04 (s, 1H), 7.94 (d, J = 2.3 Hz, 1H), 7.67 (t, J = 1.9 Hz, 1H), 7.62 (t, J = 1.9 Hz, 1H), 7.36 (d, J = 73.3 Hz, 1H), 7.01-6.91 (m, 2H), 4.48 (t, J = 12.3 Hz, 4H), 3.06 (s, 3H), 2.40 (s, 3H). |
| 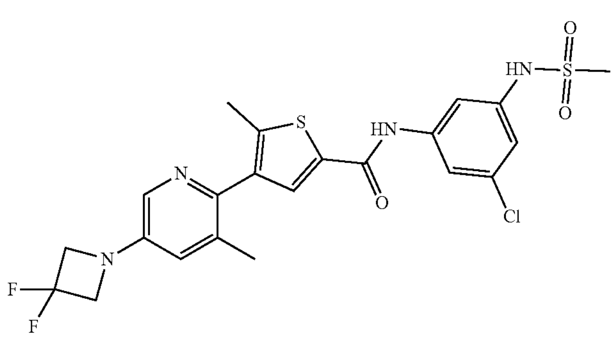 [SMILES: Cc1cc(N2CC(F)(F)C2)cnc1-c1cc(C(=O)Nc2cc(Cl)cc(NS(C)(=O)=O)c2)sc1C] | 537 | 526.85 | 1H NMR (400 MHz, DMSO-d6) δ 10.30 (s, 1H), 10.06 (s, 1H), 7.93 (s, 1H), 7.88 (d, J = 2.7 Hz, 1H), 7.66 (d, J = 1.9 Hz, 1H), 7.61 (t, J = 1.9 Hz, 1H), 6.98 (d, J = 2.7 Hz, 1H), 6.94 (t, J = 2.0 Hz, 1H), 4.39 (t, J = 12.3 Hz, 4H), 3.06 (s, 3H), 2.31 (s, 3H), 2.18 (s, 3H). |

| Structure | Compound No. | MS (ESI) [M + H]+ | 1H NMR |
|---|---|---|---|
| 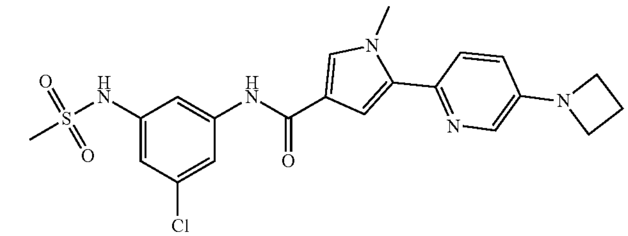 [SMILES: Cn1cc(C(=O)Nc2cc(Cl)cc(NS(C)(=O)=O)c2)cc1-c1ccc(N2CCC2)cn1] | 538 | 460 | 1H NMR (400 MHz, DMSO-d6) δ 10.05 (s, 1H), 9.77 (s, 1H), 7.82 (d, J = 2.9 Hz, 1H), 7.72 (t, J = 1.9 Hz, 1H), 7.62 (t, J = 1.9 Hz, 1H), 7.58 (d, J = 2.0 Hz, 1H), 7.48 (d, J = 8.6 Hz, 1H), 6.96 (d, J = 2.0 Hz, 1H), 6.93-6.85 (m, 2H), 3.95-3.87 (m, 7H), 3.06 (s, 3H), 2.37 (p, J = 7.3 Hz, 2H). |
| 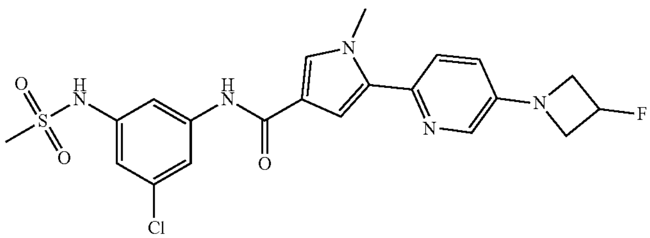 [SMILES: Cn1cc(C(=O)Nc2cc(Cl)cc(NS(C)(=O)=O)c2)cc1-c1ccc(N2CC(F)C2)cn1] | 539 | 478 | 1H NMR (300 MHz, DMSO-d6) δ 10.00 (s, 1H), 9.77 (s, 1H), 7.90 (d, J = 2.8 Hz, 1H), 7.71 (t, J = 1.8 Hz, 1H), 7.65-7.43 (m, 3H), 7.03-6.94 (m, 2H), 6.88 (t, J = 1.9 Hz, 1H), 5.53 (ddd, J = 60.0, 5.8, 2.8 Hz, 1H), 4.26 (ddd, J = 20.8, 9.8, 6.1 Hz, 2H), 4.04 (dd, J = 9.1, 2.5 Hz, 1H), 3.96 (dd, J = 10.2, 3.2 Hz, 1H), 3.90 (s, 3H), 3.05 (s, 3H). |

Example 540: N-(3-chloro-5-methanesulfonamidophenyl)-5-(3,5-difluoropyridin-2-yl)-1-methyl-1H-pyrrole-3-carboxamide

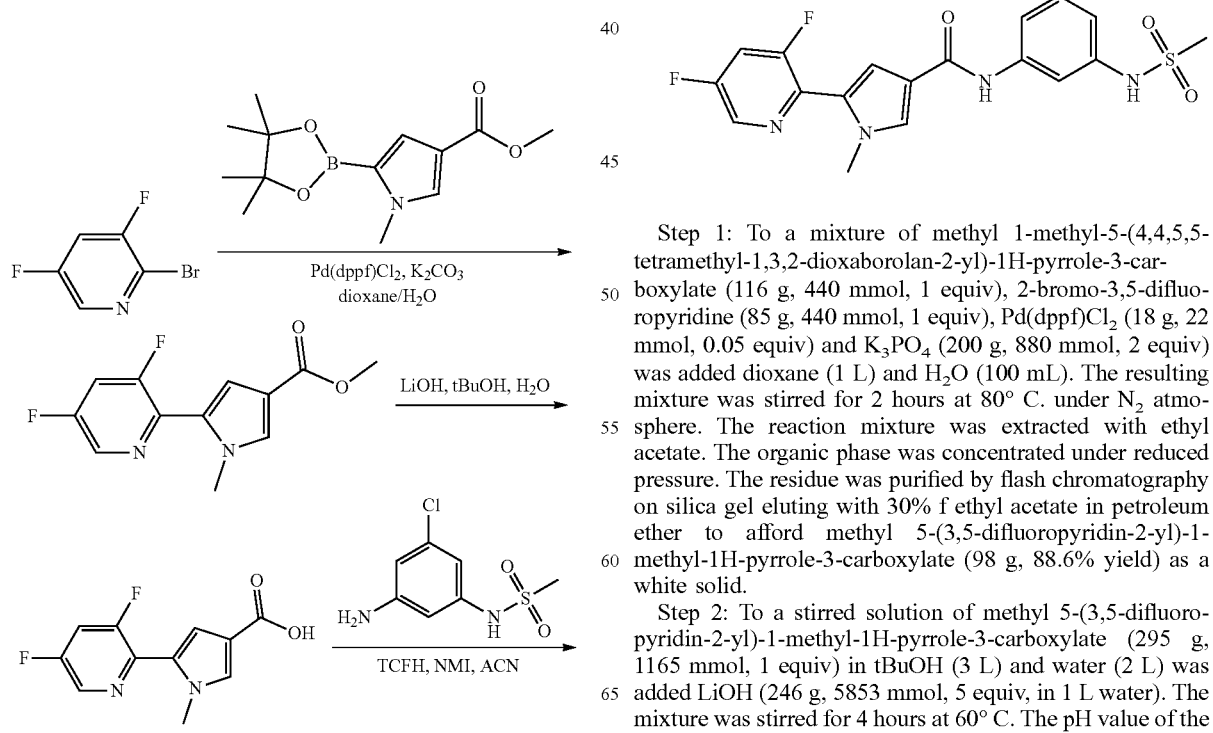

Step 1: To a mixture of methyl 1-methyl-5-(4,4,5,5-tetramethyl-1,3,2-dioxaborolan-2-yl)-1H-pyrrole-3-carboxylate (116 g, 440 mmol, 1 equiv), 2-bromo-3,5-difluoropyridine (85 g, 440 mmol, 1 equiv), Pd(dppf)Cl$_2$ (18 g, 22 mmol, 0.05 equiv) and K$_3$PO$_4$ (200 g, 880 mmol, 2 equiv) was added dioxane (1 L) and H$_2$O (100 mL). The resulting mixture was stirred for 2 hours at 80° C. under N$_2$ atmosphere. The reaction mixture was extracted with ethyl acetate. The organic phase was concentrated under reduced pressure. The residue was purified by flash chromatography on silica gel eluting with 30% f ethyl acetate in petroleum ether to afford methyl 5-(3,5-difluoropyridin-2-yl)-1-methyl-1H-pyrrole-3-carboxylate (98 g, 88.6% yield) as a white solid.

Step 2: To a stirred solution of methyl 5-(3,5-difluoropyridin-2-yl)-1-methyl-1H-pyrrole-3-carboxylate (295 g, 1165 mmol, 1 equiv) in tBuOH (3 L) and water (2 L) was added LiOH (246 g, 5853 mmol, 5 equiv, in 1 L water). The mixture was stirred for 4 hours at 60° C. The pH value of the solution was adjusted to 3 with 1M of HCl (aq). The product was precipitated from the solution. The mixture was filtered and the filter cake was washed with water (3×200 mL) to afford 5-(3,5-difluoropyridin-2-yl)-1-methyl-1H-pyrrole-3-carboxylic acid (212 g, 76.0% yield) as a white solid. LCMS [M+H]+: 239.

Step 3: A mixture of 5-(3,5-difluoropyridin-2-yl)-1-methyl-1H-pyrrole-3-carboxylic acid (212 g, 886 mmol, 1 equiv), TCFH (341 g, 1219 mmol, 137 equiv), NMI (199 g, 2438 mmol, 2.75 equiv) and N-(3-amino-5-chlorophenyl)methanesulfonamide (214 g, 487 mmol) in ACN (2 L) was stirred for two hours at room temperature. The mixture was quenched with water (2 L). The resulting mixture was extracted with DCM (3×3 L) and water. The combined organic layers were dried over anhydrous Na₂SO₄. After filtration, the filtrate was concentrated under reduced pressure. The residue was purified by silica gel column chromatography, eluted with DCM/ACN (5:1) to afford N-(3-chloro-5-methanesulfonamidophenyl)-5-(3,5-difluoropyridin-2-yl)-1-methyl-1H-pyrrole-3-carboxamide (155 g, 39.5% yield) as a white solid. LCMS [M+H]+: 441. ¹H NMR (400 MHz, DMSO-d₆) δ 10.00 (s, 1H), 9.90 (s, 1H), 8.59 (d, J=2.4 Hz, 1H), 8.08 (ddd, J=11.1, 8.9, 2.5 Hz, 1H), 7.79-7.69 (m, 2H), 7.64 (t, J=1.9 Hz, 1H), 7.21 (dd, J=3.6, 1.9 Hz, 1H), 6.91 (t, J=2.0 Hz, 1H), 3.89 (s, 3H), 3.06 (s, 3H).

Example 541: N-(3-chloro-5-(methylsulfonamido)phenyl)-4-(5-isopropoxypyrimidin-2-yl)-5-methyl-thiophene-2-carboxamide

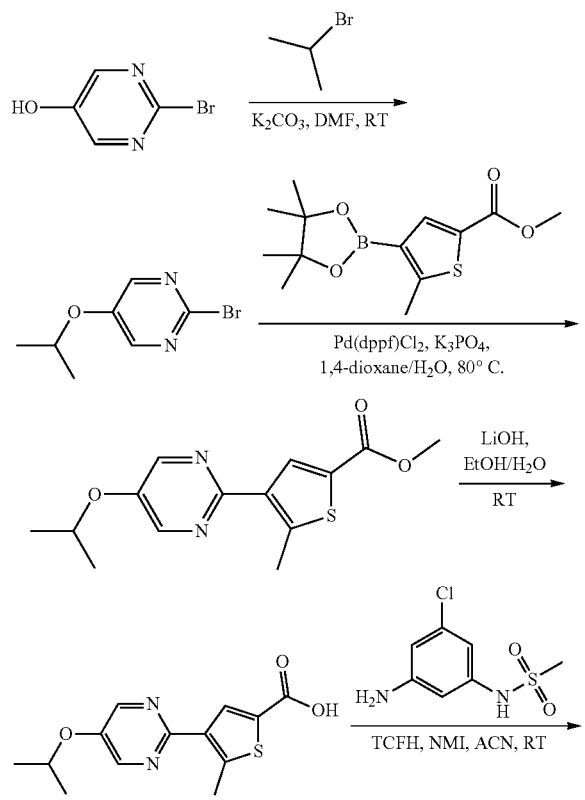

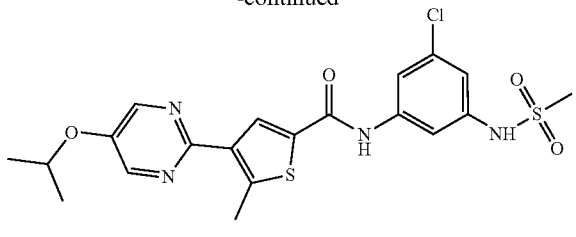

Step 1: A mixture of 2-bromopyrimidin-5-ol (15.0 g, 85.7 mmol, 1 equiv), K₂CO₃ (35.48 g, 257.1 mmol, 3 equiv) and 2-bromopropane (13.71 g, 111.5 mmol, 1.3 equiv) in DMF (150 mL) was stirred for 5 hours at room temperature. The reaction mixture was diluted with water (1 L). The resulting solution was extracted with EA (3×800 mL) and the organic layers were combined. The organic layer was dried over anhydrous sodium sulfate and concentrated under vacuum. The residue was purified by flash chromatography on silica gel column eluting with EA/PE (20%) to afford 2-bromo-5-isopropoxypyrimidine (15.0 g, 81% yield) as a white solid. LCMS (ESI) [M+H]+: 217

Step 2: A mixture of 2-bromo-5-isopropoxypyrimidine (14.0 g, 64.5 mmol, 1 equiv), Pd(dppf)Cl₂ (3.3 g, 4.5 mmol, 0.07 equiv), K₃PO₄ (41.1 g, 193.5 mmol, 3 equiv) and methyl 5-methyl-4-(4,4,5,5-tetramethyl-1,3,2-dioxaborolan-2-yl) thiophene-2-carboxylate (23.66 g, 83.8 mmol, 1.3 equiv) in 1,4-dioxane (150 mL) and H₂O (15 mL) was stirred for 2 hours at 80° C. under nitrogen atmosphere. The resulting mixture was concentrated under reduced pressure. The residue was purified by silica gel column chromatography, eluted with PE/EA (32%) to afford methyl 4-(5-isopropoxypyrimidin-2-yl)-5-methylthiophene-2-carboxylate (12.70 g, 67% yield) as a white solid. LCMS (ESI) [M+H]+: 293

Step 3: To a stirred solution of methyl 4-(5-isopropoxypyrimidin-2-yl)-5-methylthiophene-2-carboxylate (12.7 g, 43.4 mmol, 1 equiv) in EtOH (150 mL) and H₂O (150 mL) was added LiOH (10.4 g, 434.4 mmol, 10 equiv). Then the mixture was stirred for 4 hours at room temperature. The mixture was acidified to pH 5 with HCl (aq.). The precipitated solids were collected by filtration and washed with water. The resulting solid was dried under vacuum to afford 4-(5-isopropoxypyrimidin-2-yl)-5-methylthiophene-2-carboxylic acid (10.4 g, 86% yield) as a white solid. LCMS (ESI) [M+H]+: 279

Step 4: To a stirred solution of 4-(5-isopropoxypyrimidin-2-yl)-5-methylthiophene-2-carboxylic acid (10.4 g, 37.4 mmol, 1 equiv), TCFH (20.97 g, 74.7 mmol, 2 equiv) and NMI (12.27 g, 149.5 mmol, 4 equiv) in ACN (180 mL) was added N-(3-amino-5-chlorophenyl)methanesulfonamide (8.25 g, 37.4 mmol, 1 equiv). Then the mixture was stirred for 2 hours at room temperature. The mixture was concentrated and purified by reverse phase flash chromatography eluting with ACN/H₂O (56%, 0.1% FA) to afford N-(3-chloro-5-(methylsulfonamido)phenyl)-4-(5-isopropoxypyrimidin-2-yl)-5-methylthiophene-2-carboxamide (10.0113 g, 55.7% yield) as a white solid. LCMS (ESI) [M+H]+: 481. ¹H NMR (400 MHz, DMSO-d₆) δ 10.57 (s, 1H), 10.06 (s, 1H), 8.64 (d, J=2.7 Hz, 3H), 7.69 (dt, J=6.5, 1.9 Hz, 2H), 6.95 (t, J=2.0 Hz, 1H), 4.88 (p, J=6.0 Hz, 1H), 3.08 (s, 3H), 2.83 (s, 3H), 1.34 (d, J=6.0 Hz, 6H).

Examples 542-567

The compounds listed in the following table were prepared using a procedure similar to that described for examples 540 and 541:

| Structure | Compound No. | MS (ESI) [M + H]⁺ | ¹H NMR |
|---|---|---|---|
| 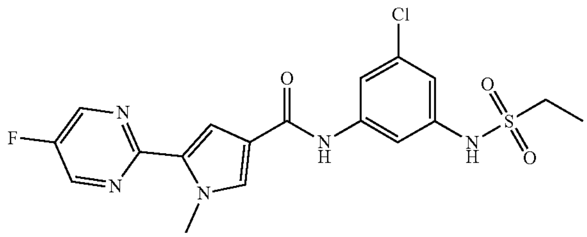 [SMILES: CCS(=O)(=O)Nc1cc(Cl)cc(NC(=O)c2cc(-c3ncc(F)cn3)n(C)c2)c1] | 542 | 437.95 | ¹H NMR (400 MHz, Methanol-d4) δ 8.70 (s, 2H), 7.59 (ddt, J = 25.9, 23.5, 2.0 Hz, 4H), 6.99 (d, J = 2.1 Hz, 1H), 4.11 (s, 3H), 3.17 (q, J = 7.4 Hz, 2H), 1.33 (t, J = 7.3 Hz, 3H). |
| 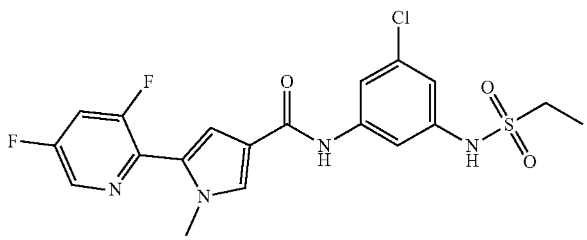 [SMILES: CCS(=O)(=O)Nc1cc(Cl)cc(NC(=O)c2cc(-c3ncc(F)cc3F)n(C)c2)c1] | 543 | 454.9 | ¹H NMR (400 MHz, DMSO-d6) δ 10.05 (s, 1H), 9.89 (s, 1H), 8.60 (d, J = 2.4 Hz, 1H), 8.09 (ddd, J = 11.1, 8.9, 2.5 Hz, 1H), 7.76 (d, J = 2.0 Hz, 1H), 7.70 (t, J = 1.9 Hz, 1H), 7.64 (t, J = 1.9 Hz, 1H), 7.20 (dd, J = 3.6, 1.9 Hz, 1H), 6.90 (t, J = 1.9 Hz, 1H), 3.88 (s, 3H), 3.16 (q, J = 7.3 Hz, 2H), 1.21 (t, J = 7.3 Hz, 3H). |
| 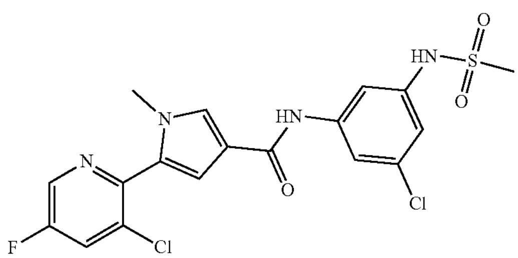 [SMILES: Cn1cc(C(=O)Nc2cc(Cl)cc(NS(C)(=O)=O)c2)cc1-c1ncc(F)cc1Cl] | 544 | 456.85 | ¹H NMR (400 MHz, DMSO-d6) δ 10.22-9.81 (m, 2H), 8.70 (d, J = 2.6 Hz, 1H), 8.25 (dd, J = 8.5, 2.6 Hz, 1H), 7.84-7.49 (m, 3H), 7.15 (d, J = 1.9 Hz, 1H), 6.90 (t, J = 2.0 Hz, 1H), 3.70 (s, 3H), 3.06 (s, 3H). |
| 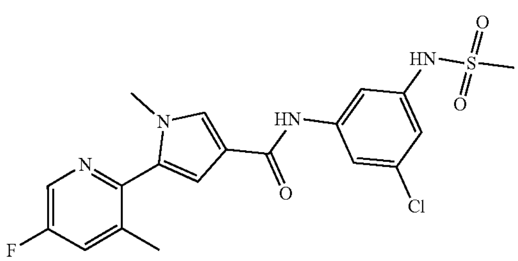 [SMILES: Cc1cc(F)cnc1-c1cc(C(=O)Nc2cc(Cl)cc(NS(C)(=O)=O)c2)cn1C] | 545 | 436.95 | ¹H NMR (400 MHz, DMSO-d6) δ 10.06 (s, 1H), 9.80 (s, 1H), 8.51 (d, J = 2.8 Hz, 1H), 7.77 (dd, J = 9.7, 2.9 Hz, 1H), 7.73-7.66 (m, 2H), 7.63 (t, J = 2.0 Hz, 1H), 6.90 (q, J = 1.9 Hz, 2H), 3.64 (s, 3H), 3.06 (s, 3H), 2.41 (s, 3H). |
| 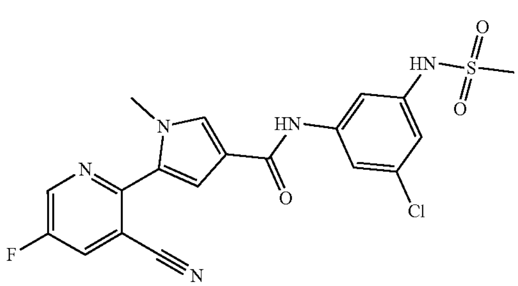 [SMILES: Cn1cc(C(=O)Nc2cc(Cl)cc(NS(C)(=O)=O)c2)cc1-c1ncc(F)cc1C#N] | 546 | 448.05 | ¹H NMR (400 MHz, DMSO-d6) δ 10.03 (s, 1H), 9.94 (s, 1H), 8.96 (d, J = 2.9 Hz, 1H), 8.56 (dd, J = 8.6, 2.9 Hz, 1H), 7.84 (d, J = 1.9 Hz, 1H), 7.71 (d, J = 1.9 Hz, 1H), 7.62 (d, J = 2.0 Hz, 1H), 7.35 (d, J = 1.9 Hz, 1H), 6.91 (d, J = 2.0 Hz, 1H), 3.83 (s, 3H), 3.06 (s, 3H). |

| Structure | Compound No. | MS (ESI) [M + H]+ | 1H NMR |
|---|---|---|---|
| 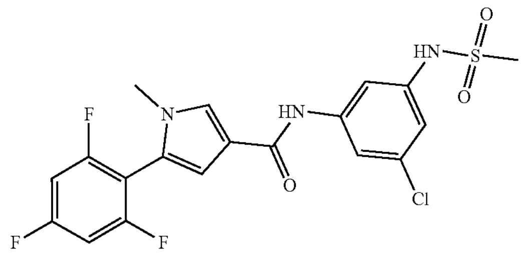 [SMILES: Cn1cc(C(=O)Nc2cc(Cl)cc(NS(C)(=O)=O)c2)cc1-c1c(F)cc(F)cc1F] | 547 | 458 | 1H NMR (300 MHz, DMSO-d6) δ 10.00 (s, 1H), 9.82 (s, 1H), 7.75 (d, J = 1.9 Hz, 1H), 7.70 (d, J = 1.8 Hz, 1H), 7.60 (d, J = 1.9 Hz, 1H), 7.40 (dd, J = 9.2, 7.8 Hz, 2H), 6.89 (t, J = 2.0 Hz, 1H), 6.82 (d, J = 1.9 Hz, 1H), 3.51 (s, 3H), 3.05 (s, 3H). |
| 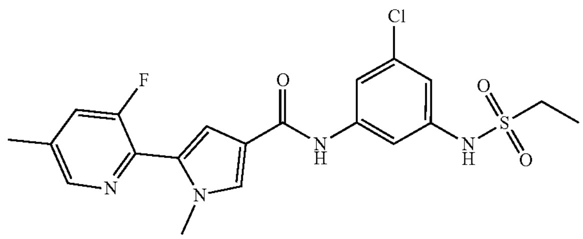 [SMILES: CCS(=O)(=O)Nc1cc(Cl)cc(NC(=O)c2cc(-c3ncc(C)cc3F)n(C)c2)c1] | 548 | 451 | 1H NMR (300 MHz, DMSO-d6) δ 10.07 (s, 1H), 9.88 (s, 1H), 8.36 (s, 1H), 7.77-7.61 (m, 4H), 7.18 (dd, J = 3.6, 1.9 Hz, 1H), 6.91 (t, J = 1.9 Hz, 1H), 3.90 (s, 3H), 3.17 (q, J = 7.3 Hz, 2H), 2.37 (s, 3H), 1.22 (t, J = 7.3 Hz, 3H). |
| 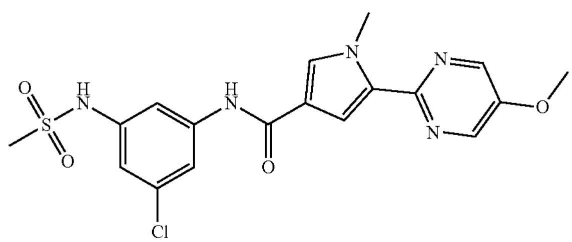 | 549 | 436.05 | 1H NMR (400 MHz, DMSO-d6) δ 10.02 (s, 1H), 9.92 (s, 1H), 8.58 (s, 2H), 7.74 (d, J = 1.9 Hz, 1H), 7.66 (d, J = 2.1 Hz, 2H), 7.56 (d, J = 2.1 Hz, 1H), 6.89 (t, J = 2.0 Hz, 1H), 4.05 (s, 3H), 3.94 (s, 3H), 3.06 (s, 3H). |
| 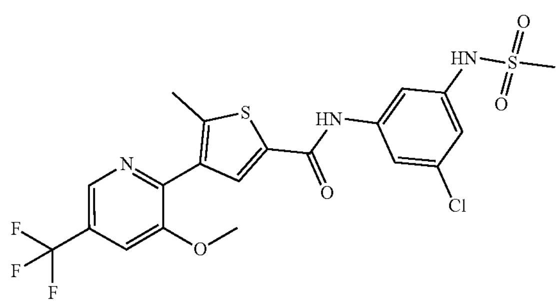 [SMILES: COc1cc(C(F)(F)F)cnc1-c1cc(C(=O)Nc2cc(Cl)cc(NS(C)(=O)=O)c2)sc1C] | 550 | 519.9 | 1H NMR (400 MHz, DMSO-d6) δ 10.41 (s, 1H), 10.06 (s, 1H), 8.63 (s, 1H), 8.16 (s, 1H), 7.92 (d, J = 1.8 Hz, 1H), 7.71-7.54 (m, 2H), 6.94 (t, J = 2.0 Hz, 1H), 3.97 (s, 3H), 3.06 (s, 3H), 2.46 (s, 3H). |
| 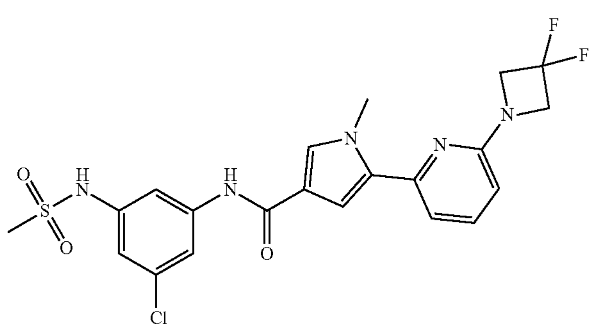 [SMILES: Cn1cc(C(=O)Nc2cc(Cl)cc(NS(C)(=O)=O)c2)cc1-c1cccc(N2CC(F)(F)C2)n1] | 551 | 495.95 | 1H NMR (400 MHz, DMSO-d6) δ 10.01 (s, 1H), 9.82 (s, 1H), 7.72 (t, J = 1.9 Hz, 1H), 7.69-7.56 (m, 3H), 7.19 (d, J = 2.0 Hz, 1H), 7.12 (d, J = 7.5 Hz, 1H), 6.89 (t, J = 1.9 Hz, 1H), 6.45 (d, J = 8.1 Hz, 1H), 4.42 (t, J = 12.4 Hz, 4H), 3.99 (s, 3H), 3.06 (s, 3H). |

| Structure | Compound No. | MS (ESI) [M + H]+ | ¹H NMR |
|---|---|---|---|
| 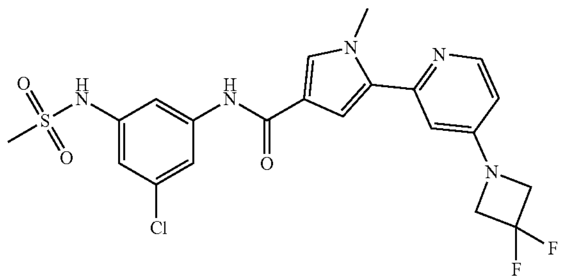 [SMILES: Cn1cc(C(=O)Nc2cc(Cl)cc(NS(C)(=O)=O)c2)cc1-c1cc(N2CC(F)(F)C2)ccn1] | 552 | 496.05 | ¹H NMR (400 MHz, Methanol-d4) δ 8.31-8.11 (m, 2H), 7.65 (t, J = 1.9 Hz, 1H), 7.61 (d, J = 2.0 Hz, 1H), 7.55 (t, J = 1.8 Hz, 1H), 7.05 (d, J = 2.0 Hz, 1H), 6.98 (t, J = 1.9 Hz, 1H), 6.76 (d, J = 2.4 Hz, 1H), 6.58 (dd, J = 6.2, 2.4 Hz, 1H), 4.51 (t, J = 11.9 Hz, 4H), 3.87 (s, 3H), 3.03 (s, 3H). |
| 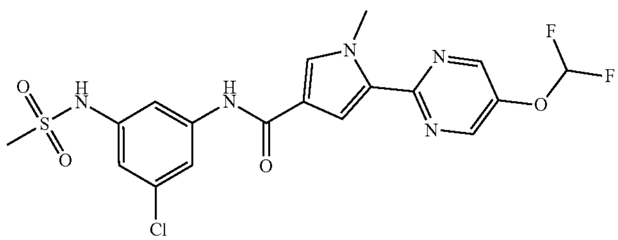 [SMILES: Cn1cc(C(=O)Nc2cc(Cl)cc(NS(C)(=O)=O)c2)cc1-c1ncc(OC(F)F)cn1] | 553 | 471.85 | ¹H NMR (400 MHz, DMSO-d6) δ 9.99 (d, J = 18.0 Hz, 2H), 8.79 (s, 2H), 7.82-7.60 (m, 4H), 7.29 (d, J = 73.0 Hz, 1H), 6.90 (d, J = 2.0 Hz, 1H), 4.07 (s, 3H), 3.07 (s, 3H). |
| 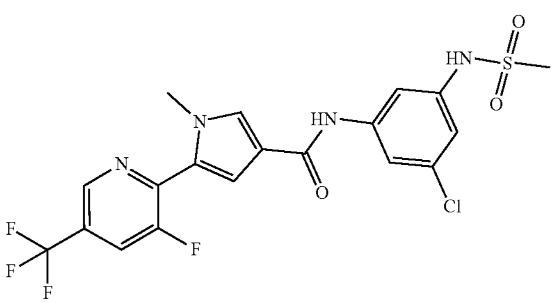 [SMILES: Cn1cc(C(=O)Nc2cc(Cl)cc(NS(C)(=O)=O)c2)cc1-c1ncc(C(F)(F)F)cc1F] | 554 | 490.9 | ¹H NMR (400 MHz, DMSO-d6) δ 10.02 (s, 1H), 9.97 (s, 1H), 8.87 (s, 1H), 8.47-8.31 (m, 1H), 7.86 (d, J = 1.9 Hz, 1H), 7.71 (q, J = 1.6 Hz, 1H), 7.65 (q, J = 1.7 Hz, 1H), 7.46 (dd, J = 4.1, 1.9 Hz, 1H), 6.92 (q, J = 1.6 Hz, 1H), 4.00 (s, 3H), 3.07 (d, J = 1.3 Hz, 3H). |
| 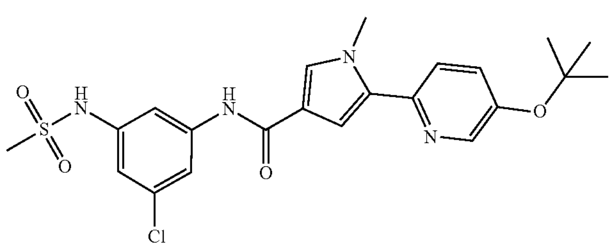 [SMILES: Cn1cc(C(=O)Nc2cc(Cl)cc(NS(C)(=O)=O)c2)cc1-c1ccc(OC(C)(C)C)cn1] | 555 | 477 | ¹H NMR (400 MHz, DMSO-d6) δ 10.03 (s, 1H), 9.84 (d, J = 2.1 Hz, 1H), 8.28 (dd, J = 2.8, 0.7 Hz, 1H), 7.73 (dq, J = 3.7, 1.8 Hz, 1H), 7.68-7.61 (m, 3H), 7.50 (ddd, J = 8.7, 3.2, 1.6 Hz, 1H), 7.18-7.11 (m, 1H), 6.93-6.75 (m, 1H), 4.11-3.81 (m, 3H), 3.16-3.04 (m, 3H), 1.34 (d, J = 0.9 Hz, 9H). |

-continued

| Structure | Compound No. | MS (ESI) [M + H]+ | 1H NMR |
|---|---|---|---|
| 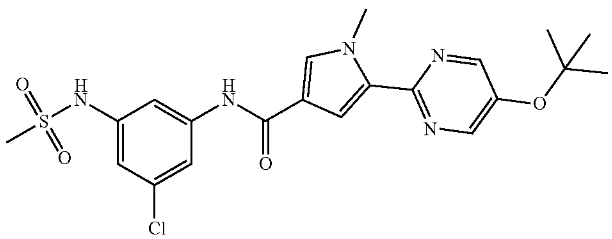 [SMILES: Cn1cc(C(=O)Nc2cc(Cl)cc(NS(C)(=O)=O)c2)cc1-c1ncc(OC(C)(C)C)cn1] | 556 | 476.15 [M − H]− | 1H NMR (400 MHz, DMSO-d6) δ 10.02 (s, 1H), 9.94 (s, 1H), 8.55 (s, 2H), 7.85-7.42 (m, 4H), 6.90 (t, J = 2.0 Hz, 1H), 4.08 (s, 3H), 3.07 (s, 3H), 1.36 (s, 9H). |
| 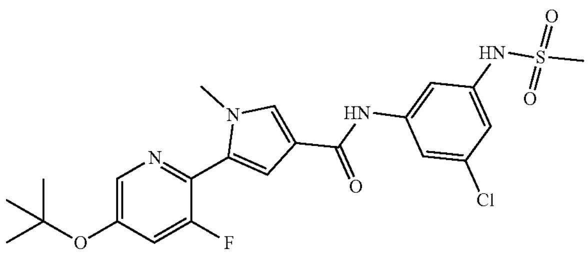 [SMILES: Cn1cc(C(=O)Nc2cc(Cl)cc(NS(C)(=O)=O)c2)cc1-c1ncc(OC(C)(C)C)cc1F] | 557 | 493.1 [M − H]− | 1H NMR (300 MHz, DMSO-d6) δ 10.02 (s, 1H), 9.88 (s, 1H), 8.23 (dd, J = 2.3, 1.2 Hz, 1H), 7.72 (q, J = 1.9 Hz, 2H), 7.67-7.53 (m, 2H), 7.15 (dd, J = 3.5, 1.9 Hz, 1H), 6.90 (t, J = 1.9 Hz, 1H), 3.89 (s, 3H), 3.07 (s, 3H), 1.39 (s, 9H). |
| 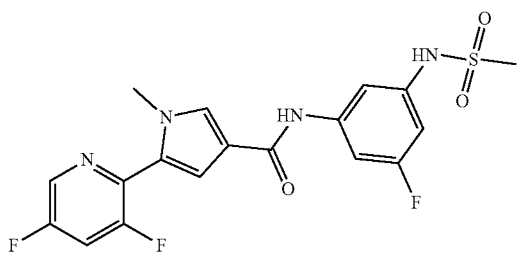 | 558 | 425.1 | 1H NMR (400 MHz, DMSO-d6) δ 10.02 (s, 1H), 9.91 (s, 1H), 8.60 (d, J = 2.4 Hz, 1H), 8.09 (ddd, J = 11.1, 8.9, 2.4 Hz, 1H), 7.76 (d, J = 1.9 Hz, 1H), 7.54-7.34 (m, 2H), 7.20 (dd, J = 3.7, 1.9 Hz, 1H), 6.67 (dt, J = 10.4, 2.2 Hz, 1H), 3.88 (s, 3H), 3.06 (s, 3H). |
| 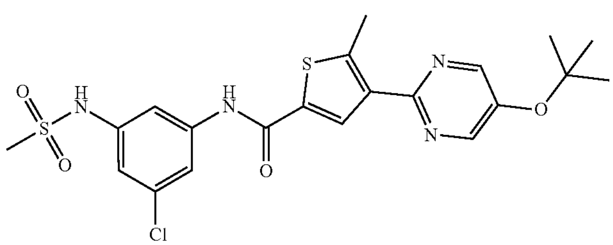 [SMILES: Cc1sc(C(=O)Nc2cc(Cl)cc(NS(C)(=O)=O)c2)cc1-c1ncc(OC(C)(C)C)cn1] | 559 | 495 | 1H NMR (400 MHz, DMSO-d6) δ 10.57 (s, 1H), 10.07 (s, 1H), 8.66 (d, J = 13.9 Hz, 3H), 7.69 (dt, J = 8.3, 1.8 Hz, 2H), 6.95 (t, J = 1.9 Hz, 1H), 3.08 (s, 3H), 2.86 (s, 3H), 1.38 (s, 9H). |
| 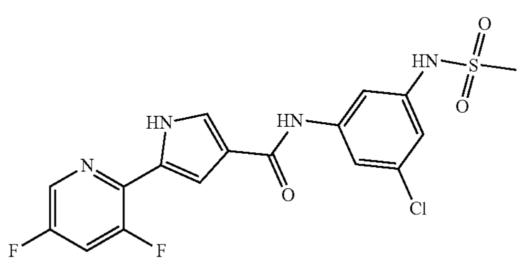 [SMILES: CS(=O)(=O)Nc1cc(Cl)cc(NC(=O)c2c[nH]c(-c3ncc(F)cc3F)c2)c1] | 560 | 427.05 | 1H NMR (400 MHz, DMSO-d6) δ 12.14 (s, 1H), 9.94 (s, 2H), 8.54 (d, J = 2.2 Hz, 1H), 8.05 (ddt, J = 11.2, 8.8, 2.4 Hz, 1H), 7.76 (dd, J = 3.3, 1.6 Hz, 1H), 7.72 (t, J = 1.9 Hz, 1H), 7.67 (t, J = 1.8 Hz, 1H), 7.31 (dt, J = 4.2, 2.1 Hz, 1H), 6.91 (t, J = 2.0 Hz, 1H), 3.07 (s, 3H). |

-continued

| Structure | Compound No. | MS (ESI) [M + H]+ | 1H NMR |
|---|---|---|---|
| 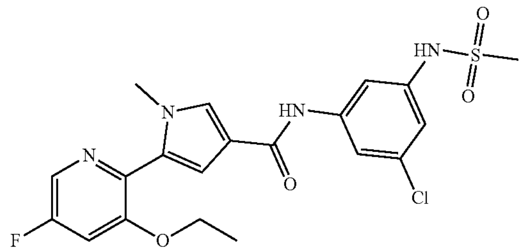 [SMILES: CCOc1cc(F)cnc1-c1cc(C(=O)Nc2cc(Cl)cc(NS(C)(=O)=O)c2)cn1C] | 561 | 466.95 | 1H NMR (400 MHz, DMSO-d6) δ 10.00 (s, 1H), 9.82 (s, 1H), 8.22 (d, J = 2.4 Hz, 1H), 7.76-7.55 (m, 4H), 7.10 (d, J = 2.0 Hz, 1H), 6.89 (t, J = 2.0 Hz, 1H), 4.18 (q, J = 6.9 Hz, 2H), 3.76 (s, 3H), 3.06 (s, 3H), 1.38 (t, J = 6.9 Hz, 3H). |
| 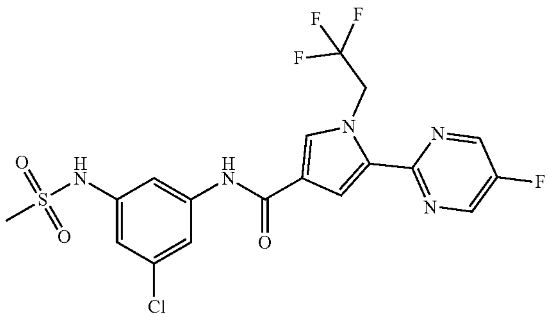 [SMILES: CS(=O)(=O)Nc1cc(Cl)cc(NC(=O)c2cc(-c3ncc(F)cn3)n(CC(F)(F)F)c2)c1] | 562 | 490 [M − H]− | 1H NMR (400 MHz, DMSO-d6) δ 10.11 (s, 1H), 10.05 (s, 1H), 8.94 (q, J = 0.9 Hz, 2H), 7.87 (d, J = 2.0 Hz, 1H), 7.80 (d, J = 2.0 Hz, 1H), 7.73 (t, J = 1.9 Hz, 1H), 7.68 (q, J = 1.6 Hz, 1H), 6.93 (td, J = 2.0, 0.7 Hz, 1H), 5.75 (q, J = 9.0 Hz, 2H), 3.08 (d, J = 0.9 Hz, 3H). |
| 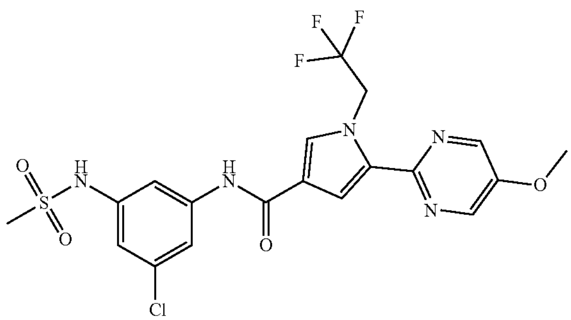 | 563 | 503.95 | 1H NMR (400 MHz, DMSO-d6) δ 10.04 (d, J = 13.6 Hz, 2H), 8.60 (s, 2H), 7.79 (d, J = 2.0 Hz, 1H), 7.73 (t, J = 1.9 Hz, 1H), 7.70-7.66 (m, 2H), 6.92 (t, J = 2.0 Hz, 1H), 5.77 (q, J = 9.1 Hz, 2H), 3.95 (s, 3H), 3.06 (s, 3H). |
| 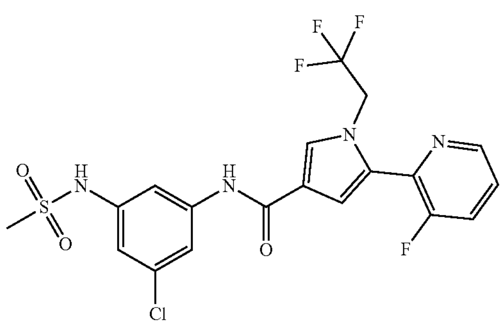 [SMILES: CS(=O)(=O)Nc1cc(Cl)cc(NC(=O)c2cc(-c3ncccc3F)n(CC(F)(F)F)c2)c1] | 564 | 491 | 1H NMR (400 MHz, DMSO-d6) δ 10.06 (s, 1H), 10.03 (s, 1H), 8.50 (dt, J = 4.7, 1.6 Hz, 1H), 7.98-7.83 (m, 2H), 7.67 (dt, J = 24.5, 2.0 Hz, 2H), 7.49-7.38 (m, 2H), 6.93 (t, J = 2.0 Hz, 1H), 5.68 (q, J = 9.2 Hz, 2H), 3.06 (s, 3H). |
| 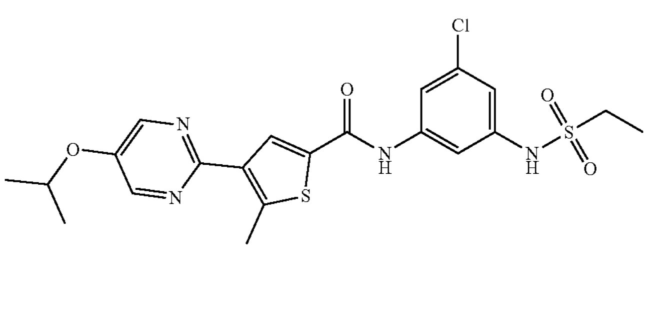 [SMILES: CCS(=O)(=O)Nc1cc(Cl)cc(NC(=O)c2cc(-c3ncc(OC(C)C)cn3)c(C)s2)c1] | 565 | 495 | 1H NMR (400 MHz, DMSO-d6) δ 10.55 (s, 1H), 10.09 (s, 1H), 8.63 (s, 3H), 7.68 (d, J = 2.0 Hz, 2H), 6.95 (t, J = 1.9 Hz, 1H), 4.88 (p, J = 6.0 Hz, 1H), 3.18 (q, J = 7.3 Hz, 2H), 2.83 (s, 3H), 1.34 (d, J = 6.0 Hz, 6H), |

| Structure | Compound No. | MS (ESI) [M + H]+ | 1H NMR |
|---|---|---|---|
| | | | 1.22 (t, J = 7.3 Hz, 3H). |
| (structure) | 566 | 509.05 | 1H NMR (400 MHz, DMSO-d6) δ 10.57 (s, 1H), 10.10 (s, 1H), 8.66 (d, J = 11.5 Hz, 3H), 7.68 (p, J = 1.9 Hz, 2H), 6.95 (t, J = 1.9 Hz, 1H), 3.18 (q, J = 7.3 Hz, 2H), 2.86 (s, 3H), 1.38 (s, 9H), 1.22 (t, J = 7.3 Hz, 3H). |
| (structure) | 567 | 457 | 1H NMR (400 MHz, DMSO-d6) δ 10.01 (s, 1H), 9.86 (s, 1H), 8.72 (dt, J = 4.0, 1.8 Hz, 1H), 7.87-7.78 (m, 2H), 7.71 (t, J = 1.8 Hz, 1H), 7.61 (t, J = 1.9 Hz, 1H), 7.01-6.72 (m, 2H), 3.57 (s, 3H), 3.06 (s, 3H). |

Example 568: N-(3-chloro-5-methanesulfonamidophenyl)-5-(5-fluoro-3-methoxypyridin-2-yl)-1-methylpyrrole-3-carboxamide

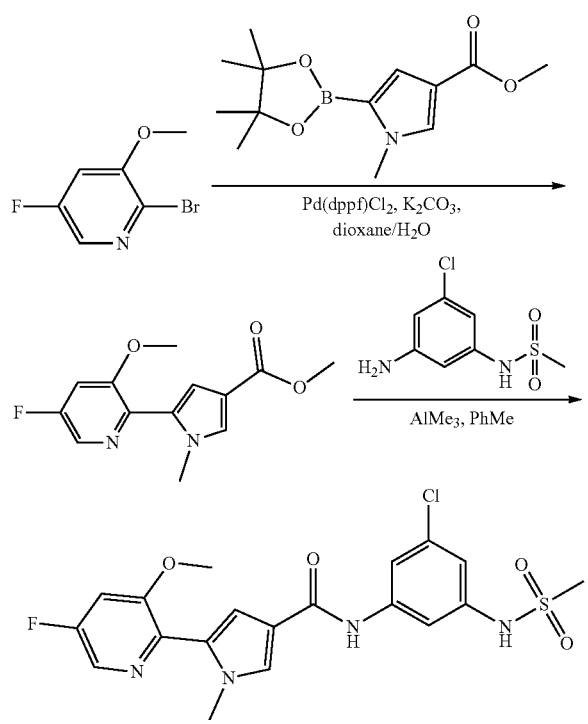

Step 1: A solution of 2-bromo-5-fluoro-3-methoxypyridine (212 mg, 1.029 mmol, 1 equiv), methyl 1-methyl-5-(4,4,5,5-tetramethyl-1,3,2-dioxaborolan-2-yl)pyrrole-3-carboxylate (273 mg, 1.029 mmol, 1 equiv), Pd(dppf)Cl$_2$ (84.04 mg, 0.103 mmol, 0.1 equiv) and K$_2$CO$_3$ (426.03 mg, 3.087 mmol, 3 equiv) in 1,4-dioxane (5 ml) and H$_2$O (1 ml) was stirred for 1.5 hours at 80° C. under nitrogen atmosphere. The mixture was allowed to cool down to room temperature. The resulting mixture was diluted with water and extracted with EtOAc (3×15 mL). The combined organic layers were washed with brine (3×10 mL), dried over anhydrous Na$_2$SO$_4$. After filtration, the filtrate was concentrated under reduced pressure. The residue was purified by silica gel column chromatography, eluted with PE/EA (1:1) to afford methyl 5-(5-fluoro-3-methoxypyridin-2-yl)-1-methylpyrrole-3-carboxylate (80 mg, 29% yield) as a white solid. LCMS (ESI) [M+H]+: 265.09

Step 2: To a stirred solution of methyl 5-(5-fluoro-3-methoxypyridin-2-yl)-1-methylpyrrole-3-carboxylate (80 mg, 0.303 mmol, 1 equiv) and N-(3-amino-5-chlorophenyl)methanesulfonamide (67 mg, 0.303 mmol, 1 equiv) in PhMe (2 ml) was added Al(Me)$_3$ (0.5 ml) dropwise at 0'° C. The resulting mixture was stirred for additional 1 hour at 80° C. The mixture was allowed to cool down to room temperature. The reaction was quenched by the addition of water (1 mL) at 0° C. The resulting mixture was concentrated under reduced pressure. The crude product (60 mg) was purified by Prep-HPLC to afford N-(3-chloro-5-methanesulfonamidophenyl)-5-(5-fluoro-3-methoxypyridin-2-yl)-1-methylpyrrole-3-carboxamide (48.8 mg, 35% yield) as a white solid. LCMS (ESI) [M+H]+: 452.85. 1H NMR (400 MHz, DMSO-d$_6$) δ 10.03 (s, 1H), 9.82 (s, 1H), 8.24 (d, J=2.4 Hz, H), 7.71 (d, J=2.2 Hz, 1H), 7.66 (d, J=2.0 Hz, H), 7.65-7.60 (m, 2H), 7.09 (d, J=2.0 Hz, 1H), 6.89 (t, J=2.0 Hz, 1H), 3.92 (s, 3H), 3.75 (s, 3H), 3.06 (s, 3H).

Examples 569-585

The compounds listed in the following table were prepared using a procedure similar to that described for example 568:

| Structure | Compound No. | MS (ESI) [M + H]+ | ¹H NMR |
|---|---|---|---|
| 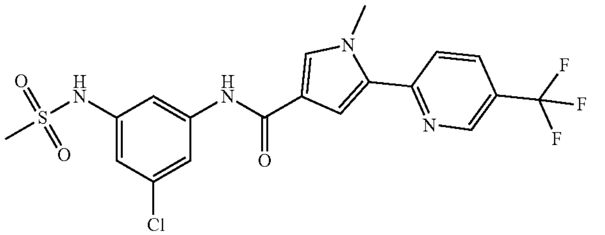 [SMILES: Cn1cc(C(=O)Nc2cc(Cl)cc(NS(C)(=O)=O)c2)cc1-c1ccc(C(F)(F)F)cn1] | 569 | 473.25 | ¹H NMR (400 MHz, DMSO-d6) δ 10.02 (s, 1H), 9.91 (s, 1H), 8.95 (s, 1H), 8.21 (dd, J = 8.9, 2.4 Hz, 1H), 7.94 (d, J = 8.4 Hz, 1H), 7.78 (d, J = 2.0 Hz, 1H), 7.72 (s, 1H), 7.63 (s, 1H), 7.46 (d, J = 2.0 Hz, 1H), 6.91 (s, 1H), 4.05 (s, 3H), 3.07 (s, 3H). |
| 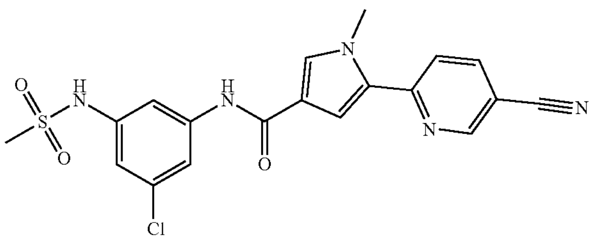 [SMILES: Cn1cc(C(=O)Nc2cc(Cl)cc(NS(C)(=O)=O)c2)cc1-c1ccc(C#N)cn1] | 570 | 429.9 | ¹H NMR (400 MHz, DMSO-d6) δ 10.01 (s, 1H), 9.93 (s, 1H), 8.99 (t, J = 1.5 Hz, 1H), 8.28 (dd, J = 8.5, 2.2 Hz, 1H), 7.95-7.88 (m, 1H), 7.81 (d, J = 1.9 Hz, 1H), 7.72 (t, J = 1.9 Hz, 1H), 7.62 (t, J = 1.9 Hz, 1H), 7.50 (d, J = 2.0 Hz, 1H), 6.91 (t, J = 1.9 Hz, 1H), 4.04 (s, 3H), 3.07 (s, 3H). |
| 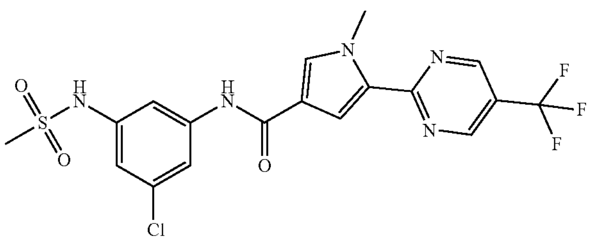 [SMILES: Cn1cc(C(=O)Nc2cc(Cl)cc(NS(C)(=O)=O)c2)cc1-c1ncc(C(F)(F)F)cn1] | 571 | 473.95 | ¹H NMR (400 MHz, DMSO-d6) δ 10.04 (s, 2H), 9.21 (s, 2H), 7.88 (dd, J = 29.9, 2.1 Hz, 2H), 7.71 (dt, J = 28.6, 1.9 Hz, 2H), 6.91 (t, J = 2.0 Hz, 1H), 4.12 (s, 3H), 3.07 (s, 3H). |
| 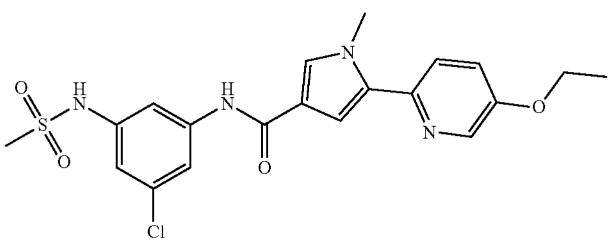 [SMILES: CCOc1ccc(-c2cc(C(=O)Nc3cc(Cl)cc(NS(C)(=O)=O)c3)cn2C)nc1] | 572 | 449.05 | ¹H NMR (300 MHz, DMSO-d6) δ 10.03 (s, 1H), 9.81 (s, 1H), 8.31 (d, J = 2.9 Hz, 1H), 7.73 (t, J = 1.8 Hz, 1H), 7.63 (t, J = 2.6 Hz, 3H), 7.45 (dd, J = 8.8, 3.0 Hz, 1H), 7.07 (d, J = 1.9 Hz, 1H), 6.90 (t, J = 1.9 Hz, 1H), 4.15 (q, J = 6.9 Hz, 2H), 3.93 (s, 3H), 3.07 (s, 3H), 1.37 (t, J = 7.0 Hz, 3H). |
| 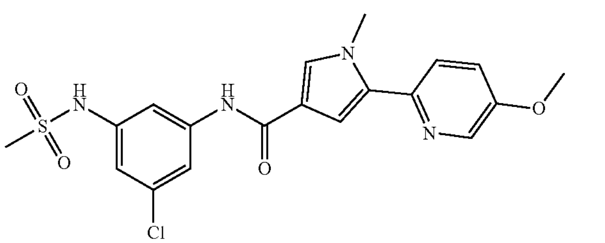 | 573 | 434.95 | ¹H NMR (400 MHz, DMSO-d6) δ 10.04 (s, 1H), 9.81 (s, 1H), 8.33 (d, J = 3.0 Hz, 1H), 7.73 (t, J = 1.9 Hz, 1H), 7.68-7.61 (m, 3H), 7.47 (dd, J = 8.8, 3.0 Hz, 1H), 7.08 (d, J = 2.0 Hz, 1H), 6.90 (t, J = 2.0 Hz, 1H), 3.93 (s, 3H), 3.87 (s, 3H), 3.07 (s, 3H). |
| 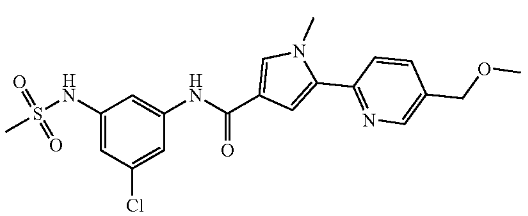 | 574 | 449 | ¹H NMR (400 MHz, DMSO-d6) δ 9.85 (s, 1H), 8.54 (d, J = 2.2 Hz, 1H), 7.79 (dd, J = 8.2, 2.2 Hz, 1H), 7.75-7.66 (m, 3H), 7.63 (t, J = 2.0 Hz, 1H), 7.24 (d, J = 2.0 Hz, 1H), 6.90 (t, J = 2.0 Hz, 1H), 4.47 (s, 2H), 4.00 (s, 3H), 3.34 (s, 3H), 3.07 (s, 3H). |

| Structure | Compound No. | MS (ESI) [M + H]⁺ | ¹H NMR |
|---|---|---|---|
| 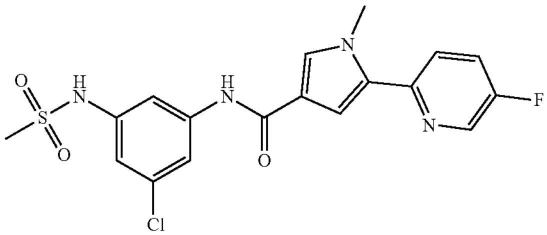 [SMILES: Cn1cc(C(=O)Nc2cc(Cl)cc(NS(C)(=O)=O)c2)cc1-c1ccc(F)cn1] | 575 | 423 | ¹H NMR (400 MHz, DMSO-d6) δ 10.02 (s, 1H), 9.84 (s, 1H), 8.60 (d, J = 2.4 Hz, 1H), 7.85-7.74 (m, 2H), 7.74-7.66 (m, 2H), 7.61 (d, J = 2.2 Hz, 1H), 7.20 (d, J = 2.0 Hz, 1H), 6.89 (d, J = 2.0 Hz, 1H), 3.95 (s, 3H), 3.06 (s, 3H) |
| 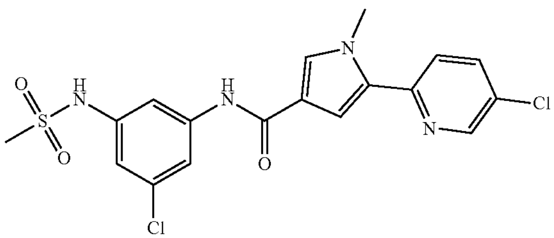 [SMILES: Cn1cc(C(=O)Nc2cc(Cl)cc(NS(C)(=O)=O)c2)cc1-c1ccc(Cl)cn1] | 576 | 438.85 | ¹H NMR (400 MHz, DMSO-d6) δ 10.00 (s, 1H), 9.86 (s, 1H), 8.63 (d, J = 2.5 Hz, 1H), 7.96 (dd, J = 8.6, 2.6 Hz, 1H), 7.79-7.59 (m, 4H), 7.28 (d, J = 2.0 Hz, 1H), 6.90 (d, J = 2.0 Hz, 1H), 3.98 (s, 3H), 3.06 (s, 3H). |
| 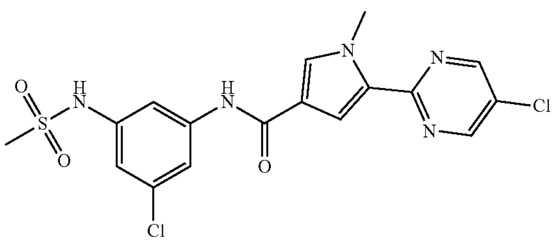 [SMILES: Cn1cc(C(=O)Nc2cc(Cl)cc(NS(C)(=O)=O)c2)cc1-c1ncc(Cl)cn1] | 577 | 438 [M − H]⁻ | ¹H NMR (400 MHz, DMSO-d6) δ 9.97 (s, 1H), 9.69 (s, 1H), 8.91 (s, 2H), 7.82-7.70 (m, 3H), 7.65 (t, J = 1.9 Hz, 1H), 6.89 (t, J = 2.0 Hz, 1H), 4.07 (s, 3H), 3.05 (s, 3H). |
| 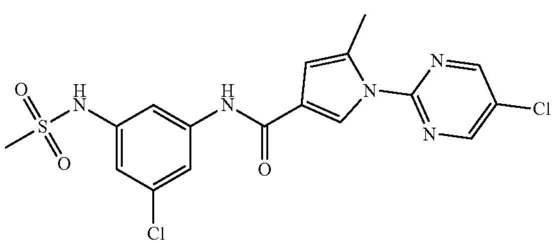 [SMILES: Cc1cc(C(=O)Nc2cc(Cl)cc(NS(C)(=O)=O)c2)cn1-c1ncc(Cl)cn1] | 578 | 439.85 | ¹H NMR (300 MHz, DMSO-d6) δ 10.03 (d, J = 12.0 Hz, 2H), 9.00 (s, 2H), 8.47 (d, J = 2.1 Hz, 1H), 7.72 (t, J = 1.9 Hz, 1H), 7.66 (t, J = 1.9 Hz, 1H), 6.91 (t, J = 1.9 Hz, 1H), 6.59 (dd, J = 2.1, 1.1 Hz, 1H), 3.06 (s, 3H), 2.58 (d, J = 1.1 Hz, 3H). |
| 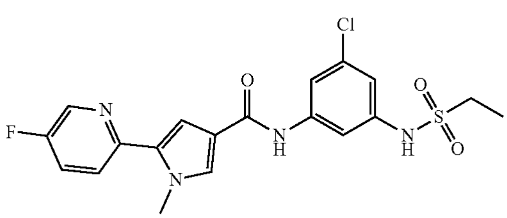 [SMILES: CCS(=O)(=O)Nc1cc(Cl)cc(NC(=O)c2cc(-c3ccc(F)cn3)n(C)c2)c1] | 579 | 437.15 | ¹H NMR (400 MHz, DMSO-d6) δ 10.06 (s, 1H), 9.85 (s, 1H), 8.60 (t, J = 1.7 Hz, 1H), 7.85-7.74 (m, 2H), 7.71 (t, J = 1.9 Hz, 1H), 7.69 (d, J = 2.0 Hz, 1H), 7.62 (t, J = 1.9 Hz, 1H), 7.20 (d, J = 2.0 Hz, 1H), 6.90 (t, J = 2.0 Hz, 1H), 3.95 (s, 3H), 3.17 (q, J = 7.3 Hz, 2H), 1.22 (t, J = 7.3 Hz, 3H). |
| 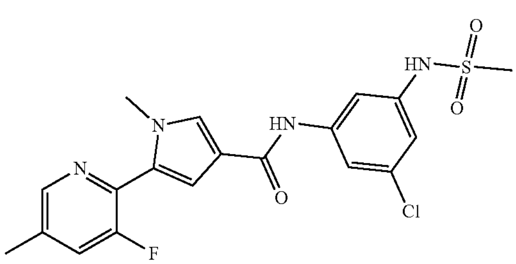 | 580 | 437.05 | ¹H NMR (300 MHz, DMSO-d6) δ 9.94 (d, J = 40.3 Hz, 2H), 8.35 (q, J = 1.5 Hz, 1H), 7.76-7.60 (m, 4H), 7.17 (dd, J = 3.5, 1.9 Hz, 1H), 6.90 (t, J = 1.9 Hz, 1H), 3.90 (s, 3H), 3.06 (s, 3H), 2.37 (s, 3H). |

| Structure | Compound No. | MS (ESI) [M + H]+ | 1H NMR |
|---|---|---|---|
| 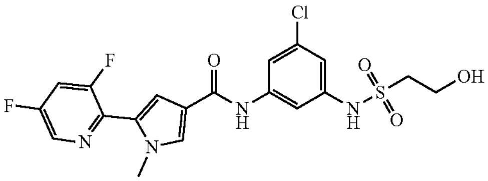 [SMILES: Cn1cc(C(=O)Nc2cc(Cl)cc(NS(=O)(=O)CCO)c2)cc1-c1ncc(F)cc1F] | 581 | 471.05 | 1H NMR (400 MHz, DMSO-d6) δ 10.00 (s, 1H), 9.90 (s, 1H), 8.60 (d, J = 2.4 Hz, 1H), 8.09 (ddd, J = 11.2, 8.9, 2.4 Hz, 1H), 7.76 (d, J = 1.9 Hz, 1H), 7.71 (t, J = 1.8 Hz, 1H), 7.63 (t, J = 1.9 Hz, 1H), 7.20 (dd, J = 3.6, 1.9 Hz, 1H), 6.90 (t, J = 1.9 Hz, 1H), 4.95 (t, J = 5.7 Hz, 1H), 3.88 (s, 3H), 3.80-3.69 (m, 2H), 3.30 (d, J = 6.5 Hz, 2H). |
| 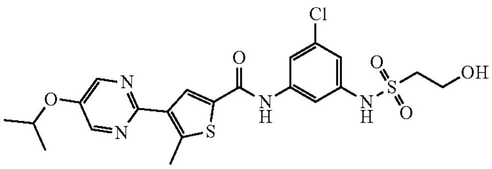 [SMILES: Cc1sc(C(=O)Nc2cc(Cl)cc(NS(=O)(=O)CCO)c2)cc1-c1ncc(OC(C)C)cn1] | 582 | 511.05 | 1H NMR (400 MHz, Methanol-d4) δ 8.51 (s, 2H), 8.45 (s, 1H), 7.65 (d, J = 2.0 Hz, 1H), 7.56 (t, J = 1.9 Hz, 1H), 7.03 (d, J = 2.0 Hz, 1H), 4.84-4.75 (m, 1H), 3.95 (t, J = 6.3 Hz, 2H), 3.35 (t, J = 6.3 Hz, 2H), 2.85 (s, 3H), 1.40 (d, J = 6.0 Hz, 6H). |
| 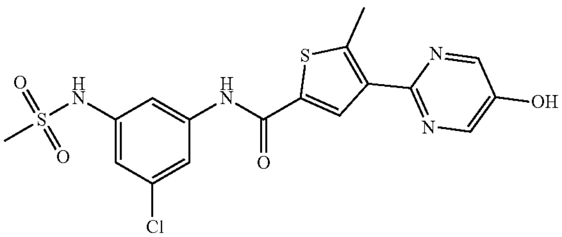 [SMILES: Cc1sc(C(=O)Nc2cc(Cl)cc(NS(C)(=O)=O)c2)cc1-c1ncc(O)cn1] | 583 | 438.95 | 1H NMR (400 MHz, DMSO-d6) δ 10.56 (d, J = 9.8 Hz, 2H), 10.06 (s, 1H), 8.61 (s, 1H), 8.45 (s, 2H), 7.69 (dt, J = 6.8, 2.0 Hz, 2H), 6.94 (t, J = 2.0 Hz, 1H), 3.07 (s, 3H), 2.81 (s, 3H). |
| 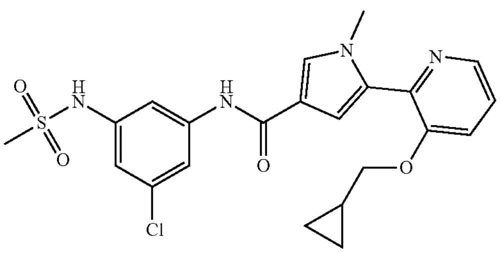 [SMILES: Cn1cc(C(=O)Nc2cc(Cl)cc(NS(C)(=O)=O)c2)cc1-c1ncccc1OCC1CC1] | 584 | 475 | 1H NMR (300 MHz, DMSO-d6) δ 9.83 (s, 1H), 8.20 (dd, J = 4.6, 1.3 Hz, 1H), 7.75-7.65 (m, 2H), 7.62 (t, J = 1.9 Hz, 1H), 7.52 (dd, J = 8.5, 1.3 Hz, 1H), 7.29 (dd, J = 8.4, 4.6 Hz, 1H), 7.17 (d, J = 2.0 Hz, 1H), 6.89 (t, J = 1.9 Hz, 1H), 3.95 (d, J = 6.9 Hz, 2H), 3.81 (s, 3H), 3.05 (s, 3H), 1.34-1.18 (m, 1H), 0.64-0.52 (m, 2H), 0.41-0.30 (m, 2H). |
| 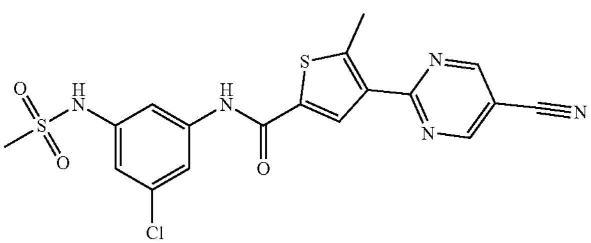 [SMILES: Cc1sc(C(=O)Nc2cc(Cl)cc(NS(C)(=O)=O)c2)cc1-c1ncc(C#N)cn1] | 585 | 448 | 1H NMR (400 MHz, DMSO-d6) δ 10.63 (s, 1H), 10.12 (s, 1H), 9.39 (s, 2H), 8.78 (s, 1H), 7.67 (dt, J = 7.2, 1.9 Hz, 2H), 6.95 (t, J = 2.0 Hz, 1H), 3.06 (s, 3H), 2.90 (s, 3H). |

Example 586: N-(3-chloro-5-methanesulfonamidophenyl)-5-ethyl-4-(5-fluoropyrimidin-2-yl)thiophene-2-carboxamide

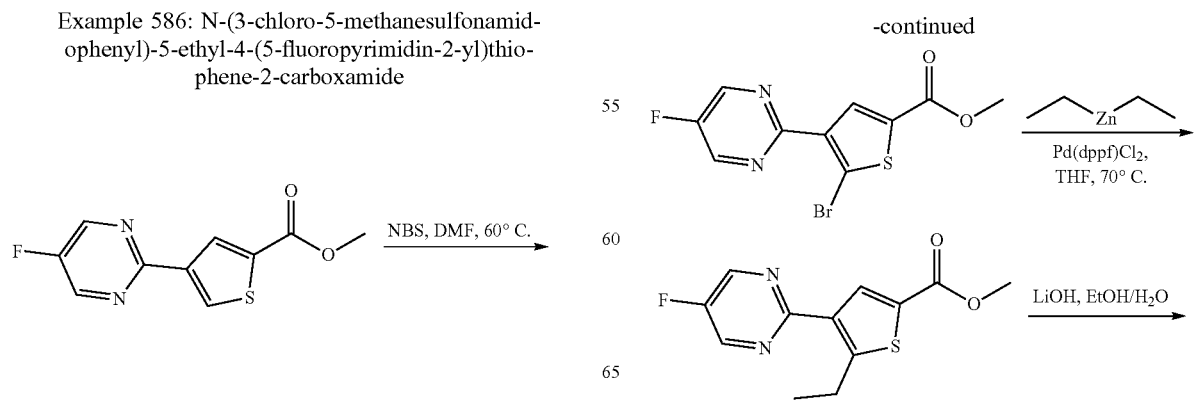

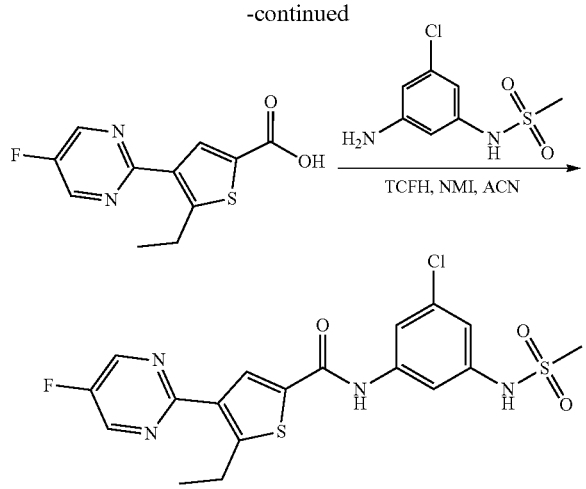

Step 1: A solution of methyl 4-(5-fluoropyrimidin-2-yl)thiophene-2-carboxylate (300 mg, 1.25 mmol) and NBS (1.33 g, 7.50 mmol) in DMF (10 mL) was stirred for 2 hours at 60° C. under nitrogen atmosphere. The resulting mixture was concentrated under reduced pressure. The residue was purified by silica gel column chromatography, eluted with PE/EA (1:1) to afford methyl 5-bromo-4-(5-fluoropyrimidin-2-yl)thiophene-2-carboxylate (280 mg, 0.882 mmol) as a white solid. LCMS (ESI) [M+H]+: 317

Step 2: A solution of methyl 5-bromo-4-(5-fluoropyrimidin-2-yl)thiophene-2-carboxylate (200 mg, 0.630 mmol), diethylzinc (1.88 mL, 1.88 mmol) and Pd(dppf)Cl$_2$ (51 mg, 0.0630 mmol) in THF (10 mL) was stirred for 2 hours at 70° C. under nitrogen atmosphere. The resulting mixture was concentrated under reduced pressure. The residue was purified by silica gel column chromatography, eluted with PE/EA (1:1) to afford methyl 5-ethyl-4-(5-fluoropyrimidin-2-yl)thiophene-2-carboxylate (107 mg, 0.401 mmol) as a white solid. LCMS (ESI) [M+H]+: 267

Step 3: To a stirred solution of methyl 5-ethyl-4-(5-fluoropyrimidin-2-yl)thiophene-2-carboxylate (107 mg, 0.401 mmol) in EtOH (5 mL) and H$_2$O (2 mL) was added LiOH (96 mg, 4.01 mmol) at 0° C. Then the mixture was stirred for 2 hours at room temperature. The mixture was acidified to pH 5 with citric acid. The precipitated solids were collected by filtration and washed with water. The resulting solid was dried under vacuum to afford 5-ethyl-4-(5-fluoropyrimidin-2-yl)thiophene-2-carboxylic acid (78.0 mg, 0.309 mmol) as a yellow solid. LCMS (ESI) [M+H]+: 253

Step 4: To a stirred solution of 5-ethyl-4-(5-fluoropyrimidin-2-yl)thiophene-2-carboxylic acid (78 mg, 0.309 mmol), TCFH (173 mg, 0.618 mmol) and NMI (74 mg, 0.926 mmol) in ACN (5 mL) was added N-(3-amino-5-chlorophenyl)methanesulfonamide (68 mg, 0.309 mmol) at room temperature. Then the mixture was stirred for 1 hour at room temperature. The mixture was concentrated under reduced pressure. The residue was purified by reversed-phase flash chromatography with the following conditions: column, C18 silica gel; mobile phase, MeCN in water (0.1% formic acid), 0% to 50% gradient in 20 min; detector, UV 254 nm. This resulted in N-(3-chloro-5-methanesulfonamidophenyl)-5-ethyl-4-(5-fluoropyrimidin-2-yl)thiophene-2-carboxamide (43.7 mg, 0.0960 mmol) as a white solid. LCMS (ESI) [M+H]+: 454.90. $^1$H NMR (400 MHz, DMSO-d$_6$) δ 10.59 (s, 1H), 10.08 (s, 1H), 9.01 (s, 2H), 8.68 (s, 1H), 7.68 (dt, J=10.2, 2.0 Hz, 2H), 6.95 (d, J=2.0 Hz, 1H), 3.43-3.35 (m, 2H), 3.07 (s, 3H), 1.32 (t, J=7.4 Hz, 3H).

Examples 587-589

The compounds listed in the following table were prepared using a procedure similar to that described for example 586:

| Structure | Compound No. | MS (ESI) [M + H]+ | $^1$H NMR |
|---|---|---|---|
| 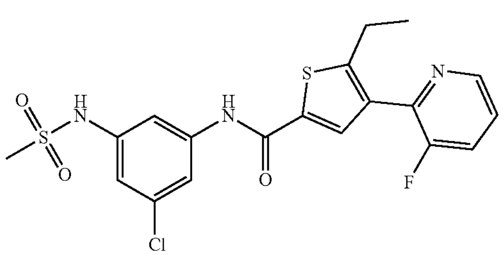 [SMILES: CCc1sc(C(=O)Nc2cc(Cl)cc(NS(C)(=O)=O)c2)cc1-c1ncccc1F] | 587 | 454.1 | $^1$H NMR (300 MHZ, DMSO-d6) δ 10.45 (s, 1H), 10.08 (s, 1H), 8.57 (dq, J = 4.6, 1.4 Hz, 1H), 8.20 (d, J = 1.9 Hz, 1H), 7.91 (ddd, J = 10.6, 8.4, 1.3 Hz, 1H), 7.68 (t, J = 1.9 Hz, 1H), 7.63 (t, J = 1.9 Hz, 1H), 7.55 (dt, J = 8.5, 4.3 Hz, 1H), 6.96 (t, J = 2.0 Hz, 1H), 3.07 (s, 3H), 2.96 (q, J = 7.5 Hz, 2H), 1.25 (t, J = 7.5 Hz, 3H). |
| 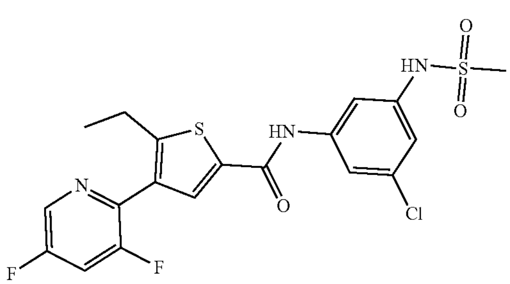 [SMILES: CCc1sc(C(=O)Nc2cc(Cl)cc(NS(C)(=O)=O)c2)cc1-c1ncc(F)cc1F] | 588 | 471.95 | $^1$H NMR (400 MHZ, DMSO-d6) δ 10.44 (s, 1H), 10.07 (s, 1H), 8.66 (d, J = 2.4 Hz, 1H), 8.23-8.03 (m, 2H), 7.64 (dt, J = 21.4, 1.9 Hz, 2H), 6.95 (t, J = 1.9 Hz, 1H), 3.06 (s, 3H), 2.93 (q, J = 7.5 Hz, 2H), 1.24 (t, J = 7.5 Hz, 3H). |

| Structure | Compound No. | MS (ESI) [M + H]+ | 1H NMR |
|---|---|---|---|
| 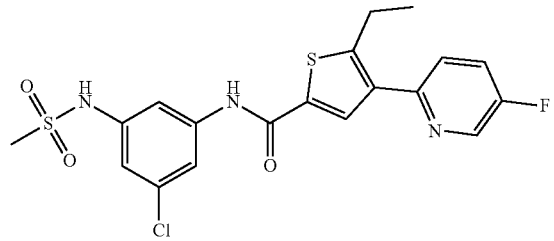 [SMILES: CCc1sc(C(=O)Nc2cc(Cl)cc(NS(C)(=O)=O)c2)cc1-c1ccc(F)cn1] | 589 | 454 | 1H NMR (400 MHZ, DMSO-d6) δ 10.43 (s, 1H), 10.07 (s, 1H), 8.68 (d, J = 3.0 Hz, 1H), 8.33 (s, 1H), 7.88 (td, J = 8.7, 3.0 Hz, 1H), 7.74 (dd, J = 8.8, 4.4 Hz, 1H), 7.65 (dt, J = 20.2, 1.9 Hz, 2H), 6.95 (t, J = 1.9 Hz, 1H), 3.14 (q, J = 7.4 Hz, 2H), 3.07 (s, 3H), 1.28 (t, J = 7.4 Hz, 3H). |
Example 590: N-(3-chloro-5-methanesulfonamidophenyl)-4-[5-(4-cyclopropanecarbonylpiperazin-1-yl)pyridin-2-yl]-5-methylthiophene-2-carboxamide
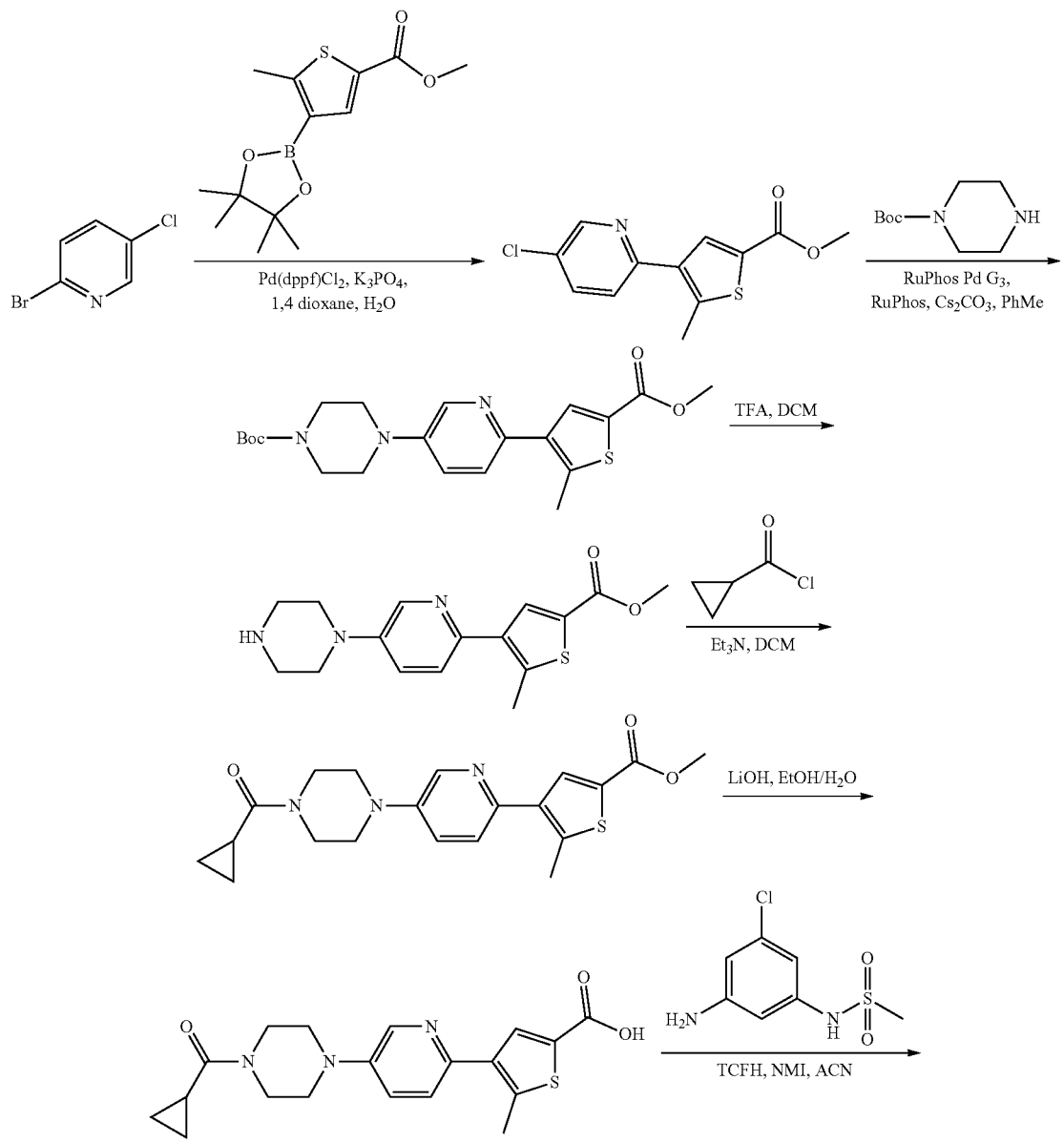

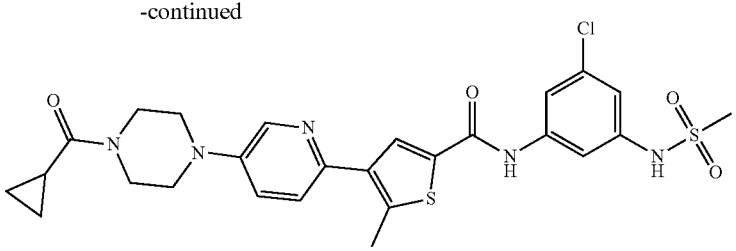

Step 1: A solution of 2-bromo-5-chloropyridine (1.02 g, 5.30 mmol), Pd(dppf)Cl$_2$ (345 mg, 0.424 mmol), K$_3$PO$_4$ (3.37 g, 15.9 mmol) and methyl 5-methyl-4-(4,4,5,5-tetramethyl-1,3,2-dioxaborolan-2-yl)thiophene-2-carboxylate (2.99 g, 10.6 mmol) in 1,4-dioxane (15 mL) and H$_2$O (1 mL) was stirred for 2 hours at 80° C. under nitrogen atmosphere. The resulting mixture was concentrated under reduced pressure. The residue was purified by silica gel column chromatography, eluted with PE/EA (1:1) to afford methyl 4-(5-chloropyridin-2-yl)-5-methylthiophene-2-carboxylate (800 mg, 2.98 mmol) as a white solid. LCMS (ESI) [M+H]$^+$: 268

Step 2: To a stirred solution of methyl 4-(5-chloropyridin-2-yl)-5-methylthiophene-2-carboxylate (800 mg, 2.98 mmol), Cs$_2$CO$_3$ (2.91 g, 8.94 mmol), RuPhos Pd G$_3$ (374 mg, 0.447 mmol), RuPhos (555 mg, 1.19 mmol) and tert-butyl piperazine-1-carboxylate (609 mg, 3.27 mmol) in PhMe (20 mL) at room temperature. Then the mixture was stirred for 5 hours at 100° C. under nitrogen atmosphere. The mixture was concentrated under reduced pressure. The residue was purified by reversed-phase flash chromatography with the following conditions: column, C18 silica gel; mobile phase, MeCN in water (0.1% formic acid), 0% to 65% gradient in 20 min; detector, UV 254 nm. This resulted in tert-butyl 4-{6-[5-(methoxycarbonyl)-2-methylthiophen-3-yl]pyridin-3-yl}piperazine-1-carboxylate (830 mg, 1.98 mmol) as a white solid. LCMS (ESI) [M+H]$^+$: 418

Step 3: To a stirred solution of tert-butyl 4-{6-[5-(methoxycarbonyl)-2-methylthiophen-3-yl]pyridin-3-yl}piperazine-1-carboxylate (830 mg, 1.98 mmol) in DCM (20 mL) was added TFA (4 mL) dropwise at 0° C. The reaction was stirred for 1 hour at room temperature. The resulting mixture was concentrated under vacuum. The mixture was basified to pH 9 with 1 M NaOH(aq). The mixture was concentrated under reduced pressure. The residue was purified by reversed-phase flash chromatography with the following conditions: column, C18 silica gel; mobile phase, MeCN in water (0.1% formic acid), 0% to 40% gradient in 20 min; detector, UV 254 nm. This resulted in methyl 5-methyl-4-[5-(piperazin-1-yl)pyridin-2-yl]thiophene-2-carboxylate (500 mg, 1.57 mmol) as a white solid. LCMS (ESI) [M+H]$^+$: 318

Step 4: To a stirred solution of methyl 5-methyl-4-[5-(piperazin-1-yl)pyridin-2-yl]thiophene-2-carboxylate (500 mg, 1.57 mmol)) and Et$_3$N (476 mg, 4.71 mmol) in DCM (15 mL) was added cyclopropanecarbonyl chloride (179 mg, 1.72 mmol) at 0° C. under nitrogen atmosphere. Then the mixture was stirred for 5 hours at room temperature. The mixture was concentrated under reduced pressure. The residue was purified by reversed-phase flash chromatography with the following conditions: column, C18 silica gel; mobile phase, MeCN in water (0.1% formic acid), 0% to 60% gradient in 20 min; detector, UV 254 nm. This resulted in methyl 4-[5-(4-cyclopropanecarbonylpiperazin-1-yl)pyridin-2-yl]-5-methylthiophene-2-carboxylate (410 mg, 1.06 mmol) as a white solid. LCMS (ESI) [M+H]$^+$: 386

Step 5: To a stirred solution of methyl 4-[5-(4-cyclopropanecarbonylpiperazin-1-yl)pyridin-2-yl]-5-methylthiophene-2-carboxylate (410 mg, 1.06 mmol) in EtOH (10 mL) and H$_2$O (2 mL) was added LiOH (253 mg, 10.6 mmol) at 0° C. Then the mixture was stirred for 2 hours at room temperature. The mixture was acidified to pH 5 with citric acid. The precipitated solids were collected by filtration and washed with water. The resulting solid was dried under vacuum to afford 4-[5-(4-cyclopropanecarbonylpiperazin-1-yl)pyridin-2-yl]-5-methylthiophene-2-carboxylic acid (300 mg, 0.807 mmol) as a yellow solid. LCMS (ESI) [M+H]$^+$: 372

Step 6: To a stirred solution of 4-[5-(4-cyclopropanecarbonylpiperazin-1-yl)pyridin-2-yl]-5-methylthiophene-2-carboxylic acid (300 mg, 0.807 mmol), TCFH (450 mg, 1.61 mmol) and NMI (193 mg, 2.42 mmol) in ACN (10 mL) was added N-(3-amino-5-chlorophenyl)methanesulfonamide (195 mg, 0.887 mmol) at room temperature. Then the mixture was stirred for 1 hour at room temperature. The mixture was concentrated under reduced pressure. The residue was purified by reversed-phase flash chromatography with the following conditions: column, C18 silica gel; mobile phase, MeCN in water (0.1% formic acid), 0% to 50% gradient in 20 min; detector, UV 254 nm. This resulted in N-(3-chloro-5-methanesulfonamidophenyl)-4-[5-(4-cyclopropanecarbonylpiperazin-1-yl)pyridin-2-yl]-5-methylthiophene-2-carboxamide (102.9 mg, 0.179 mmol) as a yellow solid. LCMS (ESI) [M+H]$^+$: 574.15. $^1$H NMR (300 MHz, DMSO-d$_6$) δ 10.43 (s, 1H), 10.07 (s, 1H), 8.42 (d, J=2.8 Hz, 1H), 8.34 (s, 1H), 7.67 (d, J=9.3 Hz, 2H), 7.60-7.45 (m, 2H), 6.95 (d, J=2.0 Hz, 1H), 3.87 (s, 2H), 3.66 (s, 2H), 3.27 (s, 4H), 3.07 (s, 3H), 2.68 (s, 3H), 2.07 (d, J=7.2 Hz, 1H), 0.76 (t, J=6.3 Hz, 4H).

Examples 591-594

The compounds listed in the following table were prepared using a procedure similar to that described for example 590:

| Structure | Compound No. | MS (ESI) [M + H]⁺ | ¹H NMR |
|---|---|---|---|
| (structure with Cl, sulfonamide, pyrrole, pyridine, piperazine, tert-butyl carbonyl) | 591 | 573.05 | ¹H NMR (300 MHZ, DMSO-d6) δ 10.05 (s, 1H), 9.79 (s, 1H), 8.32 (d, J = 2.9 Hz, 1H), 7.72 (t, J = 1.8 Hz, 1H), 7.66-7.50 (m, 3H), 7.43 (dd, J = 8.9, 2.9 Hz, 1H), 7.04 (d, J = 2.0 Hz, 1H), 6.88 (t, J = 1.9 Hz, 1H), 3.93 (s, 3H), 3.72 (t, J = 5.1 Hz, 4H), 3.23 (t, J = 5.3 Hz, 4H), 3.06 (s, 3H), 1.23 (s, 9H). |
| (structure with cyclopentyl carbonyl) | 592 | 585.05 | ¹H NMR (400 MHZ, DMSO-d6) δ 10.01 (s, 1H), 9.80 (s, 1H), 8.33 (d, J = 2.9 Hz, 1H), 7.73 (d, J = 1.9 Hz, 1H), 7.67-7.52 (m, 3H), 7.45 (dd, J = 8.9, 3.0 Hz, 1H), 7.04 (d, J = 2.0 Hz, 1H), 6.89 (t, J = 2.0 Hz, 1H), 3.93 (s, 3H), 3.65 (dt, J = 17.7, 5.4 Hz, 4H), 3.24 (dt, J = 19.8, 5.1 Hz, 4H), 3.06 (s, 4H), 1.78 (q, J = 7.6, 6.0 Hz, 2H), 1.75-1.57 (m, 2H), 1.64-1.46 (m, 4H). |
| (structure with cyclobutyl carbonyl) | 593 | 571 | ¹H NMR (400 MHZ, DMSO-d6) δ 10.00 (s, 1H), 9.79 (s, 1H), 8.32 (d, J = 2.9 Hz, 1H), 7.72 (d, J = 2.0 Hz, 1H), 7.66-7.58 (m, 2H), 7.55 (d, J = 8.8 Hz, 1H), 7.43 (dd, J = 8.9, 3.0 Hz, 1H), 7.03 (d, J = 2.0 Hz, 1H), 6.89 (d, J = 2.1 Hz, 1H), 3.93 (s, 3H), 3.64-3.57 (m, 2H), 3.48 (t, J = 5.2 Hz, 2H), 3.42 (q, J = 8.5 Hz, 1H), 3.21 (q, J = 5.1 Hz, 4H), 3.06 (s, 3H), 2.26-2.02 (m, 4H), 1.91 (dt, J = 10.9, 8.6 Hz, 1H), 1.79-1.72 (m, 1H). |
| (structure with cyclopropyl carbonyl) | 594 | 557.05 | ¹H NMR (400 MHZ, DMSO-d6) δ 10.02 (s, 1H), 9.80 (s, 1H), 8.34 (d, J = 2.9 Hz, 1H), 7.73 (t, J = 1.8 Hz, 1H), 7.66-7.59 (m, 2H), 7.56 (d, J = 8.8 Hz, 1H), 7.45 (dd, J = 8.9, 3.0 Hz, 1H), 7.04 (d, J = 2.0 Hz, 1H), 6.89 (t, J = 2.0 Hz, 1H), 3.93 (s, 3H), 3.85 (s, 2H), 3.64 (s, 2H), 3.31 (s, 2H), 3.23 (s, 2H), 3.06 (s, 3H), 2.05 (tt, J = 7.7, 4.6 Hz, 1H), 0.75 (tt, J = 7.9, 2.9 Hz, 4H). |

Example 595: N-(3-chloro-5-methanesulfonamidophenyl)-5-[5-(3,3-difluoroazetidin-1-yl)pyridin-2-yl]-1-methyl-1H-pyrrole-3-carboxamide

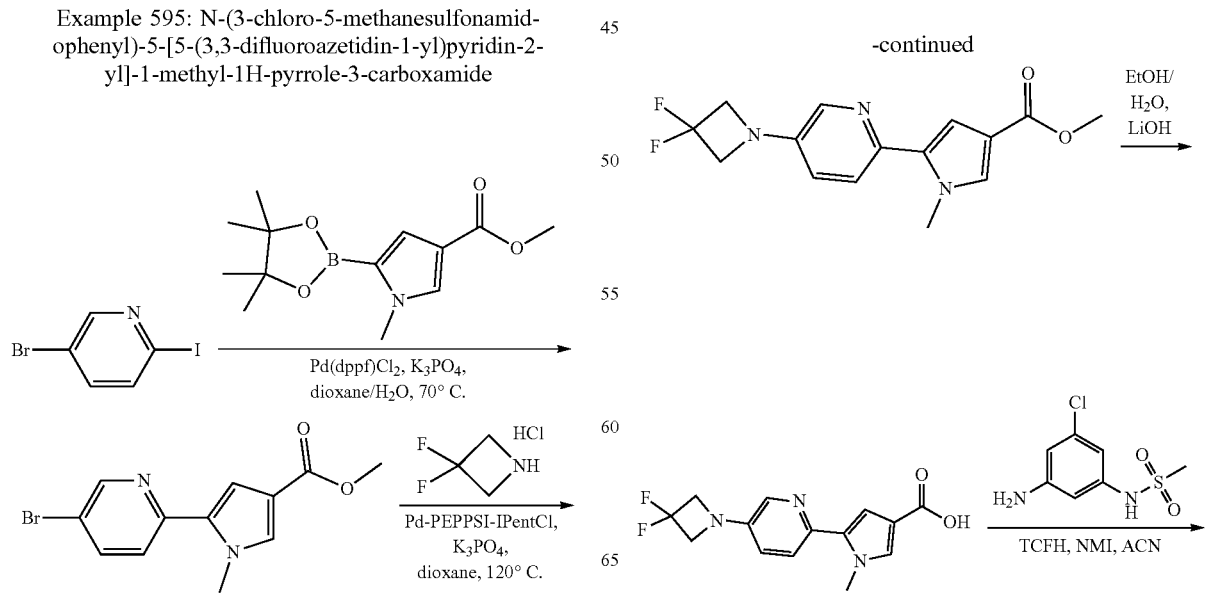

-continued

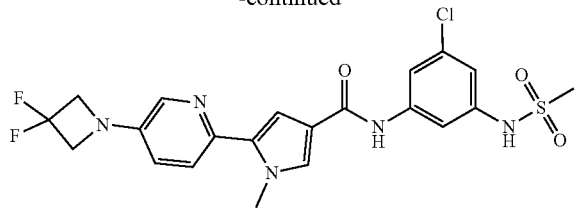

Step 1: To a mixture of 5-bromo-2-iodopyridine (5.1 g, 17.9 mmol), methyl 1-methyl-5-(4,4,5,5-tetramethyl-1,3,2-dioxaborolan-2-yl)-1H-pyrrole-3-carboxylate (5.67 g, 21.4 mmol), Pd(dppf)Cl$_2$ (1.45 g, 1.78 mmol) and K$_3$PO$_4$ (11.3 g, 53.6 mmol) was added 1,4-dioxane (60 ml) and H$_2$O (6 ml). The resulting mixture was stirred for 2 hours at 70° C. under N$_2$ atmosphere. The reaction mixture was extracted with ethyl acetate. The organic phase was concentrated under reduced pressure. The residue was purified by flash chromatography on silica gel eluting with 15% f ethyl acetate in petroleum ether to afford methyl 5-(5-bromopyridin-2-yl)-1-methyl-1H-pyrrole-3-carboxylate (5.10 g, 96.5%) as a white solid. LCMS [M+H]$^+$: 295

Step 2: To a mixture of methyl 5-(5-bromopyridin-2-yl)-1-methyl-1H-pyrrole-3-carboxylate (3.1 g, 10.5 mmol),3,3-difluoroazetidine hydrochloride (4.08 g, 31.5 mmol), Cs$_2$CO$_3$ (10.28 g, 31.6 mmol) and PEPPSI-IHeptCl (510 mg, 525 μmol) was added dioxane (30 mL). The resulting mixture was stirred for 1 hour at 120° C. under N$_2$ atmosphere. The reaction mixture was extracted with ethyl acetate. The organic phase was concentrated under reduced pressure. The residue was purified by flash chromatography on silica gel eluting with 30% f ethyl acetate in petroleum ether to afford methyl 5-[5-(3,3-difluoroazetidin-1-yl)pyridin-2-yl]-1-methyl-1H-pyrrole-3-carboxylate (2.20 g, 68.3%) as a yellow solid. LCMS [M+H]$^+$: 308

Step 3: To a stirred solution of methyl 5-[5-(3,3-difluoroazetidin-1-yl)pyridin-2-yl]-1-methyl-1H-pyrrole-3-carboxylate (2.2 g, 7.15 mmol) in 20 mL of EtOH and 20 mL of water was added LiOH (1.49 g, 35.7 mmol). The resulting mixture was stirred for 1 hour at 70° C. Then it was concentrated, and the pH value of the residue solution was adjusted to 3 with 1M of HCl (aq). The product was precipitated from the solution. The mixture was filtered and the filter cake was washed with water (20 mL) to afford 5-[5-(3,3-difluoroazetidin-1-yl)pyridin-2-yl]-1-methyl-1H-pyrrole-3-carboxylic acid (1.75 g, 83.7%) as a yellow solid. LCMS [M+H]$^+$: 294

Step 4: To a mixture of 5-[5-(3,3-difluoroazetidin-1-yl)pyridin-2-yl]-1-methyl-1H-pyrrole-3-carboxylic acid (1.6 g, 5.45 mmol) and N-(3-amino-5-chlorophenyl)methanesulfonamide (1.44 g, 6.54 mmol) in ACN (16 mL) was added TCFH (2.28 g, 8.17 mmol) and NMI (1.33 g, 16.3 mmol) at room temperature for two hours. Then it was concentrated, the residue was purified by reverse phase flash chromatography eluting with 60% f acetonitrile in water (0.1% FA) to afford N-(3-chloro-5-methanesulfonamidophenyl)-5-[5-(3,3-difluoroazetidin-1-yl)pyridin-2-yl]-1-methyl-1H-pyrrole-3-carboxamide (1.57 g, 58.1%) as a yellow solid. LCMS [M+H]$^+$: 496. $^1$H NMR (300 MHz, DMSO-d$_6$) δ 10.00 (s, 1H), 9.79 (s, 1H), 7.98 (dd, J=2.9, 0.7 Hz, 1H), 7.72 (t, J=1.8 Hz, 1H), 7.67-7.58 (m, 2H), 7.61-7.52 (m, 1H), 7.09 (dd, J=8.7, 2.9 Hz, 1H), 7.03 (d, J=2.0 Hz, 1H), 6.89 (t, J=1.9 Hz, 1H), 4.41 (d, J=12.3 Hz, 3H), 4.35 (s, 1H), 3.92 (s, 3H), 3.06 (s, 3H).

Examples 596-603

The compounds listed in the following table were prepared using a procedure similar to that described for example 595:

| Structure | Compound No. | MS (ESI) [M + H]$^+$ | $^1$H NMR |
|---|---|---|---|
| 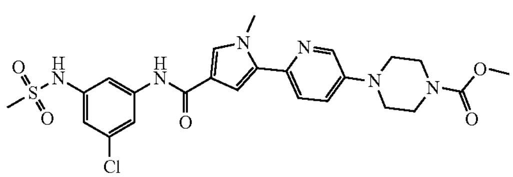 | 596 | 547.05 | $^1$H NMR (300 MHz, DMSO-d6) δ 10.01 (s, 1H), 9.79 (s, 1H), 8.32 (d, J = 2.9 Hz, 1H), 7.72 (t, J = 1.8 Hz, 1H), 7.67-7.50 (m, 3H), 7.43 (dd, J = 8.9, 2.9 Hz, 1H), 7.04 (d, J = 2.0 Hz, 1H), 6.89 (t, J = 1.9 Hz, 1H), 3.93 (s, 3H), 3.64 (s, 3H), 3.58-3.49 (m, 4H), 3.24 (d, J = 10.5 Hz, 4H), 3.06 (s, 3H). |
| 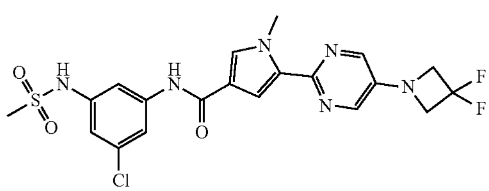 [SMILES: Cn1cc(C(=O)Nc2cc(Cl)cc(NS(C)(=O)=O)c2)cc1-c1ncc(N2CC(F)(F)C2)cn1] | 597 | 496.95 | $^1$H NMR (400 MHz, DMSO-d6) δ 9.90 (d, J = 14.2 Hz, 2H), 8.23 (s, 2H), 7.72 (t, J = 1.9 Hz, 1H), 7.65 (t, J = 1.9 Hz, 1H), 7.63 (d, J = 2.2 Hz, 1H), 7.50 (d, J = 2.1 Hz, 1H), 6.88 (t, J = 2.0 Hz, 1H), 4.46 (t, J = 12.3 Hz, 4H), 4.03 (s, 3H), 3.05 (s, 3H). |
| 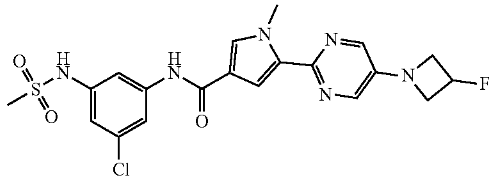 [SMILES: Cn1cc(C(=O)Nc2cc(Cl)cc(NS(C)(=O)=O)c2)cc1-c1ncc(N2CC(F)C2)cn1] | 598 | 479.05 | $^1$H NMR (300 MHz, DMSO-d6) δ 10.04 (s, 1H), 9.88 (s, 1H), 8.14 (s, 2H), 7.73 (t, J = 1.9 Hz, 1H), 7.66 (t, J = 1.9 Hz, 1H), 7.61 (d, J = 2.1 Hz, 1H), 7.46 (d, J = 2.1 Hz, 1H), 6.88 (t, J = 1.9 Hz, 1H), 5.75-5.30 (m, 1H), 4.41-4.23 (m, 2H), 4.16-3.93 (m, 5H), 3.05 (s, 3H). |

| Structure | Compound No. | MS (ESI) [M + H]+ | 1H NMR |
|---|---|---|---|
| 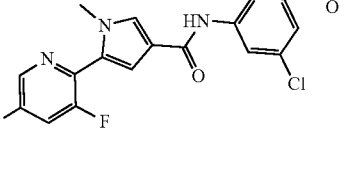 | 599 | 514 | 1H NMR (400 MHz, DMSO-d6) δ 10.00 (s, 1H), 9.83 (s, 1H), 7.89 (s, 1H), 7.67 (dd, J = 16.7, 14.7 Hz, 3H), 7.12 (dd, J = 12.4, 2.3 Hz, 1H), 7.02 (s, 1H), 6.89 (s, 1H), 4.44 (t, J = 12.3 Hz, 4H), 3.83 (s, 3H), 3.06 (s, 3H). |
| 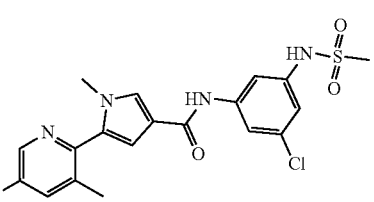 | 600 | 538.1 | ¹H NMR (300 MHz, DMSO-d6) δ 10.00 (s, 1H), 9.74 (s, 1H), 8.29 (d, J = 2.9 Hz, 1H), 7.68 (t, J = 1.9 Hz, 1H), 7.62 (t, J = 1.5 Hz, 2H), 7.38 (d, J = 2.8 Hz, 1H), 6.88 (t, J = 2.0 Hz, 1H), 6.76 (d, J = 1.9 Hz, 1H), 3.62 (s, 3H), 3.46 (t, J = 5.8 Hz, 4H), 3.05 (s, 3H), 2.33 (s, 3H), 2.09 (td, J = 13.9, 6.7 Hz, 4H). |
| 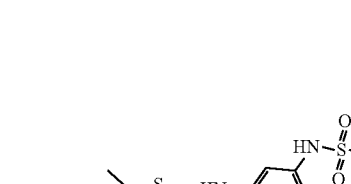 | 601 | 578.1 | ¹H NMR (400 MHz, DMSO-d6) δ 10.29 (s, 1H), 10.04 (s, 1H), 8.23 (d, J = 2.8 Hz, 1H), 7.94 (s, 1H), 7.66 (t, J = 1.9 Hz, 1H), 7.60 (t, J = 1.9 Hz, 1H), 7.38 (s, 1H), 6.94 (t, J = 2.0 Hz, 1H), 3.64 (s, 3H), 3.54 (t, J = 5.2 Hz, 4H), 3.27 (d, J = 10.7 Hz, 4H), 3.06 (s, 3H), 2.32 (s, 3H), 2.19 (s, 3H). |
| 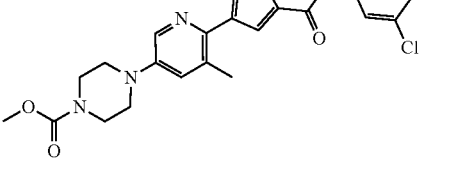 | 602 | 555 | ¹H NMR (400 MHz, DMSO- d6) δ 10.29 (s, 1H), 10.05 (s, 1H), 8.28 (d, J = 2.8 Hz, 1H), 7.94 (s, 1H), 7.66 (t, J = 1.9 Hz, 1H), 7.61 (t, J = 1.9 Hz, 1H), 7.39 (d, J = 2.7 Hz, 1H), 6.94 (t, J = 1.9 Hz, 1H), 3.45 (t, J = 5.9 Hz, 4H), 3.06 (s, 3H), 2.33 (s, 3H), 2.19 (s, 3H), 2.08 (tt, J = 13.7, 5.8 Hz, 4H). |
| 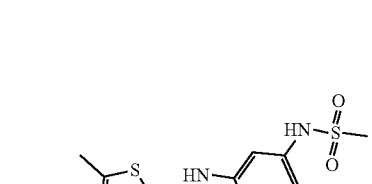 | 603 | 545 | ¹H NMR (300 MHz, DMSO-d6) δ 10.03 (s, 1H), 9.89 (s, 1H), 8.65-8.60 (m, 1H), 7.94-7.82 (m, 2H), 7.76-7.69 (m, 2H), 7.63 (s, 1H), 7.31 (d, J = 2.0 Hz, 1H), 6.91 (t, J = 1.9 Hz, 1H), 4.02 (s, 3H), 3.07 (s, 3H), 2.91 (s, 3H), 1.46 (s, 6H). |

Example 604: N-(3-chloro-5-methanesulfonamidophenyl)-5-{5,5'-difluoro-[3,3'-bipyridin]-2-yl}-1-methylpyrrole-3-carboxamide

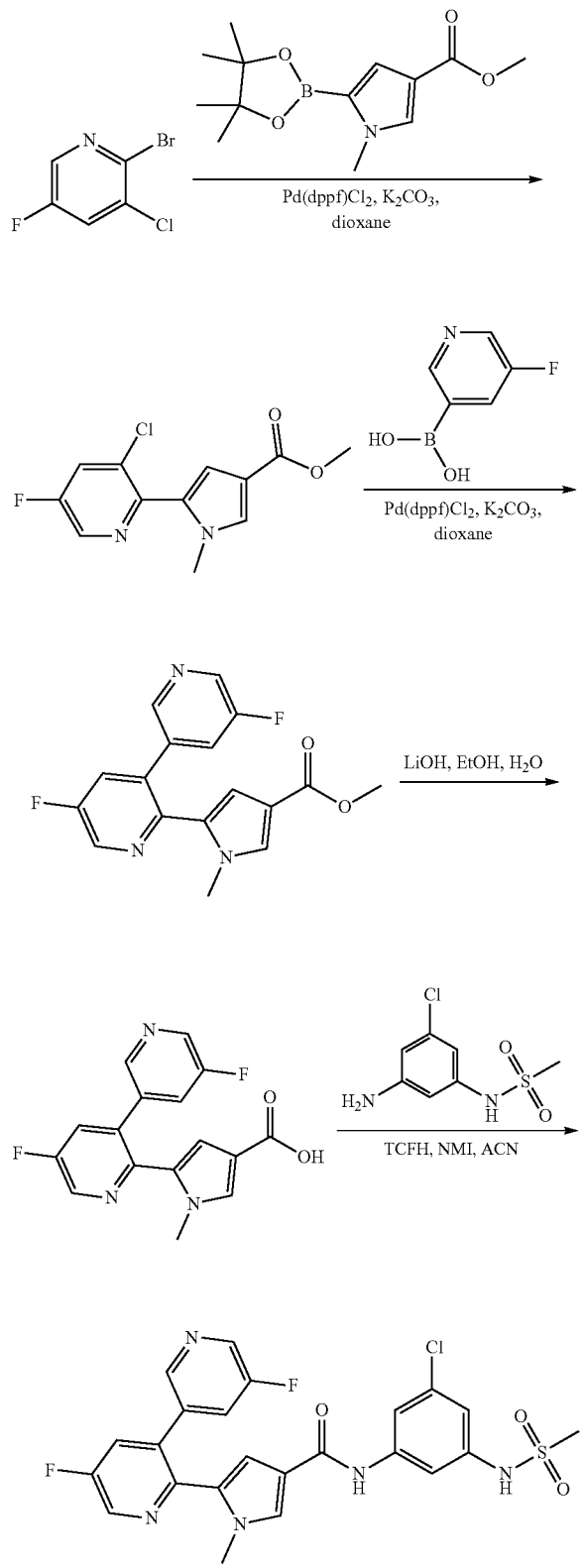

Step 1: A solution of 2-bromo-3-chloro-5-fluoropyridine (300 mg, 2 mmol, 1 equiv), methyl 1-methyl-5-(4,4,5,5-tetramethyl-1,3,2-dioxaborolan-2-yl)pyrrole-3-carboxylate (410 mg, 2 mmol, 1 equiv), Pd(dppf)Cl$_2$ (80 mg, 0.3 mmol, 0.1 equiv) and K$_2$CO$_3$ (400 mg, 8 mmol, 3 equiv) in Dioxane (10 mL) was stirred for 1 hour at 80° C. under nitrogen atmosphere. The reaction mixture was concentrated under vacuum. The residue was purified by flash chromatography on silica gel eluting with EA/PE(32%) to afford methyl 5-(3-chloro-5-fluoropyridin-2-yl)-1-methylpyrrole-3-carboxylate (200 mg, 60% yield) as a white solid. LCMS (ESI) [M+H]$^+$: 269

Step 2: A solution of methyl 5-(3-chloro-5-fluoropyridin-2-yl)-1-methylpyrrole-3-carboxylate (200 mg, 2 mmol, 1 equiv), 5-fluoropyridin-3-ylboronic acid (150 mg, 2 mmol, 1 equiv), Pd(dppf)Cl$_2$ (50 mg, 0.3 mmol, 0.1 equiv) and K$_2$CO$_3$ (200 mg, 8 mmol, 3 equiv) in Dioxane (10 mL) was stirred for 1 h at 80° C. under nitrogen atmosphere. The reaction mixture was concentrated under vacuum. The residue was purified by flash chromatography on silica gel eluting with EA/PE(22%) to afford methyl 5-{5,5'-difluoro-[3,3'-bipyridin]-2-yl}-1-methylpyrrole-3-carboxylate (120 mg, 55% yield) as a white solid. LCMS (ESI) [M+H]$^+$: 330

Step 3: A solution of ethyl methyl 5-{5,5'-difluoro-[3,3'-bipyridin]-2-yl}-1-methylpyrrole-3-carboxylate (120 mg, 0.6 mmol, 1 equiv) and LiOH (86.8 mg, 3.624 mmol, 3.00 equiv) in ethyl alcohol (2 mL)/H$_2$O (1 mL) was stirred at RT for four hours. The mixture was acidified with HCl (0.1M). The solvent was concentrated under vacuum. The residue was purified by flash chromatography on C18 column gel eluting with ACN/water (0.1% FA) (33%) to afford methyl 5-{5,5'-difluoro-[3,3'-bipyridin]-2-yl}-1-methylpyrrole-3-carboxylic acid(100 mg, 66% yield) as a white solid. LCMS (ESI) [M+H]$^+$: 316

Step 4: A solution of 5-{5,5'-difluoro-[3,3'-bipyridin]-2-yl}-1-methylpyrrole-3-carboxylic acid (100 mg, 0.2 mmol, 1 equiv), N-(3-amino-5-chlorophenyl)methanesulfonamide (80 mg, 0.2 mmol, 1 equiv) and NMI (10 mg, 0.04 mmol, 0.1 equiv), TCFH (12 mg, 0.05 mmol, 0.1 equiv) in ACN (5 mL) was stirred for 1 hour at 30° C. under nitrogen atmosphere. The reaction mixture was concentrated under vacuum. The residue (120 mg) was purified by Prep-HPLC to afford N-(3-chloro-5-methanesulfonamidophenyl)-5-{5,5'-difluoro-[3,3'-bipyridin]-2-yl}-1-methylpyrrole-3-carboxamide (18.1 mg, 20% yield) as a white solid. LCMS (ESI) [M+H]$^+$: 518. $^1$H NMR (300 MHz, DMSO-d$_6$) δ 9.67 (s, 1H), 8.79 (d, J=2.8 Hz, 1H), 8.56 (d, J=2.8 Hz, 1H), 8.32 (t, J=1.8 Hz, 1H), 8.07 (dd, J=9.3, 2.8 Hz, 1H), 7.77 (ddd, J=9.9, 2.8, 1.8 Hz, 1H), 7.66-7.56 (m, 2H), 7.52 (t, J=1.9 Hz, 1H), 6.86 (t, J=1.9 Hz, 1H), 6.24 (d, J=1.9 Hz, 1H), 3.64 (s, 3H), 3.02 (s, 3H).

Examples 605-608

The compounds listed in the following table were prepared using a procedure similar to that described for example 604:

| Structure | Compound No. | MS (ESI) [M + H]+ | 1H NMR |
|---|---|---|---|
| 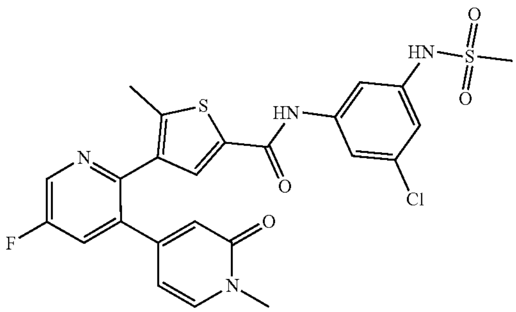 [SMILES: Cc1sc(C(=O)Nc2cc(Cl)cc(NS(C)(=O)=O)c2)cc1-c1ncc(F)cc1-c1ccn(C)c(=O)c1] | 605 | 546.9 | 1H NMR (300 MHz, DMSO-d6) δ 10.35 (s, 1H), 10.10 (s, 1H), 8.76 (d, J = 2.8 Hz, 1H), 8.02-7.86 (m, 2H), 7.66-7.55 (m, 3H), 6.93 (t, J = 1.9 Hz, 1H), 6.41 (d, J = 2.0 Hz, 1H), 5.93 (dd, J = 7.0, 2.0 Hz, 1H), 3.39 (s, 3H), 3.05 (s, 3H), 2.13 (s, 3H). |
| 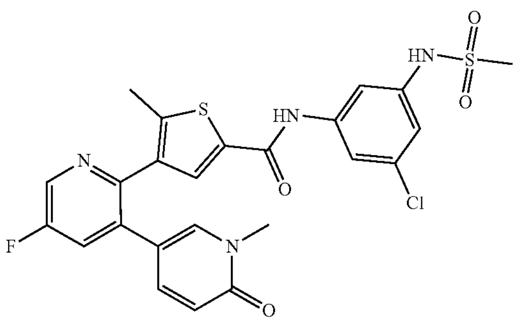 [SMILES: Cc1sc(C(=O)Nc2cc(Cl)cc(NS(C)(=O)=O)c2)cc1-c1ncc(F)cc1-c1ccc(=O)n(C)c1] | 606 | 547.05 | 1H NMR (300 MHz, DMSO-d6) δ 10.34 (s, 2H), 8.67 (d, J = 2.8 Hz, 1H), 8.00-7.86 (m, 3H), 7.61 (dt, J = 17.0, 1.9 Hz, 2H), 7.11-6.87 (m, 2H), 6.25 (d, J = 9.4 Hz, 1H), 3.44 (s, 3H), 3.05 (s, 3H), 2.08 (d, J = 5.0 Hz, 3H). |
| 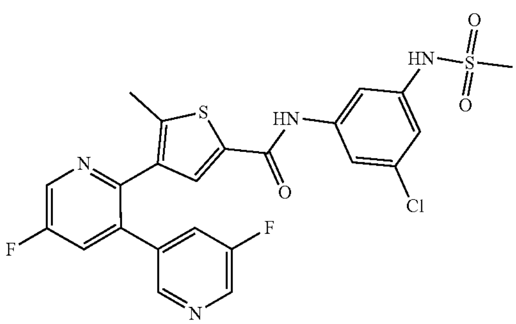 [SMILES: Cc1sc(C(=O)Nc2cc(Cl)cc(NS(C)(=O)=O)c2)cc1-c1ncc(F)cc1-c1cncc(F)c1] | 607 | 534.95 | 1H NMR (300 MHz, DMSO-d6) δ 10.33 (s, 1H), 10.06 (s, 1H), 8.80 (d, J = 2.8 Hz, 1H), 8.56 (d, J = 2.7 Hz, 1H), 8.29 (t, J = 1.8 Hz, 1H), 8.13 (dd, J = 9.4, 2.8 Hz, 1H), 7.87 (s, 1H), 7.74 (ddd, J = 9.9, 2.8, 1.8 Hz, 1H), 7.61 (dt, J = 15.5, 1.9 Hz, 2H), 6.94 (t, J = 1.9 Hz, 1H), 3.06 (s, 3H), 1.99 (s, 3H). |
| 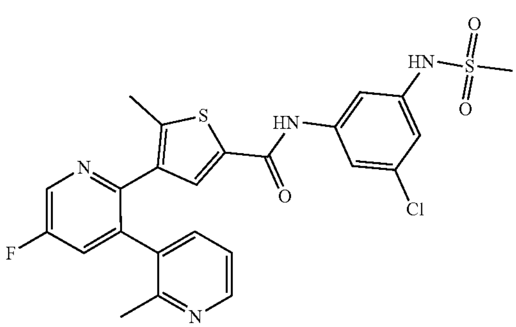 [SMILES: Cc1ncccc1-c1cc(F)cnc1-c1cc(C(=O)Nc2cc(Cl)cc(NS(C)(=O)=O)c2)sc1C] | 608 | 531 | 1H NMR (300 MHz, DMSO-d6) δ 10.25 (s, 1H), 8.78 (d, J = 2.8 Hz, 1H), 8.43 (dd, J = 4.8, 1.7 Hz, 1H), 7.97 (dd, J = 9.3, 2.8 Hz, 1H), 7.67 (s, 1H), 7.61-7.51 (m, 3H), 7.24 (dd, J = 7.7, 4.8 Hz, 1H), 6.93 (t, J = 2.0 Hz, 1H), 3.05 (s, 3H), 2.21 (s, 3H), 2.09 (s, 3H). |

Example 609: N-(3-chloro-5-methanesulfonamid-ophenyl)-5-methyl-4-{5-[(1-methylazetidin-3-yl)oxy]pyrimidin-2-yl}thiophene-2-carboxamide

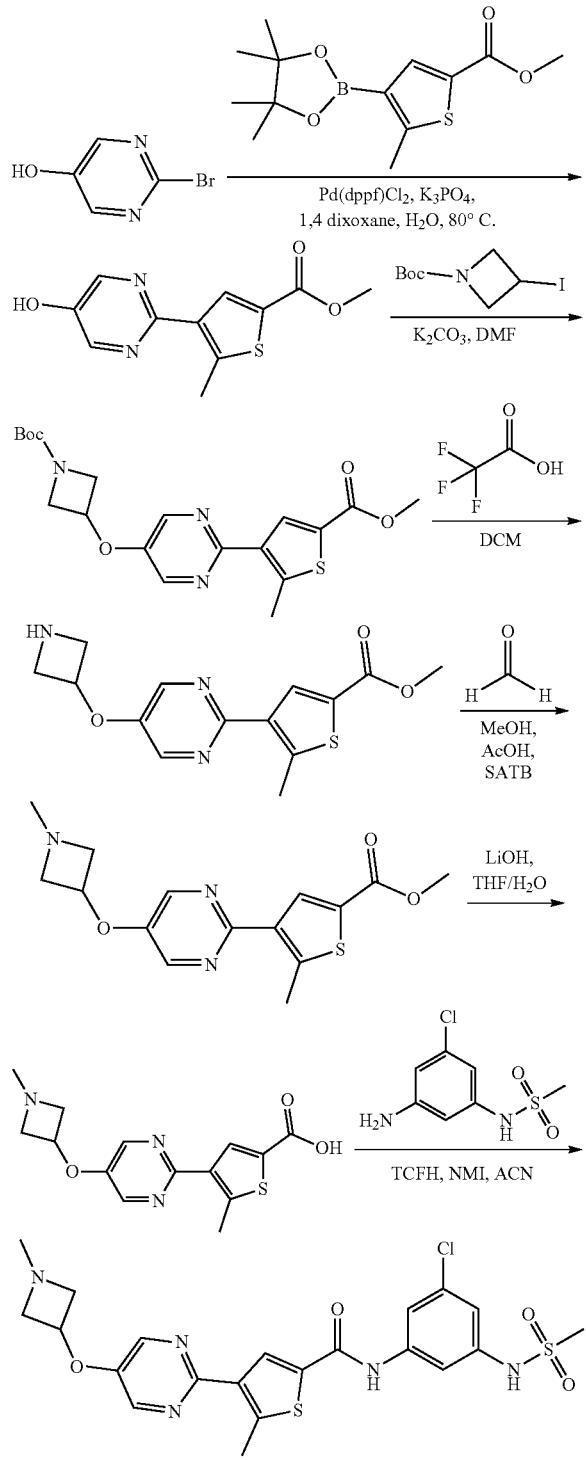

Step 1: To a stirred solution of 2-bromopyrimidin-5-ol (1.5 g, 8.57 mmol), methyl 5-methyl-4-(4,4,5,5-tetramethyl-1,3,2-dioxaborolan-2-yl)thiophene-2-carboxylate (2.41 g, 8.57 mmol), Pd(dppf)Cl₂ (699 mg, 0.857 mmol) and K₃PO₄ (5.44 g, 25.7 mmol) in 1,4-dioxane (20.00 mL) was added H₂O (3.00 mL). Then the mixture was stirred for 12 hours at 80° C. under N₂. The mixture was concentrated and purified by reverse phase flash chromatography eluting with ACN/H₂O (5-95%, acidic system) to afford methyl 4-(5-hydroxypyrimidin-2-yl)-5-methylthiophene-2-carboxylate (1.80 g, 7.19 mmol, 84.1% yield) as a white solid. LCMS (ESI) [M+H]⁺: 251.2

Step 2: To a stirred solution of methyl 4-(5-hydroxypyrimidin-2-yl)-5-methylthiophene-2-carboxylate (520 mg, 2.07 mmol), tert-butyl 3-iodoazetidine-1-carboxylate (586 mg, 2.07 mmol) and K₂CO₃ (855 mg, 6.20 mmol) in DMF (5 mL). Then the mixture was stirred for 6 hours at 80° C. under N₂. The mixture was concentrated and purified by flash chromatography on silica gel eluting with EA/PE (0-100%) to afford tert-butyl 3-({2-[5-(methoxycarbonyl)-2-methylthiophen-3-yl]pyrimidin-5-yl}oxy) azetidine-1-carboxylate (470 mg, 1.15 mmol, 56% yield) as a yellow solid. LCMS (ESI) [M+H]⁺: 406.4

Step 3: To a stirred solution of tert-butyl 3-({2-[5-(methoxycarbonyl)-2-methylthiophen-3-yl]pyrimidin-5-yl}oxy) azetidine-1-carboxylate (470 mg, 1.15 mmol) in DCM (5 ml) was added trifluoroacetic acid (655 mg, 5.75 mmol) dropwise. The reaction was stirred for 3 hours at room temperature under nitrogen atmosphere. The mixture was concentrated and purified by reverse phase flash chromatography eluting with ACN/H₂O (5-95%, acidic system) to afford methyl 4-[5-(341yridine341-3-(1-3-yloxy)pyrimidin-2-yl]-5-methylthiophene-2-carboxylate (230 mg, 0.753 mmol, 65.5% yield) as a white solid. LCMS (ESI) [M+H]⁺: 306.3

Step 4: A mixture of methyl 4-[5-(341yridine341-3-(1-3-yloxy)pyrimidin-2-yl]-5-methylthiophene-2-carboxylate (230 mg, 0.753 mmol), formaldehyde (45.0 mg, 1.50 mmol) and AcOH (135 mg, 2.25 mmol) in MeOH (3.00 mL) was stirred for 15 min at room temperature. Then sodium triacetoxyborohydride (477 mg, 2.25 mmol) was added into the mixture at room temperature. The resulting mixture was stirred for additional 1 hour at room temperature. The mixture was concentrated and purified by reverse phase flash chromatography eluting with ACN/H₂O (5-95%, acidic system) to afford methyl 5-methyl-4-{5-[(1-methylazetidin-3-yl)oxy]pyrimidin-2-yl}thiophene-2-carboxylate (200 mg, 0.626 mmol, 83.3% yield) as a white solid. LCMS (ESI) [M+H]⁺: 320.1

Step 5: To a stirred solution of methyl 5-methyl-4-{5-[(1-methylazetidin-3-yl)oxy]pyrimidin-2-yl}thiophene-2-carboxylate (200 mg, 626 μmol) and LiOH (10 mg, 2.5 mmol) in THF (10.00 mL) was added H₂O (2.00 mL) dropwise. Then the mixture was stirred for 2 hours at 60° C. The mixture was acidified to pH 5 with citric acid. The precipitated solids were collected by filtration and washed with water. The resulting solid was dried under vacuum to afford 5-methyl-4-{5-[(1-methylazetidin-3-yl)oxy]pyrimidin-2-yl}thiophene-2-carboxylic acid (150 mg, 491 μmol, 78.5% yield) as a white solid. LCMS (ESI) [M+H]⁺: 306

Step 6: To a stirred solution of 5-methyl-4-{5-[(1-methylazetidin-3-yl)oxy]pyrimidin-2-yl}thiophene-2-carboxylic acid (150 mg, 0.491 mmol), TCFH (206 mg, 0.736 mmol) and NMI (120 mg, 1.47 mmol) in ACN (5.00 mL) was added N-(3-amino-5-chlorophenyl)methanesulfonamide (108 mg, 0.491 mmol). Then the mixture was stirred for 4 hours at room temperature. The mixture was concentrated and purified by reverse phase flash chromatography eluting with ACN/H₂O (5-95%, acidic system) to afford N-(3-chloro-5-methanesulfonamidophenyl)-5-methyl-4-{5-[(1-methylazetidin-3-yl)oxy]pyrimidin-2-yl}thiophene-2-carboxamide (108.5 mg, 0.211 mmol, 42.90% yield) as an off-white solid.

LCMS (ESI) [M+H]+: 508.25. 1H NMR (400 MHz, DMSO-d6) δ 10.56 (s, 1H), 10.07 (s, 1H), 8.64 (s, 1H), 8.56 (s, 2H), 7.68 (dt, J=8.0, 1.9 Hz, 2H), 6.94 (t, J=1.9 Hz, 1H), 5.01 (p, J=5.5 Hz, 1H), 3.78 (td, J=6.1, 1.9 Hz, 2H), 3.12-2.99 (m, 5H), 2.83 (s, 3H), 2.31 (s, 3H).

Examples 610-611

The compounds listed in the following table were prepared using a procedure similar to that described for example 609:

| Structure | Compound No. | MS (ESI) [M + H]+ | 1H NMR |
|---|---|---|---|
| 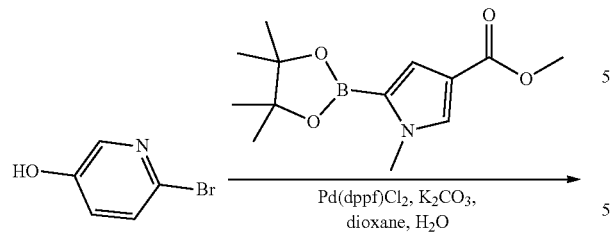 | 610 | 588.1 | 1H NMR (400 MHZ, DMSO-d6) δ 10.06 (s, 1H), 8.51 (s, 2H), 7.85-7.61 (m, 4H), 6.92 (s, 1H), 5.76 (q, J = 9.1 Hz, 2H), 4.96 (p, J = 5.7 Hz, 1H), 3.72 (t, J = 6.8 Hz, 2H), 3.06 (s, 3H), 3.00 (t, J = 6.4 Hz, 2H), 2.33 (q, J = 6.5 Hz, 1H), 0.88 (d, J = 6.1 Hz, 6H). |
| 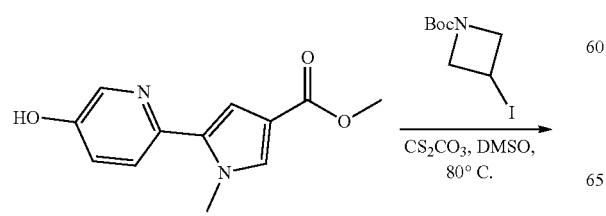 | 611 | 508 | 1H NMR (400 MHZ, DMSO-d6) δ 10.00 (s, 1H), 9.85 (s, 1H), 8.18 (dd, J = 2.6, 1.0 Hz, 1H), 7.70 (d, J = 1.9 Hz, 2H), 7.63 (d, J = 2.0 Hz, 1H), 7.47 (dd, J = 12.3, 2.5 Hz, 1H), 7.08 (dd, J = 3.4, 1.9 Hz, 1H), 6.89 (t, J = 2.0 Hz, 1H), 4.92 (p, J = 5.5 Hz, 1H), 3.84 (s, 3H), 3.77 (td, J = 6.1, 1.9 Hz, 2H), 3.05 (s, 3H), 3.04-2.98 (m, 2H), 2.30 (s, 3H). |

Example 612: N-(3-chloro-5-methanesulfonamidophenyl)-1-methyl-5-{5-[(1-methylazetidin-3-yl)oxy]pyridin-2-yl}pyrrole-3-carboxamide

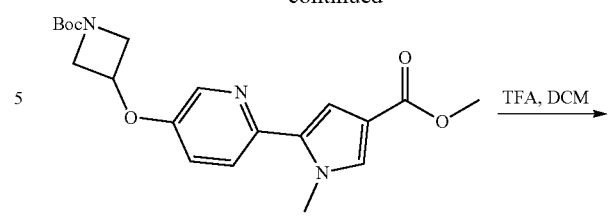

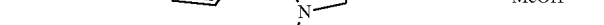

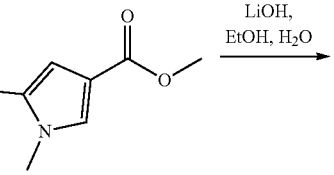

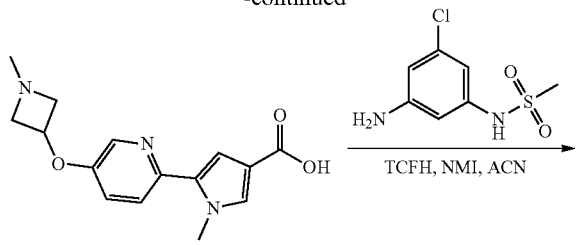

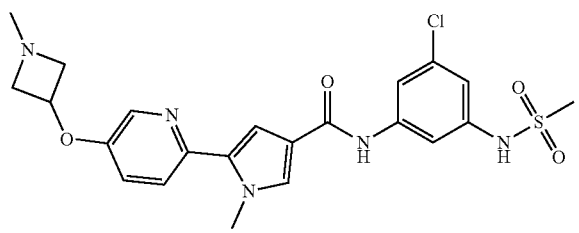

Step 1: A solution of 6-bromopyridin-3-ol (320 mg, 1.839 mmol, 1 equiv), methyl 1-methyl-5-(4,4,5,5-tetramethyl-1,3,2-dioxaborolan-2-yl)pyrrole-3-carboxylate (488 mg, 1.839 mmol, 1 equiv), Pd(dppf)Cl$_2$ (135 mg, 0.184 mmol, 0.1 equiv) and K$_2$CO$_3$ (508 mg, 3.678 mmol, 2 equiv) in dioxane (6 mL) and H$_2$O (2 mL) was stirred for 1.5 hours at 80° C. under nitrogen atmosphere. After filtration, the filtrate was concentrated under reduced pressure. The residue was purified by silica gel column chromatography, eluted with PE/EA (1:1) to afford methyl 5-(5-hydroxypyridin-2-yl)-1-methylpyrrole-3-carboxylate (280 mg, 66% yield) as a white solid. LCMS (ESI) [M+H]$^+$: 233

Step 2: A solution of methyl 5-(5-hydroxypyridin-2-yl)-1-methylpyrrole-3-carboxylate (280 mg, 1.206 mmol, 1 equiv), tert-butyl 3-iodoazetidine-1-carboxylate (410 mg, 1.447 mmol, 1.2 equiv) and Cs$_2$CO$_3$ (786 mg, 2.412 mmol, 2 equiv) in DMSO (5 mL) was stirred for 1.5 hours at 80° C. under air atmosphere. The reaction was diluted with water. The resulting mixture was extracted with EtOAc (3×50 mL). The combined organic layers were washed with brine, dried over anhydrous Na$_2$SO$_4$. After filtration, the filtrate was concentrated under reduced pressure. The residue was purified by silica gel column chromatography, eluted with PE/EA (1:1) to afford methyl 5-(5-{[1-(tert-butoxycarbonyl)azetidin-3-yl]oxy}pyridin-2-yl)-1-methylpyrrole-3-carboxylate (270 mg, 58% yield) as an off-white solid. LCMS (ESI) [M+H]$^+$: 388

Step 3: A solution of methyl 5-(5-{[1-(tert-butoxycarbonyl)azetidin-3-yl]oxy}pyridin-2-yl)-1-methylpyrrole-3-carboxylate (270 mg, 0.697 mmol, 1 equiv) in TFA (2 mL) and DCM (2 mL) was stirred for 1 hour at room temperature under air atmosphere. The mixture was concentrated under reduced pressure. The residue was purified by reverse flash chromatography with the following conditions: column, C18 silica gel; mobile phase, MeCN in water (10 mmol/L NH$_4$HCO$_3$), 0% to 100% gradient in 18 min. This resulted in methyl 5-[5-(azetidin-3-yloxy)pyridin-2-yl]-1-methylpyrrole-3-carboxylate (150 mg, 75% yield) as a white solid. LCMS (ESI) [M+H]$^+$: 288

Step 4: A solution of methyl 5-[5-(azetidin-3-yloxy)pyridin-2-yl]-1-methylpyrrole-3-carboxylate (130 mg, 0.452 mmol, 1 equiv) and formaldehyde (27 mg, 0.904 mmol, 2 equiv) in methanol (2 mL) was stirred for 1 hour at 50° C. under air atmosphere. To the above mixture was add NaBH(AcO)$_3$ (144 mg, 0.678 mmol, 1.5 equiv) at room temperature. The mixture was stirred for 30 min at room temperature under air atmosphere. The mixture was concentrated under reduced pressure. The residue was purified by silica gel column chromatography, eluted with PE/EA (5:1) to afford methyl 1-methyl-5-{5-[(1-methylazetidin-3-yl)oxy]pyridin-2-yl}pyrrole-3-carboxylate (70 mg, 51% yield) as a white solid. LCMS (ESI) [M+H]$^+$: 302

Step 5: A solution of methyl 1-methyl-5-{5-[(1-methylazetidin-3-yl)oxy]pyridin-2-yl}pyrrole-3-carboxylate (70 mg, 0.232 mmol, 1 equiv) and LiOH (11 mg, 0.464 mmol, 2 equiv) in EtOH (2 mL) and H$_2$O (1 mL) was stirred for 1 hour at 50° C. under air atmosphere. The residue was acidified to pH 5 with 1 M HCl (aq.). The mixture was concentrated under reduced pressure. The residue was purified by reverse flash chromatography with the following conditions: column, C18 silica gel; mobile phase, MeCN in water (0.1% formic acid), 0% to 40% gradient in 18 min. This resulted in 1-methyl-5-{5-[(1-methylazetidin-3-yl)oxy]pyridin-2-yl}pyrrole-3-carboxylic acid (45 mg, 67% yield) as a white solid. LCMS (ESI) [M+H]$^+$: 288

Step 6: A solution of 1-methyl-5-{5-[(1-methylazetidin-3-yl)oxy]pyridin-2-yl}pyrrole-3-carboxylic acid (45 mg, 0.157 mmol, 1 equiv), N-(3-amino-5-chlorophenyl)methanesulfonamide (41 mg, 0.188 mmol, 1.2 equiv), TCFH (66 mg, 0.235 mmol, 1.5 equiv) and NMI (39 mg, 0.471 mmol, 3 equiv) in ACN (3 mL) was stirred for 2 hours at room temperature under air atmosphere. The mixture was concentrated under reduced pressure. The residue was purified by reverse flash chromatography with the following conditions: column, C18 silica gel; mobile phase, MeCN in water (10 mmol/L NH$_4$HCO$_3$), 0% to 50% gradient in 18 min. This resulted in N-(3-chloro-5-methanesulfonamidophenyl)-1-methyl-5-{5-[(1-methylazetidin-3-yl)oxy]pyridin-2-yl}pyrrole-3-carboxamide (23.1 mg, 30% yield) as a white solid. LCMS (ESI) [M+H]$^+$: 490.00. $^1$H NMR (300 MHz, DMSO-d$_6$) δ9.96 (s, 1H), 9.77 (s, 1H), 8.21 (d, J=2.8 Hz, 1H), 7.71-7.54 (i, 4H), 7.35 (dd, J=8.8, 3.0 Hz, 1H), 7.07 (d, J=2.0 Hz, 1H), 6.86 (t, J=2.0 Hz, 1H), 4.87 (p, J=5.6 Hz, 1H), 3.92 (s, 3H), 3.76 (dd, J=8.3, 6.0 Hz, 2H), 3.12-2.89 (m, 5H), 2.30 (s, 3H).

Examples 613-615

The compounds listed in the following table were prepared using a procedure similar to that described for example 612:

| Structure | Compound No. | MS (ESI) [M + H]+ | 1H NMR |
|---|---|---|---|
| 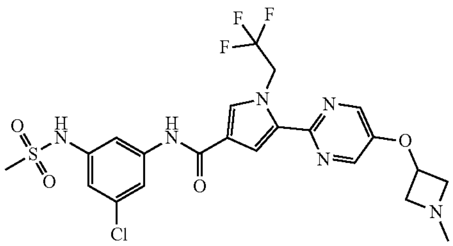 | 613 | 559.1 | 1H NMR (400 MHz, DMSO-d6) δ 10.07 (s, 1H), 8.50 (s, 2H), 7.84-7.79 (m, 1H), 7.73 (t, J = 1.8 Hz, 1H), 7.69 (p, J = 1.6 Hz, 2H), 6.93 (q, J = 1.8 Hz, 1H), 5.76 (q, J = 9.0 Hz, 2H), 5.01 (p, J = 5.5 Hz, 1H), 3.87-3.78 (m, 2H), 3.13 (qt, J = 5.0, 3.5, 3.0 Hz, 2H), 3.08 (d, J = 1.2 Hz, 3H), 2.34 (t, J = 1.5 Hz, 3H). |
| 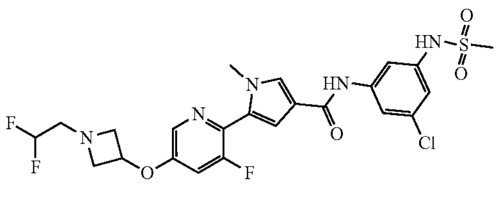 [SMILES: Cn1cc(C(=O)Nc2cc(Cl)cc(NS(C)(=O)=O)c2)cc1-c1ncc(OC2CN(CC(F)F)C2)cc1F] | 614 | 558.35 | 1H NMR (300 MHz, DMSO-d6) δ 10.00 (s, 1H), 9.86 (s, 1H), 8.23-8.10 (m, 1H), 7.71 (t, J = 1.9 Hz, 2H), 7.64 (t, J = 1.9 Hz, 1H), 7.48 (dd, J = 12.3, 2.5 Hz, 1H), 7.08 (dd, J = 3.4, 1.9 Hz, 1H), 6.90 (t, J = 1.9 Hz, 1H), 5.99 (tt, J = 55.7, 4.1 Hz, 1H), 5.00 (p, J = 5.4 Hz, 1H), 3.95-3.79 (m, 5H), 3.26 (dd, J = 8.8, 4.9 Hz, 2H), 3.06 (s, 3H), 2.91 (td, J = 16.1, 4.1 Hz, 2H). |
| 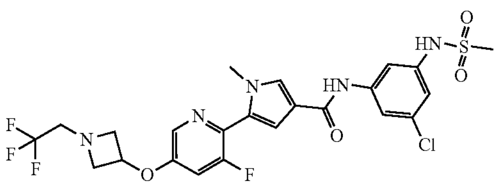 [SMILES: Cn1cc(C(=O)Nc2cc(Cl)cc(NS(C)(=O)=O)c2)cc1-c1ncc(OC2CN(CC(F)(F)F)C2)cc1F] | 615 | 576.15 | 1H NMR (400 MHz, DMSO-d6) δ 9.85 (s, 1H), 8.19 (d, J = 2.3 Hz, 1H), 7.73-7.67 (m, 2H), 7.63 (t, J = 2.0 Hz, 1H), 7.48 (dd, J = 12.3, 2.6 Hz, 1H), 7.08 (dd, J = 3.4, 2.0 Hz, 1H), 6.89 (t, J = 2.0 Hz, 1H), 5.03 (p, J = 5.5 Hz, 1H), 3.93 (dd, J = 8.3, 6.0 Hz, 2H), 3.84 (s, 3H), 3.40 (d, J = 4.6 Hz, 2H), 3.34 (d, J = 4.6 Hz, 2H), 3.05 (s, 3H). |

Example 616: N-(3-chloro-5-methanesulfonamidophenyl)-5-methyl-4-[5-(methylamino)pyrimidin-2-yl]thiophene-2-carboxamide

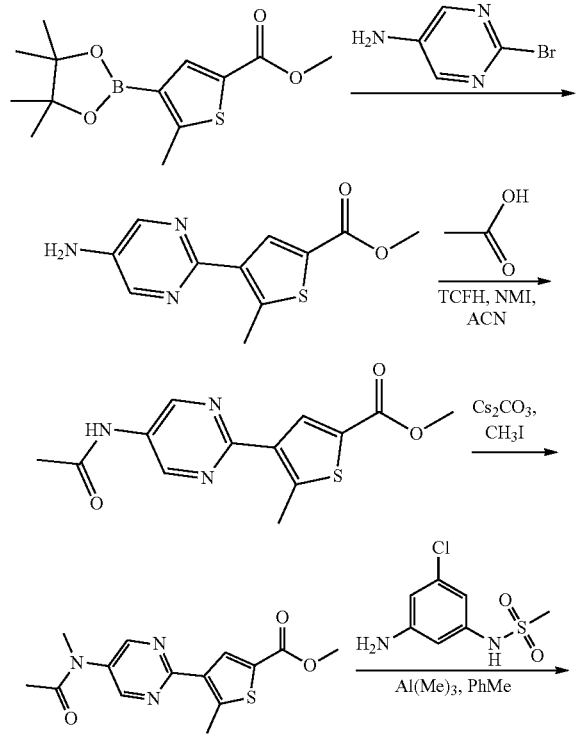

-continued

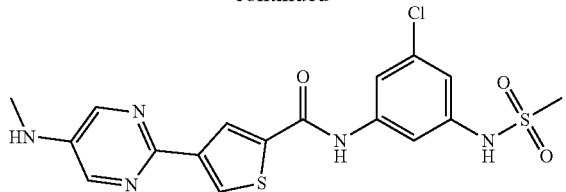

Step 1: To a stirred solution of methyl 5-methyl-4-(4,4,5,5-tetramethyl-1,3,2-dioxaborolan-2-yl)thiophene-2-carboxylate (820 mg, 2.90 mmol), 2-bromopyrimidin-5-amine (504 mg, 2.90 mmol), Pd(dppf)Cl₂ (236 mg, 0.29 mmol) and K₂CO₃ (1.20 g, 8.70 mmol) in 1,4-dioxane (10 mL) was added H₂O (2 mL). Then the mixture was stirred for 12 hours at 80° C. under N₂. The mixture was concentrated and purified by reverse phase flash chromatography eluting with ACN/H₂O (5-95%, acidic system) to afford methyl 4-(5-aminopyrimidin-2-yl)-5-methylthiophene-2-carboxylate (700 mg, 2.80 mmol, 96% yield) as a white solid. LCMS (ESI) [M+H]+: 250.2

Step 2: To a stirred solution of acetic acid (201 mg, 3.36 mmol), TCFH (944 mg, 3.36 mmol) and NMI (551 mg, 6.72 mmol) in ACN (5.00 mL) was added methyl 4-(5-aminopyrimidin-2-yl)-5-methylthiophene-2-carboxylate (560 mg, 2.24 mmol). Then the mixture was stirred for 4 hours at room temperature. The mixture was concentrated and purified by reverse phase flash chromatography eluting with ACN/H₂O (5-95%, acidic system) to afford methyl 4-(5-acetamidopyrimidin-2-yl)-5-methylthiophene-2-carboxylate (380 mg, 1.30 mmol, 58.2% yield) as a white solid. LCMS (ESI) [M+H]+: 292.3

Step 3: To a stirred mixture of methyl 4-(5-acetamidopyrimidin-2-yl)-5-methylthiophene-2-carboxylate (380 mg, 1.30 mmol) and Cs$_2$CO$_3$ (1.27 g, 3.90 mmol) in DMF (5 ml) was added CH$_3$I (276 mg, 1.95 mmol) dropwise at 80° C. under nitrogen atmosphere. Then the mixture was stirred for 4 hours at 80° C. The mixture was concentrated and purified by reverse phase flash chromatography eluting with ACN/H$_2$O (5-95%, acidic system) to afford methyl 5-methyl-4-[5-(N-methylacetamido)pyrimidin-2-yl]thiophene-2-carboxylate (270 mg, 0.884 mmol, 68.1% yield) as a white solid. LCMS (ESI) [M+H]$^+$: 306.3

Step 4: To a stirred mixture of methyl 5-methyl-4-[5-(N-methylacetamido)pyrimidin-2-yl]thiophene-2-carboxylate (120 mg, 0.392 mmol) and N-(3-amino-5-chlorophenyl)methanesulfonamide (86.5 mg, 0.392 mmol) in toluene (3 mL) was added Al(Me)$_3$ (37.1 mg, 0.509 mmol) dropwise at 80° C. under nitrogen atmosphere. Then the mixture was stirred for 4 hours at 80° C. The mixture was concentrated and purified by reverse phase flash chromatography eluting with ACN/H$_2$O (5-95%, acidic system) to afford residue. The residue was purified by Prep-HPLC with the following conditions (Column: Sunfire prep C18 column, 30*150 mm, 5 μm; Mobile Phase A: Water(0.1% FA), Mobile Phase B: ACN; Flow rate: 60 mL/min; Gradient: 45% B to 62% B in 7 min; Wave Length: 254/220 nm; RT1(min): 5.43) to afford N-(3-chloro-5-methanesulfonamidophenyl)-5-methyl-4-[5-(methylamino)pyrimidin-2-yl]thiophene-2-carboxamide (5.5 mg, 0.0118 mmol, 3% yield) as a white solid. LCMS (ESI) [M+H]$^+$: 452.05. $^1$H NMR (400 MHz, DMSO-d$_6$) δ 10.51 (s, 1H), 10.12 (s, 1H), 8.57 (s, 1H), 8.21 (s, 2H), 7.67 (dt, J=6.8, 1.9 Hz, 2H), 6.93 (t, J=2.0 Hz, 1H), 6.25 (q, J=5.0 Hz, 1H), 3.05 (s, 3H), 2.79 (t, J=2.6 Hz, 6H).

Example 617: N-(3-chloro-5-methanesulfonamidophenyl)-5-{5-1-(2,2-difluoroethyl)piperidin-4-yl]pyridin-2-yl}-1-methylpyrrole-3-carboxamide

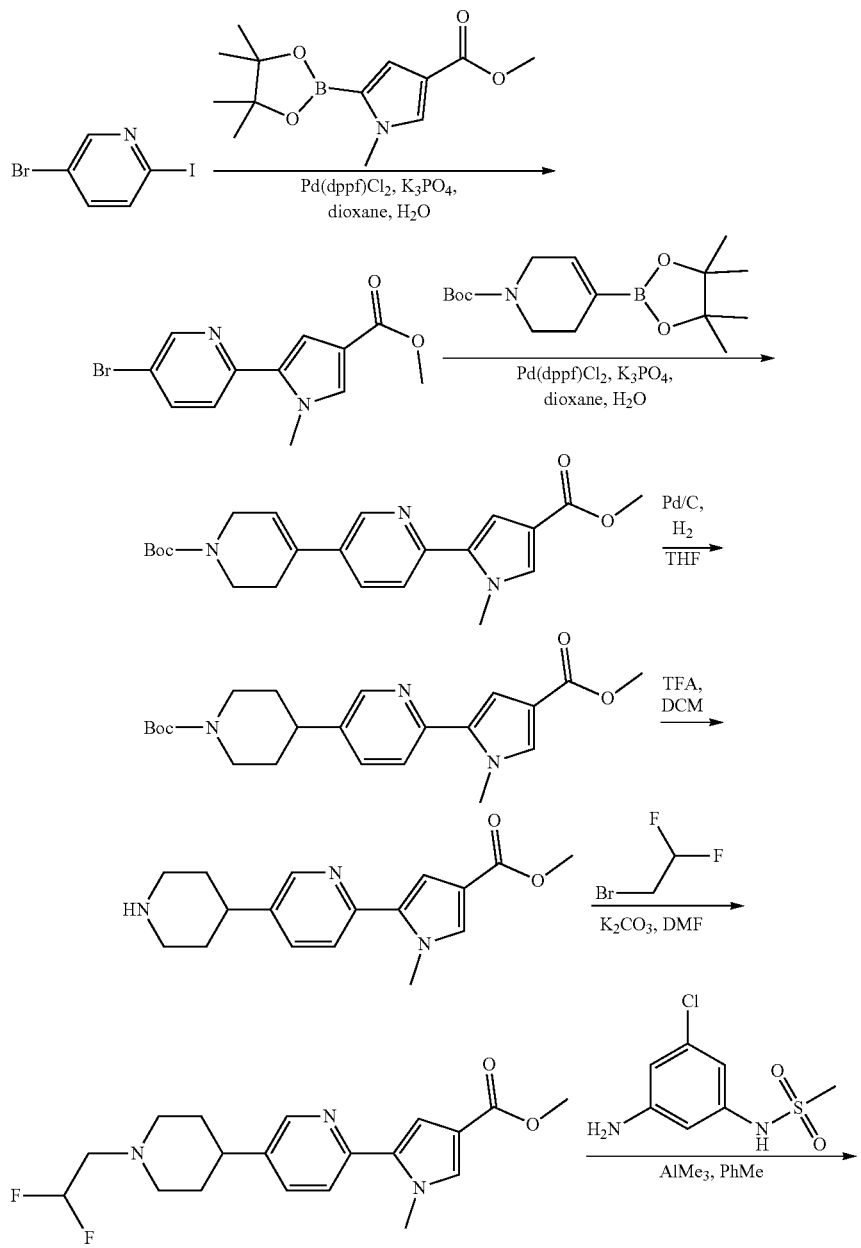

-continued

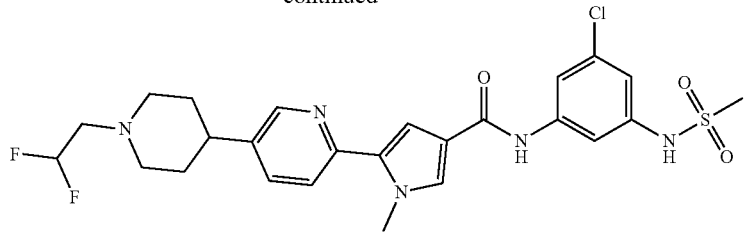

Step 1: A solution of 5-bromo-2-iodopyridine (1.5 g, 5.284 mmol, 1 equiv), methyl 1-methyl-5-(4,4,5,5-tetramethyl-1,3,2-dioxaborolan-2-yl)pyrrole-3-carboxylate (1.40 g, 5.284 mmol, 1 equiv), Pd(dppf)Cl$_2$ (0.43 g, 0.528 mmol, 0.1 equiv) and K$_3$PO$_4$ (3.36 g, 15.852 mmol, 3 equiv) in 1,4-dioxane (30 mL) and H$_2$O (6 mL) was stirred for 1 hour at 60° C. under nitrogen atmosphere. The mixture was allowed to cool down to room temperature. The resulting mixture was concentrated under reduced pressure. The residue was purified by silica gel column chromatography, eluted with PE/EA (5:1) to afford methyl 5-(5-bromopyridin-2-yl)-1-methylpyrrole-3-carboxylate (1 g, 64% yield) as a white solid. LCMS (ESI) [M+H]$^+$: 250.00.

Step 2: A solution of methyl 5-(5-bromopyridin-2-yl)-1-methylpyrrole-3-carboxylate (500 mg, 1.694 mmol, 1 equiv), tert-butyl 4-(4,4,5,5-tetramethyl-1,3,2-dioxaborolan-2-yl)-3,6-dihydro-2H-pyridine-1-carboxylate (524 mg, 1.694 mmol, 1 equiv), Pd(dppf)Cl$_2$ (138 mg, 0.169 mmol, 0.1 equiv) and K$_3$PO$_4$ (1079 mg, 5.082 mmol, 3 equiv) in 1,4-dioxane (10 mL) and H$_2$O (2 mL) was stirred for 1 hour at 80° C. under nitrogen atmosphere. The mixture was allowed to cool down to room temperature. The resulting mixture was concentrated under reduced pressure. The residue was purified by silica gel column chromatography, eluted with PE/EA (5:1) to afford tert-butyl 6-[4-(methoxycarbonyl)-1-methylpyrrol-2-yl]-3',6'-dihydro-2'H-[3,4'-bipyridine]-1'-carboxylate (350 mg, 52% yield) as a white solid. LCMS (ESI) [M+H]$^+$: 398.20.

Step 3: A solution of tert-butyl 6-[4-(methoxycarbonyl)-1-methylpyrrol-2-yl]-3',6'-dihydro-2'H-[3,4-bipyridine]-1'-carboxylate (330 mg, 0.830 mmol, 1 equiv) and Pd/C (44 mg, 0.415 mmol, 0.5 equiv) in THF (5 mL) was stirred for 1 day at room temperature under hydrogen atmosphere. The precipitated solids were collected by filtration and washed with EtOH (3×10 mL). The resulting mixture was concentrated under reduced pressure. The residue was purified by silica gel column chromatography, eluted with PE/EA (1:1) to afford tert-butyl 4-{6-[4-(methoxycarbonyl)-1-methylpyrrol-2-yl]pyridin-3-yl}piperidine-1-carboxylate (263 mg, 79% yield) as a white solid. LCMS (ESI) [M+H]$^+$: 400.22.

Step 4: A solution of tert-butyl 4-{6-[4-(methoxycarbonyl)-1-methylpyrrol-2-yl]pyridin-3-yl}piperidine-1-carboxylate (263 mg, 0.658 mmol, 1 equiv) in DCM (3 mL) and TFA (1 mL) was stirred for 1 hour at room temperature. The resulting mixture was concentrated under reduced pressure to afford methyl 1-methyl-5-[5-(piperidin-4-yl)pyridin-2-yl]pyrrole-3-carboxylate (190 mg, 96% yield) as a white solid. LCMS (ESI) [M+H]$^+$: 300.16.

Step 5: A solution of methyl 1-methyl-5-[5-(piperidin-4-yl)pyridin-2-yl]pyrrole-3-carboxylate (170 mg, 0.568 mmol, 1 equiv), 2-bromo-1,1-difluoroethane (123 mg, 0.852 mmol, 1.5 equiv) and K$_2$CO$_3$ (235 mg, 1.704 mmol, 3 equiv) in DMF (5 mL) was stirred for 1 h at 80° C. The mixture was allowed to cool down to room temperature. The resulting mixture was diluted with water and extracted with EtOAc (3×89 mL). The combined organic layers were washed with water (3×46 mL), dried over anhydrous Na$_2$SO$_4$. After filtration, the filtrate was concentrated under reduced pressure. The residue was purified by silica gel column chromatography, eluted with PE/EA (1:1) to afford methyl 5-{5-[1-(2,2-difluoroethyl)piperidin-4-yl]pyridin-2-yl}-1-methylpyrrole-3-carboxylate (133 mg, 64% yield) as a white solid. LCMS (ESI) [M+H]$^+$: 364.18.

Step 6: To a stirred solution of methyl 5-{5-[1-(2,2-difluoroethyl)piperidin-4-yl]pyridin-2-yl}-1-methylpyrrole-3-carboxylate (113 mg, 0.311 mmol, 1 equiv) and A(3-amino-5-chlorophenyl)methanesulfonamide(102.92 mg, 0.467 mmol, 1.5 equiv) in toluene (2 mL) was added Al(Me)$_3$ (0.5 mL) dropwise at 0° C. The resulting mixture was stirred for 2 hours at 80° C. The mixture was allowed to cool down to room temperature. The reaction was quenched by the addition of water (2 mL) at 0° C. The resulting mixture was concentrated under reduced pressure. The residue (200 mg) was purified by Prep-HPLC with the following conditions (Column: YMC-Actus Triart C18 ExRS, 30*150 mm, 5 μm; Mobile Phase A: Water(10 mmol/L NH$_4$HCO$_3$), Mobile Phase B: ACN; Flow rate: 60 mL/min; Gradient: 35% B to 65% B in 7 min, 65% B; Wave Length: 254/220 nm; RT1(min): 7.33; Number Of Runs: 0) to afford N-(3-chloro-5-methanesulfonamidophenyl)-5-{5-[1-(2,2-difluoroethyl)piperidin-4-yl]pyridin-2-yl}-1-methylpyrrole-3-carboxamide (106.6 mg, 62% yield) as a white solid. LCMS (ESI) [M+H]$^+$: 551.95. $^1$H NMR (300 MHz, DMSO-d$_6$) δ 10.02 (s, 1H), 9.84 (s, 1H), 8.50 (d, J=2.3 Hz, 1H), 7.80-7.69 (m, 2H), 7.69-7.56 (m, 3H), 7.17 (d, J=2.0 Hz, 1H), 6.90 (t, J=2.0 Hz, 1H), 6.17 (tt, J=55.9, 4.4 Hz, 1H), 3.98 (s, 3H), 3.07 (s, 5H), 2.77 (td, J=15.7, 4.3 Hz, 2H), 2.64-2.52 (m, 1H), 2.43-2.18 (m, 2H), 1.83-1.52 (m, 4H).

Examples 618-619

The compounds listed in the following table were prepared using a procedure similar to that described for example 617:

| Structure | Compound No. | MS (ESI) [M + H]+ | 1H NMR |
|---|---|---|---|
| 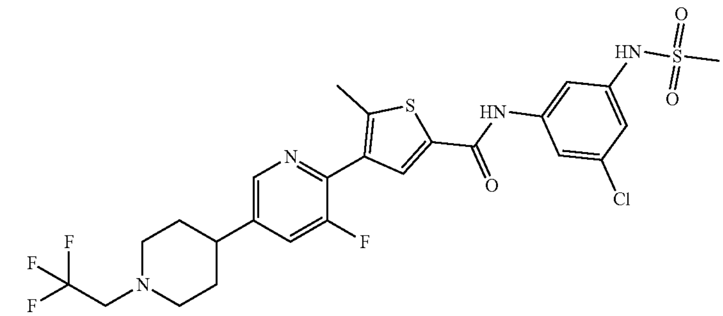 [SMILES: Cc1sc(C(=O)Nc2cc(Cl)cc(NS(C)(=O)=O)c2)cc1-c1ncc(C2CCN(CC(F)(F)F)CC2)cc1F] | 618 | 605 | 1H NMR (400 MHz, DMSO-d6) δ 10.42 (s, 1H), 10.07 (s, 1H), 8.53-8.39 (m, 1H), 8.19 (d, J = 1.7 Hz, 1H), 7.84 (dd, J = 11.8, 1.8 Hz, 1H), 7.64 (dt, J = 16.6, 1.9 Hz, 2H), 6.94 (t, J = 2.0 Hz, 1H), 3.22 (q, J = 10.3 Hz, 2H), 3.06 (s, 5H), 2.76-2.62 (m, 1H), 2.53 (d, J = 1.6 Hz, 3H), 2.47 (d, J = 8.0 Hz, 2H), 1.87-1.71 (m, 4H). |
| 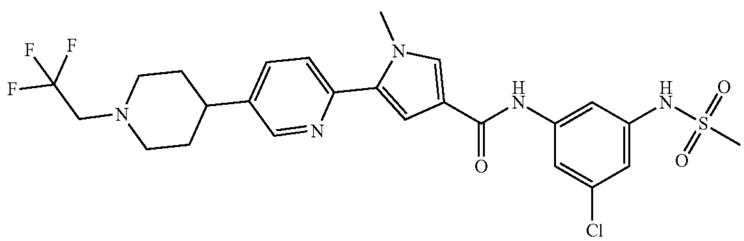 [SMILES: Cn1cc(C(=O)Nc2cc(Cl)cc(NS(C)(=O)=O)c2)cc1-c1ccc(C2CCN(CC(F)(F)F)CC2)cn1] | 619 | 570 | 1H NMR (400 MHz, DMSO-d6) δ 10.02 (s, 1H), 9.83 (s, 1H), 8.50 (d, J = 2.3 Hz, 1H), 7.79-7.69 (m, 2H), 7.69-7.60 (m, 3H), 7.17 (d, J = 2.0 Hz, 1H), 6.89 (t, J = 2.0 Hz, 1H), 3.98 (s, 3H), 3.22 (q, J = 10.2 Hz, 2H), 3.06 (s, 5H), 2.58 (dq, J = 10.7, 5.6, 4.4 Hz, 1H), 2.46 (dd, J = 11.2, 3.3 Hz, 2H), 1.87-1.56 (m, 4H). |
Example 620
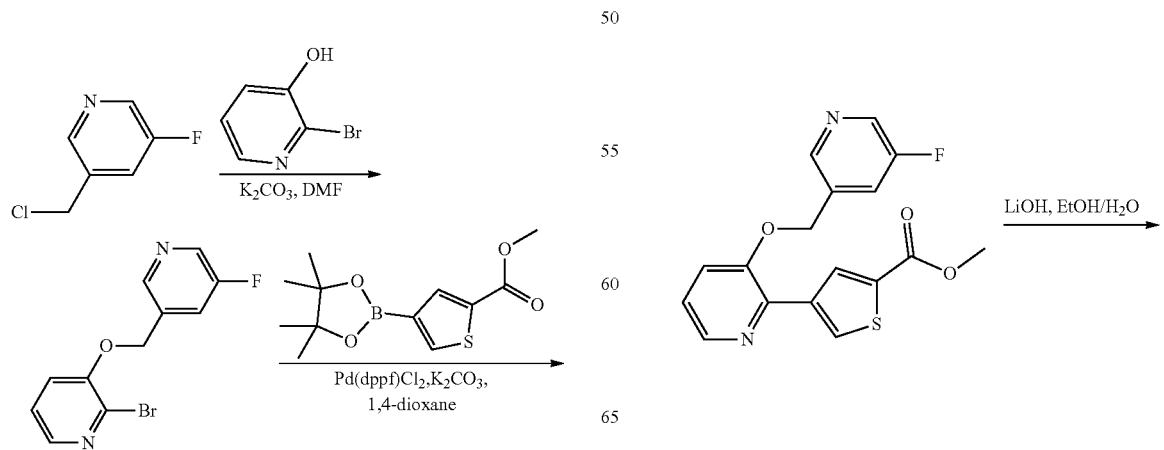
-continued -continued

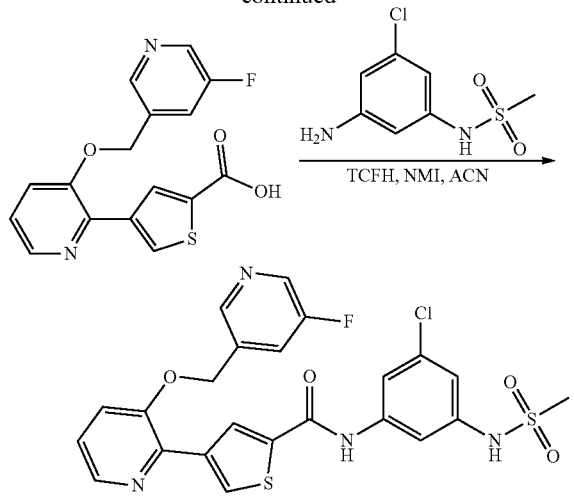

Step 1: A mixture of 3-(chloromethyl)-5-fluoropyridine (180 mg, 1.23 mmol), K$_2$CO$_3$ (508 mg, 3.68 mmol) and 2-bromopyridin-3-ol (234 mg, 1.35 mmol) in DMF (5 mL) was stirred for 2 hours at 80° C. The mixture was concentrated and purified by reverse phase flash chromatography eluting with ACN/H$_2$O (5-95%, formic acid) to afford 2-bromo-3-[(5-fluoropyridin-3-yl) methoxy]pyridine (200 mg, 0.706 mmol) as a yellow solid. LCMS (ESI) [M+H]$^+$: 283

Step 2: A mixture of 2-bromo-3-[(5-fluoropyridin-3-yl) methoxy]pyridine (200 mg, 0.706 mmol), Pd(dppf)Cl$_2$ (51.6 mg, 0.0706 mmol), K$_2$CO$_3$ (291 mg, 2.11 mmol) and methyl 4-(4,4,5,5-tetramethyl-1,3,2-dioxaborolan-2-yl)thiophene-2-carboxylate (245 mg, 0.917 mmol) in 1,4-dioxane (10 mL) was stirred for 2 hours at 80° C. under nitrogen atmosphere. The resulting mixture was concentrated under reduced pressure. The residue was purified by silica gel column chromatography, eluted with PE/EA (0-100%) to afford methyl 4-{3-[(5-fluoropyridin-3-yl)methoxy]pyridin-2-yl}thiophene-2-carboxylate (114 mg, 0.331 mmol) as a yellow solid. LCMS (ESI) [M+H]$^+$: 345

Step 3: To a stirred solution of methyl 4-{3-[(5-fluoropyridin-3-yl)methoxy]pyridin-2-yl}thiophene-2-carboxylate (140 mg, 0.406 mmol) in EtOH (3 mL) and H$_2$O (3 mL) was added LiOH (97.2 mg, 4.06 mmol). Then the mixture was stirred for 2 hours at room temperature. The mixture was acidified to pH 5 with citric acid. The precipitated solids were collected by filtration and washed with water. The resulting solid was dried under vacuum to afford 4-{3-[(5-fluoropyridin-3-yl) methoxy]pyridin-2-yl}thiophene-2-carboxylic acid (110 mg, 0.333 mmol) as a white solid. LCMS (ESI) [M+H]$^+$: 331

Step 4: To a stirred solution of 4-{3-[(5-fluoropyridin-3-yl)methoxy]pyridin-2-yl}thiophene-2-carboxylic acid (110 mg, 0.333 mmol), TCFH (1.96 g, 6.99 mmol) and NMI (163 mg, 1.99 mmol) in ACN (5 mL) was added N-(3-amino-5-chlorophenyl)methanesulfonamide (80.7 mg, 0.366 mmol). Then the mixture was stirred for 1 hour at room temperature. The mixture was concentrated and purified by reverse phase flash chromatography eluting with ACN/H$_2$O (5-95%, formic acid system) to afford N-(3-chloro-5-methanesulfonamidophenyl)-4-{3-[(5-fluoropyridin-3-yl)methoxy]pyridin-2-yl}thiophene-2-carboxamide (66.5 mg, 0.124 mmol) as a white solid. LCMS (ESI) [M+H]$^+$: 533.00. $^1$H NMR (300 MHz, DMSO-d$_6$) δ 10.63 (s, 1H), 10.07 (s, 1H), 8.81 (d, J=1.3 Hz, 1H), 8.68-8.56 (m, 2H), 8.45 (d, J=1.2 Hz, 1H), 8.31 (dd, J=4.6, 1.2 Hz, 1H), 7.93 (dt, J=9.5, 2.3 Hz, 1H), 7.78-7.66 (m, 3H), 7.40 (dd, J=8.4, 4.6 Hz, 1H), 6.96 (t, J=1.9 Hz, 1H), 5.44 (s, 2H), 3.08 (s, 3H).

Examples 621-627

The compounds listed in the following table were prepared using a procedure similar to that described for example 620:

| Structure | Compound No. | MS (ESI) [M + H]$^+$ | $^1$H NMR |
|---|---|---|---|
| 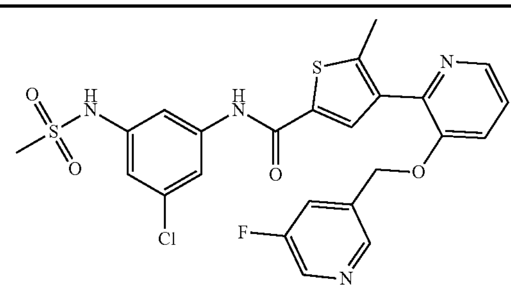 | 621 | 547 | $^1$H NMR (300 MHz, DMSO-d6) δ 10.34 (s, 1H),10.11 (s, 1H), 8.59-8.47 (m, 2H), 8.32 (dd, J = 4.7, 1.2 Hz, 1H), 8.20 (s, 1H), 7.73 (d, J = 8.5 Hz, 2H), 7.66-7.57 (m, 2H), 7.46 (dd, J = 8.4, 4.7 Hz, 1H), 6.94 (t, J = 2.0 Hz, 1H), 5.31 (s, 2H), 3.06 (s, 3H), 2.41 (s, 3H). |
| 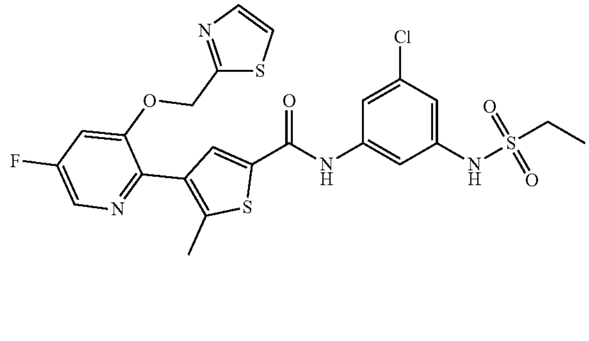 [SMILES: CCS(=O)(=O)Nc1cc(Cl)cc(NC(=O)c2cc(-c3ncc(F)cc3OCc3nccs3)c(C)s2)c1] | 622 | 567 | $^1$H NMR (300 MHz, DMSO-d6) δ 10.36 (s, 1H), 10.12 (s, 1H), 8.36 (d, J = 2.3 Hz, 1H), 8.13 (s, 1H), 7.89 (dd, J = 10.9, 2.3 Hz, 1H), 7.85 (d, J = 3.2 Hz, 1H), 7.77 (d, J = 3.2 Hz, 1H), 7.63 (d, J = 12.0 Hz, 2H), 6.94 (t, J = 1.9 Hz, 1H), 5.61 (s, 2H), 3.17 (q, J = 7.2 Hz, 2H), 2.41 (s, 3H), 1.20 (t, J = 7.3 Hz, 3H). |

| Structure | Compound No. | MS (ESI) [M + H]+ | 1H NMR |
|---|---|---|---|
| 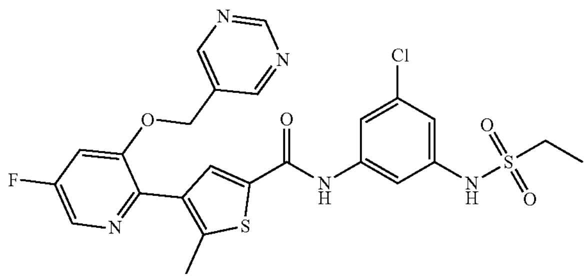 [SMILES: CCS(=O)(=O)Nc1cc(Cl)cc(NC(=O)c2cc(-c3ncc(F)cc3OCc3cncnc3)c(C)s2)c1] | 623 | 562 | 1H NMR (400 MHz, DMSO-d6) δ 10.30 (s, 1H), 10.11 (s, 1H), 9.15 (s, 1H), 8.84 (s, 2H), 8.36 (d, J = 2.3 Hz, 1H), 8.14 (s, 1H), 7.86 (dd, J = 10.8, 2.4 Hz, 1H), 7.61 (dt, J = 3.4, 1.8 Hz, 2H), 6.94 (t, J = 1.9 Hz, 1H), 5.33 (s, 2H), 3.16 (q, J = 7.3 Hz, 2H), 2.37 (s, 3H), 1.20 (t, J = 7.3 Hz, 3H). |
| 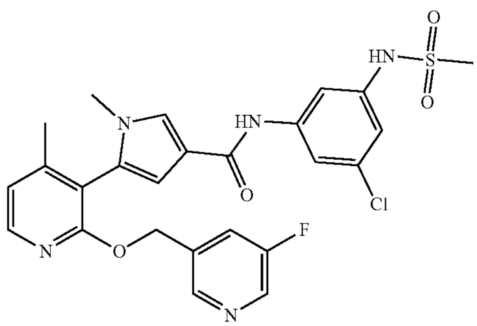 [SMILES: Cc1ccnc(OCc2cncc(F)c2)c1-c1cc(C(=O)Nc2cc(Cl)cc(NS(C)(=O)=O)c2)cn1C] | 624 | 544 | 1H NMR (300 MHz, DMSO-d6) δ 9.99 (s, 1H), 9.70 (s, 1H), 8.53 (d, J = 2.8 Hz, 1H), 8.46 (s, 1H), 7.91 (d, J = 7.0 Hz, 1H), 7.74-7.57 (m, 4H), 6.88 (t, J = 2.0 Hz, 1H), 6.52 (d, J = 1.9 Hz, 1H), 6.35 (d, J = 7.0 Hz, 1H), 5.28-5.11 (m, 2H), 3.36 (s, 3H), 3.06 (s, 3H), 2.08 (s, 3H). |
| 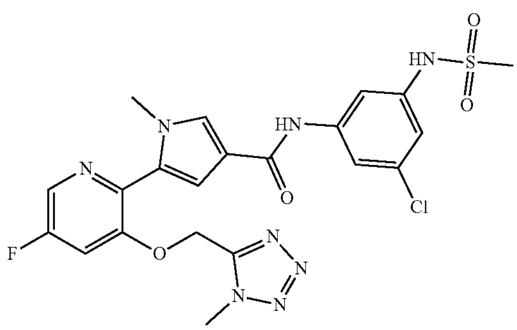 [SMILES: Cn1cc(C(=O)Nc2cc(Cl)cc(NS(C)(=O)=O)c2)cc1-c1ncc(F)cc1OCc1nnnn1C] | 625 | 535 | 1H NMR (400 MHz, DMSO-d6) δ 10.00 (s, 1H), 9.80 (s, 1H), 8.35 (d, J = 2.4 Hz, 1H), 7.88 (dd, J = 10.8, 2.4 Hz, 1H), 7.74-7.61 (m, 3H), 7.01 (d, J = 2.0 Hz, 1H), 6.89 (t, J = 2.0 Hz, 1H), 5.71 (s, 2H), 4.03 (s, 3H), 3.73 (s, 3H), 3.06 (s, 3H). |
| 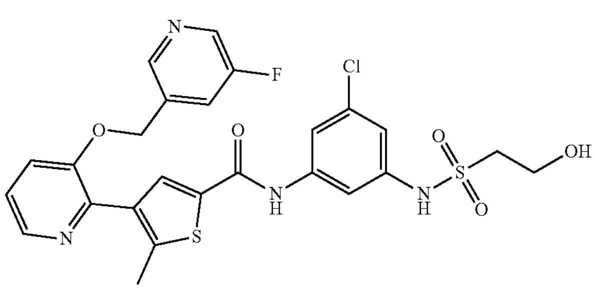 [SMILES: Cc1sc(C(=O)Nc2cc(Cl)cc(NS(=O)(=O)CCO)c2)cc1-c1ncccc1OCc1cncc(F)c1] | 626 | 577 | 1H NMR (400 MHz, DMSO-d6) δ 10.33 (s, 1H), 10.04 (s, 1H), 8.54-8.45 (m, 2H), 8.31 (dd, J = 4.6, 1.2 Hz, 1H), 8.19 (s, 1H), 7.72 (dt, J = 9.1, 1.9 Hz, 2H), 7.63 (dt, J = 4.9, 1.9 Hz, 2H), 7.45 (dd, J = 8.4, 4.7 Hz, 1H), 6.94 (t, J = 1.9 Hz, 1H), 5.31 (s, 2H), 4.94 (s, 1H), 3.75 (t, J = 6.6 Hz, 2H), 3.30 (d, J = 6.6 Hz, 2H), 2.40 (s, 3H). |

| Structure | Compound No. | MS (ESI) [M + H]+ | 1H NMR |
|---|---|---|---|
| 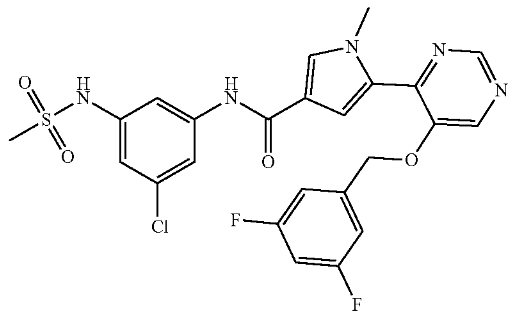 [SMILES: Cn1cc(C(=O)Nc2cc(Cl)cc(NS(C)(=O)=O)c2)cc1-c1ncncc1OCc1cc(F)cc(F)c1] | 627 | 548 | 1H NMR (400 MHz, DMSO-d6) δ 9.93 (s, 2H), 8.83 (s, 1H), 8.66 (s, 1H), 7.83 (d, J = 1.9 Hz, 1H), 7.72-7.49 (m, 3H), 7.31-7.15 (m, 3H), 6.90 (t, J = 1.9 Hz, 1H), 5.44 (s, 2H), 4.00 (s, 3H), 3.05 (s, 3H). |

Examples 628 and 629: N-(3-chloro-5-methane sulfonamidophenyl)-5-{3-[1-[3-fluoro-5-(trifluoromethyl)phenyl]ethoxy]pyridin-2-yl}-1-methyl-1H-pyrrole-3-carboxamide

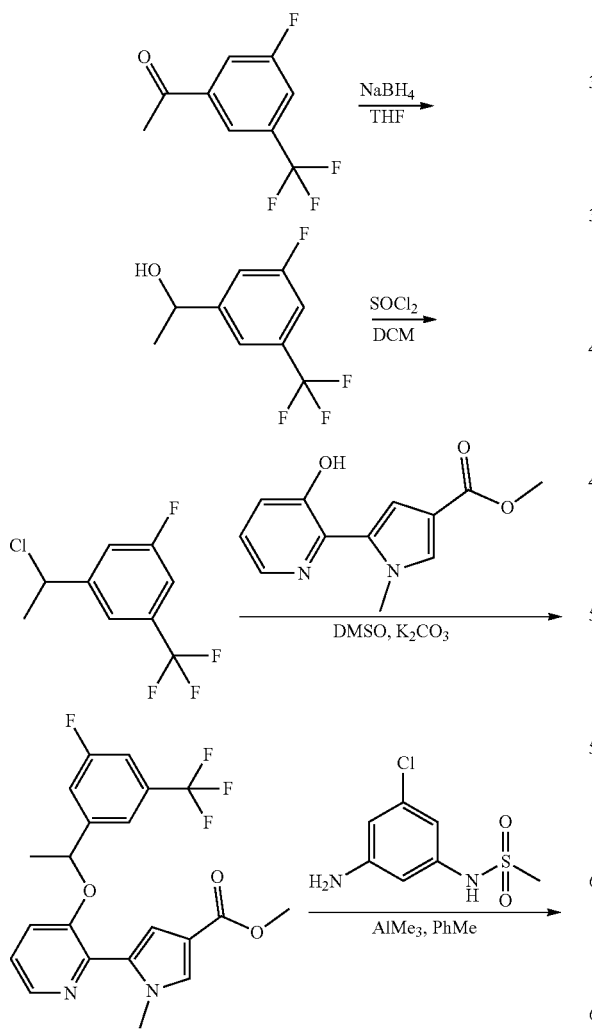

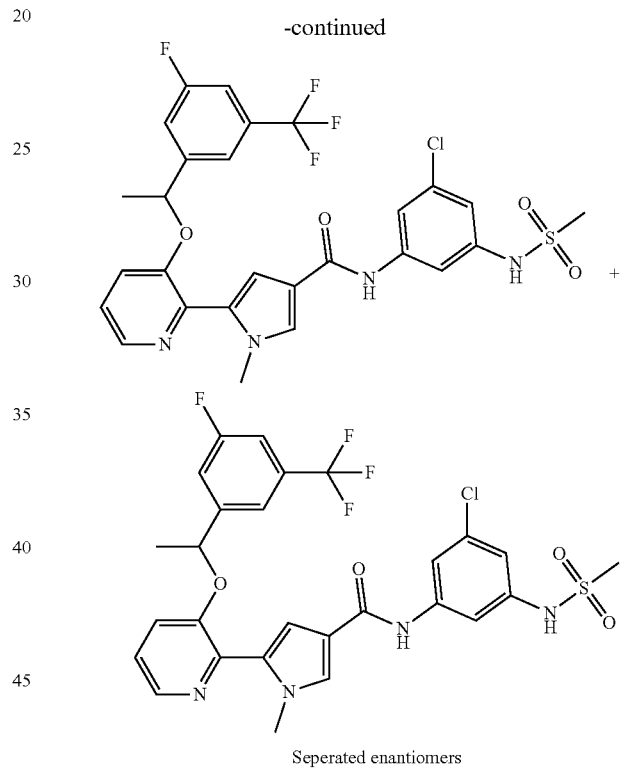

Seperated enantiomers

Step 1: To a stirred solution of 1-[3-fluoro-5-(trifluoromethyl)phenyl]ethan-1-one (2 g, 9.70 mmol) in THF (30 mL) was added NaBH$_4$ (1.10 g, 29.1 mmol) at room temperature. Then the mixture was stirred for 1 hour at 0° C. The mixture was concentrated under reduced pressure. The residue was purified by silica gel column chromatography, eluted with PE/EA (1:2) to afford 1-[3-fluoro-5-(trifluoromethyl)phenyl]ethan-1-ol (1.55 g, 7.44 mmol) as an off yellow solid. LCMS (ESI) [M+H]+: 209.05

Step 2: To a stirred solution of 1-[3-fluoro-5-(trifluoromethyl)phenyl]ethan-1-ol (1.55 g, 7.44 mmol) in DCM (5 mL) was added sulfurooyl dichloride (2.65 g, 22.3 mmol) dropwise at 0° C. under nitrogen atmosphere. Then the mixture was stirred for 1 hour at 0° C. The mixture was concentrated under reduced pressure. The residue was purified by silica gel column chromatography, eluted with PE/EA (1:1) to afford 1-(1-chloroethyl)-3-fluoro-5-(trifluoromethyl)benzene (1.30 g, 5.73 mmol) as an off yellow solid. LCMS (ESI) [M+H]$^+$: 227.06

Step 3: To a stirred solution of 1-(1-chloroethyl)-3-fluoro-5-(trifluoromethyl)benzene (420 mg, 1.85 mmol) and K$_2$CO$_3$ (765 mg, 5.55 mmol) in DMSO (10 mL) was added methyl 5-(3-hydroxypyridin-2-yl)-1-methyl-1H-pyrrole-3-carboxylate (429 mg, 1.85 mmol) at room temperature. Then the mixture was stirred for 1 hour at 60° C. The mixture was diluted with water. The resulting mixture was extracted with EA (3×100 mL). The combined organic layers were washed with brine, dried over anhydrous Na$_2$SO$_4$. After filtration, the filtrate was concentrated under reduced pressure. The residue was purified by reversed-phase flash chromatography with the following conditions: column, C18 silica gel; mobile phase, MeCN in water (0.1% formic acid), 5% to 40% gradient in 20 min; detector, UV 254 nm to afford methyl 5-(3-{1-[3-fluoro-5-(trifluoromethyl)phenyl]ethoxy}pyridin-2-yl)-1-methyl-1H-pyrrole-3-carboxylate (375 mg, 887 µmol) as an off white solid. LCMS (ESI) [M+H]$^+$: 423.13

Step 4: To a stirred solution of methyl 5-(3-{1-[3-fluoro-5-(trifluoromethyl)phenyl]ethoxy}pyridin-2-yl)-1-methyl-1H-pyrrole-3-carboxylate (375 mg, 887 µmol) and N-(3-amino-5-chlorophenyl)methanesulfonamide (195 mg, 887 µmol) in PhMe (10 mL) was added AlMe$_3$ (191 mg, 2.6 mmol) at room temperature. Then the mixture was stirred for 1 hour at 80° C. The mixture was concentrated under reduced pressure. The residue was purified by reversed-phase flash chromatography with the following conditions: column, C18 silica gel; mobile phase, MeCN in water (0.1% formic acid), 5% to 80% gradient in 20 min; detector, UV 254 nm to afford mixture products. The racemic mixture was purified Chiral-HPLC (Column: CHIRAL ART Amylose-SA, 3*25 cm, 5 m; Mobile Phase A: hexanes with 10 mM NH$_3$-MeOH, Mobile Phase B: EtOH; Flow rate: 40 mL/min; Gradient: 30% B to 30% B in 17.4 min; Sample Solvent: EtOH—HPLC; Injection Volume: 0.3 mL) to afford the separated enantiomers of N-(3-chloro-5-methane sulfonamidophenyl)-5-{3-[1-[3-fluoro-5-(trifluoromethyl)phenyl]ethoxy]pyridin-2-yl}-1-methyl-1H-pyrrole-3-carboxamide.

Example 628: N-(3-chloro-5-methane sulfonamidophenyl)-5-{3-[1-[3-fluoro-5-(trifluoromethyl)phenyl]ethoxy]pyridin-2-yl}-1-methyl-1H-pyrrole-3-carboxamide, enantiomer 1

126.7 mg, 206 µmol, white solid. Single enantiomer, arbitrarily assigned. Elution time: 11.6 min. LCMS (ESI) [M+H]$^+$: 611.10. $^1$H NMR (400 MHz, DMSO-d$_6$) δ 10.06 (s, 1H), 9.80 (s, 1H), 8.21 (d, J=2.8 Hz, 1H), 7.77 (dd, J=9.7, 2.9 Hz, 2H), 7.23-7.76 (m, 7H), 7.83 (t, J=2.0 Hz, 1H), 5.80 (q, J=1.9 Hz, 1H), 3.84 (s, 3H), 3.06 (s, 3H), 1.61 (s, 3H).

Example 629: N-(3-chloro-5-methanesulfonamidophenyl)-5-{3-[1-[3-fluoro-5-(trifluoromethyl)phenyl]ethoxy]pyridin-2-yl}-1-methyl-1H-pyrrole-3-carboxamide, enantiomer 2

122.0 mg, 199 µmol, white solid. Single enantiomer, arbitrarily assigned. Elution time: 14.6 min. LCMS (ESI) [M+H]$^+$: 611.11. $^1$HNMR(400 MHz, DMS-d$_6$) δ 10.06 (s, 1H), 9.80 (s, 1H), 8.21 (d, J=2.8 Hz, 1H), 7.77 (dd, J=9.7, 2.9 Hz, 2H), 7.23-7.76 (=, 7H), 7.83 (t, J=2.0 Hz, 1H), 5.80 (q, J=1.9 Hz, 1H), 3.84 (s, 3H), 3.06 (s, 3H), 1.61 (s, 3H).

Examples 630-633

The compounds listed in the following table were prepared using a procedure similar to that described for example 628:

| Structure | Compound No. | MS (ESI) [M + H]$^+$ | $^1$H NMR |
|---|---|---|---|
| Enantiomer 1 | 630 | 561 | $^1$H NMR (300 MHz, DMSO-d6) δ 10.36 (s, 1H), 10.08 (s, 1H), 8.56 (d, J = 1.9 Hz, 1H), 8.35 (dd, J = 4.9, 1.1 Hz, 1H), 8.28 (dd, J = 4.6, 1.2 Hz, 1H), 8.14 (s, 1H), 7.69 (t, J = 1.9 Hz, 1H), 7.63 (t, J = 1.9 Hz, 1H), 7.54 (dd, J = 8.6, 1.3 Hz, 1H), 7.35 (dd, J = 8.4, 4.6 Hz, 1H), 7.27 (dd, J = 6.3, 4.9 Hz, 1H), 6.95 (t, J = 1.9 Hz, 1H), 5.80 (q, J = 6.3 Hz, 1H), 3.08 (s, 3H), 2.45 (s, 3H), 1.58 (d, J = 6.4 Hz, 3H). |

| Structure | Compound No. | MS (ESI) [M + H]+ | ¹H NMR |
|---|---|---|---|
| (Enantiomer 2) | 631 | 561 | ¹H NMR (300 MHz, DMSO-d6) δ 10.36 (s, 1H), 10.08 (s, 1H), 8.56 (d, J = 1.9 Hz, 1H), 8.35 (dd, J = 4.9, 1.1 Hz, 1H), 8.28 (dd, J = 4.7, 1.3 Hz, 1H), 8.14 (s, 1H), 7.69 (t, J = 1.9 Hz, 1H), 7.63 (t, J = 1.9 Hz, 1H), 7.54 (dd, J = 8.5, 1.3 Hz, 1H), 7.35 (dd, J = 8.4, 4.6 Hz, 1H), 7.27 (dd, J = 6.3, 4.9 Hz, 1H), 6.95 (t, J = 1.9 Hz, 1H), 5.80 (q, J = 6.3 Hz, 1H), 3.08 (s, 3H), 2.45 (s, 3H), 1.58 (d, J = 6.4 Hz, 3H). |
| (Enantiomer 1) | 632 | 578.1 | ¹H NMR (400 MHz, DMSO-d6) δ 10.36 (s, 1H), 10.06 (s, 1H), 8.25 (dd, J = 4.7, 1.3 Hz, 1H), 8.15 (s, 1H), 7.65 (dt, J = 15.5, 1.9 Hz, 2H), 7.52 (dd, J = 8.6, 1.4 Hz, 1H), 7.34 (dd, J = 8.4, 4.6 Hz, 1H), 7.10 (tt, J = 9.3, 2.4 Hz, 1H), 7.02-6.92 (m, 3H), 5.60 (q, J = 6.3 Hz, 1H), 3.06 (s, 3H), 2.44 (s, 3H), 1.52 (d, J = 6.3 Hz, 3H). |
| (Enantiomer 2) | 633 | 578.1 | ¹H NMR (400 MHz, DMSO-d6) δ 10.36 (s, 1H), 10.06 (s, 1H), 8.25 (dd, J = 4.7, 1.3 Hz, 1H), 8.15 (s, 1H), 7.65 (dt, J = 15.5, 1.9 Hz, 2H), 7.52 (dd, J = 8.6, 1.4 Hz, 1H), 7.34 (dd, J = 8.4, 4.6 Hz, 1H), 7.10 (tt, J = 9.3, 2.4 Hz, 1H), 7.02-6.92 (m, 3H), 5.60 (q, J = 6.3 Hz, 1H), 3.06 (s, 3H), 2.44 (s, 3H), 1.52 (d, J = 6.3 Hz, 3H). |

Example 634: N-(3-chloro-5-methanesulfonamid-ophenyl)-5-{3-fluoro-5-[(1-isopropylazetidin-3-yl)oxy]pyridin-2-yl}-1-methylpyrrole-3-carboxamide

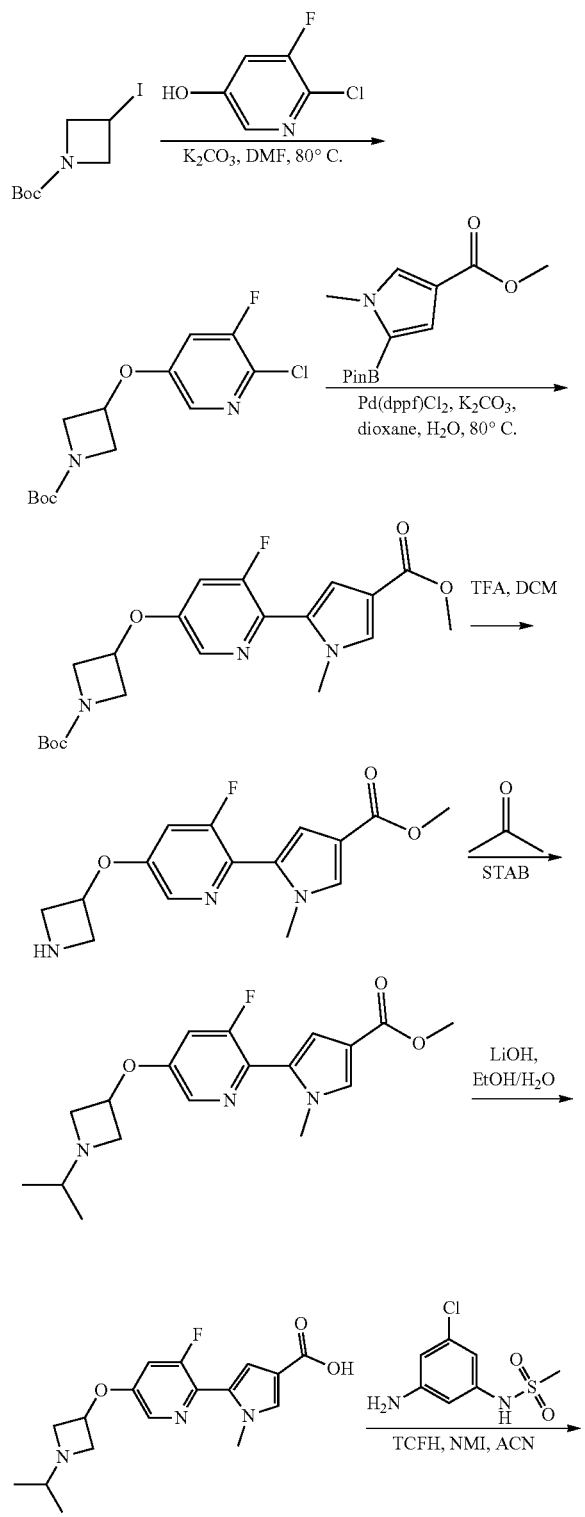

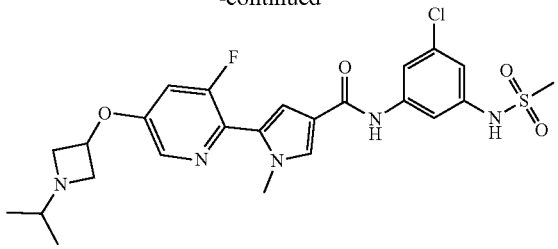

Step 1: A solution of tert-butyl 3-iodoazetidine-1-carboxylate (1.5 g, 5.29 mmol, 1 equiv), K₂CO₃ (2.20 g, 15.89 mmol, 3 equiv) and 6-chloro-5-fluoropyridin-3-ol (0.94 g, 6.35 mmol, 1.2 equiv) in DMF (15 mL) was stirred for 1 hour at 80° C. under nitrogen atmosphere. The resulting mixture was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in tert-butyl 3-[(6-chloro-5-fluoropyridin-3-yl)oxy]azetidine-1-carboxylate (1.3 g, 81% yield) as a white solid. LCMS (ESI) [M+H]⁺: 303.00.

Step 2: A solution of tert-butyl 3-[(6-chloro-5-fluoropyridin-3-yl)oxy]azetidine-1-carboxylate (1.3 g, 4.29 mmol, 1 equiv), methyl 1-methyl-5-(4,4,5,5-tetramethyl-1,3,2-dioxaborolan-2-yl)pyrrole-3-carboxylate (1.37 g, 5.15 mmol, 1.2 equiv), Pd(dppf)Cl₂ (0.31 g, 0.42 mmol, 0.1 equiv) and K₂CO₃ (1.78 g, 12.88 mmol, 3 equiv) in dioxane (10 mL) and H₂O (1 mL) was stirred for 1 hour at 80° C. under nitrogen atmosphere. The resulting mixture was concentrated under reduced pressure. The residue was purified by silica gel column chromatography, eluted with PE/EA (1:1) to afford methyl 5-(5-{[1-(tert-butoxycarbonyl)azetidin-3-yl]oxy}-3-fluoropyridin-2-yl)-1-methylpyrrole-3-carboxylate (1.08 g, 62% yield) as a white solid. LCMS (ESI) [M+H]⁺: 406.00.

Step 3: A solution of methyl 5-(5-{[1-(tert-butoxycarbonyl)azetidin-3-yl]oxy}-3-fluoropyridin-2-yl)-1-methylpyrrole-3-carboxylate (1.08 g, 2.66 mmol, 1 equiv) and TFA (5 mL) in DCM (15 mL) was stirred for 1 hour at room temperature under nitrogen atmosphere. The resulting mixture was concentrated under reduced pressure. This resulted in methyl 5-[5-(azetidin-3-yloxy)-3-fluoropyridin-2-yl]-1-methylpyrrole-3-carboxylate (930 mg, 114% yield) as a white solid. LCMS (ESI) [M+H]⁺: 306.00.

Step 4: A solution of methyl 5-[5-(azetidin-3-yloxy)-3-fluoropyridin-2-yl]-1-methylpyrrole-3-carboxylate (200 mg, 0.65 mmol, 1 equiv) and acetone (2 mL) in MeOH (2 mL) was stirred for overnight at 40° C. under nitrogen atmosphere. To the above mixture was added sodium triacetoxyborohydride (277 mg, 1.31 mmol, 2 equiv) in portions over 2 minutes at 0° C. The resulting mixture was stirred for additional 10 min at room temperature. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in methyl 5-{3-fluoro-5-[(1-isopropylazetidin-3-yl)oxy]pyridin-2-yl}-1-methylpyrrole-3-carboxylate (135 mg, 59% yield) as a white solid. LCMS (ESI) [M−H]⁺: 348.00.

Step 5: A solution of methyl 5-{3-fluoro-5-[(1-isopropylazetidin-3-yl)oxy]pyridin-2-yl}-1-methylpyrrole-3-carboxylate (135 mg, 0.39 mmol, 1 equiv) and LiOH (74 mg, 3.11 mmol, 8 equiv) in EtOH (2 mL) and H₂O (0.4 mL) was stirred for 1 hour at room temperature under nitrogen atmosphere. The resulting mixture was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in 5-{3-fluoro-5-[(1-isopropylazetidin-3-yl)oxy]pyridin-2-yl}-1-methylpyrrole-3-carboxylic acid (108 mg, 83% yield) as a white solid. LCMS (ESI) [M–H]+: 334.00.

Step 6: A solution of 5-{3-fluoro-5-[(1-isopropylazetidin-3-yl)oxy]pyridin-2-yl}-1-methylpyrrole-3-carboxylic acid (108 mg, 0.32 mmol, 1 equiv), N-(3-amino-5-chlorophenyl)methanesulfonamide (85 mg, 0.38 mmol, 1.2 equiv), TCFH (136 mg, 0.48 mmol, 1.5 equiv) and NMI (79 mg, 0.97 mmol, 3 equiv) in ACN (2 mL) was stirred for 1 hour at room temperature under nitrogen atmosphere. The resulting mixture was concentrated under reduced pressure. The residue was purified by reversed-phase flash chromatography with the following conditions: column, C18 silica gel; mobile phase, MeCN in Water (0.1% FA), 10% to 50% gradient in 10 min; detector, UV 254 nm. This resulted in N-(3-chloro-5-methanesulfonamidophenyl)-5-{3-fluoro-5-[(1-isopropylazetidin-3-yl)oxy]pyridin-2-yl}-1-methylpyrrole-3-carboxamide (103.5 mg, 60%) as a white solid. LCMS (ESI) [M–H]+: 536.20. 1H NMR (400 MHz, DMSO-d6) δ 10.00 (s, 1H), 9.86 (s, 1H), 8.19 (dt, J=2.4, 1.2 Hz, 1H), 7.71 (dt, J=4.0, 1.5 Hz, 2H), 7.64 (q, J=1.6 Hz, 1H), 7.47 (dt, J=12.2, 2.4 Hz, 1H), 7.08 (dd, J=3.5, 1.8 Hz, 1H), 6.90 (dt, J=2.2, 1.2 Hz, 1H), 4.89 (p, J=5.5 Hz, 1H), 3.84 (s, 3H), 3.76-3.68 (m, 2H), 3.06 (s, 3H), 3.03-2.95 (m, 2H), 2.39-2.28 (m, 1H), 0.88 (dd, J=6.1, 0.9 Hz, 6H).

Example 635

The compounds listed in the following table were prepared using a procedure similar to that described for example 634:

| Structure | Compound No. | MS (ESI) [M + H]+ | 1H NMR |
|---|---|---|---|
| 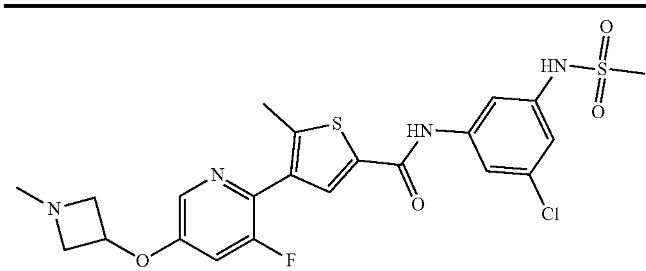 | 635 | 525 | 1H NMR (400 MHz, Methanol-d4) δ 8.39 (s, 1H), 8.20 (d, J = 2.4 Hz, 1H), 7.98 (d, J = 1.7 Hz, 1H), 7.64 (t, J = 2.0 Hz, 1H), 7.54 (t, J = 1.9 Hz, 1H), 7.35 (dd, J = 11.3, 2.5 Hz, 1H), 7.01 (t, J = 2.0 Hz, 1H), 5.14 (tt, J = 6.2, 4.4 Hz, 1H), 4.36-4.27 (m, 2H), 3.89 (dd, J = 11.1, 4.3 Hz, 2H), 3.03 (s, 3H), 2.78 (s, 3H), 2.53 (d, J = 1.2 Hz, 3H). |

Example 636: 4-[5-(azetidin-3-yloxy)pyrimidin-2-yl]-N-(3-chloro-5-methanesulfonamidophenyl)-5-methylthiophene-2-carboxamide

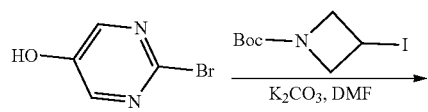

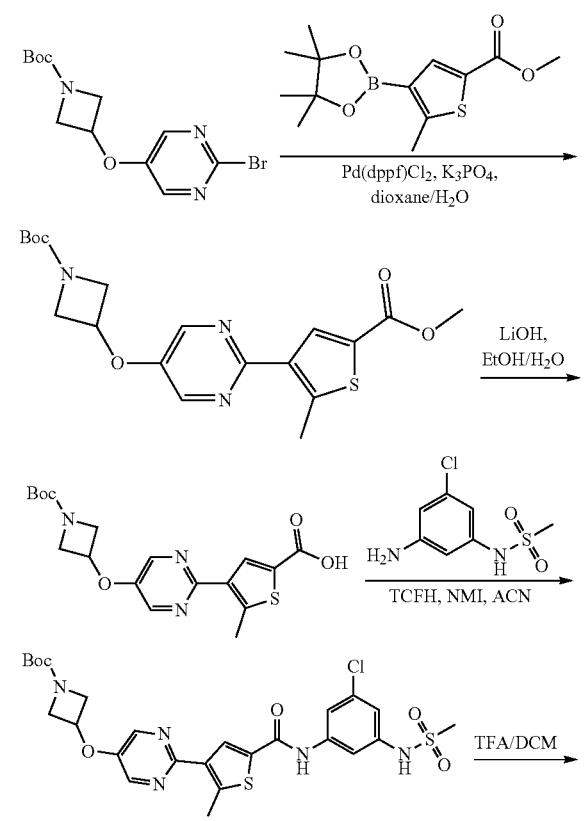

-continued

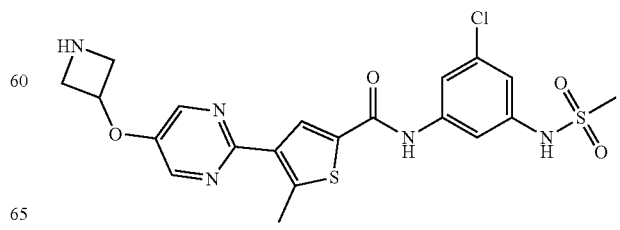

Step 1: To a stirred solution of 2-bromopyrimidin-5-ol (1 g, 5.71 mmol), K₂CO₃ (3.62 g, 17.1 mmol) and tert-butyl 3-iodoazetidine-1-carboxylate (1.61 g, 5.71 mmol) in DMF (30 mL). Then the mixture was stirred for 5 hours at 80° C. The mixture was concentrated and purified by reverse phase flash chromatography eluting with ACN/H₂O (5-95%, acidic system) to afford tert-butyl 3-[(2-bromopyrimidin-5-yl)oxy]azetidine-1-carboxylate (1.20 g, 3.63 mmol) as a white solid. LCMS (ESI) [M+H]⁺: 330

Step 2: A mixture of tert-butyl 3-[(2-bromopyrimidin-5-yl)oxy]azetidine-1-carboxylate (520 mg, 1.57 mmol), methyl 5-methyl-4-(4,4,5,5-tetramethyl-1,3,2-dioxaborolan-2-yl)thiophene-2-carboxylate (485 mg, 1.72 mmol), K₃PO₄ (0.9997 g, 4.71 mmol), Pd(dppf)Cl₂ (128 mg, 0.157 mmol) and H₂O (2 mL) in dioxane (20 mL) was stirred for 16 hours at 80° C. under nitrogen atmosphere. The residue was purified by silica gel column chromatography, eluted with PE/EA (35%) to afford tert-butyl 3-({2-[5-(methoxycarbonyl)-2-methylthiophen-3-yl]pyrimidin-5-yl}oxy)azetidine-1-carboxylate (740 mg, 1.82 mmol) as a yellow solid. LCMS (ESI) [M+H]⁺: 406

Step 3: To a stirred solution of tert-butyl 3-({2-[5-(methoxycarbonyl)-2-methylthiophen-3-yl]pyrimidin-5-yl}oxy)azetidine-1-carboxylate (420 mg, 1.03 mmol) in EtOH (15 mL) and H₂O (15 mL) was added LiOH (49.3 mg, 2.06 mmol). Then the mixture was stirred for 4 hours at room temperature. The mixture was acidified to pH 5 with hydrochloric acid. The mixture was concentrated and purified by reverse phase flash chromatography eluting with ACN/H₂O (50%, acidic system) to afford 4-[5-({1-[(tert-butoxy)carbonyl]azetidin-3-yl}oxy)pyrimidin-2-yl]-5-methylthiophene-2-carboxylic acid (366 mg, 0.935 mmol) as a white solid. LCMS (ESI) [M+H]⁺: 426

Step 4: To a stirred solution of 4-[5-({1-[(tert-butoxy)carbonyl]azetidin-3-yl}oxy)pyrimidin-2-yl]-5-methylthiophene-2-carboxylic acid (366 mg, 0.935 mmol), TCFH (785 mg, 2.80 mmol) in NMI (459 mg, 5.60 mmol) and ACN (20 mL) was added N-(3-amino-5-chlorophenyl)methanesulfonamide (247 mg, 1.12 mmol). Then the mixture was stirred for 2 hours at room temperature. The mixture was concentrated and purified by flash chromatography eluted with PE/EA (50%) to afford tert-butyl 3-[(2-{5-[(3-chloro-5-methanesulfonamidophenyl)carbamoyl]-2-methylthiophen-3-yl}pyrimidin-5-yl) oxy]azetidine-1-carboxylate (240 mg, 0.403 mmol) as a white solid. LCMS (ESI) [M+H]⁺: 594

Step 5: A mixture of tert-butyl 3-[(2-{5-[(3-chloro-5-methanesulfonamidophenyl)carbamoyl]-2-methylthio phen-3-yl}pyrimidin-5-yl)oxy]azetidine-1-carboxylate (240 mg, 0.403 mmol) and TFA (367 mg, 3.22 mmol) in DCM (20 mL) was stirred for 2 hours at ambient temperature and was concentrated under vacuum to afford 4-[5-(azetidin-3-yloxy)pyrimidin-2-yl]-N-(3-chloro-5-methanesulfonamidophenyl)-5-methylthiophene-2-carboxamide (63.2 mg, 0.127 mmol) as a light yellow oil. LCMS (ESI) [M+H]⁺: 494. ¹H NMR (300 MHz, Methanol-d₄) δ 8.45 (d, J=9.2 Hz, 3H), 7.64 (t, J=2.0 Hz, 1H), 7.55 (d, J=1.9 Hz, 1H), 7.01 (t, J=2.0 Hz, 1H), 5.28-5.18 (m, 1H), 4.04 (dd, J=10.3, 6.7 Hz, 2H), 3.77 (dd, J=10.3, 5.5 Hz, 2H), 3.03 (s, 3H), 2.84 (s, 3H).

Examples 637-638

The compounds listed in the following table were prepared using a procedure similar to that described for example 636:

| Structure | Compound No. | MS (ESI) [M + H]⁺ | ¹H NMR |
|---|---|---|---|
| 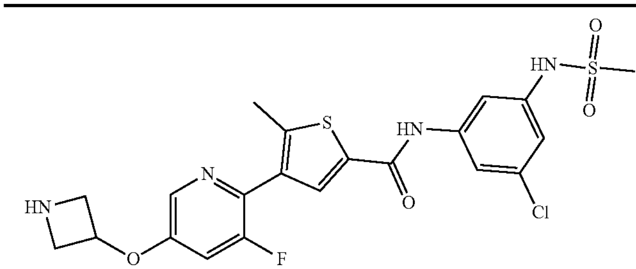 | 637 | 511 | ¹H NMR (400 MHz, Methanol-d4) δ 8.16 (d, J = 2.4 Hz, 1H), 7.97 (s, 1H), 7.63 (d, J = 2.1 Hz, 1H), 7.54 (d, J = 2.0 Hz, 1H), 7.28 (dd, J = 11.3, 2.5 Hz, 1H), 7.01 (d, J = 2.1 Hz, 1H), 5.20 (p, J = 5.9 Hz, 1H), 4.08 (dd, J = 10.2, 6.5 Hz, 2H), 3.79 (dd, J = 10.4, 5.2 Hz, 2H), 3.03 (s, 3H), 2.53 (s, 3H). |
| 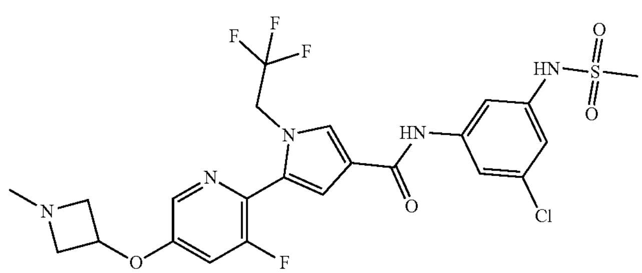 | 638 | 576 | ¹H NMR (400 MHz, DMSO-d6) δ 10.01 (s, 2H), 8.18 (d, J = 2.4 Hz, 1H), 7.84 (d, J = 1.9 Hz, 1H), 7.69 (t, J = 1.8 Hz, 1H), 7.63 (t, J = 1.9 Hz, 1H), 7.51 (dd, J = 12.4, 2.4 Hz, 1H), 7.23 (dd, J = 3.5, 1.8 Hz, 1H), 6.92 (t, J = 1.9 Hz, 1H), 5.55 (q, J = 9.1 Hz, 2H), 4.94 (p, J = 5.6 Hz, 1H), 3.77 (td, J = 6.2, 1.8 Hz, 2H), 3.12-2.96 (m, 5H), 2.30 (s, 3H). |

Example 639: N-(3-chloro-5-methanesulfonamid-ophenyl)-5-(3-fluoro-5-{[(3S)-1-methylpyrrolidin-3-yl]oxy}pyridin-2-yl)-1-methylpyrrole-3-carboxamide

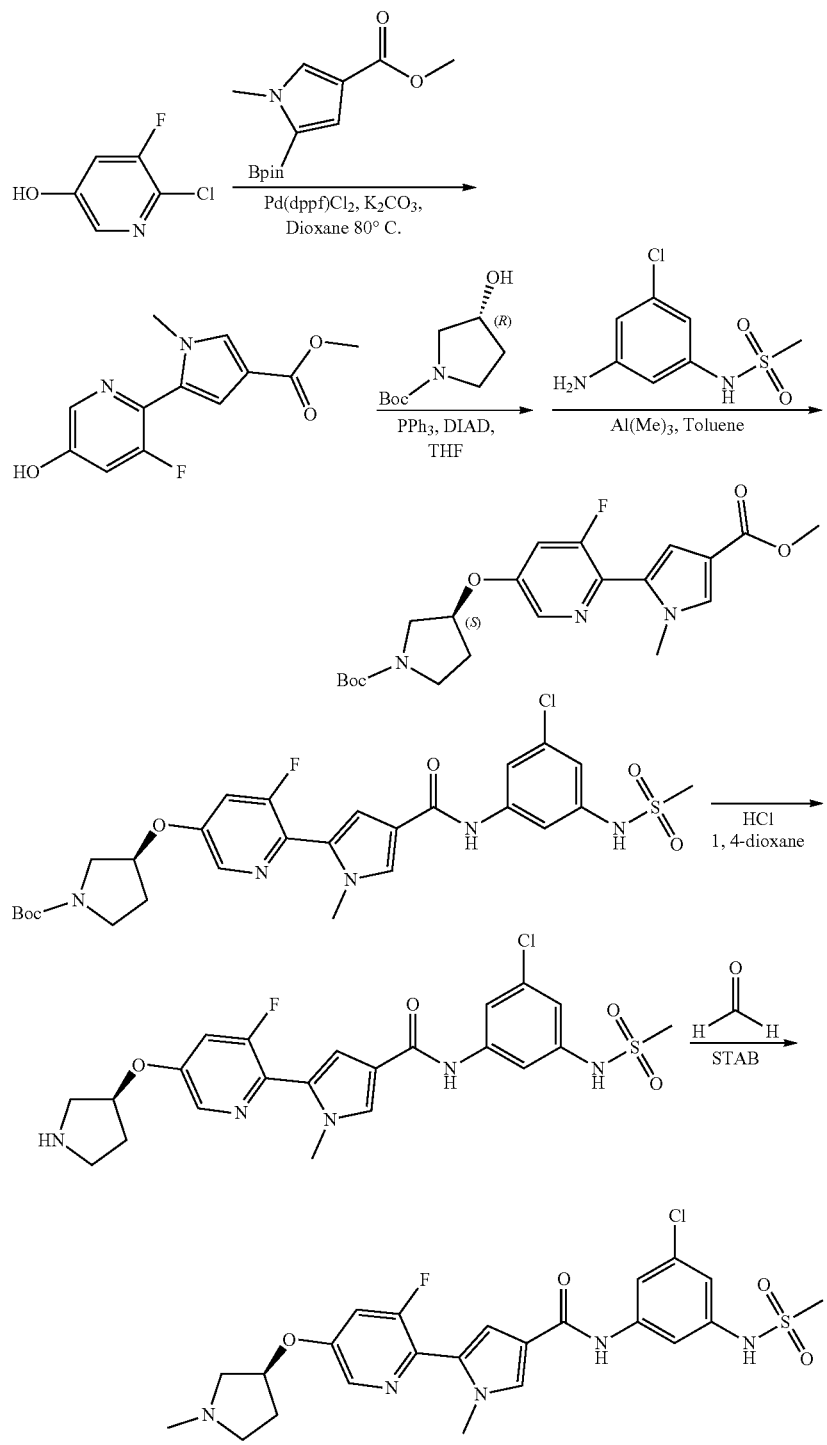

Step 1: A mixture of 6-chloro-5-fluoropyridin-3-ol (200 mg, 1.35 mmol, 1 equiv), methyl 1-methyl-5-(4,4,5,5-tetramethyl-1,3,2-dioxaborolan-2-yl)pyrrole-3-carboxylate (359 mg, 1.35 mmol, 1 equiv), $K_3PO_4$ (863 mg, 4.06 mmol, 3 equiv) and Pd(dppf)$Cl_2$ (198 mg, 0.27 mmol, 0.2 equiv) in 1,4-dioxane (5 mL) was stirred for two hours at 80° C. under $N_2$ atmosphere. The reaction mixture was concentrated under vacuum. The residue was purified by flash chroma tography on silica gel eluting with EA/PE (80%) to afford methyl 5-(3-fluoro-5-hydroxypyridin-2-yl)-1-methylpyrrole-3-carboxylate (230 mg, 68%) as a yellow solid.

LCMS (ESI) [M+H]+: 251

Step 2: Under nitrogen, a solution of methyl 5-(3-fluoro-5-hydroxypyridin-2-yl)-1-methylpyrrole-3-carboxylate (230 mg, 0.92 mmol, 1 equiv), tert-butyl (3R)-3-hydroxypyrrolidine-1-carboxylate (172 mg, 0.92 mmol, 1 equiv) and PPh$_3$ (723 mg, 2.76 mmol, 3 equiv) in THF (5 mL) was added DIAD (558 mg, 2.76 mmol, 3 equiv) at room temperature. The resulting solution was stirred for two hours at 80° C. The reaction mixture was concentrated under vacuum. The residue was purified by flash chromatography on silica gel eluting with EA/PE (40%) to afford methyl 5-(5-{[(3S)-1-(tert-butoxycarbonyl)pyrrolidin-3-yl]oxy}-3-fluoropyridin-2-yl)-1-methylpyrrole-3-carboxylate (350 mg, 91%) as a white solid.

LCMS (ESI) [M+H]+: 420

Step 3: A solution of methyl 5-(5-{[(3S)-1-(tert-butoxycarbonyl)pyrrolidin-3-yl]oxy}-3-fluoropyridin-2-yl)-1-methylpyrrole-3-carboxylate (350 mg, 0.83 mmol, 1 equiv), N-(3-amino-5-chlorophenyl)methanesulfonamide (184 mg, 0.83 mmol, 1 equiv) and Al(Me)$_3$ (0.5 mL) in Toluene (5 mL) was stirred for 1 hour at 80° C. under nitrogen atmosphere. The reaction mixture was concentrated under vacuum. The residue (500 mg) was purified by Prep-HPLC with the following conditions (Column: Sunfire prep C18 column, 30*150 mm, 5 μm; Mobile Phase A: Water(0.1% FA), Mobile Phase B: ACN; Flow rate: 60 mL/min; Gradient: 18% B to 40% B in 8 min; Wave Length: 254/220 nm; RT1(min): 5.27) to afford tert-butyl (3S)-3-[(6-{4-[(3-chloro-5-methanesulfonamidophenyl)carbamoyl]-1-methylpyrrol-2-yl}-5-fluoropyridin-3-yl)oxy]pyrrolidine-1-carboxylate (300 mg, 59% yield) as a white solid. LCMS (ESI) [M+H]+: 608

Step 4: To a stirred solution of tert-butyl (3S)-3-[(6-{4-[(3-chloro-5-methanesulfonamidophenyl)carbamoyl]-1-methyl pyrrol-2-yl}-5-fluoropyridin-3-yl)oxy]pyrrolidine-1-carboxylate (300 mg, 0.49 mmol, 1 equiv) in 1,4-dioxane (5 mL) was added a dioxane solution of HCl (5 mL, 4 M in dioxane) and the resulting mixture was stirred for 1 hour at 40° C. under nitrogen atmosphere. The reaction mixture was concentrated under vacuum. The residue was purified by flash chromatography on silica gel eluting with EA/PE (32%) to afford N-(3-chloro-5-methanesulfonamidophenyl)-5-{3-fluoro-5-[(3 S)-pyrrolidin-3-yloxy]pyridin-2-yl}-1-methylpyrrole-3-carboxamide (220 mg, 88%) as a yellow solid.

LCMS (ESI) [M+H]+: 508

Step 5: A solution of N-(3-chloro-5-methanesulfonamidophenyl)-5-{3-fluoro-5-[(3S)-pyrrolidin-3-yloxy]pyridin-2-yl}-1-methylpyrrole-3-carboxamide (220 mg, 0.43 mmol, 1 equiv), sodium triacetoxyborohydride (184 mg, 0.87 mmol, 2 equiv) in formaldehyde (3 mL) was stirred for 1 hour at 60° C. under nitrogen atmosphere. The resulting solid was dried under vacuum. The residue (150 mg) was purified by Prep-HPLC with the following conditions (Column: YMC-Actus Triart C18, 30*150 mm, 5 μm; Mobile Phase A: Water(0.1% FA), Mobile Phase B: ACN; Flow rate: 60 mL/min; Gradient: 38% B to 52% B in 7 min, 52% B; Wave Length: 254/220 nm; RT1(min): 6.38) to afford N-(3-chloro-5-methanesulfonamidophenyl)-5-(3-fluoro-5-{[(3S')-1-methylpyrrolidin-3-yl]oxy}pyridin-2-yl)-1-methylpyrrole-3-carboxamide (91.7 mg, 41%) as a white solid. LCMS (ESI) [M+H]+: 522.15. $^1$H NMR (300 MHz, DMSO-d$_6$) δ10.03 (s, 1H), 9.86 (s, 1H), 8.21 (d, J=2.3 Hz, 1H), 7.72 (q, J=2.1 Hz, 2H), 7.64 (t, J=1.9 Hz, 1H), 7.53 (dd, J=12.6, 2.4 Hz, 1H), 7.08 (t, J=2.6 Hz, 1H), 6.90 (t, J=2.0 Hz, 1H), 5.03 (s, 1H), 3.85 (s, 3H), 3.07 (s, 3H), 2.74 (ddd, J=24.9, 10.8, 7.0 Hz, 3H), 2.32 (d, J=24.2 Hz, 5H), 1.82 (d, J=10.2 Hz, 1H).

Examples 640-642

The compounds listed in the following table were prepared using a procedure similar to that described for example 639:

| Structure | Example No. | MS (ESI) [M + H]+ | $^1$H NMR |
|---|---|---|---|
| 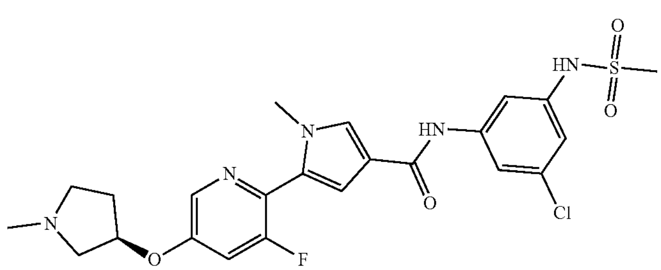 | 640 | 522 | $^1$H NMR (300 MHz, DMSO-d6) δ 9.86 (s, 1H), 8.23 (d, J = 2.4 Hz, 1H), 8.15 (s, 1H), 7.72 (q, J = 1.7 Hz, 2H), 7.68-7.62 (m, 1H), 7.57 (dd, J = 12.5, 2.4 Hz, 1H), 7.14-7.04 (m, 1H), 6.90 (t, J = 2.0 Hz, 1H), 5.10 (s, 1H), 3.85 (s, 3H), 3.06 (s, 3H), 3.02-2.89 (m, 3H), 2.78-2.57 (m, 1H), 2.46 (s, 4H), 1.93 (dd, J = 14.3, 7.0 Hz, 1H). |

-continued

| Structure | Example No. | MS (ESI) [M + H]+ | ¹H NMR |
|---|---|---|---|
| 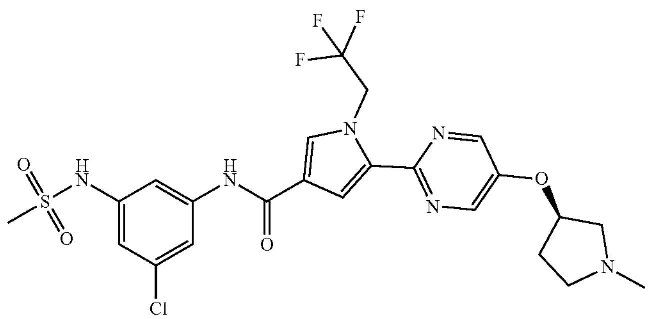 | 641 | 573 | ¹H NMR (400 MHz, DMSO-d6) δ 9.98 (s, 2H), 8.47 (s, 2H), 7.72 (d, J = 2.0 Hz, 1H), 7.65 (t, J = 1.8 Hz, 1H), 7.63-7.56 (m, 2H), 6.85 (d, J = 2.0 Hz, 1H), 5.69 (q, J = 9.1 Hz, 2H), 5.09-4.88 (m, 1H), 2.99 (s, 3H), 2.71 (dd, J = 10.7, 5.8 Hz, 1H), 2.63 (ddd, J = 10.4, 7.0, 2.9 Hz, 2H), 2.28 (dq, J = 10.6, 7.7, 6.2 Hz, 2H), 2.20 (s, 3H), 1.81-1.66 (m, 1H). |
| 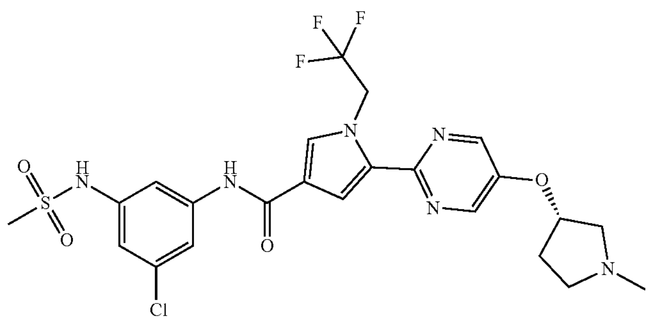 | 642 | 573 | ¹H NMR (400 MHz, DMSO-d6) δ 10.05 (s, 2H), 8.55 (s, 2H), 7.80 (d, J = 2.1 Hz, 1H), 7.72 (t, J = 1.8 Hz, 1H), 7.71-7.60 (m, 2H), 6.92 (t, J = 2.0 Hz, 1H), 5.76 (q, J = 9.1 Hz, 2H), 5.08 (t, J = 6.6 Hz, 1H), 3.06 (s, 3H), 2.78 (dd, J = 10.7, 5.8 Hz, 1H), 2.70 (ddd, J = 10.4, 6.8, 2.9 Hz, 2H), 2.43-2.30 (m, 2H), 2.27 (s, 3H), 1.87-1.73 (m, 1H). |

The following compounds were also synthesized using procedures similar to those described above.

| Structure | Example No. | MS (ESI) [M + H]+ | ¹H NMR |
|---|---|---|---|
| 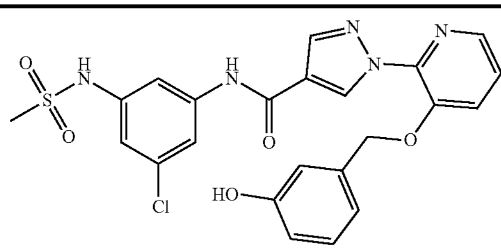 | 179 | 514 | ¹H NMR (300 MHz, DMSO-d6) δ 10.22 (s, 1H), 10.07 (s, 1H), 9.46 (s, 1H), 8.89 (s, 1H), 8.30 (s, 1H), 8.20-8.14 (m, 1H), 7.85-7.79 (m, 1H), 7.71 (t, J = 1.7 Hz, 1H), 7.64-7.60 (m, 1H), 7.54 (dd, J = 8.3, 4.6 Hz, 1H), 7.15 (t, J = 7.8 Hz, 1H), 6.95 (t, |
| 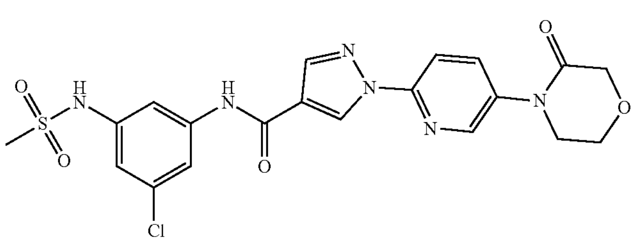 [SMILES: CS(=O)(=O)Nc1cc(Cl)cc(NC(=O)c2cnn(-c3ccc(N4CCOCC4=O)cn3)c2)c1] | 180 | 491 | ¹H NMR (400 MHz, DMSO-d6) δ 10.30 (s, 1H), 10.16 (s, 1H), 9.41 (s, 1H), 8.67 (d, J = 2.5 Hz, 1H), 8.31 (s, 1H), 8.15 (dd, J = 8.8, 2.5 Hz, 1H), 8.04 (d, J = 8.8 Hz, 1H), |

-continued

| Structure | Example No. | MS (ESI) [M + H]+ | ¹H NMR |
|---|---|---|---|
| | | | 7.71 (t, J = 1.9 Hz, 1H), 7.62 (t, J = 1.9 Hz, 1H), 6.94 (t, J = 2.0 Hz, 1H), 4.28 (s |
| 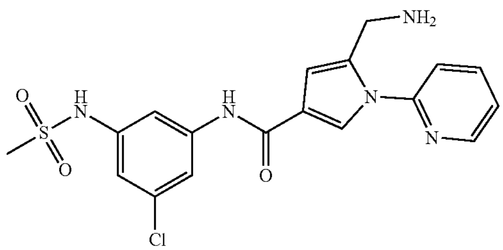 [SMILES: CS(=O)(=O)Nc1cc(Cl)cc(NC(=O)c2cc(CN)n(-c3ccccn3)c2)c1] | 181 | 420 | ¹H NMR (300 MHz, DMSO-d6) δ 9.97 (s, 1H), 8.62-8.55 (m, 1H), 8.33 (s, 1H), 8.15 (d, J = 1.9 Hz, 1H), 8.07 (td, J = 7.8, 1.8 Hz, 1H), 7.79 (d, J = 8.1 Hz, 1H), 7.71 (t, J = 1.8 Hz, 1H), 7.61 (t, J = 1.9 Hz, 1H), 7.47 (dd, J = 7.4, 4.8 Hz, 1H), 6.90 (t, J |
| 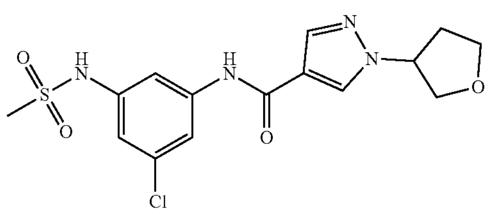 [SMILES: CS(=O)(=O)Nc1cc(Cl)cc(NC(=O)c2cnn(C3CCOC3)c2)c1] | 182 | 385 | ¹H NMR (300 MHz, DMSO-d6) δ 10.05 (s, 2H), 8.44 (s, 1H), 8.06 (s, 1H), 7.67 (s, 1H), 7.58 (s, 1H), 6.93 (s, 1H), 5.10 (s, 1H), 4.05-3.89 (m, 3H), 3.84 (q, J = 7.6 Hz, 1H), 3.06 (s, 3H), 2.42 (p, J = 7.8, 7.1 Hz, 1H), 2.34-2.20 (m, 1H). |
| 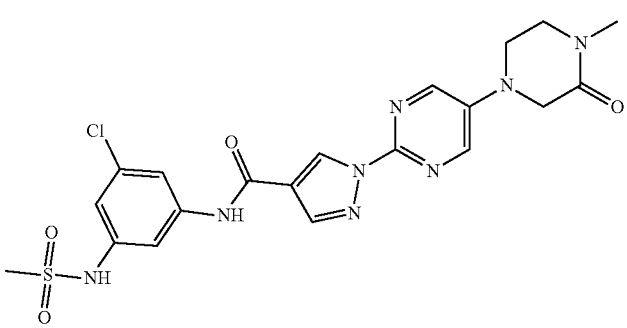 [SMILES: CN1CCN(c2cnc(-n3cc(C(=O)Nc4cc(Cl)cc(NS(C)(=O)=O)c4)cn3)nc2)CC1=O] | 183 | 505 | ¹H NMR (300 MHz, DMSO-d6) δ 10.26 (s, 1H), 10.11 (s, 1H), 9.31 (d, J = 0.8 Hz, 1H), 8.62 (s, 2H), 8.24 (d, J = 0.8 Hz, 1H), 7.68 (t, J = 1.8 Hz, 1H), 7.59 (t, J = 1.9 Hz, 1H), 6.92 (t, J = 2.0 Hz, 1H), 4.00 (s, 2H), 3.69 (dd, J = 6.5, 4.3 Hz, 2H), 3.50 (d |

-continued
| Structure | Example No. | MS (ESI) [M + H]+ | ¹H NMR |
|---|---|---|---|
| 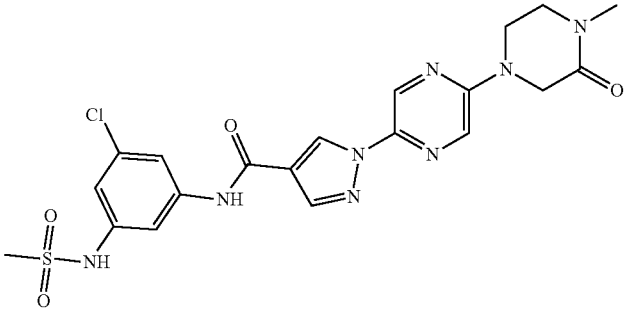 [SMILES: CN1CCN(c2cnc(-n3cc(C(=O)Nc4cc(Cl)cc(NS(C)(=O)=O)c4)cn3)cn2)CC1=O] | 184 | 505 | ¹H NMR (300 MHz, DMSO-d6) δ 10.23 (s, 1H), 9.21 (s, 1H), 8.74 (d, J = 1.4 Hz, 1H), 8.34 (s, 1H), 8.30 (d, J = 1.5 Hz, 1H), 8.27 (s, 1H), 7.68 (t, J = 1.8 Hz, 1H), 7.58 (d, J = 1.9 Hz, 1H), 6.92 (t, J = 2.0 Hz, 1H), 4.21 (s, 2H), 3.94 (t, J = 5.4 Hz, 2H), |
| 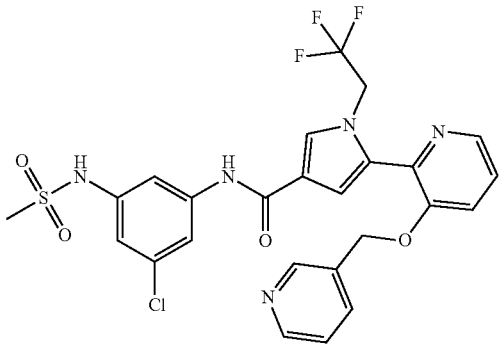 [SMILES: CS(=O)(=O)Nc1cc(Cl)cc(NC(=O)c2cc(-c3ncccc3OCc3cccnc3)n(CC(F)(F)F)c2)c1] | 185 | 580 | ¹H NMR (400 MHz, DMSO-d6) δ 10.03 (s, 1H), 9.97 (s, 1H), 8.67 (s, 1H), 8.53 (d, J = 4.0 Hz, 1H), 8.25 (d, J = 4.6 Hz, 1H), 7.86 (dt, J = 7.9, 2.0 Hz, 1H), 7.82 (s, 1H), 7.73-7.66 (m, 2H), 7.62 (t, J = 1.9 Hz, 1H), 7.41 (dd, J = 7.9, 4.8 Hz, 1H), 7.38- |
| 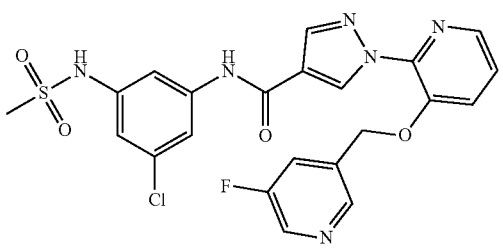 [SMILES: CS(=O)(=O)Nc1cc(Cl)cc(NC(=O)c2cnn(-c3ncccc3OCc3cncc(F)c3)c2)c1] | 186 | 517 | ¹H NMR (300 MHz, DMSO-d6) δ 10.22 (s, 1H), 10.08 (s, 1H), 8.94 (d, J = 0.7 Hz, 1H), 8.56 (d, J = 2.7 Hz, 2H), 8.32 (d, J = 0.7 Hz, 1H), 8.22 (dd, J = 4.7, 1.3 Hz, 1H), 7.91 (dd, J = 8.3, 1.0 Hz, 1H), 7.82 (dt, J = 9.5, 2.3 Hz, 1H), 7.71 (t, J = 1.8 Hz, 1H |
| 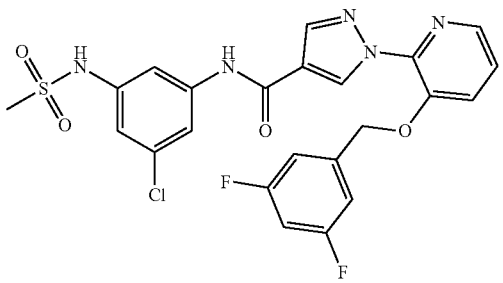 [SMILES: CS(=O)(=O)Nc1cc(Cl)cc(NC(=O)c2cnn(-c3ncccc3OCc3cc(F)cc(F)c3)c2)c1] | 187 | 534 | ¹H NMR (300 MHz, DMSO-d6) δ 10.23 (s, 1H), 10.08 (s, 1H), 8.96 (s, 1H), 8.33 (s, 1H), 8.21 (dd, J = 4.7, 1.3 Hz, 1H), 7.84 (dd, J = 8.4, 1.4 Hz, 1H), 7.71 (t, J = 1.9 Hz, 1H), 7.62 (t, J = 1.9 Hz, 1H), 7.58 (dd, J = 8.3, 4.6 Hz, 1H), 7.20 (ddd, J = 7.5, 5 |

-continued

| Structure | Example No. | MS (ESI) [M + H]+ | ¹H NMR |
|---|---|---|---|
| 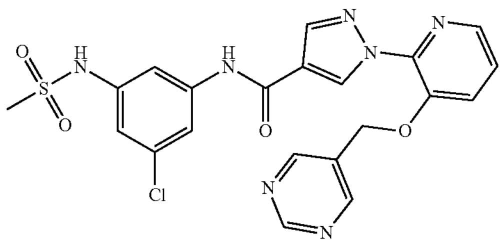 [SMILES: CS(=O)(=O)Nc1cc(Cl)cc(NC(=O)c2cnn(-c3ncccc3OCc3cncnc3)c2)c1] | 188 | 500 | ¹H NMR (300 MHz, DMSO-d6) δ 10.19 (s, 1H), 9.17 (s, 1H), 8.93 (d, J = 0.7 Hz, 1H), 8.90 (s, 2H), 8.31 (d, J = 0.7 Hz, 1H), 8.23 (dd, J = 4.7, 1.3 Hz, 1H), 8.10 (s, 1H), 7.94 (dd, J = 8.4, 1.4 Hz, 1H), 7.67 (m, 1H), 7.61 (dd, J = 8.3, 4.7 Hz, 1H), 7.57 (m, |
| 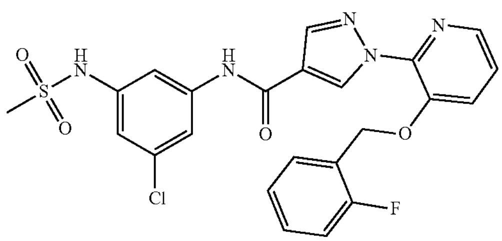 [SMILES: CS(=O)(=O)Nc1cc(Cl)cc(NC(=O)c2cnn(-c3ncccc3OCc3ccccc3F)c2)c1] | 189 | 516 | ¹H NMR (300 MHz, DMSO-d6) δ 10.20 (s, 1H), 10.08 (s, 1H), 8.86 (s, 1H), 8.29 (s, 1H), 8.21 (dd, J = 4.6, 1.3 Hz, 1H), 7.94 (dd, J = 8.4, 1.3 Hz, 1H), 7.71 (t, J = 1.9 Hz, 1H), 7.64-7.52 (m, 3H), 7.46-7.35 (m, 1H), 7.30-7.17 (m, 2H), 6.95 (t, J = 2.0 |
| 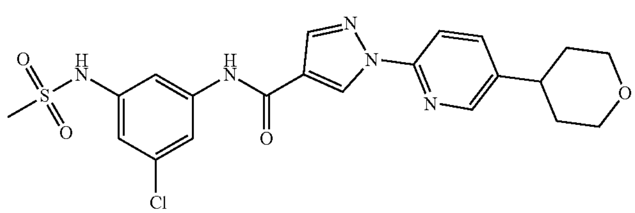 [SMILES: CS(=O)(=O)Nc1cc(Cl)cc(NC(=O)c2cnn(-c3ccc(C4CCOCC4)cn3)c2)c1] | 190 | 476 | ¹H NMR (300 MHz, DMSO-d6) δ 10.30 (s, 1H), 10.09 (s, 1H), 9.40 (s, 1H), 8.48 (d, J = 2.1 Hz, 1H), 8.29 (s, 1H), 7.99 (dd, J = 8.6, 2.2 Hz, 1H), 7.93 (d, J = 8.5 Hz, 1H), 7.73 (t, J = 1.8 Hz, 1H), 7.64 (t, J = 1.9 Hz, 1H), 6.95 (t, J = 1.9 Hz, 1H), 3.99 (d |
| 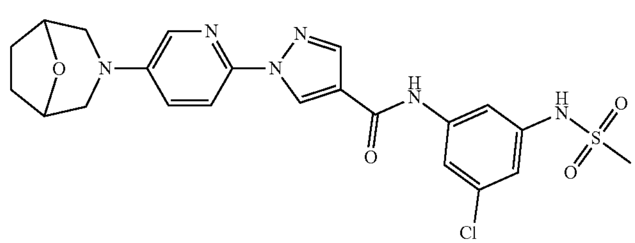 [SMILES: CS(=O)(=O)Nc1cc(Cl)cc(NC(=O)c2cnn(-c3ccc(N4CC5CCC(C4)O5)cn3)c2)c1] | 191 | 503 | ¹H NMR (400 MHz, DMSO-d6) δ 10.25 (s, 1H), 10.17 (s, 1H), 9.26 (s, 1H), 8.22 (s, 1H), 8.11 (d, J = 2.9 Hz, 1H), 7.80 (d, J = 9.0 Hz, 1H), 7.72 (t, J = 1.9 Hz, 1H), 7.62 (t, J = 1.9 Hz, 1H), 7.51 (dd, J = 9.1, 3.0 Hz, 1H), 6.93 (t, J = 1.9 Hz, 1H), 4.47 (s |

| Structure | Example No. | MS (ESI) [M + H]+ | ¹H NMR |
|---|---|---|---|
| 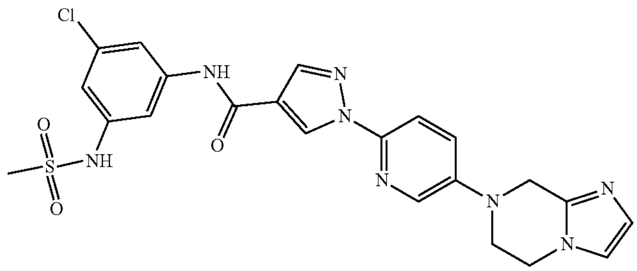 [SMILES: CS(=O)(=O)Nc1cc(Cl)cc(NC(=O)c2cnn(-c3ccc(N4CCn5ccnc5C4)cn3)c2)c1] | 192 | 513 | ¹H NMR (400 MHz, DMSO-d6) δ 10.26 (s, 1H), 9.30 (s, 1H), 8.35 (d, J = 2.9 Hz, 1H), 8.24 (s, 1H), 7.86 (d, J = 9.0 Hz, 1H), 7.76 (dd, J = 9.0, 3.0 Hz, 1H), 7.71 (s, 1H), 7.62 (s, 1H), 7.14 (s, 1H), 6.93 (d, J = 4.8 Hz, 2H), 4.55 (s, 2H), 4.23-4.07 (m, 2H |
| 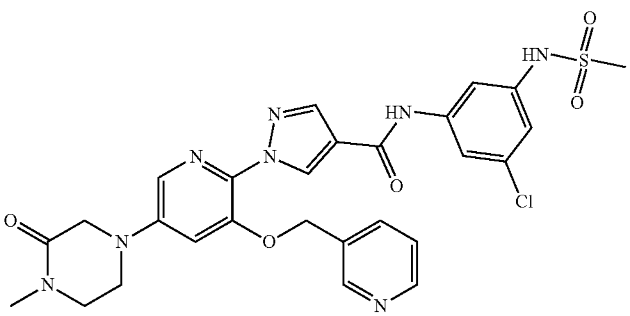 [SMILES: CN1CCN(c2cnc(-n3cc(C(=O)Nc4cc(Cl)cc(NS(C)(=O)=O)c4)cn3)c(OCc3cccnc3)c2)CC1=O] | 193 | 611 | ¹H NMR (300 MHz, DMSO-d6) δ 10.16 (s, 1H), 10.07 (s, 1H), 8.71 (s, 1H), 8.62 (d, J = 2.2 Hz, 1H), 8.52 (dd, J = 4.8, 1.6 Hz, 1H), 8.23 (s, 1H), 7.86 (d, J = 2.4 Hz, 1H), 7.81 (dt, J = 8.0, 1.9 Hz, 1H), 7.70 (t, J = 1.8 Hz, 1H), 7.61 (t, J = 1.8 Hz, 1H), 7 |
| 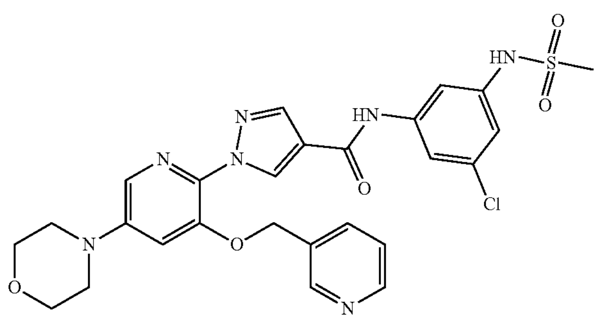 [SMILES: CS(=O)(=O)Nc1cc(Cl)cc(NC(=O)c2cnn(-c3ncc(N4CCOCC4)cc3OCc3cccnc3)c2)c1] | 194 | 584 | ¹H NMR (300 MHz, DMSO-d6) δ 8.61 (s, 1H), 8.51 (s, 1H), 8.44 (d, J = 3.3 Hz, 1H), 8.20 (s, 1H), 7.79 (d, J = 5.7 Hz, 2H), 7.60-7.55 (m, 1H), 7.52 (t, J = 1.7 Hz, 1H), 7.43-7.35 (m, 1H), 7.24 (s, 1H), 6.97-6.90 (m, 1H), 5.24 (s, 2H), 3.84-3.65 (m, |
| 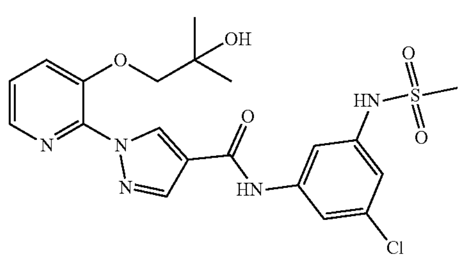 [SMILES: CC(C)(O)COc1cccnc1-n1cc(C(=O)Nc2cc(Cl)cc(NS(C)(=O)=O)c2)cn1] | 195 | 480 | ¹H NMR (300 MHz, DMSO-d6) δ 10.19 (s, 1H), 10.10 (s, 1H), 8.90 (s, 1H), 8.30 (s, 1H), 8.16 (dd, J = 4.6, 1.3 Hz, 1H), 7.81 (dd, J = 8.4, 1.4 Hz, 1H), 7.71 (t, J = 1.9 Hz, 1H), 7.62 (t, J = 1.9 Hz, 1H), 7.53 (dd, J = 8.3, 4.6 Hz, 1H), 6.94 (t, J = 1.9 Hz, |

-continued

| Structure | Example No. | MS (ESI) [M + H]+ | ¹H NMR |
|---|---|---|---|
| 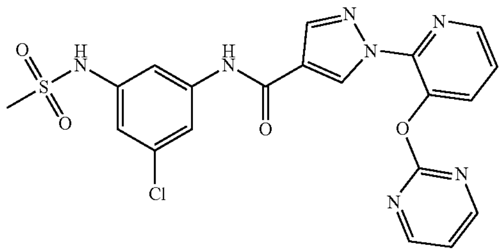 [SMILES: CS(=O)(=O)Nc1cc(Cl)cc(NC(=O)c2cnn(-c3ncccc3Oc3ncccn3)c2)c1] | 196 | 486 | ¹H NMR (300 MHz, DMSO-d6) δ 10.21 (s, 1H), 9.16 (s, 1H), 8.55 (dd, J = 14.8, 4.8 Hz, 3H), 8.12-8.00 (m, 1H), 7.96 (s, 1H), 7.71-7.58 (m, 2H), 7.57 (s, 1H), 7.23 (t, J = 4.8 Hz, 1H), 6.92 (s, 1H), 3.05 (s, 3H). |
| 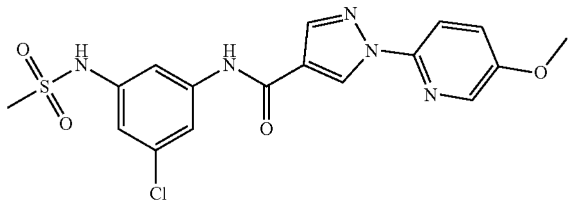 | 197 | 422 | ¹H NMR (300 MHz, DMSO-d6) δ 10.28 (s, 1H), 10.09 (s, 1H), 9.31 (s, 1H), 8.26 (m, 2H), 7.94 (d, J = 9.0 Hz, 1H), 7.73 (t, J = 1.8 Hz, 1H), 7.68 (dd, J = 9.0, 3.0 Hz, 1H), 7.63 (t, J = 1.9 Hz, 1H), 6.94 (t, J = 1.9 Hz, 1H), 3.91 (s, 3H), 3.08 (s, 3H). |
| 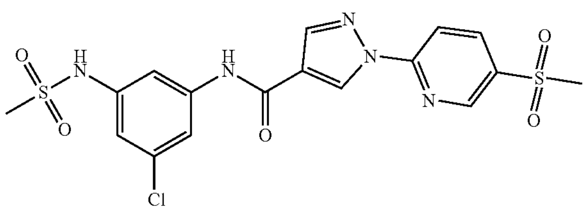 | 198 | 470 | ¹H NMR (300 MHz, DMSO-d6) δ 10.45 (s, 1H), 9.60 (s, 1H), 9.12 (s, 1H), 8.62 (d, J = 8.3 Hz, 1H), 8.47 (s, 1H), 8.29 (d, J = 8.8 Hz, 1H), 7.73 (d, J = 30.3 Hz, 2H), 7.01 (s, 1H), 3.46 (s, 3H), 3.13 (s, 3H). |
| 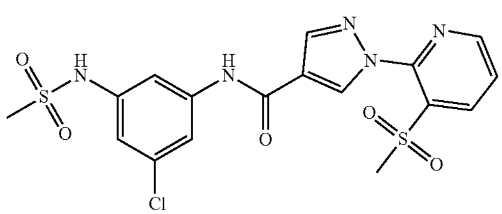 [SMILES: CS(=O)(=O)Nc1cc(Cl)cc(NC(=O)c2cnn(-c3ncccc3S(C)(=O)=O)c2)c1] | 199 | 470 | ¹H NMR (300 MHz, DMSO-d6) δ 10.34 (s, 1H), 10.12 (s, 1H), 9.08 (s, 1H), 8.90 (dd, J = 4.8, 1.7 Hz, 1H), 8.62 (dd, J = 8.0, 1.7 Hz, 1H), 8.36 (s, 1H), 7.88 (dd, J = 8.0, 4.8 Hz, 1H), 7.72 (t, J = 1.8 Hz, 1H), 7.62 (t, J = 1.9 Hz, 1H), 6.96 (t, J = 1.9 Hz, |

-continued

| Structure | Example No. | MS (ESI) [M + H]+ | ¹H NMR |
|---|---|---|---|
| 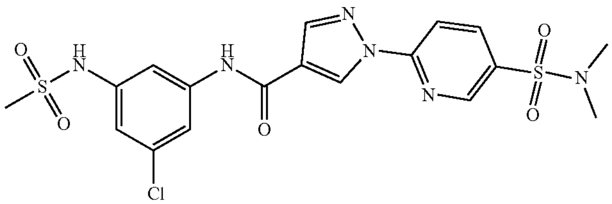 | 200 | 499 | ¹H NMR (400 MHz, DMSO-d6) δ 10.39 (s, 1H), 10.09 (s, 1H), 9.50 (s, 1H), 8.89 (dd, J = 2.4, 0.8 Hz, 1H), 8.44-8.36 (m, 2H), 8.21 (dd, J = 8.6, 0.8 Hz, 1H), 7.73 (t, J = 1.9 Hz, 1H), 7.63 (t, J = 1.9 Hz, 1H), 6.95 (t, J = 1.9 Hz, 1H), 3.07 (s, 3H), 2.71 ( |
| 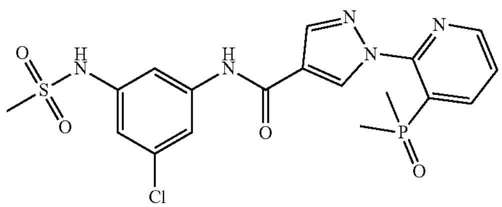 [SMILES: CP(C)(=O)c1cccnc1-n1cc(C(=O)Nc2cc(Cl)cc(NS(C)(=O)=O)c2)cn1] | 201 | 468 | ¹H NMR (300 MHz, DMSO-d6) δ 10.35 (s, 1H), 10.13 (s, 1H), 9.18 (s, 1H), 8.74 (dt, J = 4.4, 2.0 Hz, 1H), 8.65 (ddd, J = 12.3, 7.8, 1.9 Hz, 1H), 8.34 (s, 1H), 7.82-7.68 (m, 2H), 7.62 (t, J = 1.9 Hz, 1H), 6.95 (t, J = 1.9 Hz, 1H), 3.07 (s, 3H), 1.71 (d, J |
| 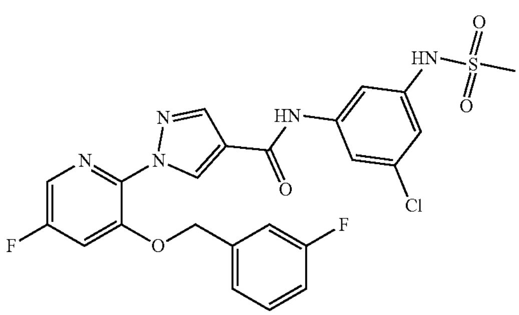 [SMILES: CS(=O)(=O)Nc1cc(Cl)cc(NC(=O)c2cnn(-c3ncc(F)cc3OCc3cccc(F)c3)c2)c1] | 202 | 534 | ¹H NMR (400 MHz, DMSO-d6) δ 10.22 (s, 1H), 10.06 (s, 1H), 8.87 (s, 1H), 8.31 (s, 1H), 8.24 (d, J = 2.4 Hz, 1H), 7.97 (dd, J = 10.1, 2.4 Hz, 1H), 7.70 (t, J = 1.9 Hz, 1H), 7.61 (t, J = 1.9 Hz, 1H), 7.43 (td, J = 8.1, 6.1 Hz, 1H), 7.30-7.22 (m, 2H), 7.16 |
| 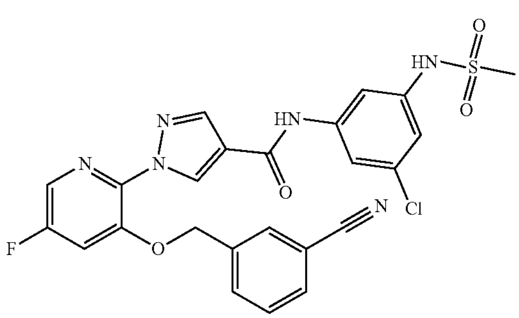 [SMILES: CS(=O)(=O)Nc1cc(Cl)cc(NC(=O)c2cnn(-c3ncc(F)cc3OCc3cccc(C#N)c3)c2)c1] | 203 | 541 | ¹H NMR (400 MHz, DMSO-d6) δ 10.21 (s, 1H), 10.05 (s, 1H), 8.87 (s, 1H), 8.30 (s, 1H), 8.25 (d, J = 2.4 Hz, 1H), 7.98 (dd, J = 10.1, 2.5 Hz, 1H), 7.89 (d, J = 1.8 Hz, 1H), 7.81 (dt, J = 7.7, 1.5 Hz, 1H), 7.77 (d, J = 7.9 Hz, 1H), 7.70 (t, J = 1.9 Hz, 1H), |

-continued

| Structure | Example No. | MS (ESI) [M + H]+ | ¹H NMR |
|---|---|---|---|
| 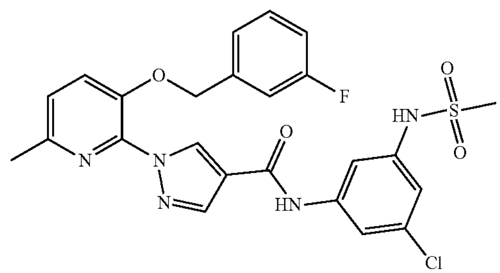 | 204 | 530 | ¹H NMR (300 MHz, DMSO-d6) δ 10.22 (s, 1H), 10.07 (s, 1H), 8.89 (s, 1H), 8.30 (s, 1H), 7.75 (d, J = 8.4 Hz, 1H), 7.72 (t, J = 1.8 Hz, 1H), 7.62 (t, J = 1.9 Hz, 1H), 7.40 (m, 2H), 7.30-7.23 (m, 2H), 7.14 (t, J = 8.1 Hz, 1H), 6.95 (t, J = 1.9 Hz, 1H), 5.29 |
| 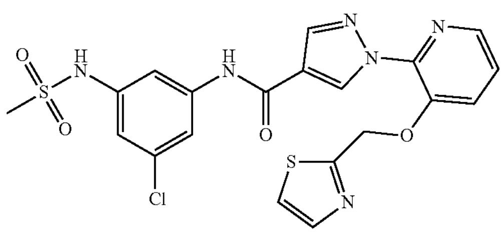 [SMILES: CS(=O)(=O)Nc1cc(Cl)cc(NC(=O)c2cnn(-c3ncccc3OCc3nccs3)c2)c1] | 205 | 505 | ¹H NMR (400 MHz, DMSO-d6) δ 10.21 (s, 1H), 10.07 (s, 1H), 8.91 (s, 1H), 8.31 (s, 1H), 8.23 (d, J = 4.6 Hz, 1H), 7.98 (dd, J = 8.4, 1.2 Hz, 1H), 7.83 (d, J = 3.2 Hz, 1H), 7.78 (d, J = 3.2 Hz, 1H), 7.71 (d, J = 1.9 Hz, 1H), 7.64-7.53 (m, 2H), 6.94 (t, J = |
| 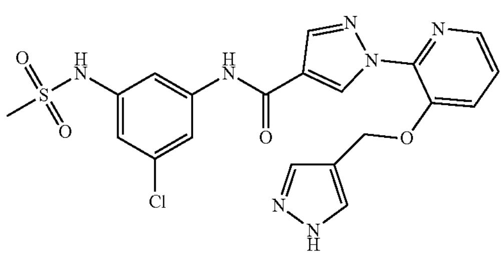 [SMILES: CS(=O)(=O)Nc1cc(Cl)cc(NC(=O)c2cnn(-c3ncccc3OCc3cn[nH]c3)c2)c1] | 206 | 488 | ¹H NMR (400 MHz, DMSO-d6) δ 12.84 (s, 1H), 10.18 (s, 1H), 10.06 (s, 1H), 8.82 (s, 1H), 8.26 (s, 1H), 8.15 (d, J = 4.6 Hz, 1H), 7.92 (d, J = 8.3 Hz, 1H), 7.80 (s, 1H), 7.70 (t, J = 1.9 Hz, 1H), 7.66-7.42 (m, 3H), 6.94 (t, J = 2.0 Hz, 1H), 5.18 (s, 2H), 3 |
| 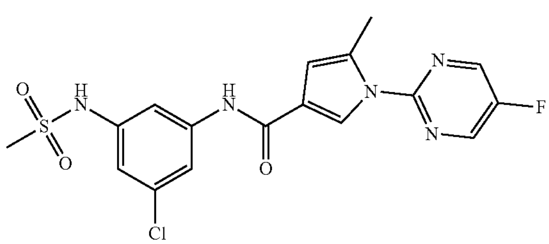 [SMILES: Cc1cc(C(=O)Nc2cc(Cl)cc(NS(C)(=O)=O)c2)cn1-c1ncc(F)cn1] | 207 | 424 | ¹H NMR (400 MHz, DMSO-d6) δ 10.03 (s, 1H), 10.01 (s, 1H), 8.99 (s, 2H), 8.42 (d, J = 2.1 Hz, 1H), 7.72 (t, J = 1.9 Hz, 1H), 7.66 (t, J = 1.9 Hz, 1H), 6.91 (t, J = 1.9 Hz, 1H), 6.58 (dd, J = 2.1, 1.2 Hz, 1H), 3.06 (s, 3H), 2.57 (s, 3H). |

-continued

| Structure | Example No. | MS (ESI) [M + H]+ | ¹H NMR |
|---|---|---|---|
| 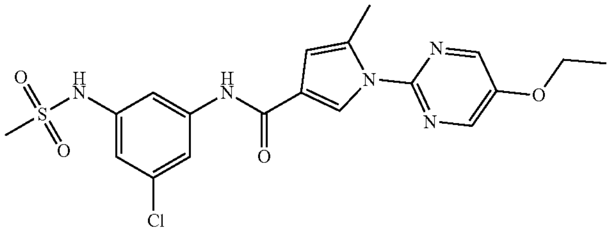 [SMILES: CCOc1cnc(-n2cc(C(=O)Nc3cc(Cl)cc(NS(C)(=O)=O)c3)cc2C)nc1] | 208 | 450 | ¹H NMR (300 MHz, DMSO-d6) δ 10.10 (s, 1H), 9.97 (s, 1H), 8.63 (s, 2H), 8.35 (d, J = 2.1 Hz, 1H), 7.71 (t, J = 1.9 Hz, 1H), 7.64 (t, J = 1.9 Hz, 1H), 6.89 (t, J = 2.0 Hz, 1H), 6.55 (s, 1H), 4.26 (q, J = 6.9 Hz, 2H), 3.05 (s, 3H), 2.55 (s, 3H), 1.39 (t, J = |
| 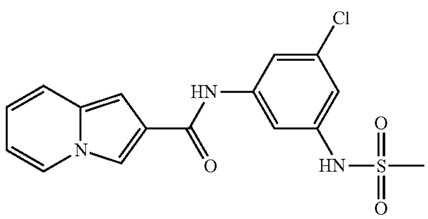 [SMILES: CS(=O)(=O)Nc1cc(Cl)cc(NC(=O)c2cc3ccccn3c2)c1] | 209 | 364 | ¹H NMR (300 MHz, DMSO-d6) δ 10.16 (s, 1H), 10.08 (s, 1H), 8.32 (dd, J = 7.0, 1.1 Hz, 1H), 8.17 (d, J = 1.6 Hz, 1H), 7.75 (t, J = 1.8 Hz, 1H), 7.68 (t, J = 1.9 Hz, 1H), 7.50 (d, J = 9.1 Hz, 1H), 6.99 (t, J = 1.2 Hz, 1H), 6.93 (t, J = 2.0 Hz, 1H), 6.78 (ddd |
| 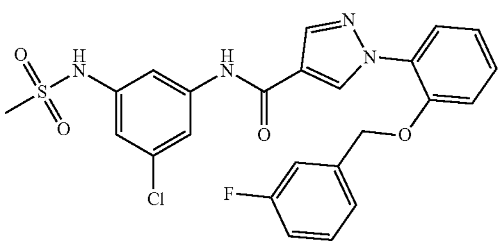 [SMILES: CS(=O)(=O)Nc1cc(Cl)cc(NC(=O)c2cnn(-c3ccccc3OCc3cccc(F)c3)c2)c1] | 210 | 515 | ¹H NMR (400 MHz, DMSO-d6) δ 10.14 (s, 1H), 10.06 (s, 1H), 8.84 (s, 1H), 8.29 (s, 1H), 7.70-7.65 (m, 2H), 7.59 (t, J = 1.9 Hz, 1H), 7.47-7.37 (m, 2H), 7.35 (dd, J = 8.5, 1.3 Hz, 1H), 7.29-7.21 (m, 2H), 7.18-7.14 (m, 1H), 7.14-7.10 (m, 1H), 6.94 ( |
| 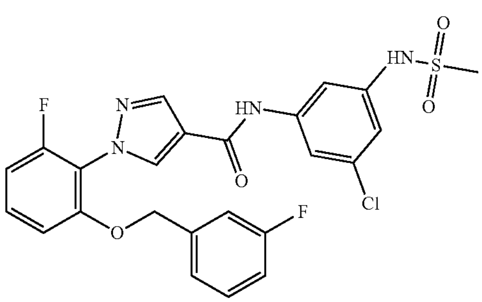 [SMILES: CS(=O)(=O)Nc1cc(Cl)cc(NC(=O)c2cnn(-c3c(F)cccc3OCc3cccc(F)c3)c2)c1] | 211 | 533 | ¹H NMR (400 MHz, DMSO-d6) δ 10.17 (s, 1H), 10.07 (s, 1H), 8.66 (s, 1H), 8.32 (s, 1H), 7.69 (t, J = 1.9 Hz, 1H), 7.59 (t, J = 1.9 Hz, 1H), 7.57-7.50 (m, 1H), 7.39 (td, J = 8.0, 5.9 Hz, 1H), 7.13 (dt, J = 24.6, 8.6 Hz, 5H), 6.94 (t, J = 2.0 Hz, 1H), 5.26 |

| Structure | Example No. | MS (ESI) [M + H]+ | ¹H NMR |
|---|---|---|---|
| 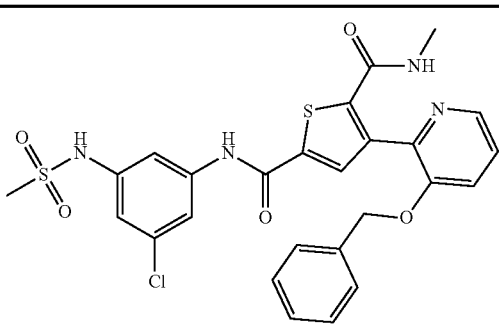 | 212 | 571 | ¹H NMR (300 MHz, DMSO-d6) δ 10.58 (s, 1H), 10.11 (s, 1H), 8.53 (q, J = 4.1 Hz, 1H), 8.29 (dd, J = 4.7, 1.2 Hz, 1H), 8.26 (s, 1H), 7.69 (t, J = 1.9 Hz, 1H), 7.65 (ddd, J = 4.4, 3.0, 1.3 Hz, 2H), 7.46 (dd, J = 8.4, 4.7 Hz, 1H), 7.42-7.25 (m, 5H), 6.98 (t, |
| 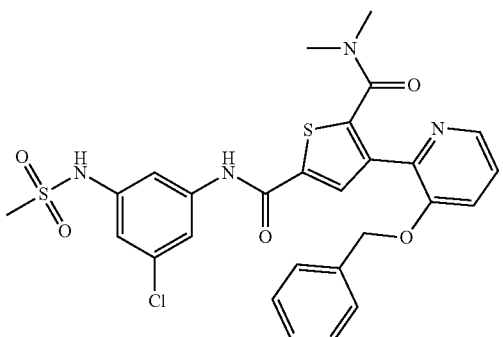 | 213 | 585 | ¹H NMR (300 MHz, DMSO-d6) δ 10.61 (s, 1H), 10.13 (s, 1H), 8.41 (s, 1H), 8.22 (d, J = 4.5 Hz, 1H), 7.70-7.63 (m, 2H), 7.60 (d, J = 8.3 Hz, 1H), 7.50-7.24 (m, 6H), 6.98 (s, 1H), 5.25 (s, 2H), 3.08 (s, 3H), 2.84 (s, 3H), 2.59 (s, 3H). |
| 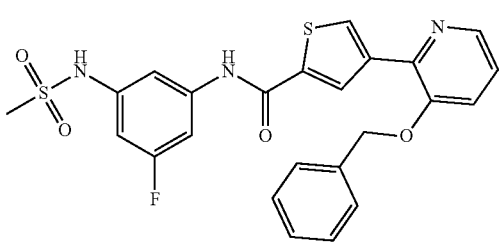 [SMILES: CS(=O)(=O)Nc1cc(F)cc(NC(=O)c2cc(-c3ncccc3OCc3ccccc3)cs2)c1] | 214 | 498 | ¹H NMR (400 MHz, DMSO-d6) δ 10.67 (s, 1H), 10.09 (s, 1H), 8.83 (s, 1H), 8.46 (s, 1H), 8.27 (dd, J = 4.6, 1.2 Hz, 1H), 7.69 (d, J = 8.4 Hz, 1H), 7.53 (d, J = 7.4 Hz, 3H), 7.50-7.45 (m, 1H), 7.42 (t, J = 7.4 Hz, 2H), 7.38-7.32 (m, 2H), 6.74 (dt, J = 10. |
| 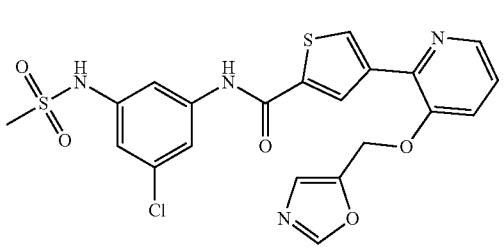 [SMILES: CS(=O)(=O)Nc1cc(Cl)cc(NC(=O)c2cc(-c3ncccc3OCc3cnco3)cs2)c1] | 215 | 505 | ¹H NMR (400 MHz, DMSO-d6) δ 10.63 (s, 1H), 10.10 (s, 1H), 8.80 (d, J = 1.3 Hz, 1H), 8.44 (s, 1H), 8.38 (d, J = 1.3 Hz, 1H), 8.31 (dd, J = 4.6, 1.2 Hz, 1H), 7.80 (dd, J = 8.5, 1.3 Hz, 1H), 7.69 (dt, J = 5.0, 1.9 Hz, 2H), 7.45-7.36 (m, 2H), 6.95 (t, J = 2 |

-continued

| Structure | Example No. | MS (ESI) [M + H]+ | ¹H NMR |
|---|---|---|---|
| 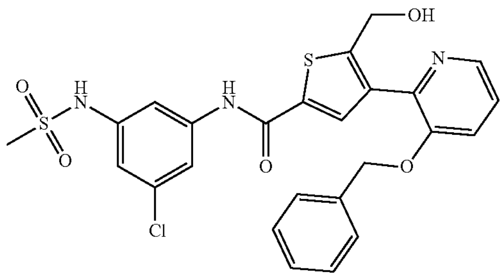 [SMILES: CS(=O)(=O)Nc1cc(Cl)cc(NC(=O)c2cc(-c3ncccc3OCc3ccccc3)c(CO)s2)c1] | 216 | 544 | ¹H NMR (400 MHz, DMSO-d6) δ 10.38 (s, 1H), 10.07 (s, 1H), 8.30 (s, 1H), 8.26 (dd, J = 4.6, 1.3 Hz, 1H), 7.70-7.62 (m, 3H), 7.47-7.42 (m, 2H), 7.40 (dd, J = 8.4, 4.7 Hz, 1H), 7.37-7.25 (m, 3H), 6.95 (t, J = 1.9 Hz, 1H), 5.80 (s, 1H), 5.23 (s, 2H), 4. |
| 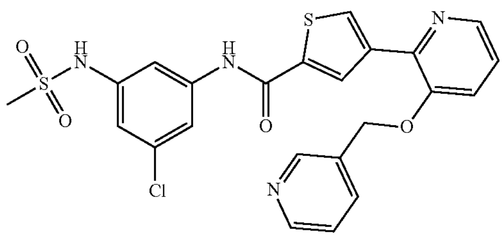 [SMILES: CS(=O)(=O)Nc1cc(Cl)cc(NC(=O)c2cc(-c3ncccc3OCc3cccnc3)cs2)c1] | 217 | 515 | ¹H NMR (400 MHz, DMSO-d6) δ 10.63 (s, 1H), 10.06 (s, 1H), 8.81 (d, J = 1.4 Hz, 1H), 8.75 (d, J = 2.2 Hz, 1H), 8.57 (dd, J = 4.8, 1.7 Hz, 1H), 8.43 (d, J = 1.3 Hz, 1H), 8.29 (dd, J = 4.6, 1.3 Hz, 1H), 7.96 (dt, J = 7.9, 2.0 Hz, 1H), 7.74 (dd, J = 8.5, 1.3 |
| 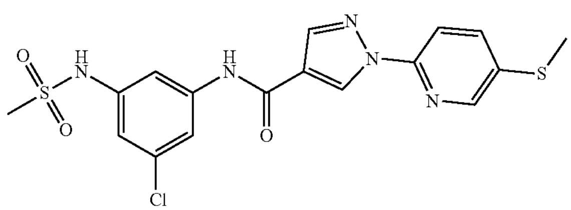 | 218 | 438 | ¹H NMR (400 MHz, DMSO-d6) δ 10.29 (s, 2H), 9.37 (s, 1H), 8.45 (d, J = 2.4 Hz, 1H), 8.29 (s, 1H), 7.99 (dd, J = 8.7, 2.4 Hz, 1H), 7.93 (d, J = 8.6 Hz, 1H), 7.70 (t, J = 1.9 Hz, 1H), 7.61 (d, J = 1.9 Hz, 1H), 6.93 (t, J = 2.0 Hz, 1H), 3.05 (s, 3H), 2.60 (s, |
| 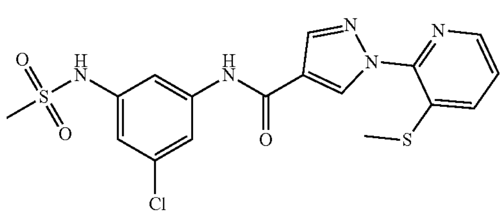 [SMILES: CSc1cccnc1-n1cc(C(=O)Nc2cc(Cl)cc(NS(C)(=O)=O)c2)cn1] | 219 | 438 | ¹H NMR (300 MHz, DMSO-d6) δ 10.33 (s, 1H), 9.17 (s, 1H), 8.41 (dd, J = 4.6, 1.5 Hz, 1H), 8.35 (s, 1H), 8.07 (dd, J = 8.1, 1.5 Hz, 1H), 7.75 (t, J = 1.9 Hz, 1H), 7.65 (t, J = 1.9 Hz, 1H), 7.61 (dd, J = 8.0, 4.6 Hz, 1H), 7.00 (t, J = 2.0 Hz, 1H), 3.11 (s, 3 |

| Structure | Example No. | MS (ESI) [M + H]+ | ¹H NMR |
|---|---|---|---|
| 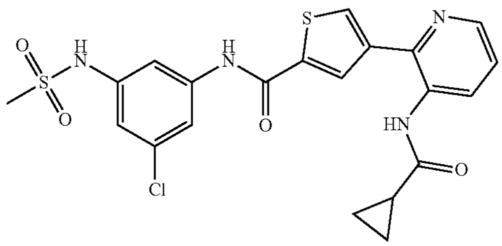 [SMILES: CS(=O)(=O)Nc1cc(Cl)cc(NC(=O)c2cc(-c3ncccc3NC(=O)C3CC3)cs2)c1] | 220 | 491 | ¹H NMR (400 MHz, DMSO-d6) δ 10.60 (s, 1H), 10.08 (s, 1H), 10.01 (s, 1H), 8.56 (d, J = 1.4 Hz, 1H), 8.49 (dd, J = 4.6, 1.6 Hz, 1H), 8.19 (d, J = 1.3 Hz, 1H), 7.90 (dd, J = 8.2, 1.6 Hz, 1H), 7.70 (t, J = 1.9 Hz, 1H), 7.65 (t, J = 1.9 Hz, 1H), 7.39 (dd, J = |
| 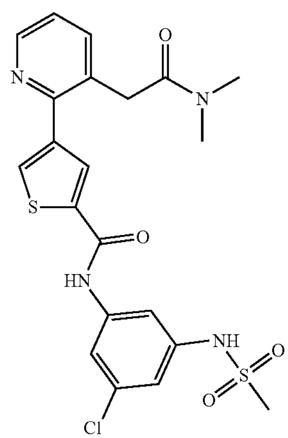 [SMILES: CN(C)C(=O)Cc1cccnc1-c1csc(C(=O)Nc2cc(Cl)cc(NS(C)(=O)=O)c2)c1] | 221 | 493 | ¹H NMR (300 MHz, DMSO-d6) δ 10.56 (s, 1H), 10.09 (s, 1H), 8.56 (dd, J = 4.7, 1.7 Hz, 1H), 8.36 (d, J = 1.4 Hz, 1H), 7.92 (d, J = 1.4 Hz, 1H), 7.74-7.63 (m, 3H), 7.37 (dd, J = 7.7, 4.7 Hz, 1H), 6.96 (t, J = 1.9 Hz, 1H), 3.88 (s, 2H), 3.08 (s, 3H), 2.99 ( |
| 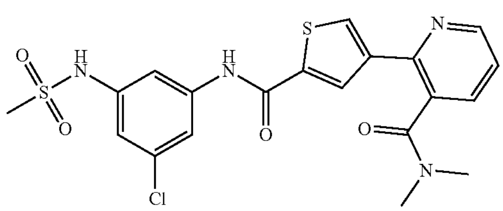 [SMILES: CN(C)C(=O)c1cccnc1-c1csc(C(=O)Nc2cc(Cl)cc(NS(C)(=O)=O)c2)c1] | 222 | 479 | ¹H NMR (300 MHz, DMSO-d6) δ 10.65 (s, 1H), 10.10 (s, 1H), 8.73 (dd, J = 4.8, 1.7 Hz, 1H), 8.56 (d, J = 1.4 Hz, 1H), 7.92 (d, J = 1.3 Hz, 1H), 7.81 (dd, J = 7.7, 1.7 Hz, 1H), 7.70 (t, J = 1.9 Hz, 1H), 7.67 (t, J = 1.9 Hz, 1H), 7.48 (dd, J = 7.7, 4.8 Hz, 1H |
| 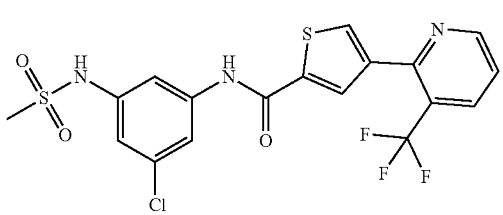 [SMILES: CS(=O)(=O)Nc1cc(Cl)cc(NC(=O)c2cc(-c3ncccc3C(F)(F)F)cs2)c1] | 223 | 476 | ¹H NMR (400 MHz, DMSO-d6) δ 10.56 (s, 1H), 10.08 (s, 1H), 8.94 (dt, J = 4.7, 1.3 Hz, 1H), 8.35 (dd, J = 8.1, 1.6 Hz, 1H), 8.32 (d, J = 1.4 Hz, 1H), 8.08 (s, 1H), 7.68 (ddd, J = 8.0, 4.4, 1.4 Hz, 2H), 7.63 (d, J = 1.9 Hz, 1H), 6.96 (t, J = 1.9 Hz, 1H), 3.0 |

-continued

| Structure | Example No. | MS (ESI) [M + H]+ | ¹H NMR |
|---|---|---|---|
| 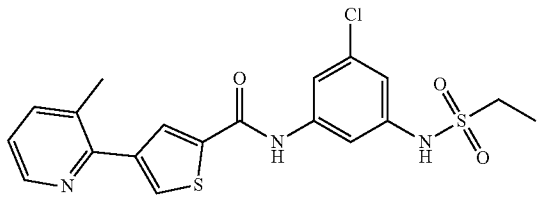 [SMILES: CCS(=O)(=O)Nc1cc(Cl)cc(NC(=O)c2cc(-c3ncccc3C)cs2)c1] | 224 | 436 | ¹H NMR (300 MHz, DMSO-d6) δ 10.57 (s, 1H), 10.13 (s, 1H), 8.51 (dd, J = 4.7, 1.6 Hz, 2H), 8.20 (d, J = 1.3 Hz, 1H), 7.81-7.72 (m, 1H), 7.68 (p, J = 1.8 Hz, 2H), 7.31 (dd, J = 7.7, 4.7 Hz, 1H), 6.97 (t, J = 1.9 Hz, 1H), 3.19 (q, J = 7.3 Hz, 2H), 2.51 (s, |
| 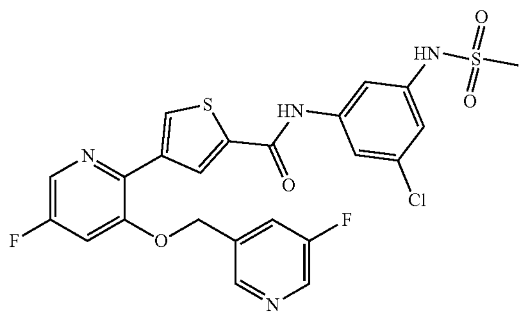 [SMILES: CS(=O)(=O)Nc1cc(Cl)cc(NC(=O)c2cc(-c3ncc(F)cc3OCc3cncc(F)c3)cs2)c1] | 225 | 551 | ¹H NMR (300 MHz, DMSO-d6) δ 10.62 (s, 1H), 10.10 (s, 1H), 8.74 (d, J = 1.3 Hz, 1H), 8.65 (d, J = 1.8 Hz, 1H), 8.61 (d, J = 2.8 Hz, 1H), 8.39 (d, J = 1.3 Hz, 1H), 8.34 (d, J = 2.2 Hz, 1H), 7.95 (dt, J = 9.6, 2.2 Hz, 1H), 7.84 (dd, J = 10.8, 2.3 Hz, 1H), 7. |
| 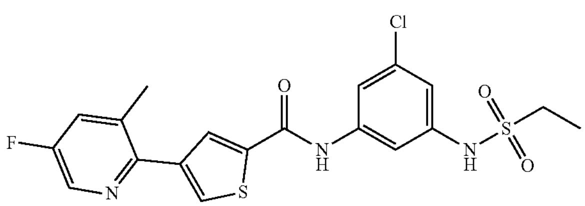 [SMILES: CCS(=O)(=O)Nc1cc(Cl)cc(NC(=O)c2cc(-c3ncc(F)cc3C)cs2)c1] | 226 | 454 | ¹H NMR (400 MHz, DMSO-d6) δ 10.55 (s, 1H), 10.11 (s, 1H), 8.51 (d, J = 2.9 Hz, 1H), 8.45 (d, J = 1.4 Hz, 1H), 8.17 (d, J = 1.4 Hz, 1H), 7.76 (dd, J = 9.7, 2.9 Hz, 1H), 7.67 (dt, J = 5.2, 1.9 Hz, 2H), 6.97 (t, J = 1.9 Hz, 1H), 3.18 (q, J = 7.3 Hz, 2H), 2.5 |
| 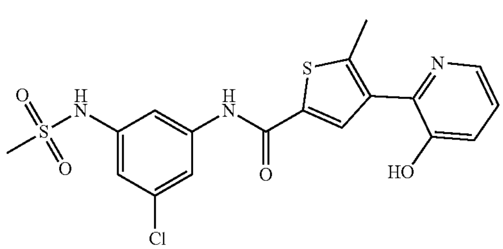 [SMILES: Cc1sc(C(=O)Nc2cc(Cl)cc(NS(C)(=O)=O)c2)cc1-c1ncccc1O] | 227 | 438 | ¹H NMR (300 MHz, DMSO-d6) δ 10.38 (s, 1H), 10.17 (s, 1H), 10.06 (s, 1H), 8.17 (s, 1H), 8.15 (dd, J = 4.6, 1.4 Hz, 1H), 7.69 (t, J = 1.9 Hz, 1H), 7.64 (t, J = 1.9 Hz, 1H), 7.36 (dd, J = 8.2, 1.5 Hz, 1H), 7.25 (dd, J = 8.2, 4.5 Hz, 1H), 6.94 (t, J = 1.9 Hz, |

| Structure | Example No. | MS (ESI) [M + H]+ | ¹H NMR |
|---|---|---|---|
| 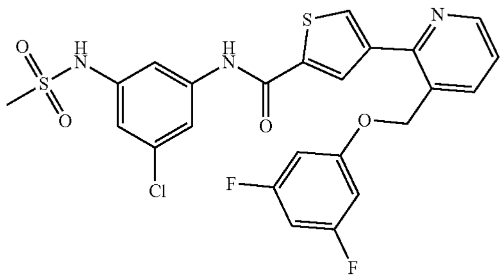 [SMILES: CS(=O)(=O)Nc1cc(Cl)cc(NC(=O)c2cc(-c3ncccc3COc3cc(F)cc(F)c3)cs2)c1] | 228 | 550 | ¹H NMR (400 MHz, DMSO-d6) δ 10.57 (s, 1H), 10.07 (s, 1H), 8.70 (d, J = 4.8 Hz, 1H), 8.50 (s, 1H), 8.11 (s, 1H), 8.08 (d, J = 7.9 Hz, 1H), 7.67 (d, J = 2.0 Hz, 2H), 7.49 (dd, J = 7.8, 4.7 Hz, 1H), 6.96 (d, J = 2.1 Hz, 1H), 6.91-6.75 (m, 3H), 5.26 (s, 2H) |
| 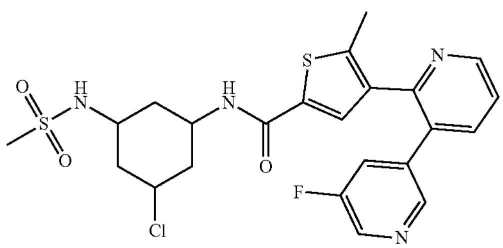 [SMILES: Cc1sc(C(=O)NC2CC(Cl)CC(NS(C)(=O)=O)C2)cc1-c1ncccc1-c1cncc(F)c1] | 229 | 517 | ¹H NMR (300 MHz, DMSO-d6) δ 10.34 (s, 1H), 10.06 (s, 1H), 8.78 (dd, J = 4.8, 1.6 Hz, 1H), 8.54 (d, J = 2.7 Hz, 1H), 8.29 (t, J = 1.7 Hz, 1H), 8.09 (dd, J = 7.8, 1.7 Hz, 1H), 7.91 (s, 1H), 7.70 (ddd, J = 9.9, 2.7, 1.7 Hz, 1H), 7.67-7.56 (m, 3H), 6.95 (t, |
| 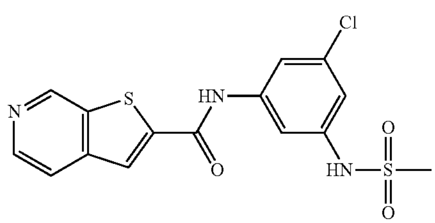 [SMILES: CS(=O)(=O)Nc1cc(Cl)cc(NC(=O)c2cc3ccncc3s2)c1] | 230 | 382 | ¹H NMR (400 MHz, DMSO-d6) δ 10.89 (s, 1H), 10.24 (s, 1H), 9.36 (s, 1H), 8.57 (d, J = 5.5 Hz, 1H), 8.42 (s, 1H), 8.00 (d, J = 5.5 Hz, 1H), 7.70 (s, 1H), 7.65 (s, 1H), 6.99 (d, J = 2.1 Hz, 1H), 3.07 (s, 3H). |
| 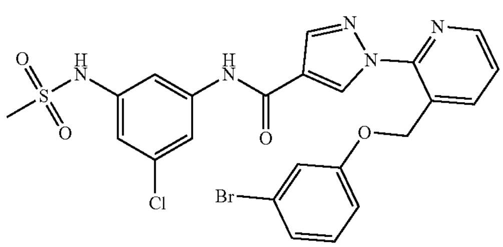 [SMILES: CS(=O)(=O)Nc1cc(Cl)cc(NC(=O)c2cnn(-c3ncccc3COc3cccc(Br)c3)c2)c1] | 231 | 576 | ¹H NMR (300 MHz, DMSO-d6) δ 10.22 (s, 1H), 10.08 (s, 1H), 8.94 (s, 1H), 8.31 (s, 1H), 8.20 (dd, J = 4.7, 1.3 Hz, 1H), 7.86 (dd, J = 8.4, 1.3 Hz, 1H), 7.71 (t, J = 1.9 Hz, 1H), 7.69 (d, J = 1.8 Hz, 1H), 7.62 (t, J = 1.9 Hz, 1H), 7.58 (dd, J = 8.3, 4.6 Hz, |

-continued

| Structure | Example No. | MS (ESI) [M + H]+ | ¹H NMR |
|---|---|---|---|
| | 232 | 436 | ¹H NMR (400 MHz, DMSO-d6) δ 10.44 (s, 1H), 10.08 (s, 1H), 8.75-8.63 (m, 1H), 8.36 (s, 1H), 7.93 (td, J = 7.7, 1.8 Hz, 1H), 7.71-7.65 (m, 2H), 7.64 (t, J = 1.9 Hz, 1H), 7.37 (ddd, J = 7.5, 4.8, 1.1 Hz, 1H), 6.95 (t, J = 1.9 Hz, 1H), 3.18 (q, J = 7.4 Hz |
| 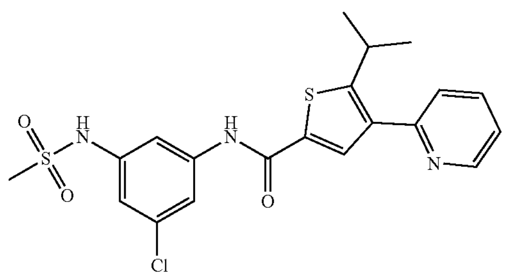 [SMILES: CC(C)c1sc(C(=O)Nc2cc(Cl)cc(NS(C)(=O)=O)c2)cc1-c1ccccn1] | 233 | 450 | ¹H NMR (400 MHz, DMSO-d6) δ 10.41 (s, 1H), 10.08 (s, 1H), 8.79-8.50 (m, 1H), 8.27 (s, 1H), 7.93 (td, J = 7.7, 1.9 Hz, 1H), 7.74-7.50 (m, 3H), 7.45-7.26 (m, 1H), 6.95 (t, J = 2.0 Hz, 1H), 3.99 (p, J = 6.7 Hz, 1H), 3.07 (s, 3H), 1.31 (d, J = 6.8 Hz, 6 |
| 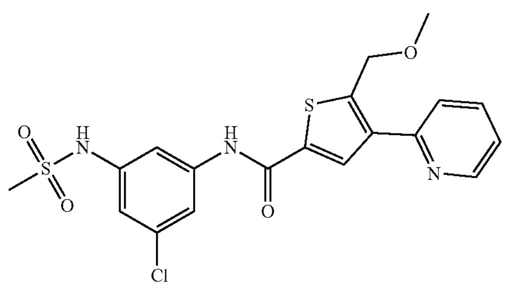 [SMILES: COCc1sc(C(=O)Nc2cc(Cl)cc(NS(C)(=O)=O)c2)cc1-c1ccccn1] | 234 | 452 | ¹H NMR (400 MHz, DMSO-d6) δ 10.46 (s, 1H), 10.06 (s, 1H), 8.68 (d, J = 4.7 Hz, 1H), 8.48 (s, 1H), 7.95 (t, J = 7.8 Hz, 1H), 7.77-7.58 (m, 3H), 7.37 (dd, J = 7.5, 4.8 Hz, 1H), 6.97 (d, J = 2.3 Hz, 1H), 4.98 (s, 2H), 3.44 (s, 3H), 3.07 (s, 3H). |
| 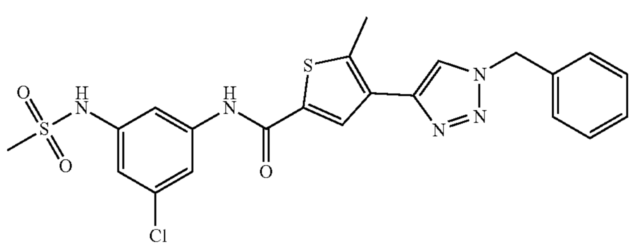 [SMILES: Cc1sc(C(=O)Nc2cc(Cl)cc(NS(C)(=O)=O)c2)cc1-c1cn(Cc2ccccc2)nn1] | 235 | 502 | ¹H NMR (400 MHz, DMSO-d6) δ 10.48 (s, 1H), 10.06 (s, 1H), 8.52 (s, 1H), 8.41 (s, 1H), 7.65 (d, J = 12.3 Hz, 2H), 7.46-7.25 (m, 5H), 6.94 (d, J = 2.1 Hz, 1H), 5.69 (s, 2H), 3.06 (s, 3H), 2.63 (s, 3H). |

-continued
| Structure | Example No. | MS (ESI) [M + H]+ | ¹H NMR |
|---|---|---|---|
| 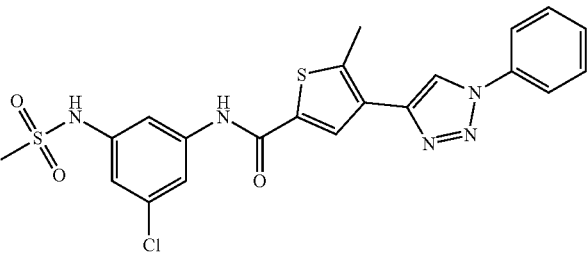 [SMILES: Cc1sc(C(=O)Nc2cc(Cl)cc(NS(C)(=O)=O)c2)cc1-c1cn(-c2ccccc2)nn1] | 236 | 488 | ¹H NMR (400 MHz, DMSO-d6) δ 10.56 (s, 1H), 10.10 (s, 1H), 9.08 (s, 1H), 8.51 (s, 1H), 8.16-7.93 (m, 2H), 7.75-7.59 (m, 4H), 7.57-7.48 (m, 1H), 6.96 (t, J = 2.0 Hz, 1H), 3.08 (s, 3H), 2.71 (s, 3H). |
| 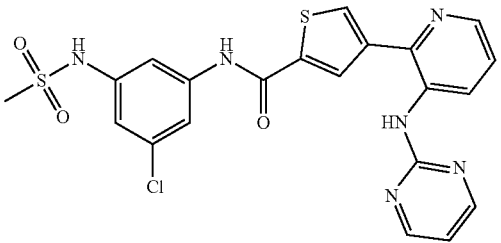 [SMILES: CS(=O)(=O)Nc1cc(Cl)cc(NC(=O)c2cc(-c3ncccc3Nc3ncccn3)cs2)c1] | 237 | 501 | ¹H NMR (300 MHz, DMSO-d6) δ 10.59 (s, 1H), 10.08 (s, 1H), 9.19 (s, 1H), 8.59 (d, J = 1.4 Hz, 1H), 8.49 (dd, J = 4.6, 1.6 Hz, 1H), 8.35 (d, J = 4.8 Hz, 2H), 8.15 (d, J = 1.3 Hz, 1H), 7.98 (dd, J = 8.2, 1.6 Hz, 1H), 7.68 (dt, J = 9.1, 1.9 Hz, 2H), 7.41 (dd, |
| 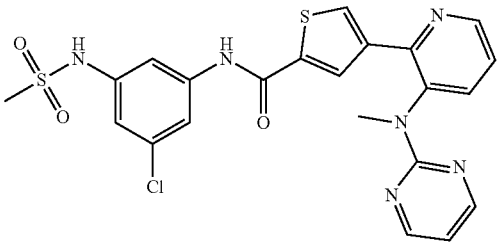 [SMILES: CN(c1ncccn1)c1cccnc1-c1csc(C(=O)Nc2cc(Cl)cc(NS(C)(=O)=O)c2)c1] | 238 | 515 | ¹H NMR (300 MHz, DMSO-d6) δ 10.60 (s, 1H), 10.10 (s, 1H), 8.67-8.52 (m, 2H), 8.33 (s, 2H), 7.86 (dd, J = 8.0, 1.6 Hz, 1H), 7.79 (d, J = 1.3 Hz, 1H), 7.67 (dt, J = 5.0, 1.9 Hz, 2H), 7.49 (dd, J = 8.0, 4.6 Hz, 1H), 6.96 (t, J = 2.0 Hz, 1H), 6.72 (t, J = 4 |
| 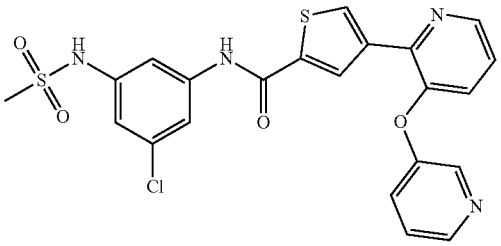 [SMILES: CS(=O)(=O)Nc1cc(Cl)cc(NC(=O)c2cc(-c3ncccc3Oc3cccnc3)cs2)c1] | 239 | 501 | ¹H NMR (300 MHz, DMSO-d6) δ 10.67 (s, 1H), 10.09 (s, 1H), 8.82 (s, 1H), 8.49 (t, J = 16.8 Hz, 4H), 7.70 (s, 2H), 7.49 (d, J = 23.5 Hz, 4H), 6.97 (s, 1H), 3.08 (s, 3H). |

-continued

| Structure | Example No. | MS (ESI) [M + H]+ | ¹H NMR |
|---|---|---|---|
| 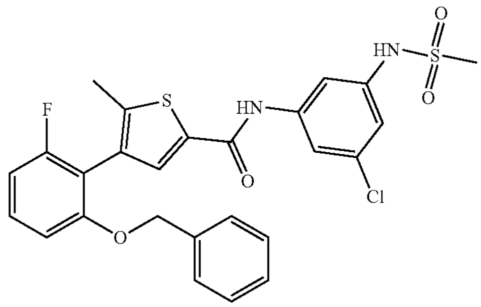 [SMILES: Cc1sc(C(=O)Nc2cc(Cl)cc(NS(C)(=O)=O)c2)cc1-c1c(F)cccc1OCc1ccccc1] | 240 | 545 | ¹H NMR (300 MHz, Methanol-d4) δ 7.81 (s, 1H), 7.65 (t, J = 1.9 Hz, 1H), 7.54 (t, J = 1.9 Hz, 1H), 7.44-7.34 (m, 1H), 7.28 (d, J = 4.0 Hz, 5H), 7.06-7.00 (m, 2H), 6.87 (t, J = 8.6 Hz, 1H), 5.13 (s, 2H), 3.05 (s, 3H), 2.32 (s, 3H). |
| 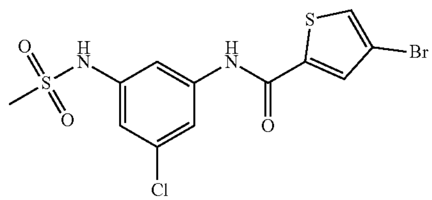 [SMILES: CS(=O)(=O)Nc1cc(Cl)cc(NC(=O)c2cc(Br)cs2)c1] | 241 | 407 | ¹H NMR (400 MHz, DMSO-d6) δ 10.50 (s, 1H), 10.12 (s, 1H), 8.10 (d, J = 1.4 Hz, 1H), 8.05 (d, J = 1.4 Hz, 1H), 7.67 (t, J = 1.9 Hz, 1H), 7.59 (t, J = 1.9 Hz, 1H), 6.97 (t, J = 2.0 Hz, 1H), 3.07 (s, 3H). |
| 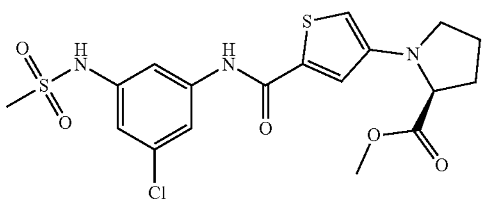 [SMILES: COC(=O)[C@@H]1CCCN1c1csc(C(=O)Nc2cc(Cl)cc(NS(C)(=O)=O)c2)c1] | 242 | 458 | ¹H NMR (300 MHz, DMSO-d6) δ 10.31 (s, 1H), 10.08 (s, 1H), 7.64-7.57 (m, 2H), 7.55 (d, J = 1.7 Hz, 1H), 6.95 (t, J = 2.0 Hz, 1H), 6.27 (d, J = 1.7 Hz, 1H), 4.22 (dd, J = 9.0, 2.4 Hz, 1H), 3.66 (s, 3H), 3.53-3.42 (m, 1H), 3.27 (d, J = 7.7 Hz, 1H), 3.06 |
| 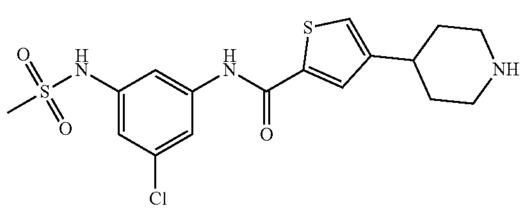 [SMILES: CS(=O)(=O)Nc1cc(Cl)cc(NC(=O)c2cc(C3CCNCC3)cs2)c1] | 243 | 414 | ¹H NMR (400 MHz, DMSO-d6) δ 10.22 (s, 1H), 7.98 (s, 1H), 7.51 (dd, J = 5.0, 3.0 Hz, 2H), 7.44 (d, J = 2.0 Hz, 1H), 6.85 (t, J = 2.0 Hz, 1H), 3.07 (d, J = 12.1 Hz, 2H), 2.93 (s, 3H), 2.66 (q, J = 12.6, 11.9 Hz, 3H), 1.87 (d, J = 12.8 Hz, 2H), 1.51 (q, J = |

-continued

| Structure | Example No. | MS (ESI) [M + H]+ | ¹H NMR |
|---|---|---|---|
| 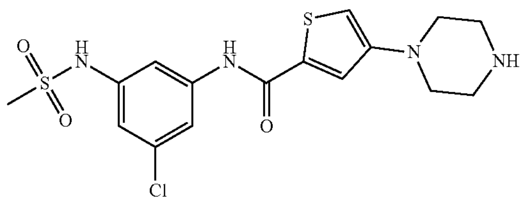 [SMILES: CS(=O)(=O)Nc1cc(Cl)cc(NC(=O)c2cc(N3CCNCC3)cs2)c1] | 244 | 415 | ¹H NMR (400 MHz, Methanol-d4) δ 8.49 (s, 1H), 7.77 (d, J = 1.8 Hz, 1H), 7.64 (t, J = 1.9 Hz, 1H), 7.56 (t, J = 1.9 Hz, 1H), 7.01 (t, J = 1.9 Hz, 1H), 6.81 (d, J = 1.7 Hz, 1H), 3.34 (dd, J = 6.5, 3.5 Hz, 8H), 3.03 (s, 3H). |
| 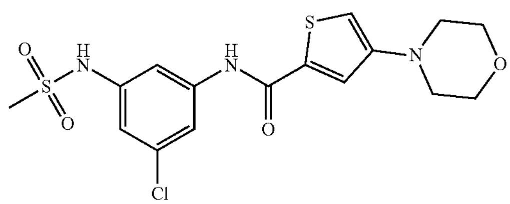 [SMILES: CS(=O)(=O)Nc1cc(Cl)cc(NC(=O)c2cc(N3CCOCC3)cs2)c1] | 245 | 416 | ¹H NMR (400 MHz, DMSO-d6) δ 10.28 (s, 1H), 10.07 (s, 1H), 7.88 (d, J = 1.7 Hz, 1H), 7.62 (dt, J = 15.9, 2.0 Hz, 2H), 6.95 (t, J = 2.0 Hz, 1H), 6.77 (d, J = 1.7 Hz, 1H), 3.82-3.64 (m, 4H), 3.06 (d, J = 7.9 Hz, 7H). |
| 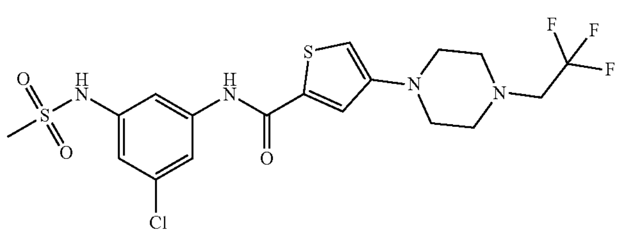 [SMILES: CS(=O)(=O)Nc1cc(Cl)cc(NC(=O)c2cc(N3CCN(CC(F)(F)F)CC3)cs2)c1] | 246 | 497 | ¹H NMR (400 MHz, DMSO-d6) δ 10.26 (s, 1H), 10.06 (s, 1H), 7.87 (d, J = 1.7 Hz, 1H), 7.61 (dt, J = 16.3, 2.0 Hz, 2H), 6.94 (t, J = 2.0 Hz, 1H), 6.73 (d, J = 1.6 Hz, 1H), 3.25 (q, J = 10.3 Hz, 2H), 3.08 (d, J = 13.9 Hz, 7H), 2.77 (t, J = 5.0 Hz, 4H). |
| 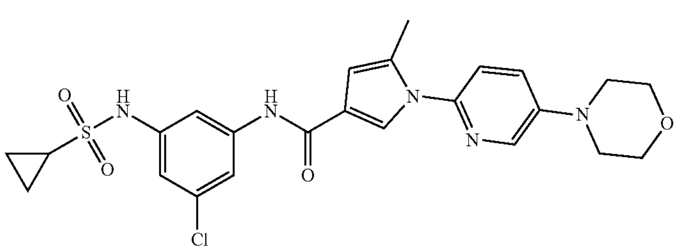 [SMILES: Cc1cc(C(=O)Nc2cc(Cl)cc(NS(=O)(=O)C3CC3)c2)cn1-c1ccc(N2CCOCC2)cn1] | 247 | 516 | ¹H NMR (400 MHz, DMSO-d6) δ 9.97 (s, 1H), 9.79 (s, 1H), 8.25 (d, J = 3.0 Hz, 1H), 7.83 (d, J = 2.1 Hz, 1H), 7.69 (q, J = 2.0 Hz, 2H), 7.55 (dd, J = 9.0, 3.1 Hz, 1H), 7.45 (d, J = 8.8 Hz, 1H), 6.90 (t, J = 2.0 Hz, 1H), 6.53 (t, J = 1.5 Hz, 1H), 3.77 (dd, J |

-continued

| Structure | Example No. | MS (ESI) [M + H]+ | ¹H NMR |
|---|---|---|---|
| 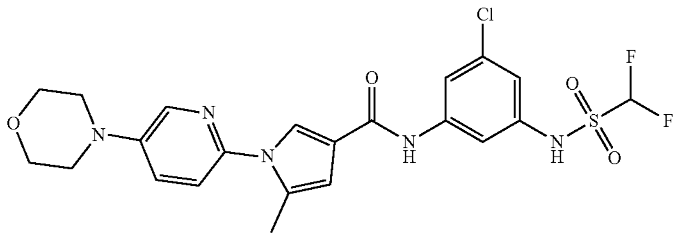 [SMILES: Cc1cc(C(=O)Nc2cc(Cl)cc(NS(=O)(=O)C(F)F)c2)cn1-c1ccc(N2CCOCC2)cn1] | 248 | 526 | ¹H NMR (400 MHz, DMSO-d6) δ 11.21 (s, 1H), 9.83 (s, 1H), 8.25 (d, J = 3.0 Hz, 1H), 7.83 (d, J = 2.0 Hz, 1H), 7.77 (s, 1H), 7.68 (s, 1H), 7.55 (dd, J = 8.9, 3.0 Hz, 1H), 7.45 (d, J = 8.8 Hz, 1H), 7.15 (t, J = 52.4 Hz, 1H), 6.92 (d, J = 2.0 Hz, 1H), 6.53 (d |
| 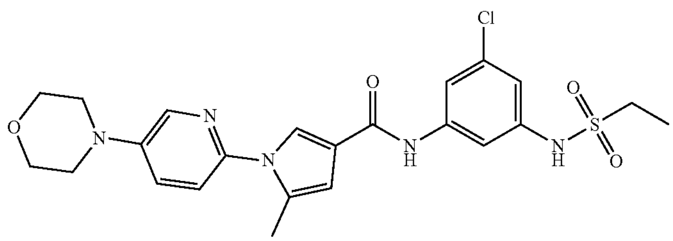 [SMILES: CCS(=O)(=O)Nc1cc(Cl)cc(NC(=O)c2cc(C)n(-c3ccc(N4CCOCC4)cn3)c2)c1] | 249 | 504 | ¹H NMR (400 MHz, DMSO-d6) δ 10.04 (s, 1H), 9.79 (s, 1H), 8.25 (d, J = 3.0 Hz, 1H), 7.83 (d, J = 2.0 Hz, 1H), 7.69 (t, J = 1.9 Hz, 1H), 7.62 (t, J = 1.9 Hz, 1H), 7.55 (dd, J = 8.9, 3.1 Hz, 1H), 7.45 (d, J = 8.8 Hz, 1H), 6.89 (t, J = 2.0 Hz, 1H), 6.53 (dd, |
| 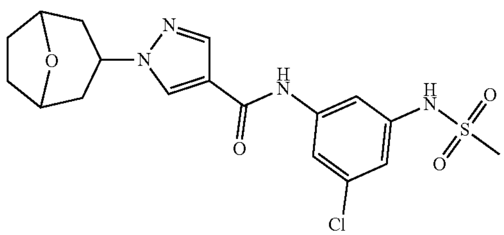 [SMILES: CS(=O)(=O)Nc1cc(Cl)cc(NC(=O)c2cnn(C3CC4CCC(C3)O4)c2)c1] | 250 | 425 | ¹H NMR (400 MHz, Methanol-d4) δ 8.30 (s, 1H), 8.04 (s, 1H), 7.62 (t, J = 1.9 Hz, 1H), 7.54 (t, J = 1.8 Hz, 1H), 6.99 (t, J = 1.9 Hz, 1H), 4.72 (dq, J = 11.6, 6.0 Hz, 1H), 4.53 (s, 2H), 3.02 (s, 3H), 2.18 (td, J = 12.3, 3.4 Hz, 2H), 2.02 (dd, J = 12.2, 5.4 |
| 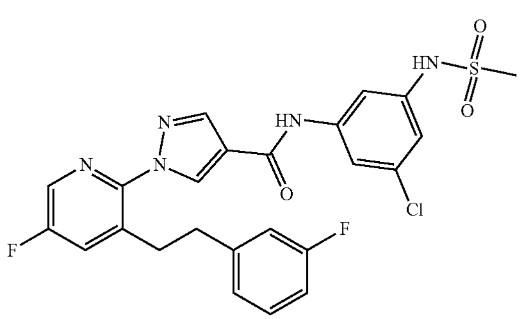 | 251 | 532 | ¹H NMR (300 MHz, DMSO-d6) δ 10.26 (s, 1H), 10.09 (s, 1H), 8.90 (s, 1H), 8.49 (s, 1H), 8.34 (s, 1H), 8.07-7.90 (m, 1H), 7.68 (d, J = 30.3 Hz, 2H), 7.43-7.14 (m, 1H), 6.98 (d, J = 12.0 Hz, 4H), 3.17 (t, J = 7.7 Hz, 2H), 3.08 (s, 3H), 2.86 (d, J = 8.3 Hz |

-continued

| Structure | Example No. | MS (ESI) [M + H]+ | ¹H NMR |
|---|---|---|---|
| 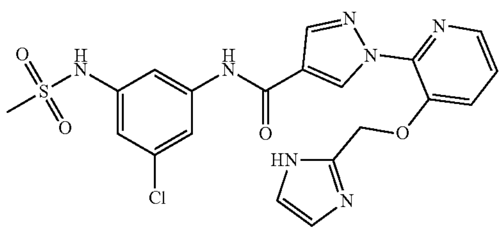 [SMILES: CS(=O)(=O)Nc1cc(Cl)cc(NC(=O)c2cnn(-c3ncccc3OCc3ncc[nH]3)c2)c1] | 252 | 488 | ¹H NMR (400 MHz, DMSO-d6) δ 12.33 (s, 1H), 10.20 (d, J = 4.7 Hz, 1H), 8.89 (d, J = 2.6 Hz, 1H), 8.31-8.12 (m, 3H), 8.05 (dd, J = 8.4, 1.4 Hz, 1H), 7.69 (d, J = 2.1 Hz, 1H), 7.62-7.46 (m, 2H), 6.93 (t, J = 2.0 Hz, 3H), 5.26 (s, 2H), 3.06 (s, 3H). |
| 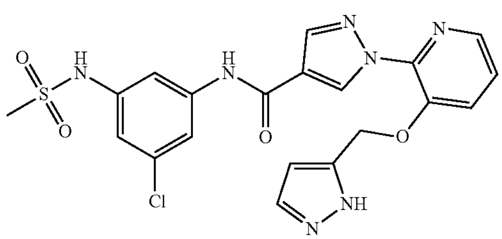 [SMILES: CS(=O)(=O)Nc1cc(Cl)cc(NC(=O)c2cnn(-c3ncccc3OCc3ccn[nH]3)c2)c1] | 253 | 488 | ¹H NMR (400 MHz, DMSO-d6) δ 12.86 (s, 1H), 10.16 (s, 1H), 8.84 (s, 1H), 8.39 (s, 1H), 8.29-8.09 (m, 2H), 7.95 (d, J = 8.4 Hz, 1H), 7.76-7.47 (m, 4H), 6.90 (s, 1H), 6.32 (d, J = 2.2 Hz, 1H), 5.27 (s, 2H), 3.01 (s, 3H). |
| 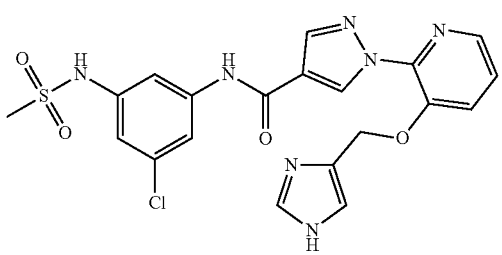 [SMILES: CS(=O)(=O)Nc1cc(Cl)cc(NC(=O)c2cnn(-c3ncccc3OCc3c[nH]cn3)c2)c1] | 254 | 488 | ¹H NMR (400 MHz, DMSO-d6) δ 12.87 (s, 1H), 10.19 (s, 1H), 10.06 (s, 1H), 8.85 (s, 1H), 8.26 (s, 1H), 8.16 (dd, J = 4.7, 1.3 Hz, 1H), 8.07-7.93 (m, 2H), 7.71 (t, J = 1.9 Hz, 1H), 7.60 (t, J = 1.9 Hz, 1H), 7.54 (dd, J = 8.3, 4.6 Hz, 1H), 7.34 (s, 1H), 6.9 |
| 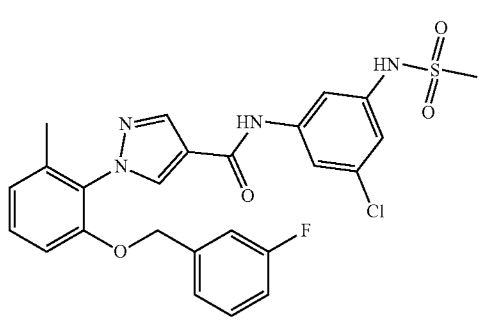 [SMILES: Cc1cccc(OCc2cccc(F)c2)c1-n1cc(C(=O)Nc2cc(Cl)cc(NS(C)(=O)=O)c2)cn1] | 255 | 529 | ¹H NMR (400 MHz, DMSO-d6) δ 10.07 (s, 2H), 8.54 (s, 1H), 8.29 (s, 1H), 7.65 (t, J = 1.9 Hz, 1H), 7.53 (t, J = 1.9 Hz, 1H), 7.45-7.26 (m, 2H), 7.15-6.97 (m, 5H), 6.90 (t, J = 1.9 Hz, 1H), 5.17 (s, 2H), 3.02 (s, 3H), 2.04 (s, 3H). |

| Structure | Example No. | MS (ESI) [M + H]+ | ¹H NMR |
|---|---|---|---|
| 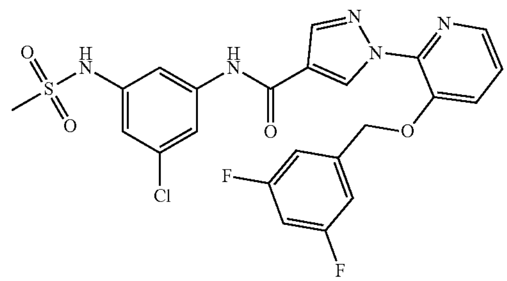 [SMILES: CS(=O)(=O)Nc1cc(Cl)cc(NC(=O)c2cnn(-c3ncccc3OCc3cc(F)cc(F)c3)c2)c1] | 256 | 534 | ¹H NMR (400 MHz, DMSO-d6) δ 10.30 (s, 1H), 10.06 (s, 1H), 9.28 (s, 1H), 8.58 (dd, J = 4.8, 1.7 Hz, 1H), 8.29 (s, 1H), 8.23-8.09 (m, 1H), 7.72 (d, J = 2.0 Hz, 1H), 7.58 (dd, J = 7.7, 4.7 Hz, 2H), 6.95 (d, J = 2.0 Hz, 1H), 6.86-6.59 (m, 3H), 5.55 (s, 2H |
| 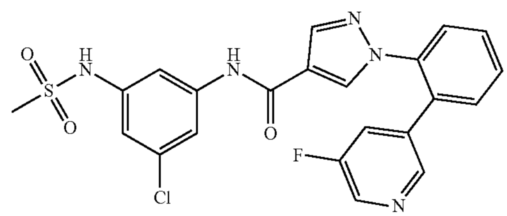 [SMILES: CS(=O)(=O)Nc1cc(Cl)cc(NC(=O)c2cnn(-c3ccccc3-c3cncc(F)c3)c2)c1] | 257 | 486 | ¹H NMR (400 MHz, DMSO-d6) δ 10.06 (d, J = 15.6 Hz, 2H), 8.51 (d, J = 2.7 Hz, 2H), 8.13 (s, 2H), 7.74-7.60 (m, 5H), 7.56-7.45 (m, 2H), 6.93 (t, J = 1.9 Hz, 1H), 3.05 (s, 3H). |
| 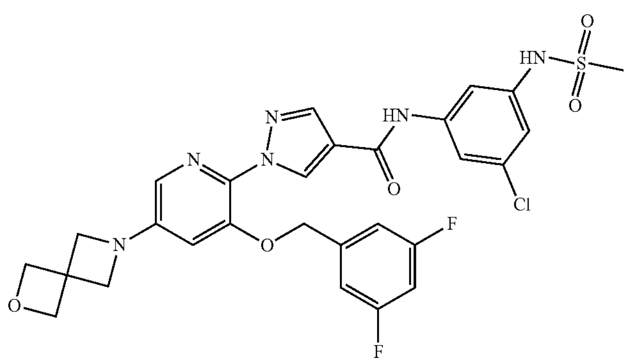 [SMILES: CS(=O)(=O)Nc1cc(Cl)cc(NC(=O)c2cnn(-c3ncc(N4CC5(COC5)C4)cc3OCc3cc(F)cc(F)c3)c2)c1] | 258 | 631 | ¹H NMR (400 MHz, DMSO-d6) δ 10.11 (d, J = 25.0 Hz, 2H), 8.70 (s, 1H), 8.23 (s, 1H), 7.69 (t, J = 1.9 Hz, 1H), 7.60 (t, J = 1.9 Hz, 1H), 7.37 (d, J = 2.3 Hz, 1H), 7.22-7.05 (m, 3H), 6.93 (t, J = 2.0 Hz, 1H), 6.77 (d, J = 2.3 Hz, 1H), 5.27 (s, 2H), 4.75 ( |
| *stereochemistry arbitrarly assigned* | 259 | 475 | ¹H NMR (400 MHz, DMSO-d6) δ 9.95 (s, 1H), 8.43 (s, 1H), 7.98 (s, 1H), 7.63 (t, J = 1.9 Hz, 1H), 7.55 (t, J = 2.0 Hz, 1H), 7.29-7.16 (m, 2H), 6.97-6.86 (m, 2H), 6.86-6.65 (m, 2H), 5.01-4.74 (m, 2H), 3.04 (s, 3H), 2.39-2.19 (m, 2H), 2.19-2.10 (m |

-continued

| Structure | Example No. | MS (ESI) [M + H]+ | ¹H NMR |
|---|---|---|---|
| *stereochemistry arbitrarly assigned* | 260 | 459 | ¹H NMR (300 MHz, DMSO-d6) δ 10.01 (s, 1H), 9.82 (s, 1H), 7.90 (s, 2H), 7.60 (t, J = 1.8 Hz, 1H), 7.53 (t, J = 1.9 Hz, 1H), 7.16-7.03 (m, 3H), 7.03-6.82 (m, 3H), 5.02 (td, J = 7.2, 3.0 Hz, 1H), 3.50-3.40 (m, 1H), 3.04 (s, 3H), 2.44-2.03 (m, 4H), 1. |
| 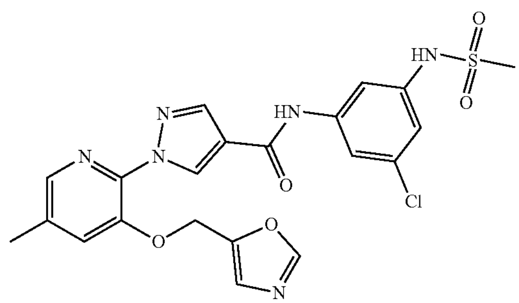 | 261 | 503 | ¹H NMR (400 MHz, Methanol-d4) δ 8.74 (s, 1H), 8.27 (s, 1H), 8.21 (s, 1H), 8.04 (d, J = 1.8 Hz, 1H), 7.80-7.75 (m, 1H), 7.64 (t, J = 1.9 Hz, 1H), 7.57 (t, J = 1.9 Hz, 1H), 7.27 (s, 1H), 7.01 (t, J = 1.9 Hz, 1H), 5.35 (s, 2H), 3.03 (s, 3H), 2.46 (s, 3H). |
| 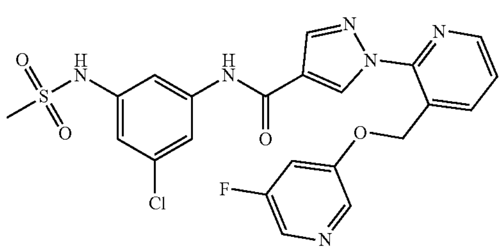 [SMILES: CS(=O)(=O)Nc1cc(Cl)cc(NC(=O)c2cnn(-c3ncccc3COc3cncc(F)c3)c2)c1] | 262 | 517 | ¹H NMR (300 MHz, DMSO-d6) δ 10.30 (s, 2H), 9.30 (d, J = 0.8 Hz, 1H), 8.59 (dd, J = 4.8, 1.7 Hz, 1H), 8.34-8.14 (m, 4H), 7.71 (t, J = 1.9 Hz, 1H), 7.64-7.55 (m, 2H), 7.50 (dt, J = 11.0, 2.4 Hz, 1H), 6.94 (t, J = 1.9 Hz, 1H), 5.63 (s, 2H), 3.07 (s, 3H). |
| 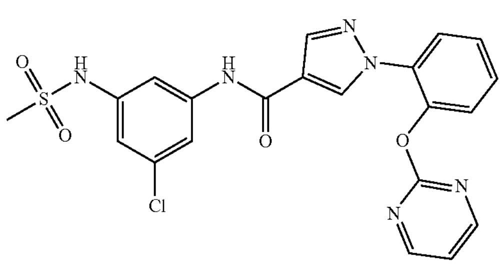 [SMILES: CS(=O)(=O)Nc1cc(Cl)cc(NC(=O)c2cnn(-c3ccccc3Oc3ncccn3)c2)c1] | 263 | 485 | ¹H NMR (400 MHz, DMSO-d6) δ 10.09 (d, J = 17.8 Hz, 2H), 8.68 (s, 1H), 8.59 (d, J = 4.8 Hz, 2H), 8.14 (s, 1H), 7.79 (dd, J = 8.2, 1.7 Hz, 1H), 7.65 (t, J = 1.9 Hz, 1H), 7.60-7.54 (m, 2H), 7.48 (ddd, J = 8.7, 3.7, 2.0 Hz, 2H), 7.24 (t, J = 4.8 Hz, 1H), 6. |

| Structure | Example No. | MS (ESI) [M + H]+ | ¹H NMR |
|---|---|---|---|
| 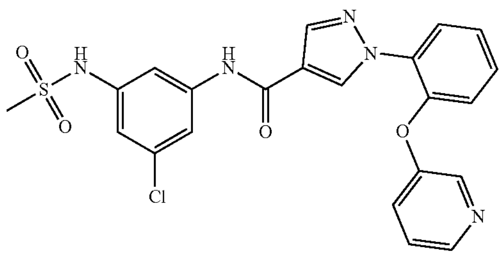 [SMILES: CS(=O)(=O)Nc1cc(Cl)cc(NC(=O)c2cnn(-c3ccccc3Oc3cccnc3)c2)c1] | 264 | 484 | ¹H NMR (300 MHz, DMSO-d6) δ 10.17 (s, 1H), 10.06 (s, 1H), 8.83 (s, 1H), 8.57-8.34 (m, 2H), 8.26 (s, 1H), 7.83 (dd, J = 7.9, 1.8 Hz, 1H), 7.67 (t, J = 1.8 Hz, 1H), 7.62-7.33 (m, 5H), 7.24 (dd, J = 8.2, 1.4 Hz, 1H), 6.94 (t, J = 2.0 Hz, 1H), 3.06 (s, 3H |
| 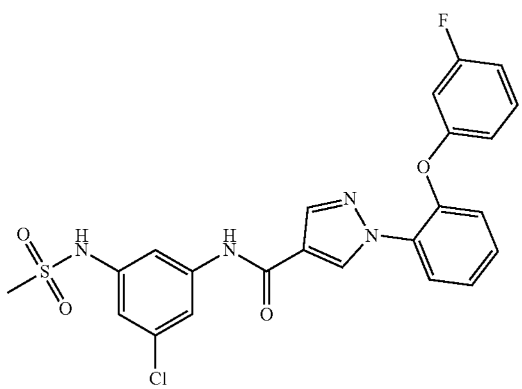 [SMILES: CS(=O)(=O)Nc1cc(Cl)cc(NC(=O)c2cnn(-c3ccccc3Oc3cccc(F)c3)c2)c1] | 265 | 501 | ¹H NMR (300 MHz, DMSO-d6) δ 10.17 (s, 1H), 10.06 (s, 1H), 8.80 (s, 1H), 8.27 (s, 1H), 7.94-7.74 (m, 1H), 7.67 (s, 1H), 7.62-7.35 (m, 4H), 7.22 (d, J = 8.1 Hz, 1H), 7.09-6.76 (m, 4H), 3.06 (s, 3H). |
| 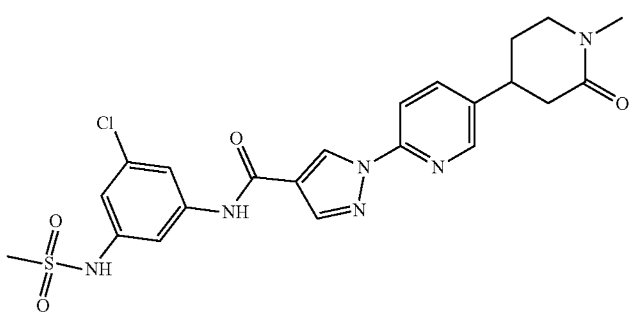 [SMILES: CN1CCC(c2ccc(-n3cc(C(=O)Nc4cc(Cl)cc(NS(C)(=O)=O)c4)cn3)nc2)CC1=O] | 266 | 503 | ¹H NMR (400 MHz, DMSO-d6) δ 10.28 (s, 1H), 9.39 (s, 1H), 8.49 (d, J = 2.3 Hz, 1H), 8.29 (s, 1H), 8.09-7.87 (m, 2H), 7.69 (t, J = 1.9 Hz, 1H), 7.59 (t, J = 1.9 Hz, 1H), 6.92 (t, J = 1.9 Hz, 1H), 3.48-3.37 (m, 1H), 3.31-3.17 (m, 2H), 3.04 (s, 3H), 2.8 |
| 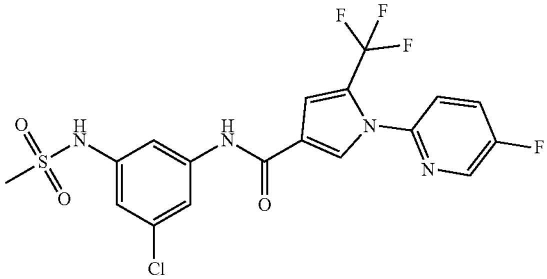 [SMILES: CS(=O)(=O)Nc1cc(Cl)cc(NC(=O)c2cc(C(F)(F)F)n(-c3ccc(F)cn3)c2)c1] | 267 | 477 | ¹H NMR (300 MHz, DMSO-d6) δ 10.13 (s, 1H), 10.07 (s, 1H), 8.65 (d, J = 3.0 Hz, 1H), 8.20 (d, J = 2.0 Hz, 1H), 8.15-8.02 (m, 1H), 7.83 (dd, J = 8.9, 3.8 Hz, 1H), 7.72 (t, J = 1.9 Hz, 1H), 7.62 (t, J = 1.9 Hz, 1H), 7.53 (s, 1H), 6.94 (t, J = 2.0 Hz, 1H), |

-continued

| Structure | Example No. | MS (ESI) [M + H]+ | 1H NMR |
|---|---|---|---|
| 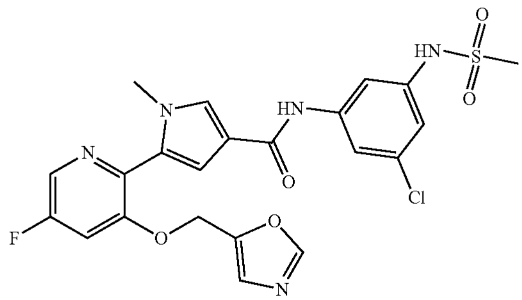 [SMILES: Cn1cc(C(=O)Nc2cc(Cl)cc(NS(C)(=O)=O)c2)cc1-c1ncc(F)cc1OCc1cnco1] | 268 | 520 | 1H NMR (400 MHz, DMSO-d6) δ 10.04 (s, 1H), 9.81 (s, 1H), 8.44 (s, 1H), 8.29 (d, J = 2.3 Hz, 1H), 7.85 (dd, J = 10.9, 2.4 Hz, 1H), 7.74-7.65 (m, 2H), 7.59 (t, J = 1.9 Hz, 1H), 7.40 (s, 1H), 6.99 (d, J = 2.0 Hz, 1H), 6.88 (t, J = 2.0 Hz, 1H), 5.39 (s, 2H) |
| 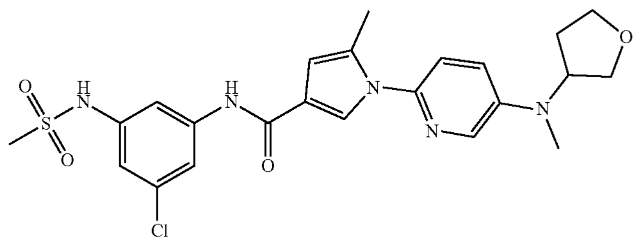 [SMILES: Cc1cc(C(=O)Nc2cc(Cl)cc(NS(C)(=O)=O)c2)cn1-c1ccc(N(C)C2CCOC2)cn1] | 269 | 504 | 1H NMR (400 MHz, DMSO-d6) δ 9.99 (s, 1H), 9.78 (s, 1H), 8.14 (d, J = 2.9 Hz, 1H), 7.79 (d, J = 2.0 Hz, 1H), 7.71 (t, J = 1.9 Hz, 1H), 7.63 (t, J = 1.9 Hz, 1H), 7.45-7.28 (m, 2H), 6.88 (t, J = 1.9 Hz, 1H), 6.52 (dd, J = 2.0, 1.1 Hz, 1H), 4.65 (dq, J = 8. |
| 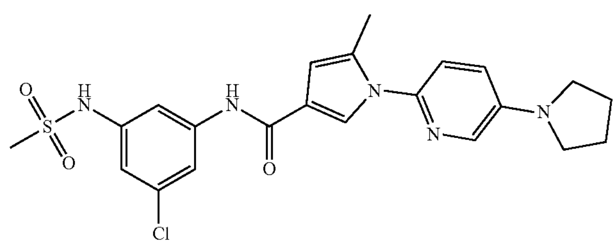 [SMILES: Cc1cc(C(=O)Nc2cc(Cl)cc(NS(C)(=O)=O)c2)cn1-c1ccc(N2CCCC2)cn1] | 270 | 474 | 1H NMR (400 MHz, DMSO-d6) δ 10.01 (s, 1H), 9.78 (s, 1H), 7.85 (d, J = 3.0 Hz, 1H), 7.76 (d, J = 2.0 Hz, 1H), 7.71 (t, J = 1.9 Hz, 1H), 7.62 (t, J = 1.8 Hz, 1H), 7.36 (d, J = 8.7 Hz, 1H), 7.09 (dd, J = 8.8, 3.1 Hz, 1H), 6.88 (t, J = 2.0 Hz, 1H), 6.50 (dd, |
| 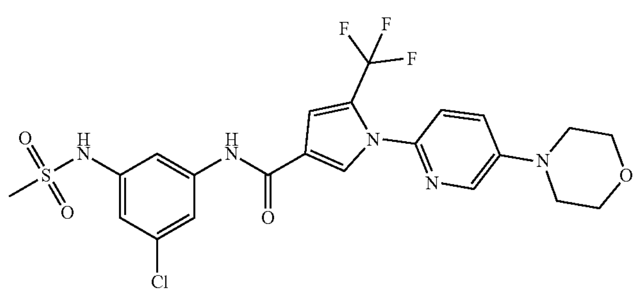 [SMILES: CS(=O)(=O)Nc1cc(Cl)cc(NC(=O)c2cc(C(F)(F)F)n(-c3ccc(N4CCOCC4)cn3)c2)c1] | 271 | 544 | 1H NMR (400 MHz, DMSO-d6) δ 10.07 (d, J = 10.3 Hz, 2H), 8.26 (d, J = 2.9 Hz, 1H), 8.07 (d, J = 2.0 Hz, 1H), 7.71 (d, J = 2.0 Hz, 1H), 7.63-7.52 (m, 2H), 7.50 (d, J = 8.8 Hz, 1H), 7.44 (d, J = 1.8 Hz, 1H), 6.93 (t, J = 2.0 Hz, 1H), 3.77 (t, J = 4.9 Hz, 4 |

-continued

| Structure | Example No. | MS (ESI) [M + H]+ | 1H NMR |
|---|---|---|---|
| 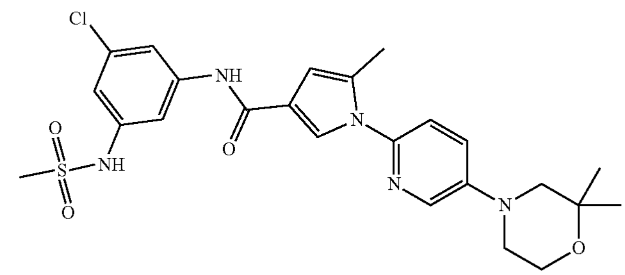 | 272 | 518 | 1H NMR (400 MHz, DMSO-d6) δ 10.00 (s, 1H), 9.81 (s, 1H), 8.23 (d, J = 3.0 Hz, 1H), 7.81 (d, J = 2.0 Hz, 1H), 7.71 (s, 1H), 7.63 (s, 1H), 7.54 (dd, J = 8.9, 2.9 Hz, 1H), 7.43 (d, J = 8.8 Hz, 1H), 6.89 (s, 1H), 6.53 (s, 1H), 3.82-3.67 (m, 2H), 3.25-3.16 |
| 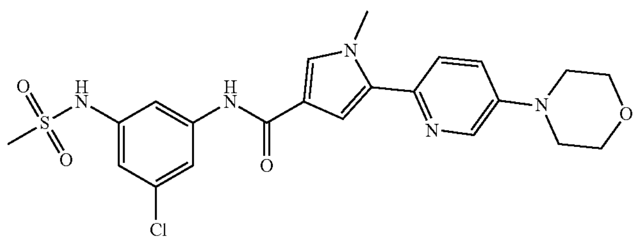 [SMILES: Cn1cc(C(=O)Nc2cc(Cl)cc(NS(C)(=O)=O)c2)cc1-c1ccc(N2CCOCC2)cn1] | 273 | 490 | 1H NMR (300 MHz, DMSO-d6) δ 10.02 (s, 1H), 9.80 (s, 1H), 8.33 (d, J = 2.9 Hz, 1H), 7.73 (t, J = 1.8 Hz, 1H), 7.65-7.60 (m, 2H), 7.56 (d, J = 8.8 Hz, 1H), 7.43 (dd, J = 8.9, 3.0 Hz, 1H), 7.04 (d, J = 2.0 Hz, 1H), 6.89 (t, J = 1.9 Hz, 1H), 3.93 (s, 3H), 3 |
| 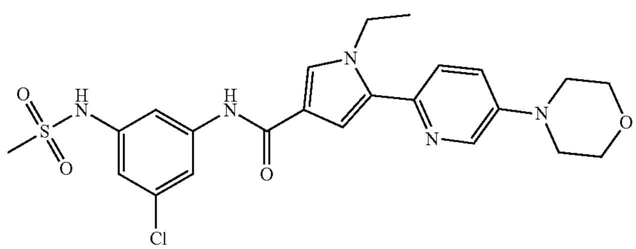 [SMILES: CCn1cc(C(=O)Nc2cc(Cl)cc(NS(C)(=O)=O)c2)cc1-c1ccc(N2CCOCC2)cn1] | 274 | 504 | 1H NMR (300 MHz, DMSO-d6) δ 10.04 (s, 1H), 9.79 (s, 1H), 8.32 (d, J = 2.8 Hz, 1H), 7.72 (t, J = 1.9 Hz, 1H), 7.67 (d, J = 2.0 Hz, 1H), 7.63 (t, J = 1.9 Hz, 1H), 7.55 (d, J = 8.8 Hz, 1H), 7.43 (dd, J = 8.9, 2.9 Hz, 1H), 7.02 (d, J = 2.0 Hz, 1H), 6.89 (t, J |
| 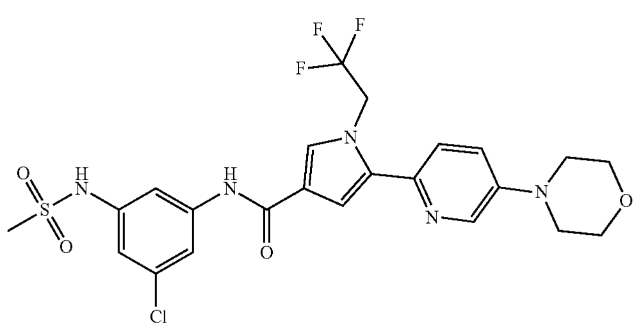 [SMILES: CS(=O)(=O)Nc1cc(Cl)cc(NC(=O)c2cc(-c3ccc(N4CCOCC4)cn3)n(CC(F)(F)F)c2)c1] | 275 | 558 | 1H NMR (300 MHz, DMSO-d6) δ 10.04 (s, 1H), 9.94 (s, 1H), 8.30 (s, 1H), 7.76-7.67 (m, 2H), 7.62 (d, J = 7.7 Hz, 2H), 7.49-7.33 (m, 1H), 7.17 (s, 1H), 6.91 (s, 1H), 5.73 (d, J = 9.4 Hz, 2H), 3.76 (d, J = 5.6 Hz, 4H), 3.25 (d, J = 5.0 Hz, 4H), 3.07 (s, 3 |

-continued

| Structure | Example No. | MS (ESI) [M + H]+ | ¹H NMR |
|---|---|---|---|
| 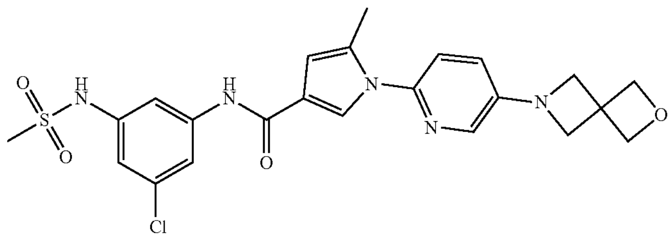 [SMILES: Cc1cc(C(=O)Nc2cc(Cl)cc(NS(C)(=O)=O)c2)cn1-c1ccc(N2CC3(COC3)C2)cn1] | 276 | 502 | ¹H NMR (400 MHz, DMSO-d6) δ 9.94 (s, 1H), 9.78 (s, 1H), 7.77 (dd, J = 5.1, 2.5 Hz, 2H), 7.69 (t, J = 1.9 Hz, 1H), 7.60 (d, J = 2.2 Hz, 1H), 7.38 (d, J = 8.6 Hz, 1H), 7.04 (dd, J = 8.6, 3.0 Hz, 1H), 6.87 (t, J = 2.0 Hz, 1H), 6.51 (s, 1H), 4.74 (s, 4H), 4.1 |
| 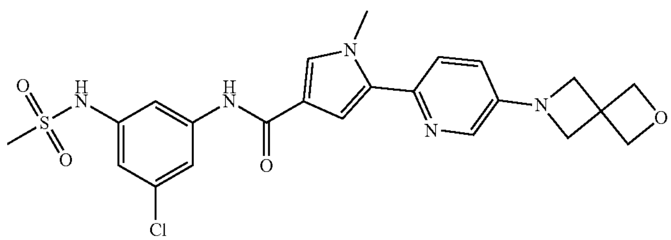 [SMILES: Cn1cc(C(=O)Nc2cc(Cl)cc(NS(C)(=O)=O)c2)cc1-c1ccc(N2CC3(COC3)C2)cn1] | 277 | 502 | ¹H NMR (300 MHz, DMSO-d6) δ 9.96 (s, 1H), 9.75 (s, 1H), 7.86 (d, J = 2.8 Hz, 1H), 7.69 (s, 1H), 7.58 (d, J = 2.0 Hz, 2H), 7.49 (d, J = 8.6 Hz, 1H), 7.03-6.91 (m, 2H), 6.87 (t, J = 1.9 Hz, 1H), 4.74 (s, 4H), 4.09 (s, 4H), 3.90 (s, 3H), 3.04 (s, 3H). |
| 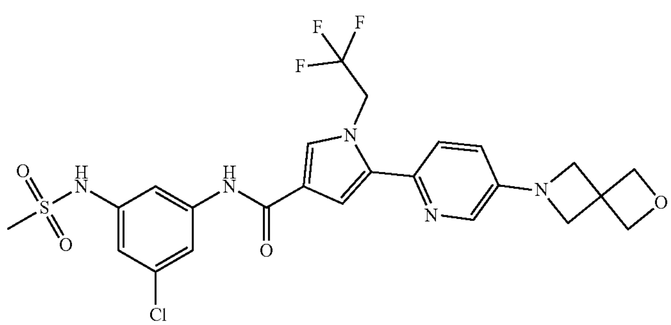 [SMILES: CS(=O)(=O)Nc1cc(Cl)cc(NC(=O)c2cc(-c3ccc(N4CC5(COC5)C4)cn3)n(CC(F)(F)F)c2)c1] | 278 | 570 | ¹H NMR (400 MHz, DMSO-d6) δ 9.93 (s, 1H), 7.83 (d, J = 2.9 Hz, 1H), 7.70 (d, J = 4.7 Hz, 2H), 7.63 (s, 1H), 7.55 (d, J = 8.6 Hz, 1H), 7.10 (d, J = 1.9 Hz, 1H), 6.95 (dd, J = 8.7, 2.9 Hz, 1H), 6.91 (d, J = 2.1 Hz, 1H), 5.68 (q, J = 9.2 Hz, 2H), 4.73 (s, 4H |
| 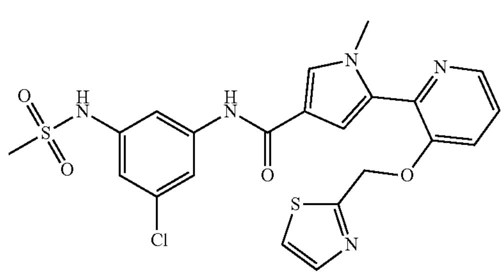 [SMILES: Cn1cc(C(=O)Nc2cc(Cl)cc(NS(C)(=O)=O)c2)cc1-c1ncccc1OCc1nccs1] | 279 | 518 | ¹H NMR (400 MHz, DMSO-d6) δ 9.82 (s, 2H), 8.38-8.20 (m, 1H), 7.85 (d, J = 3.2 Hz, 1H), 7.78 (d, J = 3.2 Hz, 1H), 7.75-7.67 (m, 3H), 7.62 (d, J = 2.0 Hz, 1H), 7.35 (dd, J = 8.4, 4.6 Hz, 1H), 7.18 (d, J = 2.0 Hz, 1H), 6.89 (d, J = 2.0 Hz, 1H), 5.59 (s, |

-continued

| Structure | Example No. | MS (ESI) [M + H]+ | 1H NMR |
|---|---|---|---|
| 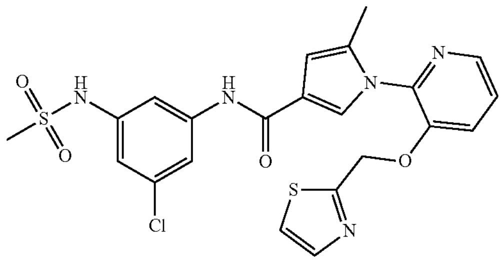 [SMILES: Cc1cc(C(=O)Nc2cc(Cl)cc(NS(C)(=O)=O)c2)cn1-c1ncccc1OCc1nccs1] | 280 | 518 | 1H NMR (400 MHz, DMSO-d6) δ 10.02 (s, 1H), 9.77 (s, 1H), 8.22 (d, J = 4.7 Hz, 1H), 7.93 (d, J = 8.3 Hz, 1H), 7.83 (d, J = 3.2 Hz, 1H), 7.76 (d, J = 3.2 Hz, 1H), 7.70 (s, 2H), 7.62-7.52 (m, 2H), 6.88 (s, 1H), 6.54 (s, 1H), 5.59 (s, 2H), 3.04 (s, 3H), 2.1 |
| 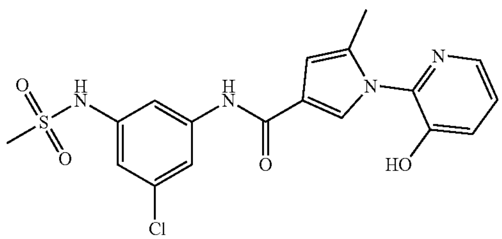 [SMILES: Cc1cc(C(=O)Nc2cc(Cl)cc(NS(C)(=O)=O)c2)cn1-c1ncccc1O] | 281 | 421 | 1H NMR (400 MHz, DMSO-d6) δ 9.73 (s, 1H), 8.00 (d, J = 4.6 Hz, 1H), 7.67 (d, J = 2.1 Hz, 2H), 7.57 (d, J = 2.1 Hz, 1H), 7.46 (d, J = 8.2 Hz, 1H), 7.35 (dd, J = 8.2, 4.6 Hz, 1H), 6.86 (d, J = 2.0 Hz, 1H), 6.49 (s, 1H), 3.02 (s, 3H), 2.12 (s, 3H). |
| 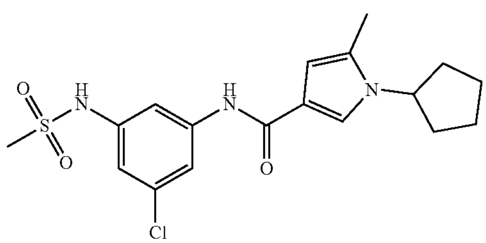 [SMILES: Cc1cc(C(=O)Nc2cc(Cl)cc(NS(C)(=O)=O)c2)cn1C1CCCC1] | 282 | 396 | 1H NMR (400 MHz, DMSO-d6) δ 9.96 (s, 1H), 9.58 (s, 1H), 7.66 (t, J = 1.9 Hz, 1H), 7.60 (t, J = 1.9 Hz, 1H), 7.55 (d, J = 2.0 Hz, 1H), 6.86 (t, J = 1.9 Hz, 1H), 6.35 (dd, J = 2.0, 1.0 Hz, 1H), 4.44 (p, J = 7.1 Hz, 1H), 3.05 (s, 3H), 2.30-2.00 (m, 5H), 1. |
| 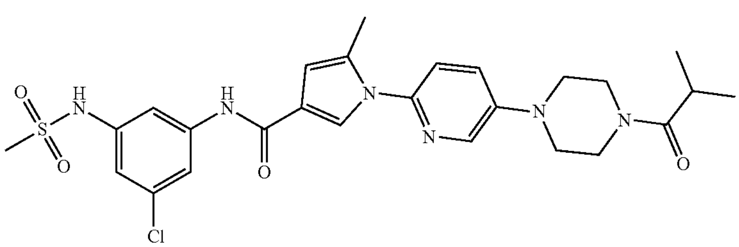 [SMILES: Cc1cc(C(=O)Nc2cc(Cl)cc(NS(C)(=O)=O)c2)cn1-c1ccc(N2CCN(C(=O)C(C)C)CC2)cn1] | 283 | 559 | 1H NMR (300 MHz, DMSO-d6) δ 10.01 (s, 1H), 9.82 (s, 1H), 8.27 (d, J = 3.0 Hz, 1H), 7.84 (s, 1H), 7.72 (s, 1H), 7.68-7.52 (m, 2H), 7.46 (d, J = 8.9 Hz, 1H), 6.89 (s, 1H), 6.54 (s, 1H), 3.66 (s, 4H), 3.27 (s, 4H), 3.06 (s, 3H), 2.94 (p, J = 6.6 Hz, 1H), 2 |

-continued

| Structure | Example No. | MS (ESI) [M + H]+ | ¹H NMR |
|---|---|---|---|
| 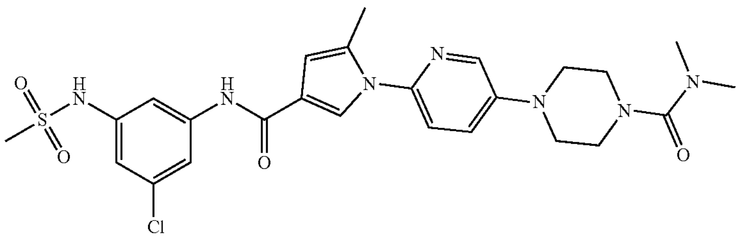 | 284 | 560 | ¹H NMR (300 MHz, DMSO-d6) δ 10.01 (s, 1H), 9.81 (s, 1H), 8.26 (d, J = 2.9 Hz, 1H), 7.84 (d, J = 2.0 Hz, 1H), 7.72 (t, J = 1.9 Hz, 1H), 7.63 (t, J = 1.9 Hz, 1H), 7.57 (dd, J = 8.9, 3.0 Hz, 1H), 7.45 (d, J = 8.8 Hz, 1H), 6.89 (t, J = 2.0 Hz, 1H), 6.53 (dd, |
| 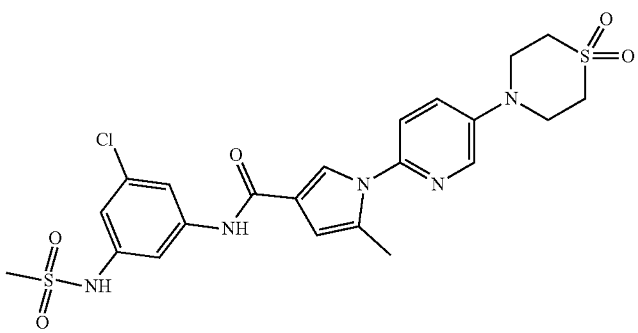 [SMILES: Cc1cc(C(=O)Nc2cc(Cl)cc(NS(C)(=O)=O)c2)cn1-c1ccc(N2CCS(=O)(=O)CC2)cn1] | 285 | 538 | ¹H NMR (400 MHz, DMSO-d6) δ 9.99 (s, 1H), 9.81 (s, 1H), 8.33 (d, J = 3.1 Hz, 1H), 7.84 (d, J = 2.0 Hz, 1H), 7.71 (q, J = 4.7, 3.3 Hz, 1H), 7.68-7.58 (m, 2H), 7.47 (d, J = 8.9 Hz, 1H), 6.89 (t, J = 2.0 Hz, 1H), 6.54 (s, 1H), 3.90 (t, J = 5.3 Hz, 4H), 3.1 |
| 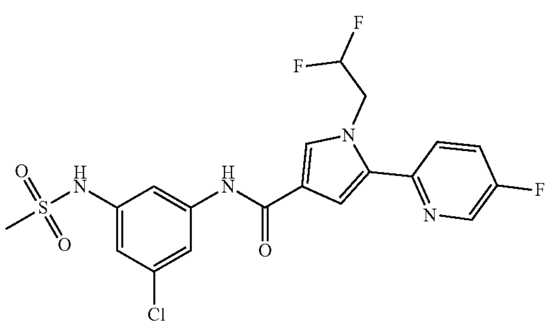 [SMILES: CS(=O)(=O)Nc1cc(Cl)cc(NC(=O)c2cc(-c3ccc(F)cn3)n(CC(F)F)c2)c1] | 286 | 473 | ¹H NMR (400 MHz, DMSO-d6) δ 9.99 (d, J = 35.0 Hz, 2H), 8.59 (t, J = 1.8 Hz, 1H), 7.83 (dd, J = 7.2, 2.2 Hz, 2H), 7.77 (d, J = 1.9 Hz, 1H), 7.72 (t, J = 1.9 Hz, 1H), 7.62 (t, J = 1.9 Hz, 1H), 7.30 (d, J = 1.9 Hz, 1H), 6.91 (t, J = 2.0 Hz, 1H), 6.56-6.16 |
| 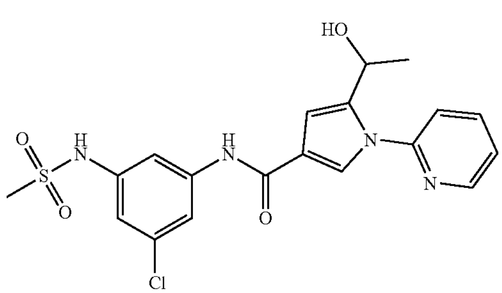 [SMILES: CC(O)c1cc(C(=O)Nc2cc(Cl)cc(NS(C)(=O)=O)c2)cn1-c1ccccn1] | 287 | 433 | ¹H NMR (400 MHz, DMSO-d6) δ 9.91 (s, 2H), 8.58 (dd, J = 5.0, 1.9 Hz, 1H), 8.06 (td, J = 7.8, 1.9 Hz, 1H), 8.01 (d, J = 2.0 Hz, 1H), 7.79 (d, J = 8.1 Hz, 1H), 7.71 (d, J = 1.9 Hz, 1H), 7.64 (d, J = 2.0 Hz, 1H), 7.47 (dd, J = 7.4, 4.9 Hz, 1H), 6.90 (t, J = |

-continued

| Structure | Example No. | MS (ESI) [M + H]+ | ¹H NMR |
|---|---|---|---|
| 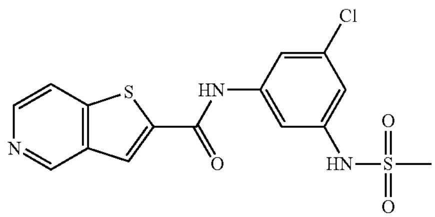 | 288 | 382 | ¹H NMR (300 MHz, Methanol-d4) δ 9.23 (s, 1H), 8.51 (d, J = 5.8 Hz, 1H), 8.37 (s, 1H), 8.12 (d, J = 14.5 Hz, 1H), 7.73 (d, J = 1.9 Hz, 1H), 7.63 (s, 1H), 7.08 (d, J = 2.3 Hz, 1H), 3.07 (s, 3H). |
| 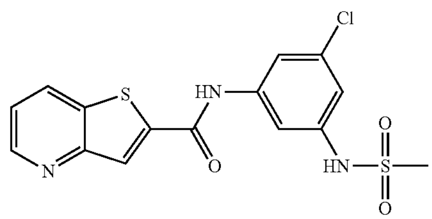 [SMILES: CS(=O)(=O)Nc1cc(Cl)cc(NC(=O)c2cc3ncccc3s2)c1] | 289 | 382 | ¹H NMR (300 MHz, DMSO-d6) δ 10.81 (s, 1H), 10.13 (s, 1H), 8.79 (dd, J = 4.5, 1.5 Hz, 1H), 8.65-8.49 (m, 2H), 7.71 (dt, J = 13.7, 1.9 Hz, 2H), 7.51 (dd, J = 8.2, 4.5 Hz, 1H), 7.00 (t, J = 1.9 Hz, 1H), 3.09 (s, 3H). |
| 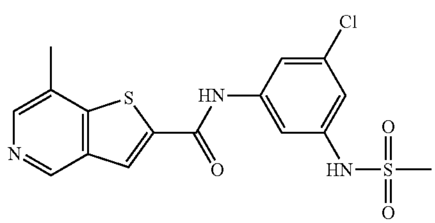 [SMILES: Cc1cncc2cc(C(=O)Nc3cc(Cl)cc(NS(C)(=O)=O)c3)sc12] | 290 | 396 | ¹H NMR (400 MHz, DMSO-d6) δ 10.86 (s, 1H), 10.14 (s, 1H), 9.15 (s, 1H), 8.55 (s, 1H), 8.39 (d, J = 1.1 Hz, 1H), 7.69 (dt, J = 28.2, 1.9 Hz, 2H), 6.99 (t, J = 1.9 Hz, 1H), 3.09 (s, 3H), 2.54 (s, 3H). |
| 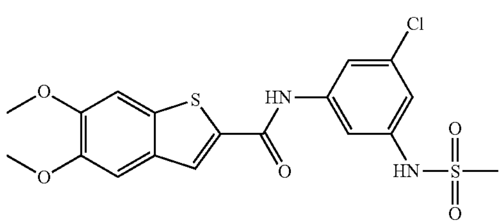 | 291 | 441 | ¹H NMR (300 MHz, DMSO-d6) δ 10.60 (s, 1H), 10.10 (s, 1H), 8.23 (s, 1H), 7.70 (t, J = 1.9 Hz, 1H), 7.66 (t, J = 1.9 Hz, 1H), 7.62 (s, 1H), 7.46 (s, 1H), 6.97 (t, J = 2.0 Hz, 1H), 3.86 (d, J = 2.4 Hz, 6H), 3.09 (s, 3H). |
| 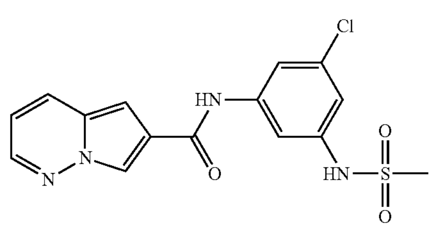 | 292 | 365 | ¹H NMR (300 MHz, DMSO-d6) δ 10.24 (s, 1H), 10.07 (s, 1H), 8.50 (dd, J = 1.8, 0.7 Hz, 1H), 8.29 (dd, J = 4.4, 1.7 Hz, 1H), 8.08 (dd, J = 9.3, 1.7 Hz, 1H), 7.72 (dt, J = 19.2, 1.9 Hz, 2H), 7.11 (d, J = 1.8 Hz, 1H), |

-continued

| Structure | Example No. | MS (ESI) [M + H]+ | ¹H NMR |
|---|---|---|---|
| | | | 6.95 (t, J = 1.9 Hz, 1H), 6.77 (dd, J = 9. |
| 6-Cl, benzothiophene-2-carboxamide, N-(3-chloro-5-methanesulfonamidophenyl) | 293 | 415 | ¹H NMR (400 MHz, DMSO-d6) δ 10.76 (s, 1H), 10.11 (s, 1H), 8.41-8.32 (m, 1H), 8.26 (d, J = 1.9 Hz, 1H), 8.05 (d, J = 8.5 Hz, 1H), 7.68 (dt, J = 20.7, 1.9 Hz, 2H), 7.52 (dd, J = 8.6, 2.0 Hz, 1H), 6.98 (t, J = 1.9 Hz, 1H), 3.08 (s, 3H). |
| 6-F, benzothiophene-2-carboxamide, N-(3-chloro-5-methanesulfonamidophenyl) | 294 | 399 | ¹H NMR (400 MHz, DMSO-d6) δ 10.72 (s, 1H), 10.12 (s, 1H), 8.38 (s, 1H), 8.04 (ddd, J = 26.0, 9.0, 3.9 Hz, 2H), 7.67 (dt, J = 21.9, 2.0 Hz, 2H), 7.37 (td, J = 9.0, 2.5 Hz, 1H), 6.97 (d, J = 2.0 Hz, 1H), 3.08 (s, 3H). |
| 5-F, benzothiophene-2-carboxamide, N-(3-chloro-5-methanesulfonamidophenyl) | 295 | 399 | ¹H NMR (400 MHz, DMSO-d6) δ 10.79 (s, 1H), 10.12 (s, 1H), 8.36 (s, 1H), 8.13 (dd, J = 8.9, 4.9 Hz, 1H), 7.89 (dd, J = 9.6, 2.6 Hz, 1H), 7.69 (dt, J = 19.0, 2.0 Hz, 2H), 7.41 (td, J = 9.0, 2.6 Hz, 1H), 6.98 (d, J = 2.0 Hz, 1H), 3.09 (s, 3H). |
| 4-F, benzothiophene-2-carboxamide, N-(3-chloro-5-methanesulfonamidophenyl) | 296 | 397 | ¹H NMR (400 MHz, DMSO-d6) δ 10.75 (s, 1H), 10.22 (s, 1H), 8.52 (s, 1H), 7.93 (d, J = 8.2 Hz, 1H), 7.67 (d, J = 23.6 Hz, 2H), 7.56-7.41 (m, 1H), 7.31 (dd, J = 10.5, 7.9 Hz, 1H), 6.97 (t, J = 1.8 Hz, 1H), 3.06 (s, 3H). |

-continued

| Structure | Example No. | MS (ESI) [M + H]+ | ¹H NMR |
|---|---|---|---|
| [7-fluorobenzo[b]thiophene-2-carboxamide with 3-chloro-5-(methylsulfonamido)phenyl] | 297 | 397 | ¹H NMR (400 MHz, DMSO-d6) δ 10.83 (d, J = 3.7 Hz, 1H), 10.14 (s, 1H), 8.48 (t, J = 3.9 Hz, 1H), 7.91 (dd, J = 8.1, 3.6 Hz, 1H), 7.69 (dq, J = 19.1, 2.3 Hz, 2H), 7.54 (dq, J = 8.3, 4.2 Hz, 1H), 7.42 (ddd, J = 11.3, 7.9, 3.5 Hz, 1H), 6.99 (p, J = 2.1 Hz, 1H |
| [5-chlorobenzo[b]thiophene-2-carboxamide with 3-chloro-5-(methylsulfonamido)phenyl] | 298 | 415 | ¹H NMR (400 MHz, DMSO-d6) δ 10.82 (s, 1H), 10.12 (s, 1H), 8.34 (s, 1H), 8.18-8.02 (m, 2H), 7.69 (dt, J = 19.5, 1.9 Hz, 2H), 7.54 (dd, J = 8.7, 2.1 Hz, 1H), 6.98 (t, J = 1.9 Hz, 1H), 3.09 (d, J = 2.4 Hz, 3H). |
| [6-chloroindolizine-2-carboxamide with 3-chloro-5-(methylsulfonamido)phenyl] | 299 | 398 | ¹H NMR (400 MHz, DMSO-d6) δ 10.23 (s, 1H), 10.05 (s, 1H), 8.63 (dd, J = 1.8, 1.0 Hz, 1H), 8.22-8.12 (m, 1H), 7.74 (d, J = 2.0 Hz, 1H), 7.68 (d, J = 2.1 Hz, 1H), 7.58 (d, J = 9.6 Hz, 1H), 7.10 (d, J = 1.5 Hz, 1H), 6.93 (q, J = 1.5, 0.9 Hz, 1H), 6.81 (dd, |
| [6-methylindolizine-2-carboxamide with 3-chloro-5-(methylsulfonamido)phenyl] | 300 | 378 | ¹H NMR (400 MHz, DMSO-d6) δ 10.10 (s, 1H), 10.03 (s, 1H), 8.11 (d, J = 1.9 Hz, 1H), 8.06 (d, J = 1.7 Hz, 1H), 7.74 (t, J = 1.9 Hz, 1H), 7.68 (t, J = 1.9 Hz, 1H), 7.41 (d, J = 9.2 Hz, 1H), 6.92 (dd, J = 5.0, 3.0 Hz, 2H), 6.65 (dd, J = 9.3, 1.5 Hz, 1H), 3.0 |

-continued

| Structure | Example No. | MS (ESI) [M + H]+ | ¹H NMR |
|---|---|---|---|
| 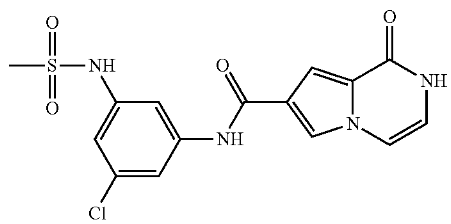 [SMILES: CS(=O)(=O)Nc1cc(Cl)cc(NC(=O)c2cc3c(=O)[nH]ccn3c2)c1] | 301 | 379 | ¹H NMR (400 MHz, DMSO-d6) δ 10.63 (d, J = 5.7 Hz, 1H), 10.14 (s, 2H), 8.04 (d, J = 1.7 Hz, 1H), 7.73 (d, J = 2.2 Hz, 1H), 7.65 (d, J = 1.8 Hz, 1H), 7.60 (s, 1H), 7.39 (d, J = 5.8 Hz, 1H), 6.92 (d, J = 1.9 Hz, 1H), 6.69 (t, J = 5.6 Hz, 1H), 3.05 (s,3H). |
| 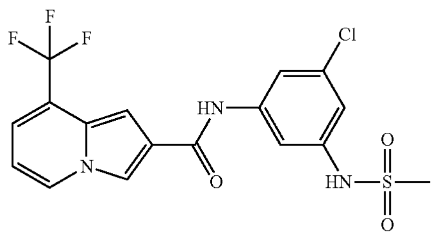 [SMILES: CS(=O)(=O)Nc1cc(Cl)cc(NC(=O)c2cc3c(C(F)(F)F)cccn3c2)c1] | 302 | 432 | ¹H NMR (400 MHz, DMSO-d6) δ 10.29 (s, 1H), 10.06 (s, 1H), 8.61 (d, J = 7.0 Hz, 1H), 8.37 (d, J = 1.6 Hz, 1H), 7.72 (dt, J = 17.5, 1.9 Hz, 2H), 7.31 (d, J = 6.9 Hz, 1H), 7.23 (s, 1H), 6.95 (t, J = 2.0 Hz, 1H), 6.81 (t, J = 7.0 Hz, 1H), 3.07 (s, 3H). |
| 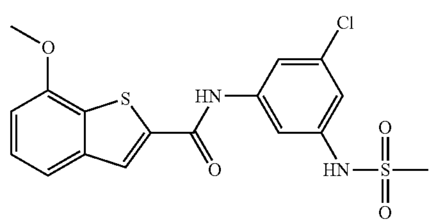 [SMILES: COc1cccc2cc(C(=O)Nc3cc(Cl)cc(NS(C)(=O)=O)c3)sc12] | 303 | 411 | ¹H NMR (400 MHz, DMSO-d6) δ 10.72 (s, 1H), 10.12 (s, 1H), 8.38 (s, 1H), 7.72 (t, J = 1.9 Hz, 1H), 7.67 (t, J = 1.9 Hz, 1H), 7.61 (d, J = 7.9 Hz, 1H), 7.45 (t, J = 7.9 Hz, 1H), 7.08 (d, J = 7.8 Hz, 1H), 6.98 (t, J = 1.9 Hz, 1H), 3.99 (s, 3H), 3.09 (s, 3H). |
| 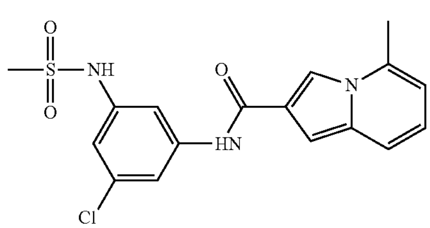 [SMILES: Cc1cccc2cc(C(=O)Nc3cc(Cl)cc(NS(C)(=O)=O)c3)cn12] | 304 | 378 | ¹H NMR (400 MHz, DMSO-d6) δ 10.15 (s, 1H), 9.88 (s, 1H), 8.05 (s, 1H), 7.72 (dt, J = 17.4, 2.0 Hz, 2H), 7.45 (d, J = 9.0 Hz, 1H), 7.06 (d, J = 1.6 Hz, 1H), 6.94 (d, J = 2.2 Hz, 1H), 6.80 (dd, J = 9.1, 6.5 Hz, 1H), 6.60 (d, J = 6.7 Hz, 1H), 3.08 (d, J = 2. |

| Structure | Example No. | MS (ESI) [M + H]+ | ¹H NMR |
|---|---|---|---|
| (8-fluoroindolizine-2-carboxamide with 3-chloro-5-methanesulfonylamino-phenyl) | 305 | 382 | ¹H NMR (400 MHz, DMSO-d6) δ 10.23 (s, 1H), 10.07 (d, J = 2.4 Hz, 1H), 8.31 (dt, J = 3.5, 1.9 Hz, 1H), 8.25-8.13 (m, 1H), 7.77 (t, J = 2.0 Hz, 1H), 7.69 (t, J = 2.0 Hz, 1H), 7.25-7.13 (m, 1H), 7.02-6.83 (m, 1H), 6.81-6.52 (m, 2H), 3.08 (d, J = 1.9 |
| (hydroxy-cyclobutyl-pyrazole carboxamide); *stereochemistry arbitrarily assigned* | 306a | 385 | ¹H NMR (400 MHz, DMSO-d6) δ = 10.03 (s, 1H), 8.46 (s, 1H), 8.07 (s, 1H), 7.67 (t, J = 1.8 Hz, 1H), 7.61-7.51 (m, 1H), 6.92 (t, J = 1.8 Hz, 1H), 5.70 (br d, J = 2.6 Hz, 1H), 4.51 (q, J = 8.4 Hz, 1H), 4.32 (br d, J = 7.4 Hz, 1H), 3.05 (s, 3H), 2.12 (br t, |
| (hydroxy-cyclobutyl-pyrazole carboxamide); *stereochemistry arbitrarily assigned* | 306b | 385 | ¹H NMR (400 MHz, DMSO-d6) δ = 10.26-9.85 (m, 2H), 8.47 (d, J = 8.8 Hz, 1H), 8.05 (d, J = 18.8 Hz, 1H), 7.69 (q, J = 1.8 Hz, 1H), 7.58 (td, J = 1.8, 7.6 Hz, 1H), 6.92 (t, J = 1.8 Hz, 1H), 5.71 (br d, J = 6.8 Hz, 1H), 5.30 (d, J = 5.4 Hz, 1H), 4.90 (br d, |
| (1-methyl-2-oxopiperidinyl-pyrazole carboxamide) | 307 | 426 | ¹H NMR (400 MHz, DMSO-d6) δ = 10.07 (s, 1H), 8.43 (s, 1H), 8.08 (s, 1H), 7.76-7.49 (m, 2H), 6.92 (t, J = 1.8 Hz, 1H), 4.89-4.69 (m, 1H), 3.31-3.18 (m, 2H), 3.05 (s, 3H), 2.84 (s, 3H), 2.78-2.69 (m, 2H), 2.31-2.14 (m, 2H) |

-continued

| Structure | Example No. | MS (ESI) [M + H]+ | ¹H NMR |
|---|---|---|---|
| (structure with methylsulfonamide, chloro, phenyl, pyrazole carboxamide, phenethyl) | 308 | 419 | ¹H NMR (400 MHz, DMSO-d6) δ = 9.99 (s, 2H), 8.25 (s, 1H), 8.06 (s, 1H), 7.67 (s, 1H), 7.57 (s, 1H), 7.36-7.08 (m, 5H), 6.92 (t, J = 1.8 Hz, 1H), 4.41 (t, J = 7.2 Hz, 2H), 3.14 (t, J = 7.2 Hz, 2H), 3.06 (s, 3H) |
| (structure with cyclopentyl pyrazole) | 309 | 383 | ¹H NMR (400 MHz, DMSO-d6) δ = 9.98 (s, 1H), δ = 8.40 (s, 1H), δ = 8.02 (s, 1H), δ = 7.65 (t, J = 1.7 Hz, 1H), δ = 7.56 (t, J = 1.7 Hz, 1H), δ = 6.91 (t, J = 1.8 Hz, 1H), δ = 4.75 (quin, J = 7.0 Hz, 1H), δ = 3.05 (s, 3H), δ = 2.04-2.18 (m, 2H), δ = 1.86- |
| (structure with spiro acetamide) | 310 | 466 | ¹H NMR (400 MHz, DMSO-d6) δ = 10.01 (s, 2H), 8.40 (s, 1H), 8.11-8.01 (m, 2H), 7.77-7.45 (m, 2H), 6.92 (t, J = 2.0 Hz, 1H), 4.82 (t, J = 8.4 Hz, 1H), 4.28-4.00 (m, 1H), 3.06 (s, 3H), 2.65-2.55 (m, 2H), 2.49-2.37 (m, 3H), 2.26 (br s, 1H), 2.06-1 |
| (structure with N-methyl azaspiro) | 311 | 424 | ¹H NMR (400 MHz, METHANOL-d4) δ = 8.53 (s, 1H), δ = 8.25 (br s, 1H), δ = 8.08 (s, 1H), δ = 7.63 (br s, 1H), δ = 7.53 (s, 1H), δ = 6.99 (s, 1H), δ = 4.76-4.86 (m, 1H), δ = 4.24 (br d, J = 14.2 Hz, 4H), δ = 3.04 (s, 3H), δ = 2.74-2.99 (m, 7H) |

-continued

| Structure | Example No. | MS (ESI) [M + H]+ | ¹H NMR |
|---|---|---|---|
| 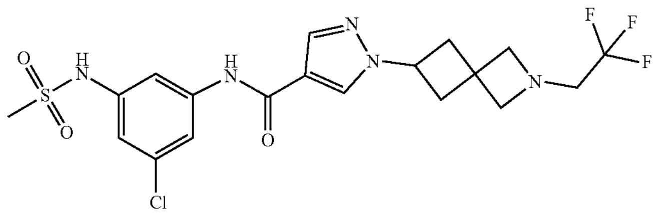 [SMILES: CS(=O)(=O)Nc1cc(Cl)cc(NC(=O)c2cnn(C3CC4(C3)CN(CC(F)(F)F)C4)c2)c1] | 312 | 492 | ¹H NMR (400 MHz, DMSO-d6)δ = 10.03 (s, 1H), δ = 8.41 (s, 1H), δ = 8.05 (s, 1H), δ = 7.65 (t, J = 1.8 Hz, 1H), δ = 7.56 (t, J = 1.8 Hz, 1H), δ = 6.91 (t, J = 1.9 Hz, 1H), δ = 4.81 (t, J = 8.1 Hz, 1H), δ = 3.45 (s, 2H), δ = 3.35 (s, 2H), δ = 3.10-3.18 (m |
| 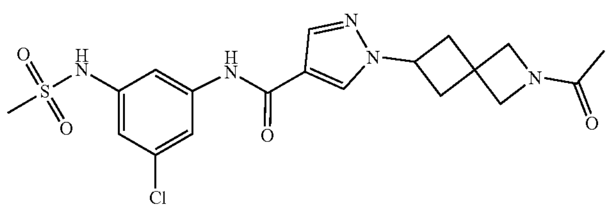 [SMILES: CC(=O)N1CC2(CC(n3cc(C(=O)Nc4cc(Cl)cc(NS(C)(=O)=O)c4)cn3)C2)C1] | 313 | 452 | ¹H NMR (400 MHz, DMSO-d6) δ = 9.96 (s, 1H), δ = 8.42 (d, J = 2.6 Hz, 1H), δ = 8.06 (s, 1H), δ = 7.59 (s, 1H), δ = 7.48 (s, 1H), δ = 6.86 (t, J = 1.8 Hz, 1H), δ = 4.85 (t, J = 8.1 Hz, 1H), δ = 4.08-4.26 (m, 2H), δ = 3.76-4.01 (m, 2H), δ = 2.99 (s, 3 |
| 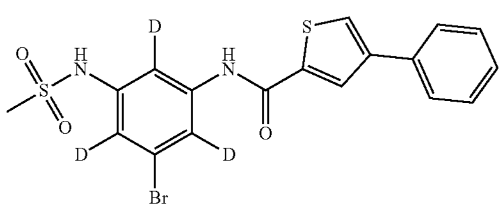 [SMILES: [2H]c1c(Br)c([2H])c(NS(C)(=O)=O)c([2H])c1NC(=O)c1cc(-c2ccccc2)cs1] | 314 | 454 | ¹H NMR (400 MHz, DMSO-d6) δ = 10.46 (s, 1H), δ = 9.91-10.23 (m, 1H), δ = 8.49 (s, 1H), δ = 8.22 (s, 1H), δ = 7.75 (d, J = 7.6 Hz, 2H), δ = 7.49 (t, J = 7.6 Hz, 2H), δ = 7.32-7.41 (m, 1H),δ = 3.07 (s, 3H) |
| 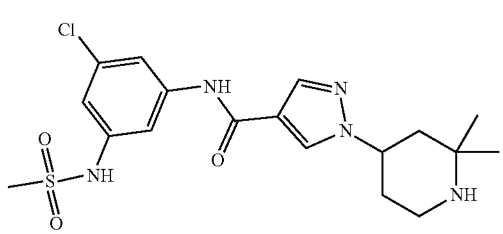 | 315 | 426 | ¹H NMR (400 MHz, DMSO-d6) δ = 10.08 (d, J = 5.6 Hz, 2H), 8.96 (br d, J = 10.0 Hz, 1H), 8.68 (br t, J = 9.6 Hz, 1H), 8.44 (s, 1H), 8.11 (s, 1H), 7.68 (t, J = 1.8 Hz, 1H), 7.58 (t, J = 1.8 Hz, 1H), 6.93 (t, J = 1.8 Hz, 1H), 4.75 (br t, J = 4.0 Hz, 1H), 3.38 |

-continued

| Structure | Example No. | MS (ESI) [M + H]+ | ¹H NMR |
|---|---|---|---|
| 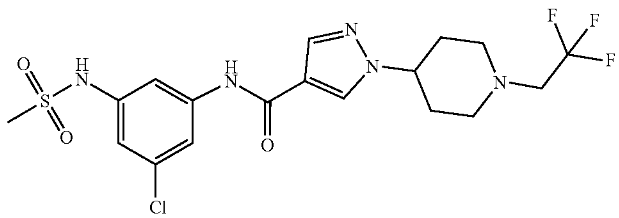 [SMILES: CS(=O)(=O)Nc1cc(Cl)cc(NC(=O)c2cnn(C3CCN(CC(F)(F)F)CC3)c2)c1] | 316 | 480 | ¹H NMR (400 MHz, DMSO-d6) δ = 9.91-10.22 (m, 2H), δ = 8.44 (s, 1H), δ = 8.06 (s, 1H), δ = 7.67 (t, J = 1.8 Hz, 1H), δ = 7.58 (s, 1H), δ = 6.92 (t, J = 1.8 Hz, 1H), δ = 4.29-4.33 (m, 1H), δ = 3.27-3.50 (m, 2H), δ = 2.94-3.19 (m, 5H), δ = 2.60 |
| 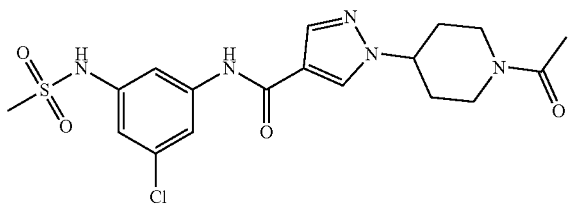 [SMILES: CC(=O)N1CCC(n2cc(C(=O)Nc3cc(Cl)cc(NS(C)(=O)=O)c3)cn2)CC1] | 317 | 440 | ¹H NMR (400 MHz, DMSO-d6) δ = 10.00 (s, 2H), δ = 8.42 (s, 1H), δ = 8.05 (s, 1H), δ = 7.66 (s, 1H), δ = 7.56 (s, 1H), δ = 6.91 (s, 1H), δ = 4.43-4.61 (m, 2H), δ = 3.92 (br d, J = 14.1 Hz, 1H), δ = 3.17-3.25 (m, 1H), δ = 3.05 (s, 3H), δ = 2.65- |
| 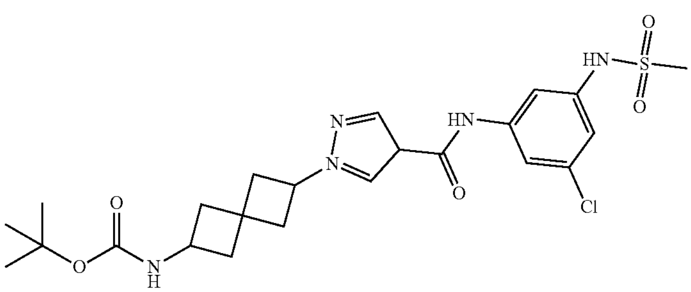 | 318 | 468 | ¹H NMR (400 MHz, DMSO-d6) δ = 10.01 (s, 1H), 8.45-8.40 (m, 1H), 8.05 (s, 1H), 7.79-7.40 (m, 2H), 7.11 (br d, J = 8.0 Hz, 1H), 6.90 (t, J = 1.8 Hz, 1H), 4.80 (t, J = 8.2 Hz, 1H), 3.87 (br d, J = 8.2 Hz, 1H), 3.02 (s, 3H), 2.49-2.30 (m, 5H), 2.27-2. |
| 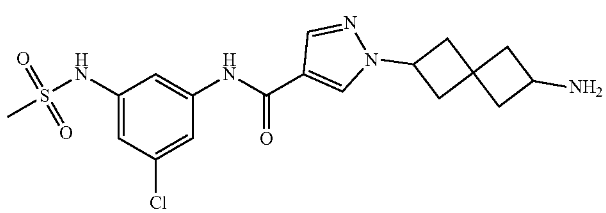 [SMILES: CS(=O)(=O)Nc1cc(Cl)cc(NC(=O)c2cnn(C3CC4(CC(N)C4)C3)c2)c1] | 319 | 424 | ¹H NMR (400 MHz, DMSO-d6) δ = 10.08 (s, 1H), 8.43 (s, 1H), 8.06 (s, 1H), 7.73-7.47 (m, 2H), 6.91 (s, 1H), 4.81 (br t, J = 8.2 Hz, 1H), 3.53 (br t, J = 7.8 Hz, 1H), 3.04 (s, 3H), 2.59 (td, J = 3.8, 7.4 Hz, 1H), 2.50-2.38 (m, 4H), 2.34-2.24 (m, 1H), 2 |

-continued

| Structure | Example No. | MS (ESI) [M + H]+ | ¹H NMR |
|---|---|---|---|
| 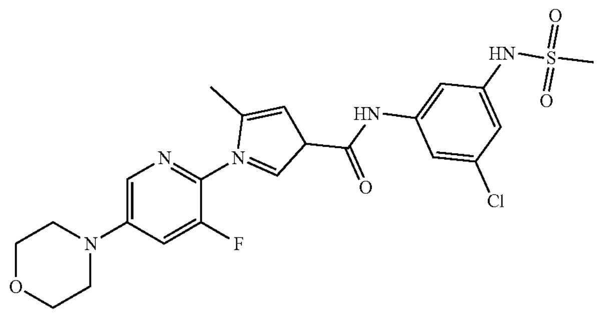 | 320 | 508 | ¹H NMR (300 MHz, DMSO-d6) δ = 9.99 (br s, 1H), 9.82 (s, 1H), 8.15 (d, J = 2.1 Hz, 1H), 7.55-7.71 (m, 4H), 6.89 (t, J = 2.0 Hz, 1H), 6.56 (d, J = 0.6 Hz, 1H), 3.77 (m, 4H), 3.32 (m, 4H), 3.06 (s, 3H), 2.12 (s, 3H) |
| 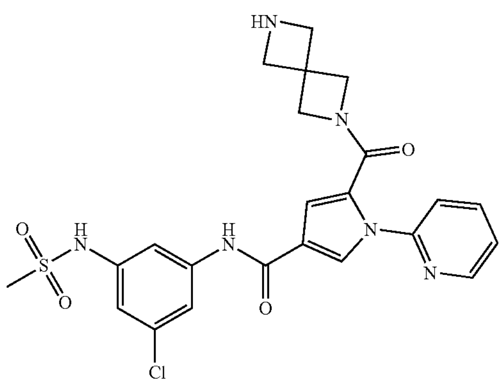 [SMILES: CS(=O)(=O)Nc1cc(Cl)cc(NC(=O)c2cc(C(=O)N3CC4(CNC4)C3)n(-c3ccccn3)c2)c1] | 643 | 515.05 | ¹H NMR (400 MHz, DMSO-d6) δ 9.96 (s, 1H), 8.50 (dd, J = 5.1, 1.8 Hz, 1H), 8.13 (d, J = 1.8 Hz, 1H), 7.96 (td, J = 7.8, 1.9 Hz, 1H), 7.57 (d, J = 1.9 Hz, 1H), 7.53-7.39 (m, 3H), 7.18 (d, J = 1.8 Hz, 1H), 6.86 (d, J = 2.0 Hz, 1H), 4.44 (s, 2H), 4.06 (s, 2H), 3.72 (s, 4H), 2.97 (s, 3H). |
| 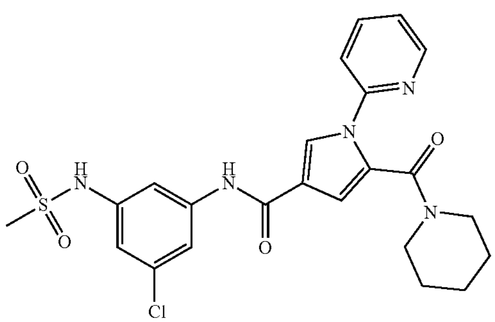 [SMILES: CS(=O)(=O)Nc1cc(Cl)cc(NC(=O)c2cc(C(=O)N3CCCCC3)n(-c3ccccn3)c2)c1] | 644 | 502 | ¹H NMR (400 MHz, DMSO-d6) δ 10.00 (s, 1H), 9.78 (s, 1H), 8.49 (d, J = 4.9 Hz, 1H), 8.21 (d, J = 1.9 Hz, 1H), 8.12-7.91 (m, 1H), 7.69 (q, J = 1.8 Hz, 1H), 7.64-7.49 (m, 2H), 7.42 (dd, J = 7.3, 5.1 Hz, 1H), 6.93 (dt, J = 18.8, 1.8 Hz, 2H), 3.47 (s, 4H), 3.04 (d, J = 1.6 Hz, 3H), 1.59 (s, 2H), 1.46 (s, 4H). |
| 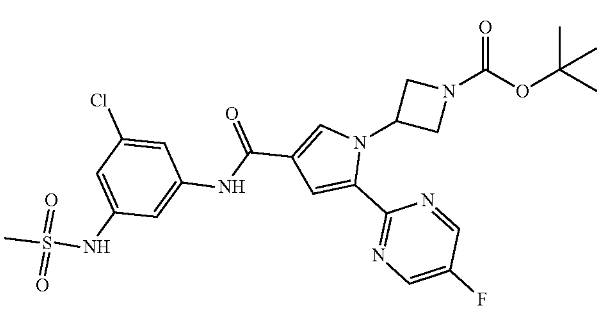 [SMILES: CC(C)(C)OC(=O)N1CC(n2cc(C(=O)Nc3cc(Cl)cc(NS(C)(=O)=O)c3)cc2-c2ncc(F)cn2)C1] | 645 | 565 | ¹H NMR (300 MHz, DMSO-d6) δ 9.97 (d, J = 12.8 Hz, 2H), 8.91 (d, J = 0.8 Hz, 2H), 8.19 (d, J = 2.0 Hz, 1H), 7.82-7.43 (m, 3H), 6.92 (t, J = 2.0 Hz, 1H), 5.85 (t, J = 6.5 Hz, 1H), 4.40 (t, J = 8.6 Hz, 2H), 4.11 (dd, J = 9.5, 5.5 Hz, 2H), 3.06 (s, 3H), 1.42 (s, |

-continued
| Structure | Example No. | MS (ESI) [M + H]+ | 1H NMR |
|---|---|---|---|
| | | | 9H). |
| 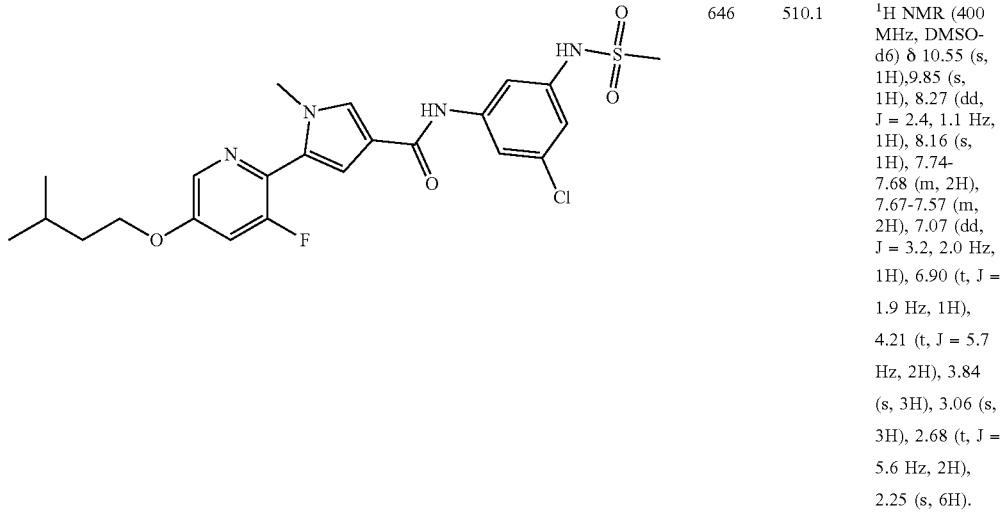 | 646 | 510.1 | 1H NMR (400 MHz, DMSO-d6) δ 10.55 (s, 1H), 9.85 (s, 1H), 8.27 (dd, J = 2.4, 1.1 Hz, 1H), 8.16 (s, 1H), 7.74-7.68 (m, 2H), 7.67-7.57 (m, 2H), 7.07 (dd, J = 3.2, 2.0 Hz, 1H), 6.90 (t, J = 1.9 Hz, 1H), 4.21 (t, J = 5.7 Hz, 2H), 3.84 (s, 3H), 3.06 (s, 3H), 2.68 (t, J = 5.6 Hz, 2H), 2.25 (s, 6H). |
| 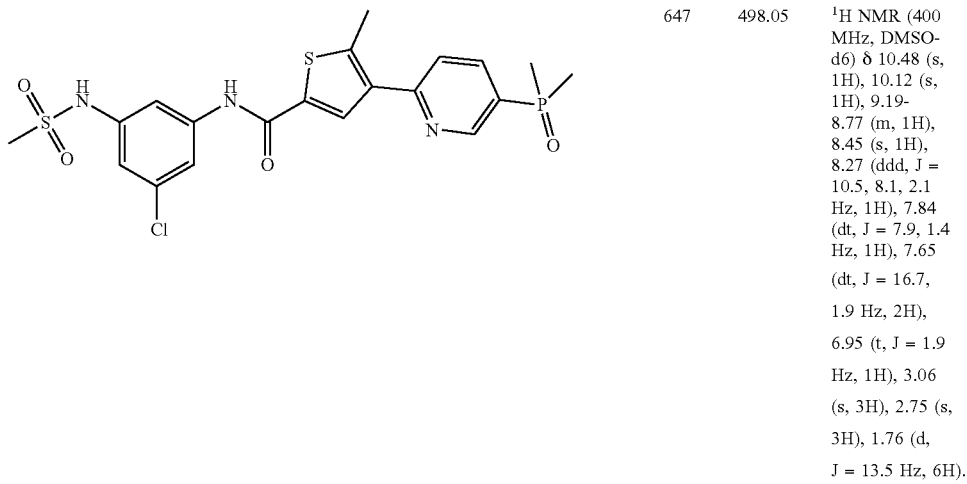 | 647 | 498.05 | 1H NMR (400 MHz, DMSO-d6) δ 10.48 (s, 1H), 10.12 (s, 1H), 9.19-8.77 (m, 1H), 8.45 (s, 1H), 8.27 (ddd, J = 10.5, 8.1, 2.1 Hz, 1H), 7.84 (dt, J = 7.9, 1.4 Hz, 1H), 7.65 (dt, J = 16.7, 1.9 Hz, 2H), 6.95 (t, J = 1.9 Hz, 1H), 3.06 (s, 3H), 2.75 (s, 3H), 1.76 (d, J = 13.5 Hz, 6H). |
| 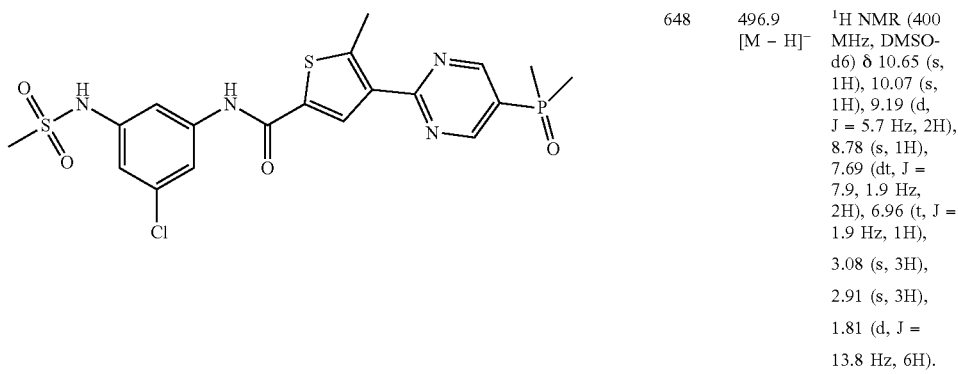 | 648 | 496.9 [M − H]− | 1H NMR (400 MHz, DMSO-d6) δ 10.65 (s, 1H), 10.07 (s, 1H), 9.19 (d, J = 5.7 Hz, 2H), 8.78 (s, 1H), 7.69 (dt, J = 7.9, 1.9 Hz, 2H), 6.96 (t, J = 1.9 Hz, 1H), 3.08 (s, 3H), 2.91 (s, 3H), 1.81 (d, J = 13.8 Hz, 6H). |

| Structure | Example No. | MS (ESI) [M + H]+ | ¹H NMR |
|---|---|---|---|
| 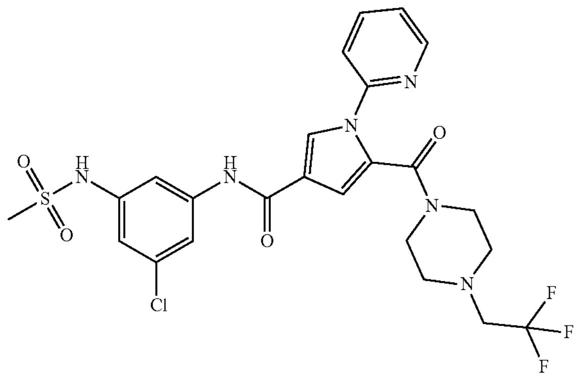 [SMILES: CS(=O)(=O)Nc1cc(Cl)cc(NC(=O)c2cc(C(=O)N3CCN(CC(F)(F)F)CC3)n(-c3ccccn3)c2)c1] | 649 | 582.9 [M − H]⁻ | ¹H NMR (400 MHz, DMSO-d6) δ 10.02 (s, 1H), 9.49 (s,1H), 8.50 (dd, J = 5.0, 1.8 Hz, 1H), 8.24 (d, J = 1.8 Hz, 1H), 8.02 (td, J = 7.8, 1.9 Hz, 1H), 7.68 (t, J = 1.9 Hz, 1H), 7.62-7.53 (m, 2H), 7.43 (dd, J = 7.4, 4.9 Hz, 1H), 6.99 (d, J = 1.8 Hz, 1H), 6.91 (t, J = 2.0 Hz, 1H), 3.53 (s, 4H), 3.24 (q, J = 10.2 Hz, 2H), 3.04 (s, 3H), 2.62 (s, 4H). |
| 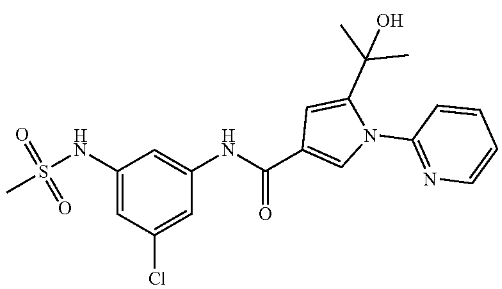 [SMILES: CC(C)(O)c1cc(C(=O)Nc2cc(Cl)cc(NS(C)(=O)=O)c2)cn1-c1ccccn1] | 650 | 447.15 [M − H]⁻ | ¹H NMR (400 MHz, DMSO-d6) δ 9.99 (s, 1H), 9.86 (s, 1H), 8.59 (ddd, J = 4.9, 1.9, 0.8 Hz, 1H), 8.10 (td, J = 7.8, 1.9 Hz, 1H), 7.87 (d, J = 2.0 Hz, 1H), 7.79 (dt, J = 8.2, 1.0 Hz, 1H), 7.68 (t, J = 1.9 Hz, 1H), 7.61 (t, J = 1.9 Hz, 1H), 7.53 (ddd, J = 7.5, 4.9, 1.0 Hz, 1H), 6.90 (t, J = 2.0 Hz, 1H), 6.76 (d, J = 2.0 Hz, 1H), 6.28 (s, 1H), 3.05 (s, 3H), 1.37 (s, 6H). |
| 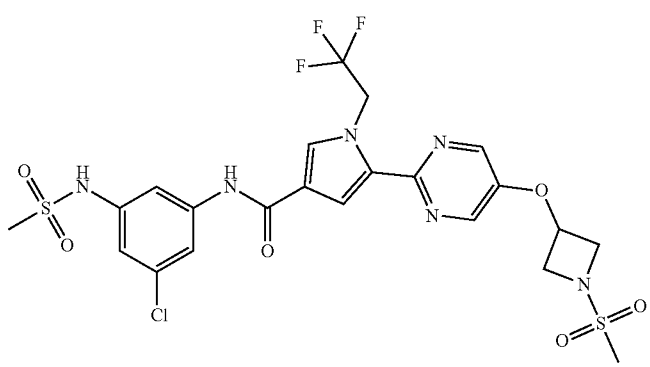 [SMILES: CS(=O)(=O)Nc1cc(Cl)cc(NC(=O)c2cc(-c3ncc(OC4CN(S(C)(=O)=O)C4)cn3)n(CC(F)(F)F)c2)c1] | 651 | 623.05 | ¹H NMR (400 MHz, DMSO-d6) δ 10.07 (s, 2H), 8.55 (s, 2H), 7.81 (s, 1H), 7.76-7.61 (m, 3H), 6.92 (s, 1H), 5.75 (t, J = 9.1 Hz, 2H), 5.26 (t, J = 5.7 Hz, 1H), 4.38 (dd, J = 9.5, 6.6 Hz, 2H), 4.03 (dd, J = 9.4, 4.6 Hz, 2H), 3.08 (d, J = 12.7 Hz, 6H), . |

-continued
| Structure | Example No. | MS (ESI) [M + H]+ | ¹H NMR |
|---|---|---|---|
| 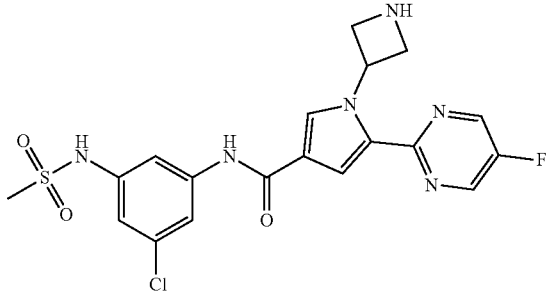 [SMILES: CS(=O)(=O)Nc1cc(Cl)cc(NC(=O)c2cc(-c3ncc(F)cn3)n(C3CNC3)c2)c1] | 652 | 464.95 | ¹H NMR (400 MHz, DMSO-d6) δ 10.25-9.75 (m, 2H), 7.72 (d, J = 1.8 Hz, 1H), 7.64 (s, 1H), 7.54 (s, 1H), 7.21 (d, J = 1.8 Hz, 1H), 6.85 (s, 1H), 6.63 (d, J = 5.0 Hz, 1H), 6.54 (s, 1H), 5.46 (s, 1H), 4.65 (d, J = 11.3 Hz, 1H), 4.20 (d, J = 13.0 Hz, 1H), 3.85 (d, J = 10.1 Hz, 1H), 3.51 (s, 1H), 3.00 (s, 4H). |
| 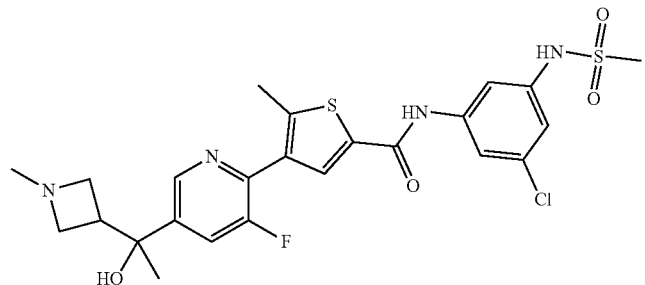 | 653 | 553.1 | ¹H NMR (400 MHz, Methanol-d4) δ 8.50 (d, J = 5.0 Hz, 1H), 8.46 (s, 1H), 7.99 (d, J = 1.8 Hz, 1H), 7.79 (t, J = 5.4 Hz, 1H), 7.65 (t, J = 1.9 Hz, 1H), 7.55 (t, J = 1.9 Hz, 1H), 7.01 (t, J = 1.9 Hz, 1H), 4.32 (d, J = 24.8 Hz, 2H), 3.91 (s, 2H), 3.46 (s, 1H), 3.03 (s, 3H), 2.88 (s, 3H), 2.53 (d, J = 1.3 Hz, 3H), 1.65-1.61 (m, 3H). |
| 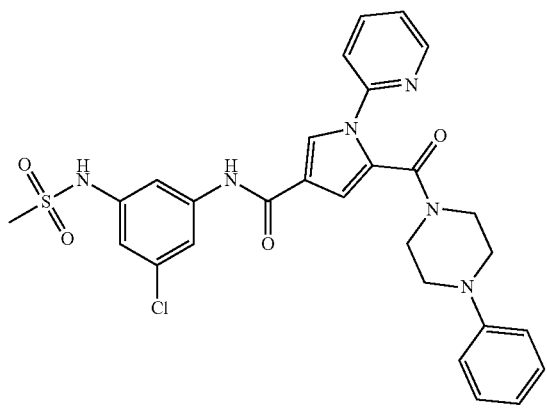 [SMILES: CS(=O)(=O)Nc1cc(Cl)cc(NC(=O)c2cc(C(=O)N3CCN(c4ccccc4)CC3)n(-c3ccccn3)c2)c1] | 654 | 579 | ¹H NMR (400 MHz, DMSO-d6) δ 10.01 (d, J = 21.2 Hz, 2H), 8.47 (dd, J = 5.3, 1.8 Hz, 1H), 8.25 (d, J = 1.8 Hz, 1H), 8.01 (td, J = 7.8, 1.9 Hz, 1H), 7.71 (t, J = 1.9 Hz, 1H), 7.63 (t, J = 1.9 Hz, 1H), 7.58 (d, J = 8.2 Hz, 1H), 7.40 (dd, J = 7.5, 4.9 Hz, 1H), 7.28-7.21 (m, 2H), 7.05 (d, J = 1.8 Hz, 1H), 6.99-6.91 (m, 3H), 6.82 (t, J = 7.3 Hz, 1H), 3.68 (s, 4H), 3.14 (q, J = 10.5, 9.0 Hz, 4H), 3.06 (s, 3H). |

| Structure | Example No. | MS (ESI) [M + H]+ | ¹H NMR |
|---|---|---|---|
| 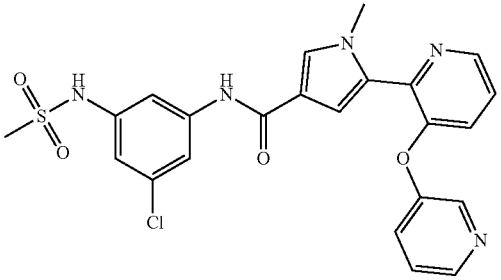 [SMILES: Cn1cc(C(=O)Nc2cc(Cl)cc(NS(C)(=O)=O)c2)cc1-c1ncccc1Oc1cccnc1] | 655 | 497.95 | ¹H NMR (400 MHz, DMSO-d6) δ 9.82 (s, 1H), 8.54-8.48 (m, 1H), 8.38 (d, J = 15.5 Hz, 2H), 7.69 (s, 2H), 7.61-7.51 (m, 2H), 7.43 (s, 3H), 7.15 (d, J = 2.0 Hz, 1H), 6.88 (s, 1H), 3.87 (s, 3H), 3.05 (d, J = 6.7 Hz, 3H). |
| 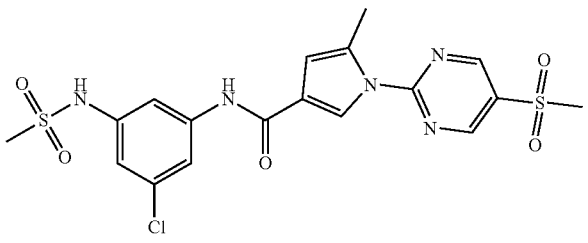 | 656 | 483.85 | ¹H NMR (300 MHz, DMSO-d6) δ 10.13 (s, 1H), 10.03 (s, 1H), 9.29 (s, 2H), 8.61 (d, J = 2.1 Hz, 1H), 7.72 (t, J = 1.8 Hz, 1H), 7.65 (t, J = 2.0 Hz, 1H), 6.92 (t, J = 2.0 Hz, 1H), 6.64 (dd, J = 2.1, 1.2 Hz, 1H), 3.44 (s, 3H), 3.06 (s, 3H), 2.64 (d, J = 1.1 Hz, 3H). |
| 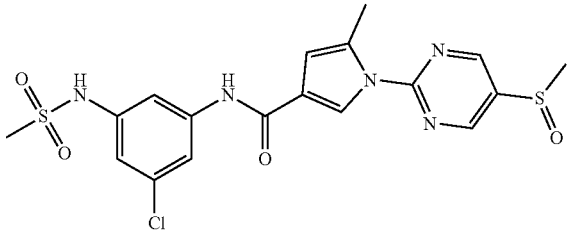 | 657 | 467.9 | ¹H NMR (300 MHz, DMSO-d6) δ 10.01 (s, 1H), 9.12 (s, 2H), 8.57 (d, J = 2.1 Hz, 1H), 7.58 (d, J = 27.8 Hz, 2H), 6.85 (s, 1H), 6.62 (d, J = 1.4 Hz, 1H), 3.00 (d, J = 10.1 Hz, 6H), 2.63 (d, J = 1.1 Hz, 3H). |
| 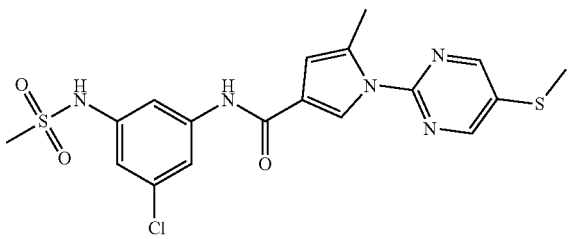 | 658 | 451.95 | ¹H NMR (300 MHz, DMSO-d6) δ 9.99 (d, J = 14.1 Hz, 2H), 8.82 (s, 2H), 8.44 (d, J = 2.1 Hz, 1H), 7.72 (t, J = 1.9 Hz, 1H), 7.65 (t, J = 1.9 Hz, 1H), 6.90 (t, J = 2.0 Hz, 1H), 6.58 (dd, J = 2.1, 1.1 Hz, 1H), 3.06 (s, 3H), 2.63 (s, 3H), 2.58 (d, J = 1.1 Hz, 3H). |

-continued

| Structure | Example No. | MS (ESI) [M + H]+ | ¹H NMR |
|---|---|---|---|
| 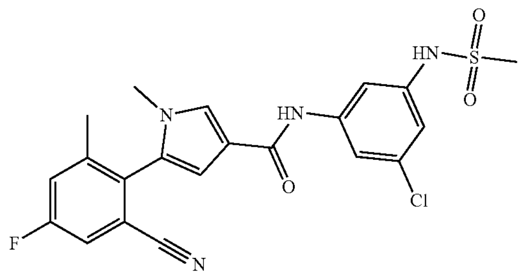 [SMILES: Cc1cc(F)cc(C#N)c1-c1cc(C(=O)Nc2cc(Cl)cc(NS(C)(=O)=O)c2)cn1C] | 659 | 460.95 | ¹H NMR (400 MHz, DMSO-d6) δ 10.00 (s, 1H), 9.83 (s, 1H), 7.84 (dd, J = 8.3, 2.8 Hz, 1H), 7.75 (d, J = 1.8 Hz, 1H), 7.71 (s, 1H), 7.67 (d, J = 8.8 Hz, 1H), 7.61 (s, 1H), 6.89 (t, J = 1.9 Hz, 1H), 6.74 (d, J = 1.9 Hz, 1H), 3.41 (s, 3H), 3.05 (s, 3H), 2.16 (s, 3H). |
| 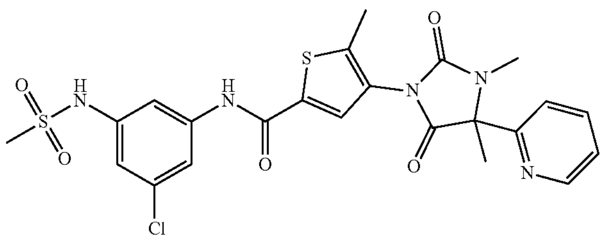 [SMILES: Cc1sc(C(=O)Nc2cc(Cl)cc(NS(C)(=O)=O)c2)cc1N1C(=O)N(C)C(C)(c2ccccn2)C1=O] | 660 | 547.9 | ¹H NMR (300 MHz, DMSO-d6) δ 10.33 (s, 1H), 10.10 (s, 1H), 8.64 (ddd, J = 4.8, 1.9, 0.9 Hz, 1H), 7.83 (td, J = 7.8, 1.8 Hz, 1H), 7.54 (dt, J = 9.8, 1.9 Hz, 2H), 7.50-7.37 (m, 3H), 6.95 (t, J = 2.0 Hz, 1H), 3.07 (d, J = 8.2 Hz, 6H), 2.01 (s, 3H), 1.92 (s, 3H). |
| 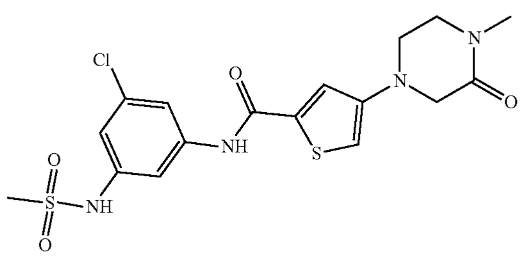 [SMILES: CN1CCN(c2csc(C(=O)Nc3cc(Cl)cc(NS(C)(=O)=O)c3)c2)CC1=O] | 661 | 441.15 [M − H]⁻ | ¹H NMR (400 MHz, DMSO-d6) δ 10.26 (s, 1H), 10.07 (s, 1H), 7.91 (d, J = 1.8 Hz, 1H), 7.61 (dt, J = 6.7, 1.9 Hz, 2H), 6.95 (t, J = 1.9 Hz, 1H), 6.84 (d, J = 1.7 Hz, 1H), 3.72 (s, 2H), 3.49-3.37 (m, 4H), 3.06 (s, 3H), 2.90 (s, 3H). |
| 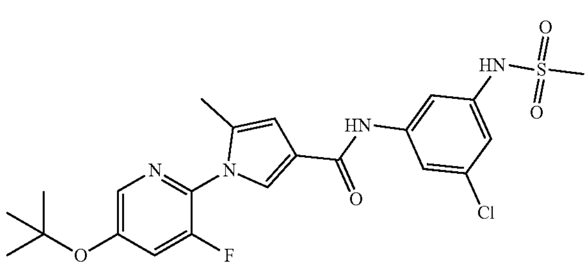 [SMILES: Cc1cc(C(=O)Nc2cc(Cl)cc(NS(C)(=O)=O)c2)cn1-c1ncc(OC(C)(C)C)cc1F] | 662 | 495.15 | ¹H NMR (300 MHz, DMSO-d6) δ 10.01 (s, 1H), 9.83 (s, 1H), 8.18 (d, J = 2.4 Hz, 1H), 7.83 (dd, J = 11.3, 2.4 Hz, 1H), 7.73 (dt, J = 10.3, 1.8 Hz, 2H), 7.62 (t, J = 1.9 Hz, 1H), 6.90 (t, J = 2.0 Hz, 1H), 6.65-6.49 (m, 1H), 3.06 (s, 3H), 2.16 (s, 3H), 1.41 (s, 9H). |

-continued

| Structure | Example No. | MS (ESI) [M + H]+ | ¹H NMR |
|---|---|---|---|
| 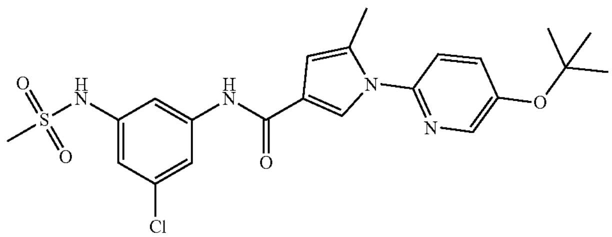 [SMILES: Cc1cc(C(=O)Nc2cc(Cl)cc(NS(C)(=O)=O)c2)cn1-c1ccc(OC(C)(C)C)cn1] | 663 | 477.1 | ¹H NMR (300 MHz, DMSO-d6) δ 10.01 (s, 1H), 9.83 (s, 1H), 8.24 (d, J = 2.8 Hz, 1H), 7.93 (d, J = 2.0 Hz, 1H), 7.72 (t, J = 1.8 Hz, 1H), 7.70-7.60 (m, 2H), 7.55 (d, J = 8.7 Hz, 1H), 6.89 (t, J = 1.9 Hz, 1H), 6.56 (d, J = 2.0 Hz, 1H), 3.06 (s, 3H), 2.47-2.30 (m, 3H), 1.36 (s, 9H). |
| 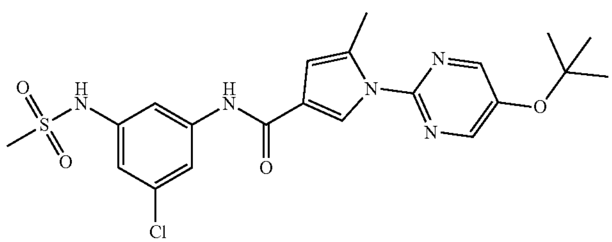 [SMILES: Cc1cc(C(=O)Nc2cc(Cl)cc(NS(C)(=O)=O)c2)cn1-c1ncc(OC(C)(C)C)cn1] | 664 | 478.1 | ¹H NMR (400 MHz, DMSO-d6) δ 10.00 (s, 2H), 8.61 (s, 2H), 8.42 (d, J = 2.1 Hz, 1H), 7.72 (t, J = 1.9 Hz, 1H), 7.65 (t, J = 1.9 Hz, 1H), 6.90 (t, J = 1.9 Hz, 1H), 6.66-6.43 (m, 1H), 3.06 (s, 3H), 2.68-2.54 (m, 3H), 1.37 (s, 9H). |
| 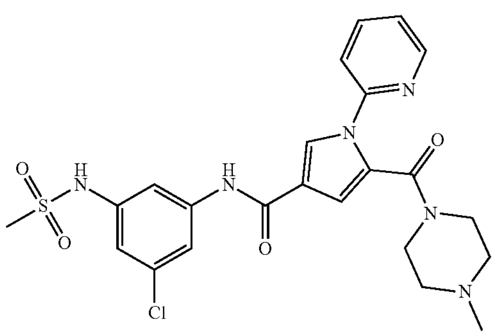 [SMILES: CN1CCN(C(=O)c2cc(C(=O)Nc3cc(Cl)cc(NS(C)(=O)=O)c3)cn2-c2ccccn2)CC1] | 665 | 516.95 | ¹H NMR (400 MHz, DMSO-d6) δ 10.01 (d, J = 3.3 Hz, 1H), 9.89 (s, 1H) 8.49 (dd, J = 5.1, 1.8 Hz, 1H), 8.22 (t, J = 2.2 Hz, 1H), 8.01 (td, J = 7.8, 1.9 Hz, 1H), 7.69 (q, J = 2.1 Hz, 1H), 7.61 (q, J = 1.8 Hz, 1H), 7.54 (d, J = 8.1 Hz, 1H), 7.43 (dd, J = 7.5, 4.8 Hz, 1H), 6.99 (d, J = 1.8 Hz, 1H), 6.91 (p, J = 2.2 Hz, 1H), 3.49 (s, 4H), 3.05 (d, J = 1.4 Hz, 3H), 2.26 (s, 4H), 2.18 (s, 3H). |

-continued

| Structure | Example No. | MS (ESI) [M + H]+ | 1H NMR |
|---|---|---|---|
| 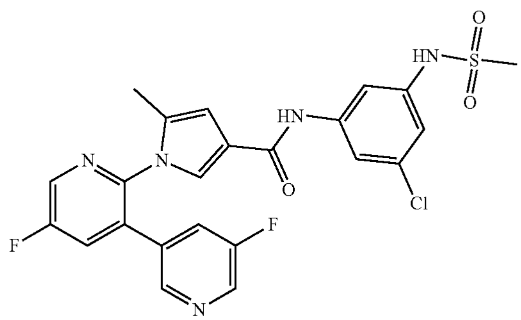 [SMILES: Cc1cc(C(=O)Nc2cc(Cl)cc(NS(C)(=O)=O)c2)cn1-c1ncc(F)cc1-c1cncc(F)c1] | 666 | 515.85 [M − H]− | 1H NMR (400 MHz, DMSO-d6) δ 9.75 (s, 2H), 8.75 (dd, J = 3.0, 1.3 Hz, 1H), 8.61-8.53 (m, 1H), 8.34 (ddd, J = 8.8, 3.0, 1.2 Hz, 1H), 8.24-8.18 (m, 1H), 7.65 (q, J = 1.7 Hz, 1H), 7.57 (dq, J = 9.7, 1.6 Hz, 2H), 7.52 (t, J = 1.7 Hz, 1H), 6.87 (q, J = 1.8 Hz, 1H), 6.49 (d, J = 1.9 Hz, 1H), 3.03 (d, J = 1.2 Hz, 3H), 1.89 (s, 3H). |
| 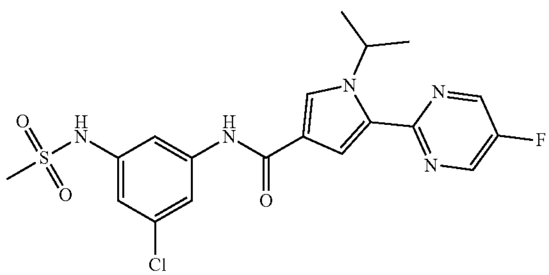 [SMILES: CC(C)n1cc(C(=O)Nc2cc(Cl)cc(NS(C)(=O)=O)c2)cc1-c1ncc(F)cn1] | 667 | 451.95 | 1H NMR (400 MHz, DMSO-d6) δ 9.99 (s, 1H), 9.91 (s, 1H), 8.91 (d, J = 0.9 Hz, 2H), 7.93 (d, J = 2.1 Hz, 1H), 7.79-7.52 (m, 3H), 6.90 (t, J = 1.9 Hz, 1H), 5.76 (p, J = 6.6 Hz, 1H), 3.06 (s, 3H), 1.46 (d, J = 6.7 Hz, 6H). |
| 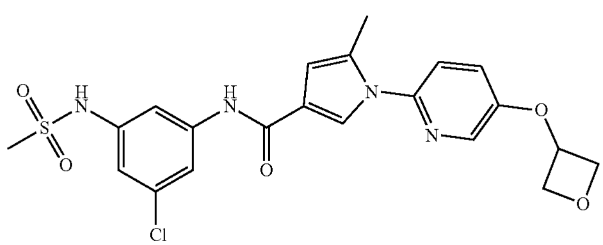 [SMILES: Cc1cc(C(=O)Nc2cc(Cl)cc(NS(C)(=O)=O)c2)cn1-c1ccc(OC2COC2)cn1] | 668 | 477 | 1H NMR (300 MHz, Methanol-d4) δ 8.11 (dd, J = 2.8, 0.9 Hz, 1H), 7.70 (d, J = 2.1 Hz, 1H), 7.65 (t, J = 1.9 Hz, 1H), 7.54 (t, J = 1.9 Hz, 1H), 7.50-7.33 (m, 2H), 6.98 (t, J = 1.9 Hz, 1H), 6.54 (dd, J = 2.1, 1.1 Hz, 1H), 5.41 (tt, J = 5.9, 4.8 Hz, 1H), 5.06 (ddd, J = 7.0, 5.9, 1.0 Hz, 2H), 4.74 (ddd, J = 7.4, 4.8, 1.0 Hz, 2H), 3.03 (s, 3H), 2.31 (d, J = 0.9 Hz, 3H). |

-continued

| Structure | Example No. | MS (ESI) [M + H]+ | ¹H NMR |
|---|---|---|---|
| 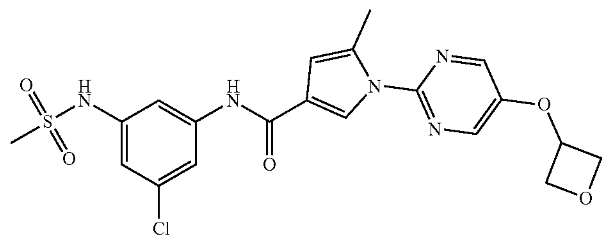 [SMILES: Cc1cc(C(=O)Nc2cc(Cl)cc(NS(C)(=O)=O)c2)cn1-c1ncc(OC2COC2)cn1] | 669 | 478.15 | ¹H NMR (300 MHz, DMSO-d6) δ 9.97 (s, 2H), 8.53 (s, 2H), 8.35 (d, J = 2.1 Hz, 1H), 7.72 (t, J = 1.8 Hz, 1H), 7.65 (t, J = 1.9 Hz, 1H), 6.90 (t, J = 1.9 Hz, 1H), 6.56 (dd, J = 2.1, 1.1 Hz, 1H), 5.51 (tt, J = 5.9, 4.7 Hz, 1H), 4.99 (ddd, J = 7.1, 5.9, 1.0 Hz, 2H), 4.63 (ddd, J = 7.5, 4.7, 1.0 Hz, 2H), 3.06 (s, 3H), 2.55 (d, J = 1.0 Hz, 3H). |
| 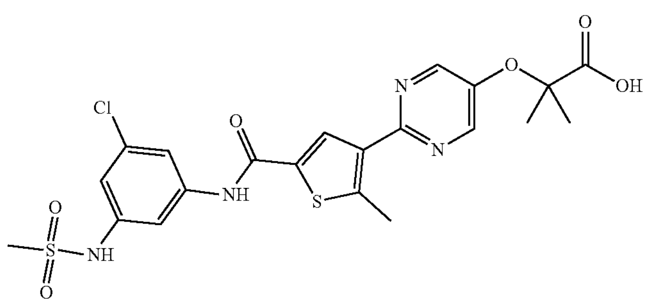 [SMILES: Cc1sc(C(=O)Nc2cc(Cl)cc(NS(C)(=O)=O)c2)cc1-c1ncc(OC(C)(C)C(=O)O)cn1] | 670 | 525.05 | ¹H NMR (400 MHz, Methanol-d4) δ 8.48 (d, J = 3.0 Hz, 3H), 7.65 (t, J = 2.0 Hz, 1H), 7.56 (t, J = 1.9 Hz, 1H), 7.02 (t, J = 2.0 Hz, 1H), 3.04 (s, 3H), 2.86 (s, 3H), 1.67 (s, 6H). |
| 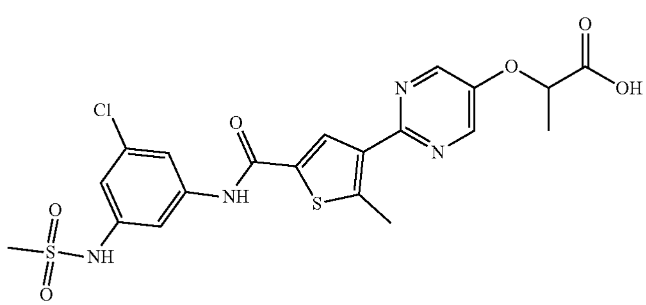 [SMILES: Cc1sc(C(=O)Nc2cc(Cl)cc(NS(C)(=O)=O)c2)cc1-c1ncc(OC(C)C(=O)O)cn1] | 671 | 511.05 | ¹H NMR (400 MHz, DMSO-d6) δ 10.55 (s, 1H), 10.05 (s, 1H), 8.63 (s, 1H), 8.56 (s, 2H), 7.68 (dt, J = 6.0, 1.8 Hz, 2H), 6.94 (t, J = 2.0 Hz, 1H), 5.06 (s, 1H), 3.07 (s, 3H), 2.82 (s, 3H), 1.54 (d, J = 6.7 Hz, 3H). |
| 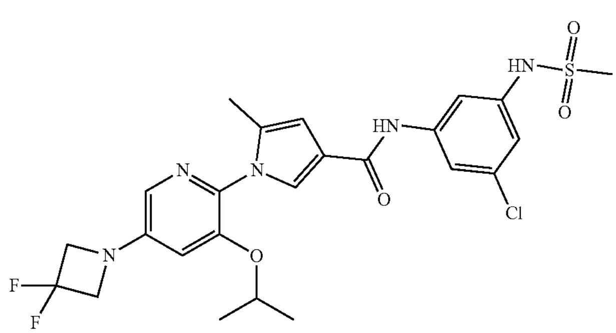 [SMILES: Cc1cc(C(=O)Nc2cc(Cl)cc(NS(C)(=O)=O)c2)cn1-c1ncc(N2CC(F)(F)C2)cc1OC(C)C] | 672 | 554.15 | ¹H NMR (400 MHz, DMSO-d6) δ 9.99 (s, 1H), 9.74 (s, 1H), 7.70 (q, J = 1.7 Hz, 1H), 7.63 (t, J = 1.9 Hz, 1H), 7.51 (t, J = 1.7 Hz, 1H), 7.47 (d, J = 2.1 Hz, 1H), 6.88 (q, J = 1.7 Hz, 2H), δ 6.46 (s, 1H), 4.67 (hept, J = 6.0 Hz, 1H), 4.44 (t, J = 12.3 Hz, 4H), 3.06 (d, J = 1.3 Hz, 3H), 2.04 (s, 3H), |

-continued

| Structure | Example No. | MS (ESI) [M + H]+ | ¹H NMR |
|---|---|---|---|
| | | | 1.20 (dd, J = 6.1, 1.3 Hz, 6H). |
| 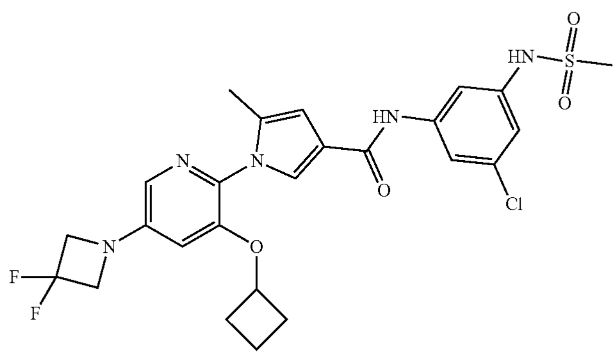 [SMILES: Cc1cc(C(=O)Nc2cc(Cl)cc(NS(C)(=O)=O)c2)cn1-c1ncc(N2CC(F)(F)C2)cc1OC1CCC1] | 673 | 566.35 | ¹H NMR (400 MHz, DMSO-d6) δ 9.99 (s, 1H), 9.75 (s, 1H), 7.70 (s, 1H), 7.62 (s, 1H), 7.53 (d, J = 2.0 Hz, 1H), 7.47 (d, J = 2.4 Hz, 1H), 6.88 (t, J = 2.0 Hz, 1H), 6.64 (d, J = 2.4 Hz, 1H), 6.48 (s, 1H), 4.86-4.72 (m, 1H), 4.44 (t, J = 12.3 Hz, 4H), 3.05 (s, 3H), 2.42 (d, J = 8.7 Hz, 2H), 2.05 (d, J = 1.0 Hz, 3H), 1.99-1.86 (m, 2H), 1.76 (d, J = 10.1 Hz, 1H), 1.61 (d, J = 9.6 Hz, 1H). |
| 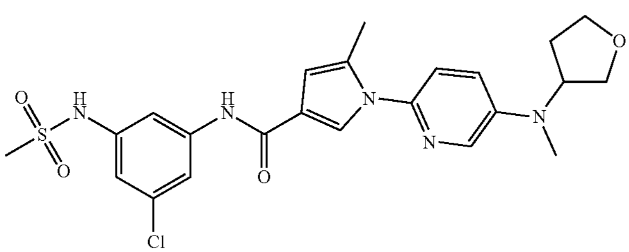 [SMILES: Cc1cc(C(=O)Nc2cc(Cl)cc(NS(C)(=O)=O)c2)cn1-c1ccc(N(C)C2CCOC2)cn1] | 674 | 504.1 | ¹H NMR (300 MHz, DMSO-d6) δ 10.04 (s, 1H), 9.79 (s, 1H), 8.14 (d, J = 3.0 Hz, 1H), 7.80 (d, J = 2.0 Hz, 1H), 7.71 (t, J = 1.9 Hz, 1H), 7.62 (d, J = 2.0 Hz, 1H), 7.48-7.34 (m, 2H), 6.88 (t, J = 2.0 Hz, 1H), 6.52 (s, 1H), 4.66 (s, 1H), 3.97 (td, J = 8.4, 5.0 Hz, 1H), 3.86-3.71 (m, 2H), 3.65 (q, J = 8.0 Hz, 1H), 3.05 (s, 3H), 2.87 (s, 3H), 2.35-2.18 (m, 4H), 1.95-1.77 (m, 1H). |
| 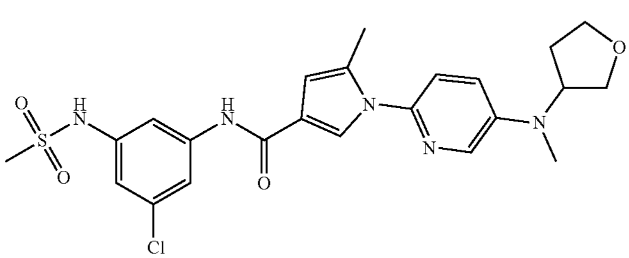 [SMILES: Cc1cc(C(=O)Nc2cc(Cl)cc(NS(C)(=O)=O)c2)cn1-c1ccc(N(C)C2CCOC2)cn1] | 675 | 504.1 | ¹H NMR (300 MHz, DMSO-d6) δ 10.02 (s, 1H), 9.80 (s, 1H), 8.14 (d, J = 2.7 Hz, 1H), 7.80 (d, J = 2.0 Hz, 1H), 7.76-7.68 (m, 1H), 7.63 (t, J = 1.9 Hz, 1H), 7.47-7.34 (m, 2H), 6.89 (t, J = 1.9 Hz, 1H), 6.56-6.49 (m, 1H), 4.66 (t, J = 7.3 |

| Structure | Example No. | MS (ESI) [M + H]+ | ¹H NMR |
|---|---|---|---|
| | | | Hz, 1H), 3.97 (td, J = 8.4, 5.1 Hz, 1H), 3.86-3.71 (m, 2H), 3.65 (q, J = 8.0 Hz, 1H), 3.06 (s, 3H), 2.87 (s, 3H), 2.35-2.17 (m, 4H), 1.94-1.77 (m, 1H). |
| 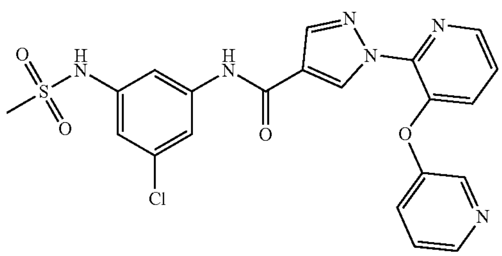 [SMILES: CS(=O)(=O)Nc1cc(Cl)cc(NC(=O)c2cnn(-c3ncccc3Oc3cccnc3)c2)c1] | 676 | 485.05 | ¹H NMR (300 MHz, DMSO-d6) δ 10.24 (s, 1H), 9.06 (d, J = 0.8 Hz, 1H), 8.48 (dd, J = 4.6, 1.4 Hz, 1H), 8.44-8.32 (m, 2H), 8.19 (d, J = 0.7 Hz, 1H), 7.85 (dd, J = 8.2, 1.5 Hz, 1H), 7.69 (t, J = 1.9 Hz, 1H), 7.65-7.57 (m, 2H), 7.50-7.35 (m, 2H), 6.94 (t, J = 1.9 Hz, 1H), 3.06 (s, 3H). |
| 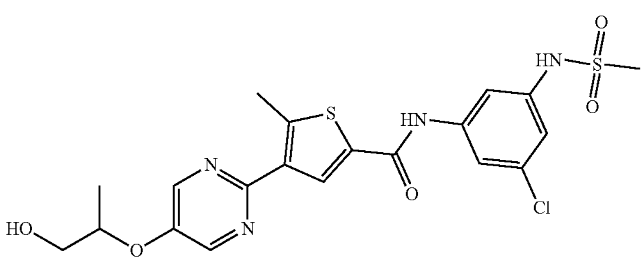 [SMILES: Cc1sc(C(=O)Nc2cc(Cl)cc(NS(C)(=O)=O)c2)cc1-c1ncc(OC(C)CO)cn1] | 677 | 497 | ¹H NMR (400 MHz, DMSO-d6) δ 10.57 (s, 1H), 10.06 (s, 1H), 8.65 (d, J = 6.9 Hz, 3H), 7.69 (dt, J = 6.4, 1.9 Hz, 2H), 6.94 (t, J = 2.0 Hz, 1H), 4.98 (t, J = 5.7 Hz, 1H), 4.71 (p, J = 5.8 Hz, 1H), 3.58 (t, J = 5.4 Hz, 2H), 3.07 (s, 3H), 2.83 (s, 3H), 1.27 (d, J = 6.2 Hz, 3H). |
| 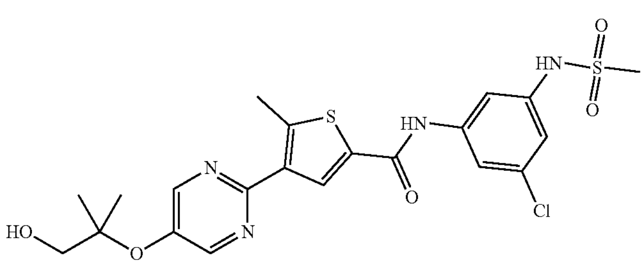 [SMILES: Cc1sc(C(=O)Nc2cc(Cl)cc(NS(C)(=O)=O)c2)cc1-c1ncc(OC(C)(C)CO)cn1] | 678 | 510.9 | ¹H NMR (400 MHz, DMSO-d6) δ 10.56 (s, 1H), 10.08 (s, 1H), 8.65 (d, J = 9.1 Hz, 3H), 7.68 (dt, J = 7.4, 1.9 Hz, 2H), 6.94 (t, J = 1.8 Hz, 1H), 4.74 (s, 1H), 3.97 (s, 2H), 3.06 (s, 3H), 2.83 (s, 3H), 1.23 (s, 6H). |

-continued

| Structure | Example No. | MS (ESI) [M + H]+ | 1H NMR |
|---|---|---|---|
| 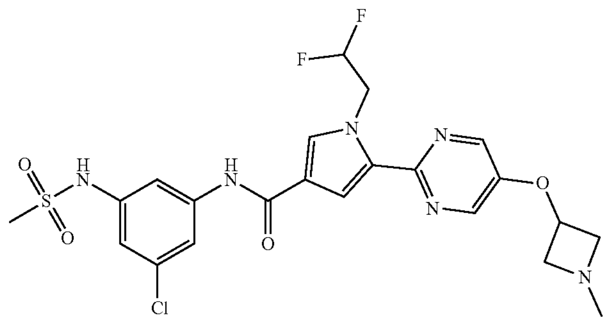 | 679 | 541.05 | 1H NMR (400 MHz, DMSO-d6) δ 10.00 (s, 1H), 8.48 (s, 2H), 7.77-7.70 (m, 2H), 7.67 (t, J = 1.9 Hz, 1H), 7.64 (d, J = 2.1 Hz, 1H), 6.91 (t, J = 2.0 Hz, 1H), 6.55-6.20 (m, 1H), 5.10 (td, J = 14.5, 3.9 Hz, 2H), 4.98 (p, J = 5.5 Hz, 1H), 3.81-3.73 (m, 2H), 3.10-2.99 (m, 5H), 2.30 (s, 3H). |
| 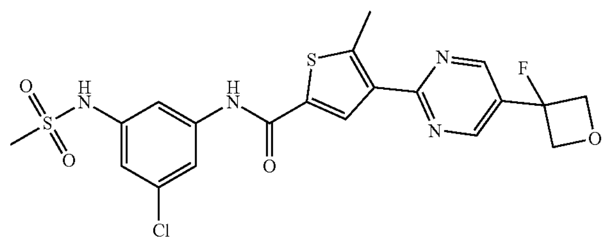 [SMILES: Cc1sc(C(=O)Nc2cc(Cl)cc(NS(C)(=O)=O)c2)cc1-c1ncc(C2(F)COC2)cn1] | 680 | 497.15 | 1H NMR (400 MHz, DMSO-d6) δ 10.64 (s, 1H), 10.07 (s, 1H), 9.11 (d, J = 1.1 Hz, 2H), 8.76 (s, 1H), 7.69 (dt, J = 8.2, 1.9 Hz, 2H), 6.95 (t, J = 1.9 Hz, 1H), 5.17-4.96 (m, 4H), 3.07 (s, 3H), 2.90 (s, 3H). |
| 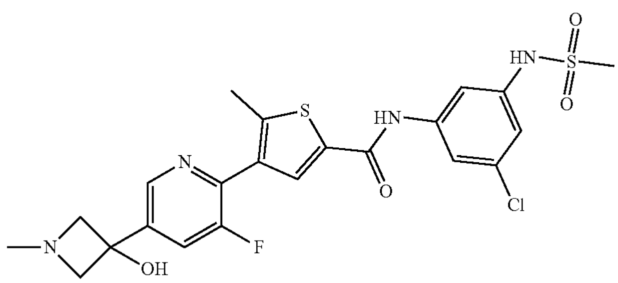 | 681 | 525.1 | 1H NMR (400 MHz, DMSO-d6) δ 10.46 (s, 1H), 10.07 (s, 1H), 8.51 (d, J = 4.8 Hz, 1H), 8.22 (d, J = 1.7 Hz, 1H), 7.67 (t, J = 1.9 Hz, 1H), 7.64 (t, J = 1.9 Hz, 1H), 7.58-7.51 (m, 1H), 6.95 (t, J = 1.9 Hz, 1H), 6.27 (s, 1H), 3.78-3.72 (m, 2H), 3.38 (d, J = 7.9 Hz, 2H), 3.06 (s, 3H), 2.54 (d, J = 1.2 Hz, 3H), 2.31 (s, 3H). |
| 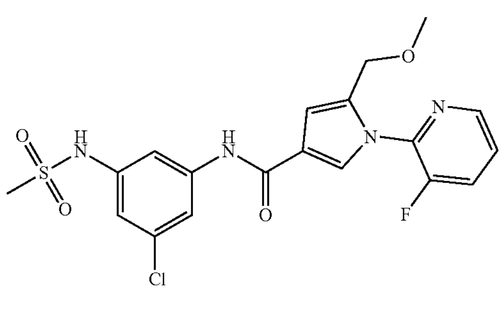 [SMILES: COCc1cc(C(=O)Nc2cc(Cl)cc(NS(C)(=O)=O)c2)cn1-c1ncccc1F] | 682 | 451.05 [M − H]− | 1H NMR (400 MHz, DMSO-d6) δ 9.92 (s, 2H), 8.44 (d, J = 4.7 Hz, 1H), 8.06 (t, J = 9.3 Hz, 1H), 7.90 (t, J = 2.1 Hz, 1H), 7.69 (s, 1H), 7.66-7.59 (m, 2H), 6.90 (d, J = 1.8 Hz, 2H), 4.48 (s, 2H), 3.03 (d, J = 4.1 Hz, 6H). |

| Structure | Example No. | MS (ESI) [M + H]+ | ¹H NMR |
|---|---|---|---|
| 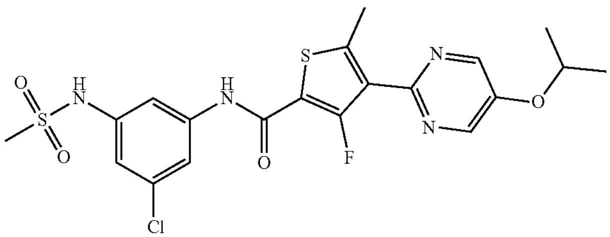 [SMILES: Cc1sc(C(=O)Nc2cc(Cl)cc(NS(C)(=O)=O)c2)c(F)c1-c1ncc(OC(C)C)cn1] | 683 | 499.05 | ¹H NMR (400 MHz, DMSO-d6) δ 10.17 (d, J = 2.0 Hz, 1H), 10.06 (s, 1H), 8.68 (s, 2H), 7.59 (dt, J = 4.2, 1.9 Hz, 2H), 6.96 (t, J = 2.0 Hz, 1H), 4.89 (p, J = 6.0 Hz, 1H), 3.07 (s, 3H), 2.65 (s, 3H), 1.35 (d, J = 6.0 Hz, 6H). |
| 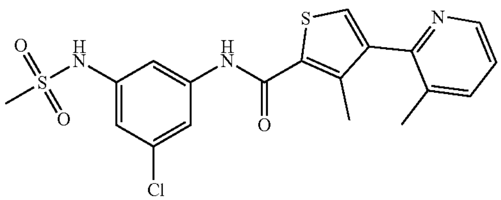 [SMILES: Cc1cccnc1-c1csc(C(=O)Nc2cc(Cl)cc(NS(C)(=O)=O)c2)c1C] | 684 | 436.05 | ¹H NMR (400 MHz, DMSO-d6) δ 10.38 (s, 1H), 10.06 (s, 1H), 8.49 (dd, J = 4.7, 1.6 Hz, 1H), 7.76 (d, J = 9.2 Hz, 2H), 7.60 (dt, J = 15.0, 1.8 Hz, 2H), 7.33 (dd, J = 7.7, 4.8 Hz, 1H), 6.96 (t, J = 1.9 Hz, 1H), 3.07 (s, 3H), 2.20 (s, 6H). |
| 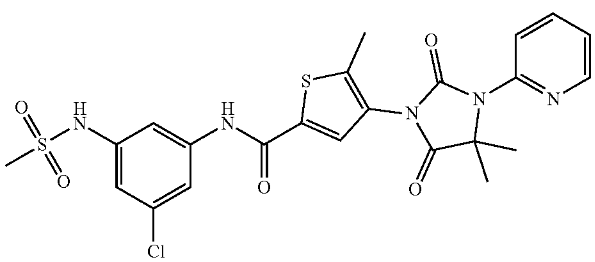 [SMILES: Cc1sc(C(=O)Nc2cc(Cl)cc(NS(C)(=O)=O)c2)cc1N1C(=O)N(c2ccccn2)C(C)(C)C1=O] | 685 | 547.9 | ¹H NMR (400 MHz, DMSO-d6) δ 10.51 (s, 1H), 10.04 (s, 1H), 8.46 (dd, J = 4.9, 1.9 Hz, 1H), 8.12-8.05 (m, 1H), 8.02 (s, 1H), 7.90 (tt, J = 8.5, 1.5 Hz, 1H), 7.67 (q, J = 1.6 Hz, 1H), 7.61 (q, J = 1.7 Hz, 1H), 7.27-7.20 (m, 1H), 6.95 (q, J = 1.7 Hz, 1H), 3.06 (d, J = 1.0 Hz, 3H), 2.41-2.35 (m, 3H), 1.87-1.80 (m, 6H). |
| 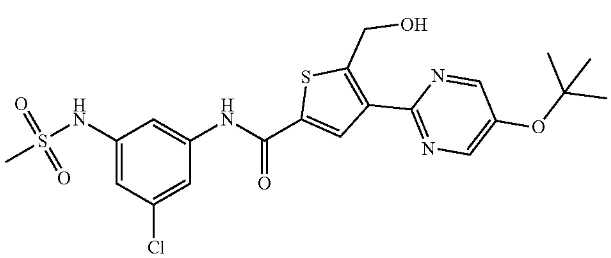 [SMILES: CC(C)(C)Oc1cnc(-c2cc(C(=O)Nc3cc(Cl)cc(NS(C)(=O)=O)c3)sc2CO)nc1] | 686 | 510.95 | ¹H NMR (300 MHz, DMSO-d6) δ 10.58 (s, 1H), 10.08 (s, 1H), 8.71 (s, 1H), 8.64 (s, 2H), 7.70 (dt, J = 5.6, 1.9 Hz, 2H), 6.95 (t, J = 2.0 Hz, 1H), 6.29-5.82 (m, 1H), 5.13 (d, J = 5.5 Hz, 2H), 3.08 (s, 3H), 1.38 (s, 9H). |

-continued
| Structure | Example No. | MS (ESI) [M + H]+ | ¹H NMR |
|---|---|---|---|
| 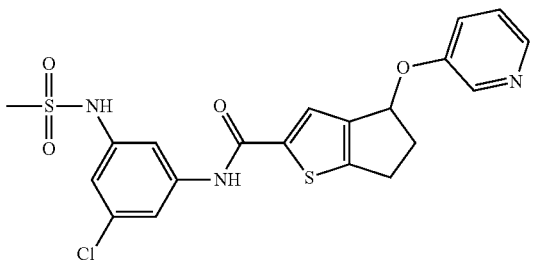 [SMILES: CS(=O)(=O)Nc1cc(Cl)cc(NC(=O)c2cc3c(s2)CCC3Oc2cccnc2)c1] | 687 | 463.9 | ¹H NMR (300 MHz, DMSO-d6) δ 10.40 (s, 1H), 10.06 (s, 1H), 8.37 (d, J = 2.9 Hz, 1H), 8.23 (dd, J = 4.6, 1.3 Hz, 1H), 7.98 (s, 1H), 7.67 (t, J = 1.8 Hz, 1H), 7.60 (t, J = 1.9 Hz, 1H), 7.55-7.50 (m, 1H), 7.39 (dd, J = 8.4, 4.5 Hz, 1H), 6.94 (t, J = 1.9 Hz, 1H), 5.92 (d, J = 5.7 Hz, 1H), 3.19-3.10 (m, 1H), 3.06 (s, 3H), 3.03-2.95 (m, 2H), 2.43 (d, J = 10.6 Hz, 1H). |
| 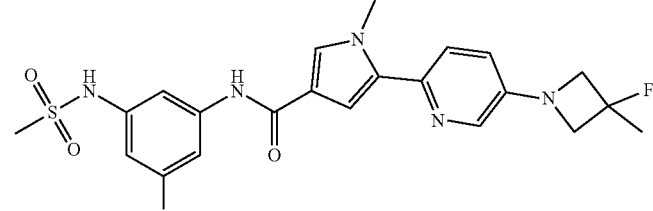 | 688 | 492.1 | ¹H NMR (300 MHz, DMSO-d6) δ 10.01 (s, 1H), 9.79 (s, 1H), 7.95-7.87 (m, 1H), 7.72 (t, J = 1.9 Hz, 1H), 7.65-7.57 (m, 2H), 7.52 (d, J = 8.6 Hz, 1H), 6.99 (q, J = 3.2 Hz, 2H), 6.89 (t, J = 1.9 Hz, 1H), 4.14-3.94 (m, 4H), 3.90 (s, 3H), 3.06 (s, 3H), 1.65 (d, J = 22.1 Hz, 3H). |
| 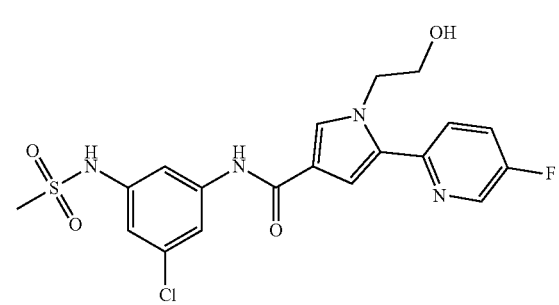 [SMILES: CS(=O)(=O)Nc1cc(Cl)cc(NC(=O)c2cc(-c3ccc(F)cn3)n(CCO)c2)c1] | 689 | 453.1 | ¹H NMR (400 MHz, DMSO-d6) δ 10.00 (s, 1H), 9.85 (s, 1H), 8.57 (d, J = 2.4 Hz, 1H), 7.83-7.76 (m, 2H), 7.75-7.69 (m, 2H), 7.63 (t, J = 2.0 Hz, 1H), 7.18 (d, J = 2.0 Hz, 1H), 6.90 (t, J = 2.0 Hz, 1H), 4.89 (t, J = 5.2 Hz, 1H), 4.47 (t, J = 5.6 Hz, 2H), 3.64 (q, J = 5.5 Hz, 2H), 3.06 (s, 3H). |

-continued

| Structure | Example No. | MS (ESI) [M + H]+ | ¹H NMR |
|---|---|---|---|
| 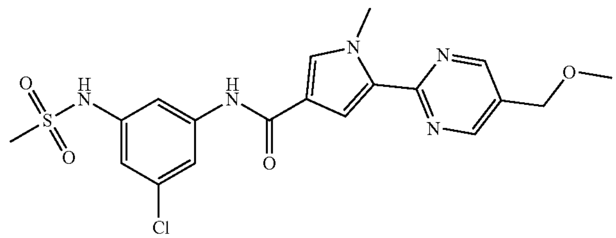 | 690 | 450 | ¹H NMR (400 MHz, DMSO-d6) δ 9.98 (d, J = 29.4 Hz, 2H), 8.76 (s, 2H), 7.95-7.47 (m, 4H), 6.90 (t, J = 2.0 Hz, 1H), 4.46 (s, 2H), 4.10 (s, 3H), 3.35 (s, 3H), 3.06 (s, 3H). |
| 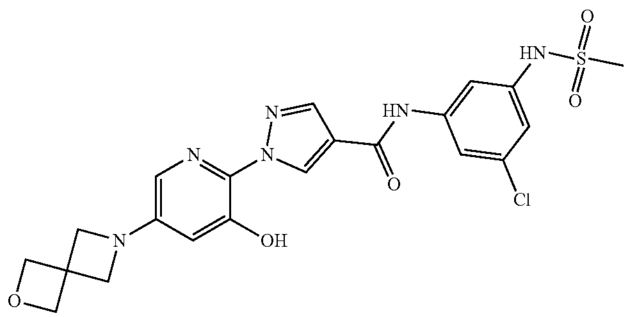 [SMILES: CS(=O)(=O)Nc1cc(Cl)cc(NC(=O)c2cnn(-c3ncc(N4CC5(COC5)C4)cc3O)c2)c1] | 691 | 505.05 | ¹H NMR (300 MHz, DMSO-d6) δ 10.72 (s, 1H), 10.25 (s, 1H), 10.09 (s, 1H), 9.06 (s, 1H), 8.28 (s, 1H), 7.72 (t, J = 1.9 Hz, 1H), 7.62 (t, J = 1.9 Hz, 1H), 7.30 (d, J = 2.4 Hz, 1H), 6.95 (t, J = 2.0 Hz, 1H), 6.54 (d, J = 2.4 Hz, 1H), 4.74 (s, 4H), 4.10 (s, 4H), 3.07 (s, 3H). |
| 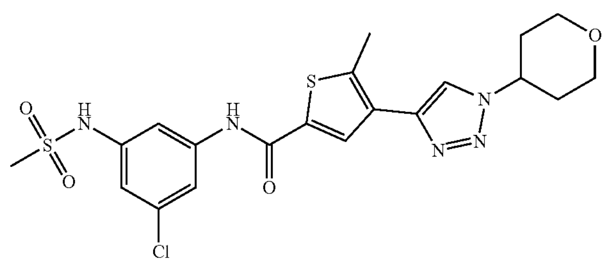 [SMILES: Cc1sc(C(=O)Nc2cc(Cl)cc(NS(C)(=O)=O)c2)cc1-c1cn(C2CCOCC2)nn1] | 692 | 496.25 | ¹H NMR (300 MHz, DMSO-d6) δ 10.51 (s, 1H), 10.07 (s, 1H), 8.52 (s, 1H), 8.42 (s, 1H), 7.68 (dt, J = 8.6, 1.9 Hz, 2H), 6.95 (t, J = 1.9 Hz, 1H), 4.85 (p, J = 8.0, 7.5 Hz, 1H), 4.06-3.95 (m, 2H), 3.54 (td, J = 11.3, 5.4 Hz, 2H), 3.08 (s, 3H), 2.64 (s, 3H), 2.18-2.02 (m, 4H). |
| 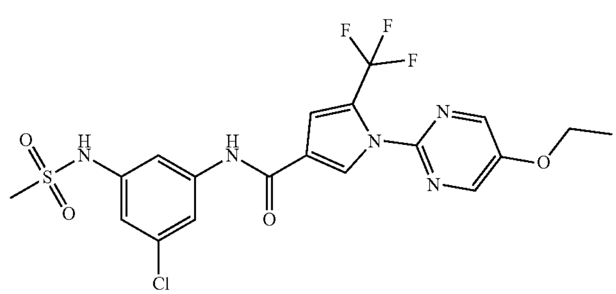 [SMILES: CCOc1cnc(-n2cc(C(=O)Nc3cc(Cl)cc(NS(C)(=O)=O)c3)cc2C(F)(F)F)nc1] | 693 | 504.1 | ¹H NMR (400 MHz, DMSO-d6) δ 10.22 (s, 1H), 10.04 (s, 1H), 8.69 (s, 2H), 8.58 (d, J = 2.1 Hz, 1H), 7.71 (t, J = 1.9 Hz, 1H), 7.63 (t, J = 1.9 Hz, 1H), 7.48 (d, J = 2.2 Hz, 1H), 6.94 (t, J = 2.0 Hz, 1H), 4.28 (q, J = 6.9 Hz, 2H), 3.06 (s, 3H), 1.39 (t, J = 6.9 Hz, 3H). |

| Structure | Example No. | MS (ESI) [M + H]+ | ¹H NMR |
|---|---|---|---|
| 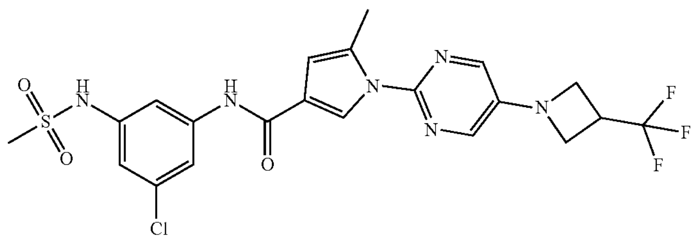 [SMILES: Cc1cc(C(=O)Nc2cc(Cl)cc(NS(C)(=O)=O)c2)cn1-c1ncc(N2CC(C(F)(F)F)C2)cn1] | 694 | 529.1 | ¹H NMR (400 MHz, DMSO-d6) δ 8.24 (d, J = 2.1 Hz, 1H), 8.19 (s, 2H), 7.68 (dt, J = 8.5, 1.9 Hz, 2H), 6.92 (t, J = 1.9 Hz, 1H), 6.54 (t, J = 1.7 Hz, 1H), 4.24 (t, J = 8.6 Hz, 2H), 4.07 (dd, J = 8.6, 5.1 Hz, 2H), 3.74 (dt, J = 9.4, 4.8 Hz, 1H), 3.06 (s, 3H), 2.50 (s, 3H). |
| 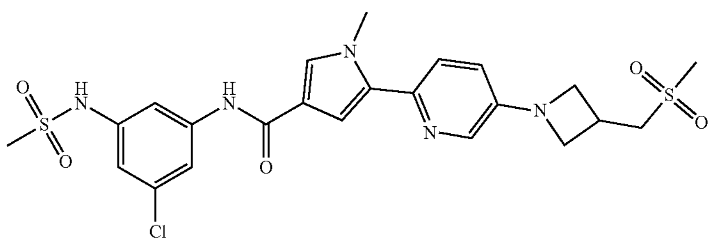 [SMILES: Cn1cc(C(=O)Nc2cc(Cl)cc(NS(C)(=O)=O)c2)cc1-c1ccc(N2CC(CS(C)(=O)=O)C2)cn1] | 695 | 552.15 | ¹H NMR (400 MHz, DMSO-d6) δ 10.00 (s, 1H), 9.78 (s, 1H), 7.85 (d, J = 2.9 Hz, 1H), 7.72 (t, J = 1.9 Hz, 1H), 7.66-7.54 (m, 2H), 7.49 (d, J = 8.6 Hz, 1H), 7.02-6.91 (m, 2H), 6.88 (t, J = 1.9 Hz, 1H), 4.14 (t, J = 7.7 Hz, 2H), 3.90 (s, 3H), 3.75 (dd, J = 7.6, 6.2 Hz, 2H), 3.57 (d, J = 7.4 Hz, 2H), 3.27 (dd, J = 14.6, 7.4 Hz, 1H), 3.03 (d, J = 24.1 Hz, 6H). |
| 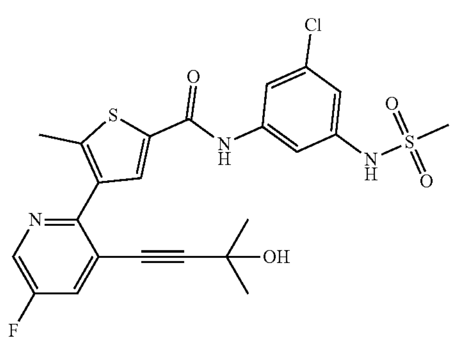 [SMILES: Cc1sc(C(=O)Nc2cc(Cl)cc(NS(C)(=O)=O)c2)cc1-c1ncc(F)cc1C#CC(C)(C)O] | 696 | 522.1 | ¹H NMR (300 MHz, DMSO-d6) δ 10.35 (s, 1H), 10.08 (s, 1H), 8.69 (d, J = 2.8 Hz, 1H), 8.23 (s, 1H), 7.96 (dd, J = 9.2, 2.9 Hz, 1H), 7.64 (dt, J = 14.4, 1.9 Hz, 2H), 6.95 (t, J = 2.0 Hz, 1H), 5.48 (s, 1H), 3.07 (s, 3H), 2.48 (s, 3H), 1.35 (s, 6H). |
| 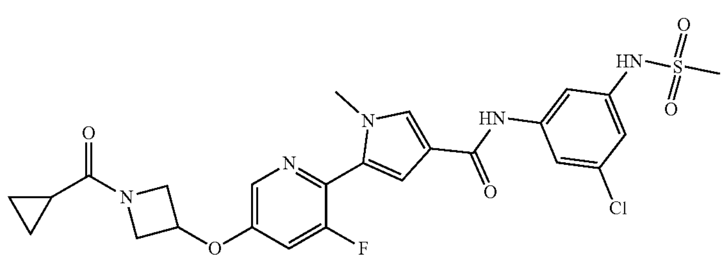 [SMILES: Cn1cc(C(=O)Nc2cc(Cl)cc(NS(C)(=O)=O)c2)cc1-c1ncc(OC2CN(C(=O)C3CC3)C2)cc1F] | 697 | 562.05 | ¹H NMR (300 MHz, DMSO-d6) δ 10.01 (s, 1H), 9.87 (s, 1H), 8.32-8.14 (m, 1H), 7.72 (q, J = 1.8 Hz, 2H), 7.64 (t, J = 1.9 Hz, 1H), 7.54 (dd, J = 12.2, 2.4 Hz, 1H), 7.11 (dd, J = 3.4, 1.9 Hz, |

| Structure | Example No. | MS (ESI) [M + H]+ | ¹H NMR |
|---|---|---|---|
| | | | 1H), 6.90 (t, J = 1.9 Hz, 1H), 5.30-5.17 (m, 1H), 4.77 (t, J = 8.1 Hz, 1H), 4.45-4.32 (m, 1H), 4.28 (d, J = 9.6 Hz, 1H), 3.87 (s, 4H), 3.06 (s, 3H), 1.67-1.51 (m, 1H), 0.73 (t, J = 5.4 Hz, 4H). |
| 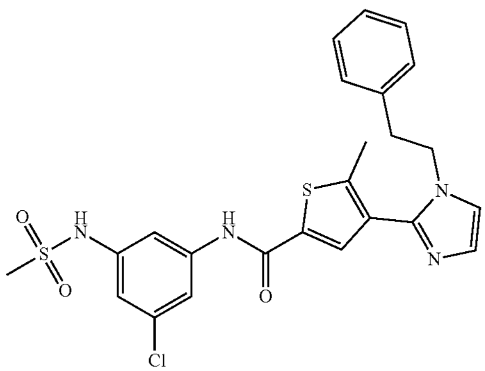 [SMILES: Cc1sc(C(=O)Nc2cc(Cl)cc(NS(C)(=O)=O)c2)cc1-c1nccn1CCc1ccccc1] | 698 | 515.1 | ¹H NMR (300 MHz, DMSO-d6) δ 10.32 (s, 1H), 7.85 (s, 1H), 7.64 (dt, J = 16.5, 1.9 Hz, 2H), 7.34 (d, J = 1.3 Hz, 1H), 7.23-7.13 (m, 3H), 7.04-6.94 (m, 4H), 4.20 (t, J = 6.9 Hz, 2H), 3.07 (s, 3H), 2.92 (t, J = 6.9 Hz, 2H), 2.27 (s, 3H). |
| 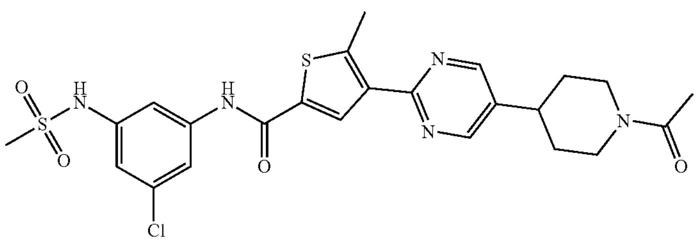 [SMILES: CC(=O)N1CCC(c2cnc(-c3cc(C(=O)Nc4cc(Cl)cc(NS(C)(=O)=O)c4)sc3C)nc2)CC1] | 699 | 548.25 | ¹H NMR (300 MHz, DMSO-d6) δ 10.59 (s, 1H), 10.07 (s, 1H), 8.84 (s, 2H), 8.71 (s, 1H), 7.70 (p, J = 1.9 Hz, 2H), 6.95 (t, J = 2.0 Hz, 1H), 4.58 (d, J = 12.9 Hz, 1H), 3.97 (d, J = 13.4 Hz, 1H), 3.16 (t, J = 12.3 Hz, 1H), 3.08 (s, 3H), 2.92 (d, J = 12.2 Hz, 1H), 2.87 (s, 3H), 2.62 (t, J = 12.5 Hz, 1H), 2.05 (s, 3H), 1.86 (d, J = 12.0 Hz, 2H), 1.79-1.54 (m, 2H). |
| 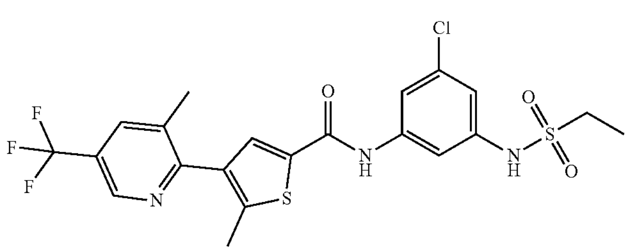 [SMILES: CCS(=O)(=O)Nc1cc(Cl)cc(NC(=O)c2cc(-c3ncc(C(F)(F)F)cc3C)c(C)s2)c1] | 700 | 517.9 | ¹H NMR (300 MHz, DMSO-d6) δ 10.35 (s, 1H), 10.14 (s, 1H), 8.89 (s, 1H), 8.25 (d, J = 2.3 Hz, 1H), 8.03 (s, 1H), 7.64 (t, J = 1.9 Hz, 1H), 7.59 (t, J = 1.9 Hz, 1H), 6.95 (t, J = 1.9 Hz, 1H), 3.16 (q, J = 7.3 Hz, 2H), 2.37 (d, J = 8.1 Hz, 6H), 1.21 (t, J = 7.3 Hz, 3H). |

-continued

| Structure | Example No. | MS (ESI) [M + H]+ | ¹H NMR |
|---|---|---|---|
| 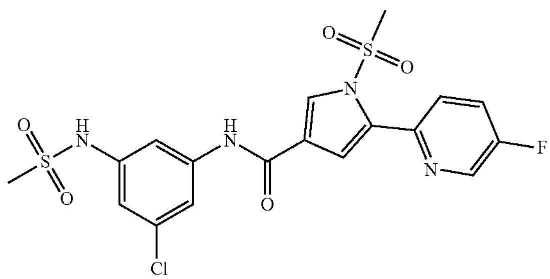 [SMILES: CS(=O)(=O)Nc1cc(Cl)cc(NC(=O)c2cc(-c3ccc(F)cn3)n(S(C)(=O)=O)c2)c1] | 701 | 486.85 | ¹H NMR (400 MHz, DMSO-d6) δ 10.22 (s, 1H), 10.14-9.93 (m, 1H), 8.68 (s, 1H) 8.28 (t, J = 1.6 Hz, 1H), 7.92-7.76 (m, 2H), 7.71 (q, J = 1.6 Hz, 1H), 7.63 (q, J = 1.7 Hz, 1H), 7.27-7.09 (m, 1H), 6.94 (q, J = 1.8 Hz, 1H), 4.08 (s, 3H), 3.07 (d, J = 1.1 Hz, 3H). |
| 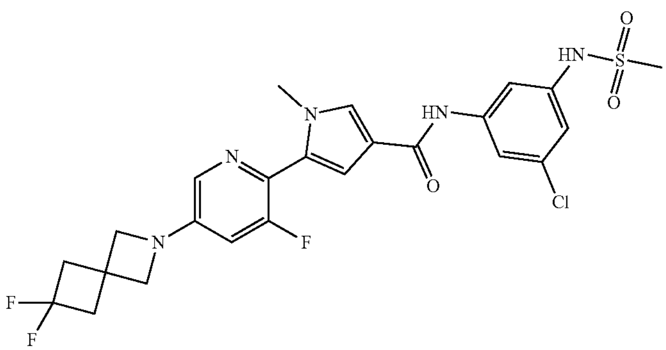 [SMILES: Cn1cc(C(=O)Nc2cc(Cl)cc(NS(C)(=O)=O)c2)cc1-c1ncc(N2CC3(C2)CC(F)(F)C3)cc1F] | 702 | 554 | ¹H NMR (400 MHz, DMSO-d6) δ 9.99 (s, 1H), 9.81 (s, 1H), 7.81-7.46 (m, 4H), 7.13-6.76 (m, 3H), 4.06 (s, 4H), 3.80 (s, 3H), 3.06 (s, 3H), 2.89 (t, J = 12.5 Hz, 4H). |
| 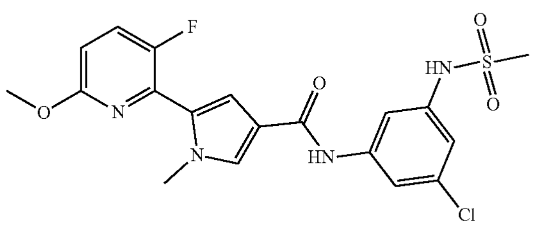 | 703 | 453.05 | ¹H NMR (400 MHz, DMSO-d6) δ 10.01 (s, 1H), 9.91 (s, 1H), 7.80-7.76 (m, 1H), 7.76-7.74 (m, 1H), 7.72 (q, J = 1.5 Hz, 1H), 7.65 (dt, J = 2.7, 1.3 Hz, 1H), 7.28 (dd, J = 3.6, 1.9 Hz, 1H), 6.90 (dt, J = 2.8, 1.4 Hz, 1H), 6.78 (ddd, J = 8.8, 2.7, 0.9 Hz, 1H), 4.01 (d, J = 1.0 Hz, 3H), 3.89 (d, J = 0.9 Hz, 3H), 3.06 (d, J = 1.0 Hz, 3H). |
| 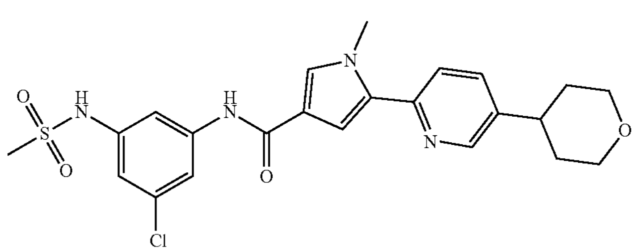 [SMILES: Cn1cc(C(=O)Nc2cc(Cl)cc(NS(C)(=O)=O)c2)cc1-c1ccc(C2CCOCC2)cn1] | 704 | 489 | ¹H NMR (300 MHz, DMSO-d6) δ 10.02 (s, 1H), 9.85 (s, 1H), 8.54-8.47 (m, 1H), 7.84-7.51 (m, 5H), 7.18 (d, J = 1.9 Hz, 1H), 6.90 (t, J = 1.9 Hz, 1H), 3.98 (s, 5H), 3.53-3.38 (m, 2H), |

| Structure | Example No. | MS (ESI) [M + H]+ | ¹H NMR |
|---|---|---|---|
| | | | 3.07 (s, 3H), 2.91-2.80 (m, 1H), 1.78-1.66 (m, 4H). |
| 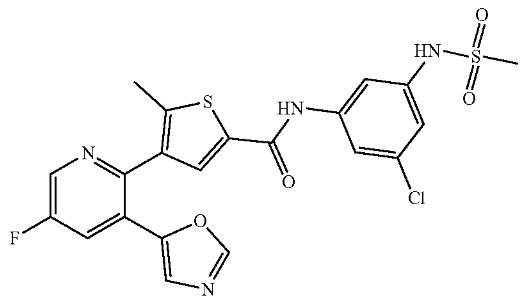 [SMILES: Cc1sc(C(=O)Nc2cc(Cl)cc(NS(C)(=O)=O)c2)cc1-c1ncc(F)cc1-c1cnco1] | 705 | 507 | ¹H NMR (400 MHz, DMSO-d6) δ 10.32 (s, 1H), 10.07 (s, 1H), 8.73 (d, J = 2.8 Hz, 1H), 8.53 (s, 1H), 8.18 (dd, J = 9.5, 2.9 Hz, 1H), 7.92 (s, 1H), 7.62 (d, J = 29.4 Hz, 2H), 6.93 (d, J = 2.1 Hz, 1H), 6.74 (s, 1H), 3.04 (s, 3H), 2.17 (s, 3H). |
| 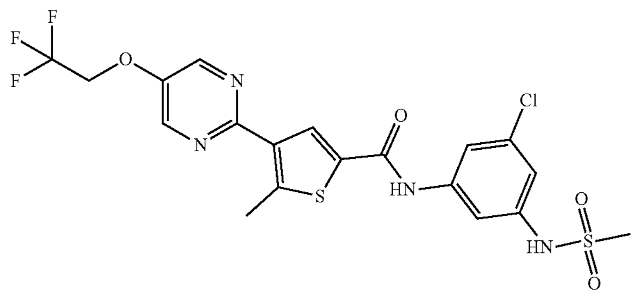 [SMILES: Cc1sc(C(=O)Nc2cc(Cl)cc(NS(C)(=O)=O)c2)cc1-c1ncc(OCC(F)(F)F)cn1] | 706 | 520.85 | ¹H NMR (400 MHz, DMSO-d6) δ 10.58 (s, 1H), 10.07 (s, 1H), 8.79 (s, 2H), 8.67 (s, 1H), 7.69 (dt, J = 5.8, 1.9 Hz, 2H), 6.95 (t, J = 1.9 Hz, 1H), 5.05 (q, J = 8.8 Hz, 2H), 3.07 (s, 3H), 2.84 (s, 3H). |
| 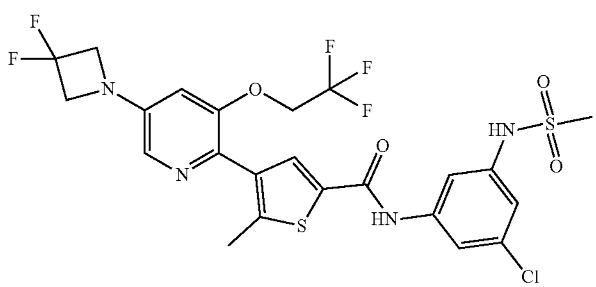 [SMILES: Cc1sc(C(=O)Nc2cc(Cl)cc(NS(C)(=O)=O)c2)cc1-c1ncc(N2CC(F)(F)C2)cc1OCC(F)(F)F] | 707 | 611.1 | ¹H NMR (300 MHz, DMSO-d6) δ 10.35 (s, 1H), 10.06 (s, 1H), 8.00 (s, 1H), 7.74 (d, J = 2.2 Hz, 1H), 7.68-7.59 (m, 2H), 6.94 (s, 2H), 4.85 (q, J = 8.9 Hz, 2H), 4.44 (t, J = 12.3 Hz, 4H), 3.06 (s, 3H), 2.38 (s, 3H). |
| 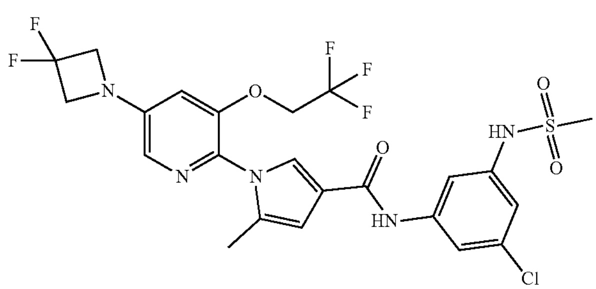 [SMILES: Cc1cc(C(=O)Nc2cc(Cl)cc(NS(C)(=O)=O)c2)cn1-c1ncc(N2CC(F)(F)C2)cc1OCC(F)(F)F] | 708 | 593.9 | ¹H NMR (400 MHz, DMSO-d6) δ 10.00 (s, 1H), 9.76 (s, 1H), 7.70 (t, J = 1.9 Hz, 1H), 7.62 (s, 1H), 7.59 (d, J = 2.3 Hz, 1H), 7.51 (d, J = 2.0 Hz, 1H), 7.07 (d, J = 2.4 Hz, 1H), 6.88 (t, J = 2.0 Hz, 1H), 6.50 (dd, J = 2.1, 1.1 Hz, 1H), 4.89 (q, J = 8.8 Hz, 2H), 4.47 (t, J = 12.3 Hz, 4H), 3.05 (s, 3H), 2.03 (d, J = 0.9 Hz, 3H). |

-continued
| Structure | Example No. | MS (ESI) [M + H]+ | ¹H NMR |
|---|---|---|---|
| 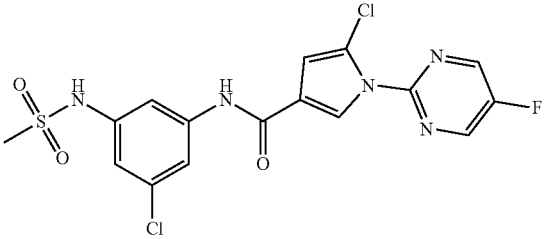 [SMILES: CS(=O)(=O)Nc1cc(Cl)cc(NC(=O)c2cc(Cl)n(-c3ncc(F)cn3)c2)c1] | 709 | 443.85 | ¹H NMR (400 MHz, DMSO-d6) δ 10.11 (s, 1H), 10.02 (s, 1H), 9.08 (s, 2H), 8.35 (d, J = 2.2 Hz, 1H), 7.69 (d, J = 2.2 Hz, 1H), 7.62 (d, J = 2.4 Hz, 1H), 6.92 (d, J = 2.3 Hz, 2H), 3.06 (s, 3H). |
| 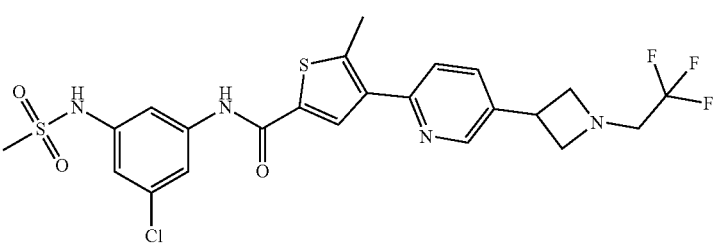 [SMILES: Cc1sc(C(=O)Nc2cc(Cl)cc(NS(C)(=O)=O)c2)cc1-c1ccc(C2CN(CC(F)(F)F)C2)cn1] | 710 | 558.95 | ¹H NMR (300 MHz, DMSO-d6) δ 10.46 (s, 1H), 10.07 (s,1H)8.65 (d, J = 2.3 Hz, 1H), 8.39 (s, 1H), 8.00 (dd, J = 8.3, 2.4 Hz, 1H), 7.77-7.60 (m, 3H), 6.95 (t, J = 1.9 Hz, 1H), 3.95-3.71 (m, 3H), 3.47-3.36 (m, 3H), 3.30 (s, 1H), 3.07 (s, 3H), 2.71 (s, 3H). |
| 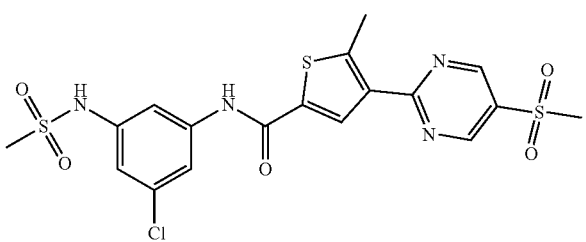 | 711 | 500.95 | ¹H NMR (300 MHz, DMSO-d6) δ 10.67 (s, 1H), 10.06 (s, 1H), 9.35 (s, 2H), 8.81 (s, 1H), 7.68 (dt, J = 8.4, 1.9 Hz, 2H), 6.95 (t, J = 1.9 Hz, 1H), 3.46 (s, 3H), 3.07 (s, 3H), 2.94 (s, 3H). |
| 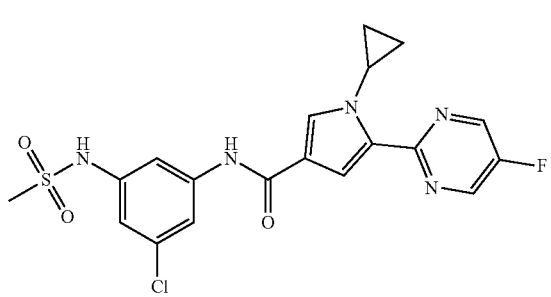 [SMILES: CS(=O)(=O)Nc1cc(Cl)cc(NC(=O)c2cc(-c3ncc(F)cn3)n(C3CC3)c2)c1] | 712 | 450 | ¹H NMR (400 MHz, DMSO-d6) δ 9.95 (d, J = 42.4 Hz, 2H), 8.91 (s, 2H), 7.75 (d, J = 2.1 Hz, 1H), 7.70 (s, 1H), 7.66 (s, 1H), 7.54 (d, J = 2.1 Hz, 1H), 6.90 (s, 1H), 4.08 (tt, J = 7.4, 4.2 Hz, 1H), 3.06 (s, 3H), 1.18-0.68 (m, 4H). |

| Structure | Example No. | MS (ESI) [M + H]+ | ¹H NMR |
|---|---|---|---|
| 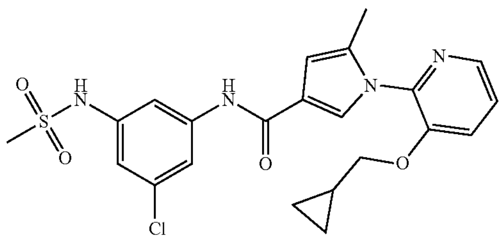 [SMILES: Cc1cc(C(=O)Nc2cc(Cl)cc(NS(C)(=O)=O)c2)cn1-c1ncccc1OCC1CC1] | 713 | 475.2 | ¹H NMR (400 MHz, DMSO-d6) δ 9.96 (s, 1H), 9.75 (s, 1H), 8.14 (dd, J = 4.7, 1.5 Hz, 1H), 7.73 (d, J = 8.2 Hz, 1H), 7.68 (dd, J = 6.4, 2.0 Hz, 2H), 7.60 (d, J = 2.6 Hz, 1H), 7.50 (dd, J = 8.3, 4.7 Hz, 1H), 6.87 (t, J = 2.0 Hz, 1H), 6.52 (d, J = 1.8 Hz, 1H), 3.96 (d, J = 6.9 Hz, 2H), 3.03 (d, J = 2.3 Hz, 3H), 2.12 (s, 3H), 1.16-1.14 (m, 1H), 0.56-0.49 (m, 2H), 0.29 (dd, J = 4.7, 1.8 Hz, 2H). |
| 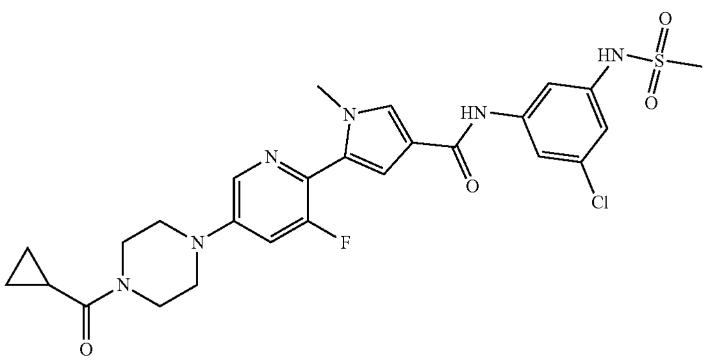 [SMILES: Cn1cc(C(=O)Nc2cc(Cl)cc(NS(C)(=O)=O)c2)cc1-c1ncc(N2CCN(C(=O)C3CC3)CC2)cc1F] | 714 | 575.25 | ¹H NMR (300 MHz, Chloroform-d) δ 8.16 (s, 1H), 8.00 (d, J = 24.0 Hz, 1H), 7.54 (d, J = 11.7 Hz, 3H), 7.44 (s, 1H), 7.02 (s, 2H), 6.93 (s, 1H), 3.84 (s, 7H), 3.36 (s, 4H), 3.05 (s, 3H), 1.28 (s, 1H), 1.06 (t, J = 3.8 Hz, 2H), 0.85 (dt, J = 7.0, 3.7 Hz, 2H). |
| 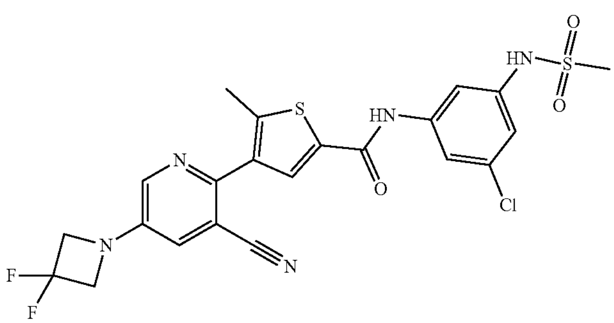 [SMILES: Cc1sc(C(=O)Nc2cc(Cl)cc(NS(C)(=O)=O)c2)cc1-c1ncc(N2CC(F)(F)C2)cc1C#N] | 715 | 538.25 | ¹H NMR (300 MHz, DMSO-d6) δ 10.44 (s, 1H), 10.08 (s, 1H), 8.31 (d, J = 2.9 Hz, 1H), 8.14 (s, 1H), 7.70-7.58 (m, 3H), 6.96 (t, J = 1.9 Hz, 1H), 4.51 (t, J = 12.3 Hz, 4H), 3.07 (s, 3H), 2.49 (s, 3H). |
| 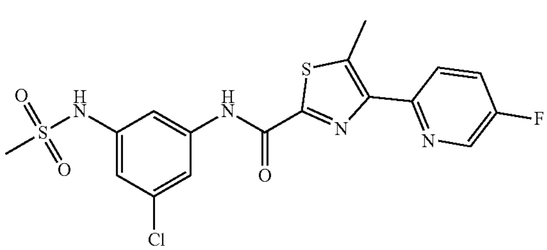 [SMILES: Cc1sc(C(=O)Nc2cc(Cl)cc(NS(C)(=O)=O)c2)nc1-c1ccc(F)cn1] | 716 | 441 | ¹H NMR (400 MHz, DMSO-d6) δ 10.78 (s, 1H), 10.12 (s, 1H), 8.69 (d, J = 3.0 Hz, 1H), 8.46 (dd, J = 8.9, 4.6 Hz, 1H), 7.95 (td, J = 8.8, 3.0 Hz, 1H), 7.79 (t, J = |

| Structure | Example No. | MS (ESI) [M + H]+ | 1H NMR |
|---|---|---|---|
| | | | 1.9 Hz, 1H), 7.73 (t, J = 1.9 Hz, 1H), 7.00 (t, J = 1.9 Hz, 1H), 3.09 (s, 3H), 2.90 (s, 3H). |
| 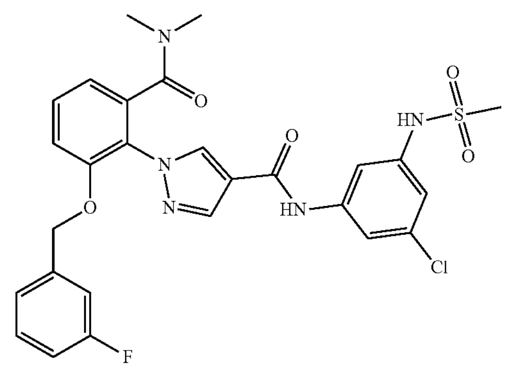 [SMILES: CN(C)C(=O)c1cccc(OCc2cccc(F)c2)c1-n1cc(C(=O)Nc2cc(Cl)cc(NS(C)(=O)=O)c2)cn1] | 717 | 586 | 1H NMR (300 MHz, DMSO-d6) δ 10.12 (s, 2H), 8.64 (s, 1H), 8.20 (s, 1H), 7.67 (t, J = 1.9 Hz, 1H), 7.58 (t, J = 2.1 Hz, 1H), 7.53 (d, J = 8.0 Hz, 1H), 7.43-7.32 (m, 2H), 7.15 (dd, J = 24.1, 8.1 Hz, 3H), 7.05 (d, J = 7.6 Hz, 1H), 6.94 (t, J = 2.0 Hz, 1H), 5.27 (s, 2H), 3.06 (s, 3H), 2.79 (d, J = 9.1 Hz, 6H). |
| 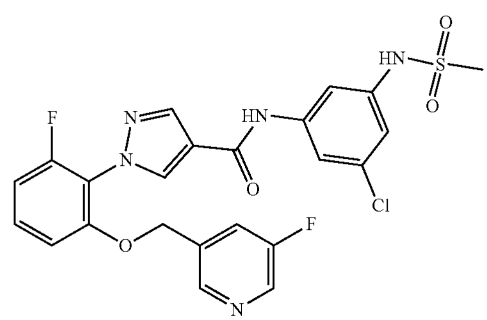 [SMILES: CS(=O)(=O)Nc1cc(Cl)cc(NC(=O)c2cnn(-c3c(F)cccc3OCc3cncc(F)c3)c2)c1] | 718 | 534 | 1H NMR (300 MHz, DMSO-d6) δ 10.16 (s, 2H), 8.68 (s, 1H), 8.52 (d, J = 2.8 Hz, 1H), 8.43 (d, J = 1.8 Hz, 1H), 8.33 (s, 1H), 7.68 (t, J = 1.9 Hz, 1H), 7.60 (ddt, J = 11.4, 9.2, 4.9 Hz, 3H), 7.23 (d, J = 8.6 Hz, 1H), 7.14 (t, J = 9.0 Hz, 1H), 6.94 (t, J = 1.9 Hz, 1H), 5.34 (s, 2H), 3.06 (s, 3H). |
| 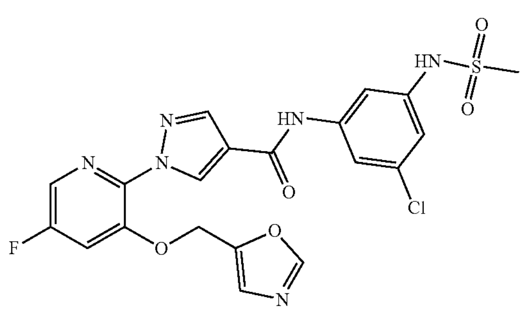 [SMILES: CS(=O)(=O)Nc1cc(Cl)cc(NC(=O)c2cnn(-c3ncc(F)cc3OCc3cnco3)c2)c1] | 719 | 507 | 1H NMR (400 MHz, DMSO-d6) δ 10.20 (s, 1H), 10.06 (s, 1H), 8.75 (s, 1H), 8.42 (s, 1H), 8.26 (d, J = 2.9 Hz, 2H), 8.11 (dd, J = 10.2, 2.5 Hz, 1H), 7.70 (t, J = 1.9 Hz, 1H), 7.60 (d, J = 2.0 Hz, 1H), 7.38 (s, 1H), 6.95 (t, J = 1.9 Hz, 1H), 5.43 (s, 2H), 3.07 (s, 3H). |

-continued
| Structure | Example No. | MS (ESI) [M + H]+ | 1H NMR |
|---|---|---|---|
| 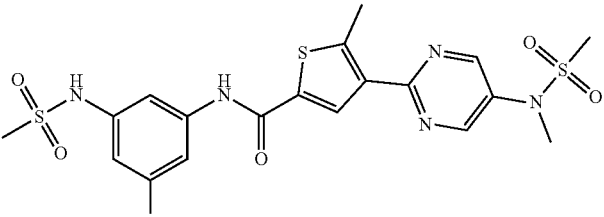 | 720 | 530.15 | 1H NMR (400 MHz, DMSO-d6) δ 10.62 (s, 1H), 10.08 (s, 1H), 8.96 (s, 2H), 8.72 (s, 1H), 7.69 (dt, J = 7.9, 1.9 Hz, 2H), 6.95 (t, J = 1.9 Hz, 1H), 3.38 (s, 3H), 3.14 (s, 3H), 3.07 (s, 3H), 2.88 (s, 3H). |
| 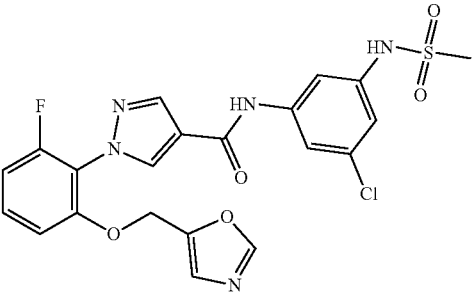 [SMILES: CS(=O)(=O)Nc1cc(Cl)cc(NC(=O)c2cnn(-c3c(F)cccc3OCc3cnco3)c2)c1] | 721 | 506 | 1H NMR (300 MHz, DMSO-d6) δ 10.15 (s, 1H), 8.52 (s, 1H), 8.38 (s, 1H), 8.27 (s, 1H), 7.76-7.47 (m, 3H), 7.32 (d, J = 15.8 Hz, 2H), 7.12 (t, J = 9.0 Hz, 1H), 6.92 (d, J = 2.1 Hz, 1H), 5.31 (s, 2H), 3.04 (s, 3H). |
| 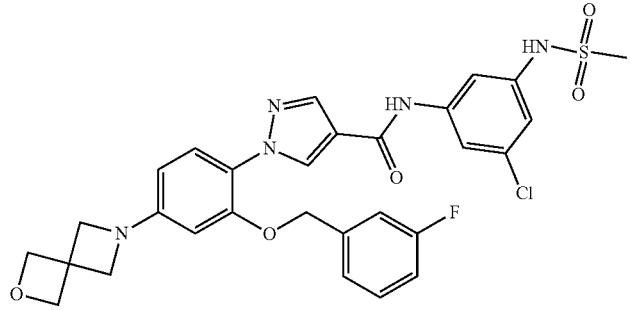 [SMILES: CS(=O)(=O)Nc1cc(Cl)cc(NC(=O)c2cnn(-c3ccc(N4CC5(COC5)C4)cc3OCc3cccc(F)c3)c2)c1] | 722 | 612 | 1H NMR (300 MHz, DMSO-d6) δ 10.07 (d, J = 5.5 Hz, 2H), 8.63 (d, J = 0.7 Hz, 1H), 8.20 (d, J = 0.7 Hz, 1H), 7.68 (t, J = 1.8 Hz, 1H), 7.59 (t, J = 1.9 Hz, 1H), 7.50-7.33 (m, 2H), 7.31-7.06 (m, 3H), 6.93 (t, J = 1.9 Hz, 1H), 6.29 (d, J = 2.3 Hz, 1H), 6.15 (dd, J = 8.6, 2.3 Hz, 1H), 5.23 (s, 2H), 4.74 (s, 4H), 4.04 (s, 4H), 3.07 (s, 3H). |
| 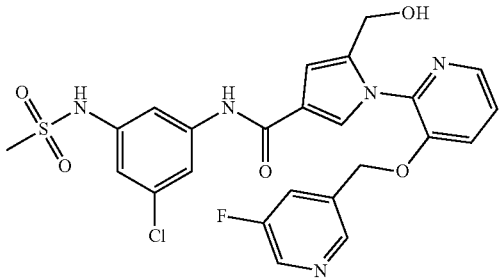 [SMILES: CS(=O)(=O)Nc1cc(Cl)cc(NC(=O)c2cc(CO)n(-c3ncccc3OCc3cncc(F)c3)c2)c1] | 723 | 546 | 1H NMR (400 MHz, DMSO-d6) δ 9.98 (s, 1H), 9.82 (s, 1H), 8.52 (d, J = 2.8 Hz, 1H), 8.47 (d, J = 1.8 Hz, 1H), 8.19 (dd, J = 4.7, 1.3 Hz, 1H), 7.92-7.81 (m, 2H), 7.75-7.66 (m, 2H), 7.62 (d, J = 2.0 Hz, 1H), 7.54 (dd, J = 8.3, 4.7 Hz, 1H), 6.89 (t, J = 2.0 Hz, 1H), 6.77 (d, J = 1.9 Hz, 1H), 5.33 (s, 2H), 4.93 (t, |

-continued

| Structure | Example No. | MS (ESI) [M + H]+ | 1H NMR |
|---|---|---|---|
| | | | J = 5.7 Hz, 1H), 4.41 (d, J = 5.7 Hz, 2H), 3.04 (s, 3H). |
| 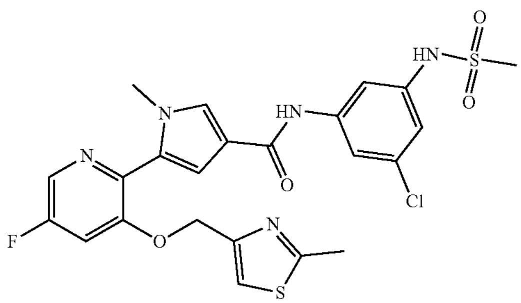 [SMILES: Cc1nc(COc2cc(F)cnc2-c2cc(C(=O)Nc3cc(Cl)cc(NS(C)(=O)=O)c3)cn2C)cs1] | 724 | 550 | 1H NMR (400 MHz, DMSO-d6) δ 9.89 (s, 1H), 9.80 (s, 1H), 8.27 (d, J = 2.4 Hz, 1H), 7.81 (dd, J = 11.0, 2.4 Hz, 1H), 7.72-7.54 (m, 4H), 7.08 (d, J = 2.0 Hz, 1H), 6.88 (t, J = 2.0 Hz, 1H), 5.29 (s, 2H), 3.74 (s, 3H), 3.05 (s, 3H), 2.65 (s, 3H). |
| 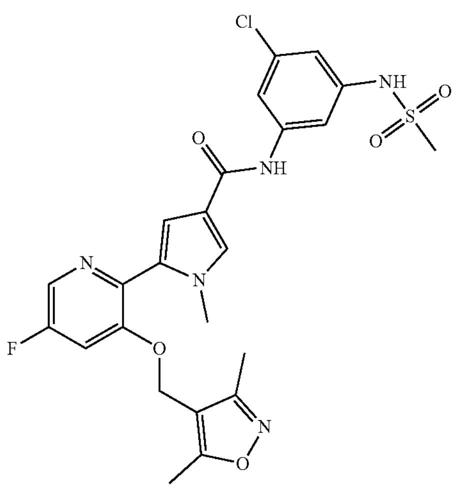 [SMILES: Cc1noc(C)c1COc1cc(F)cnc1-c1cc(C(=O)Nc2cc(Cl)cc(NS(C)(=O)=O)c2)cn1C] | 725 | 548 | 1H NMR (400 MHz, DMSO-d6) δ 9.99 (s, 1H), 9.79 (s, 1H), 8.30 (d, J = 2.3 Hz, 1H), 7.82 (dd, J = 11.0, 2.4 Hz, 1H), 7.71-7.64 (m, 2H), 7.63-7.57 (m, 1H), 6.95 (dd, J = 2.0, 0.9 Hz, 1H), 6.89 (t, J = 1.9 Hz, 1H), 5.08 (s, 2H), 3.70 (s, 3H), 3.05 (s, 3H), 2.38 (s, 3H), 2.13 (s, 3H). |
| 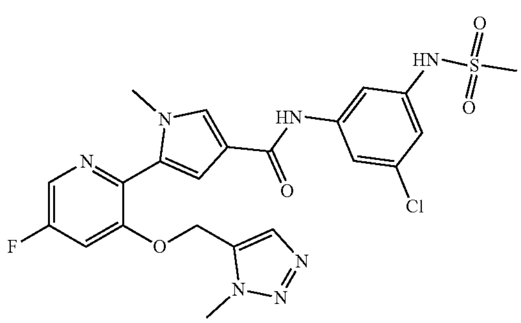 [SMILES: Cn1cc(C(=O)Nc2cc(Cl)cc(NS(C)(=O)=O)c2)cc1-c1ncc(F)cc1OCc1cnnn1C] | 726 | 534 | 1H NMR (400 MHz, DMSO-d6) δ 9.98 (s, 1H), 9.80 (s, 1H), 8.32 (d, J = 2.4 Hz, 1H), 7.88 (dd, J = 10.8, 2.4 Hz, 1H), 7.80 (s, 1H), 7.68 (d, J = 2.1 Hz, 2H), 7.59 (s, 1H), 7.00 (d, J = 2.0 Hz, 1H), 6.88 (s, 1H), 5.46 (s, 2H), 3.97 (s, 3H), 3.70 (s, 3H), 3.04 (s, 3H). |

| Structure | Example No. | MS (ESI) [M + H]+ | 1H NMR |
|---|---|---|---|
| 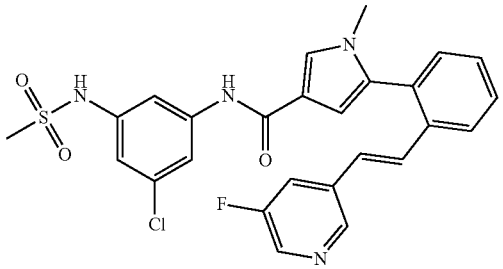 [SMILES: Cn1cc(C(=O)Nc2cc(Cl)cc(NS(C)(=O)=O)c2)cc1-c1ccccc1/C=C/c1cncc(F)c1] | 727 | 525 | 1H NMR (300 MHz, DMSO-d6) δ 10.01 (s, 1H), 9.80 (s, 1H), 8.53 (d, J = 1.8 Hz, 1H), 8.46 (d, J = 2.7 Hz, 1H), 7.91 (d, J = 8.0 Hz, 1H), 7.82 (dt, J = 10.4, 2.2 Hz, 1H), 7.76-7.68 (m, 2H), 7.62 (t, J = 1.9 Hz, 1H), 7.52-7.35 (m, 3H), 7.24-7.11 (d, J = 16.5 Hz, 2H), 6.89 (t, J = 1.9 Hz, 1H), 6.70 (d, J = 1.9 Hz, 1H), 3.44 (s, 3H), 3.06 (s, 3H). |
| 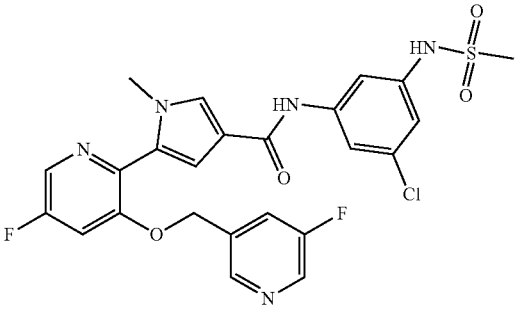 [SMILES: Cn1cc(C(=O)Nc2cc(Cl)cc(NS(C)(=O)=O)c2)cc1-c1ncc(F)cc1OCc1cncc(F)c1] | 728 | 546 | 1H NMR (300 MHz, DMSO-d6) δ 10.02 (s, 1H), 9.80 (s, 1H), 8.54 (d, J = 2.8 Hz, 1H), 8.37 (d, J = 2.8 Hz, 1H), 8.15 (t, J = 1.9 Hz, 1H), 7.87 (dd, J = 9.8, 2.9 Hz, 1H), 7.74 (dd, J = 9.8, 2.9 Hz, 1H), 7.65 (m, 1H), 7.63 (t, J = 1.9 Hz, 1H), 7.45 (ddd, J = 10.1, 2.8, 1.7 Hz, 1H), 6.94 (dd, J = 9.8, 2.9 Hz, 1H), 6.81 (m, 1H), 3.45 (s, 3H), 3.14-3.06 (s, 4H), 2.91 (dd, J = 9.0, 6.3 Hz, 2H). |
| 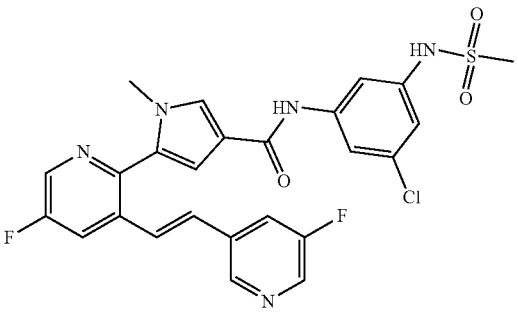 [SMILES: Cn1cc(C(=O)Nc2cc(Cl)cc(NS(C)(=O)=O)c2)cc1-c1ncc(F)cc1/C=C/c1cncc(F)c1] | 729 | 544 | 1H NMR (300 MHz, DMSO-d6) δ 9.97 (s, 1H), 9.82 (s, 1H), 8.66 (d, J = 2.7 Hz, 1H), 8.60 (d, J = 1.8 Hz, 1H), 8.50 (d, J = 2.7 Hz, 1H), 8.26 (dd, J = 10.1, 2.8 Hz, 1H), 7.98-7.87 (m, 1H), 7.77 (d, J = 1.9 Hz, 1H), 7.67 (t, J = 1.8 Hz, 1H), 7.59 (t, J = 1.9 Hz, 1H), 7.50-7.34 (m, 2H), 6.92-6.80 (m, 2H), 3.72 (s, 3H), 3.04 (s, 3H). |

-continued

| Structure | Example No. | MS (ESI) [M + H]+ | ¹H NMR |
|---|---|---|---|
| 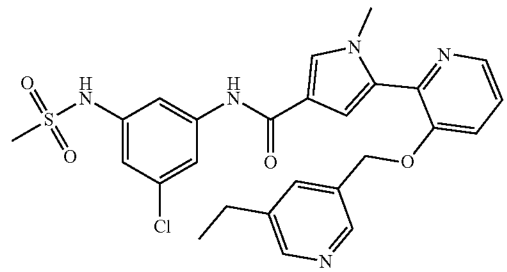 [SMILES: CCc1cncc(COc2cccnc2-c2cc(C(=O)Nc3cc(Cl)cc(NS(C)(=O)=O)c3)cn2C)c1] | 730 | 540 | ¹H NMR (400 MHz, DMSO-d6) δ 9.88 (s, 2H), 8.46 (d, J = 2.0 Hz, 1H), 8.38 (d, J = 2.1 Hz, 1H), 8.31-8.19 (m, 1H), 7.75 (d, J = 2.2 Hz, 1H), 7.73-7.62 (m, 4H), 7.36 (dd, J = 8.4, 4.6 Hz, 1H), 7.22 (d, J = 2.0 Hz, 1H), 6.90 (t, J = 2.0 Hz, 1H), 5.27 (s, 2H), 3.79 (s, 3H), 3.06 (s, 3H), 2.59 (q, J = 7.6 Hz, 2H), 1.12 (t, J = 7.6 Hz, 3H). |
| 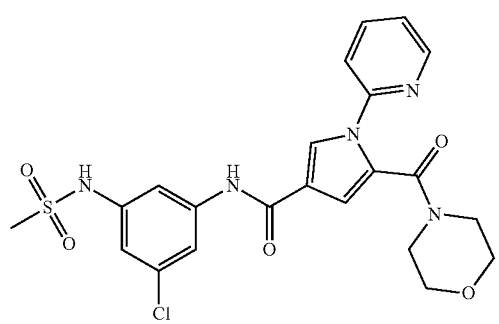 | 731 | 503.95 | ¹H NMR (300 MHz, DMSO-d6) δ 10.03 (s, 1H), 8.58-8.42 (m, 1H), 8.24 (d, J = 1.7 Hz, 1H), 8.03 (td, J = 7.8, 1.9 Hz, 1H), 7.70 (t, J = 1.8 Hz, 1H), 7.65-7.54 (m, 2H), 7.44 (dd, J = 7.5, 4.9 Hz, 1H), 7.02 (d, J = 1.8 Hz, 1H), 6.92 (t, J = 2.0 Hz, 1H), 3.54 (s, 8H), 3.06 (s, 3H). |
| 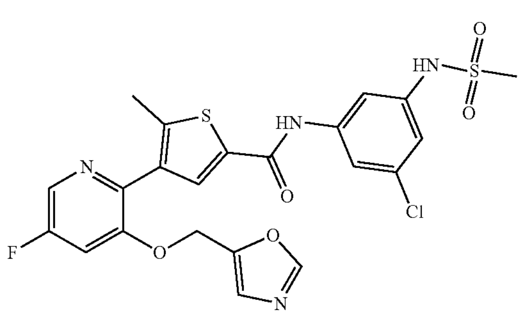 [SMILES: Cc1sc(C(=O)Nc2cc(Cl)cc(NS(C)(=O)=O)c2)cc1-c1ncc(F)cc1OCc1cnco1] | 732 | 537 | ¹H NMR (400 MHz, DMSO-d6) δ 10.34 (s, 1H), 10.06 (s, 1H), 8.40 (s, 1H), 8.33 (d, J = 2.4 Hz, 1H), 8.03 (s, 1H), 7.89 (dd, J = 10.9, 2.4 Hz, 1H), 7.66 (t, J = 1.9 Hz, 1H), 7.60 (t, J = 1.9 Hz, 1H), 7.37 (s, 1H), 6.94 (t, J = 1.9 Hz, 1H), 5.37 (s, 2H), 3.06 (s, 3H), 2.34 (s, 3H). |

| Structure | Example No. | MS (ESI) [M + H]+ | ¹H NMR |
|---|---|---|---|
| 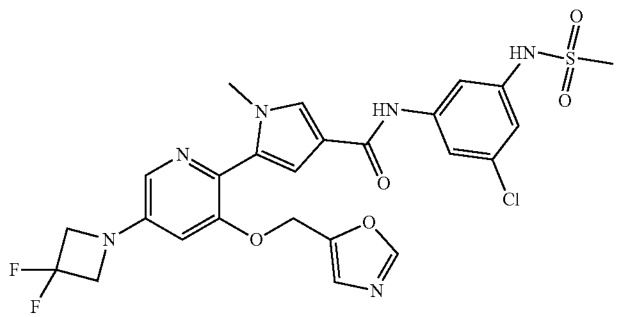 [SMILES: Cn1cc(C(=O)Nc2cc(Cl)cc(NS(C)(=O)=O)c2)cc1-c1ncc(N2CC(F)(F)C2)cc1OCc1cnco1] | 733 | 593 | ¹H NMR (400 MHz, DMSO-d6) δ 9.98 (s, 1H), 9.76 (s, 1H), 8.42 (s, 1H), 7.70 (t, J = 1.9 Hz, 1H), 7.65 (d, J = 2.2 Hz, 1H), 7.63-7.56 (m, 2H), 7.35 (s, 1H), 6.96 (d, J = 2.3 Hz, 1H), 6.88 (t, J = 2.0 Hz, 1H), 6.83 (d, J = 1.9 Hz, 1H), 5.31 (s, 2H), 4.43 (t, J = 12.2 Hz, 4H), 3.66 (s, 3H), 3.06 (s, 3H). |
| 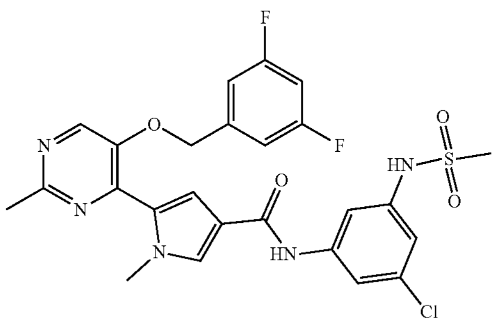 | 734 | 562.15 | ¹H NMR (400 MHz, DMSO-d6) δ 10.01 (s, 1H), 9.92 (s, 1H), 8.54 (s, 1H), 7.81 (d, J = 2.0 Hz, 1H), 7.65 (dt, J = 16.7, 1.9 Hz, 2H), 7.54 (d, J = 2.0 Hz, 1H), 7.22 (ddt, J = 9.5, 7.6, 2.8 Hz, 3H), 6.90 (t, J = 2.0 Hz, 1H), 5.39 (s, 2H), 3.99 (s, 3H), 3.06 (s, 3H), 2.58 (s, 3H). |
| 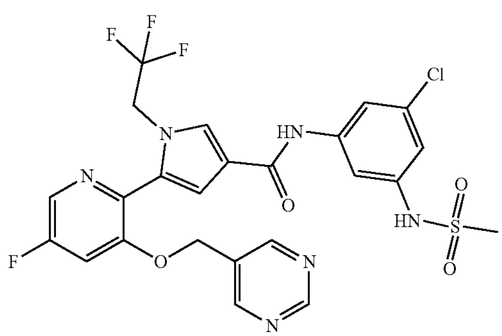 [SMILES: CS(=O)(=O)Nc1cc(Cl)cc(NC(=O)c2cc(-c3ncc(F)cc3OCc3cncnc3)n(CC(F)(F)F)c2)c1] | 735 | 599.1 | ¹H NMR (300 MHz, DMSO-d6) δ 10.04 (s, 1H), 9.98 (s, 1H), 9.18 (s, 1H), 8.90 (s, 2H), 8.32 (dd, J = 2.4, 0.6 Hz, 1H), 7.92-7.79 (m, 2H), 7.65 (dt, J = 10.5, 1.8 Hz, 2H), 7.25 (d, J = 1.9 Hz, 1H), 6.93 (t, J = 1.9 Hz, 1H), 5.51-5.36 (m, 4H), 3.07 (s, 3H). |

| Structure | Example No. | MS (ESI) [M + H]+ | 1H NMR |
|---|---|---|---|
| (structure shown) | 736 | 474 | 1H NMR (400 MHz, DMSO-d6) δ 10.41 (s, 1H), 10.18 (s, 1H), 8.75 (dt, J = 4.8, 1.9 Hz, 1H), 8.06 (s, 1H), 7.84 (td, J = 8.8, 2.3 Hz, 1H), 7.64 (t, J = 1.9 Hz, 1H), 7.57 (t, J = 1.9 Hz, 1H), 6.93 (t, J = 2.0 Hz, 1H), 3.04 (s, 3H), 2.37 (d, J = 1.1 Hz, 3H). |

Example 737. Assays

Compounds of the disclosure were assessed for their ability to inhibit DHX9 activity. The inhibitory properties of the compounds of the disclosure described herein can be evidenced by testing in any one of the following assays.

1. Biochemical Assay

Materials and Methods

Recombinant DHX9—Human recombinant DHX9 protein was custom ordered from Viva.

RNA substrate—Oligos for double-stranded RNA substrate were custom ordered from IDT Technologies. (Oligo1-GCCUGGUCCCUGUCCUUGUUAUUUCC-UUGGUUAAUU (SEQ ID NO:1). Oligo2-GAAUUAAC-CAAGGAAAAUAACAAGGACAGGGACCAGG (SEQ ID NO:2)). Each oligo was reconstituted in RNAse/DNAse-free water to achieve a 100 uM solution. The two oligo solutions were mixed in 1:1 ratio and annealed by heating at 70° C. for 5 minutes and cooling gradually to room temperature on the benchtop.

Chemicals and Assay Components—Aurintricarboxylic Acid and dimethylsulfoxide were purchased from Sigma-Aldrich (St. Louis, MO). White 384-well assay plates (Catalog #781075) were obtained from Greiner Bio-One (Frickenhausen, Germany). The ADP-Glo™ kinase assay kit from Promega Corporation is composed of ADP-Glo reagent, kinase detection reagent (made by mixing kinase detection buffer with a lyophilized kinase detection substrate), Ultra Pure ATP and ADP.

ATPase Assay

DHX9 ATPase assay was performed in small-volume, nonbinding, 384-well white plates at a final volume of 10 μL/well. Test compounds (10 mM solution in DMSO; 100 nL/well) were serially diluted on Bravo (Agilent, Santa Clara, CA) and dispensed into wells of columns 3-22 of the plates using an Echo 555 acoustic dispenser (Labcyte, Sunnyvale, CA). 100 mL of Aurintricarboxylic acid was dispensed into low control wells and 100 mL of DMSO was dispensed into high control wells. Then, a Multidrop Combi Reagent Dispenser (Thermo Fisher Scientific, Waltham, MA) was used to add a solution of DHX9 (1.25 nM, 5 μL/well) in assay buffer (40 mM HEPES [pH 7.5], 0.01% Tween 20, 0.01% BSA, 1 mM DTT, 5 mM $MgCl_2$, 0.004 U/ml RNAseOUT). The reaction was initiated by the addition of 5 μL of substrate solution (30 nM double-stranded RNA substrate, 10 μM Ultra Pure ATP in assay buffer) into the wells. The plates were incubated at room temperature for 1 h. After the indicated incubation times, 10 μL ADP-Glo reagent was added to the reactions and the plate was incubated at room temperature for 40 min. Then, 20 μL of kinase detection reagent was added and after an incubation time of 40 min, luminescence was recorded on Envision plate reader (Perkin-Elmer, Billerica, MA).

Data Processing and Analysis

All data was analyzed by Accent Therapeutics internal data analysis software developed by Scigilian (Montreal, Canada). The percentage inhibition was calculated based on the high control (DMSO) as 0% inhibition, and low control (10 μM Aurintricarboxylic acid) control as 100% inhibition and used for the calculation of $IC_{50}$ and IP (inflection point) values by fitting the dose-response curves to a four-parameter logistic model. Assay results reported IP values instead of $IC_{50}$ values since several compounds did not reach 100% inhibition at higher compound concentrations.

2. DHX9 Cellular Proliferation Assay

The CellTiter-Glo® Luminescent Cell Viability Assay is a homogeneous method to determine the number of viable cells in culture based on quantitation of the ATP present, which signals the presence of metabolically active cells.

The following cell lines were obtained from ATCC: HCT116 (CCL-247), Colo205 (CCL-222), LS411N (CRL-2159), and NCI-H747 (CCL-252). HCT116 cells were grown and assayed in McCoy's-5a growth media supplemented with 10% FBS, and Colo205, LS411N and NCI-H747 cells were grown in RPMI-1640 media supplemented with 10% FBS.

The cells are plated at pre-determined cell densities in 384-well solid white cell culture plates and incubated overnight in 37° C. at 5% $CO_2$. In a separate plate, reference and test compounds were prepared in DMSO stock solution and serially diluted 3-fold for 10 points. Compound (0.1% final DMSO concentration) was transferred to the cell plate in designated wells, and incubated 37° C. at 5% $CO_2$ for 120 hours. CellTiter-Glo reagent was prepared fresh according to manufacturer's (Promega) directions and added to each well. The plate is then shaken at 300 rpm for 10 minutes at RT, and then read on an Envision plate reader using a Luminescence protocol.

Data analysis was performed by normalizing the raw data (raw luminescence units or RSample) to an average of the positive control values for wells containing culture media only (100% cell death or RLC) and the negative control values for 0.1% DMSO (0% cell death or RHC). An $IC_{50}$ was calculated using a 4-parameter logistic nonlinear regression model in Scigilian Analyzer or GraphPad Prism, constraining the top parameter to 100 and the bottom parameter to 0.

$$\% \text{ Inhibition} = 100\% \times \left(1 - \frac{R_{Sample} - R_{LC}}{R_{HC} - R_{LC}}\right)$$

$IC_{50}$Fit formula=$(A+((B-A)/(1+((x/C)^{\wedge}D))))$ ...
whereas $A$:Bottom;$B$:Top;$C$:$IC_{50}$;$D$:Slope 3. DHX9 circBRIP1 Cellular Target Engagement SYBR Green Assay Evaluation of the circular and linear format of BRIP1 mRNA in HCT116 cells by Quantitative Polymerase Chain Reaction (qPCR). Upon DHX9 inhibition circBRIP1 levels are increased and linear BRIP1 mildly decreases or remains unchanged.

HCT116 cells were obtained from ATCC (CCL-247) and were grown and assayed in McCoy's 5a growth media supplemented with 10% FBS.

The cells are plated at pre-determined cell densities in 384-well cell culture plates and incubated overnight in 37° C. at 5% $CO_2$. In a separate plate, reference and test compounds were prepared in DMSO stock solution and serially diluted 3-fold for 10 points. Compound (0.1% final DMSO concentration) was transferred to the cell plate in designated wells, and incubated 37° C. at 5% $CO_2$ for 72 hours.

RNA is extracted from the cells using the SYBR Green Fast Advanced Cell-to-CT kit according to manufacturer's (Invitrogen) protocol, and cDNA is reverse transcribed using the High Capacity RNA-to-cDNA Kit according to the manufacturer's (Invitrogen) protocol. Using SYBR Green Master Mix and thermal cycler conditions for the QuantStudio Thermocycler, qPCR is carried out using the below custom primer sequences:

```
BRIP1-Circular-Forward (TCT GTG TGC CAG ACT GTG
AG (SEQ ID NO: 3))

BRIP1-Circular-Reverse (ACA CCA AGT TCT GAC GAA
AAG G (SEQ ID NO: 4))

BRIP1-Linear-Forward (GTC CAT CCT GAG GTA GTC
GG (SEQ ID NO: 5))

BRIP1-Linear-Reverse (TTC CCC AGG CTG ACA AGT
TC (SEQ ID NO: 6))

GAPDH-Forward (GTCTCCTCTGACTTCAACAGCG
(SEQ ID NO: 7))

GAPDH-Reverse (ACCACCCTGTTGCTGTAGCCAA
(SEQ ID NO: 8))
```

Note: Forward and Reverse primers are combined per gene, and each sample has to be run on a separate plate for each gene.

Data analysis was performed by using the QuantStudio Thermocycler software to determine threshold Ct values. ΔCt for circBRIP1 or linBRIP1 is calculated by normalizing the target gene Ct to the GAPDH housekeeping gene Ct for each sample. The inhibition activity is calculated by the following formula, whereas:

ΔCts: Mean of Ct(target gene)—Mean of Ct(GAPDH) for each sample

ΔCtc: Mean of Ct(target gene)—Mean of Ct(GAPDH) for DMSO control.

$$\% \text{ Inhibition} = 100\% \times \frac{2^{\Delta Cts}}{2^{\Delta Ctc}}$$

An $EC_{50}$ was then calculated using a 4-parameter logistic nonlinear regression model in Scigilian Analyzer or GraphPad Prism, floating both the top and bottom parameters.

$EC_{50}$Fit formula=$(A+((B-A)/(1+((x/C)^{\wedge}D))))$ ...
whereas $A$:Bottom;$B$:Top;$C$:$IC_{50}$;$D$:Slope 4. DHX9 circBRIP1 Cellular Target Engagement TaqMan Multiplex Assay:

Evaluation of the circular and linear format of BRIP1 mRNA in HCT116 cells by Quantitative Polymerase Chain Reaction (qPCR). Upon DHX9 inhibition circBRIP1 levels are increased and linear BRIP1 mildly decreases or remains unchanged.HCT116 cells were obtained from ATCC (CCL-247) and were grown and assayed in McCoy's 5a growth media supplemented with 10% FBS.

The cells are plated at pre-determined cell densities in 384-well cell culture plates and incubated overnight in 37° C. at 5% $CO_2$. In a separate plate, reference and test compounds were prepared in DMSO stock solution and serially diluted 3-fold for 10 points. Compound (0.1% final DMSO concentration) was transferred to the cell plate in designated wells, and incubated 37° C. at 5% $CO_2$ for 72 hours.

RNA is extracted from the cells using the TaqMan Gene Expression Cells-to-CT™ kit according to manufacturer's (Invitrogen) protocol, and cDNA is reverse transcribed using the High Capacity RNA-to-cDNA Kit according to the manufacturer's (Invitrogen) protocol. Using TaqMan Multiplex Mastermix and thermal cycler conditions for the QuantStudio Thermocycler, qPCR is carried out using TaqMan Gene Expression Assay with VIC Dye for Linear BRIP1 (Assay ID: Hs00908156_m1), TaqMan GAPDH primer limited assay with JUN dye/QSY probe, and the below custom TaqMan Gene Expression Assay with FAM Dye for circBRIP1:

Forward Primer: GTGAGCCAAGGAATTTTGTGTTT (SEQ ID NO:9)

Reverse Primer: GGTCTGAACTTTGCCATTAATATCTG (SEQ ID NO:10)

Probe: CCATCTTACAAGGCCTTT (SEQ ID NO:11)

Note: All target genes can be combined in one well per sample.

Data analysis was performed by using the QuantStudio Thermocycler software to determine threshold Ct values. ΔCt for circBRIP1 or linBRIP1 is calculated by normalizing the target gene Ct to the GAPDH housekeeping gene Ct for each sample. The inhibition activity is calculated by the following formula, whereas:

ΔCts: Mean of Ct(target gene)—Mean of Ct(GAPDH) for each sample
ΔCtc: Mean of Ct(target gene)—Mean of Ct(GAPDH) for DMSO control.

$$\% \text{ Inhibition} = 100\% \times \frac{2^{\Delta Cts}}{2^{\Delta Ctc}}$$

An $EC_{50}$ was then calculated using a 4-parameter logistic nonlinear regression model in Scigilian Analyzer or GraphPad Prism, floating both the top and bottom parameters.

IC50 Fit formula=$(A+((B-A)/(1+((x/C)^{\wedge}D))))$ ...
whereas $A$:Bottom;$B$:Top;$C$:IC50;$D$:Slope

DATA FOR EXAMPLES

TABLE 1

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative $IC_{50}$ | **H747 (CRC-MSS) Antiproliferative $IC_{50}$ |
|---|---|---|---|---|---|
| 1 | 0.32 | 48.3 | 16.4+ | | |
| 2 | 0.173 | 64.8 | >30+ | | |
| 3 | 0.648 | 76.4 | | | |
| 4 | 4.82 | 64.1 | | | |
| 5 | 0.215 | 74.6 | >30+ | | |
| 6 | 0.0917 | 52.5 | 9.34+ | | |
| 7 | 0.38 | 46.4 | 24.2+ | | |
| 8 | 0.395 | 54.4 | 5.52+ | | |
| 9 | 0.39 | 44.5 | 30+ | | |
| 10 | 0.133 | 61 | 12.3+ | | |
| 11 | 0.123 | 62.7 | 0.851+ | | |
| 12 | 84.7 | 58.6 | | | |
| 13 | 1.15 | 41.7 | 7.97+ | | |
| 14 | 0.353 | 59.6 | | | |
| 15 | 0.1355 | 54.8 | 0.7283+ | 0.663 | >10 |
| 16 | 0.251 | 46.3 | 3.51+ | | |
| 17 | 0.0073 | 61 | 0.0571+ | 0.2783 | 9.6533 |
| 18 | 0.0086 | 61 | 0.0984+ | 0.546 | >10 |
| 19 | 0.115 | 53.5 | 2.11+ | 1.08 | >10 |
| 20 | 0.0572 | 62.5 | 0.1+ | 0.609 | 7.22 |
| 21 | 0.0332 | 61.7 | 0.26+ | 0.791 | >10 |
| 22 | 0.0025 | 71 | 0.0358+ | 0.115 | >10 |
| 23 | 0.0032 | 69 | 0.0542+ | 0.0531 | >10 |
| 24 | 0.002 | 73.4 | 0.015+ | 0.117 | >10 |
| 25 | 0.0056 | 61.3 | 0.048+ | 0.0991 | >10 |
| 26 | 0.0018 | 65.6 | 0.0609+ | 0.217 | >10 |
| 27 | 0.0064 | 68 | 0.0497+ | 0.117 | >10 |
| 28 | 0.0042 | 68.3 | 0.0258+ | 0.0788 | >10 |
| 29 | 0.0482 | 65.2 | 0.0519+ | 0.124 | 9.28 |
| 30 | 0.787 | 40.5 | 0.687+ | | |
| 31 | 0.0038 | 72.5 | 0.0642+ | 0.0698 | >10 |
| 32 | 0.0383 | 56.3 | 0.0482+ | 0.101 | >10 |
| 33 | 0.0048 | 61.7 | 0.0215+ | 0.116 | >10 |
| 34 | 0.0063 | 75.2 | 0.013+ | 0.0141 | 8.67 |
| 35 | 0.0039 | 75.7 | 0.0372+ | 0.0768 | >10 |
| 36 | 0.028 | 56.86 | 0.3134+ | 1.085 | >10 |
| 37 | 0.0479 | 62.6 | 0.83+ | 3.47 | >10 |
| 38 | 0.0655 | 44.7 | 0.933+ | | |
| 39 | 0.0701 | 52.3 | 0.884+ | | |
| 40 | 0.0157 | 60 | 1.15+ | | |
| 41 | 0.0474 | 40.3 | 4.34+ | | |
| 42 | 0.0187 | 48.7 | 0.308+ | 0.917 | >10 |
| 43 | 0.258 | 49.8 | 4.71+ | | |
| 44 | 0.137 | 60.3 | 4.19+ | | |
| 45 | 0.0164 | 67.4 | 0.563+ | | |
| 46 | 0.0473 | 57.2 | 2.25+ | | |
| 47 | 0.269 | 64.7 | 6.73+ | | |
| 48 | 0.0931 | 54.1 | 1.41+ | | |
| 49 | 0.0497 | 58.6 | 0.4335+ | 0.901 | >10 |
| 50 | 0.045 | 55.5 | 0.895+ | | |
| 51 | 0.145 | 61.1 | 0.188+ | 0.259 | 6.47 |
| 52 | 0.198 | 37.9 | 3.01+ | | |
| 53 | 1.91 | 52.2 | 4.95+ | | |
| 54 | 0.0656 | 66.6 | 0.953+ | | |
| 55 | 0.0099 | 48.6 | 0.143+ | 1.06 | >10 |
| 56 | 0.197 | 48.8 | 7.43+ | | |
| 57 | 14.6 | 45.8 | | | |
| 58 | 0.0849 | 44.4 | 1.41+ | | |
| 59 | 0.0127 | 77.5 | 0.104+ | 0.357 | >10 |
| 60 | 0.0078 | 63 | 0.201+ | | |
| 61 | 0.0145 | 66.6 | 1.52+ | | |
| 62 | 0.211 | 58.4 | 6.8+ | | |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative $IC_{50}$ | **H747 (CRC-MSS) Antiproliferative $IC_{50}$ |
|---|---|---|---|---|---|
| 63 | 0.0839 | 66.2 | 2.43+ | | |
| 64 | 0.0599 | 61.8 | 5.64+ | | |
| 65 | 0.0055 | 72.6 | 0.0631+ | 0.109 | >10 |
| 66 | 0.0566 | 62.9 | 4.87+ | | |
| 67 | 0.154 | 54 | 0.297+ | 1.05 | >10 |
| 68 | 0.0238 | 68.7 | 0.278+ | | |
| 69 | 0.113 | 62.3 | 0.661+ | | |
| 70 | 0.0085 | 78.9 | 0.107+ | 0.375 | >10 |
| 71 | 0.171 | 77.8 | 26.3+ | | |
| 72 | 0.378 | 67.2 | | | |
| 73 | 0.189 | 63 | 11.2+ | | |
| 74 | 0.255 | 57.7 | 8.32+ | | |
| 75 | 0.0946 | 55.5 | 1.64+ | | |
| 76 | 0.0092 | 71.8 | 0.0623+ | 0.253 | >10 |
| 77 | 0.0154 | 57.8 | 0.154+ | | |
| 78 | 0.0319 | 56.2 | 0.457+ | | |
| 79 | 0.146 | 67.8 | 1.12+ | | |
| 80 | 0.493 | 71.2 | 3.09+ | | |
| 81 | 0.0326 | 66.7 | 0.29+ | 1.07 | >10 |
| 82 | 0.0092 | 69.4 | 0.0732+ | 0.134 | >10 |
| 83 | 0.0478 | 60.7 | 0.911+ | | |
| 84 | 0.0101 | 66.7 | 0.194+ | 0.385 | >10 |
| 85 | 0.099 | 59.5 | 2.76+ | | |
| 86 | 0.0184 | 51.5 | 0.585+ | | |
| 87 | 0.0261 | 55.7 | 2.46+ | | |
| 88 | 0.0071 | 54.2 | >10+ | | |
| 89 | 0.0144 | 64.9 | 0.667+ | | |
| 90 | 0.024 | 61.5 | 1.06+ | | |
| 91 | 0.0279 | 59.7 | 0.382+ | | |
| 92 | 0.0221 | 61.1 | 0.281+ | 1.1 | >10 |
| 93 | 0.0017 | 70.6 | 0.03+ | 0.253 | >10 |
| 94 | 0.0018 | 72.4 | 0.292+ | 3.2 | >10 |
| 95 | 0.0205 | 59.2 | 0.179+ | 1.02 | 7.99 |
| 96 | 0.253 | 52.8 | 9.63+ | >10 | >10 |
| 97 | 0.488 | 61.5 | 3.16+ | | |
| 98 | 0.0483 | 62.4 | 1.33+ | | |
| 99 | 0.298 | 50.9 | >10+ | | |
| 100 | 13.8 | 49.9 | | | |
| 101 | 13 | 53.6 | | | |
| 102 | 0.762 | 61.8 | >30+ | | |
| 103 | 0.452 | 49.5 | 5.31+ | | |
| 104 | 0.061 | 68 | 5.49+ | | |
| 105 | 0.0803 | 71.7 | 8.33+ | | |
| 106 | 0.078 | 58.7 | 0.414+ | | |
| 107 | 0.0622 | 53 | 0.913+ | | |
| 108 | 0.21 | 59.8 | 6.65+ | | |
| 109 | 0.0176 | 57.2 | 0.437+ | | |
| 110 | 0.04 | 53.7 | 2.71+ | | |
| 111 | 0.25 | 68.2 | 0.161+ | 0.318 | >10 |
| 112 | 0.0211 | 70.8 | 0.627+ | | |
| 113 | 0.04 | 65.9 | 7.44+ | | |
| 114 | 0.0435 | 66.4 | 1.48+ | | |
| 115 | 0.0743 | 56.5 | 0.41+ | | |
| 116 | 0.0097 | 56.6 | 0.734+ | | |
| 117 | 0.104 | 55.5 | 3.87+ | | |
| 118 | 0.0451 | 55.8 | 2.93+ | | |
| 119 | 1.16 | 82.1 | | | |
| 120 | 0.0089 | 72.5 | 0.144+ | 1.07 | 6.98 |
| 121 | 0.0406 | 63.5 | 5.43+ | | |
| 122 | 0.0288 | 67.7 | 1.29+ | | |
| 123 | 0.0148 | 72.8 | 6.59+ | | |
| 124 | 0.604 | 53.8 | 5.14+ | | |
| 125 | 0.33 | 56.7 | 16.1+ | | |
| 126 | 0.182 | 64.5 | >10+ | | |
| 127 | 0.138 | 66.4 | >10+ | | |
| 128 | 0.173 | 57.3 | >10+ | | |
| 129 | 0.0384 | 66.4 | 0.333+ | 1.09 | >10 |
| 130 | 0.0396 | 70.4 | 0.489+ | 1.16 | >10 |
| 131 | 0.151 | 55.9 | >10+ | | |
| 132 | 0.295 | 55.1 | >10+ | >10 | >10 |
| 133 | 13.6 | 41.8 | | | |
| 134 | 0.808 | 40 | | | |
| 135 | 1.07 | 44.6 | | | |
| 136 | 0.234 | 59.6 | 6.41+ | | |
| 137 | 0.0737 | 62.9 | 3.01+ | | |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative $IC_{50}$ | **H747 (CRC-MSS) Antiproliferative $IC_{50}$ |
|---|---|---|---|---|---|
| 138 | 13.5 | 42.6 | >10+ | | |
| 139 | 6.65 | 59.1 | + | | |
| 140 | 0.3 | 63.3 | >10+ | | |
| 141 | 0.442 | 54.9 | >10+ | | |
| 142 | 0.514 | 62 | >10+ | | |
| 143 | 0.0511 | 66.8 | 0.516+ | 1.09 | 8.54 |
| 144 | 0.224 | 65.1 | 5.85+ | | |
| 145 | 0.058 | 67.9 | >10+ | | |
| 146 | 0.0304 | 71.9 | >10+ | | |
| 147 | 0.0063 | 76.5 | 0.834+ | | |
| 148 | 0.0185 | 63.3 | 4.34+ | | |
| 149 | 0.0199 | 65.4 | 1.8+ | | |
| 150 | 0.147 | 65.9 | 6.56+ | | |
| 151 | 0.179 | 58.9 | >10+ | | |
| 152a | 0.138 | 63.2 | >10+ | | |
| 152b | 0.126 | 69.9 | | | |
| 153 | 0.256 | 59.7 | 6.11+ | | |
| 154 | 0.179 | 58.9 | >10+ | | |
| 155 | 0.126 | 66.4 | 3.61+ | | |
| 156 | 0.695 | 51.2 | >10+ | | |
| 157 | 0.0525 | 61.7 | 4.32+ | | |
| 158 | 0.0345 | 76.5 | 1.29+ | | |
| 159 | 4.27 | 61 | >10+ | | |
| 160 | 0.154 | 59.6 | 6.94+ | >10 | >10 |
| 161 | 0.0484 | 44.9 | 1.42+ | | |
| 162 | 0.0197 | 60.5 | 0.138+ | | |
| 163 | 0.0043 | 71.7 | 0.07+ | 0.609 | >10 |
| 164 | 9.3 | 50.5 | + | | |
| 165 | 0.0539 | 57.4 | >10+ | | |
| 166 | 0.0285 | 64 | 2.39+ | | |
| 167 | 0.386 | 58.6 | 1.75+ | | |
| 168 | 0.772 | 50.7 | 2.13+ | | |
| 169 | 0.0087 | 67.9 | 0.189+ | 2.17 | >10 |
| 170 | 0.0057 | 75.4 | 0.0447+ | 0.122 | >10 |
| 171 | 0.0145 | 61.8 | 0.0957+ | 0.372 | >10 |
| 172 | 0.0159 | 72.4 | 0.135+ | 0.237 | 6.89 |
| 173 | 0.0086 | 61.3 | 0.118+ | | |
| 174 | 0.0018 | 75.8 | 0.007+ | 0.0333 | >10 |
| 175 | 0.0036 | 78.8 | 0.0445+ | 0.0863 | >10 |
| 176 | 0.011 | 70.2 | 0.408+ | | |
| 177 | 0.0216 | 77 | 0.0848+ | 0.251 | >10 |
| 178 | 0.011 | 67.9 | 0.101+ | 0.0811 | >10 |
| 179 | 0.0272 | 72.3 | 0.997+ | | |
| 180 | 0.0202 | 67.4 | 1.2+ | | |
| 181 | 0.0096 | 57.4 | 2.09+ | | |
| 182 | 0.181 | 73.4 | >10+ | | |
| 183 | 0.0201 | 67.1 | >10+ | | |
| 184 | 0.0194 | 66.3 | >10+ | | |
| 185 | 0.0047 | 80.5 | 0.0733+ | 0.139 | 8.38 |
| 186 | 0.0039 | 87.9 | 0.161+ | 2.44 | >10 |
| 187 | 0.0032 | 82.4 | 0.0504+ | 0.0773 | >10 |
| 188 | 0.0188 | 66.2 | 1.46+ | | |
| 189 | 0.0327 | 72.1 | 0.308+ | | |
| 190 | 0.0191 | 68.8 | 0.373+ | | |
| 191 | 0.0042 | 67.6 | 0.432+ | >10 | >10 |
| 192 | 0.0165 | 72.6 | 3.6+ | | |
| 193 | 0.0111 | 65.8 | >10+ | | |
| 194 | 0.0068 | 64.3 | 2.68+ | | |
| 195 | 0.0353 | 67.1 | 0.751+ | | |
| 196 | 0.0786 | 68.9 | 6.73+ | | |
| 197 | 0.026 | 72.7 | 2.37+ | | |
| 198 | 0.0713 | 60.7 | >10+ | | |
| 199 | 0.0844 | 73.4 | >10+ | | |
| 200 | 0.0846 | 57.7 | 1.31+ | | |
| 201 | 0.184 | 66.1 | >10+ | | |
| 202 | 0.0127 | 72.3 | 0.103+ | 0.111 | 8.56 |
| 203 | 0.0281 | 76.5 | 0.341+ | | |
| 204 | 0.0096 | 68.9 | 0.0539+ | 0.0548 | >10 |
| 205 | 0.0226 | 71.4 | 0.841+ | | |
| 206 | 0.0168 | 74.9 | 1.06+ | | |
| 207 | 0.0152 | 70 | 0.508+ | | |
| 208 | 0.0155 | 79.9 | 0.125+ | 0.218 | >10 |
| 209 | 0.0894 | 64 | 3.46+ | | |
| 210 | 0.0036 | 71.3 | 0.0772+ | 0.111 | >10 |
| 211 | 0.0624 | 65.4 | 0.189+ | | |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative $IC_{50}$ | **H747 (CRC-MSS) Antiproliferative $IC_{50}$ |
|---|---|---|---|---|---|
| 212 | 0.0052 | 72.6 | 0.0326[+] | 0.202 | >10 |
| 213 | 0.0164 | 71.6 | 0.0746[+] | 0.173 | >10 |
| 214 | 0.088 | 75.9 | 0.106[+] | 0.203 | 7.15 |
| 215 | 0.004 | 75.4 | 0.0237[+] | 0.118 | >10 |
| 216 | 0.0044 | 78 | 0.0127[+] | 0.0385 | >10 |
| 217 | 0.0021 | 69.6 | 0.0136[+] | 0.0533 | >10 |
| 218 | 0.0765 | 59 | 1.39[+] | | |
| 219 | 0.0406 | 62.3 | 0.265[+] | | |
| 220 | 0.016 | 79.7 | 0.303[+] | | |
| 221 | 0.0066 | 78.3 | 0.121[+] | | |
| 222 | 0.0177 | 78.7 | 0.2[+] | | |
| 223 | 0.0565 | 75.7 | 0.421[+] | | |
| 224 | 0.0064 | 67.3 | 0.0558[+] | 0.122 | >10 |
| 225 | 0.0069 | 74.2 | 0.0199[+] | 0.0439 | >10 |
| 226 | 0.0084 | 73.6 | 0.388[+] | | |
| 227 | 0.0072 | 70.6 | 0.0403[+] | 0.879 | >10 |
| 228 | 0.0655 | 67.2 | 0.0483[+] | 0.117 | >10 |
| 229 | 0.0096 | 72.5 | 0.0781[+] | 0.051 | >10 |
| 230 | 0.093 | 65.9 | 7.25[+] | | |
| 231 | 0.0491 | 66.3 | 0.203[+] | | |
| 232 | 0.0202 | 77.5 | 0.061[+] | | |
| 233 | 0.0455 | 80.3 | 0.46[+] | 0.356 | >10 |
| 234 | 0.0095 | 84.6 | 1.18[+] | | |
| 235 | 0.0358 | 78.1 | 0.645[+] | | |
| 236 | 0.0521 | 68.9 | 0.106[+] | | |
| 237 | 0.021 | 73.5 | 1.91[+] | 0.249 | 3.78 |
| 238 | 0.0229 | 72.9 | 0.289[+] | | |
| 239 | 0.008 | 67.7 | 0.348[+] | | |
| 240 | 0.353 | 71 | 0.228[+] | | |
| 241 | 0.115 | 63.8 | 3.68[+] | | |
| 242 | 0.105 | 69.7 | 5.02[+] | | |
| 243 | 0.0923 | 73.2 | >10[+] | | |
| 244 | 0.0733 | 71.9 | >10[+] | | |
| 245 | 0.121 | 71.4 | 4.31[+] | | |
| 246 | 0.186 | 67.5 | 3.93[+] | | |
| 247 | 0.131 | 70 | 2.24[+] | | |
| 248 | 0.185 | 70.8 | >10[+] | | |
| 249 | 0.0028 | 64.1 | 0.0295[+] | | |
| 250 | 0.185 | 64.6 | 3.55[+] | | |
| 251 | 5.2 | 64.7 | >10[+] | 0.432 | >10 |
| 252 | 0.0489 | 72.1 | 1.79[+] | | |
| 253 | 0.11 | 70 | 9.23[+] | | |
| 254 | 0.0595 | 64.1 | 0.578[+] | | |
| 255 | 0.0724 | 75.8 | 0.378[+] | 0.0743 | >10 |
| 256 | 0.403 | 70.1 | 2.03[+] | | |
| 257 | 0.207 | 66.5 | 2.61[+] | | |
| 258 | 0.0047 | 72.9 | 0.291[+] | | |
| 259 | 1.94 | 69.2 | >10[+] | | |
| 260 | 0.715 | 50 | >10[+] | | |
| 261 | 0.0475 | 71 | 1.53[+] | | |
| 262 | 0.12 | 66.5 | 0.439[+] | | |
| 263 | 0.17 | 63.8 | >10[+] | | |
| 264 | 0.119 | 56.7 | 3.54[+] | | |
| 265 | 8.05 | 51.8 | 4.65[+] | | |
| 266 | 0.0131 | 64.4 | 1.16[+] | | |
| 267 | 0.248 | 66.4 | 2.26[+] | | |
| 268 | 0.0094 | 73.1 | 0.182[+] | | |
| 269 | 0.0044 | 76.9 | 0.037[+] | | |
| 270 | 0.0097 | 74.1 | 0.101[+] | | |
| 271 | 0.0865 | 66.1 | 0.761[+] | | |
| 272 | 0.0054 | 71.6 | 0.0311[+] | | |
| 273 | 0.0065 | 71.4 | 0.0375[+] | | |
| 274 | 0.0322 | 72.1 | 0.0979[+] | | |
| 275 | 0.0762 | 75.1 | 0.19[+] | | |
| 276 | 0.0047 | 73.8 | 0.0642[+] | 0.0617 | >10 |
| 277 | 0.0043 | 72.5 | 0.0476[+] | 0.0667 | 4.7 |
| 278 | 0.0442 | 74.1 | 0.251[+] | | |
| 279 | 0.004 | 73.2 | 0.0533[+] | 0.0811 | >10 |
| 280 | 0.326 | 76.3 | 0.0742[+] | 0.116 | >10 |
| 281 | 0.028 | 75.7 | 0.483[+] | 0.367 | 7.34 |
| 282 | 0.0964 | 72.4 | 1.88[+] | | |
| 283 | 0.0292 | 78 | 0.131[+] | 0.0923 | >10 |
| 284 | 0.0041 | 79.6 | 0.103[+] | 0.161 | >10 |
| 285 | 0.0054 | 70.6 | 0.503[+] | | |
| 286 | 0.24 | 72.9 | 2.63[+] | 0.131 | >10 |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative $IC_{50}$ | **H747 (CRC-MSS) Antiproliferative $IC_{50}$ |
|---|---|---|---|---|---|
| 287 | 0.0191 | 82.6 | 0.232+ | 0.165 | >10 |
| 288 | 0.132 | 58.7 | 7.8+ | | |
| 289 | 0.0806 | 66.9 | 6.55+ | | |
| 290 | 5.59 | 59.7 | >10+ | | |
| 291 | 0.144 | 59.7 | 0.803+ | 0.352 | >10 |
| 292 | 0.076 | 68.5 | 2.3+ | | |
| 293 | 0.0872 | 55 | >10+ | | |
| 294 | 1.61 | 59 | >10+ | | |
| 295 | 0.307 | 63.8 | >10+ | | |
| 296 | 0.125 | 69.9 | 1.14+ | | |
| 297 | 0.997 | 57 | >10+ | | |
| 298 | 4.21 | 58.8 | >10+ | | |
| 299 | 0.335 | 56.7 | >10+ | | |
| 300 | 0.132 | 58.5 | 3.94+ | | |
| 301 | 0.0377 | 69.5 | 2.41+ | | |
| 302 | 0.64 | 54.6 | 1.93+ | | |
| 303 | 4.02 | 57.2 | >10+ | | |
| 304 | 0.399 | 59.1 | 5.98+ | | |
| 305 | 0.0953 | 63.8 | 3.33+ | | |
| 306a | 0.127 | 70.6 | >10+ | | |
| 306b | 0.253 | 74.2 | >10+ | | |
| 307 | 0.143 | 70.4 | >10+ | | |
| 308 | 0.375 | 60.6 | >10+ | | |
| 309 | 0.162 | 60.8 | 3.73+ | | |
| 310 | 0.102 | 70.3 | >10+ | | |
| 311 | 0.0385 | 77.7 | 3.98+ | | |
| 312 | 0.22 | 69.2 | 9.97+ | | |
| 313 | 0.147 | 63.6 | >10+ | | |
| 314 | 0.119 | 58.9 | 0.844+ | | |
| 315 | 0.0753 | 66.9 | >10+ | | |
| 316 | 0.205 | 66.6 | 4.92+ | | |
| 317 | 0.272 | 63.8 | >10+ | | |
| 318 | 0.207 | 64.4 | 4.9+ | | |
| 319 | 0.0577 | 70.1 | >10+ | | |
| 320 | 0.0105 | 72.2 | 0.0961+ | | |
| 321 | 0.0135 | 79.2 | 0.241+ | | |
| 322 | 0.215 | 65.6 | >10+ | | |
| 323 | 0.282 | 58.2 | >10+ | | |
| 324 | 0.164 | 63.1 | 5.9+ | | |
| 325 | 0.591 | 63.9 | 6.09+ | | |
| 326 | 8.11 | 64.5 | >10+ | | |
| 327 | 0.264 | 63.3 | 3.54+ | | |
| 328 | 0.422 | 67.6 | 2.67+ | | |
| 329 | 0.139 | 66.5 | 4.98+ | | |
| 330 | 0.088 | 61.9 | 4.87+ | | |
| 331 | 0.194 | 57.8 | 3.75+ | | |
| 332 | 4.83 | 61.5 | 3.34+ | | |
| 333 | 0.0351 | 78.1 | 0.421+ | | |
| 334 | 0.0109 | 81.5 | 0.251+ | | |
| 335 | 0.0107 | 79 | 0.0511+ | 0.0526 | >10 |
| 336 | 0.0096 | 84 | 0.0846+ | 0.146 | >10 |
| 337 | 0.0107 | 81.2 | 0.0385+ | 0.119 | >10 |
| 338 | 0.0157 | 78 | 0.126+ | | |
| 339 | 0.0107 | 71 | 0.0918+ | 0.341 | 5.69 |
| 340 | 0.0236 | 65.6 | 0.106+ | 0.118 | >10 |
| 341 | 0.0062 | 83.05 | 0.0346+ | 0.122 | >10 |
| 342 | 0.0331 | 73.6 | 0.0478+ | 0.133 | >10 |
| 343 | 0.0552 | 54.4 | 0.189+ | | |
| 344 | 0.021 | 74.1 | 0.153+ | | |
| 345 | 0.0336 | 77.1 | 0.108+ | 0.362 | 8.45 |
| 346 | 0.0257 | 73 | 0.0438* | 0.0716 | 7.34 |
| 347 | 0.034 | 72.1 | 0.0968* | 0.16 | >10 |
| 348 | 0.0318 | 74.6 | 0.228* | | |
| 349 | 0.0237 | 76.4 | 0.0582* | 0.154 | >10 |
| 350 | 0.0539 | 67.1 | 0.257* | | |
| 351 | 0.0155 | 80.6 | 0.0286* | 0.082 | >10 |
| 352 | 0.0049 | 84.1 | 0.021* | 0.05 | 8.75 |
| 353 | 0.0242 | 69.2 | 0.094* | 0.111 | 8.49 |
| 354 | 0.0134 | 75.5 | 0.0345* | 0.0715 | 8.06 |
| 355 | 0.0341 | 69.9 | 0.362* | | |
| 356 | 0.1484 | 77.85 | 0.0448* | 0.1325 | 2.545 |
| 357 | 0.0856 | 91.7 | 0.119* | | |
| 358 | 0.0384 | 84.3 | 0.0533* | 0.129 | 6.87 |
| 359 | 0.0549 | 68.3 | 0.13* | | |
| 360 | 0.0409 | 56.5 | 0.0521* | 0.235 | 7.07 |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative IC$_{50}$ | **H747 (CRC-MSS) Antiproliferative IC$_{50}$ |
|---|---|---|---|---|---|
| 361 | 0.0191 | 88.8 | 0.0432* | 0.361 | 6.25 |
| 362 | 0.0443 | 88.6 | 0.124* | | |
| 363 | 0.0252 | 94.3 | 0.171* | | |
| 364 | 0.0156 | 79.8 | 0.387* | | |
| 365 | 0.0205 | 78.7 | 0.0339* | 0.116 | >10 |
| 366 | 0.0467 | 76.2 | 0.128* | | |
| 367 | 0.0559 | 63.5 | 0.219* | | |
| 368 | 0.118 | 67.3 | 0.31* | | |
| 369 | 0.0576 | 61.5 | 0.0868* | 0.227 | >10 |
| 370 | 0.0652 | 64.3 | 0.171* | | |
| 371 | 0.14 | 65.3 | 0.311* | | |
| 372 | 0.402 | 49.2 | 2.12* | | |
| 373 | 0.0743 | 49.9 | 0.506* | | |
| 374 | 0.579 | 60 | >10* | | |
| 375 | 0.0346 | 64.6 | 0.68* | | |
| 376 | 0.0302 | 64.1 | 0.0699* | 0.303 | >10 |
| 377 | 0.0212 | 70.6 | 0.0374* | 0.14 | >10 |
| 378 | 0.874 | 80.9 | 0.361* | | |
| 379 | 0.0418 | 65.4 | 0.0566* | 0.083 | 4.71 |
| 380 | 0.0335 | 68.7 | 0.0251* | 0.0541 | 3.62 |
| 381 | 0.0552 | 67.4 | 0.183* | 0.347 | 0.965 |
| 382 | 0.0142 | 75.9 | 0.64+ | | |
| 383 | 0.0101 | 78.3 | 0.557+ | | |
| 384 | 0.039 | 75.5 | 0.122+ | | |
| 385 | 0.0838 | 78.1 | 1.33+ | | |
| 386 | 0.42 | 59.2 | 1.97* | | |
| 387 | 0.186 | 58.2 | >10+ | | |
| 388 | 0.381 | 52.8 | 6.53+ | | |
| 389 | 0.0195 | 82.3 | 0.11+ | 0.113 | 8.04 |
| 390 | 0.0015 | 80.4 | 0.167+ | 0.0631 | >10 |
| 391 | 0.0089 | 78.5 | 0.063+ | 0.171 | >10 |
| 392 | 0.0029 | 79.3 | 2.8+ | | |
| 393 | 0.0023 | 77 | 0.133+ | | |
| 394 | 0.0248 | 73.7 | 4.23+ | | |
| 395 | 0.0066 | 77.1 | 0.0238+ | 0.117 | 9.22 |
| 396 | 0.0036 | 68.9 | 0.033+ | 0.122 | >10 |
| 397 | 0.0102 | 77.2 | 0.0263+ | 0.0465 | 6.94 |
| 398 | 0.0088 | 65.9 | 0.0411+ | 0.116 | >10 |
| 399 | 0.0114 | 72.1 | 0.0344+ | 0.0952 | 8.89 |
| 400 | 0.0237 | 74.2 | 0.0388* | 0.137 | >10 |
| 401 | 0.0106 | 70.3 | 0.135* | | |
| 402 | 0.0451 | 76.8 | 0.0686* | 0.167 | 7.05 |
| 403 | 0.186 | 84.5 | 0.1* | 0.23 | 7.41 |
| 404 | 0.0845 | 92 | 0.0356* | 0.138 | >10 |
| 405 | 0.0052 | 93.9 | 0.0261* | 0.116 | >10 |
| 406 | 0.0551 | 75.7 | 0.161* | | |
| 407 | 0.203 | 105 | 0.517* | | |
| 408 | 0.0416 | 63 | 0.0671* | 0.215 | 8.16 |
| 409 | 0.0297 | 65.7 | 0.177* | | |
| 410 | 0.0205 | 69.3 | 0.0212+ | 0.373 | >10 |
| 411 | 0.0416 | 74.2 | 0.0741+ | 0.142 | >10 |
| 412 | 0.0105 | 72.2 | 0.0961+ | | |
| 413 | 0.0133 | 64.5 | 0.0421* | 0.138 | 2.17 |
| 414 | 0.0506 | 58.3 | 0.128* | | |
| 415 | 0.0154 | 99.9 | 0.0689* | 0.502 | 7.15 |
| 416 | 0.0135 | 81.8 | 0.133* | | |
| 417 | 0.0331 | 70.1 | 0.223* | | |
| 418 | 0.017 | 70.25 | 0.0674+ | 0.139 | >10 |
| 419 | 0.0186 | 78.6 | 0.121* | | |
| 420 | 0.0177 | 95 | 0.0506* | 0.353 | 3.87 |
| 421 | 0.0108 | 81.6 | 0.0194* | 0.114 | >10 |
| 422 | 0.0753 | 56.2 | 0.125* | | |
| 423 | 0.0216 | 74.2 | 0.0512* | 0.269 | 8.03 |
| 424 | 0.0051 | 81.7 | 4.11+ | | |
| 425 | 0.0555 | 90 | 0.193+ | | |
| 426 | 0.0585 | 74.7 | 0.226+ | | |
| 427 | 0.122 | 58.4 | 0.305+ | | |
| 428 | 0.0708 | 68.9 | 0.201+ | | |
| 429 | 0.255 | 59.6 | 1.18+ | | |
| 430 | 0.142 | 74.9 | 1.17+ | | |
| 431 | 0.0086 | 73.5 | 0.447+ | | |
| 432 | 0.0121 | 75.4 | 0.112+ | 0.141 | >10 |
| 433 | 0.0241 | 71.2 | 1.41+ | | |
| 434 | 0.0511 | 67.1 | 2.32+ | | |
| 435 | 0.0087 | 79.1 | 1.15+ | | |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative $IC_{50}$ | **H747 (CRC-MSS) Antiproliferative $IC_{50}$ |
|---|---|---|---|---|---|
| 436 | 0.0157 | 81.4 | 0.0895+ | 0.272 | >10 |
| 437 | 0.0155 | 84.2 | 0.0468+ | 0.123 | >10 |
| 438 | 0.0058 | 66.9 | 0.0912+ | 0.508 | >10 |
| 439 | 0.0187 | 61.5 | 0.199+ | | |
| 440 | 0.0376 | 68.5 | 0.37+ | | |
| 441 | 0.0265 | 72.6 | 0.123+ | 0.13 | >10 |
| 442 | 0.0093 | 72.7 | 0.046+ | 0.123 | >10 |
| 443 | 0.059 | 76.6 | 0.096+ | 0.353 | 4.36 |
| 444 | 0.0391 | 72.9 | 0.16* | | |
| 445 | 0.0808 | 70.5 | 0.319* | | |
| 446 | 0.115 | 64.1 | 0.966* | | |
| 447 | 0.009 | 74.9 | 0.0278+ | 0.11 | >10 |
| 448 | 1.75 | 66.7 | 2.73+ | | |
| 449 | 0.336 | 69.5 | 0.86+ | | |
| 450 | 0.0791 | 62.8 | 0.266* | | |
| 451 | 0.0543 | 73.2 | 1.05+ | | |
| 452 | 0.0329 | 80.5 | 0.0653* | 0.223 | >10 |
| 453 | 0.0122 | 90.7 | 0.0546* | 0.218 | 6.55 |
| 454 | 0.005 | 82.9 | 0.0182* | 0.218 | 5.81 |
| 455 | 0.0342 | 67.3 | 0.0576* | 0.0886 | 6.78 |
| 456 | 0.0162 | 61.5 | 0.0328* | 0.209 | 1.94 |
| 457 | 0.0202 | 58.7 | 0.0853* | 0.0761 | 4.8 |
| 458 | 0.0641 | 60.2 | 0.199* | | |
| 459 | 0.0267 | 65.7 | 0.0582* | 0.0937 | 2.66 |
| 460 | 0.131 | 60.9 | 0.0586* | 0.221 | 3.8 |
| 461 | 0.0539 | 46.1 | 0.158* | | |
| 462 | 0.0091 | 82.4 | 0.0257* | 0.257 | >10 |
| 463 | 0.0085 | 77.1 | 0.018* | 0.0593 | >10 |
| 464 | 0.0057 | 74.8 | 0.0172* | 0.247 | >10 |
| 465 | 0.0068 | 85.3 | 0.0352* | 0.115 | >10 |
| 466 | 0.0111 | 82.2 | 0.0524* | 0.35 | 4.85 |
| 467 | 0.155 | 99.3 | 0.164* | | |
| 468 | 0.132 | 96 | 0.269* | | |
| 469 | 0.0225 | 83.4 | 0.0838* | 0.522 | 3.79 |
| 470 | 0.125 | 93.8 | 0.62* | | |
| 471 | 0.0292 | 72.1 | 0.0275* | 0.0725 | 8.87 |
| 472 | 0.211 | 60.9 | 0.127* | | |
| 473 | 0.313 | 54.5 | 0.426* | | |
| 474 | 0.0117 | 70.4 | 0.0135* | 0.0872 | 6.63 |
| 475 | 0.0136 | 64.7 | 0.0315* | 0.0812 | 8.77 |
| 476 | 0.312 | 61.1 | 0.108* | 0.14 | 4.14 |
| 477 | 0.0468 | 68 | 0.0242* | 0.0802 | 2.525 |
| 478 | 0.15 | 66.8 | 0.102* | 0.259 | 4.84 |
| 479 | 0.0175 | 69.6 | 0.0169* | 0.0374 | 7.41 |
| 480 | 0.146 | 67.4 | 0.0558* | 0.15 | >10 |
| 481 | 0.204 | 62.1 | 0.128* | | |
| 482 | 0.0665 | 63.3 | 0.0356* | 0.0668 | 1.14 |
| 483 | 0.0673 | 56.4 | 0.061* | 0.101 | 1.71 |
| 484 | 0.0335 | 66.5 | 0.0318* | 0.0662 | 2.6 |
| 485 | 0.0191 | 66.5 | 0.0124* | 0.0583 | 2.06 |
| 486 | 0.0179 | 61.7 | 0.0311* | 0.112 | 1.99 |
| 487 | 0.0253 | 64.3 | 0.654* | | |
| 488 | 0.0679 | 61.1 | 0.285* | | |
| 489 | 0.0299 | 68.7 | 0.0225* | 0.051 | 2.06 |
| 490 | 0.041 | 67.9 | 0.0198* | 0.0762 | 2.12 |
| 491 | 0.0108 | 72 | 0.0207* | 0.0591 | 2.16 |
| 492 | 0.0066 | 62.3 | 0.0444* | 0.209 | >10 |
| 493 | 0.0248 | 67 | 0.022* | 0.131 | >10 |
| 494 | 0.0269 | 55.9 | 0.0429* | 0.129 | >10 |
| 495 | 0.0854 | 61.8 | 0.142* | | |
| 496 | 0.0195 | 71.9 | 0.0233* | 0.0482 | 2.02 |
| 497 | 0.0316 | 65.2 | 0.0437* | 0.169 | 2.49 |
| 498 | 0.038 | 65.4 | 0.131* | | |
| 499 | 0.0357 | 68.1 | 0.0248* | 0.0657 | >10 |
| 500 | 0.0669 | 72 | 0.0361* | 0.0836 | 5.2 |
| 501 | 0.0709 | 73.3 | 0.0933* | 0.274 | 7.26 |
| 502 | 0.0983 | 63.6 | 0.175* | | |
| 503 | 0.0397 | 63.7 | 9.03* | | |
| 504 | 0.0235 | 65.9 | 6.86* | | |
| 505 | 0.0464 | 54.3 | 0.219* | | |
| 506 | 0.184 | 47.4 | 0.725* | | |
| 507 | 1.51 | 52.9 | 1.86* | | |
| 508 | 0.0965 | 67.1 | 0.0634* | 0.108 | 6.46 |
| 509 | 0.004 | 90.9 | 0.0177* | 0.0731 | 5.89 |
| 510 | 0.0082 | 83.7 | 0.0161* | 0.123 | >10 |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative $IC_{50}$ | **H747 (CRC-MSS) Antiproliferative $IC_{50}$ |
|---|---|---|---|---|---|
| 511 | 0.0511 | 89.8 | 0.0372* | 0.149 | 7.41 |
| 512 | 0.0109 | 74.3 | 0.0176* | 0.107 | 6.72 |
| 513 | 0.0777 | 56.4 | 0.133* | | |
| 514 | 0.0733 | 73.8 | 0.0455* | 0.149 | >10 |
| 515 | 0.0016 | 73.9 | 0.0216* | 0.0893 | 8.78 |
| 516 | 0.204 | 57.7 | 0.22* | | |
| 517 | 0.0237 | 54.1 | 0.0168* | 0.135 | 2.22 |
| 518 | 0.153 | 56.7 | 0.0573* | 0.203 | >10 |
| 519 | 0.0081 | 71.2 | 0.191* | | |
| 520 | 0.0137 | 70.8 | 0.0402+ | 0.118 | >10 |
| 521 | 0.0035 | 71.8 | 0.0351+ | 0.069 | >10 |
| 522 | 0.0408 | 71.8 | 0.109* | 0.211 | >10 |
| 523 | 0.0314 | 64.1 | 0.0572* | 0.174 | 5.95 |
| 524 | 0.0329 | 62.65 | 0.0766* | 0.138 | 6.29 |
| 525 | 0.0433 | 63.3 | 0.043* | 0.144 | 1.35 |
| 526 | 0.0174 | 61.7 | 0.0293* | 0.133 | >10 |
| 527 | 0.0424 | 65.3 | 0.109* | 0.0654 | 5.58 |
| 528 | 0.0262 | 61.5 | 0.0723* | 1.13 | 6.96 |
| 529 | 0.163 | 57.3 | 0.253* | | |
| 530 | 0.427 | 83.7 | >10* | | |
| 531 | 2.6 | 72.3 | >10* | | |
| 532 | 0.0264 | 70.8 | 0.0301* | 0.1 | 4.2 |
| 533 | 0.0072 | 83.2 | 0.0145* | 0.0739 | 4.81 |
| 534 | 0.0199 | 78.3 | 0.0876* | 0.0554 | >10 |
| 535 | 0.0034 | 84.2 | 0.0047* | 0.0933 | >10 |
| 536 | 0.0453 | 69.7 | 0.049* | 0.0704 | 6.8 |
| 537 | 0.0208 | 63 | 0.03* | 0.0828 | 6.53 |
| 538 | 0.0092 | 66.9 | 0.0574+ | 0.124 | 3.62 |
| 539 | 0.0181 | 76 | 0.0162+ | 0.0983 | 7.01 |
| 540 | 0.0174 | 67.5 | 0.0741 | 0.175 | 7.91 |
| 541 | 0.0151 | 74.1 | 0.0377* | 0.0498 | 5.9975 |
| 542 | 0.03 | 73 | 0.307* | | |
| 543 | 0.0486 | 60.2 | 0.183* | | |
| 544 | 0.059 | 66.5 | 0.538* | | |
| 545 | 0.0742 | 64.7 | 0.192* | | |
| 546 | 0.0131 | 73.6 | 0.109* | 1.09 | >10 |
| 547 | 0.126 | 81.1 | 0.127* | 0.173 | 5.43 |
| 548 | 0.0273 | 64.6 | 0.0804* | 0.226 | 6.46 |
| 549 | 0.019 | 73.6 | 0.0483* | 0.369 | >10 |
| 550 | 0.025 | 99.8 | 0.105* | 0.352 | 3.64 |
| 551 | 0.105 | 87.4 | 0.127* | 0.225 | 3.5 |
| 552 | 0.0166 | 89.7 | 0.238* | | |
| 553 | 0.0203 | 80.2 | 0.0716* | 0.211 | >10 |
| 554 | 0.0761 | 79.7 | 0.238* | | |
| 555 | 0.0436 | 61.9 | 0.0466* | 0.121 | 4.47 |
| 556 | 0.0206 | 64.8 | 0.0545* | 0.0749 | 4.52 |
| 557 | 0.0371 | 59.8 | 0.0926* | 0.131 | 2.3 |
| 558 | 0.0458 | 78 | 2.91* | | |
| 559 | 0.0334 | 72.175 | 0.0425* | 0.074 | 3.373333 |
| 560 | 0.051 | 59 | 0.148* | 0.145 | >10 |
| 561 | 0.0159 | 69.7 | 0.274* | | |
| 562 | 0.0645 | 62.3 | 0.543* | | |
| 563 | 0.0713 | 66.9 | 0.327* | | |
| 564 | 0.0701 | 77.8 | 0.761* | | |
| 565 | 0.0371 | 60 | 0.0565* | 0.0582 | 3.01 |
| 566 | 0.186 | 66 | 0.156* | | |
| 567 | 0.0584 | 77 | 0.34 * | | |
| 568 | 0.0079 | 77.3 | 0.0575+ | 0.349 | >10 |
| 569 | 0.0556 | 75.9 | 0.146+ | | |
| 570 | 0.0214 | 69.8 | 0.224+ | | |
| 571 | 0.0211 | 71.3 | 0.0621+ | 0.159 | 3.56 |
| 572 | 0.0112 | 73.3 | 0.0551+ | 0.144 | >10 |
| 573 | 0.0155 | 82.8 | 0.106+ | 0.103 | >10 |
| 574 | 0.0075 | 80.6 | 0.0395+ | 0.0922 | >10 |
| 575 | 0.0177 | 76.2 | 0.215+ | | |
| 576 | 0.0285 | 68.1 | 0.128+ | | |
| 577 | 0.0249 | 91.5 | 0.153+ | | |
| 578 | 0.149 | 70.1 | 0.491+ | | |
| 579 | 0.0311 | 65.2 | 0.103* | 0.329 | >10 |
| 580 | 0.0239 | 70.5 | 0.156* | | |
| 581 | 0.0991 | 50.5 | 1.68* | | |
| 582 | 0.287 | 49.9 | 0.21* | | |
| 583 | 0.0049 | 72.5 | 0.0431* | | |
| 584 | 0.017 | 63.5 | 0.0421+ | 0.122 | >10 |
| 585 | 0.0229 | 70.9 | 0.0651* | 0.208 | >10 |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative IC$_{50}$ | **H747 (CRC-MSS) Antiproliferative IC$_{50}$ |
|---|---|---|---|---|---|
| 586 | 0.149 | 72.2 | 0.353* | | |
| 587 | 0.0167 | 70.9 | 0.128* | | |
| 588 | 0.103 | 67.7 | 0.461* | | |
| 589 | 0.0614 | 69.7 | 0.117* | | |
| 590 | 0.0059 | 74.8 | 0.0337* | 0.533 | >10 |
| 591 | 0.0183 | 65.9 | 0.13* | | |
| 592 | 0.0541 | 77.5 | 0.303* | | |
| 593 | 0.03 | 99.9 | 0.17* | | |
| 594 | 0.0109 | 80.1 | 0.14* | | |
| 595 | 0.0175 | 69.35 | 0.0352+ | 0.167 | 7.4 |
| 596 | 0.0181 | 72.2 | 0.038* | 0.172 | 9.88 |
| 597 | 0.022 | 69.1 | 0.0648* | 0.164 | >10 |
| 598 | 0.0164 | 72.1 | 0.0506* | 0.174 | >10 |
| 599 | 0.0192 | 88.7 | 0.0378* | 0.149 | 4.33 |
| 600 | 0.0416 | 79.3 | 0.186* | | |
| 601 | 0.0212 | 72.2 | 0.106* | 0.0645 | >10 |
| 602 | 0.0578 | 92.4 | 0.18* | | |
| 603 | 0.0109 | 83.4 | 0.0458* | 1.09 | 8.37 |
| 604 | 0.037 | 69.1 | 0.16+ | | |
| 605 | 0.0246 | 67.5 | 5.33+ | | |
| 606 | 0.026 | 71.8 | 1.51+ | | |
| 607 | 0.0131 | 75.9 | 0.126+ | | |
| 608 | 0.0072 | 75.4 | 0.422+ | | |
| 609 | 0.003 | 72.7 | 0.0047* | 0.658 | >10 |
| 610 | 0.0287 | 64.1 | 0.121* | | |
| 611 | 0.0038 | 65.3 | 0.0205* | 0.133 | 8.83 |
| 612 | 0.0101 | 70 | 0.0212* | 0.281 | >10 |
| 613 | 0.0042 | 70.3 | 0.116* | 0.173 | >10 |
| 614 | 0.0146 | 70.4 | 0.0269* | 0.0531 | 3.19 |
| 615 | 0.0526 | 73.9 | 0.133* | 0.0713 | 7.56 |
| 616 | 0.0114 | 84.2 | 0.0173* | 0.348 | >10 |
| 617 | 0.0252 | 63.8 | 0.0321* | 0.0579 | 4.48 |
| 618 | 0.0592 | 66.6 | 0.0454* | 0.132 | 1.85 |
| 619 | 0.178 | 81.3 | 0.0845* | 0.178 | 3.62 |
| 620 | 0.0037 | 75.9 | 0.0062+ | 0.0264 | >10 |
| 621 | 0.0068 | 74.4 | 0.002+ | 0.0087 | >10 |
| 622 | 0.023 | 62.9 | 0.0559* | 0.0489 | >10 |
| 623 | 0.0039 | 94.5 | 0.0112* | 0.0723 | >10 |
| 624 | 0.0089 | 97.2 | 0.442* | | |
| 625 | 0.0126 | 87.8 | 1.01* | | |
| 626 | 0.0042 | 75.7 | 0.0241* | 0.137 | >10 |
| 627 | 0.0294 | 75.8 | 0.0376* | 0.0294 | >10 |
| 628 | 0.537 | 58.1 | 1.08* | | |
| 629 | 0.0289 | 74.8 | 0.112* | 0.0692 | >10 |
| 630 | 0.0229 | 67 | 0.0892* | 0.0983 | >10 |
| 631 | 0.0312 | 64.4 | 0.0593* | 0.156 | 4.88 |
| 632 | 0.241 | 71.5 | 0.112* | 0.0968 | >10 |
| 633 | 0.0526 | 71.2 | 0.046* | 0.0104 | 6.46 |
| 634 | 0.0133 | 68.2 | 0.0186* | 0.0247 | 8.98 |
| 635 | 0.002 | 68.5 | 0.0191* | 0.0792 | >10 |
| 636 | 0.0122 | 70.3 | 0.3* | 1.21 | >10 |
| 637 | 0.0034 | 71.4 | 0.427* | | |
| 638 | 0.0139 | 70.5 | 0.0621* | | |
| 639 | 0.0077 | 59.7 | 0.0266* | | |
| 640 | 0.007 | 59 | 0.0162* | | |
| 641 | 0.009 | 71 | 0.0552* | | |
| 642 | 0.0198 | 67.3 | 0.0945* | | |
| 643 | 0.0408 | 61.4 | >10+ | | |
| 644 | 0.095 | 71.2 | 8.72+ | | |
| 645 | 0.366 | 70.8 | 1.26+ | | |
| 646 | 0.0079 | 66.6 | 0.0453* | 0.0325 | >10 |
| 647 | 0.0061 | 72.9 | 0.998* | | |
| 648 | 0.0069 | 69.1 | 0.471* | | |
| 649 | 0.0503 | 67.6 | 9.93+ | | |
| 650 | 0.0524 | 80.6 | 0.859+ | | |
| 651 | 0.0706 | 59.6 | 0.535* | | |
| 652 | 0.343 | 68.1 | 3.77* | | |
| 653 | 0.002 | 75.7 | 0.292* | | |
| 654 | 0.0216 | 72.7 | 5.31+ | | |
| 655 | 0.0114 | 67.8 | 4.52+ | | |
| 656 | 0.0307 | 71.3 | 0.239+ | | |
| 657 | 0.0147 | 71.8 | 0.817+ | | |
| 658 | 0.0539 | 73.1 | 0.425+ | | |
| 659 | 0.0688 | 50.7 | >10* | | |
| 660 | 2.12 | 67.1 | >10* | | |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative $IC_{50}$ | **H747 (CRC-MSS) Antiproliferative $IC_{50}$ |
|---|---|---|---|---|---|
| 661 | 0.0032 | 78.6 | >10+ | | |
| 662 | 0.068 | 66.1 | 0.14* | | |
| 663 | 0.033 | 66.3 | 0.124* | | |
| 664 | 0.0877 | 68.8 | 0.0719* | 0.163 | >10 |
| 665 | 0.0309 | 70.1 | 4.99+ | | |
| 666 | 0.121 | 78.4 | 0.427* | | |
| 667 | 0.145 | 67.1 | 0.804* | | |
| 668 | 0.0073 | 82.3 | 0.22* | | |
| 669 | 0.0019 | 80.8 | 0.124+ | | |
| 670 | 0.0062 | 73.4 | >10* | | |
| 671 | 0.0068 | 68.8 | >10* | | |
| 672 | 0.0978 | 65.1 | 0.154* | | |
| 673 | 0.104 | 70.2 | 0.13* | | |
| 674 | 0.0039 | 66.5 | 0.0289+ | 0.119 | >10 |
| 675 | 0.0041 | 71.2 | 0.0232+ | 0.121 | >10 |
| 676 | 0.07 | 68.4 | 0.806+ | | |
| 677 | 0.0068 | 75.1 | 0.0137* | | |
| 678 | 0.0057 | 71.3 | 0.0187* | 0.391 | 3.1 |
| 679 | 0.0125 | 70.2 | 0.196* | | |
| 680 | 0.003 | 95 | 0.031* | 0.208 | 8.76 |
| 681 | 0.0024 | 77.5 | 0.133* | | |
| 682 | 0.0835 | 85.4 | 0.149+ | | |
| 683 | 1.71 | 62.5 | >10* | | |
| 684 | 8.31 | 50.6 | >10* | | |
| 685 | 0.117 | 64.3 | 0.769+ | | |
| 686 | 0.0182 | 66.6 | 0.0477* | 0.132 | 4.63 |
| 687 | 0.119 | 68.1 | 3.56+ | | |
| 688 | 0.0161 | 67.9 | 0.0475* | 0.122 | 6.36 |
| 689 | 0.0036 | 85 | 0.34+ | | |
| 690 | 0.0073 | 75.8 | 0.0557+ | 0.183 | >10 |
| 691 | 0.0359 | 68.5 | 0.291+ | | |
| 692 | 0.0027 | 81.5 | 0.142+ | | |
| 693 | 0.408 | 64.9 | 0.858+ | | |
| 694 | 0.0293 | 73 | 0.09* | 0.0804 | 7.77 |
| 695 | 0.0085 | 69.7 | 0.143* | 2.97 | >10 |
| 696 | 0.0115 | 75.4 | 0.0367* | 0.0451 | 7.7 |
| 697 | 0.0409 | 59.5 | 0.329* | | |
| 698 | 1.05 | 75.4 | 2.49+ | | |
| 699 | 0.0022 | 93.6 | 0.0219* | 0.517 | >10 |
| 700 | 0.153 | 85.6 | 0.871* | | |
| 701 | 0.115 | 66.9 | 0.638* | | |
| 702 | 0.0955 | 70.8 | 0.0316* | 0.224 | 8.12 |
| 703 | 0.0444 | 53.6 | 0.387* | | |
| 704 | 0.0125 | 78.1 | 0.0254* | 0.0569 | 7.14 |
| 705 | 0.0192 | 55.6 | 0.679+ | | |
| 706 | 0.0196 | 96.1 | 0.0517* | 0.243 | 3.88 |
| 707 | 0.0283 | 67.1 | 0.0254* | 0.0685 | 5.36 |
| 708 | 0.0691 | 73 | 0.0926* | 0.14 | 6.46 |
| 709 | 0.1 | 60.9 | 1.24+ | | |
| 710 | 0.0145 | 69 | 0.0107* | 0.0481 | 5.4 |
| 711 | 0.0321 | 69.3 | 0.17* | | |
| 712 | 0.0562 | 74.2 | 0.312* | | |
| 713 | 0.025 | 76 | 0.105+ | 0.105 | >10 |
| 714 | 0.0053 | 68.7 | 0.181* | | |
| 715 | 0.0103 | 67.8 | 0.0144* | 0.0699 | 9.76 |
| 716 | 0.128 | 55.9 | >10* | | |
| 717 | 0.199 | 68.1 | >10+ | | |
| 718 | 0.0157 | 72.7 | 0.137+ | 0.114 | >10 |
| 719 | 0.0847 | 69.7 | 2.28+ | | |
| 720 | 0.0252 | 72.6 | 0.0549* | 0.452 | 7.9 |
| 721 | 0.231 | 68.1 | 1.57+ | | |
| 722 | 0.0191 | 74.4 | 0.0511+ | 0.0506 | >10 |
| 723 | 0.0016 | 84.3 | 0.0735+ | 0.733 | >10 |
| 724 | 0.0197 | 80.4 | 0.224* | | |
| 725 | 0.0365 | 74 | 0.625* | | |
| 726 | 0.0175 | 88.1 | 0.32* | | |
| 727 | 9.03 | 55.3 | 0.71* | | |
| 728 | 0.158 | 62.5 | 1.35* | | |
| 729 | 0.114 | 45.5 | 0.382* | | |
| 730 | 0.0117 | 72.6 | 0.171* | | |
| 731 | 0.0635 | 69.1 | >10+ | | |
| 732 | 0.0105 | 70.8 | 0.0261* | 0.0341 | 4.57 |
| 733 | 0.0218 | 61.3 | 0.0883* | 0.206 | >10 |

TABLE 1-continued

| Example Number | DHX9 Biochemical Inflection Point (μM) | DHX9 Biochemical Max Inhibition (%) | DHX9 Cellular Target Engagement EC50 (μM) | **LS411N (CRC-MSI-H) Antiproliferative $IC_{50}$ | **H747 (CRC-MSS) Antiproliferative $IC_{50}$ |
|---|---|---|---|---|---|
| 734 | 0.0066 | 71.2 | 0.003* | 0.0106 | 6.17 |
| 735 | 0.007 | 80.1 | 0.0772* | 0.306 | >10 |
| 736 | 0.0549 | 70.3 | 0.372 | | |

⁺indicates the SyBr assay was used and
*indicates the Taqman assay was used.
**Anti-proliferation assay was performed at Pharmaron.

TABLE 2

| | | CRC-MSI | | CRC-MSS | |
| | | | *LS411N | | |
| Example No. | circBRIP1 EC50 (μM) | *HCT116 Anti-proliferative IC50 (μM) | Anti-proliferative Activity IC50 (μM) | *Colo205 Anti-proliferation IC50 (μM) | *NCI-H747 Anti-proliferative Activity (μM) |
|---|---|---|---|---|---|
| 15 | 0.85 | 1.03 | 2.57 | 10.59 | 23.21 |
| 17 | 0.057 | 0.11 | 0.131 | 11.82 | >30 |
| 31 | 0.054 | 0.045 | 0.041 | 7.05 | >10 |

*Anti-proliferation assay was performed at Accent Therapeutics, Inc.

Figure 4:
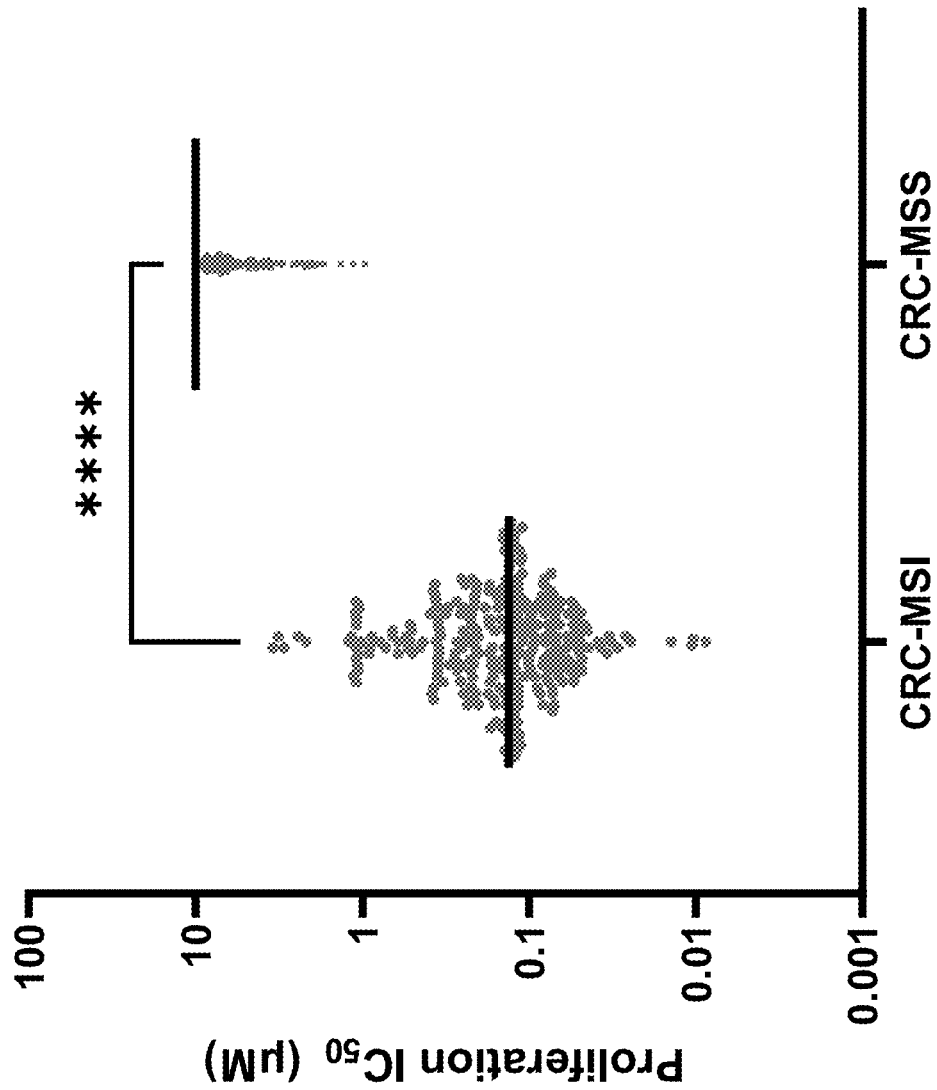
FIG. 4 shows anti-proliferation activity of 290 DHX9 inhibitor compounds described herein in CRC-MSI (LS411N) cells versus CRC-MSS (NCI-H747) cells.

As shown in Table 1, 290 DHX9 inhibitor compounds were screened in the DHX9 cellular proliferation assay in both a CRC-MSI (LS411N) and a CRC-MSS (NCI-H747) cell line. Overall DHX9 compound sensitivity is significantly greater in the CRC-MSI cell line when compared to the CRC-MSS cell line using a unpaired two-tailed t-test, p-value=<0.0001 (FIG. 4).

5. In Vivo Efficacy Demonstration for DHX9 Compounds

Experiments were performed in female BALB/c nude mice (GenPharmatech Co.). Animals were allowed to acclimate for 7 days before the study. The general health of the animals were evaluated by a veterinarian, and complete health checks were performed prior to the study. General procedures for animal care and housing were in accordance with the standard, Commission on Life Sciences, National Research Council, Standard Operating Procedures (SOPs) of Pharmaron, Inc. The mice were kept in laminar flow rooms at constant temperature and humidity with 3-5 mice in each cage. Animals were housed in polycarbonate cage which is the size of 300×180×150 mm3 and in an environmentally monitored, well-ventilated room maintained at a temperature of (23±3° C.) and a relative humidity of 40% 70%. Fluorescent lighting provided illumination approximately 12 hours per day. Animals had free access to irradiation sterilized dry granule food during the entire study period except for time periods specified by the protocol, as well as sterile drinking water in a bottle was available ad libitum during the quarantine and study periods.

The LS411N (ATCC; CRL-2159) tumor cell lines were maintained in vitro as monolayer in RPMI 1640 medium supplemented with 10% heat inactivated FBS, at 37° C. in an atmosphere of 5% $CO_2$ in air. The tumor cells were sub-cultured, not exceeding 4-5 passages, and cells growing in an exponential growth phase were harvested and counted for tumor inoculation. Each mouse was inoculated subcutaneously on the right flank with LS411N tumor cells ($2 \times 10^6$) in 0.1 mL of RPMI-1640 with Matrigel (1:1) for model development.

Depending on the target concentration, 14.4-144 mg of compound of Example 31 was dissolved in in 0.96 mL Solutol while vortexing and sonicating for 1 hour to obtain a suspension. Then 2.4 mL of 1% MC (with 100 mg/mL PVP VA64) was added and vortexed for 5 min to obtain homogeneous suspension. The mixture was kept stirring at room temperature for 5 min, and then 1.44 mL of water was added while vortexing to make the final volume of 4.8 mL. The mixture was kept stirring at RT for 30 min and homogenized for 3 min. The resulting solution was used for in vivo studies.

Treatment was started when the mean tumor size reached approximately 100-150 $mm^3$, at which time the mice were randomized into treatment groups. Animals were then treated with vehicle (20% Solutol/50% 1% MC (4000 cp) with 100 mg/mL PVP VA64/30% water) or indicated mg/kg (30-300) of Example 31 daily BID (12 hour schedule) by oral gavage at a final dosing volume of 10 mL/kg.

All study animals were monitored for not only tumor growth but also behavior such as mobility, food and water consumption (by cage side checking only), body weight (BW), eye/hair matting and any other abnormal effect. Body weights of all animals was measured and recorded twice per week throughout the study. Body weight change, expressed in %, was calculated using the following formula:

$$BW\ change(\%) = (BWDay\ PG\text{-}DX/BWDay\ PG\text{-}D1) \times 100; PG\text{-}D1\ \text{is the first day of dosing.}$$

The measurement of tumor size was conducted with a caliper and recorded twice per week. The tumor volume (TV) (mm3) was estimated using the formula: $TV = a \times b2/2$, where "a" and "b" are long and short diameters of a tumor, respectively.

The TVs were used for calculation of the tumor growth inhibition and tumor growth delay. For the tumor growth inhibition (TGI), the value using the formula:

$$\%T/C = (TreatedTVfinal - TreatedTVinitial)/(VehicleTVfinal - VehicleTVinitial) \times 100$$

$$\%TGI = [1 - (TreatedTVfinal - TreatedVTinitial)/(VehicleTVfinal - VehicleTVinitial)] \times 100$$

The "TVfinal" and "TVinitial" are the mean tumor volumes on the final day and initial day.

Tumor regression was calculated according to the following formula:

(TreatedTVfinal−TreatedTVinitial/TreatedTVinitial)×100

All statistical tests was conducted on GraphPad, and the level of significance was set at 5% r P<0.05. The group means and standard deviations was calculated for all measurement parameters. One-way Ordinary and Two-way RM ANOVA followed by Tukeys post hoc comparisons of the means was applied among groups.

Figure 1B:
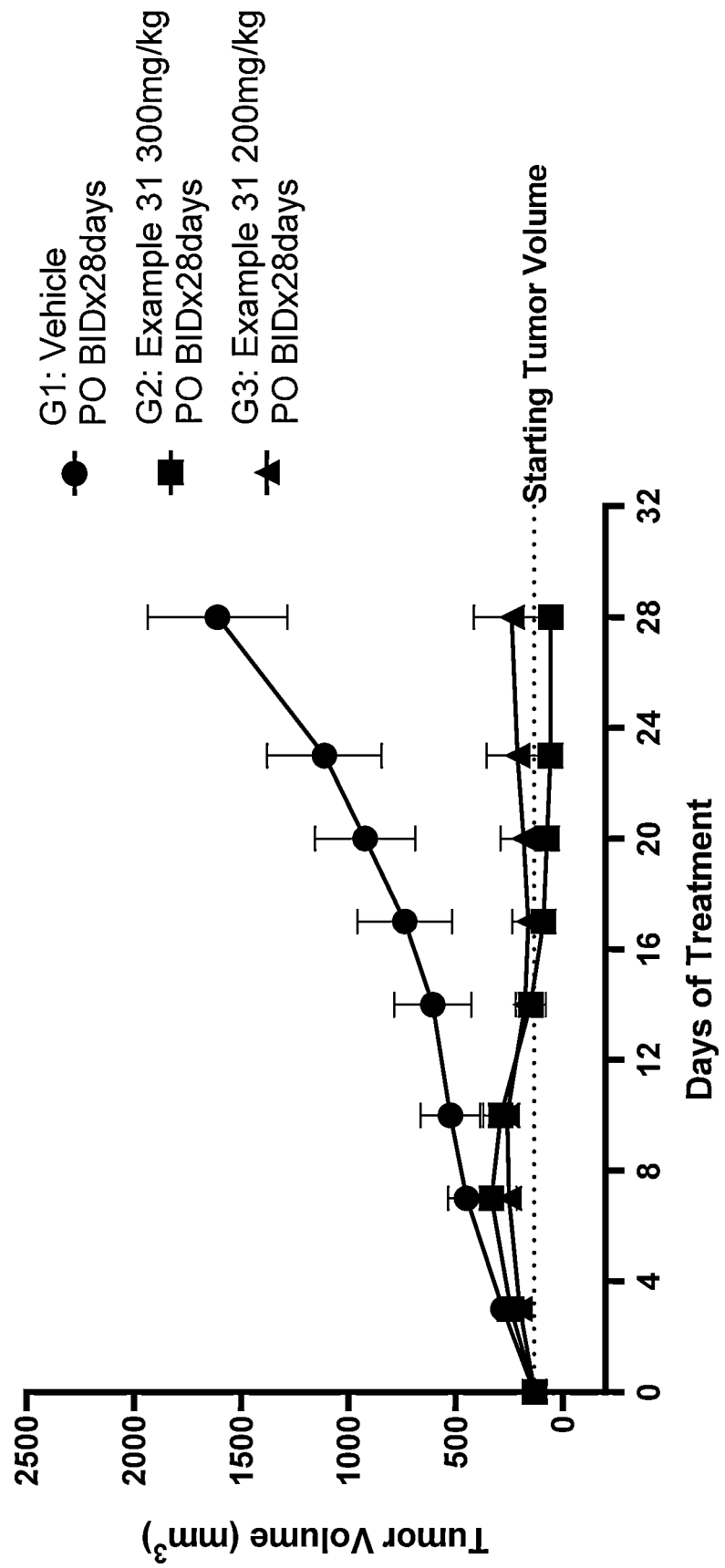
Figure 1C:
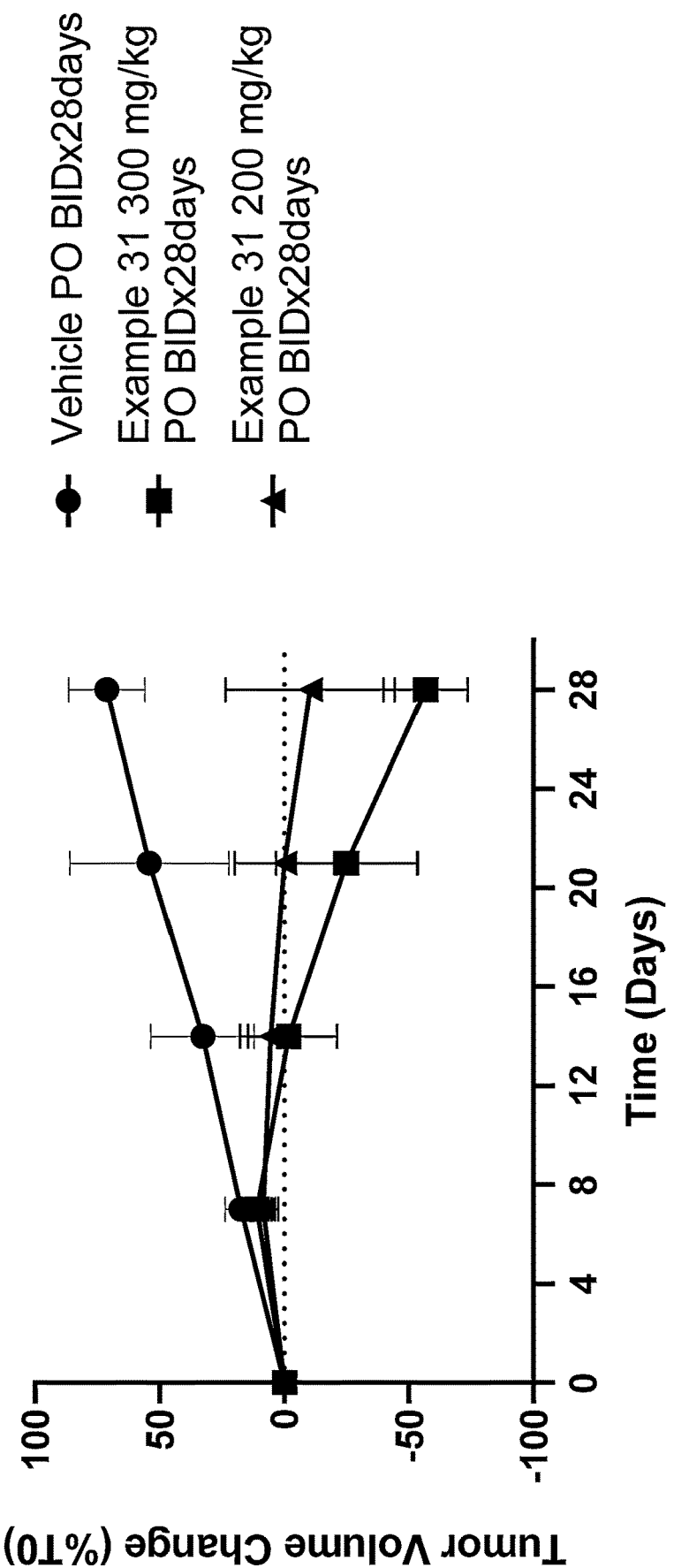
FIG. 1c shows percentage of tumor volume change over time for the in vivo efficacy study of compound of Example 31 in LS411N Xenografts.

Treatment was initiated with, for example, compound of Example 31 treated at 30, 100, 200 and 300 mg/kg using BID oral application when the tumor volume was an average of 133 mm³ (n=8/group). The initial treatment period with compound of Example 31 was 21 days, after which overall efficacy and tolerability were evaluated based on tumor volume and body weight changes observed during the treatment period (FIG. 1a and FIG. 1c).

Figure 2:
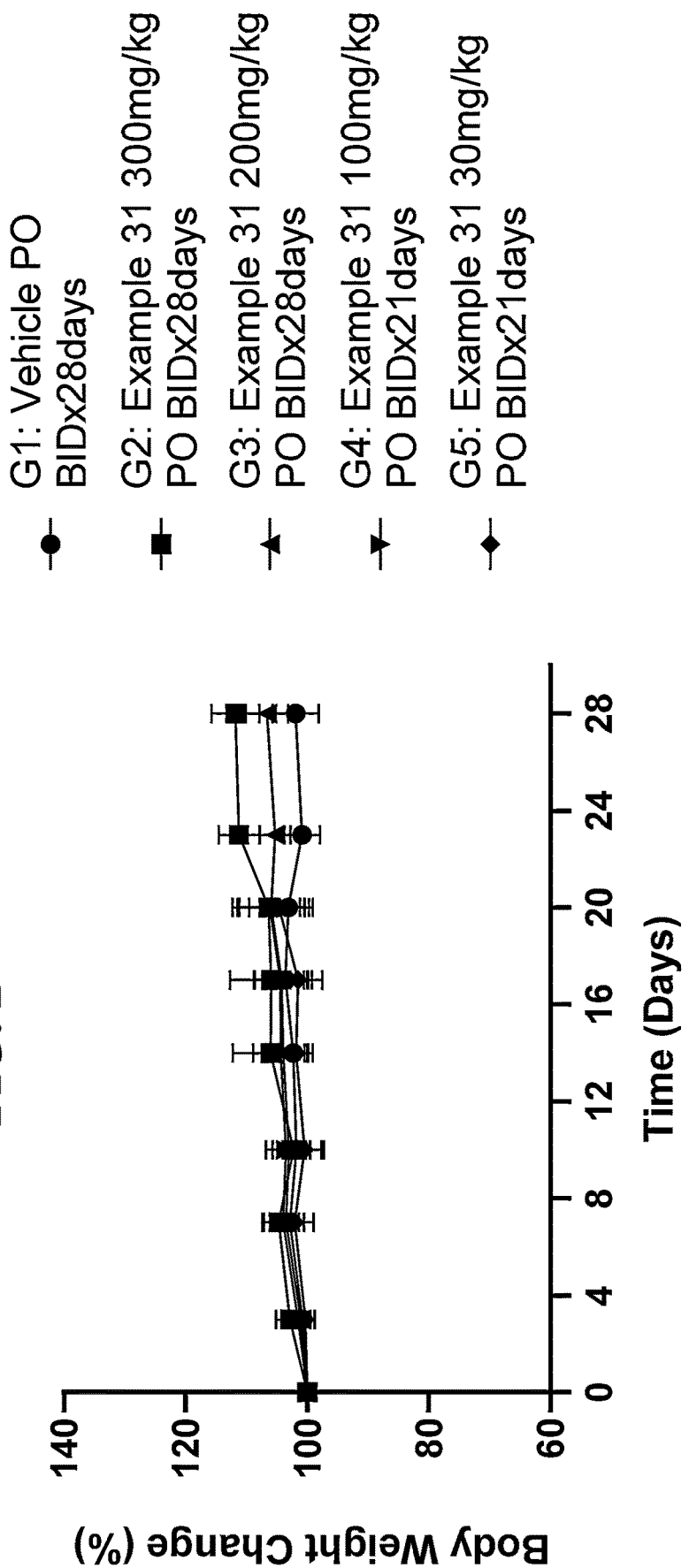
FIG. 2 shows percentage of body weight change over time for the in vivo efficacy studies of compound of Example 31 in LS411N Xenografts.

The treatment was then continued for an additional 7 days for the vehicle, 300 mg/kg and 200 mg/kg groups. On day 28, Example 31 dosed orally at 300 mg/kg BID induced an antitumor response against LS411N xenografts in nude mice, where the % T/C value was −5.2% and the % TGI was 105.2%, with a p-value=<0.0001 when compared with vehicle control using a one way ordinary ANOVA test (FIG. 1b). The mean tumor volume on day 28 for 300 mg/kg BID showed a −56% regression (FIG. 1c). Based on body weight, BID dosing of all concentrations of compound of Example 31 was well tolerated (FIG. 2).

Figure 3A:
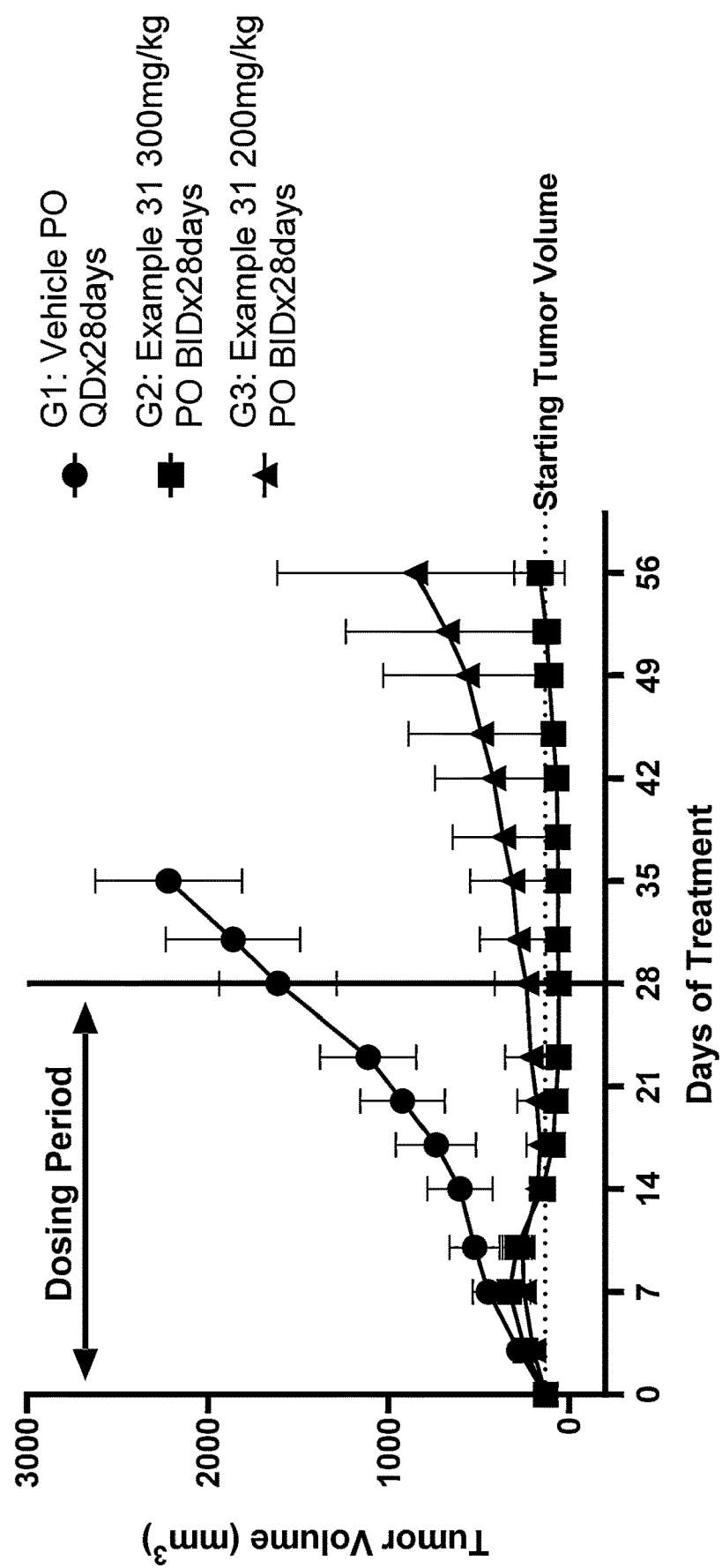
FIG. 3a. shows tumor volume over time during and after dosing period for the in vivo efficacy study of compound of Example 31 in LS411N Xenografts.
Figure 3B:
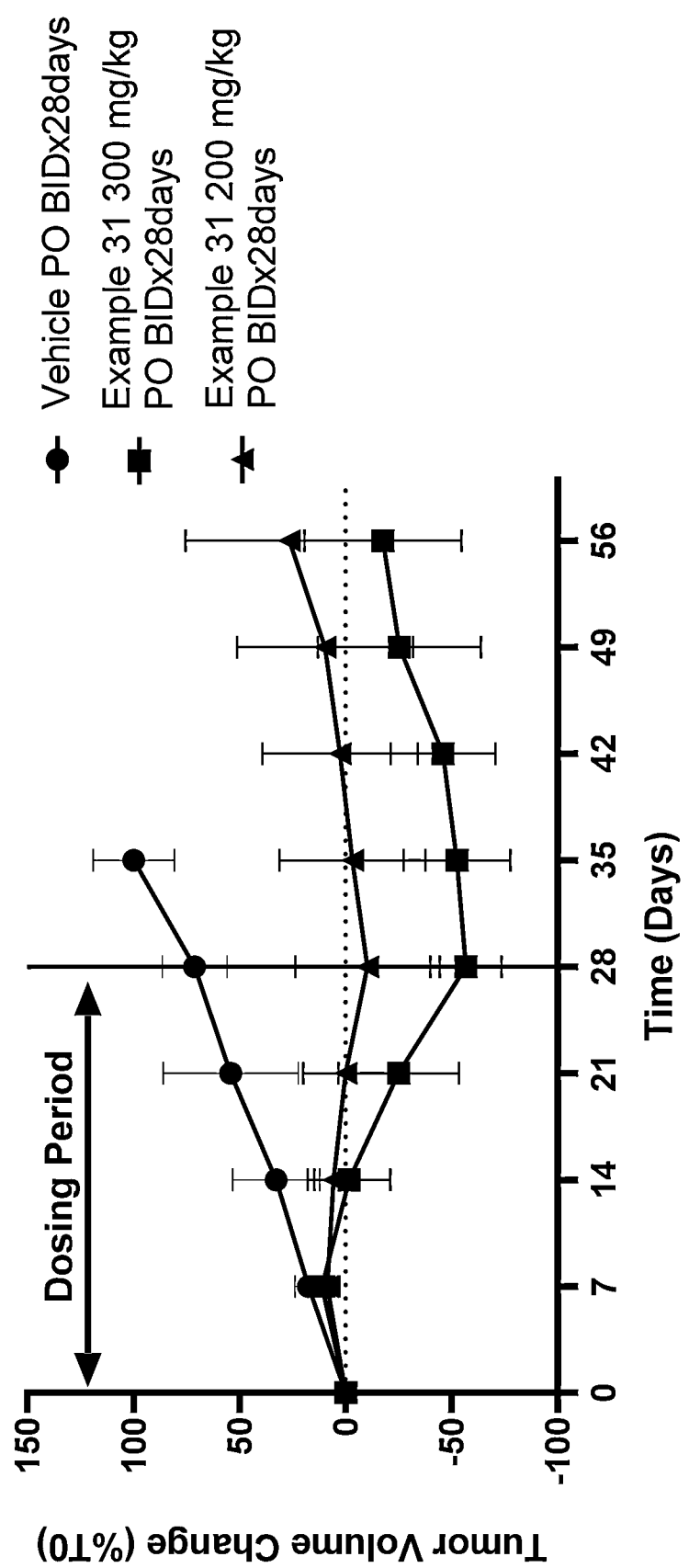
FIG. 3b shows percentage of tumor volume change over time during and after 28 days dosing period for the in vivo efficacy study of compound of Example 31 in LS411N Xenografts.

After 28 days of treatment with compound of Example 31, dosing was stopped and the animals and tumors were monitored for an additional 28 days (FIG. 3a). Vehicle animals were sacrificed on day 38 due to maximum tumor volume reaching above 2500 mm³. Regressed 300 mg/kg BID treated tumors showed little rebound with no compound treatment, going from −56% regression on day 28, to −17% regression on day 56 (FIG. 3b).

6. Cell Line Panel Proliferation Screen

Study was performed at Eurofins Discovery. The OncoPanel™ cell proliferation assay measures the proliferation response of cancer cell lines to drug treatments through bioluminescence CellTiter-Glo readout. Cell viability was measured by the bioluminescence signal generated by the production of ATP in viable cells.

Cells were grown in RPMI 1640, 10% FBS, 2 mM L-alanyl-L-glutamine, 1 mM Na pyruvate, or a special medium according to cell vendor recommendations. Cells were seeded into 384-well plates and incubated in a humidified atmosphere of 5% CO2 at 37° C. Compounds were added the day following cell seeding. At the same time, a time zero untreated cell plate was generated. After a 10-day incubation period, cells were lysed with cell viability detection reagent CellTiter-Glo® (Promega). At 7 days post-seeding, the growth media were replaced, and the plates were re-dosed with the test compound.

Compound of Example 17 was serially diluted in 3-fold steps from the highest test concentration of 10 μM, and assayed over 10 concentrations with a maximum assay concentration of 0.1% DMSO. Bioluminescence was read by a PerkinElmer Envision® microplate reader.

Cellular response parameters were calculated using non-linear regression to a sigmoidal single-site dose response model:

$$y = A + \frac{B - A}{1 + (C/x)^D}$$

Where y is a response measured at concentration x, A and B are the lower and upper limits of the response, C is the concentration at the response midpoint ($EC_{50}$), and D is the Hill Slope1.

$EC_{50}$ is the concentration of Example 17 at the curve inflection point or half the effective response (parameter C of the fitted curve solution).

Curve-fitting, calculations, and report generation was performed using a custom data reduction engine and MathIQ based software (AIM).

Figure 5A:
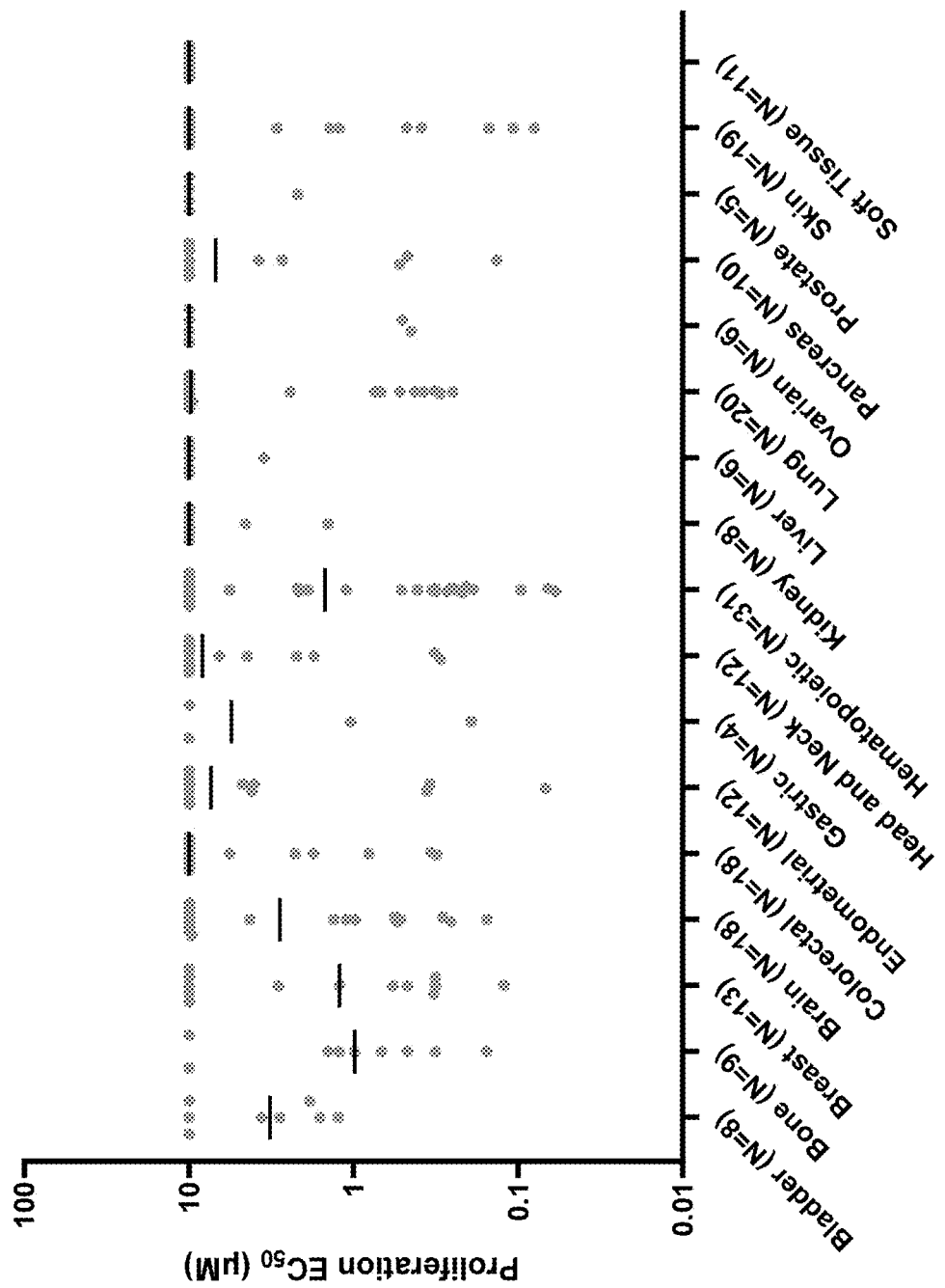
FIG. 5a shows 10-day proliferation screen for compound of Example 18 in various cancer cell line panels.
Figure 5B:
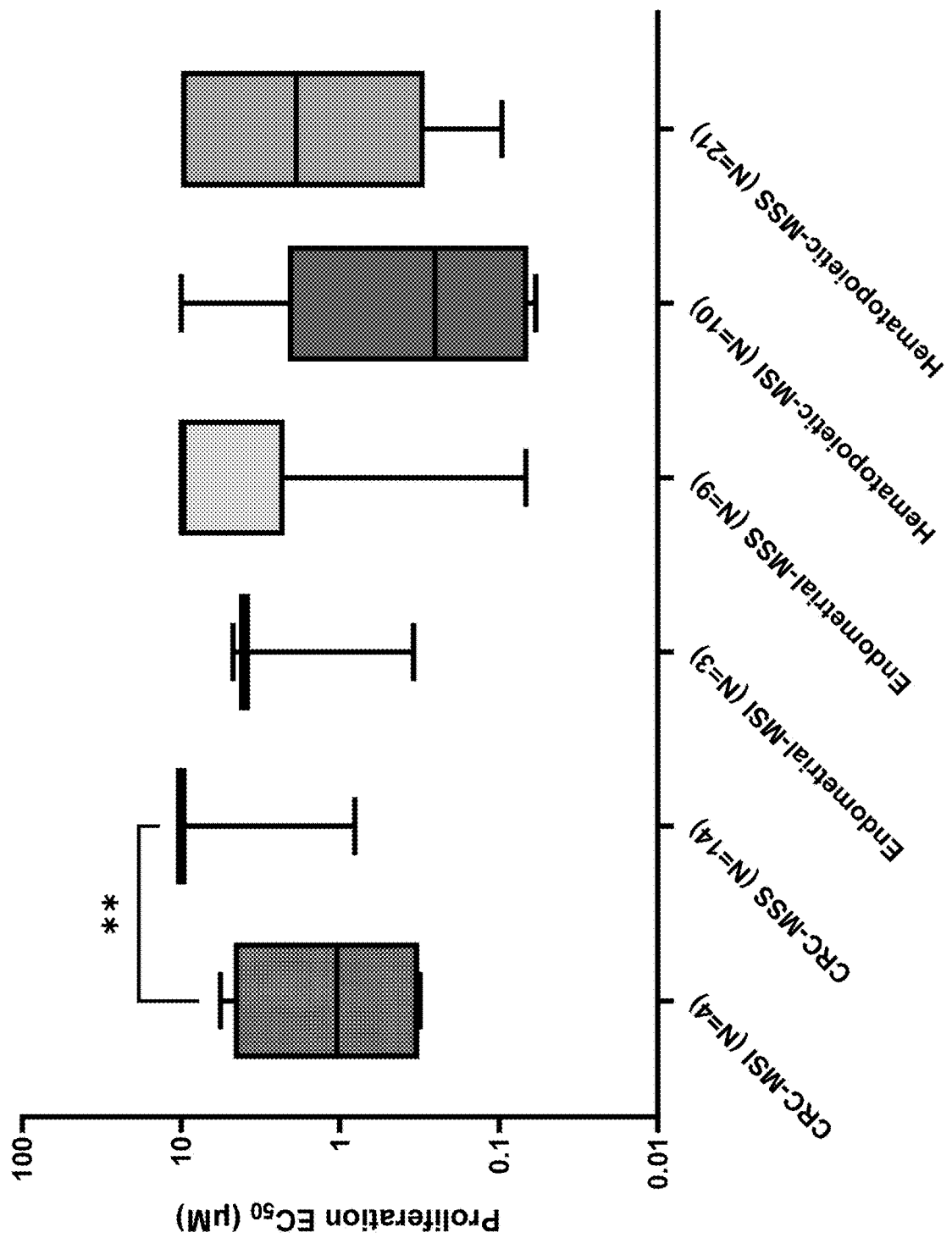
FIG. 5b shows proliferation $EC_{50}$ for compound of Example 18 in MSI cell lines vs. MSS cell lines as represented in colorectal, endometrial, and hematopoietic cancers.

A total of 214 cell lines representing 17 tumor indications were screened using Example 17. The results of this assay are shown by plotting the $EC_{50}$ values across the different indications (FIG. 5a). MSI status of the cell lines within the panel were annotated, DHX9 inhibitor Example 17 showed greater sensitivity in the MSI populations vs MSS populations as represented in colorectal, endometrial, and hematopoietic cancer. CRC-MSI sensitivity over CRC-MSS is statistically significant using an unpaired two-tailed t-test, p-value=<0.00010 (FIG. 5b).

What is claimed is:

1. A compound represented by Formula (IIB):

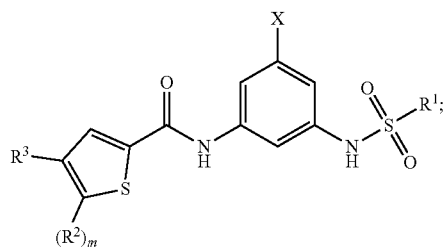

or a pharmaceutically acceptable salt thereof, wherein:
m is 1;
$R^1$ is —$CH_3$;
X is Cl;
$R^2$ is —$CH_3$;
$R^3$ is pyrimidinyl or pyridinyl, each of which is optionally substituted with 1 or 2 $R^4$;
$R^4$ is halo, —$OC_{1-3}$alkyl, or 4- to 6-membered monocyclic heterocyclyl, wherein the 4- to 6-membered monocyclic heterocyclyl is optionally substituted with 1 or 2 halo or $C_{1-3}$haloalkyl.

2. The compound of claim 1, or a pharmaceutically acceptable salt thereof, wherein $R^3$ is represented by the following structural formula:

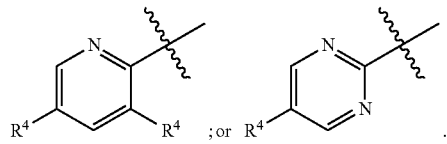

3. The compound of claim 2, or a pharmaceutically acceptable salt thereof, wherein each $R^4$ is independently —F, —$OCH(CH_3)_2$, or —$OC(CH_3)_3$, or $R^4$ is represented by the following structural formula:

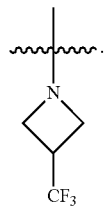 [SMILES: *N1CC(C(F)(F)F)C1]

4. The compound of claim 1, wherein the compound is:

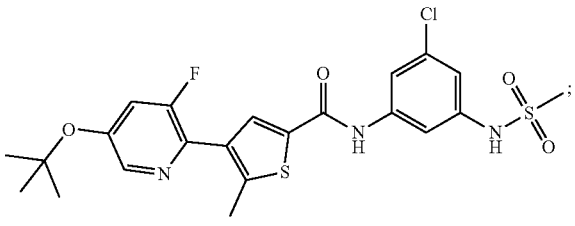 [SMILES: Cc1sc(C(=O)Nc2cc(Cl)cc(NS(C)(=O)=O)c2)cc1-c1ncc(OC(C)(C)C)cc1F]

or a pharmaceutically acceptable salt thereof.

5. The compound of claim 1, wherein the compound is:

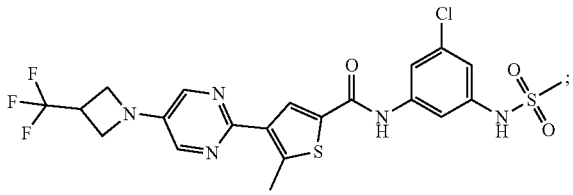 [SMILES: Cc1sc(C(=O)Nc2cc(Cl)cc(NS(C)(=O)=O)c2)cc1-c1ncc(N2CC(C(F)(F)F)C2)cn1]

or a pharmaceutically acceptable salt thereof.

6. The compound of claim 1, wherein the compound is:

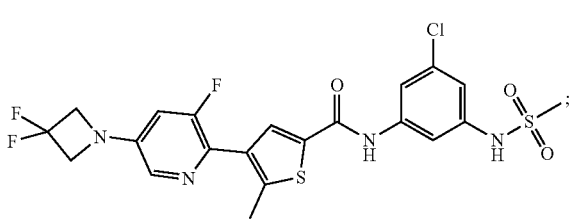 [SMILES: Cc1sc(C(=O)Nc2cc(Cl)cc(NS(C)(=O)=O)c2)cc1-c1ncc(N2CC(F)(F)C2)cc1F]

or a pharmaceutically acceptable salt thereof.

7. The compound of claim 1, wherein the compound is:

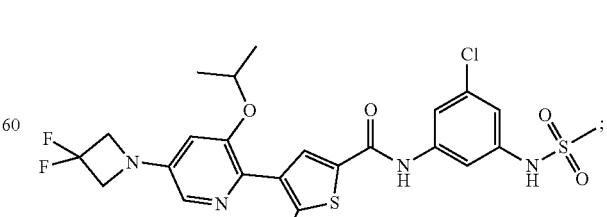

or a pharmaceutically acceptable salt thereof.

8. The compound of claim 1, wherein the compound is:

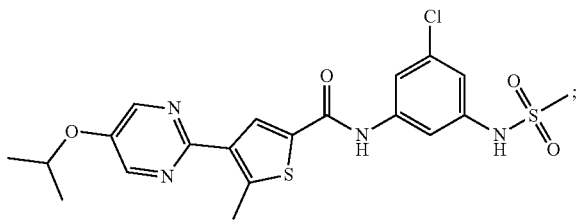 [SMILES: Cc1sc(C(=O)Nc2cc(Cl)cc(NS(C)(=O)=O)c2)cc1-c1ncc(OC(C)C)cn1]

or a pharmaceutically acceptable salt thereof.

9. The compound of claim 1, wherein the compound is:

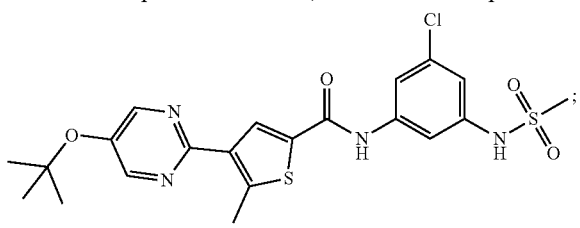

or a pharmaceutically acceptable salt thereof.

10. A pharmaceutical composition comprising a compound of claim 1, or a pharmaceutically acceptable salt thereof, and a pharmaceutically acceptable excipient.

11. A pharmaceutical composition comprising a compound of claim 4, or a pharmaceutically acceptable salt thereof, and a pharmaceutically acceptable excipient.

12. A pharmaceutical composition comprising a compound of claim 5, or a pharmaceutically acceptable salt thereof, and a pharmaceutically acceptable excipient.

13. A pharmaceutical composition comprising a compound of claim 6, or a pharmaceutically acceptable salt thereof, and a pharmaceutically acceptable excipient.

14. A pharmaceutical composition comprising a compound of claim 7, or a pharmaceutically acceptable salt thereof, and a pharmaceutically acceptable excipient.

15. A pharmaceutical composition comprising a compound of claim 8, or a pharmaceutically acceptable salt thereof, and a pharmaceutically acceptable excipient.

16. A pharmaceutical composition comprising a compound of claim 9, or a pharmaceutically acceptable salt thereof, and a pharmaceutically acceptable excipient.

* * * * *